(12) United States Patent
Kobayashi et al.

(10) Patent No.: US 6,747,023 B1
(45) Date of Patent: Jun. 8, 2004

(54) SULFONYL DERIVATIVES

(75) Inventors: Syozo Kobayashi, Tokyo (JP); Satoshi Komoriya, Tokyo (JP); Noriyasu Haginoya, Tokyo (JP); Masanori Suzuki, Tokyo (JP); Toshiharu Yoshino, Tokyo (JP); Takayasu Nagahara, Tokyo (JP); Tsutomu Nagata, Tokyo (JP); Haruhiko Horino, Tokyo (JP); Masayuki Ito, Tokyo (JP); Akiyoshi Mochizuki, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 09/762,888

(22) PCT Filed: Aug. 11, 1999

(86) PCT No.: PCT/JP99/04344

§ 371 (c)(1),
(2), (4) Date: Feb. 12, 2001

(87) PCT Pub. No.: WO00/09480

PCT Pub. Date: Feb. 24, 2000

(30) Foreign Application Priority Data

| | | |
|---|---|---|
| Aug. 11, 1998 | (JP) | 10/227449 |
| Aug. 28, 1998 | (JP) | 10/244175 |
| Sep. 4, 1998 | (JP) | 10/251674 |

(51) Int. Cl.$^7$ ................ C07D 513/04; A61K 31/542; A61P 7/02
(52) U.S. Cl. .................................. 514/224.2; 544/48
(58) Field of Search ..................... 544/48; 514/224.2

*Primary Examiner*—Richard L. Raymond
*Assistant Examiner*—Kahsay Habte
(74) *Attorney, Agent, or Firm*—Oblon, Spivak, McClelland, Maier & Neustadt, P.C.

(57) ABSTRACT

Described in the present invention are a sulfonyl derivative represented by the following formula (I):

$$Q^1—Q^2—T^1—Q^3—SO_2—Q^4 \qquad (I)$$

[wherein $Q^1$ represents a saturated or unsaturated 5- or 6-membered cyclic hydrocarbon group, 5- or 6-membered heterocyclic group, dicyclic fused ring or tricyclic fused ring group which may have a substituent;

$Q^2$ represents a single bond, an oxygen atom, a sulfur atom, a linear or branched $C_{1-6}$ alkylene group or the like;

$Q^4$ represents an arylalkenyl group which may have a substituent or a heteroarylalkenyl group which may have a substituent; and $T^1$ represents a carbonyl group or the like] and a medicament comprising the same. The compound has strong FXa inhibitory action, provides prompt, sufficient and long-lasting anti-thrombus effects when orally administered, and has low side effects and is therefore useful as an excellent anticoagulant.

24 Claims, No Drawings

SULFONYL DERIVATIVES

TECHNICAL FIELD

The present invention relates to a novel, orally-administrable sulfonyl derivative or salt thereof which inhibits an activated coagulation factor X (which will hereinafter be abbreviated as "FXa"), thereby exhibiting strong anticoagulant action; and a coagulation suppressor or preventive and/or remedy for thrombosis or embolism which comprises the derivative or salt as an effective ingredient.

BACKGROUND ART

Exasperation of coagulation activity is an important factor for unstable angina, cerebral infarction, cerebral embolism, myocardial infarction, pulmonary infarction, pulmonary embolism, Buerger's disease, deep vein thrombosis, disseminated intravascular coagulation syndrome, thrombus formation after valve replacement, reocclusion after revascularization or formation of thrombus upon extracorporeal circulation. There is accordingly a demand for an excellent anticoagulant which is excellent in dose-responsiveness, has long-lasting effects, has a low risk of hemorrhage, has less side effects and exhibits rapid and sufficient effects even by oral administration (Thrombosis Research, 68, 507–512, 1992).

Studies on anticoagulants based on various acting mechanisms suggest that a FXa inhibitor has a possibility of becoming an excellent anticoagulant. The coagulation system is a series of reactions wherein a large amount of a thrombus is produced through an amplification step due to a multi-stage enzymatic reaction and induces the formation of insoluble fibrin. In the intrinsic system, after the multi-stage reaction following the activation of a contact factor, activated Factor IX activates factor X on a phospholipid membrane in the presence of activated Factor VIII and a calcium ion, while in the extrinsic system, activated Factor VII activates Factor X in the presence of a tissue factor. In other words, the activation of Factor X into FXa in the coagulation system is an essential reaction in the formation of thrombin. Activated Factor X (FXa) in each system carries out limited proteolysis of prothrombin, thereby forming thrombin. The resulting thrombin activates the coagulation factors on the upstream side, whereby the formation of thrombin is amplified further. As described above, the coagulation system upstream of FXa is separated into intrinsic and extrinsic systems so that the inhibition of the enzyme of the coagulation system upstream of FXa does not suppress the production of FXa sufficiently, inevitably resulting in the production of thrombin. Furthermore, the coagulation occurs as a self-amplifying reaction so that the suppression of the coagulation system can be accomplished more efficiently by the inhibition of FXa which exists upstream of the thrombin than by the inhibition of the thrombin formed (Thrombosis Research, 15, 617–629(1979)).

Another merit of the FXa inhibitor is that an effective dose in a thrombus model is largely different from the dose for extending the bleeding time in an experimental hemorrhage model. From the experimental result, the FXa inhibitor is presumed to be an anticoagulant with a low risk of hemorrhage.

As a FXa inhibitor, various compounds are reported. In general, antithrombin III or antithrombin III-dependent penta-saccharide is known to have no inhibitory action against a prothrombinase complex which plays a practical role in the thrombus formation in vivo (Thrombosis Research, 68, 507–512(1992); Journal of Clinical Investigation, 71, 1383–1389(1983); Mebio, August issue, 92–97) and moreover, it does not exhibit effectiveness in oral administration. Although tick anticoagulant peptide (TAP) (Science, 248, 593–596(1990)) or antistacin (AST) (Journal of Biological Chemistry, 263, 10162–10167(1988)) isolated from a tick or leech which is a bloodsucker inhibits FXa and exhibits anti-thrombus effects on the models of from venous thrombus to arterial thrombus, it is not effective when orally administered because it is a high-molecular peptide. From such a viewpoint, a low-molecular FXa inhibitor which directly inhibits a coagulation factor without depending on antithrombin III has been developed.

An object of the present invention is to provide, as an excellent anticoagulant, a novel sulfonyl derivative or salt thereof, or a solvate thereof which has strong FXa inhibitory action, exhibits prompt, sufficient and long-lasting anti-thrombus effects even by the oral administration and has less side effects.

DISCLOSURE OF THE INVENTION

With the forgoing in view, the present inventors have carried out an extensive investigation on the synthesis of a novel FXa inhibitor and its pharmacological action. As a result, it has been found that a novel sulfonyl derivative or salt thereof, or solvate thereof exhibits strong FXa inhibitory activity and strong anticoagulant activity, inhibits FXa strongly, promptly and continuously by the oral administration, exhibits anti-coagulant action and anti-thrombus action, is highly safe and is useful as a preventive or remedy for various diseases caused by a thrombus embolus.

The present invention relates to a sulfonyl derivative represented by the below-described formula (I) or salt thereof, or a solvate thereof:

Chemical formula (I):

[wherein, $Q^1$ represents a saturated or unsaturated 5- or 6-membered cyclic hydrocarbon group which may have a substituent, a saturated or unsaturated 5- or 6-membered heterocyclic group which may have a substituent, a saturated or unsaturated dicyclic fused ring group which may have a substituent or a saturated or unsaturated tricyclic fused ring group which may have a substituent;

$Q^2$ represents a single bond, an oxygen atom, a sulfur atom, a linear or branched $C_{1-6}$ alkylene group, a linear or branched $C_{2-6}$ alkenylene group, a linear or branched $C_{2-6}$ alkynylene group,

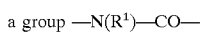

(in which $R^1$ represents a hydrogen atom or an alkyl group),

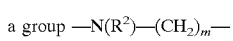

(in which $R^2$ represents a hydrogen atom or an alkyl group and m stands for an integer of 0 to 6), or a group of the following formula:

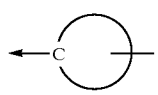

(which represents a divalent, saturated or unsaturated 5- or 6-membered cyclic hydrocarbon group which may have a substituent, a divalent, saturated or unsaturated 5- or 6-membered heterocyclic group which may have a substituent or a divalent, saturated or unsaturated dicyclic fused ring group which may have a substituent and ←C means the bonding of the carbon atom of this group to $Q^1$), $Q^3$ represents any one of the following groups:

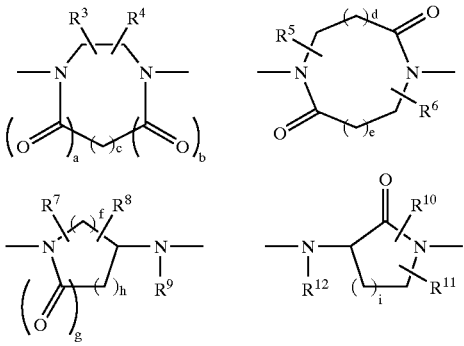

(in which when the carbon atom to which each of $R^3$, $R^4$, $R^5$, $R^6$, $R^7$, $R^8$, $R^{10}$ and $R^{11}$ has been bonded is not adjacent to a nitrogen atom, $R^3$, $R^4$, $R^5$, $R^6$, $R^7$, $R^8$, $R^{10}$ and $R^{11}$ each independently represents a hydrogen atom,
  a hydroxyl group,
  an alkyl group,
  an alkoxyl group,
  an alkoxyalkyl group,
  an alkoxyalkyloxy group,
  a hydroxyalkyl group,
  a hydroxyalkyloxy group,
  a hydroxyalkylcarbonyl group,
  a hydroxyalkylsulfonyl group,
  a formyl group,
  a formylalkyl group,
  a formylalkylcarbonyl group,
  a formylalkylsulfonyl group,
  an alkylcarbonyl group,
  an alkylsulfonyl group,
  an alkylcarbonylalkyl group,
  an alkylsulfonylalkyl group,
  a carboxyl group,
  a carboxyalkyl group,
  a carboxyalkyloxy group,
  a carboxyalkylcarbonyl group,
  a carboxyalkylsulfonyl group,
  a carboxyalkylcarbonylalkyl group,
  a carboxyalkylsulfonylalkyl group,
  an alkoxycarbonyl group,
  an alkoxycarbonylalkyl group,
  an alkoxycarbonylalkyloxy group,
  an alkoxycarbonylalkylcarbonyl group,
  an alkoxycarbonylalkylsulfonyl group,
  an amino group which may have one or two substituents,
  an aminoalkyl group which may have, at the amino moiety thereof, one or two substituents,
  an aminoalkyloxy group which may have, at the amino moiety thereof, one or two substituents,
  an aminoalkylcarbonyl group which may have, at the amino moiety thereof, one or two substituents,
  an aminoalkylcarbonyloxy group which may have, at the amino moiety thereof, one or two substituents,
  an aminocarbonyl group which may have, at the amino moiety thereof, one or two substituents,
  an aminocarbonylalkyl group which may have, at the amino moiety thereof, one or two substituents,
  an aminocarbonylalkyloxy group which may have, at the amino moiety thereof, one or two substituents,
  an alkylsulfonylaminocarbonylalkyl group which may have, at the amino moiety thereof, one substituent,
  an arylsulfonylaminocarbonyl group which may have, at the amino moiety thereof, one substituent,
  an aminosulfonylalkyl group which may have, at the amino moiety thereof, one or two substituents,
  a cyanoalkyl group,
  an alkoxyalkylaminocarbonylalkyl group which may have, at the amino moiety thereof, one substituent,
  an alkylcarbonyloxyalkyl group, or
  a group $A^1—B^1—$ (in which $A^1$ represents a saturated or unsaturated 5- or 6-membered cyclic hydrocarbon group which may have a substituent or a saturated or unsaturated 5- or 6-membered heterocyclic group which may have a substituent and $B^1$ represents a single bond, a carbonyl group, an alkylene group, a carbonylalkyl group, a group $—O—(C_{1-6}$ alkylene), a group $—COO—(C_{1-6}$ alkylene), a group $—NHCO—$ or a group $—NHCO—(C_{1-6}$ alkylene), when the carbon atom to which each of $R^3$, $R^4$, $R^5$, $R^6$, $R^7$, $R^8$, $R^{10}$ and $R^{11}$ has been bonded is adjacent to a nitrogen atom, $R^3$, $R^4$, $R^5$, $R^6$, $R^7$, $R^8$, $R^{10}$ and $R^{11}$ each independently represents
  a hydrogen atom,
  an alkyl group,
  a hydroxyalkyl group,
  a hydroxyalkylcarbonyl group,
  a hydroxyalkylsulfonyl group,
  a formyl group,
  a formylalkyl group,
  a formylalkylcarbonyl group,
  a formylalkylsulfonyl group,
  an alkylcarbonyl group,
  an alkylsulfonyl group,
  an alkylcarbonylalkyl group,
  an alkylsulfonylalkyl group,
  a carboxyl group,
  a carboxyalkyl group,
  a carboxyalkylcarbonyl group,
  a carboxyalkylsulfonyl group,
  a carboxyalkylcarbonylalkyl group,
  a carboxyalkylsulfonylalkyl group,
  an alkoxyalkyl group,
  an alkoxycarbonyl group,
  an alkoxycarbonylalkyl group,
  an alkoxycarbonylalkylcarbonyl group,
  an alkoxycarbonylalkylsulfonyl group,
  an aminoalkyl group which may have, at the amino moiety thereof, one or two substituents,
  an aminoalkylcarbonyl group which may have, at the amino moiety thereof, one or two substituents,
  an aminocarbonyl group which may have, at the amino moiety thereof, one or two substituents,
  an aminocarbonylalkyl group which may have, at the amino moiety thereof, one or two substituents
  an alkylsulfonylaminocarbonylalkyl group which may have, at the amino moiety thereof, one substituent,
  an arylsulfonylaminocarbonyl group which may have, at the amino moiety thereof, one substituent,
  an aminosulfonylalkyl group which may have, at the amino moiety thereof, one or two substituents,
  a cyanoalkyl group,
  an alkoxyalkylaminocarbonylalkyl group which may have, at the amino moiety thereof, one substituent,
  an alkylcarbonyloxyalkyl, or
  a group $A^2—B^2—$ (in which $A^2$ represents a saturated or unsaturated 5- or 6-membered cyclic hydrocarbon group which may have a substituent or a saturated or unsaturated 5- or 6-membered heterocyclic group which may have a substituent, and $B^2$ represents a single bond, a carbonyl group, an alkylene group, a carbonylalkyl group, a group —O—($C_{1-6}$ alkylene), a group —COO—($C_{1-6}$ alkylene), a group —NHCO— or a group —NHCO—($C_{1-6}$ alkylene group), each of $R^3$ and $R^4$, $R^5$ and $R^6$, $R^7$ and $R^8$, and $R^{10}$ and $R^{11}$ may be coupled together with a carbon atom which constitutes the ring and represent a saturated or unsaturated 5- to 7-membered cyclic hydrocarbon group which may have a substituent or a saturated or unsaturated 5- to 7-membered heterocyclic group which may have a substituent, $R^9$ and $R^{12}$ each independently represents:

a hydrogen atom,
an alkyl group,
a hydroxyalkyl group,
a hydroxyalkylcarbonyl group,
a hydroxyalkylsulfonyl group,
an alkoxyl group,
an alkoxyalkyl group,
an alkoxyalkylcarbonyl group,
an alkoxyalkylsulfonyl group,
a formyl group,
a formylalkyl group,
a formylalkylcarbonyl group,
a formylalkylsulfonyl group,
an alkylcarbonyl group,
an alkylcarbonylalkyl group,
an alkylsulfonyl group,
an alkylsulfonylalkyl group,
a carboxyalkyl group,
a carboxyalkylcarbonyl group,
a carboxyalkylsulfonyl group,
a carboxyalkylcarbonylalkyl group,
a carboxyalkylsulfonylalkyl group,
an alkoxycarbonyl group,
an alkoxycarbonylalkyl group,
an alkoxycarbonylalkylcarbonyl group,
an alkoxycarbonylalkylsulfonyl group,
an amino group which may have one or two substituents,
an aminoalkyl group which may have, at the amino moiety thereof, one or two substituents
an aminoalkyloxy group which may have, at the amino moiety thereof, one or two substituents,
an aminoalkylcarbonyl group which may have, at the amino moiety thereof, one or two substituents,
an aminoalkyloxycarbonyl group which may have, at the amino moiety thereof, one or two substituents,
an aminocarbonyl group which may have, at the amino moiety thereof, one or two substituents,
an aminocarbonylalkyl group which may have, at the amino moiety thereof, one or two substituents,
an aminocarbonyloxyalkyl group which may have, at the amino moiety thereof, one or two substituents,
an alkylsulfonylaminocarbonylalkyl group which may have, at the amino moiety thereof, one substituent,
an arylsulfonylaminocarbonyl group which may have, at the amino moiety thereof, one substituent,
an aminosulfonylalkyl group which may have, at the amino moiety thereof, one or two substituents,
a cyanoalkyl group,
an alkoxyalkylaminocarbonylalkyl group which may have, at the amino moiety thereof, one substituent, or
an alkylcarbonyloxyalkyl, $R^9$ and $R^7$ or $R^8$ may be coupled together with a carbon atom constituting the ring and a nitrogen atom to which $R^9$ has been bonded and represent a saturated or unsaturated 5- to 7-membered heterocyclic group which may have a substituent, $R^{12}$ and $R^{10}$ or $R^{11}$ may be coupled together with a carbon atom constituting the ring and a nitrogen atom to which $R^{12}$ has been bonded and represent a saturated or unsaturated 5- to 7-membered heterocyclic group which may have a substituent, a, b, d, e and g each independently stands for an integer of 0 or 1, c stands for an integer of 0 to 3, and f, h and i each independently represents an integer of 1 to 3, with the proviso that the sum of a, b and c stands for an integer of 2 or 3, the sum of d and e stands for an integer of 0 or 1 and the sum of f, g and h stands for an integer of 3 to 5), $Q^A$ represents an arylalkenyl group which may have a substituent, a heteroarylalkenyl group which may have a substituent, a saturated or unsaturated dicyclic fused ring group which may have a substituent, a saturated or unsaturated tricyclic fused ring group which may have a substituent, a group Ar—C(H)=N— (in which, Ar represents an aryl group which may have a substituent), or a group Het-C(H)=N— (in which, Het represents a heteroaryl group which may have a substituent), and $T^1$ represents a carbonyl group, a group —CH($R^{13}$)—

(in which $R^{13}$ represents a hydrogen atom, an alkyl group, a hydroxyalkyl group having the hydroxyl group which may be protected, an alkoxyalkyl group, a carboxyalkyl group, an alkoxycarbonylalkyl group, an aryl group, an aralkyl group, a heteroaryl group, a heteroarylalkyl group or an aminoalkyl group which may have, at the amino moiety thereof, a substituent (protecting group)), or a group —C(=NOR$^{14}$)— or —C(=N—NHR$^{14'}$)—

(in which $R^{14}$ and $R^{14'}$ each independently represents a hydrogen atom, an alkyl group, a carboxyalkyl group, an alkoxycarbonyl group, an aryl group, an aralkyl group, a heteroaryl group, a heteroarylalkyl group or an aminoalkyl group which may have, at the amino moiety thereof, a substituent.

The present invention also provides a pharmaceutical comprising as an effective ingredient a sulfonyl derivative represented by the above-described formula (I) or salt thereof, or a solvate thereof.

The present invention also provides a pharmaceutical composition comprising a sulfonyl derivative represented by the above-described formula (I) or salt thereof, or a solvate thereof and a pharmaceutically acceptable carrier.

The present invention also provides use of a sulfonyl derivative represented by the above-described formula (I) or salt thereof, or a solvate thereof as a pharmaceutical.

The present invention also provides a method for treating diseases caused by FXa, blood coagulating diseases and various diseases due to thrombosis or embolism, which comprises administering a sulfonyl derivative represented by the above-described formula (I) or salt thereof, or a solvate thereof.

BEST MODES FORM CARRYING OUT THE INVENTION

A description will next be made of the substituents in the sulfonyl group derivative of the formula (I) according to the present invention.

<About group $Q^A$>

$Q^A$ represents an arylalkenyl group which may have a substituent, a heteroarylalkenyl group which may have a substituent, a saturated or unsaturated dicyclic fused ring group which may have a substituent, a saturated or unsaturated tricyclic fused ring group which may have a substituent, a group Ar—C(H)=N— (in which, Ar represents an aryl group which may have a substituent), or a group Het-C(H)=N— (in which, Het represents a heteroaryl group which may have a substituent).

In the group $Q^A$, the term "arylalkenyl group which may have a substituent" means a group composed of an aryl group and a linear, branched or cyclic $C_{2-6}$ alkenylene group. Examples of the aryl group include phenyl, naphthyl, anthryl and phenanthryl group. Examples of the arylalkenyl group include phenylethenyl group.

The "heteroarylalkenyl group which may have a substituent" means a group composed of a heteroaryl group and a linear, branched or cyclic $C_{2-6}$ alkenylene group. The "heteroaryl group" means an aromatic monovalent group having at least one hetero atom and examples include pyridyl, furyl and thienyl groups. Examples of the heteroarylalkenyl group include pyridylethenyl group.

The "saturated or unsaturated, dicyclic or tricyclic fused ring group which may have a substituent" means: 1) a group obtained by the condensation of saturated or unsaturated 5- or 6-membered cyclic hydrocarbon groups which may have a substituent, 2) a group obtained by the condensation of a saturated or unsaturated 5- or 6-membered cyclic hydrocarbon group which may have a substituent and a saturated or unsaturated 5- or 6-membered heterocyclic group which may have a substituent and 3) a group obtained by the condensation of saturated or unsaturated 5- or 6-membered heterocyclic groups which may have a substituent.

Examples of the saturated or unsaturated 5- or 6-membered cyclic hydrocarbon group include cyclopentyl, cyclopentenyl, cyclopentadienyl, cyclohexyl, cyclohexenyl, cyclohexadienyl and phenyl groups. When the group has plural structural isomers as the cyclopentenyl group, they are all embraced in it.

The saturated or unsaturated 5- or 6-membered heterocyclic group is a cyclic group having at least one hetero atom. Examples of the hetero atom include oxygen, nitrogen and sulfur. Examples of the saturated or unsaturated 5- or 6-membered heterocyclic group include furyl, pyrrolyl, thienyl, pyrazolyl, imidazolyl, pyrazolinyl, oxazolyl, oxazolinyl, thiazolyl, thiazolinyl, oxatriazolyl, thiadiazolyl, furazanyl, pyranyl, pyridyl, pyridazinyl, pyrrolidinyl, piperazinyl, piperidinyl, oxazinyl, oxadiazinyl, morpholinyl, thiazinyl, thiadiazinyl, thiomorpholinyl, tetrazolyl, triazolyl and triazinyl. Where the group has plural structural isomers as the pyranyl, it is to be noted that they are all embraced in it.

Examples of the group 1) include indenyl, indanyl, naphthyl, tetrahydronaphthyl, anthryl and phenanthryl; those of the group 2) include benzofuranyl, benzothienyl, indolyl, indolinyl, quinolyl, benzodiazinyl, tetrahydroisoquinolyl, benzothiazolyl, tetrahydrobenzothiazolyl and isoindolyl; and those of the group 3) include naphthyridinyl, tetrahydrothienopyridyl, tetrahydrothiazolopyridyl, tetrahydropyridopyridyl, thiazolopyridazinyl, tetrahydrothiazolopyridazinyl, pyrrolopyridyl, tetrahydropyrrolopyridyl, dihydropyridoquinazolinyl, pyridopyrimidinyl, tetrahydropyridopyrimidinyl, pyranothiazolyl, dihydropyranothiazolyl, furopyridyl, tetrahydrofuropyridyl, oxazolopyridyl, and tetrahydrooxazolopyridyl.

The aryl group in the group Ar—C(H)=N (wherein Ar represents an aryl group which may have a substituent) means an aryl group similar to that described above. The group Ar—C(CH)=N— means a group composed of a phenyl group which may have a substituent and a group —C(H)=N— or the like.

The heteroaryl group in the group Het-C(H)=N— (wherein Het represents a heteroaryl group which may have a substituent) means a heteroaryl group similar to that described above. The group Het-C(H)=N— means a group composed of a pyridyl group which may have a substituent and a group Het-C(H)=N—.

Each of the arylalkenyl group, heteroarylalkenyl group, saturated or unsaturated dicyclic fused ring group, saturated or unsaturated tricyclic fused ring group, the group Ar—C(H)=N— and the group Het-C(H)=N— may have one or two substituents. Examples of the substituent include a hydroxyl group, halogen atoms such as fluorine, chlorine, bromine and iodine, halogenomethyl groups having 1 to 3 halogen atoms substituted, an amino group, a cyano group, an aminomethyl group, an amidino group, a hydroxyamidino group, linear, branched or cyclic $C_{1-6}$ alkyl groups (ex. methyl and ethyl), linear, branched or cyclic $C_{1-6}$ alkoxyl groups (ex. methoxyl and ethoxyl), linear, branched or cyclic $C_{2-7}$ alkoxycarbonylamidino groups (ex. methoxycarbonylamidino and ethoxycarbonylamidino), linear, branched or cyclic $C_{2-6}$ alkenyl groups (ex. vinyl and allyl), linear, branched or cyclic $C_{2-6}$ alkynyl groups (ex. ethynyl and propynyl), linear, branched or cyclic $C_{2-6}$ alkoxycarbonyl groups (ex. methoxycarbonyl and ethoxycarbonyl) and aminocarbonyl groups.

More specifically, the group $Q^A$ represents any one of the following groups.

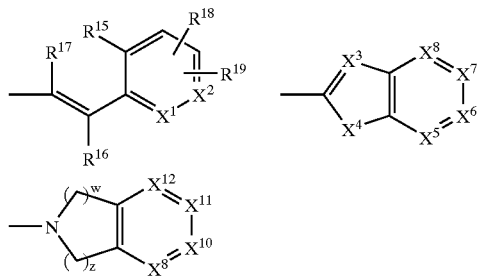

A description will next be made of the substituent in these groups.

In the group

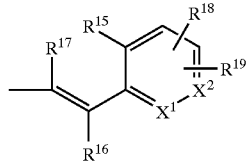

$R^{15}$ represents a hydrogen atom, a hydroxyl group, a nitro group, a cyano group, a halogen atom, an alkyl group, a hydroxyalkyl group, an alkoxyl group, an alkoxyalkyl group, a carboxyl group, a carboxyalkyl group, an alkylcarbonyl group, an alkoxycarbonyl group, an alkoxycarbonylalkyl group, an alkylcarbonyloxy group or a group $A^3$—$B^3$ (wherein, $A^3$ represents an amino group which may have one or two substituents, a saturated or unsaturated 5- or 6-membered cyclic hydrocarbon group which may have a substituent or a saturated or unsaturated 5- or 6-membered heterocyclic group which may have a substituent and $B^3$ represents a single bond, a carbonyl group, an alkylene group, a carbonylalkyl group, a carbonylalkyloxy group or an alkylenecarbonyloxy group).

In $R^{15}$, examples of the halogen atom include fluorine, chlorine, bromine and iodine.

Examples of the alkyl group include linear, branched or cyclic $C_{1-6}$ alkyl groups such as methyl, ethyl, isopropyl and cyclopropyl.

The "hydroxyalkyl group" means a group composed of a hydroxyl group and a linear, branched or cyclic $C_{1-6}$ alkylene group. Examples of the alkylene group include methylene, ethylene, trimethylene, propylene and cyclohexylene. Examples of the hydroxyalkyl group include hydroxymethyl and hydroxyethyl.

The "alkoxyl group" means a group formed of the above-described $C_{1-6}$ alkyl group and an oxygen atom. Examples include methoxyl, ethoxyl and isopropoxyl.

The "alkoxyalkyl group" means a group formed of a linear, branched or cyclic $C_{1-6}$ alkoxyl group and a linear, branched or cyclic $C_{1-6}$ alkylene group. Examples include methoxymethyl, methoxyethyl and ethoxymethyl.

The "carboxyalkyl group" means a group formed of a carboxyl group and a linear, branched or cyclic $C_{1-6}$ alkylene group. Examples include carboxymethyl and carboxyethyl.

The "alkylcarbonyl group" means a group formed of a linear, branched or cyclic $C_{1-6}$ alkyl group and a carbonyl group. Examples include methylcarbonyl and ethylcarbonyl.

The "alkoxycarbonyl group" means a group formed of a linear, branched or cyclic alkoxyl group and a carbonyl group. Examples include methoxycarbonyl and ethoxycarbonyl.

The "alkoxycarbonylalkyl group" means a group formed of a linear, branched or cyclic $C_{2-7}$ alkoxycarbonyl group and a linear, branched or cyclic $C_{1-6}$ alkylene group. Examples include methoxycarbonylethyl and ethoxycarbonylmethyl.

The "alkylcarbonyloxy group" means a group formed of a linear, branched or cyclic $C_{2-7}$ alkylcarbonyl group and an oxygen atom. Examples include methylcarbonyloxy, ethylcarbonyloxy and isopropylcarbonyloxy.

In the group $A^3$—$B^3$—, $A^3$ means an amino group which may have one or two substituents, a saturated or unsaturated 5- or 6-membered cyclic hydrocarbon group which may have a substituent or a saturated or unsaturated 5- or 6-membered heterocyclic group which may have a substituent.

When $A^3$ means an amino group which may have one or two substituents, $B^3$ represents a single bond, a carbonyl group, an alkylene group, a carbonylalkyl group, a carbonylalkyloxy group or an alkylenecarbonyloxy group. The group $A^3$—$B^3$— therefore means, for example, a group as shown in the following class (A).

Class (A):
an amino group which may have one or two substituents,
an aminocarbonyl group which may have, at the amino moiety thereof, one or two substituents,
an aminoalkyl group which may have, at the amino moiety thereof, one or two substituents,
an aminocarbonylalkyl group which may have, at the amino moiety thereof, one or two substituents,
an aminocarbonylalkyloxy group which may have, at the amino moiety thereof, one or two substituents,
an aminoalkylcarbonyl group which may have, at the amino moiety thereof, one or two substituents and
an aminoalkylcarbonyloxy group which may have, at the amino moiety thereof, one or two substituents.

A description will next be made of the groups shown in Class (A).

The "aminocarbonyl group which may have, at the amino moiety thereof, one or two substituents" means a group formed of an amino group which may have one or two substituents and a carbonyl group.

The "aminoalkyl group which may have, at the amino moiety thereof, one or two substituents" means a group formed of an amino group which may have one or two substituents and a linear, branched or cyclic $C_{1-6}$ alkylene group. Examples of the aminoalkyl group include aminomethyl and aminoethyl.

The "aminocarbonylalkyl group which may have, at the amino moiety thereof, one or two substituents" means a group formed of the above-described aminocarbonyl group and a linear, branched or cyclic $C_{1-6}$ alkylene group. Examples of the aminocarbonylalkyl group include aminocarbonylmethyl and aminocarbonylethyl.

The "aminocarbonylalkyloxy group which may have, at the amino moiety, one or two substituents" means a group formed of the above-described aminocarbonylakyl group which may have a substituent and an oxygen atom. Examples of the aminocarbonylalkyloxy group include aminocarbonylmethoxyl and aminocarbonylethoxyl.

The "aminoalkylcarbonyl group which may have, at the amino moiety thereof, one or two substituents" means a group formed of the above-described aminoalkyl group which may have a substituent and a carbonyl group. Examples of the aminoalkylcarbonyl group include aminomethylcarbonyl and aminoethylcarbonyl.

The "aminoalkylcarbonyloxy group which may have, at the amino moiety thereof, one or two substituents" means a group formed of the above-described aminoalkylcarbonyl group which may have a substituent and an oxygen atom. Examples of the aminoalkylcarbonyloxy group include aminomethylcarbonyloxy and aminoethylcarbonyloxy.

Examples of the substituent which can be substituted for an amino group (moiety) include those as shown in the following Class (1).

Class (1):
an alkyl group,
an alkenyl group,
a halogenoalkyl group,
a halogenoalkenyl group,
a hydroxyalkyl group,
a hyroxyalkylcarbonyl group,
a hydroxyalkylsulfonyl group,
an alkoxyl group,
an alkoxyalkyl group,
an alkoxyalkylcarbonyl group,
an alkoxyalkylsulfonyl group,
a formyl group,
a formylalkyl group,
a formylalkylcarbonyl group,
a formylalkylsulfonyl group,
an alkylcarbonyl group,
an alkylcarbonylalkyl group,
an alkylsulfonyl group,
an alkylsulfonylalkyl group,
a carboxyalkyl group,
a carboxyalkylcarbonyl group,
a carboxyalkylsulfonyl group,
a carboxyalkylcarbonylalkyl group,
a carboxyalkylsulfonylalkyl group,
an alkoxycarbonyl group,
an alkoxycarbonylalkyl group,
an alkoxycarbonylalkylcarbonyl group,
an alkoxycarbonylalkylsulfonyl group,
a trifluoromethylsulfonyloxyalkenyl group and
a group $a^3$-$b^3$-
(wherein $a^3$ represents a saturated or unsaturated 5- or 6-membered cyclic hydrocarbon group or saturated or unsaturated 5- or 6-membered heterocyclic group which may have one to three substituents selected from the group consisting of a halogen atom, a hydroxyl group, an amino group, an alkoxyl group, an alkyl group, a cyano group, a nitro group, a carboxyl group, an alkoxycarbonyl group and an aminocarbonyl group; and $b^3$ represents a single bond, a carbonyl group, an alkylene group, a carbonylalkyl group, a carbonylalkyloxy group, an alkylenecarbonyloxy group, an alkyleneaminocarbonyl group, an alkyleneaminocarbonylalkyl group, an alkyleneaminosulfonyl group or an alkyleneaminosulfonylalkyl group.

The substituents which can be substituted for an amino group (moiety) in Class (1) will next be described.

The "alkyl group" means a linear, branched or cyclic $C_{1-6}$ alkyl group.

The "alkenyl group" means a linear, branched or cyclic $C_{2-6}$ alkenyl group. Examples include vinyl and allyl.

The "halogenoalkyl group" means a group formed of a halogen atom and a linear, branched or cyclic $C_{1-6}$ alkylene group. Examples include chloromethyl and bromoethyl.

The "halogenoalkenyl group" means a group formed of a halogen atom and a linear or branched $C_{2-6}$ alkenylene group. Examples include chlorovinyl and bromoallyl groups. There is no particular limitation on the position of a double bond.

The "hydroxyalkyl group" means a group formed of a hydroxyl group and a linear, branched or cyclic $C_{2-6}$ alkylene group. Examples include hydroxyethyl and hydroxypropyl.

The "hydroxyalkylcarbonyl group" means a group formed of the above-described hydroxyalkyl group and a carbonyl group. Examples include hydroxymethylcarbonyl and hydroxyethylcarbonyl.

The "hydroxyalkylsulfonyl group" means a group formed of the above-described hydroxyalkyl group and a sulfonyl group. Examples include hydroxymethylsulfonyl and hydroxyethylsulfonyl. The "alkoxyl group" means a linear, branched or cyclic $C_{1-6}$ alkoxyl group.

The "alkoxyalkyl group" means a group formed of a linear, branched or cyclic $C_{1-6}$ alkoxyl group and a linear, branched or cyclic $C_{2-6}$ alkylene group. Examples include methoxyethyl, ethoxyethyl and methoxypropyl.

The "alkoxyalkylcarbonyl group" means a group formed of the above-described alkoxyalkyl group and a carbonyl group. Examples include methoxyethylcarbonyl and ethoxymethylcarbonyl.

The "alkoxyalkylsulfonyl group" means a group formed of the above-described alkoxyalkyl group and a sulfonyl group. Examples include methoxyethylsulfonyl and ethoxymethylsulfonyl.

The "formylalkyl group" means a group formed of a formyl group and a linear, branched or cyclic $C_{1-6}$ alkylene group. Examples include formylmethyl and formylethyl.

The "formylalkylcarbonyl group" means a group formed of the above-described formylalkyl group and a carbonyl group. Examples include formylmethylcarbonyl and formylethylcarbonyl.

The "formylalkylsulfonyl group" means a group formed of the above-described formylalkyl group and a sulfonyl group. Examples include formylmethylsulfonyl and formylethylsulfonyl.

The "alkylcarbonyl group" means a group formed of a linear, branched or cyclic $C_{1-6}$ alkyl group and a carbonyl group. Examples include methylcarbonyl and ethylcarbonyl.

The "alkylcarbonylalkyl group" means a group formed of the above-described alkylcarbonyl group and a linear, branched or cyclic $C_{1-6}$ alkylene group. Examples include is methylcarbonylmethyl and ethylcarbonylmethyl.

The "alkylsulfonyl group" means a group formed of the above-described alkyl group and a sulfonyl group. Examples include methylsulfonyl and ethylsulfonyl.

The "alkylsulfonylalkyl group" means a group formed of the above-described alkylsulfonyl group and a linear, branched or cyclic $C_{1-6}$ alkylene group. Examples include methylsulfonylmethyl and ethylsulfonylmethyl.

The "carboxyalkyl group" means a group composed of a carboxyl group and a linear, branched or cyclic $C_{1-6}$ alkylene group.

The "carboxyalkylcarbonyl group" means a group formed of the above-described carboxyalkyl group and a carbonyl group. Examples include carboxymethylcarbonyl and carboxyethylcarbonyl.

The "carboxyalkylsulfonyl group" means a group formed of the above-described carboxyalkyl group and a sulfonyl group. Examples include carboxymethylsulfonyl and carboxyethylsulfonyl.

The "carboxyalkylcarbonylalkyl group" means a group formed of the above-described carboxyalkylcarbonyl group and a linear, branched or cyclic $C_{1-6}$ alkylene group. Examples include carboxymethylcarbonylmethyl and carboxyethylcarbonylmethyl.

The "carboxyalkylsulfonylalkyl group" means a group formed of the above-described carboxyalkylsulfonyl group and a linear, branched or cyclic $C_{1-6}$ alkylene group. Examples include carboxymethylsulfonylmethyl and carboxyethylsulfonylmethyl.

The "alkoxycarbonyl group" means a group formed of a linear, branched or cyclic $C_{1-6}$ alkoxyl and a carbonyl group.

The "alkoxycarbonylalkyl group" means a group formed of the above-described alkoxycarbonyl group and a linear, branched or cyclic $C_{1-6}$ alkylene group.

The "alkoxycarbonylalkylcarbonyl group" means a group formed of the above-described alkoxycarbonylalkyl group and a carbonyl group. Examples include methoxycarbonylethylcarbonyl and ethoxycarbonylmethylcarbonyl.

The "alkoxycarbonylalkylsulfonyl group" means a group of the above-described alkoxycarbonylalkyl group and a sulfonyl group. Examples include methoxycarbonylethylsulfonyl and ethoxycarbonylmethylsulfonyl.

The "trifluoromethylsulfonyloxyalkenyl group" means a group formed of a trifluoromethylsulfonyloxy group and a linear or branched $C_{2-6}$ alkenylene group. Examples include trifluoromethylsulfonyloxyvinyl and trifluoromethylsulfonyloxyallyl.

In the group $a^3$-$b^3$-, $a^3$ represents a saturated or unsaturated 5- or 6-membered cyclic hydrocarbon group or saturated or unsaturated 5- or 6-membered heterocyclic group which may have a substituent such as a halogen atom. Examples of the saturated or unsaturated 5- or 6-membered cyclic hydrocarbon group include cyclopentyl, cyclopentenyl, cyclopentadienyl, cyclohexyl, cyclohexenyl, cyclohexadienyl and phenyl. Where the group has, as the cyclopentenyl, plural structural isomers, they are all embraced in it.

The saturated or unsaturated 5- or 6-membered heterocyclic group is a cyclic group having at least one hetero atom. Examples of the hetero atom include oxygen, nitrogen and sulfur. Examples of the saturated or unsaturated 5- or 6-membered heterocyclic group include furyl, pyrrolyl, thienyl, pyrazolyl, imidazolyl, pyrazolinyl, oxazolyl, oxazolinyl, thiazolyl, thiazolinyl, oxatriazolyl, thiadiazolyl, furazanyl, pyranyl, pyridyl, pyridazinyl, pyrrolidinyl, piperazinyl, piperidinyl, oxazinyl, oxadiazinyl, morpholinyl, thiazinyl, thiadiazinyl, thiomorpholinyl, tetrazolyl, triazolyl and triazinyl. Where the group has, as the pyranyl, plural structural isomers, they are all embraced in it.

$b^3$ represents a single bond or a divalent group such as carbonyl, alkylene, carbonylalkyl, carbonylalkyloxy, alkylenecarbonyloxy, alkyleneaminocarbonyl, alkyleneaminocarbonylalkyl, alkyleneaminosulfonyl or alkyleneaminosulfonylalkyl. The "alkylene group" means a linear, branched or cyclic $C_{1-6}$ alkylene group.

The "carbonylalkyl group" means a group formed of a carbonyl group and a linear, branched or cyclic $C_{1-6}$ alkylene group. Examples include carbonylmethyl and carbonylethyl.

The "carbonylalkyloxy group" means a group formed of the above-described carbonylalkyl group and an oxygen atom. Examples include carbonylmethoxy and carbonylethoxy.

The "alkylenecarbonyloxy group" means a group formed of a linear, branched or cyclic $C_{1-6}$ alkylene group, a carbonyl group and an oxygen atom. Examples include methylenecarbonyloxy and ethylenecarbonyloxy.

The "alkyleneaminocarbonyl group" means a group formed of a linear, branched or cyclic $C_{1-6}$ alkylene group, an imino group and a carbonyl group. Examples include methyleneaminocarbonyl and ethyleneaminocarbonyl.

The "alkyleneaminocarbonylalkyl group" means a group formed of the above-described alkyleneaminocarbonyl and a linear, branched or cyclic $C_{1-6}$ alkylene. Examples include methyleneaminocarbonylmethyl and ethyleneaminocarbonylmethyl.

The "alkyleneaminosulfonyl group" means a group formed of a linear, branched or cyclic $C_{1-6}$ alkylene group, an imino group and a sulfonyl group. Examples include methyleneaminosulfonyl and ethyleneaminosulfonyl.

The "alkyleneaminosulfonylalkyl group" means a group formed of the above-described alkyleneaminosulfonyl and a linear, branched or cyclic $C_{1-6}$ alkylene group. Examples include methyleneaminosulfonylmethyl and ethyleneaminosulfonylmethyl.

A description will next be made of the substituents which can be introduced into, as the above-described $a^3$, a saturated or unsaturated 5- or 6-membered cyclic hydrocarbon group or saturated or unsaturated 5- or 6-membered heterocyclic group. Examples include halogen atoms, an alkoxyl group, an alkyl group, an alkoxycarbonyl and an aminocarbonyl group.

As the group $a^3$-$b^3$-, there exist various kinds according to the combination of $a^3$ and $b^3$. Examples include:

a saturated or unsaturated, 5- or 6-membered cyclic hydrocarbon group which may have a substituent, a group formed of a saturated or unsaturated 5- or 6-membered heterocyclic group which may have a substituent and a carbonyl group, a group formed of a saturated or unsaturated 5- or 6-membered cyclic hydrocarbon group which may have a substituent and an alkylene group, a group formed of a saturated or unsaturated 5- or 6-membered heterocyclic group which may have a substituent and a carbonylalkyl group, a group formed of a saturated or unsaturated 5- or 6-membered cyclic hydrocarbon group which may have a substituent and a carbonylalkyloxy group, a group formed of a saturated or unsaturated 5- or 6-membered heterocyclic group which may have a substituent and a alkylenecarbonyloxy group, a group formed of a saturated or unsaturated 5- or 6-membered cyclic hydrocarbon group which may have a substituent and an alkyleneaminocarbonyl group, a group formed of a saturated or unsaturated 5- or 6-membered heterocyclic group which may have a substituent and an alkyleneaminocarbonylalkyl group, a group formed of a saturated or unsaturated 5- or 6-membered cyclic hydrocarbon group which may have a substituent and an alkyleneaminosulfonyl group, a group formed of a saturated or unsaturated 5- or 6-membered heterocyclic group which may have a substituent and an alkyleneaminosulfonylalkyl group, and the like.

In addition to the above-described Class (1), the following Class (2) can be given as examples of the substituent which can be substituted for the amino group (moiety).

Class (2):

an amino group which may have one or two substituents selected from Class (1), an aminoalkyl group which may have, at the amino moiety thereof, one or two substituents selected from Class (1), an aminocarbonyl group which may have, at the amino moiety thereof, one or two substituents selected from Class (1), an aminocarbonylalkyl group which may have, at the amino moiety thereof, one or two substituents selected from Class (1), an aminocarbonylalkylcarbonyl group which may have, at the amino moiety thereof, one or two substituents selected from Class (1), an aminocarbonylalkylsulfonyl group which may have, at the amino moiety thereof, one or two substituents selected from Class (1), an aminoalkylcarbonyl group which may have, at the amino moiety thereof, one or two substituents selected from Class (1), an aminosulfonyl group which may have, at the amino moiety thereof, one or two substituents selected from Class (1), an aminosulfonylalkyl group which may have, at the amino moiety thereof, one or two substituents selected from Class (1), an aminoalkylsulfonyl group which may have, at the amino moiety thereof, one or two substituents selected from Class (1), an aminosulfonylalkylcarbonyl group which may have, at the amino moiety thereof, one or two substituents selected from Class (1) and an aminosulfonylalkylsulfonyl group which may have, at the amino moiety thereof, one or two substituents selected is from Class (1).

A description will next be made of the substituents of Class (2).

The aminoalkyl, aminocarbonyl, aminocarbonylalkyl and aminoalkylcarbonyl groups in Class (2) have the same meanings as described above.

The "aminoalkyl group which may have a substituent at the amino moiety" means a group formed of an amino group which may have the above-described substituent and a linear, branched or cyclic $C_{2-6}$ alkylene group. Examples of the aminoalkyl group include aminoethyl and aminopropyl.

The "aminocarbonylalkylcarbonyl group which may have a substituent at the amino moiety" means a group formed of an aminocarbonylalkyl group which may have the above-described substituent and a carbonyl group. Examples of the aminocarbonylalkylcarbonyl group include aminocarbonylmethylcarbonyl and aminocarbonylethylcarbonyl.

The "aminocarbonylalkylsulfonyl group which may have, at the amino moiety thereof, a substituent" means a group formed of an aminocarbonylalkyl group which may have the above-described substituent and a sulfonyl group. Examples of the aminocarbonylalkylsulfonyl group include aminocarbonylmethylsulfonyl and aminocarbonylethylsulfonyl.

The "aminosulfonyl group which may have, at the amino moiety thereof, a substituent" means a group formed of an amino group which may have the above-described substituent and a sulfonyl group.

The "aminosulfonylalkyl group which may have, at the amino moiety thereof, a substituent" means a group formed of an aminosulfonyl group which may have the above-described substituent and a linear, branched or cyclic $C_{1-6}$ alkylene group. Examples of the aminosulfonylalkyl group include aminosulfonylmethyl and aminosulfonylethyl.

The "aminoalkylsulfonyl group which may have, at the amino moiety thereof, a substituent" means a group formed of an aminoalkyl group which may have the above-described substituent and a sulfonyl group. Examples of the aminoalkylsulfonyl group include aminomethylsulfonyl and aminoethylsulfonyl.

The "aminosulfonylalkylcarbonyl group which may have, at the amino moiety thereof, a substituent" means a group formed of an aminosulfonylalkyl group which may have the above-described substituent and a carbonyl group. Examples of the aminosulfonylalkylcarbonyl group include aminosulfonylmethylcarbonyl and aminosulfonylethylcarbonyl.

The "aminosulfonylalkylsulfonyl group which may have, at the amino moiety thereof, a substituent" means a group formed of an aminosulfonylalkyl group which may have the above-described substituent and a sulfonyl group. Examples of the aminosulfonylalkylsulfonyl group include aminosulfonylmethylsulfonyl and aminosulfonylethylsulfonyl.

$A^3$ also represents a saturated or unsaturated 5- or 6-membered cyclic hydrocarbon group or heterocyclic group which may have a substituent. Examples of the saturated or unsaturated 5- or 6-membered cyclic hydrocarbon group include cyclopentyl, cyclopentenyl, cyclopentadienyl, cyclohexyl, cyclohexenyl, cyclohexadienyl and phenyl groups. Where the group has plural structural isomers as the cyclopentenyl group, they are all embraced in it.

The saturated or unsaturated 5- or 6-membered heterocyclic group is a cyclic group having at least one hetero atom. Examples of the hetero atom include oxygen, nitrogen and sulfur. Examples of the saturated or unsaturated 5- or 6-membered heterocyclic group include furyl, pyrrolyl, thienyl, pyrazolyl, imidazolyl, pyrazolinyl, oxazolyl, oxazolinyl, thiazolyl, thiazolinyl, oxatriazolyl, thiadiazolyl, furazanyl, pyranyl, pyridyl, pyridazinyl, pyrrolidinyl, piperazinyl, piperidinyl, oxazinyl, oxadiazinyl, morpholinyl, thiazinyl, thiadiazinyl, thiomorpholinyl, tetrazolyl, triazolyl and triadinyl. Where the group has plural structural isomers as pyranyl, they are all embraced in it.

When $A^3$ represents a saturated or unsaturated 5- or 6-membered cyclic hydrocarbon group or heterocyclic group which may have a substituent, $B^3$ represents a single bond, a carbonyl group, an alkylene group, a carbonylalkyl group, a carbonylalkyloxy group or an alkylenecarbonyloxy group. Accordingly, the group $A^3$-$B^3$-, for example, represents a group as shown in the following Class (B):

Class (B):

a saturated or unsaturated 5- or 6-membered cyclic hydrocarbon group or heterocyclic group which may have a substituent, a group formed of a saturated or unsaturated 5- or 6-membered cyclic hydrocarbon group or heterocyclic group which may have a substituent and a carbonyl group, a group formed of a saturated or unsaturated 5- or 6-membered cyclic hydrocarbon group or heterocyclic group which may have a substituent and an alkylene group, a group formed of a saturated or unsaturated 5- or 6-membered cyclic hydrocarbon group or heterocyclic group which may have a substituent, a carbonyl group and an alkylene group, a group formed of a saturated or unsaturated 5- or 6-membered cyclic hydrocarbon group or heterocyclic group which may have a substituent, a carbonyl group, an alkylene group and an oxygen atom, a group formed of a saturated or unsaturated 5- or 6-membered cyclic hydrocarbon group or heterocyclic group which may have a substituent, an alkylene group and a carbonyl group, a group formed of a saturated or unsaturated 5- or 6-membered cyclic hydrocarbon group or heterocyclic group which may have a substituent, an alkylene group, a carbonyl group and an oxygen atom, and the like.

A description will next be made of the groups shown in Class (B).

In the group formed of a saturated or unsaturated 5- or 6-membered cyclic hydrocarbon group or heterocyclic group which may have a substituent and a carbonyl group, examples of the group formed of the cyclic hydrocarbon group and a carbonyl group include cyclopentylcarbonyl and phenylcarbonyl; while those of the group formed of the heterocyclic group and a carbonyl group include furylcarbonyl, thienylcarbonyl and pyridylcarbonyl groups.

In the group formed of a saturated or unsaturated 5- or 6-membered cyclic hydrocarbon group or heterocyclic group which may have a substituent and an alkylene group, the "group formed of a cyclic hydrocarbon group and an alkylene group" means a group formed of the above-described cyclic hydrocarbon group and $C_{1-6}$ alkylene group, for example, cyclohexylmethyl and benzyl, while the "group formed of a heterocyclic group and an alkylene group" means a group formed of the above-described heterocyclic group and linear, branched or cyclic $C_{1-6}$ alkylene group, for example, furylmethyl, thienylethyl and pyridylpropyl.

In the group formed of a saturated or unsaturated 5- or 6-membered cyclic hydrocarbon group or heterocyclic group which may have a substituent, a carbonyl group and an alkylene group, the "group formed of a cyclic hydrocarbon group, a carbonyl group and an alkylene group" means a group formed of the above-described cyclic hydrocarbon group, a carbonyl group and the above-described linear, branched or cyclic $C_{1-6}$ alkylene group, for example, cyclopentadienylcarbonylmethyl and phenylcarbonylethyl, while the "group formed of a heterocyclic group, a carbonyl group and an alkylene group" means a group formed of the above-described heterocyclic group, a carbonyl group and a linear, branched or cyclic $C_{1-6}$ alkylene group, for example, furylcarbonylmethyl, thienylcarbonylethyl and pyridylcarbonylpropyl.

In the group formed of a saturated or unsaturated 5- or 6-membered cyclic hydrocarbon group or heterocyclic group which may have a substituent, a carbonyl group, an alkylene group and an oxygen atom, the "group formed of a cyclic hydrocarbon group, a carbonyl group, an alkylene group and an oxygen atom" means a group composed of the above-described group, which is composed of a cyclic hydrocarbon group, carbonyl group and alkylene group, and an oxygen atom, for example, cyclopentylcarbonylmethoxy and phenylcarbonylethoxy, while the "group formed of a heterocyclic group, a carbonyl group, an alkylene group and an oxygen atom" means a group composed of the above-described group, which is composed of a heterocyclic group, a carbonyl group and an alkylene group, and an oxygen atom, for example, furylcarbonylmethoxy, thienylcarbonylethoxy and pyridylcarbonylpropoxy.

In the group formed of a saturated or unsaturated 5- or 6-membered cyclic hydrocarbon group or heterocyclic group which may have a substituent, an alkylene group and a carbonyl group, "the group formed of a cyclic hydrocarbon group, an alkylene group and a carbonyl group" means a group composed of the above-described group, which is formed of a cyclic hydrocarbon group and an alkylene group, and a carbonyl group, for example, cyclohexylmethylcarbonyl and phenylethylcarbonyl, while "the group formed of a heterocyclic group, an alkylene group and a carbonyl group" means a group composed of the above-described group, which is formed of a heterocyclic group and an alkylene group, and a carbonyl group, for example, furylmethylcarbonyl, thienylethylcarbonyl and pyridylpropylcarbonyl.

In the group formed of a saturated or unsaturated 5- or 6-membered cyclic hydrocarbon group or heterocyclic group which may have a substituent, an alkylene group, a carbonyl group and an oxygen atom, "the group formed of a cyclic hydrocarbon group, an alkylene group, a carbonyl group and an oxygen atom" means a group composed of the above-described group, which is formed of a cyclic hydrocarbon group, an alkylene group and a carbonyl group, and an oxygen atom, for example, cyclohexadienylmethylcarbonyloxy and phenylethylcarbonylyoxy, while "the group formed of a heterocyclic group, an alkylene group, a carbonyl group and an oxygen atom" means a group composed of the above-described group, which is formed of a heterocyclic group, an alkylene group and a carbonyl group, and an oxygen atom such as furylmethylcarbonyloxy, thienylethylcarbonyloxy and pyridylpropylcarbonyloxy.

As examples of a substituent which can be substituted for the saturated or unsaturated 5- or 6-membered cyclic hydrocarbon group or heterocyclic group, those as shown in Class (3) can be given. The number of the substituents which can be replaced is 1 to 3.

Class (3):
  a hydroxyl group,
  an alkyl group,
  an alkoxyl group,
  a hydroxyalkyl group,
  an alkoxyalkyl group,
  a halogen atom,
  a cyano group,
  a nitro group,
  a carboxyl group,
  an alkoxycarbonyl group,
  a formyl group,
  a heteroaryl group,
  a heteroarylalkyl group,
  an alkylimino group,
  an amidino group,
  a guanidino group,
  an amino(hydroxyimino)alkyl group,
  an amino(alkoxyimino)alkyl group,
  an amino(aryloxyimino)alkyl group,
  an amino group which may have one or two substituents,
  an aminocarbonyl group which may have, at the amino moiety thereof, one or two substituents,
  an aminocarbonylalkyl group which may have, at the amino moiety thereof, one or two substituents,
  an aminocarbonylalkyloxy group which may have, at the amino moiety thereof, one or two substituents,
  an aminoalkyl group which may have, at the amino moiety thereof, one or two substituents,
  an aminoalkyloxy group which may have, at the amino moiety thereof, one or two substituents,
  an aminoalkylcarbonyl group which may have, at the amino moiety thereof, one or two substituents,
  an aminoalkylcarbonyloxy group which may have, at the amino moiety thereof, one or two substituents, and
  an oxygen atom.

A description will next be made of the substituents which can be replaced for the saturated or unsaturated 5- or 6-membered cyclic hydrocarbon or heterocyclic group in Class (3).

The alkyl group, alkoxyl group, hydroxyalkyl group, alkoxyalkyl group, halogen atom, alkoxycarbonyl group, aminocarbonyl group which may have, at the amino moiety thereof, one or two substituents, aminoalkyl group which may have, at the amino moiety thereof, one or two substituents, aminocarbonylalkyl group which may have, at the amino moiety thereof, one or two substituents, aminocarbonylalkyloxy group which may have, at the amino moiety thereof, one or two substituents, aminoalkylcarbonyl group which may have, at the amino moiety thereof, one or two substituents, and aminoalkylcarbonyloxy group which may have, at the amino moiety thereof, one or two substituents have the same meanings as described above.

The "heteroaryl group" means a monovalent aromatic group having at least one hetero atom. Examples include pyridyl, furyl and thienyl.

The "heteroarylalkyl group" means a group formed of the above-described heteroaryl group and a linear, branched or cyclic $C_{1-6}$ alkylene group. Examples include pyridylmethyl, furylethyl and thienylmethyl.

The "alkylimino group" means a divalent group formed of a linear, branched or cyclic $C_{1-6}$ alkyl group and a nitrogen atom. Examples include methylimino and ethylimino.

The "amino(hydroxyimino)alkyl group" means a group having amino and hydroxyimino groups bonded to the same carbon atom of a linear, branched or cyclic $C_{1-6}$ alkyl group. Examples include amino(hydroxyimino)methyl and amino(hydroxyimino)ethyl.

The "amino(alkoxyimino)alkyl group" means a group having amino and alkoxyimino groups bonded to the same carbon atom of a linear, branched or cyclic $C_{1-6}$ alkyl group. Here, the "alkoxyimino group" means a divalent group formed of the above-described alkoxyl group and an imino group. Examples of the amino(alkoxyimino)alkyl group include amino(methoxyimino)methyl and amino(ethoxyimino)methyl.

The "amino(aryloxyimino)alkyl group" means a group having amino and aryloxyimino groups bonded to the same carbon atom of a linear, branched or cyclic $C_{1-6}$ alkyl group. Here, the "aryloxyimino group" means a divalent group formed of aryl and imino groups. Examples of the aryl group usable here include phenyl, naphthyl, anthryl and phenanthryl. Examples of the amino(aryloxyimino)alkyl group include amino(phenoxyimino)methyl and amino(naphthyloxyimino)methyl.

The "aminoalkyloxy group which may have, at the amino moiety thereof, one or two substituents" means a group formed of an amino group having a substituent, a linear, branched or cyclic $C_{2-6}$ alkylene group and an oxygen atom. Examples of the aminoalkyloxy group include aminoethyloxy and aminopropyloxy. Examples of the group which can be substituted for the amino moiety include those exemplified above.

In the case of the cyclic hydrocarbon group, an oxygen atom can serve as a substituent when the corresponding keto compound is formed, while, in the case of the heterocyclic group or dicyclic or tricyclic fused ring group, an oxygen atom can serve as a substituent when the oxygen atom is bonded to a nitrogen or sulfur atom forming the ring and the corresponding N-oxide or S-oxide or keto compound is formed.

In the present invention, when $R^{15}$ is not coupled with $R^{16}$ or $R^{17}$ to form a $C_{1-3}$ alkylene or alkenylene group, preferred examples of $R^{15}$ include a hydrogen atom, an alkyl group, a hydroxyalkyl group and a group $A^3-B^3-$.

In $R^{16}$ and $R^{17}$, examples of the halogen atom include fluorine, chlorine, bromine and iodine.

The "alkyl group" means a linear, branched or cyclic $C_{1-8}$ alkyl group. Examples include methyl, ethyl, isopropyl, cyclopropyl, heptyl and octyl.

The "hydroxyalkyl group" means a group formed of a hydroxyl group and a linear, branched or cyclic $C_{1-8}$ alkylene group. Examples include hydroxymethyl and hydroxyethyl.

The "alkoxyalkyl group" means a group formed of the above-described alkyl group, an oxygen atom and a linear, branched or cyclic $C_{1-8}$ alkylene group. Examples include methoxymethyl, methoxyethyl and ethoxymethyl.

When $R^{16}$ or $R^{17}$ is coupled with $R^{15}$ to form a $C_{1-3}$ alkylene or alkenylene group, the following group:

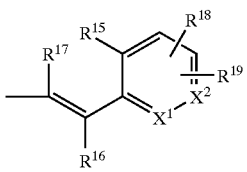

means the following group:

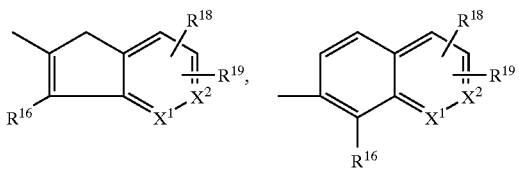

or the like.

In the present invention, when $R^{16}$ or $R^{17}$ is not coupled with $R^{15}$ to form a $C_{1-3}$ alkylene or alkenylene group, a hydrogen atom and alkyl group are preferred as $R^{16}$ or $R^{17}$.

In the present invention, it is preferred that $R^{15}$ and $R^{16}$ $R^{17}$ are coupled together to form a $C_{1-3}$ alkylene or alkenylene group.

$R^{18}$ and $R^{19}$ each independently represents a hydrogen atom, a hydroxyl group, a halogen atom, a halogenoalkyl group, an alkyl group, an alkoxyl group, an alkenyl group, an alkynyl group which may be substituted with an alkylsilyl group as a protecting group, a trifluoromethyl group, a cyano group, an amino group, an aminoalkyl group, an alkylaminoalkyl group, an amidino group, a hydroxyamidino group or an alkoxycarbonylamidino group (with the proviso that $R^{18}$ and $R^{19}$ do not represent a hydrogen atom at the same time).

In $R^{18}$ and $R^{19}$, the halogen atom, halogenoalkyl group, alkyl group, alkoxyl group, alkenyl group and aminoalkyl group mean the same meaning as described above.

The "alkylaminoalkyl group" means a group having one or two linear, branched or cyclic alkyl groups substituted with the amino group of the aminoalkyl moiety and examples include methylaminomethyl and ethylmethylaminomethyl.

The "alkynyl group which may be substituted with an alkylsilyl group as a protecting group" means an alkynyl group which may be substituted with an alkylsilyl group such as trimethylsilyl, triethylsilyl, tertiary butyldimethylsilyl or dimethylphenylsilyl group as a protecting group.

In the present invention, as $R^{18}$ or $R^{19}$, a halogen atom and alkynyl group are preferred, with a hydrogen atom, chlorine atom, bromine atom and ethynyl group are particularly preferred.

$X^3$ in the group:

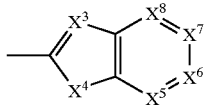

means a nitrogen atom or a group $=C(R^{100})-$
(wherein, $R^{100}$ represents a hydrogen atom, a halogen atom, an alkyl group, an alkoxycarbonyl group, an aralkyloxycarbonylalkyl group, an alkoxycarbonylalkyl group, a nitro group, an amino group which may have a protecting group or an aminoalkyl group which may have, at the amino moiety thereof, a protecting group).

The halogen atom, alkyl group, alkoxycarbonyl group, aryloxycarbonylalkyl group, alkoxycarbonylalkyl group, aryloxycarbonylalkyl group in $R^{100}$ have the same meanings as described above, respectively. The amino group which may have a protecting group or aminoalkyl group which may have, at the amino moiety thereof, a protecting group mean amino group and aminoalkyl groups which may have an ordinarily known protecting group, respectively.

$X^4$ represents an oxygen atom, a sulfur atom or a group $-N(R^{101})-$ (wherein $R^{101}$ means a hydrogen atom, an alkyl group, an alkoxycarbonyl group, an aralkyloxycarbonyl group, an alkoxycarbonylalkyl group, an alkylsulfonyl group or an arylsulfonyl group).

The alkyl group, alkoxycarbonyl group, aralkyloxycarbonyl group, alkoxycarbonylalkyl group, alkylsulfonyl group and arylsulfonyl group in $R^{101}$ have the same meanings as described above, respectively.

$X^5$ and $X^8$ each independently represents a nitrogen atom or a group $-C(R^{102})$
(wherein, $R^{102}$ represents a hydrogen atom or a halogen atom) and the halogen atom in $R^{102}$ has the same meaning as described above.

$X^6$ and $X^7$ each independently represents a nitrogen atom or a group $-C(R^{103})-$ (wherein $R^{103}$ represents a hydrogen atom, a hydroxyl group, a halogen atom, a halogenoalkyl group, an alkyl group, an alkoxyl group, alkenyl group, alkynyl group which may be substituted by an alkylsilyl group as a protecting group, a cyano group, an amino group, an aminoalkyl group, an alkylaminoalkyl group, an amidino group, a hydroxyamidino group or an alkoxycarbonylamidino group).

The halogen atom, halogenoalkyl group, alkyl group, alkoxyl group, alkenyl group, alkynyl group which may be substituted by an alkylsilyl group as a protecting group, aminoalkyl group, alkylaminoalkyl group alkoxycarbonylamidino group in $R^{103}$ have the same meanings as described above.

It is preferred that the group:

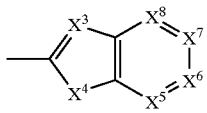

means any one of the following groups:

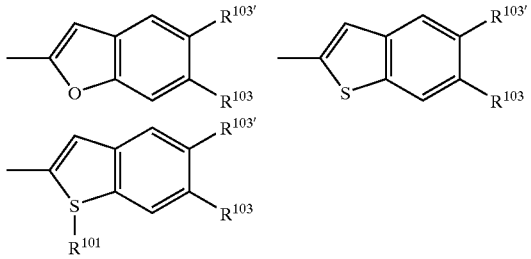

[wherein $R^{101}$ and $R^{103}$ have the same meanings as described above and $R^{103'}$ means those similar to $R^{103}$].

As $R^{101}$, a hydrogen atom is particularly preferred. It is preferred that either one of $R^{103}$ and $R^{103'}$ represents a halogen atom, an alkynyl group, an amidino group, a hydroxyamidino group or an alkoxycarbonylamidino group, with the halogen atom, ethynyl group, amidino group, hydroxyamidino group and methoxycarbonylamidino group being particularly preferred.

In the group:

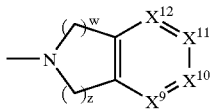

$X^9$ and $X^{12}$ each independently represents a nitrogen atom or a group —C($R^{104}$)—

(wherein $R^{104}$ represents a hydrogen atom or a halogen atom) and the halogen atom as $R^{104}$ is similar to that described above.

$X^{10}$ and $X^{11}$ each independently represents a nitrogen atom or a group —C($R^{105}$)—

(wherein $R^{105}$ represents a hydrogen atom, a hydroxyl group, a halogen atom, a halogenoalkyl group, an alkyl group, an alkoxyl group, alkenyl group, alkynyl group which may be substituted by an alkylsilyl group as a protecting group, a cyano group, an amino group, an aminoalkyl group, an alkylaminoalkyl group, an amidino group, a hydroxyamidino group or an alkoxycarbonylamidino group).

The halogen atom, halogenoalkyl group, alkyl group, alkoxyl group, alkenyl group, alkynyl group which may be substituted by an alkylsilyl group as a protecting group, aminoalkyl group, alkylaminoalkyl group alkoxycarbonylamidino group in $R^{105}$ have the same meanings as described above.

The group:

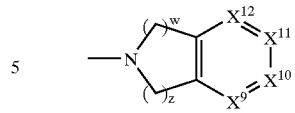

preferably represents the following group:

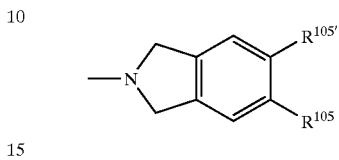

[wherein $R^{105}$ has the same meanings as described above and $R^{105'}$ is similar to that described as $R^{105}$].

It is preferred that either one of $R^{105}$ and $R^{105'}$ represents a halogen atom, an alkynyl group, an amidino group, a hydroxyamidino group or an alkoxycarbonylamidino group, with the halogen atom, ethynyl group, amidino group, hydroxyamidino group and methoxycarbonylamidino group being particularly preferred.

<About the group $Q^1$>

Q1 represents a saturated or unsaturated 5- or 6-membered cyclic hydrocarbon group which may have a substituent, a saturated or unsaturated 5- or 6-membered heterocyclic group which may have a substituent, a saturated or unsaturated dicyclic fused ring group which may have a substituent, or a saturated or unsaturated tricyclic fused ring group which may have a substituent.

Here, examples of the saturated or unsaturated 5- or 6-membered cyclic hydrocarbon group include cyclopentyl, cyclopentenyl, cyclopentadienyl, cyclohexyl, cyclohexenyl, cyclohexadienyl and phenyl. When the group has plural structural isomers as cyclopentenyl, they are all embraced in it.

The saturated or unsaturated 5- or 6-membered heterocyclic group is a cyclic group having at least one hetero atom. Examples of the hetero atom include oxygen, nitrogen and sulfur. Examples of the saturated or unsaturated 5- or 6-membered heterocyclic group include furyl, pyrrolyl, thienyl, pyrazolyl, pyrazinyl, tetrahydropyrazinyl, imidazolyl, pyrazolinyl, oxazolyl, oxazolinyl, thiazolyl, thiazolinyl, thiazolidinyl, oxatriazolyl, thiadiazolyl, furazanyl, pyranyl, pyridyl, pyrimidinyl, tetrahydropyrimidinyl, pyridazinyl, tetrahydropyridazinyl, pyrrolidinyl, piperazinyl, piperidinyl, oxazinyl, oxadiazinyl, morpholinyl, thiazinyl, thiadiazinyl, thiomorpholinyl, tetrazolyl, tetrazinyl, triazolyl and triazinyl. Where the group has plural structural isomers as pyranyl, they are all embraced in it.

The "saturated or unsaturated, dicyclic fused ring group which may have a substituent" or "saturated or unsaturated, tricylic fused ring group which may have a substituent" has the same meaning as defined in the description of the group $Q^A$. More specifically, it means: 1) a group obtained by the condensation of saturated or unsaturated 5- or 6-membered cyclic hydrocarbon groups which may have a substituent, 2) a group obtained by the condensation of a saturated or unsaturated 5- or 6-membered cyclic hydrocarbon group which may have a substituent and a saturated or unsaturated 5- or 6-membered heterocyclic group which may have a substituent and 3) a group obtained by the condensation of saturated or unsaturated 5- or 6-membered heterocyclic groups which may have a substituent. Examples of the group 1) include indenyl, indanyl, naphthyl, tetrahydronaphthyl, anthryl and phenanthryl; those of the group 2) include benzofuranyl, indolyl, indolinyl, quinolyl, benzodiazinyl, tetrahydroisoquinolyl, benzothiazolyl, tetrahydrothiazolyl and isoindolyl; and those of the group 3) include naphthyridinyl, furanopyridyl, thienopyridyl, tetrahydrothienopyridyl, pyrazolopyridyl, thiazolopyridyl, tetrahydrothiazolopyridyl, thiazolopyrazyl, tetrahydrothiazolopyrazyl, thiazolopyridazyl, tetrahydropyridopyridyl, thiazolopyridazinyl, tetrahydrothiazolopyridazinyl, pyrrolopyridyl, tetrahydropyrrolopyridyl, dihydropyridoquinazolinyl, pyridopyrimidinyl, tetrahydropyridopyrimidinyl, pyranothiazolyl, dihydropyranothiazolyl, furopyridyl, tetrahydrofuropyridyl, oxazolopyridyl and tetrahydrooxazolopyridyl.

Examples of the substituent which can be replaced for the above-described saturated or unsaturated 5- or 6-membered cyclic hydrocarbon group, saturated or unsaturated 5- or 6-membered heterocyclic group, saturated or unsaturated dicyclic fused ring group, or saturated or unsaturated tricyclic fused ring group include the groups shown in the below-described Class (4). The number of the replaceable substituents ranges from 1 to 7.

Class (4):
- a hydroxyl group,
- an alkyl group,
- an alkenyl group,
- a halogenoalkyl group,
- a halogenoalkenyl group,
- an alkoxyl group,
- a hydroxyalkyl group,
- an alkoxyalkyl group,
- a halogen atom,
- a cyano group,
- a nitro group,
- a carboxyl group,
- an alkoxycarbonyl group,
- a formyl group,
- a heteroaryl group,
- a heteroarylalkyl group,
- an alkylimino group,
- an alkylsulfonyl group,
- an amidino group,
- a guanidino group,
- an amino(hydroxyimino)alkyl group,
- an amino(alkoxyimino)alkyl group,
- an amino(aryloxyimino)alkyl group,
- a hydroxyimino group,
- an alkoxyimino group,
- an aminoimino group which may have, at the amino moiety thereof, one or two substituents,
- an amino group which may have one or two substituents,
- an aminocarbonyl group which may have, at the amino moiety thereof, one or two substituents,
- an aminocarbonylalkyl group which may have, at the amino moiety thereof, one or two substituents,
- an aminocarbonylalkyloxy group which may have, at the amino moiety thereof, one or two substituents,
- an aminosulfonyl group which may have, at the amino moiety thereof, one or two substituents,
- an aminoalkyl group which may have, at the amino moiety thereof, one or two substituents,
- an aminoalkyloxy group which may have, at the amino moiety thereof, one or two substituents,
- an aminoalkylcarbonyl group which may have, at the amino moiety thereof, one or two substituents,
- an aminoalkylcarbonyloxy group which may have, at the amino moiety thereof, one or two substituents,
- an oxygen atom,
- a trifluoromethylsulfonyloxy group,
- a trifluoromethylsulfonyloxyalkenyl group,
- a boric acid group (—B(OH)$_2$)),
- a saturated or unsaturated 5- or 6-membered cyclic hydrocarbon group which may have 1 to 3 substituents selected from the group consisting of halogen, hydroxyl, amino, alkoxyl, alkyl, cyano, nitro, carboxyl, alkoxycarbonyl, aminocarbonyl which may have, at the amino moiety thereof, one or two substituents, aminosulfonyl which may have, at the amino moiety thereof, one or two substituents, aminoalkyl which may have, at the amino moiety thereof, one or two substituents and trifluoromethyl, and saturated or unsaturated 5- or 6-membered heterocyclic group which may have 1 to 3 substituents selected from the group consisting of halogen, hydroxyl, amino, alkoxyl, alkyl, cyano, nitro, carboxyl, alkoxycarbonyl, aminocarbonyl which may have, at the amino moiety thereof, one or two substituents, aminosulfonyl which may have, at the amino moiety thereof, one or two substituents, aminoalkyl which may have, at the amino moiety thereof, one or two substituents and trifluoromethyl.

The substituents in Class (4) have the same meanings as described in Classes (1) to (3) of the description of the group $Q^A$.

In the present invention, preferred examples of $Q^1$ include a cyclopentyl group which may have a substituent, cyclohexyl group which may have a substituent, cyclopentenyl group which may have a substituent, cyclohexenyl group which may have a substituent, phenyl group which may have a substituent, pyrrolidinyl group which may have a substituent, piperidinyl group which may have a substituent, imidazolyl group which may have a substituent, thiazolyl group which may have a substituent, thiadiazolyl group which may have a substituent, pyridyl group which may have a substituent, pyrimidinyl group which may have a substituent, pyridazinyl group which may have a substituent, thiazolydinyl group which may have a substituent, morpholinyl group which may have a substituent, piperazinyl group which may have a substituent, thiomorpholinyl group which may have a substituent, pyrrolyl group which may have a substituent, thienyl group which may have a substituent, furanyl group which may have a substituent, tetrahydropyrimidinyl group which may have a substituent, tetrahydrofuranyl group which may have a substituent, tetrahydrothienyl group which may have a substituent, sulforanyl group which may have a substituent, imidazolinyl group which may have a substituent, thiazolinyl group which may have a substituent, oxazolyl group which may have a substituent, oxadiazinyl group which may have a substituent, triazinyl group which may have a substituent, tetrazinyl group which may have a substituent, pyrazinyl group which may have a substituent, pyrazolyl group which may have a substituent, pyrazolinyl group which may have a substituent, pyrazolidinyl group which may have a substituent, thienopyridyl group which may have a substituent, tetrahydrothienopyridyl group which may have a substituent, thiazolopyridyl group which may have a substituent, tetrahydrothiazolopyridyl group which may have a substituent, pyranothiazolyl group which may have a substituent, dihydropyranothiazolyl group which may have a substituent, thiazolopyridadinyl group which may have a substituent, tetrahydrothiazolopyridadinyl group which may have a substituent, furopyridyl group which may have a substituent, tetrahydrofuropyridyl group which may have a substituent, oxazolopyridyl group which may have a substituent, and tetrahydrooxazolopyridyl group which may have a substituent.

Examples of the substituent include a hydroxyl group, an alkyl group, a hydroxyalkyl group, a halogen atom, a cyano group, a nitro group, a carboxyl group, an alkoxycarbonyl group, a formyl group, an alkylsulfonyl group, an amino group which may have one or two substituents, an aminosulfonyl group which may have, at the amino moiety thereof, one or two substituents, an aminoalkyl group which may have, at the amino moiety thereof, one or two substituents, an oxygen atom, a trifluoromethyl group, a saturated or unsaturated 5- or 6-membered cyclic hydrocarbon group which may have 1 to 3 substituents selected from the group consisting of a halogen atom, a hydroxyl group, an amino group, an alkoxyl group, an alkyl group, a cyano group, a nitro group, a carboxyl group, an alkoxycarbonyl group, an aminocarbonyl group which may have, at the amino moiety thereof, one or two substituents, an aminosulfonyl group which may have, at the amino moiety thereof, one or two substituents, an aminoalkyl group which may have, at the amino moiety thereof, one or two substituents and a trifluoromethyl group, and a saturated or unsaturated 5- or 6-membered heterocyclic group which may have 1 to 3 substituents selected from the group consisting of a halogen atom, a hydroxyl group, an amino group, an alkoxyl group, an alkyl group, a cyano group, a nitro group, a carboxyl group, an alkoxycarbonyl group, an aminocarbonyl group which may have, at the amino moiety thereof, one or two substituents, an aminosulfonyl group which may have, at the amino moiety thereof, one or two substituents, an aminoalkyl group which may have, at the amino moiety thereof, one or two substituents and a trifluoromethyl group <About $Q^2$>

$Q^2$ represents a single bond, an oxygen atom, a sulfur atom, a linear or branched $C_{1-6}$ alkylene group, a linear or branched $C_{2-6}$ alkenylene group, a linear or branched $C_{2-6}$ alkynylene group, a group —N($R^1$)—CO—

(wherein, $R^1$ represents a hydrogen atom or an alkyl group), a group —N($R^2$)—(CH$_2$)$_m$—

(wherein, $R^2$ represents a hydrogen atom or an alkyl group and m stands for an integer of 0 to 6), or
a group:

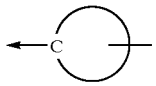

(which represents a divalent, saturated or unsaturated 5- or 6-membered cyclic hydrocarbon group which may have a substituent, a divalent, saturated or unsaturated 5- or 6-membered heterocyclic group which may have a substituent or a divalent, saturated or unsaturated dicyclic fused ring group which may have a substituent and ←C means the bonding of the carbon atom of this group to $Q^1$), In $Q^2$, examples of the linear or branched $C_{1-6}$ alkylene group include methylene, ethylene, trimethylene, propylene, tetramethylene, butylene, pentamethylene and hexamethylene.

Examples of the linear or branched $C_{2-6}$ alkenylene group include vinylene, propenylene, butenylene and pentenylene. There is no particular limitation on the position of the double bond.

Examples of the linear or branched $C_{2-6}$ alkynylene group include propynylene, butynylene, pentynylene and hexynylene.

The group of the following formula:

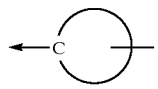

means a divalent, saturated or unsaturated 5- or 6-membered cyclic hydrocarbon group which may have a substituent a divalent, saturated or unsaturated 5- or 6-membered heterocyclic group which may have a substituent or a divalent, saturated or unsaturated dicyclic fused ring group which may have a substituent and ←C means the bonding of the carbon atom of this group to $Q^1$. Examples of the group include divalent groups derived from thiophene, furan, pyran, pyrrole, pyrrolidine, pyrroline, imidazole, imidazoline, imidazolidine, pyrazole, pyrazolidine, thiazole, oxazole, oxathiolane, benzene, pyridine, piperidine, piperazine, morpholine, thiomorpholine, pyrazine, pyrimidine, pyridazine, triazine, tetrazine, thiadiazine, dithiazine, cyclopentane, cyclopetene, cyclopentadiene, cyclohexane, cyclohexene and they may have a substituent. Examples of the substituent are similar to those exemplified in Class (4).

The alkyl group in $R^1$ or $R^2$ of the group —N($R^1$)—CO— or —N($R^2$)—(CH$_2$)$_m$— means a linear, branched or cyclic $C_{1-6}$ alkyl group. Examples include methyl, ethyl, isopropyl and cyclopropyl. As the group —N($R^1$)—CO—, a group ←N($R^1$)—CO— (wherein ← means the bonding of the nitrogen atom of this group to $Q^1$) is preferred, while as the group —N($R^2$)—(CH$_2$)$_m$—, a group ←N($R^2$)—(CH$_2$)$_m$— (wherein ← means the bonding of the nitrogen atom of this group to $Q^1$) is preferred.

In the present invention, Q2 preferably represents a single bond, a carbonyl group or a group of the following formula:

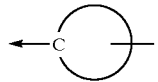

and as the group represented by the following formula:

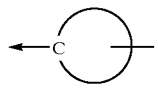

divalent groups derived from benzene, pyrimidine, tetrahydropyrimidine, pyrazine, pyridazine, triazine, tetrazine, imidazole, imidazoline, thiazole, thiazoline, furan, thiophene, pyrrole, oxazole, oxazoline, thiadiazole, cyclopentane, cyclopentene, cyclohexane or cyclohexene.

<About $Q^3$>

In $R^3$, $R^4$, $R^5$, $R^6$, $R^7$, $R^8$, $R^{10}$ and $R^{11}$ as the substituents in $Q^3$, the alkyl, alkoxyl, alkoxyalkyl, hydroxyalkyl, hydroxyalkyloxy, hydroxyalkylcarbonyl, hydroxyalkylsulfonyl, formylalkyl, formylalkylcarbonyl, formylalkylsulfonyl, alkylcarbonyl, alkylsulfonyl, alkylcarbonylalkyl, alkylsulfonylalkyl, carboxyalkyl, carboxyalkylcarbonyl, carboxyalkylsulfonyl, carboxyalkylcarbonylalkyl, carboxyalkylsulfonylalkyl, alkoxycarbonyl, alkoxycarbonylalkyl, alkoxycarbonylalkylcarbonyl, alkoxycarbonylalkylsulfonyl, amino which may have 1 to 2 substituents, aminoalkyl which may have, at the amino moiety thereof, one or two substituents, aminoalkyloxy which may have, at the amino moiety thereof, one or two substituents, aminoalkylcarbonyl which may have, at the amino moiety thereof, one or two substituents, aminoalkylcarbonyloxy which may have, at the amino moiety thereof, one or two substituents, aminocarbonyl which may have, at the amino moiety thereof, one or two substituents, aminocarbonylalkyl which may have, at the amino moiety thereof, one or two substituents, and aminocarbonylalkyloxy which may have, at the amino moiety thereof, one or two substituents have the same meanings as described above in $R^{15}$ of the description of the group $Q^A$.

The "alkoxyalkyloxy group" means a group formed of the above-described alkoxyalkyl group and an oxygen atom and examples include methoxymethyloxy, methoxyethyloxy and ethoxymethyloxy.

The "carboxyalkyloxy group" means a group formed of the above-described carboxyalkyl group and an oxygen atom and examples include carboxymethoxyl and carboxyethoxyl.

The "carboxyalkyloxy group" means a group formed of the above-described carboxyalkyl group and an oxygen atom and examples include carboxymethoxyl and carboxyethoxyl.

The "alkoxycarbonylalkyloxy group" means a group formed of the above-described alkoxycarbonylalkyl group and an oxygen atom and examples include methoxycarbonylethyl and ethoxycarbonylethyl.

The "alkylsulfonylaminocarbonylalkyl group which may have, at the amino moiety thereof, one substituent" means a group formed of the above-described alkylsulfonyl group, an imino group which may have one substituent and a carbonyl group and examples include methylsulfonylaminocarbonylmethyl.

The "arylsulfonylaminocarbonylalkyl group which may have, at the amino moiety thereof, one substituent" means a group formed of an aryl group, a sulfonyl group, an imino group which may have one substituent and a carbonyl group and examples include phenylsulfonylaminocarbonylmethyl.

The "aminosulfonylalkyl group which may have, at the amino moiety thereof, one or two substituents" means a group formed of an amino group which may have one or two substituents, a sulfonyl group and a linear, branched or cyclic $C_{1-6}$ alkylene group and examples include aminosulfonylmethyl.

The "cyanoalkyl group" means a group formed of a cyano group and a linear, branched or cyclic $C_{1-6}$ alkylene group.

The "alkylcarbonyloxyalkyl group" menas a group formed of the above-described alkylcarbonyl group, an oxygen atom and a linear, branched or cyclic $C_{1-6}$ alkylene group and examples include methylcarbonyloxyethyl.

The "alkoxyalkylaminocarbonylalkyl group which may have, at the amino moiety thereof, one substituent" means a group formed of the above-described alkoxyalkyl group, an imino group which may have one substituent and a carbonyl group and examples include ethoxymethylaminocarbonylmethyl.

In the group $A^1$—$B^1$—, $A^1$ represents a saturated or unsaturated 5- or 6-membered cyclic hydrocarbon group which may have a substituent or a saturated or unsaturated 5- or 6-membered heterocyclic group which may have a substituent. Here, examples of the saturated or unsaturated 5- or 6-membered cyclic hydrocarbon group include cyclopentyl, cyclopentenyl, cyclopentadienyl, cyclohexyl, cyclohexenyl, cyclohexadienyl and phenyl. When the group has various structural isomers as the cyclopentenyl group, they are all embraced in it.

The saturated or unsaturated 5- or 6-membered heterocyclic group is a cyclic group having at least one hetero atom. Examples of the hetero atom include oxygen, nitrogen and sulfur. Examples of the saturated or unsaturated 5- or 6-membered heterocyclic group include furyl, pyrrolyl, thienyl, pyrazolyl, imidazolyl, pyrazolinyl, oxazolyl, oxazolinyl, thiazolyl, thiazolinyl, oxatriazolyl, thiadiazolyl, furazanyl, pyranyl, pyridyl, pyridazinyl, pyrrolidinyl, piperazinyl, piperidinyl, oxazinyl, oxadiazinyl, morpholinyl, thiazinyl, thiadiazinyl, thiomorpholinyl, tetrazolyl, triazolyl and triazinyl. Where the group has plural structural isomers as the pyranyl group, they are all embraced in it.

$B^1$ represents a single bond, carbonyl group, alkylene group, carbonylalkyl group, a group —O— $C_{1-6}$ alkylene, a group —COO— $C_{1-6}$ alkylene, a group —NHCO— or a group —NHCO— $C_{1-6}$ alkylene.

Examples of the group $A^1$—$B^1$— include the following groups:

a saturated or unsaturated 5- or 6-membered cyclic hydrocarbon group which may have a substituent, a group formed of a saturated or unsaturated 5- or 6-membered heterocyclic group which may have a substituent and a carbonyl group, and a group formed of a saturated or unsaturated 5- or 6-membered cyclic hydrocarbon group which may have a substituent and an alkylene group.

Each of $R^3$ and $R^4$ $R^5$ and $R^6$ $R^7$ and $R^8$, and $R^{10}$ and $R^{11}$ are coupled together with a carbon atom which constitutes the ring and represents a saturated or unsaturated 5- to 7-membered cyclic hydrocarbon group which may have a substituent or a saturated or unsaturated 5- to 7-membered heterocyclic group which may have a substituent. Here, examples of the saturated or unsaturated 5- or 7-membered cyclic hydrocarbon group include cyclopentyl, cyclopentenyl, cyclopentadienyl, cyclohexyl, cyclohexenyl, cyclohexadienyl and phenyl. When the group has various structural isomers as the cyclopentenyl, they are all embraced in it.

The saturated or unsaturated 5- or 6-membered heterocyclic group is a cyclic group having at least one hetero atom. Examples of the hetero atom include oxygen, nitrogen and sulfur. Examples of the saturated or unsaturated 5- or 6-membered heterocyclic group include furyl, pyrrolyl, thienyl, pyrazolyl, imidazolyl, pyrazolinyl, oxazolyl, oxazolinyl, thiazolyl, thiazolinyl, oxatriazolyl, thiadiazolyl, furazanyl, pyranyl, pyridyl, pyridazinyl, pyrrolidinyl, piperazinyl, piperidinyl, oxazinyl, oxadiazinyl, morpholinyl, thiazinyl, thiadiazinyl, thiomorpholinyl, tetrazolyl, triazolyl and triazinyl. Where the group has plural structural isomers as the pyranyl, they are all embraced in it.

In $R^9$ or $R^{12}$ as the substituent in $Q^3$, the alkyl, hydroxyalkyl, alkoxyl, hydroxyalkylcarbonyl, hydroxyalkylsulfonyl, alkoxyalkyl, alkoxyalkylcarbonyl, alkoxyalkylsulfonyl, formylalkyl, formylalkylcarbonyl, formylalkylsulfonyl, alkylcarbonyl, alkylsulfonyl, alkylcarbonylalkyl, alkylsulfonylalkyl, carboxyalkylcarbonyl, carboxyalkylsulfonyl, carboxyalkylcarbonylalkyl, carboxyalkylsulfonylalkyl, alkoxycarbonyl, alkoxycarbonylalkyl, alkoxycarbonylalkylcarbonyl, alkoxycarbonylalkylsulfonyl, amino which may have 1 to 2 substituents, aminoalkyl which may have, at the amino moiety thereof, aminoalkyloxy which may have, at the amino moiety thereof, aminoalkylcarbonyl which may have, at the amino moiety thereof, one or two substituents, aminoalkyloxycarbonyl which may have, at the amino moiety thereof, 1 or 2 substituents, aminocarbonyl which may have, at the amino moiety thereof, one or two substituents, aminocarbonylalkyl which may have, at the amino moiety thereof, one or two substituents, and aminocarbonyloxyalkyl which may have, at the amino moiety thereof, one or two substituents have the same meanings as described in $Q^A$.

In the group $A^2$-$B^2$-, A represents a saturated or un-saturated 5- or 6-membered cyclic hydrocarbon group which may have a substituent or a saturated or unsaturated 5- or 6-membered heterocyclic group which may have a substituent. Here, examples of the saturated or unsaturated 5- or 6-membered cyclic hydrocarbon group include cyclopentyl, cyclopentenyl, cyclopentadienyl, cyclohexyl, cyclohexenyl, cyclohexadienyl and phenyl. When the group has plural structural isomers as the cyclopentenyl, they are all embraced in it.

The saturated or unsaturated 5- or 6-membered heterocyclic group is a cyclic group having at least one hetero atom. Examples of the hetero atom include oxygen, nitrogen and sulfur. Examples of the saturated or unsaturated 5- or 6-membered heterocyclic group include furyl, pyrrolyl, thienyl, pyrazolyl, imidazolyl, pyrazolinyl, oxazolyl, oxazolinyl, thiazolyl, thiazolinyl, oxatriazolyl, thiadiazolyl, furazanyl, pyranyl, pyridyl, pyridazinyl, pyrrolidinyl, piperazinyl, piperidinyl, oxazinyl, oxadiazinyl, morpholinyl, thiazinyl, thiadiazinyl, thiomorpholinyl, tetrazolyl, triazolyl and triazinyl. Where the group has plural structural isomers as the pyranyl, they are all embraced in it.

B2 represents a single bond, carbonyl group, alkylene group, carbonylalkyl group, a group —O— $C_{1-6}$ alkylene, a group —COO— $C_{1-6}$ alkylene, a group —NHCO— or a group —NHCO— $C_{1-6}$ alkylene.

Examples of the group $A^2$-$B^2$- include the following groups:

a saturated or unsaturated 5- or 6-membered heterocyclic group which may have a substituent, a group formed of a saturated or unsaturated 5- or 6-membered cyclic hydrocarbon group which may have a substituent and a carbonyl group, and a group formed of a saturated or unsaturated 5- or 6-membered heterocyclic group which may have a substituent and an alkylene group.

$R^9$ and $R^7$, $R^9$ and $R^8$, $R^{12}$ and $R^{10}$, and $R^{12}$ and $R^{11}$ are each coupled together with the carbon atom which constitutes the ring and the nitrogen atom to which $R^9$ or $R^{12}$ has been bonded and represent a saturated or unsaturated 5- to 7-membered heterocyclic group which may have a substituent. Here, the saturated or unsaturated 5- to 7-membered heterocyclic group is a cyclic group which has at least one nitrogen atom and may have a hetero atom. Examples of the hetero atom include oxygen, nitrogen and sulfur. Examples of the saturated or unsaturated 5- or 6-membered heterocyclic group include furyl, pyrrolyl, thienyl, pyrazolyl, imidazolyl, pyrazolinyl, oxazolyl, oxazolinyl, thiazolyl, thiazolinyl, oxatriazolyl, thiadiazolyl, furazanyl, pyranyl, pyridyl, pyridazinyl, pyrrolidinyl, piperazinyl, piperidinyl, oxazinyl, oxadiazinyl, morpholinyl, thiazinyl, thiadiazinyl, thiomorpholinyl, triazolyl and triazinyl. Where the group has plural structural isomers as the pyranyl, they are all embraced in it.

In the present invention, $Q^3$ represents a group of the following formula:

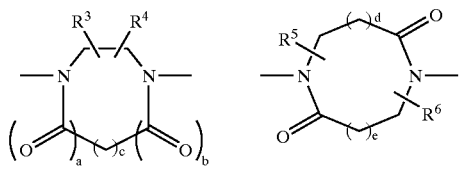

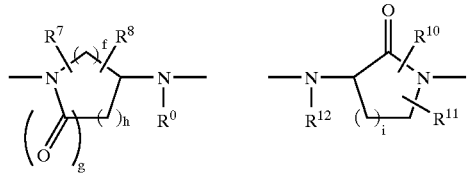

(wherein $R^3$, $R^4$, $R^5$, $R^6$, $R^7$, $R^8$, $R^9$, $R^{10}$, $R^{11}$, $R^{12}$, a, b, c, d, e, f, g, h and i have the same meanings as described above). Preferred as $Q^3$ is a group of the following formula:

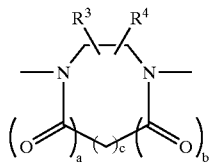

wherein $R^3$, $R^4$, a, b and c have the same meanings as described above), of which the group wherein:

$R^3$ and $R^4$ each independently represents
a hydrogen atom,
a hydroxyalkyl group,
a cyanoalkyl group,
a carboxyl group,
a carboxyalkyl group,
an alkoxycarbonyl group,
an alkoxycarbonylalkyl group,
a carboxyalkylaminocarbonyl group,
a carboxyalkylaminocarbonylalkyl group,
an alkoxycarbonylalkylaminocarbonyl group,
an alkoxycarbonylalkylaminocarbonylamino group,
a carbamoyl group,
a monoalkylcarbamoyl group,
a dialkylcarbamoyl group,
a carbamoylalkyl group,
a monoalkylcarbamoylalkyl group,
a dialkylcarbamoylalkyl group,
a morpholinylcarbonyl group
a morpholinylcarbonylalkyl group,
a tetrazolylaminocarbonyl group,
a tetrazolylaminocarbonylalkyl group,
a tetrazolylalkyl group,
a tetrazolylalkylaminocarbonyl group, or
a tetrazolylalkylaminocarbonylalkyl group,
an aminoalkyl group which may have, at the amino moiety thereof, one or two substituents,
an alkylaminosulfonylalkyl group,
an oxopyrrolidinylalkyl group,
oxopiperidinylalkyl group, or
oxooxazolidinylalkyl group, and
a stands for 0, b stands for 0 and c stands for 2 is more preferred.

<About $T^1$>

$T^1$ represents a carbonyl group, a group —CH($R^{13}$)—

(in which $R^{13}$ represents a hydrogen atom, an alkyl group, a hydroxyalkyl group, an alkoxyalkyl group, a carboxyalkyl group, an alkoxycarbonylalkyl group, an aryl group, an aralkyl group, a heteroaryl group, a heteroarylalkyl group or an aminoalkyl group which may have, at the amino moiety thereof, a substituent), or a group —C(=NOR$^{14}$)— or —C(=N—NHR$^{14'}$)—

(in which $R^{14}$ and $R^{14'}$ each independently represents a hydrogen atom, an alkyl group, a carboxyalkyl group, an alkoxycarbonyl group, an aryl group, an aralkyl group, a heteroaryl group, a heteroarylalkyl group or an aminoalkyl group which may have, at the amino moiety thereof, a substituent).

Here, in $R^{13}$ and $R^{14}$, the alkyl, carboxyalkyl, alkoxycarbonyl, aryl, aralkyl, heteroaryl, heteroarylalkyl and aminoalkyl which may have, at the amino moiety thereof, a substituent have the same meanings as described in $Q^A$. In the present invention, a carbonyl group is preferred as $T^1$.

The sulfonyl derivative of the present invention has optical isomers or stereoisomers based on an asymmetric carbon atom. These optical isomers and stereoisomers and mixtures thereof are all embraced in the present invention.

Although there is no particular limitation imposed on the salt of the sulfonyl derivative according to the present invention insofar as it is a pharmaceutically acceptable salt. Specific examples include salts of a mineral acid such as hydrochloride, hydrobromide, hydroiodide, phosphate, nitrate and sulfate, salts of an organic sulfonic acid such as benzoate, methanesulfonate, 2-hydroxyethanesulfonate and p-toluenesulfonate and salts of an organic carboxylic acid such as acetate, propanoate, oxalate, malonate, succinate, glutarate, adipate, tartrate, maleate, malate and mandelate. There is no particular limitation imposed on the solvate insofar as it is pharmaceutically acceptable. Specific examples include hydrates and ethanolates.

The following are the preferred compounds as the sulfonyl derivative of the present invention.

1-[(6-Chloronaphthalen-2-yl)sulfonyl]-4-[[5-[2-[(N,N-dimethyl)amino]ethyl]-4-methylthiazol-2-yl]carbonyl]piperazine 1-[(6-Chloronaphthalen-2-yl)sulfonyl]-4-[[5-[2-[(N,N-dimethyl)amino]ethyl]thiazol-2-yl]carbonyl]piperazine 1-[(6-Chloronaphthalen-2-yl)sulfonyl]-4-[[5-[3-[(N,N-dimethyl)amino]propyl]-4-methylthiazol-2-yl]carbonyl]piperazine 1-[(6-Chloronaphthalen-2-yl)sulfonyl]-4-[[5-[3-[(N,N-dimethyl)amino]propyl]thiazol-2-yl]carbonyl]piperazine 1-[(5-Chloroindol-2-yl)sulfonyl]-4-[[5-[2-[(N,N-dimethyl)amino]ethyl]-4-methylthiazol-2-yl]carbonyl]piperazine 1-[(5-Chloroindol-2-yl)sulfonyl]-4-[[5-[2-[(N,N-dimethyl)amino]ethyl]thiazol-2-yl]carbonyl]piperazine 1-[(5-Chloroindol-2-yl)sulfonyl]-4-[[5-[3-[(N,N-dimethyl)amino]propyl]-4-methylthiazol-2-yl]carbonyl]piperazine 1-[(5-Chloroindol-2-yl)sulfonyl]-4-[[5-[3-[(N,N-dimethyl)amino]propyl]thiazol-2-yl]carbonyl]piperazine 1-[(6-Chlorobenzo[b]thien-2-yl)sulfonyl]-4-[[5-[2-[(N,N-dimethyl)amino]ethyl]-4-methylthiazol-2-yl]carbonyl]piperazine 1-[(6-Chlorobenzo[b]thien-2-yl)sulfonyl]-4-[[5-[2-[(N,N-dimethyl)amino]ethyl]thiazol-2-yl]carbonyl]piperazine 1-[(6-Chlorobenzo[b]thien-2-yl)sulfonyl]-4-[[5-[3-[(N,N-dimethyl)amino]propyl]-4-methylthiazol-2-yl]carbonyl]piperazine 1-[(6-Chlorobenzo[b]thien-2-yl)sulfonyl]-4-[[5-[3-[(N,N-dimethyl)amino]propyl]thiazol-2-yl]carbonyl]piperazine 1-[(6-Chloronaphthalen-2-yl)sulfonyl]-4-[[5-[(1-methylpiperidin)-4-yl]thiazol-2-yl]carbonyl]piperazine 1-[(6-Chloronaphthalen-2-yl)sulfonyl]-4-[[5-[(1-methylpiperidin)-3-yl]thiazol-2-yl]carbonyl]piperazine 1-[(6-Chloronaphthalen-2-yl)sulfonyl]-4-[[5-[(1-methylpiperidin)-2-yl]thiazol-2-yl]carbonyl]piperazine 4-[(6-Chloronaphthalen-2-yl)sulfonyl]-2-[(N-methyl)carbamoyl]-1-[[5-[(1-methylpiperidin)-4-yl]thiazol-2-yl]carbonyl]piperazine 4-[(6-Chloronaphthalen-2-yl)sulfonyl]-2-[(N-methyl)carbamoyl]-1-[[5-[(1-methylpiperidin)-3-yl]thiazol-2-yl]carbonyl]piperazine 4-[(6-Chloronaphthalen-2-yl)sulfonyl]-2-[(N-methyl)carbamoyl]-1-[[5-[(1-methylpiperidin)-2-yl]thiazol-2-yl]carbonyl]piperazine 1-[(6-Chloronaphthalen-2-yl)sulfonyl]-4-[[5-(pyrrolidin-3-yl)thiazol-2-yl]carbonyl]piperazine 1-[(6-Chloronaphthalen-2-yl)sulfonyl]-4-[[5-(1-methylpyrrolidin-3-yl)thiazol-2-yl]carbonyl]piperazine 1-[[5-(1-Carbamoylpyrrolidin-3-yl)thiazol-2-yl]carbonyl]-4-[(6-chloronaphthalen-2-yl)sulfonyl]piperazine 1-[[5-(1-Acetoimidoylpyrrolidin-3-yl)thiazol-2-yl]carbonyl]-4-[(6-chloronaphthalen-2-yl)sulfonyl]piperazine 4-[(6-Chloronaphthalen-2-yl)sulfonyl]-2-[(N-methyl)carbamoyl]-1-[[5-(pyrrolidin-3-yl)thiazol-2-yl]carbonyl]piperazine 4-[(6-Chloronaphthalen-2-yl)sulfonyl]-2-[(N-methyl)carbamoyl]-1-[[5-(1-methylpyrrolidin-3-yl)thiazol-2-yl]carbonyl]piperazine 1-[[5-(1-Carbamoylpyrrolidin-3-yl)thiazol-2-yl]carbonyl]-4-[(6-chloronaphthalen-2-yl)sulfonyl]-2-[(N-methyl)carbamoyl]piperazine 1-[[5-(1-Acetoimidoylpyrrolidin-3-yl)thiazol-2-yl]carbonyl]-4-[(6-chloronaphthalen-2-yl)sulfonyl]-2-[(N-methyl)carbamoyl]piperazine 1-[(6-Chloronaphthalen-2-yl)sulfonyl]-4-[[5-[(1,2,5,6-tetrahydropyridin)-4-yl]thiazol-2-yl]carbonyl]piperazine 1-[(6-Chloronaphthalen-2-yl)sulfonyl]-4-[[5-[(1-methyl-1,2,5,6-tetrahydropyridin)-4-yl]thiazol-2-yl]carbonyl]piperazine 1-[[5-[(1-Carbamoyl-1,2,5,6-tetrahydropyridin)-4-yl]thiazol-2-yl]carbonyl]-4-[(6-chloronaphthalen-2-yl)sulfonyl]piperazine 1-[[5-[(1-Acetoimidoyl-1,2,5,6-tetrahydropyridin)-4-yl]thiazol-2-yl]carbonyl]-4-[(6-chloronaphthalen-2-yl)sulfonyl]piperazine 4-[(6-Chloronaphthalen-2-yl)sulfonyl]-2-[(N-methyl)carbamoyl]-1-[[5-[(1,2,5,6-tetrahydropyridin)-4-yl]thiazol-2-yl]carbonyl]piperazine 4-[(6-Chloronaphthalen-2-yl)sulfonyl]-2-[(N-methyl)carbamoyl]-1-[[5-[(1-methyl-1,2,5,6-tetrahydropyridin)-4-yl]thiazol-2-yl]carbonyl]piperazine 1-[[5-[(1-Carbamoyl-1,2,5,6-tetrahydropyridin)-4-yl]thiazol-2-yl]carbonyl]-4-[(6-chloronaphthalen-2-yl)sulfonyl]-2-[(N-methyl)carbamoyl]piperazine 1-[[5-[(1-Acetoimidoyl-1,2,5,6-tetrahydropyridin)-4-yl]thiazol-2-yl]carbonyl]-4-[(6-chloronaphthalen-2-yl)sulfonyl]-2-[(N-methyl)carbamoyl]piperazine 1-[(6-Chloronaphthalen-2-yl)sulfonyl]-4-[[5-(pyridin-4-yl)thiazol-2-yl]carbonyl]piperazine 4-2-[[4-[(6-Chloronaphthalen-2-yl)sulfonyl]piperazin-1-yl]carbonyl]thiazol-5-yl]pyridine N-oxide 1-[(6-Chloronaphthalen-2-yl)sulfonyl]-4-[[5-(pyridin-3-yl)thiazol-2-yl]carbonyl]piperazine 3-[2-[[4-[(6-Chloronaphthalen-2-yl)sulfonyl]piperazin-1-yl]carbonyl]thiazol-5-yl]pyridine N-oxide 1-[(6-Chloronaphthalen-2-yl)sulfonyl]-4-[[5-(pyridin-2-yl)thiazol-2-yl]carbonyl]piperazine 2-[2-[[4-[(6-Chloronaphthalen-2-yl)sulfonyl]piperazin-1-yl]carbonyl]thiazol-5-yl]pyridine N-oxide 1-[(5-Chloroindol-2-yl)sulfonyl]-4-[[5-[(1-methylpiperidin)-4-yl]thiazol-2-yl]carbonyl]piperazine 1-[(5-Chloroindol-2-yl)sulfonyl]-4-[[5-[(1-methylpiperidin)-3-yl]thiazol-2-yl]carbonyl]piperazine 1-[(5-Chloroindol-2-yl)sulfonyl]-4-[[5-[(1-methylpiperidin)-2-yl]thiazol-2-yl]carbonyl]piperazine 4-[(5-Chloroindol-2-yl)sulfonyl]-2-[(N-methyl)carbamoyl]-1-[[5-[(1-methylpiperidin)-4-yl]thiazol-2-yl]carbonyl]piperazine 4-[(5-Chloroindol-2-yl)sulfonyl]-2-[(N-methyl)carbamoyl]-1-[[5-[(1-methylpiperidin)-3-yl]thiazol-2-yl]carbonyl]piperazine 4-[(5-Chloroindol-2-yl)sulfonyl]-2-[(N-methyl)carbamoyl]-1-[[5-[(1-methylpiperidin)-2-yl]thiazol-2-yl]carbonyl]piperazine 1-[(5-Chloroindol-2-yl)sulfonyl]-4-[[5-(pyrrolidin-3-yl)thiazol-2-yl]carbonyl]piperazine 1-[(5-Chloroindol-2-yl)sulfonyl]-4-[[5-(1-methylpyrrolidin-3-yl)thiazol-2-yl]carbonyl]piperazine 1-[[5-(1-Carbamoylpyrrolidin-3-yl)thiazol-2-yl]carbonyl]-4-[(5-chloroindol-2-yl)sulfonyl]piperazine 1-[[5-(1-Acetoimidoylpyrrolidin-3-yl)thiazol-2-yl]carbonyl]-4-[(5-chloroindol-2-yl)sulfonyl]piperazine 4-[(5-Chloroindol-2-yl)sulfonyl]-2-[(N-methyl)carbamoyl]-1-[[5-(pyrrolidin-3-yl)thiazol-2-yl]carbonyl]piperazine 4-[(5-Chloroindol-2-yl)sulfonyl]-2-[(N-methyl)carbamoyl]-1-[[5-(1-methylpyrrolidin-3-yl)thiazol-2-yl]carbonyl]piperazine 1-[[5-(1-Carbamoylpyrrolidin-3-yl)thiazol-2-yl]carbonyl]-4-[(5-chloroindol-2-yl)sulfonyl]-2-[(N-methyl)carbamoyl]piperazine 1-[[5-(1-Acetoimidoylpyrrolidin-3-yl)thiazol-2-yl]carbonyl]-4-[(5-chloroindol-2-yl)sulfonyl]-2-[(N-methyl)carbamoyl]piperazine 1-[(5-Chloroindol-2-yl)sulfonyl]-4-[[5-[(1,2,5,6-tetrahydropyridin)-4-yl]thiazol-2-yl]carbonyl]piperazine 1-[(5-Chloroindol-2-yl)sulfonyl]-4-[[5-[(1-methyl-1,2,5,6-tetrahydropyridin)-4-yl]thiazol-2-yl]carbonyl]piperazine 1-[[5-[(1-Carbamoyl-1,2,5,6-tetrahydropyridin)-4-yl]thiazol-2-yl]carbonyl]-4-[(5-chloroindol-2-yl)sulfonyl]piperazine 1-[[5-[(1-Acetoimidoyl-1,2,5,6-tetrahydropyridin)-4-yl]thiazol-2-yl]carbonyl]-4-[(5-chloroindol-2-yl)sulfonyl]piperazine 4-[(5-Chloroindol-2-yl)sulfonyl]-2-[(N-methyl)carbamoyl]-1-[[5-[(1,2,5,6-tetrahydropyridin)-4-yl]thiazol-2-yl]carbonyl]piperazine 4-[(5-Chloroindol-2-yl)sulfonyl]-2-[(N-methyl)carbamoyl]-1-[[5-[(1-methyl-1,2,5,6-tetrahydropyridin)-4-yl]thiazol-2-yl]carbonyl]piperazine 1-[[5-[(1-carbamoyl-1,2,5,6-tetrahydropyridin)-4-yl]thiazol-2-yl]carbonyl]-4-[(5-chloroindol-2-yl)sulfonyl]-2-[(N-methyl)carbamoyl]piperazine 1-[[5-[(1-Acetoimidoyl-1,2,5,6-tetrahydropyridin)-4-yl]thiazol-2-yl]carbonyl]-4-[(5-chloroindol-2-yl)sulfonyl]-2-[(N-methyl)carbamoyl]piperazine 1-[(5-Chloroindol-2-yl)sulfonyl]-4-[[5-(pyridin-4-yl)thiazol-2-yl]carbonyl]piperazine 4-[2-[[4-[(5-Chloroindol-2-yl)sulfonyl]piperazin-1-yl]carbonyl]thiazol-5-yl]pyridine N-oxide 1-[(5-Chloroindol-2-yl)sulfonyl]-4-[[5-(pyridin-3-yl)thiazol-2-yl]carbonyl]piperazine 3-[2-[[4-[(5-Chloroindol-2-yl)sulfonyl]piperazin-1-yl]carbonyl]thiazol-5-yl]pyridine N-oxide 1-[(5-Chloroindol-2-yl)sulfonyl]-4-[[5-(pyridin-2-yl)thiazol-2-yl]carbonyl]piperazine 2-[2-[[4-[(5-Chloroindol-2-yl)sulfonyl]piperazin-1-yl]carbonyl]thiazol-5-yl]pyridine N-oxide 1-[(6-Chlorobenzo[b]thien-2-yl)sulfonyl]-4-[[5-[(1-methylpiperidin)-4-yl]thiazol-2-yl]carbonyl]piperazine 1-[(6-Chlorobenzo[b]thien-2-yl)sulfonyl]-4-[[5-[(1-methylpiperidin)-3-yl]thiazol-2-yl]carbonyl]piperazine 1-[(6-Chlorobenzo[b]thien-2-yl)sulfonyl]-4-[[5-[(1-methylpiperidin)-2-yl]thiazol-2-yl]carbonyl]piperazine 4-[(6-Chlorobenzo[b]thien-2-yl)sulfonyl]-2-[(N-methyl)carbamoyl]-1-[[5-[(1-methylpiperidin)-4-yl]thiazol-2-yl]carbonyl]piperazine 4-[(6-Chlorobenzo[b]thien-2-yl)sulfonyl]-2-[(N-methyl)carbamoyl]-1-[[5-[(1-methylpiperidin)-3-yl]thiazol-2-yl]carbonyl]piperazine 4-[(6-chlorobenzo[b]thien-2-yl)sulfonyl]-2-[(N-methyl)carbamoyl]-1-[[5-[(1-methylpiperidin)-2-yl]thiazol-2-yl]carbonyl]piperazine 1-[(6-Chlorobenzo[b]thien-2-yl)sulfonyl]-4-[[5-(pyrrolidin-3-yl)thiazol-2-yl]carbonyl]piperazine 1-[(6-Chlorobenzo[b]thien-2-yl)sulfonyl]-4-[[5-(1-methylpyrrolidin-3-yl)thiazol-2-yl]carbonyl]piperazine 1-[[5-(1-Carbamoylpyrrolidin-3-yl)thiazol-2-yl]carbonyl]-4-[(6-chlorobenzo[b]thien-2-yl)sulfonyl]piperazine 1-[[5-(1-Acetoimidoylpyrrolidin-3-yl)thiazol-2-yl]carbonyl]-4-[(6-chlorobenzo[b]thien-2-yl)sulfonyl]piperazine 4-[(6-Chlorobenzo[b]thien-2-yl)sulfonyl]-2-[(N-methyl)carbamoyl]-1-[[5-(pyrrolidin-3-yl)thiazol-2-yl]carbonyl]piperazine 4-[(6-Chlorobenzo[b]thien-2-yl)sulfonyl]-2-[(N-methyl)carbamoyl]-1-[[5-(1-methylpyrrolidin-3-yl)thiazol-2-yl]carbonyl]piperazine 1-[[5-(1-Carbamoylpyrrolidin-3-yl)thiazol-2-yl]carbonyl]-4-[(6-chlorobenzo[b]thien-2-yl)sulfonyl]-2-[(N-methyl)carbamoyl]piperazine 1-[[5-(1-Acetoimidoylpyrrolidin-3-yl)thiazol-2-yl]carbonyl]-4-[(6-chlorobenzo[b]thien-2-yl)sulfonyl]-2-[(N-methyl)carbamoyl]piperazine 1-[(6-Chlorobenzo[b]thien-2-yl)sulfonyl]-4-[[5-[(1,2,5,6-tetrahydropyridin)-4-yl]thiazol-2-yl]carbonyl]piperazine 1-[(6-Chlorobenzo[b]thien-2-yl)sulfonyl]-4-[[5-[(1-methyl-1,2,5,6-tetrahydropyridin)-4-yl]thiazol-2-yl]carbonyl]piperazine 1-[[5-[(1-Carbamoyl-1,2,5,6-tetrahydropyridin)-4-yl]thiazol-2-yl]carbonyl]-4-[(6-chlorobenzo[b]thien-2-yl)sulfonyl]piperazine 1-[[5-[(1-Acetoimidoyl-1,2,5,6-tetrahydropyridin)-4-yl]thiazol-2-yl]carbonyl]-4-[(6-chlorobenzo[b]thien-2-yl)sulfonyl]piperazine 4-[(6-Chlorobenzo[b]thien-2-yl)sulfonyl]-2-[(N-methyl)carbamoyl]-1-[[5-[(1,2,5,6-tetrahydropyridin)-4-yl]thiazol-2-yl]carbonyl]piperazine 4-[(6-Chlorobenzo[b]thien-2-yl)sulfonyl]-2-[(N-methyl)carbamoyl]-1-[[5-[(1-methyl-1,2,5,6-tetrahydropyridin)-4-yl]thiazol-2-yl]carbonyl]piperazine 1-[[5-[(1-Carbamoyl-1,2,5,6-tetrahydropyridin)-4-yl]thiazol-2-yl]carbonyl]-4-[(6-chlorobenzo[b]thien-2-yl)sulfonyl]-2-[(N-methyl)carbamoyl]piperazine 1-[[5-[(1-Acetoimidoyl-1,2,5,6-tetrahydropyridin)-4-yl]thiazol-2-yl]carbonyl]-4-[(6-chlorobenzo[b]thien-2-yl)sulfonyl]-2-[(N-methyl)carbamoyl]piperazine 1-[(6-Chlorobenzo[b]thien-2-yl)sulfonyl]-4-[[5-(pyridin-4-yl)thiazol-2-yl]carbonyl]piperazine 4-[2-[[4-[(6-Chlorobenzo[b]thien-2-yl)sulfonyl]piperazin-1-yl]carbonyl]thiazol-5-yl]pyridine N-oxide 1-[(6-Chlorobenzo[b]thien-2-yl)sulfonyl]-4-[[5-(pyridin-3-yl)thiazol-2-yl]carbonyl]piperazine 3-[2-[[4-[(6-chlorobenzo[b]thien-2-yl)sulfonyl]piperazin-1-yl]carbonyl]thiazol-5-yl]pyridine N-oxide 1-[(6-Chlorobenzo[b]thien-2-yl)sulfonyl]-4-[[5-(pyridin-2-yl)thiazol-2-yl]carbonyl]piperazine 2-[2-[[4-[(6-Chlorobenzo[b]thien-2-yl)sulfonyl]piperazin-1-yl]carbonyl]thiazol-5-yl]pyridine N-oxide 1-[(6-Chloronaphthalen-2-yl)sulfonyl]-4-[[1,2-dihydro-2-oxo-6-(pyridin-4-yl)pyridin-3-yl]carbonyl]piperazine 1-[(6-Chlorobenzo[b]thien-2-yl)sulfonyl]-4-[[1,2-dihydro-2-oxo-6-(pyridin-4-yl)pyridin-3-yl]carbonyl]piperazine 1-[(5-Chloroindol-2-yl)sulfonyl]-4-[[1,2-dihydro-2-oxo-6-(pyridin-4-yl)pyridin-3-yl]carbonyl]piperazine 1-[(6-Chloronaphthalen-2-yl)sulfonyl]-4-[[6-(pyridin-4-yl)-pyridazin-3-yl]carbonyl]piperazine 1-[(6-Chlorobenzo[b]thien-2-yl)sulfonyl]-4-[[6-(pyridin-4-yl)-pyridazin-3-yl]carbonyl]piperazine 1-[(5-Chloroindol-2-yl)sulfonyl]-4-[[6-(pyridin-4-yl)-pyridazin-3-yl]carbonyl]piperazine 1-[(6-Chloronaphthalen-2-yl)sulfonyl]-4-[[3-(pyridin-4-yl)-1,2,4-triazin-6-yl]carbonyl]piperazine 1-[(6-Chlorobenzo[b]thien-2-yl)sulfonyl]-4-[[3-(pyridin-4-yl)-1,2,4-triazin-6-yl]carbonyl]piperazine 1-[(5-Chloroindol-2-yl)sulfonyl]-4-[[3-(pyridin-4-yl)-1,2,4-triazin-6-yl]carbonyl]piperazine 1-[(6-Chloronaphthalen-2-yl)sulfonyl]-4-[[2,5-dihydro-5-oxo-6-(pyridin-4-yl)-1,2,4-triazin-3-yl]carbonyl]piperazine 1-[(6-Chloronaphthalen-2-yl)sulfonyl]-4-[[6-(pyridin-4-yl)-1,2,4-triazin-3-yl]carbonyl]piperazine 1-[(6-Chlorobenzo[b]thien-2-yl)sulfonyl]-4-[[6-(pyridin-4-yl)-1,2,4-triazin-3-yl]carbonyl]piperazine 1-[(5-Chloroindol-2-yl)sulfonyl]-4-[[6-(pyridin-4-yl)-1,2,4-triazin-3-yl]carbonyl]piperazine 4-[3-[[4-[(6-Chloronaphthalen-2-yl)sulfonyl]piperazin-1-yl]carbonyl]-1,2-dihydro-2-oxopyridin-6-yl]pyridine N-oxide 4-[3-[[4-[(6-chlorobenzo[b]thien-2-yl)sulfonyl]piperazin-1-yl]carbonyl]-1,2-dihydro-2-oxopyridin-6-yl]pyridine N-oxide 4-[3-[[4-[(5-Chloroindol-2-yl)sulfonyl]piperazin-1-yl]carbonyl]-1,2-dihydro-2-oxopyridin-6-yl]pyridine N-oxide 4-[6-[[4-[(6-Chloronaphthalen-2-yl)sulfonyl]piperazin-1-yl]carbonyl]pyridazin-3-yl]pyridine N-oxide 4-[6-[[4-[(6-Chlorobenzo[b]thien-2-yl)sulfonyl]piperazin-1-yl]carbonyl]pyridazin-3-yl]pyridine N-oxide 4-[6-[[4-[(5-Chloroindol-2-yl)sulfonyl]piperazin-1-yl]carbonyl]pyridazin-3-yl]pyridine N-oxide 4-[6-[[4-[(6-Chloronaphthalen-2-yl)sulfonyl]piperazin-1-yl]carbonyl]-1,2,4-triazin-3-yl]pyridine N-oxide 4-[6-[[4-[(6-Chlorobenzo[b]thien-2-yl)sulfonyl]piperazin-1-yl]carbonyl]-1,2,4-triazin-3-yl]pyridine N-oxide 4-[6-[[4-[(5-Chloroindol-2-yl)sulfonyl]piperazin-1-yl]carbonyl]-1,2,4-triazin-3-yl]pyridine N-oxide 4-[3-[[4-[(6-Chloronaphthalen-2-yl)sulfonyl]piperazin-1-yl]carbonyl]-2,5-dihydro-5-oxo-1,2,4-triazin-6-yl]pyridine N-oxide 4-[3-[[4-[(6-Chloronaphthalen-2-yl)sulfonyl]piperazin-1-yl]carbonyl]-1,2,4-triazin-6-yl]pyridine N-oxide 4-[3-[[4-[(6-Chlorobenzo[b]thien-2-yl)sulfonyl]piperazin-1-yl]carbonyl]-1,2,4-triazin-6-yl]pyridine N-oxide 4-[3-[[4-[(5-Chloroindol-2-yl)sulfonyl]piperazin-1-yl]carbonyl]-1,2,4-triazin-6-yl]pyridine N-oxide 1-[(6-Chloronaphthalen-2-yl)sulfonyl]-4-[[5-(2-methylpyridin-4-yl)pyrimidin-2-yl]carbonyl]piperazine 1-[(6-Chlorobenzo[b]thien-2-yl)sulfonyl]-4-[[5-(2-methylpyridin-4-yl)pyrimidin-2-yl]carbonyl]piperazine 1-[(5-Chloroindol-2-yl)sulfonyl]-4-[[5-(2-methylpyridin-4-yl)pyrimidin-2-yl]carbonyl]piperazine 1-[(6-Chloronaphthalen-2-yl)sulfonyl]-4-[[5-(2-hydroxymethylpyridin-4-yl)pyrimidin-2-yl]carbonyl]piperazine 1-[(6-Chlorobenzo[b]thien-2-yl)sulfonyl]-4-[[5-(2-hydroxymethylpyridin-4-yl)pyrimidin-2-yl]carbonyl]piperazine 1-[(5-Chloroindol-2-yl)sulfonyl]-4-[[5-(2-hydroxymethylpyridin-4-yl)pyrimidin-2-yl]carbonyl]piperazine 1-[(6-Chloronaphthalen-2-yl)sulfonyl]-4-[[5-(2,6-dimethylpyridin-4-yl)pyrimidin-2-yl]carbonyl]piperazine 1-[(6-Chlorobenzo[b]thien-2-yl)sulfonyl]-4-[[5-(2,6-dimethylpyridin-4-yl)pyrimidin-2-yl]carbonyl]piperazine 1-[(5-Chloroindol-2-yl)sulfonyl]-4-[[5-(2,6-dimethylpyridin-4-yl)pyrimidin-2-yl]carbonyl]piperazine 1-[(6-Chloronaphthalen-2-yl)sulfonyl]-4-[[5-(2,3-dimethylpyridin-4-yl)pyrimidin-2-yl]carbonyl]piperazine 1-[(6-Chlorobenzo[b]thien-2-yl)sulfonyl]-4-[[5-(2,3-dimethylpyridin-4-yl)pyrimidin-2-yl]carbonyl]piperazine 1-[(5-Chloroindol-2-yl)sulfonyl]-4-[[5-(2,3-dimethylpyridin-4-yl)pyrimidin-2-yl]carbonyl]piperazine 1-[(6-Chloronaphthalen-2-yl)sulfonyl]-4-[[5-(3-methylpyridin-4-yl)pyrimidin-2-yl]carbonyl]piperazine 1-[(6-Chlorobenzo[b]thien-2-yl)sulfonyl]-4-[[5-(3-methylpyridin-4-yl)pyrimidin-2-yl]carbonyl]piperazine 1-[(5-Chloroindol-2-yl)sulfonyl]-4-[[5-(3-methylpyridin-4-yl)pyrimidin-2-yl]carbonyl]piperazine 1-[(6-Chloronaphthalen-2-yl)sulfonyl]-4-[[5-(3-fluoropyridin-4-yl)pyrimidin-2-yl]carbonyl]piperazine 1-[(6-Chlorobenzo[b]thien-2-yl)sulfonyl]-4-[[5-(3-fluoropyridin-4-yl)pyrimidin-2-yl]carbonyl]piperazine 1-[(5-Chloroindol-2-yl)sulfonyl]-4-[[5-(2-fluoropyridin-4-yl)pyrimidin-2-yl]carbonyl]piperazine 1-[(6-Chloronaphthalen-2-yl)sulfonyl]-4-[[5-(2,5-dimethylpyridin-4-yl)pyrimidin-2-yl]carbonyl]piperazine 1-[(6-Chlorobenzo[b]thien-2-yl)sulfonyl]-4-[[5-(2,5-dimethylpyridin-4-yl)pyrimidin-2-yl]carbonyl]piperazine 1-[(5-Chloroindol-2-yl)sulfonyl]-4-[[5-(2,5-dimethylpyridin-4-yl)pyrimidin-2-yl]carbonyl]piperazine 4-[2-[[4-[(6-Chloronaphthalen-2-yl)sulfonyl]piperazin-1-yl]carbonyl]pyrimidin-5-yl]-2-methylpyridine N-oxide 4-[2-[[4-[(6-Chlorobenzo[b]thien-2-yl)sulfonyl]piperazin-1-yl]carbonyl]pyrimidin-5-yl]-2-methylpyridine N-oxide 4-[2-[[4-[(5-Chloroindol-2-yl)sulfonyl]piperazin-1-yl]carbonyl]pyrimidin-5-yl]-2-methylpyridine N-oxide 4-[2-[[4-[(6-Chloronaphthalen-2-yl)sulfonyl]piperazin-1-yl]carbonyl]pyrimidin-5-yl]-2-hydroxymethylpyridine N-oxide 4-[2-[[4-[(6-Chlorobenzo[b]thien-2-yl)sulfonyl]piperazin-1-yl]carbonyl]pyrimidin-5-yl]-2-hydroxymethylpyridine N-oxide 4-[2-[[4-[(5-Chloroindol-2-yl)sulfonyl]piperazin-1-yl]carbonyl]pyrimidin-5-yl]-2-hydroxymethylpyridine N-oxide 4-[2-[[4-[(6-Chloronaphthalen-2-yl)sulfonyl]piperazin-1-yl]carbonyl]pyrimidin-5-yl]-2,6-dimethylpyridine N-oxide 4-[2-[[4-[(6-Chlorobenzo[b]thien-2-yl)sulfonyl]piperazin-1-yl]carbonyl]pyrimidin-5-yl]-2,6-dimethylpyridine N-oxide 4-[2-[[4-[(5-Chloroindol-2-yl)sulfonyl]piperazin-1-yl]carbonyl]pyrimidin-5-yl]-2,6-dimethylpyridine N-oxide 4-[2-[[4-[(6-Chloronaphthalen-2-yl)sulfonyl]piperazin-1-yl]carbonyl]pyrimidin-5-yl]-2,3-dimethylpyridine N-oxide 4-[2-[[4-[(6-Chlorobenzo[b]thien-2-yl)sulfonyl]piperazin-1-yl]carbonyl]pyrimidin-5-yl]-2,3-dimethylpyridine N-oxide 4-[2-[[4-[(5-Chloroindol-2-yl)sulfonyl]piperazin-1-yl] carbonyl]pyrimidin-5-yl]-2,3-dimethylpyridine N-oxide 4-[2-[[4-[(6-Chloronaphthalen-2-yl)sulfonyl]piperazin-1-yl]carbonyl]pyrimidin-5-yl]-3-methylpyridine N-oxide 4-[2-[[4-[(6-Chlorobenzo[b]thien-2-yl)sulfonyl] piperazin-1-yl]carbonyl]pyrimidin-5-yl]-3-methylpyridine N-oxide 4-[2-[[4-[(5-Chloroindol-2-yl)sulfonyl]piperazin-1-yl] carbonyl]pyrimidin-5-yl]-3-methylpyridine N-oxide 4-[2-[[4-[(6-Chloronaphthalen-2-yl)sulfonyl]piperazin-1-yl]carbonyl]pyrimidin-5-yl]-3-fluoropyridine N-oxide 4-[2-[[4-[(6-Chlorobenzo[b]thien-2-yl)sulfonyl] piperazin-1-yl]carbonyl]pyrimidin-5-yl]-3-fluoropyridine N-oxide 4-[2-[[4-[(5-Chloroindol-2-yl)sulfonyl]piperazin-1-yl] carbonyl]pyrimidin-5-yl]-2-fluoropyridine N-oxide 4-[2-[[4-[(6-Chloronaphthalen-2-yl)sulfonyl]piperazin-1-yl]carbonyl]pyrimidin-5-yl]-2,5-dimethylpyridine N-oxide 4-[2-[[4-[(6-Chlorobenzo[b]thien-2-yl)sulfonyl] piperazin-1-yl]carbonyl]pyrimidin-5-yl]-2,5-dimethylpyridine N-oxide 4-[2-[[4-[(5-Chloroindol-2-yl)sulfonyl]piperazin-1-yl] carbonyl]pyrimidin-5-yl]-2,5-dimethylpyridine N-oxide 1-[(6-Chloronaphthalen-2-yl)sulfonyl]-4-[[2-(pyridin-4-yl)-3,4,5,6-tetrahydropyrimidin-5-yl]carbonyl]piperazine 1-[(6-Chlorobenzo[b]thien-2-yl)sulfonyl]-4-[[2-(pyridin-4-yl)-3,4,5,6-tetrahydropyrimidin-5-yl]carbonyl]piperazine 1-[(5-Chloroindol-2-yl)sulfonyl]-4-[[2-(pyridin-4-yl)-3,4,5,6-tetrahydropyrimidin-5-yl]carbonyl]piperazine 1-[(6-Chloronaphthalen-2-yl)sulfonyl]-4-[[5,6-dihydro-2-(pyridin-4-yl)oxazin-5-yl]carbonyl]piperazine 1-[(6-Chlorobenzo[b]thien-2-yl)sulfonyl]-4-[[5,6-dihydro-2-(pyridin-4-yl)oxazin-5-yl]carbonyl]piperazine 1-[(5-Chloroindol-2-yl)sulfonyl]-4-[[5,6-dihydro-2-(pyridin-4-yl)oxazin-5-yl]carbonyl]piperazine 3-[(6-Chloronaphthalen-2-yl)sulfonyl]-6,7-dihydroxy-8-[4-(pyridin-4-yl)benzoyl]-3,8-diazabicyclo[3.2.1]octane 4-[4-[[[3-[(6-Chloronaphthalen-2-yl)sulfonyl]-6,7-dihydroxy-3,8-diazabicyclo[3.2.1]octan]-8-yl]carbonyl] phenyl]pyridine N-oxide 3-[(5-Chloroindol-2-yl)sulfonyl]-6,7-dihydroxy-8-[4-(pyridin-4-yl)benzoyl]-3,8-diazabicyclo[3.2.1]octane 4-[4-[[[3-[(5-Chloroindol-2-yl)sulfonyl]-6,7-dihydroxy-3,8-diazabicyclo[3.2.1]octan]-8-yl]carbonyl]phenyl] pyridine N-oxide 3-[(6-Chlorobenzo[b]thien-2-yl)sulfonyl]-6,7-dihydroxy-8-[4-(pyridin-4-yl)benzoyl]-3,8-diazabicyclo[3.2.1]octane 4-[4-[[[3-[(6-Chlorobenzo[b]thien-2-yl)sulfonyl]-6,7-dihydroxy-3,8-diazabicyclo[3.2.1]octan]-8-yl]carbonyl] phenyl]pyridine N-oxide 3-[(6-Chloronaphthalen-2-yl)sulfonyl]-6,7-dihydroxy-8-[[5-(pyridin-4-yl)pyrimidin-2-yl]carbonyl]-3,8-diazabicyclo[3.2.1]octane 4-[2-[3-[(6-Chloronaphthalen-2-yl)sulfonyl]-3,8-diazabicyclo[3.2.1]octan-8-yl]carbonylpyrimidin-5-yl] pyridine N-oxide 3-[(6-Chloronaphthalen-2-yl)sulfonyl]-6,7-dihydroxy-[[2-(pyridin-4-yl)pyrimidin-5-yl]carbonyl]-3,8-diazabicyclo[3.2.1]octane 4-[5-[3-[(6-Chloronaphthalen-2-yl)sulfonyl]-6,7-dihydroxy-3,8-diazabicyclo[3.2.1]octan-8-yl] carbonylpyrimidin-2-yl]pyridine N-oxide 3-[(5-Chloroindol-2-yl)sulfonyl]-6,7-dihydroxy-8-[[5-(pyridin-4-yl)pyrimidin-2-yl]carbonyl]-3,8-diazabicyclo [3.2.1]octane 4-[5-[3-[(5-Chloroindol-2-yl)sulfonyl]-6,7-dihydroxy-3,8-diazabicyclo[3.2.1]octan-8-yl]carbonylpyrimidin-2-yl] pyridine N-oxide 3-[(5-Chloroindol-2-yl)sulfonyl]-6,7-dihydroxy-8-[[2-(pyridin-4-yl)pyrimidin-5-yl]carbonyl]-3,8-diazabicyclo [3.2.1]octane 4-[2-[3-[(5-Chloroindol-2-yl)sulfonyl]-6,7-dihydroxy-3,8-diazabicyclo[3.2.1]octan-8-yl]carbonylpyrimidin-5-yl] pyridine N-oxide 3-[(6-Chlorobenzo[b]thien-2-yl)sulfonyl]-6,7-dihydroxy-8-[[5-(pyridin-4-yl)pyrimidin-2-yl]carbonyl]-3,8-diazabicyclo[3.2.1]octane 4-[5-[3-[(6-Chlorobenzo[b]thien-2-yl)sulfonyl]-6,7-dihydroxy-3,8-diazabicyclo[3.2.1]octan-8-yl] carbonylpyrimidin-2-yl]pyridine N-oxide 3-[(6-Chlorobenzo[b]thien-2-yl)sulfonyl]-6,7-dihydroxy-8-[[2-(pyridin-4-yl)pyrimidin-5-yl]carbonyl]-3,8-diazabicyclo[3.2.1]octane 4-[2-[3-[(6-Chlorobenzo[b]thien-2-yl)sulfonyl]-6,7-dihydroxy-3,8-diazabicyclo[3.2.1]octan-8-yl] carbonylpyrimidin-5-yl]pyridine N-oxide 3-[(6-Chloronaphthalen-2-yl)sulfonyl]-6,7-dihydroxy-8-[[5-(pyridin-4-yl)pyrazin-2-yl]carbonyl]-3,8-diazabicyclo [3.2.1]octane 4-[5-[3-[(6-Chloronaphthalen-2-yl)sulfonyl]-6,7-dihydroxy-3,8-diazabicyclo[3.2.1]octan-8-yl] carbonylpyrazin-2-yl]pyridine N-oxide 3-[(5-Chloroindol-2-yl)sulfonyl]-6,7-dihydroxy-8-[[5-(pyridin-4-yl)pyrazin-2-yl]carbonyl]-3,8-diazabicyclo [3.2.1]octane 4-[5-[3-[(5-Chloroindol-2-yl)sulfonyl]-6,7-dihydroxy-3,8-diazabicyclo[3.2.1]octan-8-yl]carbonylpyrazin-2-yl] pyridine N-oxide 3-[(6-Chlorobenzo[b]thien-2-yl)sulfonyl]-6,7-dihydroxy-8-[[5-(pyridin-4-yl)pyrazin-2-yl]carbonyl]-3,8-diazabicyclo [3.2.1]octane 4-[5-[3-[(6-Chlorobenzo[b]thien-2-yl)sulfonyl]-6,7-dihydroxy-3,8-diazabicyclo[3.2.1]octan-8-yl] carbonylpyrazin-2-yl]pyridine N-oxide 3-[(6-Chloronaphthalen-2-yl)sulfonyl]-6,7-dihydroxy-8-[[6-(pyridin-4-yl)pyridazin-3-yl]carbonyl]-3,8-diazabicyclo [3.2.1]octane 4-[6-[3-[(6-Chloronaphthalen-2-yl)sulfonyl]-6,7-dihydroxy-3,8-diazabicyclo[3.2.1]octan-8-yl] carbonylpyridazin-3-yl]pyridine N-oxide 3-[(5-Chloroindol-2-yl)sulfonyl]-6,7-dihydroxy-8-[[6-(pyridin-4-yl)pyridazin-3-yl]carbonyl]-3,8-diazabicyclo [3.2.1]octane 4-[6-[3-[(5-Chloroindol-2-yl)sulfonyl]-6,7-dihydroxy-3,8-diazabicyclo[3.2.1]octan-8-yl]carbonylpyridazin-3-yl] pyridine N-oxide 3-[(6-Chlorobenzo[b]thien-2-yl)sulfonyl]-6,7-dihydroxy-8-[[6-(pyridin-4-yl)pyridazin-3-yl]carbonyl]-3,8-diazabicyclo[3.2.1]octane 4-[6-[3-[(6-Chlorobenzo[b]thien-2-yl)sulfonyl]-6,7-dihydroxy-3,8-diazabicyclo[3.2.1]octan-8-yl] carbonylpyridazin-3-yl]pyridine N-oxide 3-[(6-Chloronaphthalen-2-yl)sulfonyl]-6,7-dihydroxy-8-[[6-(pyridin-4-yl)-1,2,4-triazin-3-yl]carbonyl]-3,8-diazabicyclo[3.2.1]octane 4-[3-[3-[(6-Chloronaphthalen-2-yl)sulfonyl]-6,7-dihydroxy-3,8-diazabicyclo[3.2.1]octan-8-yl]carbonyl-1,2,4-triazin-6-yl]pyridine N-oxide 3-[(6-Chloronaphthalen-2-yl)sulfonyl]-6,7-dihydroxy-8-[[3-(pyridin-4-yl)-1,2,4-triazin-6-yl]carbonyl]-3,8-diazabicyclo[3.2.1]octane 4-[6-[3-[(6-Chloronaphthalen-2-yl)sulfonyl]-6,7-dihydroxy-3,8-diazabicyclo[3.2.1]octan-8-yl]carbonyl-1,2,4-triazin-3-yl]pyridine N-oxide 3-[(5-Chloroindol-2-yl)sulfonyl]-6,7-dihydroxy-8-[[6-(pyridin-4-yl)-1,2,4-triazin-3-yl]carbonyl]-3,8-diazabicyclo [3.2.1]octane 4-[3-[3-[(5-Chloroindol-2-yl)sulfonyl]-6,7-dihydroxy-3,8-diazabicyclo[3.2.1]octan-8-yl]carbonyl-1,2,4-triazin-6-yl]pyridine N-oxide 3-[(5-Chloroindol-2-yl)sulfonyl]-6,7-dihydroxy-8-[[3-(pyridin-4-yl)-1,2,4-triazin-6-yl]carbonyl]-3,8-diazabicyclo[3.2.1]octane 4-[6-[3-[(5-Chloroindol-2-yl)sulfonyl]-6,7-dihydroxy-3,8-diazabicyclo[3.2.1]octan-8-yl]carbonyl-1,2,4-triazin-3-yl]pyridine N-oxide 3-[(6-Chlorobenzo[b]thien-2-yl)sulfonyl]-6,7-dihydroxy-8-[[6-(pyridin-4-yl)-1,2,4-triazin-3-yl]carbonyl]-3,8-diazabicyclo[3.2.1]octane 4-[3-[3-[(6-Chlorobenzo[b]thien-2-yl)sulfonyl]-6,7-dihydroxy-3,8-diazabicyclo[3.2.1]octan-8-yl]carbonyl-1,2,4-triazin-6-yl]pyridine N-oxide 3-[(6-Chlorobenzo[b]thien-2-yl)sulfonyl]-6,7-dihydroxy-8-[[3-(pyridin-4-yl)-1,2,4-triazin-6-yl]carbonyl]-3,8-diazabicyclo[3.2.1]octane 4-[6-[3-[(6-Chlorobenzo[b]thien-2-yl)sulfonyl]-6,7-dihydroxy-3,8-diazabicyclo[3.2.1]octan-8-yl]carbonyl-1,2,4-triazin-3-yl]pyridine N-oxide 1-[(6-Chloronaphthalen-2-yl)sulfonyl]-4-[[5-(pyridin-2-yl)pyrimidin-2-yl]carbonyl]piperazine 2-[2-[4-[(6-Chloronaphthalen-2-yl)sulfonyl]piperazin-1-yl]carbonylpyrimidin-5-yl]pyridine N-oxide 1-[(6-Chloronaphthalen-2-yl)sulfonyl]-4-[[2-(pyridin-2-yl)pyrimidin-5-yl]carbonyl]piperazine 2-[5-[4-[(6-Chloronaphthalen-2-yl)sulfonyl]piperazin-1-yl]carbonylpyrimidin-2-yl]pyridine N-oxide 1-[(5-Chloroindol-2-yl)sulfonyl]-4-[[5-(pyridin-2-yl)pyrimidin-2-yl]carbonyl]piperazine 2-[2-[4-[(5-Chloroindol-2-yl)sulfonyl]piperazin-1-yl]carbonylpyrimidin-5-yl]pyridine N-oxide 1-[(5-Chloroindol-2-yl)sulfonyl]-4-[[2-(pyridin-2-yl)pyrimidin-5-yl]carbonyl]piperazine 2-[5-[4-[(5-Chloroindol-2-yl)sulfonyl]piperazin-1-yl]carbonylpyrimidin-2-yl]pyridine N-oxide 1-[(6-Chlorobenzo[b]thien-2-yl)sulfonyl]-4-[[5-(pyridin-2-yl)pyrimidin-2-yl]carbonyl]piperazine 2-[2-[4-[(6-Chlorobenzo[b]thien-2-yl)sulfonyl]piperazin-1-yl]carbonylpyrimidin-5-yl]pyridine N-oxide 1-[(6-Chlorobenzo[b]thien-2-yl)sulfonyl]-4-[[2-(pyridin-2-yl)pyrimidin-5-yl]carbonyl]piperazine 2-[5-[4-[(6-Chlorobenzo[b]thien-2-yl)sulfonyl]piperazin-1-yl]carbonylpyrimidin-2-yl]pyridine N-oxide 1-[(6-Chloronaphthalen-2-yl)sulfonyl]-4-[[5-(pyridin-2-yl)pyrazin-2-yl]carbonyl]piperazine 2-[5-[4-[(6-Chloronaphthalen-2-yl)sulfonyl]piperazin-1-yl]carbonylpyrazin-2-yl]pyridine N-oxide 1-[(5-Chloroindol-2-yl)sulfonyl]-4-[[5-(pyridin-2-yl)pyrazin-2-yl]carbonyl]piperazine 2-[5-[4-[(5-Chloroindol-2-yl)sulfonyl]piperazin-1-yl]carbonylpyrazin-2-yl]pyridine N-oxide 1-[(6-Chlorobenzo[b]thien-2-yl)sulfonyl]-4-[[5-(pyridin-2-yl)pyrazin-2-yl]carbonyl]piperazine 2-[5-[4-[(6-Chlorobenzo[b]thien-2-yl)sulfonyl]piperazin-1-yl]carbonylpyrazin-2-yl]pyridine N-oxide 1-[(6-Chloronaphthalen-2-yl)sulfonyl]-4-[[6-(pyridin-2-yl)pyridazin-3-yl]carbonyl]piperazine 2-[6-[4-[(6-Chloronaphthalen-2-yl)sulfonyl]piperazin-1-yl]carbonylpyridazin-3-yl]pyridine N-oxide 1-[(5-Chloroindol-2-yl)sulfonyl]-4-[[6-(pyridin-2-yl)pyridazin-3-yl]carbonyl]piperazine 2-[6-[4-[(5-Chloroindol-2-yl)sulfonyl]piperazin-1-yl]carbonylpyridazin-3-yl]pyridine N-oxide 1-[(6-Chlorobenzo[b]thien-2-yl)sulfonyl]-4-[[6-(pyridin-2-yl)pyridazin-3-yl]carbonyl]piperazine 2-[6-[4-[(6-Chlorobenzo[b]thien-2-yl)sulfonyl]piperazin-1-yl]carbonylpyridazin-3-yl]pyridine N-oxide 1-[(6-Chloronaphthalen-2-yl)sulfonyl]-4-[[6-(pyridin-2-yl)-1,2,4-triazin-3-yl]carbonyl]piperazine 2-[3-[4-[(6-Chloronaphthalen-2-yl)sulfonyl]piperazin-1-yl]carbonyl-1,2,4-triazin-6-yl]pyridine N-oxide 1-[(6-Chloronaphthalen-2-yl)sulfonyl]-4-[[3-(pyridin-2-yl)-1,2,4-triazin-6-yl]carbonyl]piperazine 2-[6-[4-[(6-Chloronaphthalen-2-yl)sulfonyl]piperazin-1-yl]carbonyl-1,2,4-triazin-3-yl]pyridine N-oxide 1-[(5-Chloroindol-2-yl)sulfonyl]-4-[[6-(pyridin-2-yl)-1,2,4-triazin-3-yl]carbonyl]piperazine 2-[3-[4-[(5-Chloroindol-2-yl)sulfonyl]piperazin-1-yl]carbonyl-1,2,4-triazin-6-yl]pyridine N-oxide 1-[(5-Chloroindol-2-yl)sulfonyl]-4-[[3-(pyridin-2-yl)-1,2,4-triazin-6-yl]carbonyl]piperazine 2-[6-[4-[(5-Chloroindol-2-yl)sulfonyl]piperazin-1-yl]carbonyl-1,2,4-triazin-3-yl]pyridine N-oxide 1-[(6-Chlorobenzo[b]thien-2-yl)sulfonyl]-4-[[6-(pyridin-2-yl)-1,2,4-triazin-3-yl]carbonyl]piperazine 2-[3-[4-[(6-Chlorobenzo[b]thien-2-yl)sulfonyl]piperazin-1-yl]carbonyl-1,2,4-triazin-6-yl]pyridine N-oxide 1-[(6-Chlorobenzo[b]thien-2-yl)sulfonyl]-4-[[3-(pyridin-2-yl)-1,2,4-triazin-6-yl]carbonyl]piperazine 2-[6-[4-[(6-Chlorobenzo[b]thien-2-yl)sulfonyl]piperazin-1-yl]carbonyl-1,2,4-triazin-3-yl]pyridine N-oxide 1-[[5-[6-(Aminomethyl)pyridin-2-yl]pyrimidin-2-yl]carbonyl]-4-[(6-chloronaphthalen-2-yl)sulfonyl]piperazine 2-(Aminomethyl)-6-[2-[4-[(6-chloronaphthalen-2-yl)sulfonyl]piperazin-1-yl]carbonylpyrimidin-5-yl]pyridine N-oxide 1-[[2-[6-(Aminomethyl)pyridin-2-yl]pyrimidin-5-yl]carbonyl]-4-[(6-chloronaphthalen-2-yl)sulfonyl]piperazine 2-(Aminomethyl)-6-[5-[4-[(6-chloronaphthalen-2-yl)sulfonyl]piperazin-1-yl]carbonylpyrimidin-2-yl]pyridine N-oxide 1-[[5-[6-(Aminomethyl)pyridin-2-yl]pyrimidin-2-yl]carbonyl]-4-[(5-chloroindol-2-yl)sulfonyl]piperazine 2-(Aminomethyl)-6-[2-[4-[(5-chloroindol-2-yl)sulfonyl]piperazin-1-yl]carbonylpyrimidin-5-yl]pyridine N-oxide 1-[[2-[6-(Aminomethyl)pyridin-2-yl]pyrimidin-5-yl]carbonyl]-4-[(5-chloroindol-2-yl)sulfonyl]piperazine 2-(Aminomethyl)-6-[5-[4-[(5-chloroindol-2-yl)sulfonyl]piperazin-1-yl]carbonylpyrimidin-2-yl]pyridine N-oxide 1-[[5-[6-(Aminomethyl)pyridin-2-yl]pyrimidin-2-yl]carbonyl]-4-[(6-chlorobenzo[b]thien-2-yl)sulfonyl]piperazine 2-(Aminomethyl)-6-[2-[4-[(6-chlorobenzo[b]thien-2-yl)sulfonyl]piperazin-1-yl]carbonylpyrimidin-5-yl]pyridine N-oxide 1-[[2-[6-(Aminomethyl)pyridin-2-yl]pyrimidin-5-yl]carbonyl]-4-[(6-chlorobenzo[b]thien-2-yl)sulfonyl]piperazine 2-(Aminomethyl)-6-[5-[4-[(6-chlorobenzo[b]thien-2-yl)sulfonyl]piperazin-1-yl]carbonylpyrimidin-2-yl]pyridine N-oxide 1-[(6-Chloronaphthalen-2-yl)sulfonyl]-4-[[5-(6-methylpyridin-2-yl)pyrimidin-2-yl]carbonyl]piperazine 2-[2-[4-[(6-Chloronaphthalen-2-yl)sulfonyl]piperazin-1-yl]carbonylpyrimidin-5-yl]-6-methylpyridine N-oxide 1-[(6-Chloronaphthalen-2-yl)sulfonyl]-4-[[2-(6-methylpyridin-2-yl)pyrimidin-5-yl]carbonyl]piperazine 2-[5-[4-[(6-Chloronaphthalen-2-yl)sulfonyl]piperazin-1-yl]carbonylpyrimidin-2-yl]-6-methylpyridine N-oxide 1-[(5-Chloroindol-2-yl)sulfonyl]-4-[[5-(6-methylpyridin-2-yl)pyrimidin-2-yl]carbonyl]piperazine 2-[2-[4-[(5-Chloroindol-2-yl)sulfonyl]piperazin-1-yl]carbonylpyrimidin-5-yl]-6-methylpyridine N-oxide 1-[(5-Chloroindol-2-yl)sulfonyl]-4-[[2-(6-methylpyridin-2-yl)pyrimidin-5-yl]carbonyl]piperazine 2-[5-[4-[(5-Chloroindol-2-yl)sulfonyl]piperazin-1-yl]carbonylpyrimidin-2-yl]-6-methylpyridine N-oxide 1-[(6-Chlorobenzo[b]thien-2-yl)sulfonyl]-4-[[5-(6-methylpyridin-2-yl)pyrimidin-2-yl]carbonyl]piperazine 2-[2-[4-[(6-Chlorobenzo[b]thien-2-yl)sulfonyl]piperazin-1-yl]carbonylpyrimidin-5-yl]-6-methylpyridine N-oxide 1-[(6-Chlorobenzo[b]thien-2-yl)sulfonyl]-4-[[2-(6-methylpyridin-2-yl)pyrimidin-5-yl]carbonyl]piperazine 2-[5-[4-[(6-Chlorobenzo[b]thien-2-yl)sulfonyl]piperazin-1-yl]carbonylpyrimidin-2-yl]-6-methylpyridine N-oxide 1-[(6-Chloronaphthalen-2-yl)sulfonyl]-4-[[4-(4-methylpyridin-2-yl)phenyl]carbonyl]piperazine 2-[4-(4-[(6-Chloronaphthalen-2-yl)sulfonyl]piperazin-1-yl]carbonylphenyl]-6-methylpyridine N-oxide 1-[(6-Chloronaphthalen-2-yl)sulfonyl]-4-[[5-(4-methylpyridin-2-yl)pyrimidin-2-yl]carbonyl]piperazine 2-[2-[4-[(6-Chloronaphthalen-2-yl)sulfonyl]piperazin-1-yl]carbonylpyrimidin-5-yl]-4-methylpyridine N-oxide 1-[(6-Chloronaphthalen-2-yl)sulfonyl]-4-[[2-(4-methylpyridin-2-yl)pyrimidin-5-yl]carbonyl]piperazine 2-[5-[4-[(6-Chloronaphthalen-2-yl)sulfonyl]piperazin-1-yl]carbonylpyrimidin-2-yl]-4-methylpyridine N-oxide 1-[(5-Chloroindol-2-yl)sulfonyl]-4-[[5-(4-methylpyridin-2-yl)pyrimidin-2-yl]carbonyl]piperazine 2-[2-[4-[(5-Chloroindol-2-yl)sulfonyl]piperazin-1-yl]carbonylpyrimidin-5-yl]-4-methylpyridine N-oxide 1-[(5-Chloroindol-2-yl)sulfonyl]-4-[[2-(4-methylpyridin-2-yl)pyrimidin-5-yl]carbonyl]piperazine 2-[5-[4-[(5-Chloroindol-2-yl)sulfonyl]piperazin-1-yl]carbonylpyrimidin-2-yl]-4-methylpyridine N-oxide 1-[(6-Chlorobenzo[b]thien-2-yl)sulfonyl]-4-[[5-(4-methylpyridin-2-yl)pyrimidin-2-yl]carbonyl]piperazine 2-[2-[4-[(6-Chlorobenzo[b]thien-2-yl)sulfonyl]piperazin-1-yl]carbonylpyrimidin-5-yl]-4-methylpyridine N-oxide 1-[(6-Chlorobenzo[b]thien-2-yl)sulfonyl]-4-[[2-(4-methylpyridin-2-yl)pyrimidin-5-yl]carbonyl]piperazine 2-[5-[4-[(6-Chlorobenzo[b]thien-2-yl)sulfonyl]piperazin-1-yl]carbonylpyrimidin-2-yl]-4-methylpyridine N-oxide 1-[(6-Chloronaphthalen-2-yl)sulfonyl]-4-[[5-[6-(hydroxymethyl)pyridin-2-yl]pyrimidin-2-yl]carbonyl]piperazine 2-[2-[4-[(6-Chloronaphthalen-2-yl)sulfonyl]piperazin-1-yl]carbonylpyrimidin-5-yl]-6-(hydroxymethyl)pyridine N-oxide 1-[(6-Chloronaphthalen-2-yl)sulfonyl]-4-[[2-[6-(hydroxymethyl)pyridin-2-yl]pyrimidin-5-yl]carbonyl]piperazine 2-[5-[4-[(6-Chloronaphthalen-2-yl)sulfonyl]piperazin-1-yl]carbonylpyrimidin-2-yl]-6-(hydroxymethyl)pyridine N-oxide 1-[(5-Chloroindol-2-yl)sulfonyl]-4-[[5-[6-(hydroxymethyl)pyridin-2-yl]pyrimidin-2-yl]carbonyl]piperazine 2-[2-[4-[(5-Chloroindol-2-yl)sulfonyl]piperazin-yl]carbonylpyrimidin-5-yl]-6-(hydroxymethyl)pyridine N-oxide 1-[(5-Chloroindol-2-yl)sulfonyl]-4-[[2-[6-(hydroxymethyl)pyridin-2-yl]pyrimidin-5-yl]carbonyl]piperazine 2-[5-[4-[(5-Chloroindol-2-yl)sulfonyl]piperazin-1-yl]carbonylpyrimidin-2-yl]-6-(hydroxymethyl)pyridine N-oxide 1-[(6-Chlorobenzo[b]thien-2-yl)sulfonyl]-4-[[5-[6-(hydroxymethyl)pyridin-2-yl]pyrimidin-2-yl]carbonyl]piperazine 2-[2-[4-[(6-Chlorobenzo[b]thien-2-yl)sulfonyl]piperazin-1-yl]carbonylpyrimidin-5-yl]-6-(hydroxymethyl)pyridine N-oxide 1-[(6-Chlorobenzo[b]thien-2-yl)sulfonyl]-4-[[2-[6-(hydroxymethyl)pyridin-2-yl]pyrimidin-5-yl]carbonyl]piperazine 2-[5-[4-[(6-Chlorobenzo[b]thien-2-yl)sulfonyl]piperazin-1-yl]carbonylpyrimidin-2-yl]-6-(hydroxymethyl)pyridine N-oxide 1-[(5-Chlorobenzimidazol-2-yl)sulfonyl]-4-[[4-(pyridin-2-yl)phenyl]carbonyl]piperazine 1-[(6-Chlorobenzimidazol-2-yl)sulfonyl]-4-[[4-(pyridin-2-yl)phenyl]carbonyl]piperazine 2-[4-[4-[(5-Chlorobenzimidazol-2-yl)sulfonyl]piperazin-1-yl]carbonylphenyl]pyridine N-oxide 2-[4-[4-[(6-Chlorobenzimidazol-2-yl)sulfonyl]piperazin-1-yl]carbonylphenyl]pyridine N-oxide 1-[(5-Chlorobenzimidazol-2-yl)sulfonyl]-4-[[5-(pyridin-2-yl)pyrimidin-2-yl]carbonyl]piperazine 1-[(6-Chlorobenzimidazol-2-yl)sulfonyl]-4-[[5-(pyridin-2-yl)pyrimidin-2-yl]carbonyl]piperazine 2-[2-[4-[(5-Chlorobenzimidazol-2-yl)sulfonyl]piperazin-1-yl]carbonylpyrimidin-5-yl]pyridine N-oxide 2-[2-[4-[(6-Chlorobenzimidazol-2-yl)sulfonyl]piperazin-1-yl]carbonylpyrimidin-5-yl]pyridine N-oxide 1-[(5-Chlorobenzimidazol-2-yl)sulfonyl]-4-[[2-(pyridin-2-yl)pyrimidin-5-yl]carbonyl]piperazine 1-[(6-Chlorobenzimidazol-2-yl)sulfonyl]-4-[[2-(pyridin-2-yl)pyrimidin-5-yl]carbonyl]piperazine 2-[5-[4-[(5-Chlorobenzimidazol-2-yl)sulfonyl]piperazin-1-yl]carbonylpyrimidin-2-yl]pyridine N-oxide 2-[5-[4-[(6-Chlorobenzimidazol-2-yl)sulfonyl]piperazin-1-yl]carbonylpyrimidin-2-yl]pyridine N-oxide 1-[(5-Chlorobenzimidazol-2-yl)sulfonyl]-4-[[5-(pyridin-2-yl)pyrazin-2-yl]carbonyl]piperazine 1-[(6-Chlorobenzimidazol-2-yl)sulfonyl]-4-[[5-(pyridin-2-yl)pyrazin-2-yl]carbonyl]piperazine 2-[5-[4-[(5-Chlorobenzimidazol-2-yl)sulfonyl]piperazin-1-yl]carbonylpyrazin-2-yl]pyridine N-oxide 2-[5-[4-[(6-Chlorobenzimidazol-2-yl)sulfonyl]piperazin-1-yl]carbonylpyrazin-2-yl]pyridine N-oxide 1-[(5-Chlorobenzimidazol-2-yl)sulfonyl)-4-[[6-(pyridin-2-yl)pyridazin-3-yl]carbonyl]piperazine 1-[(6-Chlorobenzimidazol-2-yl)sulfonyl]-4-[[6-(pyridin-2-yl)pyridazin-3-yl]carbonyl]piperazine 2-[6-[4-[(5-Chlorobenzimidazol-2-yl) sulfonyl]piperazin-1-yl]carbonylpyridazin-3-yl]pyridine N-oxide 2-[6-[4-[(6-Chlorobenzimidazol-2-yl)sulfonyl]piperazin-1-yl]carbonylpyridazin-3-yl]pyridine N-oxide 1-[(5-Chlorobenzimidazol-2-yl)sulfonyl]-4-[[6-(pyridin-2-yl)-1,2,4-triazin-3-yl]carbonyl]piperazine 1-[(6-Chlorobenzimidazol-2-yl) sulfonyl]-4-[[6-(pyridin-2-yl)-1,2,4-triazin-3-yl]carbonyl]piperazine 2-[3-[4-[(5-Chlorobenzimidazol-2-yl)sulfonyl]piperazin-1-yl]carbonyl-1,2,4-triazin-6-yl]pyridine N-oxide 2-[3-[4-[(6-Chlorobenzimidazol-2-yl)sulfonyl]piperazin-1-yl]carbonyl-1,2,4-triazin-6-yl]pyridine N-oxide 1-[(5-Chlorobenzimidazol-2-yl)sulfonyl]-4-[[3-(pyridin-2-yl)-1,2,4-triazin-6-yl]carbonyl]piperazine 1-[(6-Chlorobenzimidazol-2-yl)sulfonyl]-4-[[3-(pyridin-2-yl)-1,2,4-triazin-6-yl]carbonyl]piperazine 2-[6-[4-[(5-Chlorobenzimidazol-2-yl)sulfonyl]piperazin-1-yl]carbonyl-1,2,4-triazin-3-yl]pyridine N-oxide 2-[6-[4-[(6-Chlorobenzimidazol-2-yl)sulfonyl]piperazin-1-yl]carbonyl-1,2,4-triazin-3-yl]pyridine N-oxide 1-[[4-[6-(Aminomethyl)pyridin-2-yl]phenyl]carbonyl]-4-[(5-chlorobenzimidazol-2-yl)sulfonyl]piperazine 1-[[4-[6-(Aminomethyl)pyridin-2-yl]phenyl]carbonyl]-4-[(6-chlorobenzimidazol-2-yl)sulfonyl]piperazine 2-(Aminomethyl)-6-[4-[4-[(5-chlorobenzimidazol-2-yl)sulfonyl]piperazin-1-yl]carbonylphenyl]pyridine N-oxide 2-(Aminomethyl)-6-[4-[4-[(6-chlorobenzimidazol-2-yl)sulfonyl]piperazin-1-yl]carbonylphenyl]pyridine N-oxide yl) sulfonyl]piperazine 1-[[5-[6-(Aminomethyl)pyridin-2-yl]pyrimidin-2-yl]carbonyl]-4-[(6-chlorobenzimidazol-2-yl)sulfonyl]piperazine 2-(Aminomethyl)-6-[2-[4-[(5-chlorobenzimidazol-2-yl)sulfonyl]piperazin-1-yl]carbonylpyrimidin-5-yl]pyridine N-oxide 2-(Aminomethyl)-6-[2-[4-[(6-chlorobenzimidazol-2-yl)sulfonyl]piperazin-1-yl]carbonylpyrimidin-5-yl]pyridine N-oxide 1-[[2-[6-(Aminomethyl)pyridin-2-yl]pyrimidin-5-yl]carbonyl]-4-[(5-chlorobenzimidazol-2-yl)sulfonyl]piperazine 1-[[2-[6-(Aminomethyl)pyridin-2-yl]pyrimidin-5-yl]carbonyl]-4-[(6-chlorobenzimidazol-2-yl)sulfonyl]piperazine 2-(Aminomethyl)-6-[5-[4-[(5-chlorobenzimidazol-2-yl)sulfonyl]piperazin-1-yl]carbonylpyrimidin-2-yl]pyridine N-oxide 2-(Aminomethyl)-6-[5-[4-[(6-chlorobenzimidazol-2-yl)sulfonyl]piperazin-1-yl]carbonylpyrimidin-2-yl]pyridine N-oxide 1-[(5-Chlorobenzimidazol-2-yl)sulfonyl]-4-[[4-(6-methylpyridin-2-yl) phenyl]carbonyl]piperazine 1-[(6-Chlorobenzimidazol-2-yl)sulfonyl]-4-[[4-(6-methylpyridin-2-yl)phenyl]carbonyl]piperazine 2-[4-[4-[(5-Chlorobenzimidazol-2-yl)sulfonyl]piperazin-1-yl]carbonylphenyl]-6-methylpyridine N-oxide 2-[4-[4-[(6-Chlorobenzimidazol-2-yl)sulfonyl]piperazin-1-yl]carbonylphenyl]-6-methylpyridine N-oxide 1-[(-Chlorobenzimidazol-2-yl) sulfonyl]-4-[[5-(6-methylpyridin-2-yl)pyrimidin-2-yl]carbonylpiperazine 1-[(6-Chlorobenzimidazol-2-yl)sulfonyl]-4-[[5-(6-methylpyridin-2-yl)pyrimidin-2-yl]carbonyl]piperazine 2-[2-[4-[(5-Chlorobenzimidazol-2-yl)sulfonyl]piperazin-1-yl]carbonylpyrimidin-5-yl]-6-methylpyridine N-oxide 2-[2-[4-[(6-Chlorobenzimidazol-2yl) sulfonyl]piperazin-1-yl]carbonylpyrimidin-5-yl]-6-methylpyridine N-oxide 1-[(5-Chlorobenzimidazol-2-yl)sulfonyl]-4-[[2-(6-methylpyridin-2-yl)pyrimidin-5-yl]carbonyl]piperazine 1-[(6-Chlorobenzimidazol-2-yl)sulfonyl]-4-[[2-(6-methylpyridin-2-yl)pyrimidin-5-yl]carbonyl]piperazine 2-[5-[4-[(5-Chlorobenzimidazol-2-yl)sulfonyl]piperazin-1-yl]carbonylpyrimidin-2-yl]-6-methylpyridine N-oxide 2-[5-[4-[(6-Chlorobenzimidazol-2-yl)sulfonyl]piperazin-1-yl]carbonylpyrimidin-2-yl]-6-methylpyridine N-oxide 1-[(5-Chlorobenzimidazol-2-yl)sulfonyl]-4-[[4-(4-methylpyridin-2-yl)phenyl]carbonyl]piperazine 1-[(6-Chlorobenzimidazol-2-yl)sulfonyl]-4-[[4-(4-methylpyridin-2-yl)phenyl]carbonyl]piperazine 2-[4-[4-[(5-Chlorobenzimidazol-2-yl)sulfonyl]piperazin-1-yl]carbonylphenyl]-4-methylpyridine N-oxide 2-[4-[4-[(6-Chlorobenzimidazol-2-yl)sulfonyl]piperazin-1-yl]carbonylphenyl]-4-methylpyridine N-oxide 1-[(5-Chlorobenzimidazol-2-yl)sulfonyl]-4-[[5-(4-methylpyridin-2-yl)pyrimidin-2-yl]carbonyl]piperazine 1-[(6-Chlorobenzimidazol-2-yl)sulfonyl]-4-[[5-(4-methylpyridin-2-yl)pyrimidin-2-yl]carbonyl]piperazine 2-[2-[4-[(5-Chlorobenzimidazol-2-yl)sulfonyl]piperazin-1-yl]carbonylpyrimidin-5-yl-4-methylpyridine N-oxide 2-[2-[4-[(6-Chlorobenzimidazol-2-yl)sulfonyl]piperazin-1-yl]carbonylpyrimidin-5-yl]-4-methylpyridine N-oxide 1-[(5-Chlorobenzimidazol-2-yl)sulfonyl]-4-[[2-(4-dimethylpyridin-2-yl)pyrimidin-5-yl]carbonyl]piperazine 1-[(6-Chlorobenzimidazol-2-yl)sulfonyl]-4-[[2-(4-dimethylpyridin-2-yl)pyrimidin-5-yl]carbonyl]piperazine 2-[5-[4-[(5-Chlorobenzimidazol-2-yl)sulfonyl]piperazin-1-yl]carbonylpyrimidin-2-yl]-4-methylpyridine N-oxide 2-[5-[4-[(6-Chlorobenzimidazol-2-yl)sulfonyl]piperazin-1-yl]carbonylpyrimidin-2-yl]-4-methylpyridine N-oxide 1-[(5-Chlorobenzimidazol-2-yl)sulfonyl]-4-[[4-[6-(hydroxymethyl)pyridin-2-yl]phenyl]carbonyl]piperazine 1-[(6-Chlorobenzimidazol-2-yl)sulfonyl]-4-[[4-[6-(hydroxymethyl)pyridin-2-yl]phenyl]carbonyl]piperazine 2-[4-[4-[(5-Chlorobenzimidazol-2-yl)sulfonyl]piperazin-1-yl]carbonylphenyl]-6-(hydroxymethyl)pyridine N-oxide 2-[4-[4-[(6-Chlorobenzimidazol-2-yl)sulfonyl]piperazin-1-yl]carbonylphenyl]-6-(hydroxymethyl)pyridine N-oxide 1-[(5-Chlorobenzimidazol-2-yl)sulfonyl]-4-[[5-[6-(hydroxymethyl)pyridin-2-yl]pyrimidin-2-yl]carbonyl]piperazine 1-[(6-Chlorobenzimidazol-2-yl)sulfonyl]-4-[[5-[6-(hydroxymethyl)pyridin-2-yl]pyrimidin-2-yl]carbonyl]piperazine 2-[2-[4-[(5-Chlorobenzimidazol-2-yl)sulfonyl]piperazin-1-yl]carbonylpyrimidin-5-yl]-6-(hydroxymethyl)pyridine N-oxide 2-[2-[4-[(6-Chlorobenzimidazol-2-yl)sulfonyl]piperazin-1-yl]carbonylpyrimidin-5-yl]-6-(hydroxymethyl)pyridine N-oxide 1-[(5-Chlorobenzimidazol-2-yl)sulfonyl]-4-[[2-[6-(hydroxymethyl)pyridin-2-yl]pyrimidin-5-yl]carbonyl]piperazine 1-[(6-Chlorobenzimidazol-2-yl)sulfonyl]-4-[[2-[6-(hydroxymethyl)pyridin-2-yl]pyrimidin-5-yl]carbonyl]piperazine 2-[5-[4-[(5-Chlorobenzimidazol-2-yl)sulfonyl]piperazin-1-yl]carbonylpyrimidin-2-yl]-6-(hydroxymethyl)pyridine N-oxide 2-[5-[4-[(6-Chlorobenzimidazol-2-yl)sulfonyl]piperazin-1-yl]carbonylpyrimidin-2-yl]-6-(hydroxymethyl)pyridine N-oxide 1-[(5-Chlorobenzimidazol-2-yl)sulfonyl]-4-[[4-(pyridin-4-yl)phenyl]carbonyl]piperazine 1-[(6-Chlorobenzimidazol-2-yl)sulfonyl]-4-[[4-(pyridin-4-yl)phenyl]carbonyl]piperazine 4-[4-[4-[(5-Chlorobenzimidazol-2-yl)sulfonyl]piperazin-1-yl]carbonylphenyl]pyridine N-oxide 4-[4-[4-[(6-Chlorobenzimidazol-2-yl)sulfonyl]piperazin-1-yl]carbonylphenyl]pyridine N-oxide 1-[(5-Chlorobenzimidazol-2-yl)sulfonyl]-4-[[5-(pyridin-4-yl)pyrimidin-2-yl]carbonyl]piperazine 1-[(6-Chlorobenzimidazol-2-yl)sulfonyl]-4-[[5-(pyridin-4-yl)pyrimidin-2-yl]carbonyl]piperazine 4-[2-[4-[(5-Chlorobenzimidazol-2-yl)sulfonyl]piperazin-1-yl]carbonylpyrimidin-5-yl]pyridine N-oxide 4-[2-[4-[(6-Chlorobenzimidazol-2-yl)sulfonyl]piperazin-1-yl]carbonylpyrimidin-5-yl]pyridine N-oxide 1-[(5-Chlorobenzimidazol-2-yl)sulfonyl]-4-[[2-(pyridin-4-yl)pyrimidin-5-yl]carbonyl]piperazine 1-[(6-Chlorobenzimidazol-2-yl)sulfonyl]-4-[[2-(pyridin-4-yl)pyrimidin-5-yl]carbonyl]piperazine 4-[5-[4-[(5-Chlorobenzimidazol-2-yl)sulfonyl]piperazin-1-yl]carbonylpyrimidin-2-yl]pyridine N-oxide 4-[5-[4-[(6-Chlorobenzimidazol-2-yl)sulfonyl]piperazin-1-yl]carbonylpyrimidin-2-yl]pyridine N-oxide 1-[(5-Chlorobenzimidazol-2-yl)sulfonyl]-4-[[5-(pyridin-4-yl)pyrazin-2-yl]carbonyl]piperazine 1-[(6-Chlorobenzimidazol-2-yl)sulfonyl]-4-[[5-(pyridin-4-yl)pyrazin-2-yl]carbonyl]piperazine 4-[5-[4-[(5-Chlorobenzimidazol-2-yl)sulfonyl]piperazin-1-yl]carbonylpyrazin-2-yl]pyridine N-oxide
4-[5-[4-[(6-Chlorobenzimidazol-2-yl)sulfonyl]piperazin-1-yl]carbonylpyrazin-2-yl]pyridine N-oxide
1-[(5-Chlorobenzimidazol-2-yl)sulfonyl]-4-[[6-(pyridin-4-yl)pyridazin-3-yl]carbonyl]piperazine
1-[(6-Chlorobenzimidazol-2-yl)sulfonyl]-4-[[6-(pyridin-4-yl)pyridazin-3-yl]carbonyl]piperazine
4-[6-[4-[(5-Chlorobenzimidazol-2-yl)sulfonyl]piperazin-1-yl]carbonylpyridazin-3-yl]pyridine N-oxide
4-[6-[4-[(6-Chlorobenzimidazol-2-yl)sulfonyl]piperazin-1-yl]carbonylpyridazin-3-yl]pyridine N-oxide
1-[(5-Chlorobenzimidazol-2-yl)sulfonyl]-4-[[6-(pyridin-4-yl)-1,2,4-triazin-3-yl]carbonyl]piperazine
1-[(6-Chlorobenzimidazol-2-yl)sulfonyl]-4-[[6-(pyridin-4-yl)-1,2,4-triazin-3-yl]carbonyl]piperazine
4-[3-[4-[(5-Chlorobenzimidazol-2-yl)sulfonyl]piperazin-1-yl]carbonyl-1,2,4-triazin-6-yl]pyridine N-oxide
4-[3-[4-[(6-Chlorobenzimidazol-2-yl)sulfonyl]piperazin-1-yl]carbonyl-1,2,4-triazin-6-yl]pyridine N-oxide
1-[(5-Chlorobenzimidazol-2-yl)sulfonyl]-4-[[3-(pyridin-4-yl)-1,2,4-triazin-6-yl]carbonyl]piperazine
1-[(6-Chlorobenzimidazol-2-yl)sulfonyl]-4-[[3-(pyridin-4-yl)-1,2,4-triazin-6-yl]carbonyl]piperazine
4-[6-[4-[(5-Chlorobenzimidazol-2-yl)sulfonyl]piperazin-1-yl]carbonyl-1,2,4-triazin-3-yl]pyridine N-oxide
4-[6-[4-[(6-Chlorobenzimidazol-2-yl)sulfonyl]piperazin-1-yl]carbonyl-1,2,4-triazin-3-yl]pyridine N-oxide
1-[[4-[2-(Aminomethyl)pyridin-4-yl]phenyl]carbonyl]-4-[(5-chlorobenzimidazol-2-yl)sulfonyl]piperazine
1-[[4-[2-(Aminomethyl)pyridin-4-yl]phenyl]carbonyl]-4-[(6-chlorobenzimidazol-2-yl)sulfonyl]piperazine
2-(Aminomethyl)-4-[4-[4-[(5-chlorobenzimidazol-2-yl)sulfonyl]piperazin-1-yl]carbonylphenyl]pyridine N-oxide
2-(Aminomethyl)-4-[4-[4-[(6-chlorobenzimidazol-2-yl)sulfonyl]piperazin-1-yl]carbonylphenyl]pyridine N-oxide
1-[[5-[2-(Aminomethyl)pyridin-4-yl]pyrimidin-2-yl]carbonyl]-4-[(5-chlorobenzimidazol-2-yl)sulfonyl]piperazine
1-[[5-[2-(Aminomethyl)pyridin-4-yl]pyrimidin-2-yl]carbonyl]-4-[(6-chlorobenzimidazol-2-yl)sulfonyl]piperazine
2-(Aminomethyl)-4-[2-[4-[(5-chlorobenzimidazol-2-yl)sulfonyl]piperazin-1-yl]carbonylpyrimidin-5-yl]pyridine N-oxide
2-(Aminomethyl)-4-[2-[4-[(6-chlorobenzimidazol-2-yl)sulfonyl]piperazin-1-yl]carbonylpyrimidin-5-yl]pyridine N-oxide
1-[[2-[2-(Aminomethyl)pyridin-4-yl]pyrimidin-5-yl]carbonyl]-4-[(5-chlorobenzimidazol-2-yl)sulfonyl]piperazine
1-[[2-[2-(Aminomethyl)pyridin-4-yl]pyrimidin-5-yl]carbonyl]-4-[(6-chlorobenzimidazol-2-yl)sulfonyl]piperazine
2-(Aminomethyl)-4-[5-[4-[(5-chlorobenzimidazol-2-yl)sulfonyl]piperazin-1-yl]carbonylpyrimidin-2-yl]pyridine N-oxide
2-(Aminomethyl)-4-[5-[4-[(6-chlorobenzimidazol-2-yl)sulfonyl]piperazin-1-yl]carbonylpyrimidin-2-yl]pyridine N-oxide
1-[(5-Chlorobenzimidazol-2-yl)sulfonyl]-4-[[4-(2-methylpyridin-4-yl)phenyl]carbonyl]piperazine
1-[(6-Chlorobenzimidazol-2-yl)sulfonyl]-4-[[4-(2-methylpyridin-4-yl)phenyl]carbonyl]piperazine
4-[4-[4-[(5-Chlorobenzimidazol-2-yl)sulfonyl]piperazin-1-yl]carbonylphenyl]-2-methylpyridine N-oxide
4-[4-[4-[(6-Chlorobenzimidazol-2-yl)sulfonyl]piperazin-1-yl]carbonylphenyl]-2-methylpyridine N-oxide
1-[(5-Chlorobenzimidazol-2-yl)sulfonyl]-4-[[5-(2-methylpyridin-4-yl)pyrimidin-2-yl]carbonyl]piperazine
1-[(6-Chlorobenzimidazol-2-yl)sulfonyl]-4-[[5-(2-methylpyridin-4-yl)pyrimidin-2-yl]carbonyl]piperazine
4-[2-[4-[(5-Chlorobenzimidazol-2-yl)sulfonyl]piperazin-1-yl]carbonylpyrimidin-5-yl]-2-methylpyridine N-oxide
4-[2-[4-[(6-Chlorobenzimidazol-2-yl)sulfonyl]piperazin-1-yl]carbonylpyrimidin-5-yl]-2-methylpyridine N-oxide
1-[(5-Chlorobenzimidazol-2-yl)sulfonyl]-4-[[2-(2-methylpyridin-4-yl)pyrimidin-5-yl]carbonyl]piperazine
1-[(6-Chlorobenzimidazol-2-yl)sulfonyl]-4-[[2-(2-methylpyridin-4-yl)pyrimidin-5-yl]carbonyl]piperazine
4-[5-[4-[(5-Chlorobenzimidazol-2-yl)sulfonyl]piperazin-1-yl]carbonylpyrimidin-2-yl]-2-methylpyridine N-oxide
4-[5-[4-[(6-Chlorobenzimidazol-2-yl)sulfonyl]piperazin-1-yl]carbonylpyrimidin-2-yl]-2-methylpyridine N-oxide
1-[(5-Chlorobenzimidazol-2-yl)sulfonyl]-4-[[4-[2-(hydroxymethyl)pyridin-4-yl]phenyl]carbonyl]piperazine
1-[(6-Chlorobenzimidazol-2-yl)sulfonyl]-4-[[4-[2-(hydroxymethyl)pyridin-4-yl]phenyl]carbonyl]piperazine
4-[4-[4-[(5-Chlorobenzimidazol-2-yl)sulfonyl]piperazin-1-yl]carbonylphenyl]-2-(hydroxymethyl)pyridine N-oxide
4-[4-[4-[(6-Chlorobenzimidazol-2-yl)sulfonyl]piperazin-1-yl]carbonylphenyl]-2-(hydroxymethyl)pyridine N-oxide
1-[(5-Chlorobenzimidazol-2-yl)sulfonyl]-4-[[5-[2-(hydroxymethyl)pyridin-4-yl]pyrimidin-2-yl]carbonyl]piperazine
1-[(6-Chlorobenzimidazol-2-yl)sulfonyl]-4-[[5-[2-(hydroxymethyl)pyridin-4-yl]pyrimidin-2-yl]carbonyl]piperazine
4-[2-[4-[(5-Chlorobenzimidazol-2-yl)sulfonyl]piperazin-1-yl]carbonylpyrimidin-5-yl]-2-(hydroxymethyl)pyridine N-oxide
4-[2-[4-[(6-Chlorobenzimidazol-2-yl)sulfonyl]piperazin-1-yl]carbonylpyrimidin-5-yl]-2-(hydroxymethyl)pyridine N-oxide
1-[(5-Chlorobenzimidazol-2-yl)sulfonyl]-4-[[2-[2-(hydroxymethyl)pyridin-4-yl]pyrimidin-5-yl]carbonyl]piperazine
1-[(6-Chlorobenzimidazol-2-yl)sulfonyl]-4-[[2-[2-(hydroxymethyl)pyridin-4-yl]pyrimidin-5-yl]carbonyl]piperazine
4-[5-[4-[(5-Chlorobenzimidazol-2-yl)sulfonyl]piperazin-1-yl]carbonylpyrimidin-2-yl]-2-(hydroxymethyl)pyridine N-oxide
4-[5-[4-[(6-Chlorobenzimidazol-2-yl)sulfonyl]piperazin-1-yl]carbonylpyrimidin-2-yl]-2-(hydroxymethyl)pyridine N-oxide
1-[(5-Chloroisoindolin-2-yl)sulfonyl]-4-[4-(pyridin-4-yl)benzoyl]piperazine
4-[4-[[4-[(5-Chloroisoindolin-2-yl)sulfonyl]piperazin-1-yl]carbonyl]phenyl]pyridine N-oxide
1-[(5-Chloroisoindolin-2-yl)sulfonyl]-4-[4-(2-methylpyridin-4-yl)benzoyl]piperazine
4-[4-[[4-[(5-Chloroisoindolin-2-yl)sulfonyl]piperazin-1-yl]carbonyl]phenyl]-2-methylpyridine N-oxide
1-[(5-Chloro-1-isoindolinon-2-yl)sulfonyl]-4-[4-(pyridin-4-yl)benzoyl]piperazine
4-[4-[[4-[(5-Chloroisoindolin-2-yl)sulfonyl]piperazin-1-yl]carbonyl]phenyl]pyridine N-oxide
1-[(5-Chloro-2-isoindolinon-2-yl)sulfonyl]-4-[4-(2-methylpyridin-4-yl)benzoyl]piperazine
4-[4-[[4-[(5-Chloro-2-isoindolinon-2-yl)sulfonyl]piperazin-1-yl]carbonyl]phenyl]-2-methylpyridine N-oxide
1-[(1,2,3,4-Tetrahydro-5-chloroisoquinolin-2-yl)sulfonyl]-4-[4-(pyridin-4-yl)benzoyl]piperazine
4-[4-[[4-[(1,2,3,4-Tetrahydro-5-chloroisoquinolin-2-yl)sulfonyl]piperazin-1-yl]carbonyl]phenyl]pyridine N-oxide 1-[(1,2,3,4-Tetrahydro-5-chloroisoquinolin-2-yl)]-4-[4-(2-methylpyridin-4-yl)benzoyl]piperazine 4-[4-[[4-[(1,2,3,4-Tetrahydro-5-chloroisoquinolin-2-yl)sulfonyl]piperazin-1-yl]carbonyl]phenyl]-2-methylpyridine N-oxide 1-[(5-Chloro-3-hydroxyindol-2-yl)sulfonyl]-4-[4-(pyridin-4-yl)benzoyl]piperazine 4-[4-[[4-[(5-Chloro-3-hydroxyindol-2-yl)sulfonyl]piperazin-1-yl]carbonyl]phenyl]pyridine N-oxide 1-[(5-Chloro-3-hydroxyindol-2-yl)]-4-[4-(2-methylpyridin-4-yl)benzoyl]piperazine 4-[4-[[4-[(5-Chloro-3-hydroxyindol-2-yl)sulfonyl]piperazin-1-yl]carbonyl]phenyl]-2-methylpyridine N-oxide 1-[(5-Chloro-3-methoxyindol-2-yl)sulfonyl]-4-[4-(pyridin-4-yl)benzoyl]piperazine 4-[4-[[4-[(5-Chloro-3-methoxyindol-2-yl)sulfonyl]piperazin-1-yl]carbonyl]phenyl]pyridine N-oxide 1-[(5-Chloro-3-methoxyindol-2-yl)]-4-[4-(2-methylpyridin-4-yl)benzoyl]piperazine 4-[4-[[4-[(5-Chloro-3-methoxyindol-2-yl)sulfonyl]piperazin-1-yl]carbonyl]phenyl]-2-methylpyridine N-oxide 1-[(3-Acetoxy-5-Chloroindol-2-yl)sulfonyl]-4-[4-(pyridin-4-yl)benzoyl]piperazine 4-[4-[[4-[(3-Acetoxy-5-chloroindol-2-yl)sulfonyl]piperazin-1-yl]carbonyl]phenyl]pyridine N-oxide 1-[(3-Acetoxy-5-chloroindol-2-yl)]-4-[4-(2-methylpyridin-4-yl)benzoyl]piperazine 4-[4-[[4-[(3-Acetoxy-5-chloroindol-2-yl)sulfonyl]piperazin-1-yl]carbonyl]phenyl]-2-methylpyridine N-oxide 1-[(5-Chloro-3-hydroxymethylindol-2-yl)sulfonyl]-4-[4-(pyridin-4-yl)benzoyl]piperazine 4(4-[[4-[(5-Chloro-3-hydroxymethylindol-2-yl)sulfonyl]piperazin-1-yl]carbonyl]phenyl]pyridine N-oxide 1-[(5-Chloro-3-hydroxymethylindol-2-yl))]-4-[4-(2-methylpyridin-4-yl)benzoyl]piperazine 4-[4-[[4-[(5-Chloro-3-hydroxymethylindol-2-yl)sulfonyl]piperazin-1-yl]carbonyl]phenyl]-2-methylpyridine N-oxide 1-[(5-Chloro-3-methoxymethylindol-2-yl)sulfonyl]-4-[4-(pyridin-4-yl)benzoyl]piperazine 4-[4-[[4-[(5-Chloro-3-methoxymethylindol-2-yl)sulfonyl]piperazin-1-yl]carbonyl]phenyl]pyridine N-oxide 1-[(5-Chloro3-methoxymethylindol-2-yl))]-4-[4-(2-methylpyridin-4-yl)benzoyl]piperazine 4-[4-[[4-[(5-Chloro-3-methoxymethylindol-2-yl)sulfonyl]piperazin-1-yl]carbonyl]phenyl]-2-methylpyridine N-oxide 1-[(1-Acetyl-5-chloroindol-2-yl)sulfonyl]-4-[4-(pyridin-4-yl)benzoyl]piperazine 4-[4-[[4-[(1-Acetyl-5-chloroindol-2-yl)sulfonyl]piperazin-1-yl]carbonyl]phenyl]pyridine N-oxide 1-[(1-Acetyl-5-chloroindol-2-yl)]-4-[4-(2-methylpyridin-4-yl)benzoyl]piperazine 4-[4-[[4-[(1-Acetyl-5-chloroindol-2-yl)sulfonyl]piperazin-1-yl]carbonyl]phenyl]-2-methylpyridine N-oxide 1-[(5-Chloro-1-formylindol-2-yl)sulfonyl]-4-[4-(pyridin-4-yl)benzoyl]piperazine 4-[4-[[4-[(5-Chloro-1-formylindol-2-yl)sulfonyl]piperazin-1-yl]carbonyl]phenyl]pyridine N-oxide 1-[(5-Chloro-1-formylindol-2-yl)]-4-[4-(2-methylpyridin-4-yl)benzoyl]piperazine 4-[4-[[4-[(5-Chloro-1-formylindol-2-yl)sulfonyl]piperazin-1-yl carbonyl]phenyl]-2-methylpyridine N-oxide 1-[(5-Chloroisoindolin-2-yl)sulfonyl]-4-[[5-(pyridin-4-yl)pyrimidin-2-yl]carboxy]piperazine 4-[2-[[4-[(5-Chloroisoindolin-2-yl)sulfonyl]piperazin-1-yl]carbonyl]pyrimidin-5-yl]pyridine N-oxide 1-[(5-Chloroisoindolin-2-yl)sulfonyl]-4-[[5-(2-methylpyridin-4-yl)pyrimidin-2-yl]carboxy]piperazine 4-[2-[[4-[(5-Chloroisoindolin-2-yl)sulfonyl]piperazin-1-yl]carbonyl]pyrimidin-5-yl]-2-methylpyridine N-oxide 1-[(5-Chloro-1-isoindolinon-2-yl)sulfonyl]-4-[[5-(pyridin-4-yl)pyrimidin-2-yl]carboxy]piperazine 4-[2-[[4-[(5-Chloroisoindolin-2-yl)sulfonyl]piperazin-1-yl]carbonyl]pyrimidin-5-yl]pyridine N-oxide 1-[(5-Chloro-2-isoindolinon-2-yl)sulfonyl]-4-[[5-(2-methylpyridin-4-yl)pyrimidin-2-yl]carboxy]piperazine 4-[2-[[4-[(5-Chloro-2-isoindolinon-2-yl)sulfonyl]piperazin-1-yl]carbonyl]pyrimidin-5-yl]-2-methylpyridine N-oxide 1-[(1,2,3,4-Tetrahydro-5-chloroisoquinolin-2-yl)sulfonyl]-4-[[5-(pyridin-4-yl)pyrimidin-2-yl]carboxy]piperazine 4-[2-[[4-[(1,2,3,4-Tetrahydro-5-chloroisoquinolin-2-yl)sulfonyl]piperazin-1-yl]carbonyl]pyrimidin-5-yl]pyridine N-oxide 1-[(1,2,3,4-Tetrahydro-5-chloroisoquinolin-2-yl)]-4-[[5-(2-methylpyridin-4-yl)pyrimidin-2-yl]carboxy]piperazine 4-[2-[[4-[(1,2,3,4-Tetrahydro-5-chloroisoquinolin-2-yl)sulfonyl]piperazin-1-yl]carbonyl]pyrimidin-5-yl]-2-methylpyridine N-oxide 1-[(5-Chloro-3-hydroxyindol-2-yl)sulfonyl]-4-[[5-(pyridin-4-yl)pyrimidin-2-yl]carboxy]piperazine 4-[2-[[4-[(5-Chloro-3-hydroxyindol-2-yl)sulfonyl]piperazin-1-yl]carbonyl]pyrimidin-5-yl]pyridine N-oxide 1-[(5-Chloro-3-hydroxyindol-2-yl)]-4-[[5-(2-methylpyridin-4-yl)pyrimidin-2-yl]carboxy]piperazine 4-[2-[[4-[(5-Chloro-3-hydroxyindol-2-yl)sulfonyl]piperazin-1-yl]carbonyl]pyrimidin-5-yl]-2-methylpyridine N-oxide 1-[(5-Chloro-3-methoxyindol-2-yl)sulfonyl]-4-[[5-(pyridin-4-yl)pyrimidin-2-yl]carboxy]piperazine 4-[2-[[4-[(5-Chloro-3-methoxyindol-2-yl)sulfonyl]piperazin-1-yl]carbonyl]pyrimidin-5-yl]pyridine N-oxide 1-[(5-Chloro-3-methoxyindol-2-yl)]-4-[[5-(2-methylpyridin-4-yl)pyrimidin-2-yl]carboxy]piperazine 4-[2-[[4-[(5-Chloro-3-methoxyindol-2-yl)sulfonyl]piperazin-1-yl]carbonyl]pyrimidin-5-yl]-2-methylpyridine N-oxide 1-[(3-Acetoxy-5-chloroindol-2-yl)sulfonyl]-4-[[5-(pyridin-4-yl)pyrimidin-2-yl]carboxy]piperazine 4-[2-[[4-[(3-Acetoxy-5-chloroindol-2-yl)sulfonyl]piperazin-1-yl]carbonyl]pyrimidin-5-yl]pyridine N-oxide 1-[(3-Acetoxy-5-chloroindol-2-yl)]-4-[[5-(2-methylpyridin-4-yl)pyrimidin-2-yl]carboxy]piperazine 4-[2-[[4-[(3-Acetoxy-5-chloroindol-2-yl)sulfonyl]piperazin-1-yl]carbonyl]pyrimidin-5-yl]-2-methylpyridine N-oxide 1-[(5-Chloro-3-hydroxymethylindol-2-yl)sulfonyl]-4-[[5-(pyridin-4-yl)pyrimidin-2-yl]carboxy]piperazine 4-[2-[[4-[(5-Chloro-3-hydroxymethylindol-2-yl)sulfonyl]piperazin-1-yl]carbonyl]pyrimidin-5-yl]pyridine N-oxide 1-[(5-Chloro-3-hydroxymethylindol-2-yl)]-4-[[5-(2-methylpyridin-4-yl)pyrimidin-2-yl]carboxy]piperazine 4-[2-[[4-[(5-Chloro-3-hydroxymethylindol-2-yl)sulfonyl]piperazin-1-yl]carbonyl]pyrimidin-5-yl]-2-methylpyridine N-oxide 1-[(5-Chloro-3-methoxymethylindol-2-yl)sulfonyl]-4-[[5-(pyridin-4-yl)pyrimidin-2-yl]carboxy]piperazine 4-[2-[[4-[(5-Chloro-3-methoxymethylindol-2-yl)sulfonyl]piperazin-1-yl]carbonyl]pyrimidin-5-yl]pyridine N-oxide 1-[(5-Chloro-3-methoxymethylindol-2-yl)]-4-[[5-(2-methylpyridin-4-yl)pyrimidin-2-yl]carboxy]piperazine 4-[2-[[4-[(5-Chloro-3-methoxymethylindol-2-yl)sulfonyl]piperazin-1-yl]carbonyl]pyrimidin-5-yl]-2-methylpyridine N-oxide 1-[(1-Acetyl-5-chloroindol-2-yl)sulfonyl]-4-[[5-(pyridin-4-yl)pyrimidin-2-yl]carboxy]piperazine 4-[2-[[4-[(1-Acetyl-5-chloroindol-2-yl)sulfonyl]piperazin-1-yl]carbonyl]pyrimidin-5-yl]pyridine N-oxide 1-[(1-Acetyl-5-chloroindol-2-yl)]-4-[[5-(2-methylpyridin-4-yl)pyrimidin-2-yl]carboxy]piperazine 4-[2-[[4-[(1-Acetyl-5-chloroindol-2-yl)sulfonyl]piperazin-1-yl]carbonyl]pyrimidin-5-yl]-2-methylpyridine N-oxide 1-[(5-Chloro-1-formylindol-2-yl)sulfonyl]-4-[[5-(pyridin-4-yl)pyrimidin-2-yl]carboxy]piperazine 4-[2-[[4-[(5-Chloro-1-formylindol-2-yl)sulfonyl]piperazin-1-yl]carbonyl]pyrimidin-5-yl]pyridine N-oxide 1-[(5-Chloro-1-formylindol-2-yl)]-4-[[5-(2-methylpyridin-4-yl)pyrimidin-2-yl]carboxy]piperazine 4-[2-[[4-[(5-Chloro-1-formylindol-2-yl)sulfonyl]piperazin-1-yl]carbonyl]pyrimidin-5-yl]-2-methylpyridine N-oxide 2,6-Bis[(N-methylcarbamoyl)methyl]-4-[(6-chloronaphthalen-2-yl)sulfonyl]-1-[5-(pyridin-4-yl)pyrimidin-2-yl]piperazine 2,6-Bis[(N,N-dimethylcarbamoyl)methyl]-4-[(6-chloronaphthalen-2-yl)sulfonyl]-1-[5-(pyridin-4-yl)pyrimidin-2-yl]piperazine 2,6-Bis[(morpholin-4-yl)carbonylmethyl]-4-[(6-chloronaphthalen-2- yl)sulfonyl]-4-[5-(pyridin-4-yl)pyrimidin-2-yl]piperazine 2,6-Bis(hydroxyethyl)-4-[(6-chloronaphthalen-2-yl)sulfonyl]-1-[5-(pyridin-4-yl)pyrimidin-2-yl]piperazine 1-[(4-Chloro-2-hydroxystyryl)sulfonyl]-4-[5-(pyridin-4-yl)pyrimidin-2-yl]piperazine 2,6-Bis[(N-methylcarbamoyl)methyl]-4-[(4-chloro-2-hydroxystyryl)sulfonyl]-1-[5-(pyridin-4-yl)pyrimidin-2-yl]piperazine 2,6-Bis[(N,N-dimethylcarbamoyl)methyl]-4-[(4-chloro-2-hydroxystyryl)sulfonyl]-1-[5-(pyridin-4-yl)pyrimidin-2-yl]piperazine 2,6-Bis[(morpholin-4-yl)carbonylmethyl]-4-[(4-chloro-2-hydroxystyryl)sulfonyl]-1-[5-(pyridin-4-yl)pyrimidin-2-yl]piperazine 2,6-Bis(hydroxyethyl)-4-[(4-chloro-2-hydroxystyryl)sulfonyl]-1-[5-(pyridin-4-yl)pyrimidin-2-yl]piperazine 2,6-Bis[(N-methylcarbamoyl)methyl]-4-[(5-chloroindol-2-yl)sulfonyl]-1-[5-(pyridin-4-yl)pyrimidin-2-yl]piperazine 2,6-Bis[(N,N-dimethylcarbamoyl)methyl]-4-[(5-chloroindol-2-yl)sulfonyl]-1-[5-(pyridin-4-yl)pyrimidin-2-yl]piperazine 2,6-Bis[(morpholin-4-yl)carbonylmethyl]-4-[(5-chloroindol-2-yl)sulfonyl]-1-[5-(pyridin-4-yl)pyrimidin-2-yl]piperazine 2,6-Bis(hydroxyethyl)-4-[(5-chloroindol-2-yl)sulfonyl]-1-[5-(pyridin-4-yl)pyrimidin-2-yl]piperazine 2,6-Bis[(N-methylcarbamoyl)methyl]-4-[(6-chlorobenzo[b]thien-2-yl)sulfonyl]-1-[5-(pyridin-4-yl)pyrimidin-2-yl]piperazine 2,6-Bis[(N,N-dimethylcarbamoyl)methyl]-4-[(6-chlorobenzo[b]thien-2-yl)sulfonyl]-1-[5-(pyridin-4-yl)pyrimidin-2-yl]piperazine 2,6-Bis[(morpholin-4-yl)carbonylmethyl]-4-[(6-chlorobenzo[b]thien-2-yl)sulfonyl]-1-[5-(pyridin-4-yl)pyrimidin-2-yl]piperazine 2,6-Bis(hydroxyethyl)-4-[(6-chlorobenzo[b]thien-2-yl)sulfonyl]-1-[5-(pyridin-4-yl)pyrimidin-2-yl]piperazine 4-[5-[[2,6-Bis(carbamoylmethyl)-4-(6-chloronaphthalen-2-ylsulfonyl)piperazin-1-yl]carbonyl]pyrimidin-2-yl]pyridine N-oxide 4-[5-([2,6-Bis[(N-methylcarbamoyl)methyl]-4-(6-chloronaphthalen-2-ylsulfonyl)piperazin-1-yl]carbonyl]pyrimidin-2-yl]pyridine N-oxide 4-[5-[[2,6-Bis[(N,N-dimethylcarbamoyl)methyl]-4-(6-chloronaphthalen-2-ylsulfonyl)piperazin-1-yl]carbonyl]pyrimidin-2-yl]pyridine N-oxide 4-[5-[[2,6-Bis[(morpholin-4-yl)carbonylmethyl]-4-(6-chloronaphthalen-2-ylsulfonyl)piperazin-1-yl]carbonyl]pyrimidin-2-yl]pyridine N-oxide 4-[5-[[2,6-Bis(hydroxyethyl)-4-(6-chloronaphthalen-2-ylsulfonyl)piperazin-1-yl]carbonyl]pyrimidin-2-yl]pyridine N-oxide 4-[5-[[4-[(4-Chloro-2-hydroxystyryl)sulfonyl]piperazin-1-yl]carbonyl]pyrimidin-2-yl]pyridine N-oxide 4-[5-[[2,6-Bis(carbamoylmethyl)-4-[(4-chloro-2-hydroxystyryl)sulfonyl]piperazin-1-yl]carbonyl]pyrimidin-2-yl]pyridine N-oxide 4-[5-[[2,6-Bis[(N-methylcarbamoyl)methyl]-4-[(4-chloro-2-hydroxystyryl)sulfonyl]piperazin-1-yl]carbonyl]pyrimidin-2-yl]pyridine N-oxide 4-[5-[[2,6-Bis[(N,N-dimethylcarbamoyl)methyl]-4-[(4-chloro-2-hydroxystyryl)sulfonyl]piperazin-1-yl]carbonyl]pyrimidin-2-yl]pyridine N-oxide 4-[5-[[2,6-Bis[(morpholin-4-yl)carbonylmethyl]-4-[(4-chloro-2-hydroxystyryl)sulfonyl]piperazin-1-yl]carbonyl]pyrimidin-2-yl]pyridine N-oxide 4-[5-[[2,6-Bis(hydroxyethyl)-4-[(4-chloro-2-hydroxystyryl)sulfonyl]piperazin-1-yl]carbonyl]pyrimidin-2-yl]pyridine N-oxide 4-[5-[[2,6-Bis(carbamoylmethyl)-4-(5-chloroindol-2-ylsulfonyl)piperazin-1-yl]carbonyl]pyrimidin-2-yl]pyridine N-oxide 4-[5-[[2,6-Bis[(N-methylcarbamoyl)methyl]-4-(5-chloroindol-2-ylsulfonyl)piperazin-1-yl]carbonyl]pyrimidin-2-yl]pyridine N-oxide 4-[5-[[2,6-Bis[(N,N-dimethylcarbamoyl)methyl]-4-(5-chloroindol-2-ylsulfonyl)piperazin-1-yl]carbonyl]pyrimidin-2-yl]pyridine N-oxide 4-[5-[[2,6-Bis[(morpholin-4-yl)carbonylmethyl]-4-(5-chloroindol-2-ylsulfonyl)piperazin-1-yl]carbonyl]pyrimidin-2-yl]pyridine N-oxide 4-[5-[[2,6-Bis(hydroxyethyl)-4-(5-chloroindol-2-ylsulfonyl)piperazin-1-yl]carbonyl]pyrimidin-2-yl]pyridine N-oxide 4-[5-[[2,6-Bis(carbamoylmethyl)-4-(6-chlorobenzo[b]thien-2-ylsulfonyl)piperazin-1-yl]carbonyl]pyrimidin-2-yl]pyridine N-oxide 4-[5-[[2,6-Bis[(N-methylcarbamoyl)methyl]-4-(6-chlorobenzo[b]thien-2-ylsulfonyl)piperazin-1-yl]carbonyl]pyrimidin-2-yl]pyridine N-oxide 4-[5-[[2,6-bis[(N,N-dimethylcarbamoyl)methyl]-4-(6-chlorobenzo[b]thien-2-ylsulfonyl)piperazin-1-yl]carbonyl]pyrimidin-2-yl]pyridine N-oxide 4-[5-[[2,6-Bis[(morpholin-4-yl)carbonylmethyl]-4-(6-chlorobenzo[b]thien-2-ylsulfonyl)piperazin-1-yl]carbonyl]pyrimidin-2-yl]pyridine N-oxide 4-[5-[[2,6-Bis(hydroxyethyl)-4-(6-chlorobenzo[b]thien-2-ylsulfonyl)piperazin-1-yl]carbonyl]pyrimidin-2-yl]pyridine N-oxide 1-[(4-Chloro-2-hydroxystyryl)sulfonyl]-4-[5-(2-hydroxymethylpyridin-4-yl)pyrimidin-2-yl]piperazine 1-[(4-Chloro-2-hydroxystyryl)sulfonyl]-4-[5-(2-dimethylaminomethylpyridin-4-yl)pyrimidin-2-yl]piperazine 1-[(4-Chloro-2-hydroxystyryl)sulfonyl]-4-[5-(2-carbamoylpyridin-4-yl)pyrimidin-2-yl]piperazine 1-[(4-Chloro-2-hydroxystyryl) sulfonyl]-4-[4-(2-hydroxymethylpyridin-4-yl)benzoyl]piperazine 1-[(4-Chloro-2-hydroxystyryl)sulfonyl]-4-[4-(2-dimethylaminomethylpyridin-4-yl)benzoyl]piperazine 1-[(4-Chloro-2-hydroxystyryl)sulfonyl]-4-[4-(2-carbamoylpyridin-4-yl)benzoyl]piperazine 4-[(6-Chloronaphthalene-2-yl)sulfonyl]-2-[(N-methylcarbamoyl)methyl]-1-[5-(pyridin-4-yl)pyrimidin-2-yl]piperazine 4-[(6-Chloronaphthalen-2-yl)sulfonyl]-2-[(N,N-dimethylcarbamoyl)methyl]-1-[5-(pyridin-4-yl)pyrimidin-2-yl]piperazine 4-[(6-Chloronaphthalen-2-yl)sulfonyl]-2-[(morpholin-4-yl)carbonylmethyl]-1-[5-(pyridin-4-yl)pyrimidin-2-yl]piperazine 4-[(6-Chloronaphthalen-2-yl)sulfonyl]-2-hydroxyethyl-1-[5-(pyridin-4-yl)pyrimidin-2-yl]piperazine 3-[(6-Chloronaphthalen-2-yl)sulfonyl]-7-hydroxy-9-[4-(pyridin-4-yl)benzoyl]-3,9-diazabicyclo[3.3.1]nonane 4-[4-[[[3-[(6-Chloronaphthalen-2-yl)sulfonyl]-7-hydroxy-3,9-diazabicyclo[3.3.1]nonan]-9-yl]carbonyl]phenyl]pyridine N-oxide 3-[(5-Chloroindol-2-yl)sulfonyl]-7-hydroxy-9-[4-(pyridin-4-yl)benzoyl]-3,9-diazabicyclo[3.3.1]nonane 4-[4-[[[3-[(5-Chloroindol-2-yl)sulfonyl]-7-hydroxy-3,9-diazabicyclo[3.3.1]nonan]-9-yl]carbonyl]phenyl]pyridine N-oxide 3-[(6-Chlorobenzo[b]thien-2-yl)sulfonyl]-7-hydroxy-9-[4-(pyridin-4-yl)benzoyl]-3,9-diazabicyclo[3.3.1]nonane 4-[4-[[[3-[(6-Chlorobenzo[b]thien-2-yl)sulfonyl]-7-hydroxy-3,9-diazabicyclo[3.3.1]nonan]-9-yl]carbonyl]phenyl]pyridine N-oxide 3-[(6-Chloronaphthalen-2-yl)sulfonyl]-7-hydroxy-9-[[5-(pyridin-4-yl)pyrimidin-2-yl]carbonyl]-3,9-diazabicyclo[3.3.1]nonane 4-[2-[3-[(6-Chloronaphthalen-2-yl)sulfonyl]-7-hydroxy-3,9-diazabicyclo[3.3.1]nonan-8-yl]carbonylpyrimidin-5-yl]pyridine N-oxide 3-[(6-Chloronaphthalen-2-yl)sulfonyl]-7-methylamino-9-[4-(pyridin-4-yl)benzoyl]-3,9-diazabicyclo[3.3.1]nonane 4-[4-[[[3-[(6-Chloronaphthalen-2-yl)sulfonyl]-7-methylamino-3,9-diazabicyclo[3.3.1]nonan]-9-yl]carbonyl]phenyl]pyridine N-oxide 3-[(6-Chloronaphthalen-2-yl)sulfonyl]-7-dimethylamino-9-[4-(pyridin-4-yl)benzoyl]-3,9-diazabicyclo[3.3.1]nonane 4-[4-[[[3-[(6-Chloronaphthalen-2-yl)sulfonyl]-7-dimethylamino-3,9-diazabicyclo[3.3.1]nonan]-9-yl]carbonyl]phenyl]pyridine N-oxide 3-[(6-Chloronaphthalen-2-yl)sulfonyl]-7-piperidino-9-[4-(pyridin-4-yl)benzoyl]-3,9-diazabicyclo[3.3.1]nonane 4-[4-[[[3-[(6-Chloronaphthalen-2-yl)sulfonyl]-7-piperidino-3,9-diazabicyclo[3.3.1]nonan]-9-yl]carbonyl]phenyl]pyridine N-oxide 3-[(6-Chloronaphthalen-2-yl)sulfonyl]-7-morpholino-9-[4-(pyridin-4-yl)benzoyl]-3,9-diazabicyclo[3.3.1]nonane 4-[4-[[[3-[(6-Chloronaphthalen-2-yl)sulfonyl]-7-morpholino-3,9-diazabicyclo[3.3.1]nonan]-9-yl]carbonyl]phenyl]pyridine N-oxide 3-[(6-Chloronaphthalen-2-yl)sulfonyl]-7-(4-methylpiperazin-1-yl)-9-[4-(pyridin-4-yl)benzoyl]-3,9-diazabicyclo[3.3.1]nonane 4-[4-[[[3-[(6-Chloronaphthalen-2-yl)sulfonyl]-7-(4-methylpiperazin-1-yl)-3,9-diazabicyclo[3.3.1]nonan]-9-yl]carbonyl]phenyl]pyridine N-oxide 1-[[(6RS)-6-Aminomethyl-5,6,7,8-tetrahydronaphthalen-2-yl]carbonyl]-4-[(6-chloronaphthalen-2-yl)sulfonyl]piperazine 1-[[(6RS)-6-Aminomethyl-5,6,7,8-tetrahydronaphthalen-2-yl]methyl]-4-[(6-chloronaphthalen-2-yl)sulfonyl]piperazine 1-[[(2RS)-6-Aminomethyl-1,2,3,4-tetrahydronaphthalen-2-yl]methyl]-4-[(6-chloronaphthalen-2-yl)sulfonyl]piperazine 1-[[(2RS)-6-Aminomethyl-1,2,3,4-tetrahydronaphthalen-2-yl]carbonyl]-4-[(6-chloronaphthalen-2-yl)sulfonyl]piperazine 1-[(7-Aminomethylnaphthalen-2-yl)carbonyl]-4-[(6-chloronaphthalen-2-yl)sulfonyl]piperazine 1-[(7-Aminomethylnaphthalen-2-yl)methyl]-4-[(6-chloronaphthalen-2-yl)sulfonyl]piperazine 1-[(6-Aminomethylnaphthalen-2-yl)carbonyl]-4-[(6-chloronaphthalen-2-yl)sulfonyl]piperazine 1-[(6-Chloronaphthalen-2-yl)sulfonyl]-4-[(isoquinolin-7-yl)carbonyl]piperazine 1-[(6-Chloronaphthalen-2-yl)sulfonyl]-4-[(quinolyl-2-yl)carbonyl]piperazine 1-[(6-Chloronaphthalen-2-yl)sulfonyl]-4-[(4-hydroxyquinolin-2-yl)carbonyl]piperazine 1-[(6-Chloronaphthalen-2-yl)sulfonyl]-4-[(8-hydroxyquinolin-7-yl)carbonyl]piperazine 1-[(Benzimidazol-5-yl)carbonyl]-4-[(6-chloronaphthalen-2-yl)sulfonyl]piperazine 1-[(Benzimidazol-5-yl)carbonyl]-4-[(6-chloronaphthalen-2-yl)sulfonyl]homopiperazine 1-[(6-Chloronaphthalen-2-yl)sulfonyl]-4-[(thiazolo[5,4-c]pyridin-2-yl)carbonyl]piperazine 1-[(E)-4-Chlorostyrylsulfonyl]-4-[(thiazolo[5,4-c]pyridin-2-yl)carbonyl]piperazine 1-[(6-Chloronaphthalen-2-yl)sulfonyl]-4-[(4,5,6,7-tetrahydrothieno[3,2-c]pyridin-2-yl)methyl]piperazine 1-[(6-Chloronaphthalen-2-yl)sulfonyl]-4-[trans-3-(4,5,6,7-tetrahydrothieno[3,2-c]pyridin-2-yl)propionyl]piperazine 1-[(6-Chloronaphthalen-2-yl)sulfonyl]-4-[3-(4,5,6,7-tetrahydrothieno[3,2-c]pyridin-2-yl)propionyl]piperazine 1-[(6-Chloronaphthalen-2-yl)sulfonyl]-4-[3-(4,5,6,7-tetrahydrothieno[3,2-c]pyridin-2-yl)propyl]piperazine 1-[(6-Chloronaphthalen-2-yl)sulfonyl]-4-[N-[(4,5,6,7-tetrahydrothieno[3,2-c]pyridin-2-yl)methyl]carbamoyl]piperazine 1-[(6-Chloronaphthalen-2-yl)sulfonyl]-4-[(4,5,6,7-tetrahydrothieno[3,2-c]pyridin-2-yl)carbonyl]piperazine 4-[(6-Chloronaphthalen-2-yl)sulfonyl]-2-ethoxycarbonyl-1-[(4,5,6,7-tetrahydrothieno[3,2-c]pyridin-2-yl)carbonyl]piperazine 2-Carboxy-4-[(6-chloronaphthalen-2-yl)sulfonyl]-1-[(4,5,6,7-tetrahydrothieno[3,2-c]pyridin-2-yl)carbonyl]piperazine 1-[(6-Chloronaphthalen-2-yl)sulfonyl]-4-[(5-aminohydroxyiminomethyl-4,5,6,7-tetrahydrothieno[3,2-c]pyridin-2-yl)carbonyl]piperazine 1-[(6-Chloronaphthalen-2-yl)sulfonyl]-4-[N-(4,5,6,7-tetrahydrothieno[3,2-c]pyridin-2-yl)carbamoyl]piperazine 1-[(6-Chloronaphthalen-2-yl)sulfonyl]-4-[N-methy-N-(4,5,6,7-tetrahydrothieno[3,2-c]pyridin-2-yl)carbamoyl]piperazine 1-[(6-Chloronaphthalen-2-yl)sulfonyl]-4-[[5-(1-pyrrolin-2-yl)-4,5,6,7-tetrahydrothieno[3,2-c]pyridin-2-yl]carbonyl]piperazine 1-[(6-Chloronaphthalen-2-yl)sulfonyl]-4-[(4,5,6,7-tetrahydrothiazolo[5,4-c]pyridin-2-yl)carbonyl]piperazine 1-[(6-Chloronaphthalen-2-yl)sulfonyl]-4-[(6-aminohydroxyiminomethyl-4,5,6,7-tetrahydrothiazolo[5,4-c]pyridin-2-yl)carbonyl]piperazine 1-[(6-Carbamoyl-4,5,6,7-tetrahydrothiazolo[5,4-c]pyridin-2-yl)carbonyl]-4-[(6-chloronaphthalen-2-yl)sulfonyl]piperazine 1-[(6-Chloronaphthalen-2-yl)sulfonyl]-4-[[6-(1-pyrrolin-2-yl)-4,5,6,7-tetrahydrothiazolo[5,4-c]pyridin-2-yl]carbonyl]piperazine 1-[(6-Chloronaphthalen-2-yl)sulfonyl]-4-[(6-formyl-4,5,6,7-tetrahydrothiazolo[5,4-c]pyridin-2-yl)carbonyl]piperazine 1-[(6-Chloronaphthalen-2-yl)sulfonyl]-4-[(6-methyl-4,5,6,7-tetrahydrothiazolo[5,4-c]pyridin-2-yl)carbonyl]piperazine 2-[[4-[(6-chloronaphthalen-2-yl)sulfonyl]piperazin-1-yl]carbonyl]-6,6-dimethyl-4,5,6,7-tetrahydrothiazolo[5,4-c]pyridinium iodide 2-[[4-[(6-Chloronaphthalen-2-yl)sulfonyl]piperazin-1-yl]carbonyl]-6-methyl-4,5,6,7-tetrahydrothiazolo[5,4-c]pyridin-N-oxide 2-Carbamoyl-4-[(6-chloronaphthalen-2-yl)sulfonyl]-1-[(4,5,6,7-tetrahydrothiazolo[5,4-c]pyridin-2-yl)carbonyl]piperazine 2-Carbamoyl-4-[(6-chloronaphthalen-2-yl)sulfonyl]-1-[(6-methyl-4,5,6,7-tetrahydrothiazolo[5,4-c]pyridin-2-yl)carbonyl]piperazine 1-[(6-Chloronaphthalen-2-yl)sulfonyl]-4-[[6-(2-hydroxyethyl)-4,5,6,7-tetrahydrothiazolo[5,4-c]pyridin-2-yl]carbonyl]piperazine 1-[(6-Chloronaphthalen-2-yl)sulfonyl]-4-[[6-(pyridin-2-yl)methyl-4,5,6,7-tetrahydrothiazolo[5,4-c]pyridin-2-yl]carbonyl]piperazine 1-[(6-Chloronaphthalen-2-yl)sulfonyl]-4-[[6-(pyridin-3-yl)methyl-4,5,6,7-tetrahydrothiazolo[5,4-c]pyridin-2-yl]carbonyl]piperazine 1-[(6-Chloronaphthalen-2-yl)sulfonyl]-4-[[6-(pyridin-4-yl)methyl-4,5,6,7-tetrahydrothiazolo[5,4-c]pyridin-2-yl]carbonyl]piperazine 1-[(E)-4-Chlorostyrylsulfonyl]-4-[(4,5,6,7-tetrahydrothiazolo[5,4-c]pyridin-2-yl)carbonyl]piperazine 1-[(E)-4-Chlorostyrylsulfonyl]-4-[6-methyl-4,5,6,7-tetrahydrothiazolo[5,4-c]pyridin-2-yl)carbonyl]piperazine (3S)-3-[(6-Chloronaphthalen-2-yl)sulfonamide]-1-[(4,5,6,7-tetrahydrothieno[3,2-c]pyridin-2-yl)methyl]pyrrolidine (3S)-3-[(6-Chloronaphthalen-2-yl)sulfonamide]-1-[(4,5,6,7-tetrahydrothieno[3,2-c]pyridin-2-yl)carbonyl]pyrrolidine (3S)-1-[(6-Chloronaphthalen-2-yl)sulfonyl]-3-[[(4,5,6,7-tetrahydrothieno[3,2-c]pyridin-2-yl)methyl]amino]pyrrolidine (3S)-3-[(4,5,6,7-Tetrahydrothieno[3,2-c]pyridin-2-yl)carbonylamino]-1-[(6-chloronaphthalen-2-yl)sulfonyl]pyrrolidine 1-[(6-Chloronaphthalen-2-yl)sulfonyl]-4-[(4,5,6,7-tetrahydrothieno[3,2-c]pyridin-2-yl)carbonyl]homopiperazine 4-[(6-Chloronaphthalen-2-yl)sulfonamide]-1-[(4,5,6,7-tetrahydrothieno[3,2-c]pyridin-2-yl)carbonyl]piperidine 1-[(6-Chloronaphthalen-2-yl)sulfonyl]-4-[(6-aminohydroxyiminomethylbenzofuran-2-yl)carbonyl]piperazine 1-[(6-Chloronaphthalen-2-yl)sulfonyl]-4-[(5-aminohydroxyiminomethylbenzothiophen-2-yl)carbonyl]piperazine 1-[(6-Chloronaphthalen-2-yl)sulfonyl]-4-[(1,2,3,4-tetrahydroisoquinolin-6-yl)carbonyl]piperazine 1-[(6-Chloronaphthalen-2-yl)sulfonyl]-4-[(2-methyl-1,2,3,4-tetrahydroisoquinolin-6-yl)carbonyl]piperazine 6-[[4-[(6-Chloronaphthalen-2-yl)sulfonyl]piperazin-1-yl]carbonyl-2,2-dimethyl-1,2,3,4-tetrahydroisoquinolinium iodide 1-[(5-Chloroindol-2-yl)sulfonyl]-4-[(6-methyl-4,5,6,7-tetrahydrothiazolo[5,4-c]pyridin-2-yl)carbonyl]piperazine 4-[(5-Chloroindol-2-yl)sulfonyl]-2-(N-methylcarbamoyl)-1-[(6-methyl-4,5,6,7-tetrahydrothiazolo[5,4-c]pyridin-2-yl)carbonyl]piperazine 4-[(5-Chloroindol-2-yl)sulfonyl]-2-(N-methylcarbamoyl)-1-[(6-methyl-4,5,6,7-tetrahydrothieno[2,3-c]pyridin-2-yl)carbonyl]piperazine 1-[(5-Chlorobenzo[b]furan-2-yl)sulfonyl]-4-[(6-methyl-4,5,6,7-tetrahydrothiazolo[5,4-c]pyridin-2-yl)carbonyl]piperazine 1-[(6-Chlorobenzo[b]furan-2-yl)sulfonyl]-4-[(6-methyl-4,5,6,7-tetrahydrothiazolo[5,4-c]pyridin-2-yl)carbonyl]piperazine 1-[(5-Chlorobenzo[b]thien-2-yl)sulfonyl]-4-[(6-methyl-4,5,6,7-tetrahydrothiazolo[5,4-c]pyridin-2-yl)carbonyl]piperazine 1-[(6-Chlorobenzo[b]thien-2-yl)sulfonyl]-4-[(6-methyl-4,5,6,7-tetrahydrothiazolo[5,4-c]pyridin-2-yl)carbonyl]piperazine 1-[(6-Chloronaphthalen-2-yl)sulfonyl]-4-[(5,6,7,8-tetrahydro-1,6-naphthylidin-2-yl)carbonyl]piperazine 1-[(6-Chloronaphthalen-2-yl)sulfonyl]-4-[(6-methyl-5,6,7,8-tetrahydro-1,6-naphthylidin-2-yl)carbonyl]piperazine 1-[(6-Chloronaphthalen-2-yl)sulfonyl]-4-[(4,5,6,7-tetrahydro-1H-pyrrolo[3,2-c]pyridin-2-yl) carbonyl]piperazine 1-[(6-Chloronaphthalen-2-yl)sulfonyl]-4-[(5-methyl-4,5,6,7-tetrahydro-1H-pyrrolo [3,2-c]pyridin-2-yl) carbonyl]piperazine 1-[(6-Chloronaphthalen-2-yl)sulfonyl]-4-[(5-ethyl-4,5,6,7-tetrahydro-1H-pyrrolo [3,2-c]pyridin-2-yl)carbonyl]piperazine 1-[(6-Chloronaphthalen-2-yl)sulfonyl]-4-[(1-methyl-4,5,6,7-tetrahydro-1H-pyrrolo [3,2-c]pyridin-2-yl)carbonyl]piperazine 1-[(6-Chloronaphthalen-2-yl)sulfonyl]-4-[(1,5-dimethyl-4,5,6,7-tetrahydro-1H-pyrrolo[3,2-c]pyridin-2-yl)carbonyl]piperazine 1-[(6-Chloronaphthalen-2-yl)sulfonyl]-4-[(6-methyl-4,5,6,7-tetrahydrofro[2,3-c]pyridin-2-yl)carbonyl]piperazine 1-[(6-Chloronaphthalen-2-yl)sulfonyl]-4-[(3-hydroxy-6-methyl-4,5,6,7-tetrahydrofro[2,3-c]pyridin-2-yl)carbonyl]piperazine 1-[(6-Chloronaphthalen-2-yl)sulfonyl]-4-[(5-methyl-3-hydroxy-4,5,6,7-tetrahydro-1H-pyrrolo[3,2-c]pyridin-2-yl)carbonyl]piperazine 1-[(6-Chloronaphthalen-2-yl)sulfonyl]-4-[(5-methyl-4,5,6,7-tetrahydroxazolo[4,5-c]pyridin-2-yl)carbonyl]piperazine 4-[(5-Chloroindol-2-yl)sulfonyl]-2-(N-methylcarbamoyl)-1-[(6,7-dimethyl-4,5,6,7-tetrahydrothiazolo[5,4-c]pyridin-2-yl)carbonyl]piperazine 2,6-Bis(carbamoylmethyl)-4-[(5-chloroindol-2-yl)sulfonyl]-1-[(6,7-dimethyl-4,5,6,7-tetrahydrothiazolo[5,4-c]pyridin-2-yl)carbonyl]piperazine cis-2,6-Bis(carbamoylmethyl)-4-[(5-chloroindol-2-yl)sulfonyl]-1-[(6,7-dimethyl-4,5,6,7-tetrahydrothiazolo[5,4-c]pyridin-2-yl)carbonyl]piperazine 4-[(5-Chloroisoindol-2-yl)sulfonyl]-2-(N-methylcarbamoyl)-1-[(6-methyl-4,5,6,7-tetrahydrothiazolo[5,4-c]pyridin-2-yl)carbonyl]piperazine 2-[4-[(6-Chloronaphthalen-2-yl)sulfonyl]piperazin-1-yl]carbonyl]-6-methylthiazolo[5,4-c]pyridinium iodide 4-[(6-Chloronaphthalen-2-yl)sulfonyl]-2-[(N-methyl)carbamoyl]-1-[(6-methyl-4,5,6,7-tetrahydrothiazolo[5,4-c]pyridin-2-yl)carbonyl]piperazine 4-[(6-Chloronaphthalen-2-yl)sulfonyl]-1-[(6-methyl-4,5,6,7-tetrahydrothiazolo[5,4-c]pyridin-2-yl)carbonyl]-2-[[(morpholin-4-yl)carbonyl]methyl]piperazine N-[[4-[(6-Chloronaphthalen-2-yl)sulfonyl]-1-[(6-methyl-4,5,6,7-tetrahydrothiazolo[5,4-c]pyridin-2-yl)carbonyl]piperazin-2-yl]carbonyl]glycine ethyl ester 4-[(6-Chloronaphthalen-2-yl)sulfonyl]-1-[(6-methyl-4,5,6,7-tetrahydrothiazolo[5,4-c]pyridin-2-yl)carbonyl]-2-[N-(morpholin-4-yl)carbamoyl]piperazine Ethyl N'-[[4-[(6-chloronaphthalen-2-yl)sulfonyl]-1-[(6-methyl-4,5,6,7-tetrahydrothiazolo[5,4-c]pyridin-2-yl)carbonyl]piperazin-2-yl]carbonyl]hydrazinoacetate 4-[(6-Chloronaphthalen-2-yl)sulfonyl]-1-[(6-methyl-4,5,6,7-tetrahydrothiazolo[5,4-c]pyridin-2-yl)carbonyl]-2-[N-[[(morpholin-4-yl)carbonyl]methyl]carbamoyl]piperazine 4-[[4-[(6-Chloronaphthalen-2-yl)sulfonyl]-1-[(6-methyl-4,5,6,7-tetrahydrothiazolo[5,4-c]pyridin-2-yl)carbonyl]piperazin-2-yl]carbonyl]morpholine 4-[(6-Chloronaphthalen-2-yl)sulfonyl]-2-(ethoxycarbonyl)-1-[(6-methyl-4,5,6,7-tetrahydrothiazolo[5,4-c]pyridin-2-yl)carbonyl]piperazine Methyl [4-[(6-chloronaphthalen-2-yl)sulfonyl]-1-[(6-methyl-4,5,6,7-tetrahydrothiazolo[5,4-c]pyridin-2-yl)carbonyl]piperazin-2-yl]acetate 2-[[N-(tert-Butoxy)amino]carbonyl]-4-[(6-chloronaphthalen-2-yl)sulfonyl]-1-[(6-methyl-4,5,6,7-tetrahydrothiazolo[5,4-c]pyridin-2-yl)carbonyl]piperazine

[4-[(6-Chloronaphthalen-2-yl)sulfonyl]-1-[(6-methyl-4,5,6,7-tetrahydrothiazolo[5,4-c]pyridin-2-yl)carbonyl]piperazin-2-yl]acetamide 4-[(6-Chloronaphthalen-2-yl)sulfonyl]-2-[(N-isopropyl)carbamoyl]-1-[(6-methyl-4,5,6,7-tetrahydrothiazolo[5,4-c]pyridin-2-yl)carbonyl]piperazine 4-[(6-Chloronaphthalen-2-yl)sulfonyl]-2-[[(piperidin-1-yl)carbonyl]methyl]-1-[(6-methyl-4,5,6,7-tetrahydrothiazolo[5,4-c]pyridin-2-yl)carbonyl]piperazine 4-[(6-Chloronaphthalen-2-yl)sulfonyl]-2-[[N-(2-methoxybenzyl)]carbamoyl]-1-[(6-methyl-4,5,6,7-tetrahydrothiazolo[5,4-c]pyridin-2-yl)carbonyl]piperazine 4-[(6-Chloronaphthalen-2-yl)sulfonyl]-2-[[N-(2-methoxyethyl)]carbamoyl]-1-[(6-methyl-4,5,6,7-tetrahydrothiazolo[5,4-c]pyridin-2-yl)carbonyl]piperazine 4-[(6-Chloronaphthalen-2-yl)sulfonyl]-1-[(6-methyl-4,5,6,7-tetrahydrothiazolo[5,4-c]pyridin-2-yl)carbonyl]piperazine-2-carboxylic acid N'-[[4-[(6-Chloronaphthalen-2-yl)sulfonyl]-1-[(6-methyl-4,5,6,7-tetrahydrothiazolo[5,4-c]pyridin-2-yl)carbonyl]piperazin-2-yl]carbonyl]hydrazinoacetic acid 4-[(6-Chloronaphthalen-2-yl)sulfonyl]-1-[(6-methyl-4,5,6,7-tetrahydrothiazolo[5,4-c]pyridin-2-yl)carbonyl]-2-[[N-(tetrahydropyran-2-yloxy)]carbamoyl]piperazine 4-[(6-Chloronaphthalen-2-yl)sulfonyl]-1-[(6-methyl-4,5,6,7-tetrahydrothiazolo[5,4-c]pyridin-2-yl)carbonyl)piperazine-2-hydroxamic acid 4-[(6-Chloronaphthalen-2-yl)sulfonyl]-2-[[N-(2-hydroxybenzyl)]carbamoyl]-1-[(6-methyl-4,5,6,7-tetrahydrothiazolo[5,4-c]pyridin-2-yl)carbonyl]piperazine 1-[(6-Bromonaphthalen-2-yl)sulfonyl]-4-[(6-methyl-4,5,6,7-tetrahydrothiazolo[5,4-c]pyridin-2-yl)carbonyl]piperazine 1-[(7-Amidinonaphthalen-2-yl)sulfonyl]-4-[(6-methyl-4,5,6,7-tetrahydrothiazolo[5,4-c]pyridin-2-yl)carbonyl]piperazine 1-[(6-Amidinonaphthalen-2-yl)sulfonyl]-4-[(6-methyl-4,5,6,7-tetrahydrothiazolo[5,4-c]pyridin-2-yl)carbonyl]piperazine 1-[(6-Methyl-4,5,6,7-tetrahydrothiazolo[5,4-c]pyridin-2-yl)carbonyl]-4-[[7-[N-(methoxycarbonyl)amidino]naphthalen-2-yl]sulfonyl]piperazine 1-[(6-Methyl-4,5,6,7-tetrahydrothiazolo[5,4-c]pyridin-2-yl)carbonyl]-4-[[6-[N-(methoxycarbonyl)amidino]naphthalen-2-yl]sulfonyl]piperazine 1-[(7-[(Amino)(hydroxyimino)methyl]naphthalen-2-yl)sulfonyl]-4-[(6-methyl-4,5,6,7-tetrahydrothiazolo[5,4-c]pyridin-2-yl)carbonyl]piperazine 1-[(6-[(Amino)(hydroxyimino)methyl]naphthaien-2-yl)sulfonyl]-4-[(6-methyl-4,5,6,7-tetrahydrothiazolo[5,4-c]pyridin-2-yl)carbonyl]piperazine 1-[(6-Ethynylnaphthalen-2-yl)sulfonyl]-4-[(6-methyl-4,5,6,7-tetrahydrothiazolo[5,4-c]pyridin-2-yl)carbonyl]piperazine 1-[(5-Bromoindol-2-yl)sulfonyl]-4-[(6-methyl-4,5,6,7-tetrahydrothiazolo[5,4-c]pyridin-2-yl)carbonyl]piperazine 1-[(5-Ethynylindol-2-yl)sulfonyl]-4-[(6-methyl-4,5,6,7-tetrahydrothiazolo[5,4-c]pyridin-2-yl)carbonyl]piperazine 1-[(5-Amidinoindol-2-yl)sulfonyl]-4-[(6-methyl-4,5,6,7-tetrahydrothiazolo[5,4-c]pyridin-2-yl)carbonyl]piperazine 1-[(6-Amidinoindol-2-yl)sulfonyl]-4-[(6-methyl-4,5,6,7-tetrahydrothiazolo[5,4-c]pyridin-2-yl)carbonyl]piperazine 1-[[5-[(Amino)(hydroxyimino)methyl]indol-2-yl]sulfonyl]-4-[(6-methyl-4,5,6,7-tetrahydrothiazolo[5,4-c]pyridin-2-yl)carbonyl]piperazine 1-[[6-[(Amino)(hydroxyimino)methyl]indol-2-yl]sulfonyl]-4-[(6-methyl-4,5,6,7-tetrahydrothiazolo[5,4-c]pyridin-2-yl)carbonyl]piperazine 1-[(6-Methyl-4,5,6,7-tetrahydrothiazolo[5,4-c]pyridin-2-yl)carbonyl-4-[[5-(N-methoxycarbonylamidino)indol-2-yl]sulfonyl]piperazine 1-[(6-Methyl-4,5,6,7-tetrahydrothiazolo[5,4-c]pyridin-2-yl)carbonyl]-4-[[6-[N-(methoxycarbonyl)amidino]indol-2-yl]sulfonyl]piperazine 1-[(5-Amidinobenzo[b]thien-2-yl)sulfonyl]-4-[(6-methyl-4,5,6,7-tetrahydrothiazolo[5,4-c]pyridin-2-yl)carbonyl]piperazine 1-[(6-Amidinobenzo[b]thien-2-yl)sulfonyl]-4-[(6-methyl-4,5,6,7-tetrahydrothiazolo[5,4-c]pyridin-2-yl)carbonyl]piperazine 1-[[5-[(Amino)(hydroxyimino)methyl]benzo[b]thien-2-yl]sulfonyl]-4-[(6-methyl-4,5,6,7-tetrahydrothiazolo[5,4-c]pyridin-2-yl)carbonyl]piperazine 1-[[6-[(Amino)(hydroxyimino)methyl]benzo[b]thien-2-yl]sulfonyl]-4-[(6-methyl-4,5,6,7-tetrahydrothiazolo[5,4-c]pyridin-2-yl)carbonyl]piperazine 1-[(6-Methyl-4,5,6,7-tetrahydrothiazolo[5,4-c]pyridin-2-yl) carbonyl]-4-[[5-[N-(methoxycarbonyl) amidino]benzo[b]thien-2-yl]sulfonyl]piperazine 1-[(6-Methyl-4,5,6,7-tetrahydrothiazolo[5,4-c]pyridin-2-yl)carbonyl]-4-[[6-[N-(methoxycarbonyl)amidino]benzo[b]thien-2-yl]sulfonyl]piperazine 4-[(-Amidinoisoindol-2-yl)sulfonyl]-1-[(6-methyl-4,5,6,7-tetrahydrothiazolo[5,4-c]pyridin-2-yl)carbonyl]piperazine 4-[[5-[(Amino) (hydroxyimino)methylisoindol-2-yl]sulfonyl]-1-[(6-methyl-4,5,6,7-tetrahydrothiazolo[5,4-cpyridin-2-yl) carbonyl]piperazine 4-[[5-[N-(Methoxycarbonyl)amidino]isoindol-2-yl]sulfonyl]-1-[(6-methyl-4,5,6,7-tetrahydrothiazolo[5,4-c]pyridin-2-yl)carbonyl]piperazine 2-[[4-[(6-Chloronaphthalen-2-yl)sulfonyl]piperazin-1-yl]carbonyl]-6-methylthiazolo[5,4-c]pyridinium iodide 2-[[4-[(5-Chloroindol-2-yl)sulfonyl]piperazin-1-yl]carbonyl]-6-methylthiazolo[5,4-c]pyridinium iodide 2-[[4-[(5-Bromoindol-2-yl)sulfonyl]piperazin-1-yl]carbonyl]-6-methylthiazolo[5,4-c]pyridinium iodide 2-[[4-[(5-Ethynylindol-2-yl)sulfonyl]piperazin-1-yl]carbonyl]-6-methylthiazolo[5,4-c]pyridinium iodide 2-[[2-(Carbamoyl)-4-[(5-chloroindol-2-yl)sulfonyl]piperazin-1-yl]carbonyl]-6-methylthiazolo[5,4-c]pyridinium iodide 2-[[2-(Carbamoylmethyl)-4-[(5-chloroindol-2-yl)sulfonyl]piperazin-1-yl]carbonyl]-6-methylthiazolo[5,4-c]pyridinium iodide 2-[[2,6-Bis(carbamoylmethyl)-4-[(5-chloroindol-2-yl)sulfonyl]piperazin-1-yl]carbonyl]-6-methylthiazolo[5,4-c]pyridinium iodide 2-[[2-[[[(Tetrazol-5-ylmethyl)amino]carbonyl]-4-[(5-chloroindol-2-yl)sulfonyl]piperazin-1-yl]carbonyl]-6-methylthiazolo[5,4-c]pyridinium iodide 2-[[2-[2-(Tetrazol-5-yl)ethyl]-4-[(5-chloroindol-2-yl)sulfonyl]piperazin-1-yl]carbonyl]-6-methylthiazolo[5,4-c]pyridinium iodide 2-[[2-[(Morpholin-4-ylcarbonyl)methyl]-4-[(5-chloroindol-2-yl)sulfonyl]piperazin-1-yl]carbonyl]-6-methylthiazolo[5,4-c]pyridinium iodide 4-[(5-Chloroindol-2-yl)sulfonyl]-2-(carbamoylmethyl)-1-[(6-methyl-4,5,6,7-tetrahydrothiazolo[5,4-c]pyridin-2-yl)carbonyl]piperazine 4-[(5-Chloroindol-2-yl)sulfonyl]-1-[(6-methyl-4,5,6,7-tetrahydrothiazolo[5,4-c]pyridin-2-yl)carbonyl]-2-(N,N-dimethylcarbamoylmethyl)piperazine 4-[(5-Chloroindol-2-yl)sulfonyl]-1-[(6-methyl-4,5,6,7-tetrahydrothiazolo[5,4-c]pyridin-2-yl)carbonyl]-2-[[(tetrazol-5-yl)amino]carbonyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[[(tetrazol-5-ylmethyl)amino]carbonyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[[(tetrazol-5-ylamino)carbonyl]methyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[[[(tetrazol-5-ylmethyl)amino]carbonyl]methyl]piperazine 4-[(5-Chloroindol-2-yl)sulfonyl]-1-[(6-methyl-4,5,6,7-tetrahydrothiazolo[5,4-c]pyridin-2-yl)carbonyl]-2-(tetrazol-5-ylmethyl)piperazine 4-[(5-Chloroindol-2-yl)sulfonyl]-1-[(6-methyl-4,5,6,7-tetrahydrothiazolo[5,4-c]pyridin-2-yl)carbonyl]-2-[2-(tetrazol-5-yl)ethyl]piperazine 4-[(5-Chloroindol-2-yl)sulfonyl]-2-(N-methylcarbamoylmethyl)-1-[(6-methyl-4,5,6,7-tetrahydrothiazolo[5,4-c]pyridin-2-yl)carbonyl]piperazine 4-[(5-Chloroindol-2-yl)sulfonyl]-2-[(morpholin-4-ylcarbonyl)methyl]-1-[(6-methyl-4,5,6,7-tetrahydrothiazolo[5,4-c]pyridin-2-yl)carbonyl]piperazine 4-[(5-Ethynylindol-2-yl)sulfonyl]-2-[(morpholin-4-ylcarbonyl)methyl]-1-[(6-methyl-4,5,6,7-tetrahydrothiazolo[5,4-c]pyridin-2-yl)carbonyl]piperazine 4-[(5-Ethynylisoindol-2-yl)sulfonyl]-2-(N-methylcarbamoyl)-1-[(6-methyl-4,5,6,7-tetrahydrothiazolo[5,4-c]pyridin-2-yl)carbonyl]piperazine 4-[(5-Chloroisoindol-2-yl)sulfonyl]-2-(N-methylcarbamoyl)-1-[(6-methyl-4,5,6,7-tetrahydrothiazolo[5,4-c]pyridin-2-yl)carbonyl]piperazine 2-(Carbamoylmethyl)-4-[(5-chloroisoindol-2-yl)sulfonyl]-1-[(6-methyl-4,5,6,7-tetrahydrothiazolo[5,4-c]pyridin-2-yl)carbonyl]piperazine 2-(Carbamoylmethyl)-4-[(5-ethynylisoindol-2-yl)sulfonyl]-1-[(6-methyl-4,5,6,7-tetrahydrothiazolo[5,4-c]pyridin-2-yl)carbonyl]piperazine 4-[(5-Chloroisoindol-2-yl)sulfonyl]-2-(N-methylcarbamoylmethyl)-1-[(6-methyl-4,5,6,7-tetrahydrothiazolo[5,4-c]pyridin-2-yl)carbonyl]piperazine 4-[(5-Chloroisoindol-2-yl)sulfonyl]-1-[(6-methyl-4,5,6,7-tetrahydrothiazolo[5,4-c]pyridin-2-yl)carbonyl]-2-(N,N-dimethylcarbamoylmethyl)piperazine 4-[(5-Chloroisoindol-2-yl)sulfonyl]-1-[(6-methyl-4,5,6,7-tetrahydrothiazolo[5,4-c]pyridin-2-yl)carbonyl]-2-[(morpholin-4-ylcarbonyl)methyl]piperazine 4-[(5-Bromoisoindol-2-yl)sulfonyl]-1-[(6-methyl-4,5,6,7-tetrahydrothiazolo[5,4-c]pyridin-2-yl)carbonyl]-2-(morpholinocarbonylmethyl)piperazine 4-[(5-Ethynylisoindol-2-yl)sulfonyl]-1-[(6-methyl-4,5,6,7-tetrahydrothiazolo[5,4-c]pyridin-2-yl)carbonyl]-2-[(morpholin-4-ylcarbonyl)methyl]piperazine 1-[(6-Chloronaphthalen-2-yl)sulfonyl]-4-[(5-methyl-4,5,6,7-tetrahydroxazolo[4,5-c]pyridin-2-yl)carbonyl]piperazine 4-[(5-Chloroindol-2-yl)sulfonyl]-2-(N-methylcarbamoyl)-1-[(6,7-dimethyl-4,5,6,7-tetrahydrothiazolo[5,4-c]pyridin-2-yl)carbonyl]piperazine 4-[(5-Chloroindol-2-yl)sulfonyl]-2-(N-methylcarbamoylmethyl)-1-[(6,7-dimethyl-4,5,6,7-tetrahydrothiazolo[5,4-c]pyridin-2-yl)carbonyl]piperazine 4-[(5-Chloroindol-2-yl)sulfonyl]-2-(morpholinocarbonylmethyl)-1-[(6,7-dimethyl-4,5,6,7-tetrahydrothiazolo[5,4-c]pyridin-2-yl)carbonyl]piperazine 4-[(5-Ethynylindol-2-yl)sulfonyl]-2-(morpholinocarbonylmethyl)-1-[(6,7-dimethyl-4,5,6,7-tetrahydrothiazolo[5,4-c]pyridin-2-yl)carbonyl]piperazine 4-[(5-Bromoindol-2-yl)sulfonyl]-2-(morpholinocarbonylmethyl)-1-[(6,7-dimethyl-4,5,6,7-tetrahydrothiazolo[5,4-c]pyridin-2-yl)carbonyl]piperazine 2,6-Bis(carbamoylmethyl)-4-[(5-chloroindol-2-yl)sulfonyl]-1-[(6,7-dimethyl-4,5,6,7-tetrahydrothiazolo[5,4-c]pyridin-2-yl)carbonyl]piperazine 4-[(5-Ethynylindol-2-yl)sulfonyl]-2-(N-methylcarbamoyl)-1-[(6,7-dimethyl-4,5,6,7-tetrahydrothiazolo[5,4-c]pyridin-2-yl)carbonyl]piperazine 2,6-Bis(carbamoylmethyl)-1-[(6,7-dimethyl-4,5,6,7-tetrahydrothiazolo[5,4-c]pyridin-2-yl)carbonyl]-4-[(5-ethynylindol-2-yl)sulfonyl]piperazine 4-[(5-Chloroindol-2-yl)sulfonyl]-2-[[(ethoxycarbonylmethyl)aminocarbonyl]methyl]-1-[(6,7-dimethyl-4,5,6,7-tetrahydrothiazolo[5,4-c]pyridin-2-yl)carbonyl]piperazine 4-[(5-Chloroindol-2-yl)sulfonyl]-2-[[(ethoxycarbonylmethyl)aminocarbonyl]methyl]-1-[(6-methyl-4,5,6,7-tetrahydrothiazolo[5,4-c]pyridin-2-yl)carbonyl]piperazine 4-[(5-Chloroindol-2-yl)sulfonyl]-2-[[(carboxymethyl)aminocarbonyl]methyl]-1-[(6,7-dimethyl-4,5,6,7-tetrahydrothiazolo[5,4-c]pyridin-2-yl)carbonyl]piperazine 4-[(5-Chloroindol-2-yl)sulfonyl]-2-[[(carboxymethyl)aminocarbonyl]methyl]-1-[(6-methyl-4,5,6,7-tetrahydrothiazolo[5,4-c]pyridin-2-yl)carbonyl]piperazine 4-[(5-Chloroindol-2-yl)sulfonyl]-1-[(6,7-dimethyl-4,5,6,7-tetrahydrothiazolo[5,4-c]pyridin-2-yl)carbonyl]-2-[[[(tetrazol-5-yl)methyl]aminocarbonyl]methyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[[[(tetrazol-5-yl)methyl]aminocarbonyl]methyl]piperazine 4-[(5-Chloroindol-2-yl)sulfonyl]-1-[(6,7-dimethyl-4,5,6,7-tetrahydrothiazolo[5,4-c]pyridin-2-yl)carbonyl]-2-[(tetrazol-5-yl)methyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[(tetrazol-5-yl)methyl]piperazine 4-[(5-Chloroindol-2-yl)sulfonyl]-1-[(6,7-dimethyl-4,5,6,7-tetrahydrothiazolo[5,4-c]pyridin-2-yl)carbonyl]-2-[2-(tetrazol-5-yl)ethyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[2-(tetrazol-5-yl)ethyl]piperazine 4-[(5-Chloroindol-2-yl)sulfonyl]-1-[(6,7-dimethyl-4,5,6,7-tetrahydrothiazolo[5,4-c]pyridin-2-yl)carbonyl]-2-[(2-oxopyrrolidin-1-yl)methyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[(2-oxopyrrolidin-1-yl)methyl]piperazine 4-[(5-Chloroindol-2-yl)sulfonyl]-1-[(6,7-dimethyl-4,5,6,7-tetrahydrothiazolo[5,4-c]pyridin-2-yl)carbonyl]-2-[2-(2-oxopyrrolidin-1-yl)ethyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[2-(2-oxopyrrolidin-1-yl)ethyl]piperazine 4-[(5-Chloroindol-2-yl)sulfonyl]-2-[(4-hydroxy-2-oxopyrrolidin-1-yl)methyl]-1-[(6,7-dimethyl-4,5,6,7-tetrahydrothiazolo[5,4-c]pyridin-2-yl)carbonyl]piperazine 4-[(5-Chloroindol-2-yl)sulfonyl]-2-[(4-hydroxy-2-oxopyrrolidin-1-yl)methyl]-1-[(6-methyl-4,5,6,7-tetrahydrothiazolo[5,4-c]pyridin-2-yl)carbonyl]piperazine 4-[(5-Chloroindol-2-yl)sulfonyl]-2-[2-(4-hydroxy-2-oxopyrrolidin-1-yl)ethyl]-1-[(6,7-dimethyl-4,5,6,7-tetrahydrothiazolo[5,4-c]pyridin-2-yl)carbonyl]piperazine 4-[(5-Chloroindol-2-yl)sulfonyl]-2-[2-(4-hydroxy-2-oxopyrrolidin-1-yl)ethyl]-1-[(6-methyl-4,5,6,7-tetrahydrothiazolo[5,4-c]pyridin-2-yl)carbonyl]piperazine 4-[(5-Chloroindol-2-yl)sulfonyl]-1-[(6,7-dimethyl-4,5,6,7-tetrahydrothiazolo[5,4-c]pyridin-2-yl)carbonyl]-2-[(2,5-dioxopyrrolidin-1-yl)methyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[(2,5-dioxopyrrolidin-1-yl)methyl]piperazine 4-[(5-Chloroindol-2-yl)sulfonyl]-1-[(6,7-dimethyl-4,5,6,7-tetrahydrothiazolo[5,4-c]pyridin-2-yl)carbonyl]-2-[2-(2,5-dioxopyrrolidin-1-yl)ethyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[2-(2,5-dioxopyrrolidin-1-yl)ethyl]piperazine 2,6-Bis[2-(4-hydroxy-2-oxopyrrolidin-1-yl)ethyl]-4-[(5-chloroindol-2-yl)sulfonyl]-1-[(6,7-dimethyl-4,5,6,7-tetrahydrothiazolo[5,4-c]pyridin-2-yl)carbonyl]piperazine 2,6-Bis[2-(2-oxopyrrolidin-1-yl)ethyl]-4-[(5-chloroindol-2-yl)sulfonyl]-1-[(6,7-dimethyl-4,5,6,7-tetrahydrothiazolo[5,4-c]pyridin-2-yl)carbonyl]piperazine 2,6-Bis[2-(tetrazol-5-yl)ethyl]-4-[(5-chloroindol-2-yl)sulfonyl]-1-[(6,7-dimethyl-4,5,6,7-tetrahydrothiazolo[5,4-c]pyridin-2-yl)carbonyl]piperazine 2,6-Bis[(tetrazol-5-yl)methyl]-4-[(5-chloroindol-2-yl)sulfonyl]-1-[(6, 7-dimethyl-4, 5,6,7-tetrahydrothiazolo[5,4-c]pyridin-2-yl)carbonyl]piperazine 2,6-Bis[(N-methylcarbamoyl)methyl]-4-[(5-chloroindol-2-yl)sulfonyl]-1-[(6,7-dimethyl-4,5,6,7-tetrahydrothiazolo[5,4-c]pyridin-2-yl)carbonyl]piperazine 2,6-Bis[(2,5-di oxopyrrolidin-1-yl)methyl]-4-[(5-chloroindol-2-yl)sulfonyl]-1-[(6,7-dimethyl-4,5,6,7-tetrahydrothiazolo[5,4-c]pyridin-2-yl)carbonyl]piperazine 2,6-Bis[2-(2,5-dioxopyrrolidin-1-yl)ethyl]-4-[(5-chloroindol-2-yl)sulfonyl]-1-[(6,7-dimethyl-4,5,6,7-tetrahydrothiazolo[5,4-c]pyridin-2-yl)carbonyl]piperazine 4-[(7-Amidinonaphthalen-2-yl)sulfonyl]-1-[(6-methyl-4,5,6,7-tetrahydrothiazolo[5,4-c]pyridin-2-yl)carbonyl]piperazine-2-carboxylic acid 4-[(6-Amidinonaphthalen-2-yl)sulfonyl]-1-[(6-methyl-4,5,6,7-tetrahydrothiazolo[5,4-c]pyridin-2-yl)carbonyl]piperazine-2-carboxylic acid 1-[(6-Methyl-4,5,6,7-tetrahydrothiazolo[5,4-c]pyridin-2-yl)carbonyl]-4-[[7-[N-(methoxycarbonyl)amidino]naphthalen-2-yl]sulfonyl]piperazine-2-carboxylic acid 1-[(6-Methyl-4,5,6,7-tetrahydrothiazolo[5,4-c]pyridin-2-yl)carbonyl]-4-[[6-[N-(methoxycarbonyl)amidino]naphthalen-2-yl]sulfonyl]piperazine-2-carboxylic acid 4-[(7-[(Amino)(hydroxyimino)methyl]naphthalen-2-yl)sulfonyl]-1-[(6-methyl-4,5,6,7-tetrahydrothiazolo[5,4-c]pyridin-2-yl)carbonyl]piperazine-2-carboxylic acid 4-[(6-[(Amino)(hydroxyimino)methyl]naphthalen-2-yl)sulfonyl]-1-[(6-methyl-4,5,6,7-tetrahydrothiazolo[5,4-c]pyridin-2-yl)carbonyl]piperazine-2-carboxylic acid 4-[(5-Amidinoindol-2-yl)sulfonyl]-1-[(6-methyl-4,5,6,7-tetrahydrothiazolo[5,4-c]pyridin-2-yl)carbonyl]piperazine-2-carboxylic acid 4-[(6-Amidinoindol-2-yl)sulfonyl]-1-[(6-methyl-4,5,6,7-tetrahydrothiazolo[5,4-c]pyridin-2-yl)carbonyl]piperazine-2-carboxylic acid 4-[[5-[(Amino)(hydroxyimino)methyl]indol-2-yl]sulfonyl]-1-[(6-methyl-4,5,6,7-tetrahydrothiazolo[5,4-c]pyridin-2-yl)carbonyl]piperazine-2-carboxylic acid 4-[[6-[(Amino)(hydroxyimino)methyl]indol-2-yl]sulfonyl]-1-[(6-methyl-4,5,6,7-tetrahydrothiazolo[5,4-c]pyridin-2-yl)carbonyl]piperazine-2-carboxylic acid 1-[(6-Methyl-4,5,6,7-tetrahydrothiazolo[5,4-c]pyridin-2-yl)carbonyl]-4-[[5-[N-(methoxycarbonyl)amidino]indol-2-yl]sulfonyl]piperazine-2-carboxylic acid 1-[(6-Methyl-4,5,6,7-tetrahydrothiazolo[5,4-c]pyridin-2-yl)carbonyl]-4-[[6-[N-(methoxycarbonyl)amidino]indol-2-yl]sulfonyl]piperazine-2-carboxylic acid 4-[(5-Amidinobenzo[b]thien-2-yl)sulfonyl]-1-[(6-methyl-4,5,6,7-tetrahydrothiazolo[5,4-c]pyridin-2-yl)carbonyl]piperazine-2-carboxylic acid 4-[(6-amidinobenzo[b]thien-2-yl)sulfonyl]-1-[(6-methyl-4,5,6,7-tetrahydrothiazolo[5,4-c]pyridin-2-yl)carbonyl]piperazine-2-carboxylic acid 1-[[5-[(Amino)(hydroxyimino)methyl]benzo[b]thien-2-yl]sulfonyl]-4-[(6-methyl-4,5,6,7-tetrahydrothiazolo[5,4-c]pyridin-2-yl)carbonyl]piperazine-2-carboxylic acid 4-[[6-[(Amino)(hydroxyimino)methyl]benzo[b]thien-2-yl]sulfonyl]-1-[(6-methyl-4,5,6,7-tetrahydrothiazolo[5,4-c]pyridin-2-yl)carbonyl]piperazine-2-carboxylic acid 1-[(6-Methyl-4,5,6,7-tetrahydrothiazolo[5,4-c]pyridin-2-yl)carbonyl]-4-[[5-N-(methoxycarbonyl)amidino]benzo[b]thien-2-yl]sulfonyl]piperazine-2-carboxylic acid 1-[(6-Methyl-4,5,6,7-tetrahydrothiazolo[5,4-c]pyridin-2-yl)carbonyl]-4-[[6-(N-methoxycarbonylamidino)benzo[b]thien-2-yl]sulfonyl]piperazine-2-carboxylic acid 4-[(5-Amidinoisoindol-2-yl)sulfonyl]-1-[(6-methyl-4,5,6,7-tetrahydrothiazolo[5,4-c]pyridin-2-yl)carbonyl]piperazine-2-carboxylic acid 4-[[5-[(Amino)(hydroxyimino)methyl]isoindol-2-yl]sulfonyl]-1-[(6-methyl-4,5,6,7-tetrahydrothiazolo[5,4-c]pyridin-2-yl)carbonyl]piperazine-2-carboxylic acid 1-[(6-Methyl-4,5,6,7-tetrahydrothiazolo[5,4-c]pyridin-2-yl)carbonyl]-4-[[5-[N-(methoxycarbonyl)amidino]isoindol-2-yl]sulfonyl]piperazine-2-carboxylic acid 4-[(7-Amidinonaphthalen-2-yl)sulfonyl]-2-(ethoxycarbonyl)-1-[(6-methyl-4,5,6,7-tetrahydrothiazolo[5,4-c]pyridin-2-yl)carbonyl]piperazine 4-[(6-Amidinonaphthalen-2-yl)sulfonyl]-2-(ethoxycarbonyl)-1-[(6-methyl-4,5,6,7-tetrahydrothiazolo[5,4-c]pyridin-2-yl)carbonyl]piperazine 2-(Ethoxycarbonyl)-1-[(6-methyl-4,5,6,7-tetrahydrothiazolo[5,4-c]pyridin-2-yl)carbonyl]-4-[[7-[N-(methoxycarbonyl)amidino]naphthalen-2-yl]sulfonyl]piperazine 2-(Ethoxycarbonyl)-1-[(6-methyl-4,5,6,7-tetrahydrothiazolo[5,4-c]pyridin-2-yl)carbonyl]-4-[[6-[N-(methoxycarbonyl)amidino]naphthalen-2-yl]sulfonyl]piperazine 4-[(7-[(Amino)(hydroxyimino)methyl]naphthalen-2-yl)sulfonyl]-2-(ethoxycarbonyl)-1-[(6-methyl-4,5,6,7-tetrahydrothiazolo[5,4-c]pyridin-2-yl)carbonyl]piperazine 4-[(6-[(Amino)(hydroxyimino)methyl]naphthalen-2-yl)sulfonyl]-2-(ethoxycarbonyl)-1-[(6-methyl-4,5,6,7-tetrahydrothiazolo[5,4-c]pyridin-2-yl)carbonyl]piperazine 4-[(5-Amidinoindol-2-yl)sulfonyl]-2-(ethoxycarbonyl)-1-[(6-methyl-4,5,6,7-tetrahydrothiazolo[5,4-c]pyridin-2-yl)carbonyl]piperazine 4-[(6-Amidinoindol-2-yl)sulfonyl]-2-(ethoxycarbonyl)-1-[(6-methyl-4,5,6,7-tetrahydrothiazolo[5,4-c]pyridin-2-yl)carbonyl]piperazine 4-[[5-[(Amino)(hydroxyimino)methyl]indol-2-yl]sulfonyl]-2-(ethoxycarbonyl)-1-[(6-methyl-4,5,6,7-tetrahydrothiazolo[5,4-c]pyridin-2-yl)carbonyl]piperazine 4-[[6-[(Amino)(hydroxyimino)methyl]indol-2-yl]sulfonyl]-2-(ethoxycarbonyl)-1-[(6-methyl-4,5,6,7-tetrahydrothiazolo[5,4-c]pyridin-2-yl)carbonyl]piperazine 2-(Ethoxycarbonyl)-1-[(6-methyl-4,5,6,7-tetrahydrothiazolo[5,4-c]pyridin-2-yl)carbonyl]-4-[[5-[N-(methoxycarbonyl)amidino]indol-2-yl]sulfonyl]piperazine 2-(Ethoxycarbonyl)-1-[(6-methyl-4,5,6,7-tetrahydrothiazolo[5,4-c]pyridin-2-yl)carbonyl]-4-[[6-[N-(methoxycarbonyl)amidino]indol-2-yl]sulfonyl]piperazine 4-[(5-Amidinobenzo[b]thien-2-yl)sulfonyl]-2-(ethoxycarbonyl)-1-[(6-methyl-4,5,6,7-tetrahydrothiazolo[5,4-c]pyridin-2-yl)carbonyl]piperazine 4-[(6-Amidinobenzo[b]thien-2-yl)sulfonyl]-2-(ethoxycarbonyl)-1-[(6-methyl-4,5,6,7-tetrahydrothiazolo[5,4-c]pyridin-2-yl)carbonyl]piperazine 4-[[5-[(Amino)(hydroxyimino)methyl]benzo[b]thien-2-yl]sulfonyl]-2-(ethoxycarbonyl)-1-[(6-methyl-4,5,6,7-tetrahydrothiazolo[5,4-c]pyridin-2-yl)carbonyl]piperazine 4-[[6-[(Amino)(hydroxyimino)methyl]benzo[b]thien-2-yl]sulfonyl]-2-(ethoxycarbonyl)-1-[(6-methyl-4,5,6,7-tetrahydrothiazolo[5,4-c]pyridin-2-yl)carbonyl]piperazine 2-(Ethoxycarbonyl)-1-[(6-methyl-4,5,6,7-tetrahydrothiazolo[5,4-c]pyridin-2-yl)carbonyl]-4-[[5-[N-(methoxycarbonyl)amidino]benzo[b]thien-2-yl]sulfonyl]piperazine 2-(Ethoxycarbonyl)-1-[(6-methyl-4,5,6,7-tetrahydrothiazolo[5,4-c]pyridin-2-yl)carbonyl]-4-[[6-[N-(methoxycarbonyl)amidino]benzo[b]thien-2-yl]sulfonyl]piperazine 4-[(5-Amidinoisoindol-2-yl)sulfonyl]-2-(ethoxycarbonyl)-1-[(6-methyl-4,5,6,7-tetrahydrothiazolo[5,4-c]pyridin-2-yl)carbonyl]piperazine 4-[[5-[(Amino)(hydroxyimino)methyl]isoindol-2-yl]sulfonyl]-2-(ethoxycarbonyl)-1-[(6-methyl-4,5,6,7-tetrahydrothiazolo[5,4-c]pyridin-2-yl)carbonyl]piperazine 2-(Ethoxycarbonyl)-1-[(6-methyl-4,5,6,7-tetrahydrothiazolo[5,4-c]pyridin-2-yl)carbonyl]-4-[[5-[N-(methoxycarbonyl)amidino]isoindol-2-yl]sulfonyl]piperazine 4-[(7-Amidinonaphthalen-2-yl)sulfonyl]-1-[(6-methyl-4,5,6,7-tetrahydrothiazolo[5,4-c]pyridin-2-yl)carbonyl]-2-[(tetrazol-5-yl)methyl]piperazine 4-[(6-Amidinonaphthalen-2-yl)sulfonyl]-1-[(6-methyl-4,5,6,7-tetrahydrothiazolo[5,4-c]pyridin-2-yl)carbonyl]-2-[(tetrazol-5-yl)methyl]piperazine 1-[(6-Methyl-4,5,6,7-tetrahydrothiazolo[5,4-c]pyridin-2-yl)carbonyl]-4-[[6-[N-(methoxycarbonyl)amidino]naphthalen-2-yl]sulfonyl]-2-[(tetrazol-5-yl)methyl]piperazine 4-[(6-[(Amino)(hydroxyimino)methyl]naphthalen-2-yl)sulfonyl]-1-[(6-methyl-4,5,6,7-tetrahydrothiazolo[5,4-c]pyridin-2-yl)carbonyl]-2-[(tetrazol-5-yl)methyl]piperazine 4-[(5-Ethynylindol-2-yl)sulfonyl]-1-[(6-methyl-4,5,6,7-tetrahydrothiazolo[5,4-c]pyridin-2-yl)carbonyl]-2-[(tetrazol-5-yl)methyl]piperazine 4-[(5-Amidinoindol-2-yl)sulfonyl]-1-[(6-methyl-4,5,6,7-tetrahydrothiazolo[5,4-c]pyridin-2-yl)carbonyl]-2-[(tetrazol-5-yl)methyl]piperazine 4-[(6-Amidinoindol-2-yl)sulfonyl]-1-[(6-methyl-4,5,6,7-tetrahydrothiazolo[5,4-c]pyridin-2-yl)carbonyl]-2-[(tetrazol-5-yl)methyl]piperazine 4-[[5-[(Amino)(hydroxyimino)methyl]indol-2-yl]sulfonyl]-1-[(6-methyl-4,5,6,7-tetrahydrothiazolo[5,4-c]pyridin-2-yl)carbonyl]-2-[(tetrazol-5-yl)methyl]piperazine 4-[[6-[(Amino)(hydroxyimino)methyl]indol-2-yl]sulfonyl]-1-[(6-methyl-4,5,6,7-tetrahydrothiazolo[5,4-c]pyridin-2-yl)carbonyl]-2-[(tetrazol-5-yl)methyl]piperazine 1-[(6-Methyl-4,5,6,7-tetrahydrothiazolo[5,4-c]pyridin-2-yl)carbonyl]-4-[[5-(N-methoxycarbonylamidino)indol-2-yl]sulfonyl]-2-[(tetrazol-5-yl)methyl]piperazine 1-[(6-Methyl-4,5,6,7-tetrahydrothiazolo[5,4-c]pyridin-2-yl)carbonyl]-4-[[6-[N-(methoxycarbonyl)amidino]indol-2-yl]sulfonyl]-2-[(tetrazol-5-yl)methyl]piperazine 4-[(5-Amidinobenzo[b]thien-2-yl)sulfonyl]-4-[(6-methyl-4,5,6,7-tetrahydrothiazolo[5,4-c]pyridin-2-yl)carbonyl]-2-[(tetrazol-5-yl)methyl]piperazine 4-[[5-[(Amino)(hydroxyimino)methyl]benzo[b]thien-2-yl]sulfonyl]-1-[(6-methyl-4,5,6,7-tetrahydrothiazolo[5,4-c]pyridin-2-yl)carbonyl]-2-[(tetrazol-5-yl)methyl]piperazine 1-[(6-Methyl-4,5,6,7-tetrahydrothiazolo[5,4-c]pyridin-2-yl)carbonyl]-4-[[5-[N-(methoxycarbonyl)amidino]benzo[b]thien-2-yl]sulfonyl]-2-[(tetrazol-5-yl)methyl]piperazine 4-[(5-Amidinoisoindol-2-yl)sulfonyl]-1-[(6-methyl-4,5,6,7-tetrahydrothiazolo[5,4-c]pyridin-2-yl)carbonyl]-2-[(tetrazol-5-yl)methyl]piperazine 4-[[5-[(Amino)(hydroxyimino)methyl]isoindol-2-yl]sulfonyl]-1-[(6-methyl-4,5,6,7-tetrahydrothiazolo[5,4-c]pyridin-2-yl)carbonyl]-2-[(tetrazol-5-yl)methyl]piperazine 4-[[5-[N-(Methoxycarbonyl)amidino]isoindol-2-yl]sulfonyl]-1-[(6-methyl-4,5,6,7-tetrahydrothiazolo[5,4-c]pyridin-2-yl)carbonyl]-2-[(tetrazol-5-yl)methyl]piperazine 2-[[4-[(6-Chloronaphthalen-2-yl)sulfonyl]-2-[(tetrazol-5-yl)methyl]piperazin-1-yl]carbonyl]-6-methylthiazolo[5,4-c]pyridinium iodide 2-[[4-[(5-Chloroindol-2-yl)sulfonyl]-2-[(tetrazol-5-yl)methyl]piperazin-1-yl]carbonyl]-6-methylthiazolo[5,4-c]pyridinium iodide 4-[(7-Amidinonaphthalen-2-yl)sulfonyl]-1-[(6-methyl-4,5,6,7-tetrahydrothiazolo[5,4-c]pyridin-2-yl)carbonyl]-2-[2-(tetrazol-5-yl)ethyl]piperazine 4-[(6-Amidinonaphthalen-2-yl)sulfonyl]-1-[(6-methyl-4,5,6,7-tetrahydrothiazolo[5,4-c]pyridin-2-yl)carbonyl]-2-[2-(tetrazol-5-yl)ethyl]piperazine 1-[[(6-Methyl-4,5,6,7-tetrahydrothiazolo[5,4-c]pyridin-2-yl)carbonyl]-4-[[6-[N-(methoxycarbonyl)amidino]naphthalen-2-yl]sulfonyl]-2-[2-(tetrazol-5-yl)ethyl]piperazine 4-[(6-[(Amino)(hydroxyimino)methyl]naphthalen-2-yl)sulfonyl]-1-[(6-methyl-4,5,6,7-tetrahydrothiazolo[5,4-c]pyridin-2-yl)carbonyl]-2-[2-(tetrazol-5-yl)ethyl]piperazine 4-[(5-Ethynylindol-2-yl)sulfonyl]-1-[(6-methyl-4,5,6,7-tetrahydrothiazolo[5,4-c]pyridin-2-yl)carbonyl]-2-[2-(tetrazol-5-yl)ethyl]piperazine 4-[(5-Amidinoindol-2-yl)sulfonyl]-1-[(6-methyl-4,5,6,7-tetrahydrothiazolo[5,4-c]pyridin-2-yl)carbonyl]-2-[2-(tetrazol-5-yl)ethyl]piperazine 4-[(6-Amidinoindol-2-yl)sulfonyl]-1-[(6-methyl-4,5,6,7-tetrahydrothiazolo[5,4-c]pyridin-2-yl)carbonyl]-2-[2-(tetrazol-5-yl)ethyl]piperazine 4-[[5-[(Amino)(hydroxyimino)methyl]indol-2-yl]sulfonyl]-1-[(6-methyl-4,5,6,7-tetrahydrothiazolo[5,4-c]pyridin-2-yl)carbonyl]-2-[2-(tetrazol-5-yl)ethyl]piperazine 4-[[6-[(Amino)(hydroxyimino)methyl]indol-2-yl]sulfonyl]-1-[(6-methyl-4,5,6,7-tetrahydrothiazolo[5,4-c]pyridin-2-yl)carbonyl]-2-[2-(tetrazol-5-yl)ethyl]piperazine 1-[(6-Methyl-4,5,6,7-tetrahydrothiazolo[5,4-c]pyridin-2-yl)carbonyl]-4-[[5-(N-methoxycarbonylamidino)indol-2-yl]sulfonyl]-2-[2-(tetrazol-5-yl)ethyl]piperazine 1-[(6-Methyl-4,5,6,7-tetrahydrothiazolo[5,4-c]pyridin-2-yl)carbonyl]-4-[[6-N-(methoxycarbonyl)amidino]indol-2-yl]sulfonyl]-2-[2-(tetrazol-5-yl)ethyl]piperazine 4-[(5-Amidinobenzo[b]thien-2-yl)sulfonyl]-1-[(6-methyl-4,5,6,7-tetrahydrothiazolo[5,4-c]pyridin-2-yl)carbonyl]-2-[2-(tetrazol-5-yl)ethyl]piperazine 4-[[5-[(Amino)(hydroxyimino)methyl]benzo[b]thien-2-yl]sulfonyl]-1-[(6-methyl-4,5,6,7-tetrahydrothiazolo[5,4-c]pyridin-2-yl)carbonyl]-2-[2-(tetrazol-5-yl)ethyl]piperazine 1-[(6-Methyl-4,5,6,7-tetrahydrothiazolo[5,4-c]pyridin-2-yl)carbonyl]-4-[[5-[N-(methoxycarbonyl)amidino]benzo[b]thien-2-yl]sulfonyl]-2-[2-(tetrazol-5-yl)ethyl]piperazine 4-[(5-Amidinoisoindol-2-yl)sulfonyl]-1-[(6-methyl-4,5,6,7-tetrahydrothiazolo[5,4-c]pyridin-2-yl)carbonyl]-2-[2-(tetrazol-5-yl)ethyl]piperazine 4-[[5-[(Amino)(hydroxyimino)methyl]isoindol-2-yl]sulfonyl]-1-[(6-methyl-4,5,6,7-tetrahydrothiazolo[5,4-c]pyridin-2-yl)carbonyl]-2-[2-(tetrazol-5-yl)ethyl]piperazine 4-[[5-[N-(Methoxycarbonyl)amidino]isoindol-2-yl]sulfonyl]-1-[(6-methyl-4,5,6,7-tetrahydrothiazolo[5,4-c]pyridin-2-yl)carbonyl]-2-[2-(tetrazol-5-yl)ethyl]piperazine 2-[[4-[(6-Chloronaphthalen-2-yl)sulfonyl]-2-[2-(tetrazol-5-yl)ethyl]piperazin-1-yl]carbonyl]-6-methylthiazolo[5,4-c]pyridinium iodide 2-[[4-[(5-Chloroindol-2-yl)sulfonyl]-2-[2-(tetrazol-5-yl)ethyl]piperazin-1-yl]carbonyl]-6-methylthiazolo[5,4-c]pyridinium iodide 4-[(7-Amidinonaphthalen-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoyl]piperazine 4-[(6-Amidinonaphthalen-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoyl]piperazine 1-[(6-Methyl-4,5,6,7-tetrahydrothiazolo[5,4-c]pyridin-2-yl)carbonyl]-4-[[6-[N-(methoxycarbonyl)amidino]naphthalen-2-yl]sulfonyl]-2-[N-[(tetrazol-5-yl)methyl]carbamoyl]piperazine 4-[(6-[(Amino)(hydroxyimino)methyl]naphthalen-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoyl]piperazine 4-[(5-Ethynylindol-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoyl]piperazine 4-[(5-Amidinoindol-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoyl]piperazine 4-[(6-Amidinoindol-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoyl]piperazine 4-[[5-[(Amino)(hydroxyimino)methyl]indol-2-yl]sulfonyl]-1-[(6-methyl-4,5,6,7-tetrahydrothiazolo[5,4-c]pyridin-2-yl)carbonyl]-2-[N-[(tetrazol-5-yl)methyl]carbamoyl]piperazine 4-[[6-[(Amino)(hydroxyimino)methyl]indol-2-yl]sulfonyl]-1-[(6-methyl-4,5,6,7-tetrahydrothiazolo[5,4-c]pyridin-2-yl)carbonyl]-2-[N-[(tetrazol-5-yl)methyl]carbamoyl]piperazine 1-[(6-Methyl-4,5,6,7-tetrahydrothiazolo[5,4-c]pyridin-2-yl)carbonyl]-4-[[5-(N-methoxycarbonylamidino)indol-2-yl]sulfonyl]-2-[N-[(tetrazol-5-yl)methyl]carbamoyl]piperazine 1-[(6-Methyl-4,5,6,7-tetrahydrothiazolo[5,4-c]pyridin-2-yl)carbonyl]-4-[[6-[N-(methoxycarbonyl)amidino]indol-2-yl]sulfonyl]-2-[N-[(tetrazol-5-yl)methyl]carbamoyl]piperazine 4-[(5-Amidinobenzo[b]thien-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoyl]piperazine 4-[[5-[(Amino)(hydroxyimino)methyl]benzo[b]thien-2-yl]sulfonyl]-1-[(6-methyl-4,5,6,7-tetrahydrothiazolo[5,4-c]pyridin-2-yl)carbonyl]-2-[N-[(tetrazol-5-yl)methyl]carbamoyl]piperazine 1-[(6-Methyl-4,5,6,7-tetrahydrothiazolo[5,4-c]pyridin-2-yl) carbonyl]-4-[[5-[N-(methoxycarbonyl)amidino]benzo[b]thien-2-yl]sulfonyl]-2-[N-[(tetrazol-5-yl)methyl]carbamoyl]piperazine 4-[(5-Amidinoisoindol-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoyl]piperazine 4-[[5-[(Amino)(hydroxyimino)methyl]isoindol-2-yl]sulfonyl]-1-[(6-methyl-4,5,6,7-tetrahydrothiazolo[5,4-c]pyridin-2-yl)carbonyl]-2-[N-[(tetrazol-5-yl)methyl]carbamoyl]piperazine 4-[[5-[N-(Methoxycarbonyl)amidino]isoindol-2-yl]sulfonyl]-1-[(6-methyl-4,5,6,7-tetrahydrothiazolo[5,4-c]pyridin-2-yl)carbonyl]-2-[N-[(tetrazol-5-yl)methyl]carbamoyl]piperazine 2-[[4-[(6-Chloronaphthalen-2-yl)sulfonyl]-2-[N-[(tetrazol-5-yl)methyl]carbamoyl]piperazin-1-yl]carbonyl]-6-methylthiazolo[5,4-c]pyridinium iodide 2-[[4-[(5-Chloroindol-2-yl)sulfonyl]-2-[N-[(tetrazol-5-yl)methyl]carbamoyl]piperazin-1-yl]carbonyl]-6-methylthiazolo[5,4-c]pyridinium iodide 4-[(7-Amidinonaphthalen-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoylmethyl]piperazine 4-[(6-Amidinonaphthalen-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoylmethyl]piperazine 1-[(6-Methyl-4,5,6,7-tetrahydrothiazolo[5,4-c]pyridin-2-yl)carbonyl]-4-[[6-[N-(methoxycarbonyl)amidino]naphthalen-2-yl]sulfonyl]-2-[N-[(tetrazol-5-yl)methyl]carbamoylmethyl]piperazine 4-[(6-[(Amino)(hydroxyimino)methyl]naphthalen-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoylmethyl]piperazine 4-[(5-Ethynylindol-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoylmethyl]piperazine 4-[(5-Amidinoindol-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoylmethyl]piperazine 4-[(6-Amidinoindol-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoylmethyl]piperazine 4-[[5-[(Amino)(hydroxyimino)methyl]indol-2-yl]sulfonyl]-1-[(6-methyl-4,5,6,7-tetrahydrothiazolo[5,4-c]pyridin-2-yl)carbonyl]-2-[N-[(tetrazol-5-yl)methyl]carbamoylmethyl]piperazine 4-[[6-[(Amino)(hydroxyimino)methyl]indol-2-yl]sulfonyl]-1-[(6-methyl-4,5,6,7-tetrahydrothiazolo[5,4-c]pyridin-2-yl)carbonyl]-2-[N-[(tetrazol-5-yl)methyl]carbamoylmethyl]piperazine 1-[(6-Methyl-4,5,6,7-tetrahydrothiazolo[5,4-c]pyridin-2-yl) carbonyl]-4-[[5-(N-methoxycarbonylamidino) indol-2-yl]sulfonyl]-2-[N-[(tetrazol-5-yl)methyl]carbamoylmethyl]piperazine 1-[(6-Methyl-4,5,6,7-tetrahydrothiazolo[5,4-c]pyridin-2-yl)carbonyl]-4-[[6-[N-(methoxycarbonyl)amidino]indol-2-yl]sulfonyl]-2-[N-[(tetrazol-5-yl)methyl]carbamoylmethyl]piperazine 4-[(5-Amidinobenzo[b]thien-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoylmethyl]piperazine 4-[[5-[(Amino)(hydroxyimino)methyl]benzo[b]thien-2-yl]sulfonyl]-1-[(6-methyl-4,5,6,7-tetrahydrothiazolo[5,4-c]pyridin-2-yl)carbonyl]-2-[N-[(tetrazol-5-yl)methyl]carbamoylmethyl]piperazine 1-[(6-Methyl-4,5,6,7-tetrahydrothiazolo[5,4-c]pyridin-2-yl)carbonyl]-4-[[5-[N-(methoxycarbonyl)amidino]benzo[b]thien-2-yl]sulfonyl]-2-(N-[(tetrazol-5-yl)methyl]carbamoylmethyl]piperazine 4-[(5-Amidinoisoindol-2-yl)sulfonyl]-1-[(6-methyl-4,5,6,7-tetrahydrothiazolo[5,4-c]pyridin-2-yl)carbonyl]-2-[N-[(tetrazol-5-yl)methyl]carbamoylmethyl]piperazine 4-[[5-[(Amino)(hydroxyimino)methyl]isoindol-2-yl]sulfonyl]-1-[(6-methyl-4,5,6,7-tetrahydrothiazolo[5,4-c]pyridin-2-yl)carbonyl]-2-[N-[(tetrazol-5-yl)methyl]carbamoylmethyl]piperazine 4-[[5-[N-(Methoxycarbonyl)amidino]isoindol-2-yl]sulfonyl]-1-[(6-methyl-4,5,6,7-tetrahydrothiazolo[5,4-c]pyridin-2-yl)carbonyl]-2-[N-[(tetrazol-5-yl)methyl]carbamoylmethyl]piperazine 2-[[4-[(6-Chloronaphthalen-2-yl)sulfonyl]-2-[N-[(tetrazol-5-yl)methyl]carbamoylmethyl]piperazin-1-yl]carbonyl]-6-methylthiazolo[5,4-c]pyridinium iodide 2-[[4-[(5-Chloroindol-2-yl)sulfonyl]-2-[N-[(tetrazol-5-yl)methyl]carbamoylmethyl]piperazin-1-yl]carbonyl]-6-methylthiazolo[5,4-c]pyridinium iodide 4-[(7-Amidinonaphthalen-2-yl)sulfonyl]-2-(ethoxycarbonylmethyl)-1-[(6-methyl-4,5,6,7-tetrahydrothiazolo[5,4-c]pyridin-2-yl)carbonyl]piperazine 4-[(6-Amidinonaphthalen-2-yl)sulfonyl]-2-(ethoxycarbonylmethyl)-1-[(6-methyl-4,5,6,7-tetrahydrothiazolo[5,4-c]pyridin-2-yl)carbonyl]piperazine 2-(Ethoxycarbonylmethyl)-1-[(6-methyl-4,5,6,7-tetrahydrothiazolo[5,4-c]pyridin-2-yl)carbonyl]-4-[[6-[N-(methoxycarbonyl)amidino]naphthalen-2-yl]sulfonyl]piperazine 4-[6-[(Amino)(hydroxyimino)methyl]naphthalen-2-yl)sulfonyl]-2-(ethoxycarbonylmethyl)-1-[(6-methyl-4,5,6,7-tetrahydrothiazolo[5,4-c]pyridin-2-yl)carbonyl]piperazine 4-[(5-Ethynylindol-2-yl)sulfonyl]-2-(ethoxycarbonylmethyl)-1-[(6-methyl-4,5,6,7-tetrahydrothiazolo[5,4-c]pyridin-2-yl)carbonyl]piperazine 4-[(5-Amidinoindol-2-yl) sulfonyl]-2-(ethoxycarbonylmethyl)-1-[(6-methyl-4,5,6,7-tetrahydrothiazolo[5,4-c]pyridin-2-yl)carbonyl]piperazine 4-[(6-Amidinoindol-2-yl)sulfonyl]-2-(ethoxycarbonylmethyl)-1-[(6-methyl-4,5,6,7-tetrahydrothiazolo[5,4-c]pyridin-2-yl)carbonyl]piperazine 4-[[5-[(Amino)(hydroxyimino)methyl]indol-2-yl]sulfonyl]-2-(ethoxycarbonylmethyl)-1-[(6-methyl-4,5,6,7-tetrahydrothiazolo[5,4-c]pyridin-2-yl)carbonyl]piperazine 4-[[6-[(Amino)(hydroxyimino)methyl]indol-2-yl]sulfonyl]-2-(ethoxycarbonylmethyl)-1-[(6-methyl-4,5,6,7-tetrahydrothiazolo[5,4-c]pyridin-2-yl)carbonyl]piperazine 1-[(6-Methyl-4,5,6,7-tetrahydrothiazolo[5,4-c]pyridin-2-yl)carbonyl]-2-(ethoxycarbonylmethyl)-4-[[5-(N-methoxycarbonylamidino)indol-2-yl]sulfonyl]piperazine 1-[(6-Methyl-4,5,6,7-tetrahydrothiazolo[5,4-c]pyridin-2-yl)carbonyl]-2-(ethoxycarbonylmethyl)-4-[[6-[N-(methoxycarbonyl)amidino]indol-2-yl]sulfonyl]piperazine 4-[(5-Amidinobenzo[b]thien-2-yl)sulfonyl]-2-(ethoxycarbonylmethyl)-1-[(6-methyl-4,5,6,7-tetrahydrothiazolo[5,4-c]pyridin-2-yl)carbonyl]piperazine 4-[[5-[(Amino)(hydroxyimino)methyl]benzo[b]thien-2-yl]sulfonyl]-2-(ethoxycarbonylmethyl)-1-[(6-methyl-4,5,6,7-tetrahydrothiazolo[5,4-c]pyridin-2-yl)carbonyl]piperazine 1-[(6-Methyl-4,5,6,7-tetrahydrothiazolo[5,4-c]pyridin-2-yl)carbonyl]-2-(ethoxycarbonylmethyl)-4-[[5-[N-(methoxycarbonyl)amidino]benzo[b]thien-2-yl]sulfonyl]piperazine 4-[(5-Amidinoisoindol-2-yl)sulfonyl]-2-(ethoxycarbonylmethyl)-1-[(6-methyl-4,5,6,7-tetrahydrothiazolo[5,4-c]pyridin-2-yl)carbonyl]piperazine 4-[[5-[(Amino)(hydroxyimino)methyl]isoindol-2-yl]sulfonyl]-2-(ethoxycarbonylmethyl)-1-[(6-methyl-4,5,6,7-tetrahydrothiazolo[5,4-c]pyridin-2-yl)carbonyl]piperazine 2-(Ethoxycarbonylmethyl)-4-[[5-[N-(methoxycarbonyl)amidino]isoindol-2-yl]sulfonyl]-1-[(6-methyl-4,5,6,7-tetrahydrothiazolo[5,4-c]pyridin-2-yl)carbonyl]piperazine 2-[[4-[(6-Chloronaphthalen-2-yl)sulfonyl]-2-(ethoxycarbonylmethyl)piperazin-1-yl]carbonyl]-6-methylthiazolo[5,4-c]pyridinium iodide 2-[[4-[(5-Chloroindol-2-yl)sulfonyl]-2-(ethoxycarbonylmethyl)piperazin-1-yl]carbonyl]-6-methylthiazolo[5,4-c]pyridinium iodide 4-[(7-Amidinonaphthalen-2-yl)sulfonyl]-1-[(6-methyl-4,5,6,7-tetrahydrothiazolo[5,4-c]pyridin-2-yl)carbonyl]piperazin-2-acetic acid 4-[(6-Amidinonaphthalen-2-yl)sulfonyl]-1-[(6-methyl-4,5,6,7-tetrahydrothiazolo[5,4-c]pyridin-2-yl)carbonyl]piperazin-2-acetic acid 1-[(6-Methyl-4,5,6,7-tetrahydrothiazolo[5,4-c]pyridin-2-yl)carbonyl]-4-[[6-[N-(methoxycarbonyl)amidino]naphthalen-2-yl]sulfonyl]piperazin-2-acetic acid 4-[(6-[(Amino)(hydroxyimino)methyl]naphthalen-2-yl)sulfonyl]-1-[(6-methyl-4,5,6,7-tetrahydrothiazolo[5,4-c]pyridin-2-yl)carbonyl]piperazin-2-acetic acid 4-[(5-Ethynylindol-2-yl)sulfonyl]-1-[(6-methyl-4,5,6,7-tetrahydrothiazolo[5,4-c]pyridin-2-yl)carbonyl]piperazin-2-acetic acid 4-[(5-Amidinoindol-2-yl)sulfonyl]-1-[(6-methyl-4,5,6,7-tetrahydrothiazolo[5,4-c]pyridin-2-yl)carbonyl]piperazin-2-acetic acid 4-[(6-Amidinoindol-2-yl)sulfonyl]-1-[(6-methyl-4,5,6,7-tetrahydrothiazolo[5,4-c]pyridin-2-yl)carbonyl]piperazin-2-acetic acid 4-[[5-[(Amino)(hydroxyimino)methyl]indol-2-yl]sulfonyl]-1-[(6-methyl-4,5,6,7-tetrahydrothiazolo[5,4-c]pyridin-2-yl)carbonyl]piperazin-2-acetic acid 4-[[6-[(Amino)(hydroxyimino)methyl]indol-2-yl]sulfonyl]-1-[(6-methyl-4,5,6,7-tetrahydrothiazolo[5,4-c]pyridin-2-yl)carbonyl]piperazin-2-acetic acid 1-[(6-Methyl-4,5,6,7-tetrahydrothiazolo[5,4-c]pyridin-2-yl)carbonyl]-4-[[5-(N-methoxycarbonylamidino)indol-2-yl]sulfonyl]piperazin-2-acetic acid 1-[(6-Methyl-4,5,6,7-tetrahydrothiazolo[5,4-c]pyridin-2-yl)carbonyl]-4-[[6-[N-(methoxycarbonyl)amidino]indol-2-yl]sulfonyl]piperazin-2-acetic acid 4-[(5-Amidinobenzo[b]thien-2-yl)sulfonyl]-1-[(6-methyl-4,5,6,7-tetrahydrothiazolo[5,4-c]pyridin-2-yl)carbonyl]piperazin-2-acetic acid 4-[[5-[(Amino)(hydroxyimino)methyl]benzo[b]thien-2-yl]sulfonyl]-1-[(6-methyl-4,5,6,7-tetrahydrothiazolo[5,4-c]pyridin-2-yl)carbonyl]piperazin-2-acetic acid 1-[(6-Methyl-4,5,6,7-tetrahydrothiazolo[5,4-c]pyridin-2-yl)carbonyl]-4-[[5-[N-(methoxycarbonyl)amidino]benzo[b]thien-2-yl]sulfonyl]piperazin-2-acetic acid 4-[(5-Amidinoisoindol-2-yl)sulfonyl]-1-[(6-methyl-4,5,6,7-tetrahydrothiazolo[5,4-c]pyridin-2-yl)carbonyl]piperazin-2-acetic acid 4-[[5-[(Amino)(hydroxyimino)methyl]isoindol-2-yl]sulfonyl]-1-[(6-methyl-4,5,6,7-tetrahydrothiazolo[5,4-c]pyridin-2-yl)carbonyl]piperazin-2-acetic acid 4-[[5-[N-(Methoxycarbonyl)amidino]isoindol-2-yl]sulfonyl]-1-[(6-methyl-4,5,6,7-tetrahydrothiazolo[5,4-c]pyridin-2-yl)carbonyl]piperazin-2-acetic acid 2-[[2-(Carboxymethyl)-4-[(6-chloronaphthalen-2-yl)sulfonyl]piperazin-1-yl]carbonyl]-6-methylthiazolo[5,4-c]pyridinium iodide 2-[[2-(Carboxymethyl)-4-[(5-chloroindol-2-yl)sulfonyl]piperazin-1-yl]carbonyl]-6-methylthiazolo[5,4-c]pyridinium iodide 4-[(7-Amidinonaphthalen-2-yl)sulfonyl]-2-[(N-methylcarbamoyl)methyl]-1-[(6-methyl-4,5,6,7-tetrahydrothiazolo[5,4-c]pyridin-2-yl)carbonyl]piperazine 4-[(6-Amidinonaphthalen-2-yl)sulfonyl]-2-[(N-methylcarbamoyl)methyl]-1-[(6-methyl-4,5,6,7-tetrahydrothiazolo[5,4-c]pyridin-2-yl)carbonyl]piperazine 2-[(N-methylcarbamoyl)methyl]-1-[(6-methyl-4,5,6,7-tetrahydrothiazolo[5,4-c]pyridin-2-yl)carbonyl]-4-[[6-[N-(methoxycarbonyl)amidino]naphthalen-2-yl]sulfonyl]piperazine 4-[(6-[(Amino)(hydroxyimino)methyl]naphthalen-2-yl)sulfonyl]-2-[(N-methylcarbamoyl)methyl]-1-[(6-methyl-4,5,6,7-tetrahydrothiazolo[5,4-c]pyridin-2-yl)carbonyl]piperazine 4-[(5-Ethynylindol-2-yl)sulfonyl]-2-[(N-methylcarbamoyl)methyl]-1-[(6-methyl-4,5,6,7-tetrahydrothiazolo[5,4-c]pyridin-2-yl)carbonyl]piperazine 4-[(5-Amidinoindol-2-yl)sulfonyl]-2-[(N-methylcarbamoyl)methyl]-1-[(6-methyl-4,5,6,7-tetrahydrothiazolo[5,4-c]pyridin-2-yl)carbonyl]piperazine 4-[(6-Amidinoindol-2-yl)sulfonyl]-2-[(N-methylcarbamoyl)methyl]-1-[(6-methyl-4,5,6,7-tetrahydrothiazolo[5,4-c]pyridin-2-yl)carbonyl]piperazine 4-[[5-[(Amino)(hydroxyimino)methyl]indol-2-yl]sulfonyl]-2-[(N-methylcarbamoyl)methyl]-1-[(6-methyl-4,5,6,7-tetrahydrothiazolo[5,4-c]pyridin-2-yl)carbonyl]piperazine 4-[[6-[(Amino)(hydroxyimino)methyl]indol-2-yl]sulfonyl]-2-[(N-methylcarbamoyl)methyl]-1-[(6-methyl-4,5,6,7-tetrahydrothiazolo[5,4-c]pyridin-2-yl)carbonyl]piperazine 1-[(6-Methyl-4,5,6,7-tetrahydrothiazolo[5,4-c]pyridin-2-yl)carbonyl]-2-[(N-methylcarbamoyl)methyl]-4-[[5-(N-methoxycarbonylamidino)indol-2-yl]sulfonyl]piperazine 2-[(N-Methylcarbamoyl)methyl]-1-[(6-methyl-4,5,6,7-tetrahydrothiazolo[5,4-c]pyridin-2-yl)carbonyl]-4-[[6-[N-(methoxycarbonyl)amidino]indol-2-yl]sulfonyl]piperazine 4-[(5-Amidinobenzo[b]thien-2-yl)sulfonyl]-2-[(N-methylcarbamoyl)methyl]-1-[(6-methyl-4,5,6,7-tetrahydrothiazolo[5,4-c]pyridin-2-yl)carbonyl]piperazine 4-[[5-[(Amino)(hydroxyimino)methyl]benzo[b]thien-2-yl]sulfonyl]-2-[(N-methylcarbamoyl)methyl]-1-[(6-methyl-4,5,6,7-tetrahydrothiazolo[5,4-c]pyridin-2-yl)carbonyl]piperazine 2-[(N-Methylcarbamoyl)methyl]-1-[(6-methyl-4,5,6,7-tetrahydrothiazolo[5,4-c]pyridin-2-yl)carbonyl]-4-[[5-[N-(methoxycarbonyl)amidino]benzo[b]thien-2-yl]sulfonyl]piperazine 4-[(5-Amidinoisoindol-2-yl)sulfonyl]-2-[(N-methylcarbamoyl)methyl]-1-[(6-methyl-4,5,6,7-tetrahydrothiazolo[5,4-c]pyridin-2-yl)carbonyl]piperazine 4-[[5-[(Amino)(hydroxyimino)methyl]isoindol-2-yl]sulfonyl]-2-[(N-methylcarbamoyl)methyl]-1-[(6-methyl-4,5,6,7-tetrahydrothiazolo[5,4-c]pyridin-2-yl)carbonyl]piperazine 2-[(N-methylcarbamoyl)methyl]-4-[[5-[N-(methoxycarbonyl)amidino]isoindol-2-yl]sulfonyl]-1-[(6-methyl-4,5,6,7-tetrahydrothiazolo[5,4-c]pyridin-2-yl)carbonyl]piperazine 2-[[2-[(N-Methylcarbamoyl)methyl]-4-[(6-chloronaphthalen-2-yl)sulfonyl]piperazin-1-yl]carbonyl]-6-methylthiazolo[5,4-c]pyridinium iodide 2-[[2-[(N-methylcarbamoyl)methyl]-4-[(5-chloroindol-2-yl)sulfonyl]piperazin-1-yl]carbonyl]-6-methylthiazolo[5,4-c]pyridinium iodide 4-[(7-Amidinonaphthalen-2-yl)sulfonyl]-2-[[N-(ethoxycarbonylmethyl)carbamoyl]methyl]-4-[(6-methyl-4,5,6,7-tetrahydrothiazolo[5,4-c]pyridin-2-yl)carbonyl]piperazine 4-[(6-Amidinonaphthalen-2-yl)sulfonyl]-2-[[N-(ethoxycarbonylmethyl)carbamoyl]methyl]-4-[(6-methyl-4,5,6,7-tetrahydrothiazolo[5,4-c]pyridin-2-yl)carbonyl]piperazine 2-[[N-(Ethoxycarbonylmethyl)carbamoyl]methyl]-1-[(6-methyl-4,5,6,7-tetrahydrothiazolo[5,4-c]pyridin-2-yl)carbonyl]-4-[[6-[N-(methoxycarbonyl)amidino]naphthalen-2-yl]sulfonyl]piperazine 4-[(6-[(Amino)(hydroxyimino)methyl]naphthalen-2-yl)sulfonyl]-2-[[N-(ethoxycarbonylmethyl)carbamoyl]methyl]-1-[(6-methyl-4,5,6,7-tetrahydrothiazolo[5,4-c]pyridin-2-yl)carbonyl]piperazine 4-[(5-Ethynylindol-2-yl)sulfonyl]-2-[[N-(ethoxycarbonylmethyl)carbamoyl]methyl]-1-[(6-methyl-4,5,6,7-tetrahydrothiazolo[5,4-c]pyridin-2-yl)carbonyl]piperazine 4-[(5-Amidinoindol-2-yl)sulfonyl]-2-[[N-(ethoxycarbonylmethyl)carbamoyl]methyl]-1-[(6-methyl-4,5,6,7-tetrahydrothiazolo[5,4-c]pyridin-2-yl)carbonyl]piperazine 4-[(6-Amidinoindol-2-yl)sulfonyl]-2-[[N-(ethoxycarbonylmethyl)carbamoyl]methyl]-1-[(6-methyl-4,5,6,7-tetrahydrothiazolo[5,4-c]pyridin-2-yl)carbonyl]piperazine 4-[[5-[(Amino)(hydroxyimino)methyl]indol-2-yl]sulfonyl]-2-[[N-(ethoxycarbonylmethyl)carbamoyl]methyl]-1-[(6-methyl-4,5,6,7-tetrahydrothiazolo[5,4-c]pyridin-2-yl)carbonyl]piperazine 4-[[6-[(Amino)(hydroxyimino)methyl]indol-2-yl]sulfonyl]-2-[[N-(ethoxycarbonylmethyl)carbamoyl]methyl]-1-[(6-methyl-4,5,6,7-tetrahydrothiazolo[5,4-c]pyridin-2-yl)carbonyl]piperazine 2-[[N-(Ethoxycarbonylmethyl)carbamoyl]methyl]-1-[(6-methyl-4,5,6,7-tetrahydrothiazolo[5,4-c]pyridin-2-yl)carbonyl]-4-[[5-(N-methoxycarbonylamidino)indol-2-yl]sulfonyl]piperazine 2-[[N-(Ethoxycarbonylmethyl)carbamoyl]methyl]-1-[(6-methyl-4,5,6,7-tetrahydrothiazolo[5,4-c]pyridin-2-yl)carbonyl]-4-[[6-[N-(methoxycarbonyl)amidino]indol-2-yl]sulfonyl]piperazine 4-[(5-Amidinobenzo[b]thien-2-yl)sulfonyl]-2-[[N-(ethoxycarbonylmethyl)carbamoyl]methyl]-1-[(6-methyl-4,5,6,7-tetrahydrothiazolo[5,4-c]pyridin-2-yl)carbonyl]piperazine 4-[[5-[(Amino)(hydroxyimino)methyl]benzo[b]thien-2-yl]sulfonyl]-2-[[N-(ethoxycarbonylmethyl)carbamoyl]methyl]-1-[(6-methyl-4,5,6,7-tetrahydrothiazolo[5,4-c]pyridin-2-yl)carbonyl]piperazine 2-[[N-(Ethoxycarbonylmethyl)carbamoyl]methyl]-1-[(6-methyl-4,5,6,7-tetrahydrothiazolo[5,4-c]pyridin-2-yl)carbonyl]-4-[[5-[N-(methoxycarbonyl)amidino]benzo[b]thien-2-yl]sulfonyl]piperazine 4-[(5-Amidinoisoindol-2-yl)sulfonyl]-2-[[N-(ethoxycarbonylmethyl)carbamoyl]methyl]-1-[(6-methyl-4,5,6,7-tetrahydrothiazolo[5,4-c]pyridin-2-yl)carbonyl]piperazine 4-[[5-[(Amino)(hydroxyimino)methyl]isoindol-2-yl]sulfonyl]-2-[[N-(ethoxycarbonylmethyl)carbamoyl]methyl]-1-[(6-methyl-4,5,6,7-tetrahydrothiazolo[5,4-c]pyridin-2-yl)carbonyl]piperazine 2-[[N-(Ethoxycarbonylmethyl)carbamoyl]methyl]-4-[[5-[N-(methoxycarbonyl)amidino]isoindol-2-yl]sulfonyl]-1-[(6-methyl-4,5,6,7-tetrahydrothiazolo[5,4-c]pyridin-2-yl)carbonyl]piperazine 2-[[4-[(6-Chloronaphthalen-2-yl)sulfonyl]-2-[[N-(ethoxycarbonylmethyl)carbamoyl]methyl]piperazin-1-yl]carbonyl]-6-methylthiazolo[5,4-c]pyridinium iodide 4-[(7-Amidinonaphthalen-2-yl)sulfonyl]-2-[[N-(carboxymethyl)carbamoyl]methyl]-4-[(6-methyl-4,5,6,7-tetrahydrothiazolo[5,4-c]pyridin-2-yl)carbonyl]piperazine 4-[(6-Amidinonaphthalen-2-yl)sulfonyl]-2-[[N-(carboxymethyl)carbamoyl]methyl]-4-[(6-methyl-4,5,6,7-tetrahydrothiazolo[5,4-c]pyridin-2-yl)carbonyl]piperazine 2-[[N-(Carboxymethyl)carbamoyl]methyl]-1-[(6-methyl-4,5,6,7-tetrahydrothiazolo[5,4-c]pyridin-2-yl)carbonyl]-4-[[6-[N-(methoxycarbonyl)amidino]naphthalen-2-yl]sulfonyl]piperazine 4-[(6-[(Amino)(hydroxyimino)methyl]naphthalen-2-yl)sulfonyl]-2-[[N-(carboxymethyl)carbamoyl]methyl]-1-[(6-methyl-4,5,6,7-tetrahydrothiazolo[5,4-c]pyridin-2-yl)carbonyl]piperazine 2-[[N-(Carboxymethyl)carbamoyl]methyl]-4-[(5-ethynylindol-2-yl)sulfonyl]-1-[(6-methyl-4,5,6,7-tetrahydrothiazolo[5,4-c]pyridin-2-yl)carbonyl]piperazine 4-[(5-Amidinoindol-2-yl)sulfonyl]-2-[[N-(carboxymethyl)carbamoyl]methyl]-1-[(6-methyl-4,5,6,7-tetrahydrothiazolo[5,4-c]pyridin-2-yl)carbonyl]piperazine 4-[(6-Amidinoindol-2-yl)sulfonyl]-2-[[N-(carboxymethyl)carbamoyl]methyl]-1-[(6-methyl-4,5,6,7-tetrahydrothiazolo[5,4-c]pyridin-2-yl)carbonyl]piperazine 4-[[5-[(Amino)(hydroxyimino)methyl]indol-2-yl]sulfonyl]-yl)carbonyl]piperazine 4-[[6-[(Amino)(hydroxyimino)methyl]indol-2-yl]sulfonyl]-2-[[N-(carboxymethyl)carbamoyl]methyl]-1-[(6-methyl-4,5,6,7-tetrahydrothiazolo[5,4-c]pyridin-2-yl)carbonyl]piperazine 2-[[N-(Carboxymethyl)carbamoyl]methyl]-1-[(6-methyl-4,5,6,7-tetrahydrothiazolo[5,4-c]pyridin-2-yl)carbonyl]-4-[[5-(N-methoxycarbonylamidino) indol-2-yl]sulfonyl]piperazine 2-[[N-(Carboxymethyl)carbamoyl]methyl]-1-[(6-methyl-4,5,6,7-tetrahydrothiazolo[5,4-c]pyridin-2-yl)carbonyl]-4-[[6-[N-(methoxycarbonyl)amidino]indol-2-yl]sulfonyl]piperazine 4-[(5-Amidinobenzo[b]thien-2-yl)sulfonyl]-2-[[N-(carboxymethyl)carbamoyl]methyl]-1-[(6-methyl-4,5,6,7-tetrahydrothiazolo[5,4-c]pyridin-2-yl)carbonyl]piperazine 4-[[5-[(Amino)(hydroxyimino)methyl]benzo[b]thien-2-yl]sulfonyl]-2-[[N-(carboxymethyl)carbamoyl]methyl]-1-[(6-methyl-4,5,6,7-tetrahydrothiazolo[5,4-c]pyridin-2-yl)carbonyl]piperazine 2-[[N-(Carboxymethyl)carbamoyl]methyl]-1-[(6-methyl-4,5,6,7-tetrahydrothiazolo[5,4-c]pyridin-2-yl)carbonyl]-4-[[5-[N-(methoxycarbonyl)amidino]benzo[b]thien-2-yl]sulfonyl]piperazine 4-[(5-Amidinoisoindol-2-yl)sulfonyl]-2-[[N-(carboxymethyl)carbamoyl]methyl]-1-[(6-methyl-4,5,6,7-tetrahydrothiazolo[5,4-c]pyridin-2-yl)carbonyl]piperazine 4-[[5-[(Amino)(hydroxyimino)methyl]isoindol-2-yl]sulfonyl]-2-[[N-(carboxymethyl)carbamoyl]methyl]-1-[(6-methyl-4,5,6,7-tetrahydrothiazolo[5,4-c]pyridin-2-yl)carbonyl]piperazine 2-[[N-(Carboxymethyl)carbamoyl]methyl]-4-[[5-[N-(methoxycarbonyl)amidino]isoindol-2-yl]sulfonyl]-1-[(6-methyl-4,5,6,7-tetrahydrothiazolo[5,4-c]pyridin-2-yl)carbonyl]piperazine 2-[[2-[[N-(Carboxymethyl)carbamoyl]methyl]-4-[(6-chloronaphthalen-2-yl)sulfonyl]piperazin-1-yl]carbonyl]-6-methylthiazolo[5,4-c]pyridinium iodide 2-[[2-[[N-(Carboxymethyl)carbamoyl]methyl]-4-[(5-chloroindol-2-yl)sulfonyl]piperazin-1-yl]carbonyl]-6-methylthiazolo[5,4-c]pyridinium iodide 4-[(7-Amidinonaphthalen-2-yl)sulfonyl]-4-[(6-methyl-4,5,6,7-tetrahydrothiazolo[5,4-c]pyridin-2-yl)carbonyl]-2-[(morpholin-4-yl)carbonylmethyl]piperazine 4-[(6-Amidinonaphthalen-2-yl)sulfonyl]-4-[(6-methyl-4,5,6,7-tetrahydrothiazolo[5,4-c]pyridin-2-yl)carbonyl]-2-[(morpholin-4-yl)carbonylmethyl]piperazine 1-[(6-Methyl-4,5,6,7-tetrahydrothiazolo[5,4-c]pyridin-2-yl)carbonyl]-4-[[6-[N-(methoxycarbonyl)amidino]naphthalen-2-yl]sulfonyl]-2-[(morpholin-4-yl)carbonylmethyl]piperazine 4-[(6-[(Amino)(hydroxyimino)methyl]naphthalen-2-yl)sulfonyl]-1-[(6-methyl-4,5,6,7-tetrahydrothiazolo[5,4-c]pyridin-2-yl)carbonyl]-2-[(morpholin-4-yl)carbonylmethyl]piperazine 4-[(5-Ethynylindol-2-yl)sulfonyl]-1-[(6-methyl-4,5,6,7-tetrahydrothiazolo[5,4-c]pyridin-2-yl)carbonyl]-2-[(morpholin-4-yl)carbonylmethyl]piperazine 4-[(5-Amidinoindol-2-yl)sulfonyl]-1-[(6-methyl-4,5,6,7-tetrahydrothiazolo[5,4-c]pyridin-2-yl)carbonyl]-2-[(morpholin-4-yl)carbonylmethyl]piperazine 4-[(6-Amidinoindol-2-yl)sulfonyl]-1-[(6-methyl-4,5,6,7-tetrahydrothiazolo[5,4-c]pyridin-2-yl)carbonyl]-2-[(morpholin-4-yl)carbonylmethyl]piperazine 4-[[5-[(Amino)(hydroxyimino)methyl]indol-2-yl]sulfonyl]-1-[(6-methyl-4,5,6,7-tetrahydrothiazolo[5,4-c]pyridin-2-yl)carbonyl]-2-[(morpholin-4-yl)carbonylmethyl]piperazine 4-[[6-[(Amino)(hydroxyimino)methyl]indol-2-yl]sulfonyl]-1-[(6-methyl-4,5,6,7-tetrahydrothiazolo[5,4-c]pyridin-2-yl)carbonyl]-2-[(morpholin-4-yl)carbonylmethyl]piperazine 1-[(6-Methyl-4,5,6,7-tetrahydrothiazolo[5,4-c]pyridin-2-yl)carbonyl]-4-[[5-(N-methoxycarbonylamidino)indol-2-yl]sulfonyl]-2-[(morpholin-4-yl)carbonylmethyl]piperazine 1-[(6-Methyl-4,5,6,7-tetrahydrothiazolo[5,4-c]pyridin-2-yl)carbonyl]-4-[[6-[N-(methoxycarbonyl)amidino]indol-2-yl]sulfonyl]-2-[(morpholin-4-yl)carbonylmethyl]piperazine 4-[(5-Amidinobenzo[b]thien-2-yl)sulfonyl]-1-[(6-methyl-4,5,6,7-tetrahydrothiazolo[5,4-c]pyridin-2-yl)carbonyl]-2-[(morpholin-4-yl)carbonylmethyl]piperazine 4-[[5-[(Amino)(hydroxyimino)methyl]benzo[b]thien-2-yl]sulfonyl]-1-[(6-methyl-4,5,6,7-tetrahydrothiazolo[5,4-c]pyridin-2-yl)carbonyl]-2-[(morpholin-4-yl)carbonylmethyl]piperazine 1-[(6-Methyl-4,5,6,7-tetrahydrothiazolo[5,4-c]pyridin-2-yl)carbonyl]-4-[[5-[N-(methoxycarbonyl)amidino]benzo[b]thien-2-yl]sulfonyl]-2-[(morpholin-4-yl)carbonylmethyl]piperazine 4-[(5-Amidinoisoindol-2-yl)sulfonyl]-1-[(6-methyl-4,5,6,7-tetrahydrothiazolo[5,4-c]pyridin-2-yl)carbonyl]-2-[(morpholin-4-yl)carbonylmethyl]piperazine 4-[[5-[(Amino)(hydroxyimino)methyl]isoindol-2-yl]sulfonyl]-1-[(6-methyl-4,5,6,7-tetrahydrothiazolo[5,4-c]pyridin-2-yl)carbonyl]-2-[(morpholin-4-yl)carbonylmethyl]piperazine 4-[[5-[N-(Methoxycarbonyl)amidino]isoindol-2-yl]sulfonyl]-1-[(6-methyl-4,5,6,7-tetrahydrothiazolo[5,4-c]pyridin-2-yl)carbonyl]-2-[(morpholin-4-yl)carbonylmethyl]piperazine 2-[[4-[(6-Chloronaphthalen-2-yl)sulfonyl]-2-[(morpholin-4-yl)carbonylmethyl]piperazin-1-yl]carbonyl]-6-methylthiazolo[5,4-c]pyridinium iodide 2-[[4-[(5-Chloroindol-2-yl)sulfonyl]-2-[(morpholin-4-yl)carbonylmethyl]piperazin-1-yl]carbonyl]-6-methylthiazolo[5,4-c]pyridinium iodide 4-[(5-Chloroindol-2-yl)sulfonyl]-1-[(7-cyano-6-methyl-4,5,6,7-tetrahydrothiazolo[5,4-c]pyridin-2-yl)carbonyl]-2-[2-(2,5-dioxopyrrolidin-1-yl)ethyl]piperazine 1-[(7-Carbamoyl-6-methyl-4,5,6,7-tetrahydrothiazolo[5,4-c]pyridin-2-yl)carbonyl]-4-[(5-chloroindol-2-yl)sulfonyl]-2-[2-(2,5-dioxopyrrolidin-1-yl)ethyl]piperazine 4-[(5-Chloroindol-2-yl)sulfonyl]-1-[(7-dimethylamino-6-methyl-4,5,6,7-tetrahydrothiazolo[5,4-c]pyridin-2-yl)carbonyl]-2-[2-(2,5-dioxopyrrolidin-1-yl)ethyl]piperazine 4-[(5-Chloroindol-2-yl)sulfonyl]-1-[(7-cyano-6-methyl-4,5,6,7-tetrahydrothiazolo[5,4-c]pyridin-2-yl)carbonyl]-2-[2-(tetrazol-5-yl)ethyl]piperazine 1-[(7-Carbamoyl-6-methyl-4,5,6,7-tetrahydrothiazolo[5,4-c]pyridin-2-yl)carbonyl]-4-[(5-chloroindol-2-yl)sulfonyl]-2-[2-(tetrazol-5-yl)ethyl]piperazine 4-[(5-Chloroindol-2-yl)sulfonyl]-1-[(7-dimethylamino-6-methyl-4,5,6,7-tetrahydrothiazolo[5,4-c]pyridin-2-yl)carbonyl]-2-[2-(tetrazol-5-yl)ethyl]piperazine 4-[(5-Chloroindol-2-yl)sulfonyl]-1-[(7-cyano-6-methyl-4,5,6,7-tetrahydrothiazolo[5,4-c]pyridin-2-yl)carbonyl]-2-[[[[(ethoxycarbonyl)methyl]amino]carbonyl]methyl]piperazine 1-[(7-Carbamoyl-6-methyl-4,5,6,7-tetrahydrothiazolo[5,4-c]pyridin-2-yl)carbonyl]-4-[(5-chloroindol-2-yl)sulfonyl]-2-[[[[(ethoxycarbonyl)methyl]amino]carbonyl]methyl]piperazine 4-[(5-Chloroindol-2-yl)sulfonyl]-1-[(7-dimethylamino-6-methyl-4,5,6,7-tetrahydrothiazolo[5,4-c]pyridin-2-yl)carbonyl]-2-[[[[(ethoxycarbonyl)methyl]amino]carbonyl]methyl]piperazine 2-[[[(Carboxymethyl)amino]carbonyl]methyl]-4-[(5-chloroindol-2-yl)sulfonyl]-1-[(7-cyano-6-methyl-4,5,6,7-tetrahydrothiazolo[5,4-c]pyridin-2-yl)carbonyl]piperazine 1-[(7-Carbamoyl-6-methyl-4,5,6,7-tetrahydrothiazolo[5,4-c]pyridin-2-yl)carbonyl]-2-[[[(carboxymethyl)amino]carbonyl]methyl]-4-[(5-chloroindol-2-yl)sulfonyl]piperazine 2-[[[(Carboxymethyl)amino]carbonyl]methyl]-4-[(5-chloroindol-2-yl)sulfonyl]-1-[(7-dimethylamino-6-methyl-4,5,6,7-tetrahydrothiazolo[5,4-c]pyridin-2-yl)carbonyl]piperazine 4-[(5-Chloroindol-2-yl)sulfonyl]-1-[7-[(dimethylamino)methyl]benzothiazol-2-yl)carbonyl]-2-(N-methylcarbamoyl)piperazine 4-[(5-Chloroindol-2-yl)sulfonyl]-1-[7-[(dimethylaminomethyl)methyl]thiazolo[5,4-c]pyridin-2-yl)carbonyl]-2-(N-methylcarbamoyl)piperazine 4-[(5-Chloroindol-2-yl)sulfonyl]-1-[7-[(dimethylamino)methyl]-4,5,6,7-tetrahydrobenzothiazol-2-yl)carbonyl]-2-(N-methylcarbamoyl)piperazine 4-[(5-Chloroindol-2-yl)sulfonyl]-2-(N-methylcarbamoyl)-1-[7-[(morpholin-4-yl)methyl]benzothiazol-2-yl)carbonyl]piperazine 4-[(5-Chloroindol-2-yl)sulfonyl]-2-(N-methylcarbamoyl)-1-[6-(morpholin-4-yl)-4,5,6,7-tetrahydrobenzothiazol-2-yl)carbonyl]piperazine 4-[(5-Chloroindol-2-yl)sulfonyl]-2-(N-methylcarbamoyl)-1-[7-(piperidin-1-yl)benzothiazol-2-yl)carbonyl]piperazine 4-[(5-Chloroindol-2-yl)sulfonyl]-2-(N-methylcarbamoyl)-1-[6-(piperidin-1-yl)-4,5,6,7-tetrahydrobenzothiazol-2-yl)carbonyl]piperazine 1-[(6-Chlorobenzo[b]thien-2-yl)sulfonyl]-4-[(2-methyl-4,5,6,7-tetrahydropyrrolo[3,4-c]pyridin-5-yl)carbonyl]piperazine 1-[(6-Chlorobenzo[b]thien-2-yl)sulfonyl]-4-[(5-methyl-4,5,6,7-tetrahydropyrrolo[3,4-c]pyridin-2-yl)carbonyl]piperazine 1-[(6-Chlorobenzo[b]thien-2-yl)sulfonyl]-4-[(2-methyl-4,5,6,7-tetrahydropyrrolo[3,4-c]pyridin-5-yl)carbonyl]-2-[(morpholin-4-ylcarbonyl)methyl]piperazine 1-[(6-Chlorobenzo[b]thien-2-yl)sulfonyl]-4-[(5-methyl-4,5,6,7-tetrahydropyrrolo[3,4-c]pyridin-2-yl)carbonyl]-2-[(morpholin-4-ylcarbonyl)methyl]piperazine 4-[(6-Chlorobenzo[b]thien-2-yl)sulfonyl]-1-[(6-methoxy-4,5,6,7-tetrahydrothiazolo[5,4-c]pyridin-2-yl)carbonyl]-2-[(morpholin-4-ylcarbonyl)methyl]piperazine 4-[(6-Chlorobenzo[b]thien-2-yl)sulfonyl]-2-[(morpholin-4-ylcarbonyl)methyl]-1-[(6-sulfo-4,5,6,7-tetrahydrothiazolo[5,4-c]pyridin-2-yl)carbonyl]piperazine 4-[(6-Chlorobenzo[b]thien-2-yl)sulfonyl]-2-(2-cyanoethyl)-1-[(6-sulfo-4,5,6,7-tetrahydrothiazolo[5,4-c]pyridin-2-yl)carbonyl]piperazine 4-[(6-Chlorobenzo[b]thien-2-yl)sulfonyl]-2-[[(morpholin-4-yl)carbonyl]methyl]-1-[(4,5,6,7-tetrahydrothiazolo[5,4-c]pyridazin-2-yl)carbonyl]piperazine.

4-[(6-Ethynylbenzo[b]thien-2-yl)sulfonyl]-2-[[(morpholin-4-yl)carbonyl]methyl]-1-[(4,5,6,7-tetrahydrothiazolo[5,4-c]pyridazin-2-yl)carbonyl]piperazine.

4-[(6-Chlorobenzo[b]thien-2-yl)sulfonyl]-1-[(5,6-dimethyl-4,5,6,7-tetrahydrothiazolo[5,4-c]pyridazin-2-yl)carbonyl]-2-[[(morpholin-4-yl)carbonyl]methyl]piperazine 4-[(6-Ethynylbenzo[b]thien-2-yl)sulfonyl]-1-[(5,6-dimethyl-4,5,6,7-tetrahydrothiazolo[5,4-c]pyridazin-2-yl)carbonyl]-2-[[(morpholin-4-yl)carbonyl]methyl]piperazine 1-[(6-Chlorobenzo[b]thien-2-yl)sulfonyl]-4-[(4,5,6,7-tetrahydrothiazolo[5,4-c]pyridazin-2-yl)carbonyl]piperazine.

1-[(6-Ethynylbenzo[b]thien-2-yl)sulfonyl]-4-[(4,5,6,7-tetrahydrothiazolo[5,4-c]pyridazin-2-yl)carbonyl]piperazine.

1-[(6-Chlorobenzo[b]thien-2-yl)sulfonyl]-4-[(5,6-dimethyl-4,5,6,7-tetrahydrothiazolo[5,4-c]pyridazin-2-yl)carbonyl]piperazine 1-[(5,6-Dimethyl-4,5,6,7-tetrahydrothiazolo[5,4-c]pyridazin-2-yl)carbonyl]-4-[(6-ethynylbenzo[b]thien-2-yl)sulfonyl]piperazine 4-[(6-Chlorobenzo[b]thien-2-yl)sulfonyl]-2-(N-methylcarbamoyl)-1-[(4,5,6,7-tetrahydrothiazolo[5,4-c]pyridazin-2-yl)carbonyl]piperazine.

4-[(6-Ethynylbenzo[b]thien-2-yl)sulfonyl]-2-(N-methylcarbamoyl)-1-[(4,5,6,7-tetrahydrothiazolo[5,4-c]pyridazin-2-yl)carbonyl]piperazine.

4-[(6-Chlorobenzo[b]thien-2-yl)sulfonyl]-1-[(5,6-dimethyl-4,5,6,7-tetrahydrothiazolo[5,4-c]pyridazin-2-yl)carbonyl]-2-(N-methylcarbamoyl)piperazine 1-[(5,6-Dimethyl-4,5,6,7-tetrahydrothiazolo[5,4-c]pyridazin-2-yl)carbonyl]-4-[(6-ethynylbenzo[b]thien-2-yl)sulfonyl]-2-(N-methylcarbamoyl)piperazine 4-[(6-Chlorobenzo[b]thien-2-yl)sulfonyl]-2-[(N,N-dimethylcarbamoyl)methyl]-4-[(4,5,6,7-tetrahydrothiazolo[5,4-c]pyridazin-2-yl)carbonyl]piperazine.

2-[(N,N-Dimethylcarbamoyl)methyl]-4-[(6-ethynylbenzo[b]thien-2-yl)sulfonyl]-1-[(4,5,6,7-tetrahydrothiazolo[5,4-c]pyridazin-2-yl)carbonyl]piperazine.

4-[(6-Chlorobenzo[b]thien-2-yl)sulfonyl]-2-[(N,N-dimethylcarbamoyl)methyl]-1-[(5,6-dimethyl-4,5,6,7-tetrahydrothiazolo[5,4-c]pyridazin-2-yl)carbonyl]piperazine 2-[(N,N-Dimethylcarbamoyl)methyl]-1-[(5,6-dimethyl-4,5,6,7-tetrahydrothiazolo[5,4-c]pyridazin-2-yl)carbonyl]-4-[(6-ethynylbenzo[b]thien-2-yl)sulfonyl]piperazine 4-[(6-Chlorobenzo[b]thien-2-yl)sulfonyl]-2-(2-cyanoethyl)-1-[(4,5,6,7-tetrahydrothiazolo[5,4-c]pyridazin-2-yl)carbonyl]piperazine.

2-(2-Cyanoethyl)-4-[(6-ethynylbenzo[b]thien-2-yl)sulfonyl]-1-[(4,5,6,7-tetrahydrothiazolo[5,4-c]pyridazin-2-yl)carbonyl]piperazine.

4-[(6-Chlorobenzo[b]thien-2-yl)sulfonyl]-2-(2-cyanoethyl)-1-[(5,6-dimethyl-4,5,6,7-tetrahydrothiazolo[5,4-c]pyridazin-2-yl)carbonyl]piperazine 2-(2-Cyanoethyl)-4-[(6-ethynylbenzo[b]thien-2-yl)sulfonyl]-1-[(5,6-dimethyl-4,5,6,7-tetrahydrothiazolo[5,4-c]pyridazin-2-yl)carbonyl]piperazine 4-[(6-Chlorobenzo[b]thien-2-yl)sulfonyl]-1-[(6-hydroxy-4,5,6,7-tetrahydrothiazolo[5,4-c]pyridin-2-yl)carbonyl]-2-(N-methylcarbamoyl)piperazine 4-[(6-Ethynylbenzo[b]thien-2-yl)sulfonyl]-1-[(6-hydroxy-4,5,6,7-tetrahydrothiazolo[5,4-c]pyridin-2-yl)carbonyl]-2-(N-methylcarbamoyl)piperazine 4-[(6-Chlorobenzo[b]thien-2-yl)sulfonyl]-1-[(6-hydroxy-4,5,6,7-tetrahydrothiazolo[5,4-c]pyridin-2-yl)carbonyl]-2-[[(morpholin-4-yl)carbonyl]methyl]piperazine.

4-[(6-Ethynylbenzo[b]thien-2-yl)sulfonyl]-1-[(6-hydroxy-4,5,6,7-tetrahydrothiazolo[5,4-c]pyridin-2-yl)carbonyl]-2-[[(morpholin-4-yl)carbonyl]methyl]piperazine.

1-[(6-Chlorobenzo[b]thien-2-yl)sulfonyl]-4-[(6-hydroxy-4,5,6,7-tetrahydrothiazolo[5,4-c]pyridin-2-yl)carbonyl]piperazine.

1-[(6-Ethynylbenzo[b]thien-2-yl)sulfonyl]-4-[(6-hydroxy-4,5,6,7-tetrahydrothiazolo[5,4-c]pyridin-2-yl)carbonyl]piperazine.

4-[(6-Chlorobenzo[b]thien-2-yl)sulfonyl]-2-(2-cyanoethyl)-1-[(6-hydroxy-4,5,6,7-tetrahydrothiazolo[5,4-c]pyridin-2-yl)carbonyl]piperazine.

2-(2-Cyanoethyl)-4-[(6-ethynylbenzo[b]thien-2-yl)sulfonyl]-1-[(6-hydroxy-4,5,6,7-tetrahydrothiazolo[5,4-c]pyridin-2-yl)carbonyl]piperazine.

4-[(6-Chlorobenzo[b]thien-2-yl)sulfonyl]-2-[(N,N-dimethylcarbamoyl)methyl]-1-[(6-hydroxy-4,5,6,7-tetrahydrothiazolo[5,4-c]pyridin-2-yl)carbonyl]-2-[[(morpholin-4-yl)carbonyl]methyl]piperazine.

2-[(N,N-Dimethylcarbamoyl)methyl]-4-[(6-ethynylbenzo[b]thien-2-yl)sulfonyl]-1-[(6-hydroxy-4,5,6,7-tetrahydrothiazolo[5,4-c]pyridin-2-yl)carbonyl]piperazine.

4-[(6-Chlorobenzo[b]thien-2-yl)sulfonyl]-2-[[(morpholin-4-yl)carbonyl]methyl]-1-[(4,5,6,7-tetrahydroxazolo[5,4-c]pyridazin-2-yl)carbonyl]piperazine.

4-[(6-Ethynylbenzo[b]thien-2-yl)sulfonyl]-2-[[(morpholin-4-yl)carbonyl]methyl]-1-[(4,5,6,7-tetrahydrooxazolo[5,4-c]pyridazin-2-yl)carbonyl]piperazine.

4-[(6-Chlorobenzo[b]thien-2-yl)sulfonyl]-1-[(5,6-dimethyl-4,5,6,7-tetrahydrooxazolo[5,4-c]pyridazin-2-yl)carbonyl]-2-[[(morpholin-4-yl)carbonyl]methyl]piperazine 4-[(6-Ethynylbenzo[b]thien-2-yl)sulfonyl]-1-[(5,6-dimethyl-4,5,6,7-tetrahydrooxazolo[5,4-c]pyridazin-2-yl)carbonyl]-2-[[(morpholin-4-yl)carbonyl]methyl]piperazine 1-[(6-Chlorobenzo[b]thien-2-yl)sulfonyl]-4-[(4,5,6,7-tetrahydrooxazolo[5,4-c]pyridazin-2-yl)carbonyl]piperazine.

1-[(6-Ethynylbenzo[b]thien-2-yl)sulfonyl]-4-[(4,5,6,7-tetrahydrooxazolo[5,4-c]pyridazin-2-yl)carbonyl]piperazine.

1-[(6-Chlorobenzo[b]thien-2-yl)sulfonyl]-4-[(5,6-dimethyl-4,5,6,7-tetrahydrooxazolo[5,4-c]pyridazin-2-yl)carbonyl]piperazine 1-[(5,6-Dimethyl-4,5,6,7-tetrahydrooxazolo[5,4-c]pyridazin-2-yl)carbonyl]-4-[(6-ethynylbenzo[b]thien-2-yl)sulfonyl]piperazine 4-[(6-Chlorobenzo[b]thien-2-yl)sulfonyl]-2-(N-methylcarbamoyl)-1-[(4,5,6,7-tetrahydrooxazolo[5,4-c]pyridazin-2-yl) carbonyl]piperazine.

4-[(6-Ethynylbenzo[b]thien-2-yl)sulfonyl]-2-(N-methylcarbamoyl)-1-[(4,5,6,7-tetrahydrooxazolo[5,4-c]pyridazin-2-yl)carbonyl]piperazine 4-[(6-Chlorobenzo[b]thien-2-yl)sulfonyl]-1-[(5,6-dimethyl-4,5,6,7-tetrahydrooxazolo [5,4-c]pyridazin-2-yl)carbonyl]-2-(N-methylcarbamoyl)piperazine 1-[(5,6-Dimethyl-4,5,6,7-tetrahydrooxazolo[5,4-c]pyridazin-2-yl)carbonyl]-4-[(6-ethynylbenzo[b]thien-2-yl)sulfonyl]-2-(N-methylcarbamoyl)piperazine 4-[(6-Chlorobenzo[b]thien-2-yl)sulfonyl]-2-[(N,N-dimethylcarbamoyl)methyl]-4-[(4,5,6,7-tetrahydrooxazolo[5,4-c]pyridazin-2-yl)carbonyl]piperazine.

2-[(N,N-Dimethylcarbamoyl)methyl]-4-[(6-ethynylbenzo[b]thien-2-yl)sulfonyl]-1-[(4,5,6,7-tetrahydrooxazolo[5,4-c]pyridazin-2-yl)carbonyl]piperazine.

4-[(6-Chlorobenzo[b]thien-2-yl)sulfonyl]-2-[(N,N-dimethylcarbamoyl)methyl]-1-[(5,6-dimethyl-4,5,6,7-tetrahydrooxazolo[5,4-c]pyridazin-2-yl)carbonyl]piperazine 2-[(N,N-Dimethylcarbamoyl)methyl]-1-[(5,6-dimethyl-4,5,6,7-tetrahydrooxazolo[5,4-c]pyridazin-2-yl)carbonyl]-4-[(6-ethynylbenzo[b]thien-2-yl)sulfonyl]piperazine 4-[(6-Chlorobenzo[b]thien-2-yl)sulfonyl]-2-(2-cyanoethyl)-1-[(4,5,6,7-tetrahydrooxazolo[5,4-c]pyridazin-2-yl)carbonyl]piperazine.

2-(2-Cyanoethyl)-4-[(6-ethynylbenzo[b]thien-2-yl)sulfonyl]-1-[(4,5,6,7-tetrahydrooxazolo[5,4-c]pyridazin-2-yl)carbonyl]piperazine.

4-[(6-Chlorobenzo[b]thien-2-yl)sulfonyl]-2-(2-cyanoethyl)-1-[(5,6-dimethyl-4,5,6,7-tetrahydrooxazolo[5,4-c]pyridazin-2-yl)carbonyl]piperazine 2-(2-Cyanoethyl)-4-[(6-ethynylbenzo[b]thien-2-yl)sulfonyl]-1-[(5,6-dimethyl-4,5,6,7-tetrahydrooxazolo[5,4-c]pyridazin-2-yl)carbonyl]piperazine 4-[(6-Chlorobenzo[b]thien-2-yl)sulfonyl]-1-[(6-hydroxy-4,5,6,7-tetrahydrooxazolo[5,4-c]pyridin-2-yl)carbonyl]-2-(N-methylcarbamoyl)piperazine 4-[(6-Ethynylbenzo[b]thien-2-yl)sulfonyl]-1-[(6-hydroxy-4,5,6,7-tetrahydrooxazolo[5,4-c]pyridin-2-yl)carbonyl]-2-(N-methylcarbamoyl)piperazine 4-[(6-Chlorobenzo[b]thien-2-yl)sulfonyl]-1-[(6-hydroxy-4,5,6,7-tetrahydrooxazolo[5,4-c]pyridin-2-yl)carbonyl]-2-[[(morpholin-4-yl)carbonyl]methyl]piperazine 4-[(6-Ethynylbenzo[b]thien-2-yl)sulfonyl]-1-[(6-hydroxy-4,5,6,7-tetrahydrooxazolo[5,4-c]pyridin-2-yl)carbonyl]-2-[[(morpholin-4-yl)carbonyl]methyl]piperazine.

1-[(6-Chlorobenzo[b]thien-2-yl)sulfonyl]-4-[(6-hydroxy-4,5,6,7-tetrahydrooxazolo[5,4-c]pyridin-2-yl)carbonyl]piperazine.

1-[(6-Ethynylbenzo[b]thien-2-yl)sulfonyl]-4-[(6-hydroxy-4,5,6,7-tetrahydrooxazolo[5,4-c]pyridin-2-yl)carbonyl]piperazine.

4-[(6-Chlorobenzo[b]thien-2-yl)sulfonyl]-2-(2-cyanoethyl)-1-[(6-hydroxy-4,5,6,7-tetrahydrooxazolo[5,4-cpyridin-2-yl) carbonyl]piperazine.

2-(2-Cyanoethyl)-4-[(6-ethynylbenzo[b]thien-2-yl)sulfonyl]-1-[(6-hydroxy-4,5,6,7-tetrahydrooxazolo[5,4-c]pyridin-2-yl)carbonyl]piperazine.

4-[(6-Chlorobenzo[b]thien-2-yl)sulfonyl]-2-[(N,N-dimethylcarbamoyl)methyl]-1-[(6-hydroxy-4,5, 6,7-tetrahydrooxazolo[5,4-c]pyridin-2-yl)carbonyl]piperazine.

2-[(N,N-Dimethylcarbamoyl)methyl]-4-[(6-ethynylbenzo[b]thien-2-yl)sulfonyl]-1-[(6-hydroxy-4,5,6,7-tetrahydrooxazolo[5,4-c]pyridin-2-yl)carbonyl]piperazine.

1-[(6-Chlorobenzo[b]thien-2-yl)sulfonyl]-4-[(5,6-dihydrobenzo[f]isoquinolin-8-yl)carbonyl]piperazine 1-[(6-Chlorobenzo[b]thien-2-yl)sulfonyl]-4-[(5,6-dihydropyrido[4,3-f]quinazolin-3-yl)carbonyl]piperazine 8-[[1-[(6-Chlorobenzo[b]thien-2-yl)sulfonyl]piperazin-4-yl]carbonyl]-5,6-dihydrobenzo[f]isoquinoline N-oxide 3-[[1-[(6-Chlorobenzo[b]thien-2-yl)sulfonyl]piperazin-4-yl]carbonyl]-5,6-dihydropyrido[4,3-f]quinazoline N-oxide 1-[(6-Chlorobenzo[b]thien-2-yl)sulfonyl]-4-[(6-methanesulfonyl-4,5,6,7-tetrahydrothiazolo[5,4-c]pyridin-2-yl) carbonyl]piperazine 4-[(6-Chlorobenzo[b]thien-2-yl)sulfonyl]-1-[(6-methanesulfonyl-4,5,6,7-tetrahydrothiazolo[5,4-c]pyridin-2-yl)carbonyl]-2-(N-methylcarbamoyl)piperazine 4-[(6-Chlorobenzo[b]thien-2-yl)sulfonyl]-1-[(6-methanesulfonyl-4,5,6,7-tetrahydrothiazolo[5,4-c]pyridin-2-yl)carbonyl]-2-(morpholin-4-ylcarbonylmethyl)piperazine 4-[(6-Chlorobenzo[b]thien-2-yl)sulfonyl]-2-(2-cyanoethyl)-1-[(6-methanesulfonyl-4,5,6,7-tetrahydrothiazolo[5,4-c]pyridin-2-yl)carbonyl]piperazine 1-[(6-Chlorobenzo[b]thien-2-yl)sulfonyl]-1-[(6-methyl-4,5,6,7-tetrahydrooxazolo[4,5-c]pyridin-2-yl)carbonyl]piperazine 1-[(6-Chlorobenzo[b]thien-2-yl)sulfonyl]-4-[(6-methanesulfonyl-4,5,6,7-tetrahydrooxazolo[5,4-c]pyridin-2-yl)carbonyl]piperazine 4-[(6-Chlorobenzo[b]thien-2-yl)sulfonyl]-1-[(6-methanesulfonyl-4,5,6,7-tetrahydrooxazolo[5,4-c]pyridin-2-yl)carbonyl]-2-(N-methylcarbamoyl)piperazine 4-[(6-Chlorobenzo[b]thien-2-yl)sulfonyl]-1-[(6-methanesulfonyl-4,5,6,7-tetrahydrooxazolo[5,4-c]pyridin-2-yl)carbonyl]-2-(morpholin-4-ylcarbonylmethyl)piperazine 4-[(6-Chlorobenzo[b]thien-2-yl)sulfonyl]-2-(2-cyanoethyl)-1-[(6-methanesulfonyl-4,5,6,7-tetrahydrooxazolo[5,4-c]pyridin-2-yl)carbonyl]piperazine 1-[(6-Chlorobenzo[b]thien-2-yl)sulfonyl]-4-[(4,5,6,7-tetrahydrothiazolo[5,4-c]pyridin-6-yl)carbonyl]piperazine 1-[(6-Chlorobenzo[b]thien-2-yl)sulfonyl]-4-[(4,5,6,7-tetrahydrooxazolo[5,4-c]pyridin-6-yl)carbonyl]piperazine 1-[(6-Chlorobenzo[b]thien-2-yl)sulfonyl]-4-[(2-dimethylamino-4,5,6,7-tetrahydrothiazolo[5,4-c]pyridin-6-yl)carbonyl]piperazine 4-[(6-Chlorobenzo[b]thiophen-2-yl)sulfonyl]-1-[(6-methyl-5-oxo-4,5,6,7-tetrahydrothiazolo[5,4-c]pyridin-2-yl)carbonyl]-2-[(morpholin-4-yl)carbonylmethyl]piperazine 4-[(6-Chlorobenzo[b]thiophen-2-yl)sulfonyl]-1-[(6-methyl-5-oxo-4,5,6,7-tetrahydrooxazolo[5,4-c]pyridin-2-yl)carbonyl]-2-[(morpholin-4-yl)carbonylmethyl]piperazine 4-[(6-Chlorobenzo[b]thiophen-2-yl)sulfonyl]-1-[(5-oxo-4,5,6,7-tetrahydrothiazolo[5,4-c]pyridin-2-yl)carbonyl]-2-[(morpholin-4-yl)carbonylmethyl]piperazine 4-[(6-Chlorobenzo[b]thiophen-2-yl)sulfonyl]-1-[(5-oxo-4,5,6,7-tetrahydrooxazolo[5,4-c]pyridin-2-yl)carbonyl]-2-[(morpholin-4-yl)carbonylmethyl]piperazine 1-[(6-Amino-4,5,6,7-tetrahydrothiazolo[5,4-c]pyridin-2-yl)carbonyl]-4-[(6-chlorobenzo[b]thien-2-yl )sulfonyl]-2-(N-methylcarbamoyl)piperazine 1-[(6-Amino-4,5,6,7-tetrahydrothiazolo[5,4-c]pyridin-2-yl)carbonyl]-4-[(6-ethynylbenzo[b]thien-2-yl )sulfonyl]-2-(N-methylcarbamoyl)piperazine 1-[(6-Amino-4,5,6,7-tetrahydrothiazolo[5,4-c]pyridin-2-yl)carbonyl]-4-[(6-chlorobenzo[b]thien-2-yl)sulfonyl]-2-[[(morpholin-4-yl)carbonyl]methyl]piperazine.

1-[(6-Amino-4,5,6,7-tetrahydrothiazolo[5,4-c]pyridin-2-yl)carbonyl]-4-[(6-ethynylbenzo[b]thien-2-yl)sulfonyl]-2-[[(morpholin-4-yl)carbonyl]methyl]piperazine.

1-[(6-Amino-4,5,6,7-tetrahydrothiazolo[5,4-c]pyridin-2-yl)carbonyl]-4-[(6-chlorobenzo[b]thien-2-yl)sulfonyl]piperazine.

1-[(6-Amino-4,5,6,7-tetrahydrothiazolo[5,4-c]pyridin-2-yl)carbonyl]-4-[(6-ethynylbenzo[b]thien-2-yl)sulfonyl]piperazine.

1-[(6-Amino-4,5,6,7-tetrahydrothiazolo[5,4-c]pyridin-2-yl)carbonyl]-4-[(6-chlorobenzo[b]thien-2-yl)sulfonyl]-2-(2-cyanoethyl)piperazine.

1-[(6-Amino-4,5,6,7-tetrahydrothiazolo[5,4-c]pyridin-2-yl)carbonyl]-2-(2-cyanoethyl)-4-[(6-ethynylbenzo[b]thien-2-yl)sulfonyl]piperazine.

1-[(6-Amino-4,5,6,7-tetrahydrothiazolo[5,4-c]pyridin-2-yl)carbonyl]-4-[(6-chlorobenzo[b]thien-2-yl)sulfonyl]-2-[(N,N-dimethylcarbamoyl)methyl]piperazine.

1-[(6-Amino-4,5,6,7-tetrahydrothiazolo[5,4-c]pyridin-2-yl)carbonyl]-2-[(N,N-dimethylcarbamoyl)methyl]-4-[(6-ethynylbenzo[b]thien-2-yl)sulfonyl]piperazine.

1-[(5-Chloroindol-2-yl)sulfonyl]-4-[(2-methyl-4,5,6,7-tetrahydropyrrolo[3,4-c]pyridin-5-yl)carbonyl]piperazine 1-[(5-Chloroindol-2-yl)sulfonyl]-4-[(5-methyl-4,5,6,7-tetrahydropyrrolo[3,4-c]pyridin-2-yl)carbonyl]piperazine 1-[(5-Chloroindol-2-yl)sulfonyl]-4-[(2-methyl-4,5,6,7-tetrahydropyrrolo[3,4-c]pyridin-5-yl)carbonyl]-2-[(morpholin-4-ylcarbonyl)methyl]piperazine 1-[(5-Chloroindol-2-yl)sulfonyl]-4-[(5-methyl-4,5,6,7-tetrahydropyrrolo[3,4-c]pyridin-2-yl)carbonyl]-2-[(morpholin-4-ylcarbonyl)methyl]piperazine 1-[(5-Ethynylindol-2-yl)sulfonyl]-4-[(2-methyl-4,5,6,7-tetrahydropyrrolo[3,4-c]pyridin-5-yl)carbonyl]piperazine 1-[(5-Ethynylindol-2-yl)sulfonyl]-4-[(5-methyl-4,5,6,7-tetrahydropyrrolo[3,4-c]pyridin-5-yl)carbonyl]piperazine 1-[(5-Ethynylindol-2-yl)sulfonyl]-4-[(2-methyl-4,5,6,7-tetrahydropyrrolo[3,4-c]pyridin-5-yl)carbonyl]-2-[(morpholin-4-ylcarbonyl)methyl]piperazine 1-[(5-Ethynylindol-2-yl)sulfonyl]-4-[(5-methyl-4,5,6,7-tetrahydropyrrolo[3,4-c]pyridin-2-yl)carbonyl]-2-[(morpholin-4-ylcarbonyl)methyl]piperazine 4-[(5-Chloroindol-2-yl)sulfonyl]-1-[(6-methoxy-4,5,6,7-tetrahydrothiazolo[5,4-c]pyridin-2-yl)carbonyl]-2-[(morpholin-4-ylcarbonyl)methyl]piperazine 4-[(5-Ethynylindol-2-yl)sulfonyl]-1-[(6-methoxy-4,5,6,7-tetrahydrothiazolo[5,4-c]pyridin-2-yl)carbonyl]-2-[(morpholin-4-ylcarbonyl)methyl]piperazine 4-[(5-Chloroindol-2-yl)sulfonyl]-2-[(morpholin-4-ylcarbonyl)methyl]-1-[(6-sulfo-4,5,6,7-tetrahydrothiazolo[5,4-c]pyridin-2-yl)carbonyl]piperazine 4-[(5-Chloroindol-2-yl)sulfonyl]-2-(2-cyanoethyl)-1-[(6-sulfo-4,5,6,7-tetrahydrothiazolo[5,4-c]pyridin-2-yl)carbonyl]piperazine 4-[(5-Ethynylindol-2-yl)sulfonyl]-2-[(morpholin-4-ylcarbonyl)methyl]-1-[(6-sulfo-4,5,6,7-tetrahydrothiazolo[5,4-c]pyridin-2-yl)carbonyl]-piperazine 2-(2-Cyanoethyl)-4-[(5-ethynylindol-2-yl)sulfonyl]-1-[(6-sulfo-4,5,6,7-tetrahydrothiazolo[5,4-c]pyridin-2-yl)carbonyl]piperazine 4-[(5-Chloroindol-2-yl)sulfonyl]-2-[[(morpholin-4-yl)carbonyl]methyl]-1-[(4,5,6,7-tetrahydrothiazolo[5,4-c]pyridazin-2-yl)carbonyl]piperazine.

4-[(5-Ethynylindol-2-yl)sulfonyl]-2-[[(morpholin-4-yl)carbonyl]methyl]-1-[(4,5,6,7-tetrahydrothiazolo[5,4-c]pyridazin-2-yl)carbonyl]piperazine.

4-[(5-Chloroindol-2-yl)sulfonyl]-1-[(5,6-dimethyl-4,5,6,7-tetrahydrothiazolo[5,4-c]pyridazin-2-yl)carbonyl]-2-[[(morpholin-4-yl)carbonyl]methyl]piperazine 1-[(5,6-Dimethyl-4,5,6,7-tetrahydrothiazolo[5,4-c]pyridazin-2-yl)carbonyl]-4-[(5-ethynylindol-2-yl)sulfonyl]-2-[[(morpholin-4-yl)carbonyl]methyl]piperazine 1-[(5-Chloroindol-2-yl)sulfonyl]-4-[(4,5,6,7-tetrahydrothiazolo[5,4-c]pyridazin-2-yl)carbonyl]piperazine.

1-[(5-Ethynylindol-2-yl)sulfonyl]-4-[(4,5,6,7-tetrahydrothiazolo[5,4-c]pyridazin-2-yl)carbonyl]piperazine.

1-[(5-Chloroindol-2-yl)sulfonyl]-4-[(5,6-dimethyl-4,5,6,7-tetrahydrothiazolo[5,4-c]pyridazin-2-yl)carbonyl]piperazine 1-[(5,6-Dimethyl-4,5,6,7-tetrahydrothiazolo[5,4-c]pyridazin-2-yl)carbonyl]-4-[(5-ethynylindol-2-yl)sulfonyl]piperazine 4-[(5-Chloroindol-2-yl)sulfonyl]-2-(N-methylcarbamoyl)-1-[(4,5,6,7-tetrahydrothiazolo[5,4-c]pyridazin-2-yl)carbonyl]piperazine.

4-[(5-Ethynylindol-2-yl)sulfonyl]-2-(N-methylcarbamoyl)-1-[(4,5,6,7-tetrahydrothiazolo[5,4-c]pyridazin-2-yl)carbonyl]piperazine.

4-[(5-Chloroindol-2-yl)sulfonyl]-1-[(5,6-dimethyl-4,5,6,7-tetrahydrothiazolo[5,4-c]pyridazin-2-yl)carbonyl]-2-(N-methylcarbamoyl)piperazine 1-[(5,6-Dimethyl-4,5,6,7-tetrahydrothiazolo[5,4-c]pyridazin-2-yl)carbonyl]-4-[(5-ethynylindol-2-yl)sulfonyl]-2-(N-methylcarbamoyl)piperazine 4-[(5-Chloroindol-2-yl)sulfonyl]-2-[(N,N-dimethylcarbamoyl)methyl]-1-[(4,5,6,7-tetrahydrothiazolo[5,4-c]pyridazin-2-yl)carbonyl]piperazine.

2-[(N,N-Dimethylcarbamoyl)methyl]-4-[(5-ethynylindol-2-yl)sulfonyl]-1-[(4,5,6,7-tetrahydrothiazolo[5,4-c]pyridazin-2-yl)carbonyl]piperazine.

4-[(5-Chloroindol-2-yl)sulfonyl]-2-[(N,N-dimethylcarbamoyl)methyl]-1-[(5,6-dimethyl-4,5,6,7-tetrahydrothiazolo[5,4-c]pyridazin-2-yl)carbonyl]piperazine 2-[(N,N-Dimethylcarbamoyl)methyl]-1-[(5,6-dimethyl-4,5,6,7-tetrahydrothiazolo[5,4-c]pyridazin-2-yl)carbonyl]-4-[(5-ethynylindol-2-yl)sulfonyl]piperazine 4-[(5-Chloroindol-2-yl)sulfonyl]-2-(2-cyanoethyl)-1-[(4,5,6,7-tetrahydrothiazolo[5,4-c]pyridazin-2-yl)carbonyl]piperazine.

2-(2-Cyanoethyl)-4-[(5-ethynylindol-2-yl)sulfonyl]-1-[(4,5,6,7-tetrahydrothiazolo[5,4-c]pyridazin-2-yl)carbonyl]piperazine.

4-[(5-Chloroindol-2-yl)sulfonyl]-2-(2-cyanoethyl)-1-[(5,6-dimethyl-4,5,6,7-tetrahydrothiazolo[5,4-c]pyridazin-2-yl)carbonyl]piperazine 2-(2-Cyanoethyl)-1-[(5,6-dimethyl-4,5,6,7-tetrahydrothiazolo[5,4-c]pyridazin-2-yl)carbonyl]-4-[(5-ethynylindol-2-yl)sulfonyl]piperazine 4-[(5-Chloroindol-2-yl)sulfonyl]-1-[(6-hydroxy-4,5,6,7-tetrahydrothiazolo[5,4-c]pyridin-2-yl)carbonyl]-2-(N-methylcarbamoyl)piperazine 4-[(5-Ethynylindol-2-yl)sulfonyl]-1-[(6-hydroxy-4,5,6,7-tetrahydrothiazolo[5,4-c]pyridin-2-yl)carbonyl]-2-(N-methylcarbamoyl)piperazine 4-[(5-Chloroindol-2-yl)sulfonyl]-1-[(6-hydroxy-4,5,6,7-tetrahydrothiazolo[5,4-c]pyridin-2-yl)carbonyl]-2-[[(morpholin-4-yl)carbonyl]methyl]piperazine.

4-[(5-Ethynylindol-2-yl)sulfonyl]-1-[(6-hydroxy-4,5,6,7-tetrahydrothiazolo[5,4-c]pyridin-2-yl)carbonyl]-2-[[(morpholin-4-yl)carbonyl]methyl]piperazine.

1-[(5-Chloroindol-2-yl)sulfonyl]-4-[(6-hydroxy-4,5,6,7-tetrahydrothiazolo[5,4-c]pyridin-2-yl)carbonyl]piperazine.

1-[(5-Ethynylindol-2-yl)sulfonyl]-4-[(6-hydroxy-4,5,6,7-tetrahydrothiazolo[5,4-c]pyridin-2-yl)carbonyl]piperazine.

4-[(5-Chloroindol-2-yl)sulfonyl]-2-(2-cyanoethyl)-1-[(6-hydroxy-4,5,6,7-tetrahydrothiazolo[5,4-c]pyridin-2-yl)carbonyl]piperazine.

2-(2-Cyanoethyl)-4-[(5-ethynylindol-2-yl)sulfonyl]-1-[(6-hydroxy-4,5,6,7-tetrahydrothiazolo[5,4-c]pyridin-2-yl)carbonyl]piperazine.

4-[(5-Chloroindol-2-yl)sulfonyl]-2-[(N,N-dimethylcarbamoyl)methyl]-1-[(6-hydroxy-4,5,6,7-tetrahydrothiazolo[5,4-c]pyridin-2-yl)carbonyl]piperazine.

2-[(N,N-Dimethylcarbamoyl)methyl]-4-[(5-ethynylindol-2-yl)sulfonyl]-1-[(6-hydroxy-4,5,6,7-tetrahydrothiazolo[5,4-c]pyridin-2-yl)carbonyl]piperazine.

1-[(6-Amino-4,5,6,7-tetrahydrothiazolo[5,4-c]pyridin-2-yl)carbonyl]-4-[(5-chloroindol-2-yl)sulfonyl]-2-(N-methylcarbamoyl)piperazine 1-[(6-Amino-4,5,6,7-tetrahydrothiazolo[5,4-c]pyridin-2-yl)carbonyl]-4-[(5-ethynylindol-2-yl)sulfonyl]-2-(N-methylcarbamoyl)piperazine 1-[(6-Amino-4,5,6,7-tetrahydrothiazolo[5,4-c]pyridin-2-yl)carbonyl]-4-[(5-chloroindol-2-yl)sulfonyl]-2-[[(morpholin-4-yl)carbonyl]methyl]piperazine.

1-[(6-Amino-4,5,6,7-tetrahydrothiazolo[5,4-c]pyridin-2-yl)carbonyl]-4-[(5-ethynylindol-2-yl)sulfonyl]-2-[[(morpholin-4-yl)carbonyl]methyl]piperazine.

1-[(6-Amino-4,5,6,7-tetrahydrothiazolo[5,4-c]pyridin-2-yl)carbonyl]-4-[(5-chloroindol-2-yl)sulfonyl]piperazine.

1-[(6-Amino-4,5,6,7-tetrahydrothiazolo[5,4-c]pyridin-2-yl)carbonyl]-4-[(5-ethynylindol-2-yl)sulfonyl]piperazine.

1-[(6-Amino-4,5,6,7-tetrahydrothiazolo[5,4-c]pyridin-2-yl)carbonyl]-4-[(5-chloroindol-2-yl)sulfonyl]-2-(2-cyanoethyl)piperazine.

1-[(6-Amino-4,5,6,7-tetrahydrothiazolo[5,4-c]pyridin-2-yl)carbonyl]-2-(2-cyanoethyl)-4-[(5-ethynylindol-2-yl)sulfonyl]piperazine.

1-[(6-Amino-4,5,6,7-tetrahydrothiazolo[5,4-c]pyridin-2-yl)carbonyl]-4-[(5-chloroindol-2-yl)sulfonyl]-2-[(N,N-dimethylcarbamoyl)methyl]piperazine.

1-[(6-Amino-4,5,6,7-tetrahydrothiazolo[5,4-c]pyridin-2-yl)carbonyl]-2-[(N,N-dimethylcarbamoyl)methyl]-4-[(5-ethynylindol-2-yl)sulfonyl]piperazine.

4-[(5-Chloroindol-2-yl)sulfonyl]-2-[[(morpholin-4-yl)carbonyl]methyl]-1-[(4,5,6,7-tetrahydrooxazolo[5,4-c]pyridazin-2-yl)carbonyl]piperazine.

4-[(5-Ethynylindol-2-yl)sulfonyl]-2-[[(morpholin-4-yl)carbonyl]methyl]-1-[(4,5,6,7-tetrahydrooxazolo[5,4-c]pyridazin-2-yl)carbonyl]piperazine.

4-[(5-Chloroindol-2-yl)sulfonyl]-1-[(5,6-dimethyl-4,5,6,7-tetrahydrooxazolo[5,4-c]pyridazin-2-yl)carbonyl]-2-[[(morpholin-4-yl)carbonyl]methyl]piperazine 1-[(5,6-Dimethyl-4,5,6,7-tetrahydrooxazolo[5,4-c]pyridazin-2-yl)carbonyl]-4-[(5-ethynylindol-2-yl)sulfonyl]-2-[[(morpholin-4-yl)carbonyl]methyl]piperazine 1-[(5-Chloroindol-2-yl)sulfonyl]-4-[(4,5,6,7-tetrahydrooxazolo[5,4-c]pyridazin-2-yl)carbonyl]piperazine.

1-[(5-Ethynylindol-2-yl)sulfonyl]-4-[(4,5,6,7-tetrahydrooxazolo[5,4-c]pyridazin-2-yl)carbonyl]piperazine.

1-[(5-Chloroindol-2-yl)sulfonyl]-4-[(5,6-dimethyl-4,5,6,7-tetrahydrooxazolo[5,4-c]pyridazin-2-yl)carbonyl]piperazine 1-[(5,6-Dimethyl-4,5,6,7-tetrahydrooxazolo[5,4-c]pyridazin-2-yl)carbonyl]-4-[(5-ethynylindol-2-yl)sulfonyl]piperazine 4-[(5-Chloroindol-2-yl)sulfonyl]-2-(N-methylcarbamoyl)-1-[(4,5,6,7-tetrahydrooxazolo[5,4-c]pyridazin-2-yl)carbonyl]piperazine.

4-[(5-Ethynylindol-2-yl)sulfonyl]-2-(N-methylcarbamoyl)-1-[(4,5,6,7-tetrahydrooxazolo[5,4-c]pyridazin-2-yl)carbonyl]piperazine.

4-[(5-Chloroindol-2-yl)sulfonyl]-1-[(5,6-dimethyl-4,5,6,7-tetrahydrooxazolo[5,4-c]pyridazin-2-yl)carbonyl]-2-(N-methylcarbamoyl)piperazine 1-[(5,6-Dimethyl-4,5,6,7-tetrahydrooxazolo[5,4-c]pyridazin-2-yl)carbonyl]-4-[(5-ethynylindol-2-yl)sulfonyl]-2-(N-methylcarbamoyl)piperazine 4-[(5-Chloroindol-2-yl)sulfonyl]-2-[(N,N-dimethylcarbamoyl)methyl]-1-[(4,5,6,7-tetrahydrooxazolo[5,4-c]pyridazin-2-yl)carbonyl]piperazine.

2-[(N,N-Dimethylcarbamoyl)methyl]-4-[(5-ethynylindol-2-yl)sulfonyl]-1-[(4,5,6,7-tetrahydrooxazolo[5,4-c]pyridazin-2-yl)carbonyl]piperazine.

4-[(5-Chloroindol-2-yl)sulfonyl]-2-[(N,N-dimethylcarbamoyl)methyl]-1-[(5,6-dimethyl-4,5,6,7-tetrahydrooxazolo[5,4-c]pyridazin-2-yl)carbonyl]piperazine 2-[(N,N-Dimethylcarbamoyl)methyl]-1-[(5,6-dimethyl-4,5,6,7-tetrahydrooxazolo[5,4-c]pyridazin-2-yl)carbonyl]-4-[(5-ethynylindol-2-yl)sulfonyl]piperazine 4-[(5-Chloroindol-2-yl)sulfonyl]-2-(2-cyanoethyl)-1-[(4,5,6,7-tetrahydrooxazolo[5,4-c]pyridazin-2-yl)carbonyl]piperazine.

2-(2-Cyanoethyl)-4-[(5-ethynylindol-2-yl)sulfonyl]-1-[(4,5,6,7-tetrahydrooxazolo[5,4-c]pyridazin-2-yl)carbonyl]piperazine.

4-[(5-Chloroindol-2-yl)sulfonyl]-2-(2-cyanoethyl)-1-[(5,6-dimethyl-4,5,6,7-tetrahydrooxazolo[5,4-c]pyridazin-2-yl)carbonyl]piperazine 2-(2-Cyanoethyl)-1-[(5,6-dimethyl-4,5,6,7-tetrahydrooxazolo[5,4-c]pyridazin-2-yl)carbonyl]-4-[(5-ethynylindol-2-yl)sulfonyl]piperazine 4-[(5-Chloroindol-2-yl)sulfonyl]-1-[(6-hydroxy-4,5,6,7-tetrahydrooxazolo[5,4-c]pyridin-2-yl)carbonyl]-2-(N-methylcarbamoyl)piperazine 4-[(5-Ethynylindol-2-yl)sulfonyl]-1-[(6-hydroxy-4,5,6,7-tetrahydrooxazolo[5,4-c]pyridin-2-yl)carbonyl]-2-(N-methylcarbamoyl)piperazine 4-[(5-Chloroindol-2-yl)sulfonyl]-1-[(6-hydroxy-4,5,6,7-tetrahydrooxazolo[5,4-c]pyridin-2-yl)carbonyl]-2-[[(morpholin-4-yl)carbonyl]methyl]piperazine.

4-[(5-Ethynylindol-2-yl)sulfonyl]-1-[(6-hydroxy-4,5,6,7-tetrahydrooxazolo[5,4-c]pyridin-2-yl)carbonyl]-2-[[(morpholin-4-yl)carbonyl]methyl]piperazine.

1-[(5-Chloroindol-2-yl)sulfonyl]-4-[(6-hydroxy-4,5,6,7-tetrahydrooxazolo[5,4-c]pyridin-2-yl)carbonyl]piperazine.

1-[(5-Ethynylindol-2-yl)sulfonyl]-4-[(6-hydroxy-4,5,6,7-tetrahydrooxazolo[5,4-c]pyridin-2-yl)carbonyl]piperazine.

4-[(5-Chloroindol-2-yl)sulfonyl]-2-(2-cyanoethyl)-1-[(6-hydroxy-4,5,6,7-tetrahydrooxazolo[5,4-c]pyridin-2-yl)carbonyl]piperazine.

2-(2-Cyanoethyl)-4-[(5-ethynylindol-2-yl)sulfonyl]-1-[(6-hydroxy-4,5,6,7-tetrahydrooxazolo[5,4-c]pyridin-2-yl)carbonyl]piperazine.

4-[(5-Chloroindol-2-yl)sulfonyl]-2-[(N,N-dimethylcarbamoyl)methyl]-1-[(6-hydroxy-4,5,6,7-tetrahydrooxazolo[5,4-c]pyridin-2-yl)carbonyl]piperazine.

2-[(N,N-Dimethylcarbamoyl)methyl]-4-[(5-ethynylindol-2-yl)sulfonyl]-1-[(6-hydroxy-4,5,6,7-tetrahydrooxazolo[5,4-c]pyridin-2-yl)carbonyl]piperazine.

1-[(5-Chloroindol-2-yl)sulfonyl]-4-[(5,6-dihydrobenzo[f]isoquinolin-8-yl)carbonyl]piperazine 1-[(5,6-Dihydrobenzo[f]isoquinolin-8-yl)carbonyl]-4-[(5-ethynylindol-2-yl)sulfonyl]piperazine 1-[(5-Chloroindol-2-yl)sulfonyl]-4-[(5,6-dihydropyrido[4,3-f]quinazolin-3-yl)carbonyl]piperazine 1-[(5,6-Dihydropyrido[4,3-f]quinazolin-3-yl)carbonyl]-4-[(5-ethynylindol-2-yl)sulfonyl]piperazine 8-[[1-[(5-Chloroindol-2-yl)sulfonyl]piperazin-4-yl]carbonyl]-5,6-dihydrobenzo[f]isoquinoline N-oxide 8-[[1-[(5-Ethynylindol-2-yl)sulfonyl]piperazin-4-yl]carbonyl]-5,6-dihydrobenzo[f]isoquinoline N-oxide 3-[[1-[(5-Chloroindol-2-yl)sulfonyl]piperazin-4-yl]carbonyl]-5,6-dihydropyrido[4,3-f]quinazoline N-oxide 3-[[1-[(5-Ethynylindol-2-yl)sulfonyl]piperazin-4-yl]carbonyl]-5,6-dihydropyrido[4,3-f]quinazoline N-oxide 1-[(5-Chloroindol-2-yl)sulfonyl]-1-[(6-methyl-4,5,6,7-tetrahydrooxazolo[4,5-c]pyridin-2-yl)carbonyl]piperazine 1-[(5-Ethynylindol-2-yl)sulfonyl]-1-[(6-methyl-4,5,6,7-tetrahydrooxazolo[4,5-c]pyridin-2-yl)carbonyl]piperazine 1-[(5-Chloroindol-2-yl)sulfonyl]-4-[(6-oxo-4,5,6,7-tetrahydrobenzothiazol-2-yl)carbonyl]piperazine 1-[(5-Chloroindol-2-yl)sulfonyl]-4-[(6-hydroxyimino-4,5,6,7-tetrahydrobenzothiazol-2-yl)carbonyl]piperazine 1-[(5-Chloroindol-2-yl)sulfonyl]-4-[(6-hydroxy-4,5,6,7-tetrahydrobenzothiazol-2-yl)carbonyl]piperazine 1-[(5-Chloroindol-2-yl)sulfonyl]-4-[(6-ethylenedioxy-4,5,6,7-tetrahydrobenzothiazol-2-yl)carbonyl]piperazine 1-[(5-Chloroindol-2-yl)sulfonyl]-4-[(4,5,6,7-tetrahydrothiazolo[5,4-c]furan-2-yl)carbonyl]piperazine 1-[(6-Acetoxy-4,5,6,7-tetrahydrobenzothiazol-2-yl)carbonyl]-4-[(5-chloroindol-2-yl)sulfonyl]piperazine 1-[(5-Chloroindol-2-yl)sulfonyl]-4-[(6-methoxy-4,5,6,7-tetrahydrobenzothiazol-2-yl)carbonyl]piperazine 1-[(6-Amino-4,5,6,7-tetrahydrobenzothiazol-2-yl)carbonyl]-4-[(5-chloroindol-2-yl)sulfonyl]piperazine 1-[(5-Chloroindol-2-yl)sulfonyl]-4-[(6-dimethylamino-4,5,6,7-tetrahydrobenzothiazol-2-yl)carbonyl]piperazine 1-[(5-Chloroindol-2-yl)sulfonyl]-4-[[6-(pyrrolidin-1-yl)-4,5,6,7-tetrahydrobenzothiazol-2-yl]carbonyl]piperazine 1-[(6-Acetylamino-1-4,5,6,7-tetrahydrobenzothiazol-2-yl)carbonyl]-4-[(5-chloroindol-2-yl)sulfonyl]piperazine 1-[(5-Ethynylindol-2-yl)sulfonyl]-4-[(6-oxo-4,5,6,7-tetrahydrobenzothiazol-2-yl)carbonyl]piperazine 1-[(5-Ethynylindol-2-yl)sulfonyl]-4-[(6-hydroxyimino-4,5,6,7-tetrahydrobenzothiazol-2-yl)carbonyl]piperazine 1-[(5-Ethynylindol-2-yl)sulfonyl]-4-[(6-hydroxy-4,5,6,7-tetrahydrobenzothiazol-2-yl)carbonyl]piperazine 1-[(6-Ethylenedioxy-4,5,6,7-tetrahydrobenzothiazol-2-yl)carbonyl]-4-[(5-ethynylindol-2-yl)sulfonyl]piperazine 1-[(5-Ethynylindol-2-yl)sulfonyl]-4-[(4,5,6,7-tetrahydrothiazolo[5,4-c]furan-2-yl)carbonyl]piperazine 1-[(6-Acetoxy-4,5,6,7-tetrahydrobenzothiazol-2-yl)carbonyl]-4-[(5-ethynylindol-2-yl)sulfonyl]piperazine 1-[(5-Ethynylindol-2-yl)sulfonyl]-4-[(6-methoxy-4,5,6,7-tetrahydrobenzothiazol-2-yl)carbonyl]piperazine 1-[(6-Amino-4,5,6,7-tetrahydrobenzothiazol-2-yl)carbonyl]-4-[(5-ethynylindol-2-yl)sulfonyl]piperazine 1-[(6-Dimethylamino-4,5,6,7-tetrahydrobenzothiazol-2-yl)carbonyl]-4-[(5-ethynylindol-2-yl)sulfonyl]piperazine 4-[(5-Ethynylindol-2-yl)sulfonyl]-1-[[6-(pyrrolidin-1-yl)-4,5,6,7-tetrahydrobenzothiazol-2-yl]carbonyl]piperazine 1-[(6-Acetylamino-4,5,6,7-tetrahydrobenzothiazol-2-yl)carbonyl]-4-[(5-ethynylindol-2-yl)sulfonyl]piperazine 4-[(5-Chloroindol-2-yl)sulfonyl]-1-[(6-methyl-5-oxo-4,5,6,7-tetrahydrothiazolo[5,4-c]pyridin-2-yl)carbonyl]-2-[(morpholin-4-yl)carbonylmethyl]piperazine 4-[(5-Chloroindol-2-yl)sulfonyl]-1-[(6-methyl-5-oxo-4,5,6,7-tetrahydrooxazolo[5,4-c]pyridin-2-yl)carbonyl]-2-[(morpholin-4-yl)carbonylmethyl]piperazine 4-[(5-Chloroindol-2-yl)sulfonyl]-2-[(morpholin-4-yl)carbonylmethyl]-1-[(5-oxo-4,5,6,7-tetrahydrothiazolo[5,4-c]pyridin-2-yl)carbonyl]piperazine 4-[(5-Chloroindol-2-yl)sulfonyl]-2-[(morpholin-4-yl)carbonylmethyl]-1-[(5-oxo-4,5,6,7-tetrahydrooxazolo[5,4-c]pyridin-2-yl)carbonyl]piperazine 1-[(5-Chloroindol-2-yl)sulfonyl]-4-[(4,5,6,7-tetrahydrothieno[3,2-b]pyridin-2-yl)carbonyl]piperazine 1-[(5-Chloroindol-2-yl)sulfonyl]-4-[(4-methyl-4,5,6,7-tetrahydrothieno[3,2-b]pyridin-2-yl)carbonyl]piperazine 1-[(5-Chloroindol-2-yl)sulfonyl]-4-[(thieno[3,2-b]pyridin-2-yl)carbonyl]piperazine 2-[[4-[(5-Chloroindol-2-yl)sulfonyl]piperazin-1-yl]carbonyl]thieno[3,2-b]pyridine N-oxide 1-[(5-Ethynylindol-2-yl)sulfonyl]-4-[(4,5,6,7-tetrahydrothieno[3,2-b]pyridin-2-yl)carbonyl]piperazine 1-[(5-Ethynylindol-2-yl)sulfonyl]-4-[(4-methyl-4,5,6,7-tetrahydrothieno[3,2-b]pyridin-2-yl)carbonyl]piperazine 1-[(5-Ethynylindol-2-yl)sulfonyl]-4-[(thieno[3,2-b]pyridin-2-yl)carbonyl]piperazine 2-[[4-[(5-Ethynylindol-2-yl)sulfonyl]piperazin-1-yl]carbonyl]thieno[3,2-b]pyridine N-oxide 4-[(5-Chloroindol-2-yl)sulfonyl]-2-(2-cyanoethyl)-1-[(4,5,6,7-tetrahydrothieno[3,2-b]pyridin-2-yl)carbonyl]piperazine 4-[(5-Chloroindol-2-yl)sulfonyl]-2-(2-cyanoethyl)-1-[(4-methyl-4,5,6,7-tetrahydrothieno[3,2-b]pyridin-2-yl)carbonyl]piperazine 4-[(5-Chloroindol-2-yl)sulfonyl]-2-(2-cyanoethyl)-1-[(thieno[3,2-b]pyridin-2-yl)carbonyl]piperazine 2-[[4-[(5-Chloroindol-2-yl)sulfonyl]-2-(2-cyanoethyl)piperazin-1-yl]carbonyl]thieno[3,2-b]pyridine N-oxide 4-[(5-Ethynylindol-2-yl)sulfonyl]-2-(2-cyanoethyl)-1-[(4,5,6,7-tetrahydrothieno[3,2-b]pyridin-2-yl)carbonyl]piperazine 4-[(5-Ethynylindol-2-yl)sulfonyl]-2-(2-cyanoethyl)-1-[(4-methyl-4,5,6,7-tetrahydrothieno[3,2-b]pyridin-2-yl)carbonyl]piperazine 4-[(5-Ethynylindol-2-yl)sulfonyl]-2-(2-cyanoethyl)-1-[(thieno[3,2-b]pyridin-2-yl)carbonyl]piperazine 2-[[4-[(5-Ethynylindol-2-yl)sulfonyl]-2-(cyanoethyl)piperazin-1-yl]carbonyl]thieno[3,2-b]pyridine N-oxide 1-[(5-Chloroindol-2-yl)sulfonyl]-4-[(4,5,6,7-tetrahydrothiazolo[5,4-c]pyridin-6-yl)carbonyl]piperazine 1-[(5-Ethynylindol-2-yl)sulfonyl]-4-[(4,5,6,7-tetrahydrothiazolo[5,4-c]pyridin-6-yl)carbonyl]piperazine 1-[(5-Chloroindol-2-yl)sulfonyl]-4-[(4,5,6,7-tetrahydrooxazolo[5,4-c]pyridin-6-yl)carbonyl]piperazine 1-[(5-Ethynylindol-2-yl)sulfonyl]-4-[(4,5,6,7-tetrahydrooxazolo[5,4-c]pyridin-6-yl)carbonyl]piperazine 1-[(5-Chloroindol-2-yl)sulfonyl]-4-[(2-dimethylamino-4,5,6,7-tetrahydrothiazolo[5,4-c]pyridin-6-yl)carbonyl]piperazine 1-[(2-Dimethylamino-4,5,6,7-tetrahydrothiazolo[5,4-c]pyridin-6-yl)carbonyl]-4-[(5-ethynylindol-2-yl)sulfonyl]piperazine 1-[(5-Ethynylindol-2-yl)sulfonyl]-4-[(6-methylsulfonyl-4,5,6,7-tetrahydrothiazolo[5,4-c]pyridin-2-yl)carbonyl]piperazine 4-[(5-Ethynylindol-2-yl)sulfonyl]-1-[(6-methylsulfonyl-4,5,6,7-tetrahydrothiazolo[5,4-c]pyridin-2-yl)carbonyl]-2-(N-methylcarbamoyl)piperazine 4-[(5-Ethynylindol-2-yl)sulfonyl]-1-[(6-methylsulfonyl-4,5,6,7-tetrahydrothiazolo[5,4-c]pyridin-2-yl)carbonyl]-2-(morpholin-4-ylcarbonylmethyl)piperazine 2-(2-Cyanoethyl)-4-[(5-ethynylindol-2-yl)sulfonyl]-1-[(6-methylsulfonyl-4,5,6,7-tetrahydrothiazolo[5,4-c]pyridin-2-yl)carbonyl]piperazine 1-[(5-Chloroindol-2-yl)sulfonyl]-4-[(6-methylsulfonyl-4,5,6,7-tetrahydrooxazolo[5,4-c]pyridin-2-yl)carbonyl]piperazine 4-[(5-Chloroindol-2-yl)sulfonyl]-1-[(6-methylsulfonyl-4,5,6,7-tetrahydrooxazolo[5,4-c]pyridin-2-yl)carbonyl]-2-(N-methylcarbamoyl)piperazine 4-[(5-Chloroindol-2-yl)sulfonyl]-1-[(6-methylsulfonyl-4,5,6,7-tetrahydrooxazolo[5,4-c]pyridin-2-yl)carbonyl]-2-(morpholin-4-ylcarbonylmethyl)piperazine 4-[(5-Chloroindol-2-yl)sulfonyl]-2-(2-cyanoethyl)-1-[(6-methylsulfonyl-4,5,6,7-tetrahydrooxazolo[5,4-c]pyridin-2-yl)carbonyl]piperazine 1-[(5-Ethynylindol-2-yl)sulfonyl]-4-[(6-methylsulfonyl-4,5,6,7-tetrahydrooxazolo[5,4-c]pyridin-2-yl)carbonyl]piperazine 4-[(5-Ethynylindol-2-yl)sulfonyl]-2-(N-methylcarbamoyl)-1-[(6-methylsulfonyl-4,5,6,7-tetrahydrooxazolo[5,4-c]pyridin-2-yl)carbonyl]piperazine 4-[(5-Ethynylindol-2-yl)sulfonyl]-1-[(6-methylsulfonyl-4,5,6,7-tetrahydrooxazolo[5,4-c]pyridin-2-yl)carbonyl]-2-(morpholin-4-ylcarbonylmethyl)piperazine 2-(2-Cyanoethyl)-4-[(5-ethynylindol-2-yl)sulfonyl]-1-[(6-methylsulfonyl-4,5,6,7-tetrahydrooxazolo[5,4-c]pyridin-2-yl)carbonyl]piperazine 4-[(6-Chlorobenzo[b]thien-2-yl)sulfonyl]-1-[(6-methyl-4,5,6,7-tetrahydrooxazolo[5,4-c]pyridin-2-yl)carbonyl]-2-[2-(2-oxopyridin-1-yl)ethyl]piperazine 4-[(6-Chlorobenzo[b]thien-2-yl)sulfonyl]-1-[(6-methyl-4,5,6,7-tetrahydrooxazolo[5,4-c]pyridin-2-yl)carbonyl]-2-[2-(2-oxo-1,3-oxazolan-3-yl)ethyl]piperazine 4-[(6-Chlorobenzo[b]thien-2-yl)sulfonyl]-1-[(6-methyl-4,5,6,7-tetrahydrothiazolo[5,4-c]pyridin-2-yl)carbonyl]-2-[2-(2-oxopyridin-1-yl)ethyl]piperazine 4-[(6-Chlorobenzo[b]thien-2-yl)sulfonyl]-2-[2-[(coumarin-7-yl)oxy]ethyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-2-[2-[(coumarin-7-yl)oxy]ethyl]-1-[(6-methyl-4,5,6,7-tetrahydrooxazolo[5,4-c]pyridin-2-yl)carbonyl]piperazine 4-[(6-Chlorobenzo[b]thien-2-yl)sulfonyl]-2-[2-[(cyclopropylcarbonyl)amino]ethyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-2-[2-[(cyclopropylcarbonyl)amino]ethyl]-1-[(6-methyl-4,5,6,7-tetrahydrooxazolo[5,4-c]pyridin-2-yl)carbonyl]piperazine 4-[(6-Chlorobenzo[b]thien-2-yl)sulfonyl]-2-[[(cyclopropylcarbonyl)amino]methyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-2-[[(cyclopropylcarbonyl)amino]methyl]-1-[(6-methyl-4,5,6,7-tetrahydrooxazolo[5,4-c]pyridin-2-yl)carbonyl]piperazine 4-[(6-Chlorobenzo[b]thien-2-yl)sulfonyl]-2-(2-cyanoethyl)-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-2-(2-cyanoethyl)-1-[(6-methyl-4,5,6,7-tetrahydrooxazolo[5,4-c]pyridin-2-yl)carbonyl]piperazine 4-[(6-Chlorobenzo[b]thien-2-yl)sulfonyl]-2-[(N-cyanomethyl-N-methylcarbamoyl)methyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-2-[(N-cyanomethyl-N-methylcarbamoyl)methyl]-1-[(6-methyl-4,5,6,7-tetrahydrooxazolo[5,4-c]pyridin-2-yl)carbonyl]piperazine 2-(3-Butynyl)-4-[(6-chlorobenzo[b]thien-2-yl)sulfonyl]-4-[(6-methyl-4,5,6,7-tetrahydrothiazolo[5,4-c]pyridin-2-yl)carbonyl]piperazine 2-(3-Butynyl)-4-[(6-chlorobenzo[b]thien-2-yl)sulfonyl]-4-[(6-methyl-4,5,6,7-tetrahydrooxazolo[5,4-c]pyridin-2-yl)carbonyl]piperazine 1-[(6-Chlorobenzo[b]thien-2-yl)sulfonyl]-2-[[N-(2-hydroxyethyl)carbamoyl]methyl]-4-[(6-methyl-4,5,6,7-tetrahydrothiazolo[5,4-c]pyridin-2-yl)carbonyl]piperazine 1-[(6-Chlorobenzo[b]thien-2-yl)sulfonyl]-2-[[N-(2-hydroxyethyl)carbamoyl]methyl]-4-[(6-methyl-4,5,6,7-tetrahydrooxazolo[5,4-c]pyridin-2-yl)carbonyl]piperazine 2-[[N,N-Bis(2-hydroxyethyl)carbamoyl]methyl]-1-[(6-chlorobenzo[b]thien-2-yl)sulfonyl]-4-[(6-methyl-4,5,6,7-tetrahydrothiazolo[5,4-c]pyridin-2-yl)carbonyl]piperazine 2-[[N,N-Bis(2-hydroxyethyl)carbamoyl]methyl]-1-[(6-chlorobenzo[b]thien-2-yl)sulfonyl]-4-[(6-methyl-4,5,6,7-tetrahydrooxazolo[5,4-c]pyridin-2-yl)carbonyl]piperazine 1-[(6-Chlorobenzo[b]thien-2-yl)sulfonyl]-2-[[N-(2-methoxyethyl)carbamoyl]methyl]-4-[(6-methyl-4,5,6,7-tetrahydrothiazolo[5,4-c]pyridin-2-yl)carbonyl]piperazine 1-[(6-Chlorobenzo[b]thien-2-yl)sulfonyl]-2-[[N-(2-methoxyethyl)carbamoyl]methyl]-4-[(6-methyl-4,5,6,7-tetrahydrooxazolo[5,4-c]pyridin-2-yl)carbonyl]piperazine 2-[[N,N-Bis(2-methoxyethyl)carbamoyl]methyl]-1-[(6-chlorobenzo[b]thien-2-yl)sulfonyl]-4-[(6-methyl-4,5,6,7-tetrahydrothiazolo[5,4-c]pyridin-2-yl)carbonyl]piperazine 2-[[N,N-Bis(2-methoxyethyl)carbamoyl]methyl]-1-[(6-chlorobenzo[b]thien-2-yl)sulfonyl]-4-[(6-methyl-4,5,6,7-tetrahydrooxazolo[5,4-c]pyridin-2-yl)carbonyl]piperazine 4-[(6-Chlorobenzo[b]thien-2-yl)sulfonyl]-2-[[N-(2-hydroxyethyl)-N-methylcarbamoyl]methyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-2-[[N-(2-hydroxyethyl)-N-methylcarbamoyl]methyl]-1-[(6-methyl-4,5,6,7-tetrahydrooxazolo[5,4-c]pyridin-2-yl)carbonyl]piperazine 2-[[N-Benzyl-N-(2-hydroxyethyl)carbamoyl]methyl]-4-[(6-chlorobenzo[b]thien-2-yl)sulfonyl]-1-[(6-methyl-4,5,6,7-tetrahydrothiazolo[5,4-c]pyridin-2-yl)carbonyl]piperazine 2-[[N-Benzyl-N-(2-hydroxyethyl)carbamoyl]methyl]-4-[(6-chlorobenzo[b]thien-2-yl)sulfonyl]-1-[(6-methyl-4,5,6,7-tetrahydrooxazolo[5,4-c]pyridin-2-yl)carbonyl]piperazine 4-[(6-Chlorobenzo[b]thien-2-yl)sulfonyl]-1-[(6-methyl-4,5,6,7-tetrahydrothiazolo[5,4-c]pyridin-2-yl)carbonyl]-2-[2-[(morpholin-4-yl)carbonyl]ethyl]piperazine 4-[(6-Chlorobenzo[b]thien-2-yl)sulfonyl]-2-[2-(dimethylaminocarbonyl)ethyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-1-[(6-methyl-4,5,6,7-tetrahydrothiazolo[5,4-c]pyridin-2-yl)carbonyl]-2-[2-[(pyrrolidin-1-yl)carbonyl]ethyl]piperazine 2-[2-(Aminosulfonyl)ethyl]-4-[(6-chlorobenzo[b]thien-2-yl)sulfonyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-1-[(6-methyl-4,5,6,7-tetrahydrothiazolo[5,4-c]pyridin-2-yl)carbonyl]-2-[2-[(morpholin-4-yl)sulfonyl]ethyl]piperazine 2-[2-[(t-Butoxycarbonylamino)sulfonyl]ethyl]-4-[(6-chlorobenzo[b]thien-2-yl)sulfonyl]-1-[(6-methyl-4,5,6,7-tetrahydrothiazolo[5,4-c]pyridin-2-yl)carbonyl]piperazine 2-[2-[(n-Butoxycarbonylamino)sulfonyl]ethyl]-4-[(6-chlorobenzo[b]thien-2-yl)sulfonyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-2-[2-(ethoxycarbonylamino)sulfonyl]ethyl]-1-[(6-methyl-4,5,6,7-tetrahydrothiazolo[5,4-c]pyridin-2-yl)carbonyl]piperazine 2-[2-(Acetylamino)sulfonyl]ethyl]-4-[(6-chlorobenzo[b]thien-2-yl)sulfonyl]-1-[(6-methyl-4,5,6,7-tetrahydrothiazolo[5,4-c]pyridin-2-yl)carbonyl]piperazine 2-(Aminosulfonylmethyl)-4-[(6-chlorobenzo[b]thien-2-yl)sulfonyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-1-[(6-methyl-4,5,6,7-tetrahydrothiazolo[5,4-c]pyridin-2-yl)carbonyl]-2-[(morpholin-4-yl)sulfonylmethyl]piperazine 4-[(6-Chlorobenzo[b]thien-2-yl)sulfonyl]-1-[(6-methyl-4,5,6,7-tetrahydrothiazolo[5,4-c]pyridin-2-yl)carbonyl]-2-[(pyrrolidin-1-yl)sulfonylmethyl]piperazine 2-[(t-Butoxycarbonylamino)sulfonylmethyl]-4-[(6-chlorobenzo[b]thien-2-yl)sulfonyl]-1-[(6-methyl-4,5,6,7-tetrahydrothiazolo[5,4-c]pyridin-2-yl)carbonyl]piperazine 2-[(n-Butoxycarbonylamino)sulfonylmethyl]-4-[(6-chlorobenzo[b]thien-2-yl)sulfonyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-2-[(ethoxycarbonylamino)sulfonylmethyl]-1-[(6-methyl-4,5,6,7-tetrahydrothiazolo[5,4-c]pyridin-2-yl)carbonyl]piperazine 2-[(Acetylamino)sulfonylmethyl]-4-[(6-chlorobenzo[b]thien-2-yl)sulfonyl]-1-[(6-methyl-4,5,6,7-tetrahydrothiazolo[5,4-c]pyridin-2-yl)carbonyl]piperazine 2-[3-[(4H-5-Acetoxy-4-oxo)pyran-2-yl]propyl]-4-[(6-chlorobenzo[b]thien-2-yl)sulfonyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-2-[3-[(4H-5-hydroxy-4-oxo)pyran-2-yl]propyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-2-[3-[(4H-5-methoxy-4-oxo)pyran-2-yl]propyl]-1-[(6-methyl-4,5,6,7-tetrahydrothiazolo[5,4-c]pyridin-2-yl)carbonyl]piperazine N-methyl-N-[[4-[(6-chlorobenzo[b]thien-2-yl)sulfonyl]-1-[(6-methyl-4,5,6,7-tetrahydrothiazolo[5,4-c]pyridin-2-yl)carbonyl]piperazin-2-yl]acetyl]methanesulfonamide N-[[4-[(6-Chlorobenzo[b]thien-2-yl)sulfonyl]-1-[(6-methyl-4,5,6,7-tetrahydrothiazolo[5,4-c]pyridin-2-yl)carbonyl]piperazin-2-yl]acetyl]benzenesulfonamide N-[2-[4-[(6-Chlorobenzo[b]thien-2-yl)sulfonyl]-1-[(6-methyl-4,5,6,7-tetrahydrothiazolo[5,4-c]pyridin-2-yl)carbonyl]piperazine-2-yl]ethyl]trifluoromethanesulfonamide N-methyl-N-[2-[4-[(6-chlorobenzo[b]thien-2-yl)sulfonyl]-1-[(6-methyl-4,5,6,7-tetrahydrothiazolo[5,4-c]pyridin-2-yl)carbonyl]piperazin-2-yl]ethyl]trifluoromethanesulfonamide N-[[4-[(6-Chlorobenzo[b]thien-2-yl)sulfonyl]-1-[(6-methyl-4,5,6,7-tetrahydrothiazolo[5,4-c]pyridin-2-yl)carbonyl]piperazin-2-yl]acetyl]-N'-methanesulfonylhydrazine 4-[(6-Chlorobenzo[b]thien-2-yl)sulfonyl]-2-[2-(2,5-dihydro-5-oxo-4H-1,2,4-oxadiazol-3-yl)ethyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-2-[2-(2,5-dihydro-5-oxo-4H-1,2,4-oxadiazol-3-yl)ethyl]-1-[(6-methyl-4,5,6,7-tetrahydrooxazolo[5,4-c]pyridin-2-yl)carbonyl]piperazine 4-[(6-Chlorobenzo[b]thien-2-yl)sulfonyl]-2-[2-(2-oxo-3H-1,2,3,5-oxathiadiazol-4-yl)ethyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-2-[2-(2-oxo-3H-1,2,3,5-oxathiadiazol-4-yl)ethyl]-1-[(6-methyl-4,5,6,7-tetrahydrooxazolo[5,4-c]pyridin-2-yl)carbonyl]piperazine 4-[(6-Chlorobenzo[b]thien-2-yl)sulfonyl]-2-[2-(2,5-dihydro-5-oxo-4H-1,2,4-thiadiazol-3-yl)ethyl]-1-[(6-methyl-4,5,6,7-tetrahydrothiazolo[5,4-c]pyridin-2-yl)carbonyl]piperazine 4-[(6-Chlorobenzo[b]thien-2-yl)sulfonyl]-2-[2-(2,5-dihydro-5-oxo-4H-1,2,4-thiadiazol-3-yl)ethyl]-1-[(6-methyl-4,5,6,7-tetrahydrooxazolo[5,4-c]pyridin-2-yl)carbonyl]piperazine 4-[(6-Chlorobenzo[b]thien-2-yl)sulfonyl]-2-[2-(2,5-dihydro-5-thioxo-4H-1,2,4-oxadiazol-3-yl)ethyl]-1-[(6- methyl-4,5,6,7-tetrahydrothiazolo[5,4-c]pyridin-2-yl)carbonyl]piperazine

4-[(6-Chlorobenzo[b]thien-2-yl)sulfonyl]-2-[2-(2,5-dihydro-5-thioxo-4H-1,2,4-oxadiazol-3-yl)ethyl]-1-[(6-methyl-4,5,6,7-tetrahydrooxazolo[5,4-c]pyridin-2-yl)carbonyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[2-(2-oxo-1,3-oxazolan-3-yl)ethyl]piperazine 4-[(5-Ethynylindol-2-yl)sulfonyl]-1-[(6-methyl-4,5,6,7-tetrahydrothiazolo[5,4-c]pyridin-2-yl)carbonyl]-2-[2-(2-oxo-1,3-oxazolan-3-yl)ethyl]piperazine 4-[(5-Chloroindol-2-yl)sulfonyl]-1-[(6-methyl-4,5,6,7-tetrahydrooxazolo[5,4-c]pyridin-2-yl)carbonyl]-2-[2-(2-oxo-1,3-oxazolan-3-yl)ethyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[2-(2-oxopyridin-1-yl)ethyl]piperazine 4-[(5-Chloroindol-2-yl)sulfonyl]-1-[(6-methyl-4,5,6,7-tetrahydrooxazolo[5,4-c]pyridin-2-yl)carbonyl]-2-[2-(2-oxopyridin-1-yl)ethyl]piperazine 4-[(5-Chloroindol-2-yl)sulfonyl]-2-[2-[(coumarin-7-yl)oxy]ethyl]-1-[(6-methyl-4,5,6,7-tetrahydrothiazolo[5,4-c]pyridin-2-yl)carbonyl]piperazine 4-[(5-Chloroindol-2-yl)sulfonyl]-2-[2-[(coumarin-7-yl)oxy]ethyl]-1-[(6-methyl-4,5,6,7-tetrahydrooxazolo[5,4-c]pyridin-2-yl)carbonyl]piperazine 4-[(5-Chloroindol-2-yl)sulfonyl]-2-[2-[(cyclopropylcarbonyl)amino]ethyl]-1-[(6-methyl-4,5,6,7-tetrahydrothiazolo[5,4-c]pyridin-2-yl)carbonyl]piperazine 4-[(5-Chloroindol-2-yl)sulfonyl]-2-[2-[(cyclopropylcarbonyl)amino]ethyl]-1-[(6-methyl-4,5,6,7-tetrahydrooxazolo[5,4-c]pyridin-2-yl)carbonyl]piperazine 4-[(5-Chloroindol-2-yl)sulfonyl]-2-[[(cyclopropylcarbonyl)amino]methyl]-1-[(6-methyl-4,5,6,7-tetrahydrothiazolo[5,4-c]pyridin-2-yl)carbonyl]piperazine 4-[(5-Chloroindol-2-yl)sulfonyl]-2-[[(cyclopropylcarbonyl)amino]methyl]-1-[(6-methyl-4,5,6,7-tetrahydrooxazolo[5,4-c]pyridin-2-yl)carbonyl]piperazine 2-[2-(Aminosulfonyl)ethyl]-4-[(5-chloroindol-2-yl)sulfonyl]-1-[(6-methyl-4,5,6,7-tetrahydrothiazolo[5,4-c]pyridin-2-yl)carbonyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[2-[(morpholin-4-yl)sulfonyl]ethyl]piperazine 2-[2-[(t-Butoxycarbonylamino)sulfonyl]ethyl]-4-[(5-chloroindol-2-yl)sulfonyl]-1-[(6-methyl-4,5,6,7-tetrahydrothiazolo[5,4-c]pyridin-2-yl)carbonyl]piperazine 2-[2-[(n-Butoxycarbonylamino)sulfonyl]ethyl]-4-[(5-chloroindol-2-yl)sulfonyl]-1-[(6-methyl-4,5,6,7-tetrahydrothiazolo[5,4-c]pyridin-2-yl)carbonyl]piperazine 4-[(5-Chloroindol-2-yl)sulfonyl]-2-[2-(ethoxycarbonylamino)sulfonyl]ethyl]-1-[(6-methyl-4,5,6,7-tetrahydrothiazolo[5,4-c]pyridin-2-yl)carbonyl]piperazine 2-[2-(Acetylamino)sulfonyl]ethyl]-4-[(5-chloroindol-2-yl)sulfonyl]-1-[(6-methyl-4,5,6,7-tetrahydrothiazolo[5,4-c]pyridin-2-yl)carbonyl]piperazine 2-[2-(Aminosulfonyl)ethyl]-4-[(5-ethynylindol-2-yl)sulfonyl]-1-[(6-methyl-4,5,6,7-tetrahydrothiazolo[5,4-c]pyridin-2-yl)carbonyl]piperazine 4-[(5-Ethynylindol-2-yl)sulfonyl]-1-[(6-methyl-4,5,6,7-tetrahydrothiazolo[5,4-c]pyridin-2-yl)carbonyl]-2-[2-[(morpholin-4-yl)sulfonyl]ethyl]piperazine 2-[2-[(t-Butoxycarbonylamino)sulfonyl]ethyl]-4-[(5-ethynylindol-2-yl)sulfonyl]-1-[(6-methyl-4,5,6,7-tetrahydrothiazolo[5,4-c]pyridin-2-yl)carbonyl]piperazine 2-[2-[(n-Butoxycarbonylamino)sulfonyl]ethyl]-4-[(5-ethynylindol-2-yl)sulfonyl]-1-[(6-methyl-4,5,6,7-tetrahydrothiazolo[5,4-c]pyridin-2-yl)carbonyl]piperazine 2-[2-(Ethoxycarbonylamino)sulfonyl]ethyl]-4-[(5-ethynylindol-2-yl)sulfonyl]-1-[(6-methyl-4,5,6,7-tetrahydrothiazolo[5,4-c]pyridin-2-yl)carbonyl]piperazine 2-[2-(Acetylamino)sulfonyl]ethyl]-4-[(5-ethynylindol-2-yl)sulfonyl]-1-[(6-methyl-4,5,6,7-tetrahydrothiazolo[5,4-c]pyridin-2-yl)carbonyl]piperazine 2-(Aminosulfonylmethyl)-4-[(5-chloroindol-2-yl)sulfonyl]-1-[(6-methyl-4,5,6,7-tetrahydrothiazolo[5,4-c]pyridin-2-yl)carbonyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[(morpholin-4-yl)sulfonylmethyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[(pyrrolidin-1-yl)sulfonylmethyl]piperazine 2-[(t-Butoxycarbonylamino)sulfonylmethyl]-4-[(5-chloroindol-2-yl) sulfonyl]-1-[(6-methyl-4,5,6,7-tetrahydrothiazolo[5,4-c]pyridin-2-yl)carbonyl]piperazine 2-[(n-Butoxycarbonylamino)sulfonylmethyl]-4-[(5-chloroindol-2-yl)sulfonyl]-1-[(6-methyl-4,5,6,7-tetrahydrothiazolo[5,4-c]pyridin-2-yl)carbonyl]piperazine 4-[(5-Chloroindol-2-yl)sulfonyl]-2-[(ethoxycarbonylamino)sulfonylmethyl]-1-[(6-methyl-4,5,6,7-tetrahydrothiazolo[5,4-c]pyridin-2-yl)carbonyl]piperazine 2-[(Acetylamino)sulfonylmethyl]-4-[(5-chloroindol-2-yl)sulfonyl]-1-[(6-methyl-4,5,6,7-tetrahydrothiazolo[5,4-c]pyridin-2-yl)carbonyl]piperazine 2-(Aminosulfonylmethyl)-4-[(5-ethynylindol-2-yl)sulfonyl]-1-[(6-methyl-4,5,6,7-tetrahydrothiazolo[5,4-c]pyridin-2-yl)carbonyl]piperazine 4-[(5-Ethynylindol-2-yl)sulfonyl]-1-[(6-methyl-4,5,6,7-tetrahydrothiazolo[5,4-c]pyridin-2-yl)carbonyl]-2-[(morpholin-4-yl)sulfonylmethyl]piperazine 4-[(5-Ethynylindol-2-yl)sulfonyl]-1-[(6-methyl-4,5,6,7-tetrahydrothiazolo[5,4-c]pyridin-2-yl)carbonyl]-2-[(pyrrolidin-1-yl)sulfonylmethyl]piperazine 2-[(t-Butoxycarbonylamino)sulfonylmethyl]-4-[(5-ethynylindol-2-yl)sulfonyl]-1-[(6-methyl-4,5,6,7-tetrahydrothiazolo[5,4-c]pyridin-2-yl)carbonyl]piperazine 2-[(n-Butoxycarbonylamino)sulfonylmethyl]-4-[(5-ethynylindol-2-yl)sulfonyl]-1-[(6-methyl-4,5,6,7-tetrahydrothiazolo[5,4-c]pyridin-2-yl)carbonyl]piperazine 2-[(Ethoxycarbonylamino)sulfonylmethyl]-4-[(5-ethynylindol-2-yl)sulfonyl]-1-[(6-methyl-4,5,6,7-tetrahydrothiazolo[5,4-c]pyridin-2-yl)carbonyl]piperazine 2-[(Acetylamino)sulfonylmethyl]-4-[(5-ethynylindol-2-yl)sulfonyl]-1-[(6-methyl-4,5,6,7-tetrahydrothiazolo[5,4-c]pyridin-2-yl)carbonyl]piperazine 2-[3-[(4H-5-Acetoxy-4-oxo)pyran-2-yl]propyl]-4-[(5-chloroindol-2-yl)sulfonyl]-1-[(6-methyl-4,5,6,7-tetrahydrothiazolo[5,4-c]pyridin-2-yl)carbonyl]piperazine 4-[(5-Chloroindol-2-yl)sulfonyl]-2-[3-[(4H-5-hydroxy-4-oxo)pyran-2-yl]propyl]-1-[(6-methyl-4,5,6,7-tetrahydrothiazolo[5,4-c]pyridin-2-yl)carbonyl]piperazine 4-[(5-Chloroindol-2-yl)sulfonyl]-2-[3-[(4H-5-methoxy-4-oxo)pyran-2-yl]propyl]-1-[(6-methyl-4,5,6,7-tetrahydrothiazolo[5,4-c]pyridin-2-yl)carbonyl]piperazine N-[[4-[(5-Chloroindol-2-yl)sulfonyl]-1-[(6-methyl-4,5,6,7-tetrahydrothiazolo[5,4-c]pyridin-2-yl)carbonyl]piperazin-2-yl]acetyl]-N-methylmethanesulfonamide N-[[4-[(5-Chloroindol-2-yl)sulfonyl]-1-[(6-methyl-4,5,6,7-tetrahydrothiazolo[5,4-c]pyridin-2-yl) carbonyl]piperazin-2-yl]acetyl]benzenesulfonamide N-[2-[4-[(5-Chloroindol-2-yl)sulfonyl]-1-[(6-methyl-4,5,6,7-tetrahydrothiazolo[5,4-c]pyridin-2-yl)carbonyl]piperazin-2-yl]ethyl]trifluoromethanesulfonamide N-[2-[4-[(5-Chloroindol-2-yl)sulfonyl]-1-[(6-methyl-4,5,6,7-tetrahydrothiazolo[5,4-c]pyridin-2-yl)carbonyl]piperazin-2-yl]ethyl]-N-methyltrifluoromethanesulfonamide N-[[4-[(5-Chloroindol-2-yl)sulfonyl]-1-[(6-methyl-4,5,6,7-tetrahydrothiazolo[5,4-c]pyridin-2-yl)carbonyl]piperazin-2-yl]acetyl]-N'-methanesulfonylhydrazine 2-[3-[(4H-5-Acetoxy-4-oxo)pyran-2-yl]propyl]-4-[(5-ethynylindol-2-yl)sulfonyl]-1-[(6-methyl-4,5,6,7-tetrahydrothiazolo[5,4-c]pyridin-2-yl)carbonyl]piperazine 4-[(5-Ethynylindol-2-yl)sulfonyl]-2-[3-[(4H-5-hydroxy-4-oxo)pyran-2-yl]propyl]-1-[(6-methyl-4,5,6,7-tetrahydrothiazolo[5,4-c]pyridin-2-yl)carbonyl]piperazine 4-[(5-Ethynylindol-2-yl)sulfonyl]-2-[3-[(4H-5-methoxy-4-oxo)pyran-2-yl]propyl]-1-[(6-methyl-4,5,6,7-tetrahydrothiazolo[5,4-c]pyridin-2-yl)carbonyl]piperazine N-methyl-N-[[4-[(5-ethynylindol-2-yl)sulfonyl]-1-[(6-methyl-4,5,6,7-tetrahydrothiazolo[5,4-c]pyridin-2-yl)carbonyl]piperazin-2-yl]acetyl]methanesulfonamide N-[[4-[(5-Ethynylindol-2-yl)sulfonyl]-1-[(6-methyl-4,5,6,7-tetrahydrothiazolo[5,4-c]pyridin-2-yl)carbonyl]piperazin-2-yl]acetyl]benzenesulfonamide N-[2-[4-[(5-Ethynylindol-2-yl)sulfonyl]-1-[(6-methyl-4,5,6,7-tetrahydrothiazolo[5,4-c]pyridin-2-yl)carbonyl]piperazin-2-yl]ethyl]trifluoromethanesulfonamide N-[2-[4-[(5-Ethynylindol-2-yl)sulfonyl]-1-[(6-methyl-4,5,6,7-tetrahydrothiazolo[5,4-c]pyridin-2-yl)carbonyl]piperazin-2-yl]ethyl]-N-methyltrifluoromethanesulfonamide N-[[4-[(5-Ethynylindol-2-yl)sulfonyl]-1-[(6-methyl-4,5,6,7-tetrahydrothiazolo[5,4-c]pyridin-2-yl)carbonyl]piperazin-2-yl]acetyl]-N'-methanesulfonylhydrazine 4-[(5-Chloroindol-2-yl)sulfonyl]-2-[2-(2,5-dihydro-5-oxo-4H-1,2,4-oxadiazol-3-yl)ethyl]-1-[(6-methyl-4,5,6,7-tetrahydrothiazolo[5,4-c]pyridin-2-yl)carbonyl]piperazine 4-[(5-Ethynylindol-2-yl)sulfonyl]-2-[2-(2,5-dihydro-5-oxo-4H-1,2,4-oxadiazol-3-yl)ethyl]-1-[(6-methyl-4,5,6,7-tetrahydrothiazolo[5,4-c]pyridin-2-yl)carbonyl]piperazine 4-[(5-Chloroindol-2-yl)sulfonyl]-2-[2-(2,5-dihydro-5-oxo-4H-1,2,4-oxadiazol-3-yl) ethyl]-1-[(6-methyl-4,5,6,7-tetrahydrooxazolo[5,4-c]pyridin-2-yl)carbonyl]piperazine 4-[(5-Ethynylindol-2-yl)sulfonyl]-2-[2-(2,5-dihydro-5-oxo-4H-1,2,4-oxadiazol-3-yl)ethyl]-1-[(6-methyl-4,5,6,7-tetrahydrooxazolo[5,4-c]pyridin-2-yl)carbonyl]piperazine 4-[(5-Chloroindol-2-yl)sulfonyl]-1-[(6-methyl-4,5,6,7-tetrahydrothiazolo [5,4-c]pyridin-2-yl)carbonyl]-2-[2-(2-oxo-3H-1,2,3,5-oxathiadiazol-4-yl)ethyl]piperazine 4-[(5-Ethynylindol-2-yl)sulfonyl]-1-[(6-methyl-4,5,6,7-tetrahydrothiazolo[5,4-c]pyridin-2-yl)carbonyl]-2-[2-(2-oxo-3H-1,2,3,5-oxathiadiazol-4-yl)ethyl]piperazine 4-[(5-Chloroindol-2-yl)sulfonyl]-1-[(6-methyl-4,5,6,7-tetrahydrooxazolo[5,4-c]pyridin-2-yl)carbonyl]-2-[2-(2-oxo-3H-1,2,3,5-oxathiadiazol-4-yl)ethyl]piperazine 4-[(5-Ethynylindol-2-yl)sulfonyl]-1-[(6-methyl-4,5,6,7-tetrahydrooxazolo[5,4-c]pyridin-2-yl)carbonyl]-2-[2-(2-oxo-3H-1,2,3,5-oxathiadiazol-4-yl)ethyl]piperazine 4-[(5-Chloroindol-2-yl)sulfonyl]-2-[2-(2,5-dihydro-5-oxo-4H-1,2,4-thiadiazol-3-yl)ethyl]-1-[(6-methyl-4,5,6,7-tetrahydrothiazolo[5,4-c]pyridin-2-yl)carbonyl]piperazine 2-[2-(2,5-dihydro-5-oxo-4H-1,2,4-thiadiazol-3-yl)ethyl]-4-[(5-ethynylindol-2-yl)sulfonyl]-1-[(6-methyl-4,5,6,7-tetrahydrothiazolo[5,4-c]pyridin-2-yl)carbonyl]piperazine 4-[(5-Chloroindol-2-yl)sulfonyl]-2-[2-(2,5-dihydro-5-oxo-4H-1,2,4-thiadiazol-3-yl)ethyl]-1-[(6-methyl-4,5,6,7-tetrahydrooxazolo[5,4-c]pyridin-2-yl)carbonyl]piperazine 2-[2-(2,5-Dihydro-5-oxo-4H-1,2,4-thiadiazol-3-yl)ethyl]-4-[(5-ethynylindol-2-yl)sulfonyl]-1-[(6-methyl-4,5,6,7-tetrahydrooxazolo[5,4-c]pyridin-2-yl)carbonyl]piperazine 4-[(5-Chloroindol-2-yl)sulfonyl]-2-[2-(2,5-dihydro-5-thioxo-4H-1,2,4-oxadiazol-3-yl)ethyl]-1-[(6-methyl-4,5,6,7-tetrahydrothiazolo[5,4-c]pyridin-2-yl)carbonyl]piperazine 2-[2-(2,5-Dihydro-5-thioxo-4H-1,2,4-oxadiazol-3-yl)ethyl]-4-[(5-ethynylindol-2-yl)sulfonyl]-1-[(6-methyl-4,5,6,7-tetrahydrothiazolo[5,4-c]pyridin-2-yl)carbonyl]piperazine 4-[(5-Chloroindol-2-yl)sulfonyl]-2-[2-(2,5-dihydro-5-thioxo-4H-1,2,4-oxadiazol-3-yl)ethyl]-1-[(6-methyl-4,5,6,7-tetrahydrooxazolo[5,4-c]pyridin-2-yl)carbonyl]piperazine 4-[(5-Ethynylindol-2-yl)sulfonyl]-2-[2-(2,5-dihydro-5-thioxo-4H-1,2,4-oxadiazol-3-yl)ethyl]-1-[(6-methyl-4,5,6,7-tetrahydrooxazolo[5,4-c]pyridin-2-yl)carbonyl]piperazine 1-[(5-Chloroindol-2-yl)sulfonyl]-2-[[N-(2-hydroxyethyl)carbamoyl]methyl]-4-[(6-methyl-4,5,6,7-tetrahydrooxazolo[5,4-c]pyridin-2-yl)carbonyl]piperazine 2-[[N,N-Bis(2-hydroxyethyl)carbamoyl]methyl]-4-[(5-chloroindol-2-yl)sulfonyl]-1-[(6-methyl-4,5,6,7-tetrahydrothiazolo[5,4-c]pyridin-2-yl)carbonyl]piperazine 2-[[N,N-Bis(2-hydroxyethyl)carbamoyl]methyl]-4-[(5-chloroindol-2-yl)sulfonyl]-1-[(6-methyl-4,5,6,7-tetrahydrooxazolo[5,4-c]pyridin-2-yl)carbonyl]piperazine 4-[(5-Chloroindol-2-yl)sulfonyl]-2-[[N-(2-methoxyethyl)carbamoyl]methyl]-4-[(6-methyl-4,5,6,7-tetrahydrothiazolo[5,4-c]pyridin-2-yl)carbonyl]piperazine 4-[(5-Chloroindol-2-yl)sulfonyl]-2-[[N-(2-methoxyethyl)carbamoyl]methyl]-4-[(6-methyl-4,5,6,7-tetrahydrooxazolo[5,4-c]pyridin-2-yl)carbonyl]piperazine 2-[[N,N-Bis(2-methoxyethyl)carbamoyl]methyl]-4-[(5-chloroindol-2-yl)sulfonyl]-1-[(6-methyl-4,5,6,7-tetrahydrothiazolo[5,4-c]pyridin-2-yl)carbonyl]piperazine 2-[[N,N-Bis(2-methoxyethyl)carbamoyl]methyl]-4-[(5-chloroindol-2-yl)sulfonyl]-1-[(6-methyl-4,5,6,7-tetrahydrooxazolo[5,4-c]pyridin-2-yl)carbonyl]piperazine 4-[(5-Chloroindol-2-yl)sulfonyl]-2-[[N-(2-hydroxyethyl)-N-methylcarbamoyl]methyl]-1-[(6-methyl-4,5,6,7-tetrahydrothiazolo[5,4-c]pyridin-2-yl)carbonyl]piperazine 4-[(5-Chloroindol-2-yl)sulfonyl]-2-[[N-(2-hydroxyethyl)-N-methylcarbamoyl]methyl]-1-[(6-methyl-4,5,6,7-tetrahydrooxazolo[5,4-c]pyridin-2-yl)carbonyl]piperazine 2-[[N-Benzyl-N-(2-hydroxyethyl)carbamoyl]methyl]-4-[(5-chloroindol-2-yl)sulfonyl]-1-[(6-methyl-4,5,6,7-tetrahydrothiazolo[5,4-c]pyridin-2-yl)carbonyl]piperazine 2-[[N-benzyl-N-(2-hydroxyethyl)carbamoyl]methyl]-4-[(5-chloroindol-2-yl)sulfonyl]-1-[(6-methyl-4,5,6,7-tetrahydrooxazolo[5,4-c]pyridin-2-yl)carbonyl]piperazine 4-[(5-Chloroindol-2-yl)sulfonyl]-2-(2-cyanoethyl)-1-[(6-methyl-4,5,6,7-tetrahydrothiazolo[5,4-c]pyridin-2-yl)carbonyl]piperazine 4-[(5-Chloroindol-2-yl)sulfonyl]-2-[(N-cyanomethyl-N-methylcarbamoyl)methyl]-1-[(6-methyl-4,5,6,7-tetrahydrothiazolo[5,4-c]pyridin-2-yl)carbonyl]piperazine 4-[(5-Chloroindol-2-yl)sulfonyl]-2-[(N-cyanomethyl-N-methylcarbamoyl)methyl]-1-[(6-methyl-4,5,6,7-tetrahydrooxazolo[5,4-c]pyridin-2-yl)carbonyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[2-[(morpholin-4-yl)carbonyl]ethyl]piperazine 4-[(5-Chloroindol-2-yl)sulfonyl]-2-[2-(dimethylaminocarbonyl)ethyl]-1-[(6-methyl-4,5,6,7-tetrahydrothiazolo[5,4-c]pyridin-2-yl)carbonyl]piperazine 4-[(5-Chloroindol-2-yl)sulfonyl]-1-[(6-methyl-4,5,6,7-tetrahydrothiazolo[5,4-c]pyridin-2-yl)carbonyl]-2-[2-[(pyridin-1-yl)carbonyl]ethyl]piperazine 4-[(5-Ethynylindol-2-yl)sulfonyl]-1-[(6-methyl-4,5,6,7-tetrahydrothiazolo[5,4-c]pyridin-2-yl)carbonyl]-2-[2-[(morpholin-4-yl)carbonyl]ethyl]piperazine 4-[(5-Ethynylindol-2-yl)sulfonyl]-2-[2-(dimethylaminocarbonyl)ethyl]-1-[(6-methyl-4,5,6,7-tetrahydrothiazolo[5,4-c]pyridin-2-yl)carbonyl]piperazine 4-[(5-Ethynylindol-2-yl)sulfonyl]-1-[(6-methyl-4,5,6,7-tetrahydrothiazolo[5,4-c]pyridin-2-yl)carbonyl]-2-[2-[(pyridin-1-yl)carbonyl]ethyl]piperazine 2-(3-Butynyl)-4-[(5-chloroindol-2-yl)sulfonyl]-4-[(6-methyl-4,5,6,7-tetrahydrothiazolo[5,4-c]pyridin-2-yl)carbonyl]piperazine 2-(3-Butynyl)-4-[(5-chloroindol-2-yl)sulfonyl]-4-[(6-methyl-4,5,6,7-tetrahydrooxazolo[5,4-c]pyridin-2-yl)carbonyl]piperazine 4-[(6-Chloro-3-hydroxybenzo[b]thien-2-yl)sulfonyl]-1-[(6-methyl-4,5,6,7-tetrahydrothiazolo[5,4-c]pyridin-2-yl)carbonyl]-2-[(morpholin-4-ylcarbonyl)methyl]piperazine 4-[(6-Chloro-3-hydroxybenzo[b]thien-2-yl)sulfonyl]-1-[(6-methyl-4,5,6,7-tetrahydrooxazolo[5,4-c]pyridin-2-yl)carbonyl]-2-[(morpholin-4-ylcarbonyl)methyl]piperazine 4-[(6-Chloro-3-hydroxybenzo[b]thien-2-yl)sulfonyl]-1-[(6-methyl-4,5,6,7-tetrahydrothiazolo[5,4-c]pyridin-2-yl)carbonyl]-2-(N,N-dimethylcarbamoylmethyl)piperazine 4-[(6-Chloro-3-hydroxybenzo[b]thien-2-yl)sulfonyl]-1-[(6-methyl-4,5,6,7-tetrahydrooxazolo[5,4-c]pyridin-2-yl)carbonyl]-2-(N,N-dimethylcarbamoylmethyl)piperazine 4-[(6-Chloro-3-hydroxybenzo[b]thien-2-yl)sulfonyl]-1-[(6-methyl-4,5,6,7-tetrahydrothiazolo[5,4-c]pyridin-2-yl)carbonyl]-2-(2-cyanoethyl)piperazine 4-[(6-Chloro-3-hydroxybenzo[b]thien-2-yl)sulfonyl]-1-[(6-methyl-4,5,6,7-tetrahydrooxazolo[5,4-c]pyridin-2-yl)carbonyl]-2-(2-cyanoethyl)piperazine 4-[(3-Acetyl-6-chlorobenzo[b]thien-2-yl)sulfonyl]-1-[(6-methyl-4,5,6,7-tetrahydrothiazolo[5,4-c]pyridin-2-yl)carbonyl]-2-[(morpholin-4-ylcarbonyl)methyl]piperazine 4-[(3-Acetyl-6-chlorobenzo[b]thien-2-yl)sulfonyl]-1-[(6-methyl-4,5,6,7-tetrahydrooxazolo[5,4-c]pyridin-2-yl)carbonyl]-2-[(morpholin-4-ylcarbonyl)methyl]piperazine 4-[(3-Acetyl-6-chlorobenzo[b]thien-2-yl)sulfonyl]-1-[(6-methyl-4,5,6,7-tetrahydrothiazolo[5,4-c]pyridin-2-yl)carbonyl]-2-(N,N-dimethylcarbamoylmethyl)piperazine 4-[(3-Acetyl-6-chlorobenzo[b]thien-2-yl)sulfonyl]-1-[(6-methyl-4,5,6,7-tetrahydrooxazolo[5,4-c]pyridin-2-yl)carbonyl]-2-(N,N-dimethylcarbamoylmethyl)piperazine 4-[(3-Acetyl-6-chlorobenzo[b]thien-2-yl)sulfonyl]-1-[(6-methyl-4,5,6,7-tetrahydrothiazolo[5,4-c]pyridin-2-yl)carbonyl]-2-(2-cyanoethyl)piperazine 4-[(3-Acetyl-6-chlorobenzo[b]thien-2-yl)sulfonyl]-1-[(6-methyl-4,5,6,7-tetrahydrooxazolo[5,4-c]pyridin-2-yl)carbonyl]-2-(2-cyanoethyl)piperazine 4-[(6-Chloro-3-(hydroxymethyl)benzo[b]thien-2-yl)sulfonyl]-1-[(6-methyl-4,5,6,7-tetrahydrothiazolo[5,4-c]pyridin-2-yl) carbonyl]-2-[(morpholin-4-ylcarbonyl)methyl]piperazine 4-[(6-Chloro-3-(hydroxymethyl)benzo[b]thien-2-yl)sulfonyl]-1-[(6-methyl-4,5,6,7-tetrahydrooxazolo[5,4-c]pyridin-2-yl)carbonyl]-2-[(morpholin-4-ylcarbonyl)methyl]piperazine 4-[(6-Chloro-3-(hydroxymethyl)benzo[b]thien-2-yl)sulfonyl]-1-[(6-methyl-4,5,6,7-tetrahydrothiazolo[5,4-c]pyridin-2-yl)carbonyl]-2-(N,N-dimethylcarbamoylmethyl)piperazine 4-[(6-Chloro-3-(hydroxymethyl)benzo[b]thien-2-yl)sulfonyl]-1-[(6-methyl-4,5,6,7-tetrahydrooxazolo[5,4-c]pyridin-2-yl)carbonyl]-2-(N,N-dimethylcarbamoylmethyl)piperazine 4-[(6-Chloro-3-(hydroxymethyl)benzo[b]thien-2-yl)sulfonyl]-1-[(6-methyl-4,5,6,7-tetrahydrothiazolo[5,4-c]pyridin-2-yl)carbonyl]-2-(2-cyanoethyl)piperazine 4-[(6-Chloro-3-(hydroxymethyl)benzo[b]thien-2-yl)sulfonyl]-1-[(6-methyl-4,5,6,7-tetrahydrooxazolo[5,4-c]pyridin-2-yl)carbonyl]-2-(2-cyanoethyl)piperazine 4-[(6-Chloro-3-(N,N-dimethylaminomethyl)benzo[b]thien-2-yl)sulfonyl]-1-[(6-methyl-4,5,6,7-tetrahydrothiazolo[5,4-c]pyridin-2-yl)carbonyl]-2-[(morpholin-4-ylcarbonyl)methyl]piperazine 4-[(6-Chloro-3-(N,N-dimethylaminomethyl)benzo[b]thien-2-yl)sulfonyl]-1-[(6-methyl-4,5,6,7-tetrahydrooxazolo[5,4-c]pyridin-2-yl)carbonyl]-2-[(morpholin-4-ylcarbonyl)methyl]piperazine 4-[(6-Chloro-3-(N,N-dimethylaminomethyl)benzo[b]thien-2-yl)sulfonyl]-1-[(6-methyl-4,5,6,7-tetrahydrothiazolo[5,4-c]pyridin-2-yl)carbonyl]-2-(N,N-dimethylcarbamoylmethyl)piperazine 4-[(6-Chloro-3-(N,N-dimethylaminomethyl)benzo[b]thien-2-yl)sulfonyl]-1-[(6-methyl-4,5,6,7-tetrahydrooxazolo[5,4-c]pyridin-2-yl)carbonyl]-2-(N,N-dimethylcarbamoylmethyl)piperazine 4-[(6-Chloro-3-(N,N-dimethylaminomethyl)benzo[b]thien-2-yl)sulfonyl]-1-[(6-methyl-4,5,6,7-tetrahydrothiazolo[5,4-c]pyridin-2-yl)carbonyl]-2-(2-cyanoethyl)piperazine 4-[(6-Chloro-3-(N,N-dimethylaminomethyl)benzo[b]thien-2-yl)sulfonyl]-1-[(6-methyl-4,5,6,7-tetrahydrooxazolo[5,4-c]pyridin-2-yl)carbonyl]-2-(2-cyanoethyl)piperazine 4-[(6-Chloro-3-(cyanomethyl)benzo[b]thien-2-yl)sulfonyl]-1-[(6-methyl-4,5,6,7-tetrahydrothiazolo[5,4-c]pyridin-2-yl)carbonyl]-2-[(morpholin-4-ylcarbonyl)methyl]piperazine 4-[(6-Chloro-3-(cyanomethyl)benzo[b]thien-2-yl)sulfonyl]-1-[(6-methyl-4,5,6,7-tetrahydrooxazolo[5,4-c]pyridin-2-yl)carbonyl]-2-[(morpholin-4-ylcarbonyl)methyl]piperazine 4-[(6-Chloro-3-(cyanomethyl)benzo[b]thien-2-yl)sulfonyl]-1-[(6-methyl-4,5,6,7-tetrahydrothiazolo[5,4-c]pyridin-2-yl)carbonyl]-2-(N,N-dimethylcarbamoylmethyl)piperazine 4-[(6-Chloro-3-(cyanomethyl)benzo[b]thien-2-yl)sulfonyl]-1-[(6-methyl-4,5,6,7-tetrahydrooxazolo[5,4-c]pyridin-2-yl)carbonyl]-2-(N,N-dimethylcarbamoylmethyl)piperazine 4-[(6-Chloro-3-(cyanomethyl)benzo[b]thien-2-yl)sulfonyl]-1-[(6-methyl-4,5,6,7-tetrahydrothiazolo[5,4-c]pyridin-2-yl)carbonyl]-2-(2-cyanoethyl)piperazine 4-[(6-Chloro-3-(cyanomethyl)benzo[b]thien-2-yl)sulfonyl]-1-[(6-methyl-4,5,6,7-tetrahydrooxazolo[5,4-c]pyridin-2-yl)carbonyl]-2-(2-cyanoethyl)piperazine 4-[(6-Chloro-3-(carbamoylmethyl)benzo[b]thien-2-yl)sulfonyl]-1-[(6-methyl-4,5,6,7-tetrahydrothiazolo[5,4-c]pyridin-2-yl)carbonyl]-2-[(morpholin-4-ylcarbonyl)methyl]piperazine 4-[(6-Chloro-3-(carbamoylmethyl)benzo[b]thien-2-yl)sulfonyl]-1-[(6-methyl-4,5,6,7-tetrahydrooxazolo[5,4-c]pyridin-2-yl)carbonyl]-2-[(morpholin-4-ylcarbonyl)methyl]piperazine 4-[(6-Chloro-3-(carbamoylmethyl)benzo[b]thien-2-yl)sulfonyl]-1-[(6-methyl-4,5,6,7-tetrahydrothiazolo[5,4-c]pyridin-2-yl)carbonyl]-2-(N,N-dimethylcarbamoylmethyl)piperazine 4-[(6-Chloro-3-(carbamoylmethyl)benzo[b]thien-2-yl)sulfonyl]-1-[(6-methyl-4,5,6,7-tetrahydrooxazolo[5,4-c]pyridin-2-yl)carbonyl]-2-(N,N-dimethylcarbamoylmethyl)piperazine 4-[(6-Chloro-3-(carbamoylmethyl)benzo[b]thien-2-yl)sulfonyl]-1-[(6-methyl-4,5,6,7-tetrahydrothiazolo[5,4-c]pyridin-2-yl)carbonyl]-2-(2-cyanoethyl)piperazine 4-[(6-Chloro-3-(carbamoylmethyl)benzo[b]thien-2-yl)sulfonyl]-1-[(6-methyl-4,5,6,7-tetrahydrooxazolo[5,4-c]pyridin-2-yl)carbonyl]-2-(2-cyanoethyl)piperazine 4-[(5-Chloro-3-hydroxyindol-2-yl)sulfonyl]-1-[(6-methyl-4,5,6,7-tetrahydrooxazolo[5,4-c]pyridin-2-yl)carbonyl]-2-[(morpholin-4-ylcarbonyl)methyl]piperazine 4-[(5-Chloro-3-hydroxyindol-2-yl)sulfonyl]-1-[(6-methyl-4,5,6,7-tetrahydrothiazolo[5,4-c]pyridin-2-yl)carbonyl]-2-[(morpholin-4-ylcarbonyl)methyl]piperazine 4-[(5-Chloro-3-hydroxyindol-2-yl)sulfonyl]-1-[(6-hydroxymethyl-4,5,6,7-tetrahydrothiazolo[5,4-c]pyridin-2-yl)carbonyl]-2-[(morpholin-4-ylcarbonyl)methyl]piperazine 1-[(5-Chloro-3-hydroxyindol-2-yl)sulfonyl]-4-[(6-hydroxymethyl-4,5,6,7-tetrahydrothiazolo[5,4-c]pyridin-2-yl)carbonyl]piperazine 4-[(5-Chloro-3-hydroxyindol-2-yl)sulfonyl]-1-[(6-methyl-4,5,6,7-tetrahydrooxazolo[5,4-c]pyridin-2-yl)carbonyl]-2-(N,N-dimethylcarbamoylmethyl)piperazine 4-[(5-Chloro-3-hydroxyindol-2-yl)sulfonyl]-1-[(6-methyl-4,5,6,7-tetrahydrothiazolo[5,4-c]pyridin-2-yl)carbonyl]-2-(N,N-dimethylcarbamoylmethyl)piperazine 4-[(5-Chloro-3-hydroxyindol-2-yl)sulfonyl]-1-[(6-methyl-4,5,6,7-tetrahydrooxazolo[5,4-c]pyridin-2-yl)carbonyl]-2-(2-cyanoethyl)piperazine 4-[(5-Chloro-3-hydroxyindol-2-yl)sulfonyl]-1-[(6-methyl-4,5,6,7-tetrahydrothiazolo[5,4-c]pyridin-2-yl)carbonyl]-2-(2-cyanoethyl)piperazine 4-[(3-Acetyl-5-chloroindol-2-yl)sulfonyl]-1-[(6-methyl-4,5,6,7-tetrahydrooxazolo[5,4-c]pyridin-2-yl)carbonyl]-2-[(morpholin-4-ylcarbonyl)methyl]piperazine 4-[(3-Acetyl-5-chloroindol-2-yl)sulfonyl]-1-[(6-methyl-4,5,6,7-tetrahydrothiazolo[5,4-c]pyridin-2-yl)carbonyl]-2-[(morpholin-4-ylcarbonyl)methyl]piperazine 4-[(3-Acetyl-5-chloroindol-2-yl)sulfonyl]-1-[(6-methyl-4,5,6,7-tetrahydrooxazolo[5,4-c]pyridin-2-yl)carbonyl]-2-(N,N-dimethylcarbamoylmethyl)piperazine 4-[(3-Acetyl-5-chloroindol-2-yl)sulfonyl]-1-[(6-methyl-4,5,6,7-tetrahydrothiazolo[5,4-c]pyridin-2-yl)carbonyl]-2-(N,N-dimethylcarbamoylmethyl)piperazine 4-[(3-Acetyl-5-chloroindol-2-yl)sulfonyl]-1-[(6-methyl-4,5,6,7-tetrahydrooxazolo[5,4-c]pyridin-2-yl)carbonyl]-2-(2-cyanoethyl)piperazine 4-[(3-Acetyl-5-chloroindol-2-yl)sulfonyl]-1-[(6-methyl-4,5,6,7-tetrahydrothiazolo[5,4-c]pyridin-2-yl)carbonyl]-2-(2-cyanoethyl)piperazine 4-[(5-Chloro-3-(hydroxymethyl)indol-2-yl)sulfonyl]-1-[(6-methyl-4,5,6,7-tetrahydrooxazolo[5,4-c]pyridin-2-yl)carbonyl]-2-[(morpholin-4-ylcarbonyl)methyl]piperazine 4-[(5-Chloro-3-(hydroxymethyl)indol-2-yl)sulfonyl]-1-[(6-methyl-4,5,6,7-tetrahydrothiazolo[5,4-c]pyridin-2-yl)carbonyl]-2-[(morpholin-4-ylcarbonyl)methyl]piperazine 4-[(5-Chloro-3-(hydroxymethyl)indol-2-yl)sulfonyl]-1-[(6-methyl-4,5,6,7-tetrahydrooxazolo[5,4-c]pyridin-2-yl)carbonyl]-2-(N,N-dimethylcarbamoylmethyl)piperazine 4-[(5-Chloro-3-(hydroxymethyl)indol-2-yl)sulfonyl]-1-[(6-methyl-4,5,6,7-tetrahydrothiazolo[5,4-c]pyridin-2-yl)carbonyl]-2-(N,N-dimethylcarbamoylmethyl)piperazine 4-[(5-Chloro-3-(hydroxymethyl)indol-2-yl)sulfonyl]-1-[(6-methyl-4,5,6,7-tetrahydrooxazolo[5,4-c]pyridin-2-yl)carbonyl]-2-(2-cyanoethyl)piperazine 4-[(5-Chloro-3-(hydroxymethyl)indol-2-yl)sulfonyl]-1-[(6-methyl-4,5,6,7-tetrahydrothiazolo[5,4-c]pyridin-2-yl)carbonyl]-2-(2-cyanoethyl)piperazine 4-[(5-Chloro-3-(N,N-dimethylaminomethyl)indol-2-yl)sulfonyl]-1-[(6-methyl-4,5,6,7-tetrahydrooxazolo[5,4-c]pyridin-2-yl)carbonyl]-2-[(morpholin-4-ylcarbonyl)methyl]piperazine 4-[(5-Chloro-3-(N,N-dimethylaminomethyl)indol-2-yl)sulfonyl]-1-[(6-methyl-4,5,6,7-tetrahydrothiazolo[5,4-c]pyridin-2-yl)carbonyl]-2-[(morpholin-4-ylcarbonyl)methyl]piperazine 4-[(5-Chloro-3-(N,N-dimethylaminomethyl)indol-2-yl)sulfonyl]-1-[(6-methyl-4,5,6,7-tetrahydrooxazolo[5,4-c]pyridin-2-yl)carbonyl]-2-(N,N-dimethylcarbamoylmethyl)piperazine 4-[(5-Chloro-3-(N,N-dimethylaminomethyl)indol-2-yl)sulfonyl]-1-[(6-methyl-4,5,6,7-tetrahydrothiazolo[5,4-c]pyridin-2-yl)carbonyl]-2-(N,N-dimethylcarbamoylmethyl)piperazine 4-[(5-Chloro-3-(N,N-dimethylaminomethyl)indol-2-yl)sulfonyl]-1-[(6-methyl-4,5,6,7-tetrahydrooxazolo[5,4-c]pyridin-2-yl)carbonyl]-2-(2-cyanoethyl)piperazine 4-[(5-Chloro-3-(N,N-dimethylaminomethyl)indol-2-yl)sulfonyl]-1-[(6-methyl-4,5,6,7-tetrahydrothiazolo[5,4-c]pyridin-2-yl)carbonyl]-2-(2-cyanoethyl)piperazine 4-[(5-Chloro-3-(cyanomethyl)indol-2-yl)sulfonyl]-1-[(6-methyl-4,5,6,7-tetrahydrooxazolo[5,4-c]pyridin-2-yl)carbonyl]-2-[(morpholin-4-ylcarbonyl)methyl]piperazine 4-[(5-Chloro-3-(cyanomethyl)indol-2-yl)sulfonyl]-1-[(6-methyl-4,5,6,7-tetrahydrothiazolo[5,4-c]pyridin-2-yl)carbonyl]-2-[(morpholin-4-ylcarbonyl)methyl]piperazine 4-[(5-Chloro-3-(cyanomethyl)indol-2-yl)sulfonyl]-1-[(6-methyl-4,5,6,7-tetrahydrooxazolo[5,4-c]pyridin-2-yl)carbonyl]-2-(N,N-dimethylcarbamoylmethyl)piperazine 4-[(5-Chloro-3-(cyanomethyl)indol-2-yl)sulfonyl]-1-[(6-methyl-4,5,6,7-tetrahydrothiazolo[5,4-c]pyridin-2-yl)carbonyl]-2-(N,N-dimethylcarbamoylmethyl)piperazine 4-[(5-Chloro-3-(cyanomethyl)indol-2-yl)sulfonyl]-1-1(6-methyl-4,5,6,7-tetrahydrooxazolo[5,4-c]pyridin-2-yl)carbonyl]-2-(2-cyanoethyl)piperazine 4-[(5-Chloro-3-(cyanomethyl)indol-2-yl)sulfonyl]-1-[(6-methyl-4,5,6,7-tetrahydrothiazolo[5,4-c]pyridin-2-yl)carbonyl]-2-(2-cyanoethyl)piperazine 4-[(5-Chloro-3-(carbamoylmethyl)indol-2-yl)sulfonyl]-1-[(6-methyl-4,5,6,7-tetrahydrooxazolo[5,4-c]pyridin-2-yl)carbonyl]-2-[(morpholin-4-ylcarbonyl)methyl]piperazine 4-[(5-Chloro-3-(carbamoylmethyl)indol-2-yl)sulfonyl]-1-[(6-methyl-4,5,6,7-tetrahydrothiazolo[5,4-c]pyridin-2-yl)carbonyl]-2-[(morpholin-4-ylcarbonyl)methyl]piperazine 4-[(5-Chloro-3-(carbamoylmethyl)indol-2-yl)sulfonyl]-1-[(6-methyl-4,5,6,7-tetrahydrooxazolo[5,4-c]pyridin-2-yl)carbonyl]-2-(N,N-dimethylcarbamoylmethyl)piperazine 4-[(5-Chloro-3-(carbamoylmethyl)indol-2-yl)sulfonyl]-1-[(6-methyl-4,5,6,7-tetrahydrothiazolo[5,4-c]pyridin-2-yl)carbonyl]-2-(N,N-dimethylcarbamoylmethyl)piperazine 4-[(5-Chloro-3-(carbamoylmethyl)indol-2-yl)sulfonyl]-1-[(6-methyl-4,5,6,7-tetrahydrooxazolo[5,4-c]pyridin-2-yl)carbonyl]-2-(2-cyanoethyl)piperazine 4-[(5-Chloro-3-(carbamoylmethyl)indol-2-yl)sulfonyl]-1-[(6-methyl-4,5,6,7-tetrahydrothiazolo[5,4-c]pyridin-2-yl)carbonyl]-2-(2-cyanoethyl)piperazine 4-[(5-Chloro-1-hydroxyindol-2-yl)sulfonyl]-1-[(6-methyl-4,5,6,7-tetrahydrothiazolo[5,4-c]pyridin-2-yl)carbonyl]-2-[(morpholin-4-yl)carbonylmethyl]piperazine 4-[(5-Chloro-1-hydroxyindol-2-yl)sulfonyl]-1-[(6-methyl-4,5,6,7-tetrahydrooxazolo[5,4-c]pyridin-2-yl)carbonyl]-2-[(morpholin-4-yl)carbonylmethyl]piperazine 4-[(5-Chloro-1-methoxyindol-2-yl)sulfonyl]-1-[(6-methyl-4,5,6,7-tetrahydrothiazolo[5,4-c]pyridin-2-yl)carbonyl]-2-[(morpholin-4-yl)carbonylmethyl]piperazine 4-[(5-Chloro-1-methoxyindol-2-yl)sulfonyl]-1-[(6-methyl-4,5,6,7-tetrahydrooxazolo[5,4-c]pyridin-2-yl)carbonyl]-2-[(morpholin-4-yl)carbonylmethyl]piperazine 4-[4-[(6-Chloro-1-hydroxyindol-2-yl)sulfonyl]-1-[(6-methyl-4,5,6,7-tetrahydrothiazolo[5,4-c]pyridin-2-yl)carbonyl]-2-[(morpholin-4-yl)carbonylmethyl]piperazine 4-[4-[(6-Chloro-1-hydroxyindol-2-yl)sulfonyl]-1-[(6-methyl-4,5,6,7-tetrahydrooxazolo[5,4-c]pyridin-2-yl)carbonyl]-2-[(morpholin-4-yl)carbonylmethyl]piperazine 4-[4-[(6-chloro-1-methoxyindol-2-yl)sulfonyl]-1-[(6-methyl-4,5,6,7-tetrahydrothiazolo[5,4-c]pyridin-2-yl)carbonyl]-2-[(morpholin-4-yl)carbonylmethyl]piperazine 4-[4-[(6-Chloro-1-methoxyindol-2-yl)sulfonyl]-1-[(6-methyl-4,5,6,7-tetrahydrooxazolo[5,4-c]pyridin-2-yl)carbonyl]-2-[(morpholin-4-yl)carbonylmethyl]piperazine In the present invention, in addition to the above-exemplified compounds, salts thereof and solvates thereof can be mentioned as preferred examples.

The process for the preparation of the sulfonyl derivative of the present invention will next be described.

The sulfonyl derivative or salt thereof, or solvate thereof according to the present invention can be prepared by using general, conventionally-known chemical processes in combination. Typical synthesis processes will be described subsequently.

Upon synthesis of the sulfonyl derivative of the present invention, when it is necessary to protect a substituent such as nitrogen atom, hydroxyl group or carboxyl group, it may be protected with an ordinary, conventionally-known protecting group which can be removed as needed. Such a protecting group can be removed at need by the synthesis process ordinarily employed in the organic chemistry which will be described below.

The starting materials necessary for the synthesis can be obtained by the synthesis process ordinarily employed in the organic chemistry and such a process will be described in Referential Examples. The starting materials for the sulfonyl derivative of the present invention can also be synthesized by the application of the process described in Referential Examples.

A description will next be made of a protecting group for the substituent such as nitrogen atom, hydroxyl group or carboxyl group and deprotection process thereof.

As a protecting group for the nitrogen atom in an amino or alkylamino group, ordinary acyl-type protecting groups are suited. Examples include alkanoyl groups such as acetyl, alkoxycarbonyl groups such as methoxycarbonyl, ethoxycarbonyl and tertiary butoxy carbonyl, arylmethoxycarbonyl groups such as benzyloxycarbonyl, paramethoxybenzyloxycarbonyl and para- (ortho-)nitrobenzyloxycarbonyl groups, arylmethyl groups such as benzyl and triphenylmethyl and aroyl groups such as benzoyl. The removing process of such a protecting group differs with the chemical properties of the protecting group adopted. For example, the acyl-type protecting group such as alkanoyl, alkoxycarbonyl or aroyl can be removed by hydrolysis using an appropriate base such as alkali metal hydroxide, for example, lithium hydroxide, sodium hydroxide or potassium hydroxide.

The substituted methoxycarbonyl type protecting group such as tertiary butoxycarbonyl or paramethoxybenzyloxycarbonyl can be removed by using an appropriate acid, for example, acetic acid, hydrochloric acid, hydrobromic acid, sulfuric acid, phosphoric acid, trifluoroacetic acid or trifluoromethanesulfonic acid or combination thereof. The arylmethoxycarbonyl group such as benzyloxycarbonyl, paramethoxybenzyloxycarbonyl or para- (ortho-) nitrobenzyloxycarbonyl, or the arylmethyl group such as benzyl can be removed by hydrogenolysis in the presence of a palladium-carbon catalyst. The benzyl group can also be removed by Birch reduction, in liquid ammonia, in the presence of a metal sodium, whereby conversion into a nitrogen-hydrogen bond can be effected. The triphenylmethyl group can be removed by using an appropriate acid such as formic acid, acetic acid, hydrochloric acid, hydrobromic acid, sulfuric acid, phosphoric acid, trifluoroacetic acid or trifluoromethanesulfonic acid or combination thereof. It can also be removed by Birch reduction, in liquid ammonia, in the presence of a metal sodium or by hydrogenolysis in the presence of a palladium-carbon catalyst.

In addition to the above-described amino-protecting group, a phthaloyl type protecting group can be adopted for a primary amino group and it can be removed using hydrazine, dimethylaminopropylamine or the like. The amino group can also be protected with the nitrogen atom of indole, a phenylsulfonyl group, a toluenesulfonyl group, an acetyl group, a trifluoroacetyl group or the like and deprotection can be carried out by hydrolysis using a proper base such as sodium hydroxide, lithium hydroxide or potassium hydroxide.

As the protecting group suited for a hydroxyl group, there are acyl type and ether type ones. Examples of the acyl type protecting group include alkanoyl groups such as acetyl and aroyl groups such as benzoyl, while those of the ether type protecting group include arylmethyl groups such as benzyl, silyl ether groups such as tertiary butyl dimethylsilyl, methoxymethyl and tetrahydropyranyl. The removal of such a protecting group differs with the chemical properties of the protecting group adopted. For example, the acyl group such as alkanoyl or aroyl can be removed by the hydrolysis using an appropriate base such as an alkali metal hydroxide, for example, lithium hydroxide, sodium hydroxide or potassium hydroxide. The arylmethyl type protecting group can be removed by the hydrogenolysis using a palladium-carbon catalyst. The silyl group such as tertiary butyl dimethylsilyl can be removed using a salt of hydrofluoride such as tetrabutyl ammonium fluoride. The methoxymethyl or tetrahydropyranyl group can be removed using acetic acid, hydrochloric acid or the like. The hydroxyl group substituted for an aryl group can be protected with a methyl group and deprotection can be carried out using a Lewis acid such as aluminum chloride, boron trifluoride or phosphorus tribromide, trimethylsilyl iodide or hydrogen bromide.

A carboxyl group can be protected by the esterification of it. A methyl or ethyl ester can be deprotected by the hydrolysis using an appropriate base such as alkali metal hydroxide, e.g., lithium hydroxide, sodium hydroxide or potassium hydroxide, while from a tertiary butyl ester, the tertiary butyl group can be removed by treating with trifluoroacetic acid or hydrochloric acid. From an arylmethyl type ester such as benzyl, the arylmethyl group can be removed by the hydrogenolysis in the presence of a palladium-carbon catalyst.

As the protecting group for acetylene, an alkylsilyl group such as trimethylsilyl, tertiary-butyldimethylsilyl or tertiary-butyldiphenylsilyl can be employed and deprotection can be carried out using a proper base, for example, an alkali metal hydroxide such as sodium hydroxide, lithium hydroxide or potassium hydroxide or a salt of hydrofluoride such as tetrabutylammonium fluoride or pyridine hydrofluoride.

[Preparation Process-1]

A process for preparing a sulfonyl derivative represented by the following formula (I):

[wherein $Q^1$, $Q^2$, $Q^3$, $Q^4$ and $T^1$ have the same meanings as described above], which comprises sulfonylating the nitrogen atom of $Q^{3a}$ of the compound represented by the following formula (Ia):

[wherein $Q^1$, $Q^2$ and $T^1$ have the same meanings as described above and $Q^{3a}$ represents any one of the groups represented by the following formulas:

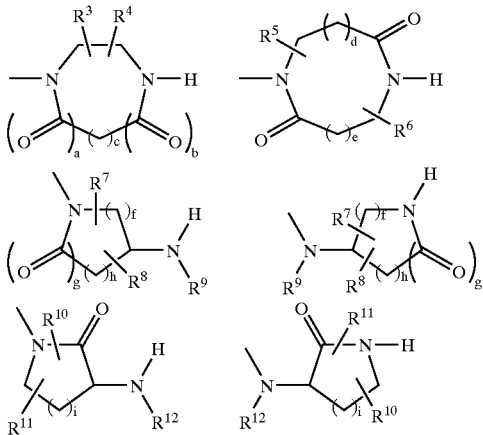

(in which $R^3$, $R^4$, $R^5$, $R^6$, $R^7$, $R^8$, $R^9$, $R^{10}$, $R^{11}$, $R^{12}$, a, b, c, d, e, f, g, h and i have the same meanings as described above)] with a sulfonic acid halide represented by the following formula (IIa):

$$\text{Halo-SO}_2\text{—Q}^A \qquad \text{(IIa)}$$

[wherein $Q^A$ has the same meaning as described above and Halo represents a halogen atom such as chlorine, bromine or iodine].

<Synthesis of the compound of the Formula (Ia)>

The compound of the formula (Ia) can be synthesized by a series of procedures in accordance with the known technique.

For example, a compound of the following formula (Ib):

$$Q^1\text{—}Q^2\text{—}T^1\text{—}Q^{3b} \qquad \text{(Ib)}$$

[wherein $Q^1$, $Q^2$ and $T^1$ have the same meanings as described above and $Q^{3b}$ represents any one of the following groups:

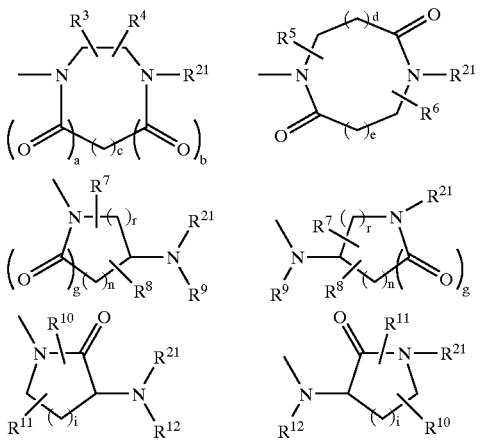

(wherein $R^3$, $R^4$, $R^5$, $R^6$, $R^7$, $R^8$, $R^9$, $R^{10}$, $R^{11}$, $R^{12}$, a, b, c, d, e, f, g, h and i have the same meanings as described above and $R^{21}$ represents an ordinary nitrogen protecting group such as tertiary butoxycarbonyl, benzyloxycarbonyl, paramethoxybenzyloxycarbonyl, paranitrobenzyloxycarbonyl or benzyl)] can be synthesized by acylating the nitrogen atom of the compound—which can be synthesized in a conventionally known manner or by application thereof and is represented by the following formula (IIIa):

$$Q^{3b}\text{—H} \qquad \text{(IIIa)}$$

(wherein $Q^{3b}$ has the same meaning as described above)—to which the hydrogen atom of $Q^{3b}$ has been bonded, with a carboxylic acid in an activated form represented by any one of the following formulas (Iva) to (Ivd):

| | |
|---|---|
| $Q^1\text{—}Q^{2b}\text{—COOH}$ | (IVa) |
| $Q^1\text{—N(R}^{20})\text{—(CH}_2)_{m1}\text{—COOH}$ | (IVb) |
| $Q^1\text{—O—(CH}_2)_{m1}\text{—COOH}$ | (IVc) |
| $Q^1\text{—S—(CH}_2)_{m1}\text{—COOH}$ | (IVd) |

[wherein $Q^1$ has the same meaning as described above, $R^{20}$ represents an ordinary nitrogen protecting group such as linear or branched alkylkylene, tertiary butoxycarbonyl, benzyloxycarbonyl, paramethoxybenzyloxycarbonyl, paranitrobenzyloxycarbonyl or benzyl, $Q^{2b}$ represents a single bond, a linear or branched $C_{1-6}$ alkylene, a linear or branched $C_{2-6}$ alkenylene, a linear or branched $C_{2-6}$ alkynylene or a group of the following formula:

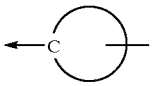

(which has the same meaning as described above) and m1 stands for an integer of 1 to 6].

When the nitrogen atom of $Q^{3b}$ of the compound represented by the formula (IIIa) forms an amide bond, the compound of the formula (Ib) can be synthesized by alkylating the nitrogen atom of $Q^{3b}$ of the compound represented by the formula (IIIa) with any one of the compounds represented by the following formulas (Va) to (Vd):

| | |
|---|---|
| $Q^1\text{—}Q^{2b}\text{—CHL}^1R^{13}$ | (Va) |
| $Q^1\text{—N(R}^{20})\text{—(CH}_2)_{m1}\text{—CHL}^1R^{13}$ | (Vb) |
| $Q^1\text{—O—(CH}_2)_{m1}\text{—CHL}^1R^{13}$ | (Vc) |
| $Q^1\text{—S—(CH}_2)_{m1}\text{—CHL}^1R^{13}$ | (Vd) |

[wherein $Q^1$, $Q^{2b}$, $R^{13}$, $R^{20}$ and m1 have the same meanings as described above, and $L^1$ represents an eliminating group frequently used in the organic chemistry, such as chlorine, bromine, iodine, methylsulfonyloxy or paratoluenesulfonyloxy].

When the nitrogen atom of $Q^{3b}$ of the compound represented by the formula (IIIa) exists as a primary or secondary amine, the compound of the formula (Ib) can be prepared by reductive alkylation, that is, by forming the corresponding imine with a carbonyl compound represented by any one of the following formulas (VIa) to (VId):

| | |
|---|---|
| $Q^1\text{—}Q^{2b}\text{—C(=O)R}^{13}$ | (VIa) |
| $Q^1\text{—N(R}^{20})\text{—(CH}_2)_{m1}\text{—C(=O) R}^{13}$ | (VIb) |
| $Q^1\text{—O—(CH}_2)_{m1}\text{—C(=O)R}^{13}$ | (VIc) |
| $Q^1\text{—S—(CH}_2)_{m1}\text{—C(=O)R}^{13}$ | (VId) |

[wherein $Q^1$, $Q^{2b}$, $R^{13}$, $R^{20}$ and m1 have the same meanings as described above], followed by reduction; by reacting the compound of the formula (IIIa) with a reagent such as phosgene, triphosgene or 1,1'-carbonyldiimidazole and a compound containing a primary amine represented by any one of the following formulas (VIIa) to (VIId) or formula (VIIe):

  (VIIa)

  (VIIb)

  (VIIc)

  (VIId)

  (VIIe)

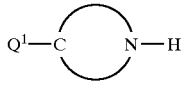

wherein $Q^1$, $Q^{2b}$ and $R^{20}$ have the same meanings as described above and m2 stands for an integer of 2 to 6 and a group of the following formula:

represents a 5- or 6-membered heterocyclic group which may have a substituent)], thereby forming the corresponding urea derivative; or by reacting the amine of the formula (IIIa) with an isocyanate derivative or an isocyanate prepared from a carboxylic acid represented by any one of the formulas (IVa) to (IVd).

When in the structure of $Q^1$ of the compound represented by the formula (Ib), a halogen- or trifluoromethanesulfonyloxy-substituted aryl group or a halogen- or trifluoromethanesulfonyloxy-substituted alkenyl group is contained, coupling reaction can be effected with a boric-acid-substituted aryl compound in the presence of a transition metal catalyst.

When in the structure of $Q^1$ of the compound represented by the formula (Ib), an alkenyl group or boric-acid-substituted alkenyl group is contained, it can be subjected to coupling reaction with a halogen- or trifluoromethanesulfonyloxy-substituted aryl group in the presence of a transition metal catalyst.

When in the structure of $Q^1$ of the compound represented by the formula (Ib), a boric-acid-substituted aryl group is contained, it can be subjected to coupling reaction with a halogen- or trifluoromethanesulfonyloxy-substituted aryl compound or a halogen- or trifluoromethanesulfonyloxy-substituted alkenyl compound. When in the structure of $Q^1$ of the compound represented by the formula (Ib), a halogen- or trifluoromethanesulfonyloxy-substituted aryl group is contained, it can be subjected to coupling reaction with an alkenyl compound in the presence of a transition metal catalyst, whereby the compound of the formula (Ib) can be obtained. If the nitrogen atom of $Q^{3b}$ of the compound (Ib) so obtained has been protected, the compound of the formula (Ia) can be obtained by deprotection as needed.

Examples of the carboxylic acids of the following formulas (IVa) to (IVd) in an activated form include acid mixed acid anhydrides available by reacting any one of the carboxylic acids of the formulas (IVa) to (IVd) with a chloroformate ester such as isobutyl chloroformate; acid halides such as acyl chloride prepared using an acid halide such as thionyl chloride; active esters obtained by reacting with a phenol such as paranitrophenol or pentafluorophenyltrifluoroacetate; active esters obtained by reacting with N-hydroxybenztriazole or N-hydroxysuccinimide; reaction products with 1-benztriazolyloxy-(pyrrolidino)-phosphonium hexafluorophosphite, N,N'-dicyclohexylcarbodiimide or N-(3-dimethylaminopropyl)-N'-ethylcarbodiimide hydrochloride which is usually employed for the peptide synthesis of amino acid, reaction products with diethyl cyanophosphonate (salting-in method) and reaction products with triphenylphosphine and 2,2'-dipyridylsulfide (Mukaiyama's method).

The resulting carboxylic acid in an activated form is then reacted with the compound of the formula (IIIa) or salt thereof generally in the presence of an appropriate base in an inert solvent at −78° C. to 150° C., whereby the compound of the formula (Ib) can be obtained.

Specific examples of the base include carbonates, alkoxides, hydroxides and hydrides of an alkali metal or alkaline earth metal, such as sodium carbonate, potassium carbonate, sodium ethoxide, potassium botoxide, sodium hydroxide, potassium hydroxide, sodium hydride and potassium hydride; organometallic base compounds typified by alkyl lithium such as n-butyl lithium and dialkylaminolithium such as lithium diisopropylamide; organometallic base of bissilylamine compounds such as lithium bis (trimethylsilyl)amide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

Examples of the inert solvent include alkyl halide solvents such as dichloromethane, chloroform and carbon tetrachloride; ether solvents such as tetrahydrofuran, 1,2-dimethoxyethane and dioxane; aromatic solvents such as benzene and toluene; and amide solvents such as N,N-dimethylformamide, N,N-dimethylacetamide and N-methylpyrrolidin-2-one. In addition to them, sulfoxide solvents such as dimethylsulfoxide and sulfolane and ketone solvents such as acetone and methyl ethyl ketone can be used if they are suited.

When the nitrogen atom of $Q^{3b}$ of the compound represented by the formula (IIIa) forms an amide bond, the alkylation of the nitrogen atom is carried out by reacting the compound (IIIa) with the compound represented by any one of the formulas (Va) to (Vd) in the presence of an appropriate base in an inert solvent at −78 to 150° C., whereby the compound of the formula (Ib) can be obtained. Specific examples of the base include alkoxides and hydrides of an alkali metal or alkaline earth metal such as sodium ethoxide, potassium butoxide, sodium hydride and potassium hydride; organometallic base compounds typified by alkyl lithium such as n-butyl lithium and dialkylaminolithium such as lithium diisopropylamide; organometallic base of bissilylamine compounds such as lithium bis(trimethylsilyl)amide; and organic bases such as diazabicyclo[5.4.0]undec-7-ene (DBU).

Examples of the inert solvent include ether solvents such as tetrahydrofuran, 1,2-dimethoxyethane and dioxane and amide solvents such as N,N-dimethylformamide.

When the nitrogen atom of $Q^{3b}$ of the compound represented by the formula (IIIa) exists as a primary or secondary amine, the compound of the formula (Ib) can be obtained by reacting the compound of the formula (IIIa) with the carbonyl compound of any one of the formulas (VIa) to (VId) to form the corresponding imine, generally in an inert solvent, optionally in the presence of an organic acid such as acetic acid, a mineral acid such as hydrochloric acid or a Lewis acid such as aluminum chloride at −20 to 150° C.; and then hydrogenating the resulting imine in an inert solvent in the presence of a boron hydride reducing agent such as sodium borohydride, sodium cyanoborohydride or sodium triacetoxyborohydride or a catalytic hyddrogenation catalyst such as palladium-carbon catalyst at 10 to 110° C.

Preferred examples of the inert solvent include carbon halides such as dichloromethane, chloroform and carbon tetrachloride, ether solvents such as tetrahydrofuran, 1,2-dimethoxyethane and dioxane, benzene solvents such as toluene and amide solvents such as N,N-dimethylformamide, N,N-dimethylacetamide and N-methylpyrrolidin-2-one.

When the nitrogen atom of $Q^{3b}$ of the compound represented by the formula (IIIa) exists as a primary or secondary amine, the reaction product of the compound of any one of the formulas (VIIa) to (VIId) containing a primary amine or the compound of the formula (VIIe) containing a secondary amine with a reagent such as phosgene, triphosgene or 1,1'-carbonyldiimidazole can be acted on the compound of the formula (IIIa) to introduce it to the corresponding urea derivative. The derivative can be synthesized by reacting the primary amine compound of any one of the formulas (VIIa) to (VIId) or the secondary amine compound of the formula (VIIe), a reagent such as phosgene, triphosgene or 1,1'-carbonyldiimidazole and the compound of the formula (IIIa) successively in this order, if necessary in the presence of a base, in an inert solvent.

Examples of the inert solvent include halogen solvents such as dichloromethane, chloroform and carbon tetrachloride; ether solvents such as tetrahydrofuran, 1,2-dimethoxyethane and dioxane; benzene solvents such as toluene; and amide solvents such as N,N-dimethylformamide, N,N-dimethylacetamide and N-methylpyrrolidin-2-one. Among them, dichloromethane, tetrahydrofuran and toluene are preferred.

Examples of the base include carbonates and hydroxides of an alkali metal or alkaline earth metal, such as sodium carbonate, potassium carbonate, sodium hydroxide and potassium hydroxide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU). The reaction is effected within a temperature range of from −70° C. to 110° C.

When the nitrogen atom of $Q^{3b}$ of the compound represented by the formula (IIIa) exists as a primary or secondary amine, the compound of the formula (Ib) can also be obtained by reacting the compound of the formula (IIIa) with an isocyanate derivative in an inert solvent at −20 to 100° C.

The isocyanate derivative can be synthesized by converting the carboxylic acid of the formula (IVa) into the corresponding acid halide by using an acid halide such as thionyl chloride or oxalyl chloride in an inert solvent such as tetrahydrofuran, chloroform or toluene at −20 to 110° C., reacting the resulting acid halide with sodium azide in an inert solvent such as tetrahydrofuran, chloroform or toluene at a temperature range of from 0 to 80° C., and then heating the reaction mixture at 20 to 100° C.; by reacting the carboxylic acid of the formula (IVa) with a chloroformate such as isobutyl chloroformate in an inert solvent such as tetrahydrofuran, chloroform or toluene at −20 to 110° C. to obtain the corresponding mixed acid anhydride, reacting the mixed acid anhydride with sodium azide within a temperature range of from 0 to 80° C. and then heating the reaction mixture at 20 to 100° C.; or by introducing the carboxylic acid of the formula (IVa) into the corresponding hydrazide through an ester in an inert solvent such as tetrahydrofuran, chloroform or toluene at −20 to 110° C., reacting the hydrazide with nitric acid or alkyl ester thereof to convert it into the corresponding acyl azide and then heating the resulting acyl azide in a solvent such as chloroform, dichloroethane, toluene, xylene or N,N-dimethylformamide at 20 to 150° C.

The compound of the formula (Ib) can also be prepared by reacting the carboxylic acid of the formula (IVa) with diphenylphosphoryl azide in the presence of a base such as triethylamine, in an inert solvent such as chloroform, tetrahydrofuran, toluene or N,N-dimethylformamide at a temperature range of 10 to 140° C. and then reacting the reaction mixture with the amine of the formula (IIIa).

When in the structure of $Q^1$ of the compound represented by the formula (Ib), a halogen- or trifluoromethanesulfonyloxy-substituted aryl group or a halogen- or trifluoromethanesulfonyoxy-substituted alkenyl group is contained, the compound can be subjected to coupling reaction with a boric-acid-substituted aryl derivative by using a transition metal catalyst such as tetrakis (triphenylphosphine)palladium (O), in a two-phase solvent such as benzene-water or toluene-water, amide solvent such as N,N-dimethylformamide or ether solvent such as tetrahydrofuran or dimethoxyethane, optionally in the presence of as sodium carbonate, sodium hydroxide, calcium hydroxide, barium hydroxide, potassium phosphate or cesium carbonate at a temperature range of 20 to 150° C. for 0.5 to 120 hours.

When an alkenyl group or boric-acid-substituted alkenyl group is contained in the structure of $Q^1$ of the compound represented by the formula (Ib), coupling reaction of the compound with a halogen- or trifluoromethanesulfonyloxy-substituted aryl group can be effected using a transition metal catalyst such as palladium acetate, in the presence of an appropriate base or cesium fluoride, in an amide solvent such as N,N-dimethylformamide, at a temperature range of 20 to 150° C. for 0.5 to 120 hours. When a boric-acid-substituted aryl group is contained in the structure of $Q^1$ of the compound represented by the formula (Ib), coupling reaction of the compound with a halogen- or trifluoromethanesulfonyloxy-substituted aryl derivative or a halogen- or trifluoromethanesulfonyloxy-substituted alkenyl derivative can be effected. When a halogen- or trifluoromethanesulfonyloxy-substituted aryl group is contained in the structure of $Q^1$ of the compound represented by the formula (Ib), coupling reaction of the compound with an alkenyl compound can be effected using a transition metal catalyst, whereby the compound of the formula (Ib) can be obtained.

If the nitrogen atom of $Q^{3b}$ of the resulting compound represented by the formula (Ib) has been protected, the compound of the formula (Ia) can be obtained by deprotection as needed.

<Synthesis of the Compound Represented by the Formula (IIa)>

The sulfonic acid halide of the formula (IIa) can be synthesized in a known matter or by application thereof. The ordinarily employed synthesis process will be described below.

Among the sulfonic acid halides represented by the formula (IIa), a sulfonic acid halide represented by the following formula (IIa-1a):

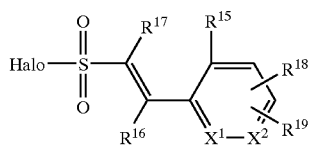

(IIa-1a)

[wherein $R^{15}$, $R^{16}$, $R^{17}$, $R^{18}$, $R^{19}$, $X^1$, $X^2$ and Halo have the same meanings as described above] can be synthesized by any one of the various processes reported to date (The Chemistry of Sulfonic Acids Esters and their Derivatives, Edited by S. Patai and Z. Rappoport, 1991, John Wiley & Sons Ltd.), for example, halogenation of a sulfonic acid of the following formula (IIa-1b):

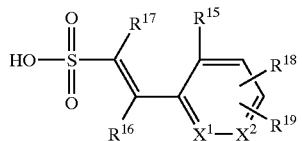

(IIa-1b)

[wherein $R^{15}$, $R^{16}$, $R^{17}$, $R^{18}$, $R^{19}$, $X^1$ and $X^2$ have the same meanings as described above] or chlorosulfonylation of the unsaturated bond represented by the following formula (IIa-1c):

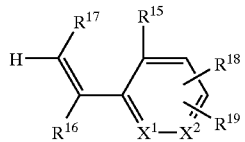

(IIa-1c)

[wherein $R^{15}$, $R^{16}$, $R^{17}$, $R^{18}$, $R^{19}$, $X^1$ and $X^2$ have the same meanings as described above].

For example, the sulfonic acid halide of the formula (IIa-1a) can be obtained by reacting the sulfonic acid of the formula (IIa-1b) with a thionyl halide in the presence of N,N-dimethylformamide at 0 to 150° C. for 0.5 to 24 hours. At this time, the reaction system may be diluted with an inert solvent such as dichloromethane, chloroform, carbon tetrachloride, N-methylpyrrolidin-2-one, dimethylsulfoxide or sulfolane.

The sulfonic acid halide of the formula (IIa-1a) can be obtained by reacting the unsaturated-bond-containing compound of the formula (IIa-1c) with a thionyl halide or chlorosulfonic acid in an inert solvent such as N,N-dimethylformamide at 0 to 150° C. for 0.5 to 24 hours.

Among the sulfonic acid halides represented by the formula (IIa), a sulfonic acid halide represented by the following formula (IIa-2a):

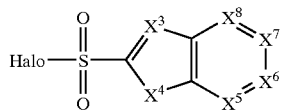

(IIa-2a)

[wherein $X^3$, $X^4$, $X^5$, $X^6$, $X^7$, $X^8$ and Halo have the same meanings as described above] can be obtained by the processes so far reported (Japanese Patent Application Laid-Open No. Sho 60-204760, Japanese Patent Application Laid-Open No. Sho 62-116575, Japanese Patent Application Laid-Open No. Hei 4-128266) or by application thereof, for example, by reacting the fused heterocycle represented by the following formula (IIa-2b):

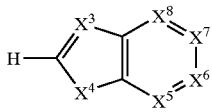

(IIa-2b)

[wherein $X^3$, $X^4$, $X^5$, $X^6$, $X^7$ and $X^8$ have the same meanings as described above] with a base and then sulfur dioxide and then reacting the reaction mixture with a halogenating agent.

The compound of the formula (IIa-2a) is obtained, for example, by reacting the fused heterocycle of the formula (IIa-2b) with an appropriate base in an ether-type inert solvent at −78° C. to 0° C., reacting the reaction mixture with sulfur dioxide at −78° C. to 0° C., and then reacting with a halogenating agent in an alkyl halide type inert solvent at −50° C. to 50° C. Specific examples of the base include alkoxides and hydrides of an alkali metal or alkaline earth metal such as sodium ethoxide, potassium botoxide, sodium hydride and potassium hydride; organometallic base compounds typified by alkyl lithium such as n-butyl lithium and dialkylaminolithium such as lithium diisopropylamide; organometallic base of bisssilylamine compounds such as lithium bis(trimethylsilyl)amide. Examples of the ether-type inert solvent include diethyl ether, tetrahydrofuran, 1,2-dimethoxyethane and dioxane. Preferred examples of the halogenating agent include chlorine, bromine, phosphorus pentachloride, thionyl chloride, N-chlorosuccinimide and N-bromosuccinimide, while those of the alkyl halide type inert solvent include dichloromethane, chloroform and tetrachloroethane.

Among the compounds represented by the formula (IIa-2a), the corresponding sulfonyl chloride of the compound represented by the following formula (IIa-2c):

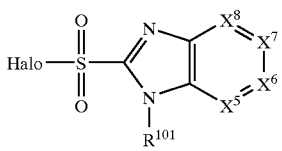

(IIa-2c)

[wherein $R^{101}$, $X^5$, $X^6$, $X^7$, $X^8$ and Halo have the same meanings as described above] can be obtained by reacting the compound of the following formula (IIa-2d):

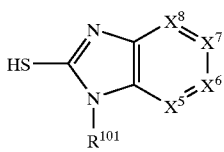

(IIa-2d)

[wherein $R^{101}$, $X^5$, $X^6$, $X^7$ and $X^8$ have the same meanings as described above] with halogen such as a chlorine gas at 0 to 30° C. for 10 minutes to 6 hours in water or a mixed solvent of water with an organic carboxylic acid such as acetic acid.

The reaction between the compound of the formula (IIa-2d) and halogen is carried out at 0 to 20° C. usually in water or a 10 to 90% aqueous solution of acetic acid if necessary in the presence of a Lewis acid such as ferric chloride as a catalyst.

<Reaction of a Compound of the Formula (Ia) with a Compound of the Formula (IIa)>

The compound of the formula (I) can be obtained generally by reacting the compound of the formula (Ia), which has been synthesized by the above-described process or the like, with the sulfonic acid halide of the formula (IIa) which has been synthesized by the above-described process or the like, in the presence of an appropriate base, in an inert solvent at −78 to 150° C.

The resulting compound of the formula (I) can be subjected to deprotection or chemical conversion of a substituent as needed.

Specific examples of the base include carbonates, alkoxides, hydroxides and hydrides of an alkali metal or alkaline earth metal, such as sodium carbonate, potassium carbonate, sodium ethoxide, potassium botoxide, sodium hydroxide, potassium hydroxide, sodium hydride and potassium hydride; organometallic base compounds typified by alkyl lithium such as n-butyl lithium and dialkylamino-lithium such as lithium diisopropylamide; organometallic base of bissilylamine compounds such as lithium bis(trimethylsilyl)amide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

Examples of the inert solvent include dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one, dimethylsulfoxide and sulfolane and mixed solvents thereof.

[Preparation Process-1-(1)]

When the nitrogen atom of $Q^{3a}$ of the compound represented by the formula (Ia), which is to be sulfonylated, exists as a primary or secondary amine, preferred examples of the base include carbonates and hydroxides of an alkali metal or an alkaline earth metal such as sodium carbonate, potassium carbonate, sodium hydroxide and potassium hydroxide and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU) and usable examples of the solvent include, in addition to inert solvents, water, alcohol solvents such as ethanol and butanol and ester solvents such as ethyl acetate.

[Preparation Process-1-(2)]

When the nitrogen atom of $Q^{3a}$ of the compound represented by the formula (Ia), which is. to be sulfonylated, forms an amide group, preferred examples of the base include alkoxides and hydrides of an alkali metal or an alkaline earth metal such as sodium ethoxide, potassium botoxide, sodium hydride and potassium hydride; organometallic base compounds typified by alkyl lithium such as n-butyl lithium and dialkylaminolithium such as lithium diisopropylamide; organometallic base of bissilylamine compounds such as lithium bis(trimethylsilyl)amide; and organic bases such as diazabicyclo[5.4.0]undec-7-ene (DBU).

Examples of the inert solvent include tetrahydrofuran, 1,2-dimethoxyethane, dioxane and N,N-dimethylformamide.

[Preparation Process-2]

A process for preparing the sulfonyl derivative (I) by acylating the nitrogen atom of $Q^{3a}$ of the compound represented by the formula (VIIIa):

$$Q^{3a}\text{—}SO_2\text{—}Q^4 \qquad \text{(VIIa)}$$

[wherein $Q^{3a}$ and $Q^4$ have the same meanings as described above] with any one of the carboxylic acids represented by the formulas (IVa) to (IVd):

$$Q^{3a}\text{—}Q^{2b}\text{—}COOH \qquad \text{(IVa)}$$

$$Q^1\text{—}N(R^{20})\text{—}(CH_2)_{m1}\text{—}COOH \qquad \text{(IVb)}$$

$$Q^1\text{—}O\text{—}(CH_2)_{m1}\text{—}COOH \qquad \text{(Ivc)}$$

$$Q^1\text{—}S\text{—}(CH_2)_{m1}\text{—}COOH \qquad \text{(Ivd)}$$

[wherein $Q^1$, $Q^2Q^{2b}$, $R^{20}$ and m1 have the same meanings as described above] or the activated form thereof which are available by the process reported to far or the chemically usual process.

The compound represented by the formula (VIIIa) can be synthesized in various processes. Some of them will next be described.

<Synthesizing Process of a Compound Represented by the Formula (VIIIa)>
<Synthesizing Process of a Compound Represented by the Formula (VIIIa-1a)>

Among the compounds represented by the formula (VIIIa), the compound of the formula (VIIIa-1a):

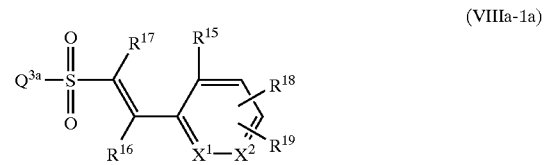

[wherein $R^{15}$, $R^{16}$, $R^{17}$, $R^{18}$, $R^{19}$, $X^1$, $X^2$ and $Q^{3a}$ have the same meanings as described above] can be synthesized as described below.

The compound of the following formula (VIIIa-1b):

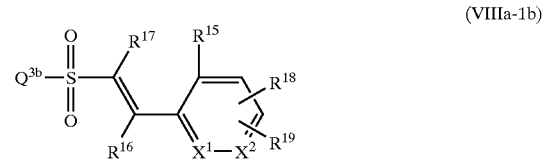

[wherein $R^{15}$, $R^{16}$, $R^{17}$, $R^{18}$, $R^{18}$, $X^1$, $X^2$ and $Q^{3b}$ have the same meanings as described above] can be obtained by sulfonylating the nitrogen atom of the primary amine, secondary amine or amide of the compound of the formula (IIIa):

$$Q^{3b}\text{—}H \qquad \text{(IIIa)}$$

[wherein $Q^{3b}$ has the same meaning as described above] with a compound represented by the following formula (IIa-1a):

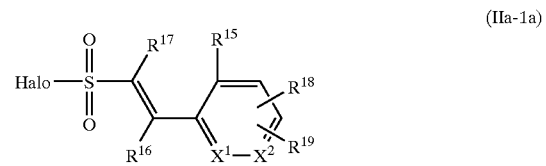

[wherein $R^{15}$, $R^{16}$, $R^{17}$, $R^{18}$, $R^{19}$, $X^1$, $X^2$ and Halo have the same meanings as described above] in the presence of an appropriate base in an inert solvent at −78 to 150° C.

Specific examples of the base include carbonates, alkoxides, hydroxides and hydrides of an alkali metal or alkaline earth metal, such as sodium carbonate, potassium carbonate, sodium ethoxide, potassium botoxide, sodium hydroxide, potassium hydroxide, sodium hydride and potassium hydride; organometallic base compounds typified by alkyl lithium such as n-butyl lithium and dialkylaminolithium such as lithium diisopropylamide; organometallic base of bissilylamine compounds such as lithium bis(trimethylsilyl)amide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

Examples of the inert solvent include dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one, dimethylsulfoxide, sulfolane and acetone.

If the nitrogen atom of $Q^{3b}$ of the resulting compound represented by the formula (VIIIa-1b) has been protected, the compound of the formula (VIIIa-1a) can be obtained by deprotection as needed.

The compound of the formula (VIIIa-1a) can be obtained by removing, in an appropriate manner, the protecting group of the nitrogen atom from the compound represented by the following formula (VIIIa-1c):

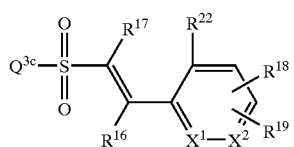

(VIIIa-1c)

[wherein $R^{15}$, $R^{16}$ $R^{17}$, $R^{18}$, $R^{19}$, $X^1$ and $X^2$ have the same meanings as described above, $R^{22}$ represents
a hydrogen atom,
an alkyl group,
a hydroxyl group protected with a methoxymethyl, tetrahydropyranyl or the like group,
a hydroxyalkyl group protected with a methoxymethyl, tetrahydropyranyl or the like group,
an alkoxyl group,
an alkoxyalkyl group,
a dialkoxyalkyl group,
a dialkylamino group,
a monoalkylamino group having an amino group protected with a tertiary butoxycarbonyl group,
a dialkylaminoalkyl group,
a monoalkylaminoalkyl group having an amino group protected with a tertiary butoxycarbonyl group,
a dialkylaminocarbonyl group,
a dialkylaminocarbonylalkyl group,
a dialkylaminoalkyloxy group,
a monoalkylaminoalkyloxy group having an amino group protected with a tertiary butoxycarbonyl group,
a dialkylaminocarbonylalkyloxy group or the like; and $Q^{3c}$ represents any one of the following groups:

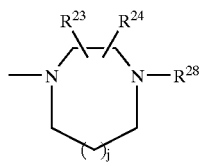
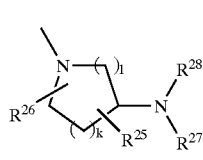

-continued

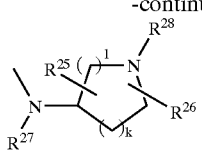

(wherein when the carbon atom to which $R^{23}$, $R^{24}$, $R^{25}$ or $R^{26}$ has been bonded is not adjacent to the nitrogen atom, $R^{23}$, $R^{24}$, $R^{25}$ and $R^{26}$ each independently represents:
a hydrogen atom,
an alkyl group,
a hydroxyl group protected with a methoxymethyl, tetrahydropyranyl or the like group,
a hydroxyalkyl group protected with a methoxymethyl, tetrahydropyranyl or the like group,
an alkoxyl group,
an alkoxyalkyl group,
a dialkoxyalkyl group,
a dialkylamino group,
a monoalkylamino group in which the amino moiety has been protected with a tertiary butoxycarbonyl group,
a dialkylaminoalkyl group,
a monoalkylaminoalkyl group having an amino group protected with a tertiary butoxycarbonyl group,
a dialkylaminocarbonyl group,
a dialkylaminocarbonylalkyl group,
a dialkylaminoalkyloxy group, or the like.

$R^{23}$ and $R^{24}$, as well as $R^{25}$ and $R^{26}$, may be coupled together to form a saturated or unsaturated 5- to 7-membered cyclic hydrocarbon group which may have a substituent or a saturated or unsaturated 5- to 7-membered heterocyclic group which may have a substituent.

$R^{27}$ represents:
an alkyl group,
a hydroxyalkyl group having the hydroxyl group protected,
a hydroxyalkylcarbonyl group having the hydroxyl group protected,
a hydroxyalkylsulfonyl having the hydroxyl group protected,
an alkoxyalkyl group,
an alkoxyalkylcarbonyl group,
an alkoxyalkylsulfonyl group,
an alkylcarbonyl group,
an alkylcarbonylalkyl group,
an alkylsulfonyl group,
an alkylsulfonylalkyl group,
an alkoxycarbonyl group,
an alkoxycarboylalkyl group,
an alkoxycarbonylalkylcarbonyl group,
an alkoxycarbonylalkylsulfonyl group,
a dialkylaminoalkyl group,
a monoalkylaminoalkyl group having the amino group protected with a tertiary butoxycarbonyl group,
a dialkylaminocarbonyl group,
a dialkylaminocarbonylalkyl group, or the like.

$R^{25}$ and $R^{27}$, or $R^{26}$ and $R^{27}$ may be coupled together to form a saturated or unsaturated 5- to 7-membered heterocyclic group which may have a substituent.

$R^{28}$ represents a tertiary butoxycarbonyl, benzyl or triphenylmethyl group which means a protecting group of the nitrogen atom, j and k each independently represents an integer of 0 or 1 and l stands for an integer of 1 to 3 with the proviso that the sum of k and l stands for an integer of 1 to 4.)]

The compound represented by the formula (VIIIa-1c) can be obtained by reacting an amino compound which is available by the known process or application thereof and is represented by the following formula (IIIb):

$$Q^{3c}—H \tag{IIIb}$$

[wherein $Q^{3c}$ has the same meaning as described above] with an alkysulfonic acid halide in the presence of an appropriate base; reacting the resulting sulfonamide represented by the following formula (IXa):

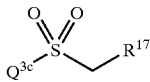
(IXa)

[wherein $R^{17}$ and $Q^3c$ have the same meanings as described above ] with a carbonyl compound represented by the following formula (XIa):

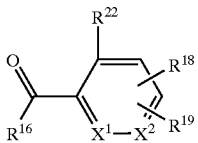
(XIa)

[wherein $R^{16}$, $R^{18}$, $R^{19}$, $R^{22}$, $X^1$ and $X^2$ have the same meanings as described above] in an inert solvent in the presence of an appropriate base to obtain the corresponding alcohol product represented by the following formula (XIIa):

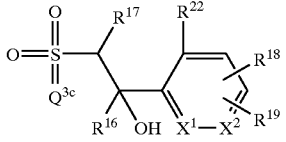
(XIIa)

[wherein $R^{16}$, $R^{17}$, $R^{18}$, $R^{19}$, $R^{22}$, $Q^{3c}$, $X^1$ and $X^2$ have the same meanings as described above]; converting the alcohol moiety of the alcohol product (XIIa) into a methanesulfonyloxy group or the like in the presence of an appropriate base, or converting the alcohol moiety into a halogen atom by using a phosphorus halide or triphenylphosphine/carbon tetrahalide, thereby forming an eliminating group; and then eliminating methanesulfonic acid or hydrogen halide in the presence of an appropriate base.

The sulfonamide compound of the formula (IXa) can be obtained by reacting the amino compound of the formula (IIIb), which is available in a known process or by application thereof, with an alkylsulfonic halide which may have a substituent, in the presence of an appropriate base, in an inert solvent at −78 to 150° C.

Examples of the base include carbonates of an alkali metal or alkaline earth metal, such as sodium carbonate and potassium carbonate and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

Examples of the inert solvent include dichloromethane, chloroform, carbon tetrachloride, tetrahydrofuran, 1,2-dimethoxyethane, dioxane, toluene, N,N-dimethylformamide, N,N-dimethylacetamide and N-methylpyrrolidin-2-one. Dimethylsulfoxide, sulfolane, acetone or the like can be used, though depending on the kind of the base employed.

The alcohol compound of the formula (XIIa) can be obtained by reacting the sulfonamide of the formula (IXa) with a carbonyl compound of the formula (XIa) in the presence of an appropriate base in an inert solvent at −78 to 110° C.

Examples of the base include hydrides of an alkali metal or alkaline earth metal such as sodium ethoxide, potassium botoxide, sodium hydride and potassium hydride; organometallic base compounds typified by alkyl lithium such as n-butyl lithium and dialkylaminolithium such as lithium diisopropylamide; organometallic base of bissilylamine compounds such as lithium bis(trimethylsilyl)amide. Examples of the inert solvent include tetrahydrofuran, 1,2-dimethoxyethane and dioxane.

The compound of the formula (VIIIa-1c) can be obtained by treating the hydroxyl group of the alcohol product of the formula (XIIa) with a phosphorus halide such as phosphorus pentachloride or a triphenylphosphine-halogen complex such as triphenylphosphine dibromide at −20 to 110° C., if necessary in the presence of an appropriate base, for example, the carbonate of an alkali metal or alkaline earth metal, such as sodium carbonate or potassium carbonate, or an organic base such as pyridine, 2,6-lutidine, collidine, 4-dimethylaminopyridine, triethylamine, N-methylmorpholine, diisopropylethylamine or diazabicyclo[5.4.0]undec-7-ene (DBU), in a solvent such as dichloromethane, chloroform, carbon tetrachloride, tetrahydrofuran, 1,2-dimethoxyethane, dioxane, toluene or N,N-dimethylformamide, thereby obtaining the corresponding halide, and then eliminating the hydrogen halide from the resulting halide under basic conditions, for example, by treating at −78 to 150° C. with a carbonate, alkoxide, hydroxide or hydride of an alkali metal or alkaline earth metal, such as sodium carbonate, potassium carbonate, sodium ethoxide, potassium butoxide, sodium hydroxide, potassium hydroxide, sodium hydride or potassium hydride, an organometallic base compound typified by alkyl lithium such as n-butyl lithium and dialkylaminolithium such as lithium diisopropylamide, an organometallic base of bissilylamine compound such as lithium bis(trimethylsilyl) amide, or an organic base such as pyridine, 2,6-lutidine, collidine, 4-dimethylaminopyridine, triethylamine, N-methylmorpholine, diisopropylethylamine and diazabicyclo[5.4.0]undec-7-ene (DBU) in dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one or dimethylsulfoxide.

The compound of the formula (VIIIa-1c) can also be obtained by treating the hydroxyl group of the alcohol product represented by the formula (XIIa) with an alkyl- or arylsulfonic acid chloride such as methanesulfonic acid chloride in the presence of an appropriate base, for example, a carbonate of an alkali metal or alkaline earth metal such as sodium carbonate or potassium carbonate or an organic base such as pyridine, 2,6-lutidine, collidine, 4-dimethylaminopyridine, triethylamine, N-methylmorpholine, diisopropylethylamine or diazabicyclo[5.4.0]undec-7-ene (DBU), in a solvent such as dichloromethane, chloroform, carbon tetrachloride, tetrahydrofuran, 1,2-dimethoxyethane, dioxane, toluene or N,N-dimethylformamide at −20 to 110° C. to obtain the corresponding alkyl- or arylsulfonate derivative; and then eliminating the alkyl- or arylsulfonic acid from the resulting alkyl- or arylsulfonate derivative under basic conditions.

Described specifically, the compound of the formula (VIIIa-1c) can be obtained by treating the resulting alkyl- or arylsulfonate derivative at −78 to 150° C. in the presence of a carbonate, alkoxide, hydroxide or hydride of an alkali metal or alkaline earth metal such as sodium carbonate, potassium carbonate, sodium ethoxide, potassium butoxide, sodium hydroxide, potassium hydroxide, sodium hydride or potassium hydride, an organometallic base compound typified by alkyl lithium such as n-butyl lithium and dialkylaminolithium such as lithium diisopropylamide, an organometallic base of bissilylamine compound such as lithium bis(trimethylsilyl)amide, or an organic base such as pyridine, 2,6-lutidine, collidine, 4-dimethylaminopyridine, triethylamine, N-methylmorpholine, diisopropylethylamine or diazabicyclo[5.4.0]undec-7-ene (DBU) in dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one or dimethylsulfoxide. The compound of the formula (VIIIa-1c) can also be obtained by treating the sulfonamide of the formula (IXa) with a silyl halide such as trimethylsilyl chloride in the presence of an appropriate base in an inert solvent to convert it to the corresponding silyl compound, reacting the resulting silyl compound with a carbonyl compound of the formula (XIa) in the presence of a base in an inert solvent and then treating the reaction product under acidic to basic aqueous conditions (Peterson's reaction).

Described specifically, the compound of the formula (VIIIa-1c) can be obtained by treating the sulfonamide of the formula (IXa) with an alkylsilyl chloride such as trimethylsilyl chloride at −78 to 110° C. in the presence of an alkoxide or hydride of an alkali metal or alkaline earth metal such as sodium ethoxide, potassium butoxide, sodium hydride or potassium hydride, an organometallic base compound typified by alkyl lithium such as n-butyl lithium and dialkylaminolithium such as lithium diisopropylamide, or an organometallic base of bissilylamine compound such as lithium bis(trimethylsilyl)amide in a solvent such as tetrahydrofuran, 1,2-dimethoxyethane or dioxane, to convert it to the corresponding silyl compound, condensing with the carbonyl compound of the formula (XIa) under the same conditions and then treating the condensate under acidic to basic aqueous conditions.

The protecting group of the nitrogen atom of the compound represented by the formula (VIIIa-1c) can be removed by the ordinarily employed process. Described specifically, when the protecting group is a tertiary butoxycarbonyl group, it can be removed by using an appropriate acid such as acetic acid, hydrochloric acid, hydrobromic acid, sulfuric acid, phosphoric acid, trifluoroacetic acid or trifluoromethanesulfonic acid or combination thereof. An arylmethyl group such as benzyl can be removed by the hydrogenolysis in the presence of a palladium-carbon catalyst. A triphenylmethyl group can be removed by using an appropriate acid such as formic acid, acetic acid, hydrochloric acid, hydrobromic acid, sulfuric acid, phosphoric acid, trifluoroacetic acid or trifluoromethanesulfonic acid or combination thereof. It can also be removed by Birch reduction with a metal sodium in liquid ammonia or by hydrogenolysis in the presence of a palladium-carbon catalyst. Thus, by the removal of the protecting group, the compound of the formula (VIIIa-1c) can be obtained.

<Synthesis of the Compound Represented by the Formula (VIIIa-2a)>

Among the compounds represented by the formula (VIIIa), the compound of the formula (VIIIa-2a):

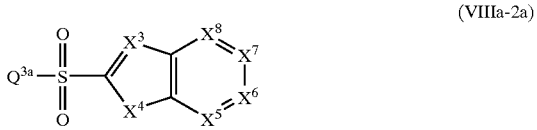

(VIIIa-2a)

[wherein $X^3$, $X^4$, $X^5$, $X^6$, $X^7$, $X^8$ and $Q^{3a}$ have the same meanings as described above] can be synthesized by the following process.

Described specifically, the compound of the following formula (VIIIa-2b):

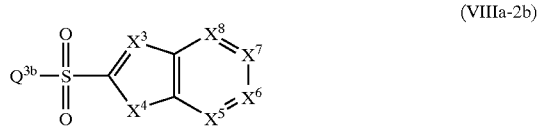

(VIIIa-2b)

[wherein $X^3$, $X^4$, $X^5$, $X^6$, $X^7$, $X^8$ and $Q^{3b}$ have the same meanings as described above] can be obtained by sulfonylating the nitrogen atom of the primary or secondary amine or amide of the compound of the formula (IIIa):

$$Q^{3b}-H \quad \quad (IIIa)$$

[wherein $Q^{3b}$ has the same meaning as described above] with a sulfonic acid halide represented by the following formula (IIa-2a):

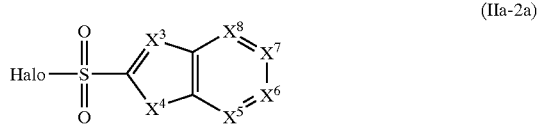

(IIa-2a)

[wherein $X^3$, $X^4$, $X^5$, $X^6$, $X^7$, $X^8$ and Halo have the same meanings as described above] in the presence of an appropriate base in an inert solvent at −78 to 150° C.

Specific examples of the base include carbonates, alkoxides, hydroxides and hydrides of an alkali metal or alkaline earth metal, such as sodium carbonate, potassium carbonate, sodium ethoxide, potassium butoxide, sodium hydroxide, potassium hydroxide, sodium hydride and potassium hydride; organometallic base compounds typified by alkyl lithium such as n-butyl lithium and dialkylaminolithium such as lithium diisopropylamide; organometallic base of bissilylamine compounds such as lithium bis(trimethylsilyl)amide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

Examples of the inert solvent include dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one, dimethylsulfoxide, sulfolane and acetone.

When the nitrogen atom of $Q^{3b}$ of the resulting compound represented by the formula (VIIIa-2b) has been protected, the compound of the formula (VIIIa-2a) can be obtained by carrying out deprotection as needed.

Alternatively, the compound of the formula (VIIIa-2a) can be obtained by removing, as needed in an appropriate manner, the protecting group of the nitrogen atom of $Q^{3d}$ from the compound which is available by the below-described preparation process and is represented by the following formula (VIIIa-2c):

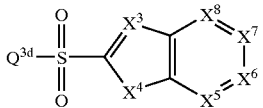

(VIIIa-2c)

[wherein $X^3$, $X^4$, $X^5$, $X^6$, $X^7$ and $X^8$ have the same meanings as described above and $Q^{3d}$ means any one of the following groups:

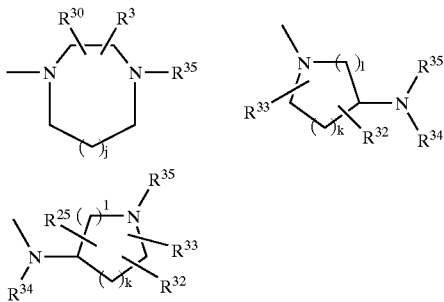

(wherein, when the carbon atom to which each of $R^{30}$, $R^{31}$, $R^{32}$ and $R^{33}$ has been bonded is not adjacent to a nitrogen atom, $R^{30}$, $R^{31}$, $R^{32}$ and $R^{33}$ each independently represents
  a hydrogen atom,
  an alkyl group;
  a hydroxyl group,
  a hydroxyl group protected with a methoxymethyl or tetrahydropyranyl or the like group,
  a hydroxyalkyl group,
  a hydroxyalkyl group having a hydroxyl group protected with a methoxymethyl or tetrahydropyranyl or the like group,
  an alkoxyl group,
  an alkoxyalkyl group,
  a dialkoxyalkyl group,
  a dialkylamino group,
  a monoalkylamino group having an amino group protected with a tertiary butoxycarbonyl group,
  a dialkylaminoalkyl group,
  a monoalkylaminoalkyl group having an amino group protected with a tertiary butoxycarbonyl group,
  a dialkylaminocarbonyl group,
  a dialkylaminocarbonylalkyl group,
  a dialkylaminoalkyloxy group,
  a monoalkylaminoalkyloxy group having an amino group protected with a tertiary butoxycarbonyl group,
  a monoalkylaminocarbonylalkyloxy group having an amino group protected with a tertiary butoxycarbonyl group,
  a dialkylaminocarbonylalkyloxy group,
  a dialkylaminoalkyloxy group,
  a monoalkylaminoalkyloxy group having an amino group protected with a tertiary butoxycarbonyl group,
  a carbamoyl group,
  a monoalkylcarbamoyl group,
  a dialkylcarbamoyl group,
  a carbamoylalkyl group,
  a monoalkylcarbamoylalkyl group,
  a dialkylcarbamoylalkyl group,
  a pyrrolidinocarbonyl group,
  a pyrrolidinocarbonylalkyl group,
  a piperidinocarbonyl group,
  a piperidinocarbonylalkyl group,
  a morpholinocarbonyl group,
  a morpholinocarbonylalkyl group,
  a dialkylaminocarbonylalkyloxy group, or the like; when the carbon atom to which each of $R^{30}$, $R^{31}$, $R^{32}$ and $R^{33}$ has been bonded is adjacent to a nitrogen atom, $R^{30}$, $R^{31}$, $R^{32}$ and $R^{33}$ each independently represents
  a hydrogen atom,
  an alkyl group,
  a hydroxyalkyl group having a hydroxy group protected with a methoxymethyl, tetrahydropyranyl or the like group,
  an alkoxyalkyl group,
  a dialkoxyalkyl group,
  a dialkylaminoalkyl group,
  a monoalkylaminoalkyl group having an amino group protected with a tertiary butoxycarbonyl group,
  a dialkylaminocarbonyl group,
  a dialkylaminocarbonylalkyl group,
  a carbamoyl group,
  a monoalkylcarbamoyl group,
  a carbamoylalkyl group,
  a monoalkylcarbamoylalkyl group,
  a pyrrolidinocarbonyl group,
  a pyrrolidinocarbonylalkyl group,
  a piperidinocarbonyl group,
  a piperidinocarbonylalkyl group,
  a morpholinocarbonyl group,
  a morpholinocarbonylalkyl group,
  a dialkylaminoalkyloxyalkyl group or the like;
$R^{30}$ and $R^{31}$, or $R^{32}$ and $R^{33}$ may be coupled together to form a saturated or unsaturated 5- to 7-membered cyclic hydrocarbon group which may have a substituent or a saturated or unsaturated 5- to 7-membered heterocyclic group which may have a substituent;
$R^{34}$ represents
  an alkyl group,
  a hydroxyalkyl group having a protected hydroxyl group,
  a hydroxyalkylcarbonyl group having a protected hydroxyl group,
  a hydroxyalkylsulfonyl group having a protected hydroxyl group,
  an alkoxyalkyl group,
  an alkoxyalkylcarbonyl group,
  an alkoxyalkylsulfonyl group,
  an alkylcarbonyl group,
  an alkylcarbonylalkyl group,
  an alkylsulfonyl group,
  an alkylsulfonylalkyl group,
  an alkoxycarbonyl group,
  an alkoxycarbonylalkyl group,
  an alkoxycarbonylalkylcarbonyl group,
  an alkoxycarbonylalkylsulfonyl group,
  a dialkylaminoalkyl group,
  a monoalkylaminoalkyl group having an amino group protected with a tertiary butoxycarbonyl group,
  a dialkylaminocarbonyl group,
  a dialkylaminocarbonylalkyl group or the like;
$R^{32}$ and $R^{34}$, or $R^{33}$ and $R^{34}$ may be coupled together to form a saturated or unsaturated 5- to 7-membered heterocyclic group which may have a substituent;
$R^{35}$ represents an ordinarily employed protecting group for a nitrogen atom such as tertiary butoxycarbonyl group, benzyl group or triphenylmethyl group; j and k independently represents 0 or an integer of 1; and l stands for an integer of 1 to 3 with the proviso that the sum of k and l stands for an integer of 1 to 4)].

The compound represented by the following formula (VIIIa-2d):

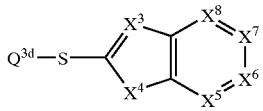

(VIIIa-2d)

[wherein $X^3$, $X^4$, $X^5$, $X^6$, $X^7$, $X^8$ and $Q^{3d}$ have the same meanings as described above] can be obtained by reacting an amino compound, which is available in a known manner or by application thereof and is represented by the following formula (IIIc)

$Q^{3d}$—H (IIIc)

[wherein $Q^{3d}$ has the same meaning as described above] with a fused heterocyclic thiol compound represented by the following formula (IIa-2e):

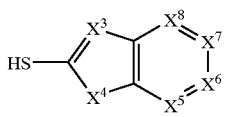

(IIa-2e)

[wherein $X^3$, $X^4$, $X^5$, $X^6$, $X^7$ and $X^8$ have the same meanings as described above] in the presence of an appropriate base and oxidizing agent.

The compound of the formula (VIIIa-2c) can be obtained by oxidizing the resulting compound of the formula (VIIIa-2d) in an inert solvent in the presence of an appropriate base.

The compound of the formula (VIIIa-2d) can be obtained by reacting an amino compound, which is represented by the formula (IIIc) and is available in a known manner or by application thereof, with a thiol represented by the formula (IIa-2e) at −10 to 50° C. in the presence of an appropriate base and oxidizing agent in water, an alcohol or dioxane or a mixed solvent thereof.

Examples of the base include carbonates and hydroxides of an alkali metal or alkaline earth metal such as sodium carbonate, potassium carbonate, sodium hydroxide and potassium hydroxide. Examples of the oxidizing agent include oxygen, chlorine, bromine, iodine and hypochlorous acid. The compound of the formula (VIIIa-2c) can be obtained by reacting the resulting compound of the formula (VIIIa-2d) with an inorganic oxidizing agent such as potassium permanganate or hydrogen peroxide or an organic oxidizing agent such as 3-chloroperbenzoic acid at −30° C. to 60° C. in the presence of an appropriate base in water, alcohol or a mixed solvent thereof.

The protecting group of the nitrogen atom can be removed from the compound of the formula (VIIIa-2c) by an ordinarily employed process. Described specifically, when the nitrogen has been protected with a tertiary butoxycarbonyl group, the protecting group can be removed using an appropriate acid, for example, acetic acid, hydrochloric acid, hydrobromic acid, sulfuric acid, phosphoric acid, trifluoroacetic acid or trifluoromethanesulfonic acid or combination thereof. An arylmethyl group such as benzyl can be removed by hydrogenolysis in the presence of a palladium-carbon catalyst. A triphenylmethyl group can be removed using an appropriate acid such as formic acid, acetic acid, hydrochloric acid, hydrobromic acid, sulfuric acid, phosphoric acid, trifluoroacetic acid or trifluoromethanesulfonic acid or combination thereof. The arylmethyl group such as benzyl can also be removed by Birch reduction, in liquid ammonia, in the presence of a metal sodium or by hydrogenolysis in the presence of a palladium-carbon catalyst. By deprotection as described above, the compound represented by the formula (VIIIa-2a) can be obtained.

Among the compounds represented by the formula (VIIIa-2a), the compound of the following formula (VIIIa-2e):

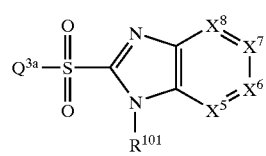

(VIIIa-2e)

[Wherein $X^3$, $X^4$, $X^5$, $X^6$, $X^7$, $X^8$, $R^{101}$ and $Q^{3a}$ have the same meanings as described above] can also be obtained by removing the protecting group of the nitrogen atom from $Q^{3d}$ of the compound which is available by the below-described preparation process and is represented by the formula (VIIIa-2f).

Described specifically, the compound of the following formula (VIIIa-2f):

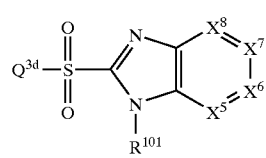

(VIIIa-2f)

[wherein $X^5$, $X^6$, $X^7$, $X^8$, $R^{101}$ and $Q^{3d}$ have the same meanings as described above] can be obtained by reacting an amino compound which is available in a known manner or by the application thereof and is represented by the following formula (IIIc):

$Q^{3d}$—H (IIIc)

[wherein $Q^{3d}$ has the same meaning as described above] with an acid halide represented by the following formula (IIa-2c):

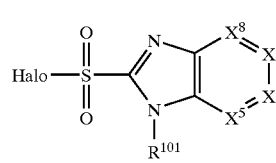

(IIa-2c)

wherein $X^5$, $X^6$, $X^7$, $X^8$, $R^{101}$ and Halo have the same meanings as described above].

The compound of the formula (VIIIa-2f) can be obtained by reacting the compound of the formula (IIa-2e) with halogen such as chlorine gas at 0 to 30° C. for 10 minutes to 60 hours in water or a mixed solvent of water with an organic carboxylic acid such as acetic acid, thereby forming the corresponding sulfonyl chloride; and then adding the resulting sulfonyl chloride to an amino compound of the formula (IIIc), which has been dissolved in an appropriate solvent, at −50 to 40° C.

The reaction between the compound of the formula (IIa-2e) and halogen is carried out at 0 to 20° C., usually in water or a 10 to 90% aqueous solution of acetic acid, if necessary in the presence of a Lewis acid such as ferric chloride as a catalyst. As the halogen, a chlorine gas is used. The reaction of the resulting acid chloride (IIa-2c) with the amine of the formula (IIIc) is carried out at −20 to 50° C., if necessary in the presence of a base, in a solvent, for example, water, an alcohol solvent such as ethanol, an ether solvent such as diethyl ether, tetrahydrofuran, dimethoxyethane or dioxane, a halogen solvent such as dichloromethane or chloroform or acetone or a mixed solvent thereof, whereby the compound of the formula (VIIIa-2f) can be obtained.

Specific examples of the base include carbonates, alkoxides and hydroxides of an alkali metal or alkaline earth metal, such as sodium carbonate, potassium carbonate, sodium hydroxide and potassium hydroxide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

The protecting group of the nitrogen atom of the compound represented by the formula (VIIIa-2f) can be removed by the ordinarily employed process. Described specifically, when the protecting group is a tertiary butoxycarbonyl group, it can be removed by using an appropriate acid such as acetic acid, hydrochloric acid, hydrobromic acid, sulfuric acid, phosphoric acid, trifluoroacetic acid or trifluoromethanesulfonic acid or combination thereof. An arylmethyl group such as benzyl can be removed by the hydrogenolysis in the presence of a palladium-carbon catalyst. A triphenylmethyl group can be removed by using an appropriate acid such as formic acid, acetic acid, hydrochloric acid, hydrobromic acid, sulfuric acid, phosphoric acid, trifluoroacetic acid or trifluoromethanesulfonic acid or combination thereof. The arylmethyl group such as benzyl group can also be removed by Birch reduction with a metal sodium in liquid ammonia or by hydrogenolysis in the presence of a palladium-carbon catalyst. Thus, by the removal of the protecting group, the compound of the formula (VIIIa-2e) can be obtained.

<Synthesis of the Compound of the Formula (VIIIa-3a)>

Among the compounds of the formula (VIIIa), the compound of the following formula (VIIIa-3a):

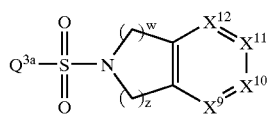

(VIIIa-3a)

[wherein $X^9$, $X^{10}$, $X^{11}$, $X^{12}$, $Q^{3a}$, w and z have the same meanings as described above] can be obtained by removing the protecting group from the nitrogen atom of $Q^{3d}$ of the compound which is available by the below-described preparation process and is represented by the following formula (VIIIa-3b):

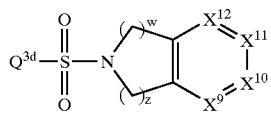

(VIIIa-3b)

[wherein $X^9$, $X^{10}$, $X^{11}$, $X^{12}$, $Q^{3d}$, w and z have the same meanings as described above].

Described specifically, the compound represented by the following formula (XIV):

$$Q^{3d}—SO_2—NHCOOR^{60} \quad (XIV)$$

[wherein $R^{60}$ and $Q^{3d}$ have the same meanings as described above] can be synthesized by reacting an amino compound represented by the following formula (IIIc):

$$Q^{3d}—H \quad (IIIc)$$

[wherein $Q^{3d}$ has the same meaning as described above] with a compound represented by the following formula (XIII):

$$Cl—SO_2—NHCOOR^{60} \quad (XIII)$$

[wherein $R^{60}$ represents an easily removable group such as tertiary butyl, benzyl, paramethoxybenzyl or paranitrobenzyl], which has been obtained from chlorosulfonyl isocyanate and an alcohol, in the presence of an appropriate base in an inert solvent.

The compound of the formula (VIIIa-3b) can be synthesized by removing the protecting group from the nitrogen atom of the compound of the formula (XIV), thereby obtaining the compound represented by the following formula (XV):

$$Q^{3d}—SO_2—NH_2 \quad (XV)$$

[wherein, $Q^{3d}$ has the same meaning as described above] and then reacting the resulting compound of the formula (XV) with a compound represented by the following formula (IIa-3a):

(IIa-3a)

[wherein, $X^9$, $X^{10}$, $X^{11}$, $X^{12}$, w and z have the same meanings as described above, $L^2$ and $L^3$ each independently represents an eliminating group frequently employed in organic chemistry such as chlorine, bromine, iodine, methylsufonyloxy or paratoluenesulfonyloxy] in the presence of an appropriate base in an inert solvent.

The reaction between the compounds of the formula (IIIc) and (XIII) is carried out at −70 to 100° C. in an solvent, for example, an ether solvent such as diethyl ether, tetrahydrofuran, dimethoxyethane or dioxane, a halogen solvent such as dichloromethane or chloroform, benzene, toluene or acetone, or a mixed solvent thereof in the presence of a base such as sodium carbonate, potassium carbonate, or an organic base such as pyridine, 2,6-lutidine, collidine, 4-dimethylaminopyridine, triethylamine, N-methylmorpholine, diisopropylethylamine and diazabicyclo[5.4.0]undec-7-ene (DBU), whereby the compound of the formula (XIV) can be obtained.

The protecting group on the nitrogen atom of the compound represented by the formula (XIV) can be removed as described below. When the protecting group is a tertiary butoxycarbonyl group, it can be removed using an appropriate acid such as acetic acid, hydrochloric acid, hydrobromic acid, sulfuric acid, phosphoric acid, trifluoroacetic acid or trifluoromethanesulfonic acid, or combination thereof. An arylmethyl group such as benzyloxycarbonyl, paranitrobenzyloxycarbonyl or paramethoxybenzyloxycarbonyl can be removed by the hydrogenolysis in the presence of a palladium-carbon catalyst. The paramethoxybenzyloxycarbonyl group can be removed using an appropriate acid such as acetic acid, hydrochloric acid, hydrobromic acid, sulfuric acid, phosphoric acid, trifluoroacetic acid or trifluoromethanesulfonic acid or combination thereof. Thus, by the removal of the protecting group, the compound of the formula (XV) can be obtained.

The reaction of the compound of the formula (XV) with the compound of the formula (IIa-3a) is carried out at −20 to 150° C. in the presence of a base in a solvent, for example, an alcohol solvent such as ethanol, an ether solvent such as diethyl ether, tetrahydrofuran, dimethoxyethane or dioxane, a halogen solvent such as dichloromethane or chloroform, a solvent such as acetone, or an amide solvent such as N,N-dimethylformamide, N-methylpyrolidin-2-one or acetamide, or a mixed solvent thereof, whereby the compound of the formula (VIII-3b) can be obtained. Examples of the base include sodium carbonate, potassium carbonate, sodium hydride, potassium hydride, and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

The protecting group of the nitrogen atom of the compound represented by the formula (VIII-3b) can be removed by the ordinarily employed process. Described specifically, when the protecting group is a tertiary butoxycarbonyl group, it can be removed using an appropriate acid such as acetic acid, hydrochloric acid, hydrobromic acid, sulfuric acid, phosphoric acid, trifluoroacetic acid or trifluoromethanesulfonic acid or combination thereof. An arylmethyl group such as benzyl can be removed by the hydrogenolysis in the presence of a palladium-carbon catalyst. A triphenylmethyl group can be removed using an appropriate acid such as formic acid, acetic acid, hydrochloric acid, hydrobromic acid, sulfuric acid, phosphoric acid, trifluoroacetic acid or trifluoromethanesulfonic acid or combination thereof. The arylmethyl group such as benzyl can also be removed by Birch reduction with a metal sodium in liquid ammonia or by hydrogenolysis in the presence of a palladium-carbon catalyst. Thus, by the removal of the protecting group, the compound of the formula (VIII-3a) can be obtained.

<Reaction of any one of the Compounds of the Formulas (IVa) to (IVd) with the Compound of the Formula (VIIIa)>

Examples of the carboxylic acid of each of the formulas (IVa) to (IVd) in an appropriate activated form include acid mixed acid anhydrides available by reacting the carboxylic acid of each of the formulas (IVa) to (IVd) with a chloroformate ester such as isobutyl chloroformate, thereby converting it into the corresponding acid anhydride, acid halides such as acyl chloride prepared by treating with an inorganic acid halide such thionyl chloride, active esters obtained by reacting with a phenol such as paranitrophenol or pentafluorophenyl-trifluoroacetate, active esters obtained by reacting it with N-hydroxybenztriazole or N-hydroxysuccinimide, reaction products with N,N'-dicyclohexylcarbodiimide or N-(3-dimethylaminopropyl)-N'-ethylcarbodiimide hydrochloride which is ordinarily employed in the synthesis of an amino acid, reaction products with diethyl cyanophosphonate (Shioiri's method) and reaction products with triphenylphosphine and 2,2'-dipyridylsulfide (Mukaiyama's method).

The resulting carboxylic acid in an activated form is reacted with the compound of the formula (VIIIa) at −78 to 150° C., usually in the presence of an appropriate base in an inert solvent, whereby the sulfonyl derivative of the formula (I) can be obtained.

Examples of the base include carbonates, alkoxides, hydroxides and hydrides of an alkali metal or alkaline earth metal, such as sodium carbonate, potassium carbonate, sodium ethoxide, potassium butoxide, sodium hydroxide, potassium hydroxide, sodium hydride and potassium hydride; organometallic base compounds typified by alkyl lithium such as n-butyl lithium and dialkylaminolithium such as lithium diisopropylamide; organometallic base of bissilylamine compounds such as lithium bis(trimethylsilyl) amide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

Examples of the inert solvent include dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one, dimethylsulfoxide and sulfolane.

[Preparation Process-2-(1)]

When the nitrogen atom of $Q^{3a}$ of the compound represented by the below-described formula (VIIIa) to be acylated:

$$Q^{3a}-S_2-Q^A \quad \text{(VIIIa)}$$

[wherein, $Q^{3a}$ and $Q^A$ have the same meanings as described above] is a primary or secondary amine, preferred examples of the base include carbonates and hydroxides of an alkali metal or alkaline earth metal, such as sodium carbonate, potassium carbonate, sodium hydroxide and potassium hydroxide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU) and usable examples of the solvent include, in addition to inert solvents, alcohol solvents such as ethanol and butanol and ester solvents such as ethyl acetate.

[Preparation Process-2-(2)]

When the nitrogen atom of $Q^{3a}$ of the compound represented by the below-described formula (VIIIa) to be acylated:

$$Q^{3a}-SO_2-Q^A \quad \text{(VIIIA)}$$

[wherein $Q^{3a}$ and $Q^A$ have the same meanings as described above] forms an amide bond, examples of the base include alkoxides and hydrides of an alkali metal or alkaline earth metal such as sodium ethoxide, potassium butoxide, sodium hydride and potassium hydride; organometallic base compounds typified by alkyl lithium such as n-butyl lithium and dialkylaminolithium such as lithium diisopropylamide; organometallic base of bissilylamine compounds such as lithium bis(trimethylsilyl)amide; and organic bases such as diazabicyclo[5.4.0]undec-7-ene (DBU). Examples of the inert solvent include tetrahydrofuran, 1,2-dimethoxyethane, dioxane and N,N-dimethylformamide.

[Preparation Process-3]

A process for preparing, in the case the nitrogen atom of $Q^{3a}$ of the compound represented by the following formula (VIIIa):

$$Q^{3a}-SO_2-Q^A \quad \text{(VIIIa)}$$

[wherein, $Q^{3a}$ and $Q^A$ have the same meanings as described above] constitutes an amide, the sulfonyl derivative of the present invention by alkylating the nitrogen atom of the formula (VIIIa) with any one of the compounds represented by the following formulas (Va) to (Vd):

$$Q^1-Q^{2b}-CHL^1R^{13} \quad \text{(Va)}$$

$$Q^1-N(R^{20})-(CH_2)_{m1}-CHL^1R^{13} \quad \text{(Vb)}$$

$$Q^1-O-(CH_2)_{m1}-CHL^1R^{13} \quad \text{(Vc)}$$

$$Q^1-S-(CH_2)_{m1}-CHL^1R^{13} \quad \text{(Vd)}$$

[wherein $Q^1$, $Q^{2b}$, $R^{13}$, $R^{20}$, m1 and $L^1$ have the same meanings as described above].

When the nitrogen atom of $Q^{3a}$ of the compound of the formula (VIIIa) is a nitrogen atom of an amide bond, the sulfonyl derivative of the formula (I) can be synthesized by alkylating the nitrogen atom of $Q^{3a}$ of the compound of the formula (VIIIa) with any one of the compounds of the formulas (Va) to (Vd). Described specifically, the sulfonyl derivative (I) can be obtained by reacting the compound of the formula (VIIIa) with any one of the compounds of the formulas (Va) to (Vd) at −78 to 150° C. for 0.5 to 120 hours in the presence of an appropriate base in an inert solvent, thereby effecting alkylation of the nitrogen atom.

Examples of the base include alkoxides and hydrides of an alkali metal or alkaline earth metal, such as sodium ethoxide, potassium butoxide, sodium hydride and potassium hydride; organometallic base compounds typified by alkyl lithium such as n-butyl lithium and dialkylaminolithium such as lithium diisopropylamide; organometallic base of bissilylamine compounds such as lithium bis(trimethylsilyl)amide; and organic bases such as diazabicyclo[5.4.0]undec-7-ene (DBU). Preferred examples of the inert solvent include tetrahydrofuran, 1,2-dimethoxyethane, toluene, dioxane and N,N-dimethylformamide.

[Preparation Process-4]

A process for preparing, in the case where the nitrogen atom of $Q^{3a}$ of the compound represented by the formula (VIIIa):

[wherein, $Q^{3a}$ and $Q^A$ have the same meanings as described above] exists as a primary or secondary amine, the sulfonyl derivative (I) by forming the corresponding imine with any one of the carbonyl compounds represented by the following formulas (VIa) to (VId):

 (VIa)

Q¹—N(R²⁰)—(CH₂)$_{m1}$—C(=O)R¹³ (VIb)

Q¹—O—(CH₂)$_{m1}$—C(=O)R¹³ (VIc)

Q¹—S—(CH₂)$_{m1}$—C(=O)R¹³ (VId)

[wherein $Q^1$, $Q^{2b}$, $R^{13}$, $R^{20}$ and m1 have the same meanings as described above], followed by reduction.

Described specifically, when the nitrogen atom of $Q^{3a}$ of the compound of the formula (VIIIa) exists as an amine, the sulfonyl derivative of the formula (I) can be prepared by reacting the compound of the formula (VIIIa) with any one of the carbonyl compounds of the formulas (VIa) to (VId) at −20 to 150° C. for 0.5 to 120 hours, usually in an inert solvent, if necessary in the presence of an organic acid such as acetic acid, a mineral acid such as hydrochloric acid or a Lewis acid such as aluminum chloride, thereby forming the corresponding imine and then hydrogenating the resulting imine with a boron hydride reducing agent such as sodium borohydride, sodium cyanoborohydride or sodium triacetoxyborohydride or a catalytic reduction catalyst such as palladium-carbon in an inert solvent at 10 to 110° C. for 0.5 to 120 hours.

Examples of the inert solvent include dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one, dimethylsulfoxide and sulfolane.

[Preparation Process-5]

A process for reacting, in the case where $Q^{3a}$ of the compound represented by the following formula (VIIIa):

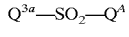 (VIIIa)

[wherein, $Q^{3a}$ and $Q^A$ have the same meanings as described above] exists as a primary or secondary amine, the compound of the formula (VIIIa) with any one of the primary-amine-containing compounds represented by the following formulas (VIIa) to (VIId):

 (VIIa)

Q¹—N(R²⁰)—(CH₂)$_{m2}$—NH₂ (VIIb)

Q¹—O—(CH₂)$_{m2}$—NH₂ (VIIc)

Q¹—S—(CH₂)$_{m2}$—NH₂ (VIId)

or a secondary-amine-containing compound represented by the following formula (VIIe):

 (VIIe)

[in the above-described formulas, $Q^1$, $Q^{2b}$, $R^{20}$, m2 and the group:

have the same meanings as described above] by using a reagent such as phosgene, triphosgene or carbonyldiimidazole, thereby forming the corresponding urea derivative.

When $Q^{3a}$ of the compound of the formula (VIIIa) exists as an amine, the compound of the formula (VIIIa) is reacted with any one of the primary-amine-containing compounds represented by the formulas (VIIa) to (VIId) or the secondary-amine-containing compound represented by the formula (VIIe) and the reagent such as phosgene, triphosgene or 1,1'-carbonyldiimidazole to introduce it into the sulfonyl derivative of the present invention represented by the formula (I), which is to be an urea derivative.

The synthesis can be carried out by successively reacting, with the reagent such as phosgene, triphosgene or 1,1'-carbonyldiimidazole, any one of the primary-amine-containing compounds of the formulas (VIIa) to (VIId) or the secondary-amine-containing compound of the formula (VIIe) and the compound of the formula (VIIIa), if necessary in the presence of a base, in an inert solvent. Examples of the inert solvent include dichloromethane, chloroform, carbon tetrachloride, tetrahydrofuran, 1,2-dimethoxyethane, dioxane, toluene, N,N-dimethylformamide, N,N-dimethylacetamide, N-methylpyrrolidin-2-one, dimethylsulfoxide and sulfolane. Among them, dichloromethane, tetrahydrofuran and toluene are preferred.

Examples of the base include carbonates and hydroxides of an alkali metal or alkaline earth metal such as sodium carbonate, potassium carbonate, sodium hydroxide and potassium hydroxide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU). The reaction may be conducted at a temperature range of from −70° C. to 110° C.

[Preparation Process-6]

A process for preparing a urea-containing sulfonyl derivative of the formula (I) by reacting, in the case where the nitrogen atom of $Q^{3a}$ of the compound represented by the formula (VIIIa):

$$Q^{3a}-SO_2-Q^A \qquad \text{(VIIIa)}$$

[wherein, $Q^{3a}$ and $Q^A$ have the same meanings as described above] exists as a primary or secondary amine, the amine of the formula (VIIIa) with a known isocyanate derivative ($Q^1-Q^{2b}-N=C=O$) [wherein, $Q^1$ and $Q^{2b}$ have the same meanings as described above] or an isocyanate prepared from any one of the carboxylic acids represented by the following formulas (IVa) to (IVd):

$$Q^1-Q^{2b}-COOH \qquad \text{(IVa)}$$

$$Q^1-N(R^{20})-(CH_2)_{m1}-COOH \qquad \text{(IVb)}$$

$$Q^1-O-(CH_2)_{m1}-COOH \qquad \text{(Ivc)}$$

$$Q^1-S-(CH_2)_{m1}-COOH \qquad \text{(Ivd)}$$

[wherein $Q^1$, $Q^{2b}$, $R^{20}$ and m1 have the same meanings as described above].

When $Q^{3a}$ of the compound represented by the formula (VIIIa) is an amine, the sulfonyl derivative of the formula (I) can be prepared by reacting the compound of the formula (VIIIa) with a known isocyanate derivative at −20 to 100° C. for 0.5 to 120 hours in an inert solvent.

The isocyanate derivative can be synthesized from any one of the carboxylic acids of the formulas (IVa) to (IVd). Described specifically, it can be obtained by introducing any one of the carboxylic acids of the formulas (IVa) to (IVd) into the corresponding acid halide with thionyl chloride, oxalyl chloride or the like, reacting the resulting acid halide with sodium azide at a temperature range of from 0 to 60° C. in an inert solvent and then, heating the reaction mixture; by reacting the carboxylic acid of the formula (IVa) with a chloroformate such as isobutyl chloroformate, reacting the resulting acid anhydride with sodium azide and then heating the reaction mixture; or introducing any one of the carboxylic acids represented by the formulas (IVa) to (IVd) into the corresponding hydrazide through an ester in an inert solvent such as tetrahydrofuran, chloroform or toluene at −20 to 110° C., reacting the resulting hydrazide with nitrous acid or alkyl ester thereof to introduce it into the corresponding acylazide and then heating at 20 to 150° C. in a solvent such as chloroform, dichloroethane, toluene, xylene or N,N-dimethylformamide.

The sulfonyl derivative of the formula (I) can also be prepared by reacting any one of the carboxylic acids of the formulas (IVa) to (IVd) with diphenylphosphorylazide at 10 to 100° C. in the presence of a base such as triethylamine in an inert solvent.

[Preparation Process-7]

The compound represented by the following formula (XVI):

$$Q^1-Q^2-T^1-Q^3-SO_2-NHCOOR \qquad \text{(XVI)}$$

[wherein, $Q^1$, $Q^2$, $Q^3$, $R^{60}$ and $T^1$ have the same meanings as described above] can be synthesized by reacting, in the case where the nitrogen atom of $Q^{3a}$ of the compound represented by the following formula (Ia) to be sulfonylated:

$$Q^1-Q^2-T^1-Q^{3a} \qquad \text{(Ia)}$$

[wherein, $Q^1$, $Q^2$, $Q^{3a}$ and $T^1$ have the same meanings as described above] exists as a primary or secondary amine, the compound of the formula (Ia) with a compound which is available from chlorosulfonyl isocyanate and an alcohol and is represented by the following formula (XIII):

$$Cl-SO_2-NHCOOR^{60} \qquad \text{(XIII)}$$

[wherein, $R^{60}$ has the same meaning as described above] in the presence of an appropriate base in an inert solvent.

The compound represented by the following formula (I-3a):

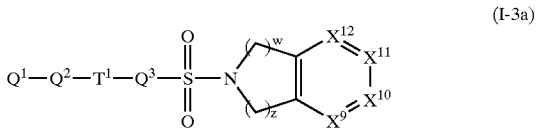

[wherein, $Q^1$, $Q^2$, $Q^3$, $T^1$, $X^9$, $X^{10}$, $X^{11}$, $X^{12}$, w and z have the same meanings as described above], one of the compounds of the formula (I), can be synthesized by removing the protecting group on the nitrogen atom of the resulting compound (XVI), thereby obtaining a compound represented by the following formula (XVII):

$$Q^1-Q^2-T^1-Q^3-SO_2-NH_2 \qquad \text{(XVII)}$$

[wherein, $Q^1$, $Q^2$, $Q^3$ and $T^1$ have the same meanings as described above]; and then reacting the resulting compound of the formula (XVII) with a compound represented by the following formula (IIa-3a):

[wherein, $X^9$, $X^{10}$, $X^{11}$, $X^{12}$, $L^2$, $L^3$, w and z have the same meanings as described above] in an appropriate base in an inert solvent.

The reaction between the compound of the formula (Ia) and the compound of the formula (XIII) to synthesize the compound of the formula (XVI) is effected at −70 to 100° C. in an solvent, for example, an ether solvent such as diethyl ether, tetrahydrofuran, dimethoxyethane or dioxane, a halogen solvent such as dichloromethane or chloroform, or a solvent such as benzene, toluene or acetone or a mixed solvent thereof and in this reaction, usable examples of the base include sodium carbonate, potassium carbonate and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

The protecting group on the nitrogen atom of the compound of the formula (XVI) can be removed as described below. When the protecting group is a tertiary butoxycarbonyl group, it can be removed using an appropriate acid such as acetic acid, hydrochloric acid, hydrobromic acid, sulfuric acid, phosphoric acid, trifluoroacetic acid or trifluoromethanesulfonic acid, or combination thereof. An arylmethyl group such as benzyloxycarbonyl, paranitrobenzyloxycarbonyl or paramethoxybenzyloxycarbonyl can be removed by the hydrogenolysis in the presence of a palladium-carbon catalyst. The paramethoxybenzyloxycarbonyl group can be removed using an appropriate acid such as acetic acid, hydrochloric acid, hydrobromic acid, sulfuric acid, phosphoric acid, trifluoroacetic acid or trifluoromethanesulfonic acid or combination thereof. Thus, by the removal of the protecting group, the compound of the formula (XVII) can be obtained.

The reaction of the compound of the formula (XVII) with the compound of the formula (IIa-3a) is carried out at −20 to 150° C. in the presence of a base in a solvent, for example, an alcohol solvent such as ethanol, an ether solvent such as diethyl ether, tetrahydrofuran, dimethoxyethane or dioxane, a halogen solvent such as dichloromethane or chloroform, a solvent such as acetone, N,N-dimethylformamide, N-methylpyrolidin-2-one or acetamide, or a mixed solvent thereof, whereby the compound of the formula (I-3a), one of the compounds of the formula (I), can be obtained.

Examples of the base include sodium carbonate, potassium carbonate, and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

From the compound of the formula (I-3a), it is possible to eliminate the protecting group in an ordinarily employed process if necessary.

[Preparation Process-8]

A process for synthesizing a sulfonyl derivative represented by the following formula (I):

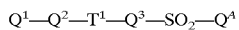  (I)

[wherein, $Q^1$, $Q^2$, $Q^3$, $Q^4$, $T^1$ have the same meanings as described above] by coupling reaction using a transition metal catalyst.

When in the structure of $Q^1$ of the sulfonyl derivative of the formula (I), a halogen- or trifluoromethanesulfonyloxy-substituted aryl group or a halogen- or trifluoromethanesulfonyloxy-substituted alkenyl group is contained, it can be subjected to coupling reaction with a boric-acid-substituted aryl compound in the presence of a transition metal catalyst.

When in the structure of $Q^1$ of the sulfonyl derivative of the formula (I), an alkenyl group is contained, it can be subjected to coupling reaction with a halogen- or trifluoromethanesulfonyloxy-substituted aryl group in the presence of a transition metal catalyst.

When in the structure of $Q^1$ of the sulfonyl derivative represented by the formula (I), a boric-acid-substituted aryl group is contained, it can be subjected to coupling reaction with a halogen- or trifluoromethanesulfonyloxy substituted aryl compound or a halogen- or trifluoromethanesulfonyloxy-substituted alkenyl compound.

When in the structure of $Q^1$ of the sulfonyl derivative of the formula (I), a halogen- or trifluoromethanesulfonyloxy-substituted aryl group or a halogen- or trifluoromethanesulfonyloxy-substituted alkenyl group is contained, it can be subjected to coupling reaction with a boric-acid-substituted aryl derivative by using a transition metal catalyst such as tetrakis(triphenylphosphine) palladium (O), in a two-phase solvent such as benzene-water or toluene-water, an amide solvent such as N,N-dimethylformamide or an ether solvent such as tetrahydrofuran or dimethoxyethane, in the presence of a base such as sodium carbonate, sodium hydroxide, barium hydroxide, potassium phosphate or cesium carbonate or a neutral salt such as cesium fluoride at a temperature range of 20 to 150° C. for 0.5 to 120 hours.

When in the structure of $Q^1$ of the sulfonyl derivative represented by the formula (I), an alkenyl group or boric-acid-substituted alkenyl group is contained, it can be subjected to coupling reaction with a halogen- or trifluoromethanesulfonyloxy-substituted aryl group by using a transition metal catalyst such as palladium acetate, in the presence of an appropriate base, in an amide solvent such as N,N-dimethylformamide at a temperature range of from 20 to 150° C. for 0.5 to 120 hours.

When in the structure of $Q^1$ of the sulfonyl derivative represented by the formula (I), a halogen- or trifluoromethanesulfonyloxy-substituted aryl group, it can be subjected to coupling reaction with an alkenyl compound by using a transition metal catalyst. By the above-described process, the sulfonyl derivative of the formula (I) can be obtained. From the sulfonyl derivative of the formula (I) can be obtained. By deprotection, the sulfonyl derivative of the formula (I) having a changed substituent can be obtained.

[Preparation Process-9]

A process for preparing each of a thioamido type sulfonamide product, an amidoxime type sulfonamide product and a hydrazono type sulfonamide product:

When $T^1$—$Q^3$ of the sulfonyl derivative represented by the following formula (I):

  (I)

[wherein $Q^1$, $Q^2$, $Q^3$, $Q^4$ and $T^1$ have the same meanings as described above] represents any one of the following formulas:

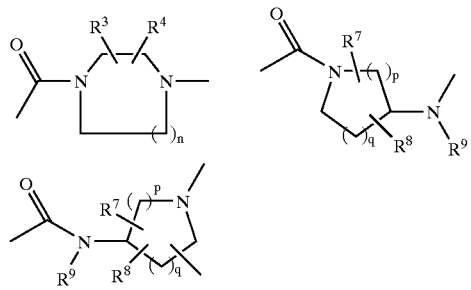

[wherein $R^3$, $R^4$, $R^7$, $R^8$ and $R^9$ have the same meanings as described above, n stands for an integer of 1 or 2, p stands for an integer of 1 to 3 and q stands for an integer of 0 to 3 with the proviso that the sum of p and q stands for an integer of 3 or 4] and none of amine-, alkylamine-, amido-, hydroxyl- and carboxylic-acid-containing substituents exist on $R^3$, $R^4$, $R^7$, $R^8$, $R^9$ or a substituent substitutable therefor in $Q^1$, $Q^2$ and $Q^3$ of the formula (I), a thioamido type sulfonamide derivative (I) can be obtained by reacting the sulfonyl derivative represented by the formula (I) with a diphosphorous pentasufide or Lawson reagent (2,4-bis(4-methoxyphenyl)-1,3-dithia-2,4-diphosphetane-2,4-disufide) at −30 to 150° C., if necessary in an inert solvent at 0 to 120° C. Examples of the inert solvent include alkyl halide solvents such as dichloromethane, chloroform and carbon tetrachloride, ether solvents such as tetrahydrofuran, 1,2-dimethoxyethane and dioxane and aromatic solvents such as benzene and toluene, and a mixture thereof.

The sulfonamide derivative represented by the formula (I) can be obtained by reacting the obtained thioamido type sulfomide with a hydroxylamine, alkoxyamine which may have a substituent, and hydrazine which may have a substituent, or a salt thereof, in the presence of a mercury catalyst such as a mercury (II) chloride at −30 to 150° C. if necessary, or in an appropriate solvent 0 to 120° C. if necessary. Examples of the solvent include alcohol solvents such as ethanol, alkyl halide solvents such as dichloromethane, chloroform and carbon tetrachloride, ether solvents such as tetrahydrofuran, 1,2-dimethoxyethane and dioxane and aromatic solvents such as benzene and toluene, and a mixture thereof.

The sulfonyl derivative represented by the formula (I) can be obtained by reacting the sulfonyl derivative of the formula (I) with a halogenating agent such as phosphorous oxychloride or phosphorus pentachloride or an alkylating agent such as Meerwein reagent at −30 to 140° C., if necessary in an inert solvent, for example, a halogen solvent such as chloroform at 0 to 80° C., to convert the derivative into the corresponding imino chloride or imino ether and then, reacting the resulting imino chloride or imino ether with hydroxylamine, alkoxyamine which may have a substituent or salt thereof at 0 to 80° C., preferably at 20 to 60° C., if necessary in the presence of a base catalyst.

Examples of the inert solvent include alkyl halide solvents such as dichloromethane, chloroform and carbon tetrachloride, ether solvents such as tetrahydrofuran, 1,2-dimethoxyethane and dioxane and aromatic solvents such as benzene and toluene. Among them, the alkyl halide solvents are particularly preferred. Examples of the base include carbonates, alkoxides, hydroxides and hydrides of an alkali metal or alkaline earth metal, such as sodium carbonate, potassium carbonate, sodium ethoxide, potassium butoxide, sodium hydroxide, potassium hydroxide, sodium hydride and potassium hydride; organometallic base compounds typified by an alkyl lithium such as n-butyl lithium and a dialkylamino lithium such as lithium diisopropylamide; organometallic base of bissilylamine compounds such as lithium bis(trimethylsilyl)amide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

[Preparation Process-10]
N-oxide Formation

When in the sulfonyl derivative of the formula (I), there exists a nitrogen-containing heterocyclic aromatic ring or aliphatic tertiary amine on $Q^1$, $Q^2$, $Q^3$, $Q^A$ or $T^1$ or a substituent substitutable therefor, the sulfonyl derivative of the formula (I) is reacted with a peroxide such as hydrogen peroxide, metachloroperbenzoic acid or tertiary butyl hydroperoxide at −40 to 60° C. for 0.5 to 120 hours preferably −20 to 20° C. in a solvent such as water, acetic acid, a benzene solvent such as benzene, toluene or xylene, an ether solvent such as tetrahydrofuran or dimethoxyethane or an alkyl halide solvent such as dichloromethane, chloroform or carbon tetrachloride, whereby the sulfonyl derivative of the formula (I) can be obtained as an N-oxide derivative.

[Preparation Process-11]
Quaternization of a Nitrogen Atom

When in the sulfonyl derivative of the formula (I), there exists a nitrogen-containing heterocyclic aromatic group or aliphatic tertiary amine on $Q^1$, $Q^2$, $Q^3$, $Q^A$ or $T^1$ or a substituent substitutable therefor, the sulfonyl derivative of the formula (I) is reacted with an alkyl halide such as methyl iodide or ethyl iodide in an ether solvent such as 1,2-dimethoxyethane or dioxane, an aromatic solvent such as benzene or toluene, an amide solvent such as N,N-dimethylformamide, N,N-dimethylacetamide or N-methylpyrrolidin-2-one or a sulfoxide solvent such as dimethyl sulfoxide or sulfolane at −10 to 150° C., preferably 0 to 80° C., whereby the sulfonyl derivative of the formula (I) can be obtained as a quaternary amino product.

[Preparation Process-12]
Sulfoxide or Sulfone Formation

When in the sulfonyl derivative of the formula (I), a sulfur-containing hetero ring or aliphatic thioether exists on $Q^1$, $Q^2$, $Q^3$, $Q^A$ or $T^1$ or a substituent substitutable therefor, the sulfonyl derivative of the formula (I) is reacted with a peroxide such as hydrogen peroxide, metachloroperbenzoic acid or tertiary butyl hydroperoxide at −40 to 60° C. for 0.5 to 120 hours, preferably −20 to 20° C. in a solvent such as water or acetic acid, a benzene solvent such as benzene, toluene or xylene, an ether solvent such as tetrahydrofuran or dimethoxyethane or an alkyl halide solvent such as dichloromethane, chloroform or carbon tetrachloride, whereby the sulfonyl derivative (I) can be obtained in the form of sulfoxide or sulfone.

[Preparation Process-13]
Amidino Formation-1

When in the sulfonyl derivative of the formula (I), a nitrile group exists on $Q^1$, $Q^2$, $Q^3$, $Q^A$ or $T^1$ or a substituent substitutable therefor, it can be converted into an amidino group by an ordinarily employed process. The amidino-containing sulfonyl derivative of the formula (I) can be obtained, for example, by allowing an equal amount to large excess of a $C_{1-4}$ alcohol such as methanol, ethanol or propanol to act on the sulfonyl derivative of the formula (I) at −10 to 60° C. for 3 to 120 hours in an aliphatic ether solvent such as diethyl ether, an alkyl halide solvent such as chloroform or dichloromethane or an aprotic solvent such as benzene or a mixed solvent thereof in the presence of a hydrogen halide such as hydrogen chloride or hydrogen bromide, thereby converting it to the corresponding imino ether; then reacting the resulting imino ether product with ammonium, a monoalkylamine which may have a substituent or a dialkylamine which may have a substituent, or a carbonate or acetate thereof at −10 to 140° C. for 0.5 to 200 hours in a $C_{1-4}$ alcohol such as ethanol or propanol, an aliphatic ether solvent such as diethyl ether, an alkyl halide solvent such as chloroform, an aprotic solvent such as benzene, a solvent such as N,N-dimethylformamide or dimethylsulfoxide or a mixed solvent thereof, preferably at −8 to 30° C. for 10 to 96 hours in ethanol.

[Preparation Process-14]
Amidino Formation-2

When in the sulfonyl derivative of the formula (I), a primary or secondary amino group exists on $Q^1$, $Q^2$, $Q^3$, $Q^A$ or $T^1$ or a substituent substitutable therefor, it can be converted into a substituted amidino group by an ordinarily employed process.

Described specifically, the amidino-containing sulfonyl derivative of the formula (I) can be obtained, for example, by reacting the sulfonyl derivative of the formula (I) with an imino ether, imino chloride or salt thereof, which has been synthesized from an amide compound or nitrile compound, in an aliphatic ether solvent such as diethyl ether, an alkyl halide solvent such as chloroform or dichloromethane or an aprotic solvent such as benzene, or a mixed solvent thereof, if necessary in the presence of a base catalyst, at −10 to 140° C. for 0.5 to 200 hours, preferably 0 to 80° C. for 10 to 96 hours. Examples of the base include carbonates and hydroxides of an alkali metal or alkaline earth metal, such as sodium carbonate, potassium carbonate, sodium hydroxide and potassium hydroxide and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

[Preparation Process-15]
N-nitrile Formation

When in the sulfonyl derivative of the formula (I), a primary or secondary amine group exists on $Q^1$, $Q^2$, $Q^3$, $Q^A$ or $T^1$ or a substituent substitutable therefor, it can be cyanated by an ordinarily employed process.

For example, the sulfonyl derivative of the formula (I) is reacted with cyan bromide in an alcohol solvent such as methanol, ethanol or propanol in the presence of a salt such as sodium acetate or a base at −10 to 110° C., preferably 0 to 60° C., whereby the sulfonyl derivative (I) having a nitrile group on its nitrogen atom can be obtained. Examples of the base include carbonates and hydroxides of an alkali metal or alkaline earth metal, such as sodium carbonate, potassium carbonate, sodium hydroxide and potassium hydroxide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

[Preparation Process-16]
Amidoxime or Carboxamido-O-alkyloxime Introduction

When in the sulfonyl derivative of the formula (I), a nitrile group exists on $Q^1$, $Q^2$, $Q^3$, $Q^4$ or $T^1$ or a substituent substitutable therefor, it can be converted into an amidoxime or carboxamido-O-alkyloxime group by an ordinarily employed process.

For example, the sulfonyl derivative of the formula (I) is reacted with hydroxylamine or an alkoxyamine which may have a substituent, or salt thereof in an alcohol solvent such as methanol, ethanol or propanol, an ether solvent such as diethyl ether or tetrahydrofuran, a halogenated hydrocarbon such as chloroform or dichloromethane, an aprotic solvent such as toluene, an amide solvent such as N,N-dimethylformamide or a solvent such as dimethylsulfoxide, or a mixed solvent thereof at −10 to 110° C., preferably 0 to 60° C., if necessary in the presence of a base catalyst, whereby the sulfonyl derivative of the formula (I) having an amidoxime or carboxamido-O-alkyloxime group can be obtained. Examples of the base include carbonates and hydroxides of an alkali metal or alkaline earth metal such as sodium carbonate, potassium carbonate, sodium hydroxide and potassium hydroxide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

[Preparation Process-17]
Guanidino Introduction

When in the sulfonyl derivative of the formula (I), a primary or secondary amino group exists on $Q^1$, $Q^2$, $Q^3$, $Q^4$ or $T^1$ or a substituent substitutable therefor, it can be converted into a substituted or unsubstituted guanidino group by an ordinarily employed process.

For example, the sulfonyl derivative of the formula (I) having a primary or secondary amino group is reacted with N,N'-di(tert-butoxy)carbonylthiourea and N,N'-dicyclohexylcarbodiimide as a condensing agent in an aliphatic ether solvent such as diethyl ether, a halogenated hydrocarbon such as chloroform or dichloromethane or an aprotic solvent such as benzene, or a mixed solvent thereof at −10 to 140° C. for 0.5 to 200 hours, preferably 0 to 80° C. for 10 to 96 hours, if necessary in the presence of a base catalyst, and then, as usual, the tertiary butoxycarbonyl group is removed, whereby the sulfonyl derivative of the formula (I) as a guanidino compound can be synthesized. Examples of the base include carbonates and hydroxides of an alkali metal or alkaline earth metal, such as sodium carbonate, potassium carbonate, sodium hydroxide and potassium hydroxide; and organic bases such as pyridine, 2,6-lutidine, collidine, 4-dimethylaminopyridine, triethylamine, N-methylmorpholine, diisopropylethylamine and diazabicyclo[5.4.0]undec-7-ene (DBU).

[Preparation Process-18]
Deprotection from the Protected Nitrogen Atom

When in the sulfonyl derivative of the formula (I), an acylamino or alkoxycarbonylamino group exists on $Q^1$, $Q^2$, $Q^3$, $Q^4$ or $T^1$ or a substituent substitutable therefor, an amino-containing derivative can be obtained by subjecting the derivative to hydrolysis at 0 to 80° C. in a solvent such as water, a lower alcohol or tetrahydrofuran, or a mixed solvent thereof in the presence of a base such as an alkali metal hydroxide e.g. lithium hydroxide, sodium hydroxide or potassium hydroxide. The nitrogen atom to which an acyl type protecting group such as tertiary butoxycarbonyl or paramethoxybenzyloxycarbonyl has been bonded can be converted into a nitrogen-hydrogen bond by using an appropriate acid such as acetic acid, hydrochloric acid, hydrobromic acid, sulfuric acid, phosphoric acid, trifluoroacetic acid or trifluoromethanesulfonic acid or combination thereof in a solvent such as water, an alcohol solvent such as methanol, an alkyl halide solvent such as dichloromethane, chloroform or carbon tetrachloride, an ether solvent such as tetrahydrofuran, 1,2-dimethoxyethane or dioxane or an aromatic solvent such as benzene or toluene and removing the acyl type protecting group from the nitrogen atom at 0 to 80° C.

The nitrogen atom to which an arylmethoxycarbonyl group such as benzyloxycarbonyl, paramethoxybenzyloxycarbonyl or para(ortho)-nitrobenzyloxycarbonyl has been bonded can be converted into a nitrogen-hydrogen bond by removing the arylmethoxycarbonyl group from the protected nitrogen atom through hydrogenolysis in the presence of a palladium-carbon catalyst in a solvent such as water, an alcohol solvent such as ethanol, an ester solvent such as ethyl acetate, an ether solvent such as diethyl ether or tetrahydrofuran, or a solvent such as acetic acid or N,N-dimethylformamide, or a mixed solvent thereof. The nitrogen atom to which a silyl type protecting group such as trimethylsilyl or tertiary butyl dimethylsilyl has been bonded can be converted into a nitrogen-hydrogen bond by reacting with hydrochloric acid or a hydrofluoride such as tetrabutylammonium fluoride at 0 to 80° C. in an alkyl halide solvent such as dichloromethane, chloroform or carbon tetrachloride, an ether solvent such as tetrahydrofuran, 1,2-dimethoxyethane or dioxane or an aromatic solvent such as benzene or toluene, thereby removing the silyl group from the protected nitrogen atom. The nitrogen atom to which a benzyl group has been bonded can be converted into a nitrogen-hydrogen bond by removing the benzyl group through the catalytic reduction at 0 to 80° C. with a palladium-carbon catalyst or the like in a solvent such as ethanol, tetrahydrofuran or acetic acid or through the Birch's reduction with a metal sodium in a liquid ammonia. The nitrogen atom to which a triphenylmethyl group has been bonded can be converted into a nitrogen-hydrogen bond by removing the triphenylmethyl group through the catalytic reduction with a palladium-carbon catalyst or the like at 0 to 80° C. in a solvent such as ethanol, tetrahydrofuran or acetic acid or through the Birch's reduction with a metal sodium in a liquid ammonia. The removal of the triphenylmethyl group and conversion into a nitrogen-hydrogen bond can also be carried out by using an appropriate acid, such as formic acid, acetic acid, hydrochloric acid, hydrobromic acid, sulfuric acid, phosphoric acid, trifluoroacetic acid or trifluoromethanesulfonic acid, or a combination thereof at 0 to 80° C.

[Preparation Process-19]
Ester Hydrolysis

When in the sulfonyl derivative of the formula (I), an alkoxycarbonyl group exists on $Q^1$, $Q^2$, $Q^3$, $Q^4$ or $T^1$ or a substituent substitutable therefor, in the case of a methyl or ethyl ester, the alkoxycarbonyl group can be converted into the corresponding carboxylic acid by the hydrolysis with an appropriate base, for example, an alkali metal hydroxide such as lithium hydroxide, sodium hydroxide or potassium hydroxide. In the case of a tertiary butyl ester, the tertiary butyl group can be removed by treating with trifluoroacetic acid or hydrochloric acid, while in the case of an arylmethyl type ester such as benzyl, the carboxylic acid can be obtained by removing the arylmethyl group by hydrogenolysis in the presence of a palladium-carbon catalyst. Conversion from an ester group to a carboxylic acid residue can be effected using potassium trimethylsilanolate.

[Preparation Process-20]

When in the sulfonyl derivative of the formula (I), an acyloxy, arylmethyloxy, silylether, methoxymethyl or tetrahydropyranyl group exists on $Q^1$, $Q^2$, $Q^3$, $Q^A$ or $T^1$ or a substituent substitutable therefor, the acyl group such as alkanoyl or aroyl can be removed by the hydrolysis with an appropriate base, for example, an alkali metal hydroxide such as lithium hydroxide, sodium hydroxide or potassium hydroxide; or alternatively can be removed by reacting with an organic base such as ammonia or methylamine. The arylmethyl type protecting group can be removed by the hydrogenolysis with a palladium-carbon catalyst. The silylether group such as tertiary butyl dimethylsilyl can be removed by a hydrofluoride salt such as tetrabutylammonium fluoride. The methoxymethyl or tetrahydropyranyl group can be removed using acetic acid or hydrochloric acid.

[Preparation Process-21]

When in the sulfonyl derivative of the formula (I), an amino group exists on $Q^1$, $Q^2$, $Q^3$, $Q^A$ or $T^1$ or a substituent substitutable therefor, it can be acylated by an ordinarily employed process which uses an acyl halide or activated carboxylic acid. Alternatively, it can be alkylated by reductive alkylation or the like process. The sulfonyl derivative of the formula (I) which is an urea derivative can be prepared by sulfonylation through sulfonic acid chloride or by reacting with isocyanate or carboxylic-acid-derived isocyanate.

[Preparation Process-22]

When in the sulfonyl derivative of the formula (I), an carboxyl group exists on $Q^1$, $Q^2$, $Q^3$, $Q^A$ or $T^1$ or a substituent substitutable therefor, it can be converted into a carbamoyl, alkylcarbamoyl or dialkylcarbamoyl group by an ordinarily employed active ester method or mixed acid anhydride method and then converted into a hydroxyl or aldehyde group by reduction. The resulting hydroxyl or aldehyde group can be subjected to conversion of a functional group, such as ether bond formation, conversion into an amino group or conversion into an alkylamino group by the process ordinarily employed in organic chemistry. The carboxyl group, after conversion into its ester or mixed acid anhydride directly or by the usual process, is reduced, whereby the corresponding alcohol can be obtained.

[Preparation-23]
Formation of Phenol

When in the sulfonyl derivative of the formula (I), an aryl-substituted methoxy group exists on $Q^1$, $Q^2$, $Q^3$, $Q^A$ or T1 or a substituent substitutable therefor, it can be converted into a hydroxyl group by removing the methyl group using trimethylsilyl iodide at −78 to 110° C. in an alkyl halide solvent such as dichloromethane, chloroform or carbon tetrachloride or a benzene solvent such as toluene, or at −78 to 110° C. in a Lewis acid such as aluminum chloride, phosphorus tribromide or boron trifluoride, an alkyl halide solvent or an ether solvent.

[Preparation Process-24]
Conversion of a Halogen Atom into an Alkynyl Group

When the compound of the formula (I), the compound of the formula (VIIIa), the compound of the formula (VIIIa-1b), the compound of the formula (VIIIa-1c), the compound of the formula (VIIIa-2a), the compound of the formula (VIIIa-2b), the compound of the formula (VIIIa-2c), the compound of the formula (VIIIa-2d), the compound of the formula (VIIIa-2e), the compound of the formula (VIIIa-3a), or the compound of the formula (VIIIa-3b) has an aromatic ring substituted with chlorine, bromine or iodine, such a halogen atom can be converted into an acetylene group by reacting with a silylacetylene compound in the presence of a transition metal catalyst.

The conversion of chlorine, bromine or iodine into a silylacetylene group can be carried out by reacting the compound of the formula (I), the compound of the formula (VIIIa), the compound of the formula (VIIIa-1b), the compound of the formula (VIIIa-1c), the compound of the formula (VIIIa-2a), the compound of the formula (VIIIa-2b), the compound of the formula (VIIIa-2c), the compound of the formula (VIIIa-2d), the compound of the formula (VIIIa-2e), the compound of the formula (VIIIa-3a), or the compound of the formula (VIIIa-3b) having an aromatic ring substituted with chlorine, bromine or iodine, with a silylacetylene such as trimethylsilylacetylene by using palladium acetate and triphenylphosphine at a temperature range of from −20 to 150° C. for 0.5 to 120 hours, if necessary in the presence of a base such as triethylamine or pyridine, in a benzene solvent such as toluene, an ether solvent such as tetrahydrofuran or an amide solvent such as N,N-dimethylformamide, or a mixed solvent thereof.

The silyl group can be removed from the resulting silylacetylene compound by treating the compound with a base such as potassium carbonate, potassium bicarbonate or sodium hydroxide in a solvent, for example, an alcohol solvent such as methanol, an ether solvent such as tetrahydrofuran, water, or a mixed solvent thereof.

[Preparation Example-25]
Conversion of a Halogen Atom into a Nitrile Group

When the compound of the formula (I), the compound of the formula (VIIIa), the compound of the formula (VIIIa-1b), the compound of the formula (VIIIa-1c), the compound of the formula (VIIIa-2a), the compound of the formula (VIIIa-2b), the compound of the formula (VIIIa-2c), the compound of the formula (VIIIa-2d), the compound of the formula (VIIIa-2e), the compound of the formula (VIIIa-3a), or the compound of the formula (VIIIa-3b) has an aromatic ring substituted with chlorine, bromine or iodine, such a halogen atom can be converted into a nitrile group by reacting with zinc cyanide in the presence of a transition metal catalyst. The conversion of chlorine, bromine or iodine into a nitrile group can be carried out by reacting the compound of the formula (I), the compound of the formula (VIIIa), the compound of the formula (VIIIa-1b), the compound of the formula (VIIIa-1c), the compound of the formula (VIIIa-2a), the compound of the formula (VIIIa-2b), the compound of the formula (VIIIa-2c), the compound of the formula (VIIIa-2d), the compound of the formula (VIIIa-2e), the compound of the formula (VIIIa-3a), or the compound of the formula (VIIIa-3b) having an aromatic ring substituted with chlorine, bromine or iodine, with zinc cyanide by using a transition metal catalyst such as tetrakis (triphenylphosphine)palladium (O) at a temperature range of from −20 to 150° C. for 0.5 to 120 hours, if necessary in the presence of a base such as triethylamine or pyridine, in a benzene solvent such as toluene, an ether solvent such as tetrahydrofuran or an amide solvent such as N,N-dimethylformamide, or a mixed solvent thereof.

[Preparation Process-26]
Conversion of a Halogen Atom into a Trifluoromethyl Group When the compound of the formula (I), the compound of the formula (VIIIa), the compound of the formula (VIIIa-1b), the compound of the formula (VIIIa-1c), the compound of the formula (VIIIa-2a), the compound of the formula (VIIIa-2b), the compound of the formula (VIIIa-2c), the compound of the formula (VIIIa-2d), the compound of the formula (VIIIa-2e), the compound of the formula (VIIIa-3a), or the compound of the formula (VIIIa-3b) contains chlorine, bromine or iodine as a substituent, such a halogen atom can be converted into a trifluoromethyl group by reacting the compound with a trifluoromethylating reagent in the presence of a metal catalyst. Described specifically, the conversion of chlorine, bromine or iodine into a trifluoromethyl group can be effected by reacting the compound of the formula (I), the compound of the formula (VIIIa), the compound of the formula (VIIIa-1b), the compound of the formula (VIIIa-1c), the compound of the formula (VIIIa-2a), the compound of the formula (VIIIa-2b), the compound of the formula (VIIIa-2c), the compound of the formula (VIIIa-2d), the compound of the formula (VIIIa-2e), the compound of the formula (VIIIa-3a), or the compound of the formula (VIIIa-3b) containing chlorine, bromine or iodine as a substituent, with a trifluoromethylating reagent such as methyl 2,2-difluoro-2-(fluorosulfonyl)acetate in the presence of a metal catalyst such as copper iodide at a temperature range of from 0 to 150° C. for 0.5 to 120 hours in a benzene solvent such as toluene, an ether solvent such as tetrahydrofuran or an amide solvent such as N,N-dimethylformamide, or a mixed solvent thereof.

[Preparation Process-27]

Conversion of a Nitrile Group into a Tetrazole Group

When the compound of the formula (I) has a nitrile group as a substituent, it can be converted into the compound of the formula (I) having a tetrazole group by reacting the former with sodium azide or trimethylsilyl azide at 0 to 170° C. in the presence of trimethylaluminum or di-n-butyltin oxide in a benzene solvent such as benzene or toluene.

[Preparation Process-28]

Conversion of an Amidino Group into an Alkoxycarbonylamidino Group

When the compound of the formula (I) contains an amidino group, it can be converted into the compound of the formula (I) containing an alkoxycarbonylamidino group by reacting the former with a reagent, for example, an acid chloride such as alkyl chlorocarbonate or alkyl p-nitrobenzylcarbonate at −78 to 100° C. in the presence of a base in an alkyl halide solvent such as dichloromethane or chloroform, an amide solvent such as N,N-dimethylformamide or an ether solvent such as tetrahydrofuran.

Examples of the base include sodium carbonate, potassium carbonate, pyridine, 2,6-lutidine, 4-dimethylaminopyridine, diazabicyclo[5.4.0]undec-7-en (DBU).

[Preparation Process-29]

The sulfonyl derivative of the formula (I) having a primary or secondary amine on $Q^1$, $Q^2$, $Q^3$, $Q^4$ or $T^1$ or a substituent substitutable therefor can be hydroxylated in a conventional manner.

For example, a sulfonyl derivative having a hydroxylated nitrogen atom can be obtained reacting the sulfonyl derivative of the formula (I) with a peroxide such as metachloroperbenzoic acid at −60 to 80° C., preferably −20 to 40° C., for 0.5 to 120 hours in a benzene solvent such as benzene, toluene or xylene, an ether solvent such as tetrahydrofuran or dimethoxyethane or an alkyl halide solvent such as dichlormethane, chloroform or carbon tetrachloride.

Alternatively, a sulfonyl derivative having a hydroxylated nitrogen atom can be obtained, for example, by reacting the sulfonyl derivative of the formula (I) with a peroxide such as benzoyl peroxide at −60 to 80° C., preferably −20 to 40° C., for 0.5 to 120 hours in a benzene solvent such as benzene, toluene or xylene, an ether solvent such as dimethoxyethane or an alkyl halide solvent such as dichlormethane, chloroform or carbon tetrachloride, thereby obtaining a sulfonyl derivative having a benzoyloxylated nitrogen atom; and then subjecting the resulting sulfonyl derivative having a benzoyloxylated nitrogen atom to hydrolysis in accordance with the process as described in [Preparation Process-19].

The sulfonyl derivative of the formula (I) according to the present invention, salt thereof or solvate thereof has peculiar and excellent FXa inhibitory activity and is therefore useful as a coagulation suppressor or a preventive and/or remedy for thrombosis or embolism.

Accordingly, the sulfonyl derivative of the present invention can treat or prevent various diseases caused by thrombosis or embolism, for example, cerebral infarction, cerebral embolism, myocardial infarction, pulmonary infarction, pulmonary embolism, Buerger's disease, deep vein thrombosis and disseminated intravascular coagulation syndrome, thrombus formation after valve replacement, reocclusion after revascularization and formation of thrombus upon extracorporeal circulation, without acting on platelets.

The sulfonyl derivative of the present invention exhibits effects even by the oral administration so that it can be administered either orally or parenterally. Upon administration, it can be formulated as a pharmaceutical composition comprising the sulfonyl derivative and a pharmaceutically acceptable carrier. The dose of the sulfonyl derivative can be changed as needed depending on the symptom, age, weight and/or the like of a patient. It is necessary to administer the derivative in an amount of 1 to 1000 mg/day, preferably 5 to 300 mg/day per adult. Although no particular limitation is imposed on the dosage form, examples include tablets, capsules, powders, granules, suspensions, syrups and dry syrups. The derivative together with ordinarily employed additives such as excipient, lubricant or binder can be formulated into the above-described dosage forms in accordance with the known formulation technique.

No particular limitation is imposed on the dosage form in the case of parenteral administration but examples include ointments, plasters, injections and suppositories. As an injection, the derivative may be administered subcutaneously or intravenously or by intravenous drip in an amount of 0.1 to 100 mg/day, preferably 0.5 to 30 mg/day per adult.

EXAMPLES

The present invention will hereinafter be described more specifically by Referential Examples, Examples and Tests. It should however be borne in mind that the present invention is not limited to or by them.

Some of the starting material compounds used for preparing the sulfonyl derivative of the present invention are novel compounds. These compounds and preparation process therefor will be described in Referential Examples.

Upon preparation of the compound, Merck Silica Gel 60 or Yamazen Silica Gel for moderate pressure liquid chromatography were employed for silica gel column chromatography.

In the nuclear magnetic resonance spectrum (NMR), tetramethylsilane was used an internal standard.

Referential Example 1

1-[(6-Chloronaphthalen-2-yl)sulfonyl]piperazine hydrochloride and trifluoroacetate In dichloromethane (20 ml), tert-butyl 1-piperazine carboxylate (856 mg) was dissolved. To the resulting solution, triethylamine (0.77 ml) and 6-chloro-2-naphthylsulfonyl chloride (WO96/10022)(1.20 g) were added, followed by stirring at room temperature for 5 hours. The reaction mixture was concentrated under reduced pressure. Ethyl acetate was added to the residue and the resulting mixture was washed with 1N hydrochloric acid. The organic layer extracted was dried over anhydrous sodium sulfate. The solvent was then distilled off under reduced pressure. The residue was dissolved in saturated hydrochloride in ethanol (10 ml), followed by concentration under reduced pressure and washing with ethyl acetate, whereby the hydrochloride (1.62 g, quant.) of the title compound was obtained as a colorless solid.

$^1$H-NMR (DMSO-d$_6$) δ: 3.1–3.4(8H,m), 7.75(1H,dd,J=8.8,2.0 Hz), 7.86(1H,dd,J=8.8,1.5 Hz), 8.22(1H,d,J=8.8 Hz), 8.26–8.32(2H,m), 8.56(1H,s), 8.63(2H,br s). MS (FAB) m/z: 311 [(M+H)$^+$, Cl$^{35}$], 313 [(M+H)$^+$, Cl$^{37}$]. Elementary analysis for C$_{14}$H$_{15}$ClN$_2$O$_2$S.HCl.0.1H$_2$O Calculated: C, 48.17; H, 4.68, Cl, 20.31; N, 8.03; S, 9.19. Found: C, 47.91; H, 4.68; Cl, 20.41; N, 7.80; S, 9.21.

Instead of the saturated solution hydrochloride in ethanol, treatment was carried out using trifluoroacetic acid, whereby the trifluoroacetate was obtained.

Elementary analysis for C$_{14}$H$_{15}$ClN$_2$O$_2$S.CF$_3$CO$_2$H Calculated: C, 45.24; H, 3.80, Cl, 8.35; F, 13.42; N, 6.59; S, 7.55. Found: C, 44.84; H, 3.80; Cl, 8.27; F, 13.72; N, 6.29; S, 7.50.

Referential Example 2

4-(4-Pridyl)benzoic acid hydrochloride

At room temperature, 4-bromopyridine hydrochloride (11.7 g) and 4-carboxyphenylboronic acid (10.0 g) were dissolved in toluene (250 ml) and water (250 ml). To the resulting solution, tetrakis(triphenylphosphine)palladium (O) (5.00 g) and anhydrous sodium carbonate (25.4 g) were added successively, followed by refluxing under heat at 120° C. for 19 hours. After allowed to cool down to room temperature, the reaction mixture was added with ethyl acetate and water, whereby the water layer was separated. The organic layer was extracted twice with water. All the water layers so obtained were combined and to the resulting solution, concentrated hydrochloric acid was added to make it acidic, followed by washing with ethyl acetate again. The solvent was distilled off from the water layer until it decreased to 100 ml. The colorless solid so precipitated was collected by filtration and dried under reduced pressure, whereby the title compound (8.37 g, 59%) was obtained.

$^1$H-NMR (DMSO-d$_6$) δ: 8.11 (2H,d,J=8.8 Hz), 8.14(2H, d,J=8.8 Hz), 8.35(2H,d,J=6.6 Hz), 8.97(2H,d,J=6.6 Hz). Elementary analysis for C$_{12}$H$_9$NO$_2$.HCl.0.3H$_2$O Calculated: C, 59.79; H, 4.43, N, 5.81 Found: C, 59.87; H, 4.35; N, 5.53. MS (FAB) m/z: 200 (M+H)$^+$.

Referential Example 3

1-tert-Butoxycarbonyl-4-[4-(4-pyridyl)benzoyl]piperazine

In N,N-dimethylformamide (40 ml), 4-(4-pyridyl)benzoic acid hydrochloride (654 mg) and tert-butyl 1-piperazinecarboxylate (569 mg) were suspended. To the resulting suspension, 1-hydroxybenzotriazole (374 mg) and N-methylmorpholine (336 μl) were added. The resulting mixture was ice cooled, followed by the addition of 1-(3-dimethylaminopropyl-3-ethylcarbodiimide hydrochloride (796 mg). After stirring at room temperature for 7 hours, the solvent was distilled off. The residue was purified by chromatography on a silica gel column (2% methanol—dichloromethane), followed by washing with hexane, whereby the title compound (905 mg, 89%) was obtained.

$^1$H-NMR (CDCl$_3$) δ: 1.48(9H,s), 3.40–3.91(8H,m), 7.51 (2H,d,J=5.9 Hz), 7.53(2H,d,J=8.1 Hz), 7.69(2H,d,J=8.1 Hz), 8.69(2H,d,J=5.9 Hz) Elementary analysis for C$_{21}$H$_{25}$N$_3$O$_3$ Calculated: C, 68.64; H, 6.86, N, 11.44. Found: C, 68.48; H, 6.84; N, 11.17.

Referential Example 4

1-[4-(4-Pyridyl)benzoyl]piperperazine ditrifluoroacetate

In dichloromethane (30 ml), 1-tert-butoxycarbonyl-4-[4-(4-pyridyl)benzoyl]piperazine (944 mg) was dissolved. Under ice cooling, trifluoroacetic acid (30 ml) was added to the resulting solution, followed by stirring at room temperature for one hour. The solvent was distilled off. Tetrahydrofuran was added to the residue to solidify the same, whereby the title compound (1.28 g, 100%) was obtained as a colorless amorphous solid.

$^1$H-NMR (DMSO-d$_6$) δ: 3.1–3.3(4H,br s), 3.5–4.0(4H, m), 7.65(2H,d,J=7.8 Hz), 7.95–8.05(4H,m), 8.79(2H,d,J= 5.4 Hz), 8.95–9.10(1H,br s)

Referential Example 5

4-tert-Butoxycarbonyl-2-ethoxycarbonyl-1-[4-(4-pyridyl)benzoyl]piperazine

In toluene (150 ml), 1,2-dibromopropionic acid (58.0 g) was dissolved. To the resulting solution, a solution of N,N'-dibenzylethylenediamine (53.5 g) and triethylamine (53 ml) in toluene (toluene: 50 ml) was added dropwise under ice cooling. Toluene (100 ml) was added again to the reaction mixture, followed by stirring at room temperature for 14 hours, addition of toluene (100 ml) again and stirring at 60 to 80° C. for 4 hours. The insoluble matter was filtered off. The filtrate was washed with water and dried over anhydrous potassium carbonate. The solvent was then distilled off under reduced pressure. The residue was dissolved in acetic acid (200 ml). To the resulting solution, 10% palladium carbon (water content: about 50%, 40 g) was added, followed by catalytic reduction under 4 atmospheric pressure for 4 hours. The catalyst was filtered off and the filtrate was distilled off under reduced pressure. To the residue, dichloromethane and a saturated aqueous solution of potassium carbonate were added to separate the organic layer, followed by drying over anhydrous potassium carbonate. The solvent was distilled off under reduced pressure. The residue was dissolved in dichloromethane (350 ml), followed by the addition of 2-(tert-butoxycarbonyloxyimino)-2-phenylacetonitrile (46.5 g) under ice cooling. The reaction mixture was heated gradually to room temperature, at which stirring was conducted for 14 hours. The solvent was distilled off under reduced pressure. The residue was purified by chromatography on a silica gel column (dichloromethane~2% methanol—dichloromethane), whereby 1-tert-butoxycarbonyl-3-ethoxycarbonylpiperazine (5.82 g, 10%) was obtained.

In the same manner as in Referential Example 3, the a reaction was conducted using the resulting product and 4-(4-pyridyl)benzoic acid hydrochloride as starting materials, whereby the title compound was obtained.

$^1$H-NMR (CDCl$_3$) δ: 1.2–1.4(3H,m), 1.46(9H,s), 2.7–5.4 (7H,m), 7.51(2H,d,J=5.2 Hz), 7.59(2H,d,J=7.6 Hz), 7.69 (2H,d,J=7.6 Hz), 8.69(2H,d,J=5.2 Hz) MS (FAB) m/z: 440 (M+H)$^+$.

Referential Example 6

6-(4-Pyridyl)nicotinic acid hydrochloride

In tetrahydrofuran (20 ml), 6-chloronicotinic acid (535 mg) and diethyl (4-pyridyl)borane (Chem. Pharm. Bull., 33, 4755, 1985) (500 mg) were dissolved. To the resulting solution, tetrabutylammonium bromide (546 mg), potassium hydrochloride (570 mg), tetrakis(triphenylphosphine) palladium (O) (392 mg) and water (0.5 ml) were added under an argon atmosphere, followed by heating under reflux for 6 hours. Dilute hydrochloric acid was added to the reaction mixture to make it acidic. Water and ethyl acetate were poured into the resulting mixture for extraction. The water layer so extracted was distilled off under reduced pressure. The residue was purified by chromatography through a synthetic adsorbent ("Diaion® HP-20", water~50% acetonitrile—water). To the resulting fraction, dilute hydrochloric acid was added to make it acidic. The solvent was then distilled off. Tetrahydrofuran was added to the residue and the precipitate was collected by filtration, whereby the title compound (269 mg, 32%) was obtained.

$^1$H-NMR (DMSO-$d_6$) δ: 8.45–8.55(2H,m), 8.65(2H,d,J=6.8 Hz), 9.03(2H,d,J=6.8 Hz), 9.27(1H,s). MS (FAB) m/z: 201 (M+H)$^+$

Referential Example 7

Methyl 4-(3-pyridyl)benzoate

In tetrahydrofuran (100 ml), methyl 4-bromobenzoate (5.04 g) and diethyl-3-pyridylborane (Chem. Pharm. Bull., 33, 4755, 1985) (2.30 g) were dissolved, followed by the addition of tetrabutylammonium bromide (2.51 g), potassium hydroxide (2.63 g), tetrakis(triphenylphosphine) palladium (O) (1.8 g) and water (1 ml) under an argon atmosphere. The resulting mixture was heated under reflux for 2 hours. After ice cooling, an aqueous ammonium chloride solution and ethyl acetate were added to the reaction mixture. The organic layer so separated was dried over anhydrous magnesium sulfate. The residue obtained by distilling off the solvent was purified by chromatography on a silica gel column (hexane: ethyl acetate=1:1). The solvent was then distilled off. To the residue, methanol and 1N aqueous hydrochloric acid in ethanol were added. The solvent was distilled off again. Tetrahydrofuran was added to the residue and the solid so precipitated was collected by filtration. After drying, the title compound (1.76 g, 45%) was obtained as a colorless solid.

$^1$H-NMR (DMSO-$d_6$) δ: 3.91(3H,s), 8.0–8.1(3H,m), 8.1–8.15(2H,m), 8.75–8.85(1H,m), 8.85–8.95(1H,m), 9.25–9.3(1H,m).

Referential Example 8

4-(3-Pyridyl)benzoic acid hydrochloride

At room temperature, methyl 4-(3-pyridyl)benzoate (1.76 g) was dissolved in a mixed solvent of 1N hydrochloric acid (50 ml) and dioxane (50 ml), followed by heating under reflux for 4 hours. The solvent was then distilled off under reduced pressure. Tetrahydrofuran was added to the residue, followed by washing, whereby the title compound (1.55 g, 93%) was obtained as a colorless solid.

$^1$H-NMR (DMSO-$d_6$) δ: 7.95–8.0(3H,m), 8.10(2H,d,J=8.3 Hz), 8.65–8.75(1H,m), 8.8–8.9(1H,m), 9.22(1H,d,J=2.0 Hz)

Referential Example 9

Methyl 4-(2-aminopyridin-5-yl)benzoate

In the same manner as in Example 2, a reaction was conducted using 5-bromo-2-aminopyridine and 4-carboxyphenyboronic acid as starting materials, whereby 4-(2-aminopyridin-5-yl)benzoic acid was obtained.

The resulting 4-(2-aminopyridin-5-yl)benzoic acid (684 mg) was dissolved in methanol (50 ml) at room temperature, followed by the addition of concentrated sulfuric acid (1 ml). After heating under reflux for 2 hours, the reaction mixture was made weakly alkaline with an aqueous solution of sodium bicarbonate. Water and ethyl acetate were added to the resulting mixture to separate the organic layer. The organic layer was then dried over anhydrous magnesium sulfate. The solvent was distilled off. Hexane was added to the residue for crystallization, whereby the title compound (243 mg, 23%) was obtained.

$^1$H-NMR (CDCl$_3$) δ: 3.94(3H,s), 4.57(2H,br s), 6.60(1H, d,J=8.8 Hz), 7.58(2H,d,J=8.8 Hz), 7.72(1H,dd,J=8.8,2.4 Hz), 8.09(2H,d,J=8.8 Hz), 8.38(1H,d,J=2.4 Hz). MS (FAB) m/z: 229 (M+H)$^+$. Elementary analysis for $C_{13}H_{12}N_2O_2$ Calculated: C, 68.41; H, 5.30, N, 12.27. Found: C, 68.78; H, 5.45; N, 12.09.

Referential Example 10

Methyl 4-[2-(tert-Butoxycarbonylamino)pyridin-5-yl]benzoate

At room temperature, methyl 4-(2-aminopyridin-5-yl) benzoate (200 mg) was suspended in tert-butanol (20 ml). To the resulting suspension, di-tert-butyl dicarbonate (286 mg) was added and the resulting mixture was stirred for 24 hours. After the solvent was distilled off, the residue was purified by chromatography on a silica gel column (1% methanol—dichloromethane), whereby the title compound (155 mg, 54%) was obtained as a colorless solid.

$^1$H-NMR (CDCl$_3$) δ: 1.55(9H,s), 3.95(3H,s), 7.63(2H,d, J=8.3 Hz), 7.92(1H,dd,J=8.8,2.4 Hz), 8.07(1H,d,J=8.8 Hz), 8.09(1H,br s), 8.12(2H,d,J=8.3 Hz), 8.55(1H,d,J=2.4 Hz). MS(FAB) m/z: 329 (M+H)$^+$. Elementary analysis for $C_{18}H_{20}N_2O_4$ Calculated: C, 65.84; H, 6.14, N, 8.53; Found: C, 65.67; H, 6.02; N, 8.40.

Referential Example 11

4-[2-(tert-Butoxycarbonylamino)pyridin-5-yl]benzoic acid

At room temperature, methyl 4-[2-(tert-butoxycarbonylamino)pyridin-5-yl]benzoate (250 mg) was suspended in a mixed solvent of tetrahydrofuran (10 ml) and methanol (10 ml), followed by the addition of a 1N aqueous sodium hydroxide solution (8 ml). The resulting mixture was stirred for 5 hours. The reaction mixture was made weakly acidic with an aqueous citric acid solution, followed by the addition of saturated saline and n-butanol to separate the organic layer. The organic layer was then dried over anhydrous magnesium sulfate. The solvent was distilled off, whereby the title compound (120 mg, 49%) was obtained as a crude purified product.

$^1$H-NMR (DMSO-$d_6$) δ: 1.49(9H,s), 7.83(2H,d,J=8.3 Hz), 7.91(1H,d,J=8.8 Hz), 8.02(2H,d,J=8.3 Hz), 8.13(1H, dd,J=8.8,2.4 Hz), 8.65(1H,d,J=2.4 Hz), 9.95(1H,s), 12.99 (1H,br s).

Referential Example 12

1-[4-[2-(tert-Butoxycarbonylamino)pyridin-5-yl]benzoyl]-4-[(6-chloronaphthalen-2-yl)sulfonyl]piperazine In a mixed solvent of dichloromethane (20 ml) and N,N-dimethylformamide (1 ml), 4-[2-(tert-butoxycarbonyl)

amino]pyridin-5-yl]benzoic acid (74 mg) and 1-[(6-chloronaphthalen-2-yl)sulfonyl]piperazine trifluoro-acetate (110 mg) were suspended. To the resulting suspension, 1-hydroxybenzotriazole (35 mg) and N-methylmorpholine (34 μl) were added, followed by the addition of 1-(3-dimethylaminopropyl)-3-ethylcarbodiimide hydrochloride (68 mg) under ice cooling. After stirring at room temperature for 6 hours, the solvent was distilled off. The residue was purified by chromatography on a silica gel column (1% methanol—dichloromethane). The solvent was then distilled off, whereby the title compound (128 mg, 90%) was obtained.

$^1$H-NMR (CDCl$_3$) δ: 1.54(9H,s), 3,00–3,30(4H,m), 3.50–4.10(4H,m), 7.39(2H,d,J=7.8 Hz), 7.54(2H,d,J=7.8 Hz), 7.60(1H,dd,J=8,8,2.0 Hz), 7.71(1H,dd,J=8.8,1.5 Hz), 7.84(1H,dd,J=8.8,2.4 Hz), 7.88(1H,br s), 7.9–8.0(3H,m), 8.03(1H,d,J=8.8 Hz), 8.31(1H,s), 8.46(1H,d,J=2.4 Hz).

Referential Example 13

4-(4-Aminophenyl)benzoic acid hydrochloride

In the same manner as in Referential Example 2, a reaction was conducted using 4-bromoaniline and 4-carboxyphenylboronic acid as starting materials, whereby the title compound was obtained.

$^1$H-NMR (DMSO-d$_6$) δ: 7.31(2H,d,J=7.3 Hz), 7.75–7.85 (4H,m), 8.09(2H,d,J=8.3 Hz) MS (FAB) m/z: 228 (M+H)$^+$. Elementary analysis for C$_{13}$H$_{11}$NO$_2$.HCl Calculated: C, 62.53; H, 4.84, N, 5.61; Cl, 14.20. Found: C, 62.33; H, 4.83; N, 5.50; Cl, 14.14.

Referential Example 14

Methyl 4-[4-(tert-butoxycarbonylamino)phenyl]benzoate

In the same manner as in Referential Example 9 or 10, a reaction was conducted using 4-(4-aminophenyl)benzoic acid hydrochloride as a starting material, whereby the title compound was obtained.

$^1$H-NMR (CDCl$_3$) δ: 1.54(9H,s), 3,94(3H,s), 6.56(1H,br s), 7.46(2H,d,J=8.8 Hz), 7.57(2H,d,J=8.8 Hz), 7.63(2H,d,J= 8.3 Hz), 8.08(2H,d,J=8.3 Hz). MS (FAB)m/z: 328 (M+H)$^+$. Elementary analysis for C$_{19}$H$_{21}$NO$_4$ Calculated: C, 69.71; H, 6.47, N, 4.28. Found: C, 69.49; H, 6.44; N, 4.42.

Referential Example 15

4-[4-(tert-Butoxycarbonylamino)phenyl]benzoic acid

In the same manner as in Referential Example 11, a reaction was conducted using methyl 4-[4-(tert-butoxycarbonylamino)phenylbenzoate (501 mg), whereby the title compound (426 mg, 89%) was obtained.

$^1$H-NMR (CDCl$_3$) δ: 1.54(9H,s), 6.57(1H,br s), 7.47(2H, d,J=8.3 Hz), 7.59(2H,d,J=8.3 Hz), 7.66(2H,d,J=8.3 Hz), 8.13(2H,d,J=8.3 Hz) MS (FAB) m/z: 314 (M+H)$^+$. Elementary analysis for C$_{18}$H$_{19}$NO4 Calculated: C, 68.99; H, 6.11, N, 4.47. Found: C, 68.91; H, 6.27; N, 4.24.

Referential Example 16

1-[4-[4-(tert-Butoxycarbonylamino) phenyl]benzoyl]-4-[(6-chloronaphthalen-2-yl)sulfonyl]piperazine In the same manner as in Referential Example 12, a reaction was conducted using 4-[4-(tert-butoxycarbonylamino)phenylbenzoic acid (150 mg) and 1-[(6-chloronaphthalen-2-yl)sulfonyl]piperazine trifluoro-acetate (203 mg) as starting materials, whereby the title compound (303 mg, 100%) was obtained.

$^1$H-NMR (CDCl$_3$) δ: 1.53(9H,s), 2.90–3.30(4H,m), 3.50–4.10(4H,m), 6.56(1H,s), 7.35(2H,d,J=8.3 Hz), 7.44 (2H,d,J=8.3 Hz), 7.49(2H,d,J=8.3 Hz), 7.54(2H,d,J=8.3 Hz), 7.59(1H,dd,J=8.8,2.0 Hz), 7.76(1H,dd,J=8.8,2.0 Hz), 7.90–7.95(3H,m), 8.30(1H,br s).

Referential Example 17

Methyl 4-acetylbenzoate

In a mixed solvent of tetrahydrofuran (100 ml) and methanol (7 ml), methyl 4-acetylbenzoate (3.28 g) was dissolved at room temperature, followed by the addition of trimethylsilyldiazomethane (a 2.0M hexane solution, 12 ml) in portions under ice cooling. After heating to room temperature and stirring for 30 minutes, the solvent was distilled off. To the residue, an aqueous solution of sodium bicarbonate and ether were added. The organic layer so separated was dried over anhydrous magnesium sulfate. After the solvent was distilled off, the residue was crystallized from hexane, whereby the title compound (2.90 g, 82%) was obtained.

$^1$H-NMR (CDCl$_3$) δ: 2.65(3H,s), 3.96(3H,s), 8.01(2H,d, J=8.3 Hz), 8.13(2H,d,J=8.3 Hz). MS (EI) m/z: 178M$^+$. Elementary analysis for C$_{10}$H$_{10}$O$_3$ Calculated: C, 67.41; H, 5.66. Found: C, 67.28; H, 5.53.

Referential Example 18

Methyl 4-bromoacetylbenzoate

At 15° C., methyl 4-acetylbenzoate (2.23 g) was dissolved in a hydrobromic acid acetic acid solution (30%, 10 ml). Bromine was gradually added dropwise to the reaction mixture to maintain its temperature at 15° C. After stirring for 10 minutes, the reaction mixture was cooled to 4° C. A mixed solvent of methanol (50 ml) and water (50 ml) was added to the reaction mixture for crystallization, followed by washing with hexane. By the collection through filtration, the title compound (2.29 g, 71%) was obtained as a colorless solid.

$^1$H-NMR (CDCl$_3$) δ: 3.96(3H,s), 4,47(2H,s), 8.05(2H,d, J=8.8 Hz), 8.16(2H,d,J=8.8 Hz). MS (FAB) m/z: 257 [(M+ H)$^+$, $^{79}$Br], 259 [(M+H)$^+$, $^{81}$Br]. Elementary analysis for C$_{10}$H$_9$BrO$_3$ Calculated: C, 46.72; H, 3.53. Found: C, 46.36; H, 3.63.

Referential Example 19

Methyl 4-(2-aminothiazol-4-yl) benzoate

At room temperature, methyl 4-bromoacetylbenzoate (1.00 g) and thiourea (296 mg) were dissolved in isopropanol (100 ml), followed by heating under reflux for 15 minutes. Under stirring at the same temperature, anhydrous sodium carbonate (206 mg) was added to the reaction mixture. The resulting mixture was heated under reflux for 20 minutes. After completion of the reaction, water (50 ml) was added under ice cooling and the solid so precipitated was collected by filtration. The solid was dissolved in water and dichloromethane. The organic layer so separated was dried over anhydrous sodium sulfate. The solvent was then distilled off. The pale yellow solid so precipitated was washed with ether, whereby the title compound (634 mg, 70%) was obtained.

¹H-NMR (CDCl₃) δ: 3.93(3H,s), 4.96(2H,br s), 6.88(1H, s), 7.85(2H,d,J=8.8 Hz), 8.05(2H,d,J=8.8 Hz). MS (FAB) m/z: 235 (M+H)⁺.

Referential Example 20

4-(2-Aminothiazol-4-yl)benzoic acid

At room temperature, methyl 4-(2-aminothiazol-4-yl) benzoate (300 mg) was suspended in a mixed solvent of tetrahydrofuran (5 ml) and methanol (5 ml), followed by the addition of a 1N aqueous sodium hydroxide solution (10 ml). The resulting mixture was stirred for one hour. To the reaction mixture, N,N-dimethylformamide (5 ml) was added, followed by heating under reflux for 6 hours. After completion of the reaction, the solvent was distilled off. To the residue, water and 1N hydrochloric acid were added successively and the pale yellow solid so precipitated was collected by filtration, whereby the title compound (229 mg, 69%) was obtained as a pale yellow solid.

¹H-NMR (DMSO-d₆) δ: 7.30(1H,br s), 7.87(2H,d,J=8.3 Hz), 7.95–8.00(2H,m). MS (FAB) m/z: 221 (M+H)⁺. Elementary analysis for $C_{10}H_8N_2O_2S\cdot 0.75HCl\cdot 0.6H_2O$ Calculated: C, 46.48; H, 3.88, N, 10.84; Cl, 10.29; S, 12.41. Found: C, 46.36; H, 4.12, N, 10.64; Cl, 10.05; S, 12.33.

Referential Example 21

Methyl 4-(imidazol-4-yl)benzoate

At room temperature, methyl 4-bromoacetylbenzoate (2 g) was dissolved in formamide (100 ml), followed by stirring at 180° C. for 90 minutes. After completion of the reaction, the reaction mixture was ice cooled and dissolved in water and 1N hydrochloric acid. The resulting solution was purified by chromatography through a synthetic adsorbent ("Diaion HP-20", water~50% acetonitrile—water). The crude product so obtained was purified further by chromatography on a silica gel column (5% methanol—dichloromethane), whereby the title compound (844 mg, 54%) was obtained as a pale yellow solid.

¹H-NMR (CDCl₃) δ: 3.93(3H,s), 7.46(1H,s), 7.75(1H,s), 7.86(2H,m), 8.07(2H,d,J=8.3 Hz). MS (FAB) m/z: 203 (M+H)⁺.

Referential Example 22

Methyl 4-[1-triphenylmethylimidazol-4(5)-yl]benzoate

Methyl 4-(imidazol-4-yl)benzoate (828 mg) was dissolved in dichloromethane (50 ml), followed by the addition of diisopropylethylamine (856 μl) and triphenylmethyl chloride (1.37 g) under ice cooling. The resulting mixture was stirred at room temperature for 16 hours. The solvent was distilled off. The residue was purified by chromatography on a silica gel column (dichloromethane), whereby the title compound (1.08 g, 59%) was obtained as a colorless glassy solid.

¹H-NMR (CDCl₃) δ: 3.90(3H,s), 7.15–7.22(6H,m), 7.23 (1H,d,J=1.5 Hz), 7.30–7.40(15H,m), 7.52(1H,d,J=1.5 Hz), 7.79(2H,d,J=8.3 Hz), 8.01(2H,d,J=8.3 Hz). MS (FAB) m/z: 445 (M+H)⁺.

Referential Example 23

4-[1-Triphenylmethylimidazol-4(5)-yl]benzoic acid

At room temperature, methyl 4-[1-triphenylmethylimidazol-4(5)-yl]benzoate (1.04 g) was dissolved in a mixed solvent of tetrahydrofuran (10 ml) and methanol (10 ml). To the resulting solution, a 3N aqueous sodium hydroxide solution (6 ml) was added, followed by stirring for 5 hours. Tetrahydrofuran and methanol were removed by distillation under reduced pressure. An aqueous citric acid solution was added to the residue to make it weakly acidic, followed by the addition of water and dichloromethane. The organic layer so separated was washed with a saturated aqueous NaCl solution and dried over anhydrous sodium sulfate. The solvent was distilled off, whereby the title compound (1.13 g, quant.) was obtained as a crude purified product in the form of a colorless glassy solid.

¹H-NMR (CDCl₃) δ: 7.15–7.22(6H,m), 7.23(1H,d,J=1.5 Hz), 7.30–7.40(9H,m), 7.69(1H,d,J=1.5 Hz), 7.81(2H,d,J= 8.3 Hz), 8.10(2H,d,J=8.3 Hz).

Referential Example 24

1-[(6-Chloronaphthalen-2-yl)sulfonyl [-4-[4-[1-triphenylmethylimidazol-4(5) -yl]benzoyl]piperazine In the same manner as in Referential Example 12, a reaction was conducted by using 4-[1-triphenylmethylimidazol-4(5)-yl]benzoic acid (371 mg) and 1-[(6-chloronaphthalen-2-yl)sulfonyl]piperazine hydrochloride (300 mg) as starting materials, whereby the title compound (560 mg, 90%) was obtained in the form of a colorless glassy solid.

¹H-NMR (CDCl₃) δ: 2.90–3.30(4H,m), 3.50–4.10(4H, m), 7.15–7.20(6H,m), 7.28(2H,d,J=8.3 Hz), 7.30–7.40(9H, m), 7.49(1H,d,J=1.0 Hz), 7.59(1H,dd,J=8.8,2.0 Hz), 7.71 (2H,d,J=8.3 Hz), 7.75(1H,dd,J=8.8,1.5 Hz), 7.90–7.95(3H, m), 8.29(1H,br s). MS (FAB) m/z: 723 (M+H)⁺.

Referential Example 25

4-[2-Aminoimidazol-4-yl]benzoic acid hydrochloride

At room temperature, methyl 4-bromoacetylbenzoate (1.37 g) and acetylguanidine (1.62 g) were suspended in acetonitrile, followed by heating under reflux for 16 hours. The solvent was then distilled off under reduced pressure. Water was added to the residue. The insoluble matter so precipitated was collected by filtration, followed by washing with ethanol, whereby methyl 4-[2-aminoimidazol-4-yl] benzoate was obtained. The resulting product was dissolved in a mixed solvent of dioxane (10 ml) and 1N hydrochloric acid (10 ml), followed by heating under reflux for 8 hours. The residue obtained by distilling off the solvent was solidified by tetrahydrofuran and then collected by filtration, whereby the title compound (500 mg, 39%) was obtained.

¹H-NMR (DMSO-d₆) δ: 7.55–7.65(3H,m), 7.80(2H,d,J= 8.3 Hz), 7.98(2H,d,J=8.3 Hz), 12.2–13.3(3H,m). MS (FAB) m/z: 204 (M+H)⁺. Elementary analysis for $C_{10}H_9N_3O_2\cdot HCl\cdot 0.5H_2O$ Calculated: C, 48.30; H, 4.46; N, 16.90; Cl, 14.26. Found: C, 48.03; H, 4.10; N, 16.49; Cl, 14.12.

Referential Example 26

1-[4-Bromo-2-(tert-butoxycarbonyl)benzoyl]-4-[(6-chloronaphthalen-2-yl)sulfonyl]piperazine In dichloromethane (200 ml), 4-bromophthalic anhydride (1.96 g) and 1-[(6-chloronaphthalen-2-yl)sulfonyl] piperazine hydrochloride (3.00 g) were suspended under ice cooling. To the resulting suspension, diisopropylethylamine (3.76 ml) was added, followed by stirring for 20 minutes. To the reaction mixture, dilute hydrochloric acid and dichloromethane were added. The organic layer so separated was dried over anhydrous sodium sulfate. The solvent was concentrated so that the volume was reduced to 200 ml. To the concentrate, N,N'-diisopropyl-O-tert-butylisourea (2.6 g) was added under ice cooling and the resulting mixture was stirred at room temperature for 3 days. Dilute hydrochloric acid and dichloromethane were added to the reaction mixture. The organic layer so separated was dried over anhydrous sodium sulfate. The residue was purified by chromatography on a silica gel column (hexane : ethyl acetate=3:1~1:1), whereby the title compound (1.78 g, 35%) was obtained as a colorless solid.

$^1$H-NMR (CDCl$_3$) δ: 1.30(9H,s), 2.90–3.40(6H,m), 3.80–4.00(2H,m), 7.01(1H,d,J=8.3 Hz), 7.59(1H,dd,J=8.3, 2.0 Hz), 7.61(1H,dd,J=8.3,2.0 Hz), 7.76(1H,dd,J=8.8,2.0 Hz), 7.85–7.95(3H,m), 8.00(1H,d,J=2.0 Hz), 8.29(1H,br s).

Referential Example 27

1-[2-tert-Butoxycarbonyl-4-(pyridin-4-yl)benzoyl]-4-[(6-chloronaphthalen-2-yl)sulfonyl]piperazine hydrochloride In the same manner as in Referential Example 7, a reaction was conducted using 1-[4-bromo-2-(tert-butoxycarbonyl)benzoyl]-4-[(6-chloronaphthalen-2-yl)sulfonyl]piperazine and diethyl(4-pyridyl)borane as starting materials, whereby the title compound was obtained.

$^1$H-NMR (CDCl$_3$) δ: 1.37(9H,s), 2.80–3.50(6H,m), 3.80–4.00(2H,m), 7.40(1H,d,J=7.8 Hz), 7.6.0(1H,dd,J=8.8, 2.0 Hz), 7.77(1H,dd,J=8.3,1.5 Hz), 7.87(1H,dd,J=7.8,2.0 Hz), 7.90–7.95(3H,m), 8.10(2H,d,J=6.8 Hz), 8.25(1H,d,J=2.0 Hz), 8.31(1H,br s), 8.90(2H,d,J=6.8 Hz). MS (FAB) m/z: 592 (M+H)$^+$. Elementary analysis for C$_{31}$H$_{30}$ClN$_3$O$_5$S.HCl.0.2H$_2$O.THF Calculated: C, 59.69; H, 5.64; N, 5.97; Cl, 10.07; S, 4.55. Found: C, 59.55; H, 5.45; N, 5.87; Cl, 9.97; S, 4.68.

Referential Example 28

5-(4-Pyridyl)thiophene-2-carboxylic acid hydrochloride

In the same manner as in Referential Example 6, a reaction was conducted using 5-bromothiophene-2-carboxylic acid and diethyl (4-pyridyl)borane as starting materials, whereby the title compound was obtained.

$^1$H-NMR (DMSO-d$_6$) δ: 7.87(1H,d,J=3.9 Hz), 8.17(1H, d,J=3.9 Hz), 8.29(2H,d,J=6.8 Hz), 8.88(2H,d,J=6.8 Hz). MS (FAB) m/z: 206 (M+H)$^+$. Elementary analysis for C$_{10}$H$_7$NO$_2$S.HCl.0.8H$_2$O Calculated: C, 46.90; H, 3.78; N, 5.47; Cl, 13.84; S, 12.52. Found: C, 46.77; H, 3.76; N, 5.27; Cl, 13.83; S, 12.56.

Referential Example 29

5-(4-Pyridyl)furan-2-carboxylic acid hydrochloride

In the same manner as in Referential Example 6, a reaction was conducted using 5-bromofuran-2-carboxylic acid and diethyl (4-pyridyl)borane as starting materials, whereby the title compound was obtained.

$^1$H-NMR (DMSO-d$_6$) δ: 7.49(1H,d,J=3.4 Hz), 7.80–7.90 (1H,m), 8.20–8.30(2H,m), 8.85–8.95(2H,m).

Referential Example 30

4-(2-Pyridyl)benzoic acid hydrochloride

To water (200 ml), 2-(p-tolyl)pyridine (17.2 g) was added. To the resulting mixture, potassium permanganate (21.0 g) was added, followed by heating under reflux for 18 hours. After the precipitate was filtered off, dichloromethane was added to the filtrate to separate the water layer. The water layer was then made acidic with 2N hydrochloric acid. The acidic aqueous solution was concentrated. The precipitate was collected by filtration, followed by washing with water and ethyl acetate, whereby the title compound (7.07 g, 35%) was obtained as a white solid.

$^1$H-NMR (DMSO-d$_6$) δ: 7.60(1H,t,J=5.9 Hz), 8.08(2H,d, J=7.8 Hz), 8.17(2H,m), 8.21(2H,d,J=7.8 Hz), 8.78(1H,d,J= 4.9 Hz). MS (EI) m/z: 199M$^+$.

Referential Example 31

1-[(E)-4-Chlorostyrylsulfonyl)piperazine hydrochloride

In the same manner as in Referential Example 1, a reaction was conducted using tert-butyl 1-piperazinecarboxylate and (E)-4-chlorostyrylsulfonyl chloride as starting materials, whereby the title compound was obtained.

$^1$H-NMR (DMSO-d$_6$) δ: 3.20(4H,br s), 3.33–3.38(4H,m), 7.47(2H,s), 7.53(1H,d,J=8.8 Hz), 7.82(1H,d,J=8.8 Hz). Elementary analysis for C$_{12}$H$_{15}$ClN$_2$O$_2$S.HCl Calculated: C, 44.59; H, 4.99, Cl, 21.94; N, 8.67; S, 9.92. Found: C, 44.42; H, 4.78, Cl, 21.83; N, 8.68; S, 9.87.

Referential Example 32

4-(2,4-Diamino-6-pyrimidyl)benzoic acid hydrochloride

In toluene (9 ml), 6-chloro-2,4-diaminopyrimidine (434 mg) was dissolved, followed by the addition of 4-carboxyphenylboronic acid (667 mg), ethanol (2.5 ml), sodium carbonate (635 mg), water (3.0 ml) and bis (triphenylphosphine)palladium (II) dichloride (65 mg). The resulting mixture was heated under reflux for 24 hours under an argon gas atmosphere. Ethyl acetate and water were added to the reaction mixture. The water layer so separated was made acidic with 2N hydrochloric acid. The insoluble matter was collected by filtration, washed with water and tetrahydrofuran and then dried, whereby the title compound (371 mg, 54%) was obtained.

$^1$H-NMR (DMSO-d$_6$) δ: 6.43(1H,s), 7.30–7.80(2H,br), 7.96(2H,d,J=7.8 Hz), 8.12(2H,d,J=7.8 Hz), 8.27(2H,br s), 12.77(1H,br), 13.33(1H,br). MS (EI) m/z: 230M$^+$. Elementary analysis for C$_{11}$H$_{10}$N$_4$O$_2$S.0.95HCl.1.9H$_2$O Calculated: C, 44.17; H, 4.97; Cl, 11.26; N, 18.73. Found: C, 44.33; H, 4.97; Cl, 11.32; N, 18.65.

Referential Example 33

1-tert-Butoxycarbonyl-4-[4-(2-pyridyl)benzoyl]piperazine

In the same manner as in Referential Example 3, a reaction was conducted using 4-(2-pyridyl)benzoic acid hydrochloride obtained in Referential Example 30 and tert-butyl 1-piperazinecarboxylate as starting materials, whereby the title compound was obtained.

$^1$H-NMR (CDCl$_3$) δ: 1.47(9H,s), 3.43(4H,br), 3.51(2H, br), 3.76(2H,br), 7.28(1H,d,J=5.9 Hz), 7.52(2H,d,J=7.8 Hz), 7.76(1H,m), 7.79(1H,m), 8.05(2H,d,J=7.8 Hz), 8.71(1H,d, J=4.9). MS (FAB) m/z: 368 (M+H)$^+$. Elementary analysis for C$_{21}$H$_{25}$N$_3$O$_3$.0.1H$_2$O Calculated: C, 68.31; H, 6.88; N, 11.38; Found: C, 68.26; H, 6.86; N, 11.42.

Referential Example 34

2-[4-[[4-(tert-Butoxycarbonyl)piperazin-1-yl]carbonyl]phenyl]pyridine N-oxide

At −10° C., metachloroperbenzoic acid (789 mg) was added to a solution of 1-tert-butoxycarbonyl-4-[4-(2-pyridyl)benzoyl]piperazine (517 mg) in dichloromethane (dichloromethane: 8 ml). The resulting mixture was stirred for 24 hours, followed by dilution with dichloromethane. A small amount of an aqueous sodium thiosulfate solution and a saturated aqueous NaCl solution were added to the dilute solution. The organic layer so separated was washed with a saturated aqueous solution of sodium bicarbonate and a saturated aqueous NaCl solution and then dried over anhydrous sodium sulfate. The residue obtained by distilling off the solvent under reduced pressure was purified by chromatography on a silica gel column (dichloromethane:methanol=20:1), whereby the title compound (415 mg, 77%) was obtained.

$^1$H-NMR (CDCl$_3$) δ: 1.48(9H,s), 3.47(6H,br), 3.76(2H,br), 7.29(1H,m), 7.34(1H,t,J=7.8 Hz), 7.44(1H,dd,J=7.8,2.0 Hz), 7.52(2H,d,J=7.8 Hz), 7.90(2H,d,J=7.8 Hz), 8.35(1H,d,J=5.9 Hz). MS (FAB) m/z: 384 (M+H)$^+$.

Referential Example 35

2-[4-[(1-Piperazinyl)carbonyl]phenyl]pyridine N-oxide hydrochloride

In dichloromethane (2.5 ml), 2-[4-[[4-(tert-butoxycarbonyl)piperazin-1-yl]carbonyl]phenyl]pyridine N-oxide was dissolved. To the resulting solution, a saturated solution of hydrochloride in ethanol (2.5 ml) was added, followed by stirring at room temperature for 1 hour. After the solvent was distilled off under reduced pressure, water was added to the residue, whereby an aqueous solution was obtained. Acetone was added to the aqueous solution until the solution became turbid. The precipitate was collected by filtration and washed with acetone, whereby the title compound (274 mg, 81%) was obtained.

$^1$H-NMR (DMSO-d$_6$) δ: 3.17(4H,br s), 3.50–3.95(4H,br), 7.43(1H,d,J=3.9 Hz), 7.44(1H,d,J=3.9 Hz), 7.57(2H,d,J=8.8 Hz), 7.66(1H,t,J=3.9 Hz), 7.92(2H,d,J=8.8 Hz), 8.36(1H,t,J=3.9 Hz), 9.21(2H,br) MS (FAB) m/z: 284 (M+H)$^+$.

Referential Example 36

1-(tert-Butoxycarbonyl)-4-[4-(3-pyridyl)benzoyl]piperazine

In the same manner as in Referential Example 3, a reaction was conducted using 4-(3-pyridyl)benzoic acid hydrochloride obtained in Referential Example 8 and tert-butyl 1-piperazinecarboxylate as starting materials, whereby the title compound was obtained.

$^1$H-NMR (CDCl$_3$) δ: 1.47(9H,s), 3.35–3.85(8H,br), 7.38 (1H,dd,J=7.8,4.9 Hz), 7.52(2H,d,J=8.3 Hz), 7.63(2H,d,J=8.3 Hz), 7.88(1H,m), 8.62(1H,dd,J=1.5,4.9 Hz), 8.84(1H,d,J=2.0 Hz).

Referential Example 37

3-[4-[[4-(tert-Butoxycarbonyl)piperazin-1-yl]carbonyl]phenyl]pyridine N-oxide

In the same manner as in Referential Example 34, the title compound was obtained as a colorless solid by using 1-(tert-butoxycarbonyl)-4-[4-(3-pyridyl)benzoyl]piperazine as a starting material.

$^1$H-NMR (CDCl$_3$) δ: 1.48(9H,s), 3.35–4.83(8H,br), 7.38 (1H,m), 7.47(1H,m), 7.49–7.65(4H,m), 8.23(1H,dd,J=6.4, 1.5 Hz), 8.47(1H,t,J=1.5 Hz). MS (FAB) m/z: 384 (M+H)$^+$. Elementary analysis for $C_{21}H_{25}N_3O_4 \cdot 0.25H_2O$ Calculated: C, 65.02; H, 6.63; N, 10.83. Found: C, 65.30; H, 6.65; N, 10.43.

Referential Example 38

2-Hydroxy-4-(4-pyridyl)benzoic acid

In water (22.5 ml) and a 47% aqueous solution of hydrobromic acid (22.5 ml), 4-amino-2-hydroxybenzoic acid (5.04 g) was dissolved. While the resulting solution mixture was maintained at 5° C. or lower, an aqueous solution (water: 15.0 ml) of sodium nitrite (2.26 g) was added dropwise thereto, followed by stirring for 30 minutes under ice cooling. The reaction mixture was added, in portions, to a solution of cuprous bromide (5.63 g) dissolved in a 47% aqueous solution of hydrobromic acid (15 ml) under ice cooling. The resulting mixture was stirred at room temperature for 150 minutes. Ethyl acetate was added to the reaction mixture for extraction. The organic layer so obtained was washed with water and then dried over anhydrous sodium sulfate. The residue obtained by distilling off the solvent under reduced pressure was purified by chromatography on a silica gel column (dichloromethane~10% methanol—dichloromethane), whereby 4-bromo-2-hydroxybenzoic acid (5.51 g) was obtained as a crudely purified product.

The crudely purified product (298 mg) was reacted as in Referential Example 6, whereby the title compound (70 mg, 21%) was obtained.

$^1$H-NMR (DMSO-d$_6$) δ: 7.30–7.40(2H,m), 7.78(2H,d,J=4.4 Hz), 7.92(1H,d,J=6.3 Hz), 8.69(2H,d,J=5.9 Hz). MS (FAB) m/z: 216 (M+H)$^+$.

Referential Example 39

4-Bromo-3-hydroxybenzoic acid

In acetic acid (24.5 ml), 3-hydroxybenzoic acid (5.00 g) was suspended. To the resulting suspension, a solution of bromine (1.9 ml) in acetic acid (acetic acid: 5 ml) was added dropwise under ice cooling, followed by stirring at room temperature for 33 hours. The reaction mixture was ice cooled. The crystals so precipitated were collected by filtration and then washed with acetic acid, whereby the title compound (1.68 g, 21%) was obtained.

$^1$H-NMR (DMSO-d$_6$) δ: 7.28(1H,dd,J=7.8,2.0 Hz), 7.51(1H,d,J=2.0 Hz), 7.59(1H,d,J=8.3 Hz), 10.54(1H,br s), 12.84(1H,br)

Referential Example 40

Methyl 4-bromo-3-methoxybenzoate

In the same manner as in Referential Example 17, a reaction was conducted using 4-bromo-3-hydroxybenzoic acid as a starting material, whereby the title compound was obtained.

$^1$H-NMR (CDCl$_3$) δ: 3.92(3H,s), 3.96(3H,s), 7.51(1H,dd, J=8.3,2.0 Hz), 7.55(1H,d,J=2.0 Hz), 7.61(1H,d,J=8.8 Hz).

Referential Example 41

3-Methoxy-4-(4-pyridyl)benzoic acid

In the same manner as in Referential Example 7, a reaction was conducted using methyl 4-bromo-3- methoxybenzoate and diethyl (4-pyridyl)borane. The crude product so obtained was reacted as in Referential Example 8, whereby the title compound was obtained.

$^1$H-NMR (CDCl$_3$) δ: 3.93(3H,s), 7.65–7.75(3H,m), 8.20 (2H,d,J=5.4 Hz), 8.94(2H,d,J=6.3 Hz). MS (FAB) m/z: 230 (M+H)$^+$.

Referential Example 42

4-tert-Butoxycarbonyl-1-[(6-chloronaphthalen-2-yl) sulfonyl]-2-ethoxycarbonylpiperazine In dichloromethane (18 ml), 1-tert-butoxycarbonyl-3-ethoxycarbonylpiperazine (517 mg) and 6-chloro-2-naphthylsulfonyl chloride (588 mg) were dissolved under ice cooling. To the resulting solution, diisopropylethylamine (0.59 ml) was added, followed by stirring at room temperature for 63 hours. The residue obtained by distilling off the solvent under reduced pressure was purified by chromatography on a silica gel column (hexane:ethyl acetate=3:1), whereby the title compound (688 mg, 71%) was obtained.

$^1$H-NMR (CDCl$_3$) δ: 1.05(3H,t,J=7.1 Hz), 1.38(9H,s), 2.80–4.70(9H,m), 7.55(1H,dd,J=8.6,2.2 Hz), 7.77(1H,dd,J=8.6,1.7 Hz), 7.85–7.90(3H,m), 8.33(1H,s). MS (FAB) m/z: 483[(M+H)$^+$, Cl$^{35}$], 485[(M+H)$^+$, Cl$^{37}$].

Referential Example 43

4-tert-Butoxycarbonyl-2-ethoxycarbonyl-1-[4-(3-pyridyl)benzoyl]piperazine

In the same manner as in Referential Example 12, a reaction was conducted using 4-(3-pyridyl)benzoic acid and 1-tert-butoxycarbonyl-3-ethoxycarbonylpiperazine as starting materials, whereby the title compound was obtained.

$^1$H-NMR (CDCl$_3$) δ: 1.20–1.40(3H,m), 1.46(9H,s), 2.70–4.80(8H,m), 5.35(1H,br), 7.35–7.70(5H,m), 7.85–7.95 (1H,m), 8.64(2H,dd,J=4.6,1.7 Hz), 8.86(1H,s). MS (FAB) m/z: 440 (M+H)$^+$.

Referential Example 44

Methyl N-tert-butoxycarbonyltranexamate

To methanol (20 ml), thionyl chloride (1 ml) was added dropwise under ice cooling, followed by the addition of tranexamic acid (2.04 g). The resulting mixture was heated under reflux for 3 hours. The residue obtained by distilling the reaction mixture under reduced pressure was pulverized in ether and then collected by filtration, whereby colorless crystals (2.31 g) were obtained.

The resulting crystals (2.10 g) were dissolved in dichloromethane (40 ml), followed by the addition of N-methylmorpholine (1.2 ml). To the resulting mixture, a solution of di-tert-butyl dicarbonate (2.51 g) in dichloromethane (dichloromethane: 3 ml) was added under ice cooling. The resulting mixture was stirred at room temperature for 18 hours. After diluted with dichloromethane, the reaction mixture was washed with water and then dried over anhydrous sodium sulfate. The residue obtained by distilling off the solvent under reduced pressure was purified by chromatography on a silica gel column (hexane:ethyl acetate=10:1~3:1), followed by recrystallization from a mixed solvent of hexane and ethyl acetate, whereby colorless crystals (2.09 g, 65%) was obtained.

$^1$H-NMR (CDCl$_3$) δ: 0.90–1.10(2H,m), 1.40–1.60(12H, m), 1.80–1.90(2H,m), 2.00–2.10(2H,m), 2.24(1H,m), 2.98 (2H,m), 3.66(3H,s), 4.58(1H,br). Elementary analysis for C$_{14}$H$_{25}$NO$_4$ Calculated: C, 61.97; H, 9.29; N, 5.16. Found: C, 62.15; H, 9.42; N, 5.12.

Referential Example 45 trans-4-(N-tert-Butoxycarbonylaminomethyl) cyclohexylmethanol

Methyl N-tert-butoxycarbonyltranexamate (1.00 g) was dissolved in a mixed solvent of tetrahydrofuran (10 ml) and methanol (2 ml). To the resulting solution, sodium borohydride (0.44 g) was added under ice cooling, followed by stirring at room temperature for 24 hours. After the addition of water, the reaction mixture was concentrated under reduced pressure. Ethyl acetate and dilute hydrochloric acid were added to the concentrate. The organic layer so separated was dried over anhydrous sodium sulfate. The residue obtained by distilling off the solvent under reduced pressure was purified by chromatography on a silica gel column in repetition (first time; dichloromethane~dichloromethane:methanol=20:1, second time; hexane:ethyl acetate=3:1), whereby colorless crystals (0.74 g, 82%) were obtained. A portion of the crystals was recrystallized from a mixed solvent of hexane and ethyl acetate, whereby colorless crystals were obtained.

$^1$H-NMR (CDCl$_3$) δ: 0.90–1.10(4H,m), 1.30–1.60(12H, m), 1.80–2.00(4H,m), 2.98(2H,m), 3.45(2H,d.J=6.4 Hz), 4.59(1H,br). Elementary analysis for C$_{13}$H$_{25}$NO$_3$ Calculated: C, 64.17; H, 10.35, N, 5.76. Found: C, 64.31; H, 10.03; N, 5.74.

Referential Example 46 trans-4-(N-tert-Butoxycarbonylaminomethyl) cyclohexanecarboxaldehyde

In dichloromethane (5 ml), trans-4-(N-tert-butoxycarbonylaminomethyl)cyclohexylmethanol (0.20 g) was dissolved, followed by the addition of pyridinium chlorochromate (0.23 g). The resulting mixture was stirred at room temperature for 3 hours. The reaction mixture was purified by chromatography on a silica gel column (hexane:ethyl acetate=3:1), whereby the title compound (0.15 g, 76%) was obtained.

$^1$H-NMR (CDCl$_3$) δ: 1.00(2H,m), 1.27(2H,m), 1.40–1.60 (1H,m), 1.44(9H,s), 1.88(2H,m), 2.02(2H,m), 2.18(1H,m), 3.00(2H,t,J=6.4 Hz), 4.61(1H,br), 9.62(1H,s). MS (FAB) m/z: 242 (M+H)$^+$.

Referential Example 47

1-[trans-4-(N-tert-Butoxycarbonylaminomethyl) cyclohexylmethyl]-4-[(6-chloronaphthalen-2-yl) sulfonyl]piperazine In dichloromethane (7 ml), trans-4-(N-tert-butoxycarbonylaminomethyl)cyclohexane carboxaldehyde (0.13 g) was dissolved, followed by the addition of 1-[(6-chloronaphthalen-2-yl)sulfonyl]piperazine trifluoroacetate (0.24 g), triethylamine (78 μl) and sodium triacetoxyborohydride (0.17 g). The resulting mixture was stirred at room temperature for 11 hours under an argon gas atmosphere. To the reaction mixture, an aqueous solution of sodium bicarbonate was added, followed by dilution with dichloromethane. The organic layer so separated was dried over anhydrous sodium sulfate. The residue obtained by distilling off the solvent under reduced pressure was purified by chromatography on a silica gel column (hexane:ethyl acetate=2:1), whereby the title compound (0.29 g, 100%) was obtained.

$^1$H-NMR (CDCl$_3$) δ: 0.70–0.90(4H,m), 1.30–1.50(2H, m), 1.42(9H,s), 1.70–1.80(4H,m), 2.09(2H,d,J=7.3 Hz), 2.46(4H,m), 2.92(2H,m), 3.08(4H,m), 4.53(1H,br), 7.56 (1H,dd,J=8.8,2.0 Hz), 7.78(1H,dd,J=8.8,2.0 Hz), 7.80–8.00 (3H,m), 8.30(1H,s). MS (FAB) m/z: 536[(M+H)$^+$, Cl$^{35}$], 538[(M+H)$^+$, Cl$^{37}$].

Referential Example 48

1-[trans-4-(N-tert-Butoxycarbonylaminomethyl) cyclohexylcarbonyl]-4-[(6-chloronaphthalen-2-yl) sulfonyl]piperazine A reaction was conducted as in Referential Examples 11 and 12, whereby the title compound was obtained.

$^1$H-NMR (CDCl$_3$) δ: 0.80–1.00(2H,m), 1.40–1.60(3H, m), 1.42(9H,s), 1.60–1.70(2H,m), 1.70–1.90(2H,m), 2.30 (1H,m), 2.95(2H,m), 3.07(4H,m), 3.58(2H,br), 3.70(2H,br), 4.57(1H,m), 7.58(1H,dd,J=8.8,2.0 Hz), 7.75(1H,dd,J=8.8, 1.5 Hz), 7.90–8.00(3H,m), 8.30(1H,s). MS (FD) m/z: 549 (M+, Cl$^{35}$), 551 (M$^+$, Cl$^{37}$).

Referential Example 49

N-[trans-4-(N-tert-Butoxycarbonylaminomethyl) cyclohexylcarbonyl]glycine benzyl ester In the same manner as in Referential Examples 11 and 12, a reaction was conducted using methyl N-tert-butoxycarbonyltranexamate and glycine benzyl ester as starting materials, whereby the title compound was obtained.

$^1$H-NMR (CDCl$_3$) δ: 0.96(2H,m), 1.44(9H,s), 1.40–1.60 (3H,m), 1.80–1.90(2H,m), 1.90–2.00(2H,m), 2.10(1H,m), 2.98(2H,m), 4.08(2H,d,J=4.9 Hz), 4.57(1H,br), 5.19(2H,s), 5.97(1H,m), 7.30–7.40(5H,m). Elementary analysis for C$_{22}$H$_{32}$N$_2$O$_5$ Calculated: C, 65.32; H, 7.97; N, 6.93. Found: C, 65.05; H, 7.89; N, 7.16.

Referential Example 50

1-[N-[trans-4-(N-tert-Butoxycarbonylaminomethyl) cyclohexylcarbonyl]glycyl]-4-[(6-chloronaphthalen-2-yl)sulfonyl]piperazine In tetrahydrofuran (11 ml), N-[trans-4-(N-tert-butoxycarbonylaminomethyl)cyclohexylcarbonyl]glycine benzyl ester (0.22 g) was suspended. To the resulting suspension, 10% palladium carbon (water content: about 50%, 50 mg) was added, followed by catalytic hydrogenation at normal pressure and room temperature for 14 hours. After the removal of the catalyst by filtration, the solvent was distilled off under reduced pressure. The residue so obtained was reacted as in Referential Example 12, whereby the title compound (0.32 g, 98%) was obtained.

$^1$H-NMR (CDCl$_3$) δ: 0.80–1.00(2H,m), 1.30–1.50(3H, m), 1.43(9H,s), 1.80–2.00(4H,m), 2.06(1H,m), 2.95(2H,m), 3.10–3.20(4H,m), 3.52(2H,m), 3.74(2H,m), 3.94(2H,d,J= 4.4 Hz), 4.54(1H,m), 6.40(1H,m), 7,59(1H,dd,J=8.8,2.0 Hz), 7.74(1H,dd,J=8.8,1.5 Hz), 7.80–8.00(3H,m), 8.30(1H, s). MS (FAB) m/z: 607 [(M+H)$^+$, Cl$^{35}$], 609 [(M+H)$^+$, Cl$^{37}$].

Referential Example 51

1-[(6-Chloronaphthalen-2-yl)sulfonyl] homopiperazine hydrochloride

Homopiperazine (5 g) was dissolved in tetrahydrofuran (100 ml) at room temperature. To the resulting solution, 2-(tert-butoxycarbonyloxyimino)-2-phenylacetonitrile (12.3 g) was added in portions, followed by stirring for 3 hours. After completion of the reaction, the solvent was distilled off. The residue was purified by chromatography on a silica gel column (10 to 20% methanol—dichloromethane), followed by the addition of 1N aqueous hydrochloric acid in ethanol. The solvent was then distilled off. The residue was solidified by the addition of ethanol, whereby powders (7.46 g) were obtained. The resulting powders were reacted as in Referential Example 1, whereby the title compound was obtained.

$^1$H-NMR (DMSO-d$_6$) δ: 2.00(2H,br s), 3.10–3.30(4H,m), 3.30–3.50(2H,m), 3.55–3.65(2H,m), 7.72(1H,d,J=8.8 Hz), 7.89(1H,d,J=8.3 Hz), 8.17(1H,d,J=8.8 Hz), 8.22–8.28(2H, m), 8.56(1H,s), 9.29(2H,br s). MS (FAB) m/z: 325 (M+H)$^+$. Elementary analysis for C$_{15}$H$_{17}$ClN$_2$O$_2$S.HCl Calculated: C, 49.89; H, 5.02; N, 7.75; Cl, 19.63. Found: C, 49.94; H, 5.05; N, 7.47; Cl, 19.65.

Referential Example 52

1-[trans-4-(N-tert-Butoxycarbonylaminomethyl) cyclohexylcarbonyl]-4-[(6-chloronaphthalen-2-yl) sulfonyl]homopiperazine In the same manner as in Referential Example 48, a reaction was conducted using methyl N-tert-butoxycarbonyltranexamate and 1-[(6-chloronaphthalen-2-yl)sulfonyl]homopiperazine hydrochloride, whereby the title compound was obtained.

$^1$H-NMR (CDCl$_3$) δ: 0.80–1.00(2H,m), 1.40–1.60(3H, m), 1.43(9H,s), 1.60–1.90(4H,m), 1.90–2.10(2H,m), 2.30–2.40(1H,m), 2.97(2H,m), 3.30–3.50(4H,m), 3.60–3.80 (4H,m), 4.64(1H,br), 7.50–7.60(1H,m), 7.70–7.80(1H,m), 7.80–8.00(3H,m), 8.33 and 8.35(1H, each s). MS (FAB) m/z: 564 [(M+H)$^+$, Cl$^{35}$], 566 [(M+H)$^+$, Cl$^{37}$].

Referential Example 53

Methyl 4-(N-tert-butoxycarbonylaminomethyl) benzoate

In the same manner as in Referential Example 44, a reaction was conducted using 4-aminomethylbenzoic acid as a starting material, whereby the title compound was obtained.

$^1$H-NMR (CDCl$_3$) δ: 1.47(9H,s), 3.91(3H,s), 4.37(2H,d, J=5.4 Hz), 4.92(1H,br), 7.35(2H,d,J=8.3 Hz), 8.00(2H,d,J= 8.3 Hz) Elementary analysis for C$_{14}$H$_{19}$NO$_4$ Calculated: C, 63.38; H, 7.22; N, 5.28. Found: C, 63.20; H, 7.02; N, 5.58.

Referential Example 54

1-[4-(N-tert-Butoxycarbonylaminomethyl)benzoyl]-4-[(6-chloronaphthalen-2-yl)sulfonyl]piperazine In the same manner as in Referential Example 48, a reaction was conducted using methyl 4-(N-tert-butoxycarbonylaminomethyl)benzoate and 1-[(6-chloronaphthalen-2-yl)sulfonyl]piperazine hydrochloride, whereby the title compound was obtained.

$^1$H-NMR (CDCl$_3$) δ: 1.45(9H,s), 3.00–3.30(4H,br), 3.40–4.00(4H,br), 4.31(2H,d,J=5.9 Hz), 4.90(1H,br), 7.27 (4H,m), 7.59(1H,dd,J=8.8,1.5 Hz), 7.75(1H,d,J=8.8 Hz), 7.90–8.00(3H,m), 8.30(1H,s). MS (FAB) m/z: 544 [(M+H)$^+$, Cl$^{35}$], 546 [(M+H)$^+$, Cl$^{37}$].

Referential Example 55

Methyl 3-(N-tert-butoxycarbonylaminomethyl) benzoate

Methyl 3-methylbenzoate (1.00 g) was dissolved in carbon tetrachloride (10 ml), followed by the addition of N-bromosuccinic imide (1.22 g) and 2,2'-azobisisobutyronitrile (catalytic amount). The resulting mixture was heated under reflux for 1 hour under exposure to a mercury lamp. After the insoluble matter was filtered off, the residue obtained by distilling off the solvent under reduced pressure was purified by chromatography on a silica gel column (hexane:ethyl acetate=20:1), whereby a colorless oil (1.34 g) was obtained.

The colorless oil (0.62 g) so obtained was dissolved in N,N-dimethylformamide (10 ml), followed by the addition of sodium azide (0.38 g). The resulting mixture was stirred at room temperature for 20 hours. After the concentration of the reaction mixture under reduced pressure, the concentrate was diluted with ethyl acetate, washed with water and then dried over anhydrous sodium sulfate. The residue obtained by distilling off the solvent under reduced pressure was dissolved in tetrahydrofuran (15 ml). Triphenylphosphine (0.75 g) was added to the resulting solution, followed by stirring at an external temperature of about 50° C. for 5 hours. After the addition of about 28% aqueous ammonia (7 ml) and stirring for further 2 hours, the reaction mixture was concentrated under reduced pressure. The concentrate was extracted with ether. Dilute hydrochloric acid was added to the extract to make it acidic. To the water layer so separated, a dilute aqueous solution of sodium hydroxide was added to make it alkaline, followed by extraction with dichloromethane. The extract was dried over anhydrous sodium sulfate. The residue obtained by distilling off the solvent under reduced pressure was dissolved in dichloromethane (7 ml). To the resulting solution, di-tert-butyl dicarbonate (0.45 g) was added under ice cooling, followed by stirring at room temperature for 3 days. The residue obtained by distilling off the solvent under reduced pressure was purified by chromatography on a silica gel column (hexane:ethyl acetate=5:1), whereby the title compound (0.29 g, 35%) was obtained.

$^1$H-NMR (CDCl$_3$) δ: 1.46(9H,s), 3.91(3H,s), 4.36(2H,d, J=5.9 Hz), 4.97(1H,br), 7.40(1H,t,J=7.8 Hz), 7.49(1H,d,J=7.8 Hz), 7,90–8,00(2H,m). MS (FAB) m/z: 266 (M+H)$^+$.

Referential Example 56

Methyl 4-cyanomethylbenzoate

In dichloromethane (20 ml), methyl 4-hydroxymethylbenzoate (1.00 g) was dissolved, followed by the addition of triethylamine (0.9 ml). Under ice cooling, a solution of methanesulfonyl chloride (0.70 g) in dichloromethane (dichloromethane: 5 ml) was added to the resulting solution. The resulting mixture was stirred at room temperature for 15 hours. After dilution with dichloromethane, the reaction mixture was washed with water and was then dried over anhydrous sodium sulfate. The residue obtained by distilling off the solvent under reduced pressure was dissolved in acetonitrile (12 ml). To the resulting solution, potassium cyanide (0.80 g) and 18-Crown-6 (0.16 g) were added, followed by stirring at room temperature for 40 hours. After concentration under reduced pressure, the concentrate was diluted with dichloromethane, washed with water and then, dried over anhydrous sodium sulfate. The residue obtained by distilling off the solvent under reduced pressure was purified by chromatography on a silica gel column (dichloromethane), whereby colorless crystals (0.91 g, 86%) was obtained. A portion of the resulting crystals was recrystallized from a mixed solvent of hexane and ethyl acetate, whereby colorless crystals were obtained.

$^1$H-NMR (CDCl$_3$) δ: 3.82(2H,s), 3.93(3H,s), 7.42(2H,d,= 8.3 Hz), 8.06(2H,d,J=8.3 Hz). Elementary analysis for $C_{10}H_9NO_2$ Calculated: C, 68.56; H, 5.18; N, 8.00. Found: C, 68.39; H, 5.29; N, 8.08.

Referential Example 57

Methyl 4-[2-(tert-butoxycarbonylamino)ethyl]benzoate

Methyl 4-cyanomethylbenzoate (0.20 g) was dissolved in a mixed solvent of methanol (15 ml) and chloroform (0.4 ml). To the resulting solution, platinum dioxide (33 mg) was added, followed by catalytic hydrogenation at room temperature under 3 atmospheric pressure for 3 hours. The catalyst was removed by filtration through Celite and the solvent was distilled off under reduced pressure. The residue was suspended in dichloromethane (5 ml), followed by the addition of triethylamine (160 μl). After the addition of a solution of di-tert-butyl dicarbonate (0.29 g) in dichloromethane (dichloromethane: 2 ml) under ice cooling, the resulting solution was stirred at room temperature for 13 hours. The reaction mixture was diluted with dichloromethane, washed with water and then dried over anhydrous sodium sulfate. The solvent was distilled off under reduced pressure. The residue was purified by chromatography on a silica gel column (hexane:ethyl acetate= 10:1~5:1), whereby the title compound (0.28 g, 88%) was obtained.

$^1$H-NMR (CDCl$_3$) δ: 1.43(9H,s), 2.86(2H,t,J=6.8 Hz), 3.39(2H,m), 3.91(3H,s), 4.53(1H,br), 7.27(2H,d,J=8.3 Hz), 7.98 (2H, d, J=8.3 Hz) Elementary analysis for $C_{15}H_{21}NO_4$ Calculated: C, 64.50; H, 7.58; N, 5.01. Found: C, 64.43; H, 7.35; N, 4.97.

Referential Example 58

1-[4-[2-(tert-Butoxycarbonylamino)ethyl]benzoyl]-4-[(6-chloronaphthalen-2-yl)sulfonyl]piperazine In the same manner as in Referential Example 48, the title compound was obtained using methyl 4-[2-(tert-butoxycarbonylamino)ethyl]benzoate and 1-[(6-chloronaphthalen-2-yl)sulfonyl]piperazine hydrochloride as starting materials.

$^1$H-NMR (CDCl$_3$) δ: 1.42(9H,s), 2.79(2H,t,J=6.8 Hz), 3.10(4H,br), 3.35(2H,m), 3.40–4.00(4H,br), 4.50(1H,br), 7.18(2H,d,J=8.3 Hz), 7.24(2H,d,J=8.3 Hz), 7.59(1H,dd,J= 8.8,2.0 Hz), 7.75(1H,dd,J=8.8,2.0 Hz), 7.90–8.00(3H,m), 8.30(1H,s). MS (FAB) m/z: 558 [(M+H)$^+$, Cl$^{35}$], 560 [(M+H)$^+$, Cl$^{37}$].

Referential Example 59

Methyl 4-[[(3S)-1-tert-butoxycarbonyl-3-pyrrolidinyl]oxy]benzoate

In tetrahydrofuran (50 ml), methyl 4-hydroxybenzoate (1.01 g), (3R)-1-tert-butoxycarbonyl-3-pyrrolidinol (1.36 g) and triphenylphosphine (1.73 g) were dissolved, followed by the dropwise addition of a 40% solution (2.87 ml) of diethyl azodicarboxylate in toluene under ice cooling. The resulting mixture was stirred at room temperature for 20 hours. To the reaction mixture, ethyl acetate and a 10% aqueous solution of potassium carbonate were added to separate the organic layer. The organic layer so separated was washed with a 10% aqueous solution of potassium carbonate and water and dried over anhydrous sodium sulfate. The solvent was then distilled off under reduced pressure. The residue was purified by chromatography on a silica gel column (hexane:ethyl acetate=2:1), whereby the title compound (1.60 g, 76%) was obtained.

$^1$H-NMR (CDCl$_3$) δ: 1.46(9H,s), 2.00–2.20(2H,m), 3.40–3.70(4H,m), 3.89(3H,s), 4.96(1H,br s), 6.88(2H,d,J= 8.8 Hz), 7.90–8.00(2H,m).

Referential Example 60

4-[[(3S)-1-tert-Butoxycarbony-3-pyrrolidinyl]oxy] benzoic acid

In the same manner as in Referential Example 11, a reaction was conducted using methyl 4-[[(3S)-1-tert-butoxycarbonyl-3-pyrrolidinyl]oxy]benzoate as a starting material, whereby the title compound was obtained.

$^1$H-NMR (CD$_3$OD) δ: 1.45 and 1.47(9H, each s), 2.10–2.20(2H,m), 3.40–3.70(4H,m), 5.00–5.10(1H,m), 6.98 (2H,d,J=8.8 Hz), 7.97(2H,d,J=8.8 Hz).

Referential Example 61

1-[4-[[(3S)-1-tert-Butoxycarbonylpyrrolidin-3-yl] oxy]benzoyl]-4-[(6-chloronaphthalen-2-yl)sulfonyl] piperazine In the same manner as in Referential Example 12, a reaction was conducted using 4-[[(3S)-1-tert-butoxycarbonyl-3-pyrrolidinyl]oxy]benzoic acid and 1-[(6-chloronaphthalen-2-yl)sulfonyl]piperazine hydrochloride as starting materials, whereby the title compound was obtained.

$^1$H-NMR (CDCl$_3$) δ: 1.46(9H,s), 2.00–2.20(2H,m), 3.00–3.20(4H,m), 3.40–3.80(8H,m), 4.88(1H,br s), 6.82 (2H,d,J=8.3 Hz), 7.20–7.30(2H,m), 7.60(1H,dd,J=8.7,1.9 Hz), 7.76(1H,dd,J=8.5,1.7 Hz), 7.90–7.95(3H,m), 8.30(1H, s). Elementary analysis for C$_{30}$H$_{34}$ClN$_3$O$_6$S Calculated: C, 60.04; H, 5.71; N, 7.00. Found: C, 60.05; H, 5.69; N, 6.80.

Referential Example 62

Methyl 3-[[(3S)-1-tert-butoxycarbonyl-3-pyrrolidinyl]oxy]benzoate

In the same manner as in Referential Example 59, the title compound was obtained using methyl 3-hydroxybenzoate as a starting material.

$^1$H-NMR (CDCl$_3$) δ: 1.45 and 1.47(9H, each s), 2.05–2.25(2H,m), 3.40–3.70(4H,m), 3.92(3H,s), 4.96(1H,br s), 7.07(1H,d,J=7.8 Hz), 7.30–7.40(1H,m), 7.53(1H,d,J=2.0 Hz), 7.65(1H,m). MS (FAB) m/z: 322 (M+H)$^+$.

Referential Example 63

3-[[(3S)-1-tert-Butoxycarbonyl-3-pyrrolidinyl]oxy] benzoic acid

In the same manner as in Referential Example 11, the title compound was obtained using methyl 3-[[(3S)-1-tert-butoxycarbonyl-3-pyrrolidinyl]oxy]benzoate as a starting material.

$^1$H-NMR (CD$_3$OD) δ: 1.45 and 1.47(9H, each s), 2.05–2.25(2H,m), 3.35–3.65(4H,m), 5.04(1H,br s), 7.05–7.15(1H,m), 7.30–7.40(1H,m), 7.53(1H,s), 7.62(1H,d, J=7.3 Hz). MS (FAB) m/z: 308 (M+H)$^+$.

Referential Example 64

1-[3-[[(3S)-1-tert-butoxycarbonylpyrrolidin-3-yl] oxy]benzoyl]-4-[(6-chloronaphthalen-2-yl)sulfonyl] piperazine In the same manner as in Referential Example 12, the title compound was obtained using 3-[[(3S)-1-tert-butoxycarbonyl-3-pyrrolidinyl]oxy]benzoic acid as a starting material.

$^1$H-NMR (CDCl$_3$) δ: 1.45 and 1.46(9H, each s), 2.00–2.20(2H,m), 2.95–3.25(4H,m), 3.40–3.90(8H,m), 4.84 (1H,br s), 6.80–6.90(3H,m), 7.20–7.30(1H,m), 7.60(1H,dd, J=8.8,1.5 Hz), 7.76(1H,dd,J=8.5,1.7 Hz), 7.90–7.95(3H,m), 8.30–8.35(1H,m). MS (FAB) m/z: 600 [(M+H)$^+$, Cl$^{35}$], 602 [(M+H)$^+$, Cl$^{37}$]

Referential Example 65

Methyl 4-[[(3R)-1-tert-butoxycarbonyl-3-pyrrolidinyl]oxy]benzoate

In the same manner as in Referential Example 59, the title compound was obtained using methyl 4-hydroxybenzoate and (3S)-1-tert-butoxycarbonyl-3-pyrrolidinol as starting materials.

$^1$H-NMR (CDCl$_3$) δ: 1.47(9H,s), 2.05–2.25(2H,m), 3.40–3.70(4H,m), 3.89(3H,s), 4.96(1H,br s), 6.88(2H,d,J= 8.8 Hz), 7.90–8.00(2H,m). MS (FAB) m/z: 322 (M+H)$^+$.

Referential Example 66

4-[[(3R)-1-tert-Butoxycarbonyl-3-pyrrolidinyl]oxy] benzoic acid

In the same manner as in Referential Example 11, the title compound was obtained using methyl 4-[[(3R)-1-tert-butoxycarbonyl-3-pyrrolidinyl]oxy]benzoate as a starting material.

$^1$H-NMR (CD$_3$OD) δ: 1.47 and 1.48(9H, each s), 2.10–2.25(2H,m), 3.40–3.70(4H,m), 4.98(1H,br s), 6.91 (2H,d,J=8.8 Hz), 8.00–8.10(2H,m). MS (FAB) m/z: 308 (M+H)$^+$.

Referential Example 67

1-[4-[[(3R)-1-tert-Butoxycarbonylpyrrolidin-3-yl] oxy]benzoyl]-4-[(6-chloronaphthalen-2-yl)sulfonyl] piperazine In the same manner as in Referential Example 12, the title compound was obtained using 4-[[(3R)-1-tert-butoxycarbonyl-3-pyrrolidinyl]oxy]benzoic acid as a starting material.

$^1$H-NMR (CDCl$_3$) δ: 1.46(9H,s), 2.00–2.20(2H,m), 3.00–3.20(4H,m), 3.40–3.80(8H,m), 4.89(1H,br s), 6.82 (2H,d,J=8.3 Hz), 7.20–7.30(2H,m), 7.58(1H,dd,J=8.8,2.0 Hz), 7.74(1H,dd,J=8.5,1.7 Hz), 7.90–7.95(3H,m), 8.30(1H, s). MS (FAB) m/z: 600 [(M+H)$^+$, Cl$^{35}$], 602 [(M+H)$^+$, Cl$^{37}$].

Referential Example 68

Methyl 3-[[(3R)-1-tert-butoxycarbonyl-3-pyrrolidinyl]oxy]benzoate

In the same manner as in Referential Example 59, the title compound was obtained using methyl 3-hydroxybenzoate and (3S)-1-tert-butoxycarbonyl-3-pyrrolidinol as starting materials.

$^1$H-NMR (CDCl$_3$) δ: 1.47(9H,s), 2.05–2.25(2H,m), 3.40–3.70(4H,m), 3.92(3H,s), 4.95(1H,br s), 7.07(1H,d,J= 7.8 Hz), 7.30–7.40(1H,m), 7.50–7.55(1H,m), 7.60–7.70(1H, m). MS (FAB) m/z: 322 (M+H)$^+$.

Referential Example 69

3-[[(3R)-1-tert-butoxycarbonyl-3-pyrrolidinyl]oxy] benzoic acid

In the same manner as in Referential Example 11, the title compound was obtained using methyl 3-[[(3R)-1-tert-butoxycarbonyl-3-pyrrolidinyl]oxy]benzoate as a starting material.

¹H-NMR (CD₃OD) δ: 1.48(9H,s), 2.05–2.25(2H,m), 3.45–3.70(4H,m), 4.97(1H,br s), 7.10–7.15(1H,m), 7.35–7.45(1H,m), 7.58(1H,s), 7.70–7.75(1H,m). MS (FAB) m/z: 308 (M+H)⁺.

Referential Example 70

1-[3-[[(3R)-1-tert-Butoxycarbonylpyrrolidin-3-yl]oxy]benzoyl]-4-[(6-chloronaphthalen-2-yl)sulfonyl]piperazine In the same manner as in Referential Example 12, the title compound was obtained using 3-[[(3R)-1-tert-butoxycarbonyl-3-pyrrolidinyl]oxy]benzoic acid as a starting material.

¹H-NMR (CDCl₃) δ: 1.45 and 1.46(9H, each s), 2.00–2.20(2H,m), 2.95–3.25(4H,m), 3.40–3.90(8H,m), 4.84 (1H,br s), 6.80–6.90(3H,m), 7.20–7.30(1H,m), 7.60(1H,dd, J=8.5,1.7 Hz), 7.76(1H,dd,J=8.5,2.0 Hz), 7.90–7.95(3H,m), 8.30–8.35(1H,m). MS (FAB) m/z: 600 [(M+H)⁺, Cl³⁵], 602 [(M+H)⁺, Cl³⁷].

Referential Example 71

4-(2-Amino-5-pyrimidyl)benzoic acid

In the same manner as in Referential Example 2, the title compound was obtained using 2-amino-5-bromopyrimidine as a starting material.

¹H-NMR (DMSO-d₆) δ: 7.81(2H,d,J=8.8 Hz), 8.00(2H, d,J=8.8 Hz), 8.84(2H,s). MS (FAB) m/z: 216 (M+H)⁺.

Referential Example 72

1-tert-Butoxycarbonyl-4-[(methoxycarbonyl)methylene]piperidine

In tetrahydrofuran (40 ml), methyl dimethylphosphonoacetate (1.8 ml) was dissolved. To the resulting solution, 60% oily sodium hydride (450 mg) was added under ice cooling, followed by stirring under the same condition. After the addition of a solution of 1-(tert-butoxycarbonyl)-4-piperidone (2.0 g) in tetrahydrofuran (tetrahydrofuran: 10 ml) and stirring at room temperature for 30 minutes, the reaction mixture was diluted with ethyl acetate. To the diluted solution, 2N hydrochloric acid was added. The organic layer was separated, washed with a saturated aqueous solution of sodium bicarbonate and saturated aqueous NaCl solution, and dried over anhydrous sodium sulfate. The solvent was then distilled off under reduced pressure. The residue was purified by chromatography on a silica gel column (hexane:ethyl acetate=6:1), whereby the title compound (2.35 g, 92%) was obtained.

¹H-NMR (CDCl₃) δ: 1.47(9H,s), 2.28(2H,t,J=5.9 Hz), 2.94(2H,t,J=5.9 Hz), 3.48(2H,t,J=5.9 Hz), 3.50(2H,t,J=5.9 Hz), 3.70(3H,s), 5.72(1H,s). Elementary analysis for C₁₃H₂₁NO₄ Calculated: C, 61.16; H, 8.29; N, 5.49. Found: C, 61.14; H, 8.34; N, 5.20.

Referential Example 73

Methyl (1-tert-butoxycarbonylpiperidin-4-yl)acetate

In ethanol (10 ml), 1-tert-butoxycarbonyl-4-[(methoxycarbonyl)methylene]piperidine (875 mg) was dissolved, followed by the addition of 10% palladium carbon (water content: about 50%, 730 mg). The resulting mixture was subjected to catalytic hydrogenation under normal pressure at room temperature for 3 days. After the removal of the catalyst by filtration, the solvent was distilled off under reduced pressure, whereby the title compound (871 mg, 99%) was obtained.

¹H-NMR (CDCl₃) δ: 1.16(2H,m), 1.45(9H,s), 1.65(2H, m), 1.93(1H,m), 2.25(2H,d,J=6.8 Hz), 2.72(2H,br), 3.68 (3H,s), 4.08(2H,br) MS (FAB) m/z: 258 (M+H)⁺.

Referential Example 74

(1-tert-Butoxycarbonylpiperidin-4-yl)acetic acid

In the same manner as in Referential Example 11, the title compound was obtained using methyl (1-tert-butoxycarbonylpiperidin-4-yl)acetate as a starting material.

¹H-NMR (CDCl₃) δ: 1.18(2H,m), 1.45(9H,s), 1.73(2H, m), 1.94(1H,m), 2.29(2H,d,J=6.8 Hz), 2.72(2H,m), 4.10(2H, br). MS (EI) m/z: 243 M⁺.

Referential Example 75

1-[(1-tert-Butoxycarbonylpiperidin-4-yl)acetyl]-4-[(6-chloronaphthalen-2-yl)sulfonyl]piperazine In the same manner as in referential Example 12, a reaction was conducted using (1-tert-butoxycarbonylpiperidin -4-yl)acetic acid and 1-[(6-chloronaphthalen-2-yl)sulfonyl]piperazine hydrochloride as starting materials, whereby the title compound was obtained.

¹H-NMR (CDCl₃) δ: 1.05(2H,m), 1.43(9H,s), 1.63(2H, m), 1.91(1H,m), 2.14(2H,d,J=6.8 Hz), 2.66(2H,m), 3.07(4H, br s), 3.56(2H,br s), 3.67(2H,br s), 4.02(2H,br), 7.58(1H, dd,J=8.8,2.0 Hz), 7.75(1H,d,J=8.8 Hz), 7.91(1H,d,J=8.8 Hz), 7.93(1H,d,J=8.8 Hz), 7.92(1H,s), 8.30(1H,s). MS (FAB) m/z: 536 [(M+H)⁺, Cl³⁵], 538 [(M+H)⁺, Cl³⁷]

Referential Example 76

3-(1-tert-Butoxycarbonylpiperidin-4-yl)propionic acid

A reaction was conducted using ethyl 1-tert-butoxycarbonylisonipecotinate and diisobutylaluminum hydride, whereby the corresponding aldehyde derivative was obtained. The resulting derivative was treated as in Referential Examples 72, 73 and 74, whereby the title compound was obtained.

¹H-NMR (CDCl₃) δ: 1.10(2H,m), 1.41(1H,m), 1.45(9H, s), 1.60(2H,q,J=7.8 Hz), 1.66(2H,m), 2.39(2H,t,J=7.8 Hz), 2.67(2H,m), 4.09(2H,br). MS (FAB) m/z: 258 (M+H)⁺.

Referential Example 77

1-[3-(1-tert-Butoxycarbonylpiperidin-4-yl]propionyl]-4-[(6-chloronaphthalen-2-yl)sulfonyl]piperazine In the same manner as in Referential Example 12, a reaction was conducted using 3-(1-tert-butoxycarbonylpiperidin-4-yl)propionic acid and 1-[(6-chloronaphthalen-2-yl)sulfonyl]-piperazine hydrochloride as starting materials, whereby the title compound was obtained.

¹H-NMR (CDCl₃) δ: 1.04(2H,m), 1.35(1H,m), 1.44(9H, s), 1.47(2H,q,J=7.8 Hz), 1.57(2H,m), 2.24(2H,t,J=7.8 Hz), 2.61(2H,m), 3.07(4H,br s), 3.56(2H,br s), 3.71(2H,br s), 4.04(2H,br), 7.58(1H,dd,J=8.8,2.0 Hz), 7.75(1H,dd,J=8.8, 2.0 Hz), 7.90(1H,d,J=8.8 Hz), 7.91(1H,s), 7.92(1H,d,J=8.8 Hz), 8.30(1H,s). MS (FAB) m/z: 550 [(M+H)⁺, Cl³⁵], 552 [(M+H)⁺, Cl³⁷].

Referential Example 78

(E)-3-(4-Pyridyl)acrylic acid

In the same manner as in Referential Examples 72 and 74, the title compound was obtained using isonicotinic aldehyde as a starting material.

$^1$H-NMR (DMSO-d$_6$) δ: 6.79(1H,d,J=16.6 Hz), 7.56(1H, d,J=16.6 Hz), 7.66(2H,d,J=5.9 Hz), 8.62(2H,d,J=5.9 Hz), 12.72(1H,br s). MS (EI) m/z: 149M$^+$.

Referential Example 79

1-Methoxycarbonyl-3-pyrroline

In dichloromethane (20 ml), 3-pyrroline (1.1 ml) was dissolved, followed by the addition of triethylamine (2.6 ml) and methyl chloroformate (1.2 ml) under ice cooling. The resulting mixture was stirred at room temperature for 17 hours. The residue obtained by distilling the reaction mixture under reduced pressure was purified by chromatography on a silica gel column (hexane:ethyl acetate=4:1), whereby the title compound (0.95 g, 52%) was obtained.

$^1$H-NMR (CDCl$_3$) δ: 3.73(3H,s), 4.00–4.20(4H,m), 5.70–5.90(2H,m).

Referential Example 80

Methyl 4-trifluoromethanesulfonyloxybenzoate

In dichloromethane (20 ml), methyl 4-hydroxybenzoate (1.99 g) was dissolved, followed by the addition of pyridine (2.4 ml) and trifluoromethanesulfonic anhydride (3.0 ml) under ice cooling. After stirring at room temperature for 6 hours, the reaction mixture was added with pyridine (1.5 ml) and trifluoromethanesulfonic anhydride (1.0 ml) again. The resulting mixture was stirred for 5 hours. Dichloromethane and an aqueous solution of sodium bicarbonate were added to the reaction mixture. The organic layer so separated was washed with a 10% aqueous citric acid solution and saturated aqueous NaCl solution and dried over anhydrous sodium sulfate. The residue obtained by distilling off the solvent under reduced pressure was purified by chromatography on a silica gel column (5% ethyl acetate—hexane), whereby the title compound (3.22 g, 86%) was obtained.

$^1$H-NMR (CDCl$_3$) δ: 3.95(3H,s), 7.36(2H,d,J=8.8 Hz), 8.15(2H,d,J=8.8 Hz). MS (FAB) m/z: 285 (M+H)$^+$.

Referential Example 81

Methyl 4-(1-methoxycarbonylpyrrolidin-3-yl)benzoate

In N,N-dimethylformamide (25 ml), methyl 4-trifluoromethanesulfonyloxybenzoate (1.05 g), 1-methoxycarbonyl-3-pyrroline (1.0 g), lithium chloride (0.51 g), palladium (II) acetate(53 mg) and tri(2-furyl)phosphine (100 mg) were dissolved, followed by the addition of diisopropylethylamine (2.8 ml). Under an argon gas atmosphere, the resulting mixture was stirred at 90° C. for 11 hours and then, at 100° C. for 7 hours. The residue obtained by distilling off the solvent under reduced pressure was added with dichloromethane and water. The organic layer so separated was washed with water and dried over anhydrous sodium sulfate. The solvent was then distilled off under reduced pressure. The residue was purified by chromatography on a silica gel column (hexane:ethyl acetate=9:1~5:1). The purified product was dissolved in methanol (30 ml), followed by the addition of 10% palladium carbon (water content: about 50%, 186 mg) and ammonium formate (197 mg). The resulting mixture was heated under reflux for 2 hours. After the removal of the catalyst by filtration, the solvent was distilled off under reduced pressure. The residue was purified by chromatography on a silica gel column (10% ethyl acetate—toluene), whereby the title compound (241 mg, 25%) was obtained.

$^1$H-NMR (CDCl$_3$) δ: 1.95–2.10(1H,m), 2.25–2.35(1H, m), 3.30–3.35(4H,m), 3.55–3.75(1H,m), 3.72 and 3.73(3H, each s), 3.80–3.90(1H,m), 3.91(3H,s), 7.30(2H,d,J=3.8 Hz), 8.00(2H,d,J=8.3 Hz). MS (FAB) m/z: 264 (M+H)$^+$.

Referential Example 82

4-(1-tert-Butoxycarbonylpyrrolidin-3-yl)benzoic acid

In methanol (10 ml), methyl 4-(1-methoxycarbonylpyrrolidin-3-yl)benzoate (0.24 g) was dissolved. The resulting solution was added with 8N hydrochloric acid (30 ml), followed by heating under reflux for 40 hours. The residue obtained by distilling off the solvent under reduced pressure was dissolved in N,N-dimethylformamide (30 ml). To the resulting solution, 2-(tert-butoxycarbonyloxyimino)-2-phenylacetonitrile (0.30 g) and then diisopropylethylamine (0.40 ml) were added, followed by stirring at room temperature for 15 hours. The residue obtained by distilling off the solvent under reduced pressure was distributed in ethyl acetate and a 10% aqueous citric acid solution. The organic layer so separated was washed with saturated aqueous NaCl solution and dried over anhydrous sodium sulfate. The solvent was then distilled off under reduced pressure. The residue was purified by chromatography on a silica gel column (dichloromethane~10% methanol—dichloromethane), whereby the title compound (234 mg) was obtained.

$^1$H-NMR (CDCl$_3$) δ: 1.48(9H,m), 1.90–2.00(1H,m), 2.20–2.30(1H,m), 3.20–3.90(5H,m), 7.20–7.30(2H,m), 8.00–8.10(2H,m). MS (EI) m/z: 291M$^+$.

Referential Example 83

1-[4-(3RS)-1-tert-Butoxycarbonylpyrrolidin-3-yl]benzoyl]-4-[(6-chloronaphthalen-2-yl)sulfonyl]piperazine In the same manner as in Referential Example 12, a reaction was conducted using 4-(1-tert-butoxycarbonylpyrrolidin-3-yl)benzoic acid and 1-[(6-chloronaphthalen-2-yl)sulfonyl]piperazine hydrochloride as starting materials, whereby the title compound was obtained.

$^1$H-NMR (CDCl$_3$) δ: 1.47 and 1.60(9H, each s), 1.80–2.00(1H,m), 2.10–2.20(1H,m), 3.00–4.00(13H,m), 7.10–7.30(4H,m), 7.55–7.65(1H,m), 7.70–7.80(1H,m), 7.85–8.00(3H,m), 8.30(1H,s).

Referential Example 84

(3S)-3-Amino-1-tert-butoxycarbonylpyrrolidine

In the same manner as in Referential Example 55, the title compound was obtained using (3R)-1-tert-butoxycarbonyl-3-methanesulfonyloxypyrrolidine (1.50 g) as a starting material.

$^1$H-NMR (CDCl$_3$) δ: 1.46(9H,s), 1.98–2.11(2H,m), 2.95–3.10(1H,m), 3.26–3.60(4H,m). MS (FAB) m/z: 187 (M+H)$^+$.

Referential Example 85

(3S)-3-[(6-Chloronaphthalen-2-yl)sulfonamide]pyrrolidine trifluoroacetate

In the same manner as in Referential Example 1, a reaction was conducted using (3S)-3-amino-1-tertbutoxycarbonylpyrrolidine as a starting material, whereby the title compound was obtained.

$^1$H-NMR (DMSO-d$_6$) δ: 1.69–1.80(1H,m), 1.88–1.99 (1H,m), 2.95–3.28(4H,m), 3.75–3.84(1H,m), 7.71(1H,m), 7.91(1H,m), 8.10–8.30(4H,m), 8.53(1H,s), 8.91(1H,br s), 9.06(1H,br s).

Referential Example 86

(3S)-3-Amino-1-[(6-chloronaphthalen-2-yl)sulfonyl]pyrrolidine

In trifluoroacetic acid, (3R)-1-tert-butoxycarbonyl-3-methanesulfonyloxypryrrolidine was dissolved. After the resulting solution was concentrated under reduced pressure, diethyl ether was added to the concentrate, followed by the removal of the supernatant. The residue was reacted as in Referential Example 1, whereby the corresponding sulfonamide derivative was obtained as a crude product. The crude product was subjected to azide formation and reduction as in Referential Example 55, whereby the title compound was obtained.

$^1$H-NMR (DMSO-d$_6$) δ: 1.38–1.53(3H,m), 1.72–1.83 (1H,m), 2.81–2.89(1H,m), 3.20–3.39(4H,m), 7.69(1H,dd,J=8.8,1.9 Hz), 7.87(1H,d,J=8.8 Hz), 8.12(1H,d,J=8.8 Hz), 8.21 (1H,s), 8.26(1H,d,J=8.8 Hz), 8.39(1H,s). MS (FAB) m/z: 311 [(M+H)$^+$, Cl$^{35}$], 313 [(M+H)$^+$, Cl$^{37}$].

Referential Example 87

4-Benzylamino-1-tert-butoxycarbonylpiperidine

In dichloromethane (500 ml), 1-tert-butoxycarbonyl-4-piperidione (7.00 g) was dissolved, followed by the addition of benzylamine (4.03 ml) and sodium triacetoxyborohydride (11.91 g). The resulting mixture was stirred overnight at room temperature. After the reaction mixture was concentrated under reduced pressure, the residue was dissolved in ethyl acetate. The resulting mixture was washed with water and saturated aqueous NaCl solution and then dried over anhydrous sodium sulfate. The solvent was then distilled off under reduced pressure. The residue was purified by chromatography on a silica gel column (hexane ethyl acetate= 1:1), whereby the title compound (7.46 g, 76%) was obtained.

$^1$H-NMR (CDCl$_3$) δ: 1.24–1.37(2H,m), 1.45(9H,s), 1.80–1.90(2H,m), 2.62–2.70(1H,m), 2.75–2.85(1H,m), 2.98–3.07(1H,m), 3.78–3.90(3H,m), 3.95–4.10(1H,m), 7.21–7.34(5H,m). MS (FD). m/z: 290M$^+$.

Referential Example 88

4-Amino-1-tert-butoxycarbonylpiperidine acetate

In methanol (2 ml) and acetic acid (30 ml), 4-benzylamino-1-tert-butoxycarbonylpiperidine (4.04 g) was dissolved, followed by the addition of 10% palladium carbon (water content: about 50%, 3.06 g). The resulting mixture was subjected to catalytic hydrogenation overnight under medium pressure (3 atmospheric pressure). After the removal of the catalyst by filtration, the filtrate was distilled off under reduced pressure. The residue was solidified in ethyl acetate, whereby the title compound (2.23 g, 57%) was obtained.

$^1$H-NMR (DMSO-d$_6$) δ: 1.10–1.23(2H,m), 1.39(9H,s), 1.69–1.77(2H,m), 1.80(3H,s), 2.50(2H,s), 2.67–2.88(2H,m), 3.80–3.90(1H,m). MS (FAB) m/z: 201(M+H)$^+$. Elementary analysis for $C_{10}H_{20}N_2O_2 \cdot CH_3CO_2H$ Calculated: C, 53.16; H, 9.37; N, 10.33. Found: C, 53.51; H, 9.10; N, 9.93.

Referential Example 89

4-[(6-Chloronaphthalen-2-yl)sulfonamido]piperidine trifluoroacetate

In the same manner as in Referential Example 1, the title compound was obtained using 4-amino-1-tert-butoxycarbonylpiperidine acetate and 6-chloro-2-naphthylsulfonyl chloride as starting materials.

$^1$H-NMR (DMSO-d$_6$) δ: 1.47–1.60(2H,m), 1.68–1.78 (2H,m), 2.81–2.95(2H,m), 3.10–3.20(2H,m), 3.29–3.40(1H, m), 7.70(1H,dd,J=8.8,2.0 Hz), 7.91(1H,dd,J=8.8,2.0 Hz), 8.11–8.15(2H,m), 8.21(1H,s), 8.31(1H,br s), 8.50(1H,s), 8.55(1H,br s). MS (FAB) m/z: 325 [(M+H)$^+$, Cl$^{35}$], 327 [(M+H)$^+$, Cl$^{37}$].

Referential Example 90

Ethyl (1RS)-4-trifluoromethanesulfonyloxy-3-cyclohexenecarboxylate

Diisopropylamine (0.99 ml) was dissolved in tetrahydrofuran (50 ml), followed by the dropwise addition of n-butyl lithium (a 1.59M hexane solution, 3.70 ml) at −78° C. After the dropwise addition of ethyl 4-oxocyclohexanecarboxylate (1.00 g) dissolved in tetrahydrofuran (5 ml) to the reaction mixture and stirring for 15 minutes, N-phenyltrifluoromethanesulfonimide (2.10 g) dissolved in tetrahydrofuran (5 ml) was added dropwise to the reaction mixture. The reaction mixture was heated to 0° C., stirred for one hour and then concentrated under reduced pressure. The residue was purified by chromatography on a neutral alumina column (hexane:ethyl acetate=9:1), whereby the title compound (838 mg, 47%) was obtained.

$^1$H-NMR (CDCl$_3$) δ: 1.27(3H,t,J=7.3 Hz), 1.88–1.99(1H, m), 2.10–2.18(1H,m), 2.38–2.50(4H,m), 2.55–2.64(1H,m), 4.16(2H,q,J=7.3 Hz), 5.77(1H,br s). MS (FAB) m/z: 303 (M+H)$^+$.

Referential Example 91

Ethyl (1RS)-4-(4-pyridyl)-3-cyclohexenecarboxylate

In the same manner as in Referential Example 7, a reaction was conducted using ethyl (1RS)-4-trifluoromethanesulfonyloxy-3-cyclohexenecarboxylate as a starting material, whereby the title compound was obtained.

$^1$H-NMR (CDCl$_3$) δ: 1.28(3H,t,J=7.3 Hz), 1.80–1.91(1H, m), 2.19–2.25(1H,m), 2.40–2.57(4H,m), 2.59–2.67(1H,m), 4.17(2H,q,J=7.3 Hz), 6.36(1H,br s), 7.26(2H,dd,J=4.9,1.5 Hz), 8.53(2H,dd,J=4.9,1.5 Hz). MS (FAB) m/z: 232 (M+H)$^+$.

Referential Example 92

(1RS)-4-(4-Pyridyl)-3-cyclohexenecarboxylic acid

In the same manner as in Referential Example 8, a reaction was conducted using ethyl (1RS)-4-(4-pyridyl)-3-cyclohexenecarboxylate as a starting material, the title compound was obtained.

$^1$H-NMR (DMSO-d$_6$) δ: 1.70–1.82(1H,m), 2.10–2.19 (1H,m), 2.42–2.65(5H,m), 6.99(1H,br s), 8.02(2H,d,J=6.8 Hz), 8.80(2H,d,J=6.8 Hz). MS (FAB) m/z: 204 (M+H)$^+$.

Referential Example 93 cis-, trans-4-(4-Pyridyl)cyclohexanecarboxylic acid

In the same manner as in Referential Example 73, the title compound was obtained using (1RS)-4-(4-pyridyl)-3-

Referential Example 94

4-(1-tert-Butoxycarbonyl-1,2,3,6-tetrahydropyridin-4-yl)benzoic acid

In 1,2-dimethoxyethane (30 ml), 4-(1-tert-butoxycarbonyl-4-trifluoromethanesulfonyloxy-1,2,3,6-tetrahydropyridine (Synthesis, 993, 1991)(3.59 g) was dissolved, followed by the addition of 4-carboxyphenylboric acid (3.60 g), lithium chloride (1.38 g), tetrakistriphenylphosphine palladium (0.62 g) and an aqueous solution of sodium carbonate (2M, 16.3 ml). The resulting mixture was heated under reflux for 2 hours under an argon gas atmosphere. To the reaction mixture, 1N hydrochloric acid was added. The resulting mixture was extracted with ethyl acetate. The extract was dried over anhydrous sodium sulfate. The residue obtained by distilling off the solvent under reduced pressure was purified by chromatography on a silica gel column (dichloromethane~dichloromethane:methanol=100:1). The purified product was pulverized and washed in a mixed solvent of hexane and ethyl acetate (hexane:ethyl acetate=5:1), whereby the title compound (462 mg, 14%) was obtained.

$^1$H-NMR (CDCl$_3$) δ: 1.50(9H,s), 2.56(2H,br s), 3.66(2H, m), 4.12(2H,br s), 6.19(1H,br s), 7.47(2H,d,J=8.3 Hz), 8.07 (2H,d,J=8.3 Hz) MS (FAB) m/z: 304 (M+H)$^+$.

Referential Example 95

4-(1-tert-Butoxycarbonylpiperidin-4-yl)benzoic acid

In the same manner as in Referential Example 73, the title compound was obtained by using 4-(1-tert-butoxycarbonyl-1,2,3,6-tetrahydropyridin-4-yl)benzoic acid as a starting material.

$^1$H-NMR (CDCl$_3$) δ: 1.48(9H,s), 1.60–1.71(2H,m), 1.80–1.89(2H,m), 2.69–2.90(3H,m), 4.20–4.35(2H,m), 7.31 (2H,d,J=8.3 Hz), 8.05(2H,d,J=8.3 Hz). MS (FAB) m/z: 306 (M+H)$^+$.

Referential Example 96

1-[4-(1-tert-butoxycarbonyl-1,2,3,6-tetrahydropyridin-4-yl)benzoyl]-4-[(6-chloronaphthalen-2-yl)sulfonyl]piperazine In the same manner as in Referential Example 12, a reaction was conducted using 4-(1-tert-butoxycarbonyl-1,2,3,6-tetrahydropyridin-4-yl)benzoic acid and 1-[(6-chloronaphthalen-2-yl)sulfonyl]piperazine hydrochloride as starting materials, whereby the title compound was obtained.

$^1$H-NMR (CDCl$_3$) δ: 1.49(9H,s), 2.48(2H,br s), 3.10(4H, br), 3.62(2H,t,J=5.9 Hz), 3.70(4H,br), 4.08(2H,br s), 6.05 (1H,br s), 7.25(2H,d,J=8.3 Hz), 7.34(2H,d,J=8.3 Hz), 7.59 (1H,dd,J=8.8,2.0 Hz), 7.75(1H,dd,J=8.8,2.0 Hz), 7.90–7.96 (3H,m), 8.30(1H,s). MS (FAB) m/z: 596 [(M+H)$^+$, Cl$^{35}$], 598 [(M+H)$^+$, Cl$^{37}$].

Referential Example 97

1-[4-(1-tert-Butoxycarbonylpiperidin-4-yl)benzoyl]-4-[(6-chloronaphthalen-2-yl)sulfonyl]piperazine In the same manner as in Referential Example 12, a reaction was conducted using 4-(1-tert-butoxycarbonylpiperidin-4-yl)benzoic acid and 1-[(6-chloronaphthalen-2-yl)sulfonyl]piperazine hydrochloride as starting materials, whereby the title compound was obtained.

$^1$H-NMR (CDCl$_3$) δ: 1.47(9H,s), 1.49–1.63(2H,m), 1.72–1.80(2H,m), 2.59–2.68(1H,m), 2.71–2.86(2H,m), 2,92–3.30(4H,m), 3.45–4.95(4H,m), 4.16–4.31(2H,m), 7.18 (2H,d,J=8.3 Hz), 7.24(2H,d,J=8.3 Hz), 7.59(1H,dd,J=8.8, 2.0 Hz), 7.75(1H,dd,J=8.8,2.0 Hz), 7.90–7.94(3H,m), 8.30 (1H,s). MS (FAB) m/z: 598 [(M+H)$^+$, Cl$^{35}$], 600 [(M+H)$^+$, Cl$^{37}$].

Referential Example 98

(3RS)-3-Amino-1-tert-butoxycarbonylpyrrolidine

In methanol (30 ml), 3-aminopyrrolidine (0.54 g) was dissolved under ice cooling, followed by the addition of diisopropylethylamine (720 μl) and 2-(tert-butoxycarbonyloxyimino)-2-phenylacetonitrile (0.84 g). The resulting mixture was gradually heated to room temperature and stirred for 11 hours. The residue obtained by distilling off the solvent under reduced pressure was purified by chromatography on a silica gel column (dichloromethane 5% methanol—dichloromethane), whereby the title compound (0.59 g, 94%) was obtained.

$^1$H-NMR (CDCl$_3$) δ: 1.45(9H,s), 2.0–2.3(2H,m), 3.1–4.0 (5H,m)

Referential Example 99

(3RS)-1-tert-Butoxycarbonyl-3-[(6-chloronaphthalen-2-yl)sulfonamide]pyrrolidine

In the same manner as in Referential Example 1, the title compound was obtained using (3RS)-3-amino-1-tert-butoxycarbonylpyrrolidine as a starting material.

$^1$H-NMR (CDCl$_3$) δ: 1.37(9H,s), 1.60–2.10(2H,m), 3.00–3.50(4H,m), 3.88(1H,br), 4.96(1H,br), 7.50–7.60(1H, m), 7.80–7.90(4H,m), 8.43(1H,s). MS (FAB) m/z: 411 [(M+H)$^+$, Cl$^{35}$], 413 (M+H)$^+$, Cl$^{37}$].

Referential Example 100

(3RS)-1-tert-Butoxycarbonyl-3-[4-(4-pyridyl)benzamide]pyrrolidine

In the same manner as in Referential Example 12, the title compound was obtained using (3RS)-3-amino-1-tert-butoxycarbonylpyrrolidine and 4-(4-pyridyl)benzoic acid as starting materials.

$^1$H-NMR (CDCl$_3$) δ: 1.48(9H,s), 1.90–2.10(1H,m), 2.20–2.30(1H,m), 3.30–3.40(1H,m), 3.40–3.60(2H,m), 3.70–3.80(1H,m), 4.65–4.75(1H,m), 6.25–6.35(1H,m), 7.52 (2H,d,J=5.9 Hz), 7.71(2H,d,J=8.3 Hz), 7.88(2H,d,J=8.3 Hz), 8.70(2H,d,J=5.4 Hz) MS (FAB) m/z: 368 (M+H)$^+$.

Referential Example 101

6-Chloro-N-methoxy-N-methylnicotinamide

Under ice cooling, 6-chloronicotinic acid (5.00 g) was suspended in dichloromethane (150 ml), followed by the addition of a catalytic amount of N,N-dimethylformamide and oxalyl chloride (5.30 ml). The resulting mixture was stirred at room temperature for 23 hours. The residue obtained by concentrating the reaction mixture was dissolved in dichloromethane (100 ml), followed by the addition of N,O-dimethylhydroxylamine hydrochloride (6.18 g) and triethylamine (13.3 ml) under ice cooling. After stirring at room temperature for 6 hours, the reaction mixture was diluted with dichloromethane (150 ml), washed with a saturated aqueous solution of sodium bicarbonate, water and saturated aqueous NaCl solution and then dried over anhydrous magnesium sulfate. The residue obtained by distilling off the solvent under reduced pressure was purified by chromatography on a silica gel column (hexane:ethyl acetate=2:1), whereby the title compound (6.08 g, 96%) was obtained.

$^1$H-NMR (CDCl$_3$) δ: 3.39(3H,s), 3.56(3H,s), 7.39(1H,d, J=8.3 Hz), 8.03 (1H,dd,J=8.3,2.4 Hz), 8.78(1H,d,J=2.4 Hz).

Referential Example 102

6-Chloronicotinaldehyde

In tetrahydrofuran (8 ml), 6-chloro-N-methoxy-N-methylnicotinamide (500 mg) was dissolved, followed by the dropwise addition of diisobutylaluminum hydride (a 0.95M hexane solution, 2.88 ml) at −78° C. in an argon gas atmosphere. The resulting mixture was stirred for 3 hours and then, at room temperature, for 2 hours. After the reaction mixture was cooled to −20° C., saturated aqueous NaCl solution (2 ml) was added thereto, followed by stirring for 30 minutes. The insoluble matter was filtered off. The residue was washed with ethyl acetate. The filtrate and the washing were combined together. The mixture was washed with saturated aqueous NaCl solution and dried over anhydrous sodium sulfate. The solvent was then distilled off under reduced pressure, whereby the title compound (346 mg, 98%) was obtained as a crude product. The product was provided for the subsequent reaction without purification.

$^1$H-NMR (CDCl$_3$) δ: 7.52(1H,d,J=8.3 Hz), 8.14(1H,dd, J=8.3,2.2 Hz), 8.87(1H,d,J=2.2 Hz), 10.10 (1H,s).

Referential Example 103

1-tert-Butoxycarbonyl-4-methanesulfonylpiperazine

In dichloromethane (40 ml), N-tert-butoxycarbonylpiperazine (2.00 g) was dissolved, followed by the addition of triethylamine (1.78 ml). To the resulting solution, methanesulfonyl chloride (0.91 ml) was added dropwise under ice cooling. After stirring for one hour under ice cooling, the reaction mixture was diluted with dichloromethane (20 ml), washed with a 5% aqueous citric acid solution, water and saturated aqueous NaCl solution and dried over anhydrous magnesium sulfate. The residue obtained by distilling off the solvent under reduced pressure was recrystallized from a mixed solvent of ethyl acetate and hexane, whereby the title compound (2.58 g, 91%) was obtained.

$^1$H-NMR (CDCl$_3$) δ: 1.47(9H,s), 2.79(3H,s), 3.19(4H,t, J=5.1 Hz), 3.55(4H,t,J=5.1 Hz).

Referential Example 104

1-tert-Butoxycarbonyl-4-[[(2RS)-2-(6-chloropyridin-3-yl)-2-hydroxyethyl]sulfonyl]piperazine In tetrahydrofuran (8 ml), 1-tert-butoxycarbonyl-4-methanesulfonylpiperazine (838 mg) was dissolved, followed by the addition of tert-butyl lithium (a 1.7M pentane solution, 1.72 ml) at −78° C. in an argon gas atmosphere. The resulting mixture was stirred for 2 hours. After the dropwise addition of a solution of 6-chloronicotinaldehyde (346 mg) in tetrahydrofuran (tetrahydrofuran: 4 ml) and stirring at −78° C. for 3 hours, the reaction mixture was added with isopropanol (1 ml). The resulting mixture was heated to room temperature and diluted with ethyl acetate. The diluted solution was washed with water and saturated aqueous NaCl solution and dried over anhydrous sodium sulfate. The residue obtained by distilling off the solvent under reduced pressure was recrystallized from ethyl acetate, whereby the title compound (532 mg, 54%) was obtained.

$^1$H-NMR (CDCl$_3$) δ: 1.46(9H,s), 3.11(1H,dd,J=14.1,2.2 Hz), 3.21(1H,dd,J=14.1,9.8 Hz), 3.23–3.33(4H,m), 3.52–3.57(4H,m), 3.70(1H,br s), 5.37(1H,br), 7.36(1H,d,J= 8.3 Hz), 7.72(1H,dd,J=8.3,2.4 Hz), 8.41(1H,d,J=2.4 Hz). MS (FAB) m/z: 405 (M+H)$^+$.

Referential Example 105

1-tert-Butoxycarbonyl-4-[[(E)-2-(6-chloropyridin-3-yl)ethylene]sulfonyl]piperazine In dichloromethane (10 ml), 1-tert-butoxycarbonyl-4-[[(2RS)-2-(6-chloropyridin-3-yl)-2-hydroxyethyl]-sulfonyl] piperazine (465 mg) was dissolved, followed by the addition of N-methylmorpholine (0.152 ml) and N,N-dimethyl-4-aminopyridine (14.1 mg). Under an argon atmosphere, p-toluenesulfonyl chloride (263 mg) was added under ice cooling. After stirring at room temperature for 2 hours, N,N-dimethyl-4-aminopyridine (141 mg) was added further and the resulting mixture was stirred at room temperature for 3 hours. After dilution with dichloromethane (20 ml), the reaction mixture was washed with a saturated aqueous solution of sodium bicarbonate, water and saturated aqueous NaCl solution and then dried over anhydrous sodium sulfate. The residue obtained by distilling off the solvent under reduced pressure was purified by chromatography on a silica gel column (dichloromethane:methanol=100:1), whereby the title compound (414 mg, 93%) was obtained.

$^1$H-NMR (CDCl$_3$) δ: 1.45(9H,s), 3.19(4H,br), 3.55(4H, br), 6.73(1H,d,J=15.6 Hz), 7.40(1H,d,J=8.3 Hz), 7.43(1H, d,J=15.6 Hz), 7.76(1H,dd,J=8.3,2.5 Hz), 8.50(1H,d,J=2.5 Hz). Elementary analysis for C$_{16}$H$_{22}$ClN$_3$O$_3$S Calculated: C, 49.54; H, 5.72; N, 10.83; Cl, 9.14; S,8.27. Found: C, 49.54; H, 5.73; N, 10.63; Cl, 9.44; S,8.15.

Referential Example 106

1-(4-Bromo-2-methylbenzoyl)-4-[(6-chloronaphthalen-2-yl)sulfonyl]piperazine

In the same manner as in Referential Example 12, a reaction was conducted using 4-bromo-2-methylbenzoic acid and 1-[(6-chloronaphthalen-2-yl)sulfonyl]piperazine hydrochloride as starting materials, whereby the title compound was obtained.

$^1$H-NMR (CDCl$_3$) δ: 2.13(3H,s), 2.80–4.10(8H,m), 6.89 (1H,d,J=8.3 Hz), 7.30(1H,dd,J=8.3,2.0 Hz), 7.35(1H,d,J= 2.0 Hz), 7.60(1H,dd,J=8.8,2.0 Hz), 7.74(1H,dd,J=8.8,2.0 Hz), 7.90–7.95(3H,m), 8.30(1H,br s). MS (FAB) m/z: 507 [(M+H)$^+$, Br$^{79}$], 509 [(M+H)$^+$, Br$^{81}$].

Referential Example 107

3-Methyl-4-(4-pyridyl)benzoic acid hydrochloride

In the same manner as in Referential Example 6, a reaction was conducted using 4-bromo-3-methylbenzoic acid as a starting material, whereby the title compound was obtained.

$^1$H-NMR (DMSO-d$_6$) δ: 2.36(3H,s), 7.50(1H,d,J=7.8 Hz), 7.92(1H,d,J=7.8 Hz), 7.97(1H,s), 8.08(2H,d,J=6.4 Hz), 8.99(2H,d,J=6.4 Hz). MS (FAB) m/z: 214 (M+H)$^+$.

Referential Example 108

4-(2-Methyl-4-pyridyl)benzoic acid hydrochloride

In the same manner as in Referential Example 2, a reaction was conducted using 4-bromo-2-methylpyridine as a starting material, whereby the title compound was obtained.

$^1$H-NMR (DMSO-d$_6$) δ: 2.81(3H,s), 8.10–8.16(4H,m), 8.23(1H,dd,J=6.4,1.5 Hz), 8.36(1H,d,J=1.5 Hz), 8.85(1H,d, J=6.4 Hz) MS (FAB) m/z: 214 (M+H)$^+$.

Referential Example 109

1,4-Dibenzyl-2-methoxycarbonylmethylpiperazine

In toluene (250 ml), N,N'-dibenzylethylenediamine (12 ml) and triethylamine (12 ml) were dissolved, followed by the dropwise addition of methyl 3-bromocrotonate (7.0 ml) under ice cooling. The resulting mixture was stirred at room temperature for 24 hours. After the addition of triethylamine (2.0 ml), the resulting mixture was stirred at room temperature for 71 hours. The insoluble matter was filtered off and the filtrate was distilled under reduced pressure. The residue was added with 10% hydrochloric acid (300 ml) and crystals so precipitated were removed by filtration. Ethyl acetate was added to the filtrate. Potassium carbonate was added to the water layer so separated to make it alkaline. Ethyl acetate was added to the resulting mixture. The organic layer so separated was washed with saturated aqueous NaCl solution and dried over anhydrous potassium carbonate. The solvent was then distilled off under reduced pressure. The residue was purified by chromatography on a silica gel column (hexane ethyl acetate=4:1), whereby the title compound (10.7 g, 62%) was obtained.

$^1$H-NMR (CDCl$_3$) δ: 2.30–2.70(8H,m), 3.11(1H,br s), 3.40–3.80(4H,m), 3.60(3H,s), 7.20–7.40(10H,m). MS (FAB) m/z: 339 (M+H)$^+$.

Referential Example 110

1-[(6-Chloronaphthalen-2-yl)sulfonyl]-3-methoxycarbonylmethylpiperazine

In acetic acid (40 ml), 1,4-dibenzyl-2-methoxycarbonylmethylpiperazine (2.04 g) was dissolved, followed by the addition of 10% palladium carbon (water content: about 50%, 2.00 g). The resulting mixture was subjected to catalytic reduction at room temperature for 4 hours under 4 atmospheric pressure. After removal of the catalyst by filtration, the residue obtained by distilling the filtrate under reduced pressure was added with dichloromethane and a saturated aqueous solution of potassium bicarbonate. The insoluble matter so precipitated was filtered off. The organic layer so separated was washed with saturated aqueous NaCl solution and dried over anhydrous sodium sulfate. The solvent was then distilled off under reduced pressure. The residue was dissolved in dichloromethane (30 ml), followed by the addition of 6-chloro-2-naphthylsulfonyl chloride (782 mg). The resulting mixture was stirred at 0° C. for 2 hours. To the reaction mixture, triethylamine (410 µl) was added, followed by stirring at 0° C. for further three hours. The residue obtained by distilling off the solvent under reduced pressure was purified by chromatography on a silica gel column (dichloromethane~3% methanol—dichloromethane), whereby the title compound (759 mg, 33%) was obtained.

$^1$H-NMR (CDCl$_3$) δ: 1.71(1H,br s), 2.15–2.55(4H,m), 2.90–3.05(2H,m), 3.15–3.25(1H,m), 3.60–3.70(5H,m), 7.55–7.60(1H,m), 7.75–7.80(1H,m), 7.85–7.95(3H,m), 8.30 (1H,s). MS (FAB) m/z: 383 [(M+H)$^+$, Cl$^{35}$], 385 [(M+H)$^+$, Cl$^{37}$].

Referential Example 111

4-tert-Butoxycarbonyl-1-[(3-chloro-1-propyl)sulfonyl]piperazine

Under an argon gas atmosphere, 1-tert-butoxycarbonylpiperazine (3.00 g) and triethylamine (2.24 ml) were dissolved in dichloromethane (40 ml) under ice cooling, followed by the addition of 3-chloro-1-propanesulfonic acid chloride (1.96 g). The resulting mixture was stirred for 20 minutes under ice cooling and then, at room temperature for 10 minutes. The reaction mixture was diluted with dichloromethane, washed with water and saturated aqueous NaCl solution and then dried over anhydrous sodium sulfate. The solvent was then distilled off under reduced pressure. The residue was recrystallized from a mixed solvent of ethyl acetate and hexane, whereby the title compound (4.36 g, 83%) was obtained.

$^1$H-NMR (CDCl$_3$) δ: 1.41(9H,s), 2.27–2.33(2H,m), 3.08 (2H,t,J=7.3 Hz), 3.26(4H,t,J=4.9 Hz), 3.53(4H,t,J=4.9 Hz), 3.69(2H,t,J=6.1 Hz) MS (FAB) m/z: 327 (M+H)$^+$ Elementary analysis for C$_{12}$H$_{23}$ClN$_2$O$_4$S Calculated: C, 44.10; H, 7.09, Cl, 10.85; N, 8.57; S, 9.81. Found: C, 44.18; H, 7.11; Cl, 10.69; N, 8.23; S, 9.76.

Referential Example 112

4-tert-Butoxycarbonyl-1-[(3-hydroxy-1-propyl)sulfonyl]piperazine

In N,N-dimethylformamide (10 ml), 4-tert-butoxycarbonyl-1-[(3-chloro-1-propyl)sulfonyl]piperazine (1.18 g) was dissolved, followed by the addition of potassium acetate (1.06 g). After stirring at room temperature for 2 hours, the reaction mixture was stirred under heat at 100° C. for 3 hours. The reaction mixture was diluted with ethyl acetate, followed by the addition of water and a saturated aqueous solution of sodium bicarbonate. After stirring, the organic layer so separated was washed with a 5% aqueous citric acid solution, water and saturated aqueous NaCl solution. After drying over anhydrous sodium sulfate, the residue obtained by distilling off the solvent under reduced pressure was dissolved in tetrahydrofuran (20 ml). To the resulting solution, water and lithium hydroxide monohydrate (221 mg) were added, followed by stirring at room temperature for 18 hours. Ethyl acetate and saturated aqueous NaCl solution were added to the reaction mixture to separate an organic layer. From the water layer, another organic layer was extracted with ethyl acetate. The organic layers were combined together, washed with saturated aqueous NaCl solution and dried over anhydrous sodium sulfate. The solvent was then distilled off under reduced pressure. The residue was recrystallized from a mixed solvent of ethyl acetate an hexane, whereby the title compound (944 mg, 84%) was obtained.

$^1$H-NMR (CDCl$_3$) δ: 1.47(9H,s), 2.04–2.11(2H,m), 3.06 (2H,t,J=7.6 Hz), 3.25(4H,t,J=4.9 Hz), 3.53(4H,t,J=4.9 Hz), 3.80(2H,q,J=5.4 Hz). MS (FAB) m/z: 309 (M+H)$^+$. Elementary analysis for C$_{12}$H$_{24}$N$_2$O$_5$S Calculated: C, 46.74; H, 7.84; N, 9.08; S, 10.40. Found: C, 46.80; H, 7.92; N, 9.05; S, 10.59.

Referential Example 113

4-tert-Butoxycarbonyl-1-[(3-methoxymethyloxy-1-propyl)sulfonyl]piperazine

In dichloromethane (60 ml), 4-tert-butoxycarbonyl-1-[(3-hydroxy-1-propyl)sulfonyl]piperazine (3.00 g) was dissolved. To the resulting solution, diisopropylethylamine (2.72 ml) was added, followed by the addition of methoxymethyl chloride (1.11 ml) under ice cooling. After stirring at room temperature for 15 hours, the reaction mixture was diluted with dichloromethane, washed with water, 5% aqueous citric acid solution and saturated aqueous NaCl solution and then dried over anhydrous sodium sulfate. The solvent was then distilled off under reduced pressure. The residue was purified by chromatography on a silica gel column (hexane:ethyl acetate=2:1), whereby the title compound (3.32 g, 97%) was obtained.

$^1$H-NMR (CDCl$_3$) δ: 1.47(9H,s), 2.06–2.13(2H,m), 3.03 (2H,m), 3.25(4H,t,J=4.9 Hz), 3.36(3H,s), 3.52(4H,t,J=4.9 Hz), 3.63(2H,t,J=5.4 Hz), 4.61(2H,s). MS (FAB) m/z: 353 (M+H)$^+$. Elementary analysis for C$_{14}$H$_{28}$N$_2$O$_6$S Calculated: C, 47.71; H, 8.01; N, 7.95; S, 9.10. Found: C, 47.77; H, 8.18; N, 7.97; S, 9.16.

Referential Example 114

4-tert-Butoxycarbonyl-1-[(E)-4-chloro-β-[2-(methoxymethyloxy)ethyl]-β-styrylsulfonyl] piperazine and 4-tert-butoxycarbonyl-1-[(Z) -4-chloro-β-[2-(methoxymethyloxy)ethyl]-β-styrylsulfonyl]piperazine Under an argon gas atmosphere, 4-tert-butoxycarbonyl -1-[(3-methoxymethyloxy-1-propyl)sulfonyl]piperazine (800 mg) was dissolved in tetrahydrofuran (10 ml), followed by the dropwise addition of tert-butyl lithium (a 1.7M hexane solution, 1.47 ml) at −78° C. The resulting mixture was stirred at −78° C. for one hour. After the addition of trimethylsilyl chloride (0.317 ml) and stirring at −78° C. for 90 minutes, tert-butyl lithium (a 1.7M hexane solution, 1.47 ml) was added dropwise to the reaction mixture and stirring was effected at −78° C. for 90 minutes. At −78° C., a solution of p-chlorobenzaldehyde (352 mg) in tetrahydrofuran (tetrahydrofuran: 8 ml) was added dropwise to the reaction mixture. After stirring for 2 hours, the temperature of the reaction mixture was allowed to rise back to room temperature over 15 hours, at which temperature it was stirred for 6 hours. Under ice cooling, a 5% citric acid solution (20 ml) and ethyl acetate (150 ml) were added to the reaction mixture. The organic layer so separated was washed with water and saturated aqueous NaCl solution and then dried over anhydrous magnesium sulfate. The residue obtained by distilling off the solvent under reduced pressure was purified by chromatography on a silica gel column (hexane:ethyl acetate=3:1~2:1), whereby the title compound was obtained as an E-form (307 mg, 28%) and Z-form (751 mg, 70%). E-form:

$^1$H-NMR (CDCl$_3$) δ: 1.42(9H,s), 2.87(2H,t,J=7.3 Hz), 3.21–3.28(4H,m), 3.35(3H,s), 3.46–3.56(4H,m), 3.80(2H,t, J=7.3 Hz), 4.60(2H,s), 7.40(2H,d,J=8.5 Hz), 7.46(2H,d,J= 8.5 Hz), 7.54(1H,s). Z-form:

$^1$H-NMR (CDCl$_3$) δ: 1.43(9H,s), 2.77(2H,dt,J=6.4,1.0 Hz), 2.91–2.98(4H,m), 3.19–3.25(4H,m), 3.38(3H,s), 3.82 (2H,t,J=6.4 Hz), 4.66(2H,s), 7.07(1H,s), 7.32(2H,d,J=8.6 Hz), 7.35(2H,d,J=8.6 Hz).

Referential Example 115

6-Chloro-1-phenylsulfonylindole

At −78° C., n-butyl lithium (a 1.61M hexane solution, 3.34 ml) was added to a solution of 6-chloroindole (777 mg) in tetrahydrofuran (25 ml), followed by heating to −40° C. over 1 hour. The reaction mixture was cooled back to −78° C. and added with benzenesulfonyl chloride (867 μl). The resulting mixture was heated to room temperature over 3 hours. Water was added to the reaction mixture, followed by extraction with dichloromethane. The organic layers were combined, dried over anhydrous sodium sulfate and concentrated under reduced pressure. The residue was purified by chromatography on a silica gel column (40 g of silica gel, hexane:ethyl acetate=5:7). The white solid so obtained was recrystallized from ethanol, whereby the title compound (826 mg, 55%) was obtained as a white solid.

$^1$H-NMR (CDCl$_3$) δ: 6.64(1H,d,J=3.9 Hz), 7.21(1H,dd, J=8.3,1.2 Hz), 7.42–7.60(5H,m), 7.88(2H,d,J=7.3 Hz), 8.03 (1H,s). Elementary analysis for C$_{14}$H$_{10}$ClNO$_2$S Calculated: C, 57.63; H, 3.45; Cl, 12.15; N, 4.80; S, 10.99. Found: C, 57.48; H, 3.75; Cl, 12.34; N, 4.87; S, 10.87.

In the same manner as in Referential Example 115, the compounds which will described below in Referential Examples 116 and 117 were synthesized.

Referential Example 116

5-Chloro-1-phenylsulfonylindole $^1$H-NMR (CDCl$_3$) δ: 6.61(1H,d,J=3.9 Hz), 7.26(1H,dd, J=8.3,2.0 Hz), 7.45(2H,t,J=7.3 Hz), 7.50(1H,d,J=2.0 Hz), 7.56(1H,m), 7.59(1H,d,J=3.9 Hz), 7.86(2H,m), 7.92(1H,d, J=8.3 Hz). Elementary analysis for C$_{14}$H$_{10}$ClNO$_2$S Calculated: C, 57.63; H, 3.45; Cl, 12.15; N, 4.80; S, 10.99. Found: C, 57.82; H, 3.58; Cl, 11.91; N, 4.79; S, 10.92.

Referential Example 117

5-Bromo-1-phenylsulfonylindole $^1$H-NMR (CDCl$_3$) δ: 6.60(1H,d,J=3.7 Hz), 7.42(1H,dd, J=8.8,2.0 Hz), 7.45(2H,t,J=8.8 Hz), 7.55(1H,d,J=8.8 Hz), 7.57(1H,d,J=3.7 Hz), 7.73(1H,d,J=2.0 Hz), 7.86(2H,d,J=8.8 Hz), 7.87(1H,d,J=1H,d,J=8.8 Hz). Elementary analysis for C$_{14}$H$_{10}$BrNO$_2$S Calculated: C, 50.01; H, 3.00; N, 4.17; Br, 23.77; S, 9.54. Found: C, 49.96; H, 2.97; N, 4.02; Br, 23.90; S, 9.53.

Referential Example 118

1-Phenylsulfonyl-5-trimethylsilylethynylindole

In tetrahydrofuran (7.00 ml), 5-bromo-1-phenylsulfonylindole (1.50 g) and triphenylphosphine (351 mg) were dissolved. Triethylamine (20 ml), N,N-dimethylformamide (7.00 ml), trimethylsilylacetylene (945 up) and palladium acetate (100 mg) were added to the resulting solution at room temperature, followed by heating under reflux for 5 hours. After the reaction mixture was allowed to cool down to room temperature, ethyl acetate and water were added to the reaction mixture to separate the organic layer. The resulting organic layer was dried over anhydrous sodium sulfate and then distilled under reduced pressure to remove the solvent. The residue was purified by chromatography on a silica gel column (hexane:ethyl acetate=20:1 to 10:1), whereby the title compound (935 mg, 59%) was obtained as a white solid.

$^1$H-NMR (CDCl$_3$) δ: 0.24(9H,s), 6.62(1H,d,J=3.9 Hz), 7.42(1H,dd,J=8.8,1.5 Hz), 7.44(2H,t,J=7.8 Hz), 7.52(1H,d, J=7.8 Hz), 7.56(1H,d,J=3.9 Hz), 7.66(1H,d,J=1.5 Hz), 7.85 (2H,d,J=7.8 Hz), 7.92(1H,d,J=8.8 Hz). MS (FAB) m/z: 354 (M+H)$^+$

Referential Example 119

5-Chloro-1-ethylindole

In benzene (10 ml), 5-chloroindole (1.52 g) was dissolved, followed by the addition of a 50% aqueous solution of sodium hydroxide (10 ml), tetrabutylammonium bromide (161 mg) and bromoethane (1.64 g). The resulting mixture was stirred at room temperature for 40 hours. After the addition of a saturated aqueous solution of ammonium chloride to the reaction mixture, water and dichloromethane were added to separate the organic layer. After the organic layer was dried over anhydrous sodium sulfate, the residue obtained by distilling off the solvent under reduced pressure was purified by chromatography on a silica gel column (ethyl acetate:hexane 1:20), whereby the title compound (1.68 g, 93%) was obtained as colorless crystals.

$^1$H-NMR (CDCl$_3$) δ: 1.46(3H,t,J=7.3 Hz), 4.16(2H,q,J=7.3 Hz), 6.43(1H,d,J=2.4 Hz), 7.14(1H,d,J=2.4 Hz), 7.15 (1H,d,J=8.3 Hz), 7.26(1H,d,J=8.3 Hz), 7.59(1H,s). MS (EI) m/z: 179 (M$^+$, Cl$^{35}$), 181 (M$^+$, Cl$^{37}$).

Referential Example 120

6-Chloro-1-phenylsulfonylindole-2-sulfonyl chloride

After the dropwise addition of tert-butyl lithium (a 1.56M pentane solution, 1.78 ml) to a solution of 6-chloro-1-phenylsulfonylindole (777 mg) in ether (12 ml) at −78° C., the mixture was heated to 0° C. over 30 minutes. The reaction mixture was stirred for 1 hour and then cooled back to −78° C. Sulfurdioxide was then introduced into the reaction mixture. After heating to room temperature over 1 hour, stirring was conducted for 1 hour. The reaction mixture was concentrated under reduced pressure. Hexane was added to the concentrate, followed by concentration under reduced pressure again. The residue was dissolved in dichloromethane. To the resulting solution, N-chlorosuccinimide (390 mg) was added at 0° C., followed by heating over 1 hour to room temperature. Stirring was then conducted for 30 minutes. Dichloromethane and water were added to the reaction mixture to separate the organic layer. The resulting organic layer was dried over anhydrous sodium sulfate and then distilled under reduced pressure to remove the solvent. The residue was recrystallized from methanol, whereby the title compound (857 mg, 79%) was obtained as a white solid.

$^1$H-NMR (CDCl$_3$) δ: 7.39(1H,dd,J=8.3,1.6 Hz), 7.48–7.67(4H,m), 7.68(1H,s), 8.08(2H,d,J=7.3 Hz), 8.35 (1H,s). Elementary analysis for C$_{14}$H$_9$ClNO$_4$S$_2$ Calculated: C, 43.09; H, 2.32; Cl, 18.17; N, 3.59; S, 16.43. Found: C, 43.32; H, 2.67; Cl, 18.25; N, 3.64; S, 16.22.

In the same manner as in Referential Example 120, compounds which will be described below in Referential Examples 121 to 128 were synthesized.

Referential Example 121

1-Phenylsulfonylindole-2-sulfonyl chloride $^1$H-NMR (CDCl$_3$) δ: 7.40(1H,t,J=7.6 Hz), 7.45–7.53(2H, m), 7.57–7.67(2H,m), 7.69(1H,d,J=7.8 Hz), 7.73(1H,s), 8.08(2H,d,J=7.3 Hz), 8.31(1H,d,J=8.8 Hz). MS (EI) m/z: 355M$^+$. Elementary analysis for C$_{14}$H$_{10}$ClNO$_4$S$_2$ Calculated: C, 47.26; H, 2.83; Cl, 9.96; N, 3.94; S, 18.02. Found: C, 47.33; H, 3.08; Cl, 10.04; N, 3.98; S, 18.18.

Referential Example 122

5-Chloro-1-phenylsulfonylindole-2-sulfonyl chloride $^1$H-NMR (CDCl$_3$) δ: 7.46–7.54(2H,m), 7.58(1H,dd,J=9.3,2.0 Hz), 7.63(1H,t,J=7.3 Hz), 7.64(1H,s), 7.67(1H,d,J=2.0 Hz), 8.06(2H,d,J=7.3 Hz), 8.26(1H,d,J=9.3 Hz). MS (EI) m/z: 291 (M$^+$, Cl$^{35}$), 293 (M$^+$, Cl$^{37}$). Elementary analysis for C$_{14}$H$_9$Cl$_2$NO$_4$S$_2$ Calculated: C, 43.09; H, 2.32; Cl, 18.27; N, 3.59; S, 16.43. Found: C, 42.98; H, 2.51; Cl, 18.36; N, 3.59 S, 16.47.

Referential Example 123

5-Chloro-1-ethylindole-2-sulfonyl chloride $^1$H-NMR (CDCl$_3$) δ: 1.52(3H,t,J=7.3 Hz), 4.59(2H,q,J=7.3 Hz), 7.36(1H,s), 7.39(1H,d,J=8.8 Hz), 7.45(1H,dd,J=8.8,2.0 Hz), 7.73(1H,d,J=2.0 Hz). MS (EI) m/z: 277 [M$^+$, Cl$^{35}$], 279 [M$^+$, Cl$^{37}$]

Referential Example 124

1-Phenylsulfonyl-5-trimethylsilylethynylindole-2-sulfonyl chloride $^1$H-NMR (CDCl$_3$) δ: 0.26(9H,s), 7.48(2H,t,J=7.8 Hz), 6.61(1H,t,J=7.8 Hz), 7.65(1H,s), 7.69(1H,dd,J=8.8,1.5 Hz), 7.79(1H,d,J=1.5 Hz), 8.04(2H,d,J=7.8 Hz), 8.24(1H,d,J=8.8 Hz). MS (FAB) m/z: 452 [(M+H)$^+$, Cl$^{35}$], 454 [(M+H)$^+$, Cl$^{37}$]

Referential Example 125

5-Chlorobenzo[b]furan-2-sulfonyl chloride $^1$H-NMR (CDCl$_3$) δ: 7.57(1H,dd,J=8.8,2.0 Hz), 7.59(1H, s), 7.61(1H,d,J=8.8 Hz), 7.76(1H,d,J=2.0 Hz). MS (EI) m/z: 250 (M$^+$, Cl$^{35}$), 252 (M$^+$, Cl$^{37}$). Elementary analysis for C8H$_4$Cl$_2$O$_3$S Calculated: C, 38.27; H, 1.61; Cl, 28.24; S, 12.77. Found: C, 38.33; H, 1.71; Cl, 28.16; S, 12.57.

Referential Example 126

6-Chlorobenzo[b]furan-2-sulfonyl chloride $^1$H-NMR (CDCl$_3$) δ: 7.43(1H,dd,J=8.8,2.0 Hz), 7.62(1H, s), 7.69(1H,s), 7.70(1H,d,J=8.8 Hz). MS (EI) m/z: 250 (M$^+$, Cl$^{35}$), 252 (M$^+$, Cl$^{37}$). Elementary analysis for C$_8$H$_4$Cl$_2$O$_3$S Calculated: C, 38.27; H, 1.61; Cl, 28.24; S, 12.77. Found: C, 38.31; H, 1.60; Cl, 28.34; S, 12.60.

Referential Example 127

5-Chlorobenzo[b]thiophene-2-sulfonyl chloride $^1$H-NMR (CDCl$_3$) δ: 7.57(1H,dd,J=8.8,2.0 Hz), 7.85(1H, d,J=8.8 Hz), 7.96(1H,d,J=2.0 Hz), 8.08(1H,s). MS (FD) m/z: 266 (M$^+$, Cl$^{35}$), 268 (M$^+$, Cl$^{37}$).

Referential Example 128

6-Chlorobenzo[b]thiophene-2-sulfonyl chloride $^1$H-NMR (CDCl$_3$) δ: 7.51(1H,dd,J=8.3,1.5 Hz), 7.90(1H, d,J=8.3 Hz), 7.92(1H,s), 8.11(1H,s). MS (FAB) m/z: 266 [(M+H)$^+$, Cl$^{35}$], 268 [(M+H)$^+$, Cl$^{37}$) ].

Referential Example 129

1-tert-Butoxycarbonyl-4-[(5-chloro-1-phenylsulfonylindol-2-yl)sulfonyl]piperazine To a solution of 5-chloro-1-phenylsulfonylindole-2-sulfonyl chloride (4.41 g) in dichloromethane (75 ml), tert-butyl-1-piperazine carboxylate (2.21 g) and triethylamine (1.65 ml) were added under ice cooling. The resulting mixture was stirred at room temperature for 3 hours. After completion of the reaction, water and dichloromethane were added to the reaction mixture. The organic layer so separated was dried over anhydrous sodium sulfate and then distilled under reduced pressure to remove the solvent. The residue was purified by chromatography on a silica gel column (ethyl acetate:n-hexane=1:20), whereby the title compound (3.63 g, 60%) was obtained as colorless crystals.

$^1$H-NMR (CDCl$_3$) δ: 1.45(9H,s), 3.35–3.42(4H,br), 3.50–3.55(4H,br), 7.40–7.48(4H,m), 7.53–7.58(2H,m), 8.00–8.05(2H,m), 8.23(1H,d,J=8.8 Hz).

In the same manner as in Referential Example 129, compounds which will described below in Referential Examples 130 to 133 were synthesized.

Referential Example 130

1-tert-Butoxycarbonyl-4-[(1-phenylsulfonylindol-2-yl)sulfonyl]piperazine $^1$H-NMR (CDCl$_3$) δ: 1.45(9H,s), 3.34–3.44(4H,br), 3.48–3.56(4H,br), 7.33(1H,t,J=7.3 Hz), 7.36–7.45(2H,m), 7.47–7.61(4H,m), 8.04(2H,d,J=7.3 Hz), 8.29(1H,d,J=8.8 Hz). MS (EI) m/z: 505M$^+$.

Referential Example 131

1-tert-Butoxycarbonyl-4-[(5-chloro-1-ethylindol-2-yl)sulfonyl]piperazine $^1$H-NMR (CDCl$_3$) δ: 1.41(3H,t,J=7.3 Hz), 1.43(9H,s), 3.16–3.23(4H,m), 3.48–3.55(4H,m), 4.45(2H,q,J=7.3 Hz), 7.03(1H,s), 7.32–7.34(2H,m), 7.66(1H,d,J=2.0 Hz). MS (EI) m/z: 427 (M$^+$, Cl$^{35}$), .429 (M$^+$, Cl$^{37}$)

Referential Example 132

1-tert-Butoxycarbonyl-4-[(5-chloro-1-phenylsulfonylindol-2-yl)sulfonyl]homopiperazine $^1$H-NMR (CDCl$_3$) δ: 1.47(9H,s), 1.98–2.17(2H,m), 3.42–3.57(8H,m), 7.28(1H,s), 7.41–7.46(3H,m), 7.53–7.57 (2H,m), 8.05(2H,d,J=7.3 Hz), 8.20(1H,d,J=9.3 Hz). MS (FAB) m/z: 554 [(M+H)$^+$, Cl$^{35}$], 556 [(M+H)$^+$, Cl$^{37}$].

Referential Example 133 cis-1-[(5-Chloro-1-phenylsulfonylindol-2-yl)sulfonyl]-3,5-dimethylpiperazine $^1$H-NMR (CDCl$_3$) δ: 1.07(6H,d,J=6.4 Hz), 2.45–2.55(2H, m), 2.95–3.05(2H,m), 3.75–3.80(2H,m), 7.35–7.50(4H,m), 7.50–7.60(2H,m), 8.00–8.05(2H,m), 8.22(1H,d,J=9.3 Hz). MS (FAB) m/z: 468 (M+H)$^+$, Cl$^{35}$], 470 [(M+H)$^+$, Cl$^{37}$].

Referential Example 134

1-[(5-Chloro-1-phenylsulfonylindol-2-yl)sulfonyl]-3-(ethoxycarbonyl)piperazine

A saturated solution of hydrochloride in ethanol was added to tert-butyl 1-(3-ethoxycarbonyl) piperazinecarboxylate (3.97 g) and the mixture was stirred for 30 minutes. After the solvent was distilled off under reduced pressure, the residue was suspended in dichloromethane (200 ml). To the resulting suspension, 5-chloro-1-phenylsulfonylindole-2-sulfonyl chloride (6.00 g) and triethylamine (6.40 ml) were added, followed by stirring at room temperature for 3 hours. Water and dichloromethane were added to the reaction mixture. The organic layer so separated was dried over anhydrous sodium sulfate and distilled under reduced pressure to remove the solvent. The residue was purified by chromatography on a silica gel column (methanol:dichloromethane=1:20), whereby the title compound (4.44 g, 56%) was obtained as colorless crystals.

$^1$H-NMR (CDCl$_3$) δ: 1.24(3H,t,J=6.8 Hz), 2.87–2.95(1H, m), 3.11–3.28(3H,m), 3.57–3.66(2H,m), 3.91–3.98(1H,m), 4.17(2H,q,J=6.8 Hz), 7.38–7.48(4H,m), 7.55–7.59(2H,m), 8.03(2H,d,J=7.8 Hz), 8.21(1H,d,J=9.3 Hz). MS (EI) m/z: 511 (M$^+$, Cl$^{35}$), 513 (M$^+$, Cl$^{37}$)+.

Referential Example 135

1-tert-Butoxycarbonyl-4-[(5-chloroindol-2-yl)sulfonyl]piperazine

To 1-tert-butoxycarbonyl-4-[(5-chloro-1-phenylsulfonylindol-2-yl)sulfonyl]piperazine (4.84 g), a 0.5N methanol solution of sodium hydroxide (20 ml) was added, followed by stirring at room temperature for 1 hour. Under ice cooling, a saturated aqueous solution of ammonium chloride was added to the reaction mixture. Water and dichloromethane were then added to separate the organic layer. The organic layer was dried over anhydrous sodium sulfate. The residue obtained by distilling off the solvent under reduced pressure was purified by chromatography on a silica gel column (methanol:dichloromethane=1:20), whereby the title compound (3.33 g, 93%) was obtained as colorless powder.

$^1$H-NMR (CDCl$_3$) δ: 1.40(9H,s), 3.05–3.14(4H,m), 3.48–3.57(4H,m), 6.96(1H,d,J=2.0 Hz), 7.33(1H,dd,J=8.8, 2.0 Hz), 7.38(1H,d,J=8.8 Hz), 7.67(1H,d,J=2.0 Hz), 8.78 (1H,br). MS (FAB) m/z: 400 [(M+H)$^+$, Cl$^{35}$], 402 [(M+H)$^+$, Cl$^{37}$].

In the same manner as in Referential Example 135, the compound shown in Referential Example 136 was synthesized.

Referential Example 136

1-[(5-Chloroindol-2-yl)sulfonyl]-3-methoxycarbonylpiperazine

In the same manner as in Referential Example 135, the title compound was obtained.

$^1$H-NMR (CDCl$_3$) δ: 2.70–2.82(1H,m), 2.84–2.97(2H, m), 3.06–3.16(1H,m), 3.37–3.46(1H,m), 3.61(1H,dd,J=8.3, 3.4 Hz), 3.69–3.80(1H,m), 3.75(3H,s), 6.98(1H,s), 7.32(1H, dd,J=8.8,2.0 Hz), 7.38(1H,d,J=8.8 Hz), 7.67(1H,s), 8.80 (1H,s). MS (EI) m/z: 357 (M$^+$, Cl$^{35}$), 359 (M$^+$, Cl$^{37}$)$^+$.

Referential Example 137

3-(N-Methylcarbamoyl)-1-[(5-chloroindol-2-yl)sulfonyl]piperazine

In tetrahydrofuran (25 ml), 1-[(5-chloroindol-2-yl) sulfonyl]-3-methoxycarbonylpiperazine (480 mg) was dissolved. After a 0.2N methanol solution (7 ml) of sodium hydroxide and water (2 ml) were added to the resulting solution and the mixture was stirred at room temperature for 1 hour, the solvent was distilled off under reduced pressure. The resulting yellow amorphous substance (520 mg) was dissolved in N,N-dimethylformamide (60 ml). At room temperature, 1-hydroxybenzotriazole (18.1 mg), 1-(3-dimethylaminopropyl)-3-ethylcarbodiimide hydrochloride (334 mg), methylamine hydrochloride (90.5 mg) and N-methylmorpholine (271 mg) were added to the resulting solution, followed by stirring at room temperature for 12 hours. The solvent was then distilled off under reduced pressure. Water and ethyl acetate were added to the residue to separate the organic layer. The organic layer was dried over anhydrous sodium sulfate and distilled under reduced pressure to remove the solvent. The residue was purified by chromatography on a silica gel column (methanol:dichloromethane=1:50), whereby the title compound (140 mg, 29%) was obtained as a brown amorphous solid.

$^1$H-NMR (DMSO-d$_6$) δ: 2.39–2.52(2H,m), 2.64(3H,d,J=3.9 Hz), 2.18–2.30(1H,m), 2.94–3.00(1H,m), 3.20–3.37(2H,m), 3.57–3.66(1H,m), 6.90–6.95(1H,br), 7.22–7.27(1H,br), 7.44–7.49(1H,m), 7.66–7.78(2H,m), 8.04–8.17(3H,m), 12.24(1H,m).

Referential Example 138

1-[(5-Chloroindol-2-yl)sulfonyl]piperazine hydrochloride

In methanol (100 ml), 1-tert-butoxycarbonyl-4-[(5-chloro-1-phenylsulfonylindol-2-yl)sulfonyl]piperazine (3.63 g) was dissolved. Under ice cooling, a 0.2N methanol solution of sodium hydroxide (100 ml) was added to the resulting solution, followed by stirring at room temperature for 12 hours. After a saturated aqueous solution of ammonium chloride was added to the reaction mixture under ice cooling, water and dichloromethane were added to separate the organic layer. The organic layer was dried over anhydrous sodium sulfate. The solvent was concentrated under reduced pressure. After the solid so precipitated was collected by filtration, it was dissolved in saturated ethanol hydrochloride, followed by stirring for 30 minutes. The reaction mixture was distilled under reduced pressure to remove the solvent, followed by drying under reduced pressure, whereby the title compound (1.25 g, 54%) was obtained as colorless powder.

$^1$H-NMR (DMSO-d$_6$) δ: 3.25–3.43(8H,br), 7.46(1H,d,J=8.8 Hz), 7.64(1H,d,J=8.8 Hz), 7.93(1H,s), 9.33(1H,br), 12.70(1H,br). MS (EI) m/z: 298 (M$^+$, Cl$^{35}$), 300 (M$^+$, Cl$^{37}$). Elementary analysis for $C_{12}H_{14}ClN_3O_2S \cdot HCl \cdot 0.5H_2O$ Calculated: C, 41.75; H, 4.67; Cl, 20.54; N, 12.17; S, 9.29. Found: C, 41.78; H, 4.98; Cl, 20.40; N, 11.88; S, 9.34.

Referential Example 139

1-tert-Butoxycarbonyl-4-[(5-chloro-1-methylindol-2-yl)sulfonyl]piperazine

Sodium hydride (about 60% in oil, 50.3 mg) washed twice with petroleum ether was suspended in tetrahydrofuran (10 ml), followed by the addition of a solution of 1-tert-butoxycarbonyl-4-[(5-chloroindol-2-yl)sulfonyl]piperazine (457 mg) in tetrahydrofuran (10 ml) under ice cooling. The resulting mixture was stirred for 30 minutes. Under ice cooling, iodomethane (179 mg) was added to the reaction mixture. The resulting mixture was heated to room temperature and stirred for 85 hours. Water and diethyl ether were added to separate the organic layer. The organic layer was dried over anhydrous magnesium sulfate and distilled under reduced pressure to remove the solvent. The residue was purified by chromatography on a silica gel column (methanol:dichloromethane=1:50), whereby the title compound (270 mg, 57%) was obtained as colorless powder.

$^1$H-NMR (CDCl$_3$) δ: 1.42(9H,s), 3.14–3.21(4H,m), 3.48–3.55(4H,m), 3.96(3H,s), 7.06(1H,s), 7.31(1H,d,J=9.3 Hz), 7.36(1H,d,J=9.3,2.0 Hz), 7.66(1H,d,J=2.0 Hz). MS (FAB) m/z: 413 [(M+H)$^+$, Cl$^{35}$], 415 [(M+H)$^+$, Cl$^{37}$].

Referential Example 140

1-tert-Butoxycarbonyl-4-[(5-chloro-1-ethoxycarbonylmethylindol-2-yl)sulfonyl]piperazine In the same manner as in Example 139, the title compound was obtained.

$^1$H-NMR (CDCl$_3$) δ: 1.27(3H,t, J=7.3 Hz), 1.43(9H,s), 3.10–3.19(4H,m), 3.45–3.53(4H,m), 4.22(2H,q,J=7.3 Hz), 5.15(2H,s), 7.15(1H,s), 7.17(1H,d,J=8.8 Hz), 7.26(1H,s), 7.36(1H,dd,J=8.8,2.0 Hz), 7.68(1H,d,J=2.0 Hz). MS (FAB) m/z: 485 [(M+H)$^+$, Cl$^{35}$], 487 [(M+H)$^+$, Cl$^{37}$].

Referential Example 141 cis-1-[(4-Bromobenzoyl)-4-[(5-chloro-1-phenylsulfonylindol-2-yl)sulfonyl]-2,6-dimethylpiperazine In dichloromethane (40 ml), cis-1-[(5-chloro-1-phenylsulfonylindol-2-yl)sulfonyl]-3,5-dimethylpiperazine (1.30 g) was dissolved. To the resulting suspension, diisopropylethylamine (645 μl) was added under ice cooling, followed by the dropwise addition of a solution of 4-bromobenzoyl chloride (0.74 g) in dichloromethane (5 ml). Stirring was then effected at room temperature for 3 hours. A saturated aqueous solution of sodium bicarbonate was added to the reaction mixture. The organic layer thus separated was washed with 0.5N hydrochloric acid and saturated aqueous NaCl solution, dried over anhydrous sodium sulfate and distilled under reduced pressure to remove the solvent. The residue was purified by chromatography on a silica gel column (hexane:ethyl acetate=2:1 to 1:1), whereby the title compound (1.8 g, 97%) was obtained as a pale yellow amorphous.

$^1$H-NMR (CDCl$_3$) δ: 1.45(6H,d,J=6.8 Hz), 3.05–3.15(2H,m), 3.74(2H,m), 4.40(2H,br), 7.23(2H,d,J=8.8 Hz), 7.40–7.50(4H,m), 7.50–7.60(4H,m), 8.00–8.05(2H,m), 8.24 (1H,d,J=9.3 Hz) MS (EI) m/z: 649 [(M+H)$^+$, Cl$^{35}$], 651 [(M+H)$^+$, Cl$^{37}$].

Referential Example 142

Ethyl-2-(4-pyridyl)-5-pyrimidinecarboxylic acid

Sodium ethoxide (590 mg) was dissolved in anhydrous ethanol (50 ml) at room temperature. To the resulting solution, 4-amidinopyridine hydrochloride (1.31 g) was added, followed by the dropwise addition of a solution of ethyl 2,2-diformylacetate (1.20 g) in anhydrous ethanol (50 ml). The resulting mixture was heated under reflux for 6 hours. To the residue obtained by distilling off the solvent under reduced pressure, dichloromethane and water were added. The organic layer thus separated was dried over anhydrous sodium sulfate. After the solvent was concentrated under reduced pressure, the residue was crystallized in ethanol, whereby the title compound (279 mg, 15%) was obtained as colorless crystals.

$^1$H-NMR (DMSO-d$_6$) δ: 1.46(3H,t,J=7.3 Hz), 4.48(2H,q, J=7.3 Hz), 8.35(2H,d,J=5.9 Hz), 8.82(2H,d,J=5.9 Hz), 9.38 (2H,s). MS (FAB) m/z: 230 (M+H)$^+$. Elementary analysis for $C_{12}H_{11}N_3O_2$ Calculated: C, 62.87; H, 4.84; N, 18.33. Found: C, 62.80; H, 4.78; N, 18.25.

Referential Example 143

2-(4-Pyridyl)-5-pyrimidinecarboxylic acid

In the same manner as in Referential Example 11, a reaction was effected using the ethyl 2-(4-pyridyl)-5-pyrimidinecarboxylate instead as a starting material, whereby the title compound was obtained.

$^1$H-NMR (DMSO-d$_6$) δ: 8.32(2H,d,J=5.9 Hz), 8.82(2H, d,J=5.9 Hz), 9.38(2H,s). MS (FAB) m/z: 201 (M+H)$^+$. Elementary analysis for $C_{10}H_7N_3O_2 \cdot 0.1H_2O$ Calculated: C, 59.17; H, 3.58; N, 20.70. Found: C, 59.09; H,. 3.49; N, 20.69.

Referential Example 144

1-[(5-Bromopyrimidin-2-yl)carbonyl]-4-[(5-chloroindol-2-yl)sulfonyl]piperazine

In the same manner as in Referential Example 12, a reaction was effected using 5-bromo-2- pyrimidinecarboxylic acid and 1-[(5-chloroindol-2-yl)sulfonyl]piperazine hydrochloride as starting materials, whereby the title compound was obtained as a colorless solid.

$^1$H-NMR (CDCl$_3$) δ: 3.14–3.17(2H,m), 3.25–3.29(2H, m), 3.52–3.55(2H,m), 3.92–3.95(2H,m), 7.97(1H,s), 7.32–7.40(2H,m), 7.69(1H,s), 8.79(1H,br,s), 8.84(2H,s). MS (FAB) m/z: 484 [(M+H)$^+$, Cl$^{35}$ and Br$^{79}$], 486 [(M+H)$^+$, Cl$^{35}$ and Br 81, Cl$^{37}$ and Br$^{79}$], 488 [(M+H)$^+$, Cl$^{37}$ and Br$^{81}$].

Referential Example 145

6-Chloro-2-mercaptobenzothiazole

Under ice cooling, a solution of p-chloroaniline (5.70 g) in acetic acid (7 ml) was added dropwise to disulfur dichloride (25.0 ml) over 30 minutes, followed by stirring at room temperature for 3 hours and then at about 80° C. for 3 hours. Benzene (50 ml) was added to the reaction mixture. The green crystals were collected by filtration and washed with benzene. The resulting crystals were dissolved in ice water (500 ml) and the solution was stirred for 1 hour. To the reaction mixture, a 6N aqueous solution of sodium hydroxide was added to make the mixture alkaline. Sodium bicarbonate (6 g) was then added and the mixture was stirred at 100° C. for 1 hour. Activated carbon was added to the reaction mixture, followed by Celite filtration. To the filtrate, carbon disulfide (2.70 ml) was added, followed by heating to about 50° C. Stirring was then conducted for 1.5 hours. After cooling to room temperature, the reaction mixture was made acidic with 1N hydrochloric acid. Colorless powder thus precipitated was collected by filtration and dried, whereby the title compound (1.30 g, 14%) was obtained.

$^1$H-NMR (DMSO-d$_6$) δ: 7.28(1H,d,J=8.3 Hz), 7.45(1H, dd,J=8.3,2.0 Hz), 7.86(1H,d,J=2.0 Hz). MS (FAB) m/z: 202 [(M+H)$^+$, Cl$^{35}$], 204 [(M+H)$^+$, Cl$^{37}$]. Elementary analysis for C$_7$H$_4$ClNS$_2$ Calculated: C, 41.68; H, 2.00; Cl, 17.58; N, 6.94; S, 31.80. Found: C, 41.64; H, 2.13; Cl, 17.83; N, 6.94; S, 31.70.

Referential Example 146

1-tert-Butoxycarbonyl-4-[(5-chloroenzothiazol-2-yl)sulphenyl]piperazine

At room temperature, tert-butyl 1-piperazine carboxylate (5.58 g), 5-chloro-2-mercaptobenzothiazole (1.21 g)and sodium hydroxide (0.48 g) were dissolved in water (25 ml), followed by the dropwise addition of an aqueous solution (25 ml) containing iodine (1.53 g) and potassium iodide (1.65 g). The colorless crystals so precipitated were collected by filtration, washed with water and dried under reduced pressure, whereby the title compound (1.1 g, 48%) was obtained.

$^1$H-NMR (CDCl$_3$) δ: 1.48(9H,s), 3.24(4H,br), 3.58(4H,br s), 7.26(1H,m), 7.70(1H,d,J=8.3 Hz), 7.81(1H,s). MS (FAB) m/z: 386 [(M+H)$^+$, Cl$^{35}$], 388 [(M+H)$^+$, Cl$^{37}$].

Referential Example 147

1-tert-Butoxycarbonyl-4-[(6-chlorobenzothiazol-2-yl)sulphenyl]piperazine

In the same manner as in Referential Example 146, the title compound was obtained.

$^1$H-NMR (CDCl$_3$) δ: 1.48(9H,s), 3.24(4H,br s), 3.58(4H, br s), 7.37(1H,dd,J=8.8,2.0 Hz), 7.73(1H,d,J=8.8 Hz), 7.77 (1H,d,J=2.0 Hz). MS (FAB) m/z: 386 [(M+H)$^+$, Cl$^{35}$], 388 [(M+H)$^+$, Cl$^{37}$].

Referential Example 148

1-tert-Butoxycarbonyl-4-[(5-chlorobenzothiazol-2-yl)sulfonyl]piperazine

At room temperature, 1-tert-butoxycarbonyl-4-[(5-chlorobenzothiazol-2-yl)sulphenyl]piperazine (1.10 g) and potassium carbonate (1.30 g) were suspended in a mixed solvent of ethanol (30 ml) and water (10 ml), followed by the dropwise addition of a solution of 3-chloroperbenzoic acid (2.11 g) in ethanol (25 ml) at 0° C. The reaction mixture was heated to room temperature and stirred for 24 hours. Sodium thiosulfate and ethyl acetate were added to separate the organic layer. The organic layer thus obtained was dried over anhydrous magnesium sulfate. The residue obtained by distilling off the solvent was purified by chromatography on a silica gel column (dichloromethane~2% methanol—dichloromethane), whereby the title compound (293 mg, 25%) was obtained.

$^1$H-NMR (CDCl$_3$) δ: 1.43(9H,s), 3.35–3.43(4H,m), 3.51–3.58(4H,m), 7.55(1H,dd,J=8.8,1.5 Hz), 7.90(1H,d,J= 8.8 Hz), 8.18(1H,d,J=1.5 Hz). MS (FAB) m/z: 418 [(M+H)$^+$, Cl$^{35}$], 420 [(M+H)$^+$, Cl$^{37}$].

Referential Example 149

1-tert-Butoxycarbonyl-4-[(6-chlorobenzothiazol-2-yl)sulfonyl]piperazine

In the same manner as in Referential Example 148, the title compound was obtained.

$^1$H-NMR (CDCl$_3$) δ: 1.43(9H,s), 3.35–3.43(4H,m), 3.50–3.58(4H,m), 7.59(1H,dd,J=8.8,2.0 Hz), 7.97(1H,d,J= 2.0 Hz), 8.10(1H,d,J=8.8 Hz) MS (FAB) m/z: 418 [(M+H)$^+$, Cl$^{35}$], 420 [(M+H)$^+$, Cl$^{37}$].

In the same manner as in Referential Example 35, compounds shown in Referential Examples 150 and 151 were synthesized, respectively.

Referential Example 150

1-[(5-Chlorobenzothiazol-2-yl)sulfonyl]piperazine hydrochloride $^1$H-NMR (DMSO-d$_6$) δ: 3.23(4H,br s), 3.56(4H,br s), 7.78(1H,dd,J=8.8,2.0 Hz), 8.39–8.43(2H,m). MS (FAB) m/z: 318 [(M+H)$^+$, Cl$^{35}$], 320 [(M+H)$^+$, Cl$^{37}$].

Referential Example 151

1-[(6-Chlorobenzothiazol-2-yl)sulfonyl]piperazine hydrochloride $^1$H-NMR (DMSO-d$_6$) δ: 3.21–3.27(4H,m), 3.52–3.57 (4H,m), 7.79(1H,dd,J=8.8,2.0 Hz), 8.28(1H,d,J=8.8 Hz), 8.53(1H,d,J=2.0 Hz). MS (FAB) m/z: 318 [(M+H)$^+$, Cl$^{35}$], 320 [(M+H)$^+$, Cl$^{37}$]. Elementary analysis for C$_{11}$H$_{12}$ClN$_3$O$_2$S$_2$.1.05HCl.0.5H$_2$O Calculated: C, 36.19; H, 3.88; Cl, 19.91; N, 11.51; S, 17.57. Found: C, 36.19; H, 4.10; Cl, 20.08; N, 11.50; S, 17.19.

In the same manner as in Referential Example 1, compounds shown in Referential Examples 152 to 155 were synthesized, respectively.

Referential Example 152

1-[(5-Chlorobenzo[b]furan-2-yl)sulfonyl]piperazine hydrochloride $^1$H-NMR (DMSO-d$_6$) δ: 3.20(4H,br), 3.45(4H,br), 7.62 (1H,d,J=8.8 Hz), 7.76(1H,s), 7.85(1H,d,J=8.8 Hz), 7.96(1H, s), 9.41(1H,br). MS (FAB) m/z: 301 [(M+H)$^+$, Cl$^{35}$], 303 [(M+H)$^+$, Cl$^{37}$]. Elementary analysis for Cl$_{12}$H$_{13}$ClN$_2$O$_3$S HCl.0.1H$_2$O Calculated: C, 42.51; H, 4.22; Cl, 20.91; N, 8.26; S, 9.46. Found: C, 42.38; H, 4.33; Cl, 20.92; N, 8.18; S, 9.58.

Referential Example 153

1-[(6-Chlorobenzo[b]furan-2-yl)sulfonyl]piperazine hydrochloride $^1$H-NMR (DMSO-d$_6$) δ: 3.20(4H,t,J=4.9 Hz), 3.42(4H,t, J=4.9 Hz), 7.51(1H,d,J=7.8 Hz), 7.82(1H,s), 7.89(1H,d,J= 7.8 Hz), 9.18(1H,br). MS (FAB) m/z: 301 [(M+H)$^+$, Cl$^{35}$], 303 [(M+H)$^+$, Cl$^{37}$]. Elementary analysis for C$_{12}$H$_{13}$ClN$_2$O$_3$S.HCl.0.5H$_2$O Calculated: C, 41.63; H, 4.37; Cl, 20.48; N, 8.09; S, 9.26. Found: C, 41.54; H, 4.32; Cl, 20.49; N, 7.90; S, 9.07.

Referential Example 154

1-[(5-Chlorobenzo[b]thien-2-yl)sulfonyl]piperazine hydrochloride $^1$H-NMR (DMSO-d$_6$) δ: 3.20–3.50(8H,m), 7.64(1H,dd, J=8.8,2.0 Hz), 8.12(1H,s), 8.20(1H,s), 8.23(1H,d,J=8.8 Hz), 9.22(2H,br s). MS (FAB) m/z: 317 [(M+H)$^+$, Cl$^{35}$], 319 [(M+H)$^+$, Cl$^{37}$]. Elementary analysis for Cl$_2$H$_{13}$ClN$_2$O$_2$S$_2$.HCl.1.6H$_2$O Calculated: C, 37.72; H, 4.54; Cl, 18.56; N, 7.33; S, 16.78. Found: C, 37.56; H, 4.67; Cl, 18.72; N, 7.17; S, 16.56.

Referential Example 155

1-[(6-Chlorobenzo[b]thien-2-yl)sulfonyl]piperazine hydrochloride $^1$H-NMR (DMSO-d$_6$) δ: 3.20–3.38(8H,m), 7.59(1H,dd, J=8.8,2.0 Hz), 8.10(1H,d,J=8.8 Hz), 8.16(1H,s), 8.36(1H,d, J=8.8 Hz), 9.29(2H,br s). MS (FAB) m/z: 317 [(M+H)$^+$, Cl$^{35}$], 319 [(M+H)$^+$, Cl$^{37}$]. Elementary analysis for C$_{12}$H$_{13}$ClN$_2$O$_2$S$_2$.HCl Calculated: C, 40.80; H, 3.99; Cl, 20.07; N, 7.93; S, 18.15. Found: C, 40.64; H, 4.04; Cl, 20.06; N, 7.90; S, 17.91.

Referential Example 156

1-[(5-Bromopyrimidin-2-yl)carbonyl]-4-[(6-chloronaphthalen-2-yl)sulfonyl]piperazine In the same manner as in Referential Example 12, the title compound was obtained.

$^1$H-NMR (CDCl$_3$) δ: 3.10–3.13(2H,m), 3.22–3.25(2H, m), 3.49–3.53(2H,m), 3.90–3.94(2H,m), 7.59(1H,dd,J=8.8, 2.0 Hz), 7.75(1H,dd,J=8.8,1.5 Hz), 7.91–7.95(3H,m), 8.30 (1H,br s), 8.82(2H,s). MS (FAB) m/z: 495 [(M+H)$^+$, Cl$^{35}$ and Br$^{79}$], 497 [(M+H)$^+$, Cl$^{35}$ and Br$^{81}$, Cl$^{37}$ and Br$^{79}$], 499 [(M+H)$^+$, Cl$^{37}$ and Br$^{81}$].

Referential Example 157

1-[(5-Bromopyrimidin-2-yl)carbonyl]-4-[(6-chlorobenzothien-2-yl)sulfonyl]piperazine $^1$H-NMR (CDCl$_3$) δ: 3.19–3.23(2H,m), 3.29–3.33(2H, m), 3.53–3.56(2H,m), 3.93–3.97(2H,m), 7.46(1H,dd,J=8.8, 1.5 Hz), 7.77(1H,s), 7.83(1H,d,J=8.8 Hz), 7.88(1H,d,J=1.5 Hz), 8.84(2H,s). MS (FAB) m/z: 501 [(M+H)$^+$, Cl$^{35}$ and Br$^{79}$], 503 [(M+H)$^+$, Cl$^{35}$ and Br81, Cl$^{37}$ and Br$^{79}$], 505 [(M+H)$^+$, Cl$^{37}$ and Br$^{81}$]. Elementary analysis for C$_{17}$H$_{14}$BrClN$_4$O$_3$S$_2$ Calculated: C, 40.69; H, 2.81; N, 11.17; S, 12.78. Found: C, 40.90; H, 2.87; N, 10.92; S, 12.87.

Referential Example 158

1-Benzyl-4-tert-butoxycarbonylpiperazine

In acetonitrile (80 ml), tert-butyl 1-piperazine carboxylate (2.50 g) was dissolved. Under ice cooling, benzyl bromide (1.59 ml) and triethylamine (1.87 ml) were added dropwise to the resulting solution, followed by stirring at room temperature for 90 minutes. After the solvent was distilled off under reduced pressure, distilled water and dichloromethane were added to the residue to separate the organic layer. The organic layer was washed with saturated aqueous NaCl solution and dried over anhydrous sodium sulfate. The residue obtained by distilling off the solvent under reduced pressure was purified by chromatography on a silica gel column (ethyl acetate:hexane=1:20 to 1:5), whereby the title compound (3.12 g, 84%) was obtained as colorless powder.

$^1$H-NMR (CDCl$_3$) δ: 1.45(9H,s), 2.38(4H,t,J=4.9 Hz), 3.42(4H,t,J=4.8 Hz), 3.51(2H,s), 7.25–7.29(1H,m), 7.30–7.33(4H,m). MS (EI) m/z: 276M$^+$.

Referential Example 159

1-Benzylpiperazine hydrochloride

To 1-benzyl-4-tert-butoxycarbonylpiperazine (3.12 g), saturated ethanol hydrochloride was added, followed by stirring for 90 minutes at room temperature. The solvent was distilled off under reduced pressure, followed by drying, whereby the title compound (2.73 g, 97%) was obtained as white powder.

$^1$H-NMR (DMSO-d$_6$) δ: 3.05–3.67(9H,m), 4.38(2H,br), 7.35–7.70(5H,m), 9.61(1H,br). MS (EI) m/z: 176M$^+$. Elementary analysis for C$_{11}$H$_{16}$N$_2$.2HCl.0.2H$_2$O Calculated: C, 52.27; H, 7.34; Cl, 28.05; N, 11.27. Found: C, 52.04; H, 7.36; Cl, 27.89; N, 11.24.

Referential Example 160

1-Benzyl-4-sulfamoylpiperazine

Chlorosulfonyl isocyanate (0.35 ml) was dissolved in dichloromethane (5 ml). Under ice cooling, tert-butanol (0.21 ml) was added dropwise to the resulting solution, followed by stirring for 30 minutes. After the reaction mixture was added dropwise to a solution of 1-benzylpiperazine dihydrochloride (0.25 g) in dichloromethane (20 ml) under ice cooling, triethylamine (0.28 ml) was added. The mixture was stirred for 30 minutes under ice cooling and then at room temperature for 1 hour. Distilled water and dichloromethane were added to separate the organic layer. The organic layer was dried over anhydrous sodium sulfate and distilled under reduced pressure to remove the solvent. The residue was purified by chromatography on a silica gel column (methanol:dichloromethane=1:50 to 1:25), whereby 1-benzyl-[4-(N-tert-butoxycarbonyl)sulfamoyl]piperazine was obtained as colorless powder. To the resulting powder, saturated solution of hydrochloride in ethanol was added and the mixture was stirred at room temperature for 1 hour. After the solvent was distilled off under reduced pressure, a saturated aqueous solution of sodium bicarbonate and dichloromethane were added to the residue to separate the organic layer. The resulting organic layer was dried over anhydrous sodium sulfate and distilled under reduced pressure to remove the solvent, whereby the title compound (0.26 g, quant.) was obtained as colorless powder.

$^1$H-NMR (CDCl$_3$) δ: 2.58(4H,t,J=4.9 Hz), 3.22(4H,t,J=4.9 Hz), 3.56(2H,s), 4.33(2H,br), 7.27–7.36(5H,m). MS (EI) m/z: 255M$^+$.

Referential Example 161

3,4-Bis(bromomethyl)-1-chlorobenzene

In acetonitrile (500 ml), 1-chloro-3,4-dimethylbenzene (20.0 ml) was dissolved and to the resulting solution, N-bromosuccinimide (53.0 g) and azoisobutyronitrile (1.20 g) were added, followed by heating under reflux for 1 hour. After cooling, the solvent was distilled off under reduced pressure and dichloromethane was then added to the residue. From the resulting mixture, the precipitate was filtered off. The filtrate was concentrated under reduced pressure. The residue was subjected to chromatography on a silica gel column (hexane), whereby the title compound (41.5 g, 93%) was obtained as a colorless oil.

$^1$H-NMR (CDCl$_3$) δ: 4.59(2H,s), 4.61(2H,s), 7.27–7.36 (3H,m). MS (EI) m/z: 295M$^+$.

Referential Example 162

1-Benzyl-4-[(5-chloroisoindol-2-yl)sulfonyl]piperazine

In ethanol (5 ml), 1-benzyl-4-sulfamoylpiperazine (251 mg) was dissolved. To the resulting solution, 3,4-bis(bromomethyl)-1-chlorobenzene (293 mg) and potassium carbonate (204 mg) were added, followed by heating under reflux for 3.5 hours. After cooling, the precipitate was filtered off. The filtrate was then distilled under reduced pressure and the residue was purified by chromatography on a silica gel column (dichloromethane~ethanol:dichloromethane=1:100), whereby the title compound (222 mg, 58%) was obtained.

$^1$H-NMR (CDCl$_3$) δ: 2.37–2.58(4H,m), 3.24–3.41(4H,m), 3.53(2H,s), 4.64(4H,m), 7.13–7.34(8H,m). MS (FAB) m/z: 392 [(M+H)$^+$, Cl$^{35}$], 394 (M+H)$^+$, Cl$^{37}$].

Referential Example 163

1-[(5-Chloroisoindol-2-yl)sulfonyl]piperazine

To a solution of 1-benzyl-4-[(5-chloroisoindol-2-yl)sulfonyl]piperazine (222 mg) in 1,2-dichloroethane (20 ml), 1-chloroethyl chloroformate (81 mg) was added under ice cooling. The resulting mixture was stirred for 15 minutes and then heated under reflux for 1 hour. After cooling, anhydrous methanol was added to the residue obtained by distilling off the solvent under reduced pressure. The mixture was heated under reflux for 11 hours. After cooling, the residue obtained by distilling off the solvent under reduced pressure was purified by chromatography on a silica gel column (ethanol:dichloromethane=1:50 to 1:10), whereby the title compound (120 mg, 70%) was obtained.

$^1$H-NMR (CDCl$_3$) δ: 2.96(4H,t,J=4.4 Hz), 3.09–3.22(1H, br), 3.30(4H,t,J=4.4 Hz), 4.65(4H,m), 7.14–7.35(3H,m). MS (FAB) m/z: 302 [(M+H)$^+$, Cl$^{35}$], 304 [(M+H)$^+$, Cl$^{37}$].

Referential Example 164

1-[(5-Bromopyrimidin-2-yl)carbonyl]-4-[(5-chloroisoindol-2-yl)sulfonyl]piperazine In the same manner as in Referential Example 12, the title compound was obtained.

$^1$H-NMR (CDCl$_3$) δ: 3.35(2H,t,J=4.9 Hz), 3.44(2H,J=4.9 Hz), 3.49(2H,t,J=4.9 Hz), 3.91(2H,t,J=4.9 Hz), 4.65–4.68(4H,m), 7.17(1H,d,J=8.3 Hz), 7.23(1H,s), 7.28 (1H,m), 8.88(2H,s). MS (EI) m/z: 486M$^+$.

Referential Example 165

2-(Furan-2-yl)-5-(pyridin-4-yl)pyrazine

At room temperature, 2-chloro-5-(furan-2-yl)pyrazine (N. Sato, J. Heterocyclic Chem., 19, 407(1982)) (1.00 g) and (pyridin-4-yl)boronic acid (1.09 g) were suspended in a mixed solvent of dimethoxyethane (50 ml) and methanol (50 ml), followed by the successive addition of tetrakis(triphenylphosphine)palladium (O) (640 mg) and cesium fluoride (5.55 g). The resulting mixture was heated under reflux for 16 hours. After cooling, the reaction mixture was concentrated. Dichloromethane and water were added to the concentrate to separate the organic layer. The organic layer was dried over anhydrous sodium sulfate, treated with activated carbon and filtered through Celite. After the filtrate was concentrated to about 5 ml, petroleum ether (50 ml) was added to the concentrate. Yellow crystalline powder thus precipitated was collected by filtration and dried, whereby the title compound (716 mg, 58%) was obtained.

$^1$H-NMR (CDCl$_3$) δ: 6.62(1H,dd,J=3.4,2.0 Hz), 7.23(1H, d,J=3.4 Hz), 7.65(1H,d,J=2.0 Hz), 7.94(2H,d,J=6.4 Hz), 8.77(2H,d,J=6.4 Hz), 9.03(1H,d,J=1.5 Hz), 9.07(1H,d,J=1.5 Hz). MS (FAB) m/z: 224 (M+H)$^+$.

Referential Example 166

5-(Pyridin-4-yl)pyrazine-2-carboxylic acid

At room temperature, potassium permanganate (700 mg) and trioctylmethylammonium chloride (one drop) were dissolved in a mixed solvent of water (20 ml) and benzene (20 ml). To the resulting solution, 2-(furan-2-yl)-5-(pyridin-4-yl)pyrazine (700 mg) was added in portions, followed by stirring at room temperature for 17 hours. After ethanol was added to the reaction mixture to decompose excess potassium permanganate, the solvent was distilled off. To the residue, water (100 ml) was added and the mixture was filtered through Celite. To the filtrate, 1N hydrochloric acid was added to adjust its pH to 6. The solvent was distilled off until the precipitation of colorless crystals. The colorless crystals were collected by filtration, whereby the title compound (491 mg, 79%) was obtained.

$^1$H-NMR (DMSO-d$_6$ with one drop of TEA) δ: 8.61(2H, d,J=5.9 Hz), 9.04(2H,d,J=5.9 Hz), 9.37(1H,s), 9.66(1H,s). MS (FAB) m/z: 202 (M+H)$^+$. Elementary analysis for C$_{10}$H$_7$N$_3$O$_2$.0.4H$_2$O Calculated: C, 57.64; H, 3.77; N, 20.16. Found: C, 57.77; H, 3.79; N, 20.33.

Referential Example 167

4-(3-Methylpyridin-4-yl)benzoic acid

In the same manner as in Referential Example 2, the title compound was obtained.

$^1$H-NMR (DMSO-d$_6$) δ: 2.41(3H,s), 7.68(2H,d,J=8.3 Hz), 7.93(1H,d,J=5.9 Hz), 8.12(2H,d,J=8.3 Hz), 8.85(1H,d, J=5.9 Hz), 8.95(1H,s).

Referential Example 168

4-Amidinobenzoic acid

In ethanol (250 ml), 4-cyanobenzoic acid (10 g) was suspended. Under ice cooling, a hydrochloric acid gas was introduced into the resulting suspension for 4 hours. After heating to room temperature, the reaction mixture was hermetically sealed and then allowed to stand for 18 hours. The reaction mixture was concentrated to dryness under reduced pressure. The residue was suspended in ethanol (250 ml) again, followed by the introduction of an ammonia gas for 4 hours under ice cooling for saturation. After heating to room temperature, the reaction mixture was hermetically sealed and allowed to stand for 3 days. To the residue obtained by distilling off the solvent under reduced pressure, dilute hydrochloric acid was added to make the residue acidic, followed by concentration. The residue was purified by chromatography through a synthetic adsorbent ("Diaion HP-20" (trade name); water~20% acetonitrile—water). The crude purified product so obtained was dissolved in 20% methanol—dichloromethane and the resulting solution was purified by chromatography on a silica gel column (20% methanol—dichloromethane). To the resulting fraction, solution of hydrochloride in ethanol was added and the mixture was concentrated. From the concentrate, colorless crystal powder was collected by filtration and dried, whereby ethyl 4-amidinobenzoate hydrochloride (5.25 g) was obtained as a crude purified product.

In 1N hydrochloric acid (100 ml), the resulting ethyl 4-amidinobenzoate hydrochloride (3.00 g) was dissolved at room temperature, followed by heating under reflux for 2 hours. The solvent was then distilled off under reduced pressure. Colorless crystalline powder so precipitated was collected by filtration and washed with a small amount of tetrahydrofuran, whereby the title compound (2.69 g, 94%) was obtained.

$^1$H-NMR (DMSO-$d_6$) δ: 7.91(2H,d,J=8.3 Hz), 8.12(2H,d,J=8.3 Hz), 9.21(2H,br s), 9.49(2H,br s), 13.50(1H,br s). MS (FAB) m/z: 165 (M+H)$^+$. Elementary analysis for $C_8H_8N_2O_2 \cdot HCl \cdot H_2O$ Calculated: C, 43.95; H, 5.07; Cl, 16.22; N, 12.81. Found: C, 44.08; H, 5.02; Cl, 16.00; N, 12.71.

Referential Example 169

Ethyl 4-(4,5-dihydroimidazol-2-yl)benzoate

In ethanol (250 ml), 4-cyanobenzoic acid (5.00 g) was suspended. A hydrochloric acid gas was blown into the resulting suspension for 4 hours under ice cooling, followed by heating to room temperature. The reaction mixture was hermetically sealed and allowed to stand for 18 hours, followed by concentration to dryness under reduced pressure. To the residue, diethyl ether was added. Coloress crystals thus precipitated were collected by filtration and dried, whereby ethyl 4-[1-(ethoxy)iminomethyl]benzoate hydrochloride (5.80 g, 66%) was obtained.

The resulting ethyl 4-[1-(ethoxy)iminomethyl]benzoate hydrochloride (2.00 g) was dissolved in ethanol (30 ml). Under ice cooling, ethylenediamine (0.52 ml) was added to the resulting solution, followed by heating to room temperature. The reaction mixture was stirred overnight. To the residue obtained by distilling off the solvent under reduced pressure, dilute hydrochloric acid was added to make it acidic, followed by concentration again. The residue was purified by chromatography through a synthetic adsorbent ("Diaion HP-20", trade name; water~50% acetonitrile-water). Solution of hydrochloride in ethanol was added to the resulting fraction and the mixture was concentrated. Colorless crystalline powder precipitated by the addition of tetrahydrofuran was collected by filtration and dried, whereby the title compound (1.63 g, 19%) was obtained.

$^1$H-NMR (DMSO-$d_6$) δ: 1.35(3H,t,J=7.3 Hz), 4.02(4H,s), 4.37(2H,q,J=7.3 Hz), 8.17(2H,d,J=8.8 Hz), 8.21(2H,d,J=8.8 Hz), 11.08(2H,br s). MS (FAB) m/z: 219 (M+H) +. Elementary analysis for $C_{12}H_{14}N_2O_2 \cdot HCl \cdot 0.2H_2O$ Calculated: C, 55.80; H, 6.01; Cl, 13.72; N, 10.84. Found: C, 55.81; H, 5.99; Cl, 13.93; N, 11.00.

Referential Example 170

5-(4,5-Dihydroimidazol-2-yl)benzoic acid hydrochloride

In the same manner as in Referential Example 8, a reaction was effected using the ethyl 4-(4,5-dihydroimidazol-2-yl)benzoate as a starting material, whereby the title compound was obtained.

$^1$H-NMR (DMSO-$d_6$) δ: 4.03(4H,s), 8.15(4H,s), 10.99 (2H,br s). MS (FAB) m/z: 191 (M+H)$^+$. Elementary analysis for $C_{10}H_{10}N_2O_2 \cdot HCl \cdot 1.2H_2O$ Calculated: C, 48.38; H, 5.44; Cl, 14.28; N, 11.28. Found: C, 48.37; H, 5.29; Cl, 14.64; N, 11.12.

Referential Example 171

4-(4-Metylphenyl)pyridine

In the same manner as in Referential Example 2, a reaction was effected, whereby the title compound was obtained.

$^1$H-NMR (CDCl$_3$) δ: 2.42(3H,s), 7.30(2H,d,J=8.3 Hz), 7.51(2H,d,J=5.9 Hz), 7.55(2H,d,J=8.3 Hz), 8.64(2H,d,J=5.9 Hz).

Referential Example 172

2-Amino-4-(4-methylphenyl)pyridine

Under an argon gas, 4-(4-methylphenyl)pyridine (2.74 g) was dissolved in N,N-dimethylaniline (10 ml), followed by the addition of sodium amide (1.40 g) at room temperature. After the resulting mixture was stirred at 110° C. for 2 days, the reaction mixture was cooled to room temperature. Brown powder precipitated by the addition of water was collected by filtration. The powder was further purified by chromatography on a silica gel column (ethyl acetate:toluene=1:1). After concentration of the resulting fraction, hexane was added and powder thus precipitated was collected by filtration and dried, whereby the title compound (1.40 g, 47%) was obtained.

$^1$H-NMR (CDCl$_3$) δ: 2.40(3H,s), 4.45(2H,br s), 6.69(1H, d,J=1.5 Hz), 6.88(1H,dd,J=5.4,1.5 Hz), 7.26(2H,d,J=8.3 Hz), 7.49(2H,d,J=8.3 Hz), 8.11(1H,d,J=5.4 Hz) MS (FAB) m/z: 185 (M+H)$^+$.

Referential Example 173

2-Diacetylamino-4-(4-methylphenyl)pyridine

2-Amino-4-(4-methylphenyl)pyridine (1.27 g) was dissolved in dichloromethane (50 ml). Under ice cooling, N,N-diisopropylethylamine (1.80 ml) and acetyl chloride (735 µl) were successively added dropwise to the resulting solution. After heating to room temperature, the reaction mixture was added again with N,N-diisopropylethylamine (0.90 ml) and acetyl chloride (800 µl). The mixture was stirred for 18 hours. Methanol was added to the reaction mixture. Dilute hydrochloric acid and ethyl acetate were then added to the residue obtained by distilling off the solvent in order to separate the organic layer. The organic layer was dried over anhydrous magnesium sulfate, followed by concentration. The residue was dissolved in methanol. Crystals precipitated by the addition of water were collected by filtration and dried, whereby the title compound (1.39 g, 75%) was obtained.

$^1$H-NMR (CDCl$_3$) δ: 2.33(6H,s), 2.42(3H,s), 7.31(2H,d, J=8.3 Hz), 7.43(1H,d,J=1.5 Hz), 7.53–7.59(3H,m), 8.61(1H, d,J=4.9 Hz). MS (FAB) m/z: 269 (M+H)$^+$. Elementary analysis for C$_{16}$H$_{16}$N$_2$O$_2$ Calculated: C, 71.62; H, 6.01; N, 10.44. Found: C, 71.28; H, 5.98; N, 10.19.

Referential Example 174

4-(2-Acetylaminopyridin-4-yl)benzoic acid

In water (4 ml), anhydrous magnesium sulfate (161 mg) was dissolved. To the resulting solution, the 2-diacetylamino-4-(4-methylphenyl)pyridine (108 mg) was suspended. Potassium permanganate (223 mg) was added to the resulting suspension, followed by heating under reflux for 2 hours. After removal of manganese dioxide, dilute hydrochloric acid and dichloromethane were added to the filtrate to separate the water layer. The water layer was concentrated to about 20 ml and the crystals thus precipitated were collected by filtration and dried, whereby the title compound (64 mg, 62%) was obtained.

$^1$H-NMR (DMSO-d$_6$) δ: 2.19(3H,s), 7.58(1H,d,J=5.9 Hz), 7.87(2H,d,J=8.3 Hz), 8.04(1H,s), 8.11(2H,d,J=8.3 Hz), 8.33(1H,s), 8.43(1H,d,J=5.9 Hz), 11.23(1H,br s). MS (FAB) m/z: 257 (M+H)$^+$.

Referential Example 175

Methyl 4-(2-aminopyridin-4-yl)benzoate

In the same manner as in Referential Example 9, a reaction was effected using the 4-(2-acetylaminopyridin-4-yl)benzoic acid as a starting material, whereby the title compound was obtained.

$^1$H-NMR (CDCl$_3$) δ: 3.95(3H,s), 4.53(2H,br s), 6.72(1H, d,J=1.5 Hz), 6.90(1H,dd,J=5.4,1.5 Hz), 7.65(2H,d,J=8.3 Hz), 8.12(2H,d,J=8.3 Hz), 8.16(1H,d,J=5.4 Hz). MS (FAB) m/z: 229 (M+H)$^+$. Elementary analysis for C$_{13}$H$_{12}$N$_2$O$_2$ Calculated: C, 68.41; H, 5.30; N, 12.27. Found: C, 68.30; H, 5.27; N, 12.36.

Referential Example 176

Methyl 4-[2-(N-tert-butoxycarbonylamino)pyridin-4-yl)benzoate

In the same manner as in Referential Example 10, the title compound was obtained.

$^1$H-NMR (DMSO-d$_6$) δ: 1.50(9H,s), 3.89(3H,s), 7.38(1H, dd,J=5.4,1.5 Hz), 7.86(2H,d,J=8.3 Hz), 8.10(2H,d,J=8.3 Hz), 8.14(1H,d,J=1.5 Hz), 8.35(1H,d,J=5.4 Hz), 9.89(1H,br s).

Referential Example 177

4-[2-(N-tert-butoxycarbonylamino)pyridin-4-yl) benzoic acid

In the same manner as in Referential Example 11, the title compound was obtained.

$^1$H-NMR (DMSO-d$_6$) δ: 1.49(9H,s), 7.38(1H,dd,J=5.4, 1.0 Hz), 7.83(2H,d,J=8.3 Hz), 8.07(2H,d,J=8.3 Hz), 8.12 (1H,d,J=1.0 Hz), 8.33(1H,d,J=5.4 Hz), 9.93(1H,br s), 13.07 (1H,br s).

Referential Example 178

1-[4-(2-Azidomethylpyridin-4-yl)benzoyl]-4-[(6-chloronaphthalen-2-yl)sulfonyl]piperazine In dichloromethane (10 ml), 1-[(6-chloronaphthalen-2-yl) sulfonyl]-4-[4-(2-hydroxymethylpyridin-4-yl)benzoyl] piperazine (300 mg) was dissolved. To the resulting solution, triphenylphosphine (301 mg) and carbon tetrabromide (572 mg) were added, followed by stirring at room temperature for 5 minutes. An aqueous solution of sodium bicarbonate and dichloromethane were added to separate the organic layer. After the organic layer was dried over anhydrous sodium sulfate, N,N-dimethylformamide (10 ml) was added and only dichloromethane was distilled off. To the N,N-dimethylformamide solution containing the bromo-compound, sodium azide (215 mg) was added, followed by stirring at an external temperature of about 100° C. for 90 minutes. The reaction mixture was distilled under reduced pressure to remove the solvent. Dichloromethane and water were added to the residue to separate the organic layer. The organic layer was dried over anhydrous sodium sulfate and distilled under reduced pressure to remove the solvent. The residue was purified by chromatography on a silica gel column (dichloromethane~2% methanol—dichloromethane), whereby the title compound (159 mg, 51%) was obtained.

$^1$H-NMR (CDCl$_3$) δ: 3.16(4H,br), 3.30–4.10(4H,br), 4.57 (2H,s), 7.40–7.45(3H,m), 7.52(1H,s), 7.60(1H,dd,J=8.8 and 2.0 Hz), 7.64(2H,d,J=8.3 Hz), 7.76(1H,dd,J=8.3 and 1.5 Hz), 7.90–7.96(3H,m), 8.31(1H,d,J=1.5 Hz), 8.65(1H,d,J= 5.4 Hz). MS (FAB) m/z: 547 [(M+H)$^+$, Cl$^{35}$], 549 [(M+H)$^+$, Cl$^{37}$].

Referential Example 179

Methyl 4-(2-methylpyridin-4-yl)benzoate hydrochloride

In methanol (100 ml), 4-(2-methylpyridin-4-yl)benzoic acid hydrochloride (5.00 g) was dissolved. To the resulting solution, thionyl chloride (1.73 ml) was added dropwise, followed by heating under reflux for 3.5 hours. The reaction mixture was distilled to remove the solvent and pale brown crystals thus precipitated were washed with ethyl acetate, whereby the title compound (4.70 g, 89%) was obtained.

Referential Example 180

Methyl 4-(2-bromomethylpyridin-4-yl)benzoate

In a mixed solution of carbon tetrachloride and an aqueous solution of sodium bicarbonate, the methyl 4-(2-methylpyridin-4-yl)benzoate hydrochloride (100 mg) was dissolved. The organic layer separated was dried over anhydrous sodium sulfate. After the insoluble matter was filtered off, N-bromosuccinic imide (68 mg) and 2,2'-azoisobutylonitrile (6 mg) were added to the filtrate, followed by heating under reflux for 1 hour. The reaction mixture was diluted with dichloromethane, washed with water and then dried over anhydrous sodium sulfate. The residue obtained by concentration under reduced pressure was purified by chromatography on a silica gel column (hexane:ethyl acetate=4:1), whereby the title compound (41 mg, 35%) was obtained.

$^1$H-NMR (CDCl$_3$) δ: 3.96(3H,s), 4.63(2H,s), 7.46(1H,dd, J=4.9,1.5 Hz), 7.68(1H,d,J=1.5 Hz), 7.71(2H,d,J=8.3 Hz), 8.16(2H,d,J=8.3 Hz), 8.69(1H,d,J=4.9 Hz). Elementary analysis for C$_{14}$H$_{12}$BrNO$_2$ Calculated: C, 54.92; H, 3.95; Br, 26.10; N, 4.58. Found: C, 54.95; H, 3.96; Br, 25.85; N, 4.33.

Referential Example 181

Methyl 4-(2-cyanomethylpyridin-4-yl)benzoate

In the same manner as in Referential Example 56, the title compound was obtained.

¹H-NMR (CDCl₃) δ: 3.97(3H,s), 4.03(2H,s), 7.51(1H,d, J=5.4 Hz), 7.67(1H,s), 7.71(2H,d,J=8.3 Hz), 8.17(2H,d,J=8.3 Hz), 8.67(1H,d,J=5.4 Hz). Elementary analysis for $C_{15}H_{12}N_2O_2$ Calculated: C, 71.42; H, 4.79; N, 11.10. Found: C, 71.13; H, 4.82; N, 11.05.

Referential Example 182

Methyl 4-[2-(2-aminoethyl)pyridin-4-yl]benzoate dihydrochloride

In methanol (5 ml), the methyl 4-(2-cyanomethylpyridin-4-yl)benzoate (190 mg) was dissolved. The resulting solution was subjected to catalytic reduction by the addition of 10% palladium-carbon (190 mg) and concentrated hydrochloric acid (5 drops) at room temperature under normal pressure for 24 hours. After the removal of the catalyst by filtration, the filtrate was concentrated under reduced pressure. Ethyl acetate was added to the concentrate. Pale yellow crystals thus precipitate were collected by filtration and then dried, whereby the title compound (141 mg, 57%) was obtained.

¹H-NMR (DMSO-d₆) δ: 3.21–3.39(4H,m), 3.90(3H,s), 7.90–8.18(8H,m), 8.76(1H,d,J=5.4 Hz). MS (FAB) m/z: 257 (M+H)⁺.

Referential Example 183

Methyl 4-[2-[2-(tert-butoxycarbonylamino)ethyl]pyridin-4-yl]benzoate

In the same manner as in Referential Example 10, the title compound was obtained.

¹H-NMR (CDCl₃) δ: 1.43(9H,s), 3.07(2H,t,J=6.4 Hz), 3.60(2H,q,J=6.4 Hz), 3.96(3H,s), 5.14(1H,br s), 7.39(1H,dd, J=5.4 and 1.5 Hz), 7.41(1H,br s), 7.70(2H,d,J=8.3 Hz), 8.15(2H,d,J=8.3 Hz), 8.62(1H,d,J=5.4 Hz). MS (FAB) m/z: 357 (M+H)⁺.

Referential Example 184

1-[(6-Chloronaphthalen-2-yl)sulfonyl]-6-methoxycarbonyl -1,2,3,4-tetrahydropyrazine At room temperature, 2-methoxycarbonylpyrazine (1.00 g) was dissolved in methanol. The resulting solution was subjected to catalytic reduction by the addition of 10% palladium-carbon (100 mg) for 2 hours under normal pressure. After the removal of the catalyst by filtration, the solvent was distilled off under reduced pressure. The residue was purified by chromatography on a silica gel column (5% methanol-dichloromethane), whereby 6-methoxycarbonyl-1,2,3,4-tetrahydropyrazine (880 mg, 86%) was obtained as a yellow oil.

The resulting 6-methoxycarbonyl-1,2,3,4-tetrahydropyrazine (440 mg) was dissolved in dichloromethane (5 ml), followed by the addition of N,N-diisopropylethylamine (594 pl) and 6-(chloronaphthalen-2-yl)sulfonyl chloride (810 mg). The resulting mixture was stirred at room temperature for 1 hour. The reaction mixture was washed with an aqueous solution of sodium bicarbonate, dried over anhydrous sodium sulfate and then concentrated. The residue thus obtained was purified by chromatography on a silica gel column (2% methanol—dichloromethane), whereby the title compound (279 mg, 25%) was obtained as a pale yellow oil.

¹H-NMR (CDCl₃) δ: 3.32(4H,s), 3.71(3H,s), 4.68(1H,br s), 7.43(1H,d,J=6.8 Hz), 7.55(1H,dd,J=8.8,2.0 Hz), 7.86–7.94(3H,m), 8.19(1H,dd,J=8.8,2.0 Hz), 8.54(1H,br s). MS (FAB) m/z: 367 [(M+H)⁺, Cl³⁵], 369 [(M+H)⁺, Cl³⁷]. Elementary analysis for $C_{16}H_{15}ClN_2O_4S$ Calculated: C, 52.39; H, 4.12; N, 7.64. Found: C, 52.31; H, 4.21; N, 7.55.

Referential Example 185

1-(4-Bromobenzoyl)-6-methoxycarbonyl-1,2,3,4-tetrahydropyrazine

In the same manner as in Referential Example 184, 6-methoxycarbonyl-1,2,3,4-tetrahydropyrazine was obtained, followed by reaction with 4-bromobenzoyl chloride, whereby the title compound was obtained.

¹H-NMR (CDCl₃) δ: 3.20–3.70(7H,m), 4.71(1H,br s), 7.16(1H,d,J=6.4 Hz), 7.48(4H,s). MS (FAB) m/z: 325 [(M+H)⁺, Br⁷⁹], 327 [(M+H)⁺, Br⁸¹].

Referential Example 186

4-(4-Bromobenzoyl)-1-[(6-chloronaphthalen-2-yl)sulfonyl-5-methoxycarbonyl-1,2,3,4-tetrahydropyrazine In the same manner as in Example A-165, the title compound was obtained.

¹H-NMR (CDCl₃) δ: 3.40–3.90(7H,m), 7.33(2H,d,J=8.3 Hz), 7.48(2H,d,J=8.3 Hz), 7.60–7.66(2H,m), 7.79(1H,dd,J=8.8,2.0 Hz), 7.92–7.99(3H,m), 8.43(1H,br s). MS (FAB) m/z: 549 [(M+H)⁺, Br⁷⁹], 551 [(M+H)⁺, Br⁸¹]. Elementary analysis for $C_{23}H_{18}BrClN_2O_5S$ Calculated: C, 50.24; H, 3.30; N, 5.10; S, 5.83. Found: C, 50.34; H, 3.37; N, 5.05; S, 5.81.

Referential Example 187

4-[3-(Aminomethyl)phenyl]benzoic acid hydrochloride

In the same manner as in Referential Example 2, the title compound was obtained.

¹H-NMR (DMSO-d₆) δ: 4.11(2H,s), 7.49–7.58(2H,m), 7.76(1H,d,J=6.8 Hz), 7.83(2H,d,J=8.8 Hz), 7.92(1H,br s), 8.05(2H,d, J=8.3 Hz).

Referential Example 188

4-[3-[(tert-Butoxycarbonylamino)methyl]phenyl]benzoic acid

In the same manner as in Referential Example 10, the title compound was obtained.

¹H-NMR (CDCl₃) δ: 1.48(9H,s), 4.41(2H,d,J=5.4 Hz), 4.94(1H,br s), 7.28–7.37(1H,m), 7.44(1H,t,J=7.3 Hz), 7.50–7.60(2H,m), 7.68(2H,d,J=8.3 Hz), 8.10–8.23(2H,m).

Referential Example 189

Ethyl 2,5-dihydro-5-oxo-3-(pyridin-4-yl)-1,2,4-triazine-6-carboxylate

In ethanol (20 ml), 4-pyridinecarboxyamidrazone (1.48 g) was dissolved. To the resulting solution, diethyl ketomalonate (1.65 ml) was added dropwise at room temperature, followed by stirring for 13 hours. After heating under reflux for 4 hours, the reaction mixture was cooled. Yellow crystals thus precipitated were collected by filtration and dried, whereby the title compound (1.50 g, 56%) was obtained.

¹H-NMR (DMSO-d₆) δ: 1.31(3H,t,J=7.3 Hz), 4.36(2H,q, J=7.3 Hz), 7.98(2H,d,J=6.3 Hz), 8.86(2H,d,J=6.3 Hz). MS (FAB) m/z: 247 (M+H)+. Elementary analysis for C$_{11}$H$_{10}$N$_4$O$_3$.0.2H$_2$O Calculated: C, 52.88; H, 4.20; N, 22.43. Found: C, 52.78; H, 4.36; N, 22.66.

Referential Example 190

2,5-Dihydro-5-oxo-3-(pyridin-4-yl)-1,2,4-triazine-6-carboxylic acid

In the same manner as in Referential Example 11, the title compound was obtained.

$^1$H-NMR (DMSO-d$_6$ (containing a small amount of trifluoroacetic acid)) δ: 8.31(2H,d,J=6.4 Hz), 8.86(2H,d,J=6.4 Hz). MS (FAB) m/z: 218 (M+H)+. Elementary analysis for C$_9$H$_6$N$_4$O$_3$.0.2H$_2$O Calculated: C, 48.74; H, 2.91; N, 25.26. Found: C, 48.58; H, 2.87; N, 25.21.

Referential Example 191

2,6-Bis(methoxycarbonylmethyl)-1,4-dibenzylpiperazine

In a shield tube, bis(3-methoxycarbonyl-2-propylenyl)benzylamine (104 mg) and benzylamine (60.0 pl) were dissolved in methanol (5 ml). After the tube was hermetically sealed, the resulting solution was stirred under heat at an external temperature of about 100 to 110° C. for 63 hours. The solvent was then distilled off under reduced pressure. The residue was purified by chromatography on a silica gel column (n-hexane:ethyl acetate=3:1), whereby the title compound (123 mg, 88%) was obtained as a yellow oil.

$^1$H-NMR (CDCl$_3$) δ: 2.25–2.60(8H,each m), 3.15–3.85 (12H,m), 7.15–7.30(10H,m). MS (FAB) m/z: 411 (M+H)+.

Referential Example 192 cis-2,6-Bis(methoxycarbonylmethyl)-4-[(6-chloronaphthalen-2-yl)sulfonyl]piperazine trans-2,6-Bis(methoxycarbonylmethyl)-4-[(6-chloronaphthalen-2-yl)sulfonyl]piperazine In methanol (70 ml) and hydrochloric acid (570 μl), 2,6-bis(methoxycarbonylmethyl)-1,4-dibenzylpiperazine (1.33 g) was dissolved. To the resulting solution, palladium hydroxide (149 mg) was added, followed by catalytic hydrogenation at room temperature for 4 hours. After the removal of the catalyst by filtration, the residue was distilled under reduced pressure to remove the solvent. Dichloromethane (70 ml) and N,N-diisopropylethylamine (2.70 ml) were added to the resulting residue to dissolve the latter in the former, followed by the addition of (6-chloronaphthalen-2-yl)sulfonyl chloride (495 mg). The mixture was stirred for 3 hours under stirring. To the reaction mixture, (6-chloronaphthalen-2-yl)sulfonyl chloride (200 mg) and N,N-diisopropylethylamine (180 μl) were added. The resulting mixture was stirred for 12.5 hours, while gradually heated to room temperature from an external temperature of about 0° C. Since the reaction was not completed, (6-chloronaphthalen-2-yl)sulfonyl chloride (101 mg) and N,N-diisopropylethylamine (90 μl) were added further and the mixture was stirred for 4.5 hours while heated gradually to room temperature from an external temperature of about 0° C. The residue obtained by distilling off the solvent under reduced pressure was purified by chromatography on a silica gel column (5% methanol—dichloromethane, n-hexane:ethyl acetate=1:2), whereby the title compounds, cis-form (226 mg, 15%) and trans-form (1.07 g, 73%), were obtained, respectively, as pale yellow amorphous powder.

cis-2,6-Bis(methoxycarbonylmethyl)-4-[(6-chloronaphthalen -2-yl)sulfonyl]piperazine $^1$H-NMR (CDCl$_3$) δ: 2.00–2.10(2H,m), 2.20–2.30(2H, m), 2.35–2.45(2H,m), 2.85(1H,br), 3.20–3.30(2H,m), 3.69 (6H,s), 3.70–3.80(2H,m), 7.50–7.60(1H,m), 7.70–7.80(1H, m), 7.85–7.95(3H,m), 8.30(1H,s).

trans-2,6-Bis(methoxycarbonylmethyl)-4-[(6-chloronaphthalen-2-yl)sulfonyl]piperazine $^1$H-NMR (CDCl$_3$) δ: 2.40–2.60(5H,m), 2.80–2.90(2H, m), 3.10–3.20(2H,m), 3.45–3.55(2H,m), 3.69(6H,s), 7.50–7.60(1H,m), 7.70–7.80(1H,m), 7.85–7.95(3H,m), 8.29 (1H,s). MS (FAB) m/z: 455 [(M+H)+, Cl$^{35}$], 457 [(M+H)+, Cl$^{37}$].

Referential Example 193 trans-2,6-Bis(methoxycarbonylmethyl)-1-(4-bromobenzoyl)-4-[(6-chloronaphthalen-2-yl)sulfonyl]piperazine In dichloromethane (8 ml), the trans-2,6-bis(methoxycarbonylmethyl)-4-[(6-chloronaphthalen-2-yl)sulfonyl]piperazine (79.7 mg) was dissolved. Under ice cooling, N,N-diisopropylethylamine (68.0 μl) and a solution of 4-bromobenzoyl chloride (51.0 mg) in dichloromethane (2 ml) were added to the resulting solution, followed by stirring at room temperature for 5.5 hours. Water was added to the reaction mixture to separate the organic layer. The organic layer was washed with saturate aqueous NaCl solution, dried over anhydrous sodium sulfate and distilled under reduced pressure to remove the solvent. The residue was purified by chromatography on a silica gel column (n-hexane:ethyl acetate=1:1), whereby the title compound (113 mg, 98%) was obtained as pale yellow amorphous powder.

$^1$H-NMR (CDCl$_3$) δ: 2.80–2.90(4H,m), 3.20–3.40(4H, m), 3.63(6H,s), 4.20–4.30(2H,m), 7.23(2H,d,J=8.3 Hz), 7.50(2H,d,J=8.3 Hz), 7.55–7.65(1H,m), 7.70–7.80(1H,m), 7.90–7.95(3H,m), 8.30(1H,s). MS (FAB) m/z: 637 [(M+H)+, Br$^{79}$, Cl$^{35}$], 639 [(M+H)+, Br$^{79}$, Cl$^{37}$ and Br$^{81}$, Cl$^{35}$], 641 [(M+H)+, Br$^{81}$, Cl$^{37}$].

Referential Example 194 cis-2,6-Bis(methoxycarbonylmethyl)-1-(4-bromobenzoyl)-4-[(6-chloronaphthalen-2-yl)sulfonyl]piperazine In the same manner as in Referential Example 193, the title compound was obtained.

$^1$H-NMR (CDCl$_3$) δ: 2.40–2.75(4H,m), 2.80–3.20(2H, m), 3.55–4.00(2H,m), 3.68(6H,s), 4.20–4.40(1H,m), 5.00–5.20(1H,m), 7.10–7.15(2H,m), 7.45–7.55(2H,m), 7.55–7.65(1H,m), 7.70–7.80(1H,m), 7.90–7.95(3H,m), 8.30 (1H,s). MS (FAB) m/z: 637 [(M+H)+, Br$^{79}$, Cl$^{35}$], 639 [(M+H)+, Br79, Cl$^{37}$ and Br$^{81}$, Cl$^{35}$], 641 [(M+H)+, Br$^{81}$, Cl$^{37}$].

Referential Example 195 trans-2,6-Bis(carbamoylmethyl) -1-(4-bromobenzoyl)-4-[(6-chloronaphthalen-2-yl)sulfonyl]piperazine In the same manner as in Example A-35, the title compound was obtained using trans-2,6-bis(methoxycarbonylmethyl)-1-(4-bromobenzoyl)-4-[(6-chloronaphthalen-2-yl)sulfonyl]piperazine as a starting material.

¹H-NMR (CDCl₃) δ: 2.5–2.65(2H,m), 3.10–3.30(4H,m), 3.40–3.50(2H,m), 4.20–4.30(2H,m), 6.34(2H,broad s), 6.59 (2H,br s), 7.14(2H,d,J=8.3 Hz), 7.31(2H,d,J=8.3 Hz), 7.50–7.60(1H,m), 7.65–7.75(1H,m), 7.85–7.95(3H,m), 8.26 (1H,s).

Referential Example 196

(2-Methylpyridin-4-yl) tributyltin

Under an argon stream, diethyl ether (100 ml) was cooled to −70° C., followed by the dropwise addition of an n-butyl lithium-hexane solution (1.52M, 14.5 ml). To the reaction mixture, a diethyl ether solution (100 ml) containing the free form of 4-bromo-2-methylpyridine was added dropwise over 15 minutes, followed by the dropwise addition of a tetrahydrofuran solution (10 ml) containing tributyltin chloride (5.40 ml) slowly. After stirring at −70° C. for 30 minutes, the reaction mixture was heated to room temperature and stirring was conducted for 1.5 hours. Water and aqueous ammonia were added to the reaction mixture and the reaction mixture was separated using diethyl ether. The organic layer was dried over anhydrous magnesium sulfate, the filtrate was concentrated and the residue was purified by chromatography on a silica gel column (hexane:ethyl acetate=29:1→19:1), whereby the title compound (3.63 g, colorless oil substance) was obtained.

¹H-NMR (CDCl₃) δ: 0.89(9H,t,J=7.3 Hz), 0.99–1.17(6H, m), 1.22–1.41(6H,m), 1.50–1.65(6H,m), 2.52(3H,s), 7.05–7.21(1H,m), 7.22(1H,s), 7.34–8.40(1H,m). MS (FAB) m/z: 382[(M+H)⁺, Sn¹¹⁸], 384[(M+H)⁺, Sn¹²⁰].

Preparation of the free form of 4-bromo-2-methylpyridine

By using an aqueous solution of sodium bicarbonate and diethyl ether, 4-bromo-2-methylpyridine hydrochloride (4.17 g) was separated. The organic layer was dried over anhydrous magnesium sulfate and concentrated. Benzene was added to the concentrate, followed by concentration again. The residue was dissolved in diethyl ether (100 ml) and the resulting solution was stored a diethyl ether solution.

Referential Example 197

(3-Fluoropyridin-4-yl)tributyltin

Under an argon stream, a solution of diisopropylamine (7.03 ml) in tetrahydrofuran (100 ml) was cooled to an internal temperature of −20° C., followed by the dropwise addition of an n-butyl lithium-hexane solution (1.52M, 32.9 ml). After stirring at 0° C. for 1 hour, the reaction mixture was cooled to −70° C. A solution of 3-fluoropyridne (4.3 ml) in tetrahydrofuran (25 ml) was added dropwise over 30 minutes. The reaction mixture was stirred at −70° C. for 5 hours. A solution of tributyltin chloride (13.5 ml) in tetrahydrofuran (25 ml) was added dropwise slowly and the reaction mixture was stirred for 2.5 hours. The reaction mixture was heated to room temperature and then, separated using diethyl ether and water. The organic layer was dried over anhydrous magnesium sulfate, the filtrate was concentrated and purified by chromatography on a silica gel column (hexane:ethyl acetate=19:1), whereby the title compound (colorless oil, 18.17 g) was obtained.

¹H-NMR (CDCl₃) δ0.89(9H,t,J=7.3 Hz), 1.06–1.27(6H, m), 1.28–1.40(6H,m), 1.43–1.70(6H,m), 7.25–7.42(1H,m), 8.30–8.40(2H,m). MS (FAB) m/z 386[(M+H)⁺, Sn¹¹⁸], 388 [(M+H)⁺, Sn¹²⁰].

In the same manner as in Referential Example 196, compounds shown in Referential Examples 198 to 199 were synthesized.

Referential Example 198

(2,6-Dimethylpyridin-4-yl)tributyltin

¹H-NMR (CDCl₃) δ0.89(9H,t,J=7.3 Hz), 0.95–1.15(6H, m), 1.26–1.38(6H,m), 1.43–1.65(6H,m), 2.49(6H,s), 6.97–7.07(2H,m). MS (FAB) m/z 396[(M+H)⁺, Sn¹¹⁸], 398 [(M+H)⁺, Sn¹²⁰].

Referential Example 199

(2,5-Dimethylpyridin-4-yl)tributyltin

¹H-NMR (CDCl₃) δ0.89(9H,t,J=7.3 Hz), 0.95–1.20(6H, m), 1.21–1.40(6H,m), 1.41–1.65(6H,m), 2.30(3H,s), 2.48 (3H,s), 7.13(1H,s), 8.24(1H,s). MS (FAB) m/z 396[(M+H)⁺, Sn¹¹⁸], 398[(M+H)⁺, Sn¹²⁰].

Referential Example 200

2,3-Dimethylpyridine N-oxide

In methylene chloride (200 ml) was dissolved 2,3-dimethylpyridine (9.50 g) and the resulting solution was. cooled to 0° C. Metachloroperbenzoic acid (21.9 g) was added to the reaction mixture, followed by heating to room temperature. Stirring was conducted for 3 days. An aqueous solution of sodium sulfite was added and the resulting mixture was separated using methylene chloride (200 ml). The organic layer was dried over anhydrous magnesium sulfate, the filtrate was concentrated and the concentrate was purified by chromatography on a silica gel column (5% methanol—methylene chloride). Petroleum ether was added to the residue. Colorless powder so precipitated was collected by filtration, followed by drying, whereby the title compound (5.47 g) was obtained.

¹H-NMR (CDCl₃) δ2.35(3H,s), 2.51(3H,s), 7.00–7.08 (2H,m), 8.17(1H,d,J=6.3 Hz) MS (FAB) m/z 124(M+H)⁺.

Referential Example 201

2,3-Dimethyl-4-nitropyridine N-oxide

In a mixed solvent of concentrated sulfuric acid (10 ml) and fuming nitric aid (10 ml) was dissolved 2,3-dimethylpyridine N-oxide (3.73 g) at 0° C. The resulting solution was stirred at 75° C. for 1.5 hours and at 100° C. for 15 minutes. The reaction mixture was charged in ice water, followed by neutralization with an aqueous solution of sodium hydroxide. The neutralized solution was separated using methylene chloride. The organic layer was dried over anhydrous magnesium sulfate and the filtrate was concentrated. Methylene chloride (1 ml) and diethyl ether (100 ml) were added to the residue. Pale yellow powder thus precipitated was collected by filtration and dried, whereby the title compound (3.31 g) was obtained.

¹H-NMR (CDCl₃) δ2.57 (3H,s), 2.58(3H,s), 7.71(1H,d, J=7.3 Hz), 8.17(1H,d,J=7.3 Hz). MS (FAB) m/z 169(M+ H)⁺.

Referential Example 202

4-Bromo-2,3-dimethylpyridine

To 2,3-Dimethyl-4-nitropyridine N-oxide (3.00 g) which had been cooled to 0° C., added was acetyl bromide (18.0 ml), followed by stirring at 50° C. for 20 minutes and then at 75° C. for 15 minutes. The reaction mixture was charged in ice water and neutralized with an aqueous solution of ammonium carbonate. The neutralized solution was separated using methylene chloride. The organic layer was dried over anhydrous sodium sulfate and the filtrate was concentrated, whereby a crudely purified product of 4-bromo-2,3-dimethylpyridine N-oxide was obtained.

The resulting product was dissolved in chloroform (50 ml), followed by cooling to 0° C. Phosphorus tribromide (5.16 ml) was added to the reaction mixture and the resulting mixture was stirred at room temperature for 30 minutes. The reaction mixture was charged in ice water and neutralized with an aqueous solution of sodium bicarbonate. Methylene chloride was added to separate the neutralized solution. The organic layer was dried over anhydrous sodium sulfate, the filtrate was concentrated and the concentrate was purified by chromatography on a silica gel column (hexane:ethyl acetate=19:1), whereby the title compound (1.90 g, 57%, pale yellow oil) was obtained.

$^1$H-NMR (CDCl$_3$) δ2.40(3H,s), 2.59(3H,s), 7.34(1H,d,J= 5.4 Hz), 8.09(1H,d,J=5.4 Hz). MS (EI) m/z 185 (M$^+$, Br$^{79}$), 187 (M$^+$, Br$^{81}$).

Referential Example 203

(2,3-Dimethylpyridin-4-yl)tributyltin

In the same manner as in Referential Example 196, the title compound was obtained.

$^1$H-NMR (CDCl$_3$) δ0.88(9H,t,J=7.3 Hz), 1.01–1.18(6H, m), 1.27–1.37(6H,m), 1.41–1.61(6H,m), 2.31(3H,s), 2.50 (3H,s), 7.07–7.20(1H,m), 8.19–8.24(1H,m). MS (FAB) m/z 396[(M+H)$^+$, Sn$^{118}$], 398[(M+H)$^+$, Sn$^{120}$].

Referential Example 204

3,5-Dimethylpyridine N-oxide

In the same manner as in Referential Example 200, the title compound was obtained.

$^1$H-NMR (CDCl$_3$) δ: 2.28(6H,s), 6.93(1H,s), 7.92(2H,s) MS (FAB) m/z: 124 (M+H)$^+$.

Referential Example 205

3,5-Dimethyl-4-nitropyridine N-oxide

In the same manner as in Referential Example 201, the title compound was obtained.

$^1$H-NMR (CDCl$_3$) δ: 2.32(6H,s), 7.99(2H,s) MS (FAB) m/z: 169 (M+H)$^+$.

Referential Example 206

4-Bromo-3,5-dimethylpyridine

In the same manner as in Referential Example 202, the title compound was obtained.

$^1$H-NMR (CDCl$_3$) δ: 2.38(6H,s), 8.23(2H,s) MS (EI) m/z: 185 (M$^+$, Br$^{79}$), 187 (M$^+$, Br$^{81}$)

In the same manner as in Referential Example 196, the compounds shown in Referential Examples 207 to 211 were synthesized.

Referential Example 207

(3,5-Dimethylpyridin-4-yl)tributyltin $^1$H-NMR (CDCl$_3$) δ: 0.88(9H,t,J=7.3 Hz), 1.04–1.21(6H, m), 1.28–1.37(6H,m), 1.41–1.59(6H,m), 2.34(6H,s), 8.13–8.18(2H,m). MS (FAB) m/z: 396 [(M+H)$^+$, Sn$^{118}$], 398[(M+H)$^+$, Sn$^{120}$].

Referential Example 208

(6-Methylpyridin-2-yl)tributyltin $^1$H-NMR (CDCl$_3$) δ: 0.88(9H,t,J=7.3 Hz), 1.01–1.18(6H, m), 1.26–1.37(6H,m). 1.43–1.63(6H,m), 2.54(3H,s), 6.95 (1H,d,J=7.3 Hz), 7.18(1H,d,J=7.3 Hz), 7.36(1H,t,J=7.3 Hz). MS (FAB) m/z: 382[(M+H)$^+$, Sn$^{118}$], 384[(M+H)$^+$, Sn$^{120}$].

Referential Example 209

(3-Methylpyridin-4-yl)tributyltin $^1$H-NMR (CDCl$_3$) δ: 0.89(9H,t,J=7.3 Hz), 1.02–1.20(6H, m), 1.27–1.37(6H,m), 1.42–1.62(6H,m), 2.35(3H,s), 7.22–7.34(1H,m), 8.28–8.38(2H,m). MS (FAB) m/z: 382 [(M+H)$^+$, Sn$^{118}$], 384 [(M+H)$^+$, Sn$^{120}$].

Referential Example 210

(5-Methylpyridin-2-yl)tributyltin $^1$H-NMR (CDCl$_3$) δ: 0.88(9H,t,J=7.3 Hz), 1.02–1.19(6H, m), 1.27–1.37(6H,m), 1.43–1.61(6H,m), 2.29(3H,s), 7.27–7.33(2H,m), 7.59(1H,s). MS (FAB) m/z: 382 [(M+H)$^+$, Sn$^{118}$], 384 [(M+H)$^+$, Sn$^{120}$].

Referential Example 211

(3-Methylpyridin-2-yl)tributyltin $^1$H-NMR (CDCl$_3$) δ: 0.87(9H,t,J=7.3 Hz), 1.05–1.23(6H, m), 1.27–1.38(6H,m), 1.46–1.60(6H,m), 2.36(3H,s), 7.02 (1H,dd,J=7.8 and 4.9 Hz), 7.33(1H,d,J=7.8 Hz), 8.54(1H,d, J=4.9 Hz). MS (FAB) m/z: 382 [(M+H)$^+$, Sn$^{118}$], 384 [(M+H), Sn$^{120}$].

Referential Example 212

1-[(6-Chlorobenzo[b]thien-2-yl)sulfonyl]piperidin-4-one

In N,N-dimethylformamide (10 ml) was suspended piperidin-4-one (monohydrochloric acid monohydrate, 1.54 g), followed by the addition of diisopropylethylamine (3.48 ml) and 6-chlorobenzo[b]thiophene-2-sulfonyl chloride (2.68 g). The resulting mixture was stirred at room temperature for 3 days. The reaction mixture was concentrated under reduced pressure. Ethyl acetate was then added to the residue, followed by washing with 1N hydrochloric acid. After extraction, the organic layer was dried over anhydrous sodium sulfate and the solvent was distilled off under reduced pressure. The residue was purified by chromatography on a silica gel column (ethyl acetate methylene chloride=3:1), followed by washing with hexane, whereby the title compound (colorless prism crystals, 1.92 g) was obtained.

$^1$H-NMR (CDCl$_3$) δ: 2.59(4H,d,J=6.4 Hz), 3.55(4H,d,J= 6.4 Hz), 7.45(1H,dd,J=8.8,2.0 Hz), 7.80–7.84(2H,m), 7.87 (1H,d,J=2.0 Hz). MS (FAB) m/z: 330 [(M+H)$^+$, Cl$^{35}$], 332 [(M+H)$^+$, Cl$^{37}$].

Referential Example 213

4-(4-Bromobenzylidene)-1-[(6-chlorobenzo[b]thien-2-yl)sulfonyl]piperidine

In a mixed solvent of tetrahydrofuran (10 ml) and ethanol (10 ml) was dissolved 4-bromobenzyl triphenylphosphonium bromide (512 mg). The resulting solution was cooled to 0° C., followed by the successive addition of sodium hydride (60% in oil, 40 mg) and 1-[(6-chlorobenzo[b]thien-2-yl)sulfonyl]piperidin-4-one (297 mg). The resulting mixture was stirred at room temperature for 16 hours and at 50° C. for 9 hours. Saturated aqueous NaCl solution and ethyl acetate were added to the reaction mixture to separate the same. The resulting organic layer was dried over anhydrous magnesium sulfate, the filtrate was concentrated and the residue was purified by chromatography on a silica gel column (hexane:ethyl acetate=4:1), whereby the title compound (colorless powder, 133 mg) was obtained.

$^1$H-NMR (CDCl$_3$) δ: 2.48(2H,d,J=5.9 Hz), 2.57(2H,d,J=5.9 Hz), 3.16(2H,d,J=5.9 Hz), 3.28(2H,d,J=5.9 Hz), 6.25(1H,s), 6.97(2H,d,J=8.3 Hz), 7.40–7.45(3H,m), 7.73(1H,s), 7.79(1H,d,J=8.5 Hz), 7.84(1H,d,J=1.2 Hz).

Referential Example 214

6-Bromobenzo[b]thiophene

To quinoline (45 ml) were added 6-bromobenzothiophene-2-carboxylic acid (14 g) and copper powder (874 mg), followed by stirring under heat at an oil temperature of 220° C. for 2 hours. After the reaction mixture was allowed to cool down, ether was added and the copper powder was filtered off. The filtrate was washed with a 1N aqueous solution of hydrochloric acid, then with a 1N aqueous solution of sodium hydroxide and finally with saturated aqueous NaCl solution, followed by drying over anhydrous sodium sulfate. The solvent was then distilled off under reduced pressure. The residue was purified by chromatography on a silica gel column (hexane), whereby the title compound (5.56 g) was obtained as a pale yellow solid. In addition, the raw material (3.15 g) was recovered.

$^1$H-NMR (CDCl$_3$) δ: 7.29(1H,d,J=5.4 Hz), 7.42(1H,d,J=5.4 Hz), 7.46(1H,dd,J=8.3,1.5 Hz), 7.67(1H,d,J=8.3 Hz), 8.01(1H,d,J=1.5 Hz). MS (EI) m/z: 214 (M$^+$, $^{81}$Br), 212 (M$^+$, $^{79}$Br)

Referential Example 215

6-Trimethylsilylethynylbenzo[b]thiophene

In tetrahydrofuran (15 ml) was dissolved 6-bromobenzo[b]thiophene (2.13 g), followed by the addition of triphenylphosphine (787 mg), triethylamine (40 ml), N,N-dimethylformamide (15 ml), trimethylsilylacetylene (1.47 g) and palladium acetate (225 mg). The resulting mixture was refluxed for 5 hours. After the reaction mixture was allowed to cool down, it was diluted with methylene chloride (150 ml). The diluted mixture was washed with water (twice) and saturated aqueous NaCl solution, dried over anhydrous sodium sulfate and distilled under reduced pressure to remove the solvent. The residue was purified by chromatography on a silica gel column (only hexane), whereby the title compound (1.38 g) was obtained.

$^1$H-NMR (CDCl$_3$) δ: 0.27(9H,s), 7.30(1H,d,J=5.7 Hz), 7.44(1H,dd,J=8.3,1.0 Hz), 7.49(1H,d,J=5.7 Hz), 7.73(1H,d, J=8.3 Hz), 8.00(1H,s). MS (EI) m/z: 230 M$^+$.

Referential Example 216

6-Trimethylsilylethynylbenzo[b]thiophene-2-sulfonyl chloride

In anhydrous diethyl ether (10 ml) was dissolved 6-trimethylsilylethynylbenzo[b]thiophene (408 mg). After the resulting solution was cooled to −78° C., tert-butyl lithium (a 1.54 mole pentane solution, 1.15 ml) was added dropwise. The reaction mixture was heated to 0° C. over 30 minutes, followed by stirring for 1 hour. The reaction mixture was cooled again to −78° C. and then, a sulfurdioxide gas was introduced thereinto. After heating to room temperature over 1 hour, the mixture was stirred for 1 hour. The unreacted portion of sulfurdioxide gas which had been dissolved in the reaction mixture was volatilized sufficiently. The solvent was then distilled off under reduced pressure. Hexane (20 ml) was added to the residue. An insoluble precipitate was collected by filtration and washed with hexane. The precipitate was then dissolved in methylene chloride (10 ml). After cooling to 0° C., N-chlorosuccinic imide (248 mg) was added and the resulting mixture was stirred for 30 minutes and after heating to room temperature, stirred for further 1 hour. Water was added to the reaction mixture to separate it into layers. The water layer was extracted with methylene chloride (5 times each with a 10 ml portion). The organic layers were combined, washed with saturated aqueous NaCl solution, dried over anhydrous sodium sulfate and distilled under reduced pressure to remove the solvent, whereby the title compound (498 mg) was obtained as a pale yellow solid.

$^1$H-NMR (CDCl$_3$) δ: 0.28(9H,s), 7.58(1H,dd,J=8.3,1.5 Hz), 7.89(1H,d,J=8.3 Hz), 8.02(1H,s), 8.10(1H,s). MS (EI) m/z: 328 M$^+$.

Referential Example 217

1-[(6-Trimethylsilylethynylbenzo[b]thien-2-yl)sulfonyl-3]-(N-methylcarbamoyl)piperazine In methanol (15 ml) was dissolved 1,4-dibenzyl-2-(N-methylcarbamoyl)piperazine (437 mg). Palladium hydroxide (22 mg) and concentrated hydrochloric acid (0.22 ml) were then added to the resulting solution. A hydrogen gas was introduced (1 atmospheric pressure) into the resulting mixture, followed by stirring at room temperature for 1 hour. After the addition of triethylamine (0.9 ml), palladium was filtered off and the solvent was distilled off under reduced pressure. The residue was dissolved in methylene chloride. Triethylamine (0.5 ml) was added to the resulting mixture, followed by the addition of 6-trimethylsilylethynylbenzo[b]thiophene-2-sulfonyl chloride (399 mg) under ice cooling. After the temperature was allowed to rise back to room temperature, stirring was conducted for 20 hours. The reaction mixture was washed (twice) with a saturated aqueous solution of sodium bicarbonate, dried over anhydrous sodium sulfate and distilled under reduced pressure to remove the solvent. The residue was purified by chromatography on a silica gel column (methanol : methylene chloride=1:19), whereby the title compound (462 mg) was obtained as a pale yellow solid.

$^1$H-NMR (CDCl$_3$) δ: 0.28(9H,s), 1.52(1H,br s), 2.57–2.66 (2H,m), 2.80, 2.79(total 3H,each s), 2.97(1H,dt,J=3.3,11.5 Hz), 3.09(1H,dt,J=13.2,3.1 Hz), 3.51(1H,dd,J=9.8,3.4 Hz), 3.59(1H,dd,J=11.7,0.98 Hz), 3.92(1H,dd,J=11.7,2.4 Hz), 6.56–6.57(1H,m), 7.52(1H,dd,J=8.3,0.98 Hz), 7.77(1H,s), 7.82(1H,d,J=8.3 Hz), 7.97(1H,s). MS (FAB) m/z: 436 (M+H)$^+$.

Referential Example 218

1-(tert-Butoxycarbonyl)-4-[(5-bromopyridin-2-yl)carbonyl]piperazine

In the same manner as in Referential Example 3, the title compound was obtained.

$^1$H-NMR (CDCl$_3$) δ: 1.47(9H,s), 3.35–3.37(2H,m), 3.45–3.48(2H,m), 3.54–3.57(2H,m), 3.77–3.79(2H,m), 8.87 (2H,s). MS (FAB) m/z: 373 [(M+H)$^+$, $^{81}$Br], 371 [(M+H)$^+$, $^{79}$Br].

Referential Example 219

1-(tert-Butoxycarbonyl)-4-[[5-(4-pyridyl)pyrimidin-2-yl]carbonyl]piperazine

To a mixed solvent of dimethoxyethane (60 ml) and methanol (120 ml) were added 1-(tert-butoxycarbonyl)-4-[(5-bromopyrimidin-2-yl)carbonyl]piperazine (2.97 g), (pyridin-4-yl)boronic acid (1.48 g), cesium fluoride (4.25 g) and tetrakis(triphenylphosphine)palladium (924 mg). After purging with argon, the reaction mixture was refluxed for 19 hours. The solvent was then distilled off under reduced pressure. The residue was purified by moderate-pressure chromatography on a silica gel column (size D, methanol methylene chloride=1:9), whereby the title compound (1.31 g) was obtained as a colorless solid.

$^1$H-NMR (CDCl$_3$) δ: 1.48(9H,s), 3.40–3.44(2H,m), 3.48–3.52(2H,m), 3.59(2H,t,J=5.4 Hz), 3.84(2H,t,J=5.4 Hz), 7.54(2H,dd,J=4.4,2.0 Hz), 8.81(2H,dd,J=4.4,2.0 Hz), 9.07(2H,s). MS (FAB) m/z: 369 M$^+$.

Referential Example 220

1-[(5-Chloro-1-phenylsulfonylindol-2-yl)sulfonyl]-3-(methoxycarbonylmethyl)piperazine To an ethanol solution (50 ml) of 1-(tert-butoxycarbonyl)-3-(3-methoxycarbonylmethyl)piperazine (5.03 g) was added a saturated solution of hydrochloride in ethanol (20 ml), followed by stirring for 30 minutes. After the solvent was distilled off under reduced pressure, the residue was dissolved in methylene chloride to obtain a methylene chloride solution (200 ml). At room temperature, 5-chloro-1-phenylsulfonylindole-2-sulfonyl chloride (7.64 g) and tri-ethylamine (9.5 ml) were added to the resulting solution, followed by stirring at room temperature for 4 hours. Distilled water and methylene chloride were added and the water layer was extracted three times. The organic layers were combined, dried over anhydrous sodium sulfate and distilled under reduced pressure to remove the solvent. The residue so obtained was subjected to chromatography on a silica gel column (methanol : methylene chloride=1:50), whereby the title compound (4.97 g) was obtained as a colorless oil.

MS (FAB) m/z: 512 [(M+H)$^+$, Cl$^{35}$], 514 [(M+H)$^+$, Cl$^{37}$].

$^1$H-NMR (CDCl$_3$) δ: 2.15–2.30(1H,br), 2.34–2.49(2H, m), 2.72–2.76(1H,m), 2.90–3.22(3H,m), 3.17–3.25(1H,m), 3.67(3H,s), 3.71–3.77(2H,m), 7.39–7.47(4H,m), 7.52–7.58 (2H,m), 8.02(2H,d,J=7.8 Hz), 8.23(1H,d,J=9.3 Hz).

Referential Example 221

1-(tert-Butoxycarbonyl)-4-[(5-chloro-1-phenylsulfonylindol-2-yl)sulfonyl]-2-(methoxycarbonylmethyl)piperazine To an ethanol solution (250 ml) of 1-[(5-chloro-1-phenylsulfonylindol-2-yl)sulfonyl]-3-(methoxycarbonylmethyl)piperazine (2.00 g) was added di-tert-butyl dicarbonate (3.91 g) at room temperature, followed by stirring for 17 hours. The reaction mixture was concentrated under reduced pressure and diethyl ether was added to the concentrate. The crystals thus precipitated were collected by filtration, washed with diethyl ether and dried under reduced pressure, whereby the title compound (2.01 g) was obtained as colorless crystals.

MS (FAB) m/z: 612 [(M+H)$^+$, Cl$^{35}$], 614 [(M+H)$^+$, Cl$^{37}$].

$^1$H-NMR (CDCl$_3$) δ: 1.45(9H,s), 2.45–2.54(1H,m), 2.74–2.86(1H,m), 2.92–3.03(1H,m), 3.07–3.27(1H,m), 3.37 (3H,s), 3.67–3.77(2H,m), 3.94–4.06(2H,m), 4.52–4.67(1H, m), 7.38–7.49(4H,m), 7.57–7.60(2H,m), 8.03(2H,d,J=6.8 Hz), 8.23(1H,d,J=9.3 Hz).

Referential Example 222

1-(tert-Butoxycarbonyl)-4-[(5-chloroindol-2-yl)sulfonyl]-2-[[(morpholin-4-yl)]carbonyl]methyl]piperazine To a 1,4-dioxane solution (100 ml) of 1-(tert-butoxycarbonyl)-4-[(5-chloro-1-phenylsulfonylindol-2-yl) sulfonyl]-2-(methoxycarbonylmethyl)piperazine (1.0 g) was added a 1N aqueous solution (4.9 ml) of sodium hydroxide at room temperature. The resulting mixture was heated to 80° C. and stirred for 6 hours. Under ice cooling, a saturated aqueous solution of ammonium chloride was added to neutralize the reaction mixture, followed by addition of distilled water. The water layer was extracted four times with methylene chloride. The organic layers were combined, dried over anhydrous sodium sulfate, and distilled under reduced pressure to remove the solvent. The residue was dissolved in methylene chloride to obtain a methylene chloride solution (150 ml). To the resulting solution were added 1-hydroxybenzotriazole (0.24 g), 1-(3-dimethylaminopropyl)-3-ethylcarbodiimide hydrochloride (0.41 g), morpholine (0.16 g) and N-methylmorpholine (0.41 g), followed by stirring at room temperature for 12 hours. Distilled water was added to the reaction mixture. The water layer was extracted three times with methylene chloride. The organic layers were combined, washed four times with distilled water, dried over anhydrous sodium sulfate and distilled under reduced pressure to remove the solvent. The resulting residue was subjected to chromatography on a silica gel column (methanol:methylene chloride 1:50), whereby the title compound (0.71 g) was obtained as a colorless solid.

$^1$H-NMR (MHz, CDCl$_3$) δ: 1.41(9H,s), 2.23–2.30(3H,m), 3.34–3.84(12H,m), 3.91–4.12(1H,m), 4.49–4.64(1H,m), 6.98(1H,s), 7.27–7.33(1H,m), 7.37(1H,d,J=8.8 Hz), 7.66 (1H,s). MS (FAB) m/z: 527 [(M+H)$^+$, Cl$^{35}$], 529 [(M+H)$^+$, Cl$^{37}$].

Referential Example 223

1-(tert-Butoxycarbonyl)-2-(carbamoylmethyl)-[(5-chloroindol-2-yl)sulfonyl]piperazine To a 1,4-dioxane solution (100 ml) of 1-(tert-butoxycarbonyl)-4-[(5-chloro-1-phenylsulfonylindol-2-yl) sulfonyl]-2-(methoxycarbonylmethyl)piperazine (800 mg) was added a 1N aqueous solution of sodium hydroxide (3.9 ml) at room temperature. The resulting mixture was heated to 80° C. and stirred for 13 hours. Under ice cooling, a saturated aqueous solution of ammonium chloride was added to neutralize the reaction mixture, followed by the addition of distilled water and methylene chloride. The water layer was extracted 4 times with methylene chloride. The organic layers were combined, dried over anhydrous sodium sulfate and distilled under reduced pressure to remove the solvent. The residue was dried overnight under reduced pressure and then, an N,N'-dimethylformamide solution (50 ml) was obtained. At room temperature, di-tert-butyl dicarbonate (856 mg, 3.92 mmol), pyridine (259 mg) and ammonium bicarbonate (233 mg) were added to the resulting solution, followed by stirring at room temperature for 15 hours. The reaction mixture was distilled under reduced pressure to remove the solvent and the residue was dissolved in methylene chloride. Hexane and diethyl ether were added to solidify the resulting solution. The resulting solid was collected by filtration, washed with hexane and dried under reduced pressure, whereby the title compound (502 mg) was obtained as a colorless solid.

MS (FAB) m/z: 457 [(M+H)$^+$, Cl$^{35}$], 459 [(M+H)$^+$, Cl$^{37}$]. $^1$H-NMR (MHz, CDCl$_3$) δ: 0.88(1H,t,J=6.4 Hz), 1.24–1.33 (1H,m), 1.35–1.44(1H,m), 1.46(9H,s), 2.32–2.59(2H,m), 2.88–3.18(2H,m), 3.69–3.88(1H,m), 3.91–4.16(1H,m), 4.35–4.82(1H,m), 5.91–6.60(1H,m), 6.97(1H,s), 7.26–7.29 (1H,m), 7.41(1H,d,J=8.8 Hz), 7.66(1H,s).

Referential Example 224

1,4-Dibenzyl-2-ethenylpiperazine

After a solution of 1,4-dibenzyl-2-(ethoxycarbonyl) piperazine (6.76 g) in methylene chloride (250 ml) was cooled to −78° C., diisobutylaluminum hydride (a 1.0 mol/l hexane solution, 39.90 ml) was added dropwise and the mixture was stirred at −78° C. for 2 hours. A saturated aqueous solution of ammonium chloride and methylene chloride were added to the reaction mixture. The water layer was extracted three times. The organic layers were combined, washed with distilled water and dried over anhydrous sodium sulfate. The residue obtained by distilling off the solvent under reduced pressure was provided for the subsequent reaction without purification. After cooling a tetrahydrofuran solution (150 ml) of methyltriphenylphosphonium iodide (8.07 g) to −78° C., n-butyl lithium (a 1.52 mole hexane solution, 13.14 ml) was added dropwise and the mixture was stirred at −78° C. for 2 hours. A solution of the residue, which residue had been obtained above, in tetrahydrofuran was then added. The reaction mixture was heated from −78° C. to 0° C. while stirring for 4 hours and then, a saturated aqueous solution of ammonium chloride was added to terminate the reaction. Diethyl ether was added and the water layer was extracted three times. The organic layers were combined, washed with saturated aqueous NaCl solution and dried over anhydrous magnesium sulfate. The residue obtained by distilling off the solvent under reduced pressure was subjected to chromatography on a silica gel column (methanol:methylene chloride=1:50), whereby the title compound (3.22 g) was obtained as a pale yellow oil.

MS (EI) m/z: 292 M$^+$. $^1$H-NMR (CDCl$_3$) δ: 2.07–2.22 (3H,m), 2.62–2.76(3H,m), 2.89–2.97(1H,m), 3.07(1H,d,J= 13.2 Hz), 3.43–3.56(2H,m), 4.04(1H,d,J=13.2 Hz), 5.15–5.32(2H,m), 5.77–5.88(1H,m), 7.20–7.33(10H,m).

Referential Example 225

2-Ethylpiperazine hydrochloride

At room temperature, concentrated hydrochloric acid (6 ml) and palladium hydroxide (1.1 g) were added to solution (600 ml) of 1,4-dibenzyl-2-ethenylpiperazine (10.9 g)in ethanol, followed by stirring for 12 hours under a hydrogen gas stream of 1 atmospheric pressure. The catalyst was filtered off and the solvent was distilled off under reduced pressure. The resulting residue was solidified using methylene chloride—diethyl ether, followed by washing with diethyl ether. The resulting solid was dried under reduced pressure, whereby the title compound (6.516 g) was obtained as a brown solid.

MS (EI) m/z: 114 M$^+$. $^1$H-NMR (DMSO-d$_6$) δ: 0.95(3H, t,J=7.8 Hz), 1.56–1.79(2H,m), 2.95–3.07(1H,m), 3.15–3.54 (6H,m), 9.75(4H,br).

Referential Example 226

1-[(5-Chloro-1-phenylsulfonylindol-2-yl)sulfonyl]-3-(ethyl)piperazine

To a methylene chloride solution (700 ml) of 2-ethylpiperazine hydrochloride (5.00 g) were added 5-chloro -1-phenylsulfonylindol-2-sulfonyl chloride (7.14 g) and triethylamine (11.16 ml) and the resulting mixture was stirred at room temperature for 3 hours. Distilled water and methylene chloride were added and the water layer was extracted three times. The organic layers were combined, dried over anhydrous sodium sulfate and distilled under reduced pressure to remove the solvent. The residue was purified by chromatography on a silica gel column (methanol:methylene chloride=1:100), whereby the title compound (5.86 g) was obtained as a pale yellow oil.

MS (EI) m/z: 468 (M$^+$, Cl$^{35}$), 470 (M$^+$, Cl$^{37}$). $^1$H-NMR (CDCl$_3$) δ: 0.94(3H,t,J=7.8 Hz), 1.33–1.46(2H,m), 2.53–2.62(1H,m), 2.56–2.74(1H,m), 2.87–3.07(3H,m), 3.75–3.83(2H,m), 7.38(1H,s), 7.40–7.47(3H,m), 7.53–7.57 (2H,m), 8.00–8.05(2H,m), 8.22(1H,d,J=8.8 Hz).

Referential Example 227

1-[(5-Chloroindol-2-yl)sulfonyl]-3-(ethyl)piperazine

A 1N aqueous solution (16 ml) of sodium hydroxide was added to a 1,4-dioxane solution (200 ml) of 1-[(5-chloro-1-phenylsulfonylindol-2-yl)sulfonyl]-3-(ethyl)piperazine (3.78 g) and the resulting mixture was stirred at 80° C. for 11.5 hours. A saturated aqueous solution of ammonium chloride was added to the reaction mixture. Distilled water and ethyl acetate were then added and the water layer was extracted three time. The organic layers were combined, dried over anhydrous magnesium sulfate and distilled under reduced pressure to remove the solvent. The residue was subjected to chromatography on a silica gel column (methanol:methylene chloride=1:100), followed by crystallization from tetrahydrofuran—diethyl ether, whereby the title compound (2.54 g) was obtained as needle crystals.

$^1$H-NMR (MHz, CDCl$_3$) δ: 0.92(3H,t,J=7.8 Hz), 1.25–1.42(2H,m), 2.09(1H,t,J=1.3 Hz), 2.47(1H,dt,J=2.9, 11.2 Hz), 2.63–2.72(1H,m), 2.92(1H,dt,J=2.9,17.2 Hz), 3.00–3.07(1H,m), 3.60–3.70(2H,m), 6.95(1H,s), 7.30(1H, dd,J=8.8,1.9 Hz), 7.37(1H,d,J=8.8 Hz), 7.67(1H,d,J=1.9 Hz), 8.98(1H,br).

Referential Example 228

1-[(5-Bromopyrimidin-2-yl)carbonyl]-4-[(5-chloroindol-2-yl)sulfonyl]-2-ethylpiperazine To an N,N-dimethylformamide solution (200 ml) of 1-[(5-chloroindol-2-yl)sulfonyl]-3-(ethyl)piperazine (2.54 g) were added benzotriazol-1-yl-oxo-tris-pyrrolidino -phosphonium hexafluorophosphite (4.84 g), 5-bromopyrimidine-2-carboxylic acid (1.83 g) and triethylamine (1.40 ml). The resulting mixture was stirred at room temperature for 12 hours. Distilled water was added and the water layer was extracted three times with ethyl acetate. The organic layers were combined, washed three times with distilled water, dried over anhydrous magnesium sulfate and distilled under reduced pressure to remove the solvent. The residue was subjected to chromatography on a silica gel column (methanol:methylene chloride=1:100), followed by crystallization from methylene chloride and washing with diethyl ether, whereby the title compound (3.18 g) was obtained as a colorless solid.

MS (FAB) m/z=512 (M$^+$), 514[(M+2)$^+$], 516 [(M+4)$^+$]. $^1$H-NMR (MHz, CDCl$_3$) δ: 0.83(1.5H,t,J=7.3 Hz), 1.03 (1.5H,t,J=7.3 Hz), 1.74–2.02(2H,m), 2.48–2.70(2H,m), 3.16–3.25(0.5H,m), 3.40–3.53(1H,m), 3.58(0.5H,m), 3.67 (1H,t,J=11.0 Hz), 3.79–3.92(1H,m), 4.65–4.70(0.5H,m), 4.78–4.85(0.5H,m), 6.94(1H,s), 7.33–7.39(1H,m), 7.68(1H, s), 8.79(1H,s), 8.83(2H,s).

Referential Example 229

1-[(6-Chlorobenzo[b]thien-2-yl)sulfonyl]-3-(ethyl) piperazine

To a methylene chloride solution (30 ml) of 2-ethylpiperazine hydrochloride (307 mg) was added (6-chlorobenzo[b]thien-2-yl)sulfonyl chloride (438 mg) and triethylamine (498 mg). The resulting mixture was stirred at room temperature for 26 hours. Distilled water and methylene chloride were added and the water layer was extracted three times. The organic layers were combined, dried over anhydrous sodium sulfate and distilled under reduced pressure to remove the solvent. The residue was subjected to chromatography on a silica gel column (methanol:methylene chloride=1:20), whereby the title compound (255 mg) was obtained as a pale yellow oil. MS (FAB) m/z: 345 [(M+H)$^+$, Cl$^{35}$], 347 [(M+H)$^+$, Cl$^{37}$]. $^1$H-NMR (CDCl$_3$) δ: 0.95(3H,t,J=7.8 Hz), 1.24–1.46(2H, m), 2.16(1H,t,J=10.7 Hz), 2.54(1H,dt,J=2.9,11.2 Hz), 2.65–2.75(1H,m), 2.95(1H,dt,J=2.9,11.2 Hz), 3.04–3.10 (1H,m), 3.65–3.72(2H,m), 7.43(1H,dd,J=8.8,2.0 Hz), 7.75 (1H,s), 7.81(1H,d,J=8.8 Hz), 7.86(1H,s).

Referential Example 230

1-[(5-Bromopyrimidin-2-yl)carbonyl]-4-[(6-chlorobenzo[b]thien-2-yl)sulfonyl]-2-ethylpiperazine Under an argon atmosphere, N,N-dimethylformamide (0.15 ml) was added to a methylene chloride solution (25 ml) of 5-bromopyrimidine-2-carboxylic acid (455 mg) was added and the resulting mixture was ice cooled. Oxalyl chloride (564 mg) was added and the resulting mixture was stirred for 30 minutes under ice cooling. The resulting solution, together with diisopropylethylamine (2.7 ml), was added to a methylene chloride solution (25 ml) of 1-[(6-chlorobenzo[b]thien-2-yl)sulfonyl]-3-ethylpiperazine (255 mg), followed by stirring at 0° C. for 1 hour. The reaction mixture was added successively with a saturated aqueous solution of ammonium chloride and distilled water. The water layer was extracted three times with methylene chloride. The organic layers were combined, washed three times with distilled water, dried over anhydrous sodium sulfate and distilled under reduced pressure to remove the solvent. The residue was subjected to chromatography on a silica gel column (methanol:methylene chloride=1:100), whereby the title compound (308 mg) was obtained as a pale yellow oil.

MS (FAB) m/z=529 (M$^+$), 531 (M+2)$^+$], 533 (M+4)$^+$]. $^1$H-NMR (CDCl$_3$) δ: 0.84(1.5H,t,J=7.3 Hz), 1.05(1.5H,t,J= 7.3 Hz), 1.17–2.03(0.5H,m), 1.76–2.04(2H,m), 2.55–2.77 (2.5H,m), 3.17–3.28(1H,m), 3.40–3.62(1.5H,m), 3.67–3.77 (1H,m), 3.82–3.94(1H,m), 4.65–4.70(0.5H,m), 4.80–4.87 (0.5H,m), 7.45(1H,dd,J=8.8,2.0 Hz), 7.75(1H,s), 7.82(1H,d, J=8.8 Hz), 7.87(1H,br), 8.83(2H,s).

Referential Example 231

1,4-Dibenzyl-2-(2-methyl-1-propenyl)piperazine

After cooling a methylene chloride solution (400 ml) of 1,4-dibenzyl-2-ethoxycarbonylpiperazine (19.57 g) to −78° C., diisobutylaluminum hydride (a 0.95 mole hexane solution, 121.7 ml) was added dropwise. The resulting mixture was stirred at −78° C. for 2.5 hours. A saturated aqueous solution of ammonium chloride and methylene chloride were added and then, the water layer was extracted three times. The organic layers were combined, washed with distilled water and dried over anhydrous sodium sulfate. The residue obtained by distilling off the solvent under reduced pressure was provided for the subsequent reaction without purification. After cooling a tetrahydrofuran solution (300 ml) of isopropyltriphenylphosphonium iodide (25.0 g) to −78° C., n-butyl lithium (a 1.53 mole hexane solution, 37.8 ml) was added dropwise, followed by stirring at −78° C. for 30 minutes. A solution of the residue, which had been obtained above, in tetrahydrofuran was added dropwise to the reaction mixture. The resulting mixture was heated gradually from −78° C. and stirred overnight. A saturated aqueous solution of ammonium chloride was added to terminate the reaction. Ethyl acetate was added and the water layer was extracted three times. The organic layers were combined, washed with saturated aqueous NaCl solution and dried over anhydrous magnesium sulfate. The residue obtained by distilling off the solvent under reduced pressure The residue was subjected to chromatography on a silica gel column (ethyl acetate:hexane=1:20), whereby the title compound (6.0 g) was obtained as a pale yellow oil.

MS (EI) m/z: 320 M$^+$. $^1$H-NMR (CDCl$_3$) δ: 0.88(3H,s), 0.91(3H,s), 2.00(1H,t,J=10.7 Hz), 2.04–2.21(2H,m), 2.64–2.72(3H,m), 3.00–3.18(2H,m), 3.40–3.55(2H,m), 4.06 (1H,d,J=13.7 Hz), 5.13(1H,d,J=8.8 Hz), 7.16–7.45(10H,m).

Referential Example 232

2-(2-Methylpropyl)piperazine hydrochloride

Concentrated hydrochloric acid (3 ml) and palladium hydroxide (683 mg) were added to an ethanol solution (300 ml) of 1,4-dibenzyl-2-(2-methyl-1-propenyl)piperazine (5.2 g), followed by stirring for 2 hours under a hydrogen gas stream of 1 atmospheric pressure. The catalyst was removed by filtration and the solvent was distilled off under reduced pressure. The residue was recrystallized from methylene chloride—hexane, followed by washing with diethyl ether and drying under reduced pressure, whereby the title compound (2.95 g) was obtained as a brown solid.

MS (EI) m/z: 143 M$^+$. $^1$H-NMR (DMSO-d$_6$) δ: 0.86–1.30 (1H,m), 1.73(3H,s), 1.76(3H,s), 3.10–3.47(7H,m), 4.36–4.45(1H,m), 5.18(1H,d,J=9.3 Hz).

Referential Example 233

1-[(5-Chloro-1-phenylsulfonylindol-2-yl)sulfonyl]-3-(2-methylpropyl)piperazine To a methylene chloride solution (150 ml) of 2-(2-methylpropyl)piperazine hydrochloride (1.50 g) were added 5-chloro-1-phenylsulfonylindole-2-sulfonyl chloride (2.72 g) and triethylamine (2.91 ml). The resulting mixture was stirred at room temperature for 13 hours. Distilled water and methylene chloride were added and the water layer was extracted three times. The organic layers were combined, washed with saturated aqueous NaCl solution, dried over anhydrous sodium sulfate and distilled under reduced pressure to remove the solvent. The residue was subjected to chromatography on a silica gel column (methanol:methylene chloride=1:20), whereby the title compound (2.69 g) was obtained as a brown oil.

MS (FAB) m/z: 496 [(M+H)$^+$, Cl$^{35}$], 498 [(M+H)$^+$, Cl$^{37}$]. $^1$H-NMR (CDCl$_3$) δ: 0.89(1H,t,J=5.9 Hz), 1.50–1.52(1H, m), 2.70–2.79(1H,m), 2.90–3.12(3H,m), 3.55–3.83(3H,m), 5.02(1H,d,J=8.3 Hz), 7.35–7.48(4H,m), 7.51–7.58(2H,m), 8.02(2H,d,J=8.3 Hz), 8.22(1H,d,J=8.8 Hz).

Referential Example 234

1-[(5-Chloroindol-2-yl)sulfonyl]-3-(2-methylpropyl) piperazine

To a solution of 1-[(5-chloro-1-phenylsulfonylindol-2-yl) sulfonyl]-3-(2-methylpropyl)piperazine (2.57 g) in a mixture of 1,4-dioxane and distilled water (100–10 ml) was added a 1N aqueous solution (10.4 ml) of sodium hydroxide. The resulting mixture was stirred at 80° C. for 3 days. After saturated ammonium chloride was added to terminate the reaction, distilled water and ethyl acetate were added. The water layer was extracted three times. The organic layers were combined, dried over anhydrous magnesium sulfate and distilled under reduced pressure to remove the solvent. The residue was subjected to chromatography on a silica gel column (methanol:methylene chloride=1:50), whereby the title compound (0.93 g) was obtained as a brown oil.

MS (FAB) m/z: 356 [(M+H)$^+$, Cl$^{35}$], 358 [(M+H)$^+$, Cl$^{37}$]. $^1$H-NMR (CDCl$_3$) δ: 0.78–1.30(2H,m), 1.69(3H,s), 1.70 (3H,s), 1.63–1.80(1H,m), 2.39–2.55(1H,M), 2.90–3.07(2H, m), 3.48–3.70(3H,m), 4.90(1H,d,J=8.3 Hz), 6.92–6.99(1H, m), 7.31(1H,dd,J=8.8,2.0 Hz), 7.36(1H,d,J=8.8 Hz), 7.65–7.69(1H,m), 8.72(1H,br).

Referential Example 235

1-[(5-Bromopyrimidin-2-yl)carbonyl]-4-[(5-chloroindol-2-yl)sulfonyl]-2-(2-methylpropyl)piperazine To an N,N-dimethylformamide solution (60 ml) of 1-[(5-chloroindol-2-yl)sulfonyl]-3-(2-methylpropyl)piperazine (0.91 g) were added benzotriazol-1-yl-oxo-tris-pyrrolidino-phosphonium hexafluorophosphite:(1.60 g), 5-bromopyrimidine-2-carboxylic acid (0.63 g) and triethylamine (0.39 g). The resulting mixture was stirred at room temperature for 14 hours. The solvent was then distilled off under reduced pressure. Distilled water was added to the residue and the water layer was extracted three times with methylene chloride. The organic layers were combined, washed three times with distilled water, dried over anhydrous magnesium sulfate and distilled under reduced pressure to remove the solvent. The residue was subjected to chromatography on a: silica gel column (methanol:methylene chloride=1:100), followed by crystallization from ethanol—diethyl ether, whereby the title compound (0.47 g) was obtained as brown crystals.

MS (FAB) m/z=538 (M$^+$), 540 [(M+2)$^{+1}$ 542 [(M+4)$^{+1}$ $^1$H-NMR (CDCl$_3$) δ: 0.70–1.28(2H,m), 1.60–1.75(1H,m), 1.79(3H,s), 1.82(3H,s), 2.53–2.90(2H,m), 3.34–3.48(0.5H, m), 3.53–3.62(0.5H,m), 3.68–3.79(1H,m), 3.83–3.97(0.5H, m), 4.54–4.66(0.5H,m), 5.64(1H,br), 6.95(1H,br), 7.34(1H, dd,J=8.8,2.0 Hz), 7.38(1H,d,J=8.8 Hz), 7.69(1H,s), 8.73 (1H,s), 8.82(2H,br).

Referential Example 236

3-(5-Thiazolyl)pyridine

At room temperature, tetrakis(triphenylphosphine) palladium (470 mg) was added to 3-bromopyridine (805 μl) and a solution of (5-thiazolyl)trimethyltin (2.07 g) in benzene (80 ml), followed by heating under reflux overnight. After the reaction mixture was allowed to cool down to room temperature, it was washed with a saturated aqueous solution (100 ml) of sodium bicarbonate. The water layer was extracted with ethyl acetate (3×20 ml). The organic layers were combine, dried over anhydrous sodium sulfate and distilled under reduced pressure to remove the solvent. The residue was purified by chromatography on a silica gel column (hexane:ethyl acetate=2:1), whereby the title compound (1.68 g, purity: 85%) was obtained as a colorless solid.

$^1$H-NMR (CDCl$_3$) δ: 7.37(1H,dd,J=7.3,4.9 Hz), 7.88(1H, dt,J=7.3,1.5 Hz), 8.14(1H,s), 8.60(1H,dd,J=4.9,1.5 Hz), 8.85 (1H,s), 8.86(1H,d,J=1.5 Hz).

Referential Example 237

1-(tert-Butoxycarboyl)-4[5-(2-methylpyridin-4-yl)thiazol-2-yl]piperazine

At room temperature, tetrakis(triphenylphosphine) palladium (470 mg) was added to a solution of 4-bromo-2-methylpyridine (1.65 g) and (5-thiazolyl)trimethyltin (1.56 g) in benzene (80 ml), followed by heating under reflux for 14 hours. After allowed to cool down to room temperature, the reaction mixture was washed with a saturated aqueous solution (100 ml) of sodium bicarbonate. The water layer was extracted with ethyl acetate (50 ml). The organic layers were combined, dried over anhydrous sodium sulfate and distilled under reduced pressure to remove the solvent. The residue was purified by chromatography on a silica gel column (methylene chloride:ethyl acetate=4:1→1:1), whereby 2-methyl-4-(5-thiazolyl)pyridine was obtained as a colorless solid. The resulting solid was dissolved in diethyl ether (30 ml) and tetrahydrofuran (30 ml), followed by the dropwise addition of n-butyl lithium (a 1.52N hexane solution, 4.35 ml) at −78° C. After stirring for 30 minutes, a carbon dioxide gas was blown into the reaction mixture. Thirty minutes later, the reaction mixture was heated gradually to room temperature. The reaction mixture was concentrated, whereby the residue of lithium 5-(2-methylpyridin-4-yl)thiazole-2-carboxylate was obtained as a colorless solid. To a solution of the resulting residue in N,N-dimethylformamide (40 ml) were added 1-(tert-butoxycarbonyl)piperazine (1.30 g), 1-hydroxybenzotriazole monohydrate (945 mg) and 1-(3-dimethylaminopropyl)-3-ethylcarbodiimide hydrochloride (1.34 g) at room temperature. After stirring for 3 days, ethyl acetate (200 ml) and water (800 ml) were added to the reaction mixture to separate it into layers. The water layer was extracted with ethyl acetate (2×100 ml). The organic layers were combined, washed with water (800 ml) and a saturated aqueous solution (200 ml) of sodium bicarbonate, dried over anhydrous sodium sulfate and distilled under reduced pressure to remove the solvent. The residue was purified by chromatography on a silica gel column (methylene chloride:acetone=6:1), whereby the title compound (810 mg) was obtained as a colorless transparent viscous substance.

$^1$H-NMR (CDCl$_3$) δ: 1.49(9H,s), 2.63(3H,s), 3.57(4H,t, J=4.9 Hz), 3.79(2H,br s), 4.43(2H,br s), 7.30(1H,d,J=4.9 Hz), 7.35(1H,s), 8.14(1H,s), 8.56(1H,d,J=4.9 Hz). MS (FAB) m/z: 389 (M+H)$^+$, 333(M+H-isobutene)$^+$, 289 (M+H-Boc)$^+$.

Referential Example 238

1-(tert-Butoxycarbonyl)-4-[5-(pyridin-4-yl)thiazol-2-yl]piperazine

Diethyl ether and a saturated aqueous solution of sodium bicarbonate were added to 4-bromopyridine hydrochloride (3.76 g). The organic layer thus separated was dried over anhydrous sodium sulfate and concentrated under reduced pressure, whereby a diethyl ether solution of 4-bromopyridine was obtained. To the resulting solution were added (5-thiazolyl)trimethyltin (4.00 g), benzene (150 ml) and tetrakis(triphenylphosphine)palladium (950 mg), followed by heating under reflux for 12 hours. After allowed to cool down to room temperature, the reaction mixture was added with a saturated aqueous solution (100 ml) of sodium bicarbonate and ethyl acetate (50 ml). The water layer thus separated was extracted with ethyl acetate (2×50 ml) and methylene chloride (2×50 ml). The organic layers were combined, dried over anhydrous sodium sulfate and distilled under reduced pressure to remove the solvent. The residue was purified by chromatography on a silica gel column (methylene chloride:ethyl acetate=5:1→2:1), whereby 4-(5-thiazolyl)pyridine was obtained as a colorless, transparent oil. The resulting oil was dissolved in diethyl ether (80 ml), followed by the dropwise addition of n-butyl lithium (a 1.52N hexane solution, 11.5 ml) at −78° C. After stirring for 30 minutes, a carbon dioxide gas was blown into the reaction mixture. Ten minutes later, the temperature was increased gradually to room temperature. The reaction mixture was concentrated, whereby the residue of lithium 5-(pyridin-4-yl)thiazole-2-carboxylate was obtained as a colorless solid. To a solution of the resulting residue in N,N-dimethylformamide (50 ml) were added 1-(tert-butoxycarbonyl)piperazine (3.30 g), 1-hydroxybenzotriazole monohydrate (2.40 g) and 1-(3-dimethylaminopropyl)-3-ethylcarbodiimide hydrochloride (3.40 g) at room temperature. The resulting mixture was stirred for 3 days. Ethyl acetate (200 ml) and water (2000 ml) were added to the reaction mixture. The water layer thus separated was extracted with ethyl acetate (2×200 ml). The organic layers were combined, washed with water (1000 ml) and a saturated aqueous solution (400 ml) of sodium bicarbonate, dried over anhydrous sodium sulfate and distilled under reduced pressure to remove the solvent. The residue was reprecipitated in a methylene chloride—hexane system, whereby the title compound (3.00 g) was obtained as pale brown powder.

$^1$H-NMR (CDCl$_3$) δ: 1.49(9H,s), 3.57(4H,t,J=5.6 Hz), 3.79(2H,br s), 4.43(2H,br s), 7.49(2H,d,J=5.9 Hz), 8.17(1H, s), 8.69(2H,d,J=5.9 Hz). MS (FAB) m/z: 375 (M+H)$^+$, 319 (M+H-isobutene)$^+$, 275 (M+H-Boc)$^+$.

Referential Example 239

5-(Pyridin-4-yl)thiazole

In a 3M aqueous solution of potassium carbonate, 4-bromopyridine hydrochloride (389 mg) was suspended, followed by extraction with diethyl ether. The organic layer thus extracted with dried over anhydrous sodium sulfate and distilled under reduced pressure to remove the solvent. The residue was dissolved in benzene (20 ml), followed by the addition of 5-trimethylstannylthiazole (496 mg) (Synthesis, 198, 757) and tetrakis(triphenylphosphine)palladium (116 mg). In an argon gas stream, the resulting mixture was heated under reflux for 48 hours. The reaction mixture was concentrated under reduced pressure. The residue was purified by chromatography on a silica gel column (hexane ethyl acetate=3:1), whereby the title compound (293 mg) was obtained as a pale yellow oil.

$^1$H-NMR (CDCl$_3$) δ: 7.47(2H,dd,J=4.9,2.0 Hz), 8.27(1H, s), 8.65(2H,dd,J=4.9,2.0 Hz), 8.89(1H,s). MS (FAB) m/z: 163 (M+H)$^+$.

Referential Example 240

Lithium 5-(pyridin-4-yl)thiazole-2-carboxylate

In diethyl ether (20 ml) was dissolved 5-(pyridin-4-yl) thiazole (290 mg), followed by the dropwise addition of an n-hexane solution (1.54M, 1.20 ml) of n-butyl lithium at −78° C. The resulting mixture was stirred for 10 minutes. After a carbon dioxide gas was blown into the reaction mixture at −78° C. for 15 minutes, the reaction mixture was heated to room temperature. The reaction mixture was concentrated under reduced pressure, whereby the title compound (409 mg) was obtained as a pale brown foam.

$^1$H-NMR (DMSO-d$_6$) δ: 7.66(2H,d,J=5.4 Hz), 8.37(1H, s), 8.59(2H,d,J=5.4 Hz),. MS (FD) m/z: 213 (M+Li+H)$^+$.

Referential Example 241

5-(Pyridin-2-yl)thiazole

In the same manner as in Referential Example 239, the title compound was obtained.

$^1$H-NMR (CDCl$_3$) δ: 7.22(1H,t,J=5.9 Hz), 7.67–7.78(3H, m), 8.34(1H,s), 8.60(1H,d,J=4.9 Hz), 8.84(1H,s). MS (FAB) m/z: 163 (M+H)$^+$.

Referential Example 242

Lithium 5-(pyridin-2-yl)thiazole-2-carboxylate

In the same manner as in Referential Example 240, the title compound was synthesized.

$^1$H-NMR (DMSO-d$_6$) δ: 7.31(1H,m), 7.85(1H,t,J=7.8 Hz), 7.94(1H,d,J=7.8 Hz), 8.36(1H,s), 8.56(1H,d,J=4.4 Hz).

Referential Example 243

(5-tert-Butyldimethylsilyloxy-4-oxo-4H-pyran-2-yl) methyl chloride

Kojic acid (5.00 g) was dissolved in methylene chloride (300 ml). To the resulting solution were added N,N-dimethylformamide (0.03 ml) and thionyl chloride (3.08 ml) under ice cooling, followed by stirring overnight at room temperature. The reaction mixture was concentrated under reduced pressure. The residue was dissolved in tetrahydrofuran (600 ml). To the resulting solution were added triethylamine (19.51 ml), N,N-dimethylaminopyridine (0.20 g) and tert-butyldimethylsilyl chloride (7.95 g), followed by stirring at room temperature for 1 hour. The reaction mixture was concentrated under reduced pressure. Methylene chloride was added to the residue. The resulting mixture was washed successively with a 0.3N aqueous solution of hydrochloric acid, a saturated aqueous solution of sodium bicarbonate and saturated aqueous NaCl solution, dried over anhydrous sodium sulfate and distilled under reduced pressure to remove the solvent. The residue was purified by chromatography on a silica gel column (hexane ethyl acetate=8:1), whereby the title compound (6.10 g) was obtained as a pale brown oil.

$^1$H-NMR (CDCl$_3$) δ: 0.23(6H,s), 0.95(9H,s), 4.30(2H,s), 6.43(1H,s), 7.67(1H,s). MS (FAB) m/z: 275 (M+H)$^+$.

Referential Example 244

[(5-tert-Butyldimethylsilyloxy-4-oxo-4H-pyran-2-yl)methyl]amine

In N,N-dimethylformamide (20 ml) was dissolved (5-tert-butyldimethylsilyloxy-4-oxo-4H-pyran-2-yl)methyl chloride (2.00 g). Sodium azide (1.00 g) was added to the resulting solution and the resulting mixture was stirred overnight at room temperature. The reaction mixture was concentrated under reduced pressure. Ethyl acetate was added to the residue, followed by washing once with water and then once with saturated aqueous NaCl solution. The organic layer thus extracted was dried over anhydrous sodium sulfate and distilled under reduced pressure to remove the solvent. The resulting residue was dissolved in methanol (100 ml), followed by the addition of 10% palladium-carbon (50% wet w/w, 800 mg). The resulting mixture was stirred overnight under a hydrogen gas stream of normal pressure. The reaction mixture was subjected to Celite filtration, the filtrate was concentrated under reduced pressure and the residue was purified by chromatography on a silica gel column (methylene chloride methanol=100:3), whereby the title compound (290 mg) was obtained as a colorless oil.

$^1$H-NMR (CDCl$_3$) δ: 0.23(6H,s), 0.95(9H,s), 3.68(2H,s), 6.35(1H,s), 7.64(1H,s). MS (FAB) m/z: 256 (M+H)$^+$.

Referential Example 245

1-(tert-Butoxycarbonyl)-2-[N-[(5-tert-butyldimethylsilyloxy-4-oxo-4H-pyran-2-yl)methyl] carbamoyl]-4-[(5-chloroindol-2-yl)sulfonyl] piperazine In the same manner as in Referential Example 5, the title compound was obtained.

$^1$H-NMR (DMSO-d$_6$) δ: 0.15(6H,s), 0.91(9H,s), 1.30(9H, br s), 2.34–2.44(1H,m), 2.56–2.71(1H,m), 3.19–3.46(1H, m), 3.55–3.68(1H,m), 3.77–3.94(1H,m), 4.03–4.32(3H,m), 4.50–4.69(1H,m), 6.22(1H,br s), 7.00(1H,s), 7.32(1H,dd,J=8.8,2.0 Hz), 7.49(1H,d,J=8.8 Hz), 7.79(1H,d,J=2.0 Hz), 8.12 (1H,s), 8.66(1H,br s), 12.43(1H,s). MS (FAB) m/z: 681 [(M+H)$^+$, Cl$^{35}$], 683 [(M+H)$^+$, Cl$^{37}$].

Referential Example 246

1-(tert-Butoxycarbonyl)-4-[(5-chloroindol-2-yl) sulfonyl]-2-[N-[(5-hydroxy-4-oxo-4H-pyran-2-yl) methyl]carbamoyl]piperazine In tetrahydrofuran (10 ml) was dissolved 1-(tert-butoxycarbonyl)-2-[N-[(5-tert-butyldimethylsilylox-4-oxo-4H-pyran-2-yl)methyl]carbamoyl]-4-[(5-chloroindol-2-yl) sulfonyl]piperazine (570 mg), followed by the addition of a 1.0 M tetrahydrofuran solution (8.37 ml) of tetrabutylammonium fluoride. The resulting mixture was stirred at room temperature for 15 minutes. The reaction mixture was concentrated under reduced pressure. The residue was purified by chromatography on a silica gel column (methylene chloride:methanol=100:3), whereby the title compound (475 mg) was obtained as a pale yellow foam.

$^1$H-NMR (DMSO-d$_6$) δ: 1.31(9H,br s), 2.30–2.86(2H,m), 3.12–3.19(1H,m), 3.52–3.68(1H,m), 3.80–3.94(1H,m), 4.00–4.30(3H,m), 4.51–4.69(1H,m), 6.23(1H,br s), 7.00 (1H,s), 7.32(1H,dd,J=8.8,2.0 Hz), 7.49(1H,d,J=8.8 Hz), 7.79(1H,d,J=2.0 Hz), 8.01(1H,s), 8.68(1H,br s), 12.44(1H, br s). MS (FAB) m/z: 567 [(M+H)$^+$, Cl$^{35}$], 569 [(M+H)$^+$, Cl$^{37}$].

Referential Example 247

2-[N-[(5-Acetoxy-4-oxo-4H-pyran-2-yl)methyl] carbamoyl]-1-(tert-butoxycarbonyl)-4-[(5-chloroindol-2-yl)sulfonyl]piperazine In acetonitrile (10 ml) was dissolved 1-(tert-butoxycarbonyl)-4-[(5-chloroindol-2-yl)sulfonyl]-2-[N-[(5-hydroxy-4-oxo-4H-pyran-2-yl)methyl]carbamoyl] piperazine (411 mg), followed by the addition of acetic anhydride (0.075 ml) and triethylamine (0.11 ml). The resulting mixture was stirred at room temperature for 15 minutes. The reaction mixture was concentrated under reduced pressure. Methylene chloride was added to the residue. The resulting mixture was washed successively with 0.2N hydrochloric acid, a saturated aqueous solution of sodium bicarbonate and saturated aqueous NaCl solution. The organic layer was then dried over anhydrous sodium sulfate. The residue obtained by distilling off the solvent under reduced pressure was purified by chromatography on a silica gel column (methylene chloride:methanol=50:5), whereby the title compound (256 mg) was obtained as a colorless foam.

$^1$H-NMR (DMSO-d$_6$) δ: 1.32(9H,br s), 2.25(3H,s), 2.31–2.70(2H,m), 3.00(1H,br s), 3.63(1H,br s), 3.86(1H,br s), 4.01–4.33(3H,m), 4.52–4.70(1H,m), 6.30(1H,br s), 7.01 (1H,s), 7.32(1H,dd,J=8.8,2.0 Hz), 7.49(1H,d,J=8.8 Hz), 7.79(1H,d,J=2.0 Hz), 8.45(1H,s), 8.72(1H,br s), 12.44(1H, s). MS (FAB) m/z: 609 [(M+H)$^+$, Cl$^{35}$], 611 [(M+H)$^+$, Cl$^{37}$].

Referential Example 248

3-[N-[(5-Acetoxy-4-oxo-4H-pyran-2-yl)methyl] carbamoyl]-1-[(5-chloroindol-2-yl)sulfonyl] piperazine trifluoroacetate In methylene chloride (5 ml), 2-[N-[(5-acetoxy-4-oxo-4H-pyran-2-yl)methyl]carbamoyl]-1-(tert-butoxycarbonyl)-4-[(5-chloroindol-2-yl)sulfonyl]piperazine was treated with trifluoroacetic acid (5 ml), followed by concentration to dryness under reduced pressure, whereby the title compound (224 mg) was obtained.

$^1$H-NMR (DMSO-d$_6$) δ: 2.26(3H,s), 2.57–2.72(2H,m), 3.14–3.23(1H,m), 3.39(1H,d,J=11.7 Hz), 3.65(1H,d,J=11.7 Hz), 4.03–4.09(1H,m), 4.17–4.26(1H,m), 4.34–4.42(1H,m), 6.46(1H,s), 7.12(1H,s), 7.36(1H,dd,J=8.8,2.0 Hz), 7.52(1H, d,J=8.8 Hz), 7.82(1H,d,J=2.0 Hz), 8.50(1H,s), 9.42(1H,br s), 12.57(1H,s). MS (FAB) m/z: 509 [(M+H)$^+$, Cl$^{35}$], 511 [(M+H)$^+$, Cl$^{37}$].

Referential Example 249

N-[[1-[(5-Chloroindol-2-yl)sulfonyl]piperazin-3-yl] acetyl]methanesulfonamide trifluoroacetate In tetrahydrofuran (5 ml) was dissolved 1-(tert-butoxycarbonyl)-2-[(carboxy)methyl]-4-[(5-chloroindol-2-yl)sulfonyl]piperazine (772 mg), followed by the addition of carbonyldiimidazole (820 mg). The resulting mixture was heated under reflux for 1 hour. After cooling to room temperature, the reaction mixture was added with methanesulfonamide (322 mg) and 1,8-diazabicyclo[5.4.0]-7-undecene (0.50 ml), followed by stirring overnight. The reaction mixture was concentrated under reduced pressure. To the residue was added a 1N aqueous solution of hydrochloric acid. After removal of the supernatant, the precipitate was washed with water and dried, whereby a colorless foam was obtained. The substance was dissolved in methylene chloride (10 ml), followed by the addition of trifluoroacetic acid (10 ml). The resulting mixture was stirred at room temperature for 10 minutes. The reaction mixture was concentrated under reduced pressure. Diethyl ether was added to the residue and the precipitate thus obtained was collected by filtration, whereby the title compound (863 mg) was obtained as a colorless solid.

$^1$H-NMR (DMSO-d$_6$) δ: 2.53–2.74(3H,m), 3.25(3H,s), 3.43–3.50(2H,m), 3.61–3.80(4H,m), 7.10(1H,s), 7.34(1H, dd,J=8.8,2.0 Hz), 7.50(1H,d,J=8.8 Hz), 7.80(1H,d,J=2.0 Hz), 12.58(1H,s). MS (FAB) m/z: 435 [(M+H)$^+$, Cl$^{35}$], 437 [(M+H)$^+$, Cl$^{37}$].

Referential Example 250

1-(tert-Butoxycarbonyl)-4-[(6-chlorobenzo[b]thien-2-yl)sulfonyl]-2-(ethoxycarbonyl)piperazine In methylene chloride (200 ml) was dissolved 2-ethoxycarbonylpiperazine acetate (2.08 g), followed by the addition of triethylamine (3.63 ml). The resulting mixture was stirred overnight at room temperature. To the reaction mixture, a methylene chloride solution (20 ml) of 6-chloroenzo[b]thiophene-2-sulfonyl chloride (2.00 g) was slowly added dropwise over 2 hours. After stirring at room temperature for 30 minutes, di-tert-butyl dicarbonate (3.27 g) was added and the resulting mixture was stirred overnight at room temperature. The reaction mixture was concentrated under reduced pressure. Ethyl acetate was added to the residue and the resulting mixture was washed successively with 1N hydrochloric acid, a saturated aqueous solution of sodium bicarbonate and saturated aqueous NaCl solution. The organic layer thus extracted was dried over anhydrous sodium sulfate and distilled under reduced pressure to remove the solvent. The residue was purified by chromatography on a silica gel column (hexane:ethyl acetate=8:1), whereby the title compound (2.26 g) was obtained as a pale yellow foam.

$^1$H-NMR (CDCl$_3$) δ: 1.30(3H,t,J=7.3 Hz), 1.36–1.49(9H, m), 2.52(1H,td,J=11.7,3.4 Hz), 2.66–2.77(1H,m), 3.20–3.42 (1H,m), 3.68–3.82(1H,m), 3.87–4.08(1H,m), 4.17–4.40(1H, m), 4.68(½H,br s), 4.87(½H,br s), 7.43(1H,dd,J=8.3,2.0 Hz), 7.77(1H,s), 7.82(1H,d,J=8.3 Hz), 7.86(1H,d,J=2.0 Hz). MS (FAB) m/z: 489 [(M+H)$^+$, Cl$^{35}$], 491 [(M+H)$^+$, Cl$^{37}$].

Referential Example 251

1-(tert-Butoxycarbonyl)-4-[(6-chlorobenzo[b]thien-2-yl)sulfonyl]piperazine-2-carboxylic acid In tetrahydrofuran (10 ml) was dissolved 1-(tert-butoxycarbonyl)-4-[(6-chlorobenzo[b]thien-2-yl)sulfonyl]-2-(ethoxycarbonyl)piperazine (2.25 g), followed by the addition of ethanol (20 ml) and a 3N aqueous solution (3 ml) of sodium hydroxide. The resulting mixture was stirred at room temperature for 3 hours. The reaction mixture was concentrated under reduced pressure. The residue was adjusted to have pH of 1 to 2 by the addition of a 1N aqueous solution of hydrochloric acid. Ethyl acetate was then added and the organic layer was collected. The organic layer was dried over anhydrous sodium sulfate and distilled under reduced pressure to remove the solvent. The solid thus precipitated was collected by filtration, whereby the title compound (2.17 g) was obtained as a colorless solid.

$^1$H-NMR (CDCl$_3$) δ: 1.44(9H,s), 2.54(1H,dt,J=11.7,3.4 Hz), 2.69–2.79(1H,m), 3.20–3.44(1H,m), 3.70–3.84(1H,m), 3.89–4.12(1H,m), 4.30–4.41(1H,m), 4.78(½H,br s), 4.98 (½H,br s), 7.45(1H,dd,J=8.3,2.0 Hz), 7.79(1H,s), 7.83(1H, d,J=8.3 Hz), 7.88(1H,d,J=2.0 Hz). MS (FAB) m/z: 461 [(M+H)$^+$, Cl$^{35}$], 463 [(M+H)$^+$, Cl$^{37}$].

Referential Example 252

1-[(6-Chlorobenzo[b]thine-2-yl)sulfonyl]-3-[(N-methyl)carbamoyl]piperazine hydrochloride In N,N-dimethylformamide (50 ml) were dissolved 1-(tert-butoxycarbonyl)-4-[(6-chlorobenzo[b]thien-2-yl)sulfonyl]piperazine-2-carboxylic acid (691 mg), N-methylamine hydrochloride (111 mg), 1-hyroxybenzotriazole monohydrate (230 mg) and 1-(3-dimethylaminopropyl)-3-ethylcarbodiimide hydrochloride (345 mg). Triethylamine (0.23 ml) was added to the resulting solution, followed by stirring overnight at room temperature. The reaction mixture was concentrated under reduced pressure. Ethyl acetate was added to the residue, followed by washing with water. The organic layer was dried over anhydrous sodium sulfate. The solvent was distilled off under reduced pressure. The residue was purified by chromatography on a silica gel column (methylene chloride:methanol=100:1), whereby a pale yellow foam was obtained. The resulting foam was dissolved in a saturated hydrochloric acid/ethanol solution (10 ml) and the resulting solution was concentrated under reduced pressure. The solid thus precipitated was collected by filtration while being washed with ethyl acetate, whereby the title compound (468 mg) was obtained as a colorless solid.

$^1$H-NMR (DMSO-d$_6$) δ: 2.67(3H,d,J=4.4 Hz), 2.77(1H, t,J=11.2 Hz), 2.87(1H,t,J=11.2 Hz), 3.15–3.25(1H,m), 3.32–3.40(1H,m), 3.70(1H,d,J=12.7 Hz), 3.98–4.03(1H,m), 4.07–4.15(1H,m), 7.62(1H,dd,J=8.8,2.0 Hz), 8.11(1H,d,J= 8.8 Hz), 8.22(1H,s), 8.40(1H,d,J=2.0 Hz), 8.80(1H,d,J=4.4 Hz) MS (FAB) m/z: 374 [(M+H)$^+$, Cl$^{35}$], 376 [(M+H)$^+$, Cl$^{37}$].

Referential Example 253

Ethyl (piperazin-1-yl)acetate hydrochloride

In N,N-dimethylformamide (50 ml) was dissolved 1-(tert-butoxycarbonyl)piperazine (942 mg). After the addition of triethylamine (1.40 ml), ethyl bromoacetate (1.13 ml) was added, followed by stirring overnight at room temperature. The reaction mixture was concentrated under reduced pressure. Ethyl acetate was added to the residue and the mixture was washed with water. The organic layer was dried over anhydrous sodium sulfate. The solvent was distilled off under reduced pressure. The residue was purified by chromatography on a silica gel column (hexane:ethyl acetate= 3:1), whereby a colorless foam was obtained. The resulting substance was dissolved in a saturated hydrochloric acid—ethanol solution (10 ml) and the resulting solution was concentrated under reduced pressure. The solid thus precipitated was collected by filtration while being washed with ethyl acetate, whereby the title compound (841 mg) was obtained as a colorless solid.

$^1$H-NMR (DMSO-d$_6$) δ: 1.24(3H,t,J=7.3 Hz), 3.36(8H,br s), 4.08(2H,br s), 4.18(2H,q,J=7.3 Hz), 9.73(2H,br s). MS (FAB) m/z: 173 (M+H)$^+$.

In the same manner as in Referential Example 252, the compounds shown in Referential Examples 254 to 255 were synthesized.

Referential Example 254

Ethyl [4-[[1-[(6-chloronaphthalen-2-yl)sulfonyl] piperazin-3-yl]carbonyl]piperazin-1-yl]acetate hydrochloride $^1$H-NMR (DMSO-d$_6$) δ: 1.26(3H,t,J=7.3 Hz), 2.51–2.78 (1H,m), 2.90–4.32(17H,m), 4.79(1H,br s), 7.76(1H,dd,J= 8.8,2.0 Hz), 7.90(1H,d,J=8.8 Hz), 8.22(1H,d,J=8.8 Hz), 8.29 (1H,s), 8.32(1H,d,J=8.8 Hz), 8.63(1H,s), 8.90(1H,br s). MS (FAB) m/z: 509 [(M+H)$^+$, Cl$^{35}$], 511 [(M+H)$^+$, Cl$^{37}$].

Referential Example 255

5-[[[[1-[(6-Chloronaphthalen-2-yl)sulfonyl] piperazin-3-yl]carbonyl]amino]methyl]tetrazole triflubroacetate $^1$H-NMR (DMSO-d$_6$) δ: 2.53–2.68(2H,m), 3.15–3.23 (1H,m), 3.30–3.37(1H,m), 3.68–3.76(1H,m), 4.12–4.20(2H, m), 4.65–4.68(2H,m), 7.76(1H,dd,J=8.8,2.0 Hz), 7.86(1H, dd,J=8.8,2.0 Hz), 8.26(1H,d,J=8.8 Hz), 8.30–8.34(2H,m), 8.56(1H,s), 9.51–9.59(1H,m). MS (FAB) m/z: 435 [(M+H)$^+$, Cl$^{35}$], 437 [(M+H)$^+$, Cl$^{37}$].

Referential Example 256

1-(tert-Butoxycarbonyl)-4-[(6-chloronaphthalen-2-yl)sulfonyl]piperazin-2-yl]acetic hydrazinamide In tetrahydrofuran (20 ml) was dissolved 1-[1-(tert-butoxycarbonyl)-4-[(6-chloronaphthalen-2-yl)sulfonyl]piperazin-2-yl]acetic acid (1.11 g). To the resulting solution, N-methylmorpholine (0.26 ml) and isobutyl chloroformate (0.31 ml) were successively added dropwise at −20° C. After stirring at −20° C. for 10 minutes, hydrazine hydrate (690 ml) was added. The reaction mixture was concentrated under reduced pressure. The residue was dissolved in ethyl acetate. The resulting solution was washed with a 1N aqueous solution of hydrochloric acid, saturated sodium bicarbonate and saturated aqueous NaCl solution, each once. The organic layer was dried over anhydrous sodium sulfate and distilled under reduced pressure to remove the solvent. The residue was purified by chromatography on a silica gel column [methylene chloride:methanol=100:0 to 100:1], whereby the title compound (513 mg) was obtained as a colorless foam.

$^1$H-NMR (DMSO-$d_6$) δ: 1.31(9H,s), 2.14–2.38(3H,m), 3.00–3.12(1H,m), 3.57–3.68(2H,m), 3.83–3.90(1H,m), 4.16 (2H,br s), 4.51(1H,br s), 7.70(1H,dd,J=8.8,2.0 Hz), 7.78(1H, d,J=8.8 Hz), 8.15(1H,d,J=8.8 Hz), 8.23(1H,s), 8.25(1H,d,J= 8.8 Hz), 8.47(1H,s), 9.08(1H,s). MS (FAB) m/z: 483 [(M+H)$^+$, Cl$^{35}$], 485 [(M+H)$^+$, Cl$^{37}$].

Referential Example 257

2-[[1-[(6-Chloronaphthalen-2-yl)sulfonyl]piperazin-3-yl]methyl]-4,5-dihydro-5-oxo-1,3,4-oxadiazole trifluoroacetate In tetrahydrofuran (2 ml) was dissolved [1-(tert-butoxycarbonyl)-4-[(6-chloronaphthalen-2-yl)sulfonyl]piperazin-2-yl]acetic hydrazinamide (505 mg), followed by the addition of carbonyl diimidazole (102 mg) and triethylamine (0.14 ml). The resulting mixture was stirred at room temperature for 30 minutes. The reaction mixture was concentrated under reduced pressure. Methylene chloride was added to the residue. The resulting mixture was washed with a 1N aqueous solution of hydrochloric acid, water and saturated aqueous NaCl solution, each once. The organic layer so extracted was dried over anhydrous sodium sulfate and distilled under reduced pressure to remove the solvent. The residue was purified by chromatography on a silica gel column (methylene chloride:methanol=100:0 to 100:1), whereby a colorless foam was obtained. The resulting substance was dissolved in methylene chloride (2 ml), followed by the addition of trifluoroacetic acid (5 ml). After stirring at room temperature for 1 minute, the reaction mixture was concentrated under reduced pressure. The residue was washed with diethyl ether. The precipitate thus obtained was collected by filtration, whereby the title compound (412 mg) was obtained as a colorless foam.

$^1$H-NMR (DMSO-$d_6$) δ: 2.60–2.79(2H,m), 2.85(1H,dd, J=16.1,6.8 Hz), 3.03(1H,dd,J=16.1,6.8 Hz), 3.20(1H,d,J= 10.2 Hz), 3.43(1H,d,J=12.7 Hz), 3.71(1H,d,J=11.2 Hz), 3.90 (1H,d,J=11.2 Hz), 7.74(1H,dd,J=8.8,2.0 Hz), 7.86(1H,dd,J= 8.8,2.0 Hz), 8.21(1H,d,J=8.8 Hz), 8.27(1H,s), 8.28(1H,d,J= 8.8 Hz), 8.55(1H,s), 12.30(1H,s). MS (FAB) m/z: 409 [(M+H)$^+$, Cl$^{35}$], 411 [(M+H)$^+$, Cl$^{37}$].

Referential Example 258

1-(tert-Butoxycarbonyl)-4-[(6-chloronaphthalen-2-yl)sulfonyl]-2-(2-hydroxylethyl)piperazine In tetrahydrofuran(100 ml) was dissolved 1-[1-(tert-butoxycarbonyl)-4-[(6-chloronaphthalen-2-yl)sulfonyl] piperazin-2-yl]acetic acid (2.00 g). The resulting solution was successively added dropwise with N-methylmorpholine (0.51 ml) and isobutyl chloroformate (0.64 ml) at −20° C. After stirring at −20° C. for 10 minutes, sodium borohydride (483 mg) and methanol (20 ml) were added successively to the reaction mixture. The resulting mixture was stirred for 10 minutes. After concentration under reduced pressure, the residue was dissolved in ethyl acetate. The resulting solution was washed with a 1N aqueous solution of hydrochloric acid, a saturated aqueous solution of sodium bicarbonate and saturated aqueous NaCl solution, each once. The organic layer was dried over anhydrous sodium sulfate and distilled under reduced pressure to remove the solvent. The residue was purified by chromatography on a silica gel column (methylene chloride:methanol 100:0 to 100:3), whereby the title compound (1.75 g) was obtained as a colorless foam.

$^1$H-NMR (CDCl$_3$) δ: 1.40(9H,s), 1.72–1.85(1H,m), 2.08–2.18(1H,m), 2.33(1H,dt,J=11.7,3.4 Hz), 2.50–2.59 (1H,m), 3.07(1H,dt,J=3.4,12.7 Hz), 3.25–3.42(1H,m), 3.60–3.78(3H,m), 3.90–3.98(1H,m), 4.37–4.44(1H,m), 7.58 (1H,dd,J=8.8,2.0 Hz), 7.74(1H,dd,J=8.8,2.0 Hz), 7.88–7.95 (3H,m), 8.29(1H,s). MS (FAB) m/z: 455 [(M+H)$^+$, Cl$^{35}$], 457 [(M+H)$^+$, Cl$^{37}$].

Referential Example 259

2-(2-Bromoethyl)-1-(tert-butoxycarbonyl)-4-[(6-chloronaphthalen-2-yl)sulfonyl]piperazine In methylene chloride (50 ml) was dissolved 1-(tert-butoxycarbonyl)-4-[(6-chloronaphthalen-2-yl)sulfonyl]-2-(2-hydroxylethyl)piperazine (1.00 g), followed by the addition of carbon tetrabromide (1.46 g) and triphenylphosphine (1.15 g). The resulting mixture was stirred at room temperature for 30 minutes. After the addition of a saturated aqueous solution of sodium sulfite, the organic layer was collected from the mixture. The organic layer was dried over anhydrous sodium sulfate and then distilled under reduced pressure to remove the solvent. The residue was purified by chromatography on a silica gel column [hexane:ethyl acetate=10:1 to 6:1], whereby the title compound (990 mg) was obtained as a colorless foam.

$^1$H-NMR (CDCl$_3$) δ: 1.41(9H,s), 2.20–2.41(3H,m), 2.44 (1H,dd,J=12.2,3.9 Hz), 3.04–3.15(1H,m), 3.43(1H,br s), 3.68(1H,d,J=12.2 Hz), 3.77(1H,d,J=10.7 Hz), 3.95–4.15 (1H,m), 4.46(1H,br s), 7.58(1H,dd,J=8.8,2.0 Hz), 7.74(1H, dd,J=8.8,2.0 Hz), 7.87–7.94(3H,m), 8.29(1H,s). MS (FAB) m/z: 518 [(M+H)$^+$, Cl$^{35}$], 520 [(M+H)$^+$, Cl$^{37}$].

Referential Example 260

1-(tert-Butoxycarbonyl)-4-[(6-chloronaphthalen-2-yl)sulfonyl]-2-(2-cyanoethyl)piperazine In N,N-dimethylformamide (20 ml) was dissolved 2-(2-bromoethyl)-1-(tert-butoxycarbonyl)-4-[(6-chloronaphthalen-2-yl)sulfonyl]piperazine (980 mg), followed by the addition of sodium cyanide (102 mg). The resulting mixture was stirred overnight at room temperature. The reaction mixture was concentrated under reduced pressure. Ethyl acetate was added to the residue and the resulting mixture was washed with water and saturated aqueous NaCl solution, each once. The organic layer thus extracted was dried over anhydrous sodium sulfate and distilled under reduced pressure to remove the solvent, whereby the title compound (842 mg) was obtained as a colorless foam.

$^1$H-NMR (CDCl$_3$) δ: 1.41(9H,s), 1.92–2.03(1H,m), 2.21–2.44(4H,m), 2.48(1H,dd,J=11.7,3.9 Hz), 3.13(1H,br s), 3.68(1H,d,J=11.7 Hz), 3.77(1H,d,J=11.7 Hz), 4.09(1H,br s), 4.38(1H,br s), 7.58(1H,dd,J=8.8,2.0 Hz), 7.73(1H,dd,J=8.8,2.0 Hz),7.88–7.95(3H,m), 8.29(1H,s). MS (FAB) m/z: 464 [(M+H)$^+$, Cl$^{35}$], 466 [(M+H)$^+$, Cl$^{37}$].

Referential Example 261

5-[2-[1-[(6-Chloronaphthalen-2-yl)sulfonyl] piperazin-3-yl]ethyl]tetrazole

In N,N-dimethylformamide (1.5 ml) was dissolved 1-(tert-butoxycarbonyl)-4-[(6-chloronaphthalen-2-yl) sulfonyl]-2-(2-cyanoethyl)piperazine (529 mg), followed by the addition of ammonium chloride (588 mg) and sodium azide (741 mg). The resulting mixture was stirred under heating at 100° C. The reaction mixture was concentrated under reduced pressure. Ethyl acetate was added to the residue and the resulting mixture was washed with water and saturated aqueous NaCl solution, each once. The organic layer thus extracted was dried over anhydrous sodium sulfate and distilled under reduced pressure to remove the solvent. The residue was purified by chromatography on a silica gel column (methylene chloride:methanol=50:1), whereby a colorless foam was obtained. The resulting substance was dissolved in methylene chloride (5 ml), followed by the addition of trifluoroacetic acid (5 ml). The mixture was stirred at room temperature for 1 minutes. The reaction mixture was concentrated under reduced pressure. The precipitate thus obtained was washed with diethyl ether and collected by filtration, whereby the title compound (141 mg) was obtained as a colorless solid.

$^1$H-NMR (DMSO-d$_6$) δ: 1.95–2.08(2H,m), 2.45–2.70 (2H,m), 2.98–3.22(3H,m), 3.35–3.51(2H,m), 3.62–3.88(2H, m), 7.75(1H,d,J=8.8 Hz), 7.88(1H,d,J=8.8 Hz), 8.20(1H,d, J=8.8 Hz), 8.27(1H,s), 8.29(1H,d,J=8.8 Hz), 8.56(1H,s). MS (FAB) m/z: 407 [(M+H)$^+$, Cl$^{35}$], 409 [(M+H)$^+$, Cl$^{37}$].

In the same manner as in Example A-4, the compounds shown in Referential Examples 262 and 263 were obtained.

Referential Example 262

1-(tert-Butoxycarbonyl)-4-[(5-chloroindol-2-yl) sulfonyl]-2-[(N-methylcabamoyl)methyl]piperazine $^1$H-NMR (CDCl$_3$) δ: 1.40(9H,s), 2.34–2.45(1H,br), 2.50–2.63(1H,br), 2.63–2.80(2H,br), 2.83(3H,d,J=4.6 Hz), 2.98–3.10(1H,m), 3.65–4.15(3H,br), 4.62(1H,br s), 6.05–6.25(1H,br), 6.97(1H,d,J=1.7 Hz), 7.29(1H,dd,J=8.8, 1.7 Hz), 7.40(1H,d,J=8.8 Hz), 7.66(1H,d,J=1.7 Hz). MS (FAB) m/z: 471 [(M+H)$^+$, Cl$^{35}$], 473 [(M+H)$^+$, Cl$^{37}$].

Referential Example 263

1-(tert-Butoxycarbonyl)-4-[(5-chloroindol-2-yl) sulfonyl]-2-[[N-(tetrahydrofurfuryl)carbamoyl] methyl]piperazine $^1$H-NMR (CDCl$_3$) δ: 1.42(9H,s), 1.50–1.70(1H,m), 1.85–2.10(3H,m), 2.25–2.35(1H,br), 2.50–2.85(3H,br), 2.89–3.20(2H,m), 3.25–3.50(1H,br), 3.55–4.17(6H,m), 4.57 (1H,br s), 6.29(1H,br s), 6.90–6.97(1H,m), 7.21–7.38(2H, m), 7.60–7.68(1H,m). MS (FAB) m/z: 541 [(M+H)$^+$, Cl$^{35}$], 543 [(M+H)$^+$, Cl$^{37}$].

Referential Example 264

1,4-Dibenzyl-2-(2-formylmethyl)piperazine

In methylene chloride (30 mL) was dissolved 1,4-dibenzyl-2-(2-hydroxyethyl)piperazine (620 mg), followed by the addition of 4-methylmorpholine N-oxide (281 mg) and tetrapropylammonium perruthenate (141 mg) under ice cooling. Ten minutes later, the resulting mixture was allowed to rise back to room temperature, followed by stirring. After 18 hours, the solvent was distilled off under reduced pressure. The residue was purified by chromatography on a silica gel column (ethyl acetate hexane=1:1), whereby the title compound (360 mg) was obtained as a colorless oil.

$^1$H-NMR (CDCl$_3$) δ: 2.33–2.82(8H,m), 3.13(1H,brs), 3.34(1H,d,J=13.2 Hz), 3.48(2H,ABq,J=13.2 Hz), 3.81(1H, d,J=13.2 Hz), 7.29(10H,m), 9.81(1H,s). MS (FAB) m/z: 309 [(M+H)$^+$].

Referential Example 265

1,4-Dibenzyl-2-[2-(1-piperidinyl)ethyl]piperazine

In methanol (10 mL) were dissolved 1,4-dibenzyl-2-(formylmethyl)piperazine (600 mg) and piperidine (200 mg). After stirring for 30 minutes, the solvent was concentrated under reduced pressure. The concentrate was dissolved in methanol (10 mL), followed by the addition of sodium borohydride (147 mg). The resulting mixture was stirred. Five hours later, the solvent was distilled off under reduced pressure. Chloroform was added to the residue and the mixture was washed with a saturated aqueous solution of sodium bicarbonate. The organic layer was dried over anhydrous magnesium sulfate and distilled under reduced pressure to remove the solvent. The residue was purified by chromatography on a silica gel column (methylene chloride:methanol=10:1→5:1), whereby the title compound (640 mg) was obtained as a colorless oil.

$^1$H-NMR (CDCl$_3$) δ: 1.42(2H,m), 1.57(4H,m), 1.85(2H, m), 2.22–2.70(13H,m), 3.22(1H,d,J=13.5 Hz), 3.46(2H, Abq,J=13.0 Hz), 3.99(1H,d,J=13.2 Hz), 7.30(10H,m). MS (FAB) m/z: 378 [(M+H)$^+$].

Referential Example 266

1-[(5-Chloro-1-phenylsulfonylindol-2-yl)sulfonyl]-3-[2-(1-piperidinyl)ethyl]piperazine To 1,4-dibenzyl-2-[2-(1-piperidinyl)ethyl]piperazine (740 mg) was added 10% palladium-carbon (100 mg). The resulting mixture was dissolved in acetic acid (5.0 ml), followed by stirring under a hydrogen gas stream of 1 atmospheric pressure. Twenty hours later, the palladium was filtered off and the filtrate was concentrated under reduced pressure. The resulting residue was dissolved in methylene chloride (10 mL), followed by the addition of triethylamine (595 mg). To the resulting mixture, 5-chloro-1-phenylsulfonylindol-2-sulfonyl chloride (765 mg) was added dropwise over 90 minutes and stirring was continued at room temperature. After 19 hours, chloroform was added and the resulting mixture was washed with a saturated aqueous solution of sodium bicarbonate. The organic layer was dried over anhydrous magnesium sulfate and distilled under reduced pressure to remove the solvent. The residue was purified by chromatography on a silica gel column (methylene chloride:methanol:isopropylamine=500:75:1), whereby the title compound (335 mg) was obtained as a colorless oil.

$^1$H-NMR (CDCl$_3$) δ: 1.46–1.86(8H,m), 2.50–3.19(11H, m), 3.74(2H,m), 7.13–7.57(6H,m), 7.99(1H,d,J=9.5 Hz), 8.02(1H,d,J=8.3 Hz), 8.22(1H,d,J=9.0 Hz). MS (FAB) m/z: 551 [(M+H)$^+$].

Referential Example 267

1,4-Dibenzyl-2-[2-(2-methoxyethyl)aminoethyl] piperazine

In the same manner as in Referential Example 265, the title compound was obtained.

¹H-NMR (CDCl₃) δ: 1.84(2H,m), 2.22(3H,m), 2.51–2.81 (8H,m), 3.23(1H,d,J=14.4 Hz), 3.35(3H,s), 3.41–3.52(4H, m), 4.02(1H,d,J=13.2 Hz), 7.30(10H,m). MS (FAB) m/z: 368 (M+H)⁺.

Referential Example 268

2-[2-[N-(tert-Butoxycarbonyl)-(2-methoxyethyl) amino]ethyl]-1,4-dibenzyl-piperazine To 1,4-dibenzyl-2-[2-[(2-methoxyethyl)amino]ethyl] piperazine (540 mg) was added di-tert-butyl dicarbonate (353 mg). The resulting mixture was dissolved in methylene chloride (10 mL), followed by the addition of triethylamine (223 mg). After stirring for 3 days, the reaction was terminated. The solvent was concentrated under reduced pressure. The residue was purified by chromatography on a silica gel column (methylene chloride:methanol=100:1), whereby the title compound (610 mg) was obtained as a colorless oil.

¹H-NMR (CDCl₃) δ: 1.40(9H,s), 1.87(2H,m), 2.21(3H, m), 2.53(2H,m), 2.68(2H,m), 3.22–3.52(9H,m), 3.29(3H,s), 4.03(1H,d,J=13.5 Hz), 7.30(10H,m). MS (FAB) m/z: 468 [(M+H)⁺].

Referential Example 269

3-[2-[N-(tert-Butoxycarbonyl)-N-(2-methoxyethyl) amino]ethyl]-1-[(5-chloro-1-phenylsulfonylindol-2-yl)sulfonyl]piperazine To 2-[2-[N-(tert-butoxycarbonyl)-2-methoxyethyl) amino]ethyl]-1,4-dibenzyl-piperazine (610 mg) was added 10% palladium-carbon (100 mg). The resulting mixture was dissolved in methanol (10 mL), followed by stirring under a hydrogen gas stream of 1 atmospheric pressure. After 3 days, palladium was filtered off and the solvent was concentrated under reduced pressure. The residue was dissolved in methylene chloride (10 mL), followed by the addition of triethylamine (390 mg). To the resulting mixture, 5-chloro-1-phenylsulfonylindole-2-sulfonyl chloride (503 mg) was added dropwise over 30 minutes. Stirring was continued at room temperature. After 22 hours, chloroform was added and the resulting mixture was washed with a saturated aqueous solution of sodium bicarbonate. The organic layer was dried over anhydrous sodium sulfate and distilled under reduced pressure to remove the solvent. The residue was purified by chromatography on a silica gel column (methylene chloride:methanol=25:1), whereby the title compound (490 mg) was obtained as a colorless oil.

¹H-NMR (CDCl₃) δ: 1.45(9H,s), 1.46–3.76(15H,m), 3.31 (3H,s), 7.21–7.56(6H,m), 8.01(2H,d,J=7.4 Hz), 8.22(1H,d, J=9.1 Hz). MS (FAB) m/z: 641 [(M+H)⁺].

Referential Example 270

Ethyl 5-hydrazino-3-(pyridin-4-yl)-1,2,4-triazine-6-carboxylate

At room temperature, ethyl 2,5-dihydro-5-oxo-3-(pyridin-4-yl)-1,2,4-triazine-6-carboxylate (246 mg) was added to phosphorus oxychloride (3 ml) in one portion, followed by stirring for 5 minutes. The reaction mixture was then heated to 90° C. and stirred for 6 hours. After completion of the reaction, the solvent was distilled off. The residue was successively added with ice water, a saturated aqueous solution of sodium bicarbonate and diethyl ether. The organic layer thus separated was dried over anhydrous magnesium sulfate. The desiccant was removed by filtration. To the filtrate was added dioxane (50 ml), followed by cooling to 0° C. Hydrazine monohydrate (146 μl) was added and the mixture was stirred for 1 minute. The solvent was distilled off and water was added to the residue. The pale yellow powder thus precipitated was collected by filtration and dried, whereby the title compound (52 mg) was obtained.

¹H-NMR (DMSO-d₆) δ: 1.36(3H,t,J=7.3 Hz), 4.41(2H,q, J=7.3 Hz), 5.32(2H,br), 8.35(2H,br s), 8.81(2H,d,J=6.4 Hz), 9.61(1H,br). MS (FAB) m/z: 261 (M+H)⁺.

Referential Example 271

Ethyl 3-(pyridin-4-yl)-1,2,4-triazine-6-carboxylate

In ethanol (5 ml) was suspended ethyl 5-hydrazino-3-(pyridin-4-yl)-1,2,4-triazine-6-carboxylate (50 mg). To the resulting suspension, mercury (II) oxide (98 mg) was added and the resulting mixture was heated under reflux for 9 hours. After completion of the reaction, the insoluble matter was removed through Celite filtration. The filtrate was concentrated and the concentrate was separated into layers by the addition of ethyl acetate and water. The organic layer thus obtained was dried over anhydrous magnesium sulfate. The filtrate was concentrated, whereby a crudely purified product of the title compound (23 mg, pale yellow powder) was obtained.

¹H-NMR (CDCl₃) δ: 1.52(3H,t,J=7.3 Hz), 4.61(2H,q,J= 7.3 Hz), 8.45(2H,d,J=6.4 Hz), 8.89(2H,d,J=6.4 Hz), 9.33 (1H,s). MS (FAB) m/z: 231 (M+H)⁺.

Referential Example 272

Ethyl bromo(pyridin-4-yl)acetate hydrochloride

At room temperature, ethyl pyridin-4-ylacetate (5.00 g) was dissolved in acetic acid (100 ml), followed by the addition of a saturated acetic acid solution (50 ml) of hydrogen bromide. Bromine (1.56 ml) was slowly added dropwise to the resulting mixture. After stirring at room temperature for 1 hour, the reaction mixture was concentrated. Acetone was added to the concentrate. Colorless powder was collected by filtration, followed by drying. The resulting powder was extracted with ethyl acetate and a saturated aqueous solution of sodium bicarbonate. The organic layer was dried over anhydrous sodium sulfate and the filtrate was concentrated. The residue was purified by chromatography on a silica gel column (hexane:ethyl acetate=1:1), followed by the addition of 1N hydrochloric acid (in ethanol) to make the mixture acidic. The acidified solution was concentrated, whereby the title compound (colorless powder, 2.68 g) was obtained.

¹H-NMR (DMSO-d₆) δ: 1.20(3H,t,J=7.3 Hz), 4.15–4.30 (2H,m), 6.28–6.29(1H,m), 8.01(2H,d,J=6.4 Hz), 8.92(2H,d, J=6.4 Hz). MS (FAB) m/z: 244 [(M+H)⁺, Br⁷⁹], 246 [(M+H)⁺, Br⁸¹].

Referential Example 273

Ethyl (pyridin-4-yl)glyoxylate hydrate

Ethyl bromo(pyridin-4-yl)acetate hydrochloride (2.05 g) was dissolved in N,N-dimethylformamide (10 ml) at room temperature, followed by the addition of sodium azide (1.43 g). The resulting mixture was stirred for 30 minutes. After the addition of water and stirring, the insoluble matter was filtered off and the filtrate was concentrated. The residue was extracted with diethyl ether and saturated aqueous NaCl solution. The organic layer thus obtained was dried over anhydrous magnesium sulfate. The filtrate was concentrated and the residue was crystallized from methylene chloride, whereby the title compound (yellow powder, 300 mg) was obtained.

$^1$H-NMR (DMSO-d$_6$) δ: 1.10(3H,t,J=7.3 Hz), 4.05(2H,d, J=7.3 Hz), 7.22(2H,s), 7.48(2H,d,J=5.9 Hz), 8.56(2H,d,J= 6.4 Hz). MS (EI) m/z: 198 (M+18)$^+$, 179 M$^+$.

Referential Example 274

Ethyl 2,5-dihydro-5-oxo-6-(pyridin-4-yl)-1,2,4-triazine-3-carboxylate

Ethyl thiooxamate (172 mg) was suspended in ethanol (5 ml) at 0° C., followed by the addition of hydrazine monohydrate (63 μl). While the resulting gas was suctioned, the resulting mixture was stirred for 30 minutes. Ethyl (pyridin-4-yl)glyoxylate hydrate (254 mg) was added to the reaction mixture and the mixture was stirred at room temperature for 30 minutes. After heating under reflux for 4 hours, the reaction mixture was concentrated. The yellow powder thus precipitated was collected by filtration and dried, whereby the title compound (140 mg) was obtained.

$^1$H-NMR (DMSO-d$_6$) δ: 1.36(3H,t,J=7.3 Hz), 4.42(2H,d, J=7.3 Hz), 8.08(2H,d,J=4.9 Hz), 8.74(2H,br s). MS (FAB) m/z: 247 (M+H)$^+$.

Referential Example 275

2,5-Dihydro-5-oxo-6-(pyridin-4-yl)-1,2,4-triazine-3-carboxylic acid

In the same manner as in Referential Example 11, the title compound was synthesized.

$^1$H-NMR (DMSO-d$_6$ with one drop of TFA) δ: 8.65(2H, d,J=5.4 Hz), 8.88(1H,s), 9.00(2H,d,J=5.4 Hz).

Referential Example 276

1-(4-Bromophenylsulfonyl)-4-(tert-butoxycarbonyl) piperazine

Diisopropylethylamine (4.00 ml) was added to a solution of 4-bromobenzenesulfonyl chloride (3.00 g) and 1-(tert-butoxycarbonyl)piperazine (2.40 g) in methylene chloride (50 ml) at room temperature. After stirring at room temperature for 30 minutes, the reaction mixture was concentrated under reduced pressure. The residue thus obtained was purified by chromatography on a silica gel column (hexane:ethyl acetate=4:1→1:1), followed by reprecipitation in a hexane—methylene chloride system, whereby the title compound (4.47 g) was obtained as a colorless solid.

$^1$H-NMR (CDCl$_3$) δ: 1.41(9H,s), 2.97(4H,t,J=5.1 Hz), 3.51(4H,t,J=5.1 Hz), 7.61(2H,d,J=8.8 Hz), 7.69(2H,d,J=8.8 Hz). MS (FAB) m/z: 405 [(M+H)$^+$, Br$^{79}$], 407 [(M+H)$^+$, Br$^{81}$], 349 [(M+H-isobutene)$^{+, Br79}$], 351 [(M+H-isobutene)$^{+, Br81}$], 305 [(M+H-isobutene-CO$_2$)$^{+, Br79}$], 307 [(M+H-isobutene-CO$_2$)$^{+, Br81}$].

Referential Example 277

1-(tert-Butoxycarbonyl)-4-[4-(pyridin-4-yl) benzenesulfonyl]piperazine

To a solution of 1-(4-bromobenzenesulfonyl)-4-(tert-butoxycarbonyl)piperazine (1.00 g) in tetrahydrofuran (50 ml) were added diethyl(pyridin-4-yl)boron (470 mg), tetrabutylammonium bromide (480 mg), potassium hydroxide (625 mg), tetrakistriphenylphosphine palladium (285 mg) and water (800 μl) at room temperature. The resulting mixture was heated under reflux for 1 hour. After allowed to cool down, the reaction mixture was added with ethyl acetate (50 ml) and water (100 ml). The water layer thus separated was extracted with ethyl acetate (50 ml). The organic layers were combined, washed with saturated aqueous NaCl solution (50 ml), dried over anhydrous sodium sulfate and distilled under reduced pressure to remove the solvent. The residue was purified by chromatography on a silica gel column (methylene chloride:ethyl acetate=1:1), whereby the title compound (540 mg) was obtained as a colorless transparent viscous substance.

$^1$H-NMR (CDCl$_3$) δ: 1.41(9H,s), 3.04(4H,t,J=5.0 Hz), 3.54(4H,t,J=5.0 Hz), 7.52(2H,d,J=5.9 Hz), 7.79(2H,d,J=8.8 Hz), 7.87(2H,d,J=8.8 Hz), 8.74(2H,d,J=5.9 Hz).

Referential Example 278

1-[(6-Chlorobenzo[b]thien-2-yl)sulfonyl]-3-(2-methylpropyl)piperazine

To a methylene chloride solution (30 ml) of 2-(2-methylpropyl)piperazine hydrochloride (353 mg) were added 6-chlorobenzo[b]thiophene-2-sulfonyl chloride (438 mg) and triethylamine (498 mg). The resulting mixture was stirred at room temperature for 3 hours. Distilled water and methylene chloride were added. The water layer thus obtained was extracted three times with methylene chloride. The organic layers were combined, dried over anhydrous sodium sulfate and distilled under reduced pressure to remove the solvent. The residue was subjected to chromatography on a silica gel column (methanol methylene chloride=1:100), whereby the title compound (363 mg) was obtained as a pale yellow oil.

$^1$H-NMR (CDCl$_3$) δ: 0.78–0.94(0.5H,m), 1.16–1.34 (0.5H,m), 1.40–1.54(1H,m), 1.70(3H,s), 1.71(3H,s), 2.24 (1H,t,J=11.2 Hz), 2.55(1H,dt,J=3.4,11.2 Hz), 2.92–3.08(2H, m), 3.52–3.62(2H,m), 3.65–3.74(1H,m), 4.92(1H,d,J=8.3 Hz), 7.43(1H,dd,J=8.8,2.0 Hz), 7.74(1H,s), 7.81(1H,d,J=8.8 Hz), 7.85(1H,d,J=2.0 Hz). MS (FAB) m/z: 383 [(M+H)$^+$, Cl$^{35}$], 385 [(M+H)$^+$, Cl$^{37}$].

Referential Example 279

1-[(5-Bromopyrimidin-2-yl)carbonyl]-4-[(6-chlorobenzo[b]thiophen-2-yl)sulfonyl]-2-(2-methylpropyl)piperazine To an N,N-dimethylformamide solution (60 ml) of 1-[(6-chlorobenzo[b]thiophen-2-yl)sulfonyl]-3-(2-methylpropyl) piperazine (2.55 mg) were added bromo-tris-pyrrolidino-phosphonium hexafluorophosphate (607 mg, 1.17 mmol), (4-bromopyrimidin-2-yl)carboxylic acid (237 mg) and triethylamine (118 mg), followed by stirring at room temperature for 13 hours. After completion of the reaction, the solvent was distilled off under reduced pressure. Distilled water and methylene chloride were added to the residue. The water layer thus obtained was extracted three times with methylene chloride. The organic layers were combined and washed with distilled water. After drying over anhydrous magnesium sulfate, the solvent was distilled under off under reduced pressure. The residue was subjected to chromatography on a silica gel column (methanol:methylene chloride= 1:100), followed by crystallization from ethyl acetate—diethyl ether, whereby the title compound (326 mg) was obtained as brown crystals.

$^1$H-NMR (CDCl$_3$) δ: 0.70–1.07(1H,m), 1.20–1.32(1H, m), 1.64–1.76(1H,m), 1.79(3H,s), 1.83(3H,s), 2.56–2.97 (2H,m), 3.36–3.66(2H,m), 3.70–3.81(1H,m), 3.85–3.94

(0.5H,m), 4.57–5.03(0.5H,m), 7.46(1H,dd,J=8.8,2.0 Hz), 7.75(1H,s), 7.82(1H,d,J=8.8 Hz), 7.88(1H,br), 8.58–8.72 (2H,m). MS (FAB) m/z=555 (M$^+$), 557 (M+2)$^{+]}$, 559 [(M+4)$^{+]}$.

Referential Example 280

1-(tert-Butoxycarbonyl)-3,3-dimethylpiperazine

To a methylene chloride solution (5.0 ml) of 2,2-dimethylpiperazine (460 mg, 4.03 mmol) (J. Med. Chem., 1995, 38, 4389) was added di-tert-butyl dicarbonate (780 µl). The resulting mixture was stirred for 3 hours. The reaction mixture was diluted with methylene chloride and then added with saturated aqueous NaCl solution to separate into two layers. The water layer thus obtained was extracted with methylene chloride. The extract was dried over anhydrous sodium sulfate and concentrated under reduced pressure. The crudely purified product was purified by chromatography on a silica gel column (methylene chloride:methanol=10:1), whereby the title compound (360 mg) was obtained as a colorless oil.

$^1$H-NMR (CDCl$_3$) δ: 1.19(6H,s), 1.46(9H,s), 2.93(2H,t, J=4.9 Hz), 3.23(2H,s), 3.42–3.48(2H,br), 3.95–4.01(1H,s).

Referential Example 281

4-(tert-Butoxycarbonyl)-1-[(6-chloronaphthalen-2-yl)sulfonyl]-2,2-dimethylpiperazine To a solution of 1-(tert-butoxycarbonyl)-3,3-dimethylpiperazine (125 mg) in methylene chloride (3.0 ml) were added triethylamine (90 ml) and 6-chloronaphthalene-2-sulfonyl chloride (167 mg). The resulting mixture was stirred at room temperature for 84 hours. The reaction mixture was diluted with methylene chloride and added with a saturated aqueous solution of sodium chloride to form two layers. The organic layer obtained by separation was dried over anhydrous sodium sulfate and concentrated under reduced pressure. The crudely purified product was purified by chromatography on a silica gel column (hexane:ethyl acetate=8:1), whereby the title compound (155 mg) was obtained as a colorless solid.

$^1$H-NMR (CDCl$_3$) δ: 1.31(6H,s), 1.44(9H,s), 3.22(2H,br s), 3.49–3.62(2H,br), 3.57–3.62(2H,br), 7.56(1H,dd,J=8.8, 2.0 Hz), 7.79(1H,d,J=8.8 Hz), 7.86(1H,s), 7.87–7.92(3H,m), 8.36(1H,s).

Referential Example 282

1-[(6-Chloronaphthalen-2-yl)sulfonyl]-2,2-dimethylpiperazine hydrochloride

To a methylene chloride solution (0.5 ml) of 4-(tert-butoxycarbonyl)-1-[(6-chloronaphthalen-2-yl)sulfonyl]-2,2-dimethylpiperazine (140 mg) was added a saturated solution (0.5 ml) of hydrochloride in ethanol. The resulting mixture was stirred at room temperature for 14 hours. Ethanol was added to the reaction mixture. After the sufficient removal of hydrochloric acid by azeotropy, the residue was dried using a vacuum pump, whereby the title compound (119 mg) was obtained as a colorless solid.

$^1$HNMR (DMSO-d$_6$) δ: 3.17(4H,br s), 3.50–3.95(4H,br), 7.44(2H,t,J=3.9 Hz), 7.57(2H,d,J=8.8 Hz), 7.66(1H,t,J=3.9 Hz), 7.92(2H,d,J=8.8 Hz), 8.36(1H,d,J=7.8 Hz), 9.21(2H,d, J=3.9 Hz). MS (FAB) m/z: 339 [(M+H)$^+$, Cl$^{35}$], 341 [(M+H)$^+$, Cl$^{37}$]

Referential Example 283

4-(tert-Butoxycarbonyl)-2,2-dimethyl-1-[4-(pyridin-4-yl)benzoyl]piperazine

To a solution of 1-(tert-butoxycarbonyl)-3,3-dimethylpiperazine (173 mg) in a mixture of N,N-dimethylformamide (2.5 ml) and triethylamine (1.0 ml) was added (4-nirophenyl) 4-(4-pyridyl)benzoate (330 mg). The resulting mixture was stirred at 60° C. for 5 days. The reaction mixture was diluted with methylene chloride and then added with a saturated aqueous solution of sodium chloride to form two layers. The organic layer obtained by separation was washed with a saturated aqueous solution of sodium bicarbonate and an aqueous solution of sodium chloride, dried over anhydrous sodium sulfate and concentrated under reduced pressure. The crudely purified product was purified by chromatography on a silica gel column (methylene chloride:methanol=50:1), whereby the title compound (199 mg) was obtained as colorless amorphous.

$^1$H-NMR (CDCl$_3$) δ: 1.49(9H,s), 1.61(6H,s), 3.45–3.56 (6H,m), 7.50(2H,d,J=5.9 Hz), 7.51(2H,d,J=7.8 Hz), 7.67 (2H,d,J=7.8 Hz), 8.69(1H,d,J=5.9 Hz). MS (FAB) m/z: 369 (M+H)$^+$.

Referential Example 284

1,4-bis(tert-Butoxycarbonyl)-2-(2-hydroxyethyl)piperazine

In methanol (200 ml) and concentrated hydrochloric acid (5.4 ml) was dissolved 1,4-dibenzyl-2-(2-hydroxyetyl) piperazine (19.2 g). Palladium hydroxide (1.02 g) was then suspended in the resulting solution. The resulting suspension was vigorously shaken at room temperature for 15.5 hours under a hydrogen gas atmosphere of 1 atmospheric pressure. The catalyst was filtered off and the filtrate was concentrated under reduced pressure. The residue thus obtained was added with methylene chloride (250 ml), methanol (50 ml) and diisopropylethylamine (20.0 ml) to dissolve the former in the latter. Under ice cooling, di-tert-butyl dicarbonate (27.0 g) was added and the resulting mixture was stirred at room temperature for 18.5 hours. The solvent was distilled off under reduced pressure. The residue was subjected to chromatography on a silica gel column (hexane:ethyl acetate=9:1→hexane:ethyl acetate=1:1). Hexane was added to the residue to solidify the same, whereby the title compound (16.1 g) was obtained as colorless powder.

$^1$H-NMR (CDCl$_3$) δ: 1.46, 1.48(18H,each s), 1.30–1.90 (2H,m), 2.70–4.40(10H,m). MS (FAB) m/z: 331 (M+H)$^+$.

Referential Example 285

1,4-Bis(tert-butoxycarbonyl)-2-formylmethylpiperazine

In methylene chloride (150 ml) was dissolved 1,4-bis(tert-butoxycarbonyl)-2-(2-hydroxyethyl)piperazine. Under ice cooling, N-methylmorpholine (2.14 g) and tetra-n-propylammonium perruthenate (0.97 g) were added to the reaction mixture, followed by stirring at room temperature for 17 hours. The reaction mixture was then distilled off under reduced pressure. The residue was subjected to chromatography on a silica gel column (hexane:ethyl acetate=9:1 to 2:1), whereby the title compound (3.11 g) was obtained as colorless powder.

$^1$H-NMR (CDCl$_3$) δ: 1.45(18H,s), 2.50–3.10(15H,m), 3.70–4.20(3H,m), 4.66(1H,br), 9.76(1H,s). MS (FAB) m/z: 329 (M+H)$^+$.

Referential Example 286

1,4-Bis(tert-butoxycarbonyl)-2-[3-(thien-2-yl)-2-propenyl]piperazine

In tetrahydrofuran (50 ml) was dissolved 1,4-bis(tert-butoxycarbonyl)-2-formylmethylpiperazine (1.01 g). Under ice cooling, a solution of [(thien-2-yl)methyl]phosphonium (1.62 g) in chloroform (100 ml) was added to the resulting solution, followed by the dropwise addition of 1,8-diazabicyclo[5.4.0]-7-undecene (620 μl). The resulting mixture was stirred at room temperature for 15 hours. The reaction mixture was distilled under reduced pressure. The residue was subjected to chromatography on a silica gel column (hexane:ethyl acetate=9:1 to 2:1), whereby the title compound (1.13 g) was obtained as a pale yellow oil.

$^1$H-NMR (CDCl$_3$) δ: 1.30–1.50(18H,m), 2.30–2.50(1H, m), 2.50–3.10(4H,m), 3.40–4.60(4H,m), 5.45–6.05(1H,m), 6.50–6.65(1H,m), 6.85–7.30(3H,m). MS (FAB) m/z: 409 (M+H)$^+$.

Referential Example 287

1,4-Bis(tert-butoxycarbonyl)-2-[3-(thien-2-yl) propyl]piperazine

In methanol (70 ml) was dissolved 1,4-bis(tert-butoxycarbonyl)-2-[3-(thien-2-yl)-2-propenyl]piperazine (1.01 g). In the resulting solution was suspended 10% palladium-carbon (50% wet, 431 mg), followed by vigorous shaking at room temperature for 6 hours under a hydrogen gas atmosphere of 1 atmospheric pressure. The catalyst was filtered off and the filtrate was concentrated under reduced pressure. The residue was subjected to chromatography on a silica gel column (hexane:ethyl acetate=9:1 to 2:1), whereby the title compound (975 mg) was obtained as colorless powder.

$^1$H-NMR (CDCl$_3$) δ: 1.45(9H,s), 1.46(9H,s), 1.50–1.80 (4H,m), 2.70–3.00(5H,m), 3.80–4.20(4H,m), 7.75–7.80(1H, m), 7.85–7.95(1H,m), 7.10(1H,d,J=5.1 Hz). MS (FAB) m/z: 411 (M+H)$^+$.

Referential Example 288

1-[(5-Chloro-1-phenylsulfonylindol-2-yl)sulfonyl]-3-[3-(thien-2-yl)propyl]piperazine In the same manner as in Referential Example 220, the title compound was obtained.

$^1$H-NMR (CDCl$_3$) δ: 1.35–1.80(4H,m), 2.55–2.65(1H, m), 2.75–3.10(6H,m), 3.77(2H,t,J=10.9 Hz), 6.70–6.80(1H, m), 6.85–6.95(1H,m), 7.05–7.15(1H,m), 7.35–7.0(4H,m), 7.50–7.60(2H,m), 8.00–8.10(2H,m), 8.22(1H,d,J=9.3 Hz). MS (FAB) m/z: 564 [(M+H)$^+$, Cl$^{35}$], 566 [(M+H)$^+$, Cl$^{37}$].

Referential Example 289

1,4-Bis(tert-butoxycarbonyl)-2-[3-(3,4-dimethoxyphenyl)-2-propenyl]piperazine

In the same manner as in Referential Example 286, the title compound was obtained.

$^1$H-NMR (CDCl$_3$) δ: 1.40–1.50(18H,m), 2.35–3.10(5H, m), 3.75–4.30(10H,m), 5.50–6.05(1H,m), 6.30–6.50(1H,m), 6.75–6.90(3H,m). MS (FAB) m/z: 463 (M+H)$^+$.

Referential Example 290

1,4-Bis(tert-butoxycarbonyl)-2-[3-(3,4-dimethoxyphenyl)propyl]piperazine

In the same manner as in Referential Example 287, the title compound was obtained.

$^1$H-NMR (CDCl$_3$) δ: 1.45(18H,s), 1.20–1.70(4H,m), 2.50–3.05(5H,m), 3.70–4.20(10H,m), 6.65–6.80(3H,m). MS (FAB) m/z: 465 (M+H)$^+$.

Referential Example 291

1-[(5-Chloro-1-phenylsulfonylindol-2-yl)sulfonyl]-3-[3-(3,4-dimethoxyphenyl)propyl]piperazine In the same manner as in Referential Example 220, the title compound was obtained.

$^1$H-NMR (CDCl$_3$) δ: 1.30–1.70(4H,m), 2.50–2.65(3H, m), 2.75–3.05(4H,m), 3.70–3.90(8H,m), 6.0–6.70(2H,m), 6.75–6.80(1H,m), 7.35–7.50(4H,m), 7.50–7.60(2H,m), 8.02 (2H,d,J=8.1 Hz), 8.22(1H,d,J=9.0 Hz). MS (FAB) m/z: 619 [(M+H)$^+$, Cl$^{35}$], 621 [(M+H)$^+$, Cl$^{37}$].

Referential Example 292

1,4-Bis(tert-butoxycarbonyl)-2-(2-bromoethyl) piperazine

In methylene chloride (70 ml) were dissolved 1,4-bis(tert-butoxycarbonyl)-2-(2-hydroxyethyl)piperazine (2.01 g) and triphenylphosphine (1.98 g). Under ice cooling, carbon tetrabromide (3.07 g) was added to the resulting solution, followed by stirring at room temperature for 2.5 hours. The reaction mixture was extracted with a 10% aqueous solution of sodium thiosulfate. The organic layer was washed with saturated aqueous NaCl solution, dried over anhydrous sodium sulfate an distilled under reduced pressure to remove the solvent. The residue was subjected to column chromatography (hexane:ethyl acetate=4:1) using as a carrier silica gel, whereby the title compound (2.20 g) was obtained as colorless powder.

$^1$H-NMR (CDCl$_3$) δ: 1.47, 1.48(18H,each s), 2.00–2.20 (2H,m), 2.70–3.00(3H,m), 3.30–3.45(2H,m), 3.80–4.40(4H, m).

Referential Example 293

1,4-Bis(tert-butoxycarbonyl)-2-[2-[(pyrrolidin-1-yl) sulfonyl]ethyl]piperazine

Sodium sulfite (1.68 g) was dissolved in water (90 ml). Under ice cooling, a solution of 1,4-bis(tert-butoxycabonyl)-2-(2-bromoethyl)piperazine (2.20 g) in N,N-dimethylformamide (90 ml) was added to the reaction mixture, followed by stirring at 50° C. for 15 hours. The reaction mixture was then concentrated under reduced pressure. The residue was added with ethanol and the insoluble matter was filtered off. The filtrate was concentrated under reduced pressure, whereby the crudely purified product (2.98 g) was obtained as a colorless paste. The crudely purified product was then dissolved in N,N-dimethylformamide (10 ml). Under ice cooling, thionyl chloride (407 μl) was added dropwise, followed by stirring at 0° C. for 0.5 hour and at room temperature for 1 hour. Ice water (40 ml) was poured into the reaction mixture. After the removal of the insoluble matter, the residue was dried. The residue was then dissolved in methylene chloride. The resulting solution was dried over anhydrous sodium sulfate and distilled under reduced pressure to remove the solvent, whereby pale yellow oil (524.9 mg) was obtained. The crudely purified product was then dissolved in methylene chloride (10 ml), followed by the addition of diisopropylethylamine (500 μl) and pyrrolidine (220 μl) under ice cooling. The resulting mixture was stirred at room temperature for 19 hours. The reaction mixture was distilled under reduced pressure. The residue was subjected to column chromatography (hexane:ethyl acetate =1:1) using silica gel as a carrier, whereby the title compound (122 mg) was obtained as a pale yellow oil.

$^1$H-NMR (CDCl$_3$) δ: 1.47, 1.47(18H,each s), 1.85–2.20 (6H,m), 2.70–3.10(5H,m), 3.30–3.40(4H,m), 3.80–4.30(4H, m).

Referential Example 294

1-[(5-Chloro-1-phenylsulfonylindol-2-yl)sulfonyl]-3-[2-[(pyrrolidin-1-yl)sulfonyl]ethyl]piperazine In the same manner as in Referential Example 220, the title compound was obtained.

$^1$H-NMR (CDCl$_3$) δ: 1.80–2.00(6H,m), 2.60–2.70(1H, m), 2.80–3.1(6H,m), 3.30–3.40(4H,m), 3.65–3.85(2H,m), 7.40–7.50(4H,m), 7.50–7.60(2H,m), 8.01(2H,d,J=7.8 Hz), 8.22(2H,d,J=8.3 Hz). MS (FAB) m/z: 601 [(M+H)$^+$, Cl$^{35}$], 603 [(M+H)$^+$, Cl$^{37}$].

Referential Example 295

4-(Chloro-2-methoxyphenyl)methanol

In tetrahydrofuran (100 ml) was dissolved 4-chloro-2-methoxyphenylcarboxylic acid (20.1 g), followed by purging with argon. A borane-methylsulfide complex (11.0 ml) was added dropwise to the reaction mixture. After completion of the dropwise addition, when reflux due to the emission of heat generated by the reaction stopped, stirring was conducted at room temperature for 2 hours. Under ice cooling, water was added to the reaction mixture. The resulting mixture was extracted with ethyl acetate and a saturated aqueous solution of sodium bicarbonate. The organic layer thus obtained was washed with saturated aqueous NaCl solution, dried over anhydrous sodium sulfate and distilled under reduced pressure to remove the solvent, whereby the title compound (17.6 g) was obtained as pale yellow powder.

$^1$H-NMR (CDCl$_3$) δ: 2.25(1H,s), 3.85(3H,s), 4.63(2H,s), 6.86(1H,d,J=1.8 Hz), 6.92(1H,dd,J=8.2,1.8 Hz), 7.21(1H,d, J=8.2 Hz).

Referential Example 296

4-Chloro-1-formyl-2-methoxybenzene

In methylene chloride (80 ml) was dissolved (4-chloro-2-methoxyphenyl)methanol (3.69 g). Under ice cooling, molecular sieve 4A (4.57 g), N-methylmorpholine (2.81 g) and tetra-n-propylammonium perruthenate (420 mg) were added to the resulting solution, followed by stirring at room temperature for 2.5 hours. The reaction mixture was distilled under reduced pressure. The residue was subjected to chromatography on a silica gel column (hexane:ethyl acetate= 9:1), whereby the title compound (3.07 g) was obtained as pale yellow oil.

$^1$H-NMR (CDCl$_3$) δ: 3.94(3H,s), 6.99(1H,d,J=2.0 Hz), 7.00–7.05(1H,m), 7.77(1H,d,J=8.3 Hz), 10.39(1H,s).

Referential Example 297

4-Chloro-2-methoxystyrene

In tetrahydrofuran (50 ml) was suspended methyltriphenylphosphonium bromide (5.03 g), followed by purging with argon. Under ice cooling, n-butyl lithium (a 1.59 mole solution, hexane) (9.80 ml) was added dropwise over 30 minutes. After completion of the dropwise addition, stirring was conducted at room temperature for 30 minutes. Under ice cooling, a solution of 4-chlorol-formyl-2-methoxybenzene (2.02 g) in tetrahydrofuran (15 ml) was added dropwise to the reaction mixture. After completion of the dropwise addition, stirring was conducted at room temperature for 3.5 hours. Then, water was added to the reaction mixture under ice cooling. The reaction mixture was extracted with ethyl acetate. The extract was washed with saturated aqueous NaCl solution, dried over anhydrous sodium sulfate and distilled under reduced pressure to remove the solvent. The residue was subjected to chromatography on a silica gel column (hexane:ethyl acetate=9:1), whereby the title compound (1.51 g) was obtained as a pale yellow oil.

$^1$H-NMR (CDCl$_3$) δ: 3.83(3H,s), 5.26(1H,dd,J=11.2,1.5 Hz), 5.70(1H,dd,J=17.8,1.2 Hz), 6.80–7.00(3H,m), 7.37 (1H,d,J=8.3 Hz). MS (FAB) m/z: 169 [(M+H)$^+$, Cl$^{35}$], 171 [(M+H)$^+$, Cl$^{37}$].

Referential Example 298

(4-Chloro-2-methoxystyryl)sulfonyl chloride

Sulfuryl chloride (1.66 ml) was charged in a container, followed by purging with argon. Under ice cooling, N,N-dimethylformamide (1.7 ml) was added, followed by stirring at room temperature for 40 minutes. To the reaction mixture was added 4-chloro-2-methoxystyrene (2.05 g) and the resulting mixture was stirred at 90° C. for 3 hours. Ice was added and the resulting mixture was extracted with methylene chloride. The extract was washed with saturated aqueous NaCl solution, dried over anhydrous sodium sulfate and distilled under reduced pressure to remove the solvent. The residue was subjected to column chromatography (hexane:ethyl acetate=9:1) using as a carrier silica gel, whereby the title compound (885 mg) was obtained as a pale yellow oil.

$^1$H-NMR (CDCl$_3$) δ: 3.96(3H,s), 6.98(1H,d,J=2.0 Hz), 7.03(1H,dd,J=8.3,2.0 Hz), 7.38(1H,d,J=8.3 Hz), 7.50(1H,d, J=15.1 Hz), 7.78(1H,d,J=15.1 Hz). MS (FAB) m/z: 266 [(M+H)$^+$, Cl$^{35}$+Cl$^{35}$].

Referential Example 299

1-(tert-Butoxycarbonyl)-4-[(E)-4-chloro-2-methoxystyrylsulfonyl]piperazine

In the same manner as in Referential Example 129, the title compound was synthesized.

$^1$H-NMR (CDCl$_3$) δ: 1.44(9H,s), 3.10–3.20(4H,m), 3.50–3.60(4H,m), 3.91(3H,s), 6.82(1H,d,J=15.6 Hz), 6.94 (1H,d,J=2.0 Hz), 6.97(1H,dd,J=8.3,2.0 Hz), 7.33(1H,d,J= 8.3 Hz), 7.56(1H,d,J=15.6 Hz). MS (FAB) m/z: 416 [(M+ H)$^+$, Cl$^{35}$], 418 [(M+H)$^+$, Cl$^{37}$].

Referential Example 300

1-(5-Bromopyrimidin-2-yl)-4-[((E)-4-chloro-1-methoxystyryl)sulfonyl]piperazine

In methylene chloride (10 ml) was dissolved 1-(tert-butoxycarbonyl)-4-[((E)-4-chloro-1-methoxystyryl) sulfonyl]piperazine (690 mg). Under ice cooling, trifluoroacetic acid (1.0 ml) was added dropwise to the resulting solution, followed by stirring at room temperature for 1 hour. Methylene chloride (10 ml) was added further to the reaction mixture and they were stirred at 0° C. for 23 hours and at room temperature for 2 hours. The solvent was distilled off under reduced pressure. The residue was extracted with methylene chloride and a saturated aqueous solution of sodium bicarbonate. The organic layer was washed with saturated aqueous NaCl solution, dried over anhydrous sodium sulfate and distilled under reduced pressure to remove the solvent. The resulting residue, that is, (5-bromopyrimidin-2-yl)carboxylic acid (467 mg) was dissolved in a mixture of N,N-dimethylformamide (15 ml) and methylene chloride (15 ml), followed by the successive addition of 1-(3-dimethylaminopropyl)-3-ethylcarbodiimide hydrochloride (366 mg), 1-hydroxybenzotriazole hydrate (266 mg) and diisopropylethylamine (1.01 ml) under ice cooling. The resulting mixture was stirred at room temperature for 25 hours. The solvent was then distilled off under reduced pressure. The residue was extracted with methylene chloride and a saturated aqueous solution of sodium bicarbonate. The organic layer was washed with saturated aqueous NaCl solution, dried over anhydrous sodium sulfate and distilled under reduced pressure to remove the solvent. The residue was subjected to column chromatography (hexane:ethyl acetate=1:1 to 1:2) using as a carrier silica gel, whereby the title compound (629 mg) was obtained as colorless powder.

$^1$H-NMR (CDCl$_3$) δ: 3.22(2H,t,J=4.5 Hz), 3.33(2H,t,J=4.6 Hz), 3.52(2H,t,J=4.4 Hz), 3.90–3.95(2H,m), 6.83(1H,d,J=15.6 Hz), 6.95(1H,s), 6.99(1H,d,J=8.3 Hz), 7.33(1H,d,J=8.3 Hz), 7.56(1H,d,J=15.6 Hz), 8.80–8.90(2H,m). MS (FAB) m/z: 501 [(M+H)$^+$, Cl$^{35}$, Br$^{79}$], 505 [(M+H)$^+$, Cl$^{35}$, Br$^{81}$ and Cl$^{37}$, Br$^{79}$], 507 [(M+H)$^+$, Cl$^{37}$, Br$^{81}$].

Referential Example 301

2,cis-6-Bis(methoxycarbonylmethyl)-1-(5-bromopyrimidin-2-yl)-4-[(6-chloronaphthalen-2-yl)sulfonyl]piperazine In a mixture of methylene chloride (30 ml) and N,N-dimethylformamide (200 pl) was dissolved 5-bromo-2-pyrimidinecarboxylic acid (736 mg), followed by purging with argon. Under an argon atmosphere and ice cooling, oxalyl chloride (0.40 ml) was added dropwise to the reaction mixture. The resulting mixture was stirred at room temperature for 0.5 hour. The reaction mixture thus obtained was designated as "Reaction Mixture A".

In methylene chloride (50 ml) was dissolved 2,cis-6-bis(methoxycarbonylmethyl)-4-[(6-chloronaphthalen-2-yl)sulfonyl]piperazine (529 mg). Diisopropylethylamine (2.00 ml) was added to the reaction mixture under ice cooling, followed by purging with argon. Reaction Mixture A prepared in advance was then added dropwise under ice cooling and the resulting mixture was stirred at room temperature for 11 hours. The reaction mixture was extracted with a saturated aqueous solution of sodium bicarbonate. The organic layer was washed successively with dilute hydrochloric acid and saturated aqueous NaCl solution, dried over anhydrous sodium sulfate and distilled under reduced pressure to remove the solvent. The residue was subjected to column chromatography (0.5%~1% methanol—methylene chloride) using as a carrier silica gel. The solvent was then distilled off under reduced pressure. A small amount of methylene chloride was added to the residue for crystallization, whereby the title compound (432 mg) was obtained as pale yellow powder.

$^1$H-NMR (CDCl$_3$) δ: 2.40–3.00(6H,m), 3.57–3.70(8H,m), 3.90–4.00(1H,m), 4.90–5.00(1H,m), 7.70–7.75(1H,m), 7.80–7.85(1H,m), 8.15–8.30(3H,m), 8.52(1H,s), 9.07(2H,s).

Referential Example 302

1-(5-Bromopyrimidin-2-yl)-4-[(6-chloronaphthalen-2-yl)sulfonyl]-2-(methoxycarbonylmethyl)piperazine In the same manner as in Referential Example 12, the title compound was synthesized.

$^1$H-NMR (CDCl$_3$) δ: 2.40–3.25(5H,m), 3.45–3.55(1H,m), 3.67, 3.72(3H,each s), 3.70–5.30(4H,m), 7.60(1H,dd,J=8.6,1.7 Hz), 7.70–7.75(1H,m), 7.90–7.95(3H,m), 8.25–8.30(1H,m), 8.80, 8.81(2H,each s). MS (FAB) m/z: 567 [(M+H)$^+$, Cl$^{35}$, Br$^{79}$], 569 [(M+H)$^+$, Cl$^{35}$, Br$^{81}$ and Cl$^{37}$, Br$^{79}$], 571 [(M+H)$^+$, Cl$^{37}$, Br$^{81}$].

Referential Example 303

1-(tert-Butoxycarbonyl)-2-[2-(tert-butyldiphenylsilyloxy)ethyl]-4-[(6-chloronaphthalen-2-yl)sulfonyl]piperazine In N,N-dimethylformamide (15 ml) was dissolved 1-tert-butoxycarbonyl-4-[(6-chloronaphthalen-2-yl)sulfonyl]-2-(2-hydroxyethyl)piperazine (739 mg) and imidazole (226 mg). Under ice cooling, tert-butylchlorodiphenylsilane (0.70 ml) was added to the resulting solution, followed by stirring at room temperature for 23 hours. The reaction mixture was distilled off under reduced pressure. The residue was extracted with methylene chloride and a saturated aqueous solution of sodium bicarbonate. The organic layer thus obtained was washed with dilute hydrochloric acid and saturated aqueous NaCl solution, dried over anhydrous sodium sulfate and distilled under reduced pressure to remove the solvent. The residue was purified by column chromatography (hexane:ethyl acetate=2:1~:2) using as a carrier silica gel, whereby the title compound (804 mg) was obtained as a pale yellow oil.

$^1$H-NMR (CDCl$_3$) δ: 1.06(9H,s), 1.31(9H,s), 1.90–2.00 (2H,m), 2.20–2.30(1H,m), 2.30–2.40(1H,m), 2.95–3.05(1H,m), 3.60–3.80(4H,m), 3.85–4.00(1H,m), 4.35–4.45(1H,m), 7.35–7.45(6H,m), 7.55–7.60(1H,m), 7.65–7.75(5H,m), 7.85–7.95(3H,m), 8.26(1H,s). MS (FAB) m/z: 693 [(M+H)$^+$, Cl$^{35}$], 695 [(M+H)$^+$, Cl$^{37}$].

Referential Example 304

3-[2-(tert-Butyldiphenylsilyloxy)ethyl]-1-[(6-chloronaphthalen-2-yl)sulfonyl]piperazine In nitrobenzene (5.0 ml) was dissolved 1-(tert-butoxycarbonyl)-2-[2-(tert-butyldiphenylsilyloxy)ethyl]-4-(6-chloronaphthalen-2-yl)piperazine (91.2 mg), followed by stirring at 170 to 185° C. for 10.5 hours. The reaction mixture was subjected to chromatography on a silica gel column (methylene chloride~5% methanol—methylene chloride), whereby the title compound (43 mg) was obtained as a pale yellow oil.

$^1$H-NMR (CDCl$_3$) δ: 1.04(9H,s), 1.50–1.65(2H,m), 2.05–2.15(1H,m), 2.35–2.45(1H,m), 2.85–3.00(3H,m), 3.65–3.75(4H,m), 7.35–7.45(6H,m), 7.55–7.60(1H,m), 7.60–7.65(4H,m), 7.70–7.80(1H,m), 7.85–7.95(3H,m), 8.28 (1H,s). MS (FAB) m/z: 593 [(M+H)$^+$, Cl$^{35}$], 595 [(M+H)$^+$, Cl$^{37}$].

Referential Example 305

1-(5-Bromopyrimidin-2-yl)-2-[2-(tert-butyldiphenylsilyloxy)ethyl]-4-[(6-chloronaphthalen-2-yl)sulfonyl]piperazine In a similar manner to Referential Example 12, the title compound was synthesized.

$^1$H-NMR (CDCl$_3$) δ: 0.90, 1.08(9H,each s), 2.00–2.20 (2H,m), 2.30–2.60(2H,m), 3.15–5.20(7H,m), 7.35–7.60 (10H,m), 7.65–7.75(2H,m), 7.85–7.95(3H,m), 8.20–8.30 (1H,m), 8.62, 8.79(2H,each s). MS (FAB) m/z: 777 [(M+H)$^+$, Cl$^{35}$, Br$^{79}$], 779 [(M+H)$^+$, Cl$^{35}$, Br$^{81}$ and Cl$^{37}$, Br$^{79}$], 781 [(M+H)$^+$, Cl$^{37}$, Br$^8$].

Referential Example 306

2,cis-6-Bis(methoxycarbonylmethyl)-4-[(6-chlorobenzo[b]thien-2-yl)sulfonyl]piperazine and 2,trans-6-bis(methoxycarbonylmethyl)-4-[(6-chlorobenzo[b]thien-2-yl)sulfonyl]piperazine In the same manner to Referential Example 192, the title compound were synthesized.
Instrumental data of 2,cis-6-Bis(methoxycarbonylmethyl)-4-[(6-chlorobenzo[b]thien-2-yl)sulfonyl]piperazine
$^1$H-NMR (CDCl$_3$) δ: 2.15–2.45(6H,m), 2.90(1H,br), 3.25–3.35(2H,m), 3.65–3.75(2H,m), 3.70(6H,s), 7.43(1H, dd,J=8.5,1.7 Hz), 7.75(1H,s), 7.82(1H,d,J=8.8 Hz), 7.85–7.90(1H,m). MS (FAB) m/z: 461 [(M+H)$^+$, Cl$^{35}$], 463 [(M+H)$^+$, Cl$^{37}$].
Instrumental data of 2,trans-6-Bis(methoxycarbonylmethyl)-4-[(6-chlorobenzo[b]thien-2-yl)sulfonyl]piperazine
$^1$H-NMR (CDCl$_3$) δ: 2.50–2.65(6H,m), 2.85–2.95(2H, m), 3.20–3.25(2H,m), 3.50–3.55(2H,m), 3.70(6H,s), 7.43 (1H,dd,J=8.6,1.7 Hz), 7.74(1H,s), 7.82(1H,d,J=8.8 Hz), 7.86(1H,br s) MS (FAB) m/z: 461 (M+H)$^+$, Cl$^{35}$], 463 [(M+H)$^+$, Cl$^{37}$].

Referential Example 307

2,cis-6-Bis(methoxycarbonylmethyl)-1-(5-bromopyrimidin-2-yl)-4-[(6-chlorobenzo[b]thien-2-yl)sulfonyl]piperazine In the same manner as in Referential Example 301, the title compound was synthesized.
$^1$H-NMR (CDCl$_3$) δ: 2.65–2.80(3H,m), 2.90–3.00(2H, m), 3.00–3.10(1H,m), 3.65–3.75(2H,m), 3.68(3H,s), 3.73 (3H,s), 4.00(1H,d,J=12.2 Hz), 4.22(1H,d,J=9.8 Hz), 5.20–5.30(1H,m), 7.40–7.50(1H,m), 7.77(1H,s), 7.80–7.90 (2H,m), 8.80(2H,s).

Referential Example 308

1,4-Dibenzyl-2-hydroxymethylpiperazine

In tetrahydrofuran (42 ml) was suspended lithium aluminum hydride (1.04 g). After a suspension of 1,4-dibenzyl-2-ethoxycarbonylpiperazine (12.5 g) in tetrahydrofuran (300 ml) was added dropwise, stirring was conducted at room temperature for 89.5 hours. The reaction mixture was ice cooled and added with a saturated aqueous solution of sodium sulfate and a 3N aqueous solution of sodium hydroxide. The insoluble matter was filtered off and the solvent was distilled off under reduced pressure. The residue was dissolved in tetrahydrofuran. The resulting solution was dried over anhydrous sodium sulfate and distilled under reduced pressure to remove the solvent.
Lithium aluminum hydride (1.5 g) was suspended in tetrahydrofuran (50 ml), followed by purging with argon. The reaction mixture was heated to 50C. To the reaction mixture, a solution of the residue, which had been obtained above, in tetrahydrofuran (50 ml) was added dropwise, followed by heating under reflux for 4.5 hours. The reaction mixture was then heated under reflux for 4.5 hours after the addition of lithium aluminum hydride (0.87 g). Lithium aluminum hydride (0.87 g) was added again and the resulting mixture was heated under reflux for 4.5 hours. The reaction mixture was ice cooled and then added with a saturated aqueous solution of sodium sulfate and a 3N aqueous solution of sodium hydroxide. The insoluble matter was filtered off and the solvent was distilled off under reduced pressure. The residue was dissolved in methylene chloride. The resulting solution was dried over anhydrous sodium sulfate and distilled under reduced pressure to remove the solvent. The residue was subjected to chromatography on a silica gel column (methylene chloride~5% methanol—methylene chloride ), whereby the title compound (8.42 g) was obtained as a pale red oil.
$^1$H-NMR (CDCl$_3$) δ: 2.30–2.70(5H,m), 2.90–3.00(1H, m), 3.40–3.50(4H,m), 3.58(1H,d,J=13.2 Hz), 3.90–4.10(2H, m), 7.20–7.35(10H,m) MS (FAB) m/z: 297 (M+H)$^+$.

Referential Example 309

2-(tert-Butyldiphenylsilyloxy)methyl-1,4-dibenzylpiperazine

In N,N-dimethylformamide (20 ml) were dissolved 1,4-dibenzyl-2-hydroxymethylpiperazine (1.11 g) and imidazole (347 mg). Under ice cooling, tert-butylchlorodiphenylsilane (1.17 ml, 1.24 g) was added to the reaction mixture, followed by stirring at room temperature for 14.5 hours. The solvent was distilled off under reduced pressure. The residue was extracted with ethyl acetate and a saturated aqueous solution of sodium bicarbonate. The organic layer was then washed with saturated aqueous NaCl solution, dried over anhydrous sodium sulfate and distilled under reduced pressure to remove the solvent. The residue was subjected to column chromatography (hexane:ethyl acetate=9:1→8:2) using as a carrier silica gel, whereby the title compound (1.42 g) was obtained.
$^1$H-NMR (CDCl$_3$) δ: 0.98(9H,s), 2.15–2.30(3H,m), 2.50–2.55(1H,m), 2.60–2.70(2H,m), 2.80–2.90(1H,m), 3.24 (1H,d,J=13.7 Hz), 3.40–3.50(2H,m), 3.60–3.70(1H,m), 3.90–4.00(2H,m), 7.15–7.45(16H,m), 7.55–7.65(4H,m). MS (FAB) m/z: 535 (M+H)$^+$.

Referential Example 310

3-(tert-Butyldiphenylsilyloxy)methyl-1-(6-chlorobenzo[b]thien-2-yl)piperazine

In the same manner as in Referential Example 192, the title compound was obtained.
$^1$H-NMR (CDCl$_3$) δ: 1.02(9H,s), 2.30–2.40(1H,m), 2.45–2.65(1H,m), 2.90–3.15(3H,m), 3.50–3,70(4H,m), 7.35–7.45(7H,m), 7.55–7.65(4H,m), 7.71(1H,s), 7.75–7.85 (2H,m). MS (FAB) m/z: 585 [(M+H)$^+$, Cl$^{35}$], 587 [(M+H)$^+$, Cl$^{37}$].

Referential Example 311

1-(5-Bromopyrimidin-2-yl)carbonyl-2-(tert-butyldiphenylsilyloxymethyl-4-(6-chlorobenzo[b]thien-2-yl)piperazine In the same manner as in Referential Example 12, the title compound was obtained.
$^1$H-NMR (CDCl$_3$) δ: 1.02, 1.08(9H,each s), 2.50–2.80 (2H,m), 2.95–3.70(2H,m), 3.80–4.25(4H,m), 4.55–5.10(1H, m), 7.35–7.50(7H,m), 7.50–7.55(1H,m), 7.60–7.65(1H,m), 7.70–7.90(5H,m), 8.65, 8.81(2H,s). MS (FAB) m/z: 769 [(M+H)$^+$, Cl$^{35}$, Br$^{79}$], 771 [(M+H)$^+$, Cl$^{35}$, Br$^{81}$ and Cl$^{37}$, Br$^{79}$], 773 [(M+H)$^+$, Cl$^{37}$, Br$^{81}$].

Referential Example 312

1,4-Dibenzyl-2-(2-hydroxyethyl)piperazine

In the same manner as in Referential Example 308, the title compound was obtained.

¹H-NMR (CDCl₃) δ: 1.80–1.90(1H,m), 2.00–2.10(1H, m), 2.25–2.35(2H,m), 2.35–2.45(1H,m), 2.45–2.55(1H,m), 2.60–2.70(1H,m), 2.75–2.85(1H,m), 2.85–2.95(1H,m), 3.39 (1H,d,J=12.7 Hz), 3.49(1H,d,J=1.5 Hz), 3.70–3.80(1H,m), 3.80–3.90(1H,m), 4.16(1H,d,J=12.7 Hz), 7.20–7.40(10H, m).

Referential Example 313

2-[2-(tert-Butyldiphenylsilyloxy)ethyl]-1,4-dibenzylpiperazine

In the same manner as in Referential Example 309, the title compound was obtained.

¹H-NMR (CDCl₃) δ: 0.99(9H,s), 1.75–1.95(2H,m), 2.10–2.20(3H,m), 2.40–2.50(1H,m), 2.50–2.65(3H,m), 3.10–3.20(1H,m), 3.30–3.50(2H,m), 3.60–3.75(2H,m), 3.83 (1H,d,J=13.2 Hz), 7.15–7.25(10H,m), 7.25–7.40(6H,m), 7.55–7.65(4H,m). MS (FAB) m/z: 549 (M+H)⁺.

Referential Example 314

3-[2-(tert-Butyldiphenylsilyloxy)ethyl]-1-[(6-chlorobenzo[b]thien-2-yl)sulfonyl]piperazine In the same manner as in Referential Example 192, the title compound was obtained.

¹H-NMR (CDCl₃) δ: 1.04(9H,s), 1.50–2.00(3H,m), 2.20–2.30(1H,m), 2.50–2.60(1H,m), 2.85–3.05(3H,m), 3.65–3.80(4H,m), 7.35–7.45(7H,m), 7.60–7.65(4H,m), 7.72 (1H,s), 7.75–7.85(2H,m). MS (FAB) m/z: 599 [(M+H)⁺, Cl³⁵], 601 [(M+H)⁺, Cl³⁷].

Referential Example 315

1-(5-Bromopyrimidin-2-yl)-2-[2-(tert-butyldiphenylsilyloxy)ethyl]-4-[(6-chlorobenzo[b]thien-2-yl)sulfonyl]piperazine In the same manner as in Referential Example 12, the title compound was obtained.

¹H-NMR (CDCl₃) δ: 0.90, 1.07(9H,each s), 2.00–2.15 (2H,m), 2.50–2.80(2H,m), 3.15–5.25(7H,m), 7.35–7.90 (16H,m), 8.64, 8.81(2H,each s). MS (FAB) m/z: 783 [(M+H)⁺, Cl³⁵, Br⁷⁹], 785 [(M+H)⁺, Cl³⁵, Br⁸¹ and Cl³⁷, Br⁷⁹], 787 [(M+H)⁺, Cl³⁷, Br⁸¹].

Referential Example 316

1-[(6-Chlorobenzo[b]thien-2-yl)sulfonyl]-3-(methoxycarbonylmethyl)piperazine

In the same manner as in Referential Example 192, the title compound was obtained.

¹H-NMR (CDCl₃) δ: 2.30–2.50(3H,m), 2.63(1H,dt,J=3.4, 11.0 Hz), 2.90–3.10(2H,m), 3.20–3.30(1H,m), 3.60–3.70 (2H,m), 3.69(3H,s), 7.44(1H,dd,J=8.8,2.0 Hz), 7.75(1H,s), 7.82(1H,d,J=8.3 Hz), 7.85–7.90(1H,m). MS (FAB) m/z: 389 [(M+H)⁺, Cl³⁵], 391 [(M+H)⁺, Cl³⁷].

Referential Example 317

1-[(5-Bromopyrimidin-2-yl)-4-[(6-chlorobenzo[b]thien-2-yl)sulfonyl]-2-(methoxycarbonylmethyl)piperazine In the same manner as in Referential Example 12, the title compound was obtained.

¹H¹H-NMR (CDCl₃) δ: 2.60–3.30(5H,m), 3.50–5.40(4H, m), 3.68, 3.73(3H,each s), 7.45(1H,dd,J=8.5,1.7 Hz), 7.76, 7.77(1H,each s), 7.80–7.85(1H,m), 7.87(1H,s), 8.83, 8.84 (2H,each s). MS (FAB) m/z: 573 [(M+H)⁺, Cl³⁵], 575 [(M+H)⁺, Cl³⁷].

Referential Example 318

(2RS)-2-(N-tert-Butoxycarbonylaminomethyl)-6-methoxycarbonyl-1,2,3,4-tetrahydronaphthalene In dimethylformamide (25 ml), (2RS)-6-methoxycarbonyl-2-toluenesulfonyloxymethyl-1,2,3,4-tetrahydronaphthalene (2.56 g) was dissolved. Sodium azide (0.92 g) was added to the resulting solution, followed by stirring at an external temperature of about 50° C. for 14 hours. The reaction mixture was concentrated under reduced pressure. The concentrate was diluted with ethyl acetate, washed with water and then dried over sodium sulfate. The residue obtained by distilling off the solvent under reduced pressure was dissolved in tetrahydrofuran (35 ml). Triphenylphosphine (1.82 g) was added to the resulting solution, followed by stirring at an external temperature of about 50° C. for 21 hours. After about 28% aqueous ammonia (15 ml) was added and the resulting mixture was stirred for 3 hours, the reaction mixture was concentrated under reduced pressure. The concentrate was extracted with diethyl ether. Dilute hydrochloric acid was added to the extract to make it acidic and water layer was separated. To the resulting water layer, a dilute aqueous solution of sodium hydroxide was added to make it alkaline, followed by extraction with dichloromethane. The extract was dried over sodium sulfate and distilled under reduced pressure to remove the solvent. The resulting residue was dissolved in dichloromethane (15 ml). To the resulting solution, a solution of di-tert-butyl dicarbonate (1.80 g) in dichloromethane (5 ml) was added under ice cooling, followed by stirring at room temperature for 2 hours. The residue obtained by distilling off the solvent under reduced pressure was purified by chromatography on a silica gel column (30 g of silica gel, dichloromethane~dichloromethane:methanol=50:1) and recrystallized from a mixed solvent of n-hexane and ethyl acetate, whereby colorless crystals (1.56 g, 71%) were obtained.

¹H-NMR (CDCl₃) δ: 1.40–1.60(1H,m), 1.46(9H,s), 1.90–2.10(2H,m), 2.50(1H,dd,J=17.1,10.7 Hz), 2.70–3.00 (3H,m), 3.10–3.30(2H,m), 3.89(3H,s), 4.68(1H,br), 7.12 (1H,d,J=7.8 Hz), 7.70–7.80(2H,m). Elementary analysis for $C_{18}H_{25}NO_4$ Calculated: C, 67.69; H, 7.89; N, 4.39. Found: C, 67.78; H, 7.61; N, 4.12.

Referential Example 319

1-[[(6RS)-6-(N-tert-Butoxycarbonylaminomethyl)-5,6,7,8-tetrahydronaphthalen-2-yl]carbonyl]-4-[(6-chloronaphthalen-2-yl)sulfonyl]piperazine In tetrahydrofuran (5 ml), (2RS)-2-(N-tert-butoxycarbonylaminomethyl)-6-methoxycarbonyl-1,2,3,4-tetrahydronaphthalene (0.14 g) was dissolved. To the resulting solution, 1N sodium hydroxide (0.50 ml) was added, followed by stirring at room temperature for 3 days and at an external temperature of about 50° C. for 20 hours. 1N Sodium hydroxide (0.40 ml) was added further, followed by stirring at an external temperature of about 50° C. for 2 days. After the reaction mixture was concentrated under reduced pressure, dichloromethane and dilute hydrochloric acid were added to separate the organic layer. The organic layer was dried over anhydrous sodium sulfate and then distilled under reduced pressure to remove the solvent. The residue was dissolved in N,N-dimethylformamide (5 ml). To the resulting solution 1-[(6-chloronaphthalen-2-yl)sulfonyl] piperazine hydrochloride (0.19 g), N-methylmorpholine (0.05 ml), 1-(3-dimethylaminopropyl-3-ethylcarbodiimide hydrochloride (86.0 mg) and 1-hydroxybenzotriazole (71.0 mg) were added, followed by stirring at room temperature for 18 hours. After the reaction mixture was concentrated under reduced pressure, the concentrate was diluted with ethyl acetate and washed with water. The mixture was dried over anhydrous sodium sulfate and distilled under reduced pressure to remove the solvent. The residue was purified by chromatography on a silica gel column (dichloromethane~dichloromethane methanol 100:1), whereby the title compound was obtained as a colorless oil (0.23 g, 86%).

$^1$H-NMR (CDCl$_3$) δ: 1.30–1.60(1H,m), 1.45(9H,s), 1.80–2.00(2H,m), 2.43(1H,dd,J=16.6,10.7 Hz), 2.70–2.90 (3H,m), 3.00–3.20(6H,m), 3.50–3.90(4H,br), 4.69(1H,br), 6.90–7.10(3H,m), 7.59(1H,dd,J=8.8,2.0 Hz), 7.75(1H,dd,J= 8.8,2.0 Hz), 7.90–8.00(3H,m), 8.30(1H,s). MS (FAB) m/z: 598 [(M+H)$^+$, Cl$^{35}$], 600 [(M+H)$^+$, Cl$^{37}$].

Referential Example 320

(2RS)-2-(N-tert-Butoxycarbonylaminomethyl)-6-hydroxymethyl-1,2,3,4-tetrahydronaphthalene In dichloromethane (10 ml), the (2RS)-2-(N-tert-butoxycarbonylaminomethyl)-6-methoxycarbonyl-1,2,3,4-tetrahydronaphthalene (0.47 g) was dissolved. Aluminum diisobutylhydride (a 0.95M hexane solution, 3.60 ml) was added dropwise to the resulting solution at an external temperature of –78° C., followed by stirring for 90 minutes without changing the temperature. Methanol was added to the reaction mixture and the mixture was heated to room temperature. The insoluble matter was filtered off from filtration through Celite. The filtrate was concentrated under reduced pressure. The concentrate was diluted with dichloromethane, washed with water and dried over anhydrous sodium sulfate. The residue obtained by distilling off the solvent under reduced pressure was purified by chromatography on a silica gel column (hexane:ethyl acetate 3:1), whereby colorless crystals (0.31 g, 72%) was obtained. A portion of the resulting crystals was recrystallized from a mixed solvent of hexane and ethyl acetate, whereby colorless crystals were obtained.

$^1$H-NMR (CDCl$_3$) δ: 1.40–1.60(1H,m), 1.46(9H,s), 1.60–1.70(1H,m), 1.90–2.00(2H,m), 2.45(1H,dd,J=16.6, 10.7 Hz), 2.70–2.90(3H,m), 3.10–3.30(2H,m), 4.62(2H,d,J= 5.9 Hz), 4.67(1H,br), 7.00–7.20(3H,m). Elementary analysis for C$_{17}$H$_{25}$NO$_3$ Calculated: C, 70.07; H, 8.65; N, 4.81. Found: C, 70.21; H, 8.49; N, 4.75.

Referential Example 321

1-[[(6RS)-6-(N-tert-Butoxycarbonylaminomethyl)-5,6,7,8-tetrahydronaphthalen-2-yl]methyl]-4-[(6-chloronaphthalen-2-yl)sulfonyl]piperazine In dichloromethane (5 ml), the (2RS)-2-(N-tert-butoxycarbonylaminomethyl)-6-hydroxymethyl-1,2,3,4-tetrahydronaphthalene (0.19 g) was dissolved. Pyridinium chlorochromate (0.17 g) was added to the resulting solution, followed by stirring at room temperature for 2 hours. The reaction mixture was purified as it was by chromatography on a silica gel column (hexane:ethyl acetate=4:1), whereby a colorless solid (0.16 g) was obtained. The resulting solid was dissolved in dichloromethane (8 ml), followed by the addition of 1-[(6-chloronaphthalen-2-yl)sulfonyl]piperazine trifluoroacetate (0.24 g), triethylamine (80.0 μl) and sodium triacetoxyboron hydride (0.17 g). The resulting mixture was stirred at room temperature for 16 hours under an argon gas atmosphere. An aqueous solution of sodium bicarbonate was added to the reaction mixture. The resulting mixture was diluted with dichloromethane to separate the organic layer. The organic layer was dried over sodium sulfate and distilled under reduced pressure to remove the solvent. The residue was purified by chromatography on a silica gel column (hexane:ethyl acetate=3:1), whereby a colorless viscous liquid (0.33 g, 86%) was obtained.

$^1$H-NMR (CDCl$_3$) δ: 1.30–1.50(1H,m), 1.44(9H,s), 1.80–2.00(2H,m), 2.40(1H,m), 2.51(4H,br), 2.60–2.90(3H, m), 3.09(6H,br), 3.39(2H,s), 4.67(1H,br), 6.90–7.00(3H,m), 7.56(1H,d,J=8.8 Hz), 7.77(1H,d,J=8.8 Hz), 7.80–8.00(3H, m), 8.28(1H,s). MS (FAB) m/z: 584 [(M+H)$^+$, Cl$^{35}$], 586 [(M+H)$^+$, Cl$^{37}$].

Referential Example 322

(2RS)-2-(tert-Butyldimethylsilyloxymethyl)-6-methoxycarbonyl-1,2,3,4-tetrahydronaphthalene In N,N-dimethylformamide (5 ml), (2RS)-2-hydroxymethyl-6-methoxycarbonyl-1,2,3,4-tetrahydronaphthalene (1.71 g) was dissolved. To the resulting solution, imidazole (0.81 g) and tert-butyldimethylsilyl chloride (1.81 g) were added under ice cooling, followed by stirring at room temperature for 14 hours. After the addition of methanol, the mixture was concentrated under reduced pressure. The concentrate was diluted with ethyl acetate, washed with water and then dried over anhydrous sodium sulfate. The residue obtained by distilling off the solvent under reduced pressure was purified by chromatography (hexane:ethyl acetate=50:1), whereby a pale yellow solid (2.20 g, 85%) was obtained.

$^1$H-NMR (CDCl$_3$) δ: 0.06(6H,s), 0.91(9H,s), 1.40–1.60 (1H,m), 1.90–2.10(2H,m), 2.53(1H,dd,J=17.1,10.3 Hz), 2.80–3.00(3H,m), 3.58(2H,d,J=5.9 Hz), 3.89(3H,s), 7.14 (1H,d,J=7.8 Hz), 7.70–7.80(2H,m). MS (FAB) m/z: 335 (M+H)$^+$.

Referential Example 323

(2RS)-2-(tert-Butyldimethylsilyloxymethyl)-6-hydroxymethyl-1,2,3,4-tetrahydronaphthalene In the same manner as in Referential Example 320, the title compound was obtained using (2RS)-2-(tert-butyldimethylsilyloxymethyl)-6-methoxycarbonyl-1,2,3,4-tetrahydronaphthalene as a starting material.

$^1$H-NMR (CDCl$_3$) δ: 0.07(6H,s), 0.91(9H,s), 1.30–1.50 (1H,m), 1.50–1.60(1H,m), 1.90–2.10(2H,m), 2.48(1H,m), 2.70–2.90(3H,m), 3.58(2H,m), 4.62(2H,d,J=5.9 Hz), 7.09 (3H,m). MS (FAB) m/z: 307 (M+H)$^+$.

Referential Example 324

(2RS)-6-(N-tert-Butoxycarbonylaminomethyl)-2-(tert-butyldimethylsilyloxymethyl)-1,2,3,4-tetrahydronaphthalene In dichloromethane (10 ml), (2RS)-2-(tert-butyldimethylsilyloxymethyl)-6-hydroxymethyl-1,2,3,4-tetrahydronaphthalene (1.00 g) was dissolved. Triethylamine (0.5 ml) was added to the resulting solution, followed by ice cooling. A solution of methanesulfonyl chloride (0.39 g) in dichloromethane (1 ml) was added to the reaction mixture and the mixture was stirred at room temperature for 9 hours. After washing with water, the reaction mixture was dried over anhydrous sodium sulfate. The residue obtained by distilling off the solvent under reduced pressure was treated In the same manner as in Referential Example 318, whereby the title compound (1.10 g, 83%) was obtained.

$^1$H-NMR (CDCl$_3$) δ: 0.06(6H,s), 0.91(9H,s), 1.40–1.60 (1H,m), 1.46(9H,s), 1.90–2.00(2H,m), 2.45(1H,m), 2.70–2.90(3H,m), 3.57(2H,m), 4.24(2H,m), 4.76(1H,br), 7.00–7.10(3H,m). MS (FAB) m/z: 406 (M+H)$^+$.

Referential Example 325

(2RS)-6-(N-tert-Butoxycarbonylaminomethyl)-2-hydroxymethyl-1,2,3,4-tetrahydronaphthalene In tetrahydrofuran (10 ml), (2RS)-6-(N-tert-butoxycarbonylaminomethyl)-2-(tert-butyldimethylsilyloxymethyl)-1,2,3,4-tetrahydronaphthalene (1.09 g) was dissolved. Tetrabutylammonium fluoride (a 1.0 M tetrahydrofuran solution, 4.0 ml) was added to the resulting solution, followed by stirring at room temperature for 2 hours. After concentration under reduced pressure, the reaction mixture was diluted with dichloromethane, washed with water an dried over anhydrous sodium sulfate. The residue obtained by distilling off the solvent under reduced pressure was purified by chromatography on a silica gel column (hexane:ethyl acetate=3:1 to 2:1), whereby a colorless solid (0.77 g, 98%) was obtained. A portion of the solid was recrystallized from a mixed solvent of hexane and ethyl acetate, whereby colorless crystals were obtained.

$^1$H-NMR (CDCl$_3$) δ: 1.40–1.60(2H,m), 1.46(9H,s), 1.90–2.10(2H,m), 2.48(1H,dd,J=16.6,10.7 Hz), 2.70–3.00 (3H,m), 3.6–3.7(2H,m), 4.24(2H,d,J=5.4 Hz), 4.78(1H,br), 7.00–7.10(3H,m). Elementary analysis for C$_{17}$H$_{25}$NO$_3$ Calculated: C, 70.07; H, 8.65; N, 4.81. Found: C, 70.02; H, 8.61; N, 4.46.

Referential Example 326

1-[[(2RS)-6-(N-tert-Butoxycarbonylaminomethyl-1,2,3,4-tetrahydronaphthalen-2-yl)methyl]-4-[(6-chloronaphthalen-2-yl)sulfonyl]piperazine In dichloromethane (5 ml), (2RS)-6-(N-tert-butoxycarbonylaminomethyl)-2-hydroxymethyl-1,2,3,4-tetrahydronaphthalene (0.17 g) was dissolved, followed by the addition of N-methylmorpholine N-oxide (0.13 g) and molecular sieves 4A (activated powder, 0.18 g). Under ice cooling, tetrapropylammonium perruthenate (10 mg) was added and the mixture was stirred at room temperature for 1 hour. Diethyl ether was added to the reaction mixture. From the resulting mixture, insoluble matter was removed by filtration through Celite. The filtrate was distilled under reduced pressure. The residue was purified by chromatography on a silica gel column (dichloromethane) to yield the aldehyde compound. In the same manner as in Referential Example 321, a reaction was effected using the resulting aldehyde compound, whereby the title compound (0.14 g, 41%) was obtained.

$^1$H-NMR (CDCl$_3$) δ: 1.20–1.40(1H,m), 1.44(9H,s), 1.80–2.00(2H,m), 2.20–2.40(3H,m), 2.50–2.60(4H,m), 2.60–2.80(3H,m), 3.11(4H,m), 4.20(2H,d,J=5.4 Hz), 4.79 (1H,br), 6.94(3H,m), 7.57(1H,dd,J=8.8,1.5 Hz), 7.79(1H,dd, J=8.8,1.5 Hz), 7.90–8.00(3H,m), 8.31(1H,s). MS (FAB) m/z: 584 [(M+H)$^+$, Cl$^{35}$], 586 [(M+H)$^+$, Cl$^{37}$].

Referential Example 327

1-[[(2RS)-6-(N-tert-Butoxycarbonylaminomethyl)-1,2,3,4-tetrahydronaphthalen-2-yl]carbonyl]-4-[(6-chloronaphthalen-2-yl)sulfonyl]piperazine In carbon tetrachloride (2 ml), acetonitrile (2 ml) and water (3 ml), (2RS)-6-(N-tert-butoxycarbonylaminomethyl)-2-hydroxymethyl-1,2,3,4-tetrahydronaphthalen (0.21 g) was dissolved. To the resulting solution, sodium periodate (0.48 g) and ruthenium trichloride hydrate (4 mg) were added, followed by stirring for 90 minutes. The reaction mixture was diluted with dichloromethane. The organic layer thus separated was dried over anhydrous sodium sulfate. The residue obtained by distilling off the solvent under reduced pressure was added with diethyl ether. After the filtration of insoluble matter, the filtrate was distilled under reduced pressure. The carboxylic acid compound thus obtained was reacted in the same manner as in Referential Example 319, whereby the title compound (0.11 g, 25%) was obtained.

$^1$H-NMR (CDCl$_3$) δ: 1.45(9H,s), 1.70–2.00(2H,m), 2.60–2.90(4H,m), 2.95(1H,m), 3.11(4H,m), 3.64(2H,m), 3.76(2H,m), 4.22(2H,d,J=5.4 Hz), 4.82(1H,br), 6.90–7.10 (3H,m), 7.59(1H,d,J=8.8 Hz), 7.77(1H,d,J=8.8 Hz), 7.90–8.00(3H,m), 8.31(1H,s). MS (FD) m/z: 597 (M$^+$, Cl$^{35}$), 599 (M$^+$, Cl$^{37}$)

Referential Example 328

2-(N-tert-Butoxycarbonylaminomethyl)-7-methoxycarbonylnaphthalene

In the same manner as in Referential Example 324, a reaction was effected using 2-hydroxymethyl-7-methoxycarbonylnaphthalene (1.01 g) as a starting material, whereby the title compound was obtained.

$^1$H-NMR (CDCl$_3$) δ: 1.49(9H,s), 3.98(3H,s), 4.50(2H,d, J=5.4 Hz), 4.99(1H,br), 7.53(1H,d,J=8.3 Hz), 7.80–7.90(3H, m), 8.04(1H,dd,J=8.3,1.0 Hz), 8.57(1H,s). Elementary analysis for C$_{18}$H$_{21}$NO$_4$ Calculated: C, 68.55; H, 6.71; N, 4.44. Found: C, 68.54; H, 6.70; N, 4.46.

Referential Example 329

1-[[7-(N-tert-Butoxycarbonylaminomethyl)naphthalen-2-yl]carbonyl]-4-[(6-chloronaphthalen-2-yl)sulfonyl]piperazine In the same manner as in Referential Example 319, a reaction was effected using 2-(N-tert-butoxycarbonylaminomethyl)-7-methoxycarbonylnaphthalene as a starting material, whereby the title compound was obtained.

$^1$H-NMR (CDCl$_3$) δ: 1.46(9H,s), 3.12(4H,br), 3.50–4.00 (4H,br), 4.45(2H,d,J=5.9 Hz), 5.01(1H,br), 7.34(1H,d,J=7.8 Hz), 7.45(1H,d,J=8.3 Hz), 7.50–7.60(1H,m), 7.66(1H,s), 7.70–7.80(4H,m), 7.90–8.00(3H,m), 8.30(1H,s). MS (FAB) m/z: 594 [(M+H)$^+$, Cl$^{35}$], 596 [(M+H)$^+$, Cl$^{37}$].

Referential Example 330

1-[[7-(N-tert-Butoxycarbonylaminomethyl)naphthalen-2-yl]methyl]-4-[(6-chloronaphthalen-2-yl)sulfonyl]piperazine In the same manner as in Referential Example 320 or Referential Example 326, a reaction was effected using 2-(N-tert7butoxycarbonylaminomethyl)-7-methoxycarbonylnaphthalene as a starting material, whereby the title compound was obtained.

$^1$H-NMR (CDCl$_3$) δ: 1.47(9H,s), 2.50–2.70(4H,m), 3.10 (4H,br), 3.61(2H,s), 4.44(2H,d,J=5.4 Hz), 4.92(1H,br), 7.30–7.40(2H,m), 7.50–7.70(3H,m), 7.70–7.90(3H,m), 7.90–8.00(3H,m), 8.29(1H,s) MS (FAB) m/z: 580 [(M+H)$^+$, Cl$^{35}$], 582 [(M+H)$^+$, Cl$^{37}$].

Referential Example 331

2-(N-tert-Butoxycarbonylaminomethyl)-6-methoxycarbonylnaphthalene

In a mixed solvent of tetrahydrofuran (40 ml) and methanol (8 ml), dimethyl 2,6-naphthalenedicarboxylate (2.00 g) was suspended. To the resulting suspension, sodium borohydride (0.98 g) was added under ice cooling, followed by stirring at room temperature for 21 hours. The reaction mixture was added with water and then concentrated under reduced pressure. Ethyl acetate and dilute hydrochloric acid were added to the residue to separate the organic layer. The organic layer was dried over anhydrous sodium sulfate. The residue obtained by distilling off the solvent under reduced pressure was purified by chromatography on a silica gel column (hexane:ethyl acetate=3:1), whereby colorless crystals (1.23 g, 70%) was obtained. The resulting crystals were reacted as in Referential Example 324, whereby the title compound was obtained.

$^1$H-NMR (CDCl$_3$) δ: 1.48(9H,s), 3.98(3H,s), 4.50(2H,d, J=5.4 Hz), 4.99(1H,br), 7.47(1H,d,J=8.3 Hz), 7.75(1H,s), 7.84(1H,d,J=8.8 Hz), 7.92(1H,d,J=8.8 Hz), 8.06(1H,d,J=8.3 Hz), 8.58(1H,s). Elementary analysis for C$_{18}$H$_{21}$NO$_4$ Calculated: C, 68.55; H, 6.71; N, 4.44. Found: C, 68.93; H, 6.70; N, 4.29.

Referential Example 332

Methyl 5-benzimidazolecarboxylate hydrochloride

Under ice cooling, thionyl chloride (2.30 ml) was added dropwise to methanol (50 ml). Then, 5-benzimidazolecarboxylic acid (5.00 g) was added, followed by heating under reflux for 5 hours. The reaction mixture was distilled under reduced pressure. The residue was pulverized in diethyl ether, followed by collection through filtration, whereby colorless crystals (6.36 g, 97%) was obtained.

$^1$H-NMR (DMSO-d$_6$) δ: 3.93(3H,s), 7.96(1H,d,J=8.8 Hz), 8.12(1H,d,J=8.8 Hz), 8.40(1H,s), 9.66(1H,s). Elementary analysis for C$_9$H$_8$N$_2$O$_2$·HCl Calculated: C, 50.84; H, 4.27; N, 13.17; Cl, 16.67. Found: C, 50.64; H, 4.22; N, 13.12; Cl, 16.59.

Referential Example 333

Methyl N-triphenylmethyl-5-benzimidazolecarboxylate

In dichloromethane (15 ml), methyl 5-benzimidazolecarboxylate hydrochloride (1.00 g) was suspended. To the resulting suspension, triethylamine (1.50 ml) and triphenylmethyl chloride (1.50 g) were added, followed by stirring at room temperature for 3 hours. The reaction mixture was diluted with dichloromethane, washed with water, and dried over anhydrous sodium sulfate. The residue obtained by distilling off the solvent under reduced pressure was purified by chromatography on a silica gel column (hexane:ethyl acetate=2:1), whereby title compound (2.10 g, quant.) was obtained as a yellow solid.

$^1$H-NMR (CDCl$_3$) δ: 3.75(2H,s), 3.89(1H,s), 6.49(⅓H,d, J=8.8 Hz), 7.1–7.4(16H,m), 7.61(⅓H,dd,J=8.8,1.5 Hz), 7.78 (⅔H,d,J=8.8 Hz), 7.87(⅔H,dd,J=8.8,1.5 Hz), 7.96(⅓H,s), 8.02(⅔H,s).

MS (FAB) m/z: 419 (M+H)$^+$.

Referential Example 334] Sodium thiazolo[5,4-c]pyridine -2-carboxylate

Ethyl thiazolo[5,4-c]pyridine-2-carboxylate (J. Heterocyclic Chem., 27, 563(1990)) (0.61 g) was dissolved in tetrahydrofuran (12 ml). To the resulting solution, a 1N aqueous sodium hydroxide solution (3 ml) was added, followed by stirring at room temperature for 30 minutes. The insoluble matter was collected by filtration. Without purification, it was provided for the subsequent reaction as it was.

$^1$H-NMR (DMSO-d$_6$) δ: 7.95(1H,d,J=5.9 Hz), 8.57(1H, d,J=5.9 Hz), 9.27(1H,s).

Referential Example 335

1-[(5-tert-Butoxycarbonyl -4,5,6,7-tetrahydrothieno [3,2-c]pyridin-2-yl)methyl]-4-[(6-chloronaphthalen-2-yl)sulfonyl]piperazine In the same manner as in Referential Example 321, the title compound was obtained using 5-tert-butoxycarbonyl-2-formyl-4,5,6,7-tetrahydrothieno[3,2-c]pyridine (WO94/21599) and 1-[(6-chloronaphthalen-2-yl)sulfonyl]piperazine hydrochloride as starting materials.

$^1$H-NMR (CDCl$_3$) δ: 1.47(9H,s), 2.53–2.62(4H,m), 2.72 (2H,br s), 3.10(4H,br s), 3.59(2H,s), 3.66(2H,br s), 4.38(2H, s), 6.54(1H,s), 7.57(1H,dd,J=8.8,2.0 Hz), 7.76(1H,dd,J=8.8, 2.0 Hz), 7.87–7.94(3H,m), 8.29(1H,s). MS (FAB) m/z: 562 [(M+H)$^+$, Cl$^{35}$], 564 [(M+H)$^+$, Cl$^{37}$].

Referential Example 336

3-(5-tert-Butoxycarbonyl -4,5,6,7-terahydrothieno[3, 2-c]pyridin-2-yl)propionic acid Under ice cooling, sodium hydride (about 60% in oil, 126 mg) was added to tetrahydrofuran (10 ml). After stirring for 5 minutes, ethyl diethylphosphonoacetate (0.42 ml) was added dropwise and the resulting mixture was stirred for 30 minutes under ice cooling. To the reaction mixture, a solution of 5-tert-butoxycarbonyl-2-formyl -4,5,6,7-tetrahydrothieno[3,2-c]pyridine (WO94/21599) (360 mg) in tetrahydrofuran (10 ml) was added dropwise, followed by stirring for 1 hour under ice cooling. The reaction mixture was then concentrated under reduced pressure. Ethyl acetate was added to the concentrate. The mixture was washed with water and saturated aqueous NaCl solution and dried over anhydrous sodium sulfate. The residue obtained by distilling off the solvent under reduced pressure was purified by chromatography on a silica gel column (hexane:ethyl acetate=5:1), whereby a yellow oil (515 mg, quant) was obtained.

The resulting oil (1.38 g, 4.09 mmol) was dissolved in methanol (40 ml), followed by the addition of 10% palladium carbon (0.20 g). The mixture was subjected to catalytic reduction for 1 hour under normal pressure. After the removal of the catalyst by filtration, the filtrate was concentrated under reduced pressure, whereby pale yellow oil (1.41 g, quant.) was obtained.

The oil (1.38 g, 4.07 mmol) was dissolved in tetrahydrofuran (15 ml), followed by the addition of ethanol (10 ml) and a 1N aqueous sodium hydroxide solution (8 ml). The resulting mixture was heated under reflux for 30 minutes. To the reaction mixture, 1N hydrochloric acid and ethyl acetate were added to separate the organic layer. The organic layer was dried over anhydrous sodium sulfate and distilled under reduced pressure to remove the solvent, whereby the title compound (1.28 g, quant.) was obtained as a colorless oil.

$^1$H-NMR (CDCl$_3$) δ: 1.48(9H,s), 2.70(2H,t,J=7.3 Hz), 2.76(2H,br s), 3.09(2H,t,J=7.3 Hz), 3.70(2H,s), 4.40(2H,s), 6.51(1H,s). MS (FD) m/z: 311M$^+$.

Referential Example 337

(E)-3-(5-tert-Butoxycarbonyl -4,5,6,7-tetrahydrothieno[3,2-c]pyridin-2-yl)acrylic acid In the same manner as in Referential Example 336 except that hydrolysis was carried out instead of catalytic hydrogenation, whereby the title compound was obtained.

¹H-NMR (CDCl₃) δ: 1.49(9H,s), 2.85(2H,br s), 3.73(2H, br s), 4.47(2H,s), 6.12(1H,d,J=15.4 Hz), 6.98(1H,s), 7.77 (1H,d,J=15.4 Hz) MS (FD) m/z: 309M⁺.

Referential Example 338

1-(E)-3-(5-tert-Butoxycarbonyl -4,5,6,7-tetrahydrothieno[3,2-c]pyridin-2-yl)propenoyl]-4[(6-chloronaphthalen-2-yl)sulfonyl]piperazine In the same manner as in Referential Example 319, a reaction was effected using (E)-3-(5-tert-butoxycarbonyl -4,5,6,7-tetrahydrothieno[3,2-c]pyridin-2-yl)acrylic acid and 1-[(6-chloronaphthalen-2-yl)sulfonyl]piperazine hydrochloride as starting materials, whereby the title compound was obtained.

¹H-NMR (CDCl₃) δ: 1.47(9H,s), 2.80(2H,br s), 3.12(4H, t,J=4.9 Hz), 3.46–3.86(6H,m), 4.41(2H,s), 6.39(1H,d,J=15.1 Hz), 6.83(1H,s), 7.55–7.78(3H,m), 7.89–7.92(3H,m), 8.30 (1H,s). MS (FD) m/z: 601 (M⁺, Cl³⁵), 603 (M⁺, Cl³⁷)

Referential Example 339

1-[3-(5-tert-Butoxycarbonyl -4,5,6,7-tetrahydrothieno[3,2-c]pyridin-2-yl)propionyl]-4-[(6-chloronaphthalen-2-yl)sulfonyl]piperazine In tetrahydrofuran (10 ml), 3-(5-tert-butoxycarbonyl -4,5,6,7-tetrahydrothieno[3,2-c]pyridin-2-yl)propionic acid (445 mg) was dissolved, followed by the successive dropwise addition of N-methylmorpholine (170 µl) and isobutyl chloroformate (210 µl) at −20° C. After stirring at −20° C. for 10 minutes, a solution of 1-[(6-chloronaphthalen-2-yl)sulfonyl] piperazine hydrochloride (607 mg) which had been dissolved in dichloromethane (10 ml) was added. After stirring at −20° C. for 10 minutes, the reaction mixture was warmed up to room temperature. The reaction mixture was concentrated under reduced pressure. The residue was then dissolved in dichloroethane. The resulting solution was washed with 1N hydrochloric acid, a saturated aqueous solution of sodium bicarbonate and saturated aqueous NaCl solution, dried over anhydrous sodium sulfate and then distilled under reduced pressure to remove the solvent. The residue was purified by chromatography on a silica gel column (hexane:ethyl acetate=4:1 to 2:1), whereby the title compound (625 mg, 72%) was obtained.

¹H-NMR (CDCl₃) δ: 1.47(9H,s), 2.53(2H,t,J=7.5 Hz), 2.68(2H,br s), 2.99–3.10(6H,m), 3.51–3.55(2H,m), 3.64 (2H,br s), 3.72–3.77(2H,m), 4.34(2H,s), 6.43(1H,s), 7.59 (1H,dd,J=8.8,2.0 Hz), 7.74(1H,dd,J=8.8,2.0 Hz), 7.88–7.94 (3H,m), 8.30(1H,s). MS (FAB) m/z: 604 [(M+H)⁺, Cl³⁵], 606 [(M+H)⁺, Cl³⁷].

Referential Example 340

3-(5-tert-Butoxycarbonyl -4,5,6,7-tetrahydrothieno [3,2-c]pyridin-2-yl)propanal

In dichloromethane (100 ml), ethyl 3-(5-tert-butoxycarbonyl-4,5,6,7-tetrahydrothieno[3,2-c]pyridin-2-yl)propionate (1.68 g) obtained in Referential Example 336 was dissolved. After stirring at −78° C. for 10 minutes, diisobutylaluminum hydride (a 0.98M hexane solution, 7.50 ml) was slowly added dropwise. After stirring at −78° C. for 10 minutes, methanol (50 ml) was added, followed by warming up to room temperature. The reaction mixture was concentrated under reduced pressure. To the residue, dichloromethane and a saturated aqueous solution of ammonium chloride were added, followed by Celite filtration. The organic layer was separated from the filtrate, washed with saturated aqueous NaCl solution, dried over anhydrous sodium sulfate and distilled to remove the solvent. The residue was purified by chromatography on a silica gel column (hexane:ethyl acetate=5:1), whereby the title compound (935 mg, 55%) was obtained.

¹H-NMR (CDCl₃) δ: 1.48(9H,s), 2.76(2H,br s), 2.81(2H, t,J=7.3 Hz), 3.09(2H,t,J=7.3 Hz), 3.69(2H,br s), 4.39(2H,s), 6.49(1H,s), 9.81(1H,s). MS (FD) m/z: 295M⁺.

Referential Example 341

1-[3-(5-tert-Butoxycarbonyl -4,5,6,7-tetrahydrothieno[3,2-c]pyridin-2-yl)propyl]-4-[(6-chloronaphthalen-2-yl)sulfonyl]piperazine In the same manner as in Referential Example 321, a reaction was effected using 3-(5-tert-butoxycarbonyl -4,5,6,7-tetrahydrothieno[3,2-c]pyridin-2-yl)propanal and 1-[(6-chloronaphthalen-2-yl)sulfonyl]piperazine hydrochloride as starting materials, whereby the title compound was obtained.

¹H-NMR (CDCl₃) δ: 1.47(9H,s), 1.69–1.79(2H,m), 2.36 (2H,t,J=7.3 Hz), 2.49–2.54(4H,m), 2.65–2.75(4H,m), 3.10 (4H,br s), 3.67(2H,br s), 4.37(2H,s), 6.39(1H,s), 7.57(1H, dd,J=8.8,2.0 Hz), 7.78(1H,dd,J=8.8,2.0 Hz), 7.88–7.95(3H, m), 8.30(1H,s).

MS (FD) m/z: 589 (M⁺, Cl³⁵), 591 (M⁺, Cl³⁷)

Referential Example 342

2-Aminomethyl-5-tert-butoxycarbonyl-4,5,6,7-tetrahydrothieno[3,2-c]pyridine

In tetrahydrofuran (100 ml), 5-tert-butoxycarbonyl-2-hydroxymethyl-4,5,6,7-tetrahydrothieno[3,2-c]pyridine (WO94/21599) (2.10 g) was dissolved. After the addition of triphenylphosphine (2.66 g) and phthalimide (1.15 g), diethyl azodicarboxylate (1.28 ml) was added dropwise, followed by stirring at room temperature for 5 hours. The reaction mixture was concentrated under reduced pressure. The residue was purified by chromatography on a silica gel column (hexane:ethyl acetate=4:1), whereby a colorless solid was obtained. The resulting solid was dissolved in ethanol (40 ml), followed by the addition of hydrazine hydrate (0.39 ml). The resulting mixture was heated under reflux for 5 hours. The precipitate was filtered off and the filtrate was concentrated under reduced pressure. The residue was purified by chromatography on a silica gel column (dichloromethane~dichloromethane:methanol=25:1), whereby the title compound (448 mg, 21%) was obtained.

¹H-NMR (DMSO-d₆) δ: 1.42(9H,s), 2.72(2H,m), 3.60 (2H,m), 3.80(2H,s), 4.32(2H,s), 6.64(1H,s). MS (FD) m/z: 268M⁺.

Referential Example 343

1-[N-[(5-tert-Butoxycarbonyl -4,5,6,7-tetrahydrothieno[3,2-c]pyridin-2-yl)methyl]carbamoyl]-4-[(6-chloronaphthalen-2-yl)sulfonyl]piperazine In tetrahydrofuran (100 ml), 5-tert-butoxycarbonyl-2-aminomethyl-4,5,6,7-tetrahydrothieno[3,2-c]pyridine (150 mg) was dissolved. Under ice cooling, carbonyl diimidazole (136 mg) was added, followed by stirring at room temperature for 1 hour. The reaction mixture was concentrated under reduced pressure and the residue was dissolved in toluene (50 ml). Under ice cooling, triethylamine (0.23 ml) and 1-[(6-chloronaphthalen-2-yl)sulfonyl]piperazine hydrochloride (356 mg) were added, followed by stirring overnight at room temperature. The reaction mixture was diluted with ethyl acetate, washed with water and saturated aqueous NaCl solution and then dried over anhydrous sodium sulfate. The solvent was then distilled off under reduced pressure and the residue was purified by chromatography on a silica gel column (hexane:ethyl acetate=3:1 to 1:1), whereby the title compound (303 mg, 89%) was obtained.

$^1$H-NMR (CDCl$_3$) δ: 1.46(9H,s), 2.70(2H,br s), 3.07(4H, t,J=4.9 Hz), 3.48(4H,t,J=4.9 Hz), 3.66(2H,br s), 4.36(2H,br s), 4.39(2H,d,J=5.4 Hz), 4.69(1H,t,J=5.4 Hz), 6.58(1H,s), 7.58(1H,dd,J=8.8,2.0 Hz), 7.74(1H,dd,J=8.8,2.0 Hz), 7.87–7.93(3H,m), 8.30(1H,s). MS (FD) m/z: 604 (M$^+$, Cl$^{35}$), 606 (M$^+$, Cl$^{37}$)

Referential Example 344

1-[(5-tert-Butoxycarbonyl -4,5,6,7-tetrahydrothieno [3,2-c]pyridin-2-yl)carbonyl]-4-[(6-chloronaphthalen-2-yl)sulfonyl]piperazine In the same manner as in Referential Example 319, the title compound was obtained using 5-tert-butoxycarbonyl -4,5,6,7-tetrahydrothieno[3,2-c]pyridine-2-carboxylic acid (WO94/21599) and 1-[(6-chloronaphthalen-2-yl)sulfonyl] piperazine hydrochloride.

$^1$H-NMR (CDCl$_3$) δ: 1.47(9H,s), 2.79(2H,br s), 3.12(4H, t,J=4.9 Hz), 3.68(2H,br s), 3.84(4H,t,J=4.9 Hz), 4.42(2H,br s), 6.91(1H,s), 7.59(1H,dd,J=8.8,2.0 Hz), 7.75(1H,dd,J=8.8, 2.0 Hz), 7.90–7.97(3H,m), 8.30(1H,s). MS (FD) m/z: 575 (M$^+$, Cl$^{35}$), 577 (M$^+$, Cl$^{37}$).

Referential Example 345

1-[(5-tert-Butoxycarbonyl -4,5,6,7-tetrahydrothieno [3,2-c]pyridin-2-yl)carbonyl]-4-[(6-chloronaphthalen-2-yl)sulfonyl]-2-ethoxycarbonylpiperazine In the same manner as in Referential Example 319, the title compound was obtained using 5-tert-butoxycarbonyl -4,5,6,7-tetrahydrothieno[3,2-c]pyridine-2-carboxylic acid (WO94/21599) and 1-[(6-chloronaphthalen-2-yl)sulfonyl]-3-ethoxycarbonylpiperazine (WO96/10022) as starting materials.

$^1$H-NMR (CDCl$_3$) δ: 1.32(3H,t,J=7.3 Hz), 1.47(9H,s), 2.35–2.46(1H,m), 2.55–2.64(1H,m), 2.80(2H,br s), 3.15–3.20(1H,m), 3.69(2H,br s), 3.75–3.85(1H,m), 4.12 (2H,q,J=7.3 Hz), 4.20–4.36(2H,m), 4.39–4.48(3H,m), 6.96 (1H,s), 7.59(1H,dd,J=8.8,2.0 Hz), 7.75(1H,dd,J=8.8,2.0 Hz), 7.88–7.94(3H,m), 8.32(1H,s). MS (FAB) m/z: 648 [(M+H)$^+$, Cl$^{35}$], 650 [(M+H)$^+$, Cl$^{37}$].

Referential Example 346

1-[(6-Chloronaphthalen-2-yl)sulfonyl]-4-[(5-cyano-4,5,6,7-tetrahydrothieno[3,2-c]pyridin-2-yl) carbonyl]piperazine In ethanol, 1-[(6-chloronaphthalen-2-yl)sulfonyl]-4-[(4,5, 6,7-tetrahydrothieno[3,2-c]pyridin-2-yl)carbonyl] piperazine hydrochloride (195 mg), triethylamine (0.2 ml) and sodium acetate (118 mg) were suspended. Cyanogen bromide (114 mg) was added to the resulting suspension, followed by stirring at room temperature for 2 hours. To the residue obtained by concentration of the reaction mixture under reduced pressure, dichloromethane was added. The mixture was washed with water and dried over anhydrous sodium sulfate. The residue obtained by distilling off the solvent under reduced pressure was purified by chromatography on a silica gel column (dichloromethane:methanol 100:1), whereby the title compound (51 mg, 28%) was obtained.

$^1$H-NMR (CDCl$_3$) δ: 2.93–2.98(2H,m), 3.11–3.14(4H,m), 3.49–3.55(2H,m), 3.81–3.84(4H,m), 4.29(2H,s), 6.89(1H,s), 7.59(1H,dd,J=8.8,2.0 Hz), 7.75(1H,dd,J=8.8,2.0 Hz), 7.90–7.94(3H,m), 8.30(1H,s). MS (FAB) m/z: 501 [(M+H)$^+$, Cl$^{35}$], 503 [(M+H)$^+$, Cl$^{37}$].

Referential Example 347

1-[N-(5-tert-Butoxycarbonyl -4,5,6,7-tetrahydrothieno[3,2-c]pyridin-2-yl)carbamoyl]-4-[(6-chloronaphthalen-2-yl)sulfonyl]piperazine In benzene (10 ml), 5-tert-butoxycarbonyl-4,5,6,7-tetrahydrothieno[3,2-c]pyridine-2-carboxylic acid (WO94/21599)(283 mg) was dissolved. To the resulting solution, triethylamine (0.14 ml) and diphenylphosphoryl azide (0.21 mg) were added, followed by heating under reflux for 2 hours. After the reaction mixture was cooled to room temperature, 1-[(6-chloronaphthalen-2-yl)sulfonyl] piperazine hydrochloride (347 mg) and triethylamine (0.28 ml) were added and the mixture was heated under reflux overnight. After cooling to room temperature, to the reaction mixture was added dichloromethane and a 3N aqueous sodium hydroxide solution. The resulting mixture was separated and aqueous layer was extracted with dichloromethane. The combined organic layer thus extracted was washed with 0.5N hydrochloric acid, a saturated aqueous solution of sodium bicarbonate and saturated aqueous NaCl solution, dried over anhydrous sodium sulfate and distilled under reduced pressure to remove the solvent. The residue was purified by chromatography on a silica gel column (hexane:ethyl acetate=3:1 to 2:1), whereby the title compound (284 mg, 48%) was obtained.

$^1$H-NMR (CDCl$_3$) δ: 1.45(9H,s), 2.65(2H,br s), 3.10(4H, t,J=4.9 Hz), 3.57(4H,t,J=4.9 Hz), 3.64(2H,br s), 4.27(2H,s), 6.15(1H,br s), 7.58(1H,dd,J=8.8,2.0 Hz), 7.73(1H,dd,J=8.8, 2.0 Hz), 7.87–7.93(3H,m), 8.28(1H,s). MS (FAB) m/z: 591 [(M+H)$^+$, Cl$^{35}$], 593 [(M+H)$^+$, Cl$^{37}$].

Referential Example 348

1-[N-(5-tert-Butoxycarbonyl -4,5,6,7-tetrahydrothieno[3,2-c]pyridin-2-yl)-N-methylcarbamoyl]-4-[(6-chloronaphthalen-2-yl) sulfonyl]piperazine In N,N-dimethylformamide (10 ml), 1-[N-(5-tert-butoxycarbonyl-4,5,6,7-tetrahydrothieno[3,2-c]pyridin-2-yl)carbamoyl]-4-[(6-chloronaphthalen-2-yl)sulfonyl] piperazine (147 mg) was dissolved. To the resulting solution, sodium hydride (60% in oil, 22 mg) was added, followed by stirring at room temperature for 30 minutes. After methyl iodide (0.023 ml) was added to the reaction mixture and the resulting mixture was stirred at room temperature for 90 minutes, the residue obtained by the concentration of the reaction mixture under reduced pressure was added with ethyl acetate. The resulting mixture was washed with water and saturated aqueous NaCl solution and then dried over anhydrous sodium sulfate. The solvent was distilled off under reduced pressure. The residue was purified by chromatography on a silica gel column (hexane:ethyl acetate= 2:1), whereby the title compound (43 mg) was obtained.

$^1$H-NMR (CDCl$_3$) δ: 1.49(9H,s), 2.63(2H,br s), 3.01(4H, t,J=4.9 Hz), 3.13(3H,s), 3.40(4H,t,J=4.9 Hz), 3.67(2H,br s), 4.31(2H,s), 6.21(1H,br s), 7.58(1H,dd,J=8.8,2.0 Hz), 7.72 (1H,dd,J=8.8,2.0 Hz), 7.88–7.95(3H,m), 8.27(1H,s). MS (FAB) m/z: 605 [(M+H)$^+$, Cl$^{35}$], 607 [(M+H)$^+$, Cl$^{37}$].

Referential Example 349

1-[(6-tert-Butoxycarbonyl -4,5,6,7-tetrahydrothiazolo[5,4-c]pyridin-2-yl)carbonyl]-4-[(6-chloronaphthalen-2-yl)sulfonyl]piperazine In the same manner as in Referential Example 319, the title compound was obtained using 6-tert-butoxycarbonyl -4,5,6,7-tetrahydrothiazolo[5,4-c]pyridine-2-carboxylic acid (WO94/21599) and 1-[(6-chloronaphthalen-2-yl)sulfonyl]piperazine hydrochloride as starting materials.

$^1$H-NMR (CDCl$_3$) δ: 1.47(9H,s), 2.84(2H,br s), 3.19(4H, br), 3.72(2H,t,J=5.4 Hz), 3.87(2H,br s), 4.54(2H,s), 4.63 (2H,br s), 7.57(1H,dd,J=8.8,2.0 Hz), 7.76(1H,dd,J=8.8,2.0 Hz), 7.87–7.94(3H,m), 8.30(1H, s) MS (FAB) m/z: 577 [(M+H)$^+$, Cl$^{35}$], 579 [(M+H)$^+$, Cl$^{37}$].

Referential Example 350

1-[(6-tert-Butoxycarbonyl -4,5,6,7-tetrahydrothiazolo[5,4-c]pyridin-2-yl)carbonyl]-4-[(6-chloronaphthalen-2-yl)sulfonyl]-2-ethoxycarbonylpiperazine In N,N-dimethylformamide (30 ml), 6-tert-butoxycarbonyl-4,5,6,7-tetrahydrothiazolo[5,4-c]pyridine-2-carboxylic acid (WO94/21599) (742 mg), 1-[(6-chloronaphthalen-2-yl)sulfonyl]-3-ethoxycarbonylpiperazine hydrochloride (WO96/10022) (1.00 g) and benzotriazol-1-yloxy-tris(pyrrolidino) phosphonium hexafluorophosphate (PyBOP®) (1.50 g) were dissolved. Triethylamine (0.40 ml) was added to the resulting solution, followed by stirring overnight at room temperature. After the reaction mixture was concentrated under reduced pressure, ethyl acetate was added to the residue. The resulting mixture was washed with water and saturated aqueous NaCl solution and then, dried over anhydrous sodium sulfate. The residue obtained by distilling off the solvent under reduced pressure was purified by chromatography on a silica gel column (hexane ethyl acetate=4:1), whereby the title compound (505 mg, 30%) was obtained.

$^1$H-NMR (CDCl$_3$) δ: 1.24–1.37(3H,m), 1.47(9H,s), 2.45–2.60(1H,m), 2.62–2.71(1H,m), 2.75–2.90(2H,m), 3.65–3.94(3H,m), 4.19–4.31(2H,m), 4.45–4.72(4H,m), 5.35 (½H,br s), 5.71–5.77(½H,m), 6.72(1H,br s), 7.58(1H,dd,J= 8.8,2.0 Hz), 7.77(1H,dd,J=8.8,2.0 Hz), 7.88–7.92(3H,m), 8.33(1H,s). MS (FAB) m/z: 649 [(M+H)$^+$, Cl$^{35}$], 651 [(M+H)$^+$, Cl$^{37}$].

Referential Example 351

1-[(6-tert-Butoxycarbonyl -4,5,6,7-tetrahydrothiazolo[5,4-c]pyridin-2-yl)carbonyl]-2-carbamoyl-4-[(6-chloronaphthalen-2-yl)sulfonyl]piperazine In tetrahydrofuran (5 ml), 1-[(6-tert-butoxycarbonyl -4,5,6,7-tetrahydrothiazolo[5,4-c]pyridin-2-yl)carbonyl]-4-[(6-chloronaphthalen-2-yl)sulfonyl]-2-ethoxycarbonylpiperazine (487 mg) was dissolved. Methanol (5 ml) and a 1N aqueous sodium hydroxide solution (3 ml) were added to the resulting solution, followed by stirring at room temperature for 4 hours. After the reaction mixture was adjusted to pH 1 to 2 by the addition of 1N hydrochloric acid, ethyl acetate was added to separate the organic layer. After drying over anhydrous sodium sulfate, the residue obtained by distilling off the solvent under reduced pressure was dissolved in tetrahydrofuran (5 ml). To the resulting solution, N-methylmorpholine (0.09 ml) and isobutyl chloroformate (0.11 ml) were added dropwise at –20° C. After stirring at –20° C. for 10 minutes, an ammoniadichloromethane solution (0.50 ml) was added to the reaction mixture. The resulting mixture was stirred at –20° C. for 10 minutes, followed by the addition of 1N aqueous hydrochloric acid solution in ethanol (10 ml). The reaction mixture was warmed up to room temperature. After the reaction mixture was concentrated under reduced pressure, the residue was dissolved in dichloroethane. The resulting solution was washed with 1N hydrochloric acid. The organic layer was dried over anhydrous sodium sulfate and distilled under reduced pressure to remove the solvent. The residue was purified by chromatography on a silica gel column (dichloromethane~dichloromethane:methanol= 100:1), whereby the title compound (317 mg, 68%) was obtained.

$^1$H-NMR (DMSO-d$_6$) δ: 1.41(9H,s), 2.39–2.86(4H,m), 3.60–3.80(4H,m), 4.25–4.34(1H,m), 4.36–4.34(½H,m), 4.62(2H,br s), 4.97(½H,br s), 5.44–5.52(½H,m), 6.19(½H, br s), 7.30–7.39(1H,m), 7.63–7.85(3H,m), 8.15(1H,d,J=8.8 Hz), 8.20–8.29(2H,m), 8.48(1H,s). MS (FAB) m/z: 620 [(M+H)$^+$, Cl$^{35}$], 622 [(M+H)$^+$, Cl$^{37}$].

Referential Example 352

1-[(6-tert-Butoxycarbonyl -4,5,6,7-tetrahydrothiazolo[5,4-c]pyridin-2-yl)carbonyl]-4-[(E)-4-chlorostyrylsulfonyl]piperazine In the same manner as in Referential Example 319, the title compound was obtained using 6-tert-butoxycarbonyl -4,5,6,7-tetrahydrothiazolo[5,4-c]pyridine-2-carboxylic acid (WO94/21599) and 1-[(E)-4-chlorostyrylsulfonyl] piperazine hydrochloride as starting materials.

$^1$H-NMR (CDCl$_3$) δ: 1.48(9H,s), 2.87(2H,br s), 3.31(4H, m), 3.75(2H,br s), 3.90(2H,br s), 4.57(2H,br s), 4.68(2H,s), 6.64(1H,d,J=15.6 Hz), 7.28–7.35(5H,m). MS (FAB) m/z: 553 [(M+H)$^+$, Cl$^{35}$], 555 [(M+H)$^+$, Cl$^{37}$].

Referential Example 353

(3S)-1-[(5-tert-Butoxycarbonyl -4,5,6,7-tetrahydrothieno[3,2-c]pyridin-2-yl)methyl]-3-[(6-chloronaphthalen-2-yl)sulfonamido]pyrrolidine In the same manner as in Referential Example 321, a reaction was effected using 5-tert-butoxycarbonyl-2-formyl -4,5,6,7-tetrahydrothieno[3,2-c]pyridine (WO94/21599) and (3S)-[(6-chloronaphthalen-2-yl)sulfonamido]pyrrolidine trifluoroacetate as starting materials, whereby the title compound was obtained.

$^1$H-NMR (CDCl$_3$) δ: 1.49(9H,s), 1.52–1.63(1H,m), 2.03–2.12(1H,m), 2.19–2.27(1H,m), 2.35–2.54(2H,m), 2.73–2.85(3H,m), 3.59(1H,d,J=13.9 Hz), 3.66(1H,d,J=13.9 Hz), 3.70(2H,br s), 3.88–3.95(1H,m), 4.39(2H,s), 4.99(½H, s), 5.02(½H,s), 6.49(1H,s), 7.55(1H,dd,J=8.8,2.0 Hz), 7.82–7.90(4H,m), 8.40(1H,s). MS (ED) m/z: 561 (M$^+$, Cl$^{35}$), 563 (M$^+$, Cl$^{37}$).

Referential Example 354

(3S)-1-[(5-tert-Butoxycarbonyl -4,5,6,7-tetrahydrothieno[3,2-c]pyridin-2-yl)carbonyl]-3-[(6-chloronaphthalen-2-yl)sulfonamido]pyrrolidine In the same manner as in Referential Example 319, the title compound was obtained using 5-tert-butoxycarbonyl -5

4,5,6,7-tetrahydrothieno[3,2-c]pyridine-2-carboxylic acid (WO94/21599) and (3S)-3-[(6-chloronaphthalen-2-yl)sulfonamido]pyrrolidine trifluoroacetate as starting materials.

$^1$H-NMR (CDCl$_3$) δ: 1.50(9H,s), 1.80–2.08(2H,m), 2.75 (2H,br s), 3.48–3.87(6H,m), 3.88–4.05(1H,m), 4.37(2H,br s), 6.09(1H,br s), 7.05–7.15(1H,m), 7.55(1H,dd,J=8.8,1.5 Hz), 7.79–7.91(4H,m), 8.41(1H,s). MS (FAB) m/z: 576 [(M+H)$^+$, Cl$^{35}$], 578 (M+H)$^+$, Cl$^{37}$].

Referential Example 355

(3S)-3-[[(5-tert-Butoxycarbonyl -4,5,6,7-tetrahydrothieno[3,2-c]pyridin-2-yl)methyl]amino]-1-[(6-chloronaphthalen-2-yl)sulfonyl]pyrrolidine In the same manner as in Referential Example 321, a reaction was effected using 5-tert-butoxycarbonyl-2-formyl-4,5,6,7-tetrahydrothieno[3,2-c]pyridine (WO94/21599) and (3S)-3-amino-1-[(6-chloronaphthalen-2-yl)sulfonyl]pyrrolidine as starting materials, whereby the title compound was obtained.

$^1$H-NMR (CDCl$_3$) δ: 1.48(9H,s), 1.60–1.69(1H,m), 1.95–2.05(1H,m), 2.72(2H,br s), 3.11(1H,dd,J=10.3,4.4 Hz), 3,30–3.46(4H,m), 3.68(2H,br s), 3.72(2H,s), 4.36(2H, s), 6.44(1H,s), 7.56(1H,dd,J=8.8,2.0 Hz), 7.86–7.91(4H,m), 8.36(1H,s). MS (FD) m/z: 561 (M$^+$, Cl$^{35}$), 563 (M$^+$, Cl$^{37}$).

Referential Example 356

(3S)-3-[(5-tert-Butoxycarbonyl -4,5,6,7-tetrahydrothieno[3,2-c]pyridin-2-yl)carbonylamino]-1-[(6-chloronaphthalen-2-yl)sulfonyl]pyrrolidine In the same manner as in Referential Example 319, the title compound was obtained using 5-tert-butoxycarbonyl-4,5,6,7-tetrahydrothieno[3,2-c]pyridine-2-carboxylic acid (WO94/21599) and (3S)-3-amino-1-[(6-chloronaphthalen-2-yl)sulfonyl]pyrrolidine as starting materials.

$^1$H-NMR (CDCl$_3$) δ: 1.48(9H,s), 1.90–2.00(1H,m), 2.11–2.22(1H,m), 2.80(2H,br s), 3.32–3.42(1H,m), 3.44–3.57(3H,m), 3.71(2H,br s), 4.38(2H,d,J=1.5 Hz), 4.40–4.49(1H,m), 5.80–5.87(1H,m), 6.96(1H,s), 7.54(1H, dd,J=8.8,1.5 Hz), 7.83–7.89(3H,m), 7.90(1H,d,J=8.8 Hz), 8.37(1H,s). MS (FAB) m/z: 576 [(M+H)$^+$, Cl$^{35}$], 578 [(M+H)$^+$, Cl$^{37}$].

Referential Example 357

1-[(5-tert-Butoxycarbonyl -4,5,6,7-tetrahydrothieno [3,2-c]pyridin-2-yl)carbonyl]-4-[(6-chloronaphthalen-2-yl)sulfonyl]homopiperazine In the same manner as in Referential Example 319, the title compound was obtained using 5-tert-butoxycarbonyl-4,5,6,7-tetrahydrothieno[3,2-c]pyridine-2-carboxylic acid (WO94/21599) and 1-[(6-chloronaphthalen-2-yl)sulfonyl]homopiperazine hydrochloride as starting materials.

$^1$H-NMR (CDCl$_3$) δ: 1.47(9H,s), 2.01(2H,br s), 2.78(2H, br s), 3.37–3.54(4H,m), 3.68(2H,br s), 3.78(2H,t,J=6.1 Hz), 3.86(2H,t,J=6.1 Hz), 4.39(2H,s), 6.88(1H,br s), 7.55(1H,dd, J=8.8,2.0 Hz), 7.75–7.80(1H,m), 7.83–7.90(3H,m), 8.33 (1H,s). MS (FD) m/z: 589 (M$^+$, Cl$^{35}$), 591 (M$^+$, Cl$^{37}$)

Referential Example 358

1-[(6-Chloronaphthalen-2-yl)sulfonyl]-4-[(6-cyanobenzofuran-2-yl)carbonyl]piperazine In the same manner as in Referential Example 319, a reaction was effected using 6-cyanobenzofuran-2-carboxylic acid and 1-[(6-chloronaphthalen-2-yl)sulfonyl]piperazine hydrochloride as starting materials, whereby the title compound was obtained.

$^1$H-NMR (CDCl$_3$) δ: 3.21(4H,s), 3.95(4H,s), 7.32(1H,d, J=1.0 Hz), 7.55(1H,dd,J=8.3,1.0 Hz), 7.59(1H,dd,J=8.8,2.0 Hz), 7.72(1H,d,J=8.3 Hz), 7.77(1H,dd,J=8.8,2.0 Hz), 7.81 (1H,s), 7.88–7.95(3H,m), 8.32(1H,s). MS (FAB) m/z: 480 [(M+H)$^+$, Cl$^{35}$], 482 [(M+H)$^+$, Cl$^{37}$].

Referential Example 359

1-[(6-Chloronaphthalen-2-yl)sulfonyl]-4-[(5-cyanobenzothiophen-2-yl)carbonyl]piperazine In the same manner as in Referential Example 319, a reaction was effected using 5-cyanobenzothiophene-2-carboxylic acid and 1-[(6-chloronaphthalen-2-yl)sulfonyl]piperazine hydrochloride as starting materials, whereby the title compound was obtained.

$^1$H-NMR (CDCl$_3$) δ: 3.18(4H,s), 3.89(4H,s), 7.43(1H,d, J=2.0 Hz), 7.60(1H,d,J=8.8 Hz), 7.73–7.80(2H,m), 7.85–7.95(4H,m), 8.10(1H,s), 8.32(1H,s). MS (FAB) m/z: 496 [(M+H)$^+$, Cl$^{35}$], 498 [(M+H)$^+$, Cl$^{37}$].

Referential Example 360

6-Methoxy-3,4-dihydroisoquinoline

In tetrahydrofuran (100 ml), 3-methoxyphenethylamine (75.0 g) was dissolved. To the resulting solution, formic acid (60 ml) and acetic anhydride (108 ml) were added under ice cooling, followed by stirring overnight at room temperature. A saturated aqueous solution of sodium bicarbonate was added to the reaction mixture to separate the organic layer. The organic layer was washed with saturated aqueous NaCl solution and then dried over anhydrous sodium sulfate. The residue obtained by distilling off the solvent under reduced pressure was dissolved in benzene (200 ml), followed by the dropwise addition of phosphorus oxychloride (140 ml) under ice cooling. After stirring at 70° C. for 15 minutes, the reaction mixture was successively added with ice and 2N hydrochloric acid. The resulting mixture was stirred for 1 hour under ice cooling. The water layer was separated from the reaction mixture, neutralized with potassium carbonate and then extracted with dichloromethane. The extract was dried over anhydrous sodium sulfate. The residue obtained by distilling off the solvent under reduced pressure was purified by chromatography on a silica gel column (dichloromethane~dichloromethane:methanol=100:1), whereby the title compound (13.5 g, 17%) was obtained.

$^1$H-NMR (CDCl$_3$) δ: 2.72(2H,t,J=7.3 Hz), 3.72(2H,t,J= 7.3 Hz), 3.83(3H,s), 6.68(1H,d,J=2.4 Hz), 6.79(1H,dd,J= 8.3,2.4 Hz), 7.22(1H,d,J=8.3 Hz), 8.25(1H,s). MS (FAB) m/z: 162 (M+H)$^+$.

Referential Example 361

6-Methoxy-1,2,3,4-tetrahydroisoquinoline

In methanol (100 ml), 6-methoxy-3,4-dihydroisoquinoline (10.4 g) was dissolved. To the resulting solution, water (10 ml) and then sodium borohydride (6.10 g) were added. The resulting mixture was stirred at room temperature for 15 minutes. The reaction mixture was concentrated under reduced pressure. The residue was dissolved in dichloromethane, followed by washing with water. The organic layer thus separated was dried over anhydrous sodium sulfate and distilled under reduced pressure to remove the solvent. The residue was purified by chromatography on a silica gel column (dichloromethane~dichloromethane:methanol=100:15), whereby the title compound (7.95 g, 76%) was obtained.

¹H-NMR (CDCl₃) δ: 2.79(2H,t,J=5.9 Hz), 3.12(2H,t,J=5.9 Hz), 3.76(3H,s), 3.96(2H,s), 6.62(1H,s), 6.70(1H,dd,J=8.3,2.4 Hz), 6.92(1H,d,J=8.3 Hz). MS (FAB) m/z: 164 (M+H)⁺.

Referential Example 362

6-Hydroxy-1,2,3,4-tetrahydroisoquinoline hydrochloride

In dimethyl sulfide (20 ml), 6-methoxy-1,2,3,4-tetrahydroisoquinoline (7.75 g) was dissolved. Under ice cooling, aluminum chloride (19.0 g) was added to the resulting solution, followed by stirring at room temperature for 3 hours. Dichloromethane and dilute hydrochloric acid were added to separate the water layer. The water layer was made basic by the addition of a saturated aqueous solution of sodium bicarbonate, followed by extraction with dichloromethane. The extract was dried over anhydrous sodium sulfate and distilled under reduced pressure to remove the solvent. The residue was dissolved in saturated solution of hydrochloride in ethanol (100 ml). To the residue obtained by distilling off the solvent under reduced pressure, ethyl acetate was added. The solid thus precipitated was collected by filtration, whereby the title compound (7.91 g, 90%) was obtained.

¹H-NMR (DMSO-d₆) δ: 3.06(2H,t,J=5.9 Hz), 3.43(2H,m), 4.25(2H,s), 6.76(1H,d,J=2.0 Hz), 6.83(1H,dd,J=8.3,2.0 Hz), 7.15(1H,d,J=8.3 Hz), 9.71(3H,br s). MS (FAB) m/z: 150 (M+H)⁺.

Referential Example 363

2-tert-Butoxycarbonyl-6-hydroxy -1,2,3,4-tetrahydroisoquinoline

In methanol (100 ml), 6-hydroxy-1,2,3,4-tetrahydroisoquinoline hydrochloride (7.87 g) was dissolved. To the resulting solution, triethylamine (4.67 ml) and di-tert-butyl dicarbonate (13.95 g) were added, followed by stirring at room temperature for 3 hours. Ethyl acetate was added to the residue obtained by concentration of the reaction mixture under reduced pressure. The resulting mixture was washed with 1N hydrochloric acid, dried over anhydrous sodium sulfate and distilled under reduced pressure to remove the solvent. The residue was purified by chromatography on a silica gel column (hexane:ethyl acetate 10:1 to 3:1), whereby the title compound (9.96 g, 94%) was obtained.

¹H-NMR (CDCl₃) δ: 1.49(9H,s), 2.75(2H,t,J=5.9 Hz), 3.61(2H,t,J=5.9 Hz), 4.48(2H,s), 6.25(1H,br s), 6.64(1H,d,J=2.4 Hz), 6.70(1H,br s), 6.93(1H,d,J=7.8 Hz).

Referential Example 364

2-tert-Butoxycarbonyl-6-trifluoromethanesulfonyloxy-1,2,3,4-tetrahydroisoquinoline In pyridine (100 ml), 2-tert-butoxycarbonyl-6-hydroxy-1,2,3,4-tetrahydroisoquinoline (9.96 g) was dissolved. To the resulting solution, trifluorosulfonic anhydride (8.10 ml) was added dropwise under ice cooling, followed by stirring at room temperature for 10 minutes. The reaction mixture was concentrated under reduced pressure and the residue was purified by chromatography on a silica gel column (hexane:ethyl acetate=10:1 to 6:1), whereby the title compound (13.47 g, 88%) was obtained as a colorless solid.

¹H-NMR (CDCl₃) δ: 1.49(9H,s), 2.87(2H,t,J=5.9 Hz), 3.66(2H,t,J=5.9 Hz), 4.59(2H,s), 7.06(1H,br s), 7.08(1H,d,J=8.3 Hz), 7.17(1H,d,J=8.3 Hz). Elementary analysis for C₁₅H₁₈F₃NO₅S Calculated: C, 47.24; H, 4.76; F, 14.94; N, 3.67; S, 8.41. Found: C, 47.34; H, 4.72; F, 15.23; N, 3.42; S, 8.65.

Referential Example 365

2-tert-Butoxycarbonyl-6-methoxycarbonyl-1,2,3,4-tetrahydroisoquinoline

In methanol (50 ml), 2-tert-butoxycarbonyl-6-trifluoromethanesulfonyloxy-1,2,3,4-tetrahydroisoquinoline (1.34 g) was dissolved, followed by the addition of triethylamine (0.73 ml), palladium (II) acetate (40 mg) and 1,3-(diphenylphosphino)propane (145 mg). Under a carbon monoxide gas stream, the resulting mixture was stirred overnight at 70° C. The reaction mixture was concentrated under reduce pressure and the residue was purified by chromatography on a silica gel column (hexane:ethyl acetate=15:1), whereby the title compound (665 mg, 65%) was obtained.

¹H-NMR (CDCl₃) δ: 1.50(9H,s), 2.88(2H,m), 3.66(2H,br s), 3.91(3H,s), 4.62(2H,s), 7.17(1H,d,J=7.8 Hz), 7.83(1H,s), 7.84(1H,d,J=7.8 Hz)

Referential Example 366

1-[(2-tert-Butoxycarbonyl -1,2,3,4-tetrahydroisoquinolin-6-yl)carbonyl]-4-[(6-chloronaphthalen-2-yl)sulfonyl]piperazine In the same manner as in Referential Example 319, the title compound was obtained using 2-tert-butoxycarbonyl-6-methoxycarbonyl-1,2,3,4-tetrahydroisoquinoline and 1-[(6-chloronaphthalen-2-yl)sulfonyl]piperazine hydrochloride as starting materials.

¹H-NMR (CDCl₃) δ: 1.48(9H,s), 2.76(2H,t,J=5.4 Hz), 3.09(4H,br), 3.60(2H,t,J=5.4 Hz), 3.77(4H,br), 4.52(2H,s), 7.12–7.25(3H,m), 7.59(1H,dd,J=8.8,2.0 Hz), 7.75(1H,dd,J=8.8,2.0 Hz), 7.88–7.95(3H,m), 8.30(1H,s). MS (FAB) m/z: 570 [(M+H)⁺, Cl³⁵], 572 [(M+H)⁺, Cl³⁷].

Referential Example 367

1-tert-Butoxycarbonyl-4-((6-chloronaphthalen-2-yl) sulfonyl]-2-ethoxycarbonylpiperazine In methanol (1000 ml), 1-[(6-chloronaphthalen-2-yl) sulfonyl]-3-[ethoxycarbonyl]piperazine hydrochloride (WO96/10022) (43.0 g) was dissolved, followed by the addition of triethylamine (17.1 ml) and di-tert-butyl dicarbonate (27.0 g). The resulting mixture was stirred at room temperature for 3 hours. The residue obtained by concentration of the reaction mixture under reduced pressure was added with ethyl acetate and the resulting mixture was washed with 1N hydrochloric acid. The organic layer thus extracted was dried over anhydrous sodium sulfate. The residue obtained by distilling off the solvent under reduced pressure was purified by chromatography on a silica gel column (hexane ethyl acetate=8:1), whereby the title compound (46.0 g, 93%) was obtained as a colorless solid.

¹H-NMR (CDCl₃) δ: 1.24–1.32(3H,m), 1.33–1.50(9H,m), 2.37(1H,m), 2.54(1H,d,J=10.7 Hz), 3.15–3.41(1H,m), 3.68–4.08(2H,m), 4.10–4.39(3H,m), 4.62(½H,br s), 4.82

(½H,br s), 7.58(1H,dd,J=8.8,2.0 Hz), 7.75(1H,dd,J=8.8,2.0 Hz), 7.87–7.94(3H,m), 8.31(1H,d,J=2.0 Hz). MS (FAB) m/z: 483 [(M+H)$^+$, Cl$^{35}$], 485 [(M+H)$^+$, Cl$^{37}$]. Elementary analysis for $C_{22}H_{27}ClNO_6S$ Calculated: C, 54.71; H, 5.63; Cl, 7.34; N, 5.80; S, 6.64. Found: C, 54.89; H, 5.42; Cl, 7.15; N, 5.76; S, 6.24.

Referential Example 368

1-tert-Butoxycarbonyl-4-[(6-chloronaphthalen-2-yl) sulfonyl]piperazine-2-carboxylic acid In tetrahydrofuran (40 ml), 1-tert-butoxycarbonyl-4-[(6-chloronaphthalen-2-yl)sulfonyl]-2-ethoxycarbonylpiperazine (23.0 g) was dissolved, followed by the addition of ethanol (40 ml) and a 3N aqueous sodium hydroxide solution (30 ml). The resulting mixture was stirred at room temperature for 3 hours. To the reaction mixture, 1N hydrochloric acid was added to make it acidic and then ethyl acetate was added to separate the organic layer. The organic layer was dried over anhydrous sodium sulfate. The solid precipitated by distilling off the solvent under reduced pressure was collected by filtration, whereby the title compound (23.8 g, quant.) was obtained as a colorless solid.

$^1$H-NMR (CDCl$_3$) δ: 2.41(1H,m), 2.59(1H,m), 3.15–3.38 (1H,m), 3.70–4.08(2H,m), 4.20–4.39(1H,m), 4.72(½H,br s), 4.91(½H,br s), 7.58(1H,dd,J=8.8,J=2.0 Hz), 7.76(1H,dd,J=8.8,2.0 Hz), 7.87–7.95(3H,m), 8.34(1H,s). Mass (FAB) m/Z: 455((M+H)$^+$, Cl$^{35}$], 457((M+H)$^+$, Cl$^{37}$]. Elementary analysis for $C_{20}H_{23}ClNO_6S$ Calculated: C, 52.80; H, 5.10; Cl, 7.79; N, 6.16; S, 7.05. Found: C, 52.62; H, 5.00; Cl, 7.75; N, 6.22; S, 6.83.

Referential Example 369

1-tert-Butoxycarbonyl-2-carboxymethyl-4-[(6-chloronaphthalen-2-yl) sulfonyl]piperazine In the same manner as in Referential Example 367 or 368, the title compound was obtained using 1-[(6-chloronaphthalen-2-yl)sulfonyl]-3-[methoxycarbonylmethyl]piperazine as a starting material.

$^1$H-NMR (DMSO-d$_6$) δ: 1.38(9H,s), 2.32(1H,dt,J=12.2, 3.4 Hz), 2.48(1H,dd,J=12.2,3.4 Hz), 2.61(1H,dd,J=15.6,5.9 Hz), 2.86(1H,dd,J=15.6,8.3 Hz), 3.13(1H,s), 3.68(3H,s), 3.74–4.08(3H,m), 7.58(1H,dd,J=8.8,2.0 Hz), 7.74(1H,dd,J=8.8,2.0 Hz), 7.89–7.94(3H,m), 8.29(1H,s). MS (FAB) m/z: 469 [(M+H)$^+$, Cl$^{35}$], 471 [(M+H)$^+$, Cl$^{37}$]. Elementary analysis for $C_{22}H_{27}ClN_2O_7S$ Calculated: C, 54.71; H, 5.63; Cl, 7.34; N, 5.80; S, 6.64. Found: C, 54.74; H, 5.69; Cl, 7.34; N, 5.84; S, 6.62.

Referential Example 370

6-Methyl-4,5,6,7-tetrahydrothiazolo[5,4-c]pyridine

In anhydrous tetrahydrofuran (500 ml), 6-ethoxycarbonyl-4,5,6,7-tetrahydrothiazolo[5,4-c]pyridine (WO94/21599) (21.0 g) was dissolved, followed by the addition of a solution of lithium aluminum hydride in tetrahydrofuran (a 1.0M solution, 200 ml) under ice cooling. The resulting mixture was stirred at room temperature for 2 hours. Water (7 ml) was then added slowly to the reaction mixture. After the termination of the reaction, a 1N aqueous potassium hydroxide solution (7 ml) and anhydrous magnesium sulfate were successively added. After removal of the insoluble matter by filtration, the filtrate was concentrated under reduced pressure. The residue thus obtained was purified by distillation under reduced pressure (1.5 mmHg, boiling point: 82 to 85° C.), whereby the title compound (6.10 g, 40%) was obtained as a colorless oil.

$^1$H-NMR (CDCl$_3$) δ: 2.52(3H,s), 2.83(2H,t,J=5.9 Hz), 2.98(2H,t,J=5.9 Hz), 3.70(2H,s), 3.87(2H,br s), 8.63(1H,s). MS (FAB) m/z: 155 [(M+H)$^+$].

Referential Example 371

Lithium 6-methyl-4,5,6,7-tetrahydrothiazolo[5,4-c] pyridine-2-carboxylate

In anhydrous tetrahydrofuran (200 ml), 6-methyl -4,5,6,7-tetrahydrothiazolo[5,4-c]pyridine (6.43 g) was dissolved, followed by the dropwise addition of a solution (1.47M, 34.00 ml) of n-butyl lithium in n-hexane at an external temperature of −78° C. The resulting mixture was stirred for 40 minutes without changing the temperature. Then a carbon dioxide gas was blown into the reaction mixture for 1 hour. After warming up to room temperature, the reaction mixture was concentrated under reduced pressure, whereby the title compound (9.42 g, quant.) was obtained as a pale brown foamy solid.

$^1$H-NMR (DMSO-d$_6$) δ: 2.37(3H,s), 2.64–2.77(4H,m), 3.54(2H,s). MS (FAB) m/z: 199 (M+H)$^+$.

Referential Example 372

N-[[1-[(6-Chloronaphthalen-2-yl)sulfonyl]piperazin-3-yl]carbonyl]glycine ethyl ester trifluoroacetate In the same manner as in Referential Example 319, an amide bond was formed using 1-tert-butoxycarbonyl-4-[(6-chloronaphthalen-2-yl)sulfonyl]piperazine-2-carboxylic acid as a starting material, followed by deprotection using trifluoroacetic acid, whereby the title compound was obtained.

$^1$H-NMR (DMSO-d$_6$) δ: 1.20(3H,t,J=7.3 Hz), 2.47–2.82 (2H,m), 3.14–3.28(1H,m), 3.30–3.39(1H,m), 3.72–3.79(1H, m), 3.95(2H,d,J=5.9 Hz), 4.08–4.18(3H,m), 4.20(1H,dd,J= 11.2,3.4 Hz), 7.75(1H,dd,J=8.8,2.0 Hz), 7.84(1H,d,J=8.8 Hz), 8.23(1H,d,J=8.8 Hz), 8.28(1H,s), 8.30(1H,d,J=8.8 Hz), 8.55(1H,s), 9.29(1H,t,J=5.9 Hz). MS (FAB) m/z: 440 [(M+H)$^+$, Cl$^{35}$], 442 [(M+H)$^+$, Cl$^{37}$].

Referential Example 373

1-[(6-Chloronaphthalen-2-yl)sulfonyl]-3-[[(morpholin-4-yl)carbonyl]methyl]piperazine hydrochloride In the same manner as in Referential Example 319, an amid bond was formed using 1-tert-butoxycarbonyl-2-carboxymethyl-4-[(6-chloronaphthalen-2-yl)sulfonyl] piperazine and morpholine as starting materials, followed by deprotection In the same manner as in Referential Example 1, whereby the title compound was obtained.

$^1$H-NMR (DMSO-d$_6$) δ: 2.65–2.91(4H,m), 3.10–3.22 (1H,m), 3.30–3.82(12H,m), 7.74(1H,d,J=8.8 Hz), 7.84(1H, d,J=8.8 Hz), 8.20(1H,d,J=8.8 Hz), 8.22–8.31(2H,m), 8.55 (1H,s), 9.18(1H,br s), 9.32(1H,br s). MS (FAB) m/z: 438 [(M+H)$^+$, Cl$^{35}$], 440 (M+H)$^+$, Cl$^{37}$].

Referential Example 374

1-[(6-Chloronaphthalen-2-yl)sulfonyl]-3-[N-(morpholin-4-yl)carbamoyl]piperazine trifluoroacetate In the same manner as in Referential Example 372, the title compound was obtained.

¹H-NMR (DMSO-d₆ at 100° C.) δ: 2.59–3.97(13H,m), 4.00–4.12(1H,m), 4.38–4.50(1H,m), 7.68(1H,dd,J=8.8,2.4 Hz), 7.84(1H,d,J=8.8 Hz), 8.15(1H,d,J=8.8 Hz), 8.18(1H,s), 8.22(1H,d,J=8.8 Hz), 8.48(1H,s), 9.18(1H,br s). MS (FAB) m/z: 439 [(M+H)⁺, Cl³⁵], 441 [(M+H)⁺, Cl³⁷].

Referential Example 375

Ethyl N'-[[1-[(6-chloronaphthalen-2-yl)sulfonyl]piperazin-3-yl]carbonyl]hydrazinoacetate hydrochloride In the same manner as in Referential Example 372, the title compound was obtained.

¹H-NMR (DMSO-d₆) δ: 1.20–1.24(3H,m), 2.55–2.90 (2H,m), 3.00–3.20(1H,m), 3.30–3.38(1H,m), 3.53–3.87(3H, m), 3.94–4.19(3H,m), 4.27(½H,d,J=9.8 Hz), 4.54–4.63(½H, m), 4.95(1H,br s), 7.75(1H,dd,J=8.8,2.0 Hz), 7.84–7.95(1H, m), 8.19–8.32(3H,m), 8.56(1H,s), 8.80–9.00(1H,m), 9.78–10.20(1H,m). MS (FAB) m/z: 455 [(M+H)⁺, Cl³⁵], 457 [(M+H)⁺, Cl³⁷].

Referential Example 376

4-(Aminoacetyl)morpholine hydrochloride

In N,N-dimethylformamide (100 ml), N-tert-butoxycarbonylglycine (2.00 g), morpholine (1.00 ml), 1-hydroxybenzotriazole monohydrate (1.74 g) and 1-(dimethylaminopropyl)-3-ethylcarbodiimide hydrochloride (2.84 g) were dissolved, followed by stirring overnight at room temperature. After concentration under reduced pressure, the residue was diluted with dichloromethane, washed with water and dried over anhydrous sodium sulfate. The residue obtained by distilling off the solvent under reduced pressure was purified by chromatography on a silica gel column (dichloromethane:methanol=100:1), whereby a colorless foam was obtained. The substance was dissolved in dichloromethane (2 ml), followed by the addition of saturated solution of hydrochloride in ethanol (10 ml). The resulting mixture was stirred at room temperature for 5 minutes. The reaction mixture was concentrated to dryness under reduced pressure, whereby the title compound (1.80 g, quant.) was obtained as a pale yellow foam was obtained.

¹H-NMR (DMSO-d₆) δ: 3.39(2H,t,J=4.5 Hz), 3.48(2H,t, J=4.5 Hz), 3.52–3.63(4H,m), 3.77–3.90(2H,m), 8.32(3H,br s). MS (FAB) m/z: 145 (M+H)⁺.

Referential Example 377

1-[(6-Chloronaphthalen-2-yl) sulfonyl]-3-[N-[[(morpholin-4-yl)carbonyl]methyl]carbamoyl]piperazine hydrochloride In the same manner as in Referential Example 372, the title compound was obtained.

¹H-NMR (DMSO-d₆) δ: 2.67(1H,d,J=11.2 Hz), 2.79(1H, d,J=11.2 Hz), 3.09–3.18(1H,m), 3.17–3.30(1H,m), 3.42(1H, d,J=13.2 Hz), 3.45–3.74(8H,m), 3.82(1H,d,J=12.2 Hz), 4.10–4.30(4H,m), 7.86(1H,d,J=8.8 Hz), 7.95(1H,d,J=8.8 Hz), 8.32(1H,d,J=8.8 Hz), 8.40(1H,s), 8.41(1H,d,J=8.8 Hz), 8.67(1H,d,J=8.8 Hz), 8.93(1H,br s), 9.12(1H,d,J=4.9 Hz), 10.03(1H,br s). MS (FAB) m/z: 481 [(M+H)⁺, Cl³⁵], 483 [(M+H)⁺, Cl³⁷].

Referential Example 378

4-[(6-Chloronaphthalen-2-yl)sulfonyl]-2-[(N-methyl)carbamoyl]piperazine trifluoroacetate In the same manner as in Referential Example 319, 1-tert-butoxycarbonyl-4-[(6-chloronaphthalen-2-yl) sulfonyl]piperazine-2-carboxylic acid was reacted with methylamine to form an amide bond and then the protecting group was removed using trifluoroacetic acid, whereby the title compound was obtained.

¹H-NMR (DMSO-d₆) δ: 2.54–2.65(2H,m), 2.67(3H,d,J= 3.9 Hz), 3.12–3.22(1H,m), 3.33(1H,d,J=13.2 Hz), 3.70(1H, d,J=12.2 Hz), 4.04(2H,d,J=8.8 Hz), 7.75(1H,dd,J=8.8,2.0 Hz), 7.87(1H,d,J=8.8 Hz), 8.20(1H,d,J=8.8 Hz), 8.27(1H,s), 8.29(1H,d,J=8.8 Hz), 8.58(1H,s), 8.70(1H,d,J=4.4 Hz), 9.06 (1H,br s) MS (FAB) m/z: 440 [(M+H)⁺, Cl³⁵], 442 [(M+H)⁺, Cl³⁷].

In the same manner as in Referential Example 378, Compounds of Referential Examples 379 to 384 were synthesized.

Referential Example 379

4-[[1-[(6-Chloronaphthalen-2-yl)sulfonyl]piperazin-3-yl]carbonyl]morpholine trifluoroacetate ¹H-NMR (DMSO-d₆) δ: 2.49–2.58(1H,m), 2.64–2.75 (1H,m), 3.09–3.81(11H,m), 3.93(1H,d,J=12.2 Hz), 4.76(1H, dd,J=10.7,2.4 Hz), 7.75(1H,d,J=8.8 Hz), 7.90(1H,d,J=8.8 Hz), 8.21(1H,d,J=8.8 Hz), 8.27(1H,s), 8.29(1H,d,J=8.8 Hz), 8.58(1H,s), 9.15(1H,br s). MS (FAB) m/z: 440 [(M+H)⁺, Cl³⁵], 442 [(M+H)⁺, Cl³⁷].

Referential Example 380

1-[(6-Chloronaphthalen-2-yl)sulfonyl]-3-[(N-tert-butoxy)carbonyl]piperazine trifluoroacetate ¹H-NMR (DMSO-d₆) δ: 2.58–2.70(2H,m), 3.14–3.23 (1H,m), 3.30–3.40(1H,m), 3.64(1H,d,J=12.2 Hz), 3.97(1H, d,J=12.2 Hz), 4.05(1H,dd,J=10.2,3.4 Hz), 7.74(1H,dd,J=8.8, 2.0 Hz), 7.87(1H,d,J=8.8 Hz), 8.21(1H,d,J=8.8 Hz), 8.27 (1H,d,J=2.0 Hz), 8.29(1H,d,J=8.8 Hz), 8.57(1H,s), 11.24 (1H,s). MS (FAB) m/z: 426 [(M+H)⁺, Cl³⁵], 428 [(M+H)⁺, Cl³⁷].

Referential Example 381

1-[(6-Chloronaphthalen-2-yl)sulfonyl]-3-[(N-isopropyl)carbamoyl]piperazine hydrochloride ¹H-NMR (DMSO-d₆) δ: 1.05–1.18(6H,m), 2.60–2.77 (2H,m), 3.08–3.16(1H,m), 3.30–3.41(1H,m), 3.67(1H,d,J= 12.2 Hz), 3.80–3.90(1H,m), 4.99(2H,d,J=7.8 Hz), 7.74(1H, dd,J=8.8,2.0 Hz), 7.87(1H,dd,J=8.8,1.5 Hz), 8.22(1H,d,J= 8.8 Hz), 8.28(1H,s), 8.31(1H,d,J=8.8 Hz), 8.58(1H,s), 8.74 (1H,d,J=7.3 Hz). MS (FAB) m/z: 396 [(M+H)⁺, Cl³⁵], 398 [(M+H)⁺, Cl³⁷].

Referential Example 382

1-[(6-Chloronaphthalen-2-yl)sulfonyl]-3-[[(piperidin-1-yl]carbonyl]methyl]piperazine hydrochloride ¹H-NMR (DMSO-d₆) δ: 1.45–1.90(8H,m), 2.78(1H,d,J= 16.1 Hz), 3.08–3.20(1H,m), 3.20–3.60(7H,m), 3.68–3.92 (3H,m), 7.58(1H,d,J=8.8 Hz), 7.71(1H,d,J=8.8 Hz), 7.85–7.98(3H,m), 8.31(1H,s), 9.09(1H,br s), 11.32(1H,br s). MS (FAB) m/z: 436 [(M+H)⁺, Cl³⁵], 438 [(M+H)⁺, Cl³⁷].

Referential Example 383

1-[(6-Chloronaphthalen-2-yl)sulfonyl]-3-[[N-(2-methoxybenzyl)]carbamoyl]piperazine hydrochloride ¹H-NMR (DMSO-d₆) δ: 2.69(1H,t,J=11.2 Hz), 2.72–2.30 (1H,m), 3.08–3.16(1H,m), 3.31–3.37(1H,m), 3.68(1H,d,J=

12.2 Hz), 4.05(1H,d,J=12.2 Hz), 4.14(1H,dd,J=10.3,3.4 Hz), 4.29(1H,d,J=5.4 Hz), 6.93(1H,t,J=7.3 Hz), 7.02(1H,d,J=7.8 Hz), 7.24(1H,d,J=7.3 Hz), 7.29(1H,t,J=7.8 Hz), 7.77(1H,dd, J=8.8,2.0 Hz), 7.88(1H,d,J=8.8 Hz), 8.23(1H,d,J=8.8 Hz), 8.30(1H,s), 8.32(1H,d,J=8.8 Hz), 8.59(1H,s), 9.17(1H,t,J= 5.4 Hz). MS (FAB) m/z: 474 [(M+H)$^+$, Cl$^{35}$], 476 [(M+H)$^+$, Cl$^{37}$].

Referential Example 384

4-[(6-Chloronaphthalen-2-yl)sulfonyl]-2-[[N-(2-methoxyethyl)]carbamoyl]piperazine $^1$H-NMR (DMSO-d$_6$) δ: 2.54–2.75(2H,m), 3.02–3.51 (7H,m), 3.70(1H,d,J=12.2 Hz), 7.75(1H,d,J=8.8 Hz), 7.87 (1H,d,J=8.8 Hz), 8.22(1H,d,J=8.8 Hz), 8.28(1H,s), 8.31(1H, d,J=8.8 Hz), 8.58(1H,s), 8.97(1H,t,J=5.4 Hz), 10.01(1H,br s). MS (FAB) m/z: 412 [(M+H)$^+$, Cl$^{35}$], 414 [(M+H)$^+$, Cl$^{37}$].

Referential Example 385

1-[(6-Chloronaphthalen-2-yl)sulfonyl]-3-[carbamoylmethyl]piperazine hydrochloride In N,N-dimethylformamide (20 ml), 1-tert-butoxycarbonyl-2-carboxymethyl-4-[(6-chloronaphthalen-2-yl)sulfonyl]piperazine (800 mg) was dissolved, followed by the addition of pyridine (0.85 ml), ammonium bicarbonate (417 mg) and di-tert-butoxy carbonate (1.15 g). The resulting mixture was stirred at room temperature for 7 hours. After concentration of the reaction mixture under reduced pressure, the residue was added with dichloromethane, washed with 1N hydrochloric acid and a saturated aqueous solution of sodium bicarbonate, each once and then dried over anhydrous sodium sulfate. The solvent was then distilled off under reduced pressure. After the addition of saturated aqueous hydrochloric acid in ethanol (30 ml) to the residue, the resulting mixture was concentrated under reduced pressure. While washing with ethanol, the solid thus precipitated was removed by filtration. The filtrate was then concentrated under reduced pressure. The residue was crystallized in methanol, whereby the title compound (426 mg) was obtained as a colorless solid.

IR(KBr)cm$^{-1}$: 3185, 2917, 2684, 2607, 1677, 1342, 1299, 1170, 1155, 1135, 755, 692, 578. $^1$H-NMR (DMSO-d$_6$) δ: 2.58–2.65(1H,m), 2.72–2.83(1H,m), 3.12–3.21(1H,m), 3.30–3.48(3H,m), 3.55–3.81(1H,m), 7.21(1H,br s), 7.66 (1H,br s), 7.73(1H,dd,J=8.8,2.0 Hz), 7.85(1H,d,J=8.8 Hz), 8.20(1H,d,J=8.8 Hz), 8.26(1H,s), 8.29(1H,d,J=8.8 Hz), 8.56 (1H,s), 9.02–9.23(2H,m). MS (FAB) m/z: 368 [(M+H)$^+$, Cl$^{35}$], 370 [(M+H)$^+$, Cl$^{37}$].

Referential Example 386

1-(3-Furyl)-2-nitroethylene

To a solution of 3-furaldehyde (10.0 g) in ethanol (200 ml), nitromethane (6.37 g) was added at room temperature, followed by the dropwise addition of a 10N-aqueous sodium hydroxide solution (11.0 ml) at 0° C. The resulting mixture was stirred for 1 hour. The reaction mixture was poured into a 15% aqueous solution of hydrochloric acid (500 ml). The precipitate so formed was collected by filtration and dried, whereby the title compound (8.01 g) was obtained as a yellowish white solid.

$^1$H-NMR (CDCl$_3$) δ: 6.57(1H,d,J=2.0 Hz), 7.39(1H,d,J= 13.4 Hz), 7.52(1H,br s), 7.83(1H,br s), 7.94(1H,d,J=13.4 Hz).

Referential Example 387

2-(t-Butoxycarbonylamino)-1-(3-furyl)ethane

In tetrahydrofuran (170 ml), lithium aluminum hydride (2.20 g) was suspended, followed by the dropwise addition of a solution of 1-(3-furyl)-3-nitroethylene (8.00 g) in tetrahydrofuran (80 ml) at room temperature over 2 hours. The resulting mixture was stirred for 30 minutes. After the reaction mixture was cooled to 0° C., ethyl acetate (50 ml) and then water (10 m) were dropwise added thereto. The mixture was stirred while gradually warmed up. The reaction mixture was subjected to Celite filtration by using ethyl acetate. After the filtrate was concentrated, the residue was dissolved in methylene chloride (200 ml). Di-t-butyl dicarbonate (12.6 g) was added to the resulting solution at room temperature and the mixture was stirred for 1 hour. The reaction mixture was concentrated and the residue was purified by chromatography on a silica gel column (400 g of silica gel, hexane:ethyl acetate=15:1→8:1), whereby the title compound (4.30 g) was obtained as a pale yellow transparent oil.

$^1$H-NMR (CDCl$_3$) δ: 1.44(9H,s), 2.61(2H,t,J=6.8 Hz), 3.25–3.37(2H,m), 4.57(1H,br s), 6.29(1H,s), 7.26(1H,s), 7.37(1H,s).

Referential Example 388

6-(t-Butoxycarbonyl)-4,5,6,7-tetrahydrofuro[2,3-c]pyridine

Paraformaldehyde (625 mg) and p-toluenesulfonic acid (49.5 mg) were added to a solution of 2-(t-butoxycarbonylamino)-1-(3-furyl)ethane (2.20 g) in toluene (300 ml), followed by heating under reflux for 2 hours while dehydrating using a Dean Stark apparatus. After the reaction mixture was allowed to cool down to room temperature, a saturated aqueous solution (200 ml) of sodium bicarbonate and ethyl acetate (200 ml) were added to the reaction mixture to cause separation. The water layer was extracted with ethyl acetate (100 ml). The organic layers were combined, washed with saturated aqueous NaCl solution (100 ml), dried over anhydrous sodium sulfate and concentrated under reduced pressure. The residue was purified by chromatography on a silica gel column (100 g of silica gel, hexane:ethyl acetate=15:1~10:1), whereby the title compound (1.04 g) was obtained as a white solid.

IR (KBr) cm$^{-1}$: 3145, 3005, 2976, 2925, 2862, 1695, 1448, 1419, 1365, 1279, 1228, 1165, 1124, 912, 895, 758. $^1$H-NMR (CDCl$_3$) δ: 1.48(9H,s), 2.52(2H,br s), 3.63(2H,br s), 4.44(2H,s), 6.25(1H,s), 7.29(1H,s). MS (FAB) m/z: 224 [(M+H)$^+$], 168 [(M+H-isobutene(56))$^+$].

Referential Example 389

6-Methyl-4,5,6,7-tetrahydrofuro[2,3-c]pyridine

To 6-(t-butoxycarbonyl)-4,5,6,7-tetrahydrofuro[2,3-c]pyridine (1.05 g), a saturated solution of hydrochloride in ethanol (30 ml) was added at room temperature. After stirring for 2 hours, the reaction mixture was concentrated. The residue thus obtained was suspended in methylene chloride (20 ml), followed by the addition of methanol (20 ml), triethylamine (1.31 ml), acetic acid (810 μl), formaldehyde (a 37% aqueous solution, 610 μl) and sodium triacetoxyborohydride (1.51 g) at room temperature. The resulting mixture was stirred for 1 hour. To the reaction mixture, a saturated aqueous solution (100 ml) of sodium bicarbonate and methylene chloride (20 ml) were added to cause separation. The water layer was extracted with methylene chloride (3×10 ml). The organic layers were combined, dried over anhydrous sodium sulfate and concentrated under reduced pressure. The residue thus obtained was purified by chromatography on a silica gel column (50 g of silica gel, methylene chloride:acetone= 1:1→1:2→methylene chloride:methanol=10:1), whereby the title compound (434 mg) was obtained as a colorless transparent oil.

$^1$H-NMR (CDCl$_3$) δ: 2.48(3H,s), 2.56(2H,t, J=5.6 Hz), 2.67(2H,t,J=5.6 Hz), 3.48(2H,s), 6.23(1H,d,J=2.0 Hz), 7.25 (1H,s).

Referential Example 390

3-Aminoacrylaldehyde

To a solution of isoxazole (5.00 g) in methanol (100 ml), Raney nickel ("R-100", product of Nikko Chemical) (about 1.0 g) was added at room temperature. Under a hydrogen atmosphere (3.05–2.65 kg/cm$^2$), the resulting mixture was stirred for 3 hours. The reaction mixture was subjected to Celite filtration and the filtrate was concentrated. The residue thus obtained was reprecipitated in a chloroform—hexane system, whereby the title compound (4.91 g, 69.1 mmol, 95%) was obtained as a yellow solid.

$^1$H-NMR (CDCl$_3$) δ: 4.60–5.20(2H,br), 5.45(1H,dd,J= 12.7,8.3 Hz), 7.15(1H,d,J=12.7 Hz), 9.18(1H,d,J=8.3 Hz) $^1$H-NMR (CD$_3$OD) δ: 5.55(1H,dd,J=12.2,9.3 Hz), 7.59(1H, d,J=12.2 Hz), 8.98(1H,d,J=9.3 Hz).

Referential Example 391

6-(t-Butoxycarbonyl)-5,6,7,8-tetrahydro-1,6-naphthylidine

Triethylamine (1.50 ml) and pyridinium acetate (30.0 mg) were added to 1-benzyl-4-piperidone (3.80 g) and 3-aminoacrylaldehyde (2.10 g), followed by stirring under heat at 120° C. After 22 hours, the reaction mixture was allowed to cool down to room temperature and the brown caramel-like substance thus obtained was dissolved in a 3N aqueous solution of hydrochloric acid. The resulting solution was extracted with chloroform (2×50 ml). To the water layer, a saturated aqueous solution (50 ml) of sodium bicarbonate was added, followed by extraction with chloroform (3×60 ml). The organic layer was dried over anhydrous sodium sulfate and distilled under reduced pressure to remove the solvent. The residue was distilled (0.90 mmHg, 145 to 150° C.), whereby about 3:2 mixture (1.98 g) of 6-benzyl-5,6,7,8-tetrahydro-1,6-naphthylidine in the form of a pale yellow transparent oil and 1-benzyl-4-piperidone as the starting material was obtained.

The mixture was dissolved in acetic acid (25 ml). To the resulting solution, 10% palladium-carbon (500 mg) was added, followed by vigorous stirring at 50 to 60° C. under a hydrogen atmosphere (about 1 atm). After the stirring was continued for 2 hours, the reaction mixture was allowed to cool down and filtered. By the concentration of the filtrate, a residue containing 5,6,7,8-tetrahydro-1,6-naphthylidine in the form of a colorless transparent oil was obtained.

The residue was dissolved in toluene (20 ml), followed by the addition of a 40% aqueous solution of sodium hydroxide (30 ml) and di-t-butyl dicarbonate (3.20 g, 14.7 mmol) at room temperature. After stirring for 10 minutes, water (30 ml) and toluene (20 ml) were added to the reaction mixture to cause separation. The water layer was extracted with toluene (30 ml). The organic layers were combined, washed with saturated aqueous NaCl solution (50 ml), dried over anhydrous sodium sulfate and distilled under reduced pressure to remove the solvent. The residue was purified by chromatography on a silica gel column (50 g of silica gel, methylene chloride:ethyl acetate=5:1→3:1), whereby the title compound (981 mg) was obtained as a colorless transparent oil.

IR(KBr)cm$^{-1}$: 2974, 1693, 1577, 1454, 1419, 1392, 1365, 1288, 1259, 1241, 1228, 1161, 1119, 1097, 989, 930, 881, 862, 789, 768, 737. $^1$H-NMR (CDCl$_3$) δ: 1.50(9H,s), 3.01 (2H,t,J=5.9 Hz), 3.76(2H,t,J=5.9 Hz), 4.59(2H,s), 7.13(1H, dd,J=7.8,4.9 Hz), 7.41(1H,d,J=7.8 Hz), 8.43(1H,d,J=4.9 Hz). MS (FAB) m/z: 235 [(M+H)$^+$], 179 [(M+H)$^+$-isobutene (56)].

Referential Example 392

6-(t-Butoxycarbonyl)-5,6,7,8-tetrahydro-1,6-naphthylidin-1-oxide

To a solution of 6-(t-butoxycarbonyl)-5,6,7,8-tetrahydro-1,6-naphthylidine (1.72 g) in methylene chloride (40 ml), metachloroperbenzoic acid (3.80 g) was added at 0° C. and the resulting mixture was stirred. Thirty minutes later, dimethyl sulfide (1.62 ml) was added to the reaction mixture, followed by stirring at room temperature for 30 minutes. To the reaction mixture, a saturated aqueous solution (150 ml) of sodium bicarbonate and methylene chloride (30 ml) were added to cause separation. The water layer was extracted with methylene chloride (3×30 ml). The organic layers were combined, dried over anhydrous sodium sulfate and distilled under reduced pressure to remove the solvent. The residue thus obtained was purified by chromatography on a silica gel column (100 g of silica gel, methylene chloride:methanol=20:1→10:1), whereby the title compound (1.80 g, 7.19 mmol, 98%) was obtained as a colorless transparent oil.

IR(KBr)cm$^{-1}$: 2976, 2929, 2860, 1697, 1431, 1365, 1263, 1240, 1167, 1115, 1028, 910, 771. $^1$H-NMR (CDCl$_3$) δ: 1.49(9H,s), 3.05(2H,t,J=5.9 Hz), 3.75(2H,t,J=5.9 Hz), 4.59 (2H,s), 7.04(1H,d,J=8.8 Hz), 7.14(1H,dd,J=8.8,5.9 Hz), 8.18(1H,d,J=5.9 Hz).

Referential Example 393

6-(t-Butoxycarbonyl)-2-cyano-5,6,7,8-tetrahydro-1,6-naphthylidine

To a solution of 6-(t-butoxycarbonyl)-5,6,7,8-tetrahydro-1,6-naphthylidin-1-oxide (760 mg) in methylene chloride (15 ml), trimethylsilyl cyanide (610 μl) was added at room temperature and the resulting mixture was stirred for 5 minutes. To the reaction mixture, N,N-dimethylcarbamoyl chloride (420 μl) was added, followed by stirring for 41 hours. To the reaction mixture, a saturated aqueous solution (50 ml) of sodium bicarbonate and chloroform (30 ml) were added to cause separation. The water layer was extracted with chloroform (30 ml). The organic layers were combined, dried over anhydrous sodium sulfate and distilled under reduced pressure to remove the solvent. The residue thus obtained was purified by chromatography on a silica gel column (50 g of silica gel, methylene chloride:ethyl acetate= 6:1~2:1), whereby the title compound (697 mg) was obtained as a white solid. The resulting white solid was recrystallized from a hexane-methylene chloride system, whereby colorless needle-like crystals were obtained.

IR(KBr)cm$^{-1}$: 2978, 2933, 2235, 1693, 1685, 1572, 1477, 1458, 1415, 1365, 1267, 1238, 1169, 1161, 1124, 1097, 935, 839, 768. $^1$H-NMR (CDCl$_3$) δ: 1.50(9H,s), 3.05(2H,t,J=5.9 Hz), 3.77(2H,t,J=5.9 Hz), 4.67(2H,s), 7.54(2H,s). MS (FAB) m/z: 260 [(M+H)$^+$], 204 [(M+H)$^+$-isobutene(56)]. Elementary analysis for C$_{14}$H$_{17}$N$_3$O$_2$ Calculated: C, 64.85; H, 6.61; N, 16.20. Found: C, 64.89; H, 6.60; N, 16.57.

Referential Example 394

6-(t-Butoxycarbonyl)-2-methoxycarbonyl-5,6,7,8-tetrahydro-1,6-naphthylidine To a solution of 6-(t-butoxycarbonyl)-2-cyano-5,6,7,8-tetrahydro-1,6-naphthylidine (1.25 g) in methanol (40 ml), concentrated hydrochloric acid (40 ml) was added at room temperature and the resulting mixture was stirred at 100° C. for 3 hours. After the reaction mixture was allowed to cool down to room temperature, it was gradually poured into tetrahydrofuran (150 ml) and an aqueous solution (250 ml) of sodium carbonate (40 g), which had been stirred in advance, followed by the addition of di-t-butyl dicarbonate (1.58 g, 7.23 mmol) at room temperature. The resulting mixture was stirred for 30 minutes. Water (200 ml) was added to the reaction mixture to cause separation. The water layer was extracted with ethyl acetate (100 ml). The organic layers were combined, dried over anhydrous sodium sulfate and distilled under reduced pressure to remove the solvent. The residue so obtained was purified by chromatography on a silica gel column (100 g of silica gel, methylene chloride:ethyl acetate=3:1→1:1), whereby the title compound (955 mg) was obtained as a colorless oil.

$^1$H-NMR (CDCl$_3$) δ: 1.50(9H,s), 3.12(2H,t,J=5.9 Hz), 3.77(2H,t,J=5.9 Hz), 4.00(3H,s), 4.67(2H,s), 7.57(1H,d,J=8.1 Hz), 7.98(1H,d,J=8.1 Hz).

Referential Example 395

6-(t-Butoxycarbonyl)-2-[[4-(chloronaphthalen-2-yl)sulfonyl]piperazin-1-yl]carbonyl]-5,6,7,8-tetrahydro-1,6-naphthylidine To a solution of 6-(t-butoxycarbonyl)-2-methoxycarbonyl-5,6,7,8-tetrahydro-1,6-naphthylidine (955 mg) in tetrahydrofuran (20 ml), a 3N aqueous solution of sodium hydroxide (20 ml) was added at room temperature. After stirring for 2 hours, ammonium sulfate (16.0 g) was added to the reaction mixture. Concentrated hydrochloric acid was added to adjust its pH to 4, followed by extraction with chloroform (2×20 ml). The organic layer was dried over anhydrous sodium sulfate and concentrated under reduced pressure, whereby the residue (874 mg),that is, 6-(t-butoxycarbonyl)-5,6,7,8-tetrahydro-1,6-naphthylidine-2-carboxylic acid was obtained as a white solid. To a solution of the resulting residue in N,N-dimethylformamide (40 ml), methylene chloride (40 ml) and 1-[(6-chloronaphthalen-2-yl)sulfonyl]piperazine hydrochloride (1.42 g) were dissolved, followed by the addition of 1-(dimethylaminopropyl)-3-ethylcarbodiimide (785 mg) and 1-hydroxybenzotriazole (555 mg) at room temperature. Then, diisopropylethylamine (1.71 ml) was added at 0° C. After stirring overnight at room temperature, a 10% aqueous solution of citric acid (200 ml) and methylene chloride (100 ml) were added to the reaction mixture to cause separation. The organic layer was extracted with methylene chloride (50 ml). The organic layers were combined, dried over anhydrous sodium sulfate and concentrated under reduced pressure. The residue was purified by chromatography on a silica gel column (100 g of silica gel, methylene chloride:acetone=10:1~5:1). The white solid thus obtained was reprecipitated in a methylene chloride—methanol—water system. After filtration and washing with water, the title compound (1.44 g) was obtained as a white solid.

IR(KBr)cm$^{-1}$: 2978, 2924, 2846, 1697, 1637, 1577, 1479, 1454, 1432, 1365, 1340, 1238, 1166, 733, 577. $^1$H-NMR (CDCl$_3$) δ: 1.50(9H,s), 2.92(2H,t,J=5.7 Hz), 3.11(2H,br t,J=4.4 Hz), 3.23(2H,br t,J=4.4 Hz), 3.74(2H,t,J=5.7 Hz), 3.78(2H,br t,J=4.4 Hz), 3.90(2H,br t,J=4.4 Hz), 4.59(2H,s), 7.42(1H,br d,J=7.8 Hz), 7.47(1H,br d,J=7.8 Hz), 7.58(1H, dd,J=2.0,8.8 Hz), 7.77(1H,dd,J=2.0,8.5 Hz), 7.90(1H,d,J=2.0 Hz), 7.92–7.95(2H,m), 8.30(1H,br s) MS (FAB) m/z: 571 [(M+H)$^+$, Cl$^{35}$], 515 [(M+H)$^+$-isobutene(56), Cl$^{35}$]. Elementary analysis for C$_{28}$H$_{31}$ClN$_4$O$_5$S Calculated: C, 58.89; H, 5.47; N, 9.81; Cl, 6.21; S, 5.61. Found: C, 58.59; H, 5.61; N, 9.84; Cl, 6.53; S, 5.66.

Referential Example 396

2-(t-Butoxycarbonylamino)-3-(t-butyldiphenylsiloxy)propanol

At room temperature, imidazole (6.43 g) was added to a solution of N-(t-butoxycarbonyl)-L-serine methyl ester (13.8 g) in N,N-dimethylformamide (140 ml), followed by the addition of t-butyldiphenylsilyl chloride (19.7 ml) at 0° C. The resulting mixture was stirred at room temperature for 39 hours. Ethyl acetate (200 ml) and water (600 ml) were added to the reaction mixture to cause separation. The water layer was extracted with ethyl acetate (100 ml). The organic layers were combined, washed with saturated aqueous NaCl solution (100 ml), dried over anhydrous sodium sulfate and concentrated under reduced pressure. The residue thus obtained was dissolved in tetrahydrofuran (100 ml) and methanol (100 ml) without purification, followed by the addition of sodium borohydride (7.20 g) in portions at 0° C. After stirring at 0° C. for 2 hours and then at room temperature for 1 hour, ethyl acetate (100 ml), an aqueous saturated solution of ammonium chloride (300 ml) and water (300 ml) were added to the reaction mixture to cause separation. The water layer was extracted with ethyl acetate (100 ml). The organic layers were combined, dried over anhydrous sodium sulfate and concentrated under reduced pressure. The residue thus obtained was purified by chromatography on a silica gel column (500 g of silica gel, hexane:ethyl acetate=10:1~1:1), whereby the title compound (24.9 g) was obtained as a white solid.

$^1$H-NMR (CDCl$_3$) δ: 1.07(9H,s), 1.44(9H,s), 2.39(1H,br s), 3.63–3.85(5H,m), 5.07(1H,br s), 7.35–7.48(6H,m), 7.60–7.67(4H,m).

Referential Example 397

2-(t-Butoxycarbonylamino)-3-(t-butyldiphenylsiloxy)propanal

To a solution of 2-(t-butoxycarbonylamino)-3-(t-butyldiphenylsiloxy)propanol (3.03 g) in methylene chloride (100 ml), Dess-Martin periodinane (3.60 g) was added at room temperature. The resulting mixture was stirred for 30 minutes. To the reaction mixture, a saturated aqueous solution (50 ml) of sodium bicarbonate and a 10% aqueous solution (50 ml) of sodium sulfite were added to cause separation. The water layer was extracted with diethyl ether (50 ml). The organic layers were combined, dried over anhydrous sodium sulfate and concentrated under reduced pressure. The residue thus obtained was purified by chromatography on a silica gel column (150 g of silica gel, hexane:ethyl acetate=4:1→3:1), whereby the title compound (2.97 g) was obtained as a colorless transparent oil.

$^1$H-NMR (CDCl$_3$) δ: 1.03(9H,s), 1.46(9H,s), 3.93(1H,dd, J=3.9,10.3 Hz), 4.18(1H,d,J=2.9,10.3 Hz), 4.27–4.35(1H, m), 5.33–5.43(1H,m), 7.32–7.48(6H,m), 7.55–7.63(4H,m), 9.66(1H,s)

Referential Example 398

1,5-Bis(t-butoxycarbonyl)-2-(t-butyldiphenylsiloxy)methyl-4,5,6,7-tetrahydro-1H-pyrrolo[3,2-c]pyridine To a solution of diisopropylamine (2.35 ml) in tetrahydrofuran (40 ml), n-butyl lithium (a 1.66 N hexane solution, 9.20 ml) was added at 0° C., followed by stirring for 30 minutes. To the reaction mixture, a solution of N-(t-butoxycarbonyl)-4-piperidone (2.77 g) in tetrahydrofuran (10 ml) was added at −78° C., and the mixture was stirred for 1.5 hours. To the reaction mixture, a solution of 2-(t-butoxycarbonylamino)-3-(t-butyldiphenylsiloxy)propanal (2.97 g) in tetrahydrofuran (10 ml) which had been cooled to −78° C. was added dropwise. The mixture was warmed up gradually and stirred for 13 hours. Water (150 ml) and diethyl ether (350 ml) were added to the reaction mixture to cause separation. The water layer was extracted with diethyl ether (100 ml). The organic layers were combined, washed with water (100 ml) and saturated aqueous NaCl solution (3×100 ml), dried over anhydrous sodium sulfate and concentrated under reduced pressure. The residue thus obtained was dissolved in methylene chloride (20 ml). Concentrated hydrochloric acid was added dropwise and the mixture was adjusted to pH 5, followed by stirring for 1 hour. Concentrated hydrochloric acid was further added dropwise to adjust its pH to 4, followed by stirring for 1 hour. A saturated aqueous solution (50 ml) of sodium bicarbonate and methylene chloride (20 ml) were added to cause separation. The water layer was extracted with diethyl ether (2×50 ml). The organic layers were combined, washed with saturated aqueous NaCl solution (50 ml), dried over anhydrous sodium sulfate and concentrated under reduced pressure. The residue thus obtained was purified by chromatography on a silica gel column (150 g of silica gel, hexane:ethyl acetate=8:1→4:1), whereby the title compound (2.20 g) was obtained as a colorless transparent caramel-like substance. IR(KBr)cm$^{-1}$: 2931, 2856, 1738, 1697, 1473, 1427, 1392, 1367, 1350, 1331, 1232, 1167, 1144, 1109, 1066, 822, 739. $^1$H-NMR (CDCl$_3$) δ: 1.08(9H,s), 1.43(9H,s), 1.49(9H,s), 2.89(2H,br s), 3.64(2H,br s), 4.32(2H,s), 4.85(2H,br s), 6.12(1H,s), 7.30–7.48(6H,m), 7.60–7.75(4H,m). MS(FAB/m-NBA/NaCl) m/z: 613[(M+Na)$^+$].

Referential Example 399

1,5-Bis(t-butoxycarbonyl)-2-hydroxymethyl-4,5,6,7-tetrahydro-1H-pyrrolo[3,2-c]pyridine To a solution of 1,5-bis(t-butoxycarbonyl)-2-(t-butyldiphenylsiloxy)methyl-4,5,6,7-tetrahydro-1H-pyrrolo[3,2-c]pyridine (2.10 g) in pyridine (20 ml), a mixture of hydrogen fluoride and pyridine was added at 0° C., followed by stirring at room temperature for 1 hour. After the reaction mixture was poured into ethyl acetate (50 ml) and ice water (300 ml) which had been stirred in advance, the resulting mixture was separated. The water layer was extracted with ethyl acetate (50 ml). The organic layers were combined, washed with a saturated aqueous solution of sodium bicarbonate, dried over anhydrous sodium sulfate and concentrated under reduced pressure. The residue thus obtained was purified by chromatography on a silica gel column (150 g of silica gel, hexane:ethyl acetate=3:1), whereby the title compound (882 mg) was obtained as a colorless, transparent caramel-like substance.

IR(KBr)cm$^{-1}$: 3432, 2976, 2931, 1736, 1695, 1419, 1365, 1350, 1323, 1234, 1167, 1144, 1105, 754.

$^1$H-NMR (CDCl$_3$) δ: 1.47(9H,s), 1.60(9H,s), 2.85(2H,br s), 3.45–3.70(1H,br), 3.64(2H,br s), 4.29(2H,s), 4.59(2H,d, J=7.3 Hz), 6.01(1H,s). MS (FAB/m-NBA/NaCl) m/z: 375 [(M+Na)$^+$].

Referential Example 400

1,5-Bis(t-butoxycarbonyl)-2-formyl-4,5,6,7-tetrahydro-1H-pyrrolo[3,2-c]pyridine

To a solution of 1,5-bis(t-butoxycarbonyl)-2-hydroxymethyl-4,5,6,7-tetrahydro-1H-pyrrolo[3,2-c]pyridine (14.0 mg) in methylene chloride (2.0 ml), Dess-Martin periodinane (34.0 mg) was added at room temperature. The resulting mixture was stirred for 1 hour. To the reaction mixture, ethyl acetate (10 ml), a 10% aqueous solution (10 ml) of sodium thiosulfate and an aqueous solution (10 ml) of sodium bicarbonate were added to cause separation. The water layer was extracted with ethyl acetate (10 ml). The organic layers were combined, dried over anhydrous sodium sulfate and concentrated under reduced pressure. The residue thus obtained was purified by thin-layer preparative chromatography on silica gel (hexane:ethyl acetate=2:1), whereby the title compound (9.8 mg) was obtained as a colorless transparent caramel-like substance. IR(KBr)cm$^{-1}$: 2976, 2933, 1741, 1697, 1660, 1479, 1413, 1367, 1346, 1298, 1281, 1234, 1165, 1146, 1103, 895, 850, 768. $^1$H-NMR (CDCl$_3$) δ: 1.48(9H,s), 1.63(9H,s), 2.96(2H,br t,J=5.4 Hz), 3.68(2H,br t,J=5.4 Hz), 4.37(2H,s), 6.97(1H,s), 10.14(1H,br s). MS (FAB/m-NBA) m/z: 351 [(M+H)$^+$], 295 [(M+H-isobutene(56))$^+$], 239 [(M+H)—2×isobutene (56))$^+$].

Referential Example 401

1,5-Bis(t-butoxycarbonyl)-2-[[4-(6-chloronaphthalen-2-yl)sulfonyl]piperazin-1-yl]carbonyl]-4,5,6,7-tetrahydro-1H-pyrrolo[3,2-c]pyridine To a solution of 1,5-bis(t-butoxycarbonyl)-2-formyl-4,5,6,7-tetrahydro-1H-pyrrolo[3,2-c]pyridine (44.0 mg) in t-butanol (2.0 ml), 2-methyl-2-butene (150 μl) and an aqueous solution (6.0 ml) of sodium chlorite (102 mg) and sodium dihydrogenphosphate (135 mg) were added at room temperature. After stirring for 21 hours, the reaction mixture was added with diethyl ether (10 ml) and water (10 ml), followed by the addition of ammonium sulfate until saturation. The resulting mixture was separated, followed by extraction with diethyl ether (10 ml). The organic layers were combined, dried over anhydrous sodium sulfate and concentrated under reduced pressure, whereby the residue, that is, 1,5-bis(t-butoxycarbonyl)-4,5,6,7-tetrahydro-1H-pyrrolo[3,2-c]pyridine-2-carboxylic acid was obtained as a white foamy substance. To a solution of the resulting residue in N,N-dimethylformamide (2.0 ml), methylene chloride (2.0 ml) and 1-[(6-chloronaphthalen-2-yl)sulfonyl]piperazine hydrochloride (55.0 mg) were dissolved, followed by the addition of 1-(dimethylaminopropyl)-3-ethyl carbodiimide (30.5 mg) and 1-hydroxybenzotriazole (21.5 mg) at room temperature. At 0° C., diisopropylethylamine (67.0 μl) was added thereto. After stirring overnight at room temperature, a 10% aqueous citric acid solution (10 ml) and methylene chloride (10 ml) were added to the reaction mixture to cause separation. The organic layer was extracted with methylene chloride (10 ml). The organic layers were combined, dried over anhydrous sodium sulfate and concentrated under reduced pressure. The resulting residue was purified by thin-layer preparative chromatography on silica gel (methylene chloride:acetone=10:1) and the white solid thus obtained was reprecipitated in a methylene chloride—methanol—water system. After filtration and washing with water, the title compound (50.0 mg) was obtained as a colorless transparent caramel-like substance. IR(KBr)cm$^{-1}$: 2981, 2929, 2860, 1743, 1693, 1647, 1456, 1421, 1367, 1348, 1325, 1279, 1236, 1165, 1103, 955, 945, 729.

$^1$H-NMR (CDCl$_3$) δ: 1.32(9H,s), 1.46(9H,s), 2.83(2H,br t,J=5.6 Hz), 3.04(2H,br), 3.17(2H,br), 3.55(2H,br), 3.62(2H, br t,J=5.6 Hz), 3.82(2H,br), 4.25(2H,s), 5.94(1H,s), 7.59 (1H,dd,J=2.0,8.8 Hz), 7.76(1H,dd,J=1.7,8.5 Hz), 7.87–7.98

(3H,m), 8.30(1H,br s). MS (FAB/m-NBA/NaCl) m/z: 681 [(M+Na)$^+$], 581 [(M+Na-Boc(100))$^+$], 525 [(M+Na-Boc(100)-isobutene(56))$^+$].

Referential Example 402

1-(tert-Butoxycarbonyl)-4-[(6-methyl-4,5,6,7-tetrahydrothiazolo[5,4-c]pyridin-2-yl)carbonyl]piperazine To a solution of lithium 6-methyl-4,5,6,7-tetrahydrothiazolo[5,4-c]pyridine-2-carboxylate (293 mg) in N,N-dimethylformamide (10 ml) were added 1-(tert-butoxycarbonyl)piperazine (294 mg), 1-hydroxybenzotriazole monohydrate (214 mg) and 1-(3-dimethylaminopropyl)-3-ethylcarbodiimide hydrochloride (303 mg) at room temperature. After stirring for 38 hours, methylene chloride (20 ml) and water (200 ml) were added to the reaction mixture to separate it into layers. The water layer thus obtained was extracted with methylene chloride (3×10 ml). The organic layers were combined, washed with a saturated aqueous solution (100 ml.) of sodium bicarbonate, dried over anhydrous sodium sulfate and distilled under reduced pressure to remove the solvent. The residue was purified by chromatography on a silica gel column (methylene chloride:acetone=2:1), whereby the title compound (300 mg) was obtained as a pale yellow viscous substance.

$^1$H-NMR (CDCl$_3$) δ: 1.48(9H,s), 2.51(3H,s), 2.83(2H,t, J=5.7 Hz), 2.94(2H,t,J=5.7 Hz), 3.53(4H,t,J=5.2 Hz), 3.71 (2H,s), 3.75(2H,br s), 4.38(2H,br s). MS (FAB) m/z: 367 (M+H)$^+$, 311 (M-isobutene+H)$^+$, 267 (M-Boc+H)$^+$.

Referential Example 403

Thiazolo[4,5-c]pyridine

In formic acid (60 ml) was dissolved 3-(tert-butoxyamino)-4-mercaptopyridine (9.20 g), followed by heating under reflux for 4 hours. After the reaction mixture was concentrated under reduced pressure and a 5N aqueous solution (100 ml) of potassium hydroxide was added to the residue, the resulting mixture was extracted with ether. The organic layer was dried over anhydrous sodium sulfate and distilled under reduced pressure to remove the solvent. Diethyl ether was added to the residue and the solid so precipitated was collected by filtration, whereby the title compound was obtained as a colorless solid (3.97 g).

$^1$H-NMR (CDCl$_3$) δ: 7.93(1H,d,J=5.4 Hz), 8.60(1H,d,J= 5.4 Hz), 9.07(1H,s), 9.46(1H,s).

Referential Example 404

5-Methyl-4,5,6,7-tetrahydrothiazolo[4,5-c]pyridine

In N,N-dimethylformamide (80 ml) was dissolved thiazolo[4,5-c]pyridine (700 mg), followed by the addition of methyl iodide (0.65 ml). The resulting mixture was stirred under heat at 80° C. for 4 hours. After concentration of the reaction mixture under reduced pressure, the residue was dissolved in water (100 ml). Sodium borohydride (583 mg) was added to the resulting solution, followed by stirring at room temperature for 1 hour. After the addition of a saturated aqueous solution of potassium carbonate, the resulting mixture was extracted with ether. The organic layer thus extracted was dried over anhydrous sodium sulfate and distilled under reduced pressure to remove the solvent. The residue was purified by chromatography on a silica gel column (methylene chloride:methanol=25:1), whereby the title compound (596 mg) was obtained as a colorless oil.

$^1$H-NMR (CDCl$_3$) δ: 2.52(3H,s), 2.77(2H,t,J=5.4 Hz), 2.92–3.00(2H,m), 3.69(2H,t,J=2.0 Hz), 8.61(1H,s). MS (FAB) m/z: 155 (M+H)$^+$.

Referential Example 405

Lithium 5-methyl-4,5,6,7-tetrahydrothiazolo[4,5-c]pyridine-2-carboxylate

In anhydrous tetrahydrofuran (10 ml) was dissolved 5-methyl-4,5,6,7-tetrahydrothiazolo[4,5-c]pyridine (583 mg), followed by the dropwise addition of a hexane solution (1.54M, 2.70 ml) of n-butyl lithium at −78° C. After stirring for 10 minutes, the reaction mixture was warmed up to 0° C. and stirring was conducted for 30 minutes. The reaction mixture was cooled to −78° C. A carbon dioxide gas was blown into the reaction mixture for 15 minutes, followed by warming up to room temperature. The reaction mixture was concentrated under reduced pressure, whereby the title compound (820 mg) was obtained as a pale brown foamy solid.

$^1$H-NMR (DMSO-d$_6$) δ: 2.38(3H,s), 2.64(2H,br s), 2.80 (2H,br s), 3.44(2H,br s). MS (FD) m/z: 199 (M+H)$^+$.

Referential Example 406

Lithium thiazolo[4,5-c]pyridine-2-carboxylate

In the same manner as in Referential Example 405, the title compound was obtained.

$^1$H-NMR (DMSO-d$_6$) δ: 8.07(1H,d,J=5.4 Hz), 8.48(1H, d,J=5.4 Hz), 9.22(1H,s).

Referential Example 407

5-Isopropyl-4,5,6,7-tetrahydrothiazolo[4,5-c]pyridine

In the same manner as in Referential Example 404, the title compound was obtained.

$^1$H-NMR (CDCl$_3$) δ: 1.16(6H,d,J=6.8 Hz), 2.80–2.92(4H, m), 2.95–3.03(1H,m), 3.83(2H,t,J=2.0 Hz), 8.60(1H,s). MS (FAB) m/z: 183 (M+H)$^+$.

Referential Example 408

Lithium 5-isopropyl-4,5,6,7-tetrahydrothiazolo[4,5-c]pyridine-2-carboxylate

In the same manner as in Referential Example 405, the title compound was obtained.

$^1$H-NMR (DMSO-d$_6$) δ: 2.64(2H,br s), 2.80(2H,br s), 3.44 (2H,br s). MS (FAB) m/z: 277 (M+H)$^+$.

Referential Example 409

1-Benzoyl-3-bromo-2-methyl-4-piperidone

In diethyl ether (50 ml) was suspended copper cyanide (197 mg), followed by the dropwise addition of a diethyl ether solution (1.10 mole, 4.00 ml) of methyl lithium at −78° C. The reaction mixture was warmed up to 0° C. After the reaction mixture was stirred for 10 minutes, it was cooled to −78° C. again. To the reaction mixture was added dropwise a diethyl ether solution (5 ml) of N-benzoylazacyclohexa-2-en-4-one (400 mg) (Can. J. Chem., 1981, 3136–3140) at −78° C., followed by stirring for 30 minutes. After trimethylsilyl chloride (0.53 ml, 4.20 mmol) was added dropwise to the reaction mixture, the resulting mixture was warmed up to room temperature. The reaction mixture was added with a saturated aqueous solution of sodium bicarbonate. The resulting solution was then extracted with ethyl acetate. The organic layer thus extracted was washed with aqueous NaCl solution. The extract was dried over anhydrous sodium sulfate and distilled to remove the solvent. The residue was dissolved in acetone (10 ml), followed by the addition of sodium acetate (135 mg), water (2 ml) and N-bromosuccinic imide (292 mg) under ice cooling. The resulting mixture was stirred overnight at room temperature. To the reaction mixture was added an aqueous solution of sodium thiosulfate (2 moles, 10 ml). After stirring for 30 minutes, ethyl acetate was added and the organic layer was collected. The organic layer thus obtained was washed with saturated aqueous NaCl solution, dried over anhydrous sodium sulfate and distilled to remove the solvent. The residue was purified by chromatography on a silica gel column (ethyl acetate:hexane=1:3), whereby the title compound (240 mg) was obtained as a yellow oil.

$^1$H-NMR (CDCl$_3$) δ: 1.39(3H,d,J=7.3 Hz), 2.20–2.40(1H, m), 2.65(1H,br s), 3.18–3.58(2H,m), 4.01(1H,br s), 4.15–4.62(½H,m), 4.80–5.28(½H,m), 7.40–7.55(5H,m). MS (FAB) m/z: 296 (M$^+$, Br$^{79}$), 298 (M$^+$, Br$^{81}$)

Referential Example 410

6-Benzoyl-7-methyl-4,5,6,7-tetrahydrothiazolo[5,4-c]pyridine

In butanol (20 ml) was dissolved 1-benzoyl-2-methyl-3-bromo-4-piperidone (240 mg), followed by the addition of thioformamide (160 mg). The resulting mixture was stirred at 100° C. for 2.5 hours. After the reaction mixture was cooled to room temperature, it was subjected to Celite filtration. The filtrate was washed with a saturated aqueous solution of sodium bicarbonate and saturated aqueous NaCl solution, dried over anhydrous sodium sulfate and distilled under reduced pressure to remove the solvent. The residue was purified by chromatography on a silica gel column (ethyl acetate:hexane=1:2), whereby the title compound (56 mg) was obtained as a yellow oil.

$^1$H-NMR (CDCl$_3$) δ: 1.39(3H,d,J=5.6 Hz), 2.88–3.10(2H, m), 3.41(1H,br s), 3.94(1H,br s), 5.97(1H,br s), 7.38–7.48 (5H,m), 8.70(1H,s). MS (FAB) m/z: 259 (M+H)$^+$.

Referential Example 411

6-tert-Butoxycarbonyl-7-methyl-4,5,6,7-tetrahydrothiazolo[5,4-c]pyridine

Under ice cooling, sodium hydride (60% in oil, 270 mg) was added to butanol (70 ml), followed by stirring for 30 minutes. A butanol solution (5 ml) of 6-benzoyl-7-methyl-4,5,6,7-tetrahydrothiazolo[5,4-c]pyridine (240 mg) was added to the reaction mixture. The resulting mixture was heated under reflux for 4 days. After water (5 ml) was added to the reaction mixture and the mixture was heated under reflux for 30 minutes, the reaction mixture was cooled to room temperature. To the reaction mixture was added di-tert-butyl dicarbonate (883 mg) and they were stirred at room temperature for 8 hours. The reaction mixture was concentrated under reduced pressure. To the residue were added 3N hydrochloric acid (10 ml) and ethyl acetate to separate the resulting mixture into layers. The organic layer thus collected was dried over anhydrous sodium sulfate and distilled to remove the solvent. The residue was purified by chromatography on a silica gel column (ethyl acetate:hexane=1:4), whereby the title compound (168 mg) was obtained as a yellow oil.

$^1$H-NMR (CDCl$_3$) δ: 1.46(3H,d,J=5.6 Hz), 1.49(9H,s), 2.85–2.92(2H,m), 3.10(1H,m), 4.27–4.50(1H,m), 5.23–5.52 (1H,m), 8.65(1H,s). MS (FAB) m/z: 255 (M+H)$^+$.

Referential Example 412

Lithium 6-(tert-butoxycarbonyl)-7-methyl-4,5,6,7-tetrahydrothiazolo[5,4-c]pyridine-2-carboxylate In the same manner as in Referential Example 405, the title compound was obtained.

$^1$H-NMR (DMSO-d$_6$) δ: 1.38–1.40(3H,m), 1.43(9H,s), 2.60–2.82(2H,m), 3.11(1H,br s), 4.15(1H,br s), 5.10–5.32 (1H,m). MS (FAB) m/z: 298 M$^+$.

Referential Example 413

4-Ethoxycarbonylthiazole

Formamide (100 ml) was stirred under ice cooling, followed by the addition of diphosphorus pentasulfide (27.48 g) in the form of a solid. The resulting mixture was stirred overnight at room temperature. Water (200 ml) was added and then the mixture was extracted with diethyl ether (8×200 ml). The organic layers were combined, washed with saturated aqueous NaCl solution, dried over anhydrous sodium sulfate and distilled under reduced pressure to remove the solvent, whereby thioformamide (35.8 g) was obtained as a yellow oil. While stirring, ethyl bromopyruvate (20.0 g) was added to the resulting oil. After the addition of ethanol (100 ml) to the reaction mixture, ethyl bromopyruvate (45.04 g) was added further. The resulting mixture was stirred at room temperature for 3 hours. The solvent was distilled off under reduced pressure. Methylene chloride was added to the residue. The resulting mixture was washed with a saturated aqueous solution of sodium bicarbonate and saturated aqueous NaCl solution, dried over anhydrous sodium sulfate and distilled under reduced pressure to remove the solvent, whereby the title compound (42.73 g) was obtained as a brown oil.

$^1$H-NMR (CDCl$_3$) δ: 1.43(3H,t,J=7.3 Hz), 4.45(2H,q,J= 7.3 Hz), 8.26(1H,d,J=2.0 Hz), 8.86(1H,d,J=2.0 Hz). MS (EI) m/z: 157 M$^+$.

Referential Example 414

4-Formylthiazole

In anhydrous tetrahydrofuran (150 ml) was dissolved 4-ethoxycarbonylthiazole (15.2 g) and the resulting solution was cooled to −78° C. Diisobutylaluminum hydride (a 0.95 mole hexane solution, 102 ml) was added dropwise, followed by stirring for 1 hour at a temperature maintained at −78° C. After the addition of methanol (20 ml) and heating to room temperature, the reaction mixture was subjected to Celite filtration. The precipitate so obtained was washed with tetrahydrofuran and ethyl acetate and then added to a saturated aqueous solution of ammonium chloride. The resulting mixture was extracted with methylene chloride. The organic layers were combined and distilled under reduced pressure to remove the solvent. The residue was then dissolved in methylene chloride. The resulting solution was washed with saturated aqueous NaCl solution, dried over anhydrous sodium sulfate and distilled under reduced pressure to remove the solvent, whereby the title compound (7.37 g) was obtained as a yellow solid.

$^1$H-NMR (CDCl$_3$) δ: 8.27(1H,d,J=2.0 Hz), 8.92(1H,d,J= 2.0 Hz), 10.15(1H,s). MS (EI) m/z: 113 M$^+$.

Referential Example 415

4-(2-Nitro-1-propenyl)thiazole

In isopropyl alcohol (100 ml) was dissolved 4-formylthiazole (10.9 g), followed by the addition of potassium fluoride (280 mg) and nitromethane (14.46 g). The resulting mixture was stirred at 60 to 65° C. for 2 hours. The reaction mixture was then stirred overnight at room temperature. The solvent was distilled off under reduced pressure. The residue was dissolved in benzene (50 ml), followed by the addition of acetic anhydride (12.29 g) and 4-(dimethylamino)pyridine (588 g). The resulting mixture was heated under reflux for 2 hours. The solvent was distilled off under reduced pressure. Methylene chloride was added to the residue. The resulting mixture was washed with a saturated aqueous solution of sodium bicarbonate. The organic layer was then dried over anhydrous sodium sulfate and distilled under reduced pressure to remove the solvent. The residue was purified by chromatography on a silica gel column (hexane : ethyl acetate=1:1), whereby the title compound (8.73 g) was obtained as vividly yellow crystals.

$^1$H-NMR (CDCl$_3$) δ: 2.78(3H,d,J=0.5Hz), 7.68(1H,d,J= 2.0 Hz), 8.03(1H,m), 8.92(1H,d,J=2.0 Hz). MS (EI) m/z: 170 M$^+$.

Referential Example 416

4-[2-[N-(tert-Butoxycarbonyl)amino]propyl]thiazole

Under ice cooling, lithium aluminum hydride (2.41 g) was suspended in anhydrous tetrahydrofuran (50 ml). An anhydrous tetrahydrofuran solution (90 ml) of 4-(2-nitro-1-propenyl)thiazole (10.8 g) was added dropwise to the resulting suspension. After stirring at the same temperature for 40 minutes, sodium sulfate 10 hydrate (15 g) was added and the resulting mixture was stirred for 45 minutes. The reaction mixture was subjected to Celite filtration. From the precipitate, an organic substance was extracted with hot methanol. The organic layers were combined and distilled under reduced pressure to remove the solvent. Methylene chloride (50 ml), sodium carbonate (3.4 g) and di-tert-butyl dicarbonate (13.86 g) were added to the residue, followed by stirring at room temperature for 2 hours. The reaction mixture was washed with water, dried over anhydrous sodium sulfate and distilled under reduced pressure to remove the solvent. The residue was purified by chromatography on a silica gel column (Φ4×20 cm, hexane:ethyl acetate=3:1→3:2), whereby the title compound (2.86 g) was obtained as a brown oil.

$^1$H-NMR (CDCl$_3$) δ: 1.13, 1.16(total 3H,d each,J=6.6,6.4 Hz), 1.42(9H,s), 2.91–3.09(2H,m), 4.00–4.11(1H,m), 5.03–5.08(1H,m), 7.05–7.10(1H,m), 8.75–8.77(1H,m). MS (FAB) m/z: 243 (M+H)$^+$.

Referential Example 417

6-(tert-Butoxycarbonyl)-5-methyl-4,5,6,7-tetrahydrothiazolo[5,4-c]pyridine

In ethanol (26 ml) was dissolved 4-[2-[N-(tert-butoxycarbonyl)amino]propyl]thiazole (1.07 g), followed by the addition of paraformaldehyde (90%, 2.94 g) and a 1N solution (13 ml) of hydrochloride in ethanol. The resulting mixture was charged in a sealed tube and stirred at 100° C. for 28 hours. During stirring, operation of cooling to room temperature, loosening the lid and thereby reducing the internal pressure of the tube was carried out several times. The solvent was then distilled off under reduced pressure. To the residue were added methylene chloride (18 ml), triethylamine (2.6 ml) and di-tert-butyl dicarbonate (1.45 g), followed by stirring at room temperature for 3 hours. The reaction mixture was washed with water, dried over anhydrous sodium sulfate and distilled under reduced pressure to remove the solvent. The residue was purified by column chromatography (hexane ethyl acetate=4:1) using, as a carrier, silica gel, whereby the title compound (625 mg) was obtained as a pale yellow solid.

$^1$H-NMR (CDCl$_3$) δ: 1.15(3H,d,J=6.8 Hz), 1.49(9H,s), 2.77(1H,d,J=16.6 Hz), 3.09–3.14(1H,m), 4.21(1H,d,J=16.8 Hz), 4.84(1H,br s), 5.06(1H,br s), 8.69(1H,s). MS (FAB) m/z: 255 (M+H)$^+$.

Referential Example 418

4-Formyl-2-(trans-β-styryl)oxazole

To a solution of 4-ethoxycarbonyl-2-(trans-β-styryl)oxazole (8.57 g) (J. Org. Chem. 1996, 61, 6496–6497) in methylene chloride (80 ml) was added dropwise diisobutylaluminum hydride (a 1.0 mole hexane solution, 66.0 ml) at −78° C. After stirring for 15 minutes, methanol (11 ml) was added dropwise and the resulting mixture was warmed up to room temperature over 1 hour. The reaction mixture was then subjected to Celite filtration. The pasty substance thus obtained was dissolved in ethyl acetate (200 ml) and a saturated aqueous solution (200 ml) of ammonium chloride. The resulting solution was separated into layers. The water layer was extracted with methylene chloride (2×100 ml). The organic layers were combined and washed with a saturated aqueous solution (100 ml) of sodium bicarbonate and saturated aqueous NaCl solution (100 ml), followed by the addition of the filtrate upon Celite filtration. The resulting mixture was dried over anhydrous sodium sulfate and distilled under reduced pressure to remove the solvent. The residue was purified by chromatography on a silica gel column (methylene chloride ethyl acetate=5:1→methylene chloride:methanol=10:1), whereby the title compound (5.86 g) was obtained as colorless needle crystals.

$^1$H-NMR (CDCl$_3$) δ: 6.96(1H,d,J=16.6 Hz), 7.35–7.45 (3H,m), 7.56(2H,d,J=6.4 Hz), 7.67(1H,d,J=16.6 Hz), 8.26 (1H,s), 9.98(1H,s). MS (FAB) m/z: 200 (M+H)$^+$.

Referential Example 419

2-(trans-β-Styryl)-4-vinyloxazole

To a solution of (methyl)triphenylphosphonium bromide (8.16 g, 22.8 mmol) in tetrahydrofuran (80 ml) was added dropwise n-butyl lithium (a 1.54N hexane solution, 14.2 ml) at 0° C., followed by stirring at room temperature for 30 minutes. The reaction mixture was cooled to 0° C. again and a solution of 4-formyl-2-(trans-β-styryl)oxazole (3.64 g) in tetrahydrofuran (20 ml) was added thereto. The resulting mixture was heated to room temperature. After stirring for 2 hours, water (200 ml) and ethyl acetate (100 ml) were added to separate the reaction mixture into layers. The water layer was extracted with ethyl acetate (50 ml). The organic layers were combined, washed with saturated aqueous NaCl solution (100 ml), dried over anhydrous sodium sulfate and distilled under reduced pressure to remove the solvent. The residue was purified by chromatography on a silica gel column (hexane:ethyl acetate=4:1→3:1), whereby the title compound (2.84 g) was obtained as a pale yellow oil.

$^1$H-NMR (CDCl$_3$) δ: 5.33(1H,dd,J=10.7,1.5 Hz), 5.98 (1H,dd,J=17.6,1.5 Hz), 6.56(1H,dd,J=17.6,10.7 Hz), 6.95 (1H,d,J=16.6 Hz), 7.31–7.42(3H,m), 7.49–7.56(4H,m). MS (FAB) m/z: 198 (M+H)$^+$.

Referential Example 420

4-(2-Hydroxyethyl)-2-(trans-β-styryl)oxazole

To a solution of 2-(trans-β-styryl)-4-vinyloxazole (13.0 g) in tetrahydrofuran (500 ml) was added 9-borabicyclo[3.3.1]

nonane (a 0.5 mole tetrahydrofuran solution, 158 ml) at 0° C. The resulting mixture was stirred at room temperature for 15 hours. At 0° C., water (10 ml), a 3N aqueous solution of sodium hydroxide (80 ml) and aqueous hydrogen peroxide (80 ml) were successively added dropwise to the reaction mixture, followed by stirring at room temperature for 6 hours. Water (600 ml) and ethyl acetate (200 ml) were added to the reaction mixture to separate the reaction mixture into layers. The water layer was extracted with ethyl acetate (200 ml). The organic layers were combined, washed with saturated aqueous NaCl solution (200 ml), dried over anhydrous sodium sulfate and distilled under reduced pressure to remove the solvent. The residue was purified by chromatography on a silica gel column (hexane:ethyl acetate= 2:1→only ethyl acetate), whereby the title compound (14.1 g) was obtained as a colorless solid.

$^1$H-NMR (CDCl$_3$) δ: 2.69(1H,br s), 2.80(2H,t,J=5.6 Hz), 3.90–3.97(2H,m), 6.91(1H,d,J=16.6 Hz), 7.30–7.42(4H,m), 7.43–7.56(3H,m). MS (FAB) m/z: 216 (M+H)$^+$.

Referential Example 421

N-[2-[2-(trans-β-styryl)oxazol-4-yl]ethyl] phthalimide

To a solution of 4-(2-hydroxyethyl)-2-(trans-β-styryl) oxazole (292 mg) in tetrahydrofuran (15 ml) were added phthalimide (200 mg), triphenylphosphine (357 mg) and diethyl azodicarboxylate (214 μl) at room temperature, followed by stirring for 4 hours. The reaction mixture was distilled under reduced pressure to remove the solvent. The residue was purified by chromatography on a silica gel column (hexane:ethyl acetate=3:1), whereby the title compound (447 mg) was obtained as a colorless solid.

$^1$H-NMR (CDCl$_3$) δ: 2.98(2H,t,J=7.2 Hz), 4.03(2H,t,J= 7.2 Hz), 6.88(1H,d,J=16.6 Hz), 7.28–7.45(5H,m), 7.48(2H, d,J=7.3 Hz), 7.71(2H,dd,J=5.4,2.9 Hz), 7.84(2H,dd,J=5.4, 2.9 Hz). MS (FAB) m/z: 345 (M+H)$^+$.

Referential Example 422

4-[2-(tert-Butoxycarbonylamino)ethyl]-2-(trans-β-styryl)oxazole

To a solution of N-[2-[2-(trans-β-styryl)oxazol-4-yl] ethyl]phthalimide (6.40 g) in ethanol (150 ml) was added hydrazine monohydrate (1.50 ml) at room temperature. After stirring for 1 hour, hydrazine monohydrate (500 μl) was added again at room temperature, followed by stirring for 2 hours. At room temperature, methylene chloride (150 ml) and a saturated aqueous solution (150 ml) of sodium bicarbonate and di-tert-butyl dicarbonate (13.4 g, 61.4 mmol) were added to the reaction mixture. After stirring for 30 minutes, the reaction mixture was separated into layers. The water layer was extracted with methylene chloride (50 ml). The organic layers were combined, dried over anhydrous sodium sulfate and distilled under reduced pressure to remove the solvent. The residue was purified by chromatography on a silica gel column (hexane:ethyl acetate= 2:1→1:1), whereby the title compound (5.06 g) was obtained as a colorless solid.

$^1$H-NMR (CDCl$_3$) δ: 1.45(9H,s), 2.75(2H,t,J=6.6 Hz), 3.46(2H,dt,J=5.9,6.6 Hz), 4.92(1H,br s), 6.91(1H,d,J=16.6 Hz), 7.29–7.45(4H,m), 7.48(1H,d,J=16.6 Hz), 7.52(2H,d,J= 7.3 Hz). MS (FAB) m/z: 315 (M+H)$^+$.

Referential Example 423

6-(tert-Butoxycarbonyl)-2-(trans-β-styryl)-4,5,6,7-tetrahydrooxazolo[5,4-c]pyridine To a solution of 4-[2-(tert-Butoxycarbonylamino)ethyl]-2-(trans-β-styryl)oxazole (190 mg) in toluene (15 ml) were added paraformaldehyde (54.5 mg) and p-toluenesulfonic acid (7.2 mg) at room temperature. After heating under reflux for 1 hour, the reaction mixture was allowed to cool down. Ethyl acetate (15 ml) and a saturated aqueous solution (15 ml) of sodium bicarbonate were added to the reaction mixture to separate it into layers. The water layer was extracted with ethyl acetate(10 ml). The organic layers were combined, dried over anhydrous sodium sulfate and distilled under reduced pressure to remove the solvent. The residue was purified by chromatography on a silica gel column (hexane:ethyl acetate=3:1→2:1), whereby the title compound (153 mg) was obtained as a colorless transparent viscous substance.

$^1$H-NMR (CDCl$_3$) δ: 1.50(9H,s), 2.67(2H,br s), 3.73(2H, br s), 4.55(2H,s), 6.90(1H,d,J=16.1 Hz), 7.29–7.42(3H,m), 7.46(1H,d,J=16.1 Hz), 7.52(2H,d,J=7.3 Hz). MS (FAB) m/z: 327 (M+H)$^+$.

Referential Example 424

6-(tert-Butoxycarbonyl)-2-formyl-4,5,6,7-tetrahydrooxazolo[5,4-c]pyridine

To a solution of 6-(tert-butoxycarbonyl)-2-(trans-β-styryl)-4,5,6,7-tetrahydrooxazol[5,4-c]pyridine (803 mg) in tetrahydrofuran (16 ml) were added acetone (8.0 ml), water (4.0 ml), N-methylmorpholine oxide (577 mg) and osmium tetraoxide (a 0.039 mole aqueous solution, 3.20 ml) at room temperature, followed by stirring overnight. Ethyl acetate (50 ml) and a 10% aqueous solution (50 ml) of sodium thiosulfate were added to the reaction mixture to separate it into layers. The water layer was extracted with ethyl acetate (30 ml). The organic layers were combined, dried over anhydrous sodium sulfate and distilled under reduced pressure to remove the solvent. A solution of the resulting residue in tetrahydrofuran (16 ml) were added methanol (8.0 ml), water (8.0 ml) and sodium metaperiodate (790 mg) at room temperature. After stirring for 3 hours, ethyl acetate (30 ml) and water (50 ml) were added to the reaction mixture to separate it into layers. The water layer was extracted with ethyl acetate (20 ml). The organic layers were combined, washed with a saturated aqueous solution of sodium bicarbonate (50 ml), dried over anhydrous sodium sulfate and distilled under reduced pressure to remove the solvent. The residue was purified by chromatography on a silica gel column (hexane:ethyl acetate=4:1→2:1), whereby the title compound (234 mg) was obtained as a colorless transparent glassy substance.

$^1$H-NMR (CDCl$_3$) δ: 1.49(9H,s), 2.77(2H,br s), 3.77(2H, br s), 4.62(2H,s), 9.70(1H,s).

The resulting aldehyde was unstable so that it was provided for the subsequent reaction immediately.

Referential Example 425

6-(tert-Butoxycarbonyl)-2-methoxycarbonyl-4,5,6,7-tetrahydrooxazol[5,4-c]pyridine To a solution of 6-(tert-butoxycarbonyl)-2-formyl-4,5,6, 7-tetrahydrooxazol[5,4-c]pyridine (225 mg) in methanol (9.0 ml) were added sodium cyanide (220 mg) and manganese dioxide (780 mg) at room temperature, followed by stirring for 30 minutes. The reaction mixture was subjected to Celite filtration by using ethyl acetate. The filtrate was washed with water (50 ml) and saturated saline (50 ml), dried over anhydrous sodium sulfate and distilled under reduced pressure to remove the solvent. The residue was purified by chromatography on a silica gel column (hexane:ethyl acetate=3:2→1:1), whereby the title compound (120 mg) was obtained as a colorless transparent glassy substance.

$^1$H-NMR (CDCl$_3$) δ: 1.49(9H,s), 2.73(2H,br s), 3.74(2H, br s), 4.01(3H,s), 4.59(2H,s). MS (FAB) m/z: 283 (M+H)$^+$.

Referential Example 426

Lithium 6-(tert-butoxycarbonyl)-4,5,6,7-tetrahydrooxazol[5,4-c]pyridine-2-carboxylate To a solution of 6-(tert-butoxycarbonyl)-2-methoxycarbonyl-4,5,6,7-tetrahydrooxazolo[5,4-c]pyridine (311 mg) in tetrahydrofuran (8.0 ml) were added water (2.0 ml) and lithium hydroxide (25.0 mg) at room temperature. After stirring for 10 minutes, the reaction mixture was distilled under reduced pressure to remove the solvent, whereby the title compound (280 mg) was obtained as a colorless solid. The residue was provided for the subsequent reaction without purification.

$^1$H-NMR (DMSO-d$_6$) δ: 1.42(9H,s), 3.31(2H,s), 3.60(2H, d,J=5.4 Hz), 4.42(2H,s).

Referential Example 427

2-Methoxycarbonyl-6-methyl-4,5,6,7-tetrahydrooxazolo[5,4-c]pyridine

To a solution of 6-(tert-butoxycarbonyl)-2-methoxycarbonyl-4,5,6,7-tetrahydrooxazolo[5,4-c]pyridine (500 mg) in methylene chloride (15 ml) was added trifluoroacetic acid (15 ml) at room temperature, followed by stirring for 10 minutes. The reaction mixture was concentrated under reduced pressure. To the resulting residue were added methylene chloride (20 ml), triethylamine (495 μl), acetic acid (205 μl), formalin (230 μl) and sodium triacetoxyborohydride (570 mg) at room temperature. After stirring for 15 minutes, methylene chloride (20 ml) and a saturated aqueous solution (50 ml) of sodium bicarbonate were added to the reaction mixture to separate it into layers. The water layer was extracted with methylene chloride (3×20 ml). The organic layers were combined, dried over anhydrous sodium sulfate and distilled under reduced pressure to remove the solvent. The residue was purified by chromatography on a silica gel column (chloroform:methanol=20:1→10:1), whereby the title compound (257 mg) was obtained as a colorless transparent oil.

$^1$H-NMR (CDCl$_3$) δ: 2.52(3H,s), 2.72–2.78(2H,m), 2.78–2.83(2H,m), 3.61(2H,t,J=1.7 Hz), 4.00(3H,s). MS (FAB) m/z: 197 (M+H)$^+$.

Referential Example 428

1-(tert-Butoxycarbonyl)-4-[(6-methyl-4,5,6,7-tetrahydrooxazolo[5,4-c]pyridin-2-yl)carbonyl]piperazine To a solution of 2-methoxycarbonyl-6-methyl-4,5,6,7-tetrahydrooxazolo[5,4-c]pyridine (250 mg) in tetrahydrofuran (8.0 ml) were added water (2.0 ml) and lithium hydroxide (30.0 mg) at room temperature. After stirring for 10 minutes, the solvent was distilled off under reduced pressure. To a solution of the resulting residue in N,N-dimethylformamide (4.0 ml) were added 1-(tert-butoxycarbonyl)piperazine (260 mg), 1-hydroxybenzotriazole monohydrate (189 mg) and 1-(3-dimethylaminopropyl)-3-ethylcarbodiimide hydrochloride (268 mg) at room temperature. After stirring for 63 hours, methylene chloride (20 ml) and a saturated aqueous solution (30 ml) of sodium bicarbonate were added to the reaction mixture to separate it into layers. The water layer was extracted with methylene chloride (2×10 ml). The organic layers were combined and washed with water (150 ml). The resulting water layer was extracted with methylene chloride (3×10 ml). The organic layers were combined, dried over anhydrous sodium sulfate and distilled under reduced pressure to remove the solvent. The residue was purified by chromatography on a silica gel column (methylene chloride acetone=1:1→1:3), whereby the title compound (359 mg) was obtained as a colorless transparent viscous substance.

$^1$H-NMR (CDCl$_3$) δ: 1.48(9H,s), 2.51(3H,s), 2.71(2H,t, J=4.5 Hz), 2.79(2H,t,J=4.5 Hz), 3.51(4H,t,J=5.0 Hz), 3.60 (2H,s), 3.75(2H,t,J=5.0 Hz), 4.22(2H,t,J=5.0 Hz). MS (FAB) m/z: 351 (M+H)$^+$.

Referential Example 429

6-(tert-Butoxycarbonyl)-2-methylthio-5,6,7,8-tetrahydropyrido[4,3-d]pyrimidine

To a solution of 1-(tert-butoxycarbonyl)-4-piperidone (9.30 g) in tetrahydrofuran (40 ml) was added N,N-dimethylformamide dimethylacetal (18.6 ml) at room temperature, followed by heating under reflux for 3 days. After the reaction mixture was allowed to cool down to room temperature, it was concentrated under reduced pressure. To a solution of the resulting residue in ethanol (120 ml) were added methylisothiourea sulfate (19.5 g) and sodium ethoxide (13.2 g) at room temperature, followed by heating under reflux for 5 hours. After the reaction mixture was allowed to cool down, water (700 ml) and ethyl acetate (200 ml) were added to the reaction mixture to separate it into layers. The water layer was then extracted with ethyl acetate (200 ml). The organic layers were combined, washed with saturated saline (200 ml), dried over anhydrous sodium sulfate and concentrated under reduced pressure. The residue was purified by chromatography on a silica gel column (methylene chloride:acetone=20:1→15:1), whereby the title compound (1.82 g) was obtained as a colorless transparent viscous substance.

$^1$H-NMR (CDCl$_3$) δ: 1.49(9H,s), 2.56(3H,s), 2.89(2H,t, J=5.9 Hz), 3.72(2H,t,J=5.9 Hz), 4.52(2H,s), 8.27(1H,s). MS (FAB) m/z: 282 (M+H)$^+$.

Referential Example 430

6-(tert-Butoxycarbonyl)-2-methylsulfonyl-5,6,7,8-tetrahydropyrido[4,3-d]pyrimidine To a solution of 6-(tert-butoxycarbonyl)-2-methylthio-5,6,7,8-tetrahydropyrido[4,3-d]pyrimidine (2.20 g) in methylene chloride (80 ml) was added metachloroperbenzoic acid (3.37 g). After stirring for 4 hours, a 10% aqueous solution (100 ml) of sodium thiosulfate and a saturated aqueous solution (100 ml) of sodium bicarbonate were added to the reaction mixture and the mixture was separated into layers. The water layer was extracted with methylene chloride (2×50 ml). The organic layers were combined, dried over anhydrous sodium sulfate and distilled under reduced pressure to remove the solvent. The residue was purified by chromatography on a silica gel column (methylene chloride:acetone=20:1→10:1), whereby the title compound (2.34 g) was obtained as a colorless solid.

$^1$H-NMR (CDCl$_3$) δ: 1.50(9H,s), 3.10(2H,t,J=5.9 Hz), 3.34(3H,s), 3.80(2H,t,J=5.9 Hz), 4.71(2H,s), 8.63(1H,s). MS (FAB) m/z: 314 (M+H)$^+$.

Referential Example 431

6-(tert-Butoxycarbonyl)-2-cyano-5,6,7,8-tetrahydrocyano[4,3-d]pyrimidine

To a solution of 6-(tert-butoxycarbonyl)-2-methylsulfonyl-5,6,7,8-tetrahydropyrido[4,3-d]pyrimidine (330 mg) in methylene chloride (10 ml) was added tetrabutylammonium cyanide (425 mg) at room temperature. After stirring at room temperature for 3 hours, the solvent was distilled off under reduced pressure. The residue was purified by chromatography on a silica gel column (methylene chloride:acetone 20:1), whereby the title compound (261 mg) was obtained as pale yellow foam.

$^1$H-NMR (CDCl$_3$) δ: 1.50 (9H,s), 3.02(2H, t,J=5.9 Hz), 3.78(2H,t,J=5.9 Hz), 4.68(2H,s), 8.55(1H,s). MS (FAB) m/z: 261 (M+H)$^+$.

Referential Example 432

6-(tert-Butoxycarbonyl)-2-methoxycarbonyl-5,6,7,8-tetrahydropyrido[4,3-d]pyrimidine To a solution of 6-(tert-butoxycarbonyl)-2-cyano-5,6,7,8-tetrahydropyrido[4,3-d]pyrimidine (814 mg) in methanol (10 ml) was added concentrated sulfuric acid (5.0 ml) at room temperature. The resulting mixture was stirred at 100° C. for 1 hour. After the reaction mixture was allowed to cool down, it was concentrated under reduced pressure. The residue was dissolved in methylene chloride (15 ml), followed by the addition of triethylamine (2.20 ml) and di-tert-butyl dicarbonate (1.03 g) at room temperature. The resulting mixture was stirred at room temperature for 1 hour. The reaction mixture was then concentrated under reduced pressure. The residue was purified by chromatography on a silica gel column (methylene chloride:acetone=6:1→3:1), whereby the title compound (619 mg) was obtained as a pale yellow viscous substance.

$^1$H-NMR (CDCl$_3$) δ: 1.50(9H,s), 3.10(2H,t,J=5.8 Hz), 3.79(2H,t,J=5.8 Hz), 4.06(3H,s), 4.71(2H,s), 8.65(1H,s). MS (FAB) m/z: 294 (M+H)$^+$.

Referential Example 433

Lithium 6-methyl-4,5,6,7-tetrahydrofuro[2,3-c]pyridine-2-carboxylate

In the same manner as in Referential Example 371, the title compound was obtained.

$^1$H-NMR (DMSO-d$_6$) δ: 2.30–2.60(4H,m), 2.35(3H,s), 3.34(2H,s), 6.50(1H,s).

Referential Example 434

1-(tert-Butoxycarbonyl)-4-[(6-methyl-4,5,6,7-tetrahydrofuro[2,3-c]pyridin-2-yl)carbonyl]piperazine In the same manner as in Example B-62, the title compound was obtained.

$^1$H-NMR (CDCl$_3$) δ: 1.48(9H,s), 2.49(3H,s), 2.55–2.65 (2H,m), 2.65–2.75(2H,m), 3.45–3.55(6H,m), 3.76(4H,br s), 6.86(1H,s). MS (FAB) m/z: 350 (M+H)$^+$.

Referential Example 435

Methyl 2-tert-butoxycarbonylisoindoline-5-carboxylate

In the same manner as in Referential Example 363, the title compound was obtained.

$^1$H-NMR (CDCl$_3$) δ: 1.52(9H,s), 3.92(3H,s), 4.65–4.72 (2H,m), 4.73(2H,s), 7.29(0.5H,d,J=7.8 Hz), 7.34(0.5H,d,J= 7.8 Hz), 7.91(0.5H,s), 7.96(1H,s), 7.98(0.5H,s). MS (FAB) m/z: 278 (M+H)$^+$. Elementary analysis for C$_{15}$H$_{19}$NO$_4$ Calculated: C, 64.97; H, 6.91; N, 5.05. Found: C, 64.94; H, 7.13; N, 4.96.

In the same manner as in Referential Example 368, compounds shown in Referential Examples 436 and 437 were obtained.

Referential Example 436

2-tert-Butoxycarbonylisoindoline-5-carboxylic acid $^1$H-NMR (CDCl$_3$) δ: 1.53(9H,s), 4.70–4.72(2H,m), 4.75 (2H,s), 7.32(0.5H,d,J=7.3 Hz), 7.38(0.5H,d,J=7.3 Hz), 7.97 (0.5H,s), 8.02(1H,s), 8.04(0.5H,s). MS (FAB) m/z: 264 (M+H)$^+$. Elementary analysis for C$_{14}$H$_{17}$NO$_4$ Calculated: C, 63.87; H, 6.51; N, 5.32. Found: C, 63.79; H, 6.65; N, 5.12.

Referential Example 437

4-tert-Butoxycarbonyl-3-carboxymethyl-1-[(5-chloroindol-2-yl)sulfonyl]piperazine $^1$H-NMR (DMSO-d$_6$) δ: 1.33(9H,s), 2.12–2.25(1H,m), 2.30–2.42(2H,m), 2.35–3.57(1H,m), 2.60–2.71(1H,m), 2.90–3.02(1H,m), 3.54–3.65(1H,m), 3.72–3.86(2H,m), 4.43 (1H,br s), 6.99(1H,s), 7.30(1H,dd,J=8.8,1.8 Hz), 7.48(1H,d, J=8.8 Hz), 7.75(1H,d,J=1.8 Hz). MS (FAB) m/z: 480 (M+Na)$^+$.

Referential Example 438

4-tert-Butoxycarbonyl-1-[(5-chloroindol-2-yl)sulfonyl]-3-[N-(2-hydroxyethyl)carbamoylmethyl]piperazine In the same manner as in Referential Example 5, the title compound was obtained.

$^1$H-NMR (CDCl$_3$) δ: 1.40(9H,s), 2.30–2.90(3H,m), 3.03–4.15(7H,m), 4.62–4.71(1H,m), 6.56(1H,br s), 6.95 (1H,s), 7.28(1H,dd,J=8.8,1.7 Hz), 7.37(1H,d,J=8.8 Hz), 7.64(1H,d,J=1.7 Hz), 10.01–10.70(1H,br m). FAB-MS m/z: 502 [(M+H)$^+$, Cl$^{35}$], 504 [(M+H)$^+$, Cl$^{37}$].

Referential Example 439

4-[(5-Chloro-1-phenylsulfonyl-indol-2-yl)sulfonyl]-1-(tert-butoxycarbonyl)-2-(2-hydroxyethyl)piperazine In tetrahydrofuran - methanol (10/1, 55 mL) was dissolved 4-(tert-butoxycarbonyl)-1-[(5-chloro-1-phenylsulfonylindol-2-yl)sulfonyl]-3-[(methoxycarbonyl)methyl]piperazine (2.5 g), followed by the addition of lithium borohydride (135 mg). The resulting mixture was stirred for 48 hours. The solvent was distilled off under reduced pressure. Water and chloroform were then added to the reaction mixture and the mixture was separated into layers. The organic layer was dried over anhydrous magnesium sulfate and distilled under reduced pressure to remove the solvent. The residue was subjected to chromatography on a silica gel column (ethyl acetate:hexane=2:3), whereby the title compound (1.84 g) was obtained as a colorless oil.

$^1$H-NMR (CDCl$_3$) δ: 1.47(9H,s), 1.60(2H,m), 2.98–4.42 (9H,m), 7.42–7.59(6H,m), 8.01(1H,d,J=1.2 Hz), 8.03(1H,d, J=1.2 Hz), 8.21(1H,d,J=9.3 Hz). MS (FAB) m/z: 584 [(M+H)$^+$].

Referential Example 440

4-[(5-Chloro-1-phenylsulfonylindol-2-yl)sulfonyl]-1-(tert-butoxycarbonyl)-2-(formylmethyl)piperazine In the same manner as in Referential Example 285, the title compound was obtained.

¹H-NMR (CDCl₃) δ: 1.45(9H,s), 2.64(1H,dd,J=5.4,17.4 Hz), 2.95–3.15(5H,m), 3.72(1H,d,J=13.2 Hz), 3.94(1H,m), 4.73(1H,m), 7.40–7.58(6H,m), 8.00(1H,d,J=1.2 Hz), 8.02 (1H,d,J=1.2 Hz), 8.20(1H,d,J=9.0 Hz), 9.62(1H,s).

Referential Example 441

4-[(5-Chloro-1-phenylsulfonylindol-2-yl)sulfonyl]-1-(tert-butoxycarbonyl)-2-[2-(1,4-dioxa-8-azaspiro[4,5]-decan-8-yl)ethyl]piperazine In the same manner as in Referential Example 265, the title compound was obtained.

¹H-NMR (CDCl₃) δ: 1.45(9H,s), 1.68(4H,t,J=6.4 Hz), 1.83–3.20(12H,m), 3.61(1H,m), 3.94(4H,s), 4.0–4.25(2H, m), 7.39–7.58(6H,m), 8.01(1H,d,J=1.5 Hz), 8.04(1H,d,J=1.0 Hz), 8.22(1H,d,J=9.3 Hz). MS (FAB) m/z: 709 [(M+H)⁺].

Referential Example 442

4-[(5-Chloro-1-phenylsulfonylindol-2-yl)sulfonyl]-1-(tert-butoxycarbonyl)-2-[(1,3-dioxolan-2-yl)methyl]piperazine In toluene (10 mL) were dissolved 4-[(5-chloro-1-phenylsulfonylindol-2-yl)sulfonyl]-1-(tert-butoxycarbonyl)-2-(formylmethyl)piperazine (440 mg) and ethylene glycol (71 mg, followed by the addition of p-TsOH.H₂O (15 mg). The resulting mixture was heated to 60° C. and stirred for 16 hours. Ethyl acetate was added to the reaction mixture. The resulting mixture was washed with a saturated aqueous solution of sodium bicarbonate. The organic layer was dried over anhydrous MgSO₄ and distilled under reduced pressure to remove the solvent, whereby the title compound (460 mg) was obtained as colorless amorphous.

¹H-NMR (CDCl₃) δ: 1.45(9H,s), 1.63(2H,m), 1.98(2H, m), 2.49–3.95(3H,m), 3.66–4.13(8H,m), 4.78(1H,t,J=4.9 Hz), 7.17(1H,m), 7.42–7.58(5H,m), 8.02(1H,d,J=1.5 Hz), 8.04(1H,d,J=1.0 Hz), 8.23(1H,d,J=9.3 Hz). MS (FAB) m/z: 626 [(M+H)⁺].

Referential Example 443

1,4-Dibenzyl-2-[(1,3-dioxoisoindol-2-yl)methyl]piperazine

To a solution of 1,4-dibenzyl-2-(hydroxymethyl)piperazine (1.51 g), phthalimide (0.790 g) and triphenylphosphine (1.40 g) in tetrahydrofuran (20 ml) was added a 40% toluene solution (2.34 ml) of diethyl azodicarboxylate under ice cooling. The resulting mixture was stirred at room temperature for 6 hours. Furthermore, 1,4-dibenzyl-2-(hydroxymethyl)piperazine (0.87 g), phthalimide (0.486 g), triphenylphosphine (0.81 g) and tetrahydrofuran (5 ml) were added to the reaction mixture, followed by the addition of a 40% toluene solution (1.34 ml) of diethyl azodicarboxylate under ice cooling. The resulting mixture was stirred at room temperature for 18.5 hours. Phthalimide (0.405 g) and a 40% toluene solution (1.10 ml) of diethyl azodicarboxylate were added under ice cooling, followed by stirring at room temperature for 20 hours. The solvent was distilled off under reduced pressure. The residue was subjected to column chromatography twice (3% methanol—methylene chloride for the first time and ethyl acetate/hexane=1/3 for the second time) using as a carrier silica gel, whereby a crude product was obtained. The crude product was crystallized from hexane - methylene chloride, collected by filtration and washed with hexane, whereby the title compound (0.243 g) was obtained as colorless powder.

¹H-NMR (CDCl₃) δ: 2.30–2.40(4H,m), 2.50–2.60(1H, m), 2.95–3.10(2H,m), 3.40–3.55(2H,m), 3.60–3.65(1H,m), 3.75–3.80(1H,m), 3.95–4.05(1H,m), 4.15–4.25(1H,m), 7.10–7.35(10H,m), 7.70–7.75(2H,m), 7.80–7.85(2H,m). MS (FAB) m/z: 426 (M+H)⁺.

Referential Example 444

1-[(5-Chloro-1-phenylsulfonyl)piperazin-2-yl]-3-[(1,4-dioxoisoindol-2-yl)methyl]piperazine In the same manner as in Referential Example 266, the title compound was obtained.

¹H-NMR (CDCl₃) δ: 2.77–2.88(2H,m), 2.98–3.09(2H, m), 3.16–3.18(1H,m), 3.69–3.72(3H,m), 3.81(1H,broad d,J=12.6 Hz), 7.36(1H,s), 7.40–7.46(3H,m), 7.52–7.56(2H, m), 7.71–7.74(2H,m), 7.83–7.86(2H,m), 7.99(2H,dd,J=1.1, 7.4 Hz), 8.22(1H,d,J=9.2 Hz). MS (FAB) m/z: 599 [(M+H)⁺, Cl³⁵], 601 [(M+H)⁺, Cl³⁷].

Referential Example 445

1,4-Di(tert-butoxycarbonyl)-2-(2-phenoxyethyl)piperazine

To a solution of 1,4-di(tert-butoxycarbonyl)-2-(2-hydroxyethyl)piperazine (0.660 g, 2 mmol) and triphenylphosphine (0.577 g, 2.2 mmol) in tetrahydrofuran (10 ml) were added a solution of phenol (0.188 g, 2 mmol) in tetrahydrofuran (5 ml) and diethyl azodicarboxylate (0.35 ml, 2.2 mmol), followed by stirring at room temperature for 4 hours. The reaction mixture was purified by flash column chromatography (ethyl acetate/n-hexane=1/4) using as a carrier silica gel, whereby the title compound (0.611 g, 75%) was obtained as a colorless solid.

¹H-NMR (CDCl₃) δ: 1.38(9H,s), 1.46(9H,s), 1.91–1.96 (1H,m), 2.06–2.12(1H,m), 2.81–3.00(2H,broad), 3.94–3.98 (6H,m), 4.40(1H,broad), 6.86(2H,d,J=7.8 Hz), 6.92(1H,dd, J=7.2,7.2 Hz), 7.23–7.27(2H,m). MS (FAB) m/z: 407 (M+H)⁺.

Referential Example 446

1-[(5-Chloro-1-phenylsulfonylindol-2-yl)sulfonyl]-3-(2-phenoxyethyl)piperazine

In the same manner as in Referential Example 220, the title compound was obtained.

¹H-NMR (CDCl₃) δ: 1.81–1.86(2H,m), 2.70–2.76(1H, m), 2.93–3.07(4H,m), 3.76–3.85(2H,m), 4.05(2H,t,J=5.8 Hz), 6.84(2H,d,J=7.8 Hz), 6.92–6.96(1H,m), 7.36(1H,s), 7.40–7.45(4H,m), 7.50–7.56(3H,m), 8.00(2H,d,J=7.5 Hz), 8.22(1H,d,J=9.2 Hz). MS (FAB) m/z: 560 [(M+H)⁺, Cl³⁵], 562 [(M+H)⁺, Cl³⁷].

Referential Example 447

1,4-Di(tert-butoxycarbonyl)-2-[2-(2-naphthoxy)ethyl]piperazine

In the same manner as in Referential Example 445, the title compound was obtained.

¹H-NMR (CDCl₃) δ: 1.38(9H,s), 1.47(9H,s), 1.99–2.04 (1H,m), 2.16(1H,m), 2.82–3.02(2H,broad), 4.00–4.12(6H, broad m), 4.46(1H,broad), 7.09–7.12(2H,m), 7.29–7.33(1H, m), 7.39–7.43(1H,m), 7.67–7.75(3H,m). MS (FAB) m/z: 457 (M+H)⁺.

Referential Example 448

1-[(5-Chloro-1phenylsulfonylindol-2-yl)sulfonyl]-3-[2-(2-naphthoxy)ethyl]piperazine In the same manner as in Referential Example 220, the title compound was obtained.

$^1$H-NMR (CDCl$_3$) δ: 1.89–1.95(2H,m), 2.73–2.79(1H, m), 2.92–3.09(4H,m), 3.79(1H,broad d,J=10.9 Hz), 3.87 (1H,broad d,J=12.2 Hz), 4.18(2H,t,J=6.0 Hz), 7.06–7.10 (2H,m), 7.31–7.35(1H,m), 7.36(1H,s), 7.39–7.48(5H,m), 7.52–7.56(1H,m), 7.69–7.72(2H,m), 7.76(1H,d,J=8.3 Hz), 8.00(2H,d,J=7.8 Hz), 8.22(1H,d,J=9.2 Hz). MS (FAB) m/z: 610 [(M+H)$^+$, Cl$^{35}$], 612 [(M+H)$^+$, Cl$^{37}$].

Referential Example 449

1-[(5-Chloro-1-phenylsulfonylindol-2-yl)sulfonyl]-3-[2-(tert-butyldiphenylsilyloxy)ethyl]piperazine In the same manner as in Referential Example 266, the title compound was obtained.

$^1$H-NMR (CDCl$_3$) δ: 1.01(9H,s), 1.55–1.61(2H,m), 2.63–2.68(1H,m), 2.88–3.01(4H,m), 3.73–3.80(4H,m), 7.33–7.45(10H,m), 7.49–7.56(2H,m), 7.61–7.64(4H,m), 8.01(2H,dd,J=1.1,8.4 Hz), 8.22(1H,d,J=9.3 Hz). MS (FAB) m/z: 722 (M+H)$^+$.

Referential Example 450

1-(tert-Butoxycarbonyl)-2-[2-(tert-butyldiphenylsilyloxy)ethyl]-4-[(1-phenylsulfonyl-5-chloroindol-2-yl)sulfonyl]piperazine In the same manner as in Example 363, the title compound was obtained.

$^1$H-NMR (CDCl$_3$) δ: 1.00(9H,s), 1.38(9H,s), 1.84–1.92 (2H,m), 2.86–2.93(1H,m), 3.02–3.14(2H,m), 3.32(1H, broad), 3.58–3.62(2H,m), 3.92(2H,broad d,J=12.4 Hz), 4.42 (1H,broad), 7.29(1H,s), 7.32–7.43(10H,m), 7.51–7.58(5H, m), 7.99–8.01(2H,m), 8.17(1H,d,J=9.0 Hz). MS (FAB) m/z: 822 (M+H)$^+$.

Referential Example 451

1-(tert-Butoxycarbonyl)-4-[(5-chloroindol-2-yl)sulfonyl]-2-(2-hydroxyethyl)piperazine To a solution of 4-[(1-benzenesulfonyl-5-chloroindol-2-yl)sulfonyl]-1-(tert-butoxycarbonyl)-2-[2-(tert-butyldiphenylsilyloxy)ethyl]piperazine (4.48 g) in tetrahydrofuran (20 ml) was added a 1.0M tetrahydrofuran solution (5.5 ml) of tetrabutylammonium fluoride, followed by stirring at room temperature for 3.5 hours. After concentration under reduced pressure, the residue was purified by flash column chromatography (ethyl acetate:hexane=1:9 to 1:0) using as a carrier silica gel, whereby the title compound (0.75 g) was obtained as a colorless solid.

$^1$H-NMR (DMSO-d$_6$) δ: 1.33(9H,s), 1.74–1.77(2H,m), 2.24–2.40(2H,m), 3.04(1H,m), 3.35–3.46(2H,m), 3.56–3.63 (2H,m), 3.85–3.88(1H,broad d,J=13.2 Hz), 4.25(1H,broad), 4.43(1H,broad), 6.98(1H,d,J=0.7 Hz), 7.29(1H,dd,J=1.9,8.8 Hz), 7.46–7.48(1H,m), 7.74(1H,m). MS (FAB) m/z: 444 (M+H)$^+$.

Referential Example 452

1,4-Bis(tert-butoxycarbonyl)-2-(2-tosyloxyethyl)piperazine

A solution of 1,4-di(tert-butoxycarbonyl)-2-(2-hydroxyethyl)piperazine (5.05 g) and p-toluenesulfonyl chloride (4.34 g) in methylene chloride (200 ml) was cooled to 0° C., followed by the dropwise addition of triethylamine (11 ml). The resulting mixture was stirred at 0° C. for 1 hour and at room temperature for 1 day. The reaction mixture was concentrated under reduced pressure. After dilution with ethyl acetate, the residue was washed with 1N hydrochloric acid, water and saturated aqueous NaCl solution, dried over anhydrous magnesium sulfate and concentrated under reduced pressure. The residue was purified by flash column chromatography (ethyl acetate/hexane=1/4 to 1/1) using, as a carrier, silica gel, whereby the title compound (4.82 g) was obtained as a colorless solid.

$^1$H-NMR (CDCl$_3$) δ: 1.44(18H,s), 1.78–1.84(1H,m), 1.94 (1H,broad), 2.44(3H,s), 2.86(3H,broad), 3.85(2H,broad), 3.97–4.07(3H,m), 4.21(1H,broad), 7.33(2H,d,J=8.3 Hz), 7.77(2H,d,J=8.3 Hz). MS (FAB) m/z: 485 (M+H)$^+$.

Referential Example 453

1,4-Bis(tert-butoxycarbonyl)-2-[2-(2-oxo-1,3-oxazolan-3-yl)ethyl]piperazine

To a suspension of sodium hydride (60%, 57 mg) in N,N-dimethylformamide (20 ml), 2-oxazolidone (0.122 g) was added, followed by stirring at 90° C. for 1 hour. A solution of 1,4-di(tert-butoxycarbonyl)-2-(2-tosyloxyethyl) piperazine (0.686 g) in N,N-dimethylformamide (15 ml) was added to the reaction mixture. The resulting mixture was stirred at 90° C. for 4 hours. The reaction mixture was concentrated under reduced pressure. The residue was diluted with ethyl acetate, washed with water and saturated aqueous NaCl solution, dried over magnesium sulfate and concentrated under reduced pressure, whereby the title compound (0.515 g) was obtained as a colorless solid.

$^1$H-NMR (CDCl$_3$) δ: 1.46(8H,s), 1.47(10H,s), 1.78–1.85 (2H,m), 2.81–2.95(3H,m), 3.39–3.64(2H,m), 3.85–4.05(2H, broad), 4.00(2H,broad d, J=13.4 Hz), 4.09–4.28(2H,m), 4.30–4.34(2H,m). MS (FAB) m/z: 400 (M+H)$^+$.

Referential Example 454

1-[(5-Chloro-1-phenylsulfonylindol-2-yl)sulfonyl]-3-[2-(2-oxo-1,3-oxazolan-3-yl)ethyl]piperazine In the same manner as in Referential Example 220, the title compound was obtained.

$^1$H-NMR (CDCl$_3$) δ: 1.51–1.76(2H,m), 2.69–2.74(1H, m), 2.77–2.85(2H,m), 2.96–3.03(2H,m), 3.20–3.27(1H,m), 3.48–3.55(2H,m), 3.59–3.69(2H,m), 3.83(1H,broad d,J= 11.7 Hz), 4.30–4.40(2H,m), 7.39–7.46(4H,m), 7.51–7.57 (2H,m), 7.99–8.02(2H,m), 8.22(1H,d,J=9.0 Hz). MS (FAB) m/z: 553 [(M+H)$^+$, Cl$^{35}$], 555 [(M+H)$^+$, Cl$^{37}$].

Referential Example 455

4,5-Bis(bromomethyl)thiazole

At room temperature, 4,5-dimethylthiazole (5.00 g), N-bromosuccinimide (15.7 g) and α,α'-azobisisobutyronitrile (362 mg) were dissolved in ethylene dichloride (500 ml), followed by heating under reflux for 1 hour. After completion of the reaction, the solvent was distilled off and the residue was purified by chromatography on a silica gel column (hexane : diethyl ether=1:4), whereby the title compound (5.24 g, 44%) was obtained.

$^1$H-NMR (CDCl$_3$) δ: 4.64(2H,s), 4.74(2H,s), 8.75(1H,s)

Referential Example 456

5,6-Dimethyl-4,5,6,7-tetrahydrothiazolo[4,5-d]pyridazine

Under ice cooling, 4,5-bis(bromomethyl)thiazole (600 mg) and 1,2-dimethylhydrazine dihydrochloride (294 mg)

were suspended in ethanol (20 ml). Triethylamine (1.23 ml) was added in one portion to the reaction mixture, followed by stirring at room temperature for 30 minutes and then, at 50° C. for 30 minutes. The solvent was distilled off and the residue was purified by chromatography on a silica gel column (5% methanol—methylene chloride), whereby the title compound (90 mg, 24%) was obtained.

$^1$H-NMR (CDCl$_3$) δ: 2.43(3H,s), 2.56(3H,s), 3.92(2H,s), 4.06(2H,br s), 8.68(1H,s). MS (FAB) m/z: 170 (M+H)$^+$.

Referential Example 457

3-(Methoxycarbonylmethyl)-1-[[1-phenylsulfonyl-5-(trimethylsilylethynyl)indol-2-yl]sulfonyl]piperazine In the same manner as in Referential Example 226, the title compound was obtained.

$^1$H-NMR (CDCl$_3$) δ: 0.25(9H,s), 2.38(1H,dd,J=16.2,8.8 Hz), 2.46(1H,dd,J=16.2,4.2 Hz), 2.76(1H,dd,J=12.5,10.0 Hz), 2.91–2.99(1H,m), 2.99–3.07(2H,m), 3.17–3.25(1H,m), 3.67(3H,s), 3.69–3.78(2H,m), 7.38–7.44(3H,m), 7.54(1H,t, J=7.6 Hz), 7.58(1H,dd,J=8.9,1.6 Hz), 7.68(1H,d,J=1.6 Hz), 7.98–8.02(2H,m), 8.22(1H,d,J=8.9 Hz). MS (FAB) m/z: 574 (M+H)$^+$.

Referential Example 458

1,4-Bis(t-butoxycarbonyl)-2-[2-[(morpholin-4-yl)sulfonyl]ethyl]piperazine

In the same manner as in Referential Example 293, the title compound was obtained.

$^1$H-NMR (CDCl$_3$) δ: 1.47(18H,s), 1.95–2.00(1H,m), 2.10–2.20(1H,m), 2.70–3.10(5H,m), 3.25(4H,t,J=4.7 Hz), 3.75(4H,t,J=4.7 Hz), 3.80–4.30(4H,m). MS (FAB) m/z: 464 (M+H)$^+$.

Referential Example 459

1-[(5-Chloro-1-phenylsulfonylindol-2-yl)sulfonyl]-3-[2-[(morpholin-4-yl)sulfonyl]ethyl]piperazine In the same manner as in Referential Example 220, the title compound was obtained.

$^1$H-NMR (CDCl$_3$) δ: 1.80–1.90(1H,m), 1.90–2.00(1H, m), 2.60–2.70(1H,m), 2.80–3.10(6H,m), 3.20–3.30(4H,m), 3.60–3.85(6H,m), 7.40–7.50(4H,m), 7.50–7.60(2H,m), 8.00–8.10(2H,m), 8.22(1H,d,J=9.1 Hz). MS (FAB) m/z: 617 [(M+H)$^+$, Cl$^{35}$], 619 [(M+H)$^+$, Cl$^{37}$].

Referential Example 460

1,4-Bis(tert-butoxycarbonyl)-2-hydroxymethylpiperazine

In the same manner as in Referential Example 284, the title compound was obtained.

$^1$H-NMR (CDCl$_3$) δ: 1.46–1.47(18H,m), 2.70–4.400 (10H).

Referential Example 461

1,4-Bis(tert-butoxycarbonyl)-2-formylpiperazine

In the same manner as in Referential Example 285, the title compound was obtained.

$^1$H-NMR (CDCl$_3$) δ: 1.45–1.50(18H,m), 2.80–3.00(1H, m), 3.00–3.20(2H,m), 3.70–4.00(2H,m), 4.40–4.70(2H,m), 9.59(1H,s). MS (FAB) m/z: 315 (M+H)$^+$.

Referential Example 462

1,4-Bis(tert-butoxycarbonyl)-2-(2-ethoxycarbonylethenyl)piperazine

In a 50-ml two-necked flask, sodium hydride (141 mg, 60% in oil) was charged, followed by purging with argon. Tetrahydrofuran (5 ml) was added and then, triethyl phosphonoacetate (700 μl) was added under ice cooling. The resulting mixture was stirred at room temperature for 15 minutes. The reaction mixture was cooled again and under ice cooling, a solution of 1,4-bis(tert-butoxycarbonyl)-2-formylpiperazine (911 mg) dissolved in tetrahydrofuran (7 ml) was added dropwise, followed by stirring at room temperature for 4 hours. After completion of the reaction, water was added and then ethyl acetate was added, whereby the mixture was separated into layers. The organic layer thus obtained was washed with saturated aqueous NaCl solution, dried over anhydrous sodium sulfate and distilled under reduced pressure to remove the solvent. The residue was subjected to flash column chromatography (hexane:ethyl acetate=2:1) using, as a carrier, silica gel, whereby the title compound (920 mg, 83%) was obtained as a pale yellow oil.

$^1$H-NMR (CDCl$_3$) δ: 1.20–1.30(3H,m), 1.40–1.50(18H, m), 2.75–3.20(3H,m), 3.80–4.80(6H,m), 5.93(1H,dd,J= 15.9,2.0 Hz), 6.82(1H,dd,J=15.9,4.4 Hz). MS (FAB) m/z: 385 (M+H)$^+$.

Referential Example 463

1,4-Bis(tert-butoxycarbonyl)-2-(2-ethoxycarbonylethyl)piperazine

In the same manner as in Referential Example 287, the title compound was obtained.

$^1$H-NMR (CDCl$_3$) δ: 1.25(3H,t,J=7.1 Hz), 1.46(9H,s), 1.46(9H,s), 1.70–1.85(1H,m), 1.85–2.00(1H,m), 2.20–2.40 (2H,m), 2.70–3.00(3H,m), 3.80–4.20(6H,m). MS (FAB) m/z: 387 (M+H)$^+$.

Referential Example 464

1-[(5-Chloro-1-phenylsulfonylindol-2-yl)sulfonyl]-3-(2-ethoxycarbonylethyl)piperazine In the same manner as in Referential Example 220, the title compound was obtained.

$^1$H-NMR (CDCl$_3$) δ: 1.25(3H,t,J=7.2 Hz), 1.30–1.80(3H, m), 2.30–2.45(2H,m), 2.55–2.65(1H,m), 2.75–3.05(4H,m), 3.70–3.80(2H,m), 4.11(2H,q,J=7.2 Hz), 7.35–7.50(4H,m), 7.50–7.60(2H,m), 8.02(2H,d,J=7.3 Hz), 8.22(1H,d,J=9.3 Hz). MS (FAB) m/z: 540 [(M+H)$^+$, Cl$^{35}$], 542 [(M+H)$^+$, Cl$^{37}$].

Referential Example 465

1,4-Bis(tert-butoxycarbonyl)-2-(2-cyanoethyl)piperazine

To an aqueous solution (3.0 ml) of potassium cyanide (85.0 mg) was added a solution of 1,4-bis(t-butoxycarbonyl)-2-(2-bromoethyl)piperazine (393 mg) in ethanol (3.0 ml), followed by stirring under heat at 110° C. for 3 hours. After the removal of ethanol by distillation under reduced pressure, methylene chloride (100 ml) was added to the residue. The organic layer was washed with distilled water until the water phase became neutral. The resulting organic layer was washed with saturated aqueous NaCl solution, dried over anhydrous sodium sulfate and concentrated under reduced pressure. The residue was subjected to chromatography on a silica gel column (silica gel 15 g, hexane:ethyl acetate=2:1), whereby the title compound (145.0 mg, 43%) was obtained as a white solid.

$^1$H-NMR (CDCl$_3$) δ: 1.47(12H,s), 1.49(6H,s), 1.75–1.88 (1H,m), 1.92–2.10(1H,m), 2.28–2.35(2H,m), 2.70–3.10(3H, m), 3.80–4.15(3H,m), 4.20–4.30(1H,m). MS (FAB) m/z: 340 (M+H)$^+$.

Referential Example 466

4-[(1-Phenylsulfonyl-5-chloroindol-2-yl)sulfonyl]-2-(2-cyanoethyl)piperazine

In the same manner as in Referential Example 220, the title compound was obtained.

$^1$H-NMR (DMSO-d$_6$) δ: 1.65–1.77(1H,m), 1.78–1.90 (1H,m), 2.48(2H,t,J=7.6 Hz), 2.70(1H,dd,J=12.5,9.5 Hz), 2.85–3.10(4H,m), 3.62–3.70(1H,m), 3.75–3.85(1H,m), 7.40–7.50(4H,m), 7.55–7.60(2H,m), 8.01(2H,dd,J=8.6,1.2 Hz), 8.22(1H,d,J=9.0 Hz). MS (FAB) m/z: 493 [(M+H)$^+$, Cl$^{35}$], 495 [(M+H)$^+$, Cl$^{37}$].

Referential Example 467

2-Amino-6,6-ethylenedioxy-4,5,6,7-tetrahydrobenzo[d]thiazole

In a 200-ml egg-plant type flask, 1,4-cyclohexanedione ethylene ketal (7.80 g) was charged and dissolved in cyclohexane (20 mL). To the resulting solution were added pyrrolidine (4.35 mL) and p-toluenesulfonic acid monohydrate (48.0 g), followed by heating under reflux while water was trapped by a Dean and Stark apparatus. After 70 minutes, the reaction mixture was cooled to room temperature and the solvent was decanted and concentrated under reduced pressure. The residue was dissolved in methanol (15 ml). While attention was paid so as not to occur a temperature rise due to water bath, sulfur powder (1.60 g) was added to the resulting solution. After 15 minutes, a solution of cyanamide (2.10 g) in methanol (10 mL) was added dropwise over 20 minutes. After 14 hours, the solvent was distilled off under reduced pressure. The residue was subjected to chromatography on a silica gel column (silica gel: 300 g, methylene chloride:methanol=100:5→10:1), whereby the title compound (8.89 g) was obtained as a dark green solid.

$^1$H-NMR (CDCl$_3$) δ: 1.96(2H,t,J=6.4 Hz), 2.74(2H,t,J=6.4 Hz), 2.81(2H,s), 4.02(4H,s), 4.77(2H,br s). MS (FAB) m/z: 213 (M+H)$^+$.

Referential Example 468

2-Chloro-6,6-ethylenedioxy-4,5,6,7-tetrahydrobenzo[d]thiazole

Copper (II) chloride (760 mg) was charged in a 100-mL egg-plant type flask and dissolved in acetonitrile (10 mL). While cooling over water bath, tert-butyl nitrite (730 mg) was added in one portion to the resulting solution. After 10 minutes, 2-amino-6,6-ethylenedioxy-4,5,6,7-tetrahydrobenzo[d]thiazole (1.00 g) was added over about 50 minutes, followed by stirring at room temperature for 1 hour. The reaction mixture was then heated to 65° C. and stirring was continued for 2 hours. After silica gel (5 g) was added to the reaction mixture, the solvent was distilled off under reduced pressure. The residue was purified by chromatography on a silica gel column (silica gel: 50 g, hexane:ethyl acetate=3:1), whereby the title compound (860 mg) was obtained as a yellow oil.

$^1$H-NMR (CDCl$_3$) δ: 2.00(2H,t,J=6.4 Hz), 2.91(4H,m), 4.03(4H,s). MS (FAB) m/z: 232 [(M+H)$^+$, Cl$^{35}$], 234 [(M+H)$^+$, Cl$^{37}$].

Referential Example 469

6,6-Ethylenedioxy-4,5,6,7-tetrahydrobenzo[d]thiazole

In a 100-mL egg-plant type flask, 2-chloro-6,6-ethylenedioxy-4,5,6,7-tetrahydrobenzo[d]thiazole (860 mg) was charged and was dissolved in methanol (10 mL). To the resulting solution were added 10% palladium-carbon (100 mg) and sodium acetate (305 mg), followed by stirring under a hydrogen gas stream of 4.5 atmospheric pressure. After 17 hours, palladium was filtered off and the solvent was distilled off under reduced pressure. The residue was subjected to chromatography on a silica gel column (silica gel: 50 g, ethyl acetate:hexane=1:1), whereby the title compound (720 mg) was obtained as a pale yellow oil.

$^1$H-NMR (CDCl$_3$) δ: 2.04(2H,t,J=6.8 Hz), 3.03(4H,m), 4.05(4H,s), 8.62(1H,s). MS (FAB) m/z: 198 (M+H)$^+$.

Referential Example 470

Lithium (6,6-ethylenedioxy-4,5,6,7-tetrahydrobenzo[d]thiazol-2-yl)carboxylate

In the same manner as in Referential Example 371, the title compound was obtained.

$^1$H-NMR (DMSO-d$_6$) δ: 1.94(2H,t,J=6.6 Hz), 3.34–3.44 (4H,m), 3.95(4H,s).

Referential Example 471

2-Amino-4,5-dihydro-7H-pyrano[4,3-d]thiazole

In the same manner as in Referential Example 467, the title compound was obtained.

$^1$H-NMR (CDCl$_3$) δ: 2.66–2.70(2H,m), 3.97(2H,t,J=5.6 Hz), 4.63(2H,s), 4.94(2H,br s). MS (FAB) m/z: 157 (M+H)$^+$.

Referential Example 472

2-Chloro-4,5-dihydro-7H-pyrano[4,3-d]thiazole

In the same manner as in Referential Example 468, the title compound was obtained.

$^1$H-NMR (CDCl$_3$) δ: 2.85–2.89(2H,m), 4.02(2H,t,J=5.6 Hz), 4.73(2H,s). MS (FAB) m/z: 175 [(M+H)$^+$, Cl$^{35}$], 177 [(M+H)$^+$, Cl$^{37}$].

Referential Example 473

4,5-Dihydro-7H-pyrano[4,3-d]thiazole

In the same manner as in Referential Example 469, the title compound was obtained.

$^1$H-NMR (CDCl$_3$) δ: 2.97–3.01(2H,m), 4.04(2H,t,J=5.6 Hz), 4.87(2H,s), 8.69(1H,s). MS (FAB) m/z: 142 (M+H)$^+$.

Referential Example 474

Lithium (4,5-dihydro-7H-pyrano[4,3-d]thiazol-2-yl)carboxylate

In a 200-mL three-necked flask, 4,5-dihydro-7H-pyrano[4,3-d]thiazole (1.14 g) was added and dissolved in ether (30 mL). After cooling to −78° C., 1.6M butyl lithium (6.6 mL) was added and the resulting mixture was stirred. After 20 minutes, a carbon dioxide gas was introduced. After about 15 minutes, the introduction was terminated. The reaction mixture was allowed to rise back to room temperature and concentrated under reduced pressure, whereby the title compound (1.65 g) was obtained as a colorless amorphous substance.

$^1$H-NMR (DMSO-$d_6$) δ: 2.83(2H,t,J=5.6 Hz), 3.92(2H,t, J=5.6 Hz), 4.73(2H,s).

Referential Example 475

4-[(5-Chloroindol-2-yl)sulfonyl]-2-[[N-(phenylsulfonyl)carbamoyl]methyl]piperazine trifluoroacetate In tetrahydrofuran (10 ml) was dissolved 1-tert-butoxycarbonyl-2-carboxymethyl-4-[(5-chloroindol-2-yl) sulfonyl]piperazine (1.00 g), followed by the addition of carbonyldiimidazole (1.06 g). The resulting mixture was heated overnight under reflux. After cooling to room temperature, the reaction mixture was added with benzenesulfonamide (685 mg), 1,8-diazabicyclo[5.4.0]-7-undecene (0.64 ml) and carbonyldiimidazole (353 mg). The resulting mixture was heated under reflux for 1 hour. The reaction mixture was then concentrated under reduced pressure. Dichloromethane was added to the residue and the solid thus precipitated was filtered off. The filtrate was washed successively with 1N hydrochloric acid and saturated aqueous NaCl solution. The organic layer was dried over anhydrous sodium sulfate and distilled under reduced pressure to remove the solvent. The residue was purified by chromatography on a silica gel column (Φ3.0×10.0 cm, dichloromethane:methanol=100:1), whereby pale brown foam was obtained. The resulting foam was dissolved in dichloromethane (10 ml), followed by the addition of trifluoroacetic acid (10 ml). After stirring at room temperature for 1 minute, the reaction mixture was concentrated under reduced pressure. Diethyl ether was added to the residue and the resulting precipitate was collected by filtration, whereby the title compound (496 mg, 31%) was obtained as colorless foam.

$^1$H-NMR (DMSO-$d_6$) δ: 2.60–2.75(3H,m), 3.10–3.20 (1H,m), 3.29–3.38(1H,m), 3.53–3.73(4H,m), 7.06(1H,d,J= 2.0 Hz), 7.34(1H,dd,J=8.8,2.0 Hz), 7.50(1H,d,J=8.8 Hz), 7.64(2H,t,J=7.1 Hz), 7.74(1H,t,J=7.1 Hz), 7.80(1H,d,J=2.0 Hz), 7.93(2H,d,J=7.1 Hz), 12.53(1H,s). MS (FAB) m/z: 497 [(M+H)$^+$, Cl$^{35}$], 499 [(M+H)$^+$, Cl$^{37}$].

Referential Example 476

1-tert-Butoxycarbonyl-4-[(5-chloroindol-2-yl) sulfonyl]-2-[(N-methylsulfonylcarbamoyl)methyl] piperazine In tetrahydrofuran (10 ml) was dissolved 1-tert-butoxycarbonyl-2-carboxymethyl-4-[(5-chloroindol-2-yl) sulfonyl]piperazine (1.00 g), followed by the addition of carbonyldiimidazole (1.06 g). The resulting mixture was heated overnight under reflux. After cooling to room temperature, methanesulfonamide (415 mg) and 1,8-diazabicyclo[5.4.0]-7-undecene (0.64 ml) were added, followed by stirring at room temperature for 1 hour. The reaction mixture was concentrated under reduced pressure. Dichloromethane was added to the residue and the resulting mixture was washed successively with 1N hydrochloric acid, and saturated aqueous NaCl solution. The organic layer was dried over anhydrous sodium sulfate and distilled under reduced pressure to remove the solvent. The residue was purified by chromatography on a silica gel column (Φ3.0× 10.0 cm, dichloromethane:methanol=100:1), whereby the title compound (518 mg, 44%) was obtained as colorless foam.

$^1$H-NMR (DMSO-$d_6$) δ: 1.33(9H,s), 2.23–2.60(3H,m), 2.62–2.78(1H,m), 3.05(1H,br s), 3.21(3H,s), 3.52–3.70(2H, m), 3.84–3.97(1H,m), 4.56(1H,br s), 7.02(1H,s), 7.32(1H, d,J=8.8 Hz), 7.49(1H,J=8.8 Hz), 7.77(1H,s), 11.84(1H,s), 12.43(1H,s). MS (FAB) m/z: 557 [(M+Na)$^+$, Cl$^{35}$], 559 [(M+Na)$^+$, Cl$^{37}$].

Referential Example 477

1-[(5-Chloroindol-2-yl)sulfonyl]-3-[(N-methyl-N-methylsulfonylcarbamoyl)methyl]piperazine trifluoroacetate In N,N-dimethylformamide (10 ml) was dissolved 1-tert-butoxycarbonyl-4-[(5-chloroindol-2-yl)sulfonyl]-2-[(N-methylsulfonylcarbamoyl)methyl]piperazine (347 mg), followed by the addition of sodium bicarbonate (55 mg) and methyl iodide (0.05 ml). The resulting mixture was stirred overnight at room temperature. The reaction mixture was then concentrated under reduced pressure. Dichloromethane was added to the residue and the resulting mixture was washed successively with water and saturated aqueous NaCl solution, each once. The organic layer was dried over anhydrous sodium sulfate and distilled under reduced pressure to remove the solvent. The residue was purified by chromatography on a silica gel column (Φ1.7×12.0 cm, dichloromethane:methanol=200:1), whereby the title compound was obtained as colorless foam. The resulting foam was dissolved in dichloromethane (1 ml), followed by the addition of trifluoroacetic acid (2 ml). After the resulting mixture was stirred at room temperature for 1 minute, the reaction mixture was concentrated under reduced pressure. Diethyl ether was added to the residue and the precipitate so formed was collected by filtration, whereby the title compound (189 mg, 43%) was obtained as colorless foam.

$^1$H-NMR (DMSO-$d_6$) δ: 2.60–2.80(2H,m), 3.02–3.11(2H, m), 3.16(3H,s), 3.20–3.30(1H,m), 3.39(3H,s), 3.61–3.80 (4H,m), 7.08(1H,d,J=1.5 Hz), 7.34(1H,dd,J=8.8,2.0 Hz), 7.50(1H,J=8.8 Hz), 7.80(1H,d,J=2.2 Hz), 12.54(1H,br s). MS (FAB) m/z: 449 [(M+H)$^+$, Cl$^{35}$], 451 [(M+H)$^+$, Cl$^{37}$].

Referential Example 478

N-methanesulfonylhydrazine hydrochloride

In pyridine (30 ml) was dissolved t-butyl carbazate (2.64 g), followed by the addition of methanesulfonyl chloride (1.62 ml) under ice cooling. The resulting mixture was stirred at room temperature for 5 hours. The reaction mixture was concentrated under reduced pressure. Ethyl acetate was added to the residue and the resulting mixture was washed successively with 1N hydrochloric acid and a saturated aqueous solution of sodium bicarbonate. The organic layer was dried over anhydrous sodium sulfate and distilled under reduced pressure to remove the solvent. The residue was solidified by the addition of hexane and ethyl acetate, whereby a pale yellow solid was obtained. The solid was dissolved in dichloromethane (20 ml), followed by the addition of saturated solution of hydrochloride in ethanol (20 ml). The resulting mixture was then concentrated under reduced pressure. The residue was solidified by the addition of ethyl acetate, whereby N-methanesulfonylhyrazine (1.67 g, 57%) was obtained as a pale yellow solid.

$^1$H-NMR (DMSO-d$_6$) δ: 3.25(3H,s), 9.80(br s,9.80). MS (FAB) m/z: 111 (M+H)$^+$.

Referential Example 479

4-[(5-Chloroindol-2-yl)sulfonyl]-2-[(2-methylsulfonylhydrazino)carbonylmethyl]-1-[(6-methyl-4,5,6,7-tetrahydrothiazolo[5,4-c]pyridin-2-yl)carbonyl]piperazine trifluoroacetate In dichloromethane (20 ml) were dissolved 1-tert-butoxycarbonyl-2-carboxymethyl-4-[(5-chloroindol-2-yl)sulfonyl]piperazine (600 mg), N-methanesulfonylhydrazine (192 mg), 1-hydroxybenzotriazole monohydrate (200 mg) and 1-(dimethylaminopropyl)-3-ethylcarbodiimide hydrochloride (301 mg), followed by the addition of triethylamine (0.21 ml). The resulting mixture was stirred overnight at room temperature. The reaction mixture was then concentrated under reduced pressure. Ethyl acetate was added to the residue and the resulting mixture was washed with water and saturated aqueous NaCl solution, each once. The organic layer was dried over anhydrous sodium sulfate and distilled under reduced pressure to remove the solvent. The residue was purified by chromatography on a silica gel column (Φ3.0×8.0 cm, dichloromethane:methanol=50:1), whereby colorless foam was obtained. The resulting foam was dissolved in dichloromethane (2 ml), followed by the addition of trifluoroacetic acid (10 ml). After the resulting mixture was stirred at room temperature for 1 minute, the reaction mixture was concentrated under reduced pressure. Diethyl ether was added to the residue and the precipitate so formed was collected by filtration, whereby the title compound (278 mg, 38%) was obtained as colorless foam.

$^1$H-NMR (DMSO-d$_6$) δ: 2.51–2.82(3H,m), 2.96(3H,s), 3.11–3.21(1H,m), 3.31–3.42(1H,m), 3.60–3.85(4H,m), 7.07 (1H,s), 7.34(1H,dd,J=8.8,2.0 Hz), 7.50(1H,J=8.8 Hz), 7.80 (1H,s), 9.52(1H,d,J=2.7 Hz), 10.39(1H,d,J=2.7 Hz), 12.51–12.57(1H,m). MS (FAB) m/z: 450 [(M+H)$^+$, Cl$^{35}$], 452 [(M+H)$^+$, Cl$^{37}$].

Referential Example 480

1-(tert-Butoxycarbonyl)-4-[(5-chloroindol-2-yl)sulfonyl]-2-[(pyrrolidin-1-ylcarbonyl)methyl]piperazine The title compound was obtained by employing the method of Referential Example 319 in which 1-(3dimethylaminopropyl-3-ethylcarbodiimide hydrochloride had been used as a condensing agent.

$^1$H-NMR (CDCl$_3$) δ: 1.41(9H,s), 1.85–1.97(2H,m), 1.98–2.18(2H,m), 2.22–2.35(1H,m), 2.50–3.00(3H,m), 2.97 (1H,dt,J=3.4,13.0 Hz), 3.40–3.60(4H,m), 3.64–3.75(1H,m), 3.80–4.20(2H,m), 4.63(1H,br d,J=10.0 Hz), 6.96(1H,d,J= 1.7 Hz), 7.27(1H,dd,J=9.1,1.7 Hz), 7.37(1H,d,J=9.1 Hz), 7.65(1H,d,J=1.7 Hz). MS (FAB) m/z: 511 [(M+H)$^+$, Cl$^{35}$], 513 [(M+H)$^+$, Cl$^{37}$].

Referential Example 481

2-[(N-Benzylcarbamoyl)methyl]-1-(tert-butoxycarbonyl)-4-[(5-chloroindol-2-yl)sulfonyl]piperazine The title compound was obtained by employing the method of Referential Example 319 in which 1-(3-dimethylaminopropyl-3-ethylcarbodiimide hydrochloride had been used as a condensing agent.

$^1$H-NMR (CDCl$_3$) δ: 1.40(9H,s), 2.35–2.48(1H,m), 2.50–2.85(3H,m), 2.95–3.07(1H,m), 3.62–3.78(1H,m), 3.80–4.15(2H,m), 4.40–4.50(2H,m), 4.60–4.70(1H,m), 6.93 (1H,s), 7.20–7.40(7H,m), 7.64(1H,s). MS (FAB) m/z: 547 [(M+H)$^+$, Cl$^{35}$], 549 [(M+H)$^+$, Cl$^{37}$].

Referential Example 482

5(6)-chloro-2-mercaptobenzimidazole

Carbon disulfide (6.60 ml) and sodium hydroxide (6.330 g) were added to the mixture of 4-chloro-1,2-phenylenediamine (14.37 g), ethanol (100 ml) and water (15 ml), and reacted under reflux for 3 hours. The reaction mixture was added by active carbon (4.0 g), refluxed for 10 minutes, and filtrated by means of suction. The precipitated substances were washed with ethanol (100 ml) and 70° C. hot water (200 ml) to obtain a solution. The obtained solution was added to the mixture of acetic acid (9.0 ml) and water (16.0 ml), concentrated under reduced pressure, purified by chromatography on a silica gel column (ethyl acetate), and solidified by acetone-water and ethyl acetate-hexane, followed by drying. Thus, the title compound (9.03 g) was obtained as pale yellow powder.

m.p. >220° C. (dec) IR (KBr) cm$^{-1}$ 3116, 3084, 3055, 2952, 1614, 1512, 1475, 1369, 1323, 1190, 1066. $^1$H-NMR (CD$_3$OD) d 7.15 (2H, s), 7.21 (1H, s). MS (EI) m/z 184 [M$^+$, C$^{135}$], 186 [M$^+$, C$^{137}$].

Referential Example 483

1-(tert-butoxycarbonyl)-4-[[5(6)-chlorobenzimidazol-2-yl]sulfonyl]piperazine

5(6)-chloro-2-mercaptobenzimidazole (1.837 g) was suspended in a 20% solution of acetic acid, and then blown by a chloride gas at a temperature less than 7° C. for 70 minutes. Yellow precipitates were obtained by filtration and thereafter, washed with cold water. The obtained yellow solid was added to the mixture of 1-(tert-butoxycarbonyl)piperazine (3.905 g), water (18 ml) and acetone (20 ml), and stirred at room temperature for 20 hours. After discarding the acetone, precipitates were filtered and dried, whereby the title compound (3.16 g) was obtained as pale yellow powder.

m.p. 210–211° C. IR (KBr) cm$^{-1}$ 3212, 2983, 1666, 1435, 1367, 1356, 1279, 1176, 1165, 1147, 1138, 974, 949. $^1$H-NMR (CDCl$_3$) d 1.44 (9H, s), 3.33–3.41 (4H, m), 3.53–3.59 (4H, m), 7.30–7.60 (2H, m), 7.72–7.88 (1H, m). MS (FAB) m/z 401 [(M$^+$+H)$^+$, C$^{135}$], 403 [(M$^+$+H)$^+$, C$^{137}$].

Referential Example 484

1-[[5(6)-chlorobenzimidazol-2-yl]sulfonyl]piperazine hydrochloride

Saturated solution of hydrochloride in ethanol (5.0 ml) was added to the mixture of 1-(tert-butoxycarbonyl)-4-[[5 (6)-chlorobenzimidazol-2-yl]sulfonyl]piperazine (1.406 g), ethanol (5.0 ml) and dichloromethane (4.0 ml), and then stirred at room temperature for 4 hours. After concentration under reduced pressure, the obtained product was purified by chromatography on a silica gel column (dichloromethane:methanol=20:1). The purified compound was added to 1N solution of hydrochloride in ethanol (1 ml), concentrated and dried, whereby the title compound (1.19 g) was obtained as a hygroscopic colorless amorphous substance.

$^1$H-NMR (DMSO-d$_6$) d 3.25–3.80 (8H, m), 7.40–7.50 (1H, br), 7.60–7.80 (2H, br), 9.20–9.55 (1H, br). MS (FAB) m/z 301 [(M +H)$^+$, C$^{135}$], 303 [(M+H)$^+$, C$^{137}$].

Example A-1

1-[(6-Chloronaphthalen-2-yl)sulfonyl]-4-[4-(pyridin-4-yl)benzoyl]piperazine hydrochloride At room temperature, 1-[4-(4-pyridyl)benzoyl]piperazine ditrifluoroacetate (1.19 g) was suspended in dichloromethane (100 ml), followed by the addition of diisopropylethylamine (1.68 ml) and 6-chloro-2-naphthylsulfonyl chloride (WO/96/10022) (691 mg). After stirring at room temperature for 2 hours, the reaction mixture was purified by chromatography on a silica gel column (2% methanol—dichloromethane). To the resulting fraction, 1N hydrochloric acid in ethanol was added to make it weakly acidic. The solvent was then distilled off. The resulting colorless solid was washed with tetrahydrofuran, whereby the title compound (1.05 g, 81%) was obtained as a colorless solid.

$^1$H-NMR (DMSO-d$_6$) δ: 2.95–3.25(4H,m), 3.43(2H,br s), 3.60(2H,br s), 7.56(2H,d,J=8.3 Hz), 7.74(1H,dd,J=8.8,2.5 Hz), 7.83(1H,dd,J=8.8,2.0 Hz), 8.01(2H,d,J=8.3 Hz), 8.19 (1H,d,J=8.8 Hz), 8.25–8.40(4H,m), 8.51(1H,s), 8.94(2H,d, J=6.8 Hz). MS (FAB) m/z: 492 [(M+H)$^+$, Cl$^{35}$], 494 [(M+H)$^+$, Cl$^{37}$]. Elementary analysis for C$_{26}$H$_{22}$N$_3$O$_3$ClS.HCl.0.5H$_2$O Calculated: C, 58.10; H, 4.50; N, 7.82; Cl, 13.19; S, 5.97. Found: C, 58.12; H, 4.67; N, 7.66; Cl, 13.12; S, 6.10.

Example A-2

4-[(6-Chloronaphthalen-2-yl)sulfonyl]-2-ethoxycarbonyl-1-[4-(pyridin-4-yl)benzoyl] piperazine hydrochloride In dichloromethane (30 ml), 4-tert-butoxycarbonyl-2-ethoxycarbonyl-1-[4-(4-pyridyl)benzoyl]piperazine (514 mg) was dissolved, followed by the addition of trifluoroacetic acid (30 ml) under ice cooling. After stirring at room temperature for 45 minutes, the residue obtained by distilling off the solvent was suspended in dichloromethane (100 ml) under ice cooling, followed by the addition of diisopropylethylamine (1.02 ml) and 6-chloro-2-naphthylsulfonyl chloride (WO96/10022) (366 mg). After stirring at room temperature for one hour, the reaction mixture was purified as was by chromatography on a silica gel column (1% methanol—dichloromethane). To the resulting fraction, 1N hydrochloric acid in ethanol was added to make it weakly acidic. The solvent was then distilled off. The resulting colorless solid was washed with ethanol, whereby the title compound (308 mg, 43%) was obtained as a colorless solid.

$^1$H-NMR (DMSO-d$_6$) δ: 1.15–1.30(3H,m), 2.60–5.40 (9H,m), 7.50(⅔H,d,J=8.3 Hz), 7.57(⅓H,d,J=7.8 Hz), 7.74 (1H,dd,J=9.0,1.7 Hz), 7.83(1H,d,J=8.8 Hz), 8.00(⅔H,d,J= 7.8 Hz), 8.04(⅓H,d,J=8.3 Hz), 8.19(1H,d,J=8.8 Hz), 8.25–8.35(4H,m), 8.55(1H,s), 8.92(2H,d,J=4.9 Hz). MS (FAB) m/z: 564 [(M+H)$^+$, Cl$^{35}$], 566 (M+H)$^+$, Cl$^{37}$]. Elementary analysis for C$_{29}$H$_{26}$N$_3$O$_5$ClS.HCl.0.5H$_2$O Calculated: C, 57.15; H, 4.63; N, 6.89; Cl, 11.63; S, 5.26. Found: C, 56.95; H, 4.68; N, 6.70; Cl, 11.36; S, 5.30.

Example A-3

4-[(6-Chloronaphthalen-2-yl)sulfonyl]-1-[4-(pyridin-4-yl)benzoyl]piperazine-2-carboxylic acid hydrochloride In a mixed solvent of ethanol (1 ml), tetrahydrofuran (1 ml) and water (1 ml), 4-[(6-chloronaphthalen-2-yl) sulfonyl]-2-ethoxycarbonyl-1-[4-(pyridin-4-yl)benzoyl] piperazine hydrochloride (152 mg) obtained in Example A-2 was dissolved under ice cooling, followed by the dropwise addition of a 1N aqueous solution of sodium hydroxide. The reaction mixture was stirred at room temperature for 90 minutes. After concentration under reduced pressure, 1N hydrochloric acid was added to the reaction mixture to make it weakly acidic. The colorless solid so precipitated was collected by filtration, followed by drying, whereby the title compound (62 mg, 42%) was obtained as a colorless solid.

$^1$H-NMR (DMSO-d$_6$) δ: 2.65–5.30(7H,m), 7.49(⅘H,d,J= 7.7 Hz), 7.56(⅕H,d,J=8.3 Hz), 7.74(1H,dd,J=8.8,2.0 Hz), 7.82(1H,d,J=8.3 Hz), 7.95–8.05(2H,m), 8.19(1H,d,J=8.3 Hz), 8.20–8.35(4H,m), 8.53(1H,s), 8.92(2H,d,J=5.4 Hz). MS (FAB) m/z: 536 [(M+H)$^+$, Cl$^{35}$], 538 [(M+H)$^+$, Cl$^{37}$]. Elementary analysis for C$_{27}$H$_{22}$N$_3$O$_5$ClS.0.9HCl.1.2H$_2$O Calculated: C, 54.92; H, 4.32; N, 7.12; Cl, 11.41; S, 5.43. Found: C, 54.94; H, 4.42; N, 6.83; Cl, 11.31; S, 5.33.

Example A-4

1-[(6-Chloronaphthalen-2-yl)sulfonyl]-4-[4-(pyridin-4-yl)nicotinyl]piperazine hydrochloride In dichloromethane (10 ml), 6-(4-pyridyl)nicotinic acid hydrochloride (96 mg) and 1-[(6-chloronaphthalen-2-yl) sulfonyl]piperazine trifluoroacetate (150 mg) were suspended, followed by the addition of 1-hydroxybenzotriazole (48 mg) and N-methylmorpholine (155 μl). After the addition of 1-(3-dimethylaminopropyl)-3-ethylcarbodiimide hydrochloride (102 mg) under ice cooling, the resulting mixture was stirred at room temperature for 16 hours. Owing to the slow reaction, N,N-dimethylformamide (10 ml) was added to the reaction mixture and the resulting mixture was stirred for 3 days. After completion of the reaction, the solvent was distilled off. The residue was purified by chromatography on a silica gel column (1% methanol—dichloromethane). The solvent was then distilled off. To the residue, tetrahydrofuran and 1N hydrochloric acid in ethanol were added and the solid so precipitated was collected by filtration and dried, whereby the title compound (105 mg, 55%) was obtained as a colorless solid.

$^1$H-NMR (DMSO-d$_6$) δ: 3.00–3.25(4H,m), 3.46(2H,br s), 3.76(2H,br s), 7.74(1H,dd,J=8.5,1.7 Hz), 7.83(1H,d,J=8.8 Hz), 8.07(1H,dd,J=7.8,1.5 Hz), 8.19(1H,d,J=8.8 Hz), 8.28 (1H,s), 8.29(1H,d,J=8.8 Hz), 8.42(1H,d,J=8.3 Hz), 8.51(1H, s), 8.65(2H,d,J=6.4 Hz), 8.80(1H,m), 9.01(2H,d,J=5.9 Hz). MS (FAB) m/z: 493 [(M+H)$^+$, Cl$^{35}$], 495 [(M+H)$^+$, Cl$^{37}$]. Elementary analysis for C$_{25}$H$_{21}$N$_4$O$_3$ClS.HCl.H$_2$O Calculated: C, 54.85; H, 4.42; N, 10.23; Cl, 12.95; S, 5.86. Found: C, 54.57; H, 4.51; N, 10.06; Cl, 13.08; S, 5.87.

Example A-5

1-[(6-Chloronaphthalen-2-yl)sulfonyl]-4-[4-(pyridin-3-yl)benzoyl]piperazine hydrochloride In the same manner as in Example A-4, a reaction was conducted using 4-(3-pyridyl)benzoic acid hydrochloride and 1-[(6-chloronaphthalen-2-yl)sulfonyl]piperazine trifluoroacetate as starting materials, whereby the title compound was obtained as a colorless solid.

$^1$H-NMR (DMSO-d$_6$) δ: 3.00–3.25(4H,m), 3.47(2H,br s), 3.73(2H,br s), 7.51(2H,d,J=8.3 Hz), 7.73(1H,dd,J=8.8,2.0 Hz), 7.8–7.9(3H,m), 7.92(1H,dd,J=7.8,5.4 Hz), 8.19(1H,d, J=8.8 Hz), 8.25–8.30(2H,m), 8.50(1H,s), 8.55–8.65(1H,m), 8.75–8.85(1H,m), 9.14(1H,d,J=2.0 Hz). MS (FAB) m/z: 492 [(M+H)$^+$, Cl$^{35}$], 494 [(M+H)$^+$, Cl$^{37}$]. Elementary analysis for C$_{26}$H$_{22}$N$_3$O$_3$ClS.0.85HCl.H$_2$O Calculated: C, 57.72; H, 4.63; N, 7.77; Cl, 12.12; S, 5.93. Found: C, 57.44; H, 4.62; N, 7.68; Cl, 11.99; S, 5.83.

Example A-6

4-[4-[[4-[(6-Chloronaphthalen-2-yl)sulfonyl] piperazin-1-yl]carbonyl]phenyl]pyridine N-oxide In dichloromethane (10 ml), 1-[(6-chloronaphthalen-2-yl) sulfonyl]-4-[4-(pyridin-4-yl)benzoyl]piperazine (300 mg)

obtained in Example A-1 was dissolved, followed by the addition of 3-chloroperbenzoic acid (382 g) at −20° C. The resulting mixture was stirred at −20° C. for 21 hours. An aqueous solution of sodium sulfite was added to decompose an excess peroxide. Dichloromethane and a saturated aqueous solution of sodium bicarbonate were added to separate an organic layer. After drying the organic layer over anhydrous magnesium sulfate, the residue obtained by distilling off the solvent was purified by chromatography on a silica gel column (2–5% methanol—dichloromethane). After the solvent was distilled off, ether was added to the residue to solidify it, followed by collection through filtration, whereby the title compound (200 mg, 63%) was obtained as a colorless solid.

$^1$H-NMR (CDCl$_3$) δ: 2.90–3.40(4H,m), 3.40–4.20(4H, m), 7.43(2H,d,J=8.3 Hz), 7.47(2H,d,J=7.3 Hz), 7.55–7.65 (3H,m), 7.76(1H,dd,J=8.8,1.5 Hz), 7.90–8.00(3H,m), 8.26 (2H,d,J=7.3 Hz), 8.31(1H,s). MS (FAB) m/z: 508 [(M+H)$^+$, Cl$^{35}$], 510 [(M+H)$^+$, Cl$^{37}$]. Elementary analysis for C$_{26}$H$_{22}$N$_3$O$_4$ClS.0.8H$_2$O Calculated: C, 59.78; H, 4.55; N, 8.04; Cl, 6.79; S, 6.14. Found: C, 59.82; H, 4.45; N, 7.94; Cl, 6.85; S, 6.29.

Example A-7

1-[4-(2-Aminopyridin-5-yl)benzoyl]-4-[(6-chloronaphthalen-2-yl)sulfonyl]piperazine hydrochloride In a mixed solvent of dichloromethane (1 ml) and ethanol (1 ml), 1-[4-[2-tert-butoxycarbonylamino]pyridin-5-yl] benzoyl]-4-[(6-chloronaphthalen-2-yl)sulfonyl]piperazine (128 mg) was dissolved, followed by the addition of a saturated hydrochloride solution in ethanol (10 ml) under ice cooling. After stirring at room temperature for 1 minute, the solvent was distilled off. Isopropanol was added to the residue for crystallization. The crystals so obtained were collected by filtration and dried, whereby the title compound (88 mg, 68%) was obtained as a colorless solid.

$^1$H-NMR (DMSO-d$_6$) δ: 3.00–3.20(4H,m), 3.30–3.90 (4H,m), 7.05(½H,d,J=8.8 Hz), 7.06(½H,d,J=8.8 Hz), 7.43 (2H,d,J=8.3 Hz), 7.67(2H,d,J=8.3 Hz), 7.73(1H,d,J=8.3 Hz), 7.82(1H,d,J=8.8 Hz), 7.90–8.10(2H,br), 8.18(1H,d,J=8.3 Hz), 8.25–8.35(4H,m), 8.50(1H,s). MS (FAB) m/z: 507 [(M+H)$^+$, Cl$^{35}$], 509 [(M+H)$^+$, Cl$^{37}$]. Elementary analysis for C$_{26}$H$_{23}$ClN$_4$O$_3$S.HCl.1.2H$_2$O.0.8iPrOH Calculated: C, 55.56; H, 5.52; N, 9.13; Cl, 11.55; S, 5.22. Found: C, 55.40; H, 5.24; N, 8.85; Cl, 11.79; S, 5.50.

Example A-8

1-[4-(4-Aminophenyl)benzoyl]-4-[(6-chloronaphthalen-2-yl)sulfonyl]piperazine hydrochloride In the same manner as in Example A-7, a reaction was conducted using 1-[4-[4-(tert-butoxycarbonylamino)phenyl] benzoyl]-4-[(6-chloronaphthalen-2-yl)sulfonyl]piperazine as a starting material, whereby the title compound was obtained as a colorless solid.

$^1$H-NMR (DMSO-d$_6$) δ: 2.90–3.20(4H,m), 3.25–3.80 (4H,m), 6.68(2H,d,J=8.3 Hz), 7.32(2H,d,J=8.3 Hz), 7.39 (2H,d,J=8.3 Hz), 7.54(2H,d,J=8.3 Hz), 7.73(1H,dd,J=8.8, 2.0 Hz), 7.82(1H,dd,J=8.8,2.0 Hz), 8.18(1H,dd,J=8.8 Hz), 8,25–8.40(2H,m), 8.50(1H,br s). MS (FAB) m/z: 506 [(M+H)$^+$, Cl$^{35}$], 508 [(M+H)$^+$, Cl$^{37}$]. Elementary analysis for C$_{27}$H$_{24}$ClN$_3$O$_3$S.0.2HCl Calculated: C, 63.18; H, 4.75; N, 8.19; Cl, 8.29; S, 6.25. Found: C, 62.93; H, 4.93; N, 7.91; Cl, 7.99; S, 6.36.

Example A-9

1-[4-(2-Aminothiazol-4-yl)benzoyl]-4-[(6-chloronaphthalen-2-yl)sulfonyl]piperazine hydrochloride In the same manner as in Example A-4, a reaction was effected using 4-(2-aminothiazol-4-yl)benzoic acid and 1-[(6-chloronaphthalen-2-yl)sulfonyl]piperazine hydrochloride as starting materials, whereby the title compound was obtained.

$^1$H-NMR (DMSO-d$_6$) δ: 2.90–3.20(4H,m), 3.30–3.90 (4H,m), 7.26(1H,s), 7.41(2H,d,J=8.3 Hz), 7.73(1H,dd,J=8.8, 2.0 Hz), 7.79(2H,d,J=8.3 Hz), 7.82(1H,dd,J=8.8,2.0 Hz), 8.18(1H,d,J=8.8 Hz), 8.25–8.30(2H,m), 8.50(1H,br s). MS (FAB) m/z: 513 [(M+H)$^+$, Cl$^{35}$], 515 [(M+H)$^+$, Cl$^{37}$]. Elementary analysis for C$_{24}$H$_{21}$N$_4$O$_3$ClS2.HCl.0.3H$_2$O Calculated: C, 51.95; H, 4.11; N, 10.10; Cl, 12.78; S, 11.56. Found: C, 51.99; H, 4.19; N, 10.03; Cl, 12.61; S, 11.45.

Example A-10

1-[(6-Chloronaphthalen-2-yl)sulfonyl]-4-[4-[imidazol-4(5)-yl]benzoyl]piperazine hydrochloride In dichloromethane (5 ml), 1-[(6-chloronaphthalen-2-yl) sulfonyl]-4-[4-[1-triphenylmethylimidazol-4(5)-yl]benzoyl] piperazine (303 mg) was dissolved, followed by the addition of a saturated hydrochloride solution in ethanol (30 ml) under ice cooling. After stirring at room temperature for 3 hours, the solvent was distilled off. Ether was added to the residue for crystallization and the resulting crystals were collected by filtration, whereby the title compound (307 mg, 76%) was obtained as a colorless solid.

$^1$H-NMR (DMSO-d$_6$) δ: 2.90–3.20(4H,m), 3.30–3.90 (4H,m), 7.47(2H,d,J=8.3 Hz), 7.74(1H,dd,J=8.8,2.0 Hz), 7.82(1H,dd,J=8.8,2.0 Hz), 7.89(2H,d,J=8.3 Hz), 8.19(1H,d, J=8.8 Hz), 8.22(1H,d,J=1.0 Hz), 8.25–8.30(2H,m), 8.50(1H, m), 9.22(1H,d,J=1.0 Hz). MS (FAB) m/z: 481 [(M+H)$^+$, Cl$^{35}$], 483 [(M+H)$^+$, Cl$^{37}$]. Elementary analysis for C$_{24}$H$_{21}$ClN$_4$O$_3$S.HCl.0.4H$_2$O Calculated: C, 54.94; H, 4.38; N, 10.68; Cl, 13.52; S, 6.11. Found: C, 54.98; H, 4.29; N, 10.62; Cl, 13.56; S, 6.14.

Example A-11

1-[4-(2-Aminoimidazol-4-yl)benzoyl]-4-[(6-chloronaphthalen-2-yl)sulfonyl]piperazine hydrochloride In the same manner as in Example A-4, a reaction was conducted using 4-[2-aminoimidazol-4-yl]benzoic acid hydrochloride and 1-[(6-chloronaphthalen-2-yl)sulfonyl] piperazine hydrochloride as starting materials, whereby the title compound was obtained.

$^1$H-NMR (DMSO-d$_6$) δ: 2.90–3.20(4H,m), 3.30–3.90 (4H,m), 7.39(2H,d,J=8.3 Hz), 7.47(1H,s), 7.49(2H,br s), 7.67(2H,d,J=8.3 Hz), 7.73(1H,dd,J=8.8,2.5 Hz), 7.82(1H, dd,J=8.8,2.0 Hz), 8.18(1H,d,J=8.8 Hz), 8.25–8.30(2H,m), 8.50(1H,br s). MS (FAB) m/z: 496 [(M+H)$^+$, Cl$^{35}$], 498 [(M+H)$^+$, Cl$^{37}$]. Elementary analysis for C$_{24}$H$_{22}$N$_5$O$_3$ClS.HCl Calculated: C, 54.14; H, 4.35; N, 13.15; Cl, 13.32; S, 6.02. Found: C, 53.94; H, 4.39; N, 12.82; Cl, 13.27; S, 6.07.

Example A-12

4-[4-[[4-[(6-Chloronaphthalen-2-yl)sulfonyl] piperazin-1-yl]carbonyl]phenyl]-1-methylpyridinium iodide In a mixed solvent of benzene (10 ml) and methanol (10 ml), 1-[(6-chloronaphthalen-2-yl)sulfonyl]-4-[4-(pyridin-4- yl)benzoyl]piperazine (300 mg) obtained in Example A-1 was dissolved at room temperature, followed by the addition of methyl iodide (1 ml). To the resulting mixture, the same amount of methyl iodide was added three times at intervals of 24 hours, followed by heating under reflux for 4 days. The reaction mixture was distilled under reduced pressure and the residue was washed with methanol, collected by filtration and dried, whereby the title compound (229 mg, 58%) was obtained as a yellow solid.

$^1$H-NMR (DMSO-$d_6$) δ: 3.03(2H,br s), 3.13(2H,br s), 3.43(2H,br s), 3.75(2H,br s), 4.34(3H,s), 7.59(2H,d,J=8.8 Hz), 7.74(1H,dd,J=8.8,2.4 Hz), 7.85(1H,dd,J=8.8,2.0 Hz), 8.08(2H,d,J=8.8 Hz), 8.19(1H,d,J=8.8 Hz), 8.25–8.30(2H, m), 8.45–8.55(3H,m), 9.03(2H,d,J=6.8 Hz). Elementary analysis for $C_{27}H_{25}N_3O_3ClIS.H_2O$ Calculated: C, 49.74; H, 4.17; N, 6.45. Found: C, 49.60; H, 4.09; N, 6.23.

Example A-13

3-[4-[[4-[(6-Chloronaphthalen-2-yl)sulfonyl] piperazin-1-yl]carbonyl]phenyl]pyridine N-oxide In the same manner as in Example A-6, a reaction was conducted using 1-[(6-chloronaphthalen-2-yl)sulfonyl]-4-[4-(pyridin-3-yl)benzoyl]piperazine, which had been obtained in Example A-5, as a starting material, whereby the title compound was obtained.

$^1$H-NMR (CDCl$_3$) δ: 2.90–3.40(4H,m), 3.40–4.20(4H, m), 7.50–7.60(1H,m), 7.40–7.45(3H,m), 7.54(2H,d,J=8.3 Hz), 7.60(1H,dd,J=8.8,2.0 Hz), 7.76(1H,dd,J=8.8,2.0 Hz), 7.90–8.00(3H,m), 8.22(1H,d,J=5.9 Hz), 8.31(1H,d,J=2.0 Hz), 8.43(1H,br s). MS (FAB) m/z: 508 [(M+H)$^+$, Cl$^{35}$], 510 [(M+H)$^+$, Cl$^{37}$]. Elementary analysis for $C_{26}H_{22}N_3O_4ClS.H_2O$ Calculated: C, 59.37; H, 4.60; N, 7.99; Cl, 6.74; S, 6.10. Found: C, 59.48; H, 4.69; N, 7.74; Cl, 6.73; S, 6.07.

Example A-14

1-[2-Carboxy-4-(pyridin-4-yl)benzoyl]-4-[(6-chloronaphthalen-2-yl)sulfonyl]piperazine In dichloromethane (50 ml), 1-[2-tert-butoxycarbonyl-4-(pyridin-4-yl)benzoyl]-4-[(6-chloronaphthalen-2-yl) sulfonyl]piperazine hydrochloride (250 g) was dissolved, followed by the dropwise addition of trifluoroacetic acid (50 ml) under ice cooling. After stirring at room temperature for 5 hours, the solvent was distilled off. The residue was dissolved in methanol and the resulting solution was allowed to stand in a refrigerator for one day. The colorless solid so precipitated was collected by filtration and dried, whereby the title compound (550 mg, 28%) was obtained as a colorless solid.

$^1$H-NMR (DMSO-$d_6$) δ: 2.90–3.40(6H,m), 3.65–3.75 (2H,m), 7.41(1H,d,J=7.8 Hz), 7.70–7.75(3H,m), 7.82(1H, dd,J=8.8,2.0 Hz), 8.00(1H,dd,J=7.8,1.5 Hz), 8.15–8.30(4H, m), 8.50(1H,br s), 8.67(2H,d,J=5.9 Hz), 13.29(1H,br s). MS (FAB) m/z: 536 [(M+H)$^+$, Cl$^{35}$], 538 [(M+H)$^+$, Cl$^{37}$]. Elementary analysis for $C_{27}H_{22}ClN_3O_5S$ 0.5H$_2$O Calculated: C, 59.50; H, 4.25; N, 7.71; Cl, 6.50; S, 5.88. Found: C, 59.54; H, 4.30; N, 7.37; Cl, 6.35; S, 5.89.

Example A-15

1-[(6-Chloronaphthalen-2-yl)sulfonyl]-4-[[5-(pyridin-4-yl)thiophen-2-yl]carbonyl]piperazine hydrochloride In the same manner as in Example A-4, a reaction was conducted using 5-(pyridin-4-yl)thiophene-2-carboxylic acid hydrochloride obtained in Referential Example 28 and 1-[(6-chloronaphthalen-2-yl)sulfonyl]piperazine hydrochloride as starting materials, whereby the title compound was obtained.

$^1$H-NMR (DMSO-$d_6$) δ: 3.11(4H,br s), 3.74(4H,br s), 7.52(1H,d,J=3.9 Hz), 7.73(1H,dd,J=8.8,2.5 Hz), 7.83(1H, dd,J=8.8,2.0 Hz), 8.03(1H,d,J=3.9 Hz), 8.10–8.15(2H,m), 8.18(1H,d,J=8.8 Hz), 8.25–8.30(2H,m), 8.51(1H,s), 8.88 (2H,d,J=6.8 Hz). MS (FAB) m/z: 498 [(M+H)$^+$, Cl$^{35}$], 500 [(M+H)$^+$, Cl$^{37}$]. Elementary analysis for $C_{24}H_{20}ClN_3O_3S_2.HCl.H_2O$ Calculated: C, 52.17; H, 4.20; N, 7.61; Cl, 12.83; S, 11.61. Found: C, 52.04; H, 4.22; N, 7.22; Cl, 12.74; S, 11.57.

Example A-16

1-[(6-Chloronaphthalen-2-yl)sulfonyl]-4-[[5-(pyridin-4-yl)furan-2-yl]carbonyl]piperazine hydrochloride In the same manner as in Example A-4, a reaction was conducted using 5-(pyridin-4-yl)furan-2-carboxylic acid hydrochloride obtained in Referential Example 29 and 1-[(6-chloronaphthalen-2-yl)sulfonyl]piperazine hydrochloride as starting materials, whereby the title compound was obtained.

$^1$H-NMR (DMSO-$d_6$) δ: 3.13(4H,br s), 3.30–4.00(4H,m), 7.21(1H,d,J=3.9 Hz), 7.71(1H,d,J=8.8 Hz), 7.75–7.80(1H, m), 7.83(1H,d,J=8.8 Hz), 8.10–8.30(5H,m), 8.51(1H,s), 8.85–8.90(2H,m). MS (FAB) m/z: 482 [(M+H)$^+$, Cl$^{35}$], 484 [(M+H)$^+$, Cl$^{37}$]. Elementary analysis for $C_{24}H_{20}ClN_3O_4S.HCl.H_2O$ Calculated: C, 53.74; H, 4.32; N, 7.83; Cl, 13.22; S, 5.98. Found: C, 53.51; H, 4.36; N, 7.57; Cl, 13.21; S, 5.97.

Example A-17

1-[(6-Chloronaphthalen-2-yl)sulfonyl]-4-[4-(pyridin-2-yl)benzoyl]piperazine hydrochloride In the same manner as in Example A-4, a reaction was conducted using 4-(pyridin-2-yl)benzoic acid hydrochloride obtained in Referential Example 30 and 1-[(6-chloronaphthalen-2-yl)sulfonyl]piperazine hydrochloride as starting materials, whereby the title compound was obtained.

$^1$H-NMR (DMSO-$d_6$) δ: 3.07(4H,br), 3.60–4.00(4H,br), 7.46(3H,br), 7.73(1H,dd,J=8.8,2.0 Hz), 7.82(1H,dd,J=8.8, 2.0 Hz), 7.94–8.05(2H,br), 8.08(2H,d,J=8.8 Hz), 8.18(1H, d,J=8.8 Hz), 8.28(2H,d,J=8.8 Hz), 8.50(1H,s), 8.70(1H,br). MS (FAB) m/z: 492 [(M+H)$^+$, Cl$^{35}$], 494 [(M+H)$^+$, Cl$^{37}$]. Elementary analysis for $C_{26}H_{22}ClN_3O_3S.0.9HCl.H_2O$ Calculated: C, 57.53; H, 4.62; Cl, 12.41; N, 7.74; S, 5.91. Found: C, 57.55; H, 4.52; Cl, 12.64; N, 7.61; S, 6.03.

Example A-18

1-[(E)-4-Chlorostyrylsulfonyl]-4-[4-(pyridin-2-yl) benzoyl]piperazine hydrochloride In the same manner as in Example A-17, a reaction was conducted using 4-(2-pyridyl)benzoic acid hydrochloride and 1-[(E)-4-chlorostyrylsulfonyl]piperazine hydrochloride as starting materials, whereby the title compound was obtained.

$^1$H-NMR (DMSO-$d_6$) δ: 3.19(4H,br), 3.46(2H,br), 3.75 (2H,br), 7.36(1H,d,J=15.6 Hz), 7.44(1H,d,J=15.6 Hz), 7.50–7.58(1H,br), 7.53(2H,d,J=7.8 Hz), 7.57(2H,d,J=7.8 Hz), 7.82(2H,d,J=7.8 Hz), 8.13(2H,m), 8.15(2H,d,J=7.8 Hz), 8.75(1H,d,J=4.9 Hz). MS (FAB) m/z: 468 [(M+H)$^+$,

Cl³⁵], 470 [(M+H)⁺, Cl³⁷]. Elementary analysis for C₂₄H₂₂ClN₃O₃S.HCl.0.3EtOH.0.3H₂O Calculated: C, 56.42 H, 4.89; Cl, 13.54; N, 8.02; S, 6.12. Found: C, 56.51 H, 4.83; Cl, 13.46; N, 8.10; S, 5.99.

Example A-19

2-[4-[[4-[(6-Chloronaphthalen-2-yl)sulfonyl]piperazin-1-yl]carbonyl]phenyl]pyridine N-oxide In the same manner as in Example A-6, a reaction was conducted using 1-[(6-chloronaphthalen-2-yl)sulfonyl]-4-[4-(pyridin-2-yl)benzoyl]piperazine, which had been obtained in Example A-17, as a starting material, whereby the title compound was obtained.

¹H-NMR (CDCl₃) δ: 3.11(4H,br), 3.63(2H,br), 3.87(2H,br), 7.27(1H,m), 7.33(1H,t,J=8.8 Hz), 7.39–7.41(1H,br), 7.40(2H,d,J=7.8 Hz), 7.60(1H,d,J=8.8 Hz), 7.77(1H,d,J=8.8 Hz), 7.83(2H,d,J=7.8 Hz), 7.93(1H,d,J=3.8 Hz), 7.94(1H,s), 8.31(1H,s), 8.33(1H,d,J=5.9 Hz). MS (FAB) m/z: 508 [(M+H)⁺, Cl³⁵], 510 [(M+H)⁺, Cl³⁷]. Elementary analysis for C₂₆H₂₂ClN₃O₄S Calculated: C, 61.47; H, 4.37; Cl, 6.98; N, 8.27; S, 6.31. Found: C, 61.32; H, 4.46; Cl, 7.21; N, 8.13; S, 6.02.

Example A-20

2-[4-[[4-[(6-Chloronaphthalen-2-yl)sulfonyl]piperazin-1-yl]carbonyl]phenyl]-1-methylpyridinium iodide In the same manner as in Example A-12, a reaction was conducted using 1-[(6-chloronaphthalen-2-yl)sulfonyl]-4-[4-(pyridin-2-yl)benzoyl]piperazine, which had been obtained in Example A-17, as a starting material, whereby the title compound was obtained.

¹H-NMR (DMSO-d₆) δ: 2.93–3.23(4H,br), 3.54(2H,br), 3.82(2H,br), 4.30(3H,s), 7.50(2H,d,J=8.8 Hz), 7.53(1H,m), 7.70(2H,d,J=8.8 Hz), 7.70(1H,br), 7.84–7.92(4H,m), 8.15 (1H,t,J=6.8 Hz), 8.26(1H,s), 8.52(1H,t,J=6.8 Hz), 9.29(1H,d,J=5.9 Hz). Elementary analysis for C₂₇H₂₅ClIN₃O₃S.1.6H₂O Calculated: C, 48.93; H, 4.29; N, 6.34. Found: C, 48.81; H, 4.06; N, 6.31.

Example A-21

1-[(6-Chloronaphthalen-2-yl)sulfonyl]-4-[4-(2,4-diaminopyrimidin-6-yl)benzoyl]piperazine hydrochloride In the same manner as in Example A-4, a reaction was conducted using 4-(2,4-diamino-6-pyrimidyl)benzoic acid hydrochloride and 1-[(6-chloronaphthalen-2-yl)sulfonyl]piperazine hydrochloride as starting materials, whereby the title compound was obtained.

¹H-NMR (DMSO-d₆) δ: 3.14(4H,br), 3.45(2H,br s), 3,73 (2H,br s), 6,36(1H,s), 7,54(2H,d,J=7.8 Hz), 7.74(1H,dd,J=8.8,2.0 Hz), 7.82(1H,d,J=8.8 Hz), 7.83(1H,s), 7.84(2H,d,J=7.8 Hz), 8.18(1H,J=8.8 Hz), 8.18–8.35(3H,br), 8.27(1H,s), 8.28(1H,d,J=8.8 Hz), 8.50(1H,s), 12.64(1H,br s). MS (FAB) m/z: 523 [(M+H)⁺, Cl³⁵], 525 [(M+H)⁺, Cl³⁷]. Elementary analysis for C₂₅H₂₃ClN₆O₃S.HCl.1.4H₂O Calculated: C, 51.36; H, 4.62; Cl, 12.13; N, 14.37; S, 5.48. Found: C, 51.38; H, 4.54; Cl, 12.24; N, 14.23; S, 5.55.

Example A-22

1-[(E)-4-Chlorostyrylsulfonyl]-4-[4-(2,4-diaminopyrimidin-6-yl)benzoyl]piperazine hydrochloride In the same manner as in Example A-21, a reaction was conducted using 4-(2,4-diamino-6-pyrimidyl)benzoic acid hydrochloride and 1-[(E)-4-chlorostyrylsulfonyl)piperazine hydrochloride obtained in Referential Example 31 as starting materials, whereby the title compound was obtained.

¹H-NMR (DMSO-d₆) δ: 3.18(4H,br), 3.43(2H,br), 3.76 (2H,br), 4.0(2H,br), 6.37(1H,s), 7.84(2H,d,J=15.6 Hz), 7.44 (1H,J=15.6 Hz), 7.53(2H,d,J=8.8 Hz), 7.63(2H,d,J=8.8 Hz), 7.82(1H,d,J=8.8 Hz), 7.88(1H,d,J=8.8 Hz), 8.23(1H,br s), 8.32(1H,br s), 12.58(1H,br s). MS (FAB) m/z: 499 [(M+H)⁺, Cl³⁵], 501 [(M+H)⁺, Cl³⁷]. Elementary analysis for C₂₃H₂₃ClN₆O₃S.1.2HCl.1.4H₂O Calculated: C, 48.64; H, 4.79; Cl, 13.73; N, 14.80; S, 5.65. Found: C, 48.46; H, 4.56; Cl, 13.53; N, 14.54; S, 5.72.

Example A-23

2-[4-[[4-[(E)-4-Chlorostyrylsulfonyl]piperazin-1-yl]carbonyl]phenyl]pyridine N-oxide In the same manner as in Example A-1, a reaction was conducted using 2-[1-4-[(1-piperazyl)carbonyl]phenyl]pyridine N-oxide hydrochloride and (E)-4-chlorostyrylsulfonyl chloride (WO/96/10022) as starting materials, whereby the title compound was obtained.

¹H-NMR (CDCl₃) δ: 3.10–3.40(4H,br), 3.66(2H,br), 3.89 (2H,br), 6.65(1H,d,J=15.6 Hz), 7.28(1H,m), 7.34(1H,t,J=7.8 Hz), 7.39–7.48(6H,m), 7.50(2H,d,J=7.8 Hz), 7.88(2H,d,J=7.8 Hz), 8.34(1H,d,J=5.9 Hz). MS (FD) m/z: 483 (M⁺, Cl³⁵), 485 (M⁺, Cl³⁷). Elementary analysis for C₂₄H₂₂ClN₃O₄S.0.5H₂O Calculated: C, 58.47; H, 4.70; Cl, 7.19; N, 8.52; S, 6.50. Found: C, 58.49; H, 4.80; Cl, 7.29; N, 8.31; S, 6.34.

Example A-24

1-[(E)-4-Chlorostyrylsulfonyl]-4-[4-(pyridin-4-yl)benzoyl]piperazine hydrochloride Under ice cooling, piperazine (727 mg) was dissolved in dichloromethane (10 ml), followed by the addition of (E)-4-chlorostyrylsulfonyl chloride (WO96/10022) (500 mg) in portions. After stirring at room temperature for one hour, the reaction mixture was diluted with dichloromethane (100 ml), washed with a saturated aqueous NaCl solution solution of sodium bicarbonate, a 5% aqueous solution of nitric acid, water and saturated saline and then dried over anhydrous magnesium sulfate. The residue obtained by distilling off the solvent under reduced pressure was suspended in N,N-dimethylformamide (10 ml), followed by the addition of 4-(4-pyridyl)benzoic acid (420 mg) obtained in Referential Example 2 and N,N-dimethyl-4-aminopyridine (309 mg). Under ice cooling, 1-(3-dimethylaminopropyl)-3-ethylcarbodiimide hydrochloride (405 mg) was added and the resulting mixture was stirred at room temperature for 68 hours. After concentration, the residue was purified by chromatography on a silica gel column (dichloromethane methanol=70:1). The colorless solid so obtained was recrystallized from a mixed solvent of ethyl acetate and hexane, followed by recrystallization from ethyl acetate to obtain colorless needle crystals (185 mg). To the filtrate, on the other hand, saturated hydrochloric acid-ethanol (4 ml) was added. After concentration, the residue was recrystallized from methanol-ethyl acetate, whereby the title compound (200 mg) was obtained as colorless needle crystals.

¹H-NMR (DMSO-d₆) δ: 3.17(2H,br s), 3.23(2H,br s), 3.48(2H,br s), 3.77(2H,br s), 7.36(1H,d,J=15.3 Hz), 7.44 (1H,d,J=15.3 Hz), 7.53(2H,d,J=8.8 Hz),7.64(2H,d,J=8.3 Hz), 7.82(2H,d,J=8.3 Hz), 8.06(2H,d,J=8.8 Hz), 8.32(2H,d,J=6.6 Hz), 8.95(2H,d,J=6.6 Hz). MS (FAB) m/z: 468 [(M+

H)$^+$, Cl$^{35}$], 470 [(M+H)$^+$, C$^{137}$]. Elementary analysis for C$_{24}$H$_{22}$ClN$_3$O$_3$S.HCl.0.2H$_2$O.0.22CH$_3$CO$_2$CH$_2$CH$_3$ Calculated: C, 56.66; H, 4.81; Cl, 13.44; N, 7.97; S, 6.08. Found: C, 56.68; H, 4.79; Cl, 13.43; N, 8.04; S, 6.14.

Example A-25

4-[4-[[4-[(E)-4-Chlorostyrylsulfonyl]piperazin-1-yl]carbonyl]phenyl]-1-methylpyridinium iodide In the same manner as in Example A-12, a reaction was conducted using 1-[(E)-4-chlorostyrylsulfonyl]-4-[4-(pyridin-4-yl)benzoyl]piperazine, which had been obtained in Example A-24, as a starting material, whereby the title compound was obtained.

$^1$H-NMR (DMSO-d$_6$) δ: 3.04–3.87(8H,br), 4.35(3H,s), 7.35(1H,d,J=15.6 Hz), 7.44(1H,d,J=15.6 Hz), 7.53(2H,d,J=8.3 Hz), 7.67(2H,d,J=8.3 Hz), 7.82(2H,d,J=8.8 Hz), 8.13 (2H,d,J=8.3 Hz), 8.53(2H,d,J=6.8 Hz), 9.05(2H,d,J=7.3 Hz). Elementary analysis for C$_{25}$H$_{25}$ClIN$_3$O$_3$S.0.5H$_2$O Calculated: C, 48.52; H, 4.23; N, 6.79. Found: C, 48.68; H, 4.13; N, 6.41.

Example A-26

3-[4-[[4-[(E)-4-Chlorostyrylsulfonyl]piperazin-1-yl]carbonyl]phenyl]pyridine N-oxide After the protective group was removed by the reaction as in Example A-7, the reaction with (E)-4-chlorostyrylsulfonyl chloride (WO96/10022) was effected in the same manner as in Example A-23, whereby the title compound was obtained.

$^1$H-NMR (CDCl$_3$) δ: 3.26(4H,br), 3.52–4.00(4H,br), 6.64 (1H,d,J=15.6 Hz), 7.45–7.52(7H,m), 7.52(2H,d,J=2.0 Hz), 7.57(2H,d,J=2.0 Hz), 8.22(1H,dt,J=6.3,1.6 Hz), 8.44(1H,t, J=1.6 Hz). MS (FAB) m/z: 484 [(M+H)$^+$, Cl$^{35}$], 486 [(M+H)$^+$, C$^{37}$]. Elementary analysis for C$_{24}$H$_{22}$ClN$_3$O$_3$S.0.5H$_2$O Calculated: C, 58.47; H, 4.70; Cl, 7.19; N, 8.52; S, 6.50. Found: C, 58.49; H, 4.66; Cl, 7.40; N, 8.54; S, 6.56.

Example A-27

1-[(E)-4-Chlorostyrylsulfonyl]-4-[4-(pyridin-3-yl)benzoyl]piperazine hydrochloride In the same manner as in Example A-17 except for the use, as starting materials, of 4-(3-pyridyl)benzoic acid hydrochloride and 1-[(E)-4-chlorostyrylsulfonyl]piperazine hydrochloride, a reaction was conducted, whereby the title compound was obtained.

$^1$H-NMR (DMSO-d$_6$) δ: 3.08–3.29(4H,br), 3.42–3.85 (4H,br), 7.35(1H,d,J=15.6 Hz), 7.43(1H,d,J=15.6 Hz), 7.52 (2H,d,J=8.3 Hz), 7.59(2H,d,J=8.3 Hz), 7.80–7.93(5H,m), 8.54(1H,d,J=6.8 Hz), 8.78(1H,d,J=4.5 Hz), 9.13(1H,d,J=2.0 Hz). MS (FAB) m/z: 468 [(M+H)$^+$, Cl$^{35}$], 470 [(M+H)$^+$, Cl$^{37}$]. Elementary analysis for C$_{24}$H$_{22}$ClN$_3$O$_3$S.HCl.1.3H$_2$O Calculated: C, 54.61; H, 4.89; N, 7.96; Cl, 13.43; S, 6.07. Found: C, 54.82; H, 4.80; N, 7.91; Cl, 13.14; S, 6.14.

Example A-28

3-[4-[[4-[(6-Chloronaphthalen-2-yl)sulfonyl]piperazin-1-yl]carbonyl]phenyl]-1-methylpyridinium iodide In the same manner as in Example A-12, a reaction was conducted using 1-[(6-chloronaphthalen-2-yl)sulfonyl]-4-[4-(pyridin-3-yl)benzoyl]piperazine, which had been obtained in Example A-5, as a starting material, whereby the title compound was obtained.

$^1$H-NMR (DMSO-d$_6$) δ: 2.50–3.80(8H,m), 4.44(3H,s), 7.57(2H,d,J=8.3 Hz), 7.74(1H,dd,J=8.8,2.0 Hz), 7.84(1H, dd,J=8.8,1.5 Hz), 7.94(2H,d,J=8.3 Hz), 8.10–8.30(4H,m), 8.51(1H,s), 8.90(1H,d,J=7.8 Hz), 9.01(1H,d,J=5.9 Hz), 9.45 (1H,s). MS (FAB) m/z: 506 [(M+H)$^+$, Cl$^{35}$], 508 [(M+H)$^+$, Cl$^{37}$].

Example A-29

1-[(6-Chloronaphthalen-2-yl)sulfonyl]-4-[2-hydroxy-4-(pyridin-4-yl)benzoyl]piperazine hydrochloride In the same manner as in Example A-4, a reaction was conducted using 2-(hydroxy-4-(4-pyridyl)benzoic acid and 1-[(6-chloronaphthalen-2-yl)sulfonyl]piperazine hydrochloride as starting materials, whereby the title compound was obtained.

$^1$H-NMR (DMSO-d$_6$) δ: 2.90–3.40(8H,m), 7.25–7.40 (3H,m), 7.70–7.80(1H,m), 7.80–7.90(1H,m), 8.15–8.25(3H, m), 8.25–8.35(2H,m), 8.50–8.60(1H,m), 8.91(2H,d,J=6.4 Hz), 10.41(1H,br s). MS (FAB) m/z: 535 [(M+H)$^+$, Cl$^{35}$], 537 [(M+H)$^+$, C$^{137}$]. Elementary analysis for C$_{26}$H$_{22}$ClN$_3$O$_4$S.1.1HCl.1.7H$_2$O Calculated: C, 53.96; H, 4.62; N, 7.26; Cl, 12.86; S, 5.54. Found: C, 53.62; H, 4.58; N, 7.34; Cl, 13.10; S, 5.94.

Example A-30

1-[(6-Chloronaphthalen-2-yl)sulfonyl]-4-[3-methoxy-4-(pyridin-4-yl)benzoyl]piperazine hydrochloride In the same manner as in Example A-4, a reaction was conducted using 3-methoxy-4-(4-pyridyl)benzoic acid and 1-[(6-chloronaphthalen-2-yl)sulfonyl]piperazine hydrochloride as starting materials, whereby the title compound was obtained.

$^1$H-NMR (DMSO-d$_6$) δ: 3.00–4.00(8H,m), 3.81(3H,s), 7.08(1H,d,J=8.8 Hz), 7.17(1H,s), 7.55(1H,d,J=8.8 Hz), 7.74 (1H,dd,J=8.8,2.0 Hz), 7.83(1H,d,J=8.3 Hz), 8.04(2H,d,J= 6.3 Hz), 8.19(1H,d,J=8.8 Hz), 8.25–8.30(2H,m), 8.52(1H,s), 8.85(2H,d,J=6.3 Hz). MS (FAB) m/z: 522 [(M+H)$^+$, Cl$^{35}$], 524 [(M+H)$^+$, Cl$^{37}$]. Elementary analysis for C$_{27}$H$_{24}$ClN$_3$O$_4$S.0.8HCl.1.7H$_2$O Calculated: C, 55.74; H, 4.89; N, 7.22; Cl, 10.97; S, 5.51. Found: C, 55.59; H, 4.90; N, 7.23; Cl, 10.90; S, 5.52.

Example A-31

1-[(6-Chloronaphthalen-2-yl)sulfonyl]-4-[3-hydroxy-4-(pyridin-4-yl)benzoyl]piperazine hydrochloride In dichloromethane (1 ml), boron tribromide (115 µl) was dissolved, followed by the dropwise addition of a solution of 1-[(6-chloronaphthalen-2-yl)sulfonyl]-4-[3-methoxy-4-(pyridin-4-yl)benzoyl]piperazine, which had been obtained in Example A-30, in dichloromethane (dichloromethane: 4 ml) at an external temperature of about −78° C. While heating gradually to room temperature, the resulting mixture was stirred for 23 hours. After dichloromethane and water were added to the reaction mixture and the resulting mixture was stirred for a while, sodium bicarbonate was added to make alkaline the reaction mixture, which was separated into an organic layer and a water layer. From the water layer, another organic layer was extracted with dichloromethane. These organic layers were combined together, washed with saturated aqueous NaCl solution and then dried over anhydrous sodium sulfate. The residue obtained by distilling off the solvent under reduced pressure was purified by chromatography on a silica gel column (dichloromethane~3% methanol—dichloromethane). The crudely purified product so obtained was dissolved in tetrahydrofuran. Solution of hydrochloride in ethanol was added to the resulting solution to solidify the same. The resulting solid was collected by filtration and then dissolved in a mixed solvent of water and methanol. After the removal of the insoluble matter by filtration, the filtrate was distilled under reduced pressure, whereby the title compound (36 mg, 30%) was obtained.

$^1$H-NMR (DMSO-$d_6$) δ: 3.00–3.80(8H,m), 6.85–6.95 (1H,m), 7.01(1H,d,J=1.4 Hz), 7.49(1H,d,J=8.8 Hz), 7.72 (1H,dd,J=8.8,2.0 Hz), 7.81(1H,dd,J=8.5,1.7 Hz), 7.94(2H, d,J=6.4 Hz), 8.19(1H,d,J=8.8 Hz), 8.25–8.30(2H,m), 8.51 (1H,s), 8.75(2H,d,J=5.9 Hz), 10.67(1H,s). MS (FAB) m/z: 508 [(M+H)$^+$, Cl$^{35}$], 510 [(M+H)$^+$, Cl$^{37}$].

Example A-32

1-[(6-Chloronaphthalen-2-yl)sulfonyl]-2-ethoxycarbonyl-4-[4-(pyridin-4-yl)benzoyl] piperazine In the same manner as in Example A-7, a reaction was effected using 4-tert-butoxycarbonyl-1-[(6-chloronaphthalen-2-yl)sulfonyl]-2-ethoxycarbonylpiperazine as a starting material and the protective group was removed. The residue was then reacted with 4-(4-pyridyl)benzoic acid hydrochloride as in Example A-4, whereby the title compound was obtained.

$^1$H-NMR (CDCl$_3$) δ: 0.80–1.10(3H,m), 3.00–4.00(8H, m), 4.60–4.80(1H,m), 7.42(2H,d,J=7.8 Hz), 7.47(2H,d,J= 5.9 Hz), 7.50–7.60(1H,m), 7.64(2H,d,J=8.3 Hz), 7.70–7.80 (1H,m), 7.85–7.95(3H,m), 8.33(1H,s), 8.69(2H,s). MS (FAB) m/z: 564 [(M+H)$^+$, Cl$^{35}$], 566 [(M+H)$^+$, Cl$^{37}$]. Elementary analysis for C$_{29}$H$_{26}$ClN$_3$O$_5$S.0.3H$_2$O Calculated: C, 60.78; H, 4.70; N, 7.33; Cl, 6.80; S, 5.60. Found: C, 60.84; H, 4.84; N, 6.98; Cl, 7.03; S, 5.70.

Example A-33

1-[(6-Chloronaphthalen-2-yl)sulfonyl]-4-[4-(pyridin-4-yl)benzoyl]piperazine-2-carboxylic acid In the same manner as in Example A-3, the title compound was obtained using 1-[(6-chloronaphthalen-2-yl) sulfonyl]-2-ethoxycarbonyl-4-[4-(pyridin-4-yl)benzoyl] piperazine as a starting material.

$^1$H-NMR (DMSO-$d_6$) δ: 2.70–5.00(7H,m), 7.40–7.50 (2H,m), 7.65–7.75(2H,m), 7.85–8.25(8H,m), 8.50–8.60(2H, m), 8.80–8.95(2H,m). MS (FAB) m/z: 536 [(M+H)$^+$, Cl$^{35}$], 538 [(M+H)$^+$, Cl$^{37}$]. Elementary analysis for C$_{27}$H$_{22}$ClN$_3$O$_5$S.0.3HCl.H$_2$O Calculated: C, 57.40; H, 4.34; N, 7.44; Cl, 8.16; S, 5.68. Found: C, 57.16; H, 4.35; N, 7.36; Cl, 7.92; S, 6.08.

Example A-34

4-[(6-Chloronaphthalen-2-yl)sulfonyl]-2-ethoxycarbonyl-1-[4-(pyridin-3-yl)benzoyl] piperazine In the same manner as in Example A-2, a reaction was effected, whereby the title compound was obtained.

$^1$H-NMR (CDCl$_3$) δ: 1.15–1.30(3H,m), 2.60–4.60(8H, m), 5.33(1H,br), 7.40–7.55(3H,m), 7.70–7.85(4H,m), 8.05–8.10(1H,m), 8.19(1H,d,J=8.8 Hz), 8.25–8.30(2H,m), 8.50–8.65(2H,m), 8.91(1H,s). MS (FAB) m/z: 564 [(M+H)$^+$, Cl$^{35}$], 566 [(M+H)$^+$, Cl$^{37}$]. Elementary analysis for C$_{29}$H$_{26}$ClN$_3$O$_5$S.0.3HCl.0.5H$_2$O Calculated: C, 60.40; H, 4.74; N, 7.29; Cl, 6.76; S, 5.56. Found: C, 60.67; H, 4.61; N, 7.30; Cl, 6.89; S, 5.51.

Example A-35

2-Carbamoyl-4-[(6-chloronaphthalen-2-yl)sulfonyl]-1-[4-(pyridin-3-yl)benzoyl]piperazine hydrochloride In the same manner as in Example A-3, with 4-[(6-chloronaphthalen-2-yl)sulfonyl]-2-ethoxycarbonyl-1-[4-(pyridin-3-yl)benzoyl]piperazine (426 mg) as a starting material, a crude product was obtained by the hydrolysis of the ester, followed by suspension in N,N-dimethylformamide (35 ml). Under ice cooling, di-tert-butyl dicarbonate (646 mg), pyridine (370 µl) and ammonium bicarbonate (196 mg) were added to the resulting suspension. The resulting mixture was stirred at room temperature for 19 hours. The residue obtained by distilling off the solvent under reduced pressure was purified by chromatography on a silica gel column (4% methanol—dichloromethane) and the eluate was dissolved in tetrahydrofuran. Solution of hydrochloride in ethanol was added to the resulting solution to solidify the same. The resulting solid was collected by filtration and dissolved in a mixed solvent of water and methanol. The insoluble matter was filtered off and the filtrate was distilled under reduced pressure, whereby the title compound (302 mg, 65%) was obtained.

$^1$H-NMR (DMSO-$d_6$) δ: 2.30–4.50(6H,m), 5.08(1H,br), 7.40–7.60(2H,m), 7.65–7.85(3H,m), 7.92(2H,d,J=7.8 Hz), 8.00–8.10(1H,m), 8.20(2H,d,J=8.8 Hz), 8.25–8.35(2H,m), 8.49(1H,s), 8.80(1H,d,J=7.8 Hz), 8.88(1H,d,J=5.4 Hz), 9.25 (1H,s). MS (FAB) m/z: 535 [(M+H)$^+$, Cl$^{35}$], 537 [(M+H)$^+$, Cl$^{37}$]. Elementary analysis for C$_{27}$H$_{23}$ClN$_4$O$_4$S.1.1HCl.1.7H$_2$O Calculated: C, 53.54; H, 4.58; N, 9.25; Cl, 12.29; S, 5.29. Found: C, 53.36; H, 4.71; N, 9.07; Cl, 12.17; S, 5.50.

Example A-36

2-Carbamoyl-4-[(6-chloronaphthalen-2-yl)sulfonyl]-1-[4-(pyridin-4-yl)benzoyl]piperazine hydrochloride In the same manner as in Example A-35, the title compound was obtained using 4-[(6-chloronaphthalen-2-yl) sulfonyl]-2-ethoxycarbonyl-1-[4-(pyridin-4-yl)benzoyl] piperazine as a starting material.

$^1$H-NMR (DMSO-$d_6$) δ: 2.30–2.70(2H,m), 3.20–3.80 (2H,m), 4.10–4.50(2H,m), 5.07(1H,br s), 7.40–7.55(2H,m), 7.60–7.65(1H,m), 7.67(1H,s), 7.72(1H,dd,J=8.8,2.4 Hz), 7.78(1H,dd,J=8.8,2.4 Hz), 8.04(2H,d,J=8.8 Hz), 8.20(1H,d, J=8.8 Hz), 8.25–8.35(4H,m), 8.49(1H,s), 8.95(2H,d,J=5.4 Hz). MS (FAB) m/z: 535 [(M+H)$^+$, Cl$^{35}$], 537 [(M+H)$^+$, Cl$^{37}$]. Elementary analysis for C$_{27}$H$_{23}$ClN$_4$O$_4$S HCl.1.8H$_2$O Calculated: C, 53.70; H, 4.61; N, 9.28; Cl, 11.74; S, 5.31. Found: C, 53.87; H, 4.40; N, 8.89; Cl, 11.81; S, 5.23.

Example A-37

4-[4-[[2-Carbamoyl-4-[(6-chloronaphthalen-2-yl) sulfonyl]piperazin-1-yl]carbonyl]phenyl]pyridine N-oxide In the same manner as in Example A-6, a reaction was conducted using 2-carbamoyl-4-[(6-chloronaphthalen-2-yl)

sulfonyl]-1-[4-pyridin-4-yl)benzoyl]piperazine as a starting material, whereby the title compound was obtained.

$^1$H-NMR (DMSO-d$_6$) δ: 2.30–4.50(6H,m), 5.04(1H,br), 7.30–7.90(10H,m), 8.10–8.30(5H,m), 8.48(1H,s). MS (FAB) m/z: 551 [(M+H)$^+$, Cl$^{35}$], 553 [(M+H)$^+$, Cl$^{37}$]. Elementary analysis for C$_{27}$H$_{23}$ClN$_4$O$_5$S.0.8H$_2$O Calculated: C, 57.35; H, 4.39; N, 9.91; Cl, 6.27; S, 5.67. Found: C, 57.64; H, 4.50; N, 9.48; Cl, 6.37; S, 5.71.

Example A-38

4-[4-[[4-[(6-Chloronaphthalen-2-yl)sulfonyl]-2-ethoxycarbonylpiperazin-1-yl]carbonyl]phenyl] pyridine N-oxide In the same manner as in Example A-37, a reaction was conducted, whereby the title compound was obtained.

$^1$H-NMR (CDCl$_3$) δ: 1.30–1.40(3H,m), 2.30–4.70(8H,m), 5.47(1H,br s), 7.40–7.80(8H,m), 7.92(1H,s), 7.94(2H,s), 8.26(2H,d,J=6.8 Hz), 8.48(1H,s). MS (FAB) m/z: 580 [(M+H)$^+$, Cl$^{35}$], 582 [(M+H)$^+$, Cl$^{37}$]. Elementary analysis for C$_{29}$H$_{26}$ClN$_3$O$_6$S.1.3H$_2$O Calculated: C, 57.72; H, 4.78; N, 6.96; Cl, 5.87; S, 5.31. Found: C, 57.99; H, 4.75; N, 6.56; Cl, 5.98; S, 5.43.

Example A-39

4-[4-[[2-Carboxy-4-[(6-Chloronaphthalen-2-yl) sulfonyl]piperazin-1-yl]carbonyl]phenyl]pyridine N-oxide In the same manner as in Example A-3, the title compound was obtained.

$^1$H-NMR (CDCl$_3$) δ: 2.30–4.50(6H,m), 5.22(1H,br s), 7.35–7.50(2H,m), 7.70–7.90(6H,m), 8.19(1H,d,J=8.8 Hz), 8.25–8.30(4H,m), 8.53(1H,s), 13.42(1H,br). Elementary analysis for C$_{27}$H$_{22}$ClN$_3$O$_6$S.0.2HCl.1.7H$_2$O Calculated: C, 54.97; H, 4.37; N, 7.12; Cl, 7.21; S, 5.44. Found: C, 55.07; H, 4.40; N, 6.82; Cl, 7.16; S, 5.47.

Example A-40

2-Carbamoyl-4-[(E)-4-chlorostyrylsulfonyl]-1-[4-(pyridin-4-yl)benzoyl]piperazine hydrochloride, and 2-Carbamoyl-4-[[2-(4-chlorophenyl)-2-ethoxyethyl] sulfonyl]-1-[4-(pyridin-4-yl)benzoyl]piperazine hydrochloride In the same manner as in Example A-35, a reaction was conducted, whereby the title compounds were obtained.
2-Carbamoyl-4-[(E)-4-chlorostyrylsulfonyl]-1-[4-(pyridin-4-yl)benzoyl]piperazine hydrochloride $^1$H-NMR (CD$_3$OD) δ: 2.80–4.80(6H,m), 5.32(1H,br), 7.04(1H,d,J=15.6 Hz), 7.40–7.50(3H,m), 7.60–7.80(4H,m), 7.95–8.05(2H,m), 8.20(2H,br), 8.81(2H,br). MS (FAB) m/z: 511 [(M+H)$^+$, Cl$^{35}$], 513 [(M+H)$^+$, Cl$^{37}$]. Elementary analysis for C$_{25}$H$_{23}$ClN$_4$O$_4$S.0.9HCl.1.8H$_2$O Calculated: C, 52.11; H, 4.81; N, 9.72; Cl, 11.69. Found: C, 52.28; H, 4.83; N, 9.44; Cl, 11.51.
2-Carbamoyl-4-[[2-(4-chlorophenyl)-2-ethoxyethyl] sulfonyl]-1-[4-(pyridin-4-yl)benzoyl]piperazine hydrochloride $^1$H-NMR (CD$_3$OD) δ: 1.10–1.20(3H,m), 2.95–4.70(6H,m), 5.34(1H,br), 7.38(4H,s), 7.65–7.85(2H,m), 8.05–8.15(2H,m), 8.40–8.50(2H,m), 8.91(2H,d,J=5.9 Hz). MS (FAB) m/z: 557 [(M+H)$^+$, Cl$^{35}$], 559 [(M+H)$^+$, Cl$^{37}$]. Elementary analysis for C$_{27}$H$_{29}$ClN$_4$O$_5$S.HCl.2.5H$_2$O Calculated: C, 50.78; H, 5.52; N, 8.77; Cl, 11.10; S, 5.02. Found: C, 50.61; H, 5.38; N, 8.68; Cl, 11.27; S, 5.07.

Example A-41

1-[trans-4-(Aminomethyl)cyclohexylmethyl]-4-[(6-chloronaphthalen-2-yl)sulfonyl]piperazine hydrochloride In the same manner as in Example A-7, a reaction was conducted, whereby the title compound was obtained.

$^1$H-NMR (DMSO-d$_6$) δ: 0.80–1.00(4H,m), 1.48(1H,m), 1.60–1.90(5H,m), 2.60(2H,m), 2.90–3.10(4H,m), 3.14(2H,m), 3.52(2H,m), 3.77(2H,m), 7.75(1H,dd,J=8.8,2.0 Hz), 7.85(1H,d,J=8.8 Hz), 7.99(3H,br), 8.21(1H,d,J=8.8 Hz), 8.30–8.40(2H,m), 8.56(1H,s), 10.46(1H,br). MS (FAB) m/z: 436 [(M+H)$^+$, Cl$^{35}$], 438 [(M+H)$^+$, Cl$^{37}$]. Elementary analysis for C$_{22}$H$_{30}$ClN$_3$O$_2$S.2HCl.¾H$_2$O Calculated: C, 50.58; H, 6.46; N, 8.04; Cl, 20.36; S, 6.14. Found: C, 50.74; H, 6.48; N, 7.76; Cl, 20.09; S, 6.19.

Example A-42

1-[trans-4-(Aminomethyl)cyclohexylcarbonyl]-4-[(6-chloronaphthalen-2-yl)sulfonyl]piperazine hydrochloride In the same manner as in Example A-7, the title compound was obtained using 1-[trans-4-(N-tert-butoxycarbonylaminomethyl)cyclohexylcarbonyl]-4-[(6-chloronaphthalen-2-yl)sulfonyl]piperazine as a starting material.

$^1$H-NMR (DMSO-d$_6$) δ: 0.90–1.00(2H,m), 1.20–1.40 (2H,m), 1.48(1H,m), 1.50–1.70(2H,m), 1.70–1.90(2H,m), 2.44(1H,m), 2.59(2H,m), 2.96(4H,m), 3.55(4H,m), 7.72 (1H,dd,J=8.8,2.0 Hz), 7.81(1H,d,J=8.3 Hz), 7.90(3H,br), 8.16(1H,d,J=8.8 Hz), 8.20–8.30(2H,m), 8,49(1H,s). MS (FAB) m/z: 450 [(M+H)$^+$, Cl$^{35}$], 452 [(M+H)$^+$, Cl$^{37}$]. Elementary analysis for C$_{22}$H$_{28}$ClN$_3$O$_3$S.0.9HCl.1.5H$_2$O Calculated: C, 51.83; H, 6.31; N, 8.24; Cl, 13.21; S, 6.29. Found: C, 51.63; H, 6.22; N, 7.97; Cl, 13.32; S, 6.17.

Example A-43

1-[N-[trans-4-(Aminomethyl)cyclohexylcarbonyl] glycyl]]-4-[(6-chloronaphthalen-2-yl)sulfonyl] piperazine hydrochloride In the same manner as in Example A-7, a reaction was conducted using 1-[N-[trans-4-(N-tert-butoxycarbonylaminomethyl)cyclohexylcarbonyl]glycyl]-4-[(6-chloronaphthalen-2-yl)sulfonyl]piperazine as a starting material, whereby the title compound was obtained.

$^1$H-NMR (DMSO-d$_6$) δ: 0.80–1.00(2H,m), 1.20–1.40 (2H,m), 1.50(1H,m), 1.60–1.80(4H,m), 2.10(1H,m), 2.62 (2H,m), 2.90–3.10(4H,m), 3.40–3.60(4H,m), 3.83(2H,d,J= 5.4 Hz), 7.70–7.90(3H,m), 7.93(3H,br), 8.17(1H,d,J=8.3 Hz), 8.20–8.30(2H,m), 8.49(1H,s). MS (FAB) m/z: 507 [(M+H)$^+$, Cl$^{35}$], 509 [(M+H)$^+$, Cl$^{37}$]. Elementary analysis for C$_{24}$H$_{31}$ClN$_4$O$_4$S.HCl Calculated: C, 53.04; H, 5.93; N, 10.31; Cl, 13.05; S, 5.90. Found: C, 52.90; H, 5.98; N, 10.29; Cl, 12.98; S, 5.91.

Example A-44

1-[trans-4-(Aminomethyl)cyclohexylcarbonyl]-4-[(6-chloronaphthalen-2-yl)sulfonyl]homopiperazine hydrochloride In the same manner as in Example A-7, the title compound was obtained using 1-[trans-4-(N-tert-butoxycarbonylaminomethyl)cyclohexylcarbonyl]-4-[(6- chloronaphthalen-2-yl)sulfonyl]homopiperazine as a starting material.

$^1$H-NMR (DMSO-d$_6$) δ: 0.90–1.10(2H,m), 1.30–1.50 (2H,m), 1.50–1.90(7H,m), 2.40–2.80(3H,m), 3.20–3.70(8H, m), 7.60–7.70(1H,m), 7.80–8.00(4H,m), 8.10–8.20(1H,m), 8.20–8.30(2H,m), 8.52 and 8.53(1H, each s). MS (FAB) m/z: 464 [(M+H)$^+$, Cl$^{35}$], 466 [(M+H)$^+$, Cl$^{37}$]. Elementary analysis for C$_{23}$H$_{30}$ClN$_3$O$_3$S.HCl Calculated: C, 55.20; H, 6.24; N, 8.40; Cl, 14.17; S, 6.41. Found: C, 55.42; H, 6.18; N, 8.26; Cl, 14.11; S, 6.53.

Example A-45

1-[4-(Aminomethyl)benzoyl]-4-[(6-chloronaphthalen-2-yl)sulfonyl]piperazine hydrochloride In the same manner as in Example A-7, the title compound was obtained using 1-[4-(N-tert-butoxycarbonylaminomethyl)benzoyl]-4-[(6-chloronaphthalen-2-yl)sulfonyl]piperazine as a starting material.

$^1$H-NMR (DMSO-d$_6$) δ: 3.00–3.20(4H,br), 3.30–3.80 (4H,br), 4.03(2H,s), 7.37(2H,d,J=7.3 Hz), 7.50(2H,d,J=7.3 Hz), 7.72(1H,d,J=8.8 Hz), 7.82(1H,d,J=8.8 Hz), 8.18(1H,d, J=8.8 Hz), 8.20–8.40(2H,m), 8.43(3H,br), 8.49(1H,s). MS (FAB) m/z: 444 [(M+H)$^+$, Cl$^{35}$], 446 [(M+H)$^+$, Cl$^{37}$]. Elementary analysis for C$_{22}$H$_{22}$ClN$_3$O$_3$S.HCl.H$_2$O Calculated: C, 53.02; H, 5.06; N, 8.43; Cl, 14.23; S, 6.43. Found: C, 53.06; H, 5.30; N, 8.32; Cl, 14.20; S, 6.44.

Example A-46

1-[3-(Aminomethyl)benzoyl]-4-[(6-chloronaphthalen-2-yl)sulfonyl]piperazine hydrochloride In the same manner as in Example A-3, the ester was hydrolyzed using methyl 3-(N-tert-butoxycarbonylaminomethyl)benzoate as a starting material. Reaction was then effected as in Example A-4 or A-7, whereby the title compound was obtained.

$^1$H-NMR (DMSO-d$_6$) δ: 3.07(4H,br), 3.20–3.80(4H,br), 4.00(2H,s), 7.30–7.60(4H,m), 7.73(1H,d,J=8.8 Hz), 7.83 (1H,d,J=8.8 Hz), 8.10–8.60(7H,m). MS (FAB) m/z: 444 [(M+H)$^+$, Cl$^{35}$], 446 [(M+H)$^+$, Cl$^{37}$]. Elementary analysis for C$_{22}$H$_{22}$ClN$_3$O$_3$S.HCl.¼H$_2$O Calculated: C, 54.49; H, 4.88; N, 8.67; Cl, 14.62; S, 6.61. Found: C, 54.64; H, 4.95; N, 8.52; Cl, 14.59; S, 6.70.

Example 47

1-[(6-Chloronaphthalen-2-yl)sulfonyl]-4-[3-[N-(1-pyrrolin-2-yl)aminomethyl]benzoyl]piperazine hydrochloride In dimethylformamide (2 ml), 2-methoxy-1-pyrroline (35 mg) was dissolved, followed by the addition of 1-[3-(aminomethyl)benzoyl]-4-[(6-chloronaphthalen-2-ylsulfonyl]piperazine hydrochloride (0.10 g) and triethylamine (44 μl). The resulting mixture was stirred at room temperature for 3 days. After the reaction mixture was concentrated under reduced pressure, the concentrate was diluted with methanol, followed by the addition of 1N hydrochloric acid. The solvent was then distilled off under reduced pressure. The residue was purified by gel permeation chromatography ("Sephadex LH-20", Ø15×300 mm, methanol), followed by solidification in a mixed solvent of methanol and ether, whereby a colorless solid (0.11 g, 91%) was obtained.

$^1$H-NMR (DMSO-d$_6$) δ: 2.04(2H,m), 2.81(2H,t,J=7.8 Hz), 3.18(4H,br), 3.20–3.80(5H,m), 4.10(1H,br), 4.51(2H, d,J=5.9 Hz), 7.30–7.50(4H,m), 7.72(1H,dd,J=8.8,2.0 Hz), 7.82(1H,d,J=8.8 Hz), 8.18(1H,d,J=8.8 Hz), 8.20–8.30(2H, m), 8.50(1H,s), 10.0l(1H,t,J=5.9 Hz), 10.06(1H,s). MS (FAB) m/z: 511 [(M+H)$^+$, Cl$^{35}$], 513 [(M+H)$^+$, Cl$^{37}$]. Elementary analysis for C$_{26}$H$_{27}$ClN$_4$O$_3$S.HCl.CH$_3$OH.⅕H$_2$ Calculated: C, 54.60; H, 5.70; N, 9.43; Cl, 11.94; S, 5.40. Found: C, 54.84; H, 5.47; N, 9.13; Cl, 11.86; S, 5.48.

Example A-48

1-[4-(2-Aminoethyl)benzoyl]-4-[(6-chloronaphthalen-2-yl)sulfonyl]piperazine hydrochloride In the same manner as in Example A-7, the title compound was obtained using 1-[4-(2-(tert-butoxycarbonylamino)ethyl]benzoyl]-4-[(6-chloronaphthalen-2-yl)sulfonyl]piperazine as a starting material.

$^1$H-NMR (DMSO-d$_6$) δ: 2.90–3.20(8H,m), 3.40–3.90 (4H,br), 7.28(4H,s), 7.72(1H,dd,J=8.8,2.4 Hz), 7.81(1H,dd, J=8.8,2.0 Hz), 8.02(3H,br), 8.17(1H,d,J=8.3 Hz), 8.20–8.30 (2H,m), 8.49(1H,s). MS (FAB) m/z: 458 [(M+H)$^+$, Cl$^{35}$], 460 [(M+H)$^+$, Cl$^{37}$]. Elementary analysis for C$_{23}$H$_{24}$ClN$_3$O$_3$S.HCl.½CH$_3$OH.½H$_2$O Calculated: C, 54.34; H, 5.43; N, 8.09; Cl, 13.65; S, 6.17. Found: C, 54.43; H, 5.26; N, 7.92; Cl, 13.58; S, 6.24.

Example A-49

1-[(6-Chloronaphthalen-2-yl]sulfonyl]-4-[4-[[(3S)-pyrrolidin-3-yl]oxy]benzoyl]piperazine hydrochloride In the same manner as in Example A-7, the title compound was obtained using 1-[4-[[(3S)-1-tert-butoxycarbonylpyrrolidin-3-yl]oxy]benzoyl]-4-[(6-chloronaphthalen-2-yl)sulfonyl]piperazine as a starting material.

$^1$H-NMR (DMSO-d$_6$) δ: 2.05–2.25(2H,m), 3.00–3.10 (4H,m), 3.20–3.70(8H,m), 5.16(1H,br s), 6.95(2H,d,J=8.8 Hz), 7.31(2H,d,J=8.3 Hz), 7.70–7.75(1H,m), 7.82(1H,dd,J= 8.5,1.7 Hz), 8.18(2H,d,J=8.8 Hz), 8.20–8.30(2H,m), 8.50 (1H,s). MS (FAB) m/z: 500 [(M+H)$^+$, Cl$^{35}$], 502[(M+H)$^+$, Cl$^{37}$].

Example A-50

1-[(6-Chloronaphthalen-2-yl]sulfonyl]-4-[3-[[(3S)-pyrrolidin-3-yl]oxy]benzoyl]piperazine hydrochloride In the same manner as in Example 7, the title compound was obtained using 1-[3-[[(3S)-1-tert-butoxycarbonylpyrrolidin-3-yl]oxy]benzoyl]-4-[(6-chloronaphthalen-2-yl)sulfonyl]piperazine as a starting material.

$^1$H-NMR (DMSO-d$_6$) δ: 2.00–2.20(2H,m), 2.95–3.15 (4H,m), 3.20–3.80(8H,m), 5.11(1H,br s), 6.90–6.95(3H,m), 7.00–7.05(1H,m), 7.30–7.35(1H,m), 7.72(1H,dd,J=8.8,2.0 Hz), 7.81(1H,dd,J=8.5,1.7 Hz), 8.18(2H,d,J=8.8 Hz), 8.25–8.30(2H,m), 8.50(1H,s). MS (FAB) m/z: 500 [(M+H)$^+$, Cl$^{35}$], 502 [(M+H)$^+$, Cl$^{37}$]. Elementary analysis for C$_{25}$H$_{26}$ClN$_3$O$_4$S.HCl H$_2$O Calculated: C, 54.15; H, 5.27; N, 7.58; Cl, 12.79; S, 5.78. Found: C, 53.84; H, 5.19; N, 7.33; Cl, 12.72; S, 5.86.

Example A-51

1-[(6-Chloronaphthalen-2-yl]sulfonyl]-4-[4-[[(3R)-pyrrolidin-3-yl]oxy]benzoyl]piperazine hydrochloride In the same manner as in Example A-7, the title compound was obtained using 1-[4-[[(3R)-1-tertbutoxycarbonylpyrrolidin-3-yl]oxy]benzoyl]-4-[(6-chloronaphthalen-2-yl)sulfonyl]piperazine as a starting material.

$^1$H-NMR (DMSO-d$_6$) δ: 2.05–2.25(2H,m), 3.00–3.10 (4H,m), 3.20–3.70(8H,m), 5.16(1H,br s), 6.96(2H,d,J=8.8 Hz), 7.31(2H,d,J=8.8 Hz), 7.74(1H,dd,J=8.8,2.0 Hz), 7.82 (1H,dd,J=8.8,1.5 Hz), 8.18(1H,d,J=8.8 Hz), 8.25–8.30(2H, m), 8.50(1H,s). MS (FAB) m/z: 500 [(M+H)$^+$, Cl$^{35}$], 502 [(M+H)$^+$, Cl$^{37}$]. Elementary analysis for C$_{25}$H$_{26}$ClN$_3$O$_4$S.1.2HCl.0.8H$_2$O Calculated: C, 53.80; H, 5.20; N, 7.53; Cl, 13.97; S, 5.74. Found: C, 53.84; H, 5.05; N, 7.51; Cl, 13.79; S, 5.74.

Example A-52

1-[(6-Chloronaphthalen-2-yl]sulfonyl]-4-[3-[[(3R)-pyrrolidin-3-yl]oxy]benzoyl]piperazine hydrochloride In the same manner as in Example A-7, the title compound was obtained using 1-[3-[[(3R)-1-tert-butoxycarbonylpyrrolidin-3-yl]oxy]benzoyl]-4-[(6-chloronaphthalen-2-yl)sulfonyl]piperazine as a starting material.

$^1$H-NMR (DMSO-d$_6$) δ: 2.00–2.20(2H,m), 2.95–3.15 (4H,m), 3.20–3.80(8H,m), 5.11(1H,br s), 6.90–6.95(2H,m), 7.00–7.05(1H,m), 7.30–7.35(1H,m), 7.74(1H,dd,J=8.8,2.0 Hz), 7.82(1H,dd,J=8.8,1.5 Hz), 8.18(2H,d,J=8.8 Hz), 8.25–8.30(2H,m), 8.50(1H,s). MS (FAB) m/z: 500 [(M+H)$^+$, Cl$^{35}$], 502 [(M+H)$^+$, Cl$^{37}$]. Elementary analysis for C$_{25}$H$_{26}$ClN$_3$O$_4$S.HCl.H$_2$O Calculated: C, 54.15; H, 5.27; N, 7.58; Cl, 12.79; S, 5.78. Found: C, 53.91; H, 5.14; N, 7.37; Cl, 12.62; S, 5.67.

Example A-53

1-[4-(2-Aminopyrimidin-5-yl)benzoyl]-4-[(6-chloronaphthalen-2-yl]sulfonyl]piperazine hydrochloride In the same manner as in Example A-4, a reaction was conducted using 4-(2-amino-5-pyrimidyl)benzoic acid and 1-[(6-chloronaphthalen-2-yl)sulfonyl]piperazine hydrochloride as starting materials, whereby the title compound was obtained.

$^1$H-NMR (DMSO-d$_6$) δ: 3.06(4H,br), 3.56 and (each 2H,br), 4.70–5.45(3H,br), 7.40(2H,d,J=8.8 Hz), 7.67(2H,d, J=8.8 Hz), 7.73(1H,dd,J=8.8,2.0 Hz), 7.82(1H,d,J=8.8 Hz), 8.18(1H,d,J=8.8 Hz), 8.27(1H,s), 8.28(1H,d,J=8.8 Hz), 8.50 (1H,s), 8.72(1H,s). MS (FAB) m/z: 508 [(M+H)$^+$, Cl$^{35}$], 510 [(M+H)$^+$, Cl$^{37}$]. Elementary analysis for C$_{25}$H$_{22}$ClN$_5$O$_3$S.1.1HCl.0.7H$_2$O Calculated: C, 53.55; H, 4.40; Cl, 13.28; N, 12.49; S, 5.72. Found: C, 53.59; H, 4.58; Cl, 13.02; N, 12.58; S, 5.89.

Example A-54

1-[(6-Chloronaphthalen-2-yl]sulfonyl]-4-[(piperidin-4-yl)acetyl]piperazine hydrochloride In the same manner as in Example A-7, the title compound was obtained using 1-[(1-tert-butoxycarbonylpiperidin-4-yl)acetyl]-4-[(6-chloronaphthalen-2-yl)sulfonyl]piperazine as a starting material.

$^1$H-NMR (DMSO-d$_6$) δ: 1.25(2H,m), 1.71(2H,m), 1.87 (1H,m), 2.20(2H,d,J=6.8 Hz), 2.78(2H,br), 2.96(4H,br s), 3.14(2H,m), 3.52(4H,br s), 4.02(2H,br), 7.73(1H,dd,J=8.8, 2.0 Hz), 7.81(1H,d,J=8.8 Hz), 8.17(1H,d,J=8.8 Hz), 8.28 (1H,d,J=8.8 Hz), 8.26(1H,s), 8.50(1H,s), 8.54(1H,br), 8.75 (1H,br). MS (FAB) m/z: 436 [(M+H)$^+$, Cl$^{35}$], 438 [(M+H)$^+$, Cl$^{37}$]. Elementary analysis for C$_{21}$H$_{26}$ClN$_3$O$_3$S.1.1HCl.1.1H$_2$O Calculated: C, 50.86; H, 5.96; Cl, 15.01; N, 8.47; S, 6.47. Found: C, 51.07; H, 5.74; Cl, 14.75; N, 8.36; S, 6.50.

Example A-55

1-[(6-Chloronaphthalen-2-yl]sulfonyl]-4-[3-(piperidin-4-yl)propionyl]piperazine hydrochloride In the same manner as in Example A-7, the title compound was obtained using 1-[3-(1-tert-butoxycarbonylpiperidin-4-yl)propionyl]-4-[(6-chloronaphthalen-2-yl)sulfonyl]piperazine as a starting material.

$^1$H-NMR (CD$_3$OD) δ: 1.29(2H,m), 1.50(1H,m), 1.51(2H, m), 1.89(2H,m), 2.36(2H,m), 2.88(2H,m), 3.08(4H,m), 3.64 (4H,m), 4.04(2H,br), 7.58(1H,dd,J=8.8,2.0 Hz), 7.82(1H,dd, J=8.8,2.0 Hz), 8.05(1H,d,J=8.8 Hz), 8.06(1H,s), 8.09(1H,d, J=8.8 Hz), 8.42(1H,s). MS (FAB) m/z: 450 [(M+H)$^+$, Cl$^{35}$], 452 [(M+H)$^+$, Cl$^{37}$]. Elementary analysis for C$_{22}$H$_{28}$ClN$_3$O$_3$S.1.8HCl.0.9H$_2$O Calculated: C, 49.68; H, 5.99; Cl, 18.66; N, 7.90; S, 6.03. Found: C, 49.45; H, 5.70; Cl, 18.63; N, 7.72; S, 6.04.

Example A-56

1-[(6-Chloronaphthalen-2-yl]sulfonyl]-4-[(E)-3-(pyridin-3-yl)propenoyl]piperazine hydrochloride In the same manner as in Example A-4, the title compound was obtained using (E)-3-(3-pyridyl)acrylic acid and 1-[(6-chloronaphthalen-2-yl)sulfonyl]piperazine hydrochloride as starting materials.

$^1$H-NMR (DMSO-d$_6$) δ: 3.03(4H,m), 3.69(2H,br), 3.85 (2H,br), 7.51(2H,s), 7.70(1H,dd,J=8.8,2.0 Hz), 7.83(1H,dd, J=8.8,2.0 Hz), 7.89(1H,dd,J=7.8,5.4 Hz), 8.16(1H,d,J=8.8 Hz), 8.22(1H,d,J=2.0 Hz), 8.26(1H,d,J=8.8 Hz), 8.51(1H,s), 8.67(1H,d,J=7.8 Hz), 8.77(1H,d,J=5.4 Hz), 9.13(1H,s). MS (FAB) m/z: 442 [(M+H)$^+$, Cl$^{35}$], 444 [(M+H)$^+$, Cl$^{37}$]. Elementary analysis for C$_{22}$H$_{20}$ClN$_3$O$_3$S.HCl.¼H$_2$O Calculated: C, 54.72; H, 4.49; N, 8.70; Cl, 14.68; S, 6.64. Found: C, 54.81; H, 4.43; N, 8.54; Cl, 14.68; S, 6.74.

Example A-57

1-[(6-Chloronaphthalen-2-yl]sulfonyl]-4-[(E)-3-(pyridin-4-yl)propenoyl]piperazine hydrochloride In the same manner as in Example A-4, the title compound was obtained using (E)-3-(4-pyridyl)acrylic acid and 1-[(6-chloronaphthalen-2-yl)sulfonyl]piperazine hydrochloride as starting materials.

$^1$H-NMR (DMSO-d$_6$) δ: 3.03(4H,m), 3.68(2H,br), 3.82 (2H,br), 5.76(1H,s), 7.48(1H,d,J=15.1 Hz), 7.65(1H,d,J= 15.1 Hz), 7.72(1H,dd,J=8.8,2.0 Hz), 7.83(1H,dd,J=8.8,2.0 Hz), 8.11(2H,br s), 8.16(1H,d,J=8.8 Hz), 8.24(1H,s), 8.27 (1H,d,J=8.8 Hz), 8.52(1H,s), 8.82(2H,d,J=5.9 Hz). MS (FAB) m/z: 442 [(M+H)$^+$, Cl$^{35}$], 444 [(M+H)$^+$, Cl$^{37}$]. Elementary analysis for C$_{22}$H$_{20}$ClN$_3$O$_3$S.HCl.⅓H$_2$O Calculated: C, 54.82; H, 4.48; Cl, 14.71; N, 8.72; S, 6.65. Found: C, 54.77; H, 4.41; Cl, 14.71; N, 8.50; S, 6.77.

Example A-58

1-[(6-Chloronaphthalen-2-yl]sulfonyl]-4-[(pyridin-4-yl)acetyl]piperazine hydrochloride In the same manner as in Example A-4, the title compound was obtained using 4-pyridylacetic acid hydrochloride and 1-[(6-chloronaphthalen-2-yl)sulfonyl]piperazine hydrochloride as starting materials.

$^1$H-NMR (DMSO-d$_6$) δ: 2.99(2H,br), 3.04(2H,br), 3.57 (2H,br), 3.62(2H,br), 4.00(2H,s), 7.71(2H,d,J=5.9 Hz), 7.74 (1H,dd,J=8.8,3.0 Hz), 7.83(1H,dd,J=8.8,2.0 Hz), 8.18(1H, d,J=8.8 Hz), 8.27(1H,s), 8.29(1H,d,J=8.8 Hz), 8.53(1H,s), 8.72(2H,d,J=5.9 Hz). MS (FAB) m/z: 430 [(M+H)$^+$, Cl$^{35}$], 432 [(M+H)$^+$, Cl$^{37}$]. Elementary analysis for C$_{21}$H$_{20}$ClN$_3$O$_3$S HCl.0.3H$_2$O Calculated: C, 53.46; H, 4.61; Cl, 15.03; N, 8.91; S, 6.80. Found: C, 53.28; H, 4.49; Cl, 15.18; N, 8.91; S, 6.75.

Example A-59

1-[(6-Chloronaphthalen-2-yl]sulfonyl]-4-[4-[(3RS)-pyrrolidin-3-yl)benzoyl]piperazine hydrochloride In the same manner as in Example A-7, the title compound was obtained using 1-[4-[(3RS)-1-tert-butoxycarbonylpyrrolidin-3-yl)benzoyl]-4-[(6-chloronaphthalen-2-yl)sulfonyl]piperazine as a starting material.

$^1$H-NMR (DMSO-d$_6$) δ: 1.85–1.95(1H,m), 2.30–2.40 (1H,m), 3.00–3.90(13H,m), 7.72(1H,dd,J=8.6,2.2 Hz), 7.80 (1H,dd,J=8.8,2.0 Hz), 7.29(2H,d,J=8.3 Hz), 7.35(2H,d,J= 8.3 Hz), 8.18(1H,d,J=8.8 Hz), 8.25–8.30(2H,m), 8.49(1H,s). MS (FAB) m/z: 484 [(M+H)$^+$, Cl$^{35}$], 486 [(M+H)$^+$, Cl$^{37}$]. Elementary analysis for C$_{25}$H$_{26}$ClN$_3$O$_3$S.HCl.½H$_2$O Calculated: C, 54.84; H, 5.52; N, 7.67; Cl, 12.95; S, 5.86. Found: C, 55.00; H, 5.53; N, 7.48; Cl, 13.23; S, 5.97.

Example A-60

1-[(6-Chloronaphthalen-2-yl)sulfonyl]-4-[[(1RS)-4-(pyridin-4-yl)-3-cyclohexene]carbonyl]piperazine hydrochloride In the same manner as in Example A-4, a reaction was conducted using (1RS)-4-(4-pyridyl)-3-cyclohexenecarboxylic acid and 1-[(6-chloronaphthalen-2-yl)sulfonyl]piperazine hydrochloride as starting materials, whereby the title compound was obtained.

$^1$H-NMR (DMSO-d$_6$) δ: 1.50–1.60(1H,m), 1.80–1.90 (1H,m), 2.25–2.58(5H,m), 2.80–2.90(1H,m), 2.91–3.10(1H, m), 3.46–3.72(4H,m), 6.94(1H,br s), 7.71(1H,dd,J=8.8,2.0 Hz), 7.82(1H,dd,J=8.8,2.0 Hz), 7.96(2H,d,J=6.8 Hz), 8.15 (1H,J=8.8 Hz), 8.24(1H,J=2.0 Hz), 8.27(1H,J=8.8 Hz), 8.50 (1H,s), 8.76(2H,d,J=6.8 Hz). MS (FAB) m/z: 496 [(M+H)$^+$, Cl$^{35}$], 498 [(M+H)$^+$, Cl$^{37}$]. Elementary analysis for C$_{26}$H$_{26}$ClN$_3$O$_3$S.HCl.1.3H$_2$O Calculated: C, 56.18; H, 5.37; Cl, 12.75; N, 7.56; S, 5.77. Found: C, 56.03; H, 5.29; Cl, 12.67; N, 7.41; S, 5.77.

Example A-61

1-[(E)-4-Chlorostyrylsulfonyl]-4-[[(1RS)-4-(pyridin-4-yl)-3-cyclohexene]carbonyl]piperazine hydrochloride In the same manner as in Example A-4, a reaction was conducted using (1RS)-4-(4-pyridyl)-3-cyclohexenecarboxylic acid and 1-[(E)-4-chlorostyrylsulfonyl)piperazine hydrochloride as starting materials, whereby the title compound was obtained.

$^1$H-NMR (DMSO-d$_6$) δ: 1.59–1.70(1H,m), 1.90–1.98 (1H,m), 2.31–2.56(4H,m), 2.90–3.00(1H,m), 3.13(4H,br s), 3.50–3.63(4H,m), 6.98(1H,br s), 7.35(1H,d,J=15.6 Hz), 7.44(1H,d,J=15.6 Hz), 7.51(2H,d,J=8.3 Hz), 7.80(1H,J=8.3 Hz), 7.97(1H,J=6.8 Hz), 8.77(1H,J=6.8 Hz). MS (FAB) m/z: 472 [(M+H)$^+$, Cl$^{35}$], 474 [(M+H)$^+$, Cl$^{37}$]. Elementary analysis for C$_{24}$H$_{26}$ClN$_3$O$_3$S.0.9HCl.2.3H$_2$O Calculated: C, 52.77; H, 5.81; Cl, 12.33; N, 7.69; S, 5.87. Found: C, 52.61; H, 5.80; Cl, 12.54; N, 7.44; S, 6.05.

Example A-62 cis, trans-1-[(6-Chloronaphthalen-2-yl)sulfonyl]-4-[[4-(pyridin-4-yl)cyclohexane]carbonyl]piperazine hydrochloride In the same manner as in Example A-4, a reaction was conducted using cis, trans-4-(4-pyridyl)cyclohexanecarboxylic acid and 1-[(6-chloronaphthalen-2-yl)sulfonyl]piperazine hydrochloride as starting materials, whereby the title compound was obtained. MS (FAB) m/z: 498 [(M+H)$^+$, Cl$^{35}$], 500 [(M+H)$^+$, Cl$^{37}$]. Elementary analysis for C$_{26}$H$_{28}$ClN$_3$O$_3$S.1.3HCl.2H$_2$O Calculated: C, 53.71; H, 5.77; Cl, 14.02; N, 7.23; S, 5.51. Found: C, 53.70; H, 5.70; Cl, 14.21; N, 7.13; S, 5.72.

Example A-63 cis, trans-1-[(E)-4-Chlorostyrylsulfonyl]-4-[[4-(pyridin-4-yl)cyclohexane]carbonyl]piperazine hydrochloride In the same manner as in Example A-4, a reaction was conducted using cis, trans-4-(4-pyridyl)cyclohexanecarboxylic acid and 1-[(E)-4-chlorostyrylsulfonyl)piperazine hydrochloride as starting materials, whereby the title compound was obtained. MS (FAB) m/z: 474 [(M+H)$^+$, Cl$^{35}$], 476 [(M+H)$^+$, Cl$^{37}$]. Elementary analysis for C$_{24}$H$_{28}$ClN$_3$O$_3$S.1. 2HCl.0.8H$_2$O Calculated: C, 54.17; H, 5.83; Cl, 14.66; N, 7.80; S, 6.03. Found: C, 54.21; H, 6.20; Cl, 15.03; N, 7.51; S, 6.18.

Example A-64

1-[(6-Chloronaphthalen-2-yl)sulfonyl]-4-[4-(1,2,3,6-tetrahydropyridin-4-yl)benzoyl]piperazine hydrochloride In the same manner as in Example A-7, the title compound was obtained using 1–4-(1-tert-butoxycarbonyl-1,2, 3,6-tetrahydropyridin-4-yl)benzoyl]-4-[(6-chloronaphthalen-2-yl)sulfonyl]piperazine as a starting material.

$^1$H-NMR (DMSO-d$_6$) δ: 2.67(2H,br s), 3.05(4H,br), 3.30 (2H,br s), 3.35–3.78(6H,m), 6.24(1H,br s), 7.32(2H,d,J=8.3 Hz), 7.47(2H,d,J=8.3 Hz), 7.71(1H,dd,J=8.8,2.0 Hz), 7.81 (1H,dd,J=8.8,2.0 Hz), 8.17(1H,d,J=8.8 Hz), 8.22–8.28(2H, m), 8.49(1H,s), 9.25(2H,br s). MS (FAB) m/z: 496 [(M+H)$^+$, Cl$^{35}$], 498 [(M+H)$^+$, Cl$^{37}$]. Elementary analysis for C$_{26}$H$_{26}$ClN$_3$O$_3$S.HCl.⅖H$_2$O Calculated: C, 57.86; H, 5.19; Cl, 13.14; N, 7.79; S, 5.94. Found: C, 57.91; H, 5.19; Cl, 12.91; N, 7.75; S, 5.78.

Example A-65

1-[(6-Chloronaphthalen-2-yl)sulfonyl]-4-[4-(piperidin-4-yl)benzoyl]piperazine hydrochloride In the same manner as in Example A-7, the title compound was obtained using 1-[4-(1-tert-butoxycarbonylpiperidin-4-yl)benzoyl]-4-[(6-chloronaphthalen-2-yl)sulfonyl]piperazine as a starting material.

$^1$H-NMR (DMSO-d$_6$) δ: 1.78–1.94(4H,m), 2.80–3.21 (7H,m), 3.30–3.84(6H,m), 7.23(2H,d,J=8.3 Hz), 7.28(2H,d,

J=8.3 Hz), 7.71(1H,dd,J=8.8,2.0 Hz), 7.80(1H,dd,J=8.8,2.0 Hz), 8.17(1H,d,J=8.8 Hz), 8.22–8.27(2H,m), 8.49(1H,s), 8.78–9.00(2H,m). MS (FAB) m/z: 498 [(M+H)$^+$, Cl$^{35}$], 500 [(M+H)$^+$, Cl$^{37}$]. Elementary analysis for C$_{26}$H$_{28}$ClN$_3$O$_3$S.HCl.⅗H$_2$O Calculated: C, 57.27; H, 5.58; Cl, 13.00; N, 7.71; S, 5.88. Found: C, 57.23; H, 5.52; Cl, 12.90; N, 7.60; S, 5.83.

Example A-66

(3RS)-3-[(6-Chloronaphthalen-2-yl)sulfonamido]-1-[4-(pyridin-4-yl)benzoyl]pyrrolidine hydrochloride In saturated solution of hydrochloride in ethanol, (3RS)-1-tert-butoxycarbonyl-3-[(6-chloronaphthalen-2-yl)sulfonamido]pyrrolidine was dissolved, followed by stirring at room temperature for 8 hours. The solvent was then distilled off under reduced pressure. In the same manner as in Example A-4, a reaction was conducted using the resulting residue and 4-(4-pyridyl)benzoic acid as starting materials, whereby the title compound was obtained.

$^1$H-NMR (DMSO-d$_6$) δ: 1.70–2.10(2H,m), 3.00–3.65 (4H,m), 3.75–3.90(1H,m), 7.50–8.40(13H,m), 8.95–9.05 (2H,m). MS (FAB) m/z: 492 [(M+H)$^+$, Cl$^{35}$], 494 [(M+H)$^+$, Cl$^{37}$]. Elementary analysis for C$_{26}$H$_{22}$ClN$_3$O$_3$S HCl.1.8H$_2$O Calculated: C, 55.68; H, 4.78; N, 7.49; Cl, 12.64; S, 5.72. Found: C, 55.62; H, 4.94; N, 7.67; Cl, 12.76; S, 5.79.

Example A-67

(3RS)-1-[(6-Chloronaphthalen-2-yl)sulfonyl]-3-[4-(pyridin-4-yl)benzamido]pyrrolidine hydrochloride In saturated solution of hydrochloride in ethanol, (3RS)-1-tert-butoxycarbonyl-3-[4-(4-pyridyl)benzamido]pyrrolidine was dissolved, followed by stirring at room temperature for 4 hours. The solvent was then distilled off under reduced pressure. In the same manner as in Example A-1, a reaction was conducted using the resulting residue and 6-chloro-2-naphthylsulfonyl chloride as starting materials, whereby the title compound was obtained as a hydrochloride.

$^1$H-NMR (DMSO-d$_6$) δ: 1.90–2.10(2H,m), 3.00–3.60 (4H,m), 4.15–4.25(1H,M), 7.57(1H,dd,J=8.8,2.0 Hz), 7.73 (2H,d,J=8.8 Hz), 7.85(1H,dd,J=8.8,2.0 Hz), 7.90(2H,d,J= 8.8 Hz), 7.95–8.05(2H,m), 8.18(1H,d,J=8.8 Hz), 8.30–8.40 (3H,m), 8.50(1H,s), 8.98(2H,d,J=6.4 Hz). MS (FAB) m/z: 492 [(M+H)$^+$, Cl$^{35}$], 494 [(M+H)$^+$, Cl$^{37}$]. Elementary analysis for C$_{26}$H$_{22}$ClN$_3$O$_3$S.0.8HCl.0.8H$_2$O Calculated: C, 58.31; H, 4.59; N, 7.85; Cl, 11.92; S, 5.99. Found: C, 58.27; H, 4.68; N, 7.80; Cl, 11.94; S, 6.04.

Example A-68

1-[[(E)-2-(6-Chloropyridin-3-yl)ethylene]sulfonyl]-4-[4-(pyridin-4-yl)benzoyl]piperazine To a suspension of 1-tert-butoxycarbonyl-4-[[(E)-2-(6-chloropyridin-3-yl)ethylene]sulfonyl]piperazine (390 mg) in ethanol (2 ml), saturated hydrochloric acid-ethanol (6 ml) was added, followed by stirring for 3 hours. The reaction mixture was concentrated and the residue was dissolved in N,N-dimethylformamide (10 ml). To the resulting solution, 4-(4-pyridyl)benzoic acid hydrochloride (262 mg) and N-methylmorpholine (1.00 ml) were added. Under ice cooling, 1H-benzotriazoyl-1-yloxytripyrrolidinophosphonium hexafluorophosphate was added, followed by stirring at room temperature for 4 hours. The reaction mixture was diluted with ethyl acetate, washed successively with water, a saturated aqueous solution of sodium bicarbonate and saturated aqueous NaCl solution and then dried over anhydrous sodium sulfate. The residue obtained by distilling off the solvent under reduced pressure was recrystallized from a mixed solvent of dichloromethane and ethyl acetate. The resulting crystals were suspended in ethanol. Saturated hydrochloric acid-ethanol (6 ml) was added to the resulting suspension, followed by concentration into its hydrochloride. The resulting solid was recrystallized from ethanol, whereby the title compound (245 mg, 47%) was obtained as a colorless solid.

$^1$H-NMR (DMSO-d$_6$) δ: 3.10–3.31(4H,br), 3.40–3.84 (4H,br), 7.50(1H,d,J=15.9 Hz), 7.52(1H,d,J=15.9 Hz), 7.46 (3H,d,J=8.3 Hz), 8.06(2H,d,J=8.3 Hz), 8.28–8.33(3H,m), 8.79(1H,d,J=2.0 Hz), 8.94(2H,d,J=6.4 Hz). MS (FAB) m/z: 469 [(M+H)$^+$, Cl$^{35}$], 471 [(M+H)$^+$, Cl$^{37}$]. Elementary analysis for C$_{23}$H$_{21}$ClN$_4$O$_3$S HCl.0.4H$_2$O Calculated: C, 53.89; H, 4.48; N, 10.93; Cl, 13.83; S, 6.26. Found: C, 53.95; H, 4.47; N, 11.02; Cl, 13.91; S, 6.39.

Example A-69

1-[(6-Chloronaphthalen-2-yl)sulfonyl]-4-[2-methyl-4-(pyridin-4-yl)benzoyl]piperazine hydrochloride In the same manner as in Referential Example 7, a reaction was conducted using 1-(4-bromo-2-methylbenzoyl)-4-[(6-chloronaphthalen-2-yl)sulfonyl]piperazine as a starting material, whereby the title compound was obtained.

$^1$H-NMR (DMSO-d$_6$) δ: 2.20(3H,s), 2.80–4.00(8H,m), 7.36(1H,d,J=8.3 Hz), 7.73(1H,dd,J=8.8,2.4 Hz), 7.75–7.85 (2H,m), 7.88(1H,s), 8.18(1H,d,J=8.8 Hz), 8.20–8.30(4H,m), 8.50(1H,br s), 8.90(2H,d,J=6.8 Hz). MS (FAB) m/z: 506 [(M+H)$^+$, Cl$^{35}$], 508 [(M+H)$^+$, Cl$^{37}$].

Example A-70

4-[4-[4[-[(6-Chloronaphthalen-2-yl)sulfonyl]piperazin-1-yl]carbonyl]-3-methylphenyl]pyridine N-oxide In the same manner as in Example A-6, a reaction was conducted using 1-[(6-chloronaphthalen-2-yl)sulfonyl]-4-[2-methyl-4-(pyridin-4-yl)benzoyl]piperazine as a starting material, whereby the title compound was obtained.

$^1$H-NMR (CDCl$_3$) δ: 2.27(3H,s), 2.80–4.20(8H,m), 7.16 (1H,d,J=8.3 Hz), 7.38(1H,J=8.3 Hz), 7.41(1H,br s), 7.48 (2H,d,J=6.8 Hz), 7.61(1H,dd,J=8.8,1.5 Hz), 7.75(1H,d,J= 8.8 Hz), 7.91–7.97(3H,m), 8.28(2H,d,J=6.8 Hz), 8.31(1H,br s). MS (FAB) m/z: 522 [(M+H)$^+$, Cl$^{35}$], 524 [(M+H)$^+$, Cl$^{35}$]. Elementary analysis for C$_{27}$H$_{24}$ClN$_3$O$_4$S.H$_2$O Calculated: C, 60.05; H, 4.85; Cl, 6.56; N, 7.78; S, 5.94. Found: C, 59.98; H, 4.89; Cl, 6.51; N, 7.48; S, 5.92.

Example A-71

1-[(6-Chloronaphthalen-2-yl)sulfonyl]-4-[3-methyl-4-(pyridin-4-yl)benzoyl]piperazine hydrochloride In the same manner as in Example A-4, a reaction was conducted using 3-methyl-4-(4-pyridyl)benzoic acid hydrochloride as a starting material, whereby the title compound was obtained.

$^1$H-NMR (DMSO-d$_6$) δ: 2.27(3H,s), 3.08(4H,br), 3.47 (2H,br), 3.72(2H,br), 7.26–7.37(3H,m), 7.73(1H,dd,J=8.8, 2.0 Hz), 7.83(1H,dd,J=8.8,2.0 Hz), 7.86(2H,d,J=6.8 Hz), 8.18(1H,d,J=8.8 Hz), 8.25–8.29(2H,m), 8.50(1H,br s), 8.87

(2H,d,J=6.8 Hz). MS (FAB) m/z: 506 [(M+H)$^+$, Cl$^{35}$], 508 [(M+H)$^+$, Cl$^{35}$]. Elementary analysis for C$_{27}$H$_{24}$ClN$_3$O$_3$S.0.9HCl.1.7H$_2$O Calculated: C, 56.95; H, 5.01; Cl, 11.83; N, 7.38; S, 5.63. Found: C, 57.08; H, 5.04; Cl, 11.75; N, 7.37; S, 5.49.

Example A-72

4-4-[[4-[(6-Chloronaphthalen-2-yl)sulfonyl]-piperazin-1-yl]carbonyl]-2-methylphenyl]pyridine N-oxide In the same manner as in Example A-6, a reaction was conducted using 1-[(6-chloronaphthalen-2-yl)sulfonyl]-4-[3-methyl-4-(pyridin-4-yl)benzoyl piperazine as a starting material, whereby the title compound was obtained.

$^1$H-NMR (CDCl$_3$) δ: 2.28(3H,s), 3.13(4H,br), 3.63(2H, br), 3.86(2H,br), 7.15–7.28(5H,m), 7.60(1H,d,J=8.8 Hz), 7.76(1H,d,J=8.8 Hz), 7.90–7.96(3H,m), 8.26(2H,d,J=6.8 Hz), 8.31(1H,s). MS (FAB) m/z: 522 [(M+H)$^+$, Cl$^{35}$], 524 [(M+H)$^+$, Cl$^{35}$]. Elementary analysis for C$_{27}$H$_{24}$ClN$_3$O$_4$S.H$_2$O Calculated: C, 60.05; H, 4.85; Cl, 6.56; N, 7.78; S, 5.94. Found: C, 59.71; H, 4.68; Cl, 6.87; N, 7.63; S, 5.91.

Example A-73

1-[(6-Chloronaphthalen-2-yl)sulfonyl]-4-[4-(2-methylpyridin-4-yl)benzoyl]piperazine hydrochloride In the same manner as in Example A-4, a reaction was conducted using 4-(2-methyl-4-pyridyl)benzoic acid hydrochloride as a starting material, whereby the title compound was obtained.

$^1$H-NMR (DMSO-d$_6$) δ: 2.76(3H,s), 3.00–3.90(8H,m), 7.56(2H,d,J=8.3 Hz), 7.74(1H,dd,J=8.8,2.4 Hz), 7.38(1H, dd,J=8.8,2.0 Hz), 8.00(2H,d,J=8.3 Hz), 8.14(1H,d,J=6.4 Hz), 8.19(1H,d,J=8.8 Hz), 8.22–8.29(3H,m), 8.51(1H,br s), 8.80(1H,d,J=6.4 Hz). MS (FAB) m/z: 506 [(M+H)$^+$, Cl$^{35}$], 508 [(M+H)$^+$, Cl$^{35}$]. Elementary analysis for C$_{27}$H$_{24}$ClN$_3$O$_3$S.HCl.2H$_2$O Calculated: C, 56.06; H, 5.05; Cl, 12.26; N, 7.26; S, 5.54. Found: C, 55.84; H, 5.03; Cl, 12.26; N, 6.87; S, 5.54.

Example A-74

4-4-[[4-[(6-Chloronaphthalen-2-yl)sulfonyl]-piperazin-1-yl]carbonyl]phenyl]-2-methylpyridine N-oxide In the same manner as in Example A-6, a reaction was conducted using 1-[(6-chloronaphthalen-2-yl)sulfonyl]-4-[4-(2-methylpyridin-4-yl)benzoyl]piperazine as a starting material, whereby the title compound was obtained.

$^1$H-NMR (CDCl$_3$) δ: 2.58(3H,s), 3.13(4H,br), 3.65(2H, br), 3.84(2H,br), 7.34(1H,dd,J=6.8,2.4 Hz), 7.41(2H,d,J=8.3 Hz), 7.45(1H,d,J=2.4 Hz), 7.56–7.62(3H,m), 7.76(1H,dd,J=8.8,2.0 Hz), 7.91–7.96(3H,m), 8.28–8.32(2H,m). MS (FAB) m/z: 522 [(M+H)$^+$, Cl$^{35}$], 524 [(M+H)$^+$, Cl$^{35}$]. Elementary analysis for C$_{27}$H$_{24}$ClN$_3$O$_4$S.H$_2$O.0.05CH$_2$Cl$_2$ Calculated: C, 59.69; H, 4.83; Cl, 7.16; N, 7.72; S, 5.89. Found: C, 59.47; H, 4.87; Cl, 6.98; N, 7.48; S, 6.10.

Example A-75

4-4-[[4-[(6-Chloronaphthalen-2-yl)sulfonyl]-2-[[2-(morpholin-4-yl)ethylamino]carbonyl]piperazin-1-yl]carbonyl]phenyl]pyridine N-oxide In the same manner as in Example A-4, a reaction was conducted using 4-[4-[[2-carboxy-4-[(6-chloronaphthalen-2-yl)sulfonyl]piperazin-1-yl]carbonyl]phenyl]pyridine N-oxide and 4-(2-aminoethyl)morpholine as starting materials, whereby the title compound was obtained.

$^1$H-NMR (CDCl$_3$) δ: 2.22(4H,s), 2.35–2.80(6H,br), 3.20–3.90(3H,br), 3.74(4H,s), 4.20–4.60(1H,br), 5.25–5.50 (1H,br), 6.80–7.20(1H,br), 7.45–7.70(7H,m), 7.76(1H,d,J= 8.8 Hz), 7.85–7.95(3H,m), 8.26(2H,d,J=6.9 Hz), 8.32(1H,s). MS (FAB) m/z: 664 [(M+H)$^+$, Cl$^{35}$], 666 [(M+H)$^+$, Cl$^{37}$].

Example A-76

4-4-[[4-[(6-Chloronaphthalen-2-yl)sulfonyl]-2-[[2-(dimethylamino)ethylamino]carbonyl]piperazin-1-yl]carbonyl]phenyl]pyridine N-oxide In the same manner as in Example A-4, a reaction was conducted using 4-[4-[[2-carboxy-4-[(6-chloronaphthalen-2-yl)sulfonyl]piperazin-1-yl]carbonyl]phenyl]pyridine N-oxide and 2-(dimethylamino)ethylamine as starting materials, whereby the title compound was obtained.

$^1$H-NMR (CDCl$_3$) δ: 2.29(6H,s), 2.35–2.75(6H,br), 3.35–3.90(3H,br), 4.40–4.60(1H,br), 5.25–5.50(1H,br), 7.00–7.20(1H,br), 7.45–7.65(7H,m), 7.77(1H,dd,J=8.8,1.4 Hz), 7.85–7.95(3H,m), 8.26(2H,d,J=7.3 Hz), 8.34(1H,s). MS (FAB) m/z: 622 [(M+H)$^+$, Cl$^{35}$], 624 [(M+H)$^+$, Cl$^{35}$]. Elementary analysis for C$_{31}$H$_{32}$N$_5$O$_5$S.0.05CH$_2$Cl$_2$.2H$_2$O Calculated: C, 56.30; H, 5.49; N, 10.57; Cl, 5.89; S, 4.84. Found: C, 56.27; H, 5.37; N, 10.39; Cl, 6.01; S, 4.91.

Example A-77

4-[(6-Chloronaphthalen-2-yl)sulfonyl]-2-methoxycarbonylmethyl-1-[4-(pyridin-2-yl)benzoyl] piperazine In the same manner as in Example A-68, a reaction was conducted using 1-[(6-chloronaphthalen-2-yl)sulfonyl]-3-methoxycarbonylmethylpiperazine (723 mg) and 4-(2-pyridyl)benzoic acid hydrochloride as starting materials, whereby the title compound was obtained.

$^1$H-NMR (DMSO-d$_6$) δ: 2.30–4.50(11H,m), 5.06(1H,br s), 7.30–7.50(3H,m), 7.72(1H,dd,J=8.8,2.0 Hz), 7.80–7.85 (1H,m), 7.85–7.95(1H,m), 7.98(1H,d,J=7.8 Hz), 8.10(2H,d, J=8.3 Hz), 8.18(1H,d,J=8.8 Hz), 8.25–8.30(2H,m), 8.51(1H, s), 8.65–8.70(1H,m). MS (FAB) m/z: 564 [(M+H)$^+$, Cl$^{35}$], 566 [(M+H)$^+$, Cl$^{35}$]. Elementary analysis for C$_{29}$H$_{26}$ClN$_3$O$_5$S.1.1H$_2$O Calculated: C, 59.66; H, 4.87; N, 7.20; Cl, 6.07; S, 5.49. Found: C, 59.53; H, 4.61; N, 7.05; Cl, 6.33; S, 5.70.

Example A-78

4-[(6-Chloronaphthalen-2-yl)sulfonyl]-2-carboxymethyl-1-[4-(pyridin-2-yl)benzoyl] piperazine hydrochloride In the same manner as in Example A-3, a reaction was conducted using 4-[(6-chloronaphthalen-2-yl)sulfonyl]-2-methoxycarbonylmethyl-1-[4-(pyridin-2-yl)benzoyl] piperazine as a starting material, whereby the title compound was obtained.

$^1$H-NMR (DMSO-d$_6$) δ: 2.30–4.50(8H,m), 5.05(1H,br s), 7.35–7.40(1H,m), 7.43(2H,d,J=8.8 Hz), 7.72(1H,d,J=8.3 Hz), 7.81(1H,d,J=8.8 Hz), 7.85–7.90(1H,m), 7.97(1H,d,J= 7.8 Hz), 8.08(2H,d,J=8.8 Hz), 8.17(1H,d,J=8.8 Hz), 8.25–8.30(2H,m), 8.49(1H,s), 8.65–8.70(1H,m). MS (FAB) m/z: 550 [(M+H)$^+$, Cl$^{35}$], 552 [(M+H)$^+$, Cl$^{35}$]. Elementary analysis for C$_{28}$H$_{24}$ClN$_3$O$_5$S.0.4HCl.0.9H$_2$O Calculated: C,

Example A-79

2-Carbamoylmethyl-4-[(6-chloronaphthalen-2-yl)sulfonyl]-1-[4-(pyridin-2-yl)benzoyl]piperazine hydrochloride In the same manner as in Example A-35, a reaction was conducted using 4-[(6-chloronaphthalen-2-yl)sulfonyl]-2-carboxymethyl-1-[4-(pyridin-2-yl)benzoyl]piperazine as a starting material, whereby the title compound was obtained.

$^1$H-NMR (DMSO-$d_6$) δ: 2.20–4.50(8H,m), 5.10(1H,br s), 6.96(2H,br s), 7.45–7.55(3H,m), 7.70–7.85(3H,m), 8.05–8.35(6H,m), 8.50(1H,s), 8.81(1H,d,J=4.9 Hz). MS (FAB) m/z: 549 [(M+H)$^+$, Cl$^{35}$], 551 [(M+H)$^+$, Cl$^{35}$]. Elementary analysis for $C_{28}H_{25}ClN_4O_4S.1.3HCl.1.5H_2O$ Calculated: C, 53.94; H, 4.74; N, 8.99; Cl, 13.08; S, 5.14. Found: C, 53.85; H, 4.87; N, 8.80; Cl, 13.19; S, 5.27.

Example A-80

1-[(Z)-4-Chloro-β-(2-hydroxyethan-1-yl)-β-styrylsulfonyl]-4-[4-(pyridin-2-yl)benzoyl]piperazine hydrochloride Under ice cooling, 4-tert-butoxycarbonyl-1-[(Z)-4-chloro-β-[2-(methoxymethyloxy)ethyl]-β-styrylsulfonyl]piperazine (355 mg) was dissolved in ethanol (3 ml), followed by the addition of saturated solution of hydrochloride (6 ml) in ethanol. The resulting mixture was stirred at room temperature for 1 hour. After the reaction mixture was concentrated under reduced pressure, a reaction was effected in the same manner as in Example A-4 by using the resulting residue, whereby the title compound (285 mg, 65%) was obtained.

$^1$H-NMR (DMSO-$d_6$) δ: 2.58(2H,t,J=6.6 Hz), 3.06(4H,br s), 3.15–3.60(4H,br), 3.68(2H,t,J=6.6 Hz), 7.24(1H,s), 7.38 (2H,d,J=8.6 Hz), 7.40(2H,d,J=8.6 Hz), 7.47–7.57(3H,m), 8.02–8.10(2H,m), 8.14(2H,d,J=8.3 Hz), 8.74(1H,d,J=4.4 Hz). MS (FAB) m/z: 512 (M+H)$^+$.

Example A-81

1-[(E)-4-Chloro-β-(2-hydroxyethan-1-yl)-β-styrylsulfonyl]-4-[4-(pyridin-2-yl)benzoyl]piperazine hydrochloride In the same manner as in Example A-80, the title compound (240 mg, 74%) was obtained using 4-tert-butoxycarbonyl-1-[(E)-4-chloro-β-[2-(methoxymethyloxy)ethyl]-β-styrylsulfonyl]piperazine (355 mg) as a starting material.

$^1$H-NMR (DMSO-$d_6$) δ: 2.74(2H,t,J=7.3 Hz), 3.27(4H,br s), 3.37–3.85(6H,m), 7.45(1H,s), 7.50–7.60(5H,m), 7.68 (2H,d,J=8.3 Hz), 8.06–8.17(4H,m), 8.75(1H,d,J=4.9 Hz). MS (FAB) m/z: 512 (M+H)$^+$. Elementary analysis for $C_{26}H_{26}ClN_3O_4S.1.1HCl.0.8H_2O$ Calculated: C, 55.12; H, 5.11; N, 7.42; Cl, 13.14; S, 5.66. Found: C, 55.22; H, 5.21; N, 7.20; Cl, 12.97; S, 5.66.

In the same manner as in Example A-7 or Example A-1, the compounds shown in Examples A-82 to A-86 were synthesized.

Example A-82

1-[(6-Chloro-1-phenylsulfonylindol-2-y)sulfonyl]-4-[4-(pyridin-4-yl)benzoyl]piperazine $^1$H-NMR (CDCl$_3$) δ: 2.80–4.30(8H,br), 7.34(1H,d, J=8.5, 1.7 Hz), 7.43–7.62(9H,m), 7.69(2H,d,J=7.8 Hz), 8.04(2H, d,J=7.8 Hz), 8.33(1H,s), 8.70(2H,br s). Elementary analysis for $C_{30}H_{25}ClN_4O_5S_2$ Calculated: C, 58.01; H, 4.06; Cl, 5.71; N, 9.02; S, 10.32. Found: C, 58.34; H, 4.23; Cl, 5.78; N, 8.85; S, 9.96.

Example A-83

1-[(5-Chloro-3-methylbenzo[b]thien-2-yl)sulfonyl]-4-[4-(piridin-4-yl)benzoyl]piperazine $^1$H-NMR (DMSO-$d_6$) δ: 2.67(3H,s), 3.15–3.31(4H,br), 3.37–3.84(4H,br), 7.58(1H,m), 7.65(1H,dd,J=8.8,2.0 Hz), 7.92–8.03(2H,br), 8.13(1H,d,J=2.0 Hz), 8.15–8.24(4H,m), 8.79–8.92(2H,br). MS (FAB) m/z: 512 [(M+H)$^+$, Cl$^{35}$], 514 [(M+H)$^+$, Cl$^{37}$]. Elementary analysis for $C_{25}H_{22}ClN_3O_3S_2.HCl.0.3H_2O$ Calculated: C, 54.21; H, 4.29; Cl, 12.80; N, 7.59; S, 11.58. Found: C, 54.25; H, 4.25; Cl, 12.98; N, 7.52; S, 11.52.

Example A-84

1-[(1-Phenylsulfonyl-5-trimethylsilylethynylindol-2-yl)sulfonyl]-4-[4-(pyridin-4-yl)benzoyl]piperazine $^1$H-NMR (CDCl$_3$) δ: 0.25(9H,s), 3.35–4.00(8H,m), 7.43 (2H,t,J=8.1 Hz), 7.47–7.64(7H,m), 7.64–7.74(3H,m), 8.00 (2H,d,J=8.1 Hz), 8.23(1H,d,J=8.8 Hz), 8.71(2H,br s).

Example A-85

1-[(5-Chlorobenzo[b]furan-2-yl)sulfonyl]-4-[4-(pyridin-4-yl)benzoyl]piperazine $^1$H-NMR (DMSO-$d_6$) δ: 3.20–3.55(6H,br), 3.60–3.90 (2H,br), 7.61(1H,dd,J=8.8,2.0 Hz), 7.61(2H,d,J=8.8 Hz), 7.68(1H,s), 7.84(1H,d,J=8.8 Hz), 7.94(1H,d,J=2.0 Hz), 8.05 (2H,d,J=8.8 Hz), 8.34(2H,d,J=5.9 Hz), 8.95(2H,d,J=5.9 Hz). MS (FAB) m/z: 482 [(M+H)$^+$, Cl$^{35}$], 484 [(M+H)$^+$, Cl$^{37}$]. Elementary analysis for $C_{24}H_{20}ClN_3O_4S.HCl.0.6H_2O$ Calculated: C, 54.47; H,4.23 ; Cl, 13.40; N, 7.94; S, 6.06. Found: C, 54.48; H, 4.14; Cl, 13.41; N, 7.83; S, 6.17.

Example A-86

1-[(6-Chlorobenzo[b]furan-2-yl)sulfonyl]-4-[4-(pyridin-4-yl)benzoyl]piperazine $^1$H-NMR (DMSO-$d_6$) δ: 3.20–3.45(4H,br), 3.35–3.55 (2H,br), 3.65–3.85(2H,br), 7.48(1H,d,J=8.8 Hz), 7.59(2H,d, J=7.8 Hz), 7.73(1H,s), 7.80–8.10(1H,m), 7.86(1H,d,J=8.8 Hz), 7.98(1H,s), 8.04(2H,d,J=7.8 Hz), 8.20–8.32(½H,m), 8.60–9.49(1H,br), 8.90–8.93(½H,m). MS (FAB) m/z: 482 [(M+H)$^+$, Cl$^{35}$], 484 [(M+H)$^+$, Cl$^{37}$]. Elementary analysis for $C_{24}H_{20}ClN_3O_4S.HCl.0.3H_2O$ Calculated: C, 55.03; H, 4.16; Cl, 13.54; N, 8.02; S, 6.12. Found: C, 55.06; H, 4.12; Cl, 13.62; N, 7.89; S, 6.11.

In the same manner as in Example A-7 or Example A-4, the compounds shown in Examples A-87 to A-93 were synthesized.

Example A-87

1-[(5-Chloro-1-phenylsulfonylindol-2-yl)sulfonyl]-4-[4-(pyridin-4-yl)benzoyl]piperazine $^1$H-NMR (CDCl$_3$) δ: 3.45–3.53(4H,br), 3.53–3.98(4H, br), 7.40–7.50(4H,m), 7.52–7.60(6H,m), 7.70(2H,d,J=8.3 Hz), 8.01(2H,d,J=8.3 Hz), 8.24(1H,d,J=9.3 Hz), 8.73(2H, br). MS (FAB) m/z: 621 [(M+H)$^+$, Cl$^{35}$], 623 [(M+H)$^+$, Cl$^{37}$]. Elementary analysis for $C_{30}H_{25}ClN_4O_5S_2.0.1CH_2Cl_2$ Calculated: C, 57.42; H, 4.03; Cl, 6.76; N, 8.90; S, 10.19. Found: C, 57.10; H, 4.35; Cl, 6.58; N, 8.80; S, 10.04.

Example A-88

1-[(1-Phenylsulfonyl-2-yl)sulfonyl]-4-[4-(pyridin-4-yl)benzoyl]piperazine $^1$H-NMR (CDCl$_3$) δ: 3.43–3.53(4H,br), 3.53–3.94(4H,br), 7.43(1H,t,J=7.6 Hz), 7.40–7.46(2H,m), 7.48–7.65(10H,m), 7.69(2H,d,J=8.3 Hz), 8.04(3H,m), 8.30(1H,d,J=8.3 Hz), 8.69(2H,m). MS (FAB) m/z: 587 (M+H)$^+$ Elementary analysis for C$_{30}$H$_{26}$N$_4$O$_5$S$_2$.0.5H$_2$O Calculated: C, 60.49; H, 4.57; N, 9.41; S, 10.77. Found: C, 60.32; H, 4.73; N, 9.41; S, 10.43.

Example A-89

1-[(1-Phenylsulfonyl-5-chloroindol-2-yl)sulfonyl]-4-[4-(pyridin-4-yl)benzoyl]homopiperazine $^1$H-NMR (CDCl$_3$) δ: 1.85–1.92(1H,m), 2.13–2.20(1H,m), 3.47–3.76(1H,m), 3.54–3.73(5H,m), 3.87–3.98(2H,m), 7.38–7.60(11H,m), 7.69(2H,d,J=6.8 Hz), 8.02–8.08(2H,m), 8.18–8.23(1H,m), 8.69(2H,d,J=5.9 Hz). MS (FAB) m/z: 635 [(M+H)$^+$, Cl$^{35}$], 637 [(M+H)$^+$, Cl$^{37}$].

Example A-90

1-[(5-Chloroindol-2-yl)sulfonyl]-4-[4-(pyridin-2-yl)benzoyl]piperazine hydrochloride $^1$H-NMR (DMSO-d$_6$) δ: 2.92–3.26(4H,br), 3.35–3.78(4H,br), 7.03(1H,d,J=2.0 Hz), 7.34(1H,dd,J=8.8,2.4 Hz), 7.47–7.56(4H,m), 7.80(1H,d,J=2.0 Hz), 8.02–8.16(4H,m), 8.73(1H,d,J=4.9 Hz), 12.40(1H,s). MS (FAB) m/z: 481 [(M+H)$^+$, Cl$^{35}$], 483 [(M+H)$^+$, Cl$^{37}$]. Elementary analysis for C$_{24}$H$_{21}$ClN$_4$O$_3$S.0.9HCl.1.6H$_2$O Calculated: C, 53.13; H, 4.66; Cl, 12.41; N, 10.33; S, 5.91. Found: C, 53.29; H, 4.89; Cl, 12.40; N, 10.15; S, 5.92.

Example A-91

1-[(5-Chloro-1-methylindol-2-yl)sulfonyl]-4-[4-(pyridin-4-yl)benzoyl]piperazine $^1$H-NMR (CDCl$_3$) δ: 3.09–3.45(4H,br), 3.49–4.03(4H,br), 3.70(3H,s), 7.08(1H,m), 7.33(1H,d,J=8.8 Hz), 7.37(2H,d,J=7.8 Hz), 7.44–7.53(3H,m), 7.64–7.69(3H,m), 8.69(2H,br). MS (FAB) m/z: 495 [(M+H)$^+$, Cl$^{35}$], 497 [(M+H)$^+$, Cl$^{37}$]. Elementary analysis for C$_{25}$H$_{23}$ClN$_4$O$_3$S.0.1HCl.0.2H$_2$O Calculated: C, 56.12; H, 4.60; Cl, 13.25; N, 10.47; S, 5.99. Found: C, 56.13; H, 4.54; Cl, 13.25; N, 10.40; S, 5.99.

Example A-92

1-[(5-Chloro-1-ethylindol-2-yl)sulfonyl]-4-[4-(pyridin-4-yl)benzoyl]piperazine $^1$H-NMR (DMSO-d$_6$) δ: 1.30(3H,t,J=6.8 Hz), 3.15–3.37(4H,br), 3.38–3.57(2H,br), 3.65–3.87(2H,br), 4.47(2H,q,J=6.8 Hz), 7.17(1H,s), 7.41(1H,dd,J=8.8,2.0 Hz), 7.63(2H,d,J=8.3 Hz), 7.73(1H,d,J=8.8 Hz), 7.81(1H,d,J=2.0 Hz), 8.05(2H,d,J=8.3 Hz), 8.31(2H,d,J=6.4 Hz), 8.94(2H,d,J=6.4 Hz). MS (FAB) m/z: 509 [(M+H)$^+$, Cl$^{35}$], 511 [(M+H)$^+$, Cl$^{37}$]. Elementary analysis for C$_{26}$H$_{25}$ClN$_4$O$_3$S.1.1HCl.1.2H$_2$O Calculated: C, 54.71; H, 5.03; Cl, 13.04; N, 9.82; S, 5.62. Found: C, 54.51; H, 5.11; Cl, 13.06; N, 9.68; S, 5.71.

Example A-93

1-[(5-Chloro-1-ethoxycarbonylmethylindol-2-yl)sulfonyl]-4-[4-(pyridin-4-yl)benzoyl]piperazine $^1$H-NMR (DMSO-d$_6$) δ: 1.19(3H,t,J=6.8 Hz), 3.00–3.29(4H,br), 3.30–3.85(4H,br), 4.14(2H,q,J=6.8 Hz), 5.30(2H,s), 7.17–7.27(1H,m), 7.42(1H,d,J=8.8 Hz), 7.59(2H,d,J=7.8 Hz), 7.73(1H,d,J=8.8 Hz), 7.84(1H,s), 8.01(2H,d,J=7.8 Hz), 8.21(2H,d,J=6.3 Hz), 8.88(2H,d,J=6.3 Hz). MS (FAB) m/z: 567 [(M+H)$^+$, Cl$^{35}$], 569 [(M+H)$^+$, Cl$^{37}$]. Elementary analysis for C$_{28}$H$_{27}$ClN$_4$O$_5$S.0.9HCl.0.5H$_2$O Calculated: C, 55.23; H, 4.78; Cl, 11.06; N, 9.20; S, 5.27. Found: C, 54.91; H, 5.06; Cl, 10.78; N, 9.22; S, 5.45.

In the same manner as in Example A-4, the compounds shown in Examples A-94 to A-98 were synthesized.

Example A-94

1-[(5-Chlorobenzothiazol-2-yl)sulfonyl]-4-[4-(pyridin-4-yl)benzoyl]piperazine hydrochloride 1H-NMR (DMSO-d$_6$) δ: 3.28–3.90(8H,m), 7.61(2H,d,J=8.3 Hz), 7.77(1H,dd,J=8.8,2.0 Hz), 8.04(2H,d,J=8.8 Hz), 8.28(2H,d,J=6.4 Hz), 8.38(1H,d,J=8.8 Hz), 8.43(1H,d,J=2.0 Hz), 8.93(2H,d,J=6.4 Hz). MS (FAB) m/z: 499 [(M+H)$^+$, Cl$^{35}$], 501 [(M+H)$^+$, Cl$^{37}$]. Elementary analysis for C$_{23}$H$_{19}$ClN$_4$O$_3$S$_2$.HCl.0.6H$_2$O Calculated: C, 50.57; H, 3.91; Cl, 12.98; N, 10.26; S, 11.74. Found: C, 50.72; H, 3.90; Cl, 13.22; N, 9.99; S, 11.35.

Example A-95

1-[(6-Chlorobenzothiazol-2-yl)sulfonyl]-4-[4-(pyridin-4-yl)benzoyl]piperazine $^1$H-NMR (DMSO-d$_6$) δ: 3.28–3.90(8H,m), 7.55(2H,d,J=8.3 Hz), 7.77(1H,dd,J=8.8,2.0 Hz), 7.85–7.93(4H,m), 8.29(1H,d,J=8.8 Hz), 8.50(1H,d,J=2.0 Hz), 8.73(2H,d,J=6.4 Hz). MS (FAB) m/z: 499 [(M+H)$^+$, Cl$^{35}$], 501 [(M+H)$^+$, Cl$^{37}$]. Elementary analysis for C$_{23}$H$_{19}$ClN$_4$O$_3$S$_2$.0.25HCl.0.5H$_2$O Calculated: C, 53.42; H, 3.95; Cl, 8.57; N, 10.83; S, 12.40. Found: C, 53.22; H, 3.91; Cl, 8.41; N, 10.70; S, 12.59.

Example A-96

1-[(5-Chlorobenzo[b]thien-2-yl)sulfonyl]-4-[4-(pyridin-4-yl)benzoyl]piperazine hydrochloride $^1$H-NMR (DMSO-d$_6$) δ: 3.02–4.00(8H,m), 7.51(2H,d,J=8.8 Hz), 7.62(1H,dd,J=8.8,2.0 Hz), 7.71(2H,d,J=5.4 Hz), 7.82(2H,d,J=8.8 Hz), 8.04(1H,s), 8.17(1H,d,J=2.0 Hz), 8.19(1H,d,J=8.8 Hz), 8.65(2H,d,J=5.4 Hz). MS (FAB) m/z: 498 [(M+H)$^+$, Cl$^{35}$], 499 [(M+H)$^+$, Cl$^{37}$]. Elementary analysis for C$_{24}$H$_{20}$ClN$_3$O$_3$S$_2$.HCl Calculated: C, 53.93; H, 3.96; Cl, 13.27; N, 7.86; S, 12.00. Found: C, 53.79; H, 4.07; Cl, 13.37; N, 7.70; S, 12.07.

Example A-97

1-[(6-Chlorobenzo[b]thien-2-yl)sulfonyl]-4-[4-(pyridin-4-yl)benzoyl]piperazine hydrochloride $^1$H-NMR (DMSO-d$_6$) δ: 3.03–3.88(8H,m), 7.56–7.61(3H,m), 8.02(2H,d,J=8.8 Hz), 8.09(2H,d,J=8.8 Hz), 8.29(2H,d,J=6.3 Hz), 8.34(1H,d,J=2.0 Hz), 8.94(2H,d,J=6.3 Hz). MS (FAB) m/z: 498 [(M+H)$^+$, Cl$^{35}$], 500 [(M+H)$^+$, Cl$^{37}$]. Elementary analysis for C$_{24}$H$_{20}$ClN$_3$O$_3$S$_2$.HCl.H$_2$O Calculated: C, 52.17; H, 4.20; Cl, 12.83; N, 7.61; S, 11.61. Found: C, 52.18; H, 4.14; Cl, 12.84; N, 7.56; S, 11.70.

Example A-98

1-[(6-Chlorobenzo[b]thien-2-yl)sulfonyl]-4-[4-(pyridin-2-yl)benzoyl]piperazine hydrochloride $^1$H-NMR (DMSO-d$_6$) δ: 3.02–3.90(8H,m), 7.55(2H,d,J=8.3 Hz), 7.58(1H,dd,J=8.3,1.5 Hz), 7.62(1H,t,J=6.3 Hz), 8.07–8.20(6H,m), 8.33(1H,d,J=1.5 Hz), 8.77(1H,d,J=5.4 Hz). MS (FAB) m/z: 498 [(M+H)$^+$, Cl$^{35}$], 500 [(M+H)$^+$, Cl$^{37}$]. Elementary analysis for $C_{24}H_2OClN_3O_3S_2$·HCl·0.8H$_2$O Calculated: C, 52.52; H, 4.15; Cl, 12.92; N, 7.66; S, 11.68. Found: C, 52.69; H, 4.18; Cl, 12.63; N, 7.46; S, 11.68.

Example A-99

1-[(6-Chloroindol-2-yl)sulfonyl]-4-[4-(pyridin-4-yl)benzoyl]piperazine

In tetrahydrofuran (4.0 ml), 1-[(1-phenylsulfonyl-6-chloroindol-2-yl)sulfonyl]-4-[4-(pyridin-4-yl)benzoyl]piperazine (380 mg) was dissolved, followed by the addition of methanol (4.0 ml) and potassium hydroxide (34.3 mg) at room temperature. The resulting mixture was stirred for 2 hours. To the reaction mixture, a saturated aqueous solution (30 ml) of ammonium chloride was added to make it weakly acidic. Then, a saturated aqueous solution (40 ml) of sodium bicarbonate was added to make the resulting mixture to weakly alkaline. The resulting mixture was added with dichloromethane (30 ml). The organic layer thus separated was extracted further with dichloromethane. The organic layers were combined, dried over anhydrous sodium sulfate and distilled under reduced pressure. The residue thus obtained was purified by preparative thin-layer chromatography on a silica gel (dichloromethane:acetone:methanol=20:2:1), followed by recrystallization from a mixed solvent of hexane and dichloromethane, whereby the title compound (157 mg, 53%) was obtained as a white solid.

$^1$H-NMR (CDCl$_3$) δ: 2.70–4.20(8H,br), 7.02(1H,br s), 7.23(1H,dd,J=8.3,1.8 Hz), 7.42–7.50(5H,m), 7.62–7.68(3H, m), 8.69(2H,d,J=5.9 Hz), 8.78(1H,br s).

In the same manner as in Example A-99, the compounds shown in Examples A-100 to A-103 were synthesized.

Example A-100

1-[(Indol-2-yl)sulfonyl]-4-[4-(pyridin-4-yl)benzoyl]piperazine $^1$H-NMR (DMSO-d$_6$) δ: 3.00–3.20(4H,br), 3.42–3.84 (4H,br), 7.05(1H,s), 7.16(1H,t,J=7.3 Hz), 7.33(1H,m), 7.50 (3H,m), 7.72(2H,d,J=6.3 Hz), 7.82(2H,d,J=7.8 Hz), 7.65 (2H,d,J=4.9 Hz), 12.20(1H,s). MS (FAB) m/z: 447 (M+H)$^+$ Elementary analysis for $C_{24}H_{22}N_4O_3S$·0.2H$_2$O Calculated: C, 64.04; H, 5.02; N, 12.45; S, 7.12. Found: C, 64.23; H, 5.30; N, 12.06; S, 7.07.

Example A-101

1-[(5-Chloroindol-2-yl)sulfonyl]-4-[4-(pyridin-4-yl)benzoyl]piperazine $^1$H-NMR (DMSO-d$_6$) δ: 2.94–3.25(4H,br), 3.30–3.41 (4H,br), 7.03(1H,s), 7.33(1H,d,J=8.8 Hz), 7.52(1H,d,J=8.8 Hz), 7.59(2H,d,J=7.3 Hz), 7.80(1H,s), 8.03(2H,d,J=7.3 Hz), 8.33(2H,d,J=5.9 Hz), 8.95(2H,d,J=5.9 Hz), 12.5(1H,s). MS (FAB) m/z: 481 [(M+H)$^+$, Cl$^{35}$], 483 [(M+H)$^+$, Cl$^{37}$]. Elementary analysis for $C_{24}H_{21}ClN_4O_3S$·HCl·1.5H$_2$O Calculated: C, 52.95; H, 4.63; Cl, 13.02; N, 10.29; S, 5.89. Found: C, 53.34; H, 4.74; Cl, 12.87; N, 9.92; S, 5.77.

Example A-102

1-[(5-Chloroindol-2-yl)sulfonyl]-4-[4-(pyridin-4-yl)benzoyl]homopiperazine $^1$H-NMR (DMSO-d$_6$) δ: 1.75–1.85(1H,br), 2.02–2.13 (1H,br), 3.50–3.73(6H,m), 3.92–3.96(1H,br), 7.00(1H,m), 7.28–7.35(1H,m), 7.43–7.52(2H,m), 7.58(1H,d,J=7.8 Hz), 7.74–7.78(1H,m), 7.93–8.07(2H,m), 8.14–8.36(2H,m), 8.83–8.95(2H,m), 12.43(1H,m). MS (FAB) m/z: 495 [(M+H)$^+$, Cl$^{35}$], 497 [(M+H)$^+$, Cl$^{37}$]. Elementary analysis for $C_{25}H_{23}ClN_4O_3S$·1.05HCl·0.85H$_2$O Calculated: C, 54.73; H, 4.73; Cl, 13.25; N, 10.21; S, 5.85. Found: C, 55.04; H, 5.03; Cl, 13.23; N, 9.89; S, 5.61.

Example A-103

1-[(5-Ethynylindol-2-yl)sulfonyl]-4-[4-(pyridin-4-yl)benzoyl]piperazine $^1$H-NMR (CDCl$_3$) δ: 2.85–3.40(4H,br), 3.06(1H,s), 3.40–4.10(4H,br), 7.01(1H,br s), 7.39(1H,d,J=8.8 Hz), 7.45 (2H,d,J=8.3 Hz), 7.45–7.50(3H,m), 7.64(2H,d,J=8.3 Hz), 7.89(1H,br s), 8.70(2H,d,J=6.8 Hz), 9.55(1H,br s). MS (FAB) m/z: 471 (M+H)$^+$ Example A-104 cis-4-[(5-Chloroindol-2-yl)sulfonyl]-2,6-dimethyl-1-[4-(pyridin-4-yl)benzoyl]piperazine In tetrahydrofuran (50 ml), cis-1-(4-Bromobenzoyl)-4-[(5-chloro-1-phenylsulfonylindol-2-yl)sulfonyl]-1-(4-bromobenzoyl)-2,6-dimethylpiperazine (800 mg), diethyl 4-pyridylbolan (255 mg), tetrabutylammonium bromide (275 mg) and tetrakis(triphenylphosphine) palladium (0) (175 mg) were dissolved, followed by the addition of potassium hydroxide (289 mg) and water (0.745 ml). The resulting mixture was heated under reflux for 3 hours. The reaction mixture was concentrated under reduced pressure. Ethyl acetate and water were added to the residue to separate the organic layer. The organic layer thus obtained was washed with saturated aqueous NaCl solution, dried over anhydrous sodium sulfate. The residue obtained by distilling off the solvent under reduced pressure was purified by chromatography on a silica gel column (2% methanol—dichloromethane), followed by crystallization from ethanol, whereby the title compound (580 mg, 53%) was obtained as colorless amorphous.

$^1$H-NMR (DMSO-d$_6$) δ: 1.33(6H,br), 2.60–2.70(2H,m), 3.40–3.60(2H,m), 3.70–4.10(1H,br), 4.40–4.90(1H,br), 7.02 (1H,s), 7.30–7.35(1H,m), 7.45–7.55(3H,m), 7.72(2H,d,J= 5.4 Hz), 7.75–7.85(3H,m), 8.65(2H,d,J=5.4 Hz), 12.43(1H, s). Elementary analysis for $C_{26}H_{25}ClN_4O_3S$·0.3H$_2$O Calculated: C, 60.70; H, 5.02; Cl, 6.89; N, 10.89; S, 6.23. Found: C, 61.03; H, 5.06; Cl, 7.09; N, 10.51; S, 6.09.

Example A-105

1-[(5-Chloroindol-2-yl)sulfonyl]-4-[[5-(pyridin-4-yl)pyrimidin-2-yl]carbonyl]piperazine In a mixed solvent of dimethoxyethane (10 ml) and methanol (10 ml), 1-[(5-bromopyrimidin-2-yl)carbonyl]-4-[(5-chloroindol-2-yl)sulfonyl]piperazine (485 mg) and 4-pyridylboric acid (197 mg) were suspended at room temperature, followed by the successive addition of tetrakis (triphenylphosphine) palladium (0) (116 mg) and cesium fluoride (1.00 g). The resulting mixture was heated under reflux for 1 week. After the reaction mixture was cooled to room temperature, it was concentrated under reduced pressure. Dichloromethane and water were added to the concentrate to separate the organic layer. The organic layer thus obtained was dried over anhydrous sodium sulfate. The residue obtained by distilling off the solvent under reduced pressure was purified by chromatography on a silica gel column (2% methanol—dichloromethane). The pale yellow crystals precipitated in ethanol were collected by filtration and dissolved in dichloromethane. To the resulting solution, 1N aqueous hydrochloride in ethanol was added and the resulting mixture was distilled under reduced pressure to remove the solvent. The yellow crystals precipitated in ethyl acetate were collected by filtration and dried, whereby the title compound (40%) was obtained.

$^1$H-NMR (DMSO-$d_6$) δ: 2.96(2H,br s), 3.16(2H,br s), 3.38(2H,br s), 3.81(2H,br s), 7.05(1H,d,J=2.0 Hz), 7.35(1H, dd,J=8.8,2.0 Hz), 7.51(1H,d,J=8.8 Hz), 7.81(1H,d,J=2.0 Hz), 8.13(2H,d,J=5.9 Hz), 8.87(2H,d,J=5.9 Hz), 9.37(2H,s), 12.48(1H,s). MS (FAB) m/z: 483 [(M+H)$^+$, Cl$^{35}$], 485 [(M+H)$^+$, Cl$^{37}$]. Elementary analysis for $C_{22}H_{19}ClN_6O_3S \cdot 0.9HCl \cdot 1.4H_2O$ Calculated: C, 48.84; H, 4.23; Cl, 12.45; N, 15.53; S, 5.93. Found: C, 49.11; H, 4.27; Cl, 12.26; N, 15.34; S, 5.91.

In the same manner as in Example A-6, the compounds shown in Examples A-106 to A-120 were synthesized.

Example A-106

4-[4-[[4-[(6-Chloroindol-2-yl)sulfonyl]piperazin-1-yl]carbonyl]phenyl]pyridine N-oxide $^1$H-NMR (CDCl$_3$) δ: 2.90–4.10(8H,br), 7.02(1H,d,J=1.0 Hz), 7.22(1H,dd,J=8.8,1.7 Hz), 7.46(2H,d,J=8.3 Hz), 7.47 (1H,s), 7.50(2H,d,J=7.3 Hz), 7.60(2H,d,J=8.3 Hz), 8.63(1H, d,J=8.8 Hz), 8.29(2H,d,J=7.3 Hz), 9.32(1H,br s). Elementary analysis for $C_{24}H_{21}ClN_4O_4S \cdot 1.7H_2O$ Calculated: C, 54.64; H, 4.66; Cl, 6.72; N, 10.62; S, 6.08. Found: C, 54.63; H, 4.65; Cl, 6.91; N, 10.42; S, 6.07.

Example A-107

4-[4-[[4-[(5-Chloroindol-2-yl)sulfonyl]piperazin-1-yl]carbonyl]phenyl]pyridine N-oxide $^1$H-NMR (DMSO-$d_6$) δ: 3.00–3.20(4H,br), 3.34–3.58 (2H,br), 3.60–3.84(2H,br), 7.03(1H,s), 7.34(1H,d,J=8.8 Hz), 7.47(2H,d,J=7.3 Hz), 7.51(1H,d,J=8.8 Hz), 7.79(2H,d, J=5.9 Hz), 7.80(1H,s), 7.81(2H,d,J=7.3 Hz), 8.28(2H,d,J= 5.9 Hz), 12.43(1H,br). MS (FAB) m/z: 497 [(M+H)$^+$, Cl$^{35}$], 499 [(M+H)$^+$, Cl$^{37}$]. Elementary analysis for $C_{24}H_{21}ClN_4O_4S \cdot 0.2H_2O$ Calculated: C, 57.59; H, 4.31; Cl, 7.08; N, 11.19; S, 6.41. Found: C, 57.60; H, 4.38; Cl, 7.26; N, 11.09; S, 6.16.

Example A-108

4-[4-[[4-[(5-Chloro-1-methylindol-2-yl)sulfonyl] piperazin-1-yl]carbonyl]phenyl]pyridine N-oxide $^1$H-NMR (CDCl$_3$) δ: 3.06–3.45(4H,br), 3.48–4.06(4H, br), 4.00(3H,s), 7.07(1H,m), 7.33(1H,d,J=8.8 Hz), 7.35(2H, dd,J=8.8,1.8 Hz), 7.45–7.57(4H,m), 7.61(2H,d,J=8.3 Hz), 7.66(1H,d,J=2.0 Hz), 8.27(2H,d,J=6.8 Hz). MS (FAB) m/z: 511 [(M+H)$^+$, Cl$^{35}$], 513 [(M+H)$^+$, Cl$^{37}$]. Elementary analysis for $C_{25}H_{23}ClN_4O_4S \cdot 0.9H_2O \cdot 0.05CH_2Cl_2$ Calculated: C, 56.61; H, 4.72; Cl, 7.34; N, 10.54; S, 6.03. Found: C, 56.51; H, 4.71; Cl, 7.51; N, 10.37; S, 6.29.

Example A-109

2-[4-[[4-[(5-Chloroindol-2-yl)sulfonyl]piperazin-1-yl]carbonyl]phenyl]pyridine N-oxide $^1$H-NMR (DMSO-$d_6$) δ: 3.04–3.18(4H,br), 3.37–3.83 (4H,br), 7.03(1H,s), 7.33(1H,d,J=8.8 Hz), 7.38–7.44(2H,m), 7.45(2H,d,J=7.3 Hz), 7.50(1H,d,J=8.8 Hz), 7.61–7.67(1H, m), 7.80(1H,s), 7.85(2H,d,J=7.3 Hz), 8.33(1H,m), 12.40 (1H,br). MS (FAB) m/z: 497 [(M+H)$^+$, Cl$^{35}$], 499 [(M+H)$^+$, Cl$^{37}$]. Elementary analysis for $C_{24}H_{21}ClN_4O_4S \cdot 0.2H_2O$ Calculated: C, 57.59; H, 4.31; Cl, 7.08; N, 11.19; S, 6.41. Found: C, 57.72; H, 4.58; Cl, 7.13; N, 10.86; S, 6.29.

Example A-110

4-[4-[[4-[(5-Chloro-1-ethylindol-2-yl)sulfonyl] piperazin-1-yl]carbonyl]phenyl]pyridine N-oxide $^1$H-NMR (DMSO-$d_6$) δ: 1.30(3H,t,J=6.8 Hz), 3.18–3.38 (4H,br), 3.40–3.61(2H,br), 3.62–3.84(2H,br), 4.46(2H,q,J= 6.8 Hz), 7.16(1H,s), 7.41(1H,dd,J=8.8,2.0 Hz), 7.52(2H,d, J=7.3 Hz), 7.72(1H,d,J=8.8 Hz), 7.78–7.88(5H,m), 8.28(2H, d,J=7.3 Hz). MS (FAB) m/z: 525 [(M+H)$^+$, Cl$^{35}$], 527 [(M+H)$^+$, Cl$^{37}$]. Elementary analysis for $C_{26}H_{25}ClN_4O_4S \cdot 0.4H_2O$ Calculated: C, 58.67; H, 4.89; Cl, 6.66; N, 10.53; S, 6.02. Found: C, 58.73; H, 4.91; Cl, 6.88; N, 10.26; S, 5.96.

Example A-111

4-[4-[[4-[(5-Chloro-3-methylbenzo[b]thien-2-yl) sulfonyl]piperazin-1-yl]carbonyl]phenyl]pyridine N-oxide $^1$H-NMR (DMSO-$d_6$) δ: 2.67(3H,s), 3.12–3.29(4H,br), 3.37–3.86(4H,br), 7.48(2H,d,J=8.3 Hz), 7.65(1H,dd,J=8.8, 2.0 Hz), 7.80(2H,d,J=7.3 Hz), 7.81(2H,d,J=8.3 Hz), 8.12 (1H,d,J=2.0 Hz), 8.15(1H,d,J=8.8 Hz), 8.27(2H,d,J=7.3 Hz). MS (FAB) m/z: 528 [(M+H)$^+$, Cl$^{35}$], 530 [(M+H)$^+$, Cl$^{37}$]. Elementary analysis for $C_{25}H_{22}ClN_3O_4S_2 \cdot 0.7H_2O$ Calculated: C, 55.54; H, 4.36; Cl, 6.56; N, 7.77; S, 11.86. Found: C, 55.73; H, 4.40; Cl, 6.67; N, 7.52; S, 11.72.

Example A-112

4-[4-[[cis-4-[(5-Chloroindol-2-yl)sulfonyl]-2,6-dimethylpiperazin-1-yl]carbonyl]phenyl]pyridine N-oxide $^1$H-NMR (DMSO-$d_6$) δ: 1.32(6H,br), 2.60–2.70(2H,m), 3.40–3.60(2H,m), 3.80–4.10(1H,br), 4.50–4.90(1H,br), 7.01 (1H,s), 7.30–7.35(1H,m), 7.45–7.55(3H,m), 7.75–7.85(5H, m), 8.27(2H,d,J=6.8 Hz), 12.44(1H,s). Elementary analysis for $C_{26}H_{25}ClN_4O_4S \cdot 0.5H_2O$ Calculated: C, 58.48; H, 4.91; Cl, 6.64; N, 10.49; S, 6.00. Found: C, 58.68; H, 5.02; Cl, 6.72; N, 10.51; S, 6.04.

Example A-113

4-[4-[[4-[(5-Chlorobenzo[b]furan-2-yl)sulfonyl] piperazin-1-yl]carbonyl]phenyl]pyridine N-oxide $^1$H-NMR (CDCl$_3$) δ: 3.20–3.50(4H,br), 3.50–4.05(4H, br), 7.34(1H,s), 7.45–7.53(6H,m), 7.62(2H,d,J=7.8 Hz), 7.69(1H,s). MS (FAB) m/z: 498 [(M+H)$^+$, C$^{35}$], 500 [(M+H)$^+$, Cl$^{37}$]. Elementary analysis for $C_{24}H_{20}ClN_3O_5S \cdot 0.25H_2O$ Calculated: C, 57.37; H, 4.11; Cl, 7.06; N, 8.36; S, 6.38. Found: C, 57.31; H, 4.30; Cl, 7.17; N, 8.22; S, 6.40.

Example A-114

4-[4-[[4-[(6-Chlorobenzo[b]furan-2-yl)sulfonyl] piperazin-1-yl]carbonyl]phenyl]pyridine N-oxide $^1$H-NMR (CDCl$_3$) δ: 3.20–3.50(4H,br), 3.50–4.10(4H, br), 3.65–3.85(2H,br), 7.35–7.41(2H,br), 7.46–7.55(5H,br), 7.58–7.67(5H,m), 8.27(2H,d,J=5.9 Hz). HRMS (FAB) m/z: 498.0901 (M+H)⁺ (calcd for $C_{24}H_{21}ClN_3O_5S$ 498.0890).

Example A-115

4-[4-[[4-[(5-Chlorobenzo[b]thien-2-yl)sulfonyl]piperazin-1-yl]carbonyl]phenyl]pyridine N-oxide $^1$H-NMR (DMSO-d$_6$) δ: 3.02–3.90(8H,m), 7.59(2H,d,J=8.3 Hz), 7.64(1H,d,J=2.0 Hz), 8.01–8.05(3H,m), 8.18(1H,d,J=2.0 Hz), 8.20(1H,d,J=8.8 Hz), 8.31(2H,d,J=6.3 Hz), 8.94(2H,d,J=6.3 Hz). MS (FAB) m/z: 514 [(M+H)⁺, Cl$^{35}$], 516 [(M+H)⁺, Cl$^{37}$]. Elementary analysis for $C_{24}H_{20}ClN_3O_3S_2 \cdot 0.8H_2O$ Calculated: C, 54.55; H, 4.12; Cl, 6.71; N, 7.95; S, 12.14. Found: C, 54.66; H, 4.09; Cl, 6.95; N, 7.77; S, 11.87.

Example A-116

4-[4-[[4-[(6-Chlorobenzo[b]thien-2-yl)sulfonyl]piperazin-1-yl]carbonyl]phenyl]pyridine N-oxide $^1$H-NMR (DMSO-d$_6$) δ: 3.16–3.88(8H,m), 7.48(2H,d,J=8.3 Hz), 7.58(1H,dd,J=8.8,2.0 Hz), 7.77(1H,d,J=7.3 Hz), 7.79(1H,s), 7.81(2H,d,J=8.8 Hz), 8.08(2H,d,J=8.8 Hz), 8.27(1H,d,J=7.3 Hz), 8.33(1H,s). MS (FAB) m/z: 514 [(M+H)⁺, Cl$^{35}$], 516 [(M+H)⁺, Cl$^{37}$]. Elementary analysis for $C_{24}H_{20}ClN_3O_4S_2 \cdot 1.2H_2O$ Calculated: C, 53.82; H, 4.22; Cl, 6.62; N, 7.84; S, 11.97. Found: C, 53.66; H, 4.22; Cl, 6.81; N, 7.61; S, 11.72.

Example A-117

2-[4-[[4-[(6-Chlorobenzo[b]thien-2-yl)sulfonyl]piperazin-1-yl]carbonyl]phenyl]pyridine N-oxide $^1$H-NMR (DMSO-d$_6$) δ: 3.06–3.94(8H,m), 7.38–7.42(2H,m), 7.46(2H,d,J=8.3 Hz), 7.54–7.63(2H,m), 7.86(2H,d,J=8.3 Hz), 8.07(2H,t,J=4.4 Hz), 8.27–8.34(2H,m). MS (FAB) m/z: 514 [(M+H)⁺, Cl$^{35}$], 516 [(M+H)⁺, Cl$^{37}$]. Elementary analysis for $C_{24}H_{20}ClN_3O_4S_2 \cdot 0.5H_2O \cdot 0.1CH_2Cl_2$ Calculated: C, 54.56; H, 4.01; Cl, 7.99; N, 7.89; S, 12.04. Found: C, 54.93; H, 3.95; Cl, 7.90; N, 7.74; S, 11.71.

Example A-118

4-[4-[[4-[(5-Chlorobenzothiazol-2-yl)sulfonyl]piperazin-1-yl]carbonyl]phenyl]pyridine N-oxide $^1$H-NMR (CDCl$_3$) δ: 3.40–4.00(8H,m), 7.50(2H,d,J=7.3 Hz), 7.51(2H,d,J=8.3 Hz), 7.58(1H,dd,J=8.8,2.0 Hz), 7.63(2H,d,J=8.3 Hz), 7.93(1H,d,J=8.8 Hz), 8.19(1H,d,J=2.0 Hz), 8.27(2H,d,J=7.3 Hz). MS (FAB) m/z: 515 [(M+H)⁺, Cl$^{35}$], 517 [(M+H)⁺, Cl$^{37}$]. Elementary analysis for $C_{23}H_{19}ClN_4O_4S_2 \cdot 0.1H_2O$ Calculated: C, 53.45; H, 3.74; Cl, 6.86; N, 10.84; S, 12.41. Found: C, 53.19; H, 3.72; Cl, 7.09; N, 10.70; S, 12.29.

Example A-119

4-[4-[[4-[(6-Chlorobenzothiazol-2-yl)sulfonyl]piperazin-1-yl]carbonyl]phenyl]pyridine N-oxide $^1$H-NMR (DMSO-d$_6$) δ: 3.30–3.85(8H,m), 7.50(2H,d,J=8.3 Hz), 7.77(1H,dd,J=8.8,2.0 Hz), 7.80(2H,d,J=7.3 Hz), 7.83(2H,d,J=8.3 Hz), 8.28(2H,d,J=7.3 Hz), 8.29(1H,d,J=8.8 Hz), 8.50(1H,d,J=2.0 Hz). MS (FAB) m/z: 515 [(M+H)⁺, Cl$^{35}$], 517 [(M+H)⁺, Cl$^{37}$]. Elementary analysis for $C_{23}H_{19}ClN_4O_4S_2$ Calculated: C, 53.64; H, 3.72; Cl, 6.88; N, 10.88; S, 12.45. Found: C, 53.64; H, 3.99; Cl, 6.63; N, 10.90; S, 12.30.

Example A-120

4-[4-[[4-[(5-Ethynylindol-2-yl)sulfonyl]piperazin-1-yl]carbonyl]phenyl]pyridine N-oxide $^1$H-NMR (CDCl$_3$) δ: 2.80–3.90(8H,br), 4.05(1H,s), 7.06(1H,br s), 7.39(1H,d,J=8.8 Hz), 7.43–7.52(3H,m), 7.77–7.86(4H,m), 7.89(1H,br s), 8.27(2H,d,J=6.8 Hz), 12.43(1H,br s). MS (FAB) m/z: 487 (M+H)⁺. Elementary analysis for $C_{26}H_{22}N_4O_4S \cdot H_2O$ Calculated: C, 61.89; H, 4.79; N, 11.10; S, 6.36. Found: C, 62.00; H, 4.67; N, 11.08; S, 6.35.

Example A-121

1-[(6-Chloronaphthalen-2-yl)sulfonyl]-4-[[2-(pyridin-4-yl)pyrimidin-5-yl]carbonyl]piperazine In the same manner as in Example A-4, a reaction was effected, whereby the title compound was obtained.

$^1$H-NMR (DMSO-d$_6$) δ: 3.06(2H,br), 3.14(2H,br), 3.45–3.85(4H,m), 7.74(1H,d,J=8.3 Hz), 7.83(1H,d,J=8.8 Hz), 8.19(1H,d,J=8.3 Hz), 8.25–8.29(2H,m), 8.31(2H,d,J=5.9 Hz), 8.52(1H,br s), 8.89(2H,d,J=5.9 Hz), 9.02(2H,s). MS (FAB) m/z: 494 [(M+H)⁺, Cl$^{35}$], 496 [(M+H)⁺, Cl$^{37}$]. Elementary analysis for $C_{24}H_{20}ClN_5O_3S \cdot HCl \cdot H_2O$ Calculated: C, 52.56; H, 4.23; Cl, 12.93; N, 12.77; S, 5.85. Found: C, 52.47; H, 4.20; Cl, 13.09; N, 12.60; S, 5.98.

Example A-122

4-[5-[[4-[(6-Chloronaphthalen-2-yl)sulfonyl]piperazin-1-yl]carbonyl]pyrimidin-2-yl]pyridine N-oxide In the same manner as in Example A-6, a reaction was effected, whereby the title compound was obtained.

$^1$H-NMR (CDCl$_3$) δ: 3.05–3.30(4H,br), 3.55–4.00(4H,br), 7.61(1H,dd,J=8.3 and 2.0 Hz), 7.76(1H,dd,J=8.8 and 2.0 Hz), 7.91–7.97(3H,m), 8.25–8.29(2H,m), 8.31–8.35(3H,m), 8.77(2H,s). MS (FAB) m/z: 510 [(M+H)⁺, Cl$^{35}$], 512 [(M+H)⁺, Cl$^{37}$]. Elementary analysis for $C_{24}H_{20}ClN_5O_4S \cdot 0.8H_2O$ Calculated: C, 54.97; H, 4.15; Cl, 6.76; N, 13.36; S, 6.11. Found: C, 54.99; H, 4.08; Cl, 6.75; N, 13.24; S, 6.20.

Example A-123

1-[(6-Chloronaphthalen-2-yl)sulfonyl]-4-[[5-(pyridin-4-yl)pyrimidin-2-yl]carbonyl]piperazine In the same manner as in Example A-105, the title compound was obtained.

$^1$H-NMR (DMSO-d$_6$) δ: 2.94(2H,br s), 3.13(2H,br s), 3.37(2H,br s), 3.80(2H,br s), 7.74(1H,dd,J=8.8,2.4 Hz), 7.83(1H,dd,J=8.8,2.0 Hz), 8.05–8.18(2H,br), 8.19(1H,d,J=8.8 Hz), 8.25–8.32(2H,m), 8.52(1H,br s), 8.82–8.91(2H,br), 9.33–9.38(2H,m). MS (FAB) m/z: 494 [(M+H)⁺, Cl$^{35}$], 496 [(M+H)⁺, Cl$^{37}$]. Elementary analysis for $C_{24}H_{20}ClN_5O_3S \cdot 0.95HCl \cdot 0.5H_2O$ Calculated: C, 53.62; H, 4.12; Cl, 12.86; N, 13.03; S, 5.96. Found: C, 53.50; H, 4.09; Cl, 12.76; N, 12.87; S, 5.91.

Example A-124

4-[2-[[4-[(6-Chloronaphthalen-2-yl)sulfonyl]piperazin-1-yl]carbonyl]pyrimidin-5-yl]pyridine N-oxide In the same manner as in Example A-6, the title compound was obtained.

$^1$H-NMR (CDCl$_3$) δ: 3.14–3.17(2H,m), 3.25–3.28(2H, m), 3.55–3.58(2H,m), 3.94–3.98(2H,m), 7.50(2H,d,J=7.3 Hz), 7.60(1H,dd,J=8.8,2.0 Hz), 7.76(1H,dd,J=8.8,2.0 Hz), 7.91–7.96(3H,m), 8.30–8.35(3H,m), 8.98(2H,s). MS (FAB) m/z: 510 [(M+H)$^+$, Cl$^{35}$], 512 [(M+H)$^+$, Cl$^{37}$]. Elementary analysis for C$_{24}$H$_{20}$ClN$_5$O$_4$S.0.6H$_2$O Calculated: C, 55.35; H, 4.10; Cl, 6.81; N, 13.45; S, 6.16. Found: C, 55.01; H, 4.01; Cl, 7.00; N, 13.28; S, 6.28.

Example A-125

4-[4-[[4-[(6-Bromonaphthalen-2-yl)sulfonyl]piperazin-1-yl]carbonyl]phenyl]pyridine N-oxide In the same manner as in Example A-1, the title compound was obtained using 4-[4-[(piperazin-1-yl)carbonyl]phenyl]pyridine N-oxide hydrochloride and (6-bromonaphthalen-2-yl)sulfonyl chloride as starting materials.

$^1$H-NMR (CDCl$_3$) δ: 2.80–3.40(4H,br), 3.40–4.05(4H, br), 7.43(2H,d,J=7.8 Hz), 7.47(2H,d,J=7.1 Hz), 7.58(2H,d, J=7.8 Hz), 7.70–7.78(2H,m), 7.85(1H,d,J=8.8 Hz), 7.92(1H, d,J=8.8 Hz), 8.13(1H,s), 8.26(2H,d,J=7.1 Hz), 8.30(1H,s). MS (FAB) m/z: 552 [(M+H)$^+$, Br$^{79}$], 554 [(M+H)$^+$, Br$^{81}$9. Elementary analysis for C$_{26}$H$_{22}$BrN$_3$O$_4$S.0.5H$_2$O Calculated: C, 55.62; H, 4.13; N, 7.48; Br, 14.23; S, 5.71. Found: C, 55.36; H, 3.89; N, 7.41; Br, 14.20; S, 5.59.

Example A-126

1-[(6-Bromonaphthalen-2-yl)sulfonyl]-4-[4-(pyridin-4-yl)benzoyl]piperazine

In the same manner as in Example A-1, a reaction was effected, whereby the title compound was obtained.

$^1$H-NMR (CDCl$_3$) δ: 2.80–3.40(4H,br), 3.40–4.10(4H, br), 7.43(2H,d,J=8.3 Hz), 7.47(2H,d,J=5.6 Hz), 7.63(2H,d, J=8.3 Hz), 7.72–7.78(2H,m), 7.86(1H,d,J=8.8 Hz), 7.92(1H, d,J=8.8 Hz), 8.13(1H,d,J=1.5 Hz), 8.30(1H,s), 8.68(2H,d,J= 5.6 Hz). MS (FAB) m/z: 536 [(M+H)$^+$, Br$^{79}$], 538 [(M+H)$^+$, Br$^{81}$]. Elementary analysis for C$_{26}$H$_{22}$BrN$_3$O$_3$S.0.5H$_2$O Calculated: C, 57.25; H, 4.25; N, 7.70; Br, 14.65; S, 5.88. Found: C, 57.51; H, 3.96; N, 7.67; Br, 14.76; S, 6.01.

Example A-127

1-[(6-Ethynylnaphthalen-2-yl)sulfonyl]-4-(4-(pyridin-4-yl)benzoyl]piperazine

To a solution of 1-[(6-bromonaphthalen-2-yl)sulfonyl]-4-[4-(pyridin-4-yl)benzoyl]piperazine (310 mg) and triphenylphosphine (455 mg) in tetrahydrofuran (1.0 ml), triethylamine (3.0 ml), N,N-dimethylformamide (1.0 ml), trimethylsilylacetylene (130 ml) and palladium acetate (13.0 mg) were added, followed by heating under reflux for 2 hours. After the reaction mixture was allowed to cool down to room temperature, dichloromethane (15 ml) and water (30 ml) were added to separate the organic layer. The organic layer thus obtained was dried over anhydrous sodium sulfate and distilled under reduced pressure to remove the solvent. The residue was purified by chromatography on a silica gel column (dichloromethane:acetone=3:1), whereby colorless amorphous was obtained. The resulting product was dissolved in methanol (25 ml), followed by the addition of tetrahydrofuran (5.0 ml) and potassium carbonate (300 mg). The resulting mixture was stirred for 30 minutes. Dichloromethane (30 ml) and water (50 ml) were added to the reaction mixture to separate the organic layer. The organic layer thus obtained was dried over anhydrous sodium sulfate and distilled under reduced pressure to remove the solvent. The residue was purified by chromatography on a silica gel column (dichloromethane acetone=4:1), followed by pulverization and washing in a mixed solvent of dichloromethane, acetone and water, whereby the title compound (210 mg, 75%) was obtained.

$^1$H-NMR (CDCl$_3$) δ: 2.80–4.10(8H,br), 7.43(2H,d,J=8.3 Hz), 7.47(2H,d,J=6.4 Hz), 7.67(2H,d,J=8.3 Hz), 7.68(1H, dd,J=8.8,1.5 Hz), 7.75(1H,dd,J=8.3,1.5 Hz), 7.93(1H,d,J= 8.3 Hz), 7.97(1H,d,J=8.8 Hz), 8.11(1H,s), 8.30(1H,s), 8.68 (2H,d,J=6.4 Hz). MS (FAB) m/z: 482 (M+H)$^+$. Elementary analysis for C$_{28}$H$_{23}$N$_3$O$_3$S.0.4H$_2$O Calculated: C, 68.81; H, 4.91; N, 8.60; S, 6.56. Found: C, 68.96; H, 4.91; N, 8.47; S, 6.52.

Example A-128

4-[4-[[4-[(6-Ethynylnaphthalen-2-yl)sulfonyl]piperazin-1-yl]carbonyl]phenyl]pyridine N-oxide In the same manner as in Example A-6, the title compound was obtained.

$^1$H-NMR (CDCl$_3$) δ: 2.95–4.00(8H,br), 7.42(2H,d,J=8.3 Hz), 7.46(2H,d,J=6.8 Hz), 7.58(2H,d,J=8.3 Hz), 7.68(1H, dd,J=8.8,1.5 Hz), 7.75(1H,dd,J=8.3,1.5 Hz), 7.92(1H,d,J= 8.8 Hz), 7.95(1H,d,J=8.3 Hz), 8.10(1H,s), 8.25(2H,d,J=6.8 Hz), 8.30(1H,s). MS (FAB) m/z: 498 [(M+H)$^+$]. Elementary analysis for C$_{28}$H$_{23}$N$_3$O$_4$S.H$_2$O Calculated: C, 65.23; H, 4.89; N, 8.15; S, 6.22. Found: C, 65.41 H, 5.14; N, 8.19; S, 6.11.

Example A-129

2-Carbamoylmethyl-4-[(5-chloro-1-phenylsulfonyl-5-chloroindol-2-ylsulfonyl]-1-[4-(pyridin-4-yl)benzoyl]piperazine In the same manner as in Example A-7 or Example A-1, a reaction was effected, whereby the title compound was obtained.

$^1$H-NMR (CDCl$_3$) δ: 2.44–3.28(4H,m), 3.50–4.14(2H, m), 4.45–4.78(1H,m), 5.58–5.79(1H,m), 7.44–7.65(13H,m), 7.69(2H,d,J=8.3 Hz), 8.05(2H,d,J=8.3 Hz), 8.13–8.17(1H, m), 8.69(2H,d,J=5.9 Hz). MS (FAB) m/z: 678 [(M+H)$^+$, Cl$^{35}$], 680 [(M+H)$^+$, Cl$^{37}$].

Example A-130

2-Carbamoylmethyl-4-[(5-chloroindol-2-yl)sulfonyl]-1-[4-(pyridin-4-yl)benzoyl]piperazine In the same manner as in Example A-99, the title compound was obtained.

$^1$H-NMR (DMSO-d$_6$) δ: 2.55–2.80(2H,m), 3.00–4.56 (6H,m), 5.05–5.17(1H,m), 6.90–7.05(2H,m), 7.34(1H,dd,J= 8.8,2.2 Hz), 7.40–7.63(4H,m), 7.79(1H,m), 7.99(1H,m), 8.24(2H,br), 8.90(1H,m), 12.43(1H,s). MS (FAB) m/z: 538 [(M+H)$^+$, Cl$^{35}$], 540 [(M+H)$^+$, Cl$^{37}$]. Elementary analysis for C$_{26}$H$_{24}$ClN$_5$O$_4$S.1.2HCl.2.5H$_2$O Calculated: C, 49.82; H, 4.86; Cl, 12.44; N, 11.17; S, 5.12. Found: C, 50.14; H, 5.07; Cl, 12.54; N, 10.80; S, 5.18.

Example A-131

1-[(5-Chloroindol-2-yl)sulfonyl]-4-[[2-(pyridin-4-yl)pyrimidin-5-yl]carbonyl]piperazine In the same manner as in Example A-4, a reaction was effected, whereby the title compound was obtained.

¹H-NMR (DMSO-d₆) δ: 3.08(2H,br), 3.18(2H,br), 3.52 (2H,br), 3.77(2H,br), 7.04(1H,d,J=1.5 Hz), 7.34(1H,dd,J= 8.8,2.0 Hz), 7.50(1H,d,J=8.8 Hz), 7.80(1H,d,J=2.0 Hz), 8.48–8.53(2H,m), 8.91–8.95(2H,m), 9.07(2H,s), 12.46(1H, br s). MS (FAB) m/z: 483 [(M+H)⁺, Cl³⁵], 485 [(M+H)⁺, Cl³⁷]. Elementary analysis for C₂₂H₁₉ClN₆O₃S.HCl.1.3H₂O.0.2EtOH Calculated: C, 48.74; H, 4.35; Cl, 12.84; N, 15.22; S, 5.81. Found: C, 48.87; H, 4.38; Cl, 12.82; N, 15.02; S, 5.86.

Example A-132

1-[(6-Chlorobenzothiophen-2-yl)sulfonyl]-4-[[5-(pyridin-4-yl)pyrimidin-2-yl]carbonyl]piperazine In the same manner as in Example A-105, the title compound was obtained.

¹H-NMR (DMSO-d₆) δ: 3.03–3.06(2H,m), 3.20–3.23 (2H,m), 3.41–3.44(2H,m), 3.83–3.86(2H,m), 7.61(1H,dd,J= 8.8,2.0 Hz), 8.10(1H,d,J=8.8 Hz), 8.13(1H,s), 8.30–8.40 (3H,m), 8.90–9.02(2H,br), 9.40–9.46(2H,m). MS (FAB) m/z: 500 [(M+H)⁺, Cl³⁵], 502 [(M+H)⁺, Cl³⁷]. Elementary analysis for C₂₂H₁₈ClN₅O₃S.HCl.0.7H₂O Calculated: C, 48.13; H, 3.74; Cl, 12.91; N, 12.75; S, 11.68. Found: C, 47.95; H, 3.78; Cl, 13.13; N, 12.65; S, 11.53.

Example A-133

4-[2-[[4-[(6-Chlorobenzo[b]thien-2-yl)sulfonyl] piperazin-1-yl]carbonyl]pyrimidin-5-yl]pyridine N-oxide In the same manner as in Example A-6, a reaction was effected, whereby the title compound was obtained.

¹H-NMR (CDCl₃) δ: 3.24(2H,br), 3.34(2H,br), 3.60(2H, br), 3.98(2H,br), 7.47(1H,dd,J=8.8,2.0 Hz), 7.52(2H,d,J=7.3 Hz), 7.79(1H,s), 7.83(1H,d,J=8.8 Hz), 7.88(1H,br s), 8.33 (2H,d,J=7.3 Hz), 9.00(2H,s). MS (FAB) m/z: 516 [(M+H)⁺, Cl³⁵], 518 [(M+H)⁺, Cl³⁷]. Elementary analysis for C₂₂H₁₈ClN₅O₄S.0.4H₂O Calculated: C, 50.50; H, 3.62; Cl, 6.78; N, 13.39; S, 12.26. Found: C, 50.24; H, 3.62; Cl, 7.14; N, 13.19; S, 12.04.

Example A-134

4-[2-[[4-[(5-Chloroindol-2-yl)sulfonyl]piperazin-1-yl]carbonyl]pyrimidin-5-yl]pyridine N-oxide In the same manner as in Example A-6, a reaction was effected, whereby the title compound was obtained.

¹H-NMR (DMSO-d₆) δ: 2.95(2H,br), 3.15(2H,br), 3.37 (2H,br), 3.79(2H,br), 7.05(1H,s), 7.34(1H,dd,J=8.8,1.5 Hz), 7.51(1H,d,J=8.8 Hz), 7.80(1H,d,J=1.5 Hz), 7.95(2H,d,J=7.3 Hz), 8.37(2H,d,J=7.3 Hz), 9.28(2H,s), 12.47(1H,s). MS (FAB) m/z: 499 [(M+H)⁺, Cl³⁵], 501 [(M+H)⁺, Cl³⁷]. Elementary analysis for C₂₂H₁₉ClN₆O₄S.0.5H₂O.0.2EtOH Calculated: C, 52.02; H, 4.13; Cl, 6.86; N, 16.25; S, 6.20. Found: C, 52.03; H, 3.99; Cl, 7.18; N, 15.99; S, 6.16.

Example A-135

4-[5-[[4-[(5-Chloroindol-2-yl)sulfonyl]piperazin-1-yl]carbonyl]pyrimidin-2-yl]pyridine N-oxide In the same manner as in Example A-6, a reaction was effected, whereby the title compound was obtained.

¹H-NMR (DMSO-d₆) δ: 3.09(2H,br), 3.16(2H,br), 3.53 (2H,br), 3.75(2H,br), 7.03(1H,s), 7.32(1H,dd,J=8.8,2.0 Hz), 7.50(1H,d,J=8.8 Hz), 7.79(1H,d,J=2.0 Hz), 8.27(2H,d,J=7.3 Hz), 8.34(2H,d,J=7.3 Hz), 8.95(2H,s), 12.42(1H,br s). MS (FAB) m/z: 499 [(M+H)⁺, Cl³⁵], 501 [(M+H)⁺, C³⁷]. Elementary analysis for C₂₂H₁₉ClN₆O₄S.H₂O Calculated: C, 51.11; H, 4.09; Cl, 6.86; N, 16.26; S, 6.20. Found: C, 51.29; H, 4.34; Cl, 6.80; N, 15.90; S, 6.08.

Example A-136

1-[(5-Chloroindol-2-yl)sulfonyl]-4-[[5-(pyridin-4-yl) pyrimidin-2-yl]carbonyl]piperazine In the same manner as in Example A-105, the title compound was obtained.

¹H-NMR (DMSO-d₆) δ: 3.20(2H,t,J=4.9 Hz), 3.62–3.78 (2H,m), 3.45–3.60(2H,m), 3.78(2H,t,J=4.9 Hz), 4.63(2H,s), 4.64(2H,s), 7.35(1H,d,J=8.3 Hz), 7.38(1H,d,J=8.3 Hz), 7.42 (1H,s), 8.22(2H,d,J=5.4 Hz), 8.92(2H,d,J=5.4 Hz), 9.44(2H, s). MS (FAB) m/z: 485 [(M+H)⁺, Cl³⁵], 487 [(M+H)⁺, Cl³⁷]. Elementary analysis for C₂₂H₂₁ClN₆O₃S HCl.1.8H₂O Calculated: C, 47.71; H, 4.66; Cl, 12.80; N, 15.17; S, 5.79. Found: C, 48.01; H, 4.39; Cl, 13.19; N, 14.74; S, 573.

In the same manner as in Example A-4, the compounds shown in Examples A-137 and A-138 were synthesized.

Example A-137

1-[(6-Chloronaphthalen-2-yl)sulfonyl]-4-[[5-(pyridin-4-yl)pyrazin-2-yl]carbonyl]piperazine ¹H-NMR (DMSO-d₆) δ: 3.01(2H,br), 3.14(2H,br), 3.62 (2H,br), 3.81(2H,br), 7.74(1H,dd,J=8.8,2.0 Hz), 7.84(1H, dd,J=8.8,2.0 Hz), 8.19(1H,d,J=8.8 Hz), 8.25–8.31(2H,m), 8.46(2H,d,J=5.4 Hz), 8.52(1H,br s), 8.91(3H,m), 9.47(1H, s). MS (FAB) m/z: 494 [(M+H)⁺, Cl³⁵], 496 [(M+H)⁺, Cl³⁷]. Elementary analysis for C₂₄H₂₀ClN₅O₃S.HCl-H₂O.0.2AcOEt Calculated: C, 52.62; H, 4.38; Cl, 12.53; N, 12.37; S, 5.66. Found: C, 52.47; H, 4.51; Cl, 12.87; N, 12.09; S, 5.68.

Example A-138

1-[(5-Chloroindol-2-yl)sulfonyl]-4-[[5-(pyridin-4-yl) pyrazin-2-yl]carbonyl]piperazine ¹H-NMR (DMSO-d₆) δ: 3.04(2H,br), 3.18(2H,br), 3.63 (2H,br), 3.81(2H,br), 7.05(1H,s), 7.33(1H,dd,J=8.8,2.0 Hz), 7.50(1H,d,J=8.8 Hz), 7.79(1H,d,J=2.0 Hz), 8.11(2H,d,J=6.4 Hz), 8.77(2H,d,J=6.4 Hz), 8.93(1H,d,J=1.5 Hz), 9.34(1H,d, J=1.5 Hz), 12.43(1H,br s). MS (FAB) m/z: 483 [(M+H)⁺, Cl³⁵], 485 [(M+H)⁺, Cl³⁷]. Elementary analysis for C₂₂H₁₉ClN6O₃S.H₂O Calculated: C, 52.75; H, 4.23; Cl, 7.08; N, 16.78; S, 6.40. Found: C, 52.78; H, 4.27; Cl, 7.17; N, 16.67; S, 6.37.

In the same manner as in Example A-6, reaction was effected, whereby the compounds shown in Examples A-139 and A-140 were synthesized.

Example A-139

4-[5-[[4-[(6-Chloronaphthalen-2-yl)sulfonyl] piperazin-1-yl]carbonyl]pyrazin-2-yl]pyridine N-oxide ¹H-NMR (CDCl₃) δ: 3.19(2H,br), 3.26(2H,br), 3.88(2H, br), 3.94(2H,br), 7.59(1H,dd,J=8.8,2.0 Hz), 7.78(1H,dd,J= 8.8,2.0 Hz), 7.91–7.95(3H,m), 7.98(2H,d,J=7.3 Hz), 8.30 (2H,d,J=7.3 Hz), 8.32(1H,d,J=2.0 Hz), 8.90(1H,d,J=1.5 Hz), 8.99(1H,d,J=1.5 Hz). MS (FAB) m/z: 510 [(M+H)⁺, Cl³⁵], 512 [(M+H)⁺, Cl³⁷]. Elementary analysis for $C_{24}H_{20}ClN_5O_4S\cdot1.1H_2O$ Calculated: C, 54.41; H, 4.22; Cl, 6.69; N, 13.22; S, 6.05. Found: C, 54.27; H, 4.61; Cl, 6.99; N, 13.28; S, 6.12.

Example A-140

4-[5-[[4-[(5-Chloroindol-2-yl)sulfonyl]piperazin-1-yl]carbonyl]pyrazin-2-yl]pyridine N-oxide $^1$H-NMR (DMSO-d$_6$) δ: 3.03(2H,br), 3.17(2H,br), 3.63 (2H,br), 3.80(2H,br), 7.04(1H,s), 7.33(1H,dd,J=8.8,2.0 Hz), 7.50(1H,d,J=8.8 Hz), 7.80(1H,d,J=2.0 Hz), 8.19(2H,d,J=7.3 Hz), 8.37(2H,d,J=7.3 Hz), 8.87(1H,d,J=1.5 Hz), 9.31(1H,d, J=1.5 Hz), 12.45(1H,br s). MS (FAB) m/z: 499 [(M+H)$^+$, Cl$^{35}$], 501 [(M+H)$^+$, Cl$^{37}$]. Elementary analysis for $C_{22}H_{19}ClN_6O_4S\cdot H_2O$ Calculated: C, 51.11; H, 4.09; Cl, 6.86; N, 16.26; S, 6.20. Found: C, 50.92; H, 4.05; Cl, 6.96; N, 15.88; S, 6.10.

Example A-141

1-[(6-Chloronaphthalen-2-yl)sulfonyl]-4-[4-(3-methylpyridin-4-yl)benzoyl]piperazine hydrochloride In the same manner as in Example A-4, a reaction was effected, whereby the title compound was obtained.

$^1$H-NMR (DMSO-d$_6$) δ: 2.36(3H,s), 2.95–3.30(4H,br), 3.35–3.90(4H,br), 7.50(2H,d,J=8.8 Hz), 7.53(2H,d,J=8.8 Hz), 7.71(1H,d,J=5.4 Hz), 7.73(1H,dd,J=8.8,2.0 Hz), 7.83 (1H,dd,J=8.8,2.0 Hz), 8.18(1H,d,J=8.8 Hz), 8.24–8.30(2H, m), 8.50(1H,br s), 8.72(1H,d,J=5.4 Hz), 8.80(1H,s). MS (FAB) m/z: 506 [(M+H)$^+$, Cl$^{35}$], 508 [(M+H)$^+$, Cl$^{37}$]. Elementary analysis for $C_{27}H_{24}ClN_3O_3S\cdot0.8HCl\cdot1.5H_2O$ Calculated: C, 57.68; H, 4.98; Cl, 11.35; N, 7.48; S, 5.70. Found: C, 57.50; H, 5.06; Cl, 11.35; N, 7.28; S, 5.95.

Example A-142

4-[4-[[4-[(6-Chloronaphthalen-2-yl)sulfonyl]piperazin-1-yl]carbonyl]phenyl]-3-methylpyridine N-oxide In the same manner as in Example A-6, a reaction was effected, whereby the title compound was obtained.

$^1$H-NMR (CDCl$_3$) δ: 2.21(3H,s), 3.14(4H,br), 3.68(2H, br), 3.85(2H,br), 7.09(1H,d,J=6.8 Hz), 7.32(2H,d,J=8.3 Hz), 7.41(2H,d,J=8.3 Hz), 7.60(1H,dd,J=8.8,2.0 Hz), 7.77(1H, dd,J=8.8,2.0 Hz), 7.90–7.96(3H,m), 8.11(1H,dd,J=6.4,1.5 Hz), 8.15(1H,br s), 8.31(1H,br s). MS (FAB) m/z: 522 [(M+H)$^+$, Cl$^{35}$], 524 [(M+H)$^+$, Cl$^{37}$]. Elementary analysis for $C_{27}H_{24}ClN_3O_4S\cdot0.1H_2O$ Calculated: C, 61.92; H, 4.66; Cl, 6.77; N, 8.02; S, 6.12. Found: C, 61.76; H, 4.72; Cl, 7.04; N, 7.76; S, 6.30.

Example A-143

1-(4-Amidinobenzoyl)-4-[(6-chloronaphthalen-2-yl)sulfonyl]piperazine

In the same manner as in Example A-4, a reaction was effected, whereby the title compound was obtained.

$^1$H-NMR (DMSO-d$_6$) δ: 3.03(2H,br s), 3.13(2H,br s), 3.30(2H,br s), 3.73(2H,br s), 7.56(2H,d,J=8.3 Hz), 7.73(1H, dd,J=8.8,2.0 Hz), 7.78–7.85(3H,m), 8.18(1H,d,J=8.3 Hz), 8.25–8.30(2H,m), 8.50(1H,s), 9.10(2H,br s), 9.38(2H,br s). MS (FAB) m/z: 457 [(M+H)$^+$, Cl$^{35}$], 459 [(M+H)$^+$, Cl$^{37}$].

Example A-144

1-[(6-Chloronaphthalen-2-yl)sulfonyl]-4-[4-(4,5-dihydroimidazol-2-yl)benzoyl]piperazine $^1$H-NMR (DMSO-d$_6$) δ: 3.04(2H,br s), 3.13(2H,br s), 3.37(2H,br s), 3.74(2H,br s), 4.00(4H,s), 7.60(2H,d,J=8.3 Hz), 7.73(1H,dd,J=8.8,2.0 Hz), 7.83(1H,d,J=8.8 Hz), 8.11 (2H,d,J=8.3 Hz), 8.19(1H,d,J=8.8 Hz), 8.26(1H,d,J=2.0 Hz), 8.28(1H,d,J=8.8 Hz), 8.50(1H,s), 11.00(2H,br s). MS (FAB) m/z: 483 [(M+H)$^+$, Cl$^{35}$], 485 [(M+H)$^+$, Cl$^{37}$].

Example A-145

1-[(6-Chloronaphthalen-2-yl)sulfonyl]-4-[4-[2-(N-tert-butoxycarbonylamino)pyridin-4-yl]benzoyl]piperazine In the same manner as in Example A-4, the title compound was obtained.

$^1$H-NMR (CDCl$_3$) δ: 1.54(9H,s), 3.00–3.30(4H,m), 3.40–4.10(4H,m), 7.14(1H,dd,J=5.4,1.5 Hz), 7.38(2H,d,J= 8.3 Hz), 7.53(1H,br s), 7.60(1H,dd,J=8.8,2.0 Hz), 7.67(2H, d,J=8.3 Hz), 7.77(1H,dd,J=8.3,1.5 Hz), 7.91–7.98(3H,m), 8.18(1H,d,J=1.5 Hz), 8.29(1H,d,J=5.4 Hz), 8.32(1H,s).

Example A-146

1-[4-(2-Aminopyridin-4-yl)benzoyl]-4-[(6-chloronaphthalen-2-yl)sulfonyl]piperazine In the same manner as in Example A-7, the title compound was obtained.

$^1$H-NMR (DMSO-d$_6$) δ: 2.95–3.25(4H,m), 3.30–3.93 (4H,m), 7.14–7.23(2H,m), 7.51(2H,d,J=8.3 Hz), 7.66–7.75 (1H,m), 7.76(2H,d,J=8.8 Hz), 7.82(1H,m), 8.03(1H,d,J=6.8 Hz), 8.05–8.12(2H,m), 8.13–8.30(3H,m), 8.50(1H,s), 13.60 (1H,br). MS (FAB) m/z: 507 [(M+H)$^+$, Cl$^{35}$], 509 [(M+H)$^+$, Cl$^{37}$]. Elementary analysis for $C_{26}H_{23}ClN_4O_3S\cdot HCl\cdot3.6H_2O$ Calculated: C, 51.34; H, 5.17; Cl, 11.66; N, 9.21; S, 5.27. Found: C, 51.07; H, 5.24; Cl, 11.85; N, 9.10; S, 5.75.

Example A-147

2-tert-Butoxycarbonylamino-4-[4-[[4-[(6-chloronaphthalen-2-yl)sulfonyl]piperazin-1-yl]carbonyl]phenyl]pyridine N-oxide In the same manner as in Example A-6, the title compound was obtained.

$^1$H-NMR (CDCl$_3$) δ: 1.55(9H,s), 2.95–3.35(4H,br), 3.50–4.00(4H,m), 7.11(1H,dd,J=6.8,2.5 Hz), 7.40(2H,d,J= 8.3 Hz), 7.60(1H,dd,J=8.8,2.0 Hz), 7.64(2H,d,J=8.3 Hz), 7.77(1H,dd,J=8.8,2.0 Hz), 7.91–7.98(3H,m), 8.25(1H,d,J= 6.8 Hz), 8.31(1H,d,J=2.0 Hz), 8.42(1H,d,J=2.5 Hz), 9.28 (1H,s). MS (FAB) m/z: 623 [(M+H)$^+$, Cl$^{35}$], 625 [(M+H)$^+$, Cl$^{37}$]. Elementary analysis for $C_{31}H_{31}ClN_4O_6S\cdot0.1H_2O$ Calculated: C, 59.58; H, 5.03; Cl, 5.67; N, 8.97; S, 5.13. Found: C, 59.43; H, 5.04; Cl, 5.95; N, 8.89; S, 5.17.

Example A-148

2-Amino-4-[4-[[4-[(6-chloronaphthalen-2-yl)sulfonyl]piperazin-1-yl]carbonyl]phenyl]pyridine N-oxide In the same manner as in Example A-7, the title compound was obtained.

$^1$H-NMR (DMSO-d$_6$) δ: 2.95–3.25(4H,br), 3.30–3.90 (4H,m), 7.14(1H,dd,J=6.8,2.0 Hz), 7.28(1H,d,J=2.0 Hz), 7.49(2H,d,J=8.3 Hz), 7.70–7.78(3H,m), 7.82(1H,dd,J=8.8, 2.0 Hz), 8.16(2H,br), 8.18(1H,d,J=8.8 Hz), 8.25–8.30(2H, m), 8.32(1H,d,J=6.8 Hz), 8.50(1H,br s). MS (FAB) m/z: 523 [(M+H)$^+$, Cl$^{35}$], 525 [(M+H)$^+$, Cl$^{37}$]. Elementary analysis for $C_{26}H_{23}ClN_4O_4S\cdot HCl\cdot1.5H_2O$ Calculated: C, 53.25; H, 4.64; Cl, 12.09; N, 9.55; S, 5.47. Found: C, 53.21; H, 4.67; Cl, 11.96; N, 9.53; S, 5.61.

Example A-149

4-[5-[[4-[(6-Chloronaphthalen-2-yl)sulfonyl]piperazin-1-yl]carbonyl]pyridin-2-yl]pyridine N-oxide In the same manner as in Example A-6, the title compound was obtained.

$^1$H-NMR (CDCl$_3$) δ: 3.00–3.40(4H,br s), 3.50–4.05(4H,m), 7.61(1H,dd,J=8.8,2.0 Hz), 7.73–7.83(3H,m), 7.90–7.97(5H,m), 8.27(2H,d,J=7.3 Hz), 8.31(1H,br s), 8.63(1H,m). MS (FAB) m/z: 509 [(M+H)$^+$, Cl$^{35}$], 511 [(M+H)$^+$, Cl$^{37}$]. Elementary analysis for C$_{25}$H$_{21}$ClN$_4$O$_4$S.0.5H$_2$O Calculated: C, 57.97; H, 4.28; Cl, 6.84; N, 10.82; S, 6.19. Found: C, 57.99; H, 4.51; Cl, 6.99; N, 10.54; S, 6.53.

Example A-150

1-[(6-Chloronaphthalen-2-yl)sulfonyl]-4-[[1-oxo-6-(1-oxopyridin-4-yl)pyridin-3-yl]carbonyl]piperazine In the same manner as in Example A-6, the title compound was obtained.

$^1$H-NMR (CDCl$_3$) δ: 3.15(4H,br s), 3.50–4.00(4H,m), 7.20–7.30(1H,m), 7.52(1H,d,J=8.3 Hz), 7.61(1H,dd,J=8.8,2.0 Hz), 7.76(1H,dd,J=8.8,2.0 Hz), 7.89(2H,d,J=7.3 Hz), 7.91–7.97(3H,m), 8.21(1H,d,J=1.5 Hz), 8.26(2H,d,J=7.3 Hz), 8.31(1H,br s). MS (FAB) m/z: 525 [(M+H)$^+$, Cl$^{35}$], 527 [(M+H)$^+$, Cl$^{37}$]. Elementary analysis for C$_{25}$H$_{21}$ClN$_4$O$_5$S.0.1H$_2$O Calculated: C, 57.00; H, 4.06; Cl, 6.73; N, 10.64; S, 6.09. Found: C, 57.03; H, 4.23; Cl, 6.82; N, 10.34; S, 6.15.

Example A-151

1-[4-(2-Acetoxymethylpyridin-4-yl)benzoyl]-4-[(6-chloronaphthalen-2-yl)sulfonyl]piperazine hydrochloride In acetic anhydride (25 ml), 4-[4-[[4-[(6-chloronaphthalen-2-yl)sulfonyl]piperazin-1-yl]carbonyl]phenyl]-2-methylpyridine N-oxide (900 mg) was dissolved, followed by heating under reflux for 15 minutes. Ethanol (25 ml) was added to the reaction mixture and the resulting mixture was heated under reflux for further 1 hour. To the reaction mixture, dichloromethane and an aqueous solution of sodium bicarbonate were added to separate the organic layer. The organic layer thus obtained was dried over anhydrous sodium sulfate and 775 concentrated under reduced pressure to remove the solvent. The residue was purified by chromatography on a silica gel column (dichloromethane~1.5% methanol—dichloromethane), followed by crystallization from ethanol. The crystals were dissolved in dichloromethane and the resulting solution was made acidic by the addition of hydrochloric acid in ethanol. The resulting acidic mixture was concentrated, whereby the title compound (842 mg, 87%, pale yellow powder) was obtained.

$^1$H-NMR (DMSO-d$_6$) δ: 2.12(3H,s), 3.06(4H,br), 3.30–3.80(4H,br), 5.23(2H,s), 7.48(2H,d,J=8.3 Hz), 7.72(1H,dd,J=8.8,2.4 Hz), 7.78(1H,d,J=5.4 Hz), 7.79–7.87(4H,m), 8.17(1H,d,J=8.8 Hz), 8.23–8.29(2H,m), 8.49(1H,br s), 8.67(1H,d,J=5.4 Hz). MS (FAB) m/z: 564 [(M+H)$^+$, Cl$^{35}$], 566 [(M+H)$^+$, Cl$^{37}$]. Elementary analysis for C$_{29}$H$_{26}$ClN$_3$O$_5$S.0.4HCl.0.7H$_2$O Calculated: C, 58.91; H, 4.74; Cl, 8.39; N, 7.11; S, 5.42. Found: C, 58.86; H, 4.69; Cl, 8.29; N, 6.99; S, 5.41.

Example A-152

1-[(6-Chloronaphthalen-2-yl)sulfonyl]-4-[4-(2-hydroxymethylpyridin-4-yl)benzoyl]piperazine In the same manner as in Example A-3, the title compound was obtained.

$^1$H-NMR (DMSO-d$_6$) δ: 3.08(4H,br), 3.47(2H,br), 3.71(2H,br), 4.66(2H,s), 7.49(2H,d,J=8.3 Hz), 7.64(1H,d,J=5.4 Hz), 7.73(1H,dd,J=8.8,2.0 Hz), 7.78–7.85(4H,m), 8.18(1H,d,J=8.8 Hz), 8.23–8.30(2H,m), 8.50(1H,br s), 8.58(1H,d,J=5.4 Hz). MS (FAB) m/z: 522 [(M+H)$^+$, Cl$^{35}$], 524 [(M+H)$^+$, Cl$^{37}$]. Elementary analysis for C$_{27}$H$_{24}$ClN$_3$O$_4$S.0.25HCl.1.2H$_2$O Calculated: C, 58.67; H, 4.86; Cl, 8.02; N, 7.60; S, 5.80. Found: C, 58.73; H, 4.77; Cl, 7.94; N, 7.39; S, 5.82.

Example A-153

2-Acetoxymethyl-4-[4-[[4-[(6-chloronaphthalen-2-yl)sulfonyl]piperazin-1-yl]carbonyl]phenyl]pyridine N-oxide In the same manner as in Example A-6, the title compound was obtained.

$^1$H-NMR (CDCl$_3$) δ: 2.21(3H,s), 3.14(4H,br), 3.30–4.10(4H,br), 5.42(2H,s), 7.40–7.46(3H,m), 7.54–7.64(4H,m), 7.76(1H,d,J=7.3 Hz), 7.90–7.97(3H,m), 8.29(1H,d,J=6.4 Hz), 8.31(1H,br s). MS (FAB) m/z: 580 [(M+H)$^+$, Cl$^{35}$], 582 [(M+H)$^+$, Cl$^{37}$]. Elementary analysis for C$_{29}$H$_{26}$ClN$_3$O$_6$S.0.3H$_2$O Calculated: C, 59.49; H, 4.58; Cl, 6.06; N, 7.18; S, 5.48. Found: C, 59.33; H, 4.63; Cl, 6.18; N, 7.26; S, 5.49.

Example A-154

4-[4-[[4-[(6-Chloronaphthalen-2-yl)sulfonyl]piperazin-1-yl]carbonyl]phenyl]-2-hydroxymethylpyridine N-oxide In the same manner as in Example A-3, the title compound was obtained.

$^1$H-NMR (CDCl$_3$) δ: 3.06(4H,br), 3.30–3.90(4H,br), 4.63(2H,d,J=5.4 Hz), 5.66(1H,t,J=5.4 Hz), 7.46(2H,d,J=8.3 Hz), 7.70(1H,dd,J=6.8,2.9 Hz), 7.73(1H,dd,J=8.8,2.0 Hz), 7.78(2H,d,J=8.3 Hz), 7.80–7.84(2H,m), 8.18(1H,d,J=8.8 Hz), 8.25–8.32(3H,m), 8.50(1H,br s). MS (FAB) m/z: 538 [(M+H)$^+$, Cl$^{35}$], 540 [(M+H)$^+$, Cl$^{37}$]. Elementary analysis for C$_{27}$H$_{24}$ClN$_3$O$_5$S.0.4H$_2$O Calculated: C, 59.48; H, 4.58; Cl, 6.50; N, 7.71; S, 5.88. Found: C, 59.60; H, 4.56; Cl, 6.50; N, 7.52; S, 5.92.

Example A-155

1-[4-(2-Aminomethylpyridin-4-yl)benzoyl]-4-[(6-chloronaphthalen-2-yl)sulfonyl]piperazine hydrochloride At room temperature, 1-[4-(2-azidomethylpyridin-4-yl)benzoyl]-4-[(6-chloronaphthalen-2-yl)sulfonyl]piperazine (159 mg) was dissolved in tetrahydrofuran (5 ml), followed by the addition of water (0.5 ml) and triphenylphosphine (114 mg). The resulting mixture was stirred for 18 hours. The residue obtained by distilling off the solvent under reduced pressure was purified by chromatography on a silica gel column (10% methanol—dichloromethane), followed by dissolution in dichloromethane. To the resulting solution, 1N hydrochloric acid in ethanol and water were added. The resulting mixture was then concentrated. The crystals were collected by filtration and washed with ethyl acetate, whereby the title compound (53 mg, 30%) was obtained.

$^1$H-NMR (DMSO-$d_6$) δ: 3.07(4H,br), 3.30–4.20(4H,m), 4.24(1H,d,J=5.8 Hz), 4.27(1H,d,J=5.8 Hz), 7.51(2H,d,J=8.3 Hz), 7.71–7.78(2H,m), 7.80–7.87(3H,m), 7.89(1H,br s), 8.19(1H,d,J=8.8 Hz), 8.25–8.30(2H,m), 8.42(2H,br s), 8.50 (1H,br s), 8.69(1H,d,J=5.4 Hz). MS (FAB) m/z: 521 [(M+H)$^+$, Cl$^{35}$], 523 [(M+H)$^+$, Cl$^{37}$]. Elementary analysis for $C_{27}H_{25}ClN_4O_3S \cdot 1.5HCl \cdot 2.1H_2O$ Calculated: C, 52.85; H, 5.04; Cl, 14.45; N, 9.13; S, 5.23. Found: C, 52.69; H, 4.93; Cl, 14.60; N, 9.21; S, 5.25.

Example A-156

1-[(6-Chloronaphthalen-2-yl)sulfonyl]-4-[4-[2-(dimethylaminomethyl)pyridin-4-yl]benzoyl]piperazine hydrochloride In the same manner as in Referential Example 178, the corresponding brome compound was obtained using 1-[(6-chloronaphthalen-2-yl)sulfonyl]-4-[4-(2-hydroxymethylpyridin-4-yl)benzoyl]piperazine (300 mg). To the resulting compound, dimethylamine hydrochloride (469 mg) and potassium carbonate (795 mg) were added, followed by stirring for 24 hours. The solvent was then distilled off under reduced pressure. Ethyl acetate and water were added to the residue to separate the organic layer. The organic layer thus obtained was dried over anhydrous sodium sulfate. The residue obtained by distilling off the solvent under reduced pressure was purified by chromatography on a silica gel column (3 to 5% methanol—dichloromethane). Hydrochloric acid in ethanol was added and the resulting mixture was concentrated. Ethyl acetate was added to the concentrate. The colorless powder thus obtained was collected by filtration and dried, whereby the title compound (74 mg, 21%) was obtained.

$^1$H-NMR (DMSO-$d_6$) δ: 2.82(6H,s), 3.07(4H,br), 3.30–3.90(4H,m), 4.50(2H,br s), 7.51(2H,d,J=7.8 Hz), 7.73 (1H,dd,J=8.8,2.0 Hz), 7.79–7.85(2H,m), 7.86(2H,d,J=7.8 Hz), 8.00(1H,br s), 8.19(1H,d,J=8.8 Hz), 8.25–8.30(2H,m), 8.50(1H,br s), 8.73(1H,d,J=4.9 Hz). MS (FAB) m/z: 549 [(M+H)$^+$, Cl$^{35}$], 551 [(M+H)$^+$, Cl$^{37}$]. Elementary analysis for $C_{29}H_{29}ClN_4O_3S \cdot 1.1HCl \cdot 2H_2O$ Calculated: C, 55.71; H, 5.50; Cl, 11.91; N, 8.96; S, 5.13. Found: C, 55.61; H, 5.49; Cl, 11.89; N, 9.18; S, 5.27.

Example A-157

1-[4-[2-[(tert-Butoxycarbonylamino)methyl]pyridin-4-yl]benzoyl]-4-[(6-chloronaphthalen-2-yl)sulfonyl]piperazine hydrochloride In the same manner as in Referential Example 10, a reaction was effected, whereby the title compound was obtained.

$^1$H-NMR (CDCl$_3$) δ: 1.47(9H,s), 3.13(4H,br), 3.40–4.00 (4H,m), 4.50(2H,d,J=5.4 Hz), 5.57(1H,br s), 7.35(1H,dd,J= 5.4,1.5 Hz), 7.41(2H,d,J=8.3 Hz), 7.44(1H,br s), 7.57–7.65 (3H,m), 7.76(1H,dd,J=8.3,1.5 Hz), 7.90–7.97(3H,m), 8.31 (1H,d,J=1.5 Hz), 8.59(1H,d,J=5.4 Hz). MS (FAB) m/z: 621 [(M+H)$^+$, Cl$^{35}$], 623 [(M+H)$^+$, Cl$^{37}$].

Example A-158

2-[(tert-Butoxycarbonylamino)methyl]-4-[4-[[4-[(6-chloronaphthalen-2-yl)sulfonyl]piperazin-1-yl]carbonyl]phenyl]pyridine N-oxide In the same manner as in Example A-6, the title compound was obtained.

$^1$H-NMR (CDCl$_3$) δ: 1.42(9H,s), 3.13(4H,br), 3.40–4.00 (4H,m), 4.52(2H,d,J=6.3 Hz), 5.86(1H,br s), 7.39–7.44(3H, m), 7.56–7.63(4H,m), 7.77(1H,dd,J=8.8,2.0 Hz), 7.91–7.97 (3H,m), 8.27(1H,d,J=6.8 Hz), 8.31(1H,d,J=2.0 Hz). MS (FAB) m/z: 637 [(M+H)$^+$, Cl$^{35}$], 639 [(M+H)$^+$, Cl$^{37}$]. Elementary analysis for $C_{32}H_{33}ClN_4O_6S \cdot 0.7H_2O$ Calculated: C, 59.15; H, 5.34; Cl, 5.46; N, 8.62; S, 4.94. Found: C, 58.92; H, 5.41; Cl, 5.56; N, 8.52; S, 5.05.

Example A-159

2-Aminomethyl-4-[4-[[4-[(6-chloronaphthalen-2-yl)sulfonyl]piperazin-1-yl]carbonyl]phenyl]pyridine N-oxide In the same manner as in Example A-7, the title compound was obtained.

$^1$H-NMR (DMSO-$d_6$) δ: 3.07(4H,br), 3.35–3.95(4H,m), 4.24(2H,d,J=5.4 Hz), 7.49(2H,d,J=8.3 Hz), 7.73(1H,dd,J= 8.8,2.0 Hz), 7.80–7.87(3H,m), 7.89(1H,dd,J=6.8,2.4 Hz), 8.17–8.22(2H,m), 8.25–8.30(2H,m), 8.45(1H,d,J=6.8 Hz), 8.51(1H,br s), 8.71(3H,br s). MS (FAB) m/z: 537 [(M+H)$^+$, Cl$^{35}$], 539 [(M+H)$^+$, Cl$^{37}$]. Elementary analysis for $C_{27}H_{25}ClN_4O_4S \cdot 1.7HCl \cdot H_2O$ Calculated: C, 52.56; H, 4.69; Cl, 15.51; N, 9.08; S, 5.20. Found: C, 52.69; H, 4.85; Cl, 15.51; N, 8.90; S, 5.13.

Example A-160

1-[(6-Chloronaphthalen-2-yl)sulfonyl]-4-[4-(2-cyanopyridin-4-yl)benzoyl]piperazine In dichloromethane (100 ml), 4-[4-[[4-[(6-chloronaphthalen-2-yl)sulfonyl]piperazin-1-yl]carbonyl]phenyl]pyridine N-oxide (1.67 g) was dissolved, followed by the addition of trimethylsilycynanide (0.42 ml) and dimethylcarbamoyl chloride (0.30 ml). The resulting mixture was stirred at room temperature for 24 hours. An aqueous solution of sodium bicarbonate and dichloromethane were added to the reaction mixture to separate the organic layer. The organic layer thus obtained was dried over anhydrous sodium sulfate. The residue obtained by distilling off the solvent under reduced pressure was purified by chromatography on a silica gel column (1% methanol—dichloromethane), whereby the title compound (1.44 g, 84%) was obtained.

$^1$H-NMR (CDCl$_3$) δ: 3.14(4H,br s), 3.49(2H,br s), 3.89 (2H,br s), 7.47(2H,d,J=8.3 Hz), 7.55–7.72(4H,m), 7.76(1H, dd,J=8.8,1.5 Hz), 7.87(1H,s), 7.90–8.04(3H,m), 8.31(1H,br s), 8.77(1H,d,J=4.9 Hz). MS (FAB) m/z: 517 [(M+H)$^+$, Cl$^{35}$], 519 [(M+H)$^+$, Cl$^{37}$]. Elementary analysis for $C_{27}H_{21}ClN_4O_3S \cdot 0.05CH_2Cl_2$ Calculated: C, 62.33; H, 4.08; Cl, 7.48; N, 10.75; S, 6.15. Found: C, 62.16; H, 4.20; Cl, 7.65; N, 10.69; S, 6.04.

Example A-161

4-[4-[[4-[(6-Chloronaphthalen-2-yl)sulfonyl]piperazin-1-yl]carbonyl]phenyl]-2-cyanopyridine N-oxide In the same manner as in Example A-6, the title compound was obtained.

$^1$H-NMR (CDCl$_3$) δ: 3.13(4H,br s), 3.60(2H,br s), 3.87 (2H,br s), 7.46(2H,d,J=8.3 Hz), 7.54–7.65(4H,m), 7.76(1H, dd,J=8.3,1.5 Hz), 7.83(1H,d,J=2.9 Hz), 7.90–7.97(3H,m), 8.28–8.33(2H,m). MS (FAB) m/z: 533 [(M+H)$^+$, Cl$^{35}$], 535 [(M+H)$^+$, Cl$^{37}$]. Elementary analysis for $C_{27}H_{21}ClN_4O_4S$ Calculated: C, 60.84; H, 3.97; Cl, 6.65; N, 10.51; S, 6.02. Found: C, 60.76; H, 4.04; Cl, 6.64; N, 10.39; S, 6.05.

Example A-162

1-[4-[2-[2-(tert-Butoxycarbonylamino)ethyl]pyridin-4-yl]benzoyl]-4-[(6-chloronaphthalen-2-yl)sulfonyl]piperazine In a similar manner to Example A-3 and Example A-4, a reaction was effected using methyl 4-[2-[2-(tert-butoxycarbonylamino)ethyl]pyridin-4-yl]benzoate as a starting material, whereby the title compound was obtained.

$^1$H-NMR (CDCl$_3$) δ: 1.42(9H,s), 3.04(2H,t,J=6.4 Hz), 3.12(4H,br), 3.45–4.00(6H,m), 5.11(1H,br s), 7.31(1H,dd,J=5.4,2.0 Hz), 7.35(1H,br s), 7.41(2H,d,J=8.3 Hz), 7.58–7.65(3H,m), 7.77(1H,dd,J=8.3,1.5 Hz), 7.90–7.97(3H,m), 8.31(1H,s), 8.59(1H,d,J=5.4 Hz). MS (FAB) m/z: 635 [(M+H)$^+$, Cl$^{35}$], 637 [(M+H)$^+$, Cl$^{37}$]. Elementary analysis for C$_{33}$H$_{35}$ClN$_4$O$_5$S Calculated: C, 62.40; H, 5.55; N, 8.82. Found: C, 62.78; H, 5.93; N, 8.51.

Example A-163

4-[4-[[4-[(6-Chloronaphthalen-2-yl)sulfonyl]piperazin-1-yl]carbonyl]phenyl]-2-[2-(tert-butoxycarbonylamino)ethyl]pyridine N-oxide In the same manner as in Example A-6, the title compound was obtained.

$^1$H-NMR (CDCl$_3$) δ: 1.39(9H,s), 3.00–3.30(6H,m), 3.50–4.00(6H,m), 5.28(1H,br s), 7.37(1H,dd,J=6.8,2.9 Hz), 7.41(2H,d,J=8.3 Hz), 7.51(1H,br s), 7.56–7.63(3H,m), 7.77(1H,dd,J=8.3,1.5 Hz), 7.91–7.97(3H,m), 8.28(1H,d,J=6.8 Hz), 8.31(1H,d,J=1.5 Hz). MS (FAB) m/z: 651 [(M+H)$^+$, Cl$^{35}$], 653 [(M+H)$^+$, Cl$^{37}$]. Elementary analysis for C$_{33}$H$_{35}$ClN$_4$O$_6$S.0.8H$_2$O Calculated: C, 59.55; H, 5.54; N, 8.42. Found: C, 59.75; H, 5.61; N, 8.07.

Example A-164

2-(2-Aminoethyl)-4-[4-[[4-[(6-chloronaphthalen-2-yl)sulfonyl]piperazin-1-yl]carbonyl]phenyl]pyridine N-oxide In the same manner as in Example A-7, the title compound was obtained using 4-[4-[[4-[(6-chloronaphthalen-2-yl)sulfonyl]piperazin-1-yl]carbonyl]phenyl]-2-[2-(tert-butoxycarbonylamino)ethyl]pyridine N-oxide as a starting material.

$^1$H-NMR (DMSO-d$_6$) δ: 2.95–3.30(6H,m), 3.30–3.90(6H,m), 7.47(2H,d,J=8.3 Hz), 7.71–8.10(8H,m), 8.19(1H,d,J=8.8 Hz), 8.26–8.30(2H,m), 8.37(1H,d,J=6.8 Hz), 8.51(1H,br s). MS (FAB) m/z: 551 [(M+H)$^+$, Cl$^{35}$], 553 [(M+H)$^+$, Cl$^{37}$]. Elementary analysis for C$_{28}$H$_{27}$ClN$_4$O$_4$S.1.1HCl.1.6H$_2$O Calculated: C, 54.24; H, 5.09; Cl, 12.01; N, 9.04; S, 5.17. Found: C, 54.40; H, 5.36; Cl, 11.90; N, 8.97; S, 5.27.

Example A-165

4-[(6-Chloronaphthalen-2-yl)sulfonyl]-5-methoxycarbonyl-1-[4-(pyridin-4-yl)benzoyl]-1,2,3,4-tetrahydropyrazine In N,N-dimethylformamide (1 ml), 1-[(6-chloronaphthalen-2-yl)sulfonyl]-6-methoxycarbonyl-1,2,3,4-tetrahydropyrazine (60 mg) and p-nitrophenyl 4-(pyridin-4-yl)benzoate (52 mg) were dissolved, followed by the addition of sodium hydride (60% in oil, 7.20 mg) under ice cooling. The resulting mixture was stirred for 1 hour. Water and ethyl acetate were added to the reaction mixture to separate the organic layer. The organic layer was dried over anhydrous magnesium sulfate and the solvent was concentrated under reduced pressure. The residue was purified by chromatography on a silica gel column (ethyl acetate:hexane=2:1), followed by dissolution in ethanol. To the resulting solution, 1N aqueous hydrochloric acid in ethanol was added and the resulting mixture was concentrated, whereby the title compound (58 mg, 60%) was obtained as pale yellow powder.

$^1$H-NMR (CDCl$_3$) δ: 3.51(2H,s), 3.79(3H,s), 3.99(2H,s), 7.60(1H,dd,J=8.8,2.0 Hz), 7.68(1H,br), 7.76(2H,d,J=7.8 Hz), 7.90(2H,d,J=7.8 Hz), 7.92–7.99(3H,m), 8.12(2H,d,J=5.4 Hz), 8.16(1H,dd,J=8.8,1.5 Hz), 8.58(1H,br s), 8.93(2H,d,J=5.4 Hz). MS (FAB) m/z: 548 [(M+H)$^+$, Cl$^{35}$], 550 [(M+H)$^+$, Cl$^{37}$]. Elementary analysis for C$_{28}$H$_{22}$ClN$_3$O$_5$S.0.8HCl.1.3H$_2$O Calculated: C, 55.99; H, 4.26; Cl, 10.63; N, 7.00; S, 5.34. Found: C, 55.96; H, 4.31; Cl, 10.43; N, 6.94; S, 5.56.

Example A-166

1-[(6-Chloronaphthalen-2-yl)sulfonyl]-5-methoxycarbonyl-4-[4-(pyridin-4-yl)benzoyl-1,2,3,4-tetrahydropyrazine In the same manner as in Referential Example 7, the title compound was obtained using 4-(4-bromobenzoyl)-1-[(6-chloronaphthalen-2-yl)sulfonyl]-5-methoxycarbonyl-1,2,3,4-tetrahydropyrazine as a starting material.

$^1$H-NMR (DMSO-d$_6$) δ: 3.10–3.90(7H,m), 7.43(1H,s), 7.66(2H,d,J=8.3 Hz), 7.78(1H,dd,J=8.8,2.0 Hz), 7.96(1H,dd,J=8.8,2.0 Hz), 8.02(2H,d,J=8.3 Hz), 8.20–8.38(5H,m), 8.74(1H,br s), 8.94(2H,d,J=6.3 Hz). MS (FAB) m/z: 548 [(M+H)$^+$, Cl$^{35}$], 550 [(M+H)$^+$, Cl$^{37}$]. Elementary analysis for C$_{28}$H$_{22}$ClN$_3$O$_5$S.0.8HCl.0.5H$_2$O Calculated: C, 57.37; H, 4.09; Cl, 10.89; N, 7.17; S. 5.47. Found: C, 57.24; H, 4.15; Cl, 10.88; N, 6.97; S, 5.29.

Example A-167 cis-1-[(6-Chloronaphthalen-2-yl)sulfonyl]-4-[4-(2-cyanopyridin-4-yl)benzoyl]-2,6-dimethylpiperazine In the same manner as in Example A-160, the title compound was obtained.

$^1$H-NMR (CDCl$_3$) δ: 1.40–1.60(6H,m), 2.40–2.60(2H,m), 3.40–3.90(3H,m), 4.40–4.90(1H,br), 7.43(2H,d,J=8.3 Hz), 7.60(1H,dd,J=8.8,2.0 Hz), 7.64(2H,d,J=8.3 Hz), 7.69(1H,dd,J=5.4,2.0 Hz), 7.76(1H,dd,J=8.8,1.5 Hz), 7.88(1H,d,J=2.0 Hz), 7.90–7.95(3H,m), 8.31(1H,d,J=1.5 Hz), 8.78(1H,d,J=5.4 Hz). MS (FAB) m/z: 545 [(M+H)$^+$, Cl$^{35}$], 547 [(M+H)$^+$, Cl$^{37}$]. Elementary analysis for C$_{29}$H$_{25}$ClN$_4$O$_3$S Calculated: C, 63.90; H, 4.62; Cl, 6.50; N, 10.28; S, 5.88. Found: C, 63.87; H, 4.98; Cl, 6.33; N, 9.96; S, 5.75.

Example A-168

4-[4-[[cis-4-[(6-Chloronaphthalen-2-yl)sulfonyl]-2,6-dimethylpiperazin-1-yl]carbonyl]phenyl]-2-cyanopyridine N-oxide In the same manner as in Example A-6, the title compound was obtained.

$^1$H-NMR (CDCl$_3$) δ: 1.42–1.55(6H,m), 2.43–2.60(2H,m), 3.40–3.90(3H,m), 4.40–4.90(1H,br), 7.42(2H,d,J=8.3 Hz), 7.58(2H,d,J=8.3 Hz), 7.60–7.65(2H,m), 7.76(1H,dd,J=8.8,2.0 Hz), 7.83(1H,d,J=2.9 Hz), 7.90–7.95(3H,m), 8.29–8.32(2H,m). MS (FAB) m/z: 561 [(M+H)$^+$, Cl$^{35}$], 563

[(M+H)⁺, Cl³⁷]. Elementary analysis for C₂₉H₂₅ClN₄O₄S.0.3H₂O Calculated: C, 61.49; H, 4.56; Cl, 6.26; N, 9.89; S, 5.66. Found: C, 61.47; H, 4.63; Cl, 6.13; N, 9.72; S, 5.73.

Example A-169

1-[4-[(3-Aminomethyl)phenyl]benzoyl]-4-[(6-chloronaphthalen-2-yl)sulfonyl]piperazine hydrochloride In the same manner as in Example A-4 and Example A-7, a reaction was effected, whereby the title compound was obtained.

¹H-NMR (DMSO-d₆) δ: 3.07(4H,br), 3.51(2H,br), 3.69(2H,br), 4.09(2H,s), 7.45(2H,d,J=8.3 Hz), 7.47–7.55(2H,m), 7.66–7.76(4H,m), 7.80–7.87(2H,m), 8.19(2H,d,J=8.8 Hz), 8.25–8.42(4H,m), 8.51(1H,br s). MS (FAB) m/z: 520 [(M+H)⁺, Cl³⁵], 522 [(M+H)⁺, Cl³⁷]. Elementary analysis for C₂₈H₂₆ClN₃O₃S.HCl Calculated: C, 60.34; H, 4.89; Cl, 12.74; N, 7.55; S, 5.76. Found: C, 60.15; H, 4.89; Cl, 12.44; N, 7.52; S, 5.80.

Example A-170

1-[(6-Chloronaphthalen-2-yl)sulfonyl]-4-[[2,5-dihydro-5-oxo-3-(pyridin-4-yl)-1,2,4-triazin-6-yl]carbonyl]piperazine In the same manner as in Example A-4, the title compound was obtained.

¹H-NMR (DMSO-d₆) δ: 2.94(2H,br s), 3.07(2H,br s), 3.52(2H,br s), 3.73(2H,br s), 7.74(1H,dd,J=8.8,2.4 Hz), 7.84(1H,dd,J=8.8,2.0 Hz), 7.99(2H,d,J=6.3 Hz), 8.20(1H,d,J=8.8 Hz), 8.26–8.31(2H,m), 8.53(1H,br s), 8.87(2H,d,J=6.3 Hz). MS (FAB) m/z: 511 [(M+H)⁺, Cl³⁵], 513 [(M+H)⁺, Cl³⁷]. Elementary analysis for C₂₃H₁₉ClN₆O₄S.0.6HCl.1.5H₂O Calculated: C, 49.34; H, 4.07; Cl, 10.13; N, 15.01; S, 5.73. Found: C, 49.25; H, 4.01; Cl, 10.12; N, 15.07; S, 5.59.

Example A-171 trans-2,6-Bis(methoxycarbonylmethyl)-4-[(6-chloronaphthalen-2-yl)sulfonyl]-1-[4-(pyridin-4-yl)benzoyl]piperazine In the same manner as in Example A-105, the title compound was obtained as colorless amorphous powder by using trans-2,6-bis(methoxycarbonylmethyl)-1-(4-bromobenzoyl)-4-[(6-chloronaphthalen-2-yl)sulfonyl]piperazine as a starting material.

¹H-NMR (DMSO-d₆) δ: 2.50–2.65(2H,m), 3.70–3.80(2H,m), 3.30–3.40(4H,m), 3.46(6H,s), 4.23(2H,br), 7.60(2H,d,J=8.3 Hz), 7.74(1H,d,J=8.8 Hz), 7.85(1H,d,J=8.3 Hz), 8.03(2H,d,J=8.3 Hz), 8.15–8.40(4H,m), 8.53(1H,s), 8.90–9.00(2H,m). MS (FAB) m/z: 636 [(M+H)⁺, Cl³⁵], 638 [(M+H)⁺, Cl³⁷]. Elementary analysis for C₃₂H₃₀ClN₃O₇S.HCl.2.6H₂O Calculated: C, 53.42; H, 5.07; Cl, 9.86; N, 5.84; S, 4.46. Found: C, 53.21; H, 4.75; Cl, 9.91; N, 5.80; S, 4.54.

Example A-172 cis-2,6-Bis(methoxycarbonylmethyl)-4-[(6-chloronaphthalen-2-yl)sulfonyl]-1-[4-(pyridin-4-yl)benzoyl]piperazine In the same manner as in Example A-171, the title compound was obtained.

¹H-NMR (DMSO-d₆) δ: 2.70–3.00(6H,m), 3.40–3.80(2H,m), 3.51(3H,s), 3.68(3H,s), 4.13(1H,br), 4.97(1H,br), 7.58(2H,d,J=7.8 Hz), 7.70–7.75(1H,m), 7.80–7.90(1H,m), 8.03(2H,d,J=8.3 Hz), 8.19(1H,d,J=8.8 Hz), 8.25–8.35(4H,m), 8.55(1H,s), 8.90–8.95(2H,m). MS (FAB) m/z: 636 [(M+H)⁺, Cl³⁵], 638 [(M+H)⁺, Cl³⁷]. Elementary analysis for C₃₂H₃₀ClN₃O₇S.HCl.0.3H₂O Calculated: C, 56.69; H, 4.70; Cl, 10.46; N, 6.20; S, 4.73. Found: C, 56.72; H, 4.66; Cl, 10.31; N, 6.03; S, 4.71.

Example A-173 cis-2,6-Bis(carbamoylmethyl)-4-[(6-chloronaphthalen-2-yl)sulfonyl]-1-[4-(pyridin-4-yl)benzoyl]piperazine In the same manner as in Example A-35, the title compound was obtained using cis-2,6-bis(methoxycarbonylmethyl)-4-[(6-chloronaphthalen-2-yl)sulfonyl]-1-[4-(pyridin-4-yl)benzoyl]piperazine as a starting material.

¹H-NMR (DMSO-d₆) δ: 2.30–2.60(10H,m), 2.80–2.90(2H,m), 3.45–3.55(1H,m), 3.75–3.85(1H,m), 4.10–4.20(1H,m), 4.95–5.05(1H,m), 6.85(1H,br s), 7.03(1H,br s), 7.40(1H,br s), 7.45(1H,br s), 7.56(2H,d,J=8.3 Hz), 7.70–7.75(1H,m), 7.80–7.85(1H,m), 8.02(2H,d,J=8.3 Hz), 8.18(1H,d,J=8.8 Hz), 8.25–8.40(4H,m), 8.52(1H,s), 8.95(2H,d,J=6.8 Hz). MS (FAB) m/z: 606 [(M+H)⁺, Cl³⁵], 608 [(M+H)⁺, Cl³⁷]. Elementary analysis for C₃₀H₂₈ClN₅O₅S.1.2HCl.2.8H₂O Calculated: C, 51.45; H, 5.01; N, 11.14; Cl, 10.00; S, 4.58. Found: C, 51.52; H, 5.30; N, 11.33; Cl, 10.01; S, 4.72.

Example A-174

4-[4-[[cis-2,6-Bis(carbamoylmethyl)-4-[(6-chloronaphthalen-2-yl)sulfonyl]piperazin-1-yl]carbonyl]phenyl]pyridine N-oxide In the same manner as in Example A-6, the title compound was obtained.

¹H-NMR (DMSO-d₆) δ: 2.30–2.60(4H,m), 2.75–2.90(2H,m), 3.45–3.55(1H,m), 3.75–3.85(1H,m), 4.10–4.20(1H,m), 4.90–5.00(1H,m), 6.86(1H,br), 7.02(1H,br), 7.30–7.50(4H,m), 7.70–7.85(6H,m), 8.18(1H,d,J=8.8 Hz), 8.25–8.35(4H,m), 8.52(1H,s). MS (FAB) m/z: 622 [(M+H)⁺, Cl³⁵], 624 [(M+H)⁺, Cl³⁷]. Elementary analysis for C₃₀H₂₈ClN₅O₆S.1.6H₂O Calculated: C, 55.36; H, 4.83; Cl, 5.45; N, 10.76; S, 4.93. Found: C, 55.05; H, 4.77; Cl, 5.77; N, 10.51; S, 4.90.

Example A-175

4-[4-[[cis-2,6-Bis(ethoxycarbonylmethyl)-4-[(6-chloronaphthalen-2-yl)sulfonyl]piperazin-1-yl]carbonyl]phenyl]pyridine N-oxide In the same manner as in Example A-6, the title compound was obtained.

¹H-NMR (CDCl₃) δ: 2.85–2.95(4H,m), 3.20–3.40(4H,m), 3.63(6H,s), 4.25–4.35(2H,m), 7.45–7.50(4H,m), 7.55–7.65(3H,m), 7.70–7.80(1H,m), 7.90–7.95(3H,m), 8.25–8.35(3H,m). MS (FAB) m/z: 652 [(M+H)⁺, Cl³⁵], 654 [(M+H)⁺, Cl³⁷]. Elementary analysis for C₃₂H₃₀ClN₃O₈S.2.3H₂O Calculated: C, 55.42; H, 5.03; Cl, 5.11; N, 6.06; S, 4.62. Found: C, 55.50; H, 4.93; Cl, 5.12; N, 5.89; S, 4.54.

Example A-176 trans-2,6-Bis(carbamoylmethyl)-4-[(6-chloronaphthalen-2-yl)sulfonyl]-1-[4-(pyridin-4-yl)benzoyl]piperazine In the same manner as in Example A-105, the title compound was obtained using trans-2,6-bis (carbamoylmethyl)-1-(4-bromobenzoyl)-4-[(6-chloronaphthalen-2-yl)sulfonyl]piperazine as a starting material.

$^1$H-NMR (DMSO-d$_6$) δ: 2.50–2.60(4H,m), 3.20–3.30 (4H,m), 4.15–4.25(2H,m), 6.87(2H,br s), 7.40(2H,br s), 7.62(2H,d,J=8.8 Hz), 7.72(1H,d,J=8.3 Hz), 7.82(1H,d,J=8.8 Hz), 8.02(2H,d,J=8.3 Hz), 8.16(1H,d,J=8.8 Hz), 8.20–8.40 (4H,m), 8.51(1H,s), 8.90–9.00(2H,m). MS (FAB) m/z: 606 [(M+H)$^+$, Cl$^{35}$], 608 [(M+H)$^+$, Cl$^{37}$]. Elementary analysis for C$_{30}$H$_{28}$ClN$_5$O$_5$S.1.2HCl.3H$_2$O Calculated: C, 51.19; H, 5.04; Cl, 11.08; N, 9.95; S, 4.56. Found: C, 51.10; H, 4.97; Cl, 11.17; N, 9.71; S, 4.64.

Example A-177

4-[4-[[trans-2,6-Bis(carbamoylmethyl)-4-[(6-chloronaphthalen-2-yl)sulfonyl]piperazin-1-yl]carbonyl]phenyl]pyridine N-oxide In the same manner as in Example A-6, the title compound was obtained.

$^1$H-NMR (DMSO-d$_6$) δ: 2.55–2.65(2H,m), 2.65–2.80 (2H,m), 3.20–3.60(4H,m), 4.25–4.35(2H,m), 4.90–5.00(1H, m), 6.98(2H,br), 7.48(2H,br), 7.55–7.65(2H,m), 7.80–8.00 (6H,m), 8.20–8.40(5H,m), 8.60(1H,s). MS (FAB) m/z: 622 [(M+H)$^+$, Cl$^{35}$], 624 [(M+H)$^+$, Cl$^{37}$].

Example A-178 trans-2,6-bis(carboxymethyl)-4-[(6-chloronaphthalen-2-yl)sulfonyl]-1-[4-(pyridin-4-yl)benzoyl]piperazine In the same manner as in Example A-3, the title compound was obtained.

$^1$H-NMR (DMSO-d$_6$) δ: 2.50–2.75(4H,m), 3.25–3.45 (4H,m), 4.15–4.25(2H,m), 7.52(2H,d,J=8.3 Hz), 7.70–7.75 (3H,m), 7.80–7.85(3H,m), 8.16(1H,d,J=8.8 Hz), 8.20–8.30 (2H,m), 8.51(1H,s), 8.60–8.70(2H,m), 12.32(2H,s). MS (FAB) m/z: 608 [(M+H)$^+$, Cl$^{35}$], 610 [(M+H)$^+$, Cl$^{37}$]. Elementary analysis for C$_{30}$H$_{26}$ClN$_3$O$_7$S.0.2HCl.0.5H$_2$O Calculated: C, 57.71; H, 4.39; Cl, 6.81; N, 6.73; S, 5.14. Found: C, 57.78; H, 4.35; Cl, 6.73; N, 6.68; S, 5.11.

Example A-179 trans-2,6-Bis(2-hydroxyethyl)-4-[(6-chloronaphthalen-2-yl)sulfonyl]-1-[4-(pyridin-4-yl)benzoyl]piperazine In tetrahydrofuran (40 ml), trans-2,6-bis(carboxymethyl)-4-[(6-chloronaphthalen-2-yl)sulfonyl]-1-[4-(pyridin-4-yl)benzoyl]piperazine (269 mg) was suspended, followed by the addition of N,N-diisopropylethylamine (480 μl) and 1-benzotriazolyloxy-tris(pyrrolidino)phosphonium hexafluorophosphate (672 mg) under ice cooling. The resulting mixture was stirred for 3.5 hours at room temperature. Under ice cooling, sodium borohydride (297 mg) was added and the resulting mixture was stirred for 15 hours at room temperature. The reaction mixture was ice cooled and added with water and ethyl acetate to separate the organic layer. The organic layer thus obtained was washed with aqueous NaCl solution, dried over anhydrous sodium sulfate. The residue obtained by distilling off the solvent under reduced pressure was purified by chromatography on a silica gel column (4% methanol—dichloromethane), followed by dissolution in tetrahydrofuran. Saturated hydrochloride in methanol was added to the resulting solution and the resulting mixture was concentrated to dryness. Ethyl acetate was then added to the residue to crystallize the same, whereby the title compound was obtained.

$^1$H-NMR (DMSO-d$_6$) δ: 1.60–1.80(2H,m), 1.80–1.95 (2H,m), 3.20–3.40(6H,m), 3.95–4.05(2H,m), 7.59(2H,d,J= 8.3 Hz), 7.70–7.75(3H,m), 7.80–7.90(31H,m), 7.99(2H,d,J= 8.3 Hz), 8.17(1H,d,J=8.8 Hz), 8.20–8.30(4H,m), 8.54(1H,s), 8.85–8.95(2H,m). HRMS (FAB) m/z: 580.1633 (M+H)$^+$ (calcd for C$_{30}$H$_{30}$ClN$_3$O$_5$S 580.1673).

Example A-180

1-[(5-Chloroindol-2-yl)sulfonyl]-4-[4-(2-methylpyridin-4-yl)benzoyl]piperazine

In the same manner as in Example A-4, the title compound was obtained.

$^1$H-NMR (DMSO-d$_6$) δ: 2.74(3H,s), 2.99–3.81(8H,br), 7.71(1H,s), 7.33(1H,dd,J=8.8,2.0 Hz), 7.51(1H,d,J=8.8 Hz), 7.58(2H,d,J=8.3 Hz), 7.79(1H,d,J=2.0 Hz), 8.00(2H,d,J=8.3 Hz), 8.77–8.84(1H,m), 8.79(1H,d,J=6.3 Hz), 12.50(1H,s). MS (FAB) m/z: 495 [(M+H)$^+$, Cl$^{35}$], 497 [(M+H)$^+$, Cl$^{37}$]. Elementary analysis for C$_{25}$H$_{23}$ClN$_4$O$_3$S.0.9HCl.H$_2$O Calculated: C, 55.01; H, 4.78; Cl, 12.34; N, 10.26; S, 5.87. Found: C, 54.99; H, 5.01; Cl, 12.12; N, 10.03; S, 5.88.

Example A-181

4-[4-[[4-[(5-Chloroindol-2-yl)sulfonyl]piperazin-1-yl]carbonyl]phenyl]-2-methylpyridine N-oxide In the same manner as in Example A-6, the title compound was obtained. MS (FAB) m/z: 511 [(M+H)$^+$, Cl$^{35}$], 513 [(M+H)$^+$, Cl$^{37}$].

$^1$H-NMR (DMSO-d$_6$) δ: 2.95–3.18(4H,br), 3.37–3.81 (4H,br), 7.03(1H,s), 7.34(1H,dd,J=8.8,2.0 Hz), 7.47(2H,d, J=8.3 Hz), 7.51(1H,d,J=8.8 Hz), 7.66(1H,dd,J=6.8,2.9 Hz), 7.79(1H,s), 7.80(2H,d,J=8.3 Hz), 7.91(1H,d,J=2.9 Hz), 8.30 (1H,d,J=6.8 Hz), 12.42(1H,s). Elementary analysis for C$_{25}$H$_{23}$ClN$_4$O$_4$S.0.8H$_2$O Calculated: C, 57.15; H, 4.72; Cl, 6.75; N, 10.66; S, 6.10. Found: C, 57.22; H, 4.64; Cl, 7.04; N, 10.42; S, 6.17.

Example A-182

1-[(5-Chloroindol-2-yl)sulfonyl]-4-[[5-(pyridin-2-yl)pyrimidin-2-yl]carbonyl]piperazine At room temperature, 1-[(5-bromopyrimidin-2-yl)carbonyl]-4-[(5-chloroindol-2-yl)sulfonyl]piperazine (500 mg) and (pyridin-2-yl)tributyltin (418 mg) were dissolved in N,N-dimethylformamide (10 ml). To the reaction mixture was added tetrakis(triphenylphosphine)palladium(0) (69 mg), followed by stirring at 100° C. for 9 hours. After cooling to room temperature, ethyl acetate and ammonia solution were added. The resulting mixture was separated by ethyl acetate and water. The organic layer was dried over anhydrous sodium sulfate. The filtrate was concentrated and the residue was purified by chromatography on a silica gel column (4% methanol—methylene chloride). The resulting fraction was added with ethanol, followed by concentration. Diethyl ether was then added to the concentrate. Colorless powder thus precipitated was collected by filtration and dried, whereby the free form (254 mg) of the title compound was obtained. The resulting free form was dissolved in methylene chloride, followed by the addition of 1N hydrochloric acid (in ethanol) to make the solution acidic. After concentration, ethyl acetate and diethyl ether were added, followed by concentration. Colorless powder thus precipitated was collected by filtration and dried, whereby the title compound was obtained.

¹H-NMR (DMSO-d₆) δ: 2.90–2.98(2H,m), 3.10–3.15 (2H,m), 3.30–3.41(2H,m), 3.75–3.85(2H,m), 7.05(1H,d,J= 2.0 Hz), 7.35(1H,dd,J=2.0 and 8.8 Hz), 7.47–7.53(2H,m), 7.80(1H,d,J=2.0 Hz), 8.00(1H,dt,J=2.0 and 8.3 Hz), 8.17 (1H,d,J=8.3 Hz), 8.76(1H,d,J=4.4 Hz), 9.47(2H,s), 12.47 (1H,s). MS (FAB) m/z: 483 [(M+H)⁺, Cl³⁵], 485 [(M+H)⁺, Cl³⁷].

Example A-183

2-[2-[[4-[(5-Chloroindol-2-yl)sulfonyl]piperazin-1-yl]carbonyl]pyrimidin-5-yl]pyridine N-oxide In the same manner as in Example A-6, the title compound was obtained.

¹H-NMR (CDCl₃) δ: 3.10–3.20(2H,m), 3.20–3.30(2H, m), 3.50–3.60(2H,m), 3.85–3.95(2H,m), 6.97(1H,s), 7.30–7.52(5H,m), 7.68(1H,s), 8.39(1H,d,J=5.9 Hz), 9.28 (2H,s), 9.50(1H,s). MS (FAB) m/z: 499 [(M+H)⁺, Cl³⁵], 501 [(M+H)⁺, Cl³⁷].

Example A-184

1-[(6-Chlorobenzo[b]thien-2-yl)sulfonyl]-4-[[5-(pyridin-2-yl)pyrimidin-2-yl]carbonyl]piperazine In the same manner as in Example A-182, the title compound was obtained.

¹H-NMR (DMSO-d₆) δ: 3.01–3.10(2H,m), 3.17–3.26 (2H,m), 3.39–3.47(2H,m), 3.79–3.87(2H,m), 7.52(1H,dd,J= 7.3 and 4.9 Hz), 7.61(1H,d,J=8.8 Hz), 8.01(1H,dt,J=1.5 and 7.3 Hz), 8.10(1H,d,J=8.8 Hz), 8.12(1H,s), 8.18(1H,d,J=7.3 Hz), 8.35(1H,s), 8.76(1H,d,J=4.9 Hz), 9.48(2H,s). MS (FAB) m/z: 500 [(M+H)⁺, Cl³⁵], 502 [(M+H)⁺, Cl³⁷].

Example A-185

2-[2-[[4-[(6-Chlorobenzo[b]thien-2-yl)sulfonyl] piperazin-1-yl]carbonyl]pyrimidin-5-yl]pyridine N-oxide In the same manner as in Example A-6, the title compound was obtained.

¹H-NMR (CDCl₃) δ: 3.24(2H,t,J=4.9 Hz), 3.33(2H,t,J= 4.9 Hz), 3.63(2H,t,J=4.9 Hz), 3.99(2H,t,J=4.9 Hz), 7.36–7.53(4H,m), 7.78(1H,s), 7.84(1H,d,J=8.3 Hz), 7.88 (1H,br s), 8.36–8.39(1H,m), 9.29(2H,s). MS (FAB) m/z: 516 [(M+H)⁺, Cl³⁵], 518 [(M+H)⁺, Cl³⁷].

Example A-186

1-[(5-Chloroindol-2-yl)sulfonyl]-4-[[5-(2-methylpyridin-4-yl)pyrimidin-2-yl]carbonyl] piperazine In the same manner as in Example A-182, the title compound was obtained.

¹H-NMR (DMSO-d₆) δ: 2.71(3H,s), 2.96(2H,br s), 3.16 (2H,br s), 3.30(2H,br s), 3.81(2H,br s), 7.05(1H,s), 7.35(1H, d,J=8.8 Hz), 7.51(1H,d,J=8.8 Hz), 7.81(1H,s), 8.13(1H,br s), 8.23(1H,br s), 8.84(1H,br s), 9.40(2H,s), 12.50(1H,s). MS (FAB) m/z: 497 [(M+H)⁺, Cl³⁵], 499 [(M+H)⁺, Cl³⁷].

Example A-187

4-[2-[[4-[(5-Chloroindol-2-yl)sulfonyl]piperazin-1-yl]carbonyl]pyrimidin-5-yl]-2-methylpyridine N-oxide In the same manner as in Example A-6, the title compound was obtained.

¹H-NMR (DMSO-d₆) δ: 2.77(3H,s), 3.16–3.20(2H,m), 3.28–3.31(2H,m), 3.57–3.60(2H,m), 3.95–3.98(2H,m), 6.97 (1H,d,J=1.5 Hz), 7.32–7.42(3H,m), 7.50(1H,d,J=2.9 Hz), 7.69(1H,s), 8.39(1H,d,J=6.8 Hz), 8.92–9.05(3H,m). MS (FAB) m/z: 513 [(M+H)⁺, Cl³⁵], 515 [(M+H)⁺, Cl³⁷].

Example A-188

1-[(6-Chlorobenzo[b]thien-2-yl)sulfonyl]-4-[[5-(2-methylpyridin-4-yl)pyrimidin-2-yl]carbonyl] piperazine In the same manner as in Example A-182, the title compound was obtained.

¹H-NMR (DMSO-d₆) δ: 2.74(3H,s), 3.01–3.09(2H,m), 3.17–3.25(2H,m), 3.38–3.45(2H,m), 3.80–3.90(2H,m), 7.61 (1H,dd,J=8.8,2.0 Hz), 8.10(1H,d,J=8.8 Hz), 8.13(1H,s), 8.20(1H,d,J=5.9 Hz), 8.31(1H,br s), 8.36(1H,d,J=2.0 Hz), 8.87(1H,d,J=5.9 Hz), 9.43(2H,s). MS (FAB) m/z: 514 [(M+H)⁺, Cl³⁵], 516 [(M+H)⁺, Cl³⁷].

Example A-189

4-[2-[[4-[(6-Chlorobenzo[b]thien-2-yl)sulfonyl] piperazin-1-yl]carbonyl]pyrimidin-5-yl]-2-methylpyridine N-oxide In the same manner as in Example A-6, the title compound was obtained.

¹H-NMR (CDCl₃) δ: 2.60(3H,s), 3.24(2H,br), 3.34(2H, br), 3.60(2H,br), 3.99(2H,br), 7.39(1H,dd,J=2.4 and 6.8 Hz), 7.47(1H,dd,J=1.5 and 8.8 Hz), 7.50(1H,d,J=2.4 Hz), 7.78 (1H,s), 7.83(1H,d,J=8.8 Hz), 7.88(1H,d,J=1.5 Hz), 8.38(1H, d,J=6.8 Hz), 8.99(2H,s). MS (FAB) m/z: 530 [(M+H)⁺, Cl³⁵], 532 [(M+H)⁺, Cl³⁷].

Example A-190

1-[(6-Chlorobenzo[b]thien-2-yl)sulfonyl]-4-[[5-(3-fluoropyridin-4-yl)pyrimidin-2-yl]carbonyl] piperazine In the same manner as in Example A-182, the title compound was obtained.

¹H-NMR (DMSO-d₆) δ: 3.06(2H,br s), 3.21(2H,br s), 3.44(2H,br s), 3.84(2H,br s), 7.60(1H,dd,J=8.8,2.0 Hz), 7.84 (1H,dd,J=6.4,4.9 Hz), 8.09(1H,d,J=8.8 Hz), 8.12(1H,s), 8.35(1H,d,J=2.0 Hz), 8.62(1H,d,J=4.9 Hz), 8.79(1H,d,J=2.0 Hz), 9.20(2H,s). MS (FAB) m/z: 518 [(M+H)⁺, Cl³⁵], 520 [(M+H)⁺, Cl³⁷].

Example A-191

4-[2-[[4-[(6-Chlorobenzo[b]thien-2-yl)sulfonyl] piperazin-1-yl]carbonyl]pyrimidin-5-yl]-3-fluoropyridine N-oxide In the same manner as in Example A-6, the title compound was obtained.

¹H-NMR (CDCl₃) δ: 3.23–3.27(2H,m), 3.32–3.36(2H, m), 3.59–3.63(2H,m), 3.98–4.01(2H,m), 7.36–7.43(1H,m), 7.47(1H,d,J=8.3 Hz), 7.78(1H,s), 7.83(1H,d,J=8.3 Hz), 7.88 (1H,s), 8.18(1H,d,J=6.8 Hz), 8.30(1H,d,J=5.9 Hz), 9.00(2H, s). HRMS (FAB) m/z: 534.0468 [(M+H)⁺ calcd for C₂₂H₁₈ClFN₅O₄S₂, 534.0473].

Example A-192

1-[(5-Chloroindol-2-yl)sulfonyl]-4-[[5-(2,6-dimethylpyridin-4-yl)pyrimidin-2-yl]carbonyl] piperazine In the same manner as in Example A-182, the title compound was obtained.

¹H-NMR (DMSO-d₆) δ: 2.71(6H,s), 2.95(2H,br s), 3.16 (2H,br s), 3.37(2H,br s), 3.81(2H,br s), 7.05(1H,s), 7.35(1H, dd,J=8.8,2.0 Hz), 7.51(1H,d,J=8.8 Hz), 7.80(1H,br s), 8.14 (2H,br s), 9.39(2H,s), 12.50(1H,s). MS (FAB) m/z: 511 [(M+H)⁺, Cl³⁵], 513 [(M+H)⁺, Cl³⁷].

Example A-193

4-[2-[[4-[(5-Chloroindol-2-yl)sulfonyl]piperazin-1-yl]carbonyl]pyrimidin-5-yl]-2,6-dimethylpyridine N-oxide In the same manner as in Example A-6, the title compound was obtained.

¹H-NMR (CDCl₃) δ: 2,61(6H,s), 3.18(2H,d,J=4.9 Hz), 3.29(2H,d,J=4.9 Hz), 3.59(2H,d,J=4.9 Hz), 3.97(2H,d,J=4.9 Hz), 6.97(1H,d,J=1.5 Hz), 7.35(1H,dd,J=8.8 and 2.0 Hz), 7.38–7.43(3H,m), 7.69(1H,d,J=2.0 Hz), 8.89(1H,br s), 8.98 (2H,s). MS (FAB) m/z: 527 [(M+H)⁺, Cl³⁵], 529 [(M+H)⁺, Cl³⁷].

Example A-194

1-[(5-Chloroindol-2-yl)sulfonyl]-4-[[5-(2,5-dimethylpyridin-4-yl)pyrimidin-2-yl]carbonyl]piperazine In the same manner as in Example A-182, the title compound was obtained.

¹H-NMR (DMSO-d₆) δ: 2.39(3H,s), 2.68(3H,s), 2.97(2H, br s), 3.16(2H,br s), 3.40(2H,br s), 3.81(2H,br s), 7.06(1H, s), 7.34(1H,dd,J=8.8 and 2.0 Hz), 7.52(1H,d,J=8.8 Hz), 7.79–7.83(2H,m), 8.76(1H,s), 9.32(2H,s), 12.52(1H,s). MS (FAB) m/z: 511 [(M+H)⁺, Cl³⁵], 513 [(M+H)⁺, Cl³⁷].

Example A-195

4-[2-[[4-[(5-Chloroindol-2-yl)sulfonyl]piperazin-1-yl]carbonyl]pyrimidin-5-yl]-2,5-dimethylpyridine N-oxide In the same manner as in Example A-6, the title compound was obtained.

¹H-NMR (CDCl₃) δ: 2.25(3H,s), 2.54(3H,s), 3.15–3.25 (2H,m), 3.25–3.38(2H,m), 3.55–3.65(2H,m), 3.90–4.05(2H, m), 6.97(1H,s), 7.13(1H,s), 7.34(1H,dd,J=8.8 and 1.5 Hz), 7.41(1H,d,J=8.8 Hz), 7.68(1H,d,J=1.5 Hz), 8.28(1H,s), 8.78 (2H,s), 9.20(1H,s). MS (FAB) m/z: 527 [(M+H)⁺, Cl³⁵], 529 [(M+H)⁺, Cl³⁷].

Example A-196

1-[(5-Chloroindol-2-yl)sulfonyl]-4-[[5-(2,3-dimethylpyridin-4-yl)pyrimidin-2-yl]carbonyl]piperazine In the same manner as in Example A-182, the title compound was obtained.

¹H-NMR (DMSO-d₆) δ: 2.33(3H,s), 2.76(3H,s), 2.97(2H, br s), 3.17(2H,br s), 3.43(2H,br s), 3.82(2H,br s), 7.06(1H, s), 7.34(1H,dd,J=8.8 and 2.0 Hz), 7.52(1H,d,J=8.8 Hz), 7.78–7.85(2H,m), 8.72(1H,d,J=5.9 Hz), 9.01(2H,s), 12.52 (1H,s). MS (FAB) m/z: 511 [(M+H)⁺, Cl³⁵], 513 [(M+H)⁺, Cl³⁷].

Example A-197

4-[2-[[4-[(5-Chloroindol-2-yl)sulfonyl]piperazin-1-yl]carbonyl]pyrimidin-5-yl]-2,3-dimethylpyridine N-oxide In the same manner as in Example A-6, the title compound was obtained.

¹H-NMR (CDCl₃) δ: 2.27(3H,s), 2.61(3H,s), 3.20(2H,t, J=4.9 Hz), 3.31(2H,t,J=4.9 Hz), 3.62(2H,t,J=4.9 Hz), 3.98 (2H,t,J=4.9 Hz), 6.97(1H,d,J=1.5 Hz), 7.00(1H,d,J=6.8 Hz), 7.35(1H,dd,J=8.8 and 2.0 Hz), 7.40(1H,d,J=8.8 Hz), 7.68 (1H,d,J=2.0 Hz), 8.29(1H,d,J=6.8 Hz), 8.75(2H,s), 9.02(1H, s). MS (FAB) m/z: 527 [(M+H)⁺, Cl³⁵], 529 [(M+H)⁺, Cl³⁷].

Example A-198

1-[(6-Chlorobenzo[b]thien-2-yl)sulfonyl-4-[[5-(2,3-dimethylpyridin-4-yl)pyridimin-2-yl]carbonyl]piperazine In the same manner as in Example A-182, the title compound was obtained.

¹H-NMR (DMSO-d₆) δ: 2.31(3H,s), 2.73(3H,s), 3.05(2H, br s), 3.21(2H,br s), 3.46(2H,br s), 3.84(2H,br s), 7.59(1H, dd,J=8.5,2.0 Hz), 7.78(1H,d,J=5.4 Hz), 8.08(1H,d,J=8.5 Hz), 8.12(1H,s), 8.34(1H,d,J=2.0 Hz), 8.70(1H,d,J=5.4 Hz), 9.00(2H,s). MS (FAB) m/z: 528 [(M+H)⁺, Cl³⁵], 530 [(M+H)⁺, Cl³⁷].

Example A-199

4-[2-[[4-[(6-Chlorobenzo[b]thien-2-yl)sulfonyl]piperazin-1-yl]carbonyl]pyrimidin-5-yl]-2,3-dimethylpyridine N-oxide In the same manner as in Example A-182, the title compound was obtained.

¹H-NMR (CDCl₃) δ: 2.28(3H,s), 2.60(3H,s), 3.26(2H,d, J=4.9 Hz), 3.35(2H,d,J=4.9 Hz), 3.64(2H,d,J=4.9 Hz), 4.00 (2H,d,J=4.9 Hz), 7.01(1H,d,J=6.6 Hz), 7.47(1H,dd,J=1.7 and 8.8 Hz), 7.78(1H,s), 7.83(1H,d,J=8.8 Hz), 7.88(1H,d,J= 1.7 Hz), 8.28(1H,d,J=6.6 Hz), 8.76(2H,s). MS (FAB) m/z: 544 [(M+H)⁺, Cl³⁵], 546 [(M+H)⁺, Cl³⁷].

Example A-200

1-[(5-Chloroindol-2-yl)sulfonyl]-4-[[5-(3,5-dimethylpyridin-4-yl)pyrimidin-2-yl]carbonyl]piperazine In the same manner as in Example A-182, the title compound was obtained.

¹H-NMR (DMSO-d₆) δ: 2.16(6H,s), 2.99(2H,br s), 3.17 (2H,br s), 3.42(2H,br s), 3.82(2H,br s), 7.06(1H,s), 7.34(1H, d,J=8.8 Hz), 7.51(1H,d,J=8.8 Hz), 7.80(1H,s), 8.72(2H,br s), 8.91(2H,s), 12.50(1H,s). MS (FAB) m/z: 511 [(M+H)⁺, Cl³⁵], 513 [(M+H)⁺, Cl³⁷].

Example A-201

1-[(5-Chloroindol-2-yl)sulfonyl]-4-[[5-(6-methylpyridin-2-yl)pyrimidin-2-yl]carbonyl]piperazine In the same manner as in Example A-182, the title compound was obtained.

¹H-NMR (DMSO-d₆) δ: 2.57(3H,s), 2.96(2H,br s), 3.15 (2H,br s), 3.36(2H,br s), 3.80(2H,br s), 7.05(1H,d,J=2.0 Hz), 7.35(1H,dd,J=8.8,2.0 Hz), 7.38(1H,d,J=7.3 Hz), 7.51(1H,d, J=8.8 Hz), 7.81(1H,d,J=2.0 Hz), 7.89(1H,t,J=7.3 Hz), 7.96 (1H,d,J=7.3 Hz), 9.44(2H,s), 12.49(1H,s). MS (FAB) m/z: 497 [(M+H)⁺, Cl³⁵], 499 [(M+H)⁺, Cl³⁷].

Example A-202

2-[2-[[4-[(5-Chloroindol-2-yl)sulfonyl]piperazin-1-yl]carbonyl]pyrimidin-5-yl]-6-methylpyridine N-oxide In the same manner as in Example A-6, the title compound was obtained.

¹H-NMR (CDCl₃) δ: 2.59(3H,s), 3.15(2H,d,J=4.9 Hz), 3.26(2H,d,J=4.9 Hz), 3.56(2H,d,J=4.9 Hz), 3.94(2H,d,J=4.9 Hz), 6.97(1H,s), 7.30–7.41(5H,m), 7.69(1H,s), 9.07(1H,s), 9.25(2H,s). MS (FAB) m/z: 513 [(M+H)$^+$, Cl$^{35}$], 515 [(M+H)$^+$, Cl$^{37}$].

Example A-203

1-[(5-Chloroindol-2-yl)sulfonyl]-4-[[5-(3methylpyridin-4-yl)pyrimidin-2-yl]carbonyl] piperazine In the same manner as in Example A-182, the title compound was obtained.

¹H-NMR (DMSO-d₆) δ: 2.41(3H,s), 2.97(2H,br s), 3.16 (2H,br s), 3.40(2H,br s), 3.80(2H,br s), 7.05(1H,s), 7.33(1H, dd,J=8.8,2.0 Hz), 7.50(1H,d,J=8.8 Hz), 7.79(1H,d,J=2.0 Hz), 7.84(1H,d,J=5.4 Hz), 8.79(1H,d,J=5.4 Hz), 8.85(1H,s), 9.04(2H,s), 12.49(1H,s). MS (FAB) m/z: 497 [(M+H)$^+$, Cl$^{35}$], 499 [(M+H)$^+$, Cl$^{37}$].

Example A-204

1-[(5-Chloroindol-2-yl)sulfonyl]-4-[[5-(5-methylpyridin-2-yl)pyrimidin-2-yl]carbonyl] piperazine In the same manner as in Example A-182, the title compound was obtained.

¹H-NMR (DMSO-d₆) δ: 2.37(3H,s), 2.94–2.97(2H,m), 3.13–3.16(2H,m), 3.35–3.39(2H,m), 3.78–3.81(2H,m), 7.05 (1H,d,J=2.0 Hz), 7.34(1H,dd,J=8.8,2.0 Hz), 7.51(1H,d,J= 8.8 Hz), 7.78–7.83(2H,m), 8.07(1H,d,J=8.3 Hz), 8.60(1H, d,J=1.5 Hz), 9.44(2H,s), 12.47(1H,s). MS (FAB) m/z: 497 [(M+H)$^+$, C$^{35}$], 499 (M+H)$^+$, Cl$^{37}$].

Example A-205

2-[2-[[4-[(5-Chloroindol-2-yl)sulfonyl]piperazin-1-yl]carbonyl]pyrimidin-5-yl]-5-methylpyridine N-oxide In the same manner as in Example A-6, the title compound was obtained.

¹H-NMR (CDCl₃) δ: 2.40(3H,s), 3.16–3.19(2H,m), 3.26–3.29(2H,m), 3.58–3.61(2H,m), 3.95–3.98(2H,m), 6.98 (1H,s), 7.20–7.41(4H,m), 7.70(1H,s), 8.24(1H,s), 9.04(1H, s), 9.27(2H,s). MS (FAB) m/z: 513 [(M+H)$^+$, Cl$^{35}$], 515 [(M+H)$^+$, Cl$^{37}$]. HRMS (FAB) m/z: 513.1144 (M+H)$^+$ (calcd for C₂₃H₂₂ClN₆O₄S, 513.1112).

Example A-206

1-[(5-Chloroindol-2-yl)sulfonyl]-4-[[5-(3-methylpyridin-2-yl)pyrimidin-2-yl]carbonyl] piperazine In the same manner as in Example A-182, the title compound was obtained.

¹H-NMR (DMSO-d₆) δ: 2.41(3H,s), 2.98(2H,br s), 3.15 (2H,br s), 3.40(2H,br s), 3.81(2H,br s), 7.05(1H,s), 7.34(1H, dd,J=8.8,2.0 Hz), 7.45(1H,dd,J=7.8,4.9 Hz), 7.51(1H,d,J= 8.8 Hz), 7.80(1H,s), 7.85(1H,d,J=7.8 Hz), 8.59(1H,d,J=4.9 Hz), 9.09(2H,s), 12.49(1H,s). MS (FAB) m/z: 497 [(M+H)$^+$, Cl$^{35}$], 499 [(M+H)$^+$, Cl$^{37}$].

Example A-207

1-[(5-Chloroindol-2-yl)sulfonyl]-4-[[5-(pyridin-4-yl)pyrimidin-2-yl]thiocarbonyl]piperazine In a mixed solvent of dimethoxyethane (10 ml) and toluene (10 ml) was suspended 1-[(5-chloroindol-2-yl) sulfonyl]-4-[[5-(pyridin-4-yl)pyrimidin-2-yl]carbonyl] piperazine (100 mg) at room temperature, followed by the addition of Lawesson's reagent (2,4-bis(4-methoxyphenyl)-1,3-dithia-2,4-diphosphetane-2,4-disulfide, 42 mg). The resulting mixture was heated under reflux for 2 days. After cooling to room temperature, the reaction mixture was concentrated and the residue was purified by chromatography on a silica gel column (3→5% methanol—methylene chloride). 1N hydrochloric acid (in ethanol) was added to make acidic the purified product. After concentration, ethyl acetate was added. Yellow powder so precipitated was collected by filtration and dried, whereby the title compound (34 mg) was obtained.

¹H-NMR (DMSO-d₆) δ: 3.00(3H,br s), 3.28(2H,br s), 3.59(2H,br s), 4.44(2H,br s), 7.06(1H,s), 7.34(1H,dd,J=9.0, 2.0 Hz), 7.51(1H,d,J=9.0 Hz), 7.80(1H,d,J=2.0 Hz), 8.21 (2H,d,J=6.1 Hz), 8.90(2H,d,J=6.1 Hz), 9.33(2H,s), 12.51 (1H,s). MS (FAB) m/z: 499 [(M+H)$^+$, Cl$^{35}$], 501 [(M+H)$^+$, Cl$^{37}$].

Example A-208

1-[(5-Chloroindol-2-yl)sulfonyl]-4-[(hydroxyimino) [5-(pyridin-4-yl)pyrimidin-2-yl]methyl]piperazine In ethanol (50 ml) was suspended 1-[(5-chloroindol-2-yl) sulfonyl]-4-[[5-(pyridin-4-yl)pyrimidin-2-yl]thiocarbonyl] piperazine (243 mg) at room temperature, followed by the successive addition of hydroxylamine hydrochloride (338 mg), sodium acetate (399 mg) and mercury (II) chloride (132 mg). The resulting mixture was stirred at room temperature for 6 hours. The insoluble matter was filtered off through Celite filtration. The residue was purified by chromatography on a silica gel column (7% methanol—methylene chloride), whereby two fractions were obtained. They were concentrated, respectively, whereby a low-polarity compound (20 mg, colorless powder) and a high-polarity compound (20 mg, colorless powder) were obtained. Low-polarity compound:

¹H-NMR (DMSO-d₆) δ: 3.01(4H,br s), 3.09(4H,br s), 7.00(1H,s), 7.25–7.35(1H,m), 7.49(1H,d,J=9.0 Hz), 7.78 (1H,br s), 7.89(2H,d,J=6.1 Hz), 8.73(2H,d,J=6.1 Hz), 9.30 (2H,s). HRMS (FAB) m/z: 498.1115 (M+H)$^+$ (calcd for C₂₂H₂₁ClN₇O₃S, 498.1115).

High-polarity Compound:

¹H-NMR (DMSO-d₆) δ: 3.06(4H,br s), 3.30–3.32(4H, unclear because of the overlapping with that of water), 7.03(1H,s), 7.33(1H,d,J=8.8 Hz), 7.51(1H,d,J=8.8 Hz), 7.80 (1H,br s), 7.87(2H,d,J=6.1 Hz), 8.73(2H,d,J=6.1 Hz), 9.24 (2H,s). HRMS (FAB) m/z: 498.1110 (M+H)$^+$ (calcd for C₂₂H₂₁ClN₇O₃S, 498.1115).

Example A-209

1-[(5-Chloroindol-2-yl)sulfonyl]-4-[(hydrazono)[5-(pyridin-4-yl)pyrimidin-2-yl]methyl]piperazine In a mixed solvent of ethanol (100 ml) and methylene chloride (100 ml) was suspended 1-[(5-chloroindol-2-yl) sulfonyl]-4-[[5-(pyridin-4-yl)pyrimidin-2-yl]thiocarbonyl] piperazine (499 mg) at room temperature, followed by the successive addition of hydrazine monohydrate (146 μg) and mercury (II) chloride (272 mg). The resulting mixture was stirred at room temperature for 4 hours. After the solvent was distilled off, the residue was purified by chromatography on a silica gel column (8% methanol—methylene chloride). Methylene chloride was added and the resulting mixture was concentrated. Yellow crystals thus precipitated were collected by filtration and dried, whereby the title compound (100 mg) was obtained.

$^1$H-NMR (DMSO-d$_6$) δ: 3.03(8H,br s), 6.77(2H,br s), 7.04(1H,s), 7.34(1H,dd,J=8.8 and 2.0 Hz), 7.52(1H,d,J=8.8 Hz), 7.81(1H,d,J=2.0 Hz), 7.88(2H,d,J=6.3 Hz), 8.73(2H,d, J=6.3 Hz), 9.35(2H,s), 12.45(1H,s). MS (FAB) m/z: 497 [(M+H)$^+$, Cl$^{35}$], 499 [(M+H)$^+$, Cl$^{37}$].

Example A-210

1-[(6-Chlorobenzo[b]thien-2-yl)sulfonyl]-4-[4-(pyridin-4-yl)benzylidene]piperazine In the same manner as in Referential Example 7, the title compound was obtained.

$^1$H-NMR (DMSO-d$_6$) δ: 2.45–2.52(2H,m), 2.57–2.61 (2H,m), 3.12–3.16(2H,m), 3.20–3.24(2H,m), 6.44(1H,s), 7.37(2H,d,J=8.3 Hz), 7.56(1H,dd,J=8.5,2.0 Hz), 7.91(2H,d, J=8.3 Hz), 8.05(1H,d,J=8.5 Hz), 8.07(1H,s), 8.16(2H,d,J= 6.6 Hz), 8.31(1H,s), 8.82(2H,d,J=6.6 Hz). HRMS (FAB) m/z: 481.0783 (M+H)$^+$ (calcd for C$_{25}$H$_{22}$ClN$_2$O$_2$S$_2$, 481.0811).

Example A-211

1-[(6-Chloronaphthalen-2-yl)sulfonyl]-4-[[5-(2-methylpyridin-4-yl)pyrimidin-2-yl]carbonyl]piperazine In the same manner as in Example A-182, the title compound was obtained.

$^1$H-NMR (DMSO-d$_6$) δ: 2.69(3H,s), 2.93(2H,br s), 3.13 (2H,br s), 3.37(2H,br s), 3.80(2H,br s), 7.75(1H,dd,J=8.8 and 2.0 Hz), 7.84(1H,d,J=7.8 Hz), 8.10(1H,br s), 8.18–8.23 (2H,m), 8.26–8.32(2H,m), 8.53(1H,br s), 8.82(1H,d,J=5.9 Hz), 9.38(2H,s). MS (FAB) m/z: 508 [(M+H)$^+$, Cl$^{35}$], 510 [(M+H)$^+$, Cl$^{37}$].

Example A-212

4-[2-[[4-[(6-Chloronaphthalen-2-yl)sulfonyl]piperazin-1-yl]carbonyl]pyrimidin-5-yl]-2-methylpyridine N-oxide In the same manner as in Example A-6, the title compound was obtained.

$^1$H-NMR (CDCl$_3$) δ: 2.60(3H,s), 3.13–3.17(2H,m), 3.25–3.28(2H,m), 3.55–3.59(2H,m), 3.94–3.98(2H,m), 7.37 (1H,dd,J=6.8 and 2.9 Hz), 7.49(1H,d,J=2.9 Hz), 7.60(1H, dd,J=8.8 and 2.0 Hz), 7.76(1H,dd,J=8.8 and 2.0 Hz), 7.90–7.97(3H,m), 8.31(1H,d,J=2.0 Hz), 8.37(1H,d,J=6.8 Hz), 8.97(2H,s). MS (FAB) m/z: 524 [(M+H)$^+$, Cl$^{35}$], 526 [(M+H)$^+$, Cl$^{37}$].

Example A-213

1-[(6-Chloronaphthalen-2-yl)sulfonyl]-4-[[5-(pyridin-2-yl)pyrimidin-2-yl]carbonyl]piperazine In the same manner as in Example A-182, the title compound was obtained.

$^1$H-NMR (DMSO-d$_6$) δ: 2.93(2H,br s), 3.12(2H,br s), 3.36(2H,br s), 3.81(2H,br s), 7.50(1H,dd,J=7.3 and 4.9 Hz), 7.74(1H,dd,J=8.8 and 2.0 Hz), 7.83(1H,dd,J=8.8 and 1.5 Hz), 7.96–8.03(1H,m), 8.16(1H,d,J=8.3 Hz), 8.19(1H,d,J= 8.8 Hz), 8.25–8.31(2H,m), 8.52(1H,br s), 8.75(1H,d,J=4.9 Hz), 9.46(2H,s). MS (FAB) m/z: 494 [(M+H)$^+$, Cl$^{35}$], 496 [(M+H)$^+$, Cl$^{37}$].

Example A-214

2-[2-[[4-[(6-Chloronaphthalen-2-yl)sulfonyl]piperazin-1-yl]carbonyl]pyrimidin-5-yl]pyridine N-oxide In the same manner as in Example A-6, the title compound was obtained.

$^1$H-NMR (CDCl$_3$) δ: 3.13–3.16(2H,m), 3.24–3.27(2H, m), 3.57–3.60(2H,m), 3.93–3.97(2H,m), 7.38–7.44(2H,m), 7.46–7.50(1H,m), 7.59(1H,dd,J=8.8 and 2.0 Hz), 7.77(1H, dd,J=8.8 and 2.0 Hz), 7.91–7.96(3H,m), 8.31(1H,br s), 8.35–8.38(1H,m), 9.26(2H,s). MS (FAB) m/z: 510 [(M+H)$^+$, Cl$^{35}$], 512 [(M+H)$^+$, Cl$^{37}$].

Example A-215

1-[[5-(Pyridin-4-yl)pyrimidin-2-yl]carbonyl]-4-[(6-trimethylsilylethynylbenzo[b]thien-2-yl)sulfonyl]piperazine In a 1N aqueous hydrochloric acid in ethanol was dissolved 1-(tert-butoxycarbonyl)-4-[[5-(pyridin-4-yl)pyrimidin-2-yl]carbonyl]piperazine (739 mg), followed by stirring at room temperature for 30 minutes. The solvent was distilled off under reduced pressure. To the residue were added N,N-dimethylformamide (15 ml), triethylamine (2 ml) and 6-trimethylsilylethynylbenzo[b]thiophen-2-sulfonyl chloride (740 mg) and the resulting mixture was stirred at room temperature for 3 hours. The reaction mixture was diluted with methylene chloride, washed with water (thrice), dried over anhydrous sodium sulfate and purified by chromatography on a silica gel column (hexane:ethyl acetate= 1:0→1:1→ethyl acetate:methylene chloride= 3:1→0:1→methylene chloride:methanol=100:2→100:7), whereby the title compound (167 mg) was obtained as a white solid.

$^1$H-NMR (CDCl$_3$) δ: 0.28(9H,s), 3.25(2H,t,J=4.9 Hz), 3.35(2H,t,J=4.9 Hz), 3.61(2H,t,J=4.9 Hz), 4.00(2H,t,J=4.9 Hz), 7.51(2H,dd,J=4.4,1.5 Hz), 7.55(1H,dd,J=8.3,1.5 Hz), 7.78(1H,s), 7.83(1H,d,J=8.3 Hz), 8.00(1H,s), 8.80(2H,dd,J= 4.4,1.5 Hz), 9.03(2H,s). MS (FAB) m/z: 567 (M+H)$^+$.

Example A-216

4-[[5-(Pyridin-4-yl)pyrimidin-2-yl]carbonyl]-1-[(6-ethynylbenzo[b]thien-2-yl)sulfonyl]piperazine In a mixed solvent of tetrahydrofuran (5 ml) and methanol (7 ml) was dissolved 1-[[5-(4-pyridyl)pyrimidin-2-yl]carbonyl]-4-[(6-trimethylsilylethynylbenzo[b]thien-2-yl)sulfonyl]piperazine (167 mg), followed by the addition of potassium hydroxide (34 mg). The resulting mixture was stirred at room temperature for 30 minutes. The reaction mixture was made weakly acidic with a saturated aqueous solution of ammonium chloride, and then made weakly alkaline with a saturated aqueous solution of sodium bicarbonate. After concentration under reduced pressure, the concentrate was extracted (4 times) with methylene chloride. The organic layers were combined, dried over anhydrous sodium sulfate and distilled under reduced pressure to remove the solvent. The residue was purified by chromatography on a silica gel column (methylene chloride:methanol=1:0→24:1). The resulting amorphous was dissolved in methylene chloride, followed by the dropwise addition to hexane to precipitate the resulting mixture as powder. The title compound (112 mg) was obtained as a white solid.

$^1$H-NMR (CDCl$_3$) δ: 3.23(1H,s), 3.25(2H,t,J=5.1 Hz), 3.35(2H,t,J=5.1 Hz), 3.61(2H,t,J=5.1 Hz), 4.00(2H,t,J=5.1 Hz), 7.51(2H,dd,J=4.4,1.5 Hz), 7.58(1H,dd,J=8.3,0.98 Hz), 7.79(1H,s), 7.86(1H,d,J=8.3 Hz), 8.02(1H,s), 8.80(2H,dd,J= 4.4,1.5 Hz), 9.02(2H,s). MS (FAB) m/z: 490 (M+H)$^+$.

Example A-217

1-[(5-Chloroisoindolin-2-yl)sulfonyl]-4-[4-(pyridin-4-yl)benzoyl]piperazine

In the same manner as in Example A-4, the title compound was obtained.

¹H-NMR (CDCl₃) δ: 3.22–3.80(8H,m), 4.63–4.65(4H, m), 7.37(1H,d,J=8.3 Hz), 7.37(1H,m), 7.43(1H,s), 7.64(2H, d,J=8.3 Hz), 8.04(2H,d,J=8.3 Hz), 8.20–8.14(2H,br), 8.9 (2H,d,J=5.4 Hz). MS (FAB) m/z: 483 [(M+H)⁺, Cl³⁵], 485 [(M+H)⁺, Cl³⁷].

Example A-218

4-[4-[[4-[(5-Chloroisoindolin-2-yl)sulfonyl] piperazin-1-yl]carbonyl]phenyl]pyridine N-oxide In the same manner as in Example A-6, the title compound was obtained.

¹H-NMR (DMSO-d₆) δ: 3.25–3.77(8H,m), 4.62–4.65 (4H,m), 7.33–7.39(2H,m), 7.43(1H,s), 7.54(2H,d,J=8.3 Hz), 7.81(1H,d,J=6.8 Hz), 7.86(2H,d,J=8.3 Hz), 8.28(2H,d,J=6.8 Hz). MS (FAB) m/z: 499 [(M+H)⁺, Cl³⁵], 501 [(M+H)⁺, Cl³⁷].

Example A-219

4-[(5-Chloroindol-2-yl)sulfonyl]-2-ethyl -1-[[5-pyridin-4-yl)pyrimidin-2-yl]carbonyl]piperazine In the same manner as in Example A-182, the title compound was obtained.

¹H-NMR (DMSO-d₆) δ: 0.75(1.5H,t,J=7.8 Hz), 0.94 (1.5H,t,J=7.8 Hz), 1.60–1.89(2H,m), 2.23–2.57(2H,m), 3.14 (0.5H,m), 3.25–3.43(1H,m), 3.45–3.90(2.5H,m), 4.44–4.53 (0.5H,m), 4.65–4.72(0.5H,m), 7.04(1H,t,J=2.4 Hz), 7.34 (1H,dt,J=8.8,2.4 Hz), 7.50(1H,dd,J=8.8,2.4 Hz), 7.80(1H,t, J=2.4 Hz), 8.18(2H,br), 8.90(2H,br), 9.39(2H,t,J=2.4 Hz), 12.48(1H,br). MS (FAB) m/z: 511 [(M+H)⁺, Cl³⁵], 513 [(M+H)⁺, Cl³⁷].

Example A-220

4-[2-[[4-[(5-Chloroindol-2-yl)sulfonyl]-2-ethylpiperazin-1-yl]carbonyl]pyrimidin-5-yl] pyridine N-oxide In the same manner as in Example A-6, the title compound was obtained.

¹H-NMR (DMSO-d₆) δ: 0.74(1.5H,t,J=7.3 Hz), 0.93 (1.5H,t,J=7.3 Hz), 1.03–1.09(0.5H,m), 1.58–1.68(0.5H,m), 1.70–1.90(1.5H,m), 2.13–2.57(2H,m), 3.13–3.21(0.5H,m), 3.25–3.60(2H,m), 3.70–3.76(0.5H,m), 3.78–3.86(0.5H,m), 4.45–4.52(0.5H,m), 4.67(0.5H,br), 7.04(1H,m), 7.34(1H,dt, J=8.8,2.4 Hz), 7.50(1H,dd,J=8.8,2.4 Hz), 7.80(1H,t,J=2.4 Hz), 7.90(2H,dd,J=7.3,2.4 Hz), 8.38(2H,t,J=7.3,3.4 Hz), 9.29(2H,d,J=4.5 Hz), 12.46(1H,br). MS (FAB) m/z: 517 [(M+H)⁺, Cl³⁵], 519 [(M+H)⁺, Cl³⁷].

Example A-221

4-[(6-Chlorobenzo[b]thien-2-yl)sulfonyl]-2-ethyl-1-[(5-(pyridin-4-yl)pyrimidin-2-yl]carbonyl]piperazine In the same manner as in Example A-182, the title compound was obtained.

¹H-NMR (DMSO-d₆) δ: 0.77(1.5H,t,J=7.8 Hz), 0.95 (1.5H,t,J=7.8 Hz), 1.62–1.70(0.5H,m), 1.73–1.82(0.5H,m), 1.83–1.93(1H,m), 2.44–2.71(2H,m), 3.14–3.24(0.5H,m), 3.35–3.62(2H,m), 3.67–3.76(1H,m), 3.79–3.85(0.5H,m), 4.47–4.53(0.5H,m), 4.67–4.74(0.5,m), 7.57–7.62(1H,m), 8.03–8.14(4H,m), 8.33–8.37(1H,m), 8.83(1H,d,J=4.6 Hz), 9.36(2H,d,J=3.7 Hz). MS (FAB) m/z: 528 [(M+H)⁺, Cl³⁵], 530 [(M+H)⁺, Cl³⁷].

Example A-222

4-[2-[[4-[(6-Chlorobenzo[b]thien-2-yl)sulfonyl]-2-ethylpiperazin-1-yl]carbonyl]pyrimidin-5-yl] pyridine N-oxide In the same manner as in Example A-6, the title compound was obtained.

¹H-NMR (DMSO-d₆) δ: 0.76(1.5H,t,J=7.3 Hz), 0.94 (1.5H,t,J=7.3 Hz), 1.15–1.28(0.5H,m), 1.60–1.69(0.5H,m), 1.70–1.92(1.5H,m), 2.50–2.60(1H,m), 2.62–2.71(1H,m), 3.12–3.24(0.5H,m), 3.35–3.45(1H,m), 3.50–3.61(1H,m), 3.64–3.87(1H,m), 4.47–4.54(0.5H,m), 4.67–4.74(0.5H,m), 7.58–7.63(1H,m), 7.94–8.00(2H,m), 8.06–8.13(2H,m), 8.34–8.40(3H,m), 9.30(2H,d,J=2.0 Hz). MS (FAB) m/z: 544 [(M+H)⁺, Cl³⁵], 546 [(M+H)⁺, Cl³⁷].

Example A-223

4-[(5-Chloroindol-2-yl)sulfonyl]-2-ethyl-1-[(5-(pyridin-2-yl)pyrimidin-2-yl]carbonyl]piperazine In the same manner as in Example A-182, the title compound was obtained.

¹H-NMR (DMSO-d₆) δ: 0.74(1.5H,t,J=7.3 Hz), 0.94 (1.5H,t,J=7.3 Hz), 1.02–1.13(0.5H,m), 1.57–1.68(0.5H,m), 1.70–1.89(2H,m), 2.25–2.49(1H,m), 3.10–3.23(0.5H,m), 3.27–3.59(2.5H,m), 3.68–3.87(1H,m), 4.45–4.52(0.5H,m), 4.63–4.71(0.5H,m), 7.03–7.05(1H,m), 7.32–7.36(1H,m), 7.50(2H,d,J=8.3,2.4 Hz), 7.79(1H,br), 7.98–8.02(1H,m), 8.16(1H,d,J=7.8 Hz), 8.75–8.77(1H,m), 9.48(2H,br), 12.46 (1H,br). MS (FAB) m/z: 511 [(M+H)⁺, Cl³⁵], 513 [(M+H)⁺, Cl³⁷].

Example A-224

2-[2-[[4-[(5-Chloroindol-2-yl)sulfonyl]-2-ethylpiperazin-1-yl]carbonyl]pyrimidin-5-yl] pyridine N-oxide To a methylene chloride solution (50 ml) of 4-[(5-chloroindol-2-yl)sulfonyl]-2-(ethyl)-1-[(5-(pyridin-2-yl) pyrimidin-2-yl]carbonyl]piperazine (234 mg) was added metachloroperbenzoic acid (1.58 g) at room temperature. The resulting mixture was stirred for 5 hours. An aqueous solution (20 ml) of sodium sulfite was added, followed by stirring for 1 hour. To the reaction mixture were added a saturated aqueous solution of sodium bicarbonate and methylene chloride. The water layer was extracted thrice with methylene chloride. The organic layers were combined, dried over anhydrous sodium sulfate and distilled under reduced pressure to remove the solvent. The residue was subjected to chromatography on a silica gel column (methanol:methylene chloride=1:50). The oil thus obtained was solidified from ethanol-diethyl ether, whereby the title compound (44.1 mg) was obtained as a pale yellow solid. MS (FAB) m/z: 527 [(M+H)⁺, Cl³⁵], 529 [(M+H)⁺, Cl³⁷].

¹H-NMR (DMSO-d₆) δ: 0.75(1.5H,t,J=7.3 Hz), 0.93 (1.5H,t,J=7.3 Hz), 1.05–1.13(0.5H,m), 1.58–1.92(2.5H,m), 2.29–2.78(1H,m), 3.13–3.89(4H,m), 4.40–4.52(0.5H,m), 4.62–4.71(0.5H,m), 7.04(1H,d,J=3.4 Hz), 7.32–7.37(1H,m), 7.47–7.55(3H,m), 7.78–7.82(1H,m), 7.86–7.90(1H,m), 8.42 (1H,d,J=5.9 Hz), 9.33(2H,br), 12.44(1H,br).

Example A-225

1-[(5-Chloroindol-2-yl)sulfonyl]-4-[5-(pyridin-3-yl) thiazol-2-yl]piperazine

To a solution of 3-(5-thiazolyl)pyridine (400 mg) in diethyl ether (15 mg), n-butyl lithium (a 1.52 N hexane solution, 1.45 ml) was added dropwise at −78° C. After stirring for 30 minutes, a carbon dioxide gas was blown into the reaction mixture. After 10 minutes, a cooling bath was removed and the temperature of the reaction mixture was allowed to rise back slowly to room temperature. The reaction mixture was concentrated, whereby the residue of lithium 5-(3-pyridyl)thiazole-2-carboxylate was obtained as a white solid. To a solution of the resulting residue in N,N-dimethylformamide (10 ml) were added 1-[(5-chloroindol-2-yl)sulfonyl]piperazine hydrochloride (600 mg), 1-hydroxybenzotriazole monohydrate (255 mg) and 1-(3-dimethylaminopropyl)-3-ethylcarbodiimide hydrochloride (360 mg) at room temperature. After stirring for 3 days, ethyl acetate (50 ml) and water (100 ml) were added to the reaction mixture. The white precipitate thus obtained was collected by filtration and washed with water and ethyl acetate, whereby the title compound (727 mg) was obtained as a pale brown solid. A portion of the compound was added with an aqueous solution of hydrochloric acid, followed by concentration and drying. The product thus obtained showed the following data.

$^1$H-NMR (DMSO-$d_6$) δ: 3.32(4H,br s), 3.94(2H,br s), 4.59(2H,br s), 7.20(1H,s), 7.47(1H,d,J=8.8 Hz), 7.65(1H,d, J=8.8 Hz), 7.66–7.76(1H,m), 7.93(1H,s), 8.36(1H,d,J=8.3 Hz), 8.63(1H,br s), 8.78(1H,s), 9.16(1H,s), 12.61(1H,s). MS (FAB) m/z: 488 (M+H)$^+$.

Example A-226

3-[2-[[4-[(5-Chloroindol-2-yl)sulfonyl]piperazin-1-yl]carbonyl]thiazol-5-yl]pyridine N-oxide In the same manner as in Example A-6, the title compound was obtained.

$^1$H-NMR (DMSO-$d_6$) δ: 3.31(4H,br s), 3.93(2H,br s), 4.57(2H,br s), 7.19(1H,s), 7.46(1H,d,J=8.8 Hz), 7.50–7.70 (2H,m), 7.80(1H,d,J=8.3 Hz), 7.92(1H,s), 8.05(1H,s), 8.39 (1H,d,J=6.4 Hz), 8.67(1H,br s), 8.93(1H,s), 12.61(1H,br s). MS (FAB) m/z: 504 (M+H)$^+$, 488 (M+H–O)$^+$.

Example A-227

1-[(5-Chloro-1-phenylsulfonylindol-2-yl)sulfonyl]-4-[5-(2-methylpyridin-4-yl)thiazol-2-yl]piperazine A saturated solution of hydrochloride in methanol (12 ml) was added to 1-(t-butoxycarbonyl)-4-[5-(2-methylpyridin-4-yl)thiazol-2-yl]piperazine (400 mg) at room temperature. After stirring for 10 minutes, the reaction mixture was concentrated under reduced pressure, whereby 1-[5-(2-methylpyridin-4-yl)thiazol-2-yl]piperazine hydrochloride was obtained as a white solid. In a solution of the resulting hydrochloride in methylene chloride (12 ml) was dissolved 5-chloro-1-phenylsulfonylindol-2-sulfonyl chloride (522 mg), followed by the addition of diisopropylethylamine (538 µl) at room temperature. After stirring for 3 hours, a saturated aqueous solution (50 ml) of sodium bicarbonate was added to the reaction. mixture to separate it into layers. The water layer was extracted with methylene chloride (2×15 ml). The organic layers were combined, dried over anhydrous sodium sulfate and distilled under reduced pressure to remove the solvent. The residue was purified by chromatography on a silica gel column (methylene chloride:acetone=7:1), whereby the title compound (240 mg) was obtained as a foam.

$^1$H-NMR (CDCl$_3$) δ: 2.63(3H,s), 3.55(2H,s), 3.60(2H,s), 3.92(2H,s), 4.60(2H,s), 7.31(1H,d,J=5.4 Hz), 7.35(1H,s), 7.40–7.52(4H,m), 7.52–7.65(2H,m), 8.03(2H,d,J=7.3 Hz), 8.14(1H,s), 8.23(1H,d,J=9.3 Hz), 8.56(1H,d,J=5.4 Hz).

Example A-228

1-[(5-Chloroindol-2-yl)sulfonyl]-4-[5-(2-methylpyridin-4-yl)thiazol-2-yl]piperazine In the same manner as in Example A-99, the title compound was obtained.

$^1$H-NMR (DMSO-$d_6$) δ: 2.88(3H,s), 3.33(4H,br s), 3.95 (2H,br s), 4.57(2H,br s), 7.20(1H,d,J=2.0 Hz), 7.47(1H,dd, J=8.8,2.0 Hz), 7.66(1H,d,J=8.8 Hz), 7.93(1H,d,J=2.0 Hz), 8.32(1H,d,J=6.4 Hz), 8.40(1H,br s), 8.94(1H,d,J=6.4 Hz), 9.02(1H,d,J=2.0 Hz), 12.66(1H,s). MS (FAB) m/z: 502 [(M+H)$^+$, Cl$^{35}$], 504 [(M+H)$^+$, Cl$^{37}$].

Example A-229

4-[2-[[4-[(5-Chloroindol-2-yl)sulfonyl]piperazin-1-yl]carbonyl]thiazol-5-yl]-2-methylpyridine N-oxide In the same manner as in Example A-6, the title compound was obtained.

$^1$H-NMR (DMSO-$d_6$) δ: 3.28(4H,br s), 3.47(3H,s), 3.91 (2H,br), 4.56(2H,br.s), 7.17(1H,s), 7.44(1H,dd,J=8.8,2.0 Hz), 7.62(1H,d,J=8.8 Hz), 7.81(1H,dd,J=6.8,2.7 Hz), 7.90 (1H,d,J=2.0 Hz), 8.04(1H,d,J=2.7 Hz), 8.43(1H,d,J=6.8 Hz), 8.59(1H,s), 12.57(1H,br s). MS (FAB) m/z: 518 (M+H)$^+$, 502 (M+H–O)$^+$.

Example A-230

1-[(5-Ethynylindol-2-yl)sulfonyl]-4-[5-(pyridin-4-yl)thiazol-2-yl]piperazine

A saturated solution of hydrochloride in methanol (12 ml) was added to 1-(tert-butoxycarbonyl)-4-[5-(pyridin-4-yl)thiazol-2-yl]piperazine (400 mg) at room temperature. After stirring for 1 hour, the reaction mixture was concentrated under reduced pressure, whereby the residue, that is, 1-[5-(pyridin-4-yl)thiazol-2-yl]piperazine hydrochloride was obtained as a white solid. In a solution of the resulting residue in methylene chloride (15 ml) was dissolved [1-phenylsulfonyl-5-(trimethylsilylethynyl)indol-2-yl] sulfonyl chloride (630 mg), followed by the addition of diisopropylethylamine (746 µl) at 0° C. After stirring for 4 hours, methylene chloride (10 ml) and a saturated aqueous solution (30 ml) of sodium bicarbonate were added to the reaction mixture to separate it into layers. The water layer was extracted with methylene chloride (2×10 ml). The organic layers were combined, dried over anhydrous sodium sulfate and distilled under reduced pressure to remove the solvent. The residue was purified by chromatography on a silica gel column (methylene chloride acetone=6:1), whereby 1-[5-(2-methylpyridin-4-yl)thiazol-2-yl)-4-[[1-phenylsulfonyl-5-(trimethylsilylethynyl)indol-2-yl] sulfonyl]piperazine (214 mg) was obtained as a foam.

To a solution of the resulting residue in tetrahydrofuran (10 ml) were added methanol (10 ml), morpholine (54.0 µl) and potassium hydroxide (52.0 mg), followed by stirring at room temperature for 3 hours. A saturated aqueous solution (30 ml) of sodium bicarbonate, methylene chloride (30 ml) and water (10 ml) were added to the reaction mixture to separate it into layers. The water layer was extracted with methylene chloride (10 ml). The organic layers were combined, dried over anhydrous sodium sulfate and distilled under reduced pressure to remove the solvent. The residue was purified by preparative thin-layer chromatography (methylene chloride:acetone=6:1) using silica gel, whereby the title compound (84.8 mg) was obtained as a white solid. The solid was dissolved in tetrahydrofuran, followed by the addition of water. The resulting mixture was concentrated, whereby a white solid was obtained. The solid showed the following data:

$^1$H-NMR (DMSO-d$_6$) δ: 3.15(4H,br s), 3.77(2H,br s), 4.01(1H,s), 4.41(2H,br s), 7.05(1H,s), 7.34(1H,d,J=8.5 Hz), 7.44(1H,d,J=8.5 Hz), 7.72(2H,d,J=4.9 Hz), 7.85(1H,s), 8.58 (1H,s), 8.63(2H,d,J=4.9 Hz), 12.42(1H,br s). MS (FAB) m/z: 478 (M+H)$^+$.

Example A-231

4-[2-[[4-[(5-Ethynylindol-2-yl)sulfonyl]piperazin-1-yl]carbonyl]thiazol-5-yl]pyridine N-oxide In the same manner as in Example A-6, the title compound was obtained.

$^1$H-NMR (DMSO-d$_6$) δ: 3.16(4H,br s), 3.77(2H,br s), 4.02(1H,s), 4.41(2H,br s), 7.06(1H,s), 7.36(1H,d,J=8.5 Hz), 7.46(1H,d,J=8.5 Hz), 7.78(2H,d,J=6.9 Hz), 7.86(1H,s), 8.26 (2H,d,J=6.9 Hz), 8.48(1H,s), 12.43(1H,br s). MS (FAB) m/z: 494 (M+H)$^+$, 478 (M+H−O)$^+$.

Example A-232

1-[(6-Chloronaphthalen-2-yl)sulfonyl]-4-[[5-(pyridin-4-yl)thiazol-2-yl]carbonyl]piperazine hydrochloride In the same manner as in Example A-7, the title compound was obtained.

$^1$H-NMR (DMSO-d$_6$) δ: 3.14(4H,br s), 3.79(2H,br s), 4.41(2H,br s), 7.71(1H,dd,J=8.8,2.0 Hz), 7.83(1H,dd,J=8.8, 2.0 Hz), 8.11(2H,d,J=5.9 Hz), 8.15(1H,d,J=8.8 Hz), 8.22 (1H,d,J=2.0 Hz), 8.25(1H,d,J=8.8 Hz), 8.51(1H,s), 8.77(1H, s), 8.79–8.85(2H,m). MS (FAB) m/z: 499 [(M+H)$^+$, Cl$^{35}$], 501 [(M+H)$^+$, Cl$^{37}$].

Example A-233

4-[2-[[4-[(6-Chloronaphthalen-2-yl)sulfonyl]piperazin-1-yl]carbonyl]thiazol-5-yl]pyridine N-oxide In the same manner as in Example A-6, the title compound was obtained.

$^1$H-NMR (DMSO-d$_6$) δ: 3.13(4H,br s), 3.77(2H,br s), 4.43(2H,br s), 7.69(1H,d,J=8.8 Hz), 7.76(2H,d,J=6.4 Hz), 7.82(1H,d,J=8.8 Hz), 8.15(1H,d,J=8.8 Hz), 8.20–8.28(5H, m), 8.46(1H,s), 8.50(1H,s). MS (FAB) m/z: 515 [(M+H)$^+$, Cl$^{35}$], 517 [(M+H)$^+$, Cl$^{37}$].

Example A-234

1-[(6-Chloronaphthalen-2-yl)sulfonyl]-4-[[5-(pyridin-2-yl)thiazol-2-yl]carbonyl]piperazine hydrochloride In the same manner as in Example A-4, the title compound was obtained.

$^1$H-NMR (DMSO-d$_6$) δ: 3.13(4H,br s), 3.77(2H,br s), 4.42(2H,br s), 7.37(1H,m), 7.69(1H,dd,J=8.8,2.0 Hz), 7.81 (1H,d,J=8.8 Hz), 7.89(1H,m), 8.03(1H,d,J=7.8 Hz), 8.15 (1H,d,J=8.8 Hz), 8.21(1H,d,J=2.0 Hz), 8.25(1H,d,J=8.8 Hz), 8.50(1H,s), 8.56(1H,s), 8.57(1H,d,J=4.4 Hz). MS (FAB) m/z: 499 [(M+H)$^+$, Cl$^{35}$], 501 [(M+H)$^+$, Cl$^{37}$].

Example A-235

2-[2-[[4-[(6-Chloronaphthalen-2-yl)sulfonyl]piperazin-1-yl]carbonyl]thiazol-5-yl]pyridine N-oxide In the same manner as in Example A-6, the title compound was obtained.

$^1$H-NMR (DMSO-d$_6$) δ: 3.14(4H,br s), 3.78(2H,br s), 4.41(2H,br s), 7.47(1H,t,J=7.8 Hz), 7.54(1H,t,J=7.8 Hz), 7.68(1H,dd,J=8.8,2.0 Hz), 7.84(1H,d,J=8.8 Hz), 8.15(1H,d, J=8.8 Hz), 8.20(1H,s), 8.25(1H,d,J=8.8 Hz), 8.42–8.51(3H, m), 8.95(1H,s). MS (FAB) m/z: 515 [(M+H)$^+$, Cl$^{35}$], 517 [(M+H)$^+$, Cl$^{37}$].

Example A-236

1-[(5-Chloroindol-2-yl)sulfonyl]-4-[[5-(pyridin-4-yl)thiazol-2-yl]carbonyl]piperazine hydrochloride In the same manner as in Example A-4, the title compound was obtained.

$^1$H-NMR (DMSO-d$_6$) δ: 3.18(4H,br s), 3.80(2H,br s), 4.41(2H,br s), 7.04(1H,s), 7.30(1H,dd,J=8.8,1.5 Hz), 7.49 (1H,d,J=8.8 Hz), 7.76(1H,s), 8.15(2H,d,J=5.9 Hz), 8.79(1H, s), 8.84(2H,d,J=5.9 Hz), 12.44(1H,s). MS (FAB) m/z: 488 [(M+H)$^+$, Cl$^{35}$], 490 [(M+H)$^+$, Cl$^{37}$].

Example A-237

4-[2-[[4-[(5-Chloroindol-2-yl)sulfonyl]piperazin-1-yl]carbonyl]thiazol-5-yl]pyridine N-oxide In the same manner as in Example A-6, the title compound was obtained.

$^1$H-NMR (DMSO-d$_6$) δ: 3.16(4H,br s), 3.78(2H,br s), 4.43(2H,br s), 7.03(1H,s), 7.30(1H,dd,J=8.8,2.0 Hz), 7.47 (1H,d,J=8.8 Hz), 7.75(1H,d,J=2.0 Hz), 7.77(2H,d,J=7.3 Hz), 8.25(2H,d,J=7.3 Hz), 8.30(1H,s), 8.47(1H,s), 12.41(1H,s). MS (FAB) m/z: 504 [(M+H)$^+$, Cl$^{35}$], 506 [(M+H)$^+$, Cl$^{37}$].

Example A-238

1-[(6-Chlorobenzo[b]thien-2-yl)sulfonyl]-4-[[5-(pyridin-4-yl)thiazol-2-yl]carbonyl]piperazine hydrochloride In the same manner as in Example A-4, the title compound was obtained.

$^1$H-NMR (DMSO-d$_6$) δ: 3.24(4H,br s), 3.84(2H,br s), 4.46(2H,br s), 7.50–7.65(3H,m), 8.03–8.10(2H,m), 8.30 (1H,s), 8.76(1H,s), 8.80(2H,m). MS (FAB) m/z: 505 [(M+H)$^+$, Cl$^{35}$], 507 [(M+H)$^+$, Cl$^{37}$].

Example A-239

4-[2-[[4-[(6-Chlorobenzo[b]thien-2-yl)sulfonyl]piperazin-1-yl]carbonyl]thiazol-5-yl]pyridine N-oxide In the same manner as in Example A-6, the title compound was obtained.

$^1$H-NMR (DMSO-d$_6$) δ: 3.22(4H,br s), 3.82(2H,br s), 4.47(2H,br s), 7.54(1H,dd,J=8.8,2.0 Hz), 7.78(2H,d,J=7.3 Hz), 8.05(1H,d,J=8.8 Hz), 8.09(1H,s), 8.25(2H,d,J=7.3 Hz), 8.29(1H,s), 8.48(1H,s). MS (FAB) m/z: 521 [(M+H)$^+$, Cl$^{35}$], 523 [(M+H)$^+$, Cl$^{37}$].

Example A-240

1-[(5-Chloroindol-2-yl)sulfonyl]-4-[[3-(pyridin-4-yl)-1,2,4-triazin-6-yl]carbonyl]piperazine hydrochloride Ethyl 3-(pyridin-4-yl)-1,2,4-triazin-6-carboxylate (200 mg) was dissolved in a mixed solvent of tetrahydrofuran (5 ml) and methanol (5 ml) at room temperature. A 1N aqueous solution (1.00 ml) of sodium hydroxide was added to the reaction mixture in one portion. After stirring for 5 minutes, the reaction mixture was distilled under reduced pressure to remove tetrahydrofuran and methanol, followed by neutralization with 1N hydrochloric acid. The reaction mixture was concentrated to dryness, whereby 3-(pyridin-4-yl)-1,2,4-triazine-6-carboxylic acid was obtained as a crudely purified product.

In N,N-dimethylformamide (10 ml) were suspended 3-(pyridin-4-yl)-1,2,4-triazine-6-carboxylic acid and 1-[(5-chloroindol-2-yl)sulfonyl]piperazine hydrochloride (292 mg) at room temperature. To the reaction mixture were successively added 1-hydroxybenzotriazole (117 mg), N-methylmorpholine (191 µl) and 1-(3-dimethylaminopropyl)-3-ethylcarbodiimide hydrochloride (250 mg), followed by stirring overnight. After completion of the reaction, the solvent was distilled off under reduced pressure. Water and ethyl acetate were added to the residue to separate into layers. The organic layer was dried over magnesium sulfate and the filtrate was concentrated. Ethanol was added to the residue. Yellow crystals thus precipitated were collected by filtration and dried, whereby the free form (282 mg) of the title compound was obtained. The free form was suspended in ethanol and the resulting suspension was made acidic by the addition of 1N hydrochloric acid (in ethanol) and a small amount of water. After concentration of the resulting solution, ethanol and ethyl acetate were added and the resulting mixture was concentrated again. Crystals thus precipitated were collected by filtration and dried, whereby the title compound was obtained.

$^1$H-NMR (DMSO-$d_6$) δ: 3.05–3.09(2H,m), 3.18–3.21 (2H,m), 3.69–3.72(2H,m), 3.84–3.88(2H,m), 7.05(1H,d,J= 1.5 Hz), 7.33(1H,dd,J=8.8,2.0 Hz), 7.50(1H,d,J=8.8 Hz), 7.79(1H,d,J=2.0 Hz), 8.45–8.52(2H,m), 8.92–8.98(2H,m), 9.17(1H,d,J=1.0 Hz), 12.47(1H,s). MS (FAB) m/z: 484 [(M+H)$^+$, Cl$^{35}$], 486 [(M+H)$^+$, Cl$^{37}$].

Example A-241

4-[6-[[4-[(5-Chloroindol-2-yl)sulfonyl]piperazin-1-yl]carbonyl]-1,2,4-triazin-3-yl]pyridine N-oxide In the same manner as in Example A-6, the title compound was obtained.

$^1$H-NMR (DMSO-$d_6$) δ: 3.06(2H,br), 3.18(2H,br), 3.70 (2H,br), 3.85(2H,br), 7.05(1H,s), 7.32(1H,dd,J=8.8,2.0 Hz), 7.49(1H,d,J=8.8 Hz), 7.79(1H,d,J=2.0 Hz), 8.34(2H,d,J=7.3 Hz), 8.40(2H,d,J=7.3 Hz), 9.06(1H,s), 12.45(1H,s). MS (FAB) m/z: 500 [(M+H)$^+$, Cl$^{35}$], 502 [(M+H)$^+$, Cl$^{37}$].

Example A-242

1-[(6-Chloronaphthalen-2-yl)sulfonyl]-4-[[2,5-dihydro-5-oxo-6-(pyridin-4-yl)-1,2,4-triazin-3-yl] carbonyl]piperazine hydrochloride In the same manner as in Example A-4, the title compound was obtained.

$^1$H-NMR (DMSO-$d_6$) δ: 3.00–3.09(2H,m), 3.10–3.17 (2H,m), 3.75–3.81(4H,m), 7.74(1H,dd,J=8.8 and 2.0 Hz), 7.86(1H,d,J=8.8 Hz), 8.20(1H,d,J=8.8 Hz), 8.25–8.35(4H, m), 8.55(1H,br s), 8.86(2H,d,J=5.4 Hz). MS (FAB) m/z: 511 [(M+H)$^+$, Cl$^{35}$], 513 [(M+H)$^+$, Cl$^{37}$].

Example A-243

1-[(6-Chloronaphthalen-2-yl)sulfonyl]-4-[[5-(2,6-dimethylpyridin-4-yl)pyrimidin-2-yl]carbonyl] piperazine hydrochloride In the same manner as in Example A-182, the title compound was obtained.

$^1$H-NMR (DMSO-$d_6$) δ: 2.71(6H,s), 2.94(2H,br s), 3.13 (2H,br s), 3.37(2H,br s), 3.80(2H,br s), 7.74(1H,dd,J=8.8, 2.0 Hz), 7.83(1H,d,J=8.8 Hz), 8.13(2H,br s), 8.13(1H,d,J= 8.8 Hz), 8.27–8.30(2H,m), 8.52(1H,s), 9.38(2H,s). MS (FAB) m/z: 522 [(M+H)$^+$, Cl$^{35}$], 524 [(M+H)$^+$, Cl$^{37}$].

Example A-244

4-[2-[[4-[(6-Chloronaphthalen-2-yl)sulfonyl] piperazin-1-yl]carbonyl]pyrimidin-5-yl]-2,6-dimethylpyridine N-oxide In the same manner as in Example A-6, the title compound was obtained.

$^1$H-NMR (CDCl$_3$) δ: 2.61(6H,s), 3.15(2H,d,J=4.8 Hz), 3.26(2H,d,J=4.8 Hz), 3.57(2H,d,J=4.8 Hz), 3.96(2H,d,J=4.9 Hz), 7.37(2H,s), 7.60(1H,dd,J=8.8,2.0 Hz), 7.76(1H,dd,J= 8.8,1.5 Hz), 7.91–7.97(3H,m), 8.31(1H,s), 8.96(2H,s). MS (FAB) m/z: 538 [(M+H)$^+$, Cl$^{35}$], 540 [(M+H)$^+$, Cl$^{37}$].

Example A-245

1-[(5-Chloro-1-phenylsulfonylindol-2-yl)sulfonyl]-4-[4-(pyridin-4-yl)phenylsulfonyl]piperazine A saturated solution of hydrochloride in methanol (10 ml) was added to 1-(tert-butoxycarbonyl)-4-[4-(pyridin-4-yl) phenylsulfonyl]piperazine (180 mg). After stirring for 30 minutes, the solvent was distilled off under reduced pressure. To the residue were added methylene chloride (10 ml), 5-chloro-1-phenylsulfonylindol-2-sulfonyl chloride (260 mg) and diisopropylethylamine (235 µg) at room temperature. After stirring for 4 hours, methylene chloride (10 ml) and a saturated aqueous solution (30 ml) of sodium bicarbonate were added the reaction mixture to separate it into layers. The water layer was extracted with methylene chloride. The organic layers were combined, dried over anhydrous sodium sulfate and distilled under reduced pressure to remove the solvent. The residue was purified by chromatography on a silica gel column (methylene chloride:acetone=5:1→3:1), whereby the title compound (131 mg) was obtained as a pale yellow foam.

$^1$H-NMR (CDCl$_3$) δ: 3.18(4H,s), 3.57(4H,s), 7.37–7.46 (4H,m), 7.50–7.59(4H,m), 7.80(2H,d,J=8.3 Hz), 7.85(2H,d, J=8.3 Hz), 7.86(2H,d,J=8.3 Hz), 8.12(1H,d,J=8.8 Hz), 8.76 (2H,br d,J=4.4 Hz).

Example A-246

1-[(5-Chloroindol-2-yl)sulfonyl]-4-[4-(pyridin-4-yl) phenylsulfonyl]piperazine hydrochloride In the same manner as in Example A-103, the title compound was obtained.

$^1$H-NMR (DMSO-$d_6$) δ: 3.05(4H,br t,J=4.0 Hz), 3.18(4H, br t,J=4.0 Hz), 6.97(1H,d,J=1.5 Hz), 7.16(1H,dd,J=8.8,1.9 Hz), 7.40(1H,d,J=8.8 Hz), 7.68(1H,d,J=1.9 Hz), 7.83(2H,d, J=8.5 Hz), 8.09(2H,d,J=8.5 Hz), 8.19(2H,d,J=6.6 Hz), 8.97 (2H,d,J=6.6 Hz), 12.40(1H,br s). MS (FAB) m/z: 517 (M+H)$^+$.

Example A-247

4-[4-[[4-[(5-Chloroindol-2-yl)sulfonyl]piperazin-1-yl]sulfonyl]phenyl]pyridine N-oxide In the same manner as in Example A-6, the title compound was obtained.

$^1$H-NMR (DMSO-$d_6$) δ: 3.00(4H,br t,J=4.6 Hz), 3.17(4H, br t,J=4.0 Hz), 6.96(1H,s), 7.18(1H,dd,J=9.1,1.7 Hz), 7.39

(1H,d,J=9.1 Hz), 7.69(1H,d,J=1.7 Hz), 7.73(2H,d,J=8.3 Hz), 7.82(2H,d,J=6.8 Hz), 7.93(2H,d,J=8.3 Hz), 8.34(2H,d,J=6.8 Hz), 12.35(1H,br s). MS (FAB) m/z: 533 (M+H)$^+$.

Example A-248

1-[(5-Chloroindol-2-yl)carbonyl]-4-[4-(pyridin-4-yl) phenylsulfonyl]piperazine hydrochloride A saturated solution of hydrochloride in methanol (10 ml) was added to 1-(tert-butoxycarbonyl)-4-[4-(pyridin-4-yl) phenylsulfonyl]piperazine (180 mg). After stirring for 30 minutes, the solvent was distilled off under reduced pressure. To a solution of the residue in N,N-dimethylformamide (10 ml) were added (5-chloroindol-2-yl)carboxylic acid (90.0 mg), 1-hydroxybenzotriazole (75.5 mg) and 1-(dimethylaminopropyl)-3-ethylcarbodiimide hydrochloride (107 mg) and diisopropylethylamine (233 µg) at room temperature. After stirring for 3 days, methylene chloride (100 ml) and water (500 ml) were added to the reaction mixture to separate it into layers. The water layer was extracted with methylene chloride (50 ml). The organic layers were combined, washed with water (500 ml) and a saturated aqueous solution (100 ml) of sodium bicarbonate, dried over anhydrous sodium sulfate and distilled under reduced pressure to remove the solvent. The residue was purified by chromatography on a silica gel column (silica gel: 20 g, methylene chloride:acetone=3:1→1:1), whereby the title compound (97.5 mg) was obtained as a white solid. The resulting compound was dissolved in hydrochloric acid-methanol-methylene chloride-tetrahydrofuran, followed by concentration, whereby the title compound was obtained.

Hydrochloride:
$^1$H-NMR (DMSO-d$_6$) δ: 3.10(4H,br s), 3.84(4H,br s), 6.76(1H,d,J=1.5 Hz), 7.17(1H,dd,J=8.8,2.0 Hz), 7.39(1H,d,J=8.8 Hz), 7.62(1H,d,J=2.0 Hz), 7.96(2H,d,J=8.3 Hz), 8.22(2H,d,J=8.3 Hz), 8.30(2H,d,J=6.4 Hz), 8.97(2H,d,J=6.4 Hz), 11.76(1H,br s). MS (FAB) m/z: 481 (M+H)$^+$.

Example A-249

4-[4-[[4-[(5-Chloroindol-2-yl)carbonyl]piperazin-1-yl]sulfonyl]phenyl]pyridine N-oxide In the same manner as in Example A-6, the title compound was obtained.

$^1$H-NMR (DMSO-d$_6$) δ: 3.07(4H,br s), 3.83(4H,br s), 6.75(1H,s), 7.18(1H,br d,J=8.8 Hz), 7.39(1H,d,J=8.8 Hz), 7.62(1H,br s), 7.85(2H,d,J=8.3 Hz), 7.88(2H,d,J=6.6 Hz), 8.07(2H,d,J=8.3 Hz), 8.33(2H,d,J=6.6 Hz), 11.74(1H,br s). MS (FAB) m/z: 497 (M+H)$^+$.

Example A-250

4-[(5-Chloroindol-2-yl)sulfonyl]-1-[(5-(pyridin-4-yl)pyrimidin-2-yl]carbonyl]-2-(2-methlpropyl)piperazine In the same manner as in Example A-182, the title compound was obtained.

$^1$H-NMR (DMSO-d$_6$) δ: 0.84–1.62(2H,m), 1.75(3H,s), 1.77(3H,s), 2.26–2.41(1H,m), 2.55–2.70(1H,m), 3.18–3.50 (2H,m), 3.55–3.68(1H,m), 3.70–4.45(2H,m), 5.36–5.58(1H, m), 7.04(1H,s), 7.34(1H,d,J=8.8 Hz), 7.51(1H,d,J=8.8 Hz), 7.80(1H,s), 8.16(2H,br), 8.90(2H,br), 9.37(2H,s), 12.48(1H, br). MS (FAB) m/z: 539 [(M+H)$^+$, Cl$^{35}$], 541 [(M+H)$^+$, Cl$^{37}$].

Example A-251

4-[(6-Chlorobenzo[b]thien-2-yl)sulfonyl]-1-[(5-(pyridin-4-yl)pyrimidin-2-yl)carbonyl]-2-(2-methylpropyl)piperazine In the same manner as in Example A-182, the title compound was obtained.

$^1$H-NMR (DMSO-d$_6$) δ: 0.64–1.68(3H,m), 1.75(3H,s), 1.77(3H,s), 2.25–2.58(1H,m), 2.60–2.83(1H,m), 2.87–4.23 (4H,m), 4.40–4.53(1H,m), 7.06(1H,s), 7.34(1H,d,J=8.8 Hz), 7.49(1H,d,J=8.8 Hz), 7.81(1H,s), 8.15(2H,br), 8.88(2H,br), 9.37(2H,br), 12.48(1H,s). MS (FAB) m/z: 556 [(M+H)$^+$, Cl$^{35}$], 558 [(M+H)$^+$, Cl$^{37}$].

Example A-252

1-[(6-Chloronaphthalen-2-yl)sulfonyl]-2,2-dimethyl-4-[4-(pyridin-4-yl)benzoyl]piperazine In the same manner as in Example A-4, the title compound was obtained.

$^1$H-NMR (DMSO-d$_6$) δ: 1.14(3H,br s), 1.28(3H,br s), 3.20–3.90(6H,br), 7.53–7.70(2H,br), 7.71(1H,dd,J=8.8,2.0 Hz), 7.90(1H,br), 7.96–8.08(2H,m), 8.14(1H,d,J=8.8 Hz), 8.20–8.33(4H,m), 8.57(1H,s), 8.92(2H,br). MS (FAB) m/z: 520 [(M+H)$^+$, Cl$^{35}$], 522 [(M+H)$^+$, Cl$^{37}$].

Example A-253

4-[4-[[4-[(6-Chloronaphthalen-2-yl)sulfonyl]-3,3-dimethylpiperazin-1-yl]carbonyl]phenyl]pyridine N-oxide In the same manner as in Example A-6, the title compound was obtained.

$^1$H-NMR (CDCl$_3$) δ: 1.26(3H,br), 1.39(3H,br), 3.26(1H, br), 3.50–3.95(5H,br), 7.45–7.55(4H,br), 7.58(1H,dd,J=8.8, 2.0 Hz), 7.62(2H,d,J=7.8 Hz), 7.79(1H,d,J=7.8 Hz), 7.89 (2H,d,J=7.8 Hz), 7.92(1H,s), 8.27(2H,br), 8.37(1H,s). MS (FAB) m/z: 536 [(M+H)$^+$, Cl$^{35}$], 538 [(M+H)$^+$, Cl$^{37}$].

Example A-254

4-[(6-Chloronaphthalen-2-yl)sulfonyl]-2,2-dimethyl-1-[4-(pyridin-4-yl)benzoyl]piperazine In the same manner as in Example A-26, the title compound was obtained.

$^1$H-NMR (DMSO-d$_6$) δ: 1.50(6H,s), 3.10(2H,s), 3.20–3.30(2H,br t), 3.50(2H,br), 7.58(2H,d,J=7.8 Hz), 7.73 (1H,dd,J=8.8,2.0 Hz), 7.87(1H,dd,J=8.8,2.0 Hz), 7.98(2H, d,J=7.8 Hz), 8.19(1H,d,J=8.8 Hz), 8.20–8.30(3H,m), 8.30 (1H,d,J=7.8 Hz), 8.53(1H,s), 8.90(2H,d,J=5.9 Hz). MS (FAB) m/z: 520 [(M+H)$^+$, Cl$^{35}$], 522 [(M+H)$^+$, Cl$^{37}$].

Example A-255

4-[4-[[4-[(6-Chloronaphthalen-2-yl)sulfonyl]-2,2-dimethylpiperazin-1-yl]carbonyl]phenyl]pyridine N-oxide In the same manner as in Example A-6, the title compound was obtained.

$^1$H-NMR (CDCl$_3$) δ: 1.60(5H,br), 3.04(2H,s), 3.20(2H,t, J=4.9 Hz), 3.48(2H,t,J=4.9 Hz), 7.40–7.50(4H,m), 7.56(2H, d,J=8.8 Hz), 7.61(1H,dd,J=8.8,2.0 Hz), 7.79(1H,dd,J=8.8, 2.0 Hz), 7.88–7.96(1H,m), 7.95(2H,d,J=7.8 Hz), 8.25(2H, d,J=7.8 Hz), 8.34(1H,s). MS (FAB) m/z: 536 [(M+H)$^+$, Cl$^{35}$], 538 [(M+H)$^+$, Cl$^{37}$].

Example A-256

4-[(5-Chloroindol-2-yl)sulfonyl]-2-(methoxycarbonylmethyl)-1-[[4-(pyridin-4-yl)-3-cyclohexen-1-yl]carbonyl]piperazine In a mixture of methylene chloride (30 mL) and N,N-dimethylformamide (30 mL) was dissolved 4-(pyridin-4-yl)-

3-hexenic acid hydrochloride (480 mg). Under ice cooling, 1-[(5-chloro-1-phenylsulfonylindol-2-yl)sulfonyl]-2-(methoxycarbonylmethyl)piperazine (1.024 g), 1-hydroxybenzotriazole (405 mg), N-methylmorpholine (607 mg) and 1-ethyl-3-(3-dimethylaminopropyl) carbodiimide hydrochloride (575 mg) were added to the resulting solution. After 10 minutes, the mixture was allowed to rise back to room temperature, followed by stirring. After 48 hours, the reaction was terminated and the solvent was distilled off under reduced pressure. Ethyl acetate was added to the residue. The resulting mixture was washed with a saturated aqueous solution of sodium bicarbonate and saturated saline, dried over anhydrous magnesium sulfate and distilled under reduced pressure to remove the solvent. The residue was subjected to chromatography on a silica gel column (methylene chloride:methanol=20:1), whereby the title compound (680 mg, colorless oil) was obtained.

$^1$H-NMR (CDCl$_3$) δ: 1.14(1H,t,J=7.1 Hz), 1.22(1H,t,J=7.1 Hz), 1.64–3.87(14H,m), 3.69(3H,s), 6.33–6.42(1H,m), 6.97(1H,m), 7.21–7.40(4H,m), 7.67(1H,d,J=2 Hz), 8.54(2H, m). MS (FAB) m/z: 557 (M+H)$^+$.

Example A-257

Sodium [4-[(5-chloroindol-2-yl)sulfonyl]-1-[[4-(pyridin-4-yl)-3-cyclohexen-1-yl]carbonyl]piperazin-2-yl]acetate In a 100-mL egg-plant type flask was charged 4-[(5-chloroindo-2-yl)sulfonyl]-2-(methoxycarbonylmethyl)-1-[[4-(pyridin-4-yl)-3-hexen-1-yl]carbonyl]piperazine (680 mg), followed by dissolution in methanol (20 mL). A 1N sodium hydroxide solution (5 mL) was added to the resulting solution and the resulting mixture was stirred at 70° C. After 23 hours, the reaction was terminated. After concentration, the crystals were collected by filtration, whereby the title compound (320 mg, colorless solid) was obtained as a sodium salt.

$^1$H-NMR (CDCl$_3$) δ: 1.10–3.90(16H,m), 6.40–6.48(1H, m), 6.95(1H,d,J=2.9 Hz), 7.19(1H,dd,J=8.8,2.0 Hz), 7.41 (3H,m), 7.64(1H,d,J=2.5 Hz), 8.40(2H,m).

Example A-258

4-[(5-Chloroindol-2-yl)sulfonyl]-2-[(piperidin-1-yl) carbonylmethyl]-1-[[4-(pyridin-4-yl)-3-cyclohexen-1-yl]carbonyl]piperazine In the same manner as in Example A-4, the title compound was obtained.

$^1$H-NMR (CDCl$_3$) δ: 1.61–3.82(24H,m), 4.65–4.93(2H, m), 6.96–7.68(5H,m), 8.02(1H,s), 8.51(2H,m).

Example A-259

4-[4-[[4-[(5-Chloroindol-2-yl)sulfonyl]-2-[(piperidin-1-yl)carbonylmethyl]piperazin-1-yl] carbonyl]-1-cyclohexen-1-yl]pyridine N-oxide In the same manner as in Example A-6, the title compound was obtained.

$^1$H-NMR (DMSO-d$_6$) δ: 1.63–4.94(26H,m), 6.28(1H,m), 6.99(1H,m), 7.18–7.40(4H,m), 7.65(1H,d,J=15.4 Hz), 8.13 (1H,d,J=4.9 Hz). MS (FAB) m/z: 626 [(M+H)$^+$, Cl$^{35}$].

Example A-260

1-[((E)-4-Chloro-2-methoxystyryl)sulfonyl]-4-[[5-(pyridin-4-yl)pyrimidin-2-yl]carbonyl]piperazine hydrochloride In the same manner as in Example A-105, the title compound was obtained.

$^1$H-NMR (DMSO-d$_6$) δ: 3.07(2H,br), 3.24(2H,br), 3.39 (2H,br), 3.82(2H,br), 3.92(2H,s), 7.10(1H,dd,J=8.3,1.5 Hz), 7.23(1H,d,J=1.5 Hz), 7.29(1H,d,J=15.6 Hz), 7.56(1H,d,J= 15.6 Hz), 7.84(1H,d,J=8.3 Hz), 8.34(2H,d,J=6.1 Hz), 8.98 (2H,d,J=6.1 Hz), 9.46(2H,s). MS (FAB) m/z: 500 [(M+H)$^+$, Cl$^{35}$], 502 [(M+H)$^+$, Cl$^{37}$].

Example A-261

1-[((E)-4-Chloro-2-hydroxystyryl)sulfonyl]-4-[[5-(pyridin-4-yl)pyrimidin-2-yl]carbonyl]piperazine hydrochloride In methylene chloride (18 ml) was dissolved 1-[((E)-4-chloro-2-methoxystyryl)sulfonyl]-4-[[5-(pyridin-4-yl) pyrimidin-2-yl]carbonyl]piperazine (366 mg), followed by the addition of boron tribromide (a 1.0 mole solution, methylene chloride) at −78° C. in an argon atmosphere. The resulting mixture was stirred at −78° C. for 0.5 hour and 0° C. for 2 hours. The reaction mixture was distilled under reduced pressure. After a saturated aqueous solution of sodium bicarbonate and water were added to the residue and the insoluble matter was filtered off, methylene chloride was added for extraction. The organic layer was washed with saturated saline, dried over anhydrous sodium sulfate and distilled under reduced pressure to remove the solvent. The residue was subjected to column chromatography (10% methanol—methylene chloride) using as a carrier silica gel and then chromatography on a silica gel column (methylene chloride~5% methanol—methylene chloride), whereby a crudely purified product (146 mg) was obtained. A portion (81.0 mg) of the product was dissolved in tetrahydrofuran. To the resulting solution was added 1N aqueous hydrochloric acid in ethanol. The resulting mixture was solidified, followed by collection by filtration. The resulting solid was then dissolved in methanol. After filtration of the resulting solution, water was added. The solvent was distilled off under reduced pressure, whereby the title compound (68.5 g) was obtained as colorless powder.

$^1$H-NMR (DMSO-d$_6$) δ: 3.00–3.10(2H,m), 3.20–3.25 (2H,m), 3.35–3.45(2H,m), 3.80–3.85(2H,m), 6.94(1H,d,J= 8.3 Hz), 7.05(1H,s), 7.24(1H,d,J=15.6 Hz), 7.55(1H,d,J= 15.6 Hz), 7.74(1H,d,J=8.3 Hz), 8.36(2H,br s), 8.95–9.05 (2H,m), 9.47(2H,s), 11.10(1H,br s). MS (FAB) m/z: 486 [(M+H)$^+$, Cl$^{35}$], 488 [(M+H)$^+$, Cl$^{37}$].

Example A-262

4-[2-[[4-[((E)-4-Chloro-2-hydroxystyryl)sulfonyl] piperazin-1-yl]carbonyl]pyrimidin-5-yl]pyridine N-oxide In the same manner as in Example A-105, the title compound was obtained.

$^1$H-NMR (DMSO-d$_6$) δ: 3.00–3.10(2H,m), 3.15–3.25 (2H,m), 3.35–3.40(2H,m), 3.75–3.85(2H,m), 6.90–7.00(2H, m), 7.23(1H,d,J=15.6 Hz), 7.54(1H,d,J=15.6 Hz), 7.74(1H, d,J=8.3 Hz), 7.97(2H,d,J=7.8 Hz), 8.45–50(2H,m), 9.32(2H, s), 10.95(1H,br s). MS (FAB) m/z: 502 [(M+H)$^+$, Cl$^{35}$], 504 [(M+H)$^+$, Cl$^{37}$].

Example A-263

2,cis-6-Bis(methoxycarbonylmethyl)-4-[(6-chloronaphthalen-2-yl)sulfonyl]-1-[5-(pyridin-4-yl) pyrimidin-2-yl]piperazine In the same manner as in Example A-105, the title compound was obtained.

$^1$H-NMR (CDCl$_3$) δ: 2.50–2.80(3H,m), 2.95–3.05(2H, m), 3.10–3.20(1H,m), 3.65–3.75(1H,m), 3.68(3H,s), 3.75 (3H,s), 4.00–4.10(1H,m), 4.15–4.25(1H,m), 5.15–5.25(1H, m), 7.40–7.50(2H,m), 7.55–7.60(1H,m), 7.70–7.75(1H,m), 7.90–7.95(3H,m), 8.30(1H,s), 8.75–8.85(2H,m), 8.96(2H,s).

Example A-264

2,cis-6-Bis(carbamoylmethyl)-4-[(6-chloronaphthalen-2-yl)sulfonyl]-1-[5-(pyridin-4-yl)pyrimidin-2-yl]piperazine In tetrahydrofuran (10 ml) and methanol (5 ml) were dissolved 2,cis-6-bis(methoxycarbonylmethyl)-4-[(6-chloronaphthalen-2-yl)sulfonyl]-1-[5-(pyridin-4-yl)pyrimidin-2-yl]piperazine (372 mg), followed by the dropwise addition of a mixture of sodium hydroxide (310 ml) and water (1.6 ml) under ice cooling. The resulting mixture was stirred at room temperature for 23.5 hours. After concentrated hydrochloric acid was added to the reaction mixture to make it acidic, the solvent was distilled off under reduced pressure. The residue was suspended in N,N-dimethylformamide (15 ml), followed by the addition of di-tert-butyl dicarbonate (665 mg), pyridine (290 μl) and ammonium bicarbonate (304 mg) under ice cooling. The resulting mixture was stirred at room temperature for 19 hours. After completion of the the stirring, the solvent was distilled off under reduced pressure. The residue was subjected to chromatography on a silica gel column (methylene chloride~20% methanol—methylene chloride), whereby a crudely purified product (182 mg) was obtained. A 62.3 mg portion of the resulting product was subjected to chromatography on a silica gel column (methylene chloride~15% methanol—methylene chloride). The solvent was then distilled off under reduced pressure. Ethyl acetate was added to the residue to solidify the same, whereby the title compound (23 mg) was obtained as pale yellow powder.

$^1$H-NMR (DMSO-d$_6$) δ: 2.25–2.35(1H,m), 2.40–2.60 (3H,m), 2.80–3.00(2H,m), 3.50–3.60(1H,m), 3.8–3.95(2H, m), 4.90–5.00(1H,m), 6.90(1H,br s), 7.06(1H,br s), 7.45(1H, br s), 7.53(1H,br s), 7.70–7.75(1H,m), 7.75–7.85(1H,m), 7.85–7.95(2H,m), 8.17(1H,d,J=8.8 Hz), 8.25–8.35(2H,m), 8.51(1H,s), 8.70–8.75(1H,m), 9.31(2H,s). MS (FAB) m/z: 608 [(M+H)$^+$, Cl$^{35}$], 610 [(M+H)$^+$, Cl$^{37}$].

Example A-265

4-[2-[[2,cis-6-Bis(carbamoylmethyl)-4-[(6-chloronaphthalen-2-yl)sulfonyl]piperazin-1-yl]carbonyl]pyrimidin-5-yl]pyridine N-oxide In the same manner as in Example A-6, the title compound was obtained.

$^1$H-NMR (DMSO-d$_6$) δ: 2.25–2.35(1H,m), 2.40–2.60 (3H,m), 2.80–3.00(2H,m), 3.55–3.60(1H,m), 3.85–3.95(2H, m), 4.90–5.00(1H,m), 6.89(1H,br s), 7.06(1H,br s), 7.43(1H, br s), 7.51(1H,br s), 7.70–7.75(1H,m), 7.75–7.85(1H,m), 7.97(2H,d,J=7.3 Hz), 8.16(1H,d,J=8.8 Hz), 8.20–8.40(4H, m), 8.51(1H,s), 9.29(2H,s). MS (FAB) m/z: 624 [(M+H)$^+$, Cl$^{35}$], 626 [(M+H)$^+$, Cl$^{37}$].

Example A-266

4-[(6-Chloronaphthalen-2-yl)sulfonyl]-2-(methoxycarbonylmethyl)-1-[5-(pyridin-4-yl)pyrimidin-2-yl]piperazine In the same manner as in Example A-105, the title compound was obtained.

$^1$H-NMR (CDCl$_3$) δ: 2.45–3.30(6H,m), 3.50–5.40(6H, m), 3.67, 3.74(3H,each s), 7.45–7.50(2H,m), 7.55–7.65(1H, m), 7.70–7.80(1H,m), 7.90–7.95(3H,m), 8.29(1H,br s), 8.78 (2H,d,J=5.4 Hz), 8.99, 9.00(2H,each s).

Example A-267

4-[(6-Chloronaphthalen-2-yl)sulfonyl]-2-[[(morpholin-4-yl)carbonyl]methyl]-1-[5-(pyridin-4-yl)pyrimidin-2-yl]piperazine hydrochloride In tetrahydrofuran (10 ml) and methanol (5.0 ml) was dissolved 4-[(6-chloronaphthalen-2-yl)sulfonyl]-2-(methoxycarbonylmethyl)-1-[5-(pyridin-4-yl)pyrimidin-2-yl]piperazine (583 mg). Under ice cooling, a mixture of sodium hydroxide (200 mg) and water (1.0 ml) was added dropwise to the resulting solution under ice cooling, followed by stirring at room temperature for 5 hours. Under ice cooling, concentrated hydrochloric acid (420 μl) was added to the reaction mixture to make it weakly acidic. The reaction mixture was then distilled under reduced pressure. To the residue were added morpholine (102 μl), 1-(3-dimethylaminopropyl)-3-ethylcarbodiimide hydrochloride (239 mg) and 1-hydroxybenzotriazole hydrate (159 mg). The resulting mixture was dissolved in N,N-dimethylformamide (60 ml) and methylene chloride (30 ml). Diisopropylethylamine (760 μl) was added dropwise to the resulting solution under ice cooling, followed by stirring at room temperature for 12.5 hours. The reaction mixture was distilled under reduced pressure. A 100% aqueous solution of citric acid was added to the residue and it was extracted with methylene chloride. The organic layer was washed with a saturated aqueous solution of sodium bicarbonate and saturated aqueous NaCl solution, dried over anhydrous sodium sulfate and distilled under reduced pressure to remove the solvent. The residue was subjected to column chromatography (10% methanol—methylene chloride) using as a carrier silica gel, followed by crystallization from methylene chloride-tetrahydrofuran, whereby a crudely purified product (349 mg) was obtained. A portion (161 mg) of then product was dissolved in methylene chloride-methanol. To the resulting solution was added 1N aqueous hydrochloride in ethanol (260 μl) and the mixture was concentrated to dryness. Ethyl acetate was added to the concentrate and the solid thus obtained was collected by filtration, washed with ethyl acetate and dried, whereby the title compound (117 mg) was obtained as colorless powder.

$^1$H-NMR (CDCl$_3$) δ: 2.25–5.15(17H,m), 7.70–7.75(1H, m), 7.82(1H,d,J=8.8 Hz), 8.15–8.30(5H,m), 8.51(1H,br s), 8.90–9.00(2H,m), 9.35–9.45(2H,m). MS (FAB) m/z: 621 [(M+H)$^+$, Cl$^{35}$], 623 [(M+H)$^+$, Cl$^{37}$].

Example A-268

2,cis-6-Bis[(N-methylcarbamoyl)methyl]-4-[(6-chloronaphthalen-2-yl)sulfonyl]-1-[5-(pyridin-4-yl)pyrimidin-2-yl]piperazine hydrochloride In the same manner as in Example A-264, the title compound was obtained.

$^1$H-NMR (DMSO-d$_6$) δ: 2.20–2.70(10H,m), 2.70–2.90 (2H,m), 3.40–4.10(3H,m), 4.90–5.00(1H,m), 7.73(1H,d,J= 7.8 Hz), 7.81(1H,d,J=7.8 Hz), 7.94(1H,d,J=4.4 Hz), 8.01 (1H,d,J=4.4 Hz), 8.17(1H,d,J=8.3 Hz), 8.20–8.40(4H,m), 8.52(1H,s), 8.98(2H,d,J=5.9 Hz), 9.43(2H,s). MS (FAB) m/z: 636 [(M+H)$^+$, Cl$^{35}$], 638 [(M+H)$^+$, Cl$^{37}$].

Example A-269

2,cis-6-Bis[(N,N-dimethylcarbamoyl)methyl]-4-[(6-chloronaphthalen-2-yl)sulfonyl]-1-[5-(pyridin-4-yl)pyrimidin-2-yl]piperazine hydrochloride In the same manner as in Example A-264, the title compound was obtained.

¹H-NMR (DMSO-d₆) δ: 2.50–3.10(6H,m), 2.73(3H,s), 2.86(3H,s), 2.97(3H,s), 3.04(3H,s), 3.53(1H,d,J=11.7 Hz), 3.84(1H,d,J=12.2 Hz), 3.99(1H,d,J=9.8 Hz), 5.02(1H,d,J=10.8 Hz), 7.71(1H,dd,J=9.0,2.2 Hz), 7.79(1H,dd,J=8.5,1.7 Hz), 8.17(1H,d,J=8.8 Hz), 8.20–8.35(4H,m), 8.51(1H,s), 8.90–8.95(2H,m), 9.35–9.45(2H,m). MS (FAB) m/z: 664 [(M+H)⁺, Cl³⁵], 666 [(M+H)⁺, Cl³⁷].

Example A-270

4-[2-[[4-[(6-Chloronaphthalen-2-yl)sulfonyl]-2-[[(morpholin-4-yl)carbonyl]methyl]piperazin-1-yl]carbonyl]pyrimidin-5-yl]pyridine N-oxide In the same manner as in Example A-6, the title compound was obtained.

¹H-NMR (CDCl₃) δ: 2.25–5.15(17H,m), 7.70–7.75(1H, m), 7.80–7.85(1H,m), 7.90–8.00(2H,m), 8.18(1H,d,J=8.8 Hz), 8.20–8.30(2H,m), 8.30–8.40(2H,m), 8.49(1H,br s), 9.26(2H,d,J=7.8 Hz). MS (FAB) m/z: 637 [(M+H)⁺, Cl³⁵], 639 [(M+H)⁺, Cl³⁷].

Example A-271

4-[2-[[2,cis-6-Bis(N,N-dimethycarbamoylmethyl)-4-(6-chloronaphthalen-2-ylsulfonyl)piperazin-1-yl]carbonyl]pyrimidin-5-yl]pyridine N-oxide In the same manner as in Example A-6, the title compound was obtained.

¹H-NMR (CDCl₃) δ: 2.50–3.30(6H,m), 2.91(3H,m), 3.00 (3H,m), 3.08(3H,m), 3.12(3H,m), 3.70(1H,d,J=12.2 Hz), 4.16(1H,d,J=12.7 Hz), 4.37(1H,d,J=10.7 Hz), 5.20–5.30 (1H,m), 7.50(2H,d,J=7.3 Hz), 7.57(1H,dd,J=8.8,2.0 Hz), 7.72(1H,dd,J=8.6,1.7 Hz), 7.85–7.95(3H,m), 8.25–8.35(3H, m), 8.91(2H,s). MS (FAB) m/z: 680 [(M+H)⁺, Cl³⁵], 682 [(M+H)⁺, Cl³⁷].

Example A-272

4-[2-[[2,cis-6-Bis(N-methylcarbamoylmethyl)-4-(6-chloronaphthalen-2-ylsulfonyl)piperazin-1-yl]carbonyl]pyrimidin-5-yl]pyridine N-oxide In the same manner as in Example A-6, the title compound was obtained.

¹H-NMR (CD₃OD) δ: 2.50–2.80(4H,m), 2.66(3H,s), 2.78 (3H,s), 2.90–3.00(2H,m), 3.64(1H,d,J=12.7 Hz), 4.01(1H, d,J=12.2 Hz), 4.20(1H,d,J=9.8 Hz), 5.10–5.15(1H,m), 7.62 (1H,dd,J=8.8,2.0 Hz), 7.78(1H,dd,J=8.8,1.5 Hz), 7.97(2H, d,J=7.3 Hz), 8.00–8.10(3H,m), 8.35–8.45(3H,m), 9.20(2H, s). MS (FAB) m/z: 652 [(M+H)⁺, Cl³⁵], 654 [(M+H)⁺, Cl³⁷].

Example A-273

2-[2-(tert-Butyldiphenylsilyloxy)ethyl]-4-[(6-chloronaphthalen-2-yl)sulfonyl]-1-[5-(pyridin-4-yl)pyrimidin-2-yl]piperazine In the same manner as in Example A-105, the title compound was obtained.

¹H-NMR (CDCl₃) δ: 0.84, 1.09(9H,each s), 2.10–2.20 (2H,m), 2.35–2.65(2H,m), 3.15–5.25(7H,m), 7.10–7.80 (14H,m), 7.85–8.00(3H,m), 8.20–8.30(1H,m), 8.65–9.00 (4H,m). MS (FAB) m/z: 776 [(M+H)⁺, Cl³⁵], 778 [(M+H)⁺, Cl³⁷].

Example A-274

4-(6-Chloronaphthalen-2-ylsulfonyl)-2-(2-hydroxyethyl)-1-[[5-(pyridin-4-yl)pyrimidin-2-yl]carbonyl]piperazine hydrochloride In pyridine (6.0 ml) was dissolved 2-[(tert-butyldiphenylsilyloxy)methyl]-4-[(6-chloronaphthalen-2-yl)sulfonyl]-1-[5-(pyridin-4-yl)pyrimidin-2-yl]piperazine (150 mg). A hydrogen fluoride-pyridine complex (2.0 ml) was added dropwise to the resulting solution under ice cooling, followed by stirring at 0° C. for 1.5 hours. Ethyl acetate (40 ml) was added to the reaction mixture to dilute it. Then, the diluted mixture was poured into ice. The resulting mixture was extracted. The organic layer was washed with saturated saline, dried over anhydrous sodium sulfate and distilled under reduced pressure to remove the solvent. The residue was subjected to column chromatography (5% methanol—methylene chloride~10% methanol—methylene chloride) using as a carrier silica gel, whereby a crudely purified product (97.9 mg) was obtained. The resulting product was dissolved in methylene chloride, followed by the addition of 1N hydrochloric acid in ethanol (182 μl) for solidification. Tetrahydrofuran was added to the residue to solidify the same, whereby the title compound (62.7 mg) was obtained as colorless crystalline powder.

¹H-NMR (DMSO-d₆) δ: 2.20–5.20(9H,m), 6.90–7.05 (1H,m), 7.50–7.60(2H,m), 7.70–7.90(2H,m), 8.00–8.10(1H, m), 8.19(1H,d,J=8.3 Hz), 8.25–8.35(2H,m), 8.40–8.50(3H, m), 9.00(2H,d,J=5.9 Hz). MS (FAB) m/z: 538 [(M+H)⁺, Cl³⁵], 540 [(M+H)⁺, Cl³⁷].

Example A-275

2-cis,6-Bis(methoxycarbonylmethyl)-4-[(6-chlorobenzo[b]thien-2-yl)sulfonyl]-1-[[5-(pyridin-4-yl)pyrimidin-2-yl]piperazine In the same manner as in Example A-105, the title compound was obtained.

¹H-NMR (CDCl₃) δ: 2.70–2.85(3H,m), 2.95–3.15(3H, m), 3.65–3.75(1H,m), 3.67(3H,s), 3.75(3H,s), 4.02(1H,d,J=12.7 Hz), 4.29(1H,d,J=9.8 Hz), 5.25–5.35(1H,m), 7.45–7.55 (3H,m), 7.75–7.90(3H,m), 8.75–8.85(2H,m), 8.98(2H,s). MS (FAB) m/z: 644 [(M+H)⁺, Cl³⁵], 646 [(M+H)⁺, Cl³⁷].

Example A-276

2-[(tert-Butyldiphenylsilyloxy)methyl]-4-[(6-chlorobenzo[b]thien-2-yl)sulfonyl]-1-[5-(pyridin-4-yl)pyrimidin-2-yl]piperazine hydrochloride In the same manner as in Example A-105, the title compound was obtained.

¹H-NMR (DMSO-d₆) δ: 0.95(9H×0.5,s), 1.04(9H×0.5,s), 2.50–3.60(4H,m), 3.70–3.90(2H,m), 3.95–4.10(2H,m), 4.45–5.00(1H,m), 7.30–7.55(7H,m), 7.55–7.65(2H,m), 7.70–7.75(2H,m), 8.05–8.15(2H,m), 8.25–8.40(3H,m), 8.95–9.05(2H,m), 9.25–9.35(1H,m), 9.40–9.45(1H,m). MS (FAB) m/z: 768 [(M+H)⁺, Cl³⁵], 770 [(M+H)⁺, Cl³⁷].

Example A-277

4-[(6-Chlorobenzo[b]thien-2-yl)sulfonyl]-2-(hydroxymethyl)-1-[5-(pyridin-4-yl)pyrimidin-2-yl]piperazine hydrochloride In the same manner as in Example A-274, the title compound was obtained.

¹H-NMR (DMSO-d₆) δ: 2.40–2.70(2H,m), 3.10–4.00 (6H,m), 4.45–4.75(1H,m), 7.55–7.65(1H,m), 8.05–8.15(2H, m), 8.35(1H,s), 8.40–8.45(2H,m), 9.03(2H,d,J=4.4 Hz), 9.46(2H,s). MS (FAB) m/z: 530 [(M+H)⁺, C³⁵], 532 [(M+H)⁺, Cl³⁷].

Example A-278

2,cis-6-Bis[(N,N-dimethylcarbamoyl)methyl]-4-[(6-chlorobenzo[b]thien-2-yl)sulfonyl]-1-[[5-(pyridin-4-yl)pyrimidin-2-yl]carbonyl]piperazine hydrochloride In the same manner as in Example A-264, the title compound was obtained.

¹H-NMR (DMSO-d₆) δ: 2.40–3.80(7H,m), 2.74(3H,s), 2.87(3H,s), 2.98(3H,s), 3.05(3H,s), 3.83(1H,d,J=12 Hz), 4.00–4.05(1H,m), 5.06(1H,d,J=8.7 Hz), 7.58(1H,dd,J=8.8, 2.0 Hz), 8.07(1H,d,J=8.8 Hz), 8.10–8.20(3H,m), 8.35(1H,s), 8.87(2H,d,J=5.4 Hz), 9.39(2H,s). MS (FAB) m/z: 670 [(M+H)⁺, Cl³⁵], 672 [(M+H)⁺, Cl³⁷].

Example A-279

4-[2-[[2,cis-6-Bis[(N,N-dimethylcarbamoyl)methyl]-4-[(6-chlorobenzo[b]thien-2-yl)sulfonyl]piperazin-1-yl]carbonyl]pyrimidin-5-yl]pyridine N-oxide In the same manner as in Example A-6, the title compound was obtained.

¹H-NMR (DMSO-d₆) δ: 2.40–3.10(4H,m), 2.74(3H,s), 2.87(3H,s), 3.04(3H,s), 3.33(3H,s), 3.40–3.50(2H,m), 3.52 (1H,d,J=11.7 Hz), 3.82(1H,d,J=12.7 Hz), 4.03(1H,d,J=6.8 Hz), 5.05(1H,d,J=10.3 Hz), 7.59(1H,dd,J=8.8,2.0 Hz), 7.99 (2H,d,J=7.3 Hz), 8.07(1H,d,J=8.3 Hz), 8.12(1H,s), 8.30–8.40(3H,m), 9.30(2H,s). MS (FAB) m/z: 686 [(M+H)⁺, Cl³⁵], 688 [(M+H)⁺, Cl³⁷].

Example A-280

4-[2-[[4-[(6-Chlorobenzo[b]thien-2-yl) sulfonyl]-2-(hydroxymethyl)piperazin-1-yl]carbonyl]pyrimidin-5-yl]pyridine N-oxide In the same manner as in Example A-6, the title compound was obtained.

¹H-NMR (DMSO-d₆) δ: 2.40–2.70(2H,m), 3.10–4.00 (6H,m), 4.47(1H,d,J=13.7 Hz), 4.67(1H,br s), 4.89(1H,t,J= 5.4 Hz), 5.16(1H,t,J=5.4 Hz), 7.55–7.65(1H,m), 7.90–8.00 (2H,m), 8.05–8.15(2H,m), 8.30–8.40(3H,m), 9.30(2H,s). MS (FAB) m/z: 546 [(M+H)⁺, Cl³⁵], 548 [(M+H)⁺, Cl³⁷].

Example A-281

2-[2-(tert-Butyldiphenylsilyloxy)ethyl]-4-[(6-chlorobenzo[b]thien-2-yl)sulfonyl]-1-[5-(pyridin-4-yl)pyrimidin-2-yl]piperazine hydrochloride In the same manner as in Example A-105, the title compound was obtained.

¹H-NMR (DMSO-d₆) δ: 0.79, 1.02(9H,each s), 1.70–5.10 (11H,m), 7.35–7.70(12H,m), 8.05–8.40(4H,m), 8.90–9.05 (2H,m), 9.35, 9.45(2H,each s). MS (FAB) m/z: 782 [(M+H)⁺, Cl³⁵], 784 [(M+H)⁺, Cl³⁷].

Example A-282

4-[(6-Chlorobenzo[b]thien-2-yl)sulfonyl]-2-(2-hydroxyethyl)-1-[5-(pyridin-4-yl)pyrimidin-2-yl] piperazine hydrochloride In the same manner as in Example A-274, the title compound was obtained.

¹H-NMR (DMSO-d₆) δ: 1.80–2.00(2H,m), 2.40–3.90 (9H,m), 4.45–5.00(1H,m), 7.55–7.65(1H,m), 8.05–8.15(2H, m), 8.35–8.45(3H,m), 9.01(2H,d,J=7.8 Hz), 9.45(2H,d,J= 2.4 Hz). MS (FAB) m/z: 544 [(M+H)⁺, Cl³⁵], 546 [(M+H)⁺, Cl³⁷].

Example A-283

2-[2-(tert-Butyldiphenylsilyloxy)ethyl]-4-[(6-chlorobenzo[b]thien-2-yl)sulfonyl]-1-[5-(pyridin-2-yl)pyrimidin-2-yl]piperazine In the same manner as in Example A-182, the title compound was obtained.

¹H-NMR (DMSO-d₆) δ: 0.82, 1.09(9H,each s), 2.05–2.20 (2H,m), 2.55–2.80(2H,m), 3.15–4.25(6H,m), 4.70–5.30(1H, m), 7.10–7.55(11H,m), 7.70–7.90(6H,m), 8.70–8.80(1H,m), 9.22, 9.34 (2H,each s). MS (FAB) m/z: 782 [(M+H)⁺, Cl³⁵], 784 [(M+H)⁺, Cl³⁷].

Example A-284

4-[(6-Chlorobenzo[b]thien-2-yl)sulfonyl]-2-(2-hydroxyethyl)-1-[5-(pyridin-2-yl)pyrimidin-2-yl] piperazine hydrochloride In the same manner as in Example A-274, the title compound was obtained.

¹H-NMR (DMSO-d₆) δ: 1.80–2.00(2H,m), 2.40–3.90 (9H,m), 4.45–5.00(1H,m), 7.50–7.65(2H,m), 8.00–8.15(3H, m), 8.15–8.25(1H,m), 8.34(1H,s), 8.77(1H,d,J=4.4 Hz), 9.48(2H,s). MS (FAB) m/z: 544 [(M+H)⁺, Cl³⁵], 546 [(M+H)⁺, Cl³⁷].

Example A-285

4-[(6-Chlorobenzo[b]thien-2-yl)sulfonyl]-2-[(methoxycarbonyl)methyl]-1-[5-(pyridin-2-yl) pyrimidin-2-yl]piperazine In the same manner as in Example A-182, the title compound was obtained.

¹H-NMR (CDCl₃) δ: 2.60–3.30(5H,m), 3.50–5.45(7H, m), 7.20–7.55(2H,m), 7.70–7.90(5H,m), 8.76(1H,d,J=4.9 Hz), 8.76(2H,d,J=2.4 Hz). MS (FAB) m/z: 572 [(M+H)⁺, Cl³⁵], 574 [(M+H)⁺, Cl³⁷].

Example A-286

2-[2-[[4-[(6-Chlorobenzo[b]thien-2-yl)sulfonyl]-2-[(methoxycarbonyl)methyl]piperazin-1-yl]carbonyl] pyrimidin-5-yl]pyridine N-oxide In the same manner as in Example A-6, the title compound was obtained.

¹H-NMR (CDCl₃) δ: 2.60–3.30(4H,m), 3.50–5.40(5H, m), 3.67, 3.74(3H,each s), 7.30–7.55(4H,m), 7.70–7.90(3H, m), 8.30–8.40(1H,m), 9.29(2H,d,J=12.2 Hz). MS (FAB) m/z: 572 [(M+H)⁺, Cl³⁵], 574 [(M+H)⁺, Cl³⁷].

Example A-287

2-[2-[[4-[(6-Chlorobenzo[b]thien-2-yl)sulfonyl]-2-[(N,N-dimethylcarbamoyl)methyl]piperazin-1-yl] carbonyl]pyrimidin-5-yl]pyridine N-oxide In the same manner as in Example A-267, the title compound was obtained.

¹H-NMR (DMSO-d₆) δ: 2.30–2.80(3H,m), 2.74(3H,s), 2.85(3H,s), 2.92(3H,s), 3.01(3H,s), 3.10–4.15(5H,m), 4.50–5.15(1H,m), 7.45–7.65(3H,m), 7.85–7.95(1H,m), 8.05–8.15(2H,m), 8.34(1H,s), 8.40–8.45(1H,m), 9.35(2H,s). MS (FAB) m/z: 601 [(M+H)⁺, Cl³⁵], 603 [(M+H)⁺, Cl³⁷].

Example A-288

2-[2-[[2-(2-tert-Butyldiphenylsilyloxyethyl)-4-[(6-chlorobenzo[b]thien-2-yl)sulfonyl]piperazin-1-yl] carbonyl]pyrimidin-5-yl]pyridine N-oxide In the same manner as in Example A-6, the title compound was obtained.

¹H-NMR (CDCl₃) δ: 0.80–1.10(9H,m), 2.00–2.20(2H, m), 2.50–2.80(2H,m), 3.10–4.30(6H,m), 4.65–5.30(1H,m), 7.05–7.90(17H,m), 8.30–8.40(1H,m), 9.10–9.30(2H,m). MS (FAB) m/z: 798 [(M+H)$^+$, Cl$^{35}$], 800 [(M+H)$^+$, Cl$^{37}$].

Example A-289

2-[2-[[4-[(6-Chlorobenzo[b]thien-2-yl)sulfonyl]-2-(2-hydroxyethyl)piperazin-1-yl]carbonyl]pyrimidin-5-yl]pyridine N-oxide In the same manner as in Example A-274, the title compound was obtained.

$^1$H-NMR (CDCl$_3$) δ: 1.80–2.05(1H,m), 2.25–2.45(1H,m), 2.60–2.95(2H,m), 3.00–4.20(7H,m), 4.70–5.10(1H,m), 7.40–7.55(4H,m), 7.70–7.90(3H,m), 8.30–8.40(1H,m), 9.30 (2H,s). MS (FAB) m/z: 560 [(M+H)$^+$, Cl$^{35}$], 562 [(M+H)$^+$, Cl$^{37}$].

Example A-290

2-[2-[[4-[(6-Chlorobenzo[b]thien-2-yl)sulfonyl]-2-[[(pyrrolidin-1-yl) carbonyl]methyl]piperazin-1-yl]carbonyl]pyrimidin-5-yl]pyridine N-oxide In the same manner as in Example A-267, the title compound was obtained.

$^1$H-NMR (DMSO-d$_6$) δ: 1.70–1.90(4H,m), 2.30–4.20 (12H,m), 4.50–5.20(1H,m), 7.45–7.65(3H,m), 7.85–7.90 (1H,m), 8.05–8.15(2H,m), 8.34(1H,s), 8.43(1H,d,J=6.3 Hz), 9.35(2H,s). MS (FAB) m/z: 627 [(M+H)$^+$, Cl$^{35}$], 629 [(M+H)$^+$, Cl$^{37}$].

Example A-291

2-[2-[[4-[(6-Chlorobenzo[b]thien-2-yl)sulfonyl]-2-[(N-methylcarbamoyl)methyl]piperazin-1-yl]carbonyl]pyrimidin-5-yl]pyridine N-oxide In the same manner as in Example A-267, the title compound was obtained.

$^1$H-NMR (DMSO-d$_6$) δ: 2.30–2.90(5H,m), 3.15–4.25 (6H,m), 4.50–5.20(1H,m), 7.45–7.60(3H,m), 7.85–8.00(1H,m), 8.05–8.15(2H,m), 8.34(1H,s), 8.43(1H,d,J=6.3 Hz), 9.35(2H,d,J=4.9 Hz). MS (FAB) m/z: 587 [(M+H)$^+$, Cl$^{35}$], 589 [(M+H)$^+$, Cl$^{37}$].

Example A-292

2-[2-[[4-[(6-Chlorobenzo[b]thien-2-yl)sulfonyl]-2-[[(thiomorpholin-4-yl)carbonyl]methyl]piperazin-1-yl]carbonyl]pyrimidin-5-yl]pyridine N-oxide In the same manner as in Example A-267, the title compound was obtained.

$^1$H-NMR (CDCl$_3$) δ: 2.50–2.90(7H,m), 3.10–4.85(9H,m), 4.45–5.45(1H,m), 7.35–7.55(4H,m), 7.75–7.90(3H,m), 8.30–8.40(1H,m), 9.30(2H,d,J=10.5 Hz). MS (FAB) m/z: 659 [(M+H)$^+$, Cl$^{35}$], 661 [(M+H)$^+$, Cl$^{37}$].

Example A-293

2-[2-[[4-[(6-Chlorobenzo[b]thien-2-yl)sulfonyl]-2-[(N-cyclopropylcarbamoyl)methyl]piperazin-1-yl]carbonyl]pyrimidin-5-yl]pyridine N-oxide In the same manner as in Example A-267, the title compound was obtained.

$^1$H-NMR (CDCl$_3$) δ: 0.50–0.90(4H,m), 2.60–6.20(11H,m), 7.35–7.55(4H,m), 7.70–7.90(3H,m), 8.30–8.40(1H,m), 9.25–9.35(2H,m). MS (FAB) m/z: 613 [(M+H)$^+$, Cl$^{35}$], 615 [(M+H)$^+$, Cl$^{37}$].

Example A-294

2-[2-[[4-[(6-Chlorobenzo[b]thien-2-yl)sulfonyl]-2-[[(morpholin-4-yl)carbonyl]methyl]piperazin-1-yl]carbonyl]pyrimidin-5-yl]pyridine N-oxide In the same manner as in Example A-267, the title compound was obtained.

$^1$H-NMR (CDCl$_3$) δ: 2.55–2.85(4H,m), 3.10–5.45(13H,m), 7.35–7.55(4H,m), 7.70–7.90(3H,m), 8.30–8.40(1H,m), 9.25–9.35(2H,m). MS (FAB) m/z: 643 [(M+H)$^+$, Cl$^{35}$], 645 [(M+H)$^+$, Cl$^{37}$].

Example A-295

2-[2-[[2-[(N-Benzylcarbamoyl)methyl]-4-[(6-chlorobenzo[b]thien-2-yl)sulfonyl]piperazin-1-yl]carbonyl]pyrimidin-5-yl]pyridine N-oxide In the same manner as in Example A-267, the title compound was obtained.

$^1$H-NMR (CDCl$_3$) δ: 2.65–2.85(3H,m), 2.95–5.45(8H,m), 6.10–6.30(1H,m), 7.25–7.55(9H,m), 7.70–7.90(3H,m), 8.30–8.40(1H,m), 9.25–9.30(2H,m). MS (FAB) m/z: 663 [(M+H)$^+$, Cl$^{35}$], 665 [(M+H)$^+$, Cl$^{37}$].

Example A-296

1-[(5-Chloroindol-2-yl)sulfonyl]-4-[4-methyl-2-(pyridin-4-yl)thiazol-5-yl]piperazine In the same manner as in Example A-4, the title compound was obtained.

$^1$H-NMR (DMSO-d$_6$) δ: 2.35(3H,s), 3.00–3.15(4H,br), 3.55–3.73(4H,br), 7.01(1H,s), 7.30(1H,dd,J=8.8,2.2 Hz), 7.49(1H,d,J=8.8 Hz), 7.765(1H,d,J=2.0 Hz), 7.82(2H,d,J=6.2 Hz), 8.69(2H,d,J=6.2 Hz). MS (FAB) m/z: 502 [(M+H)$^+$, Cl$^{35}$], 504 [(M+H)$^+$, Cl$^{37}$].

Example A-297

4-[(5-Chloroidol-2-yl)sulfonyl]-1-[[5-(pyridin-4-yl)thiazol-2-yl]carbonyl]-2-[(pyrrolidin-1-yl)carbonylmethyl]piperazine In the same manner as in Example A-66, the title compound was obtained.

$^1$H-NMR (CDCl$_3$) δ: 1.85–2.05(4H,m), 2.50–3.30(5H,m), 3.40–3.60(4H,m), 3.81,3.90,4.03,4.23,4.64,5.62(3H, each br d,J=12.5 Hz), 5.15–6.21(1H,m), 6.99(1H,s), 7.25–7.50(4H,m), 7.64(1H,d,J=5.6 Hz), 8.60–8.70(3H,m), 10.38,10.95(1H,each s). FAB-MS m/z: 599 [(M+H)$^+$, Cl$^{35}$], 601 [(M+H)$^+$, Cl$^{37}$].

Example A-298

4-[2-[[4-[(5-Chloroidol-2-yl)sulfonyl]-2-[(pyrrolidin-1-yl)carbonylmethyl]piperazin-1-yl]carbonyl]thiazol-5-yl]pyridine N-oxide In the same manner as in Example A-4, the title compound was obtained.

$^1$H-NMR (DMSO-d$_6$) δ: 1.65–1.90(4H,m), 2.30–3.50 (9H,m), 3.50–3.88(2H,m), 4.41, 5.40(1H,each br d,J=12.5 Hz), 5.02–5.95(1H,m), 7.02(1H,s), 7.31(1H,dd,J=8.8,2.0 Hz), 7.48(1H,d,J=8.8 Hz), 7.75–7.83(3H,m), 8.26(2H,d,J=7.1 Hz), 8.45,8.49(1H,each s), 12.42(1H,br s). MS (FAB) m/z: 615 [(M+H)$^+$, Cl$^{35}$], 617 [(M+H)$^+$, Cl$^{37}$].

Example A-299

2-[(N-Benzylcarbamoyl)methyl]-4-[(5-chloroindol-2-yl)sulfonyl]-1-[[5-(pyridin-4-yl)thiazol-2-yl]carbonyl]piperazine In the same manner as in Example A-66, the title compound was obtained.

¹H-NMR (CDCl₃) δ: 2.60–3.06(4H,m), 3.12–3.57(1H, m), 3.78–3.95(1H,m), 3.98–4.12(1H,m), 4.38–4.56(2H,m), 4.57–6.01(2H,m), 6.47,6.58(1H,each br s), 6.97(1H,s), 7.25–7.52(8H,m), 7.65(2H,d,J=6.6 Hz), 8.64–8.71(3H,m), 10.24(1H,s). FAB-MS m/z: 635 [(M+H)⁺, Cl³⁵], 637 [(M+ H)⁺, Cl³⁷].

Example A-300

4-[2-[[2-(N-Benzylcarbamoyl)methyl]-4-[(5-chloroindol-2-yl)sulfonyl]piperazin-1-yl]carbonyl]thiazol-5-yl]pyridine N-oxide In the same manner as in Example A-4, the title compound was obtained.

¹H-NMR (DMSO-d₆) δ: 2.30–2.92(3H,m), 3.20–3.63 (2H,m), 3.65–3.85(2H,m), 4.15–4.35(2H,m), 4.41,5.41(1H, each br d,J=13.5 Hz), 5.15,5.98(1H,each br s), 7.02(1H,s), 7.15–7.33(6H,m), 7.48(1H,d,J=8.6 Hz), 7.73–7.81(3H,m), 8.26(2H,d,J=6.6 Hz), 8.38–8.60(2H,m), 12.41(1H,br s). MS (FAB) m/z: 651 [(M+H)⁺, Cl³⁵], 653 [(M+H)⁺, Cl³⁷].

Example A-301

1-[4-[2-(2-Aminoethyl)pyridin-4-yl]benzoyl]-4-[(6-chloronaphthalen-2-yl)sulfonyl]piperazine In the same manner as in Example A-7, the title compound was obtained.

¹H-NMR (DMSO-d₆) δ: 3.08(4H,s), 3.23(2H,br), 3.30 (2H,br), 3.45(2H,br), 3.73(2H,br), 7.52(2H,d,J=8.3 Hz), 7.74(1H,dd,J=5.4,2.0 Hz), 7.80–7.87(5H,m), 8.06(2H,br), 8.19(1H,d,J=8.8 Hz), 8.25–8.31(2H,m), 8.51(1H,br s), 8.69 (1H,d,J=4.4 Hz). MS (FAB) m/z: 535 [(M+H)⁺, Cl³⁵], 537 [(M+H)⁺, Cl³⁷].

Elementary analysis for C₂₈H₂₇ClN₄O₃S.1.85HCl.1.4H₂O Calculated: C, 53.57; H, 5.08; Cl, 16.10; N, 8.93; S, 5.11. Found: C, 53.39; H, 5.06; Cl, 15.99;N, 8.81; S, 5.08.

Example A-302

1-[[5(6)-Chloroimidazol-2-yl]sulfonyl]-4-[4-(pyridin-4-yl)benzoyl]piperazine hydrochloride 1-[[5(6)-Chlorobenzimidazol-2-yl]sulfonyl]piperazine (507 mg), 1-hydroxybenzotriazole (220 mg), N-methylmorpholine (480 μl) and 1-ethyl-3-(3-dimethylaminopropyl)-carbodiimide (309 mg) were successively added to the mixture of 4-[(pyridin-4-yl)benzoic acid (314 mg), dichloromethane (5.0 ml) and N,N-dimethylformamide (2.0 ml), stirred at room temperature for 5 hours. The mixture was diluted with dichloromethane, and then divided into two layers by adding a saturated sodium chloride solution. The organic layer was washed with a saturated sodium chloride solution, dried over sodium sulfate, and concentrated under reduced pressure. The obtained product was purified by chromatography on a silica gel column (dichloromethane:methanol=15:1). After dichloromethane was removed from the mixture of dichloromethane and methanol under reduced pressure, 1-[[5(6)-chloroimidazol-2-yl]sulfonyl]-4-[4-(pyridin-4-yl)benzoyl] piperazine (396 mg) was obtained as precipitated powder by filtration. 140 mg of this obtained compound was concentrated by adding 1N aqueous hydrochloride in ethanol (3 ml) and ethanol (3 ml), and dried, whereby the title compound (152 mg) was obtained as colorless amorphous.

IR (KBr) cm⁻¹ 1631, 1431, 1365, 1282, 1155. ¹H-NMR (DMSO-d₆) δ, 3.30–4.00 (8H, br), 7.43 (1H, d, J=8.8, 2.0 Hz), 7.62 (2H, d, J=7.8 Hz), 7.75 (1H, d, J=8.8 Hz), 7.80 (1H, s), 8.07 (2H, d, J=8.8 Hz), 8.38 (2H, d, J=5.9 Hz), 8.97 (2H, d, J=5.9 Hz). MS (FAB) m/z 482 [(M +H)⁺, Cl³⁵], 484 [(M +H)⁺, Cl³⁷].

Example A-303

4-[4-[[5(6)-chlorobenzimidazol-2-yl]sufonyl]piperazin-1-yl]carbonylphenyl]piridine N-oxide Metachloroperbenzoic acid (0° C.; 121 mg) was added to the mixture of 1-[[5(6)-chloroimidazol-2-yl]sulfonyl]-4-[4-(pyridin-4-yl)benzoyl]piperazine (191 mg) obtained by Example A-302, N,N-dimethylformamide (5.0 ml) and chloroform (15 ml) at a temperature of 0° C., and stirred at a temperature of 0° C. for 3 hours, thereto was added dichloromethane (50 ml), followed by stirring at room temperature for 64 hours. The mixture was divided into two layers by adding a small quantity of sodium thiosulfate solution, and saturated sodium chloride solution. The organic layer was washed with a saturated sodium hydrogencarbonate solution and a saturated sodium chloride solution, dried over sodium sulfate, and concentrated under reduced pressure. The obtained product was purified by chromatography on a silica gel column (dichloromethane:methanol=20:1). The mixture of dichloromethane and methanol was concentrated under reduced pressure, filtered and dried to obtain solid. Thus, the title compound (141 mg) was obtained as colorless amorphous.

IR (KBr) cm⁻¹ 1645, 1433, 1371, 1248, 1180, 966, 933. ¹H-NMR (DMSO-d₆) 6, 3.30–3.85 (8H, br), 7.41 (1H, dd, J=8.8, 2.0 Hz), 7.49 (2H, d, J=7.8 Hz), 7.68–7.83 (2H, br), 7.80 (2H, d, J=6.8 Hz), 7.83 (2H, d, J=7.8 Hz), 8.27 (2H, d, J=6.8 Hz). MS (FAB) m/z 498 [(M +H)⁺, Cl³⁵], 500 [(M +H)⁺, Cl³⁷].

Example B-1

1-[[(6RS)-6-Aminomethyl-5,6,7,8-tetrahydronaphthalen-2-yl]carbonyl]-4-[(6-chloronaphthalen-2-yl)sulfonyl]piperazine hydrochloride In saturated aqueous hydrochloric acid in ethanol (5 ml), 1-[[(6RS)-6-(N-tert-butoxycarbonylaminomethyl)-5,6,7,8-tetrahydronaphthalen-2-yl]carbonyl]-4-[(6-chloronaphthalen-2-yl)sulfonyl]piperazine (0.22 g) was dissolved, followed by stirring at room temperature for 90 minutes. The residue obtained by distilling off the solvent under reduced pressure was recrystallized from a mixed solvent of ethanol and diethyl ether, whereby the title compound (0.14 g, 68%) was obtained.

¹H-NMR (DMSO-d₆) δ: 1.30–1.50(1H,m), 1.90–2.10 (2H,m), 2.40–2.60(1H,m), 2.60–3.00(5H,m), 3.03(4H,m), 3.40–3.80(4H,br), 7.00–7.10(3H,m), 7.73(1H,dd,J=8.8,2.0 Hz), 7.81(1H,dd,J=8.8,1.5 Hz), 8.05(3H,br), 8.18(1H,d,J= 8.3 Hz), 8.20–8.30(2H,m), 8.49(1H,s). MS (FAB) m/z: 498 [(M+H)⁺, Cl³⁵], 500 [(M+H)⁺, Cl³⁷]. Elementary analysis for C₂₆H₂₈ClN₃O₃S.HCl.½H₂O Calculated: C, 55.61; H, 5.74; N, 7.48; Cl, 12.63; S, 5.71. Found: C, 55.64; H, 5.53; N, 7.77; Cl, 12.79; S, 5.76.

Example B-2

1-[[(6RS)-6-Aminomethyl-5,6,7,8-tetrahydronaphthalen-2-yl]methyl]-4-[(6-chloronaphthalen-2-yl)sulfonyl]piperazine hydrochloride In the same manner as in Example B-1, the title compound was obtained using 1-[[(6RS)-6-(N-tertbutoxycarbonylaminomethyl)-5,6,7,8-tetrahydronaphthalen-2-yl]methyl]-4-[(6-chloronaphthalen-2-yl)sulfonyl]piperazine as a starting material.

$^1$H-NMR (DMSO-d$_6$) δ: 1.30–1.50(1H,m), 2.00–2.10 (2H,m), 2.40–2.60(1H,m), 2.60–3.00(7H,m), 3.00–3.20(2H, m), 3.30–3.50(2H,m), 3.82(2H,m), 4.22(2H,br), 7.00–7.10 (1H,m), 7.25(2H,s), 7.73(1H,dd,J=8.8,2.4 Hz), 7.81(1H,dd, J=8.8,1.5 Hz), 8.00–8.40(6H,m), 8.52(1H,s), 11.08(1H,br). MS (FAB) m/z: 484 [(M+H)$^+$, Cl$^{35}$], 486[(M+H)$^+$, Cl$^{37}$]. Elementary analysis for C$_{26}$H$_{20}$ClN$_3$O$_2$S.2HCl Calculated: C, 56.07; H, 5.79; N, 7.54; Cl, 19.10; S, 5.76. Found: C, 56.04; H, 5.79; N, 7.52; Cl, 18.95; S, 5.80.

Example B-3

1-[[(2RS)-6-Aminomethyl-1,2,3,4-tetrahydronaphthalen-2-yl]methyl]-4-[(6-chloronaphthalen-2-yl)sulfonyl]piperazine hydrochloride In the same manner as in Example B-1, the title compound was obtained using 1-[[(2RS)-6-(N-tert-butoxycarbonylaminomethyl)-1,2,3,4-tetrahydronaphthalen-2-yl]methyl]-4-[(6-chloronaphthalen-2-yl)sulfonyl]piperazine as a starting material.

$^1$H-NMR (DMSO-d$_6$) δ: 1.30–1.50(1H,m), 2.00–2.20 (1H,m), 2.20–2.40(1H,m), 2.40–2.60(1H,m), 2.75(2H,m), 2.90–3.30(7H,m), 3.60–3.70(2H,m), 3.70–4.00(4H,m), 7.04 (1H,d,J=7.8 Hz), 7.10–7.30(2H,m), 7.74(1H,m), 7.86(1H,d, J=8.8 Hz), 8.20–8.50(6H,m), 8.56(1H,s), 10.69(1H,br). MS (FAB) m/z: 484 [(M+H)$^+$, Cl$^{35}$], 486 [(M+H)$^+$, Cl$^{37}$]. Elementary analysis for C$_{26}$H$_{30}$ClN$_3$O$_2$S.2HCl.½H$_2$O Calculated: C, 55.18; H, 5.88; N, 7.42; Cl, 18.79; S, 5.66. Found: C, 55.34; H, 5.70; N, 7.31; Cl, 18.76; S, 5.85.

Example B-4

1-[[(2RS)-6-Aminomethyl-1,2,3,4-tetrahydronaphthalen-2-yl]carbonyl]-4-[(6-chloronaphthalen-2-yl)sulfonyl]piperazine hydrochloride In the same manner as in Example B-1, the title compound was obtained using 1-[[(2RS)-6-(N-tert-butoxycarbonylaminomethyl)-1,2,3,4-tetrahydronaphthalen-2-yl]carbonyl]-4-[(6-chloronaphthalen-2-yl)sulfonyl]piperazine as a starting material.

$^1$H-NMR (DMSO-d$_6$) δ: 1.55(1H,m), 1.80-1.90(1H,m), 2.60–2.90(4H,m), 2.90–3.10(5H,m), 3.50–3.80(4H,m), 3.90 (2H,s), 7.05(1H,d,J=7.8 Hz), 7.10–7.20(2H,m), 7.71(1H,d, J=8.8 Hz), 7.82(1H,d,J=8.3 Hz), 8.10–8.40(6H,m), 8.50(1H, s). MS (FAB) m/z: 498 [(M+H)$^+$, Cl$^{35}$], 500 [(M+H)$^+$, Cl$^{37}$]. Elementary analysis for C$_{26}$H$_{28}$ClN$_3$O$_3$S.1.2HCl.0.8H$_2$O Calculated: C, 56.15; H, 5.58; N, 7.55; Cl, 14.02; S, 5.76. Found: C, 55.93; H, 5.22; N, 7.37; Cl, 14.26; S, 5.70.

Example B-5

1-[(7-Aminomethylnaphthalen-2-yl)carbonyl]-4-[(6-chloronaphthalen-2-yl)sulfonyl]piperazine hydrochloride In the same manner as in Example B-1, the title compound was obtained using 1-[[7-(N-tert-butoxycarbonylaminomethyl)naphthalen-2-yl]carbonyl]-4-[(6-chloronaphthalen-2-yl)sulfonyl]piperazine as a starting material.

$^1$H-NMR (DMSO-d$_6$) δ: 3.10(4H,br), 3.30–3.90(4H,br), 4.18(2H,s), 7.46(1H,d,J=8.8 Hz), 7.69(1H,d,J=8.8 Hz), 7.73 (1H,d,J=8.8 Hz), 7.83(1H,d,J=8.8 Hz), 7.89(1H,s), 7.90–8.00(3H,m), 8.19(1H,d,J=8.8 Hz), 8.20–8.30(2H,m), 8.50(4H,br s). MS (FAB) m/z: 494 [(M+H)$^+$, Cl$^{35}$], 496 [(M+H)$^+$, Cl$^{37}$]. Elementary analysis for C$_{26}$H$_{24}$ClN$_3$O$_3$S.HCl.¾H$_2$O Calculated: C, 57.41; H, 4.91; N, 7.72; Cl, 13.03; S, 5.89. Found: C, 57.40; H, 4.87; N, 7.71; Cl, 13.09; S, 5.89.

Example B-6

1-[(7-Aminomethylnaphthalen-2-yl)methyl]-4-[(6-chloronaphthalen-2-yl)sulfonyl]piperazine hydrochloride In the same manner as in Example B-1, the title compound was obtained using 1-([7-(N-tert-butoxycarbonylaminomethyl)naphthalen-2-yl]methyl]-4-[(6-chloronaphthalen-2-yl)sulfonyl]piperazine as a starting material.

$^1$H-NMR (DMSO-d$_6$) δ: 2.92(2H,m), 3.22(2H,m), 3.83 (2H,m), 4.20(2H,d,J=5.4 Hz), 4.51(2H,br), 7.60–7.90(4H, m), 7.90–8.40(7H,m), 8.52(1H,s), 8.57(3H,br), 11.52(1H, br). MS (FAB) m/z: 480 [(M+H)$^+$, Cl$^{35}$], 482 [(M+H)$^+$, Cl$^{37}$]. Elementary analysis for C$_{26}$H26ClN3O2S.2HCl.¼H$_2$O Calculated: C, 56.02; H, 5.15; N, 7.54; Cl, 19.08; S, 5.75. Found: C, 55.88; H, 5.45; N, 7.34; Cl, 18.90; S, 5.69.

Example B-7

1-[(6-Aminomethylnaphthalen-2-yl)carbonyl]-4-[(6-chloronaphthalen-2-yl)sulfonyl]piperazine hydrochloride In tetrahydrofuran (5 ml), 2-(N-tert-butoxycarbonylaminomethyl)-6-methoxycarbonylnaphthalene (0.15 g) was dissolved, followed by the addition of 1N sodium hydroxide (0.70 ml). The resulting mixture was stirred at room temperature for 16 hours. After the reaction mixture was concentrated under reduced pressure, the concentrate was diluted with dichloromethane and added with dilute hydrochloric acid to separate the organic layer. The organic layer thus obtained was dried over anhydrous sodium sulfate. The residue obtained by distilling off the solvent under reduced pressure was dissolved in N,N-dimethylformamide (5 ml), followed by the addition of 1-[(6-chloronaphthalen-2-yl)sulfonyl] piperazine hydrochloride (0.21 g), N-methylmorpholine (54.0 μl), 1-(3-dimethylaminopropyl)-3-ethylcarbodiimide hydrochloride (94.0 mg) and 1-hydroxybenzotriazole (77.0 mg). The resulting mixture was stirred at room temperature for 21 hours. The reaction mixture was concentrated under reduced pressure. The concentrate was diluted with ethyl acetate, washed with water and dried over anhydrous sodium sulfate. The residue obtained by distilling off the solvent under reduced pressure was purified by chromatography on a silica gel column (dichloromethane~dichloromethane:methanol=100:1), followed by the reaction in the same manner as in Example B-1, whereby the title compound (77.0 g, 29%) was obtained as colorless crystals.

$^1$H-NMR (DMSO-d$_6$) δ: 3.09(4H,br), 3.40–3.90(4H,br), 4.19(2H,s), 7.47(1H,d,J=8.3 Hz), 7.66(1H,d,J=8.3 Hz), 7.73 (1H,d,J=9.3 Hz), 7.83(1H,d,J=8.8 Hz), 7.90–8.10(4H,m), 8.19(1H,d,J=8.8 Hz), 8.20–8.30(2H,m), 8.40–8.60(4H,m). MS (FAB) m/z: 494 [(M+H)$^+$, Cl$^{35}$], 496 [(M+H)$^+$, Cl$^{37}$]. Elementary analysis for C$_{26}$H$_{24}$ClN$_3$O$_3$S.HCl.¾H$_2$O.⅓Et$_2$O Calculated: C, 57.60;

H, 5.14; N, 7.52; Cl, 12.69; S, 5.74. Found: C, 57.64; H, 5.10; N, 7.12; Cl, 12.69; S, 5.82.

Example B-8

1-[(6-Chloronaphthalen-2-yl)sulfonyl]-4-[(isoquinolin-7-yl)carbonyl]piperazine hydrochloride In 4N hydrochloric acid, methyl 7-isoquinolinecarboxylate (J. Org. Chem., 38(21), 3701, 1973) (206 mg) was dissolved, followed by heating under reflux for 4 hours. In the same manner as in Example B-7, a reaction was effected using the residue obtained by distilling off the solvent under reduced pressure and 1-[(6-chloronaphthalen-2-yl)sulfonyl]piperazine hydrochloride as starting materials, whereby the title compound (298 mg, 62%) was obtained.

$^1$H-NMR (DMSO-d$_6$) δ: 2.95–3.25(4H,m), 3.40–3.60 (2H,m), 3.70–3.90(2H,m), 7.73(1H,dd,J=8.8,2.0 Hz), 7.84 (1H,d,J=8.8 Hz), 8.05(1H,d,J=7.3 Hz), 8.20(1H,d,J=8.8 Hz), 8.25–8.35(3H,m), 8.41(1H,d,J=6.4 Hz), 8.45(1H,s), 8.52 (1H,s), 8.71(1H,d,J=6.4 Hz), 9.79(1H,s). MS (FAB) m/z: 465 [(M+H)$^+$, Cl$^{35}$], 467 [(M+H)$^+$, Cl$^{37}$]. Elementary analysis for C$_{24}$H$_{20}$ClN$_3$O$_3$S.HCl.2.2H$_2$O Calculated: C, 53.18; H, 4.72; N, 7.75; Cl, 13.08; S, 5.92. Found: C, 53.11; H, 4.70; N, 7.60; Cl, 13.01; S, 6.16.

Example B-9

1-[(6-Chloronaphthalen-2-yl)sulfonyl]-4-[(quinolyl-2-yl)carbonyl]piperazine hydrochloride In the same manner as in Example B-7, the title compound was obtained using quinoline-2-carboxylic acid and 1-[(6-chloronaphthalen-2-yl)sulfonyl]piperazine hydrochloride as starting materials.

$^1$H-NMR (DMSO-d$_6$) δ: 3.05(2H,m), 3.17(2H,m), 3.62 (2H,m), 3.83(2H,m), 7.61(1H,d,J=8.3 Hz), 7.60–7.80(2H, m), 7.80–7.90(2H,m), 7.95(1H,d,J=8.3 Hz), 8.00(1H,d,J= 7.3 Hz), 8.18(1H,d,J=8.8 Hz), 8.20–8.40(2H,m), 8.43(1H, d,J=8.3 Hz), 8.51(1H,s). Elementary analysis for C$_{24}$H$_{20}$ClN$_3$O$_3$S Calculated: C, 61.87; H, 4.33; N, 9.02; Cl, 7.61; S, 6.88. Found: C, 61.76; H, 4.20; N, 8.73; Cl, 7.65; S, 6.99.

Example B-10

1-[(6-Chloronaphthalen-2-yl)sulfonyl]-4-[(4-hydroxyquinolin-2-yl)carbonyl]piperazine hydrochloride In the same manner as in Example B-7, the title compound was obtained using 4-hydroxyquionoline-2-carboxylic acid and 1-[(6-chloronaphthalen-2-yl)sulfonyl] piperazine hydrochloride as starting materials.

$^1$H-NMR (DMSO-d$_6$) δ: 3.00–3.30(4H,br), 3.53(2H,br), 3.77(2H,br), 6.45(1H,s), 7.48(1H,t,J=7.3 Hz), 7.70–7.90 (4H,m), 8.10–8.40(4H,m), 8.52(1H,s). MS (FAB) m/z: 482 [(M+H)$^+$, Cl$^{35}$], 484 [(M+H)$^+$, Cl$^{37}$]. Elementary analysis for C$_{24}$H$_{20}$ClN$_3$O$_4$S.9/10HCl.1/3CH$_3$OH, 3/2H$_2$O Calculated: C, 52.90; H, 4.60; N, 7.61; Cl, 12.19; S, 5.80. Found: C, 53.17; H, 4.59; N, 7.39; Cl, 12.31; S, 6.07.

Example B-11

1-[(6-Chloronaphthalen-2-yl)sulfonyl]-4-[(8-hydroxyquinolin-7-yl)carbonyl]piperazine hydrochloride In the same manner as in Example B-7, the title compound was obtained using 8-hydroxyquionoline-7-carboxylic acid and 1-[(6-chloronaphthalen-2-yl)sulfonyl] piperazine hydrochloride as starting materials.

$^1$H-NMR (DMSO-d$_6$) δ: 2.90–3.30(4H,br), 3.35(2H,br), 3.79(2H,br), 7.39(1H,d,J=8.3 Hz), 7.53(1H,d,J=8.3 Hz), 7.60–7.90(3H,m), 8.10–8.40(3H,m), 8.50(1H,s), 8.60(1H,d, J=7.8 Hz), 8.96(1H,d,J=4.4 Hz). MS (FAB) m/z: 482 [(M+H)$^+$, Cl$^{35}$], 484 [(M+H)$^+$, Cl$^{37}$]. Elementary analysis for C$_{24}$H$_{20}$ClN$_3$O$_4$S.HCl.CH$_2$OH.1/4H$_2$O Calculated: C, 54.11; H, 4.63; N, 7.57; Cl, 12.78; S, 5.78. Found: C, 54.40; H, 4.84; N, 7.66; Cl, 13.04; S, 5.99.

Example B-12

1-[(Benzimidazol-5-yl)carbonyl]-4-[(6-chloronaphthalen-2-yl)sulfonyl]piperazine hydrochloride In the same manner as in Example B-7, the title compound was obtained using methyl N-triphenylmethyl-5-benzimidazolecarboxylate and 1-[(6-chloronaphthalen-2-yl) sulfonyl]piperazine hydrochloride as starting materials.

$^1$H-NMR (DMSO-d$_6$) δ: 3.08(4H,br), 3.30–4.00(4H,br), 7.48(1H,d,J=8.3 Hz), 7.60–7.90(4H,m), 8.10–8.30(3H,m), 8.50(1H,s), 9.51(1H,s). MS (FAB) m/z: 455 [(M+H)$^+$, Cl$^{35}$], 457 [(M+H)$^+$, Cl$^{37}$]. Elementary analysis for C$_{22}$H$_{19}$ClN$_4$O$_3$S.HCl.5/4H$_2$O Calculated: C, 51.42; H, 4.41; N, 10.90; Cl, 13.80; S, 6.24. Found: C, 51.53; H, 4.40; N, 10.71; Cl, 13.61; S, 6.40.

Example B-13

1-[(Benzimidazol-5-yl)carbonyl]-4-[(6-chloronaphthalen-2-yl)sulfonyl]homopiperazine hydrochloride In the same manner as in Example B-12, the title compound was obtained using methyl N-triphenylmethyl-5-benzimidazolecarboxylate and 1-[(6-chloronaphthalen-2-yl) sulfonyl]homopiperazine hydrochloride as starting materials.

$^1$H-NMR (DMSO-d$_6$) δ: 1.67(1H,m), 1.93(1H,m), 3.20–3.90(8H,m), 7.44(½H,m), 7.54(½H,m), 7.68(1H,m), 7.80–8.00(3H,m), 8.10–8.30(3H,m), 8.49(½H,s), 8.55(½H, s), 9.56 and 9.57(1H,each s). MS (FAB) m/z: 469 [(M+H)$^+$, Cl$^{35}$], 471 [(M+H)$^+$, Cl$^{37}$]. Elementary analysis for C$_{23}$H$_{21}$ClN$_4$O$_3$S.HCl.0.3CH$_3$OH.H$_2$O Calculated: C, 52.50; H, 4.76; N, 10.51; Cl, 13.30; S, 6.01. Found: C, 52.31; H, 4.66; N, 10.50; Cl, 13.34; S, 6.01.

Example B-14

1-[(6-Chloronaphthalen-2-yl)sulfonyl]-4-[(thiazolo [5,4-c]pyridin-2-yl)carbonyl]piperazine hydrochloride In the same manner as in Example B-7, the title compound was obtained using sodium thiazolo[5,4-c]pyridine-2-carboxylate and 1-[(6-chloronaphthalen-2-yl)sulfonyl] piperazine hydrochloride as starting materials.

$^1$H-NMR (DMSO-d$_6$) δ: 3.10–3.30(4H,m), 3.84(2H,m), 4.32(2H,m), 7.69(1H,dd,J=8.8,2.0 Hz), 7.83(1H,dd,J=8.8, 2.0 Hz), 8.10–8.30(4H,m), 8.51(1H,s), 8.79(1H,d,J=5.9 Hz), 9.62(1H,s). MS (FAB) m/z: 473 [(M+H)$^+$, Cl$^{35}$], 475 [(M+H)$^+$, Cl$^{37}$]. Elementary analysis for C$_{21}$H$_{17}$ClN$_4$O$_3$S$_2$.HCl Calculated: C, 49.51; H, 3.56; N, 11.00; Cl, 13.92; S, 12.59. Found: C, 49.45; H, 3.71; N, 11.20; Cl, 13.67; S, 12.55.

Example B-15

1-[(E)-4-Chlorostyrylsulfonyl]-4-[(thiazolo[5,4-c] pyridin-2-yl)carbonyl]piperazine hydrochloride In the same manner as in Example B-7, the title compound was obtained using sodium thiazolo[5,4-c]pyridine- 2-carboxylate and 1-[(E)-4-chlorostyrylsulfonyl]piperazine hydrochloride as starting materials.

$^1$H-NMR (DMSO-d$_6$) δ: 3.30(4H,m), 3.87(2H,m), 4.35 (2H,m), 7.35(1H,d,J=15.6 Hz), 7.40–7.50(3H,m), 7.79(1H, d,J=8.3 Hz), 8.22(1H,d,J=5.9 Hz), 8.77(1H,d,J=5.9 Hz), 9.59(1H,s). MS (FAB) m/z: 449 ( (M+H)$^+$, Cl$^{35}$], 451 [(M+H)$^+$, Cl$^{37}$]. Elementary analysis for C$_{19}$H$_{17}$ClN$_4$O$_3$S$_2$.½HCl Calculated: C, 48.85; H, 3.78; N, 11.99; Cl, 11.38; S, 13.73. Found: C, 49.18; H, 3.80; N, 12.20; Cl, 11.05; S, 13.84.

Example B-16

1-[(6-Chloronaphthalen-2-yl)sulfonyl]-4-[(4,5,6,7-tetrahydrothieno[3,2-c]pyridin-2-yl)methyl] piperazine hydrochloride In the same manner as in Example B-1, the title compound was obtained using 1-[(5-tert-butoxycarbonyl-4,5,6,7-tetrahydrothieno[3,2-c]pyridin-2-yl)methyl]-4-[(6-chloronaphthalen-2-yl)sulfonyl]piperazine as a starting material.

$^1$H-NMR (DMSO-d$_6$) δ: 2.82–2.88(4H,m), 2.91–2.99 (4H,m), 3.28–3.36(2H,m), 3.47–3.55(4H,m), 4.02(2H,br s), 6.58(1H,s), 7.71(1H,dd,J=8.8,2.0 Hz), 7.81(1H,dd,J=8.8,2.0 Hz), 7.23–7.28(3H,m), 8.49(1H,s), 9.42(2H,br s). MS (FAB) m/z: 462 [(M+H)$^+$, Cl$^{35}$], 464 [(M+H)$^+$, Cl$^{37}$].

Example B-17

1-[(6-Chloronaphthalen-2-yl)sulfonyl]-4-[trans-3-(4,5,6,7-tetrahydrothieno[3,2-c]pyridin-2-yl)propenoyl] piperazine hydrochloride In the same manner as in Example B-1, the title compound was obtained using 1-[trans-3-(5-tert-butoxycarbonyl-4,5,6,7-tetrahydrothieno[3,2-c]pyridin-2-yl)propenoyl]-4-[(6-chloronaphthalen-2-yl)sulfonyl] piperazine as a starting material.

$^1$H-NMR (DMSO-d$_6$) δ: 2.95–3.10(6H,m), 3.32–3.51 (3H,m), 3.60–3.80(3H,m), 4.12(2H,s), 6.75(1H,d,J=15.1 Hz), 7.19(1H,s), 7.50(1H,d,J=15.1 Hz), 7.70(1H,dd,J=8.8, 2.4 Hz), 7.81(1H,dd,J=8.8,2.0 Hz), 8.15(1H,d,J=8.8 Hz), 8.22(1H,d,J=2.0 Hz), 8.50(1H,s), 9.53(2H,br s). MS (EAB) m/z: 502 [(M+H)$^+$, Cl$^{35}$], 504 [(M+H)$^+$, Cl$^{37}$]. Elementary analysis for C$_{24}$H$_{24}$ClN$_3$O$_3$S$_2$.HCl.0.5H$_2$O Calculated: C, 52.65; H, 4.79; Cl, 12.95; N, 7.67; S, 11.71. Found: C, 52.36; H, 4.88; Cl, 12.63; N, 8.01; S, 11.39.

Example B-18

1-[(6-Chloronaphthalen-2-yl)sulfonyl]-4-[3-(4,5,6,7-tetrahydrothieno[3,2-c]pyridin-2-yl)propionyl] piperazine hydrochloride In the same manner as in Example B-1, the title compound was obtained using 1-[3-(5-tert-butoxycarbonyl-4,5,6,7-tetrahydrothieno[3,2-c]pyridin-2-yl)propionyl]-4-[(6-chloronaphthalen-2-yl)sulfonyl]piperazine as a starting material.

$^1$H-NMR (DMSO-d$_6$) δ: 2.80–3.60(16H,m), 4.12(2H,br s), 7.11(1H,br s), 7.74(1H,dd,J=8.8,2.0 Hz), 7.83(1H,dd,J= 8.8,2.0 Hz), 8.20(1H,s), 8.25–8.30(2H,m), 8.53(1H,s), 9.67 (2H,br s). MS (FAB) m/z: 504 [(M+H)$^+$, Cl$^{35}$], 506 [(M+H)$^+$, Cl$^{37}$]. Elementary analysis for C$_{24}$H$_{26}$ClN$_3$O$_3$S$_2$.1.2HCl.1.3H$_2$O Calculated: C, 50.46; H, 5.26; N, 7.36. Found: C, 50.83; H, 5.26; Cl, 13.43; N, 6.97.

Example B-19

1-[(6-Chloronaphthalen-2-yl)sulfonyl]-4-[3-(4,5,6,7-tetrahydrothieno[3,2-c]pyridin-2-yl)propyl] piperazine hydrochloride In the same manner as in Example B-1, the title compound was obtained using 1-[3-(5-tert-butoxycarbonyl-4,5,6,7-tetrahydrothieno[3,2-c]pyridin-2-yl)propyl]-4-[(6-chloronaphthalen-2-yl)sulfonyl]piperazine as a starting material.

$^1$H-NMR (DMSO-d$_6$) δ: 1.90–2.07(2H,m), 2.72–2.80 (2H,m), 2.82–3.21(8H,m), 3.35(2H,br s), 3.51(2H,d,J=11.5 Hz), 3.82(2H,d,J=11.5 Hz), 4.06(2H,s), 6.66(1H,s), 7.74 (1H,dd,J=8.8,1.5 Hz), 7.85(1H,dd,J=8.8,1.5 Hz), 8.20(1H, d,J=8.8 Hz), 8.25–8.39(2H,m), 8.55(1H,s), 9.50(2H,br s), 11.26(1H,br s). MS (FAB) m/z: 490 ((M+H)$^+$, Cl$^{35}$], 492 [(M+H)$^+$, Cl$^{37}$]. Elementary analysis for C$_{24}$H$_{28}$ClN$_3$O$_2$S$_2$.2HCl.1.6H$_2$O Calculated: C, 48.71; H, 5.65; Cl, 17.97; N, 7.10; S, 10.84. Found: C, 49.01; H, 5.77; Cl, 17.62; N, 6.96; S, 10.82.

Example B-20

1-[(6-chloronaphthalen-2-yl)sulfonyl]-4-[N-[(4,5,6,7-tetrahydrothieno[3,2-c]pyridin-2-yl)methyl] carbamoyl]piperazine hydrochloride In the same manner as in Example B-1, the title compound was obtained using 1-[N-[(5-tert-butoxycarbonyl-4,5,6,7-tetrahydrothieno[3,2-c]pyridin-2-yl)methyl] carbamoyl]-4-[(6-chloronaphthalen-2-yl)sulfonyl] piperazine as a starting material.

$^1$H-NMR (DMSO-d$_6$) δ: 2.78–2.86(2H,br s), 2.88–2.94 (4H,m), 3.29–3.35(2H,m), 3.37–3.42(4H,m), 4.03(2H,br s), 4.19(2H,d,J=5.4 Hz), 6.62(1H,s), 7.25(1H,t,J=5.4 Hz), 7.72 (1H,dd,J=8.8,2.0 Hz), 7,82(1H,dd,J=8.8,2.0 Hz), 8.16(1H, d,J=8.8 Hz), 8.22–8.26(2H,m), 8.50(1H,s), 9.27(2H,br s). Elementary analysis for C$_{23}$H$_{25}$ClN$_4$O$_3$S$_2$.HCl.1.3H$_2$O Calculated: C, 48.90; H, 5.10; Cl, 12.55; N, 9.92. Found: C, 49.02; H, 5.20; Cl, 12.50; N, 9.76.

Example B-21

1-[(6-Chloronaphthalen-2-yl)sulfonyl]-4-[(4,5,6,7-tetrahydrothieno[3,2-c]pyridin-2-yl)carbonyl] piperazine hydrochloride In the same manner as in Example B-1, the title compound was obtained using 1-[(5-tert-butoxycarbonyl-4,5,6,7-tetrahydrothieno[3,2-c]pyridin-2-yl)carbonyl]-4-[(6-chloronaphthalen-2-yl)sulfonyl]piperazine as a starting material.

$^1$H-NMR (DMSO-d$_6$) δ: 2.99–3.05(2H,m), 3.08(4H,t,J= 4.6 Hz), 3.35–3.40(2H,m), 3.71(4H,t,J=4.6 Hz), 4.11(2H,s), 7.17(1H,s), 7.71(1H,dd,J=8.8,2.0 Hz), 7.82(1H,dd,J=8.8,2.0 Hz), 8.22–8.28(3H,m), 8.50(1H,s), 9.38(2H,br s). MS (FAB) m/z: 476 [(M+H)$^+$, Cl$^{35}$], 478 [(M+H)$^+$, Cl$^{37}$]. Elementary analysis for C$_{22}$H$_{23}$ClN$_3$O$_3$S$_2$.HCl.½H$_2$O Calculated: C, 48.98; H, 4.86; Cl, 13.14; N, 7.79; S, 11.89. Found: C, 48.96; H, 4.67; Cl, 13.21; N, 7.74; S, 11.93.

Example B-22

4-[(6-Chloronaphthalen-2-yl)sulfonyl]-2-ethoxycarbonyl-1-[(4,5,6,7-tetrahydrothieno[3,2-c] pyridin-2-yl)carbonyl]piperazine hydrochloride In the same manner as in Example B-1, the title compound was obtained using 1-[(5-tert-butoxycarbonyl-4,5,6, 7-tetrahydrothieno[3,2-c]pyridin-2-yl)carbonyl]-4-[(6-chloronaphthalen-2-yl)sulfonyl]-2-ethoxycarbonylpiperazine as a starting material.

$^1$H-NMR (DMSO-d$_6$) δ: 1.22(3H,t,J=7.0 Hz), 2.38–2.58 (1H,m), 2.65–2.72(1H,m), 3.04(2H,br s), 3.29–3.43(3H,m), 3.70(1H,br s), 4.01–4.30(6H,m), 5.18(1H,br s), 7.27(1H,s), 7.73(1H,dd,J=8.8,2.0 Hz), 7.82(1H,d,J=8.8 Hz), 8.26(1H,s), 8.29(1H,s), 8.54(1H,s), 9.59(2H,br s). MS (FAB) m/z: 548 [(M+H)$^+$, Cl$^{35}$], 550 [(M+H)$^+$, Cl$^{37}$]. Elementary analysis for C$_{25}$H$_{26}$N$_3$ClO$_5$S$_2$.1.2HCl.0.6H$_2$O Calculated: C, 49.83; H, 4.75; Cl, 12.94; N, 6.97; S, 10.64. Found: C, 49.62; H, 4.71; Cl, 13.30; N, 7.19; S, 10.56.

Example B-23

2-Carboxy-4-[(6-chloronaphthalen-2-yl)sulfonyl]-1-((4,5,6,7-tetrahydrothieno[3,2-c]pyridin-2-yl)carbonyl]piperazine hydrochloride In tetrahydrofuran (1 ml), 4-[(6-chloronaphthalen-2-yl)sulfonyl]-2-ethoxycarbonyl-1-[(4,5,6,7-tetrahydrothieno[3,2-c]pyridin-2-yl)carbonyl]piperazine hydrochloride (95 mg) was dissolved, followed by the addition of ethanol (2 ml) and 1N sodium hydroxide (3 ml). The resulting mixture was heated under reflux for 30 minutes. To the reaction mixture, 4N hydrochloric acid (2 ml) was added and the precipitate thus obtained was collected by filtration, whereby the title compound (83 mg, 90%) was obtained as a colorless foam.

$^1$H-NMR (DMSO-d$_6$) δ: 2.30–2.53(1H,m), 2.58–2.69 (1H,m), 3.04(2H,br s), 3.29–3.83(4H,m), 4.07–4.32(4H,m), 4.90–5.20(1H,m), 7.03–7.30(1H,m), 7.71(1H,dd,J=8.8,2.4 Hz), 7.81(1H,d,J=8.8 Hz), 8.81(1H,d,J=8.8 Hz), 8.20–8.29 (2H,m), 8.52(1H,s), 9.58(2H,br s). MS (FAB) m/z: 520 [(M+H)$^+$, Cl$^{35}$], 522 [(M+H)$^+$, Cl$^{37}$]. Elementary analysis for C$_{23}$H$_{22}$N$_3$ClO$_5$S$_2$.1.2HCl.0.8H$_2$O Calculated: C, 47.78; H, 4.32; Cl, 13.49; N, 7.27; S, 11.09. Found: C, 47.41; H, 4.36; Cl, 13.81; N, 7.14; S, 11.01.

Example B-24

1-[(6-Chloronaphthalen-2-yl)sulfonyl]-4-[(5-aminohydroxyiminomethyl-4,5,6,7-tetrahydrothieno[3,2-c]pyridin-2-yl)carbonyl]piperazine To methanol (4 ml), a solution of 1-[(6-chloronaphthalen-2-yl)sulfonyl]-4-[(5-cyano-4,5,6,7-tetrahydrothieno[3,2-c]pyridin-2-yl)carbonyl]piperazine (41 mg) in dichloromethane (1 ml) was added, followed by the addition of hydroxylamine hydrochloride (28 mg) and triethylamine (0.55 ml). The resulting mixture was stirred at room temperature for 2 hours. The residue obtained by concentrating the reaction mixture under reduced pressure was purified by chromatography on a silica gel column (dichloromethane~dichloromethane:methanol=100:3), whereby the title compound (14 mg, 32%) was obtained.

$^1$H-NMR (DMSO-d$_6$) δ: 2.74–2.79(2H,m), 3.06(4H,s), 3.35–3.38(2H,m), 3.71(4H,s), 4.07(2H,s), 5.32(2H,s), 7.08 (1H,s), 7.71(1H,dd,J=8.8,1.6 Hz), 7.81(1H,dd,J=8.8,1.6 Hz), 8.16(1H,s), 8.23–8.25(2H,m), 8.33(1H,br s), 8.49(1H, s). MS (FAB) m/z: 534 [(M+H)$^+$, Cl$^{35}$], 536 [(M+H)$^+$, Cl$^{37}$].

Example B-25

1-[(6-Chloronaphthalen-2-yl)sulfonyl]-4-[N-(4,5,6,7-tetrahydrothieno[3,2-c]pyridin-2-yl) carbamoyl]piperazine hydrochloride In the same manner as in Example B-1, the title compound was obtained using 1-[N-(5-tert-butoxycarbonyl-4,5, 6,7-tetrahydrothieno[3,2-c]pyridin-2-yl)carbamoyl]-4-[(6-chloronaphthalen-2-yl)sulfonyl]piperazine as a starting material.

$^1$H-NMR (DMSO-d$_6$) δ: 2.83(2H,br s), 2.99(4H,br s), 3.30(2H,br s), 3.54(4H,br s), 4.00(2H,s), 6.33(1H,s), 7.70 (1H,dd,J=8.8,2.0 Hz), 7.82(1H,d,J=8.8 Hz), 8.16(1H,d,J= 8.8 Hz), 8.22(1H,s), 8.26(1H,d,J=8.8 Hz), 8.50(1H,s), 9.18 (2H,br s), 9.82(1H,s). MS (FAB) m/z: 491 [(M+H)$^+$, Cl$^{35}$], 493 [(M+H)$^+$, Cl$^{37}$]. Elementary analysis for C$_{22}$H$_{23}$N$_4$ClO$_3$S$_2$.HCl.0.3H$_2$O Calculated: C, 49.59; H, 4.65; Cl, 13.31; N, 10.51; S, 12.03. Found: C, 49.32; H, 4.63; Cl, 13.34; N, 10.81; S, 12.03.

Example B-26

1-[(6-Chloronaphthalen-2-yl)sulfonyl]-4-[N-methyl-N-(4,5,6,7-tetrahydrothieno[3,2-c]pyridin-2-yl)carbamoyl]piperazine hydrochloride In the same manner as in Example B-1, the title compound was obtained using 1-[N-(5-tert-butoxycarbonyl-4,5, 6,7-tetrahydrothieno[3,2-c]pyridin-2-yl)-N-methylcarbamoyl]-4-[(6-chloronaphthalen-2-yl)sulfonyl]piperazine as a starting material.

$^1$-NMR (DMSO-d$_6$) δ: 2.83(2H,d,J=5.4 Hz), 2.97(4H,br s), 3.10(3H,s), 3.28–3.41(6H,m), 4.00(2H,s), 6.35(1H,s), 7.72(1H,dd,J=8.8,2.0 Hz), 7.81(1H,dd,J=8.8,2.0 Hz), 8.17 (1H,d,J=8.8 Hz), 8.23–8.31(2H,m), 8.50(1H,s), 9.28(2H,br s). MS (FAB) m/z: 505 [(M+H)$^+$, Cl$^{35}$], 507 [(M+H)$^+$, Cl$^{37}$]. Elementary analysis for C$_{23}$H$_{25}$N$_4$ClO$_3$S$_2$.1.1HCl.0.5H$_2$O Calculated: C, 49.85; H, 4.93; Cl, 13.43; N, 10.11; S, 11.57. Found: C, 49.55; H, 4.92; Cl, 13.23; N, 10.13; S, 11.83.

Example B-27

1-[(6-Chloronaphthalen-2-yl)sulfonyl]-4-[[5-(1-pyrrolin-2-yl)-4,5,6,7-tetrahydrothieno[3,2-c]pyridin-2-yl]carbonyl]piperazine hydrochloride In N,N-dimethylformamide (20 ml), 1-[(6-chloronaphthalen-2-yl)sulfonyl]-4-[(4,5,6,7-tetrahydrothieno[3,2-c]pyridin-2-yl)carbonyl]piperazine hydrochloride (400 mg) was dissolved, followed by the addition of triethylamine (0.16 ml) and 2-methoxypyrroline (464 mg). The resulting mixture was stirred at room temperature for 3 days. The reaction mixture was concentrated under reduced pressure. To the residue, 1N hydrochloric acid was added and the precipitate thus formed was collected by filtration, whereby the title compound (411 mg, 88%) was obtained as a pale yellow foamy solid.

$^1$H-NMR (DMSO-d$_6$) δ: 2.07–2.18(2H,m), 2.90–3.11(8H, m), 3.62(2H,t,J=6.8 Hz), 3.72(4H,br), 3.80(2H,t,J=5.9 Hz), 3.99(2H,t,J=5.9 Hz), 4.62(1H,br s), 4.73(1H,br s), 7.10(1H, s), 7.50(1H,s), 7.72(1H,dd,J=8.8,2.0 Hz), 7.82(1H,dd,J=8.8, 2.0 Hz), 8.18(1H,d,J=8.8 Hz), 8.22–8.28(2H,m), 8.51(1H,s), 10.37(1H,br s), 10.53(1H,br s). MS (FAB) m/z: 542 [(M+ H)$^+$, Cl$^{35}$], 544 [(M+H)$^+$, Cl$^{37}$]. Elementary analysis for C$_{26}$H$_{27}$ClN$_4$O$_3$S$_2$.1.3HCl.0.4H$_2$O Calculated: C, 52.25; H, 4.91; Cl, 13.64; N, 9.37; S. 10.73. Found: C, 52.34; H, 5.03; Cl, 13.56; N, 9.36; S, 10.74.

Example B-28

1-[(6-Chloronaphthalen-2-yl)sulfonyl]-4-[(4,5,6,7-tetrahydrothiazolo[5,4-c]pyridin-2-yl)carbonyl]piperazine hydrochloride In the same manner as in Example B-1, the title compound was obtained using 1-[(6-tert-butoxycarbonyl-4,5,6, 7-tetrahydrothiazolo[5,4-c]pyridin-2-yl)carbonyl]-4-[(6-chloronaphthalen-2-yl)sulfonyl]piperazine as a starting material.

$^1$H-NMR (DMSO-d$_6$) δ: 3.01(2H,t,J=5.9 Hz), 3.11(4H, br), 3.44(2H,br s), 3.74(2H,br s), 4.32–4.46(4H,m), 7.71 (1H,dd,J=8.8,2.0 Hz), 7.83(1H,dd,J=8.8,2.0 Hz), 8.15(1H, d,J=8.8 Hz), 8.23(1H,s), 8.26(1H,d,J=8.8 Hz), 8.30(1H,s). MS (FAB) m/z: 477 ((M+H)$^+$, Cl$^{35}$], 479 [(M+H)$^+$, Cl$^{37}$]. Elementary analysis for C$_{21}$H$_{21}$ClN$_4$O$_3$S$_2$.HCl.0.2H$_2$O Calculated: C, 48.78; H, 4.37; Cl, 13.71; N, 10.84; S, 12.40. Found: C, 48.60; H, 4.50; Cl, 13.58; N, 10.62; S, 12.29.

Example B-29

1-[(6-Chloronaphthalen-2-yl)sulfonyl]-4-[(6-aminohydroxyiminomethyl-4,5,6,7-tetrahydrothiazolo[5,4-c]pyridin-2-yl)carbonyl]piperazine hydrochloride; and 1-[(6-carbamoyl-4,5,6,7-tetrahydrothiazolo[5,4-c]pyridin-2-yl)carbonyl]-4-[(6-chloronaphthalen-2-yl)sulfonyl]piperazine In a similar manner to Referential Example 33 and Example B-24 by using 1-[(6-chloronaphthalen-2-yl)sulfonyl]-4-[(4,5,6,7-tetrahydrothiazolo[5,4-c]pyridin-2-yl)carbonyl]piperazine hydrochloride as a starting material, 1-[(6-chloronaphthalen-2-yl)sulfonyl]-4-[(6-aminohydroxyiminomethyl-4,5,6,7-tetrahydrothiazolo[5,4-c]pyridin-2-yl)carbonyl]piperazine hydrochloride and also 1-[(6-carbamoyl-4,5,6,7-tetrahydrothiazolo[5,4-c]pyridin-2-yl)carbonyl]-4-[(6-chloronaphthalen-2-yl)sulfonyl]piperazine were obtained. 1-[(6-Chloronaphthalen-2-yl)sulfonyl]-4-[(6-aminohydroxyiminomethyl-4,5,6,7-tetrahydrothiazolo[5,4-c]pyridin-2-yl)carbonyl]piperazine hydrochloride:

$^1$H-NMR (DMSO-d$_6$) δ: 2.77(2H,br s), 3.09(4H,br), 3.48 (2H,t,J=5.4 Hz), 3.73(2H,br s), 4.30–4.50(4H,m), 5.61(1H, br s), 7.71(1H,dd,J=8.8 Hz,2.0 Hz), 7.82(1H,dd,J=8.8,2.0 Hz), 8.15(1H,d,J=8.8 Hz), 8.22(1H,d,J=1.5 Hz), 8.25(1H,d, J=8.8 Hz), 8.50(1H,s), 8.53(1H,br s). MS (FAB) m/z: 535 [(M+H)$^+$, Cl$^{35}$], 537 [(M+H)$^+$, Cl$^{37}$].
1-[(6-Carbamoyl-4,5,6,7-tetrahydrothiazolo[5,4-c]pyridin-2-yl)carbonyl]-4-[(6-chloronaphthalen-2-yl)sulfonyl]piperazine:

$^1$H-NMR (DMSO-d$_6$) δ: 2.75(2H,br s), 3.09(4H,br), 3.63 (2H,t,J=5.9 Hz), 3.73(2H,br s), 4.39(2H,br s), 4.59(2H,s), 6.17(2H,s), 7.70(1H,dd,J=8.8,2.0 Hz), 7.82(1H,dd,J=8.8,2.0 Hz), 8.14(1H,d,J=8.8 Hz), 8.21(1H,d,J=1.5 Hz), 8.25(1H,d, J=8.8 Hz), 8.50(1H,s). MS (FAB) m/z: 520 [(M+H)$^+$, Cl$^{35}$], 522 [(M+H)$^+$, Cl$^{37}$]. Elementary analysis for C$_{22}$H$_{22}$ClN$_5$O$_4$S$_2$.H$_2$O Calculated: C, 49.11; H, 4.50; N, 13.02. Found: C, 48.98; H, 4.12; N, 12.83.

Example B-30

1-[(6-Chloronaphthalen-2-yl)sulfonyl]-4-[[6-(1-pyrrolin-2-yl)-4,5,6,7-tetrahydrothiazolo[5,4-c]pyridin-2-yl]carbonyl]piperazine hydrochloride In the same manner as in Example B-27, the title compound was obtained using 1-[(6-chloronaphthalen-2-yl)sulfonyl]-4-[(4,5,6,7-tetrahydrothiazolo[5,4-c]pyridin-2-yl)carbonyl]piperazine hydrochloride as a starting material.

$^1$H-NMR (DMSO-d$_6$) δ: 2.07–2.15(2H,m), 2.94–3.16 (8H,m), 3.63(2H,t,J=7.3 Hz), 3.75(2H,br s), 3.90(2H,br s), 4.39(2H,br s), 4.93(2H,s), 7.70(1H,dd,J=8.8,2.0 Hz), 7.83 (1H,dd,J=8.8,2.0 Hz), 8.15(1H,d,J=8.8 Hz), 8.22(1H,d,J= 2.0 Hz), 8.25(1H,d,J=8.8 Hz), 8.50(1H,s). MS (FAB) m/z: 544 [(M+H)$^+$, Cl$^{35}$], 546 [(M+H)$^+$, Cl$^{37}$]. Elementary analysis for C$_{25}$H$_{26}$ClN$_5$O$_3$S$_2$.1.4HCl.CH$_3$OH Calculated: C, 49.79; H, 5.05; Cl, 13.57; N, 11.17; S, 10.23. Found: C, 49.44; H, 4.78; Cl, 13.63; N, 10.83; S, 10.15.

Example B-31

1-[(6-Chloronaphthalen-2-yl)sulfonyl]-4-[(6-formyl-4,5,6,7-tetrahydrothiazolo[5,4-c]pyridin-2-yl)carbonyl]piperazine In the same manner as in Example B-7, the title compound was obtained using 1-[(6-chloronaphthalen-2-yl)sulfonyl]-4-[(4,5,6,7-tetrahydrothiazolo[5,4-c]pyridin-2-yl)carbonyl]piperazine hydrochloride and formic acid as starting materials.

$^1$H-NMR (DMSO-d$_6$) δ: 2.74–2.88(2H,m), 3.10(4H,br), 3.31(2H,s), 3.66–3.86(4H,m), 4.64–4.73(2H,m), 7.69(1H, dd,J=8.8,2.0 Hz), 7.82(1H,dd,J=8.8,2.0 Hz), 8.14(1H,d,J= 8.8 Hz), 8.15–8.22(2H,m), 8.24(1H,d,J=8.8 Hz), 8.50(1H,s). MS (FAB) m/z: 505 [(M+H)$^+$, Cl$^{35}$], 507 [(M+H)$^+$, Cl$^{37}$]. Elementary analysis for C$_{22}$H$_{21}$ClN$_4$O$_4$S$_2$.⅓H$_2$O Calculated: C, 51.95; H, 4.24; Cl, 6.97; N, 11.02; S, 12.61. Found: C, 52.18; H, 4.30; Cl, 6.69; N, 10.71; S, 12.21.

Example B-32

1-[(6-Chloronaphthalen-2-yl)sulfonyl]-4-[(6-methyl-4,5,6,7-tetrahydrothiazolo[5,4-c]pyridin-2-yl)carbonyl]piperazine hydrochloride In dichloromethane (10 ml), 1-[(6-chloronaphthalen-2-yl)sulfonyl]-4-[(4,5,6,7-tetrahydrothiazolo[5,4-c]pyridin-2-yl)carbonyl]piperazine hydrochloride (400 mg) was suspended, followed by the addition of triethylamine (0.22 ml) and acetic acid (0.05 ml). The resulting mixture was stirred at room temperature for 5 minutes. To the reaction mixture, a 30% aqueous solution (0.08 ml) of formaldehyde and sodium triacetoxyborohydride (264 mg) were added. The resulting mixture was stirred at room temperature for 10 minutes. The reaction mixture was concentrated under reduced pressure. Ethyl acetate was added to the residue. The resulting mixture was washed with water and saturated aqueous NaCl solution, dried over anhydrous sodium sulfate and distilled under reduced pressure to remove the solvent. The residue was dissolved in a saturated hydrochloride solution in ethanol (1 ml), followed by concentration under reduced pressure. The residue thus obtained was crystallized from hexane and ethyl acetate, whereby the title compound (298 mg, 71%) was obtained.

$^1$H-NMR (DMSO-d$_6$) δ: 2.89(3H,s), 3.10(6H,br), 3.32–3.81(4H,m), 4.30–4.81(4H,m), 7.71(1H,dd,J=8.8,2.0 Hz), 7.82(1H,dd,J=8.8,2.0 Hz), 8.15(1H,d,J=8.8 Hz), 8.20–8.28(2H,m), 8.50(1H,s), 11.28(1H,br s). MS (FAB) m/z: 491 [(M+H)$^+$, Cl$^{35}$], 493 (M+H)$^+$, Cl$^{37}$]. Elementary analysis for C$_{22}$H$_{23}$ClN$_4$O$_3$S$_2$.HCl.0.6H$_2$O Calculated: C, 49.09; H, 4.72; Cl, 13.17; N, 10.41; S, 11.91. Found: C, 48.88; H, 4.78; Cl, 13.26; N, 10.42; S, 12.03.

Example B-33

2-[[4-[(6-Chloronaphthalen-2-yl)sulfonyl]piperazin-1-yl]carbonyl]-6,6-dimethyl-4,5,6,7-tetrahydrothiazolo[5,4-c]pyridinium iodide In N,N-dimethylformamide (20 ml), 1-[(6-chloronaphthalen-2-yl)sulfonyl]-4-[(6-methyl-4,5,6,7-tetrahydrothiazolo[5,4-c]pyridin-2-yl)carbonyl]piperazine hydrochloride (200 mg) was dissolved, followed by the addition of methyl iodide (0.05 ml) and potassium carbonate (79.0 mg). The resulting mixture was stirred overnight at 80° C. The reaction mixture was concentrated under reduced pressure. Water was added to the residue and the precipitate so formed was collected by filtration. The precipitate was dissolved in a 1:1 mixed solution of dichloromethane and methanol. Ethyl acetate was added to the resulting solution and the precipitate thus formed was collected by filtration, whereby the title compound (144 mg, 56%) was obtained.

$^1$H-NMR (DMSO-d$_6$) δ: 3.05–3.23(12H,m), 3.77(2H,t,J= 5.9 Hz), 4.40(2H,br s), 4.79(2H,br s), 7.71(1H,dd,J=8.8,2.0 Hz), 7.83(1H,dd,J=8.8,2.0 Hz), 8.15(1H,d,J=8.8 Hz), 8.20–8.27(2H,m), 8.52(1H,s). MS (FD) m/z: 505 (M$^+$, Cl$^{35}$), 507 (M$^+$, Cl$^{37}$). Elementary analysis for C$_{23}$H$_{26}$ClIN$_4$O$_3$S$_2$·½CH$_3$CO$_2$CH$_2$CH$_3$ Calculated: C, 44.35; H, 4.47; N, 8.28. Found: C, 44.52; H, 4.23; N, 8.01.

Example B-34

2-[[4-[(6-Chloronaphthalen-2-yl)sulfonyl]piperazin-1-yl]carbonyl]-6-methyl-4,5,6,7-tetrahydrothiazolo [5,4-c]pyridine N-oxide In acetone (10 ml), 1-[(6-chloronaphthalen-2-yl)sulfonyl]-4-[(6-methyl-4,5,6,7-tetrahydrothiazolo[5,4-c]pyridin-2-yl)carbonyl]piperazine hydrochloride (400 mg) was suspended, followed by the addition of a 1N aqueous solution (0.38 ml) of sodium hydroxide and a 30% aqueous solution (3.50 ml) of hydrogen peroxide. The resulting mixture was stirred at room temperature for 8 days. After the reaction mixture was concentrated under reduced pressure, the residue was purified by chromatography through a synthetic adsorbent ("Diaion® HP-20", trade name; water~water : acetonitrile=2:5), whereby the title compound (84 mg, 39%) was obtained.

$^1$H-NMR (DMSO-d$_6$) δ: 2.83–2.90(1H,m), 3.10(5H,br), 3.20–3.47(4H,m), 3.61–3.83(3H,m), 4.28–4.50(3H,m), 4.78–4.85(1H,m), 7.69(1H,dd,J=8.8,2.0 Hz), 7.82(1H,dd,J= 8.8,2.0 Hz), 8.14(1H,d,J=8.8 Hz), 8.19–8.27(2H,m), 8.50 (1H,s). MS (FD) m/z: 506 (M$^+$, Cl$^{35}$), 508 (M$^+$, Cl$^{37}$).

Example B-35

2-Carbamoyl-4-[(6-chloronaphthalen-2-yl)sulfonyl]-1-[(4,5,6,7-tetrahydrothiazolo[5,4-c]pyridin-2-yl) carbonyl]piperazine trifluoroacetate To trifluoroacetic acid (1 ml), a solution of 1-[(6-tert-butoxycarbonyl-4,5,6,7-tetrahydrothiazolo[5,4-c]pyridin-2-yl)carbonyl]-2-carbamoyl-4-[(6-chloronaphthalen-2-yl) sulfonyl]piperazine (303 mg) dissolved in dichloromethane (1 ml) was added, followed by concentration under reduced pressure. The precipitate thus formed was collected by filtration and washed with diethyl ether, whereby the title compound (263 mg, 83%) was obtained.

$^1$H-NMR (DMSO-d$_6$) δ: 2.39–2.70(2H,m), 2.92–3.06 (2H,m), 3.42–3.77(4H,m), 4.25–4.50(⅞H,m), 4.97(½H,br s), 5.35–5.44(½H,m), 6.14(½H,br s), 7.30–7.39(1H,m), 7.66–7.73(2H,m), 7.77–7.82(1H,m), 8.16(1H,d,J=8.8 Hz), 8.21–8.28(2H,m), 8.49(1H,s), 9.26(2H,br s). MS (FAB) m/z: 520 [(M+H)$^+$, Cl$^{35}$], 522 [(M+H)$^+$, Cl$^{37}$]. Elementary analysis for C$_{22}$H$_{22}$ClN$_5$O$_4$S$_2$·CF$_3$CO$_2$H·0.6H$_2$O Calculated: C, 44.29; H, 3.73; Cl, 5.40; F, 9.55; N, 10.67; S, 9.77. Found: C, 44.59; H, 3.79; Cl, 5.26; F, 9.54; N, 10.28; S 9.72.

Example B-36

2-Carbamoyl-4-[(6-chloronaphthalen-2-yl)sulfonyl]-1-[(6-methyl-4,5,6,7-tetrahydrothiazolo[5,4-c] pyridin-2-yl)carbonyl]piperazine hydrochloride In the same manner as in Example B-32, the title compound was obtained using 2-carbamoyl-4-[(6-chloronaphthalen-2-yl)sulfonyl]-1-[(4,5,6,7-tetrahydrothiazolo[5,4-c]pyridin-2-yl)carbonyl]piperazine trifluoroacetate as a starting material.

$^1$H-NMR (DMSO-d$_6$) δ: 2.37–2.70(2H,m), 2.91(3H,s), 3.00–3.78(6H,m), 4.28–4.77(⅞H,m), 4.97(½H,br s), 5.40–5.50(½H,m), 6.14(½H,br s), 7.32–7.40(1H,m), 7.68–7.75(2H,m), 7.77–7.83(1H,m), 8.15(1H,d,J=8.8 Hz), 8.21–8.28(2H,m), 8.49(1H,s). MS (FAB) m/z: 534 [(M+H)$^+$, Cl$^{35}$], 536 [(M+H)$^+$, Cl$^{37}$]. Elementary analysis for C$_{23}$H$_{24}$ClN$_5$O$_4$S$_2$·HCl·2.5H$_2$O Calculated: C, 44.88; H, 4.91; Cl, 11.52; N, 11.38; S, 10.42. Found: C, 44.83; H, 4.89; Cl, 11.65; N, 11.31; S, 10.46.

Example B-37

1-[(6-Chloronaphthalen-2-yl)sulfonyl]-4-[[6-(2-hydroxyethyl)-4,5,6,7-tetrahydrothiazolo[5,4-c] pyridin-2-yl]carbonyl]piperazine hydrochloride The crude product, which had been obtained by the reaction in the same manner as in Example B-32 by using 1-[(6-chloronaphthalen-2-yl)sulfonyl]-4-[(4,5,6,7-tetrahydrothiazolo[5,4-c]pyridin-2-yl)carbonyl]piperazine hydrochloride (132 mg) and glyoxylic hydrate (82 mg) as starting materials, was suspended in tetrahydrofuran (50 ml). Triethylamine (0.22 ml) and ethyl chloroformate (0.03 ml) were added to the resulting suspension under ice cooling, followed by stirring at room temperature for 15 minutes. To the reaction mixture, sodium borohydride (50 mg) and water (10 ml) were added to the reaction mixture and the resulting mixture was stirred at room temperature for 1 hour. The reaction mixture was concentrated under reduced pressure. The residue was diluted with dichloromethane, washed with saturated aqueous NaCl solution and dried over anhydrous sodium sulfate. The residue obtained by distilling off the solvent under reduced pressure was purified by chromatography on a silica gel column (dichloromethane~dichloromethane:methanol 100:3), followed by dissolution in saturated hydrochloride in ethanol (1 ml). The resulting solution was then concentrated under reduced pressure. The concentrate was pulverized and washed in ethyl acetate, whereby the title compound (52 mg, 33%) was obtained.

$^1$H-NMR (DMSO-d$_6$) δ: 3.11(4H,br s), 3.20–3.57(6H,m), 3.69–3.87(4H,m), 4.34–4.82(4H,m), 5.38(1H,br s), 7.71 (1H,dd,J=8.8,2.0 Hz), 7.82(1H,dd,J=8.8,2.0 Hz), 8.15(1H, d,J=8.8 Hz), 8.22(1H,s), 8.25(1H,d,J=8.8 Hz), 8.50(1H,s), 10.48(1H,br s). MS (FAB) m/z: 521 [(M+H)$^+$, Cl$^{35}$], 523 [(M+H)$^+$, Cl$^{37}$].

In the same manner as in Example B-32, the compounds of Examples B-38, B-39 and B-40 were obtained, respectively by using 1-[(6-chloronaphthalen-2-yl)sulfonyl]-4-[(4,5,6,7-tetrahydrothiazolo[5,4-c]pyridin-2-yl)carbonyl] piperazine hydrochloride as a starting material.

Example B-38

1-[(6-Chloronaphthalen-2-yl)sulfonyl]-4-[[6-(pyridin-2-yl)methyl-4,5,6,7-tetrahydrothiazolo[5,4-c]pyridin-2-yl]carbonyl]piperazine hydrochloride $^1$H-NMR (DMSO-d$_6$) δ: 3.07–3.17(6H,m), 3.63(2H,t,J= 6.3 Hz), 3.74(2H,br s), 4.39(2H,br s), 4.58(2H,s), 4.61(2H, s), 7.50–7.64(1H,m), 7.67–7.73(2H,m), 7.82(1H,dd,J=8.8, 1.5 Hz), 7.97(1H,m), 8.15(1H,d,J=8.8 Hz), 8.22(1H,d,J=1.5 Hz), 8.25(1H,d,J=8.8 Hz), 8.50(1H,s), 8.69(1H,d,J=4.9 Hz). MS (FAB) m/z: 568 [(M+H)$^+$, Cl$^{35}$], 570 [(M+H)$^+$, Cl$^{37}$]. Elementary analysis for C$_{27}$H$_{26}$ClN$_5$O$_3$S$_2$·2HCl·0.8H$_2$O Calculated: C, 49.48; H, 4.55; Cl, 16.23; N, 10.68; S, 9.78. Found: C, 49.72; H, 4.48; Cl, 16.31; N, 10.86; S, 9.53.

Example B-39

1-[(6-Chloronaphthalen-2-yl)sulfonyl]-4-[[6-(pyridin-3-yl)methyl-4,5,6,7-tetrahydrothiazolo[5,4-c]pyridin-2-yl]carbonyl]piperazine hydrochloride $^1$H-NMR (DMSO-$d_6$) δ: 3.03–3.27(6H,m), 3.40–3.81 (4H,m), 3.74(2H,br s), 4.40(2H,br s), 4.50(2H,s), 4.70(2H, s), 7.70(1H,dd,J=8.8,2.4 Hz), 7.82(1H,d,J=8.8 Hz), 8.15 (1H,d,J=8.8 Hz), 8.22(1H,s), 8.25(1H,d,J=8.8 Hz), 8.50(1H, s), 8.73(1H,d,J=7.8 Hz), 8.93(1H,d,J=4.4 Hz). MS (FAB) m/z: 568 [(M+H)$^+$, Cl$^{35}$], 570 [(M+H)$^+$, Cl$^{37}$]. Elementary analysis for $C_{27}H_{26}ClN_5O_3S_2$·2.9HCl·4.5H$_2$O Calculated: C, 42.96; H, 5.06; Cl, 18.32; N, 9.28. Found: C, 42.97; H, 4.84; Cl, 18.19; N, 9.23.

Example B-40

1-[(6-Chloronaphthalen-2-yl)sulfonyl]-4-[[6-(pyridin-4-yl)methyl-4,5,6,7-tetrahydrothiazolo[5,4-c]pyridin-2-yl]carbonyl]piperazine hydrochloride $^1$H-NMR (DMSO-$d_6$) δ: 3.11(4H,br s), 3.19(2H,br s), 3.64(2H,br s), 3.74(2H,br s), 4.41(2H,br s), 4.49(2H,s), 4.80(2H,s), 7.69(1H,dd,J=8.8,2.0 Hz), 7.82(1H,dd,J=8.8,2.0 Hz), 8.15(1H,d,J=8.8 Hz), 8.21(1H,d,J=2.0 Hz), 8.25(1H,d, J=8.8 Hz), 8.41(2H,d,J=6.3 Hz), 8.50(1H,s), 9.04(2H,d,J= 6.3 Hz). MS (FAB) m/z: 568 [(M+H)$^+$, Cl$^{35}$], 570 ((M+H)$^+$, Cl$^{37}$]. Elementary analysis for $C_{27}H_{26}ClN_5O_3S_2$·2.7HCl·6.0H$_2$O Calculated: C, 41.86; H, 5.30; Cl, 16.93; N, 9.04; S, 8.28. Found: C, 42.05; H, 4.98; Cl, 16.92; N, 9.37; S, 8.61.

Example B-41

1-[(E)-4-Chlorostyrylsulfonyl]-4-[(4,5,6,7-tetrahydrothiazolo[5,4-c]pyridin-2-yl)carbonyl]piperazine hydrochloride In the same manner as in Example B-1, the title compound was obtained using 1-[(6-tert-butoxycarbonyl-4,5,6,7-tetrahydrothiazolo[5,4-c]pyridin-2-yl)carbonyl]-4-[(E)-4-chlorostyrylsulfonyl]piperazine as a starting material.

$^1$H-NMR (DMSO-$d_6$) δ: 3.04(2H,br s), 3.23(4H,br), 3.47 (2H,br s), 3.77(2H,br s), 4.35–4.50(2H,m), 7.33(1H,d,J= 15.6 Hz), 7.43(1H,d,J=15.6 Hz), 7.49(1H,d,J=8.3 Hz), 7.79 (1H,d,J=8.3 Hz), 9.57(2H,br s). MS (FAB) m/z: 453 [(M+H)$^+$, Cl$^{35}$], 455 [(M+H)$^+$, Cl$^{37}$]. Elementary analysis for $C_{19}H_{21}ClN_4O_3S_2$·HCl·0.3H$_2$O Calculated: C, 46.12; H, 4.60; Cl, 14.33; N, 11.32; S, 12.96. Found: C, 46.42; H, 4.66; Cl, 14.38; N, 11.02; S, 13.02.

Example B-42

1-[(E)-4-Chlorostyrylsulfonyl]-4-[6-methyl-4,5,6,7-tetrahydrothiazolo[5,4-c]pyridin-2-yl)carbonyl]piperazine hydrochloride In the same manner as in Example B-32, the title compound was obtained using 1-[(E)-4-chlorostyrylsulfonyl]-4-[(4,5,6,7-tetrahydrothiazolo[5,4-c]pyridin-2-yl)carbonyl]piperazine hydrochloride as a starting material.

$^1$H-NMR (DMSO-$d_6$) δ: 2.92(3H,s), 3.01–3.32(6H,br), 3.35–3.88(4H,m), 4.29–4.84(4H,m), 7.33(1H,d,J=15.6 Hz), 7.49(1H,d,J=15.6 Hz), 7.49(1H,d,J=8.3 Hz), 7.79(1H,d,J= 8.3 Hz), 11.31(1H,br s). MS (FAB) m/z: 467 [(M+H)$^+$, Cl$^{35}$], 469 [(M+H)$^+$, Cl$^{37}$]. Elementary analysis for $C_{20}H_{23}ClN_4O_3S_2$·HCl·0.2H$_2$O Calculated: C, 47.37; H, 4.85; Cl, 13.98; N, 11.05; S, 12.65. Found: C, 47.30; H, 4.92; Cl, 14.05; N, 11.03; S, 12.49.

Example B-43

(3S)-3-[(6-Chloronaphthalen-2-yl)sulfonamido]-1-[(4,5,6,7-tetrahydrothieno[3,2-c]pyridin-2-yl)methyl]pyrrolidine hydrochloride In the same manner as in Example B-1, the title compound was obtained using (3S)-1-[(5-tert-butoxycarbonyl-4,5,6,7-terahydrothieno[3,2-c]pyridin-2-yl)methyl]-3-[(6-chloronaphthalen-2-yl)sulfonamido]pyrrolidine as a starting material.

$[α]_D$=−69.72° (25° C., c=1.00, CH$_3$OH). $^1$H-NMR (DMSO-$d_6$ at 100° C.) δ: 1.88–1.89(1H,m), 2.10–2.25(1H, m), 3.02–3.07(2H,m), 3.10–3.50(6H,m), 4.02(1H,s), 4.12 (2H,s), 4.45(2H,s), 7.12(1H,s), 7.65(1H,d,J=8.3 Hz), 7.91 (1H,d,J=8.3 Hz), 8.10(1H,d,J=8.3 Hz), 8.14(1H,s), 8.16(1H, d,J=8.3 Hz), 8.18(1H,br s), 8.48(1H,s), 9.65(2H,br s). MS (FD) m/z: 461 (M$^+$, Cl$^{35}$), 463 (M$^+$, Cl$^{37}$). Elementary analysis for $C_{22}H_{24}ClN_3O_2S_2$·2.1HCl·H$_2$O Calculated: C, 47.47; H, 5.09; Cl, 19.74; N, 7.55; S, 11.52. Found: C, 47.55; H, 5.13; Cl, 19.85; N, 7.45; S, 11.48.

Example B-44

(3S)-3-[(6-Chloronaphthalen-2-yl)sulfonamido]-1-[(4,5,6,7-tetrahydrothieno[3,2-c]pyridin-2-yl)carbonyl]pyrrolidine hydrochloride In the same manner as in Example B-1, the title compound was obtained using (3S)-1-[(5-tert-butoxycarbonyl-4,5,6,7-tetrahydrothieno[3,2-c]pyridin-2-yl)carbonyl]-3-[(6-chloronaphthalen-2-yl)sulfonamido]pyrrolidine as a starting material.

$[α]_D$=−62.70° (25° C., c=1.00, CH$_3$OH). $^1$H-NMR (DMSO-$d_6$ at 100° C.) δ: 1.82–1.90(1H,m), 1.96–2.05(1H, m), 3.05(2H,t,J=6.0 Hz), 3.42–3.57(2H,m), 3.60–3.72(2H, m), 3.84–3.90(1H,m), 4.12(2H,s), 4.45(2H,s), 7.25(1H,s), 7.64(1H,dd,J=8.3,1.6 Hz), 7.90(1H,dd,J=8.3,1.6 Hz), 7.97 (1H,d,J=5.6 Hz), 8.08(1H,d,J=8.7 Hz), 8.12(1H,s), 8.14(1H, d,J=8.7 Hz), 8.47(1H,s), 9.55(2H,br s). MS (FAB) m/z: 476 [(M+H)$^+$, Cl$^{35}$], 478 [(M+H)$^+$, Cl$^{37}$]. Elementary analysis for $C_{22}H_{22}ClN_3O_3S_2$·HCl Calculated: C, 51.56; H, 4.52; Cl, 13.84; N, 8.20; S, 12.51. Found: C, 51.25; H, 4.61; Cl, 13.68; N, 7.98; S, 12.36.

Example B-45

(3S)-1-[(6-Chloronaphthalen-2-yl)sulfonyl]-3-[[(4,5,6,7-tetrahydrothieno[3,2-c]pyridin-2-yl)methyl]amino]pyrrolidine hydrochloride In the same manner as in Example B-1, the title compound was obtained using (3S)-3-[[(5-tert-butoxycarbonyl-4,5,6,7-tetrahydrothieno[3,2-c]pyridin-2-yl)methyl]amino]-1-[(6-chloronaphthalen-2-yl)sulfonyl]pyrrolidine as a starting material.

$[α]_D$=+34.82° (25° C., c=1.00, CH$_3$OH). $^1$H-NMR (DMSO-$d_6$) δ: 1.98–2.20(2H,m), 2.99–3.04(2H,m), 3.19–3.26(1H,m), 3.30–3.50(3H,m), 3.61–3.72(1H,m), 3.52–3.60(1H,m), 4.13(2H,s), 4.29(2H,s), 7.09(1H,s), 7.71 (1H,dd,J=8.8,2.0 Hz), 7.89(1H,dd,J=8.8,2.0 Hz), 8.17(1H, d,J=8.8 Hz), 8.25(1H,d,J=2.0 Hz), 8.30(1H,s), 8.57(1H,s), 9.55(2H,br s), 9.7–10.0(1H,m). MS (FD) m/z: 461 (M$^+$, Cl$^{35}$), 463 (M$^+$, Cl$^{37}$). Elementary analysis for $C_{22}H_{24}ClN_3O_2S_2 \cdot 2HCl \cdot 0.2H_2O$ Calculated: C, 49.06; H, 4.94; Cl, 19.75; N, 7.80; S, 11.91. Found: C, 48.88; H, 4.97; Cl, 19.65; N, 7.67; S, 11.84.

Example B-46

(3S)-3-[(4,5,6,7-Tetrahydrothieno[3,2-c]pyridin-2-yl)carbonylamino]-1-[(6-chloronaphthalen-2-yl)sulfonyl]pyrrolidine hydrochloride In the same manner as in Example B-1, the title compound was obtained using (3S)-3-[(5-tert-butoxycarbonyl-4,5,6,7-tetrahydrothieno[3,2-c]pyridin-2-yl)carbonylamino]-1-[(6-chloronaphthalen-2-yl)sulfonyl]pyrrolidine as a starting material.

$[\alpha]_D = +33.56°$ (25° C., c=1.00, $CH_3OH$). $^1$H-NMR (DMSO-$d_6$) δ: 1.85–1.95(1H,m), 1.95–2.05(1H,m), 3.04 (2H,m), 3.24–3.40(1H,m), 3.41–3.53(3H,m), 4.04–4.24(3H, m), 7.34(1H,s), 7.67(1H,d,J=8.8 Hz), 7.84(1H,d,J=8.8 Hz), 8.03(1H,d,J=8.8 Hz), 8.17(1H,s), 8.22(1H,d,J=8.8 Hz), 8.27 (1H,d,J=5.7 Hz), 8.50(1H,s), 9.59(1H,br s), 9.71(1H,br s). MS (FD) m/z: 476 [(M+H)$^+$, $Cl^{35}$], 478 [(M+H)$^+$, $Cl^{37}$].

Example B-47

1-[(6-Chloronaphthalen-2-yl)sulfonyl]-4-[(4,5,6,7-tetrahydrothieno[3,2-c]pyridin-2-yl)carbonyl]homopiperazine hydrochloride In the same manner as in Example B-1, the title compound was obtained using 1-[(5-tert-butoxycarbonyl-4,5,6,7-tetrahydrothieno[3,2-c]pyridin-2-yl)carbonyl]-4-[(6-chloronaphthalen-2-yl)sulfonyl]homopiperazine as a starting material.

$^1$H-NMR (DMSO-$d_6$) δ: 1.83(2H,br s), 3.04(2H,t,J=5.4 Hz), 3.30–3.59(6H,m), 3.60–3.88(4H,m), 4.14(2H,s), 7.20 (1H,br s), 7.69(1H,dd,J=8.8,2.0 Hz), 7.84(1H,d,J=8.8 Hz), 8.10(1H,d,J=8.8 Hz), 8.17–8.21(2H,m), 8.50(1H,s), 9.57 (2H,br s). MS (FAB) m/z: 490 [(M+H)$^+$, $Cl^{35}$], 492 [(M+H)$^+$, $Cl^{37}$]. Elementary analysis for $C_{23}H_{25}ClN_3O_3S_2 \cdot 1.1HCl \cdot 0.2H_2O$ Calculated: C, 51.66; H, 4.99; Cl, 13.92; N, 7.86. Found: C, 51.46; H, 4.61; Cl, 13.55; N, 8.05.

Example B-48

4-[(6-Chloronaphthalen-2-yl)sulfonamido]-1-[(4,5,6,7-tetrahydrothieno[3,2-c]pyridin-2-yl)carbonyl]piperidine hydrochloride In the same manner as in Examples B-7 and B-1, the title compound was obtained using 5-tert-butoxycarbonyl-4,5,6,7-tetrahydrothieno[3,2-c]pyridin-2-carboxylic acid (WO94/21599) and 4-[(6-chloronaphthalen-2-yl)sulfonamido]piperidine trifluoroacetate as starting materials.

$^1$H-NMR (DMSO-$d_6$) δ: 1.26–1.38(2H,m), 1.58–1.65 (2H,m), 2.93–3.13(4H,m), 3.29–3.40(3H,m), 3.90–4.05(2H, m), 4.11(2H,s), 7.16(1H,s), 7.68(1H,dd,J=8.0,2.0 Hz), 7.92 (1H,dd,J=8.8,2.0 Hz), 8.07(1H,d,J=7.3 Hz), 8.13(2H,d,J= 8.8 Hz), 8.20(1H,d,J=7.3 Hz), 8.23(1H,s), 8.51(1H,s), 9.71 (2H,br s). MS (FAB) m/z: 490 [(M+H)$^+$, $Cl^{35}$], 492 [(M+H)$^+$, $Cl^{37}$]. Elementary analysis for $C_{23}H_{25}ClN_3O_3S_2 \cdot 2.4HCl \cdot 3H_2O$ Calculated: C, 43.67; H, 5.32; Cl, 19.05; N, 6.64. Found: C, 43.85; H, 5.10; Cl, 19.07; N, 6.63.

Example B-49

1-[(6-Chloronaphthalen-2-yl)sulfonyl]-4-[(6-aminohydroxyiminomethylbenzofuran-2-yl)carbonyl]piperazine In the same manner as in Example B-24, the title compound was obtained using 1-[(6-chloronaphthalen-2-yl)sulfonyl]-4-[(6-cyanobenzofuran-2-yl)carbonyl]piperazine as a starting material.

$^1$H-NMR (DMSO-$d_6$) δ: 3.11(4H,s), 3.83(4H,br), 5.90 (2H,br s), 7.34(1H,s), 7.64–7.75(3H,m), 7.83(1H,dd,J=8.8, 2.0 Hz), 7.89(1H,s), 8.17(1H,d,J=8.8 Hz), 8.23(1H,d,J=1.5 Hz), 8.26(1H,d,J=8.8 Hz), 8.51(1H,s), 9.77(1H,s). MS (FAB) m/z: 513 [(M+H)$^+$, $Cl^{35}$], 515 [(M+H)$^+$, $Cl^{37}$]. Elementary analysis for $C_{24}H_{21}ClN_4O_5S \cdot \frac{1}{3}H_2O$ Calculated: C, 55.80; H, 4.18; Cl, 6.86; N, 10.70; S, 6.21. Found: C, 55.65; H, 4.25; Cl, 6.81; N, 10.70; S, 6.37.

Example B-50

1-[(6-Chloronaphthalen-2-yl)sulfonyl]-4-[(5-aminohydroxyiminomethylbenzothiophen-2-yl)carbonyl]piperazine In the same manner as in Example B-24, the title compound was obtained using 1-[(6-chloronaphthalen-2-yl)sulfonyl]-4-[(5-cyanobenzothiophen-2-yl)carbonyl]piperazine as a starting material.

$^1$H-NMR (DMSO-$d_6$) δ: 3.11(4H,s), 3.77(4H,s), 5.87(2H, br s), 7.67(1H,s), 7.71(1H,d,J=2.0 Hz), 7.75(1H,d,J=8.8 Hz), 7.83(1H,dd,J=8.8,2.0 Hz), 7.94(1H,d,J=8.8 Hz), 8.15 (1H,s), 8.17(1H,d,J=8.8 Hz), 8.25(1H,d,J=8.8 Hz), 8.29(1H, d,J=8.3 Hz), 8.50(1H,s), 9.68(1H,s). MS (FAB) m/z: 529 [(M+H)$^+$, $Cl^{35}$], 531 [(M+H)$^+$, $Cl^{37}$]. Elementary analysis for $C_{24}H_{21}N_4ClO_4S_2 \cdot 0.3H_2O$ Calculated: C, 53.94; H, 4.07; N, 10.48. Found: C, 54.22; H, 4.17; N, 10.23.

Example B-51

1-[(6-Chloronaphthalen-2-yl)sulfonyl]-4-[(1,2,3,4-tetrahydroisoquinolin-6-yl)carbonyl]piperazine hydrochloride In the same manner as in Example B-1, the title compound was obtained using 1-[(2-tert-butoxycarbonyl-1,2,3,4-tetrahydroisoquinolin-6-yl)carbonyl]-4-[(6-chloronaphthalen-2-yl)sulfonyl]piperazine as a starting material.

$^1$H-NMR (DMSO-$d_6$) δ: 2.89–3.29(4H,m), 3.20–3.83 (8H,m), 4.25(2H,s), 7.10–7.25(3H,m), 7.71(1H,d,J=8.3 Hz), 7.81(1H,d,J=8.3 Hz), 8.17(1H,d,J=8.8 Hz), 8.15–8.25(2H, m), 8.49(1H,s), 9.54(2H,br s). MS (FAB) m/z: 470 [(M+H)$^+$, $Cl^{35}$], 472 [(M+H)$^+$, $Cl^{37}$]. Elementary analysis for $C_{24}H_{24}ClN_3O_3S \cdot HCl \cdot 2.0H_2O$ Calculated: C, 53.14; H, 5.39; Cl, 13.07; N, 7.75; S, 5.91. Found: C, 53.43; H, 5.43; Cl, 13.15; N, 8.07; S, 5.55.

Example B-52

1-[(6-Chloronaphthalen-2-yl)sulfonyl]-4-[(2-methyl-1,2,3,4-tetrahydroisoquinolin-6-yl)carbonyl]piperazine hydrochloride In the same manner as in Example B-32, the title compound was obtained using 1-[(6-chloronaphthalen-2-yl)sulfonyl]-4-[(1,2,3,4-tetrahydroisoquinolin-6-yl)carbonyl]piperazine hydrochloride as a starting material.

$^1$H-NMR (DMSO-$d_6$) δ: 2.88(3H,s), 2.90–3.80(13H,m), 4.12–4.56(1H,m), 7.19(1H,s), 7.20(2H,d,J=6.8 Hz), 7.72 (1H,dd,J=8.8,2.0 Hz), 7.81(1H,d,J=8.8 Hz), 8.17(1H,d,J= 8.8 Hz), 8.24–8.28(2H,m), 8.49(1H,s), 10.93(1H,br s). MS (FAB) m/z: 484 [(M+H)$^+$, $Cl^{35}$], 486 [(M+H)$^+$, $Cl^{37}$]. Elementary analysis for $C_{24}H_{24}ClN_3O_3S \cdot HCl \cdot 2.3H_2O$ Calculated: C, 53.44; H, 5.67; Cl, 12.62; N, 7.48; S, 5.71. Found: C, 53.71; H, 5.81; Cl, 12.37; N, 7.26; S, 5.62.

Example B-53

6-[[4-[(6-Chloronaphthalen-2-yl)sulfonyl]piperazin-1-yl]carbonyl]-2,2-dimethyl-1,2,3,4-tetrahydroisoquinolinium iodide In the same manner as in Example B-33, the title compound was obtained using 1-[(6-chloronaphthalen-2-yl)sulfonyl]-4-[(2-methyl-1,2,3,4-tetrahydroisoquinolin-6-yl)carbonyl]piperazine hydrochloride as a starting material.

$^1$H-NMR (DMSO-d$_6$) δ: 2.90–3.85(18H,m), 4.61(2H,s), 7.19(1H,d,J=7.8 Hz), 7.24(1H,d,J=7.8 Hz), 7.28(1H,s), 7.72 (1H,dd,J=8.8,1.5 Hz), 7.81(1H,d,J=8.8 Hz), 8.17(1H,d,J= 8.8 Hz), 8.20–8.31(2H,m), 8.50(1H,s). Elementary analysis for C$_{26}$H$_{29}$ClIN$_3$O$_3$S.H$_2$O Calculated: C, 48.49; H, 4.85; N, 6.53. Found: C, 48.66; H, 4.96; N, 6.39.

Example B-54

1-[(5-Chloroindol-2-yl)sulfonyl]-4-[(6-methyl-4,5,6,7-tetrahydrothiazolo[5,4-c]pyridin-2-yl)carbonyl]piperazine hydrochloride A reaction was effected in the same manner as in Example B-7 by using 1-[(5-chloroindol-2-yl)sulfonyl]piperazine and lithium 6-methyl-4,5,6,7-tetrahydrothiazolo[5,4-c]pyridin-2-carboxylate as starting materials, whereby the title compound was obtained as brown amorphous.

$^1$H-NMR (CDCl$_3$) δ: 2.49(3H,s), 2.78–2.83(2H,m), 2.85–2.94(2H,m), 3.15–3.28(4H,br), 3.67(2H,s), 3.82–3.95 (2H,br), 4.50–4.65(2H,br), 6.96(1H,d,J=2.0 Hz), 7.32(1H, dd,J=8.8,2.0 Hz), 7.36(1H,d,J=8.8 Hz), 7.67(1H,s), 8.71 (1H,br). MS (FAB) m/z: 480 [(M+H)$^+$, Cl$^{35}$], 482 [(M+H)$^+$, Cl$^{37}$]. Elementary analysis for C$_{20}$H$_{22}$ClN$_5$O$_3$S$_2$.HCl.0.5H$_2$O Calculated: C, 44.64; H, 4.76; Cl, 13.18; N, 13.02; S, 11.92. Found: C, 44.69; H, 4.72; Cl, 13.36; N, 12.76; S, 11.76.

In a similar manner to Example B-54, the compounds shown in Examples B-55 to B-60 were synthesized.

Example B-55

4-[(5-Chloroindol-2-yl)sulfonyl]-2-(N-methylcarbamoyl)-1-[(6-methyl-4,5,6,7-tetrahydrothiazolo[5,4-c]pyridin-2-yl)carbonyl]piperazine hydrochloride $^1$H-NMR (DMSO-d$_6$) δ: 2.50–2.63(3H,m), 2.65–2.74 (2H,m), 2.92(3H,s), 3.00–3.14(2H,m), 3.22–3.42(2H,m), 3.63–3.78(2H,m), 4.23–4.29(1H,m), 4.35–4.47(1H,m), 4.64–4.80(1H,m), 4.97–5.02(½H,m), 5.45–5.51(1H,m), 6.13–6.17(½H,m), 7.02(1H,br), 7.32(1H,dd,J=8.8,2.0 Hz), 7.47(1H,d,J=8.3 Hz), 7.77(1H,br), 8.07–8.16(1H,m), 12.41 (1H,s). MS (FAB) m/z: 537 [(M+H)$^+$, Cl$^{35}$], 539 [(M+H)$^+$, Cl$^{37}$]. Elementary analysis for C$_{22}$H$_{25}$ClN$_6$O$_4$S$_2$.HCl.1.7H$_2$O Calculated: C, 43.74; H, 4.90; Cl, 11.74; N, 13.91; S, 10.62. Found: C, 44.02; H, 5.07; Cl, 11.83; N, 13.59; S, 10.52.

Example B-56

4-[(5-Chloroindol-2-yl)sulfonyl]-2-(N-methylcarbamoyl)-1-[(6-methyl-4,5,6,7-tetrahydrothieno[2,3-c]pyridin-2-yl)carbonyl]piperazine hydrochloride $^1$H-NMR (DMSO-d$_6$) δ: 2.65(3H,d,J=4.5 Hz), 2.85–3.22 (7H,m), 3.22–3.38(2H,m), 3.66(1H,d,J=12.2 Hz), 3.55–3.68 (2H,m), 4.17–4.40(3H,m), 4.55–4.68(1H,m), 6.99(1H,d,J= 2.0 Hz), 7.27–7.31(2H,m), 7.48(1H,d,J=8.8 Hz), 7.77(1H, d,J=2.0 Hz), 8.09(1H,br s), 10.60(1H,br s), 12.41(1H,s). MS (FAB) m/z: 536 [(M+H)$^+$, Cl$^{35}$], 538 [(M+H)$^+$, Cl$^{37}$]. Elementary analysis for C$_{23}$H$_{26}$ClN$_5$O$_4$S$_2$.1.3HCl.0.6H$_2$O.1.5EtOH Calculated: C, 47.07; H, 5.70; Cl, 12.29; N, 10.56; S, 9.67. Found: C, 46.68; H, 5.63; Cl, 12.16; N, 10.20; S, 10.06.

Example B-57

1-[(5-Chlorobenzo[b]furan-2-yl)sulfonyl]-4-[(6-methyl-4,5,6,7-tetrahydrothiazolo[5,4-c]pyridin-2-yl)carbonyl]piperazine $^1$H-NMR (DMSO-d$_6$) δ: 2.91(3H,s), 3.11(2H,br), 3.25–3.90(4H,m), 3.76(2H,br), 5.35–4.80(2H,br), 4.41(2H, br), 7.46(1H,d,J=8.8 Hz), 7.73(1H,s), 7.84(1H,d,J=8.8 Hz), 7.96(1H,s), 11.48(1H,br). MS (FAB) m/z: 481 [(M+H)$^+$, Cl$^{35}$], 483 [(M+H)$^+$, Cl$^{37}$]. Elementary analysis for C$_{20}$H$_{21}$ClN$_4$O$_4$S$_2$.1.1HCl.0.3H$_2$O Calculated: C, 45.63; H, 4.35; Cl, 14.14; N, 10.64; S, 12.18. Found: C, 45.81; H, 4.29; Cl, 13.93; N, 10.44; S, 12.26.

Example B-58

1-[(6-Chlorobenzo[b]furan-2-yl)sulfonyl]-4-[(6-methyl-4,5,6,7-tetrahydrothiazolo[5,4-c]pyridin-2-yl)carbonyl]piperazine $^1$H-NMR (DMSO-d$_6$) δ: 2.91(3H,s), 3.00–3.55(7H,m), 3.60–3.85(3H,m), 4.42(3H,br), 4.67(1H,br), 7.46(1H,d,J= 8.8 Hz), 7.73(1H,s), 7.84(1H,d,J=8.8 Hz), 7.96(1H,s), 11.48 (1H,br). MS (FAB) m/z: 481 [(M+H)$^+$, Cl$^{35}$], 483 [(M+H)$^+$, Cl$^{37}$]. Elementary analysis for C$_{20}$H$_{21}$ClN$_4$O$_4$S$_2$.HCl.0.17H$_2$O Calculated: C, 46.15; H, 4.33; Cl, 13.62; N, 10.76; S, 12.32. Found: C, 46.45; H, 4.41; Cl, 13.61; N, 10.58; S, 12.02.

Example B-59

1-[(5-Chlorobenzo[b]thien-2-yl)sulfonyl]-4-[(6-methyl-4,5,6,7-tetrahydrothiazolo[5,4-c]pyridin-2yl)carbonyl]piperazine hydrochloride $^1$H-NMR (DMSO-d$_6$) δ: 2.91(3H,s), 2.98–3.90(10H,m), 4.24–4.77(4H,m), 7.60(1H,d,J=8.8 Hz), 8.05(1H,s), 8.10–8.21(2H,m), 11.72(1H,br s). MS (FAB) m/z: 497 [(M+H)$^+$, Cl$^{35}$], 499 [(M+H)$^+$, Cl$^{37}$]. Elementary analysis for C$_{20}$H$_{21}$ClN$_4$O$_3$S$_3$.HCl.0.9H$_2$O Calculated: C, 43.70; H, 4.36; Cl, 12.90; N, 10.19; S, 17.50. Found: C, 43.82; H, 4.49; Cl, 13.27; N, 9.86; S, 17.32.

Example B-60

1-[(6-Chlorobenzo[b]thien-2-yl)sulfonyl]-4-[(6-methyl-4,5,6,7-tetrahydrothiazolo[5,4-c]pyridin-2-yl)carbonyl]piperazine hydrochloride $^1$H-NMR (DMSO-d$_6$) δ: 2.91(3H,s), 3.02–3.25(5H,m), 3.32–3.90(6H,m), 4.33–4.55(2H,m), 4.64–4.75(1H,m), 7.55 (1H,dd,J=8.8,2.0 Hz), 8.06(1H,d,J=8.8 Hz), 8.09(1H,s), 11.42(1H,br s). MS (FAB) m/z: 497 [(M+H)$^+$, Cl$^{35}$], 499 [(M+H)$^+$, Cl$^{37}$]. Elementary analysis for C$_{20}$H$_{21}$ClN4O$_3$S$_3$.1.1HCl.1.4H$_2$O Calculated: C, 42.71; H, 4.46; Cl, 13.24; N, 9.96; S, 17.11. Found: C, 42.49; H, 4.51; Cl, 13.01; N, 9.76; S, 16.95.

Example B-61

2-[4-[(6-Chloronaphthalen-2-yl)sulfonyl]piperazin-1-yl]carbonyl]-6-methylthiazolo[5,4-c]pyridinium iodide 1-[(6-Chloronaphthalen-2-yl)sulfonyl]-4-[(thiazolo[5,4-c]pyridin-2-yl)carbonyl]piperazine was treated and purified in the same manner as in Example B-33, whereby the title compound was obtained.

IR(KBr)cm$^{-1}$: 3016, 1631, 1450, 1432, 1344, 1328, 1276, 1267, 1162, 1135, 998, 727, 578. $^1$H-NMR (DMSO-d$_6$) δ: 3.10–3.23(4H,m), 3.85(2H,br s), 4.29(2H,br s), 4.48(3H,s), 7.70(1H,dd,J=8.8,2.0 Hz), 7.83(1H,d,J=8.8,2.0 Hz), 8.17 (1H,d,J=8.8 Hz), 8.23(1H,d,J=2.0 Hz), 8.26(1H,d,J=8.8 Hz), 8.52(1H,s), 8.71(1H,d,J=6.8 Hz), 8.98(1H,d,J=6.8,2.0 Hz), 9.92(1H,d, J=2.0 Hz). MS (FAB) m/z: 487 [M$^+$, Cl$^{35}$], 489 [M$^+$, Cl$^{37}$].

Example B-62

4-[(6-Chloronaphthalen-2-yl)sulfonyl]-2-[(N-methyl)carbamoyl]-1-[(6-methyl-4,5,6,7-tetrahydrothiazolo[5,4-c]pyridin-2-yl)carbonyl] piperazine hydrochloride In N,N-dimethylformamide (100 ml), lithium 6-methyl-4,5,6,7-tetrahydrothiazolo[5,4-c]pyridine-2-carboxylate (616 mg), 4-[(6-chloronaphthalen-2-yl)sulfonyl]-2-[(N-methyl) carbamoyl]piperazine trifluoroacetate (1.12 g), 1-hydroxybenzotriazole monohydrate (36 mg) and 1-(dimethylaminopropyl)-3-ethylcarbodiimide hydrochloride (579 mg) were dissolved and the resulting solution was stirred overnight at room temperature. The reaction mixture was concentrated under reduced pressure. Dichloromethane was then added to the residue, followed by washing with water. The organic layer was dried over anhydrous sodium sulfate and distilled under reduced pressure to remove the solvent. The residue was purified by chromatography on a silica gel column [Φ3.0×(1.5+8) cm, ethyl acetate:methanol=100:4], whereby a colorless foam was obtained. The resulting foam was dissolved in 1N HCl (20 ml), followed by concentration under reduced pressure, whereby the title compound (845 mg) was obtained as a pale yellow foam.

IR(KBr)cm$^{-1}$: 3380, 1668, 1623, 1542, 1415, 1342, 1330, 1159, 1135, 1078, 952, 941, 723, 578. $^1$H-NMR (DMSO-d$_6$) δ: 2.42–2.80(5H,m), 2.90(3H,s), 2.95–3.80(6H,m), 4.23–4.50(5/2H,m), 4.60–4.77(1H,m), 4.98(½H,br s), 5.45–5.55(1H,m), 6.15(½H,br s), 7.71(1H,d,J=8.8 Hz), 7.78–7.82(1H,m), 8.07–8.13(1H,m), 8.15(1H,d,J=8.8 Hz), 8.23(1H,s), 8.25(1H,d,J=8.8 Hz), 8.49(1H,s), 11.70–12.00 (1H,m). MS (FAB) m/z: 548 [(M+H)$^+$, Cl$^{35}$], 550 [(M+H)$^+$, Cl$^{37}$].

In a similar manner to Example B-62, the compounds of Examples B-63 to B-76 were obtained.

Example B-63

4-[(6-Chloronaphthalen-2-yl)sulfonyl]-1-[(6-methyl-4,5,6,7-tetrahydrothiazolo[5,4-c]pyridin-2-yl) carbonyl]-2-[[(morpholin-4-yl)carbonyl]methyl] piperazine hydrochloride Starting materials: lithium 6-methyl-4,5,6,7-tetrahydrothiazolo[5,4-c]pyridine-2-carboxylate, 1-[(6-chloronaphthalen-2-yl)sulfonyl]-3-[[(morpholin-4-yl) carbonyl]methyl]piperazine hydrochloride $^1$H-NMR (DMSO-d$_6$) δ: 2.35–2.83(2H,m), 2.89(3H,s), 2.95–3.88(18H,m), 4.31–4.45(3/2H,m), 4.67(2H,d,J=15.1 Hz), 5.03(0.5H,br s), 5.37(0.5H,d,J=13.7 Hz), 5.79(½H,br s), 7.70(1H,dd,J=8.8,2.0 Hz), 7.81(1H,d,J=8.8 Hz), 8.15 (1H,d,J=8.8 Hz), 8.23(1H,s), 8.27(1H,d,J=8.8 Hz), 8.50(1H, s), 11.50–11.75(1H,m). MS (FAB) m/z: 618 [(M+H)$^+$, Cl$^{35}$], 620 [(M+H)$^+$, Cl$^{37}$]. Elementary analysis for C$_{28}$H$_{32}$ClN$_5$O$_5$S$_2$.1.5HCl.3H$_2$O Calculated: C, 46.27; H, 5.48; Cl, 12.19; N, 9.63; S, 8.82. Found: C, 46.49; H, 5.20; Cl, 12.16; N, 9.67; S, 8.88.

Example B-64

N-[[4-[(6-chloronaphthalen-2-yl)sulfonyl]-1-[(6-methyl-4,5,6,7-tetrahydrothiazolo[5,4-c]pyridin-2-yl)carbonyl]piperazin-2-yl]carbonyl]glycine ethyl ester Starting materials: lithium 6-methyl-4,5,6,7-tetrahydrothiazolo[5,4-c]pyridine-2-carboxylate, N-[[1-[(6-chloronaphthalen-2-yl)sulfonyl]piperazin-3-yl]carbonyl] glycine ethyl ester trifluoroacetate $^1$H-NMR (DMSO-d$_6$) δ: 1.17–1.24(3H,m), 2.38(3H,s), 2.39–2.53(1H,m), 2.58–2.84(5H,m), 3.20–3.29(1H,m), 3.54–3.81(4H,m), 3.90–4.00(1H,m), 4.06–4.17(1H,m), 4.32 (1H,d,J=11.7 Hz), 4.47(½H,d,J=13.7 Hz), 5.14(½H,s), 5.66 (½H,d,J=13.7 Hz), 6.42(1H,br s), 7.68(1H,d,J=8.3 Hz), 7.79 (1H,d,J=8.3 Hz), 8.12(1H,dd,J=8.8,3.4 Hz), 8.19(1H,s), 8.23(1H,d,J=8.8 Hz), 8.48(1H,s), 8.52(½H,t,J=5.4 Hz), 8.61 (½H,t,J=5.4 Hz). MS (FD) m/z: 619 [M$^+$, Cl$^{35}$], 621 [M$^+$, Cl$^{37}$]. Elementary analysis for C$_{27}$H$_{30}$ClN$_5$O$_6$S$_2$.0.2HCl.0.1H$_2$O Calculated: C, 51.54; H, 4.87; Cl, 6.76; N, 11.13; S, 10.19. Found: C, 51.31; H, 4.92; Cl, 6.74; N, 10.92; S, 10.01.

In the present reaction, the below-described compound whose ester bond had been hydrolyzed was obtained. N-[[4-[(6-Chloronaphthalen-2-yl)sulfonyl]-1-[(6-methyl-4, 5,6,7-tetrahydrothiazolo[5,4-c]pyridin-2-yl)carbonyl] piperazin-2-yl]carbonyl]glycine $^1$H-NMR (DMSO-d$_6$) δ: 2.37(3H,s), 2.59–2.83(6H,m), 3.20–3.32(1H,m), 3.52–3.77(4H,m), 3.82–3.95(1H,m), 4.28–4.35(1H,m), 4.45(½H,d,J=13.7 Hz), 5.13(½H,br s), 5.63(½H,d,J=13.7 Hz), 6.36(1H,br s), 7.69(1H,d,J=8.3 Hz), 7.80(1H,d,J=8.3 Hz), 8.12(1H,dd,J=8.8,3.4 Hz), 8.20(1H,s), 8.23(1H,d,J=8.8 Hz), 8.41(½H,t,J=5.4 Hz), 8.45–8.50(3/2H, m). MS (FD) m/z: 592 [(M+H)$^+$, Cl$^{35}$], 594 [(M+H)$^+$, Cl$^{37}$]. Elementary analysis for C$_{27}$H$_{30}$ClN$_5$O$_6$S$_2$.H$_2$O Calculated: C, 49.22; H, 4.63; Cl, 5.81; N, 11.48; S, 10.51. Found: C, 49.11; H, 4.78; Cl, 6.02; N, 11.41; S, 10.25.

Example B-65

4-[(6-Chloronaphthalen-2-yl)sulfonyl]-1-[(6-methyl-4,5,6,7-tetrahydrothiazolo[5,4-c]pyridin-2-yl) carbonyl]-2-[N-(morpholin-4-yl)carbamoyl] piperazine hydrochloride Starting materials: lithium 6-methyl-4,5,6,7-tetrahydrothiazolo[5,4-c]pyridine-2-carboxylate, 1-[(6-chloronaphthalen-2-yl)sulfonyl]-3-[N-(morpholin-4-yl) carbamoyl]piperazine trifluoroacetate $^1$H-NMR (DMSO-d$_6$ at 100° C.) δ: 2.58–2.84(8H,m), 2.89(3H,s), 2.98–3.58(3H,m), 3.40–3.80(8H,m), 4.10–4.70 (4H,m), 7.65(1H,dd,J=8.6,2.4 Hz), 7.79(1H,dd,J=8.6,1.2 Hz), 8.09(1H,d,J=8.6 Hz), 8.14(1H,s), 8.18(1H,d,J=8.6 Hz), 8.42(1H,s), 8.58(1H,br s). MS (FAB) m/z: 619 [(M+H)$^+$, Cl$^{35}$], 621 [(M+H)$^+$, Cl$^{37}$]. Elementary analysis for C$_{24}$H$_{26}$ClN$_4$O$_5$S$_2$.1.7HCl.1.7H$_2$O Calculated: C, 45.56; H, 5.11; Cl, 13.45; N, 10.57; S, 8.93. Found: C, 45.35; H, 5.34; Cl, 13.46; N, 12.01; S, 8.93.

Example B-66

Ethyl N'-[[4-[(6-chloronaphthalen-2-yl)sulfonyl]-1-[(6-methyl-4,5,6,7-tetrahydrothiazolo[5,4-c]pyridin-2-yl)carbonyl]piperazin-2-yl]carbonyl] hydrazinoacetate hydrochloride Starting materials: lithium 6-methyl-4,5,6,7-tetrahydrothiazolo[5,4-c]pyridine-2-carboxylate, ethyl N'-

[[1-[(6-chloronaphthalen-2-yl)sulfonyl]piperazin-3-yl]carbonyl]hydrazinoacetate hydrochloride $^{1}$H-NMR (DMSO-d$_{6}$) δ: 1.18–1.28(3H,m), 2.36(3H,s), 2.65–2.85(5H,m), 3.23–3.28(1H,m), 3.31(2H,s), 3.44–3.75(4H,m), 4.08–4.24(3H,m), 4.38(½H,d,J=13.7 Hz), 5.01(½H, s), 5.22–5.31(1H,m), 5.52(½H,d,J=13.7 Hz), 6.10(½H,br s), 7.69(1H,d,J=8.8,2.0 Hz), 7.72–7.80(1H,m), 7.72–7.80(3H, m), 8.47(1H,s), 9.77–9.85(1H,m). MS (FAB) m/z: 635 [(M+H)$^{+}$, Cl$^{35}$], 637 [(M+H)$^{+}$, Cl$^{37}$]. Elementary analysis for C$_{27}$H$_{31}$ClN$_{6}$O$_{6}$S$_{2}$·1.6HCl H$_{2}$O Calculated: C, 45.58; H, 4.90; Cl, 12.95; N, 11.81; S, 9.01. Found: C, 45.71; H, 5.09; Cl, 12.83; N, 11.46; S, 8.94.

Example B-67

4-[(6-Chloronaphthalen-2-yl)sulfonyl]-1-[(6-methyl-4,5,6,7-tetrahydrothiazolo[5,4-c]pyridin-2-yl)carbonyl]-2-[N-[[(morpholin-4-yl)carbonyl]methyl]carbamoyl]piperazine hydrochloride Starting materials : lithium 6-methyl-4,5,6,7-tetrahydrothiazolo[5,4-c]pyridine-2-carboxylate, 1-[(6-chloronaphthalen-2-yl)sulfonyl]-3-[N-[[(morpholin-4-yl)carbonyl]methyl]carbamoyl]piperazine hydrochloride $^{1}$H-NMR (DMSO-d$_{6}$) δ: 2.35–2.82(2H,m), 2.90(3H,s), 2.95–3.30(2H,m), 3.32–3.86(13H,m), 4.05–4.20(1H,m), 4.23–4.50(2.5H,m), 4.59–4.70(1H,m), 5.15(0.5H,s), 5.50(0.5H,d,J=12.2 Hz), 6.30(0.5H,s), 7.70(1H,dd,J=8.8,2.0 Hz), 7.80(1H,d,J=8.8 Hz), 8.12–8.38(4H,m), 8.48(1H,s), 11.45–11.75(1H,m). MS (FAB) m/z: 661 [(M+H)$^{+}$, Cl$^{35}$], 663 [(M+H)$^{+}$, Cl$^{37}$]. Elementary analysis for C$_{29}$H$_{33}$ClN$_{6}$O$_{6}$S$_{2}$·HCl·H$_{2}$O Calculated: C, 48.67; H, 5.07; Cl, 9.91; N, 11.74; S, 8.96. Found: C, 48.70; H, 5.03; Cl, 10.23; N, 11.55; S, 9.32.

Example B-68

4-[[4-[(6-Chloronaphthalen-2-yl)sulfonyl]-1-[(6-methyl-4,5,6,7-tetrahydrothiazolo[5,4-c]pyridin-2-yl)carbonyl]piperazin-2-yl]carbonyl]morpholine hydrochloride Starting materials: lithium 6-methyl-4,5,6,7-tetrahydrothiazolo[5,4-c]pyridine-2-carboxylate, 4-[[1-[(6-chloronaphthalen-2-yl)sulfonyl]piperazin-3-yl]carbonyl]morpholine trifluoroacetate IR(KBr)cm$^{-1}$: 3396, 2919, 2854, 1652, 1623, 1457, 1112, 954, 723, 578. $^{1}$H-NMR (DMSO-d$_{6}$) δ: 2.62–2.79(1H,m), 2.85–3.92(19H,m), 4.02–4.13(½H,m), 4.30–4.49(⅔H,m), 4.58–4.80(1H,m), 5.24–5.46(1H,m), 6.28–6.45(1H,m), 7.71(1H,dd,J=8.8,2.0 Hz), 7.83(1H,d,J=8.8 Hz), 8.12–8.28(3H, m), 8.53(1H,s), 11.30–11.80(1H,m). MS (FAB) m/z: 604 [(M+H)$^{+}$, Cl$^{35}$], 606 [(M+H)$^{+}$, Cl$^{37}$].

Example B-69

4-[(6-Chloronaphthalen-2-yl)sulfonyl]-2-(ethoxycarbonyl)-1-[(6-methyl-4,5,6,7-tetrahydrothiazolo[5,4-c]pyridin-2-yl)carbonyl]piperazine Starting materials: lithium 6-methyl-4,5,6,7-tetrahydrothiazolo[5,4-c]pyridine-2-carboxylate, 1-[(6-chloronaphthalen-2-yl)sulfonyl]-3-[ethoxycarbonyl]piperazine $^{1}$H-NMR (CDCl$_{3}$) δ: 1.25–1.35(3H,m), 2.43–2.94(9H, m), 3.31(½H,dt,J=12.7,3.4 Hz), 3.60–3.76(2.5H,m), 3.83(½H,d,J=11.7 Hz), 3.89(½H,d,J=11.7 Hz), 4.19–4.30(2H, m), 4.42–4.50(1H,m), 4.55(½H,14.2 Hz), 5.76(½H,14.2 Hz), 7.57(1H,dd,J=8.3,1.5 Hz), 7.77(1H,dd,J=8.3,1.5 Hz), 7.89–7.94(3H,m), 8.34(1H,s). MS (FAB) m/z: 563 [(M+H)$^{+}$, Cl$^{35}$], 565 [(M+H)$^{+}$, Cl$^{37}$].

Example B-70

Methyl [4-[(6-chloronaphthalen-2-yl)sulfonyl]-1-[(6-methyl-4,5,6,7-tetrahydrothiazolo[5,4-c]pyridin-2-yl)carbonyl]piperazin-2-yl]acetate Starting materials: lithium 6-methyl-4,5,6,7-tetrahydrothiazolo[5,4-c]pyridine-2-carboxylate, 1-[(6-chloronaphthalen-2-yl)sulfonyl]-3-[methoxycarbonylmethyl]piperazine IR(KBr)cm$^{-1}$: 2944, 2846, 2788, 1735, 1619, 1455, 1164. $^{1}$H-NMR (CDCl$_{3}$) δ: 2.40–2.92(10H,m), 3.04(1H,dd,J=16.1,8.8 Hz), 3.16–3.27(½H,m), 3.42–3.55(½H,m), 3.60–3.72(5H,m), 3.83–3.97(2H,m), 4.60(½H,d,J=13.2 Hz), 5.21(½H,br s), 5.70(½H,d,J=13.2 Hz), 6.15(½H,br s), 7.57(1H,dd,J=8.8,2.0 Hz), 7.75(1H,dd,J=8.8,2.0 Hz), 7.87–7.95(3H,m), 8.30(1H,s). MS (FAB) m/z: 563 [(M+H)$^{+}$, Cl$^{35}$], 565 [(M+H)$^{+}$, Cl$^{37}$].

Example B-71

2-[[N-(tert-butoxy)amino]carbonyl]-4-[(6-chloronaphthalen-2-yl)sulfonyl]-1-[(6-methyl-4,5,6,7-tetrahydrothiazolo[5,4-c]pyridin-2-yl)carbonyl]piperazine trifluoroacetate Starting materials: lithium 6-methyl-4,5,6,7-tetrahydrothiazolo[5,4-c]pyridine-2-carboxylate, 1-[(6-chloronaphthalen-2-yl)sulfonyl]-3-[(N-tert-butoxy)carbonyl]piperazine trifluoroacetate IR(KBr)cm$^{-1}$: 2979, 1675, 1465, 1199, 1184, 1166, 1135, 721. $^{1}$H-NMR (DMSO-d$_{6}$) δ: 1.15–1.25(9H,m), 2.36(3H,s), 2.37–2.49(1H,m), 2.67–2.84(5H,m), 3.25–3.35(1H,m), 3.59–3.78(3H,m), 4.13–4.25(1H,m), 4.38(1H,d,J=13.2 Hz), 5.01(½H,br s), 5.52(½H,d,J=13.2 Hz), 5.14(½H,s), 6.21(½H,br s), 7.69(1H,dd,J=8.8,2.0 Hz), 7.76–7.74(1H,m), 8.14(1H,d,J=8.8 Hz), 8.21(1H,s), 8.24(1H,d,J=8.8 Hz), 8.47–8.53(1H,m), 10.75–10.78(1H,m). MS (FAB) m/z: 606 [(M+H)$^{+}$, Cl$^{35}$], 608 [(M+H)$^{+}$, Cl$^{37}$].

Example B-72

[4-[(6-Chloronaphthalen-2-yl)sulfonyl]-1-[(6-methyl-4,5,6,7-tetrahydrothiazolo[5,4-c]pyridin-2-yl)carbonyl]piperazin-2-yl]acetamide hydrochloride Starting materials: lithium 6-methyl-4,5,6,7-tetrahydrothiazolo[5,4-c]pyridine-2-carboxylate, 1-[(6-chloronaphthalen-2-yl)sulfonyl]-3-[carbamoylmethyl]piperazine hydrochloride IR(KBr)cm$^{-1}$: 1671, 1616, 1465, 1457, 1419, 1332, 1162, 1133, 1124, 1078, 956, 701, 578. $^{1}$H-NMR (DMSO-d$_{6}$) δ: 2.30–2.80(4H,m), 2.90(3H,s), 2.93–3.25(2H,m), 3.30–3.55(1H,m), 3.62–3.88(3H,m), 4.05–4.43(2.5H,m), 4.60–4.71(1H,m), 5.05(0.5H,br s), 5.34(0.5H,d,J=13.2 Hz), 5.69–5.84(0.5H,m), 6.82(0.5H,br s), 6.93(0.5H,br s), 7.37–7.50(1H, m), 7.70(1H,d,J=8.8 Hz), 7.80(1H,d,J=8.8 Hz), 8.10–8.29(3H,m), 8.49(1H,s). MS (FAB) m/z: 576 [(M+H)$^{+}$, Cl$^{35}$], 578 [(M+H)$^{+}$, Cl$^{37}$].

Example B-73

4-[(6-chloronaphthalen-2-yl)sulfonyl]-2-[(N-isopropyl)carbamoyl]-1-[(6-methyl-4,5,6,7-tetrahydrothiazolo[5,4-c]pyridin-2-yl)carbonyl]piperazine hydrochloride Starting materials: lithium 6-methyl-4,5,6,7-tetrahydrothiazolo[5,4-c]pyridine-2-carboxylate, 1-[(6- chloronaphthalen-2-yl)sulfonyl]-3-[(N-isopropyl) carbamoyl]piperazine hydrochloride IR(KBr)cm$^{-1}$: 2967, 2933, 1666, 1625, 1542, 1463, 1344, 1332, 1159, 1135, 954, 725, 578. $^1$H-NMR (DMSO-d$_6$) δ: 1.00–1.10(6H,m), 2.50–2.80(2H,m), 2.91(3H,s), 2.93–3.50 (4H,m), 3.60–3.79(2H,m), 3.82–3.95(1H,m), 4.18–4.30(1H, m), 4.32–4.50(1.5H,m), 4.60–4.77(1H,m), 4.97(0.5H,s), 5.03(0.5H,d,J=13.2 Hz), 5.90(0.5H,s), 7.70(1H,d,J=8.8 Hz), 7.79(1H,d,J=8.8 Hz), 7.92–8.00(1H,m), 8.22(1H,d,J=8.8 Hz), 8.18–8.28(2H,m), 8.48(1H,s). MS (FAB) m/z: 576 [(M+H)$^+$, Cl$^{35}$], 578 [(M+H)$^+$, Cl$^{37}$].

Example B-74

4-[(6-Chloronaphthalen-2-yl)sulfonyl]-2-[[(piperidin-1-yl)carbonyl]methyl]-1-[(6-methyl-4,5,6,7-tetrahydrothiazolo[5,4-c]pyridin-2-yl)carbonyl]piperazine hydrochloride Starting materials: lithium 6-methyl-4,5,6,7-tetrahydrothiazolo[5,4-c]pyridine-2-carboxylate, 1-[(6-chloronaphthalen-2-yl)sulfonyl]-3-[[(piperidin-1-yl)carbonyl]methyl]piperazine hydrochloride IR(KBr)cm$^{-1}$: 2931, 2854, 1623, 1455, 1334, 1159, 1135, 1124, 1078, 954, 700, 578. $^1$H-NMR (DMSO-d$_6$) δ: 1.20–1.70(8H,m), 2.35–2.82(2H,m), 2.90(3H,s), 2.95–3.88 (11H,m), 4.31–4.45(1.5H,m), 4.62–4.76(1H,m), 5.03(0.5H, br s), 5.34(0.5H,d,J=13.2 Hz), 5.70(0.5H,br s), 7.70(1H,d, J=8.8 Hz), 7.81(1H,d,J=8.8 Hz), 8.15(1H,d,J=8.8 Hz), 8.22 (1H,s), 8.27(1H,d,J=8.8 Hz), 8.50(1H,s). MS (FAB) m/z: 616 [(M+H)$^+$, Cl$^{35}$], 618 [(M+H)$^+$, Cl$^{37}$].

Example B-75

4-[(6-Chloronaphthalen-2-yl)sulfonyl]-2-[[N-(2-methoxybenzyl)]carbamoyl]-1-[(6-methyl-4,5,6,7-tetrahydrothiazolo[5,4-c]pyridin-2-yl)carbonyl]piperazine hydrochloride Starting materials: lithium 6-methyl-4,5,6,7-tetrahydrothiazolo[5,4-c]pyridine-2-carboxylate, 1-[(6-chloronaphthalen-2-yl)sulfonyl]-3-[[N-(2-methoxybenzyl)]carbamoyl]piperazine hydrochloride $^1$H-NMR (DMSO-d$_6$) δ: 2.42–3.54(9H,m), 3.62–3.85 (5H,m), 4.12–4.50(3.5H,m), 4.60–4.77(1H,m), 5.09(½H,br s), 5.43–5.52(½H,m), 6.11–6.19(½H,m), 6.85–7.00(2H,m), 7.16–7.29(2H,m), 7.72(1H,d,J=10.7 Hz), 7.80–7.86(1H,m), 8.16(1H,d,J=8.8 Hz), 8.22–8.28(2H,m), 8.50(1H,s), 8.65–8.72(1H,m). MS (FAB) m/z: 654 [(M+H)$^+$, Cl$^{35}$], 656 [(M+H)$^+$, Cl$^{37}$].

Example B-76

4-[(6-Chloronaphthalen-2-yl)sulfonyl]-2-[[N-(2-methoxyethyl)]carbamoyl]-1-[(6-methyl-4,5,6,7-tetrahydrothiazolo[5,4-c]pyridin-2-yl)carbonyl]piperazine hydrochloride Starting materials: lithium 6-methyl-4,5,6,7-tetrahydrothiazolo[5,4-c]pyridine-2-carboxylate, 4-[(6-chloronaphthalen-2-yl)sulfonyl]-2-[[N-(2-methoxyethyl)]carbamoyl]piperazine IR(KBr)cm$^{-1}$: 2931, 1544, 1463, 1423, 1344, 1332, 1157, 1133, 1078, 954, 943, 723, 578. $^1$H-NMR (DMSO-d$_6$) δ: 2.42–2.82(2H,m), 2.92(3H,s), 2.95–3.79(13H,m), 4.21–4.80 (3.5H,m), 5.02(½H,br s), 5.47(½H,d,J=12.2 Hz), 6.07(½H, br s), 7.70(1H,dd,J=8.8,2.0 Hz), 7.79(1H,d,J=8.8 Hz), 8.13 (1H,d,J=8.8 Hz), 8.17–8.32(3H,m), 8.48(1H,s), 11.09–11.40 (1H,m). MS (FAB) m/z: 592 [(M+H)$^+$, Cl$^{35}$], 594 [(M+H)$^+$, Cl$^{37}$].

Example B-77

4-[(6-Chloronaphthalen-2-yl)sulfonyl]-1-[(6-methyl-4,5,6,7-tetrahydrothiazolo[5,4-c]pyridin-2-yl) carbonyl]piperazine-2-carboxylic acid In tetrahydrofuran (10 ml), 4-[(6-chloronaphthalen-2-yl) sulfonyl]-2-(ethoxycarbonyl)-1-[(6-methyl-4,5,6,7-tetrahydrothiazolo[5,4-c]pyridin-2-yl)carbonyl]piperazine (2.08 g) was dissolved, followed by the addition of ethanol (20 ml) and a 1N aqueous solution (3.70 ml) of sodium hydroxide. The resulting mixture was stirred at room temperature for 1 hour. After concentration of the reaction mixture under reduced pressure, the residue was added with water (20 ml). The precipitate thus formed was collected by filtration, whereby the title compound (1.39 g) was obtained as a pale yellow foam.

IR(KBr)cm$^{-1}$: 1731, 1625, 1461, 1346, 1332, 1315, 1159, 1135, 1078, 954, 943, 723, 580. $^1$H-NMR (DMSO-d$_6$) δ: 2.32–3.86(11H,m), 4.27(1H,d,J=11.7 Hz), 4.35–4.48(⅜H, m), 4.59–4.78(1H,m), 5.21(½H,m), 5.38–5.52(½H,m), 6.34–6.47(½H,m), 7.71(1H,dd,J=8.8,2.0 Hz), 7.83(1H,d,J= 8.8 Hz), 8.16(1H,d,J=8.8 Hz), 8.23(1H,s), 8.27(1H,d,J=8.8 Hz), 8.53(1H,s), 11.60–11.90(1H,m). Elementary analysis for C$_{23}$H$_{23}$ClN$_4$O$_5$S$_2$.1.3HCl.1.5H$_2$O Calculated: C, 45.33; H, 4.51; Cl, 13.38; N, 9.19; S, 10.52. Found: C, 45.69; H, 4.55; Cl, 13.29; N, 9.21; S, 10.21.

Example B-78

N'-[[4-[(6-Chloronaphthalen-2-yl)sulfonyl]-1-[(6-methyl-4,5,6,7-tetrahydrothiazolo[5,4-c]pyridin-2-yl)carbonyl]piperazin-2-yl]carbonyl]hydrazinoacetic acid In the same manner as in the Example B-77, the title compound was obtained using ethyl N'-[[4-[(6-chloronaphthalen-2-yl)sulfonyl]-1-[(6-methyl-4,5,6,7-tetrahydrothiazolo[5,4-c]pyridin-2-yl)carbonyl]piperazin-2-yl]carbonyl]hydrazinoacetate hydrochloride as a starting material. MS (FAB) m/z: 607 [(M+H)$^+$, Cl$^{35}$], 609 [(M+H)$^+$, Cl$^{37}$].

$^1$H-NMR (DMSO-d$_6$ at 100° C.) δ: 2.41(3H,s), 2.65–3.30 (6H,m), 3.37–3.77(8H,m), 4.16(1H,d,J=12.7 Hz), 7.64(1H, dd,J=8.7,2.4 Hz), 7.78(1H,dd,J=8.7,1.6 Hz), 8.07(1H,d,J= 8.7 Hz), 8.11(1H,d,J=1.6 Hz), 8.16(1H,d,J=8.7 Hz), 8.42 (1H,s). Elementary analysis for C$_{25}$H$_{27}$ClN$_6$O$_6$S$_2$.2H$_2$O Calculated: C, 46.69; H, 4.86; N, 13.07; S, 9.97. Found: C, 46.87; H, 4.86; N, 12.82; S, 9.62.

Example B-79

4-[(6-Chloronaphthalen-2-yl)sulfonyl]-1-[(6-methyl-4,5,6,7-tetrahydrothiazolo[5,4-c]pyridin-2-yl) carbonyl]-2-[[N-(tetrahydropyran-2-yloxy)] carbamoyl]piperazine In N,N-dimethylformamide (20 ml), 4-[(6-chloronaphthalen-2-yl)sulfonyl]-1-[(6-methyl-4,5,6,7-tetrahydrothiazolo[5,4-c]pyridin-2-yl)carbonyl]piperazine-2-carboxylic acid (141 mg), 2-tetrahydropyranyloxyamine (180 mg), 1-hydroxybenzotriazole monohydrate (11 mg), 1-(dimethylaminopropyl)-3-ethylcarbodiimide hydrochloride (145 mg) and potassium carbonate (129 mg) were dissolved, followed by stirring overnight at room temperature. The reaction mixture was concentrated under reduced pressure. Dichloromethane was added to the residue, followed by washing with water. The organic layer was dried over anhydrous sodium sulfate. The solvent was distilled off under reduced pressure. The residue was purified by chromatography on a silica gel column (Φ0.7×25.0 cm, dichloromethane:methanol=100:3), whereby the title compound (308 mg) was obtained as a colorless foam.

$^1$H-NMR (CDCl$_3$) δ: 1.50–1.89(6H,m), 2.45–2.55(3H, m), 2.72–3.00(6H,m), 3.57–3.97(5H,m), 4.28(0.5H,d,J= 12.2 Hz), 4.35(0.5H,d,J=12.2 Hz), 4.52–4.61(0.5H,m), 4.92 (0.5H,s), 5.02(0.5H,br s), 5.06–5.10(0.5H,m), 5.55–5.65 (0.5H,m), 5.88(0.5H,br s), 6.21(0.5H,br s), 7.51–7.58(1H, m), 7.77–7.93(4H,m), 8.35(1H,s), 9.61(0.5H,br s), 10.10 (1H,br s). MS (FAB) m/z: 634 [(M+H)$^+$, Cl$^{35}$], 636 [(M+H)$^+$, Cl$^{37}$].

Example B-80

4-[(6-Chloronaphthalen-2-yl)sulfonyl]-1-[(6-methyl-4,5,6,7-tetrahydrothiazolo[5,4-c]pyridin-2-yl)carbonyl]piperazine-2-carbohydroxamic acid In methanol (10 ml), 4-[(6-chloronaphthalen-2-yl)sulfonyl]-1-[(6-methyl-4,5,6,7-tetrahydrothiazolo[5,4-c]pyridin-2-yl)carbonyl]-2-[[N-(tetrahydropyran-2-yloxy)]carbamoyl]piperazine (297 mg) was dissolved, followed by the addition of 1N hydrochloric acid (10 ml). The resulting mixture was stirred at room temperature for 1 hour. The reaction mixture was concentrated under reduced pressure. The residue was purified by "HP-20" (Φ1.7×20.0 cm, acetonitrile:water=1:5), whereby the title compound (65 mg) was obtained as a pale yellow foam.

$^1$H-NMR (CDCl$_3$) δ: 2.32–2.73(2H,m), 2.91(3H,s), 2.97–3.30(3H,m), 3.35–3.50(1H,m), 3.63–3.76(2H,m), 4.22–4.48(2.5H,m), 4.61–4.75(1H,m), 4.99(0.5H,s), 5.47 (0.5H,d,J=12.2 Hz), 6.24(0.5H,s), 7.70(1H,d,J=8.8 Hz), 7.75–7.85(1H,m), 8.15(1H,d,J=8.8 Hz), 8.23(1H,s), 8.25 (1H,d,J=8.8 Hz), 8.48(1H,s), 10.26(1H,br s), 10.97(1H,br s). MS (FAB) m/z: 550 [(M+H)$^+$, Cl$^{35}$], 552 [(M+H)$^+$, Cl$^{37}$].

Example B-81

4-[(6-Chloronaphthalen-2-yl)sulfonyl]-2-[[N-(2-hydroxybenzyl)]carbamoyl]-1-[(6-methyl-4,5,6,7-tetrahydrothiazolo[5,4-c]pyridin-2-yl)carbonyl]piperazine In dichloromethane (10 ml), 4-[(6-chloronaphthalen-2-yl)sulfonyl]-2-[[N-(2-methoxybenzyl)]carbamoyl]-1-[(6-methyl-4,5,6,7-tetrahydrothiazolo[5,4-c]pyridin-2-yl)carbonyl]piperazine hydrochloride (195 mg) was dissolved, followed by the dropwise addition of a boron tribromide-dichloromethane solution (1.0M, 2.08 ml) at −78° C. The reaction mixture was heated to room temperature and stirred overnight. To the reaction mixture, methanol (2 ml), sodium carbonate (200 mg) and water (3 ml) were added to extract the organic layer, followed by drying over anhydrous sodium sulfate. The solvent was then distilled off under reduced pressure. The solid thus precipitated was collected by filtration while being washed with 1N hydrochloric acid, whereby the title compound (50 mg, 24%) was obtained as a pale yellow solid.

$^1$H-NMR (DMSO-d$_6$) δ: 2.36–2.87(9H,m), 3.11–3.28(1H, m), 3.59–3.80(3H,m), 4.12–4.45(3.5H,m), 4.48–4.57(½H, m), 5.08(½H,br s), 6.19(½H,br s), 6.63–6.81(2H,m), 6.98–7.15(2H,m), 7.70(1H,dd,J=8.3,1.5 Hz), 7.78–7.84(1H, m), 8.13(1H,d,J=8.8 Hz), 8.20–8.28(2H,m), 8.49(1H,s), 8.50–8.62(1H,m), 9.45(½H,s), 9.50(½H,s). MS (FAB) m/z: 640 [(M+H)$^+$, Cl$^{35}$], 642 [(M+H)$^+$, Cl$^{37}$].

Example B-82

2-[[4-[(6-Chloronaphthalen-2-yl)sulfonyl]piperazin-1-yl]carbonyl]-6-methyl-4,5,6,7-tetrahydrofuro[2,3-c]pyridine hydrochloride To a solution of 6-methyl-4,5,6,7-tetrahydrofuro[2,3-c]pyridine (58.1 mg) in tetrahydrofuran (3.2 ml), n-butyl lithium (a 1.59N hexane solution, 320 μl) was added at −78° C., followed by stirring for 1 hour and then at 0° C. for 30 minutes. The reaction mixture was cooled to −78° C. and a carbon dioxide gas was introduced thereinto for 1 hour. After the reaction mixture was heated to room temperature over 30 minutes, it was concentrated. To a solution of the resulting residue in N,N-dimethylformamide (6.0 ml), 1-[(6-chloronaphthalen-2-yl)sulfonyl]piperazine hydrochloride (177 mg, 510 μmol) was dissolved, followed by the addition of 1-(dimethylaminopropyl)-3-ethylcarbodiimide (98.0 mg, 511 μmol) and 1-hydroxybenzotriazole (69.0 mg, 511 μmol) at room temperature and then, diisopropylethylamine (185 μl, 1.06 mmol) at 0° C. After stirring overnight at room temperature, the reaction mixture was added with methylene chloride (20 ml) and a saturated aqueous solution (50 ml) of sodium bicarbonate, whereby the organic layer was separated. The resulting organic layer was extracted with methylene chloride (2×10 ml). The organic layers were combined, washed with water (50 ml), dried over anhydrous sodium sulfate and concentrated under reduced pressure. The residue thus obtained was purified twice by preparative thin-layer chromatography on a silica gel (methylene chloride:acetone:methanol=10:5:1). The white solid thus obtained was dissolved in a 1N ethanol hydrochloride solution and the resulting solution was concentrated. After the addition of water, the mixture was concentrated again, whereby the title compound (74.7 mg) was obtained as a white solid.

IR(KBr)cm$^{-1}$: 3396, 2918, 2850, 2538, 1620, 1456, 1432, 1344, 1329, 1282, 1161, 955, 941, 729. $^1$H-NMR (DMSO-d$_6$) δ: 2.68(1H,br d,J=15.1 Hz), 2.78–2.92(1H,br), 2.85(3H, s), 3.04(4H,br s), 3.26(1H,br s), 3.52(1H,br s), 3.72(4H,br s), 4.20(1H,br d,J=15.1 Hz), 4.43(1H,br d,J=15.1 Hz), 6.92 (1H,s), 7.71(1H,dd,J=2.0,8.8 Hz), 7.80(1H,d,J=8.8 Hz), 8.15(1H,d,J=8.8 Hz), 8.23(1H,s), 8.25(1H,d,J=8.8 Hz), 8.48 (1H,s), 11.64(1H,br s). MS (FAB) m/z: 474 [(M+H)$^+$]. Elementary analysis for C$_{23}$H$_{24}$ClN$_3$O$_4$S.1.1HCl.1.7H$_2$O Calculated: C, 50.72; H, 5.27; N, 7.71; Cl, 13.67; S, 5.89. Found: C, 50.58; H, 5.39; N, 7.69; Cl, 13.94; S, 5.85.

Example B-83

2-[[4-[(6-Chloronaphthalen-2-yl)sulfonyl]piperazin-1-yl]carbonyl]-5,6,7,8-tetrahydro-1,6-naphthyridine hydrochloride To 6-(t-butoxycarbonyl)-2-[[4-(chloronaphthalen-2-yl)sulfonyl]piperazin-1-yl]carbonyl]-5,6,7,8-tetrahydro-1,6-naphthyridine (1.28 g, 2.24 mmol), a saturated ethanol hydrochloride solution (50 ml) was added at room temperature. The resulting mixture was stirred for 20 minutes, followed by concentration, whereby the title compound (1.26 g) was obtained as a white solid.

IR(KBr)cm$^{-1}$: 3396, 2924, 2615, 2544, 1957, 1655, 1610, 1473, 1454, 1425, 1448, 1336, 1286, 1157, 941, 731, 580. $^1$H-NMR (DMSO-d$_6$) δ: 3.02(2H,br t,J=5.3 Hz), 3.05(2H,t, J=6.4 Hz), 3.42–3.49(2H,brm), 3.52(2H,br t,J=5.3 Hz), 3.75 (2H,br t,J=5.3 Hz), 4.33(2H,br t,J=5.3 Hz), 7.56(1H,br d,J= 8.3 Hz), 7.89(1H,d,J=8.3 Hz), 7.89(1H,dd,J=1.5,8.8 Hz), 7.98(1H,dd,J=2.0,8.8 Hz), 8.34(1H,d,J=8.8 Hz), 8.43(1H,s), 8.44(1H,d,J=8.8 Hz), 8.67(1H,br s), 9.87(2H,br s). MS (FAB) m/z: 471 [(M+H)$^+$, Cl$^{35}$]. Elementary analysis for C$_{23}$H$_{23}$ClN$_4$O$_3$S.1.9HCl.0.9H$_2$O Calculated: C, 49.64; H, 4.84; Cl, 10.07; N, 18.48; S, 5.76. Found: C, 49.64; H, 4.96; Cl, 10.01; N, 18.73; S, 5.93.

Example B-84

2-[[4-(6-Chloronaphthalen-2-yl)sulfonyl]piperazin-1-yl]carbonyl]-6-methyl-5,6,7,8-tetrahydro-1,6-naphthyridine hydrochloride To a solution of 2-[[4-(chloronaphthalen-2-yl)sulfonyl]piperazin-1-yl]carbonyl]-5,6,7,8-tetrahydro-1,6- naphthyridine (174 mg) in methylene chloride (3.5 ml), triethylamine (95.6 μl), acetic acid (58.9 μl), formaldehyde (a 37% aqueous solution, 42.0 μl) and sodium triacetoxyborohydride (110 mg) were added at room temperature, followed by stirring for 15 minutes. To the reaction mixture, a saturated aqueous solution (10 ml) of sodium bicarbonate and methylene chloride (10 ml) were added to separate the water layer. The resulting water layer was extracted with methylene chloride (10 ml). The organic layers were combined, dried over anhydrous sodium sulfate and concentrated under reduced pressure. The residue was purified by preparative thin-layer chromatography on a silica gel (methylene chloride methanol=15:1). The white solid thus obtained was dissolved in a 1N aqueous hydrochloride in ethanol, followed by concentration, whereby the title compound (170 mg) was obtained as a white solid.

IR(KBr)cm$^{-1}$: 3359, 2918, 2544, 1655, 1641, 1475, 1431, 1342, 1331, 1284, 1155, 953, 941, 727, 579. $^1$H-NMR (DMSO-d$_6$) δ: 3.04(3H,d,J=3.9 Hz), 3.17(2H,br s), 3.26(2H, br s), 3.38–3.65(2H,m), 3.68(2H,br s), 3.39(2H,br s), 4.40–4.70(2H,m), 4.57(2H,br s), 7.57(1H,d,J=7.8 Hz), 7.84–7.92(2H,m), 7.98(1H,d,J=8.8 Hz), 8.33(1H,d,J=8.3 Hz), 8.42(1H,s), 8.43(1H,d,J=8.8 Hz), 8.67(1H,s), 11.86 (1H,br s). MS (FAB) m/z: 485 [(M+H)$^+$, Cl$^{35}$].

Example B-85

2-[[4-[(6-Chloronaphthalen-2-yl)sulfonyl]piperazin-1-yl]carbonyl]-4,5,6,7-tetrahydro-1H-pyrrolo[3,2-c]pyridine hydrochloride A saturated solution of hydrochloride in ethanol (25 ml) was added to 1,5-bis(t-butoxycarbonyl)-2-[[4-[(6-chloronaphthalen-2-yl)sulfonyl]piperazin-1-yl]carbonyl]-4,5,6,7-tetrahydro-1H-pyrrolo[3,2-c]pyridine (300 mg) at room temperature, followed by stirring for 1 hour. The reaction mixture was concentrated and water was added to the concentrate. The resulting mixture was concentrated under reduced pressure. To the residue, a saturated solution of hydrochloride in methanol (25 ml) was added at room temperature, followed by stirring for 1 hour. After concentration of the reaction mixture, water was added and the resulting mixture was concentrated under reduced pressure, whereby the title compound (200 mg) was obtained as a white solid.

IR(KBr)cm$^{-1}$: 3290, 2918, 2762, 2559, 1614, 1483, 1454, 1381, 1340, 1323, 1244, 1155, 1147, 1136, 978, 955, 727, 575. $^1$H-NMR (DMSO-d$_6$) δ: 2.77(2H,br t,J=5.9 Hz), 3.03 (4H,t,J=5.3 Hz), 3.30(2H,br t,J=5.9 Hz), 3.73(4H,br t,J=5.3 Hz), 3.99(2H,br s), 6.32(1H,d,J=2.0 Hz), 7.73(1H,dd,J=2.0, 8.8 Hz), 7.83(1H,dd,J=2.0,8.8 Hz), 8.17(1H,d,J=8.8 Hz), 8.25(1H,d,J=2.0 Hz), 8.28(1H,d,J=8.8 Hz), 8.50(1H,br s), 9.07(2H,br), 11.38(1H,br). MS (FAB) m/z: 459 [(M+H)$^+$, Cl$^{35}$]. Elementary analysis for C$_{22}$H$_{23}$ClN$_4$O$_3$S.1.1HCl.0.3H$_2$O Calculated: C, 52.38; H, 4.94; N, 11.11; Cl, 14.76; S, 6.36. Found: C, 52.48; H, 4.92; N, 11.07; Cl, 14.48; S, 6.65.

Example B-86

2-[[4-[(6-Chloronaphthalen-2-yl)sulfonyl]piperazin-1-yl]carbonyl]-5-methyl-4,5,6,7-tetrahydro-1H-pyrrolo[3,2-c]pyridine hydrochloride In methylene chloride (4.5 ml), 2-[[4-[(6-chloronaphthalen-2-yl)sulfonyl]piperazin-1-yl]carbonyl]-4,5,6,7-tetrahydro-1H-pyrrolo[3,2-c]pyridine hydrochloride (200 mg) was suspended, followed by the addition of triethylamine (125 μl), acetic acid (77.0 μl), formaldehyde (a 37% aqueous solution, 56.1 μl) and sodium triacetoxyborohydride (139 mg) at room temperature. The resulting mixture was stirred for 15 minutes. To the reaction mixture, a saturated aqueous solution (20 ml) of sodium bicarbonate and methylene chloride (10 ml) were added to separate the water layer. The resulting water layer was extracted with methylene chloride (2×10 ml). The organic layers were combined, dried over anhydrous sodium sulfate and concentrated under reduced pressure. The residue thus obtained was purified by chromatography on a silica gel column (25 g of silica gel, methylene chloride:methanol 10:1→7:1). The resulting solid was dissolved in a 1N aqueous hydrochloride in ethanol. After concentration of the resulting solution, water was added to the concentrate and the mixture was concentrated again, whereby the title compound (133 mg) was obtained as a white solid.

IR(KBr)cm$^{-1}$: 3213, 2918, 2650, 2530, 1604, 1585, 1508, 1491, 1456, 1342, 1331, 1157, 727, 579. $^1$H-NMR (DMSO-d$_6$) δ: 2.72–2.86(1H,m), 2.83(3H,d,J=4.9 Hz), 2.87–2.99 (1H,m), 3.03(4H,br t,J=4.4 Hz), 3.19–3.31(1H,m), 3.46–3.64(1H,m), 3.74(4H,br t,J=4.4 Hz), 3.97(1H,dd,J= 7.8,14.2 Hz), 4.20(1H,br d,J=14.2 Hz), 6.32(1H,d,J=2.4 Hz), 7.72(1H,dd,J=2.4,8.8 Hz), 7.82(1H,dd,J=2.0,8.8 Hz), 8.16(1H,d,J=8.8 Hz), 8.25(1H,d,J=2.0 Hz), 8.27(1H,d,J=8.8 Hz), 8.51(1H,br s), 10.84(1H,br s), 11.42(1H,br s). MS (FAB) m/z: 473 [(M+H)$^+$, Cl$^{35}$]. Elementary analysis for C$_{23}$H$_{25}$ClN$_4$O$_3$S.1. 3HCl.0. 7H$_2$O Calculated: C, 51.83; H, 5.24; N, 10.51; Cl, 15.30; S, 6.02. Found: C, 51.83; H, 5.37; N, 10.30; Cl, 15.35; S, 6.09.

Example B-87

2-[[4-[(6-Chloronaphthalen-2-yl)sulfonyl]piperazin-1-yl]carbonyl]-5-ethyl-4,5,6,7-tetrahydro-1H-pyrrolo[3,2-c]pyridine hydrochloride In methylene chloride (3.0 ml), 2-[[4-[(6-chloronaphthalen-2-yl)sulfonyl]piperazin-1-yl]carbonyl]-4,5,6,7-tetrahydro-1H-pyrrolo[3,2-c]pyridine hydrochloride (149 mg) was suspended, followed by the addition of methanol (0.6 ml), triethylamine (82.5 μl), acetic acid (51.0 μl, 891 μmol), acetaldehyde (19.5 μl) and sodium triacetoxyborohydride (74.0 mg) at room temperature. The resulting mixture was stirred for 15 minutes. To the reaction mixture, a saturated aqueous solution (30 ml) of sodium bicarbonate and methylene chloride (15 ml) were added to separate the water layer. The resulting water layer was extracted with methylene chloride (2×10 ml). The organic layers were combined, dried over anhydrous sodium sulfate and concentrated under reduced pressure. The residue thus obtained was purified by chromatography on a silica gel column (30 g of silica gel, methylene chloride:methanol=10:1). The resulting white solid was dissolved in a 1N aqueous hydrochloride in ethanol (10 ml). After concentration of the resulting solution, water (30 ml) was added to the concentrate and the mixture was concentrated again, whereby the title compound (81.7 mg) was obtained as a white solid.

IR(KBr)cm$^{-1}$: 3386, 3226, 2918, 2586, 1603, 1585, 1491, 1454, 1427, 1344, 1331, 1163, 1136, 1078, 933, 727, 579. $^1$H-NMR (DMSO-d$_6$) δ: 1.26(3H,t,J=7.3 Hz), 2.72–2.82 (1H,m), 2.86–3.00(1H,m), 3.02(4H,br s), 3.12–3.64(6H,m), 3.73(4H,br s), 3.96(1H,dd,J=7.8,14.1 Hz), 4.22(1H,br d,J= 14.1 Hz), 6.31(1H,d,J=2.4 Hz), 7.71(1H,br d,J=8.8 Hz), 7.81(1H,br d,J=8.8 Hz), 8.16(1H,d,J=8.8 Hz), 8.23(1H,br s), 8.26(1H,d,J=8.8 Hz), 8.50(1H,br s), 10.39(1H,br s), 11.40 (1H,br s). MS (FAB) m/z: 486 [(M+H)$^+$, Cl$^{35}$]. Elementary analysis for C$_{24}$H$_{27}$ClN$_4$O$_3$S.1.2HCl.2.0H$_2$O Calculated: C, 50.86; H, 5.73; N, 9.88; Cl, 13.76; S, 5.66. Found: C, 51.11; H, 5.71; N, 9.58; Cl, 13.60; S, 5.66.

Example B-88

5-(t-Butoxycarbonyl)-2-[[4-[(6-chloronaphthalen-2-yl)sulfonyl]piperazin-1-yl]carbonyl]-4,5,6,7-tetrahydro-1H-pyrrolo[3,2-c]pyridine In methylene chloride (15 ml), 2-[[4-[(6-chloronaphthalen-2-yl)sulfonyl]piperazin-1-yl]carbonyl]-4,5,6,7-tetrahydro-1H-pyrrolo[3,2-c]pyridine hydrochloride (780 mg) was suspended, followed by the addition of a saturated aqueous solution (15 ml) of sodium bicarbonate and di-t-butyl dicarbonate (506 ml) at room temperature. The resulting mixture was stirred for 1 hour. To the reaction mixture, water (30 ml) and methylene chloride (30 ml) were added to separate the water layer. The resulting water layer was extracted with methylene chloride (2×20 ml). The organic layers were combined, dried over anhydrous sodium sulfate and concentrated under reduced pressure. The residue thus obtained was purified by chromatography on a silica gel column (75 g of silica gel, methylene chloride:acetone=8:1→2:1). The resxulting white solid was dissolved in a 1N aqueous hydrochloride in ethanol. After concentration of the resulting solution, water was added to the concentrate and the mixture was concentrated again, whereby the title compound (641 mg) was obtained as a white solid.

$^1$H-NMR (CDCl$_3$) δ: 1.46(9H,s), 2.61(2H,br s), 3.12(4H, br t,J=4.9 Hz), 3.66(2H,br s), 3.90(4H,br t,J=4.9 Hz), 4.36 (2H,br s), 6.19(1H,d,J=2.0 Hz), 7.57(1H,dd,J=1.7,9.0 Hz), 7.76(1H,br d,J=8.8 Hz), 7.86–7.97(3H,m), 8.29(1H,br s), 9.24 (1H,br s).

Example B-89

5-(t-Butoxycarbonyl)-2-[[4-[(6-chloronaphthalen-2-yl)sulfonyl]piperazin-1-yl]carbonyl]-1-methyl-4,5,6,7-tetrahydro-1H-pyrrolo[3,2-c]pyridine To a solution of 5-(t-butoxycarbonyl)-2-[[4-[(6-chloronaphthalen-2-yl)sulfonyl]piperazin-1-yl]carbonyl]-4,5,6,7-tetrahydro-1H-pyrrolo[3,2-c]pyridine (33.0 mg) in N,N-dimethylformamide (15 ml), sodium hydride (60% in oil, 3.5 mg) was added at 0° C. After stirring for 10 minutes, methyl iodide (4.5 μl) was added and the resulting mixture was stirred at 0° C. for 1 hour. To the reaction mixture, a saturated aqueous solution (10 ml) of ammonium chloride, methylene chloride (20 ml) and water (30 ml) were added to separate the organic layer. The resulting water layer was extracted with methylene chloride (10 ml). The organic layers were combined, dried over anhydrous sodium sulfate and concentrated under reduced pressure. The residue was purified by preparative thin-layer chromatography on a silica gel (methylene chloride:acetone=9:1), whereby the title compound (32.3 mg) was obtained as a colorless, transparent viscous substance.

$^1$H-NMR (CDCl$_3$) δ: 1.46(9H,s), 2.58(2H,br s), 3.12(4H, br t,J=4.5 Hz), 3.50(3H,s), 3.68(2H,br s), 3.84(4H,br t,J=4.5 Hz), 4.32(2H,br s), 6.02(1H,s), 7.58(1H,dd,J=2.0,8.8 Hz), 7.77(1H,dd,J=1.7,8.5 Hz), 7.88–7.97(3H,m), 8.32(1H,br s).

Example B-90

2-[[4-[(6-Chloronaphthalen-2-yl)sulfonyl]piperazin-1-yl]carbonyl]-1-methyl-4,5,6,7-tetrahydro-1H-pyrrolo[3,2-c]pyridine hydrochloride To 5-(t-butoxycarbonyl)-2-[[4-[(6-chloronaphthalen-2-yl)sulfonyl]piperazin-1-yl]carbonyl]-1-methyl-4,5,6,7-tetrahydro-1H-pyrrolo[3,2-c]pyridine (280 mg), a saturated solution hydrochloride in ethanol (25 ml) was added at room temperature, followed by stirring for 1 hour. The reaction mixture was then concentrated. Water (10 ml) was added to the concentrate, followed by concentration under reduced pressure, whereby the title compound (210 mg) was obtained as a white solid.

IR(KBr)cm$^{-1}$: 3381, 2918, 2748, 1622, 1583, 1495, 1454, 1342, 1331, 1248, 1163, 1136, 953, 935, 879, 726, 579, 476. $^1$H-NMR (DMSO-d$_6$) δ: 2.81(2H,br t,J=5.6 Hz), 3.05(4H,br s), 3.35(2H,br t,J=5.6 Hz), 3.42(3H,s), 3.69(4H,br s), 3.97 (2H,br s), 6.18(1H,s), 7.73(1H,dd,J=2.0,8.8 Hz), 7.83(1H, dd,J=2.0,8.8 Hz), 8.18(1H,d,J=8.8 Hz), 8.27(1H,br s), 8.28 (1H,d,J=8.8 Hz), 8.50(1H,br s), 9.34(1H,br d,J=27.4 Hz). MS (FAB) m/z: 473 [(M+H)$^+$, Cl$^{35}$]. Elementary analysis for C$_{23}$H$_{25}$ClN$_4$O$_3$S.1.4HCl.1.2H$_2$O Calculated: C, 50.63; H, 5.32; N, 10.27; Cl, 15.59; S, 5.88. Found: C, 50.71; H, 5.53; N, 10.14; Cl, 15.53; S, 5.90.

Example B-91

2-[[4-[(6-Chloronaphthalen-2-yl)sulfonyl]piperazin-1-yl]carbonyl]-1,5-methyl-4,5,6,7-tetrahydro-1H-pyrrolo[3,2-c]pyridine hydrochloride In methylene chloride (10 ml), 2-[[4-(6-chloronaphthalen-2-yl)sulfonyl]piperazin-1-yl]carbonyl]-1-methyl-4,5,6,7-tetrahydro-1H-pyrrolo[3,2-c]pyridine hydrochloride (170 mg) was suspended, followed by the addition of methanol (10 ml), triethylamine (100 μl), acetic acid (62.0 μl), formaldehyde (a 37% aqueous solution, 46.5 μl) and sodium triacetoxyborohydride (115 mg) at room temperature. The resulting mixture was stirred for 30 minutes. To the reaction mixture, a saturated aqueous solution (50 ml) of sodium bicarbonate and methylene chloride (30 ml) were added to separate the water layer. The water layer thus obtained was extracted with methylene chloride (2×10 ml). The organic layers were combined, dried over anhydrous sodium sulfate and concentrated under reduced pressure. The residue was purified by chromatography on a silica gel column (30 g of silica gel, methylene chloride:methanol=10:1→7:1). The resulting white solid was dissolved in a 1N aqueous hydrochloride in ethanol. After the concentration of the resulting solution, water was added to the concentrate and the resulting mixture was concentrated again, whereby the title compound (162 mg) was obtained as a white solid.

IR(KBr)cm$^{-1}$: 3396, 2924, 2663, 2586, 1622, 1581, 1456, 1342, 1329, 1248, 1163, 1136, 955, 937, 727, 579. $^1$H-NMR (DMSO-d$_6$) δ: 2.77–3.00(5H,m), 3.06(4H,br s), 3.23–3.37 (1H,m), 3.43(3H,s), 3.55–3.65(1H,m), 3.69(4H,br s), 3.90–4.03(1H,m), 3.93(3H,s), 4.19(1H,br d,J=11.7 Hz), 6.18 (1H,s), 7.74(1H,dd,J=2.0,8.8 Hz), 7.83(1H,dd,J=2.0,8.8 Hz), 8.18(1H,d,J=8.8 Hz), 8.27(1H,br s), 8.28(1H,d,J=8.8 Hz), 8.51(1H,br s), 11.00(1H,br s). MS (FAB) m/z: 487 [(M+H)$^+$, Cl$^{35}$]. Elementary analysis for C$_{24}$H$_{27}$ClN$_4$O$_3$S.1.4HCl.1.4H$_2$O Calculated: C, 51.18; H, 5.58; N, 9.95; Cl, 15.11; S, 5.69. Found: C, 51.09; H, 5.83; N, 9.78; Cl, 15.37; S, 5.79.

Example B-92

2-(N-Methylcarbamoyl)-1-[(6-methyl-4,5,6,7-tetrahydrothiazolo[5,4-c]pyridin-2-yl)carbonyl]-4-[(6-trimethylsilylethynylbenzo[b]thien-2-yl)sulfonyl]piperazine In N,N-dimethylformamide (5 ml) was dissolved 3-(N-methylcarbamoyl)-1-[(6-trimethylsilylethynylbenzo[b]

thien-2-yl)sulfonyl]piperazine (218 mg), followed by the addition of lithium 6-methyl-4,5,6,7-tetrahydrothiazolo[5,4-c]pyridine-2-carboxylate (188 mg), 1-ethyl-3-(3-dimethylaminopropyl)carbodiimide hydrochloride (240 mg) and 1-hyroxybenzotriazole (68 mg). The resulting mixture was stirred at room temperature for 30 minutes. The reaction mixture was diluted with methylene chloride, washed with water (twice) and then with a saturated aqueous solution of sodium bicarbonate. After drying over anhydrous sodium sulfate, the solvent was distilled off under reduced pressure. The residue was purified by chromatography on a silica gel column (methanol:methylene chloride=3:97→5:95→7:93), whereby the title compound (90 mg) was obtained. MS (FAB) m/z: 616 (M+H)$^+$.

Example B-93

4-[(6-Ethynylbenzo[b]thien-2-yl)sulfonyl]-2-[N-methylcarbamoyl)-1-[(6-methyl-4,5,6,7-tetrahydrothiazolo[5,4-c]pyridin-2-yl)carbonyl] piperazine In a mixed solvent of tetrahydrofuran (0.5 ml) and methanol (0.5 ml) was dissolved 2-(N-methylcarbamoyl)-1-[(6-methyl-4,5,6,7-tetrahydrothiazolo[5,4-c]pyridin-2-yl)carbonyl]-4-[(6-trimethylsilylethynylbenzo[b]thien-2-yl)sulfonyl]piperazine (90 mg), followed by the addition of a 1N aqueous solution (0.3 ml) of sodium hydroxide. The resulting mixture was stirred at room temperature for 2 hours. The reaction mixture was made weakly acidic with a saturated aqueous solution of ammonium chloride and then made weakly alkaline with a saturated aqueous solution of sodium bicarbonate. The solution was extracted (four times) with methylene chloride. The organic layers were combined, dried over anhydrous sodium sulfate and distilled under reduced pressure to remove the solvent. The residue was purified by preparative thin-layer chromatography (methanol:methylene chloride=1:9). Similar reaction and post treatment were repeated three times and the purified products were combined, followed by purification through Sephadex LH-20 (elution with methanol). The amorphous substance thus obtained was dissolved in methylene chloride. Hexane was added dropwise to the resulting solution, whereby the title compound (82 mg) was obtained as a light gray solid.

$^1$H-NMR (CDCl$_3$) δ: 2.49(3H,s), 2.80–2.90(10H,m), 3.15–3.18(1H,m), 3.22(1H,s), 3.53–3.62(1H,m), 3.67(1H,s), 4.49(1H,d,J=12.2 Hz), 4.65, 5.74(total 1H,each d,J=13.7 Hz), 5.26, 6.18(total 1H,each s), 6.45, 6.49(total 1H,each s), 7.54(1H,d,J=8.3 Hz), 7.80(1H,s), 7.82(1H,d,J=8.3 Hz), 7.97 (1H,s). MS (FAB) m/z: 544 (M+H)$^+$.

Example B-94

1-[(6-tert-Butoxycarbonyl-4,5,6,7-tetrahydrothiazolo [5,4-c]pyridin-2-yl)carbonyl]-4-[(5-chloroindol-2-yl) sulfonyl]-2-[[(morpholin-4-yl)carbonyl]methyl] piperazine In methylene chloride (5 ml) was dissolved 1-(tert-butoxycarbonyl)-4-[(5-chloroindol-2-yl)sulfonyl]-2-[[(morpholin-4-yl)carbonyl]methyl]piperazine (930 mg), followed by the addition of trifluoroacetic acid (2 ml). The resulting mixture was stirred at room temperature for 30 minutes. A saturated aqueous solution of sodium bicarbonate was added and the resulting mixture was extracted with methylene chloride. The organic layer was dried over anhydrous sodium sulfate and distilled under reduced pressure to remove the solvent. The residue was dissolved in N,N-dimethylformamide (10 ml), followed by the addition of lithium 6-tert-butoxycarbonyl-4,5,6,7-tetrahydrothiazolo[5,4-c]pyridine-2-carboxylate (695 mg), 1-ethyl-3-(3-dimethylainopropyl)carbodiimide hydrochloride (506 mg) and 1-hydroxybenzotriazole (119 mg). The resulting mixture was stirred overnight at room temperature. A saturated aqueous solution of sodium bicarbonate was added and the resulting mixtures was extracted with methylene chloride. The extract was dried over anhydrous sodium sulfate and distilled under reduced pressure to remove the solvent. The residue was purified by chromatography on a silica gel column (hexane:ethyl acetate=1:1), whereby the title compound (585 mg) was obtained as an orange foam.

$^1$H-NMR (CDCl$_3$) δ: 1.48(9H,s), 2.58–3.96(19H,m), 4.60–6.02(4H,m), 6.98(1H,s), 7.27(1H,d,J=9.0 Hz), 7.38 (1H,d,J=9.0 Hz), 7.64(H,s), 10.39(1H,s).

Example B-95

4-[(5-Chloroindol-2-yl)sulfonyl]-1-[(6-methylsulfonyl-4,5,6,7-tetrahydrothiazolo[5,4-c] pyridin-2-yl)carbonyl]-2-[[(morpholin-4-yl) carbonyl]methyl]piperazine In methylene chloride (5 ml) was dissolved 1-[(6-tert-butoxycarbonyl-4,5,6,7-tetrahydrothiazolo[5,4-c]pyridin-2-yl)carbonyl]-4-[(5-chloroindol-2-yl)sulfonyl]-2-[[(morpholin-4-yl)carbonyl]methyl]piperazine (585 mg), followed by the addition of trifluoroacetic acid (2 ml). The resulting mixture was stirred at room temperature for 30 minutes. A saturated aqueous solution of sodium bicarbonate was added and the resulting mixture was extracted with methylene chloride (to which N,N-dimethylformamide was added in a small amount). The organic layer was dried over anhydrous sodium sulfate and distilled under reduced pressure to remove the solvent. To the residue was added a 1N aqueous hydrochloride in ethanol (1 ml) and the solvent was distilled off under reduced pressure, whereby the hydrochloride (585 mg, containing two molecules of N,N-dimethylformamide). A 100 mg portion of the resulting hydrochloride was added to methylene chloride (3 ml), followed by the addition of triethylamine (0.5 ml) and methanesulfonyl chloride (20 mg). The resulting mixture was stirred at room temperature for 2 hours. A saturated aqueous solution of sodium bicarbonate was added to the reaction mixture. The resulting mixture was extracted with methylene chloride. The extract was dried over anhydrous sodium sulfate and distilled under reduced pressure to remove the solvent. The residue was purified by preparative thin-layer chromatography (methylene chloride:methanol= 9:1). The solid thus obtained was dissolved in methylene chloride, followed by the addition of ether for crystallization, whereby the title compound (34.2 mg) was obtained as a white solid.

$^1$H-NMR (DMSO-d$_6$) δ: 2.33–3.57(20H,m), 3.72–3.79 (2H,m), 4.38, 5.39(total 1H,each d,J=12.2,13.7 Hz), 4.55 (2H,s), 5.06, 5.82(total 1H,each br s), 7.02(1H,s), 7.30(1H, d,J=8.8 Hz), 7.47(1H,d,J=8.8 Hz), 7.76(1H,s), 12.41 (1H,s). MS (FAB) m/z: 671 (M+H)$^+$.

Example B-96

4-[(6-Chloronaphthalen-2-yl)sulfonyl]-2-(N-methylcarbamoyl)-1-[(4,5,6,7-tetrahydrothiazolo[5, 4-c]pyridin-2-yl)carbonyl]piperazine trifluoroacetate In N,N-dimethylformamide (50 ml) were dissolved 6-(tert-butoxycarbonyl)-4,5,6,7-tetrahydrothiazolo[5,4-c]

pyridine-2-carboxylic acid (530 mg), 4-[(5-chloronaphthalen-2-yl)sulfonyl]-2-[(N-methyl)carbamoyl]piperazine hydrochloride (527 mg) and 1-hydroxybenzotriazole monohydrate (200 mg) and 1-(dimethylaminopropyl)-3-ethylcarbodiimide hydrochloride (324 mg), followed by the addition of triethylamine (0.18 ml). The resulting mixture was stirred overnight at room temperature. The reaction mixture was concentrated under reduced pressure. Methylene chloride was added to the residue and the resulting mixture was washed with water and saturated aqueous NaCl solution, each once. The organic layer was dried over anhydrous sodium sulfate and distilled under reduced pressure to remove the solvent. The residue was purified by chromatography on a silica gel column (methylene chloride:methanol=100:1), whereby pale yellow foam (577 mg) was obtained. The resulting foam was dissolved in methylene chloride (3 ml), followed by the addition of trifluoroacetic acid (6 ml). The resulting mixture was concentrated under reduced pressure. The precipitate so formed was collected by filtration while being washed with diethyl ether, whereby the title compound (596 mg) was obtained as colorless foam.

$^1$H-NMR (DMSO-$d_6$) δ: 2.53–2.62(3H,m), 2.63–2.74 (1H,m), 2.90–3.06(2H,m), 3.12–3.22(0.5H,m), 3.39–3.59 (1.5H,s), 3.68–3.77(1H,m), 4.28(1H,d,J=11.7 Hz), 4.28–4.50(1.5H,m), 4.97(0.5H,br s), 5.44(0.5H,d,J=13.2 Hz), 6.13(0.5H,br s), 7.72(1H,dd,J=8.8,2.0 Hz), 7.80(1H,d, J=8.8 Hz), 8.07–8.18(2H,m), 8.22–8.27(2H,m), 8.50(1H,s), 9.16–9.40(1H,m). MS (FAB) m/z: 534 [(M+H)$^+$, Cl$^{35}$], 536 [(M+H)$^+$, Cl$^{37}$].

Example B-97

4-[(6-Chloronaphthalen-2-yl)sulfonyl]-2-(N-methylcarbamoyl)-1-[(6-methylsulfonyl-4,5,6,7-tetrahydrothiazolo[5,4-c]pyridin-2-yl)carbonyl]piperazine In the same manner as in Example B-95, the title compound was obtained.

$^1$H-NMR (CDCl$_3$) δ: 2.61–2.87(1H,m), 2.88(6H,br s), 2.89–3.24(3H,m), 3.45–3.90(4H,m), 4.43–4.60(3H,m), 4.74, 5.21(total 1H,each br s), 5.60–6.09(total 1H,m), 6.30, 6.42(total 1H,br s), 7.58(1H,d,J=7.6 Hz), 7.80(1H,d,J=9.0 Hz), 7.89–7.91(3H,m), 8.35(1H,s). MS (FAB) m/z: 612 (M+H)$^+$.

Example B-98

4-[(5-Chloroindol-2-yl)sulfonyl]-1-[(6-dimethylaminosulfonyl-4,5,6,7-tetrahydrothiazolo[5,4-c]pyridin-2-yl)carbonyl]-2-[[(morpholin-4-yl)carbonyl]methyl]piperazine In the same manner as in Example B-95, the title compound was obtained.

$^1$H-NMR (DMSO-$d_6$) δ: 2.60–3.79(25H,m), 4.38,5.37 (total 1H,each d,J=13.5,14.5 Hz), 4.53(2H,s), 5.04,5.75(total 1H,each br), 7.02(1H,s), 7.30(1H,dd,J=8.8,2.0 Hz), 7.47 (1H,d,J=8.8 Hz), 7.76(1H,s), 12.41(1H,s). MS (FAB) m/z: 700 (M+H)$^+$.

Example B-99

4-[(5-Chloroindol-2-yl)sulfonyl]-1-[(6-methyl-4,5,6,7-tetrahydrothiazolo[5,4-c]pyridin-2-yl)carbonyl]-2-[[(morpholin-4-yl)carbonyl]methyl]piperazine hydrochloride To an ethanol solution (50 ml) of 1-(tert-butoxycarbonyl)-4-[(5-chloroindol-2-yl)sulfonyl]-2-[[(morpholin-4-yl)carbonyl]methyl]piperazine (710 mg) was added a saturated ethanol hydrochloride solution (20 ml) at room temperature. The resulting mixture was stirred for 3 hours. After concentration of the reaction mixture under reduced pressure, diethyl ether and ethanol were added to precipitate crystals. The resulting crystals were collected by filtration, washed with ethanol and then dried under reduced pressure. The crystals were dissolved in N,N-dimethylformamide to form an N,N-dimethylformamide solution (50 ml), followed by the addition of 1-hydroxybenzotriazole (68.8 mg), 1-(3-dimethylaminopropyl-3-ethylcarbodiimide hydrochloride (115.4 mg), lithium 6-methyl-4,5,6,7-tetrahydrothiazolo[5,4-c]pyridine-2-carboxylate (189.0 mg) and N-methylmorpholine (140.5 mg) at room temperature. The resulting mixture was stirred at room temperature for 19 hours. The reaction solvent was distilled off under reduced pressure. Distilled water and ethyl acetate were added to the residue and the water layer was extracted three times. The organic layers were combined, washed four times with distilled water, dried over anhydrous sodium sulfate and distilled under reduced pressure to remove the solvent. The residue was subjected to chromatography on a silica gel column (methanol : ethyl acetate=1:50). Diethyl ether and methylene chloride were added to the purified product to precipitate crystals. The resulting crystals were collected by filtration, followed by washing with diethyl ether. A 1N aqueous hydrochloric acid in ethanol (0.5 ml) and a small amount of distilled water were added. The solvent was then distilled off under reduced pressure. The residue was dried under heat at 60° C. under reduced pressure, whereby the title compound (187 mg) was obtained as a yellow amorphous solid. MS (FAB+) m/z: 607 [(M+H)$^+$, Cl$^{35}$], 609 [(M+H)$^+$, Cl$^{37}$].

$^1$H-NMR (DMSO-$d_6$) δ: 2.66–2.89(1H,m), 2.99(3H,s), 3.03–3.29(2H,m), 3.34–3.46(1H,m), 3.52–3.92(8H,m), 4.42–4.53(1.5H,m), 4.73–4.81(1H,m), 5.10–5.17(0.5H,m), 5.39–5.47(1H,m), 5.82–5.92(0.5H,m), 7.12(1H,br), 7.41 (1H,dd,J=2.0,8.8 Hz), 7.58(1H,d,J=8.8 Hz), 7.87(1H,br), 12.57(1H,s).

Example B-100

2-(Carbamoylmethyl)-4-[(5-chloroindol-2-yl)sulfonyl]-1-[(6-methyl-4,5,6,7-tetrahydrothiazolo[5,4-c]pyridin-2-yl)carbonyl]piperazine hydrochloride In the same manner as in Example B-98, the title compound was obtained. MS (FAB+) m/z: 537 [(M+H)$^+$, Cl$^{35}$], 539 [(M+H)$^+$, Cl$^{37}$].

$^1$H-NMR (DMSO-$d_6$) δ: 1.00–1.08(1H,m), 2.65–2.68 (1H,m), 2.88–2.94(2H,m), 3.00–3.12(1H,m), 3.27–3.46(3H, m), 3.62–3.73(1H,m), 4.32–4.39(1H,m), 5.04–5.37(1H,m), 6.83–6.86(1H,m), 7.01(1H,s), 7.27–7.33(1H,m), 7.46(1H,d, J=8.5 Hz), 7.76(1H,s), 12.42(1H,s).

Example B-101

1-[(5-Chloroisoindolin-2-yl)sulfonyl]-4-[(6-methyl-4,5,6,7-tetrahydrothiazolo[5,4-c]pyridin-2-yl)carbonylpiperazine hydrochloride In the same manner as in Example B-62, the title compound was obtained. MS (FAB+) m/z: 482 [(M+H)$^+$, Cl$^{35}$], 484 [(M+H)$^+$, Cl$^{37}$].

$^1$H-NMR (CDCl$_3$) δ: 2.93(3H,s), 3.08–3.19(1H,m), 3.28–3.40(8H,m), 3.40–3.53(1H,br), 3.68–3.77(2H,br), 4.28–4.46(2H,m), 4.63–4.65(4H,m), 7.33(1H,d,J=8.3 Hz), 7.37(1H,dd,J=2.0,8.3 Hz), 7.41(1H,s).

Example B-102

1-[(5-Ethynylindol-2-yl)sulfonyl]-4-[(6-methyl-4,5,6,7-tetrahydrothizolo[5,4-c]pyridin-2-yl)carbonyl]piperazine A saturated solution of hydrochloride in ethanol (8.0 ml) was added to 1-(tert-butoxycarbonyl)-4-[(6-methyl-4,5,6,7-tetrahydrothiazolo[5,4-c]pyridin-2-yl)carbonyl]piperazine (300 mg). After stirring for 1 hour, the reaction mixture was concentrated under reduced pressure. To the residue were added N,N-dimethylformamide (8.0 ml) and 1-phenylsulfonyl-5-trimethylsilylethynylindol-2-sulfonyl chloride (450 mg) at room temperature, followed by the addition of diisopropylethylamine (860 μl) at 0° C. After stirring at room temperature for 1 hour, the reaction mixture was concentrated under reduced pressure. The residue was purified by chromatography on a silica gel column (methylene chloride:acetone:methanol 30:10:1→10:10:1), whereby 4-[(6-methyl-4,5,6,7-tetrahydrothizolo[5,4-c]pyridin-2-yl)carbonyl]-1-[(1-phenylsulfonyl-5-trimethylsilylethynylindol-2-yl)carbonyl]piperazine (123 mg) was obtained as a colorless viscous substance. The resulting substance was dissolved in tetrahydrofuran (3.0 ml), followed by the addition of methanol (3.0 ml) and potassium hydroxide (22.5 mg) at room temperature. After stirring for 2 hours, a saturated aqueous solution (10 ml) of ammonium chloride was added. A saturated aqueous solution (15 ml) of sodium bicarbonate and methylene chloride (10 ml) were added and the mixture was separated into layers. The water layer was extracted with methylene chloride (10 ml). The organic layers were combined, dried over anhydrous sodium sulfate and distilled under reduced pressure to remove the solvent. The residue was purified by preparative thin-layer chromatography (methylene chloride:acetone:methanol=40:10:1) using silica gel, whereby the title compound (39.4 mg) was obtained as a colorless solid. The resulting compound was dissolved in methylene chloride, methanol and water. The resulting solution was concentrated under reduced pressure, followed by drying, whereby the title compound was obtained as a colorless solid.

$^1$H-NMR (CDCl$_3$) δ: 2.49(3H,s), 2.81(2H,t,J=5.5 Hz), 2.90(2H,t,J=5.5 Hz), 3.04(1H,s), 3.22(4H,br s), 3.68(2H,s), 3.88(2H,br s), 4.57(2H,br s), 7.00(1H,s), 7.37(1H,d,J=8.6 Hz), 7.47(1H,dd,J=8.6,1.5 Hz), 7.86(1H,s), 8.88(1H,br s) MS (FAB) m/z: 470 (M+H)$^+$.

Example B-103

2-(N-Methylcarbamoyl)-1-[(6-methyl-4,5,6,7-tetrahydrothiazolo[5,4-c]pyridin-2-yl)carbonyl]-4-[(1-phenylsulfonyl-5-trimethylsilylethynylindol-2-yl)sulfonyl]piperazine A saturated solution of hydrochloride in methanol (20 ml) was added to 4-(tert-butoxycarbonyl)-2-(N-methylcarbamoyl)-1-[(6-methyl-4,5,6,7-tetrahydrothiazolo[5,4-c]pyridin-2-yl)carbonyl]piperazine (410 mg) at room temperature. After stirring for 1 hour, the reaction mixture was concentrated under reduced pressure. To the residue were added methylene chloride (15 ml) and 1-phenylsulfonyl-5-trimethylsilylethynylindol-2-sulfonyl chloride (450 mg) at room temperature, followed by the addition of diisopropylethylamine (590 μl) at room temperature. After stirring for 12 hours, diisopropylethylamine (590 μl) was added again at room temperature. The resulting mixture was stirred at room temperature for 4 hours. A saturated aqueous solution (50 ml) of sodium bicarbonate and methylene chloride (50 ml) were added to the reaction mixture and the mixture was separated into layers. The water layer was extracted with methylene chloride (2×20 ml). The organic layers were combined, dried over anhydrous sodium sulfate and distilled under reduced pressure to remove the solvent. The residue was purified by chromatography on a silica gel column (methylene chloride:methanol=20:1), whereby the title compound (389 mg) was obtained as a colorless transparent glassy substance.

$^1$H-NMR (CDCl$_3$) δ: 0.25(9H,s), 2.50(3H,d,J=8.3 Hz), 2.65–3.02(8H,m), 3.05–3.30(2H,m), 3.70(2H,br s), 4.13 (1H,d,J=13.4 Hz), 4.40(1H,d,J=13.4 Hz), 4.67(½H,d,J=13.4 Hz), 5.24(½H,br s), 5.66(½H,d,J=14.0 Hz), 6.08(½H,br s), 6.39(1H,br s), 7.41(2H,t,J=7.7 Hz), 7.47–7.63(3H,m), 7.71 (1H,s), 8.02(2H,d,J=7.8 Hz), 8.18(1H,d,J=8.8 Hz). MS (FAB) m/z: 739 (M+H)$^+$.

Example B-104

4-[(5-Ethynylindol-2-yl)sulfonyl]-2-(N-methylcarbamoyl)-1-[(6-methyl-4,5,6,7-tetrahydrothiazolo[5,4-c]pyridin-2-yl)carbonyl]piperazine In tetrahydrofuran (5.0 ml) was dissolved 2-[-(N-methylcarbamoyl)-1-[(6-methyl-4,5,6,7-tetrahydrothiazolo[5,4-c]pyridin-2-yl)carbonyl]-4-[(1-phenylsulfonyl-5-trimethylsilylethynylindol-2-yl)carbonyl]piperazine (350 mg), followed by the addition of methanol (5.0 ml) and potassium hydroxide (102 mg) at room temperature. After stirring for 4 hours, a saturated aqueous solution (50 ml) of sodium bicarbonate and methylene chloride (50 ml) were added to the reaction mixture to separate the mixture into layers. The water layer was extracted with methylene chloride (50 ml). The organic layers were combined, dried over anhydrous sodium sulfate and distilled under reduced pressure to remove the solvent. The residue was purified twice by chromatography on a silica gel column (methylene chloride:methanol=20:1), whereby the title compound (126 mg) was obtained as a colorless solid. The resulting solid was dissolved in methylene chloride, methanol and water, followed by concentration under reduced pressure and drying, whereby the title compound was obtained as a colorless solid.

$^1$H-NMR (CDCl$_3$) δ: 2.51(3H,s), 2.75–3.30(11H,m), 3.58–3.85(3H,m), 4.50–4.70(2H,m), 5.25(½H,brs), 5.64 (½H,d,J=11.5 Hz), 6.10(½H,br s), 6.53(½H,br s), 7.10(1H, s), 7.43(2H,s), 7.85(1H,s), 10.78(1H,d,J=9.5 Hz). MS (FAB) m/z: 527 (M+H)$^+$.

Example B-105

1-[(6-Chloronaphthalen-2-yl)sulfonyl]-4-[(5-methyl-4,5,6,7-tetrahydrothiazolo[4,5-c]pyridine-2-yl)carbonyl]piperazine hydrochloride In the same manner as in Example B-62, the title compound was obtained.

$^1$H-NMR (DMSO-d$_6$) δ: 2.92(3H,s), 3.04–3.28(6H,m), 3.35–3.90(4H,m), 4.12–4.70(4H,m), 7.69(1H,dd,J=8.8,2.0 Hz), 7.82(1H,dd,J=8.8,2.0 Hz), 8.14(1H,d,J=8.8 Hz), 8.21 (1H,s), 8.25(1H,dd,dd,J=8.8,2.0 Hz), 8.50(1H,s), 11.27(1H, br s). MS (FAB) m/z: 491 [(M+H)$^+$, Cl$^{35}$], 493 [(M+H)$^+$, Cl$^{37}$].

Example B-106

4-[(5-Chloronaphthalen-2-yl)sulfonyl]-2-(N-methylcarbamoyl)-1-[(5-methyl-4,5,6,7-tetrahydrothiazolo[4,5-c]pyridin-2-yl)carbonyl]piperazine hydrochloride In the same manner as in Example B-62, the title compound was obtained.

¹H-NMR (DMSO-d₆) δ: 2.43–2.81(5H,m), 2.89–2.95 (4H,m), 3.22–3.80(6H,m), 4.16–4.65(2.5H,m), 5.01(0.5H, s), 5.36–5.45(0.5H,m), 6.06(0.5H,br s), 7.00(1H,s), 7.29 (1H,d,J=8.8 Hz), 7.48(1H,d,J=8.8 Hz), 7.75(1H,s), 11.25–11.40(1H,m), 12.43(1H,s). MS (FAB) m/z: 537 [(M+H)⁺, Cl³⁵], 539 [(M+H)⁺, Cl³⁷].

Example B-107

4-[(5-Chloroindol-2-yl)sulfonyl]-2-(N-methylcarbamoyl)-1-[(5-isopropyl-4,5,6,7-tetrahydrothiazolo[4,5-c]pyridin-2-yl)carbonyl]piperazine hydrochloride In the same manner as in Example B-62, the title compound was obtained.

¹H-NMR (DMSO-d₆) δ: 1.31–1.40(6H,m), 2.38–2.75 (5H,m), 3.10–3.80(8H,m), 4.22–4.50(2.5H,m), 4.97(½H,br s), 5.35–5.49(½H,m), 6.13(¼H,br s), 6.19(¼H,br s), 7.70 (1H,d,J=8.8 Hz), 7.79(1H,d,J=8.8 Hz), 8.09–8.28(4H,m), 8.49(1H,s), 10.80–11.34(1H,m). MS (FAB) m/z: 576 [(M+H)⁺, Cl³⁵], 578 [(M+H)⁺, Cl³⁷].

Example B-108

1-[(5-Chloroindol-2-yl)sulfonyl]-4-[(thiazolo[5,4-c]pyridin-2-yl)carbonyl]piperazine In the same manner as in Example B-62, the title compound was obtained.

¹H-NMR (DMSO-d₆) δ: 3.20(4H,br s), 3.84(2H,br s), 4.35(2H,br s), 7.28(1H,dd,J=8.8,2.5 Hz), 7.47(1H,dd,J=8.8, 2.0 Hz), 7.74(1H,d,J=2.0 Hz), 8.05(1H,d,J=5.4 Hz), 8.67 (1H,d,J=5.4 Hz), 9.44(1H,s), 12.41(1H,s). MS (FAB) m/z: 462 [(M+H)⁺, Cl³⁵], 464 [(M+H)⁺, Cl³⁷].

Example B-109

2-[[4-[(5-Chloroindol-2-yl)sulfonyl]piperazin-1-yl]carbonyl]-6-methylthiazolo[5,4-c]pyridinium iodide In the same manner as in Example B-62, the title compound was obtained.

¹H-NMR (DMSO-d₆) δ: 3.14–3.28(4H,m), 3.86(2H,br s), 4.29(2H,br s), 4.49(3H,s), 7.04(1H,s), 7.30(1H,dd,J=8.8,2.0 Hz), 7.48(1H,d,J=8.8 Hz), 7.76(1H,s), 8.72(1H,d,J=6.8 Hz), 9.00(1H,d,J=6.8 Hz), 9.94(1H,s), 12.44(1H,br s). MS (FAB) m/z: 476, 478.

Example B-110

1-[(6-tert-Butoxycarbonyl-7-methyl-4,5,6,7-tetrahydrothiazolo[5,4-c]pyridin-2-yl)carbonyl]-4-[(5-chloroindol-2-yl)sulfonyl]-2-(N-methylcarbamoyl)piperazine hydrochloride In the same manner as in Example B-62, the title compound was obtained.

¹H-NMR (DMSO-d₆) δ: 1.38(3H,d,J=6.6 Hz), 1.42(9H, s), 2.55–2.80(5H,m), 3.31(3H,s), 3.46–3.56(½H,m), 3.61–3.72(1H,m), 3.81–3.90(1H,m), 4.18–4.29(2H,m), 4.43–4.48(½H,m), 4.91–5.05(1H,m), 5.26–5.45(1H,m), 6.15–6.25(2H,m), 6.98–7.03(1H,m), 7.26–7.33(1H,m), 7.41–7.50(1H,m), 7.73–7.80(1H,m), 8.02–8.17(1H,m), 12.40(1H,s). MS (FAB) m/z: 637 [(M+H)⁺, Cl³⁵], 639 [(M+H)⁺, Cl³⁷].

Example B-111

4-[(5-Chloroindol-2-yl)sulfonyl]-2-(N-methylcarbamoyl)-1-[(7-methyl-4,5,6,7-tetrahydrothiazolo[5,4-c]pyridin-2-yl)carbonyl]piperazine trifluoroacetate In the same manner as in Example B-35, the title compound was obtained.

¹H-NMR (DMSO-d₆) δ: 1.55(3H,d,J=6.4 Hz), 2.28–2.76 (5H,m), 2.88–3.10(2H,m), 3.25–3.65(1H,m), 4.20–4.30(1H, m), 4.40–4.50(½H,m), 4.83(1H,br s), 4.92–5.02(½H,m), 5.40–5.50(½H,m), 6.13(½H,s), 7.00(1H,s), 7.30(1H,d,J=8.8 Hz), 7.46(1H,d,J=8.8 Hz), 7.76(1H,s), 8.06–8.14(1H,m), 8.93–9.62(2H,m), 12.40(1H,s). MS (FAB) m/z: 537 [(M+H)⁺, Cl³⁵], 539 [(M+H)⁺, Cl³⁷].

Example B-112

4-[(5-Chloroindol-2-yl)sulfonyl]-1-[(6,7-dimethyl-4,5,6,7-tetrahydrothiazolo[5,4-c]pyridin-2-yl)carbonyl]-2-(N-methylcarbamoyl)piperazine hydrochloride In the same manner as in Example B-32, the title compound was obtained.

¹H-NMR (DMSO-d₆) δ: 1.40–1.70(3H,m), 2.40–2.80 (4H,m), 2.92(3H,br s), 3.00–3.25(2H,m), 3.40–3.80(1H,m), 4.19–4.30(1H,m), 4.39–4.50(½H,m), 4.66–4.82(½H,br s), 5.00(½H,br s), 5.40–5.55(½H,m), 5.73(½H,br s), 6.17(½H, br s), 7.00(1H,s), 7.30(1H,d,J=8.8 Hz), 7.46(1H,d,J=8.8 Hz), 7.76(1H,s), 8.05–8.20(1H,m), 12.41(1H,s). MS (EI) m/z: 550 (M⁺, Cl³⁵) , 552 (M⁺, Cl³⁷).

Example B-113

2-[N-[(5-Acetoxy-4-oxo-4H-pyran-2-yl)methyl]carbamoyl]-4-[(5-chloroindol-2-yl)sulfonyl]-1-[(6-methyl-4,5,6,7-tetrahydrothiazolo[5,4-c]pyridin-2-yl)carbonyl]piperazine In the same manner as in Example B-62, the title compound was obtained.

¹H-NMR (DMSO-d₆ at 100° C.) δ: 2.22(3H,s), 2.38(3H, s), 2.65–2.89(8H,m), 3.64(2H,s), 3.70(1H,d,J=11.0 Hz), 4.28(1H,d,J=12.4 Hz), 6.30(1H,s), 6.98(1H,s), 7.26(1H,dd, J=9.2,1.8 Hz), 7.46(1H,d,J=9.2 Hz), 7.70(1H,d,J=1.8 Hz), 8.28(1H,s), 8.51(1H,s), 12.00(1H,br s). MS (FAB) m/z: 689 [(M+H)⁺, Cl³⁵], 691 [(M+H)⁺, Cl³⁷].

Example B-114

4-[(5-Chloroindol-2-yl)sulfonyl]-2-[N-[(5-hydroxy-4-oxo-4H-pyran-2-yl)methyl]carbamoyl]-1-[(6-methyl-4,5,6,7-tetrahydrothiazolo[5,4-c]pyridin-2-yl)carbonyl]piperazine hydrochloride In the same manner as in Example B-23, the title compound was obtained.

¹H-NMR (DMSO-d₆ at 100° C.) δ: 2.71–2.84(1H,m), 2.90(3H,s), 3.00(1H,dd,J=12.2,4.3 Hz), 3.06–3.28(4H,m), 3.54(2H,br s), 3.74(1H,d,J=12.0 Hz), 4.09–4.28(4H,m), 4.52(2H,br s), 7.00(1H,d,J=1.2 Hz), 7.29(1H,dd,J=9.2,1.8 Hz), 7.50(1H,d,J=9.2 Hz), 7.73(1H,d,J=1.8 Hz), 7.91(1H,s), 8.60(1H,s), 12.14(1H,br s). MS (FAB) m/z: 647 [(M+H)⁺, Cl³⁵], 649 [(M+H)⁺, Cl³⁷].

Example B-115

N-[[4-[(5-Chloroindol-2-yl)sulfonyl]-1-[(6-methyl-4,5,6,7-tetrahydrothiazolo[5,4-c]pyridin-2-yl)carbonyl]piperazin-2-yl]acetyl]methanesulfonamide hydrochloride In the same manner as in Example B-62, the title compound was obtained.

¹H-NMR (DMSO-d₆) δ: 2.61–3.10(8H,m), 3.15(3H,s), 3.34–3.81(4H,m), 3.90–4.48(2.5H,m), 4.60–4.72(1H,m), 5.10(0.5H,br s), 5.29–5.39(0.5H,m), 5.80–6.00(0.5H,m), 7.02(1H,s), 7.30(1H,d,J=8.8 Hz), 7.48(1H,d,J=8.8 Hz), 7.75 (1H,s), 11.45–11.70(1H,m), 11.85–12.00(1H,m), 12.46(1H, br s). MS (FAB) m/z: 615 [(M+H)$^+$, Cl$^{35}$], 617 [(M+H)$^+$, Cl$^{37}$].

Example B-116

N-[[1-[(6-tert-Butoxycarbonyl-4,5,6,7-tetrahydrothiazolo[5,4-c]pyridin-2-yl)carbonyl]-4-[(5-chloroindol-2-yl)sulfonyl]piperazin-2-yl]acetyl]methanesulfonamide In the same manner as in Example B-62, the title compound was obtained.

$^1$H-NMR (DMSO-d$_6$) δ: 1.40(9H,s), 2.62–2.93(6H,m), 3.09–3.20(3H,m), 3.40–3.50(0.5H,m), 3.60–3.78(4.5H,m), 4.35–4.43(0.5H,m), 4.61(2H,s), 5.07–5.14(0.5H,m), 5.30–5.40(0.5H,m), 5.90–6.00(0.5H,m), 7.03(1H,s), 7.29 (1H,dd,J=8.8,2.0 Hz), 7.45(1H,d,J=8.8 Hz), 7.74(1H,s), 11.84(1H,br s), 12.39(1H,br s). MS (FAB) m/z: 701 [(M+H)$^+$, Cl$^{35}$], 703 [(M+H)$^+$, Cl$^{37}$].

Example B-117

N-[[4-[(5-Chloroindol-2-yl)sulfonyl]-1-[(4,5,6,7-tetrahydrothiazolo[5,4-c]pyridin-2-yl)carbonyl]piperazin-1-yl]acetyl]methanesulfonamide trifluoroacetate In the same manner as in Example B-35, the title compound was obtained.

$^1$H-NMR (DMSO-d$_6$) δ: 2.64–3.04(6H,m), 3.15(3H,d,J=7.1 Hz), 3.41–3.53(2H,m), 3.60–3.80(4H,m), 4.35–4.43 (0.5H,m), 4.44(2H,s), 5.06–5.12(0.5H,m), 5.25–5.35(0.5H, m), 5.86(0.5H,br s), 7.02(1H,s), 7.29(1H,dd,J=8.8,2.0 Hz), 7.46(1H,d,J=8.8 Hz), 7.75(1H,s), 9.25(2H,br s), 11.86(1H,br s), 12.42(1H,br s). MS (FAB) m/z: 601 [(M+H)$^+$, Cl$^{35}$], 603 [(M+H)$^+$, Cl$^{37}$].

Example B-118

N-[[1-[[6-(1-Acetoxyethoxy)carbonyl-4,5,6,7-tetrahydrothiazolo[5,4-c]pyridin-2-yl)carbonyl]-4-[(5-chloroindol-2-yl)sulfonyl]piperazin-2-yl]acetyl]methanesulfonamide In ethanol (2 ml) was dissolved N-[[4-[(5-chloroindol-2-yl)sulfonyl]-1-[(4,5,6,7-tetrahydrothiazolo[5,4-c]pyridin-2-yl)carbonyl]piperazin-2-yl]acetyl]methanesulfonamide trifluoroacetate (97 mg), followed by the addition of triethylamine (0.63 ml) and 1-acetoxyethyl p-nitrophenyl carbonate (110 mg). The resulting mixture was stirred at room temperature for 4 hours. The reaction mixture was concentrated under reduced pressure. Methylene chloride was added to the residue. The resulting mixture was washed with water, dried over anhydrous sodium sulfate and distilled to remove the solvent. The residue was purified by chromatography on a silica gel column (methylene chloride:methanol=50:1), whereby the title compound (50 mg) was obtained as a colorless foam.

$^1$H-NMR (DMSO-d$_6$) δ: 1.42(3H,br s), 2.01(3H,br s), 2.60–2.90(6H,m), 3.07–3.16(3H,m), 3.64–3.80(4H,m), 4.09–4.12(0.5H,m), 4.35–4.41(0.5H,m), 4.63–4.77(2.5H, m), 5.05–5.11(0.5H,m), 5.32–5.39(0.5H,m), 5.89–5.96 (0.5H,m), 6.62–6.70(1H,m), 7.02(1H,s), 7.29(1H,d,J=8.8 Hz), 7.46(1H,d,J=8.8 Hz), 7.75(1H,s), 11.88(1H,br s), 12.44 (1H,br s). MS (FAB) m/z: 731 [(M+H)$^+$, Cl$^{35}$], 733 [(M+H)$^+$, Cl$^{37}$].

Example B-119

4-[(6-Chlorobenzo[b]thien-2-yl)sulfonyl]-2-(N-methylcarbamoyl)-1-[(6-methyl-4,5,6,7-tetrahydrothiazolo[5,4-c]pyridin-2-yl)carbonyl]piperazine hydrochloride In the same manner as in Example B-62, the title compound was obtained.

$^1$H-NMR (DMSO-d$_6$) δ: 2.62(3H,s), 2.66–4.49(13.5H, m), 4.60–4.76(1H,m), 5.05(½H,br s), 5.50–5.62(½H,m), 6.15–6.27(½H,m), 7.57(1H,d,J=8.8 Hz), 8.07(1H,d,J=8.8 Hz), 8.08(1H,s), 8.17(½H,br s), 8.23(½H,br s), 8.37(1H,s). MS (FAB) m/z: 554 [(M+H)$^+$, Cl$^{35}$], 556 [(M+H)$^+$, Cl$^{37}$].

Example B-120

4-[(6-Chloronaphthalen-2-yl)sulfonyl]-1-[(thiazolo[4,5-c]pyridin-2-yl)carbonyl]piperazine In the same manner as in Example B-62, the title compound was obtained.

$^1$H-NMR (CDCl$_3$) δ: 3.27(4H,br s), 3.90–4.03(2H,m), 4.61–4.73(2H,m), 7.58(1H,dd,J=8.8,2.0 Hz), 7.79(1H,dd,J=8.8,2.0 Hz), 7.85–8.01(4H,m), 8.34(1H,s), 8.59(1H,d,J=5.4 Hz), 9.35(1H,d,J=1.0 Hz). MS (FAB) m/z: 473 [(M+H)$^+$, Cl$^{35}$], 475 [(M+H)$^+$, Cl$^{37}$].

Example B-121

2-[[4-[(6-Chloronaphthalen-2-yl)sulfonyl]piperazin-1-yl]carbonyl]thiazolo[4,5-c]pyridine N-oxide In the same manner as in Example B-34, the title compound was obtained.

$^1$H-NMR (DMSO-d$_6$) δ: 3.15(4H,br s), 3.80(2H,br s), 4.32(2H,br s), 7.70(1H,dd,J=8.8,2.0 Hz), 7.83(1H,dd,J=8.8, 2.0 Hz), 8.15(1H,d,J=8.8 Hz), 8.18(1H,d,J=8.8 Hz), 8.22 (1H,s), 8.25(1H,d,J=8.8 Hz), 8.30(1H,d,J=2.0 Hz), 8.32(1H, d,J=1.5 Hz), 8.51(1H,s), 9.03(1H,d,J=1.5 Hz). MS (FAB) m/z: 489 [(M+H)$^+$, Cl$^{35}$], 491 [(M+H)$^+$, Cl$^{37}$].

Example B-122

2-[[4-[(6-Chloronaphthalen-2-yl)sulfonyl]piperazin-1-yl]carbonyl]-5-methylthiazolo[4,5-c]pyridinium iodide In the same manner as in Example B-33, the title compound was obtained.

$^1$H-NMR (DMSO-d$_6$) δ: 3.10–3.25(4H, m), 3.85(2H,br s), 4.29(2H,br s), 4.47(3H,s), 7.71(1H,dd,J=8.8,2.0 Hz), 7.84 (1H,d,J=8.8 Hz), 8.17(1H,d,J=8.8 Hz), 8.23(1H,s), 8.26(1H, d,J=8.8 Hz), 8.53(1H,s), 8.86(1H,d,J=6.8 Hz), 8.90(1H,d,J=6.8 Hz), 10.03(1H,s). MS (FAB) m/z: 487, 489.

Example B-123

4-[(6-Chloronaphthalen-2-yl)sulfonyl]-2-(N-methylcarbamoyl)-1-[(thiazolo[4,5-c]pyridin-2-yl)carbonyl]piperazine In the same manner as in Example B-62, the title compound was obtained.

$^1$H-NMR (DMSO-d$_6$ at 100° C.) δ: 2.61(3H,d,J=4.9 Hz), 2.75–2.88(1H,m), 2.98(1H,dd,J=12.7,4.9 Hz), 3.20–3.80 (1H,m), 4.29(1H,d,J=2.7 Hz), 4.90–5.48(1H,m), 7.61(1H, dd,J=8.8,2.0 Hz), 7.79(1H,br s), 7.81(1H,dd,J=8.8,2.0 Hz), 8.04–8.10(2H,m), 8.12(1H,d,J=5.4 Hz), 8.15(1H,d,J=8.8

Hz), 8.44(1H,d,J=1.0 Hz), 8.56(1H,d,J=5.4 Hz), 9.28(1H,br s). MS (FAB) m/z: 530 [(M+H)$^+$, Cl$^{35}$], 532 [(M+H)$^+$, Cl$^{37}$].

Example B-124

2-[[4-[(6-Chloronaphthalen-2-yl)sulfonyl]-2-(N-methylcarbamoyl)piperazin-1-yl]carbonyl]-5-methylthiazolo[4,5-c]pyridinium Iodide In the same manner as in Example B-33, the title compound was obtained.

$^1$H-NMR (DMSO-d$_6$ at 100° C.) δ: 2.62(3H,d,J=4.4 Hz), 2.77–2.87(1H,m), 2.94–3.03(1H,m), 3.10–3.90(2H,m), 4.31 (1H,d,J=12.7 Hz), 4.50(3H,s), 4.85–5.85(2H,m), 7.64(1H, dd,J=8.8,2.0 Hz), 7.80(1H,dd,J=8.8,2.0 Hz), 7.82–7.90(1H, m), 8.10(1H,d,J=8.8 Hz), 8.12(1H,d,J=2.0 Hz), 8.17(1H,d, J=8.8 Hz), 8.45(1H,s), 8.86(2H,d,J=1.5 Hz), 9.93(1H,br s). MS (FAB) m/z: 544 (M$^+$, Cl$^{35}$), 546 (M$^+$, Cl$^{37}$)

Example B-125

4-[(6-Chloronaphthalen-2-yl)sulfonyl]-2-(N-methylcarbamoyl)-1-[(5-methyl-4,5,6,7-tetrahydrothiazolo[4,5-c]pyridin-2-yl)carbonyl]piperazine hydrochloride The title compound was obtained in the same manner as in Referential Example 404 in which reduction by sodium borohydride had been employed.

$^1$H-NMR (DMSO-d$_6$) δ: 2.41–2.80(5H,m), 3.12–3.78 (7H,m), 4.15–4.60(2.5H,m), 4.97(0.5H,br s), 5.35–5.48 (0.5H,m), 6.03(0.5H,br s), 7.70(1H,dd,J=8.8,2.0 Hz), 7.79 (1H,d,J=8.8 Hz), 8.06–8.20(2H,m), 8.22(1H,s), 8.24(1H,d, J=8.8 Hz), 8.48(1H,s), 11.20–11.63(1H,m). MS (FAB) m/z: 548 [(M+H)$^+$, Cl$^{35}$], 550 [(M+H)$^+$, Cl$^{37}$].

Example B-126

4-[(6-Chloronaphthalen-2-yl)sulfonyl]-1-[(6-ethyl-4,5,6,7-tetrahydrothiazolo[4,5-c]pyridin-2-yl)carbonyl-2-(N-methylcarbamoyl)piperazine hydrochloride In the same manner as in Referential Example 404, the title compound was obtained.

$^1$H-NMR (DMSO-d$_6$) δ: 1.28–1.40(3H,m), 2.40–2.79 (5H,m), 3.10–3.83(10H,m), 4.15–4.60(2.5H,m), 4.97(0.5H, br s), 5.35–5.45(0.5H,m), 6.05–6.12(0.5H,m), 7.70(1H,dd, J=8.8,2.0 Hz), 7.79(1H,d,J=8.8 Hz), 8.05–8.17(2H,m), 8.22 (1H,s), 8.24(1H,d,J=8.8 Hz), 8.49(1H,s), 11.01–11.20(1H, m). MS (FAB) m/z: 562 [(M+H)$^+$, Cl$^{35}$], 564 [(M+H)$^+$, Cl$^{37}$].

Example B-127 tert-Butyl [2-[[4-[(6-chloronaphthalen-2-yl)sulfonyl]piperazin-1-yl]carbonyl]-4,5,6,7-tetrahydrothiazolo[5,4-c]pyridin-6-yl)acetate In N,N-dimethylformamide (50 ml) was dissolved 1-[(6-chloronaphthalen-2-yl)sulfonyl]-4-[(4,5,6,7-tetrahydrothiazolo[5,4-c]pyridin-2-yl)carbonyl]piperazine hydrochloride (240 mg), followed by the addition of triethylamine (0.28 ml) and then tert-butyl bromoacetate (0.14 ml). The resulting mixture was stirred overnight at room temperature. After concentration of the reaction mixture under reduced pressure, ethyl acetate was added to the residue. The resulting mixture was washed with water, dried over anhydrous sodium sulfate and distilled under reduced pressure to remove the solvent. The residue was purified by chromatography on a silica gel column (Φ3.0×12.0 cm, hexane:ethyl acetate 3:2), whereby the title compound (207 mg) was obtained as a colorless foam.

$^1$H-NMR (CDCl$_3$) δ: 1.47(9H,s), 2.86–2.92(2H,m), 3.00 (2H,t,J=5.4 Hz), 3.18(4H,br s), 3.35(2H,s), 3.87(2H,br s), 3.90(2H,s), 4.55(2H,br s), 7.57(1H,dd,J=8.8,2.0 Hz), 7.76 (1H,dd,J=8.8,2.0 Hz), 7.87–7.93(3H,m), 8.31(1H,s). MS (FAB) m/z: 591 [(M+H)$^+$, Cl$^{35}$], 593 [(M+H)$^+$, C$^{37}$].

Example B-128

Ethyl [2-[[4-[(6-Chloronaphthalen-2-yl)sulfonyl]piperazin-1-yl]carbonyl]-4,5,6,7-tetrahydrothiazolo[5,4-c]pyridin-6-yl)acetate In the same manner as in Example B-127, the title compound was obtained.

$^1$H-NMR (CDCl$_3$) δ: 1.28(3H,t,J=7.3 Hz), 2.85–2.95(2H, m), 2.97–3.07(2H,m), 3.18(4H,br s), 3.46(2H,s), 3.87(2H,br s), 3.92(2H,s), 4.20(2H,q,J=7.3 Hz), 4.55(2H,br s), 7.57(1H, d,J=8.8 Hz), 7.76(1H,d,J=8.8 Hz), 7.82–7.95(3H,m), 8.31 (1H,s). MS (FAB) m/z: 477 [(M+H)$^+$, Cl$^{35}$], 479 [(M+H)$^+$, Cl$^{37}$].

Example B-129

[2-[[4-[(6-Chloronaphthalen-2-yl)sulfonyl]piperazin-1-yl]carbonyl]-4,5,6,7-tetrahydrothiazolo[5,4-c]pyridin-6-yl)acetic acid trifluoroacetate In methylene chloride (1 ml) was dissolved tert-butyl [2-[[4-[(6-chloronaphthalen-2-yl)sulfonyl]piperazin-1-yl]carbonyl]-4,5,6,7-tetrahydrothiazolo[5,4-c]pyridin-6-yl)acetate (200 mg), followed by the addition of trifluoroacetic acid (2 ml). The resulting mixture was stirred at room temperature for 2 hours. After concentration under reduced pressure, diethyl ether was added to the residue. The precipitate so formed was collected by filtration, whereby the title compound (193 mg) was obtained as a colorless foam.

$^1$H-NMR (DMSO-d$_6$) δ: 2.96(2H,br s), 3.08(4H,br s), 3.27–3.96(6H,m), 4.37(4H,br s), 7.70(1H,dd,J=8.8,2.0 Hz), 7.82(1H,d,J=8.8 Hz), 8.20–8.28(3H,m), 8.50(1H,s). MS (FAB) m/z: 535 [(M+H)$^+$, Cl$^{35}$], 537 [(M+H)$^+$, Cl$^{37}$].

Example B-130

N-[[2-[[4-(6-Chloronaphthalen-2-yl)sulfonyl]piperazin-1-yl]carbonyl]-4,5,6,7-tetrahydrothiazolo[5,4-c]pyridin-6-yl]acetyl]methanesulfonamide hydrochloride In tetrahydrofuran (20 ml) was dissolved [2-[[4-[(6-chloronaphthalen-2-yl)sulfonyl]piperazin-1-yl]carbonyl]-4,5,6,7-tetrahydrothiazolo[5,4-c]pyridin-6-yl]acetic acid trifluoroacetate (110 mg), followed by the addition of carbonyldiimidazole (60 mg). The resulting mixture was heated under reflux for 1 hour. After the reaction was cooled to room temperature, methanesulfonamide (34 mg) and 1,8-diazabicyclo[5.4.0]-7-undecene (0.05 ml) were added and they were stirred for 30 minutes. The reaction mixture was concentrated under reduced pressure. To the residue was added methylene chloride, followed by washing with water, 0.2N hydrochloric acid and saturated aqueous NaCl solution, each once. The organic layer thus extracted was dried over anhydrous sodium sulfate and distilled under reduced pressure to remove the solvent. The residue was purified by chromatography on a silica gel column (methylene chloride:methanol=100:4), whereby colorless foam was obtained. The resulting foam was suspended in a 1N aqueous hydrochloric acid in ethanol solution (1 ml), followed by concentration under reduced pressure and azeotropy with water, whereby the title compound (44 mg) was obtained as pale yellow foam.

$^1$H-NMR (DMSO-d$_6$) δ: 3.00(2H,br s), 3.11(4H,br s), 3.28(3H,s), 3.32–4.06(6H,m), 4.40(4H,br s), 7.70(1H,dd,J=8.8,2.0 Hz), 7.82(1H,d,J=8.8 Hz), 8.14(1H,d,J=8.8 Hz), 8.22 (1H,s), 8.25(1H,d,J=8.8 Hz), 8.50(1H,s). MS (FAB) m/z: 612 [(M+H)$^+$, Cl$^{35}$], 614 [(M+H)$^+$, Cl$^{37}$].

Example B-131

Ethyl [4-[[4-[(6-chloronaphthalen-2-yl)sulfonyl]-1-[(6-methyl-4,5,6,7-tetrahydrothiazolo[5,4-c]pyridin-2-yl)carbonyl]piperazin-2-yl]carbonyl]piperazin-1-yl]acetate hydrochloride In the same manner as in Example B-62, the title compound was obtained.

$^1$H-NMR (DMSO-d$_6$ at 100° C.) δ: 1.26(3H,t,J=7.2 Hz), 2.80–3.35(13H,m) 3.44–3.89(11H,m), 4.20(2H,q,J=7.2 Hz), 4.52(2H,br s), 7.67(1H,dd,J=8.8,1.7 Hz), 7.81(1H,d,J=8.8, 1.7 Hz), 8.11(1H,d,J=8.8 Hz), 8.16(1H,s), 8.19(1H,d,J=8.8 Hz), 8.47(1H,s). MS (FAB) m/z: 689 [(M+H)$^+$, Cl$^{35}$], 691 [(M+H)$^+$, Cl$^{37}$].

Example B-132

[4-[[4-[(6-Chloronaphthalen-2-yl)sulfonyl]-1-[(6-methyl-4,5,6,7-tetrahydrothiazolo[5,4-c]pyridin-2-yl)carbonyl]piperazin-2-yl]carbonyl]piperazin-1-yl] acetic acid hydrochloride In the same manner as in Example B-23, the title compound was obtained.

$^1$H-NMR (DMSO-d$_6$ at 100° C.) δ: 2.84–2.93(5H,m), 3.10–3.34(7H,m), 3.45–3.61(2H,m), 3.70–4.70(12H,m), 7.67(1H,dd,J=8.8,2.0 Hz), 7.81(1H,d,J=8.8,1.7 Hz), 8.11 (1H,d,J=8.8 Hz), 8.17(1H,s), 8.20(1H,d,J=8.8 Hz), 8.48(1H, s). MS (FAB) m/z: 661 [(M+H)$^+$, Cl$^{35}$], 663 [(M+H)$^+$, Cl$^{37}$].

Example B-133

N-[[4-[(6-Chloronaphthalen-2-yl)sulfonyl]-1-[(6-methyl-4,5,6,7-tetrahydrothiazolo[5,4-c]pyridin-2-yl)carbonyl]piperazin-2-yl]carbonyl] methanesulfonamide hydrochloride In tetrahydrofuran (30 ml) was dissolved 2-carbamoyl-4-[(6-chloronaphthalen-2-yl)sulfonyl]-1-[(6-methyl-4,5,6,7-tetrahydrothiazolo[4,5-c]pyridin-2-yl)carbonyl]piperazine (300 mg), followed by the addition of a 0.5 mole toluene solution (1.12 ml) of potassium bis(trimethylsilyl)amide. The resulting mixture was stirred for 10 minutes under ice cooling. After the addition of methanesulfonyl chloride (0.04 ml), the resulting mixture was warmed up to room temperature and stirred for 1 hour. The reaction mixture was concentrated under reduced pressure. Methylene chloride was added to the residue and the resulting mixture was washed once with water and once with saturated aqueous NaCl solution. The organic layer thus extracted was dried over anhydrous sodium sulfate and distilled under reduced pressure to remove the solvent. The residue was purified by chromatography on a silica gel column (methylene chloride:methanol=100:0→100:3), whereby colorless foam was obtained. The resulting foam was suspended in 1N hydrochloric acid (1 ml). The resulting suspension was concentrated under reduced pressure, whereby the title compound (96 mg) was obtained as pale yellow foam.

$^1$H-NMR (DMSO-d$_6$) δ: 2.73–2.84(1H,m), 2.90(6H,s), 3.09–3.77(8H,m), 3.99–4.27(1H,m), 4.39–4.51(1H,m), 4.69–4.79(1H,m), 4.99(1H,s), 7.64–7.73(2H,m), 8.06–8.10 (1H,m), 8.12–8.19(1H,m), 8.44(1H,s), 11.41(1H,br s), 11.52 (1H,s). MS (FAB) m/z: 612 [(M+H)$^+$, Cl$^{35}$], 614 [(M+H)$^+$, Cl$^{37}$].

Example B-134

5-[2-[4-[(6-Chloronaphthalen-2-yl)sulfonyl]-1-[(4,5,6,7-tetrahydrothiazolo[5,4-c]pyridin-2-yl)carbonyl] piperazin-2-yl]ethyl]tetrazole trifluoroacetate In N,N-dimethylformamide (10 ml) were dissolved lithium 6-tert-butoxycarbonyl-4,5,6,7-tetrahydrothiazolo[5,4-c]pyridine-2-carboxylate (329 mg), 5-[2-[4-[(6-chloronaphthalen-2-yl)sulfonyl]piperazin-2-yl]ethyl]tetrazole trifluoroacetate (295 mg), 1-hydroxybenzotriazole monohydrate (9 mg) and 1-(3-dimethylaminopropyl)-3-ethylcarbodiimide hydrochloride (114 mg), followed by stirring overnight at room temperature. The reaction mixture was concentrated under reduced pressure. Methylene chloride was added to the residue and the resulting mixture was washed with water and saturated aqueous NaCl solution, each once. The organic layer was then dried over anhydrous sodium sulfate and distilled under reduced pressure to remove the solvent. The residue was purified by chromatography on a silica gel column (methylene chloride:methanol=25:2), whereby pale yellow foam (48 mg) was obtained. The resulting foam was dissolved in methylene chloride (1 ml), followed by the addition of trifluoroacetic acid (1 ml). After concentration under reduced pressure, the precipitate so formed was collected by filtration while being washed with diethyl ether, whereby the title compound (48 mg) was obtained as a colorless solid.

$^1$H-NMR (DMSO-d$_6$) δ: 1.12–1.40(2H,m), 1.95–3.00 (7H,m), 3.42–3.47(1H,m), 3.60–3.88(2.5H,m), 4.10–4.15 (0.5H,br s), 4.38–4.45(2H,m), 4.67–4.80(1H,m), 5.25–5.31 (0.5H,m), 5.58–5.65(0.5H,m), 7.70(1H,d,J=8.8 Hz), 7.82 (1H,d,J=8.8 Hz), 8.14(1H,d,J=8.8 Hz), 8.18–8.26(2H,m), 8.46–8.50(1H,m). MS (FAB) m/z: 573 [(M+H)$^+$, Cl$^{35}$], 575 [(M+H)$^+$, Cl$^{37}$].

Example B-135

5-[2-[4-[(6-Chloronaphthalen-2-yl)sulfonyl]-1-[(6-methyl-4,5,6,7-tetrahydrothiazolo[5,4-c]pyridin-2-yl)carbonyl]piperazin-2-yl]ethyl]tetrazole In the same manner as in Example B-32, the title compound was obtained.

$^1$H-NMR (DMSO-d$_6$) δ: 1.08–1.40(2H,m), 1.90–3.84 (15.5H,m), 4.10(0.5H,br s), 4.32–4.43(0.5H,m), 4.72–4.80 (0.5H,m), 5.35–5.43(0.5H,m), 5.69–5.80(0.5H,m), 7.68(1H, dd,J=8.8,2.0 Hz). MS (FAB) m/z: 587 [(M+H)$^+$, Cl$^{35}$], 589 [(M+H)$^+$, Cl$^{37}$].

Example B-136

5-[[[[4-[(6-Chloronaphthalen-2-yl)sulfonyl]-1-[(4,5,6,7-tetrahydrothiazolo[5,4-c]pyridin-2-yl)carbonyl] piperazin-2-yl]carbonyl]amino]methyl]tetrazole trifluoroacetate In the same manner as in Example B-134, the title compound was obtained.

$^1$H-NMR (DMSO-d$_6$) δ: 2.63–2.78(1H,m), 2.85–2.93 (1H,m), 2.99–3.05(1H,m), 3.28–3.79(6H,m), 4.27–4.34(1H, m), 4.40–4.70(3.5H,m), 5.13–5.16(0.5H,m), 5.48–5.56

(0.5H,m), 6.10–6.13(0.5H,m), 7.70(1H,d,J=8.8 Hz), 7.79 (1H,d,J=8.8 Hz), 8.08–8.26(3H,m), 8.48(1H,s), 8.89–9.00 (1H,m). MS (FAB) m/z: 602 [(M+H)$^+$, Cl$^{35}$], 604 [(M+H)$^+$, Cl$^{37}$].

Example B-137

5-[[[[4-[(6-Chloronaphthalen-2-yl)sulfonyl]-1-[(6-methyl-4,5,6,7-tetrahydrothiazolo[5,4-c]pyridin-2-yl)carbonyl]piperazin-2-yl]carbonyl]amino]methyl]tetrazole In the same manner as in Example B-32, the title compound was obtained.

$^1$H-NMR (DMSO-d$_6$) δ: 2.36(3H,s), 3.59(1H,d,J=12.2 Hz), 3.65–3.75(1H,m), 4.16–4.56(4.5H,m), 5.06(0.5H,br s), 5.48–5.57(0.5H,m), 6.20(0.5H,br s), 7.67(1H,dd,J=8.8,2.0 Hz), 7.80(1H,d,J=8.8 Hz), 8.05–8.35(4H,m), 8.49(1H,s).

Example B-138

2-[[4-[(6-Chloronaphthalen-2-yl)sulfonyl]-1-[(4,5,6,7-tetrahydrothiazolo[5,4-c]pyridin-2-yl)carbonyl]piperazin-2-yl]methyl]-4,5-dihydro-5-oxo-1,3,4-oxadiazole trifluoroacetate In the same manner as in Example B-134, the title compound was obtained.

$^1$H-NMR (DMSO-d$_6$) δ: 2.38–2.69(2H,m), 2.92–3.11(3H, m), 3.18–3.34(1H,m), 3.40–3.88(5H,m), 4.39–4.47(2.5H, m), 4.99(0.5H,br s), 5.38–5.44(0.5H,m), 5.72–5.88(0.5H,br s), 7.70(1H,d,J=8.8 Hz), 7.81(1H,d,J=8.8 Hz), 8.15(1H,d,J= 8.8 Hz), 8.22(1H,s), 8.24(1H,d,J=8.8 Hz), 8.50(1H,s), 9.23 (2H,br s), 12.03(0.5H,s), 12.08(0.5H,s). MS (FAB) m/z: 575 [(M+H)$^+$, Cl$^{35}$], 577 [(M+H)$^+$, Cl$^{37}$].

Example B-139

2-[[4-[(6-Chloronaphthalen-2-yl)sulfonyl]-[(6-methyl-4,5,6,7-tetrahydrothiazolo[5,4-c]pyridin-2-yl)carbonyl]piperazin-2-yl]methyl]-4,5-dihydro-5-oxo-1,3,4-oxadiazole In the same manner as in Example B-32, the title compound was obtained.

$^1$H-NMR (DMSO-d$_6$) δ: 2.35(3H,s), 2.37–2.82(6H,m), 2.97–3.36(2.5H,m), 3.45–3.88(4.5H,m), 4.40–4.46(0.5H, m), 4.98(0.5H,br s), 5.45–5.55(0.5H,br s), 5.93(0.5H,br s), 7.70(1H,dd,J=8.8,2.0 Hz), 7.81(1H,dd,J=8.8,2.0 Hz), 8.15 (1H,d,J=8.8 Hz), 8.22(1H,s), 8.24(1H,d,J=8.8 Hz), 8.50(1H, s), 11.91–12.10(1H,m). MS (FAB) m/z: 589 [(M+H)$^+$, Cl$^{35}$], 591 [(M+H)$^+$, Cl$^{37}$].

Example B-140

4-[(5-Chloroindol-2-yl)sulfonyl]-2-[[(morpholin-4-yl)carbonyl]methyl]-1-[(4,5,6,7-tetrahydrothiazolo[5,4-c]pyridin-2-yl)carbonyl]piperazine hydrochloride In the same manner as in Example B-1, the title compound was obtained.

$^1$H-NMR (DMSO-d$_6$) δ: 2.33–3.85(19H,m), 4.35–4.50 (2.5H,m), 5.01–5.08(0.5H,m), 5.27–5.37(0.5H,m), 5.68–5.78(0.5H,m), 7.03(1H,s), 7.32(1H,d,J=8.8 Hz), 7.48 (1H,d,J=8.8 Hz), 7.77(1H,s), 9.54(2H,br s), 12.45(1H,s). MS (FAB) m/z: 593 [(M+H)$^+$, Cl$^{35}$], 595 [(M+H)$^+$, C$^{37}$].

Example B-141

1-[[6-(1-Acetoxyethoxy)carbonyl-4,5,6,7-tetrahydrothiazolo[5,4-c]pyridin-2-yl]carbonyl]-4-[(5-chloroindol-2-yl)sulfonyl]-2-[[(morpholin-4-yl)carbonyl]methyl]piperazine In ethanol (6 ml) was dissolved 4-[(5-chloroindol-2-yl)sulfonyl]-2-[[(morpholin-4-yl)carbonyl]methyl]-1-[(4,5,6,7-tetrahydrothiazolo[5,4-c]pyridin-2-yl)carbonyl]piperazine hydrochloride (200 mg), followed by the addition of diisopropylethylamine (83 μl) and 1-acetoxyethyl p-nitrophenyl carbonate (128 mg). The resulting mixture was stirred at room temperature for 5 hours. The solvent was distilled off under reduced pressure. Methylene chloride and an aqueous solution of sodium bicarbonate were added and the mixture was separated into layers. The organic layer was dried over anhydrous sodium sulfate and the filtrate was concentrated. The residue was purified by chromatography on a silica gel column (1–2% methanol-methylene chloride). The product was dissolved in ethyl acetate, followed by crystallization from diethyl ether, whereby the title compound (100 mg) was obtained as colorless powder.

$^1$H-NMR (DMSO-d$_6$) δ: 1.43(3H,br s), 2.00–2.03(3H,m), 2.30–3.80(19H,m), 4.35–4.45(0.5H,m), 4.61–4.77(2H,m), 5.01–5.08(0.5H,m), 5.27–5.37(0.5H,m), 5.71–5.82(0.5H, m), 6.65–6.68(1H,m), 7.01(1H,s), 7.30(1H,d,J=8.8 Hz), 7.47(1H,d,J=8.8 Hz), 7.75(1H,s), 12.40(1H,s). MS (FAB) m/z: 723 [(M+H)$^+$, Cl$^{35}$], 725 [(M+H)$^+$, Cl$^{37}$].

Example B-142

1-[[6-(tert-Butoxycarbonyl)-4,5,6,7-tetrahydrothiazolo[5,4-c]pyridin-2-yl]carbonyl]-4-[(5-chloroindol-2-yl)sulfonyl]-2-(N-methylcarbamoyl)piperazine In the same manner as in Example B-62, the title compound was obtained.

$^1$H-NMR (DMSO-d$_6$) δ: 1.41(9H,s), 2.43–2.85(5H,m), 3.15–3.75(6H,m), 4.20–4.27(1H,m), 4.40–4.48(0.5H,m), 4.60–4.67(2H,m), 5.01(0.5H,s), 5.52–5.57(0.5H,m), 6.19 (0.5H,br s), 6.99–7.01(1H,m), 7.30(1H,d,J=8.8 Hz), 7.44–7.48(1H,m), 7.76(1H,s), 8.04–8.12(1H,m), 12.39(1H, s). MS (FAB) m/z: 623 [(M+H)$^+$, Cl$^{35}$], 625 [(M+H)$^+$, Cl$^{37}$].

Example B-143

4-[(5-Chloroindol-2-yl)sulfonyl]-2-(N-methylcarbamoyl)-1-[(4,5,6,7-tetrahydrothiazolo[5,4-c]pyridin-2-yl]carbonyl]piperazine hydrochloride In the same manner as in Example B-1, the title compound was obtained.

$^1$H-NMR (DMSO-d$_6$) δ: 2.43–2.75(5H,m), 2.95(1H,br s), 3.02(1H,br s), 3.15–3.25(0.5H,m), 3.38–3.50(2H,m), 3.50–3.62(0.5H,m), 3.63–3.75(1H,m), 4.20–4.27(1H,m), 4.35–4.50(2.5H,m), 5.00(0.5H,br s), 5.42–5.53(0.5H,m), 6.15(0.5H,br s), 7.01(1H,s), 7.30(1H,d,J=8.8 Hz), 7.47(1H, d,J=8.8 Hz), 7.77(1H,s), 8.09–8.14(1H,m), 9.43(1H,br s), 12.42(1H,s). MS (FAB) m/z: 523 [(M+H)$^+$, Cl$^{35}$], 525 [(M+H)$^+$, Cl$^{37}$].

Example B-144

4-[(5-Chloroindol-2-yl)sulfonyl]-1-[(6-hydroxy-4,5,6,7-tetrahydrothiazolo[5,4-c]pyridin-2-yl)carbonyl]-2-(N-methylcarbamoyl)piperazine In methylene chloride (25 ml) were dissolved 4-[(5-chloroindol-2-yl)sulfonyl]-2-(N-methylcarbamoyl)-1-[(4,5,6,7-tetrahydrothiazolo[5,4-c]pyridin-2-yl)carbonyl]piperazine (209 mg) and benzoyl peroxide (70%, 138 mg) at room temperature, followed by heating under reflux for 9 hours. By the purification by chromatography on a silica gel column (4% methanol—methylene chloride), a crudely purified product of 1-[(6-benzoyloxy-4,5,6,7-tetrahydrothiazolo [5,4-c]pyridin-2-yl)carbonyl]-4-[(5-chloroindol-2-yl)

sulfonyl]-2-(N-methylcarbamoyl)piperazine (190 mg) was obtained as a colorless glassy solid. The resulting solid was dissolved in a mixed solvent of tetrahydrofuran (20 ml) and methanol (20 ml), followed by the addition of a 1N aqueous solution (2.00 ml) of sodium hydroxide. The resulting mixture was stirred at room temperature for 10 minutes. The solvent was distilled off and the residue was separated into layers by the addition of chloroform and water. The organic layer was dried over anhydrous sodium sulfate and the filtrate was concentrated. The residue was purified by preparative thin-layer chromatography (4% methanol—methylene chloride) using silica gel, whereby the title compound (19 mg) was obtained as colorless powder.

$^1$H-NMR (CDCl$_3$) δ: 2.75–3.25(7H,m), 3.34(2H,br s), 3.58–3.68(1H,m), 4.05–4.45(2H,br), 4.53–4.73(2H,m), 5.25 (0.5H,br s), 5.50–5.75(2.5H,m), 6.11(0.5H,br s), 6.50(0.5H, s), 7.05(1H,br s), 7.25–7.32(1H,m), 7.35–7.45(1H,m), 7.64 (1H,s), 10.73(1H,s). HRMS (FAB) m/z: 539.0920 (M+H)$^+$ (calcd for C$_{21}$H$_{24}$ClN$_6$O$_5$S$_2$, 539.0938).

Example B-145

4-[(5-Chloroindol-2-yl)sulfonyl]-2-[(N-methylcarbamoyl)methyl]-1-[(6-methyl-4,5,6,7-tetrahydrothiazolo[5,4-c]pyridin-2-yl)carbonyl] piperazine hydrochloride In the same manner as in Example B-94, the title compound was obtained.

$^1$H-NMR (DMSO-d$_6$) δ: 2.40–2.85(7H,m), 2.89(3H,s), 3.00–3.30(3H,br), 3.40–3.82(4H,m), 4.30–4.80(2.5H,br), 5.06(0.5H,br s), 5.26–5.40(0.5H,m), 5.81(0.5H,br s), 7.02 (1H,s), 7.31(1H,d,J=8.6 Hz), 7.48(1H,d,J=8.6 Hz), 7.76(1H, s), 7.89–7.94(1H,m), 11.16(1H,br s), 12.44(1H,s). MS (FAB) m/z: 551 [(M+H)$^+$, Cl$^{35}$], 553 [(M+H)$^+$, Cl$^{37}$].

Example B-146

4-[(5-Chloroindol-2-yl)sulfonyl]-2-[(methoxycarbonyl)methyl]-1-[(6-methyl-4,5,6,7-tetrahydrothiazolo[5,4-c]pyridin-2-yl)carbonyl] piperazine In the same manner as in Example B-62, the title compound was obtained.

$^1$H-NMR (CDCl$_3$) δ: 2.49(3H,s), 2.50–2.90(7H,m), 2.95–3.06(1H,m), 3.10–3.25(0.5H,m), 3.35–3.50(0.5H,m), 3.50–3.70(5H,m), 3.70–3.95(2H,br), 4.60–4.64(0.5H,br), 5.22(0.5H,br s), 5.71–5.75(0.5H,m), 6.18(0.5H,br s), 6.96 (1H,s), 7.31(1H,dd,J=8.8,1.7 Hz), 7.36(1H,d,J=8.8 Hz), 7.65(1H,d,J=1.7 Hz), 9.15–9.20(1H,br). MS (FAB) m/z: 552 [(M+H)$^+$, Cl$^{35}$], 554 [(M+H)$^+$, Cl$^{37}$].

Example B-147

2-(Carboxymethyl)-4-[(5-chloroindol-2-yl)sulfonyl]-1-[(6-methyl-4,5,6,7-tetrahydrothiazolo[5,4-c]pyridin-2-yl)carbonyl]piperazine In the same manner as in Example B-77, the title compound was obtained.

$^1$H-NMR (DMSO-d$_6$) δ: 2.38(3H,s), 2.40–3.81(13H,m), 4.36–4.41(0.5H,br), 5.01(0.5H,br s), 5.41–5.44(0.5H,m), 5.86(0.5H,br s), 7.03(1H,s), 7.31(1H,dd,J=8.8,1.7 Hz), 7.47 (1H,d,J=8.8 Hz), 7.76(1H,d,J=1.7 Hz), 12.42(1H,s). MS (FAB) m/z: 538 [(M+H)$^+$, Cl$^{35}$], 540 [(M+H)$^+$, Cl$^{37}$].

Example B-148

4-[(5-Chloroindol-2-yl)sulfonyl]-2-[[N-[(1,3-dioxolan-2-yl)methyl]carbamoyl]methyl]-1-[(6-methyl-4,5,6,7-tetrahydrothiazolo[5,4-c]pyridin-2-yl)carbonyl]piperazine In the same manner as in Example B-79, the title compound was obtained.

$^1$H-NMR (CDCl$_3$) δ: 2.50(3H,s), 2.51–3.10(7H,m), 3.30–3.65(3H,m), 3.68(2H,s), 3.70–4.12(6H,m), 4.46–4.57 (0.5H,m), 4.90–5.00(1H,m), 5.10–5.20(0.5H,m), 5.55–5.70 (0.5H,m), 5.87(0.5H,s), 6.28(0.5H,s), 6.52(0.5H,s), 6.99 (1H,s), 7.28(1H,d,J=8.8 Hz), 7.37(1H,d,J=8.8 Hz), 7.64(1H, s), 10.38(0.5H,br s), 10.62(0.5H,s). MS (FAB) m/z: 623 [(M+H)$^+$, Cl$^{35}$], 625 [(M+H)$^+$, Cl$^{37}$].

Example B-149

1-[[4-[(5-Chloroindol-2-yl)sulfonyl]-1-[(6-methyl-4,5,6,7-tetrahydrothiazolo[5,4-c]pyridin-2-yl) carbonyl]piperazin-2-yl)acetyl]piperidin-4-one ethyleneketal In the same manner as in Example B-79, the title compound was obtained.

$^1$H-NMR (CDCl$_3$) δ: 1.60(4H,s), 2.49(3H,s), 2.55–3.20 (7H,m), 3.20–3.35(0.5H,m), 3.50–3.85(8H,m), 4.00(5H,br s), 4.12–4.23(0.5H,m), 4.55–4.67(0.5H,m), 4.95–5.07(0.5H, m), 5.45–5.60(0.5H,m), 5.95–6.07(0.5H,m), 7.00(1H,s), 7.22–7.31(1H,m), 7.37(1H,d,J=8.8 Hz), 7.64(1H,s), 10.37 (0.5H,br s), 11.14 (0.5H,s). MS (FAB) m/z: 663 [(M+H)$^+$, Cl$^{35}$], 665 [(M+H)$^+$, Cl$^{37}$].

Example B-150

4-[( 5-Chloroindol-2-yl)sulfonyl]-2-[(N,N-dimethylcarbamoyl)methyl]-1-[(6-methyl-4,5,6, 7tetrahydrothiazolo[5,4-c]pyridin-2-yl]carbonyl] piperazine hydrochloride In the same manner as in Example B-79, the title compound was obtained.

$^1$H-NMR (DMSO-d$_6$) δ: 2.40–2.80(6H,m), 2.81–3.20 (9H,m), 3.35–3.85(5H,m), 4.30–4.80(2.5H,br), 5.00(0.5H, br s), 5.26–5.40(0.5H,m), 5.75(0.5H,br s), 7.01(1H,s), 7.30 (1H,d,J=8.6 Hz), 7.47(1H,d,J=8.6 Hz), 7.75(1H,s), 11.22 (1H,br s), 12.42(1H,s). MS (FAB) m/z: 565 [(M+H)$^+$, Cl$^{35}$], 567 [(M+H)$^+$, Cl$^{37}$].

Example B-151

4-[(5-Chloroindol-2-yl)sulfonyl]-2-[[N-(2,2-diethoxyethyl)carbamoyl]methyl]-1-[(6-methyl-4,5, 6,7-tetrahydrothiazolo[5,4-c]pyridin-2-yl)carbonyl] piperazine In the same manner as in Example B-79, the title compound was obtained.

$^1$H-NMR (CDCl$_3$) δ: 1.15–1.27(6H,m), 2.50(3H,s), 2.55–3.10(8H,m), 3.30–3.90(10H,m), 4.00–4.15(1H,m), 4.45–4.60(1.5H,m), 5.12(0.5H,br s), 5.55–5.70(0.5H,m), 5.82(0.5H,br s), 6.19(0.5H,br s), 6.59(0.5H,br s), 7.01(1H, s), 7.22–7.31(1H,m), 7.36(1H,d,J=9.0 Hz), 7.65(1H,s), 10.21(0.5H,br s), 10.72(0.5H,s). MS (FAB) m/z: 653 [(M+H)$^+$, Cl$^{35}$], 655 [(M+H)$^+$, Cl$^{37}$].

Example B-152

4-[(5-Chloroindol-2-yl)sulfonyl]-1-[(6-methyl-4,5,6, 7-tetrahydrothiazolo[5,4-c]pyridin-2-yl)carbonyl]-2-[[N-(tetrahydrofurfuryl)carbamoyl]methyl] piperazine hydrochloride In the same manner as in Example B-62, the title compound was obtained.

$^1$H-NMR (DMSO-d$_6$) δ: 1.40–1.55(1H,m), 1.65–1.90 (3H,m), 2.40–2.89(3H,br), 2.90(3H,s), 3.00–3.40(5H,m), 3.41–3.85(9H,m), 4.25–4.70(1.5H,m), 5.08(0.5H,br s), 5.26–5.37(0.5H,m), 5.83(0.5H,br s), 7.03(1H,s), 7.31(1H,d, J=9.0 Hz), 7.48(1H,d,J=9.0 Hz), 7.77(1H,s), 8.07(1H,br s), 11.00–11.30(1H,br), 12.43(1H,s). MS (FAB) m/z: 621 [(M+H)$^+$, Cl$^{35}$], 623 [(M+H), Cl$^{37}$].

Example B-153

1-[[6-(tert-Butoxycarbonylaminosulfonyl)-4,5,6,7-tetrahydrothiazolo[5,4-c]pyridin-2-yl]carbonyl]-4-[(5-chloroindol-2-yl)sulfonyl]-2-[[(morpholin-4-yl)carbonyl]methyl]piperazine To methylene chloride (3 ml) was added tert-butyl alcohol (53 mg). While cooling to 0° C., chlorosulfonylisocyanate (88 mg) was added to the resulting mixture, followed by stirring for 10 minutes. To the reaction mixture was added a solution of 4-[(5-chloroindol-2-yl)sulfonyl]-2-[[(morpholin-4-yl)carbonyl]methyl]-1-[(4,5,6,7-tetrahydrothiazolo[5,4-c]pyridin-2-yl]carbonyl]]piperazine (300 mg) and triethylamine (475 mg) in methylene chloride (3 ml). After stirring at room temperature for 1 hour, water was added to the reaction mixture and the resulting mixture was extracted with methylene chloride. The organic layer was dried over anhydrous sodium sulfate and distilled under reduced pressure to remove the solvent. The residue was purified by column chromatography (methanol:methylene chloride= 1:19) using as a carrier silica gel, whereby the title compound (311 mg) was obtained. A portion of the compound was purified further by preparative thin-layer chromatography (methanol:methylene chloride=1:9) using silica gel, followed by the addition of ether. The instrumental data on the resulting pale yellow solid was as follows:

$^1$H-NMR (DMSO-d$_6$) δ: 1.23, 1.24(total 9H,each s), 2.33–3.75(19H,m), 4.37–5.86(4H,m), 7.03(1H,s), 7.31(1H, d,J=8.8 Hz), 7.47(1H,d,J=8.8 Hz), 7.76(1H,s), 11.21(1H,s), 12.42(1H,s). MS (FAB) m/z: 772 (M+H)$^+$.

Example B-154

1-[[6-(Aminosulfonyl)-4,5,6,7-tetrahydrothiazolo[5,4-c]pyridin-2-yl]carbonyl]-4-[(5-chloroindol-2-yl)sulfonyl]-2-[[(morpholin-4-yl)carbonyl]methyl]piperazine In methylene chloride (3 ml) was dissolved 1-[[6-(tert-butoxycarbonylaminosulfonyl)-4,5,6,7-tetrahydrothiazolo[5,4-c]pyridin-2-yl]carbonyl]-4-[(5-chloroindol-2-yl)sulfonyl]-2-[[(morpholin-4-yl)carbonyl]methyl]piperazine (275 mg), followed by the addition of trifluoroacetic acid (3 ml). The resulting mixture was stirred at room temperature for 30 minutes. The solvent was distilled off under reduced pressure. A saturated solution of hydrochloride. in ethanol (3 ml) was added and the resulting mixture was stirred at room temperature for 1.5 hours. The residue obtained by distilling off the solvent under reduced pressure was added with methylene chloride and water to separate into layers. The water layer was extracted with methylene chloride. The organic layer was dried over anhydrous sodium sulfate and distilled under reduced pressure to remove the solvent. The residue was purified by preparative thin-layer chromatography (methanol:methylene chloride=1:9) using silica gel. The solid thus obtained was dissolved in a small amount of methylene chloride, followed by solidification by the addition of diethyl ether, whereby the title compound (50 mg) was obtained as a pale yellow solid.

$^1$H-NMR (DMSO-d$_6$) δ: 2.33–3.75(19H,m), 4.35–5.84 (4H,m), 7.01–7.02(3H,m), 7.31(1H,d,J=8.8 Hz), 7.48(1H,d, J=9.0 Hz), 7.76(1H,s), 12.41(1H,s). MS (FAB) m/z: 672 (M+H)$^+$.

Example B-155

4-[(5-Chloroindol-2-yl)sulfonyl]-2-[[(morpholin-4-yl)carbonyl]methyl]-1-[6-[phenylsulfonyl]-4,5,6,7-tetrahydrothiazolo[5,4-c]pyridin-2-yl]carbonyl]piperazine In the same manner as in Example B-95, the title compound was obtained.

$^1$H-NMR (DMSO-d$_6$) δ: 2.33–3.74(19H,m), 4.34–5.71 (4H,m), 7.02(1H,s), 7.31(1H,d,J=8.6 Hz), 7.47(1H,d,J=9.0 Hz), 7.57–7.61(2H,m), 7.65–7.67(1H,m), 7.76(1H,s), 7.80 (2H,d,J=7.8 Hz), 12.40(1H,s). HRMS (FAB) m/z: 733.1333 (M+H)$^+$ (calcd for C$_{31}$H$_{33}$ClN$_6$O$_7$S$_3$, 733.1340).

Example B-156

5-Methyl-4,5,6,7-tetrahydrothiazolo[5,4-c]pyridin-2-yl]carbonyl]-4-[(5-chloroindol-2-yl)sulfonyl]-2-(N-methylcarbamoyl)-1-[[6-(tert-butoxycarbonyl)piperazine In diethyl ether (8 ml) dried by a molecular sieve was dissolved 6-(tert-butoxycarbonyl)-5-methyl-4,5,6,7-tetrahydrothiazolo[5,4-c]pyridine (203 mg). After the container employed was purged with argon, the temperature was cooled to −78° C. To the resulting solution, n-butyl lithium (a 1.66 mole n-hexane solution, 506 µl) was added dropwise, followed by stirring at the same temperature for 1.5 hours. While a carbon dioxide gas was blown into the reaction mixture, the mixture was stirred at the same temperature for 1 hour. After warming up to room temperature, the solvent was distilled off under reduced pressure, whereby crude lithium 6-(tert-butoxycarbonyl)-5-methyl-4,5,6,7-tetrahydrothiazolo[5,4-c]pyridine-2-carboxylate was obtained. This product was provided for the subsequent reaction without purification. In N,N-dimethylformamide (4 ml) was dissolved 3-(N-methylcarbamoyl)-1-[(5-chloro-1-phenylsulfonylindol-2-yl)sulfonyl]piperazine (248 mg), followed by the addition of the crude lithium 6-(tert-butoxycarbonyl)-5-methyl-4,5,6,7-tetrahydrothiazolo[5,4-c] pyridine-2-carboxylate (ca. 550 µmol), which had been obtained above, 1-(3-dimethylaminopropyl)-3-ethylcarbodiimide (144 mg) and 1-hydroxybenzotriazole (34 mg). The resulting mixture was stirred overnight at room temperature. Methylene chloride was added to the reaction mixture. The resulting mixture was washed with a saturated aqueous solution of sodium bicarbonate, dried over anhydrous sodium sulfate and distilled under reduced pressure to remove the solvent. The residue was purified by flash column chromatography (hexane ethyl acetate=2:1) using as a carrier silica gel, whereby the title compound (121 mg) was obtained as a white solid.

$^1$H-NMR (CDCl$_3$) δ: 1.12–1.17(3H,m), 1.49(9H,s), 2.62–3.23(7H,m), 3.63(1H,d,J=12.3 Hz), 4.22(1H,d,J=17.9 Hz), 4.55–4.74(2H,m), 4.83–4.89(1H,m), 5.09–5.16(1H,m), 5.25–6.49(2H,m), 7.06(1H,s), 7.27–7.30(2H,m), 7.38–7.42 (1H,m), 7.64(1H,s), 10.62–10.67(1H,m).

Example B-157

4-[(5-Chloroindol-2-yl)sulfonyl]-2-(N-methylcarbamoyl)-1-[(5-methyl-4,5,6,7-tetrahydrothiazolo[5,4-c]pyridin-2-yl)carbonyl]piperazine hydrochloride In the same manner as in Example B-1, the title compound was obtained.

$^1$H-NMR (DMSO-d$_6$) δ: 1.39–1.40(3H,m), 2.32–3.68 (10H,m), 4.21–5.00(4H,m), 5.44–6.15(1H,m), 7.01(1H,s), 7.31(1H,dd,J=8.5,2.0 Hz), 7.48(1H,d,J=8.5 Hz), 7.77(1H,s), 8.11–8.14(1H,m), 9.38–9.75(2H,m), 12.42(1H,s). HRMS (FAB) m/z: 537.1140 (M+H)$^+$ (calcd for $C_{22}H_{26}N_6O_4ClS_2$, 537.1145).

Example B-158

4-[(5-Chloroindol-2-yl)sulfonyl]-1-[(5,6-dimethyl-4,5,6,7-tetrahydrothiazolo[5,4-c]pyridin-2-yl) carbonyl]-2-(N-methylcarbamoyl)piperazine hydrochloride In a saturated solution of hydrochloride in ethanol (2 ml) was dissolved 1-[[6-(tert-butoxycarbonyl)-5-methyl-4,5,6,7-tetrahydrothiazolo[5,4-c]pyridin-2-yl]carbonyl]-4-[(5-chloroindol-2-yl)sulfonyl]-2-(N-methylcarbamoyl) piperazine (40 mg), followed by stirring at room temperature for 1 hour. Diethyl ether was added to the reaction mixture. The precipitate so formed was collected by filtration and washed with diethyl ether. Methylene chloride (7 ml) and triethylamine (81 μl) were added, followed by the addition of acetic acid (34 μl). To the resulting mixture were added a 30% aqueous solution (21 μl) of formaldehyde and sodium triacetoxyborohydride (64 mg), followed by stirring at room temperature for 30 minutes. The solvent was distilled off under reduced pressure. Methylene chloride was added and the resulting mixture was washed with water and saturated aqueous NaCl solution. The organic layer was dried over anhydrous sodium sulfate and distilled under reduced pressure to remove the solvent. The residue was dissolved in a 1N ethanol hydrochloride solution. After stirring at room temperature for 5 minutes, the solvent was distilled off under reduced pressure. The precipitate so formed was collected by filtration and washed with diethyl ether, whereby the title compound (68 mg) was obtained as a white solid.

$^1$H-NMR (DMSO-$d_6$) δ: 1.32–1.40(3H,m), 2.33–3.94 (13H,m), 4.23–4.26(1H,m), 4.44–5.01(3H,m), 5.50–6.16 (1H,m), 7.02(1H,s), 7.31(1H,dd,J=8.8,2.0 Hz), 7.48(1H,d, J=8.8 Hz), 7.77(1H,s), 8.10–8.16(1H,m), 11.15–11.54(1H, m), 12.43(1H,s).

Example B-159

4-[(6-Chloronaphthalen-2-yl)sulfonyl]-2-(N-methylcarbamoyl)-1-[(4,5,6,7-tetrahydrooxazolo[5,4-c]pyridin-2-yl)carbonyl]piperazine trifluoroacetate To a solution of 6-(tert-butoxycarbonyl)-2-methoxycarbonyl-4,5,6,7-tetrahydrooxazolo[5,4-c]pyridine (120 mg) in tetrahydrofuran (4.0 ml) were added water (1.0 ml) and lithium hydroxide (18.0 mg) at room temperature. After stirring for 10 minutes, the solvent was distilled off under reduced pressure. To a solution of the residue in N,N-dimethylformamide were added 1-[(6-chloronaphthalen-2-yl)sulfonyl]-3-(N-methylcarbamoyl) piperazine hydrochloride (190 mg), 1-hyroxybenzotriazole monohydrate (11.5 mg) and 1-(3-dimethylaminopropyl)-3-ethylcarbodiimide (90.0 mg) at room temperature. After stirring for 4 hours, methylene chloride (30 ml) and water (250 ml) were added to the reaction mixture to separate it into layers. The water layer was extracted with methylene chloride (20 ml). The organic layers were combined, washed with a saturated aqueous solution (50 ml) of sodium bicarbonate, dried over anhydrous sodium sulfate and distilled under reduced pressure to remove the solvent. The residue was purified by chromatography on a silica gel column (silica gel: 25 g, methylene chloride:acetone 5:1→3:1), whereby a colorless transparent oil was obtained. To a solution of the resulting substance in methylene chloride (4.0 ml) was added trifluoroacetic acid (4.0 ml) at room temperature and the resulting mixture was stirred for 1 hour. The reaction mixture was concentrated under reduced pressure. The residue was reprecipitated from a methylene chloride-methanol-diethyl ether system, whereby the title compound (165 mg) was obtained as a pale brown solid.

$^1$H-NMR (DMSO-$d_6$) δ: 2.30–2.70(2H,m), 2.58(3H,d,J= 3.9 Hz), 2.77(2H,br d,J=16.1 Hz), 3.05–3.60(3H,m), 3.71 (1H,br d,J=11.2 Hz), 4.29(1H,br d,J=11.7 Hz), 4.35–4.50 (2H+½ of 1H,m), 4.96(½ of 1H,br s), 5.05(½ of 1H,br d,J=13.2 Hz), 5.78(½ of 1H,br s), 7.71(1H,d,J=8.3 Hz), 7.73–7.83(1H,m), 8.00–8.20(1H,m), 8.15(1H,d,J=8.3 Hz), 8.24(1H,s), 8.25(1H,d,J=8.3 Hz), 8.48(½ of 1H,s), 8.49(½ of 1H,s), 9.34(2H,br s). MS (FAB) m/z: 518 (M+H)$^+$.

Example B-160

4-[(6-Chloronaphthalen-2-yl)sulfonyl]-2-(N-methylcarbamoyl)-1-[(6-methyl-4,5,6,7-tetrahydrooxazolo[5,4-c]pyridin-2-yl)carbonyl] piperazine In the same manner as in Example B-32, the title compound was obtained.

$^1$H-NMR (DMSO-$d_6$) δ: 2.48(3H,s), 2.52–2.80(6H,m), 2.80–3.00(3H,m), 3.10(½ of 1H,t,J=11.2 Hz), 3.49(½ of 1H,t,J=11.2 Hz), 3.54(2H,s), 3.78(½ of 1H,br d,J=10.3 Hz), 3.86(½ of 1H,br d,J=11.2 Hz), 4.45(1H,t,J=11.4 Hz), 4.63(½ of 1H,br d,J=12.7 Hz), 5.24(½ of 1H,s), 5.38(½ of 1H,br d,J=12.7 Hz), 6.12(½ of 1H,br s), 6.16(½ of 1H,s), 6.40(½ of 1H,br s), 7.58(1H,d,J=7.8 Hz), 7.80(1H,d,J=7.8 Hz), 7.86–7.96(3H,m), 8.34(1H,s). MS (FAB) m/z: 532 (M+H)$^+$.

Example B-161

1-[[6-(tert-Butoxycarbonyl)-4,5,6,7-tetrahydrooxazolo[5,4-c]pyridin-2-yl]carbonyl]-4-[(5-chloroindol-2-yl)sulfonyl]piperazine In the same manner as in Example B-62, the title compound was obtained.

$^1$H-NMR (CDCl$_3$) δ: 1.46(9H,s), 2.64(2H,br s), 3.22(4H, br s), 3.71(2H,br s), 3.90(2H,br s), 4.42(2H,br s), 4.53(2H,br s), 6.97(1H,d,J=2.0 Hz), 7.33(1H,dd,J=8.8,2.0 Hz), 7.37 (1H,d,J=8.8 Hz), 7.67(1H,s), 8.71(1H,br s).

Example B-162

1-[[6-(tert-Butoxycarbonyl)-4,5,6,7-tetrahydrooxazolo[5,4-c]pyridin-2-yl]carbonyl]-4-[(5-chloroindol-2-yl)sulfonyl]-2-[[(morpholin-4-yl) carbonyl]methyl]piperazine In the same manner as in Example B-62, the title compound was obtained.

$^1$H-NMR (CDCl$_3$) δ: 1.47(9H,s), 2.50–2.70(2H,m), 2.70–3.20(2H+½ of 1H,m), 3.38(½ of 1H,t,J=11.2 Hz), 3.50–3.95(11H+½ of 1H,m), 3.99(½ of 1H,br d,J=12.7 Hz), 4.40–4.60(½ of 1H,br), 4.53(2H,s), 4.64(½ of 2H,s), 4.64(½ of 1H,br d,J= 13.7 Hz), 5.02(½ of 1H,br s), 5.24(½ of 1H,br s), 5.79(½ of 1H,br s), 7.00(1H,s), 7.20–7.35(1H,m), 7.38(1H,d,J=8.8 Hz), 7.65(½ of 1H,s), 7.67(½ of 1H,s), 9.89(½1H,br s), 10.60–11.00(½ of 1H,br).

Example B-163

1-[(5-Chloroindol-2-yl)sulfonyl]-4-[(6-methyl-4,5,6,7-tetrahydrooxazolo[5,4-c]pyridin-2-yl)carbonyl] piperazine hydrochloride To a solution of 1-[[6-(tert-butoxycarbonyl)-4,5,6,7-tetrahydrooxazolo[5,4-c]pyridin-2-yl]carbonyl]-4-[(5- chloroindol-2-yl)sulfonyl]piperazine (100 mg) in methylene chloride (3.0 ml) was added trifluoroacetic acid (3.0 ml) at room temperature, followed by stirring for 15 minutes. The reaction mixture was concentrated under reduced pressure. To the residue were added methylene chloride (4.0 ml), triethylamine (50.0 µl), acetic acid (21.0 µl), formalin (23.5 µl) and sodium triacetoxyborohydride (58.0 mg) at room temperature. After stirring for 1 hour, methylene chloride (20 ml) and a saturated aqueous solution (50 ml) of sodium bicarbonate were added to the reaction mixture to separate it into layers. The water layer was extracted with methylene chloride (20 ml). The organic layers were combined, dried over anhydrous sodium sulfate and distilled under reduced pressure to remove the solvent. The residue was purified by preparative thin-layer chromatography (chloroform : methanol=10:1) using silica gel, whereby the free form (82.6 mg) of the title compound was obtained as a colorless solid. To the resulting compound were added a 1N aqueous solution of hydrochloric acid, tetrahydrofuran and methanol, followed by concentration under reduced pressure, whereby the title compound was obtained as a colorless solid.

$^1$H-NMR (DMSO-d$_6$) δ: 2.90(4H,s), 3.11(3H,br s), 3.25–3.75(2H,br), 3.35(2H,s), 3.75(2H,br s), 4.16(2H,br s), 4.20–4.75(2H,br), 7.04(1H,s), 7.32(1H,dd,J=8.8,1.0 Hz), 7.50(1H,d,J=8.8 Hz), 7.78(1H,d,J=1.0 Hz), 11.51(1H,br s), 12.46(1H,s). MS (FAB) m/z: 464 (M+H)$^+$.

Example B-164

4-(5-Chloroindol-2-yl)sulfonyl]-1-[(6-methyl-4,5,6,
7-tetrahydrooxazolo[5,4-c]pyridin-2-yl]carbonyl]-2-
[[(morpholin-4-yl)carbonyl]methyl]piperazine
hydrochloride In the same manner as in Example B-163, the title compound was obtained.

$^1$H-NMR (DMSO-d$_6$) δ: 2.30–2.75(2H,m), 2.75–3.20 (2H,m), 2.90(3H,s), 3.20–3.90(15H,m), 4.30–4.45(1H+½ of 1H,m), 4.55–4.70(1H,m), 4.89(½ of 1H,br s), 5.05(½ of 1H,br s), 5.47(½ of 1H,br s), 7.04(1H,s), 7.29–7.35(1H,m), 7.50(1H,dd,J=8.8,2.9 Hz), 7.76–7.80(1H,m), 11.45–11.95 (1H,br), 12.49(1H,br s). MS (FAB) m/z: 591 (M+H)$^+$.

Example B-165

1-[[6-(tert-Butoxycarbonyl)-4,5,6,7-
tetrahydrooxazolo[5,4-c]pyridin-2-yl]carbonyl]-4-
[(6-chlorobenzo[b]thien-2-yl)sulfonyl]piperazine To a solution of lithium 6-(tert-butoxycarbonyl)-4,5,6,7-tetrahydrothiazolo[5,4-c]pyridine-2-carboxylate (70.0 mg) in N,N-dimethylformamide (4.0 ml) were added 1-[(6-chlorobenzo[b]thien-2-yl)sulfonyl]piperazine hydrochloride (90.0 mg), 1-hydroxybenzotriazole monohydrate (7.0 mg) and 1-(3-dimethylaminopropyl)-3-ethylcarbodiimide (64.0 mg) at room temperature. After stirring for 2 days, ethyl acetate (30 ml) and water (500 ml) were added to the reaction mixture to separate it into layers. The water layer was extracted with ethyl acetate (30 ml). The organic layers were combined, washed with a saturated aqueous solution of sodium bicarbonate (100 ml), dried over anhydrous sodium sulfate and distilled under reduced pressure to remove the solvent. The residue was purified by preparative thin-layer chromatography (hexane:ethyl acetate=1:1) using silica gel, whereby the title compound (37.9 mg) was obtained as a colorless transparent glassy substance.

$^1$H-NMR (CDCl$_3$) δ: 1.47(9H,s), 2.65(2H,s), 3.27(4H,t, J=5.0 Hz), 3.70(2H,s), 3.91(2H,s), 4.42(2H,s), 4.53(2H,s), 7.45(1H,dd,J=8.8,1.5 Hz), 7.77(1H,s), 7.81(1H,d,J=8.8 Hz), 7.86(1H,d,J=1.5 Hz). MS (FAB) m/z: 567 (M+H)$^+$.

Example B-166

1-[(6-Chlorobenzo[b]thien-2-yl)sulfonyl]-4-[(6-
methyl-4,5,6,7-tetrahydrooxazolo[5,4-c]pyridin-2-yl)
carbonyl]piperazine hydrochloride In the same manner as in Example B-163, the title compound was obtained.

$^1$H-NMR (DMSO-d$_6$) δ: 2.90(3H,s), 2.94(1H,br s), 3.10–3.25(4H,m), 3.49(2H,s), 3.64(1H,br s), 3.79(2H,s), 4.21(2H,s), 4.39(1H,br s), 4.60(1H,br s), 7.58(1H,dd,J=8.8, 2.0 Hz), 8.07(1H,d,J=8.8 Hz), 8.10(1H,s), 8.34(1H,d,J=2.0 Hz), 11.70(1H,br s). MS (FAB) m/z: 481 (M+H)$^+$.

Example B-167

1-[(6-Methyl-4,5,6,7-tetrahydrooxazolo[5,4-c]
pyridin-2-yl)carbonyl]-4-[(1-phenylsulfonyl-5-
trimethylsilylethynylindol-2-yl)sulfonyl]piperazine In the same manner as in Example B-103, the title compound was obtained.

$^1$H-NMR (CDCl$_3$) δ: 0.25(9H,s), 2.51(3H,s), 2.69(2H,t, J=5.4 Hz), 2.78(2H,t,J=5.4 Hz), 3.52(2H,br s), 3.55(2H,br s), 3.59(2H,s), 3.89(2H,br s), 4.41(2H,br s), 7.42(2H,t,J=7.6 Hz), 7.47(1H,s), 7.55(1H,t,J=7.6 Hz), 7.59(1H,dd,J=8.8,1.7 Hz), 7.69(1H,d,J=1.7 Hz), 8.00(2H,d,J=7.6 Hz), 8.22(1H,d, J=8.8 Hz).

Example B-168

1-[(5-Ethynylindol-2-yl)sulfonyl]-4-[(6-methyl-4,5,
6,7-tetrahydrooxazolo[5,4-c]pyridin-2-yl)carbonyl]
piperazine In the same manner as in Example B-104, the title compound was obtained.

$^1$H-NMR (CDCl$_3$) δ: 2.48(3H,s), 2.66(2H,t,J=5.4 Hz), 2.75(2H,t,J=5.4 Hz), 3.04(1H,s), 3.21(4H,t,J=4.4 Hz), 3.54 (2H,s), 3.89(2H,br s), 4.43(2H,br s), 7.00(1H,s), 7.37(1H,d, J=8.6 Hz), 7.47(1H,dd,J=8.6,1.5 Hz), 7.86(1H,br s), 8.85 (1H,br s). MS (FAB/glycerol) m/z: 454 (M+H)$^+$.

Example B-169

1-[[6-(tert-Butoxycarbonyl)-4,5,6,7-
tetrahydrooxazolo[5,4-c]pyridin-2-yl]carbonyl]-4-
[(5-chloroindol-2-yl)sulfonyl]-2-ethylpiperazine In the same manner as in Example B-165, the title compound was obtained.

$^1$H-NMR (CDCl$_3$) δ: 0.90(½ of 3H,t,J=7.1 Hz), 0.96(½ of 3H,t,J=7.1 Hz), 1.47(9H,s), 1.78–2.03(2H,m), 2.45–2.73 (4H,m), 3.18(½ of 1H,t,J=11.5 Hz), 3.51(½ of 1H,t,J=11.5 Hz), 3.60–3.92(4H,m), 4.52(2H,s), 4.62(½ of 1H,d,J=13.0 Hz), 4.79(½ of 1H,br s), 5.20(½ of 1H,br s), 5.40(½ of 1H,br s), 6.94(1H,d,J=1.5 Hz), 7.31(1H,dd,J=8.8,2.0 Hz), 7.37 (1H,d,J=8.8 Hz), 7.66(1H,d,J=2.0 Hz), 8.87(1H,br s). MS (FAB) m/z: 578 (M+H)$^+$.

Example B-170

4-[(5-Chloroindol-2-yl)sulfonyl]-2-ethyl-1-[(4,5,6,7-
tetrahydrooxazolo[5,4-c]pyridin-2-yl)carbonyl]
piperazine trifluoroacetate To a solution of 1-[[6-(tert-butoxycarbonyl)-4,5,6,7-tetrahydrooxazolo[5,4-c]pyridin-2-yl]carbonyl]-4-[(5- chloroindol-2-yl)sulfonyl]-2-ethylpiperazine (320 mg) in methylene chloride (5.0 ml) was added trifluoroacetic acid (5.0 ml) at room temperature, followed by stirring for 10 minutes. The reaction mixture was concentrated under reduced pressure, whereby the title compound (423 mg) was obtained as a pale brown solid.

$^1$H-NMR (DMSO-d$_6$) δ: 0.78(½ of 3H,t,J=6.9 Hz), 0.83(½ of 3H,t,J=6.9 Hz), 1.47(9H,s), 1.65–1.95(2H,m), 2.30–2.70(2H,m), 2.80(2H,s), 3.13(½ of 1H,t,J=12.7 Hz), 3.37–4.00(2H +½ of 1H,m), 3.42(2H,s), 4.30–4.47(2H+½ of 1H,m), 4.60(½ of 1H,br s), 4.73(½ of 1H,d,J=14.0 Hz), 4.91(½ of 1H,br s), 8.01(1H,s), 7.30(1H,d,J=8.8 Hz), 7.47 (1H,d,J=8.8 Hz), 7.76(1H,s), 9.36(2H,br s), 12.42(1H,s). MS (FAB) m/z: 478 (M+H)$^+$.

Example B-171

4-[(5-Chloroindol-2-yl)sulfonyl]-2-ethyl-1-[(6-methyl-4,5,6,7-tetrahydrooxazolo[5,4-c]pyridin-2-yl)carbonyl]piperazine hydrochloride In the same manner as in Example B-32, the title compound was obtained.

$^1$H-NMR (DMSO-d$_6$) δ: 0.73–0.83(3H,m), 1.60–1.92 (2H,m), 2.30–2.70(2H,m), 2.75–3.03(2H,m), 2.89(3H,s), 3.03–3.53(2H+½ of 1H,m), 3.53–3.80(2H+½ of 1H,m), 4.20–4.45(1H+½ of 1H,br), 4.60(1H+½ of 1H,br s), 4.76(½ of 1H,d,J=13.0 Hz), 4.92(½ of 1H,br s), 7.00(1H,s), 7.30 (1H,dd,J=8.8,2.0 Hz), 7.47(1H,d,J=8.8 Hz), 7.75(1H,d,J=2.0 Hz), 11.57(1H,br s), 12.43(1H,s). MS (FAB) m/z: 492 (M+H)$^+$.

Example B-172

1-[[6-(tert-Butoxycarbonyl)-5,6,7,8-tetrahydropyrido[4,3-d]pyrimidin-2-yl]carbonyl]-4-[(5-chloroindol-2-yl)sulfonyl]piperazine In the same manner as in Example B-159, the title compound was obtained.

$^1$H-NMR (CDCl$_3$) δ: 1.49(9H,s), 2.96(2H,t,J=5.9 Hz), 3.14(2H,t,J=5.0 Hz), 3.27(2H,t,J=5.1 Hz), 3.53(2H,t,J=5.0 Hz), 3.75(2H,t,J=5.9 Hz), 3.93(2H,t,J=5.1 Hz), 4.62(2H,s), 6.96(1H,s), 7.35(1H,dd,J=8.5,1.7 Hz), 7.38(1H,d,J=8.5 Hz), 7.69(1H,d,J=1.7 Hz), 8.48(1H,s), 8.77(1H,br s). MS (FAB) m/z: 561 (M+H)$^+$.

Example B-173

1-[(5-Chloroindol-2-yl)sulfonyl]-4-[(5,6,7,8-tetrahydropyrido[4,3-d]pyrimidin-2-yl]carbonyl]piperazine trifluoroacetate In the same manner as in Example B-170, the title compound was obtained.

$^1$H-NMR (DMSO-d$_6$) δ: 2.96(2H,t,J=4.5 Hz), 3.03(2H,t,J=6.0 Hz), 3.11(2H,t,J=4.5 Hz), 3.29(2H,t,J=4.5 Hz), 3.49 (2H,br s), 3.75(2H,t,J=4.5 Hz), 4.36(2H,s), 7.03(1H,s), 7.32 (1H,dd,J=8.8,1.7 Hz), 7.49(1H,d,J=8.8 Hz), 7.78(1H,d,J=1.7 Hz), 8.70(1H,s), 9.25(2H,br s), 12.46(1H,s). MS (FAB) m/z: 461 (M+H)$^+$.

Example B-174

1-[(5-Chloroindol-2-yl)sulfonyl]-4-[(6-methyl-5,6,7,8-tetrahydropyrido[4,3-d]pyrimidin-2-yl]carbonyl]piperazine hydrochloride In the same manner as in Example B-32, the title compound was obtained.

$^1$H-NMR (DMSO-d$_6$) δ: 2.92(3H,s), 2.98(2H,br s), 3.06 (1H,br s), 3.13(2H,t,J=5.0 Hz), 3.28(1H,br s), 3.32(2H,t,J=5.0 Hz), 3.46(1H,br s), 3.70(1H,br s), 3.77(2H,br s), 4.34 (1H,br d,J=15.4 Hz), 4.57(1H,br d,J=15.4 Hz), 7.04(1H,d,J=1.6 Hz), 7.34(1H,dd,J=8.8,2.0 Hz), 7.62(1H,d,J=8.8 Hz), 7.79(1H,d,J=2.0 Hz), 8.71(1H,s), 11.67(1H,br s), 12.50(1H,d,J=1.6 Hz). MS (FAB) m/z: 475 (M+H)$^+$.

Example B-175

1-[[6-(tert-Butoxycarbonyl)-5,6,7,8-tetrahydropyrido[4,3-d]pyrimidin-2-yl]carbonyl]-4-[(5-chloroindol-2-yl)sulfonyl]-2-(N-methylcarbamoyl)piperazine In the same manner as in Example B-159, the title compound was obtained.

$^1$H-NMR (CDCl$_3$) δ: 1.49(½ of 9H,s), 1.50(½ of 9H,s), 2.60–2.72(½ of 1H,m), 2.85–3.12(6H,m), 3.12–3.30(1H,m), 3.45–3.70(1H,m), 3.70–3.90(2H+½ of 1H,m), 4.32(½ of 1H,br s), 4.60–4.75(½ of 1H+2H,m), 4.81(½ of 1H,d,J=12.9 Hz), 5.31–5.35(½ of 1H,m), 6.68(½ of 1H,br s), 7.04(½ of 1H,s), 7.07(½ of 1H,s), 7.20–7.35(1H,m), 7.39(½ of 1H,d,J=8.8 Hz), 7.40(½ of 1H,d,J=8.3 Hz), 7.62(½ of 1H,s), 7.66(½ of 1H,s), 7.87(½ of 1H,br s), 10.47(½ of 1H,br s), 10.70(½ of 1H,br s). MS (FAB) m/z: 618 (M+H)$^+$.

Example B-176

4-[(5-Chloroindol-2-yl)sulfonyl]-2-(N-methylcarbamoyl)-1-[(5,6,7,8-tetrahydropyrido[4,3-d]pyrimidin-2-yl]carbonyl]piperazine trifluoroacetate In the same manner as in Example B-170, the title compound was obtained.

$^1$H-NMR (DMSO-d$_6$) δ: 2.30–2.58(2H,m), 2.60(½ of 3H,d,J=4.4 Hz), 2.64(½ of 3H,d,J=4.2 Hz), 2.65–2.75(1H,m), 3.00(½ of 2H,t,J=5.4 Hz), 3.06(½ of 2H,t,J=6.2 Hz), 3.29(½ of 1H,br t,J=11.0 Hz), 3.39(½ of 1H,br d,J=13.5 Hz), 3.50(2H,br s), 3.53–3.80(½ of 1H+1H,m), 4.10–4.30(½ of 1H,m), 4.35(½ of 2H,s), 4.38(½ of 2H,s), 4.50(½ of 1H,br d,J=13.5 Hz), 5.05(½ of 1H,br s), 7.00(½ of 1H,s), 7.01(½ of 1H,s), 7.28–7.38(1H,m), 7.48(½ of 1H,d,J=8.8 Hz), 7.49(½ of 1H,d,J=8.8 Hz), 7.77(½ of 1H,d,J=1.7 Hz), 7.78(½ of 1H,d,J=1.7 Hz), 7.90–8.03(½ of 1H,m), 8.07–8.17(½ of 1H,m), 8.69(½ of 1H,s), 8.73(½ of 1H,s), 9.24(2H,br s), 12.43(1H,s). MS (FAB) m/z: 518 (M+H)$^+$.

Example B-177

4-[(5-Chloroindol-2-yl)sulfonyl]-2-(N-methylcarbamoyl)-1-[(6-methyl-5,6,7,8-tetrahydropyrido[4,3-d]pyrimidin-2-yl]carbonyl]piperazine hydrochloride In the same manner as in Example B-32, the title compound was obtained.

$^1$H-NMR (DMSO-d$_6$) δ: 2.30–2.55(2H,m), 2.61(½ of 3H,d,J=3.5 Hz), 2.65(½ of 3H,d,J=4.2 Hz), 2.68–2.77(1H,m), 2.93(3H,br s), 2.97–3.18(1H,m), 3.20–3.80(6H,m), 4.04–4.65(3H,m), 5.07(½ of 1H,br s), 7.00(½ of 1H,d,J=1.5 Hz), 7.02(½ of 1H,d,J=1.7 Hz), 7.30–7.37(1H,m), 7.50(½ of 1H,d,J=8.8 Hz), 7.51(½ of 1H,d,J=8.8 Hz), 7.78(½ of 1H,d,J=1.7 Hz), 7.80(½ of 1H,d,J=2.0 Hz), 8.05(½ of 1H,br s), 8.15(½ of 1H,br d,J=4.2 Hz), 8.70(½ of 1H,s), 8.74(½ of 1H,s), 11.68(1H,br s), 12.48(1H,s). MS (FAB) m/z: 532 (M+H)$^+$.

Example B-178

4-(5-Chloroindol-2-yl)sulfonyl]-1-[(6-methyl-4,5,6,7-tetrahydrothiazolo[5,4-c]pyridin-2-yl]carbonyl]-2-[2-(piperidin-1-yl)ethyl]piperazine hydrochloride In the same manner as in Example B-62, the title compound was obtained.

$^1$H-NMR (DMSO-d$_6$) δ: 1.16–3.79(26H,m), 4.37–4.45 (1H,m), 4.68–4.75(2H,m), 5.40–5.47(1H,m), 7.02(1H,d,J= 5.1 Hz), 7.32(1H,dd,J=2.2,8.8 Hz), 7.49(1H,d,J=8.8 Hz), 7.77(1H,s). MS (FAB) m/z: 591 [(M+H)$^+$, Cl$^{35}$], 593 [(M+H)$^+$, Cl$^{37}$].

Example B-179

4-[(5-Chloroindol-2-yl)sulfonyl]-2-[2-[N-(2-methoxyethyl)amino]ethyl]-1-[(6-methyl-4,5,6,7-tetrahydrothiazolo[5,4-c]pyridin-2-yl]carbonyl] piperazine hydrochloride In the same manner as in Example B-62, the title compound was obtained.

$^1$H-NMR (DMSO-d$_6$) δ: 2.33–4.77(21H,m), 3.29(3H,s), 3.34(3H,s), 5.39–5.43(1H,m), 7.01(1H,d,J=4.4 Hz), 7.30 (1H,dd,J=7.8,2.0 Hz), 7.49(1H,d,J=8.8 Hz), 7.76(1H,s). MS (FAB) m/z: 581 (M+H)$^+$, Cl$^{35}$], 583 [(M+H)$^+$, Cl$^{37}$].

Example B-180

1-[[6-(tert-Butoxycarbonyl)-4,5,6,7-tetrahydrothiazolo[5,4-c]pyridin-2-yl]carbonyl]-4-[(5-chloroindol-2-yl)sulfonyl]-2-[2-(piperidin-1-yl)ethyl]piperazine In the same manner as in Example B-62, the title compound was obtained.

$^1$H-NMR (CDCl$_3$) δ: 1.48(9H,s), 1.16–3.79(23H,m), 4.45–4.59(1H,m), 4.65–4.75(2H,m), 6.70–6.80(1H,m), 6.96 (1H,s), 7.28–7.31(1H,m), 7.64(1H,d,J=1.7 Hz), 8.02(1H,s). MS (FAB) m/z: 677 (M+H)$^+$.

Example B-181

4-[(5-Chloroindol-2-yl)sulfonyl]-1-[(6-methylsulfonyl-4,5,6,7-tetrahydrothiazolo[5,4-c]pyridin-2-yl]carbonyl]-2-[2-(piperidin-1-yl)ethyl]piperazine In the same manner as in Example B-95, the title compound was obtained.

$^1$H-NMR (CDCl$_3$) δ: 1.54–3.83(23H,m), 2.89(3H,s), 4.59 (2H,s), 4.55–4.84(1H,m), 5.61–5.84(1H,m), 7.00(1H,d,J= 15.0 Hz), 7.27–7.29(1H,m), 7.50–7.57(1H,m), 7.63(1H,s). MS (FAB) m/z: 655 [(M+H)$^+$, Cl$^{35}$], 657 [(M+H)$^+$, Cl$^{37}$].

Example B-182

4-[(5-Chloroindol-2-yl)sulfonyl]-1-[(6-methyl-4,5,6,7-tetrahydrothiazolo[5,4-c]pyridin-2-yl]carbonyl]-2-[3-(thien-2-yl)propyl]piperazine hydrochloride In N,N-dimethylformamide (15 ml) were dissolved 1-[(5-chloro-1-phenylsulfonylindol-2-yl)sulfonyl]-3-[3-(thien-2-yl)propyl]piperazine (257 mg), lithium 6-methyl-4,5,6,7-tetrahydrothiazolo[5,4-c]pyridine-2-carboxylate (129 mg), 1-(3-dimethylaminopropyl)-3-ethylcarbodiimide hydrochloride (131 mg) and 1-hydroxybenzotriazole hydrate (76.4 mg). Under ice cooling, diisoproylethylamine (180 μl) was added dropwise to the resulting solution, followed by stirring at room temperature for 15.5 hours. The reaction mixture was extracted with methylene chloride and water. The organic layer was washed with saturated aqueous NaCl solution, dried over anhydrous sodium sulfate and distilled under reduced pressure to remove the solvent. The residue was subjected to column chromatography (2% methanol—methylene chloride) using as a carrier silica gel. After conversion into the corresponding hydrochloride by the addition of 1N aqueous hydrochloric acid in ethanol, methylene chloride-methanol-ether was added to solidify the hydrochloride. The resulting solid was purified again by subjecting it to thin-layer chromatography (10% methanol—methylene chloride), followed by the addition of 1N aqueous hydrochloric acid in ethanol to form the corresponding hydrochloride. Methylene chloride-methanol-ether was added to solidify the hydrochloride. The resulting solid was collected by filtration, washed with ether and then dried, whereby the title compound (62.6 mg) was obtained as colorless powder.

$^1$H-NMR (DMSO-d$_6$) δ: 1.45–2.00(4H,m), 2.30–3.80 (11H,m), 4.30–4.80(3H,m), 5.15–5.65(1H,m), 6.75–6.85 (1H,m), 6.85–6.95(1H,m), 7.01(1H,s), 7.20–7.35(2H,m), 7.48(1H,d,J=9.0 Hz), 7.75(1H,s), 11.42(1H,br), 12.44(1H, s). MS (FAB) m/z: 604 [(M+H)$^+$, Cl$^{35}$], 606 [(M+H)$^+$, Cl$^{37}$].

Example B-183

4-[(5-Chloroindol-2-yl)sulfonyl]-2-[3-(3,4-dimethoxyphenyl)propyl]-1-[(6-methyl-4,5,6,7-tetrahydrothiazolo[5,4-c]pyridin-2-yl]carbonyl] piperazine hydrochloride In the same manner as in Example B-182, the title compound was obtained.

$^1$H-NMR (DMSO-d$_6$) δ: 1.40–1.90(4H,m), 2.40–2.70 (1H,m), 2.90(3H,s), 3.00–3.20(2H,m), 3.30–3.80(16H,m), 4.30–4.80(3H,m), 5.20–5.60(1H,m), 6.60–6.70(1H,m), 6.82 (1H,d,J=8.1 Hz), 7.01(1H,s), 7.25–7.35(1H,m), 7.48(1H,d, J=8.8 Hz), 7.70–7.80(1H,m), 11.20–11.50(1H,br), 12.43 (1H,s). MS (FAB) m/z: 658 [(M+H)$^+$, Cl$^{35}$], 660 [(M+H)$^+$, Cl$^{37}$].

Example B-184

4-[(5-Chloroindol-2-yl)sulfonyl]-1-[(6-methyl-4,5,6,7-tetrahydrothiazolo[5,4-c]pyridin-2-yl]carbonyl]-2-[2-[(pyrrolidin-1-yl)sulfonyl]ethyl]piperazine hydrochloride In the same manner as in Example B-182, the title compound was obtained.

$^1$H-NMR (DMSO-d$_6$) δ: 1.80–1.90(4H,m), 2.10–2.30 (2H,m), 2.40–3.85(15H,m), 2.90(3H,s), 4.30–4.90(3H,m), 5.30–5.50(1H,m), 7.02(1H,s), 7.25–7.35(1H,m), 7.48(1H,d, J=8.8 Hz), 7.76(1H,s), 11.27(1H,br), 12.44(1H,s). MS (FAB) m/z: 641 [(M+H)$^+$, Cl$^{35}$], 642 [(M+H)$^+$, Cl$^{37}$].

Example B-185

1-[[6-Methyl-4,5,6,7-tetrahydrofuro[2,3-c]pyridin-2-yl]carbonyl]-4-[(1-phenylsulfonyl-5-trimethylsilylethynylindol-2-yl)sulfonyl]piperazine In the same manner as in Example B-103, the title compound was obtained.

$^1$H-NMR (CDCl$_3$) δ: 0.25–0.35(9H,m), 2.45–2.55(3H, m), 2.55–2.65(2H,m), 2.65–2.75(2H,m), 3.45–3.55(6H,m), 3.85–3.95(4H,m), 7.40–7.65(6H,m), 7.70–7.75(1H,m), 8.00–8.05(2H,m), 8.20–8.25(1H,m). MS (FAB) m/z: 665 (M+H)$^+$.

Example B-186

1-[(5-Ethynylindol-2-yl)sulfonyl]-4-[(6-methyl-4,5,6,7-tetrahydrofuro[2,3-c]pyridin-2-yl)carbonyl] piperazine In the same manner as in Example B-104, the title compound was obtained.

¹H-NMR (CDCl₃) δ: 2.47(3H,s), 2.50–2.60(2H,m), 2.65 (2H,t,J=5.6 Hz), 3.17(4H,t,J=5.0 Hz), 3.46(2H,s), 3.90(4H, br s), 6.84(1H,s), 7.00(1H,d,J=1.0 Hz), 7.35–7.40(1H,m), 7.45–7.50(1H,m), 7.87(1H,s), 8.92(1H,br s). MS (FAB) m/z: 453 (M+H)⁺.

Example B-187

1-[(5-Chloroindol-2-yl)sulfonyl]-4-[(6-methyl-4,5,6,7-tetrahydrofuro[2,3-c]pyridin-2-yl)carbonyl]piperazine hydrochloride In the same manner as in Example B-62, the title compound was obtained.

¹H-NMR (DMSO-d₆) δ: 2.76(2H,br), 2.89(3H,s), 3.05–3.10(2H,m), 3.35–3.50(2H,m), 3.74(4H,br), 4.10–4.60 (2H,m), 6.97(1H,s), 7.00–7.05(1H,m), 7.30–7.35(1H,m), 7.49(1H,d,J=9.0 Hz), 7.78(1H,d,J=2.0 Hz), 10.88(1H,br s), 12.45(1H,s). MS (FAB) m/z: 463 [(M+H)⁺, Cl³⁵], 465 [(M+H)⁺, Cl³⁷].

Example B-188

1-[(2-tert-Butoxycarbonylisoindolin-5-yl)carbonyl]-4-[(5-chloroindol-2-yl)sulfonyl]piperazine In the same manner as in Example B-62, the title compound was obtained.

¹H-NMR (CDCl₃) δ: 1.51(9H,s), 3.13(4H,br s), 3.72(4H, br s), 4.60–4.70(4H,m), 6.96(1H,s), 7.18–7.30(3H,m), 7.31–7.40(2H,m), 7.69(1H,s), 8.93(1H,s). MS (FAB) m/z: 545 [(M+H)⁺, Cl³⁵], 547 [(M+H)⁺, Cl³⁷]. Elementary analysis for C₂₆H₂₉ClN₄O₅S.H₂O Calculated: C, 55.46; H, 5.55; N, 9.95. Found: C, 55.69; H, 5.35; N, 9.85.

Example B-189

1-[(5-Chloroindol-2-yl)sulfonyl]-4-[(isoindolin-5-yl)carbonyl]piperazine

In the same manner as in Example B-1, the title compound was obtained.

m.p. 196–199° C. (dec). ¹H-NMR (DMSO-d₆) δ: 3.08 (4H,br s), 3.44(2H,br s), 3.69(2H,br s), 4.47(2H,s), 4.50(2H, s), 7.02(1H,s), 7.30–7.45(4H,m), 7.51(1H,d,J=8.8 Hz), 7.79 (1H,d,J=2.0 Hz), 9.65(2H,br s), 12.44(1H,s). MS (FAB) m/z: 445 [(M+H)⁺, Cl³⁵], 447 [(M+H)⁺, Cl³⁷]. Elementary analysis for C₂₁H₂₁ClN₄O₃S Calculated: C, 48.75; H, 5.06; Cl, 13.70; N, 10.83; S, 6.20. Found: C, 49.06; H, 4.96; Cl, 13.61; N, 10.63; S, 6.08.

Example B-190

1-[(5-Chloroindol-2-yl)sulfonyl]-4-[(2-methylisoindolin-5-yl)carbonyl]piperazine In the same manner as in Example B-32, the title compound was obtained.

m.p. 175–180° C. (dec). ¹H-NMR (DMSO-d₆) δ: 2.97 (3H,br s), 3.09(4H,br s), 3.43(2H,br s), 3.68(2H,br s), 4.57 (4H,br s), 7.02(1H,s), 7.30–7.45(4H,m), 7.51(1H,d,J=9.0 Hz), 7.79(1H,s), 11.58(1H,br s), 12.46(1H,s). MS (FAB) m/z: 459 [(M+H)⁺, Cl³⁵], 461 [(M+H)⁺, Cl³⁷]. Elementary analysis for C₂₂H₂₃ClN₄O₃S.0.95HCl.1.6H₂O Calculated: C, 50.58; H, lfonyl]-4-[(5,6-dimethyl-4,5,6,7-tetrahydrothiazolo[4,5-d]pyridazin-2-yl]carbonyl]piperazine hydrochloride In the same manner as in Example B-82, the title compound was obtained.

¹H-NMR (DMSO-d₆) δ: 2.65(3H,br s), 2.76(3H,br s), 3.13(4H,br s), 3.74(2H,br s), 4.10–4.50(6H,br), 7.03(1H,d, J=1.5 Hz), 7.31(1H,dd,J=8.8,2.0 Hz), 7.48(1H,d,J=8.8 Hz), 7.76(1H,d,J=2.0 Hz), 12.42(1H,br s). MS (FAB) m/z: 495 [(M+H)⁺, Cl³⁵], 497 [(M+H)⁺, Cl³⁷].

Example B-200

2-[[(4-tert-Butoxycarbonylpiperazin-1-yl)carbonyl]methyl]-4-[(5-chloroindol-2-yl)sulfonyl]-1-[(6-methyl-4,5,6,7-tetrahydrothiazolo[5,4-c]pyridin-2-yl)carbonyl]piperazine In the same manner as in Example B-79, the title compound was obtained.

¹H-NMR (CDCl₃) δ: 1.49(9H,s), 2.49(3H,s), 2.55–3.20 (8H,m), 3.30–3.85(12H,m), 3.95–4.04(0.5H,m), 4.10–4.18 (0.5H,m), 4.55–4.67(0.5H,m), 4.95–5.07(0.5H,m), 5.55–5.65(0.5H,m), 6.00–6.10(0.5H,m), 7.00(1H,s), 7.25–7.31(1H,m), 7.37(1H,d,J=8.8 Hz), 7.65(1H,s). MS (FAB) m/z: 706 [(M+H)⁺, Cl³⁵], 708 [(M+H)⁺, Cl³⁷].

Example B-201

4-[(5-Chloroindol-2-yl)sulfonyl]-1-[(6-methyl-4,5,6,7-tetrahydrothiazolo[5,4-c]pyridin-2-yl)carbonyl]-2-[[(piperazin-1-yl)carbonyl]methyl]piperazine hydrochloride In the same manner as in Example B-1, the title compound was obtained.

¹H-NMR (DMSO-d₆) δ: 2.50–3.85(23H,m), 4.30–4.45 (1H,m), 4.60–4.75(0.5H,m), 5.00–5.10(0.5H,m), 5.30–5.40 (0.5H,m), 5.80–5.95(0.5H,m), 7.03(1H,s), 7.32(1H,d,J=8.8 Hz), 7.50(1H,d,J=8.8 Hz), 7.78(1H,s), 9.20–9.45(1H,br), 12.46(1H,br s). MS (FAB) m/z: 606 [(M+H)⁺, Cl³⁵], 608 [(M+H)⁺, Cl³⁷].

Example B-202

4-[(5-Chloroindol-2-yl)sulfonyl]-2-[(N-furfurylcarbamoyl)methyl]-1-[(6-methyl-4,5,6,7-tetrahydrothiazolo[5,4-c]pyridin-2-yl)carbonyl]piperazine hydrochloride In the same manner as in Example B-79, the title compound was obtained.

¹H-NMR (DMSO-d₆) δ: 2.50–3.50(13H,m), 3.60–3.85 (2H,m), 4.12–4.50(3H,m), 4.60–4.75(0.5H,m), 5.05–5.10 (0.5H,m), 5.30–5.40(0.5H,m), 5.78–5.90(0.5H,m), 6.17–6.25(1H,br), 6.35–6.42(1H,m), 7.03(1H,s), 7.31(1H,d, J=8.8 Hz), 7.48(1H,d,J=8.8 Hz), 7.51–7.58(1H,m), 7.77(1H, s), 8.41–8.55(1H,br), 12.44(1H,br s). MS (FAB) m/z: 617 [(M+H)⁺, Cl³⁵], 619 [(M+H)⁺, Cl³⁷]. HRMS (FAB) m/z: 617.1418 (M+H)⁺ (calcd for C₂₇H₂₉ClN₆O₅S₂, 617.1408).

Example B-203

4-[(5-Chloroindol-2-yl)sulfonyl]-2-[(N-methoxy-N-methylcarbamoyl)methyl]-1-[(6-methyl-4,5,6,7-tetrahydrothiazolo[5,4-c]pyridin-2-yl)carbonyl]piperazine hydrochloride In the same manner as in Example B-79, the title compound was obtained.

¹H-NMR (DMSO-d₆) δ: 2.50–3.83(20H,m), 4.30–4.80 (2.5H,br), 5.07(0.5H,br s), 5.31–5.36(0.5H,br), 5.78(0.5H,br s), 7.03(1H,s), 7.31(1H,d,J=9.2 Hz), 7.48(1H,d,J=9.2 Hz), 7.77(1H,s), 11.04(1H,br s), 12.45(1H,br s). MS (FAB) m/z: 581 [(M+H)⁺, Cl³⁵], 583 [(M+H)⁺, Cl³⁷].

Example B-204

1-[(6-(tert-Butoxycarbonyl)-4,5,6,7-tetrahydrothiazolo[5,4-c]pyridin-2-yl)carbonyl]-4-[(5-chloroindol-2-yl)sulfonyl]piperazine In the same manner as in Example B-62, the title compound was obtained.

$^1$H-NMR (CDCl$_3$) δ: 1.48(9H,s), 2.85(2H,br s), 3.22(4H, br s), 3.73(2H,br s), 3.89(2H,br s), 4.58(2H,br s), 4.65(2H,br s), 6.97(1H,s), 7.32(1H,dd,J=8.8,2.0 Hz), 7.37(1H,d,J=8.8 Hz), 7.66(1H,d,J=2.0 Hz), 8.72(1H,s). MS (FAB) m/z: 566 [(M+H)$^+$, Cl$^{35}$], 568 [(M+H)$^+$, Cl$^{37}$].

Example B-205

1-[(5-Chloroindol-2-yl)sulfonyl]-4-[(4,5,6,7-tetrahydrothiazolo[5,4-c]pyridin-2-yl)carbonyl]piperazine hydrochloride In the same manner as in Example B-1, the title compound was obtained.

$^1$H-NMR (DMSO-d$_6$) δ: 3.01(2H,t,J=6.1 Hz), 3.13(4H,br s), 3.44(2H,t,J=6.1 Hz), 3.75(2H,br s), 4.36(2H,br s), 4.42 (2H,s), 7.04(1H,s), 7.31(1H,dd,J=8.8,2.0 Hz), 7.49(1H,d,J=8.8 Hz), 7.77(1H,d,J=2.0 Hz), 9.46(2H,br s), 12.43(1H,s). MS (FAB) m/z: 466 [(M+H)$^+$, Cl$^{35}$], 468 [(M+H)$^+$, Cl$^{37}$].

Example B-206

1-[(5-Chloroindol-2-yl)sulfonyl]-4-[(6-hydroxy-4,5,6,7-tetrahydrothiazolo[5,4-c]pyridin-2-yl]carbonyl]piperazine In the same manner as in Example B-144, the title compound was obtained.

$^1$H-NMR (DMSO-d$_6$) δ: 2.70–3.05(2H,br), 3.05–3.25 (6H,br), 3.65–4.50(6H,br), 7.03(1H,s), 7.30(1H,dd,J=8.8, 2.0 Hz), 7.47(1H,d,J=8.8 Hz), 7.76(1H,d,J=2.0 Hz), 8.35 (1H,s), 12.40(1H,s). MS (FAB) m/z: 482 [(M+H)$^+$, Cl$^{35}$], 84 [(M+H)$^+$, Cl$^{37}$].

Example B-207

4-[(5-Chloroindol-2-yl)sulfonyl]-2-[(ethoxycarbonyl)methyl]-1-[(6-methylsulfonyl-4,5,6,7-tetrahydrothiazolo[5,4-c]pyridin-2-yl)carbonyl]piperazine In a saturated solution of hydrochloride in ethanol was dissolved 1-(tert-butoxycarbonyl)-4-[(5-chloroindol-2-yl)sulfonyl]-2-[(methoxycarbonyl)methyl]piperazine (1.15 g), followed by stirring at room temperature for 1 hour. The solvent was distilled off under reduced pressure. Methylene chloride and a saturated aqueous solution of sodium bicarbonate were added to the residue to separate into layers. The organic layer was dried over anhydrous sodium sulfate and distilled under reduced pressure to remove the solvent. A portion (519 mg) of the residue (0.97 g) was dissolved in N,N-dimethylformamide (2 ml), followed by the addition of lithium (6-tert-butoxycarbonyl-4,5,6,7-tetrahydrothiazolo [5,4-c]pyridin-2-yl)carboxylate (328 mg), 1-ethyl-3-(3-dimethylaminopropyl)carbodiimide hydrochloride (288 mg) and 1-hydroxybenzotriazole (363 mg). The resulting mixture was stirred at room temperature for 3 days. Methylene chloride and water were added and the organic layer was collected. The organic layer was dried over anhydrous sodium sulfate and distilled under reduced pressure to remove the solvent. The residue was purified by flash column chromatography (hexane:ethyl acetate=1:1) using as a carrier silica gel.

The resulting purified product was dissolved in a saturated solution (5 ml) of hydrochloride in ethanol, followed by stirring at room temperature for 1 hour. After the addition of methylene chloride, the resulting mixture was washed with a saturated aqueous solution of sodium bicarbonate. The organic layer was dried over anhydrous sodium sulfate and distilled under reduced pressure to remove the solvent. The residue was dissolved in methylene chloride (5 ml), followed by the addition of methanesulfonyl chloride (105 μl) and triethylamine (0.5 ml). The resulting mixture was stirred at room temperature for 15 minutes and washed with water. The organic layer was dried over anhydrous sodium sulfate and distilled under reduced pressure to remove the solvent. The residue was purified by flash column chromatography (methylene chloride:methanol 49:1) using as a carrier silica gel, whereby the title compound (207 mg) was obtained.

$^1$H-NMR (DMSO-d$_6$) δ: 1.07–1.16(3H,m), 2.67–2.90 (5H,m), 2.96(3H,s), 3.20–3.24(2H,m), 3.53–3.78(4H,m), 3.95–4.04(2H,m), 4.39, 5.04(1H,each d,J=14.4,14.9 Hz), 4.55(2H,s), 5.03, 5.95(1H,each br s), 7.03(1H,s), 7.31(1H, dd,J=8.8,1.7 Hz), 7.47(1H,d,J=8.8 Hz), 7.76(1H,d,J=1.7 Hz), 12.41(1H,s). MS (FAB) m/z: 630 (M+H)$^+$.

Example B-208

2-[Carboxymethyl]-4-[(5-chloroindol-2-yl)sulfonyl]-1-[(6-methylsulfonyl-4,5,6,7-tetrahydrothiazolo[5,4-c]pyridin-2-yl)carbonyl]piperazine In the same manner as in Example B-77, the title compound was obtained.

$^1$H-NMR (DMSO-d$_6$) δ: 2.32–3.74(14H,m), 4.38,5.37 (1H,each d,J=12.2,12.4 Hz), 4.54(2H,s), 5.00,5.83(1H,each br s), 7.02(1H,s), 7.30(1H,d,J=8.8 Hz), 7.47(1H,d,J=8.8 Hz), 7.75(1H,s), 12.51(1H,s). HRMS (FAB) m/z: 602.0612 (M+H)$^+$ (calcd for C$_{22}$H$_{25}$N$_5$O$_7$ClS$_3$, 602.0605).

Example B-209

4-[(5-Chloroindol-2-yl)sulfonyl]-2-[[N-methylsulfonyl)carbamoyl]methyl]-1-[(6-methylsulfonyl)-4,5,6,7-tetrahydrothiazolo[5,4-c]pyridin-2-yl]carbonyl]piperazine In tetrahydrofuran (5 ml) was dissolved 2-[carboxymethyl]-4-[(5-chloroindol-2-yl)sulfonyl]-1-[(6-methylsulfonyl-4,5,6,7-tetrahydrothiazolo[5,4-c]pyridin-2-yl)carbonyl]piperazine (115 mg), followed by the addition of carbonyldiimidazole (58 mg). The resulting mixture was heated under reflux for 2 hours. After cooling to room temperature, methanesulfonamide (34 mg) and 1,8-diazabicyclo[5.4.0]-7-undecene (55 mg) were added, followed by stirring for 1.5 hours. The solvent was distilled off under reduced pressure. The residue was dissolved in methylene chloride and the solution was washed with water, 0.2N hydrochloric acid and saturated aqueous NaCl solution. The organic layer was dried over anhydrous sodium sulfate and distilled under reduced pressure to remove the solvent. The residue was purified by preparative TLC (methylene chloride:methanol=9:1). The solvent was distilled off under reduced pressure. The solid thus obtained was washed with ether, whereby the title compound (62 mg) was obtained as a colorless solid.

$^1$H-NMR (DMSO-d$_6$) δ: 2.50–3.56(15H,m), 3.65–3.77 (2H,m), 4.40, 5.40(1H,each d,J=15.4,11.8 Hz), 4.55(2H,s), 5.10, 5.98(1H,each br s), 7.04(1H,s), 7.31(1H,d,J=8.8,2.0

Hz), 7.47(1H,d,J=8.8 Hz), 7.76(1H,d,J=2.0 Hz), 11.88(1H, s), 12.44(1H,s). MS (FAB) m/z: 602 (M+H)+.

Example B-210

1-[(6-Chlorobenzo[b]thien-2-yl)sulfonyl]-4-[(4,5,6,7-tetrahydrothiazolo[5,4-c]pyridin-2-yl)carbonyl]piperazine To a solution of lithium 6-(tert-butoxycarbonyl-4,5,6,7-tetrahydrothiazolo[5,4-c]pyridine-2-carboxylate (1.89 g) in N,N-dimethylformamide (40 ml) were added 1-[(6-chlorobenzo[b]thien-2-yl)sulfonyl]piperazine (2.50 g), 1-hydroxybenzotriazole monohydrate (1.20 g) and 1-(dimethylaminopropyl)-3-ethylcarbodiimide hydrochloride (1.70 g) at room temperature. After stirring for 2 days, ethyl acetate (200 ml) and water (1.0 l) were added to the reaction mixture to separate it into layers. The water layer was extracted with ethyl acetate (2×150 ml). The organic layers were combined, washed with water (1.0 l) and a saturated aqueous solution (200 ml) of sodium bicarbonate, dried over anhydrous sodium sulfate and distilled under reduced pressure to remove the solvent. The residue was purified by chromatography on a silica gel column (silica gel: 200 g, methylene chloride:ethyl acetate=7:1→1:1), whereby 1-[[6-(tert-butoxycarbonyl)-4,5,6,7-tetrahydrothiazolo[5,4-c]pyridin-2-yl)carbonyl]-4-[(6-chlorobenzo[b]thien-2-yl)sulfonyl]piperazine was obtained as pale yellow foam. A solution of the boc form in methylene chloride (15 ml) was added trifluoroacetic acid (15 ml) at room temperature. After stirring for 10 minutes, the solvent was distilled off under reduced pressure. Methylene chloride (50 ml) and a saturated aqueous solution (150 ml) of sodium bicarbonate were added to the residue to separate it into layers. The water layer was extracted with methylene chloride (6×25 ml). The organic layers were combined, dried over anhydrous sodium sulfate and distilled under reduced pressure to remove the solvent. The residue was purified by chromatography on a silica gel column (silica gel: 100 g, methylene chloride:methanol=25:1→10:1), whereby the title compound (754 mg) was obtained as a pale brown solid.

$^1$H-NMR (DMSO-d$_6$) δ: 2.67(2H,t,J=5.7 Hz), 2.96(2H,t, J=5.7 Hz), 3.18(4H,t,J=4.9 Hz), 3.31(1H,s), 3.77(2H,br s), 3.90(2H,s), 4.44(2H,br s), 7.57(1H,dd,J=8.8,2.0 Hz), 8.05 (1H,d,J=8.8 Hz), 8.09(1H,s), 8.31(1H,d,J=2.0 Hz). MS (FAB) m/z: 483 (M+H)+.

Example B-211

1-[(6-Chlorobenzo[b]thien-2-yl)sulfonyl]-4-[[6-(pyridin-4-yl)-4,5,6,7-tetrahydrothiazolo[5,4-c]pyridin-2-yl]carbonyl]piperazine hydrochloride To a solution of 1-[(6-chlorobenzo[b]thien-2-yl)sulfonyl]-4-[(4,5,6,7-tetrahydrothiazolo[5,4-c]pyridin-2-yl]carbonyl]piperazine (200 mg) in N,N-dimethylformamide (2.0 ml) were added 4-bromopyridine (87.0 mg) and triethylamine (150 μl) at room temperature. The resulting mixture was stirred under heat at 120° C. for 12 hours. After concentration of the reaction mixture, methylene chloride (20 ml), a saturated aqueous solution (50 ml) of sodium bicarbonate and water (50 ml) were added to the concentrate to separate it into layers. The water layer thus obtained was extracted with methylene chloride (4×20 ml). The organic layers were combined, dried over anhydrous sodium sulfate and distilled under reduced pressure to remove the solvent. The residue was purified by preparative thin-layer chromatography (methylene chloride:methanol=20:1) using silica gel, followed by purification by preparative thin-layer chromatography (methylene chloride:acetone:methanol=15:5:1) using silica gel. The purified product was dissolved in methylene chloride, methanol and 1N hydrochloric acid. The resulting solution was concentrated under reduced pressure and dried, whereby the title compound (56.5 mg) was obtained as a pale yellow solid.

$^1$H-NMR (DMSO-d$_6$) δ: 2.97(2H,t,J=5.6 Hz), 3.17(4H,br s), 3.77(2H,br s), 4.05(2H,t,J=5.6 Hz), 4.41(2H,br s), 5.01 (2H,s), 7.31(2H,br s), 7.56(1H,d,J=8.4 Hz), 8.05(1H,d,J=8.4 Hz), 8.08(1H,s), 8.30(2H,s), 8.32(1H,s), 13.70(1H,br s). MS (FAB) m/z: 560 (M+H)+.

Example B-212

2-(Methoxycarbonylmethyl)-1-[(6-methyl-4,5,6,7-tetrahydrothiazolo[5,4-c]pyridin-2-yl)carbonyl]-4-[[5-(trimethylsilylethynyl)indol-2-yl]sulfonyl]piperazine In the same manner as in Example B-62, the title compound was obtained.

$^1$H-NMR (CDCl$_3$) δ: 0.26(9H,s), 2.49(3H,s), 2.53–2.68 (1H,m), 2.74(1H,dd,J=12.0,2.7 Hz), 2.77–2.83(3H,m), 2.87 (2H,br s), 3.00(1H,dd,J=15.8,8.7 Hz), 3.11–3.26(½H,br), 3.39–3.54(½H,br), 3.59–3.67(5H,m), 3.72–3.96(2H,m), 4.61(½H,br d,J=13.2 Hz), 5.22(½H,br s), 5.71(½H,br d,J= 13.2 Hz), 6.16(½H,br s), 6.97(1H,s), 7.34(1H,d,J=8.6 Hz), 7.43(1H,dd,J=8.6,1.5 Hz), 7.81(1H,s), 9.35(1H,br d,J=11.0 Hz). MS (FAB) m/z: 614 (M+H)+.

Example B-213

4-[(5-Ethynylindol-2-yl)sulfonyl-2-(methoxycarbonylmethyl)-1-[(6-methyl-4,5,6,7-tetrahydrothiazolo[5,4-c]pyridin-2-yl)carbonyl]piperazine In the same manner as in Example B-104, the title compound was obtained.

$^1$H-NMR (CDCl$_3$) δ: 2.49(3H,s), 2.53–2.95(7H,m), 2.95–3.05(1H,m), 3.04(1H,s), 3.20(½H,br t,J=11.6 Hz), 3.46(½H,br t,J=11.6 Hz), 3.59–3.75(5H,m), 3.75–3.97(2H, m), 4.62(½H,br d,J=12.8 Hz), 5.22(½H,br s), 5.73(½H,br d,J=13.6 Hz), 6.18(½H,br s), 7.00(1H,s), 7.37(1H,d,J=8.6 Hz), 7.45(1H,dd,J=8.6,1.2 Hz), 7.85(1H,s), 9.28(1H,br d,J= 13.2 Hz). MS (FAB) m/z: 542 (M+H)+.

Example B-214

4-[(5-Chloroindol-2-yl)sulfonyl]-1-[(6-methyl-4,5,6,7-tetrahydrothiazolo[5,4-c]pyridin-2-yl)carbonyl]-2-[2-(morpholin-4-yl)sulfonyl]ethyl]piperazine hydrochloride In the same manner as in Example B-182, the title compound was obtained.

$^1$H-NMR (DMSO-d$_6$) δ: 2.10–2.40(2H,m), 2.50–2.80 (2H,m), 2.90(3H,s), 3.00–3.30(8H,m), 3.30–3.90(9H,s), 4.30–4.90(3H,m), 5.30–5.50(1H,m), 7.03(1H,s), 7.31(1H, dd,J=8.8,1.5 Hz), 7.48(1H,d,J=8.8 Hz), 7.76(1H,d,J=1.5 Hz), 11.42(1H,br), 12.45(1H,s). MS (FAB) m/z: 657 [(M+H)+, Cl$^{35}$], 659 [(M+H)+, Cl$^{37}$].

Example B-215

4-[(5-Chloroindol-2-yl)sulfonyl]-2-(2-ethoxycarbonylethyl)-1-[(6-methyl-4,5,6,7-tetrahydrothiazolo[5,4-c]pyridin-2-yl)carbonyl]piperazine In the same manner as in Example B-62, the title compound was obtained.

¹H-NMR (CDCl₃) δ: 1.15–1.25(3H,m), 1.40–1.80(1H, m), 2.05–2.15(1H,m), 2.25–2.45(3H,m), 2.49(3H,s), 2.50–3.55(6H,m), 3.67(2H,s), 3.70–3.90(2H,m), 4.00–4.20 (2H,m), 4.55–6.10(2H,m), 6.95(1H,s), 7.30–7.40(2H,m), 7.65(1H,d,J=1.6 Hz), 9.03(1H,br). MS (FAB) m/z: 580 [(M+H)⁺, Cl³⁵], 582 [(M+H)⁺, Cl³⁷].

Example B-216

4-[(5-Chloroindol-2-yl)sulfonyl]-1-[(6-methyl-4,5,6, 7-tetrahydrothiazolo[5,4-c]pyridin-2-yl)carbonyl]-2-[[2-(morpholin-4-yl)carbonyl]ethyl]piperazine In the same manner as in Referential Example 319, the title compound was obtained.

¹H-NMR (DMSO-d₆) δ: 1.85–2.00(1H,m), 2.05–2.20 (1H,m), 2.20–2.35(2H,m), 2.55–2.70(1H,m), 3.80–2.95(4H, m), 3.00–3.80(14H,m), 4.25–5.55(5H,m), 7.02(1H,s), 7.30 (1H,dd,J=8.8,2.0 Hz), 7.48(1H,d,J=8.8 Hz), 7.75(1H,d,J= 2.0 Hz), 11.45(1H,br s), 12.43(1H,s). MS (FAB) m/z: 621 [(M+H)⁺, Cl³⁵], 623 [(M+H)⁺, Cl³⁷].

Example B-217

4-[(5-Chloroindol-2-yl)sulfonyl]-2-[[2-(N,N-dimethylaminocarbonyl)ethyl]-1-[(6-methyl-4,5,6,7-tetrahydrothiazolo[5,4-c]pyridin-2-yl)carbonyl] piperazine In the same manner as in Referential Example 319, the title compound was obtained.

¹H-NMR (DMSO-d₆) δ: 1.85–2.00(1H,m), 2.05–2.20 (1H,m), 2.20–2.35(2H,m), 2.50–2.65(1H,m), 2.70–3.80 (17H,m), 4.30–5.55(4H,m), 7.02(1H,s), 7.29(1H,dd,J=8.8, 2.0 Hz), 7.48(1H,d,J=8.8 Hz), 7.75(1H,d,J=2.0 Hz), 11.49 (1H,br s), 12.44 (1H,s). MS (FAB) m/z: 579 [(M+H)⁺, Cl³⁵], 581 [(M+H)⁺, Cl³⁷].

Example B-218

4-[(5-Chloroindol-2-yl)sulfonyl]-2-(2-cyanoethyl)-1-[(6-methyl-4,5,6,7-tetrahydrothiazolo[5,4-c]pyridin-2-yl)carbonyl]piperazine hydrochloride In the same manner as in Example B-182, the title compound was obtained.

¹H-NMR (DMSO-d₆) δ: 1.90–2.18(2H,m), 2.20–2.90 (4H,m), 2.90(3H,s), 3.12(2H,br s), 3.21–3.82(6H,m), 4.30–4.85(2H,m), 5.31–5.43(0.5H,m), 5.55–5.70(0.5H,m), 7.02(1H,d,J=2.0 Hz), 7.31(1H,dd,J=8.9,2.1 Hz), 7.48(1H,d, J=8.8 Hz), 7.76(1H,d,J=1.7 Hz), 11.18(1H,br s), 12.44(1H, br s). MS (FAB) m/z: 533 [(M+H)⁺, Cl³⁵], 535 [(M+H)⁺, Cl³⁷].

Example B-219

1-[(5-Chloroindol-2-yl)sulfonyl]-4-[(6,6-ethylenedioxy-4,5,6,7-tetrahydrobenzo[d]thiazol-2-yl)carbonyl]piperazine In the same manner as in Example B-62, the title compound was obtained.

¹H-NMR (DMSO-d₆) δ: 1.93(2H,t,J=6.6 Hz), 2.73–3.32 (10H,m), 3.73(1H,br s), 3.93(4H,s), 3.95(1H,br s), 6.97, 7.03(1H,s), 7.30(1H,dd,J=8.8,2.2 Hz), 7.45–7.47(1H,m), 7.76(1H,s). MS (FAB) m/z: 523 [(M+H)⁺, Cl³⁵], 525 [(M+H)⁺, Cl³⁷].

Example B-220

1-[(5-Chloroindol-2-yl)sulfonyl]-4-[(6-oxo-4,5,6,7-tetrahydrobenzo[d]thiazol-2-yl)carbonyl]piperazine In a 300-mL egg-plant type flask was charged 1-[(5-chloroindol-2-yl)sulfonyl]-4-[(6,6-ethylenedioxy-4,5,6,7-tetrahydrobenzo[d]thiazol-2-yl)carbonyl]piperazine (740 mg), followed by dissolution in methanol (150 mL). To the resulting solution was added p-toluenesulfonic monohydrate (100 mg), followed by heating under reflux. After 16 hours, the reaction was terminated and the solvent was distilled off under reduced pressure. The residue was purified by chromatography on a silica gel column (silica gel: 75 g, ethyl acetate:hexane=1:1), whereby the title compound (110 mg) was obtained as a pale yellow amorphous solid.

¹H-NMR (CDCl₃) δ: 2.76(2H,t,J=6.8 Hz), 3.18(2H,t,J= 6.8 Hz), 3.19–3.22(6H,m), 3.65(2H,s), 3.89(1H,br s), 4.59 (1H,br s), 6.97(1H,s), 7.31–7.39(2H,m), 7.66(1H,d,J=2.0 Hz). MS (FAB) m/z: 479 [(M+H)⁺, Cl³⁵], 481 [(M+H)⁺, Cl³⁷].

Example B-221

1-[(5-Chloroindol-2-yl)sulfonyl]-4-[(4,5-dihydro-7H-pyrano[4,3-d]thiazol-2-yl)carbonyl]piperazine In the same manner as in Example B-62, the title compound was obtained.

¹H-NMR (DMSO-d₆) δ: 2.82(2H,t,J=5.6 Hz), 3.12(4H,t, J=4.9 Hz), 3.28–3.35(2H,m), 3.73(1H,br s), 3.93(2H,t,J=5.6 Hz), 4.39(1H,br s), 4.79(2H,s), 7.03(1H,s), 7.30(1H,dd,J= 8.8,2.2 Hz), 7.47(1H,d,J=8.8 Hz), 7.76(1H,s). MS (FAB) m/z: 467 [(M+H)⁺, Cl³⁵], 469 [(M+H)⁺, Cl³⁷].

Example B-222

4-[(5-Chloroindol-2-yl)sulfonyl]-1-[(6-methyl-4,5,6, 7-tetrahydrothiazolo[5,4-c]pyridin-2-yl)carbonyl]-2-[[N-(phenylsulfonyl)carbamoyl]methyl]piperazine hydrochloride In the same manner as in Example B-62, the title compound was obtained.

¹H-NMR (DMSO-d₆) δ: 2.52–3.77(12H,m), 3.88–4.20 (2H,m), 4.24–4.48(1.5H,m), 4.52–4.75(1H,m), 5.00(0.5H, m), 5.23–5.32(0.5H,m), 5.57(0.25H,br s), 5.79(0.25H,br s), 6.97(1H,s), 7.28(1H,d,J=8.8 Hz), 7.45(1H,d,J=8.8 Hz), 7.49–7.53(1H,m), 7.61(2H,br s), 7.72(1H,s), 7.85(2H,br s), 11.54–11.98(1H,m), 12.20–12.50(2H,m). MS (FAB) m/z: 677 [(M+H)⁺, Cl³⁵], 679 [(M+H)⁺, Cl³⁷].

Example B-223

1-[(5-Chloroindol-2-yl)sulfonyl]-2-[(N-methyl-N-methylsulfonylcarbamoyl)methyl]-4-[(6-methyl-4,5, 6,7-tetrahydrothiazolo[5,4-c]pyridin-2-yl]carbonyl] piperazine hydrochloride In the same manner as in Example B-62, the title compound was obtained.

¹H-NMR (DMSO-d₆) δ: 3.12–4.53(21H,m), 3.75–3.82 (0.5H,m), 4.35–4.45(1H,m), 5.09(0.5H,br s), 5.32–5.49 (0.5H,m), 5.85(0.5H,br s), 7.02(1H,s), 7.30(1H,dd,J=8.8,2.0 Hz), 7.47(1H,dd,J=8.8,2.0 Hz), 7.75(1H,s), 12.44(1H,br s). MS (FAB) m/z: 629 [(M+H)⁺, Cl³⁵], 631 [(M+H)⁺, Cl³⁷].

Example B-224

4-(5-Chloroindol-2-yl)sulfonyl]-2-[(2-methylsulfonylhyrazino)carbonylmethyl]-1-[(6-methyl-4,5,6,7-tetrahydrothiazolo[5,4-c]pyridin-2-yl]carbonyl]piperazine hydrochloride In the same manner as in Example B-62, the title compound was obtained.

$^1$H-NMR (DMSO-d$_6$) δ: 3.10–4.60(17H,m), 5.10–5.25 (1.5H,m), 5.40–5.55(1H,m), 5.90(0.5H,br s), 6.11–6.20 (0.5H,m), 6.74(0.5H,br s), 7.81(1H,s), 8.10(1H,d,J=8.6 Hz), 8.27(1H,d,J=8.6 Hz), 8.56(1H,s), 10.15–10.25(1H,m), 11.08 (1H,s), 11.99(1H,s), 13.22(1H,s). MS (FAB) m/z: 630 [(M+H)$^+$, Cl$^{35}$], 632 [(M+H)$^+$, Cl$^{37}$].

Example B-225

1-[[5(6)-chlorobenzimidazol-2-yl-]sulfonyl]-4-[(6-methyl-4,5,6,7-tetrahydrothiazolo[5,4-c]pyridin-2-yl)carbonyl]piperazine 1-[[5(6)-chlorobenzimidazol-2-yl-]sulfonyl]pyperazine (225 mg), 1-hydroxybenztriazole (11 mg) and 1-ethyl-3-(3-dimethylaminopropyl)-carbodiimide (148 mg) were successively added to a N,N-dimethylformamide solution (3.0 ml) containing lithium 6-methyl-4,5,6,7-tetrahydrothiazolo[5,4-c]pyridin-2-yl)carboxylate (153 mg), and stirred at room temperature for 28 hours. After concentration under reduced pressure, the reaction solution was divided into two layers by adding a dichloromethane and saturated sodium chloride solution. The organic layer was washed with a saturated sodium chloride solution, dried over sodium sulfate, and concentrated under reduced pressure. The obtained product was purified by chromatography on a silica gel column (dichloromethane:methanol=20:1), concentrated by adding ethanol (2 ml) and a 1N aqueous hydrochloride in ethanol (1.5 ml), and dried. Thus, the title compound (168 mg) was obtained as colorless amorphous.

IR (KBr) cm$^{-1}$ 1622, 1429, 1365, 1279, 1157, 1055, 1005, 970, 939, 922. $^1$H-NMR (DMSO-d$_6$) d, 2.90 (3H, s), 3.03–4.00 (10H, br), 4.40 (3H, br s), 4.63–4.77 (1H, m), 7.40 (1H, dd, J=8.8, 2.0 Hz), 7.72 (1H, d, J=8.8 Hz), 7.78 (1H, s), 11.48–11.65 (1H, br s). MS (FAB) m/z 481 [(M+H)$^+$, Cl$^{35}$], 483 [(M +H)$^+$, Cl$^{37}$].

Test 1

Measurement of FXa Inhibitory Action (IC$_{50}$)

In a 96-well microtiter plate, 10 μl of a sample solution, 40 μl of a 100 mM tris 200 mM sodium chloride 0.2% BSA (pH: 7.4) buffer and 10 μl of 0.05 U/ml human FXa ("Cosmobio-ERL HFXa-1011", dissolved in and diluted with a measuring buffer) were poured in portions, followed by the addition of 40 ml of 750 μM S2222 (product of Chromogenix). An increase (mOD/min) in the absorbance at 405 nm was measured at room temperature. From the below-described equation, an inhibitory ratio % of each sample was determined. On a logarithmic probability paper, the final concentration of the sample and inhibitory ratio % were plotted along the abscissa and the ordinate, respectively, whereby a 50% inhibitory concentration (IC$_{50}$) was determined.

Inhibitory ratio (%)=(1−OD of sample÷OD of control)×100

(Results)

The compound of the formula (I) having, in the structure thereof, an unsubstituted pyridylphenyl group as the group Q$^1$—Q$^2$— and a 7-chloronaphthyl, 5-chlorobenzofuranyl, 6-chlorobenzofuranyl, 5-chlorobenzothienyl or 5-chloro-1-methylindole group as the group Q$^A$ is found to have FXa activity 50% inhibitory concentration (IC$_{50}$) of 100 nM or greater (refer to Table 1).

TABLE 1

| Sample compound | Concentration (nM) of the sample at which 50% of Fxa activity is inhibited |
|---|---|
| Compound of Example A-1 | 123 |
| Compound of Example A-17 | 180 |
| Compound of Example A-83 | 2800 |
| Compound of Example A-85 | 1000 |
| Compound of Example A-86 | >10000 |
| Compound of Example A-91 | 7000 |
| Compound of Example A-96 | 450 |
| Compound of Example A-106 | 420 |

The compound similar to the compound of Example A-1 except for having a substituted pyridylphenyl group, pyridylpyrimidinyl group, pyridylpyrazyl group or pyridylpyridyl group instead of the pyridylphenyl group is found to have FXa inhibitory action improved by several times as much as that of the compound of Example A-1 (refer to Table 2).

TABLE 2

| Sample compound | Concentration (nM) of the sample at which 50% of Fxa activity is inhibited |
|---|---|
| Compound of Example A-152 | 38 |
| Compound of Example A-155 | 28 |
| Compound of Example A-123 | 23 |
| Compound of Example A-137 | 60 |
| Compound of Example A-4 | 54 |

The compound similar to that of Example A-1 except for having, as the group Q$^A$, a 6-chlorobenzothienyl group, 5-ethynylindolyl group or 5-chloroindolyl group instead of chloronaphthyl group is found to be particularly excellent in FXa inhibitory action (refer to Table 3).

| Sample compound | Concentration (nM) of the sample at which 50% of Fxa activity is inhibited |
|---|---|
| Compound of Example A-90 | 16 |
| Compound of Example A-101 | 9.5 |
| Compound of Example A-103 | 27 |
| Compound of Example A-181 | 15 |
| Compound of Example A-97 | 82 |
| Compound of Example A-98 | 125 |

The compound having, as the group Q$^1$—Q$^2$— a pyridylphenyl group is found to show a drastic improvement in the FXa inhibitory action when the nitrogen atom on the pyridine ring has been converted into N-oxide and the group $Q^A$ represents a 6-chlorobenzothienyl group, 5-ethynylindolyl group or 5-chloroindolyl group (refer to Table 4).

TABLE 4

| Sample compound | Concentration (nM) of the sample at which 50% of Fxa activity is inhibited |
|---|---|
| Compound of Example A-107 | 4.7 |
| Compound of Example A-117 | 10.5 |
| Compound of Example A-109 | 6.9 |
| Compound of Example A-116 | 8.6 |
| Compound of Example A-181 | 2.9 |
| Compound of Example A-120 | 14 |

The compound having, as the group $Q^1$—$Q^2$—, a heteroaryl group such as pyridylpyrimidinyl, pyridylpyrazinyl or pyridylthiazolyl group and, as the group $Q^A$, a 6-chlorobenzothienyl, 6-ethynylbenzothienyl, 5-chloroindolyl or 5-ethynylindolyl group is found to be improved in FXa inhibitory action (refer to Table 5).

TABLE 5

| Sample compound | Concentration (nM) of the sample at which 50% of Fxa activity is inhibited |
|---|---|
| Compound of Example A-132 | 5.6 |
| Compound of Example A-133 | 10 |
| Compound of Example A-105 | 2.4 |
| Compound of Example A-134 | 4.6 |
| Compound of Example A-138 | 5 |
| Compound of Example A-140 | 6.8 |
| Compound of Example A-131 | 19 |
| Compound of Example A-135 | 14 |
| Compound of Example A-183 | 4.7 |
| Compound of Example A-185 | 6.3 |
| Compound of Example A-186 | 1.9 |
| Compound of Example A-229 | 1.6 |
| Compound of Example A-231 | 2.3 |
| Compound of Example A-239 | 3.5 |
| Compound of Example A-216 | 15 |
| Compound of Example A-296 | 1.3 |

The compound having one or two substituents introduced in the group $Q^3$ is found to exhibit strong FXa inhibitory activity (refer to Table 6).

TABLE 6

| Sample compound | Concentration (nM) of the sample at which 50% of Fxa activity is inhibited |
|---|---|
| Compound of Example A-130 | 3.6 |
| Compound of Example A-173 | 10 |
| Compound of Example A-105 | 20 |
| Compound of Example A-224 | 7.6 |
| Compound of Example A-259 | 3.5 |
| Compound of Example A-277 | 2.7 |
| Compound of Example A-279 | 10 |
| Compound of Example A-293 | 1.9 |
| Compound of Example A-298 | 0.7 |

Compounds of Examples B-32, B-54, B-61, B-63 and B-99 exhibited FXa 50% inhibitory concentrations of 20 nM, 5.0 nM, 30 nM, 12.5 nM and 1.7 nM, respectively.

Test 2

Measurement of Thrombin Inhibitory Action ($IC_{50}$)

In a 96-well microtiter plate, 10 µl of a sample solution, 40 µl of a 100 mM tris.200 mM sodium chloride 0.2% BSA (pH: 7.4) buffer and 10 µl of 4 U/ml human thrombin (Sigma Chemical, dissolved in and diluted with a measuring buffer) were poured in portions, followed by the addition of 40 µl of 500 µM S2266 (product of Chromogenix). An increase (mOD/min) in the absorbance at 405 nm was measured at room temperature. From the below-described equation, an inhibitory ratio % of each sample was determined. On a logarithmic probability paper, the final concentration of the sample and inhibitory ratio % were plotted along the abscissa and the ordinate, respectively, whereby a 50% inhibitory concentration ($IC_{50}$) was found.

Inhibitory ratio (%)=(1−OD of sample÷OD of control)×100

The compound having, in the structure thereof, a heteroaryl group such as pyridylpyrimidinyl or pyridylpyrazinyl, a 6-chlorobenzothienyl group, a 6-ethynylbenzothienyl, a 5-ethynylindolyl group or a 5-chloroindolyl group; or the compound having, in the structure thereof, a 6-chlorobenzothienyl, 6-ethynylbenzothienyl, 5-ethynylindolyl or 5-chloroindolyl group, in addition to a heteroaryl group such as pyridylpyrimidinyl or pyridylpyrazinyl is found to exhibit markedly low thrombin-activity inhibitory action compared with excellent FXa inhibitory action (refer to Tables 7 and 8).

TABLE 7

| Sample compound | Concentration (nM) of the sample at which 50% of thrombin activity is inhibited |
|---|---|
| Compound of Example A-117 | 4100 |
| Compound of Example A-137 | 4100 |

TABLE 7-continued

| Sample compound | Concentration (nM) of the sample at which 50% of thrombin activity is inhibited |
|---|---|
| Compound of Example A-123 | 16000 |
| Compound of Example A-109 | 1550 |
| Compound of Example A-132 | >100000 |
| Compound of Example A-133 | 7700 |
| Compound of Example A-216 | >50000 |

TABLE 8

| Sample compound | Concentration (nM) of the sample at which 50% of thrombin action is inhibited |
|---|---|
| Compound of Example A-105 | 19000 |
| Compound of Example A-134 | 10200 |
| Compound of Example A-138 | 5900 |
| Compound of Example A-140 | 1370 |
| Compound of Example A-103 | 2220 |

The compound of Example B-54 exhibited a thrombin 50% inhibitory concentration of 1.05 μM.

Test 3

Measurement of Coagulation Extending Action (Measurement of Prothrombin Time)

Plasma (20 μl) and 20 μl of a sample solution were mixed. To the resulting mixture, 40 ml of cynplastin (product of Organon Teknika) was added and the coagulation time was measured. The concentration of the sample (CT2) at which the coagulation time of the plasma was increased twice was found and it was designated as an index of anticoagulant action.

The compound of Example 33 showed CT2 of 0.35 μM.

Test 4

Test of Oral Administration

1) Method

A sample was dissolved or suspended in a 0.5% (w/v) methyl cellulose solution and the resulting solution or suspension was orally administered (10 ml/kg) to a 8 to 11 week-old rat (Wistar male rat (Nippon SLC Co., Ltd.)) which had been fasted overnight. After administration of the sample, the blood to which 1/10 part by weight of 3.13% (w/v) sodium citrate had been added was collected from the cervical vein under anesthesia with halothane. The rat was awakened except during the blood collection. Feeding was re-started 6 hours after the blood collection. From each blood sample, the plasma was separated by centrifugal separation and anti-FXa activity in the blood and prothrombin time extending action were measured.

2) Measuring Method 2-1) Measurement of anti-FXa Activity in the Plasma

In a 96-well plate, 5 μl of the plasma was poured in portions, followed by the addition of 55 μl of a 8:1:2 mixture of 100 mM tris.200 mM sodium chloride.0.2% BSA (pH 7.4) buffer, water and 0.1 U/ml human Factor Xa solution (dissolved in and diluted with a measuring buffer) and 40 μl of 750 μM S-2222. After stirring for 10 seconds in a plate mixer, an increase (mOD/min) of the absorbance at 405 nm was measured at room temperature. The inhibitory ratio was calculated as follows:

An inhibitory ratio (%)=(1−OD of sample÷OD of control on average relative to blood-collecting time of sample)×100

2-2) Measurement of Coagulation Extending Action in Oral Administration (Measurement of Prothrombin Time)

To 20 μl of the plasma, 40 μl of cynplastin (Organon Teknika/USA) was added and the coagulation time was measured. The ratio of the prothrombin time after the administration of the sample relative to the prothrombin time before the administration of the sample was designated as an index of the coagulation extending action.

3) Results

The compound of Example A-60 showed an anti-FXa activity of 70% in the plasma one hour after the oral administration of 30 mg/kg of the sample. It extended the prothrombin time by 1.18 times.

The compound of Example B-36 showed an anti-FXa activity of 68% in the plasma one hour after the oral administration of 30 mg/kg of the sample. It extended the thrombin time.

Test 5

Testing Method of Anti-thrombus Effects in a Tissue Thromboplastin-derived Rat DIC Model A rat was anesthetized with halothane. After the collection of the blood (for measurement of the number of platelets, anti-FXa activity and TAT) from its cervical vein by using 1/10 part by weight of 3.13% (w/v) sodium citrate, the sample was administered orally. At an appropriate time after the administration, the rat was intraperitoneally anesthetized (1 mg/kg) with Nembutal (50 mg/ml pentobarbital sodium, Abott Laboratories), followed by intravenous drip of 0.2 U/ml of tissue thromboplastin (Thromboplastin C plus, Dade Diagnostics of P. R. Inc.,) from the femoral vein for one minute at a rate of 2.5 to 3.0 ml/kg/min. The blood was collected (for measuring the number of platelets and anti-FXa activity) from the cervical vein 10 minutes after the intravenous drip and the blood was collected (for measuring TAT) from the cervical vein 20 minutes after the blood collection. The number of platelets, anti-FXa activity in the plasma and TAT concentration of each blood sample were measured. The number of the platelets was measured by an automatic cytometer, while the anti-FXa activity in the plasma was measured in a similar manner to that described in Test 4.

For the measurement of TAT (Thrombin-anti Thrombin= complex), EnzygnostR TAT micro kit (Boering Verke) was employed.

As a result of the oral administration of 30 mg/kg of the compound of Example B-36, apparent anti-FXa action in the plasma was recognized and a decrease in the number of the platelets and an increase in the TAT concentration were suppressed (the tissue thromboplastin was administered one hour after the administration of the sample).

Capability of Exploitation in Industry

The compound according to the present invention has peculiar and excellent FXa inhibitory action so that it is useful as a coagulation suppressor, or a preventive and/or remedy for thrombosis or embolism.

Use of the compound of the present invention as a pharmaceutical can therefore treat or prevent various diseases caused by a thrombus or embolus such as cerebral infarction, cerebral embolism, myocardial infarction, pulmonary infarction, pulmonary embolism, Buerger's disease, deep vein thrombosis, disseminated intravascular coagulation syndrome, thrombus formation after valve replacement, reocclusion after revascularization, formation of a thrombus upon extracorporeal circulation or coagulation upon blood collection.

What is claimed is:

1. A compound represented by formula (I):

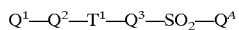     (I)

wherein

Q1 represents a saturated 5- or 6-membered cyclic hydrocarbon that is substituted or unsubstituted, an unsaturated 5- or 6-membered cyclic hydrocarbon that is substituted or unsubstituted, a saturated 5- or 6-membered heterocycle that is substituted or unsubstituted, an unsaturated 5- or 6-membered heterocycle that is substituted or unsubstituted, a saturated dicyclic fused ring that is substituted or unsubstituted, an unsaturated dicyclic fused ring that is substituted or unsubstituted, a saturated tricyclic fused ring group that is substituted or unsubstituted, or an unsaturated tricyclic fused ring group that is substituted or unsubstituted;

$Q^2$ represents a single bond or a group of the following formula:

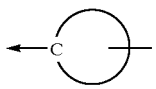

which represents a divalent saturated 5- or 6-membered cyclic hydrocarbon that is substituted or unsubstituted, a divalent unsaturated 5- or 6-membered cyclic hydrocarbon that is be substituted or unsubstituted, a divalent saturated 5- or 6-membered heterocycle that is substituted or unsubstituted, a divalent unsaturated 5- or 6-membered heterocycle that is substituted or unsubstituted, a divalent saturated dicyclic fused ring that is substituted or unsubstituted, a divalent unsaturated dicyclic fused ring that is substituted or unsubstituted, and wherein ←C is a bonding of a carbon atom to $Q^1$;

$T^1$ is a carbonyl group, a salt thereof, or a solvate thereof;

$Q^3$ represents the following formula

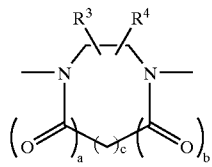

wherein a and b are 0, c is 2, and wherein $R^3$ and $R^4$ independently are a hydrogen atom, a hydroxyalkyl group, a cyanoalkyl group, a carboxyl group, a carboxyalkyl group, an alkoxycarbonyl group, an alkoxycarbonylalkyl group, a carboxyalkylaminocarbonyl group, a carboxyalkylaminocarbonylalkyl group, an alkoxycarbonylalkylaminocarbonyl group, an alkoxycarbonylalkylaminocarbonylamino group, a carbamoyl group, a monoalkylcarbamoyl group, a dialkylcarbamoyl group, a carbamoylalkyl group, a monoalkylcarbamoylalkyl group, a dialkylcarbamoylalkyl group, a morpholinylcarbonyl group, a morpholinylcarbonylalkyl group, a tetrazolylaminocarbonyl group, a tetrazolylaminocarbonylalkyl group, a tetrazolylalkyl group, a tetrazolylalkylaminocarbonyl group, a tetrazolylalkylaminocarbonylalkyl group, an unsubstituted aminoalkyl group, an aminoalkyl group that is singly or doubly substituted at the amino moiety thereof, an alkylaminosulfonylalkyl group, an oxopyrrolidinylalkyl group, oxopiperidinylalkyl group, or oxooxazolidinylalkyl group; and $Q^A$ is a substitute or unsubstituted phenylethylenyl moiety.

2. The compound according to claim 1, wherein $Q^A$ is

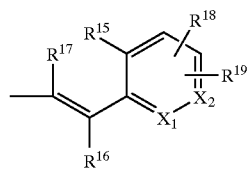

wherein $R^{15}$ is a hydrogen atom, a hydroxyl group, a nitro group, a cyano group, a halogen atom, an alkyl group, a hydroxyalkyl group, an alkoxyl group, an alkoxyalkyl group, a carboxyl group, a carboxyalkyl group, an alkylcarbonyl group, an alkoxycarbonyl group, an alkoxycarbonylalkyl group, an alkylcarbonyloxy group or a $A^3$—$B^3$— group wherein $A^3$ is a singly or doubly substituted amino group, a saturated 5- or 6-membered cyclic hydrocarbon that is substituted or unsubstituted, an unsaturated 5- or 6-membered cyclic hydrocarbon that is substituted or unsubstituted, a saturated 5- or 6-membered heterocycle that is substituted or unsubstituted, an unsaturated 5- or 6-membered heterocycle that is substituted or unsubstituted and $B^3$ is a single bond, a carbonyl group, an alkylene group, a carbonylalkyl group, a carbonylalkyloxy group or an alkylenecarbonyloxy group, $R^{16}$ and $R^{17}$ independently are a hydrogen atom, a halogen atom, an alkyl group, a hydroxyalkyl group having a protected or unprotected hydroxyl group, or an alkoxyalkyl group, $R^{18}$ and $R^{19}$ independently are a hydrogen atom, a hydroxyl group, a halogen atom, a halogenoalkyl group, an alkyl group, an alkoxyl group, an alkenyl group, an unsubstituted alkynyl group, an alkynyl group substituted by an alkylsilyl group, a trifluoromethyl group, a cyano group, an amino group, an aminoalkyl group, an alkylaminoalkyl group, an amidino group, a hydroxyamidino group or an alkoxycarbonylamidino group, with the proviso that $R^{18}$ and $R^{19}$ do not represent a hydrogen atom at the same time, and $X^1$ and $X^2$ each independently represents a methine group;

a salt thereof; or a solvate thereof.

3. The compound according to claim 2, wherein $R^{18}$ is a halogen atom or an ethynyl group; a salt thereof; or a solvate thereof.

4. The compound according to claims 1, wherein $Q^1$ is a substituted or unsubstituted cyclopentyl group, substituted or unsubstituted cyclohexyl group, substituted or unsubstituted cyclopentenyl group, substituted or unsubstituted cyclohexenyl group, substituted or unsubstituted phenyl group, substituted or unsubstituted pyrrolidinyl group, substituted or unsubstituted piperidinyl group, substituted or unsubstituted imidazolyl group, substituted or unsubstituted thiazolyl group, substituted or unsubstituted thiadiazolyl group, substituted or unsubstituted pyridyl group, substituted or unsubstituted pyrimidinyl group, substituted or unsubstituted pyridazinyl group, substituted or unsubstituted thiazolydinyl group, substituted or unsubstituted morpholinyl group, substituted or unsubstituted piperazinyl group, substituted or unsubstituted thiomorpholinyl group, substituted or unsubstituted pyrrolyl group, substituted or unsubstituted thienyl group, substituted or unsubstituted furanyl group, substituted or unsubstituted tetrahydropyrimidinyl group, substituted or unsubstituted tetrahydrofuranyl group, substituted or unsubstituted tetrahydrothienyl group, substituted or unsubstituted sulfolanyl group, substituted or unsubstituted imidazolinyl group, substituted or unsubstituted thiazolinyl group, substituted or unsubstituted oxazolyl group, substituted or unsubstituted oxadiazinyl group, substituted or unsubstituted triazinyl group, substituted or unsubstituted tetrazinyl group, substituted or unsubstituted pyrazinyl group, substituted or unsubstituted pyrazolyl group, substituted or unsubstituted pyrazolinyl group, substituted or unsubstituted pyrazolidinyl group, substituted or unsubstituted thienopyridyl group, substituted or unsubstituted tetrahydrothienopyridyl group, substituted or unsubstituted thiazolopyridyl group, substituted or unsubstituted tetrahydrothiazolopyridyl group, substituted or unsubstituted pyranothiazolyl group, substituted or unsubstituted dihydropyranothiazolyl group, substituted or unsubstituted thiazolopyridadinyl group, substituted or unsubstituted tetrahydrothiazolopyridadinyl group, substituted or unsubstituted furopyridyl group, substituted or unsubstituted tetrahydrofuropyridyl group, substituted or unsubstituted oxazolopyridyl group, or substituted or unsubstituted tetrahydrooxazolopyridyl group.

5. A medicament, comprising the compound according to claim 1.

6. A pharmaceutical composition, comprising the compound according to claim 1 and a pharmaceutically acceptable carrier.

7. An inhibitor for an activated coagulation factor X, comprising the compound according to claim 1.

8. A coagulation suppressor comprising the compound according to claim 1.

9. A method of treating, reducing, or arresting, thrombosis or embolism in a patient, comprising administering the compound according to claim 1 to a patient in need thereof.

10. A method of treating, reducing, or arresting cerebral infarction, cerebral embolism, myocardial infarction, pulmonary infarction, pulmonary embolism, Buerger's disease, deep vein thrombosis, disseminated intravascular coagulation syndrome, thrombus formation after valve replacement, reocclusion after revascularization, formation of thrombus upon extracorporeal circulation, or coagulation upon blood collection, comprising administering the compound according to claim 1 to a patient in need thereof.

11. A method of treating, reducing, or arresting, symptoms of thrombosis or embolism in a patient, comprising administering the compound according to claim 1 to a patient in need thereof.

12. A method of treating, reducing, or arresting symptoms of cerebral infarction, cerebral embolism, myocardial infarction, pulmonary infarction, pulmonary embolism, Buerger's disease, deep vein thrombosis, disseminated intravascular coagulation syndrome, thrombus formation after valve replacement, reocclusion after revascularization, formation of thrombus upon exgulation upon blood collection, comprising administering the compound according to claim 1 to a patient in need thereof.

13. A method of treating, inhibiting, reducing, or arresting, activated coagulation factor X, comprising administering the compound according to claim 1 to a patient in need thereof.

14. A method of treating, inhibiting, reducing, or arresting, coagulation, comprising administering the compound according to claim 1 to a patient in need thereof.

15. A method for treating, reducing, or arresting diseases caused by an activated coagulation factor X in a patient, comprising administering the compound according to claim 1 to a patient in need thereof.

16. A method for treating, reducing, or arresting diseases caused by coagulation in a patient, comprising administering the compound according to claim 1 to a patient in need thereof.

17. A method of treating, inhibiting, reducing, or arresting, symptoms of activated coagulation factor X in a patient, comprising administering the compound according to claim 1 to a patient in need thereof.

18. A method of treating, inhibiting, reducing, or arresting, symptoms of coagulation in a patient, comprising administering the compound according to claim 1 to a patient in need thereof.

19. A method for treating, reducing, or arresting symptoms diseases caused by an activated coagulation factor X in a patient, comprising administering the compound according to claim 1 to a patient in need thereof.

20. A method for treating, reducing, or arresting symptoms diseases caused by coagulation in a patient, comprising administering the compound according to claim 1 to a patient in need thereof.

21. A method, comprising contacting the compound according to claim 1 with a pharmaceutically acceptable carrier.

22. The compound according to claim 1, having the following chemical formula B-15

B-15:

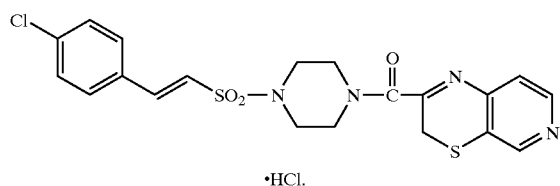

·HCl.

23. The compound according to claim 1, having the following chemical formula B-41

B-41:

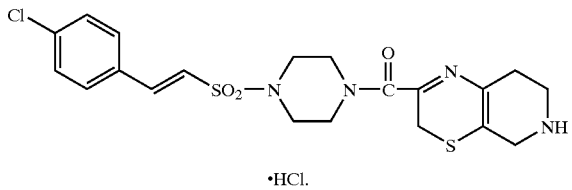

·HCl.

24. The compound according to claim 1, having the following chemical formula B-42

B-42:

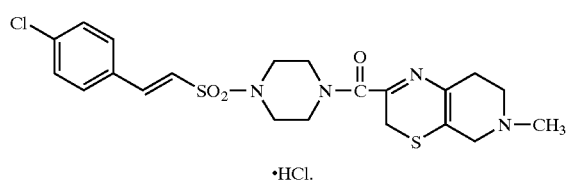

·HCl.

* * * * *